US010080809B2

(12) United States Patent
Thess

(10) Patent No.: US 10,080,809 B2
(45) **Date of Patent: *Sep. 25, 2018**

(54) ARTIFICIAL NUCLEIC ACID MOLECULES COMPRISING A 5'TOP UTR

(71) Applicant: CureVac AG, Tubingen (DE)

(72) Inventor: Andreas Thess, Kusterdingen (DE)

(73) Assignee: CureVac AG, Tübingen (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/388,224

(22) PCT Filed: Mar. 27, 2013

(86) PCT No.: PCT/EP2013/000938

§ 371 (c)(1),
(2) Date: Sep. 25, 2014

(87) PCT Pub. No.: WO2013/143700

PCT Pub. Date: Oct. 3, 2013

(65) Prior Publication Data

US 2015/0050302 A1 Feb. 19, 2015

(30) Foreign Application Priority Data

Mar. 27, 2012 (WO) ................. PCT/EP2012/001334
Jun. 8, 2012 (WO) ................. PCT/EP2012/002448

(51) Int. Cl.

| | |
|---|---|
| ***C12N 15/00*** | (2006.01) |
| ***C12N 15/67*** | (2006.01) |
| ***A61K 48/00*** | (2006.01) |
| ***C12N 15/85*** | (2006.01) |
| ***A61K 39/00*** | (2006.01) |
| *A61K 38/00* | (2006.01) |

(52) U.S. Cl.

CPC .......... *A61K 48/0066* (2013.01); *A61K 39/00* (2013.01); *C12N 15/67* (2013.01); *C12N 15/85* (2013.01); *A61K 38/00* (2013.01); *C12N 2830/50* (2013.01); *C12N 2830/85* (2013.01); *C12N 2840/105* (2013.01)

(58) Field of Classification Search

None

See application file for complete search history.

(56) References Cited

U.S. PATENT DOCUMENTS 5,908,779 A * 6/1999 Carmichael .......... C12N 15/113
435/320.1
8,217,016 B2 7/2012 Hoerr et al.
8,383,340 B2 2/2013 Ketterer et al.
8,703,906 B2 4/2014 Baumhof et al.
8,968,746 B2 3/2015 Baumhof et al.
9,155,788 B2 10/2015 Hoerr et al.
9,447,431 B2 9/2016 Thess et al.
2005/0009028 A1 1/2005 Heintz et al.
2005/0032730 A1 2/2005 Von Der Mülbe et al.
2005/0048549 A1 3/2005 Cao et al.
2005/0059624 A1 3/2005 Hoerr et al.
2005/0250723 A1 11/2005 Hoerr et al.
2006/0188490 A1 8/2006 Hoerr et al.
2007/0111203 A1* 5/2007 Cao ........................ C07K 14/52
435/6.12
2007/0172949 A9 7/2007 Liu et al.
2008/0025944 A1 1/2008 Hoerr et al.
2008/0267873 A1 10/2008 Hoerr et al.
2009/0324584 A1 12/2009 Hoerr et al.
2010/0048883 A1 2/2010 Ketterer et al.
2010/0120152 A1 5/2010 Wooddell et al.
2010/0129392 A1 5/2010 Shi et al.
2010/0189729 A1 7/2010 Hoerr et al.
2010/0203076 A1 8/2010 Fotin-Mleczek et al.
2010/0239608 A1 9/2010 Von Der Mülbe et al.
2010/0291156 A1 11/2010 Barner et al.
2010/0303851 A1 12/2010 Hoerr et al.
2010/0305196 A1 12/2010 Probst et al.
2011/0053829 A1 3/2011 Baumhof et al.
2011/0077287 A1 3/2011 Von Der Mülbe et al.
2011/0250225 A1 10/2011 Fotin-Mleczek et al.

(Continued)

FOREIGN PATENT DOCUMENTS

EA 010056 6/2008
WO WO 1995/015394 6/1995

(Continued)

OTHER PUBLICATIONS

Lorenzi et al., Intranasal vaccination with messenger RNA as a new approach in gene therapy: Use against tuberculosis. BMC Biotechnology 2010, 10:77.*
Kudla et al., High Guanine and Cytosine Content Increases mRNA Levels in Mammalian Cells. PLoS Biology, 2006, 4:0933-0942.*
Dugaiczyk et al., Nucleotide sequence and the encoded amino acids of human serum albumin mRNA. Proc. Nati Acad. Sci. USA vol. 79, pp. 71-75, Jan. 1982. (Year: 1982).*
Avni et al., "The 5' terminal oligopyrimidine tract confers translational control on TOP mRNAs in a cell type-and sequence context-dependent manner," *Nucleic Acids Research*, 25(5):995-1001, 1997.
Avni et al., "Vertebrate mRNAs with a 5'-terminal pyrimidine tract are candidates for translational repression in quiescent cells: characterization of the translational cis-regulatory element," *Mol. Cell. Biol.*, 14(6):3822-3833, 1994.

(Continued)

*Primary Examiner* — Scott Long
*Assistant Examiner* — Arthur S Leonard
(74) *Attorney, Agent, or Firm* — Parker Highlander PLLC

(57) ABSTRACT

The invention relates to an artificial nucleic acid molecule comprising at least one 5'UTR element which is derived from a TOP gene, at least one open reading frame and optionally at least one 3'UTR element comprising a nucleic acid sequence which is preferably derived from the 3'UTR of a gene providing a stable mRNA, such as an albumin gene, or from a variant of the 3'UTR of a gene providing a stable mRNA. The invention further relates to the use of such an artificial nucleic acid molecule in gene therapy and/or genetic vaccination.

17 Claims, 30 Drawing Sheets

Specification includes a Sequence Listing.

(56) References Cited

U.S. PATENT DOCUMENTS

| | | | |
|---|---|---|---|
| 2011/0269950 | A1 | 11/2011 | Von Der Mülbe et al. |
| 2011/0311472 | A1 | 12/2011 | Hoerr et al. |
| 2012/0009221 | A1 | 1/2012 | Hoerr et al. |
| 2012/0021043 | A1 | 1/2012 | Kramps et al. |
| 2012/0213818 | A1 | 8/2012 | Hoerr et al. |
| 2012/0258046 | A1 | 10/2012 | Mutzke |
| 2013/0121988 | A1 | 5/2013 | Hoerr et al. |
| 2013/0129754 | A1 | 5/2013 | Thess et al. |
| 2013/0195867 | A1 | 8/2013 | Hoerr et al. |
| 2013/0202645 | A1 | 8/2013 | Barner et al. |
| 2013/0251742 | A1 | 9/2013 | Probst et al. |
| 2013/0259879 | A1 | 10/2013 | Baumhof et al. |
| 2013/0273001 | A1 | 10/2013 | Hoerr et al. |
| 2013/0280283 | A1 | 10/2013 | Lorenz et al. |
| 2013/0295043 | A1 | 11/2013 | Kallen et al. |
| 2013/0336998 | A1 | 12/2013 | Kallen et al. |
| 2014/0037660 | A1 | 2/2014 | Fotin-Mleczek et al. |
| 2014/0147454 | A1 | 5/2014 | Chakraborty et al. |
| 2014/0294877 | A1 | 10/2014 | Baumhof et al. |
| 2015/0050302 | A1 | 2/2015 | Thess et al. |
| 2015/0057340 | A1 | 2/2015 | Thess et al. |
| 2015/0093413 | A1 | 4/2015 | Thess |
| 2015/0104476 | A1 | 4/2015 | Von Der Mülbe et al. |
| 2015/0118183 | A1 | 4/2015 | Baumhof |
| 2015/0118264 | A1 | 4/2015 | Baumhof et al. |
| 2015/0141498 | A1 | 5/2015 | Mutzke |
| 2015/0165006 | A1 | 6/2015 | Thess et al. |
| 2015/0184195 | A1 | 7/2015 | Thess et al. |
| 2015/0218554 | A1 | 8/2015 | Thess |
| 2015/0258214 | A1 | 9/2015 | Baumhof et al. |
| 2015/0306249 | A1 | 10/2015 | Baumhof et al. |
| 2015/0320847 | A1 | 11/2015 | Thess et al. |

FOREIGN PATENT DOCUMENTS

| | | | |
|---|---|---|---|
| WO | WO 1998/042856 | 10/1998 | |
| WO | WO 2001/012824 | 2/2001 | |
| WO | WO 2002/098443 | 12/2002 | |
| WO | WO 2005/035771 | 4/2005 | |
| WO | WO 2006/008154 | 1/2006 | |
| WO | WO 2006/024518 | 3/2006 | |
| WO | WO 2007/024708 | * 3/2007 | ............ A61K 48/00 |
| WO | WO 2009/030481 | 3/2009 | |
| WO | WO 2009/095226 | 8/2009 | |
| WO | WO 2010/023260 | 3/2010 | |
| WO | WO 2010/132867 | 11/2010 | |
| WO | WO 2011/069529 | 6/2011 | |
| WO | WO 2012/013326 | 2/2012 | |
| WO | WO 2012/019630 | 2/2012 | |
| WO | WO 2012/019780 | 2/2012 | |
| WO | WO 2012/116714 | 9/2012 | |
| WO | WO 2013/120626 | 8/2013 | |
| WO | WO 2013/120627 | 8/2013 | |
| WO | WO 2013/120628 | 8/2013 | |
| WO | WO 2013/120629 | 8/2013 | |
| WO | WO 2015/024665 | 2/2015 | |
| WO | WO 2015/024668 | 2/2015 | |

OTHER PUBLICATIONS

Battle and Doudna, "The stem-loop binding protein forms a highly stable and specific complex with the 3' stem-loop of histone mRNAs," *RNA*, 7:123-132, 2001.

Caldarola et al., "Translational regulation of terminal oligopyrimidine mRNAs induced by serum and amino acids involves distinct signaling events," *The Journal of Biological Chemistry*, 279(14):13522-135531, 2004.

Cameron et al., "Recent advances in transgenic technology," *Molecular Biotechnology*, 7:253-265, 1997.

Chakrabarti et al., "The mammalian target of rapamycin complex 1 regulates leptin biosynthesis in adipocytes at the level of translation: the role of the 5'-untranslated region in the expression of leptin messenger ribonucleic acid," *Molecular Endocrinology*, 22(10):2260-2267, 2008.

Collart et al., "A human histone H2B.1 variant gene, located on chromosome 1, utilizes alternative 3' end processing," *Journal of Cellular Biochemistry*, 50:374-385, 1992.

Damgaard and Lykke-Andersen, "Translational coregulation of 5'TOP mRNAs by TIA-1 and TIAR," *Genes Dev.*, 25:2057-2068, 2011.

Database EMBL Accession No. EM_STD:AB063609, "Homosapiens RPL36AL mRNA for ribosomal protein L36a-like, complete cds," 2002.

Database Geneseq Accession No. ATN08647, "Human transcriptional regulatory element SEQ ID No. 6587," 2008.

Davuluri et al., "CART classification of human 5' UTR sequences," *Genome Research*, 10(11):1807-1816, 2000.

Gallie et al., "The histone 3'-terminal stem-loop is necessary for translation in Chinese hamster ovary cells," *Nucleic Acids Res.*, 24(10):1954-1962, 1996.

Gerwitz et al., "Nucleic acid therapeutics: state of the art and future prospects," *Blood*, 92(3):712-736, 1998.

Ginn et al., "Gene therapy clinical trails worldwide to 2012—an update," *Journal of Gene Medicine*, 15:65-77, 2013.

Holtkamp et al., "Modification of antigen-encoding RNA increases stability, translational efficacy, and T-cell stimulatory capacity of dendritic cells," *Blood*, 108(13):4009-17, 2006.

Iadevaia et al., "All translation elongation factors and the e, f, and h subunits of translation initiation factor 3 are encoded by 5'-terminal oligopyrimidine (TOP) mRNAs," *RNA*, 14:1730-1736, 2008.

Kato et al., "Histone H2B as an antigen recognized by lung cancer-specific human monoclonal antibody HB4C5," *Human Antibodies and Hybridomas*, 2(2):94-101, 1991.

Knapinska et al., "Molecular mechanisms regulation mRNA stability: physiological and pathological significance," *Current Genomics*, 6(6):1-16, 2005.

Ledda et al., "Effect of 3' UTR length on the translational regulation of 5'-terminal oligopyrimidine mRNAs," *Gene*, 344:213-220, 2005.

Levy et al., "Oligopyrimidine tract at the 5' end of mammalian ribosomal protein mRNAs is required for their translational control," *Proc. Natl. Acad. Sci. USA*, 88:3319-3323, 1991.

Levy et al., "Sequence and functional characterization of the terminal exon of the human insulin receptor gene," *Biochim Biophys Acta.*, 1263(3):253-257, 1995.

Ling et al., "The histone 3'-terminal stem-loop-binding protein enhances translation through a functional and physical interaction with eukaryotic initiation factor 4G (eIF4G) and eIF3," *Mol Cell Biol.*, 22:7853-7867, 2002.

Lopez and Samuelsson, "Early evolution of histone mRNA 3' end processing," *Bioinformatics*, 14(1):1-10, 2008.

Meyuhas, "Synthesis of the translational apparatus is regulated at the translational level," *Eur. J Biochem.*, 267:6321-6330, 2000.

Montoliu, "Gene transfer strategies in animal transgenesis," *Cloning and Stem Cells*, 4(1):39-46, 2002.

Narita et al., "NELF interacts with CDC and participates in 3' end processing of replication-dependent histone mRNAs," *Molecular Cell*, 26(3):349-365, 2007.

Niemann, "Transgenic farm animals get off the ground," *Transgenic Research*, 7:73-75, 1998.

Office Action issued in U.S. Appl. No. 13/321,474, dated Apr. 6, 2015.

Office Action issued in U.S. Appl. No. 13/321,474, dated May 20, 2014.

Office Action issued in U.S. Appl. No. 14/378,538, dated Nov. 12, 2015.

Office Action issued in U.S. Appl. No. 14/378,606, dated May 27, 2015.

Office Action issued in U.S. Appl. No. 14/378,606, dated Nov. 13, 2015.

Office Action issued in U.S. Appl. No. 14/388,226, dated Nov. 6, 2015.

Orom et al., "MicroRNA-10a binds the 5'UTR of ribosomal protein mRNAs and enhances their translation," *Molecular Cell*, 30:460-471, 2008.

(56) References Cited

OTHER PUBLICATIONS

Pandey et al., "Introns in histone genes alter the distribution of 3' ends," *Nucleic Acids Res.*, 18(11):3161-3170, 1990.
PCT International Search Report and Written Opinion issued in International Application No. PCT/EP2013/000938, dated Nov. 13, 2013.
PCT International Search Report and Written Opinion issued in International Application No. PCT/EP2013/000461, dated Apr. 16, 2013.
PCT International Search Report and Written Opinion issued in International Application No. PCT/EP2013/000458, dated Apr. 24, 2013.
PCT International Search Report and Written Opinion issued in International Application No. PCT/EP2013/000459, dated Apr. 23, 2013.
PCT International Search Report and Written Opinion issued in International Application No. PCT/EP2013/000460, dated Apr. 22, 2013.
PCT International Search Report and Written Opinion issued in International Application No. PCT/EP2011/004077, dated Nov. 10, 2011.
PCT International Search Report and Written Opinion issued in International Application No. PCT/EP2013/000937, dated Aug. 30, 2013.
Prelle et al., "Establishment of pluripotent cell lines from vertebrate species—present status and future prospects," *Cells Tissues Organs*, 165:220-236, 1999.
Ristevski, "Making better transgenic models," *Molecular Biotechnology*, 29:153-163, 2005.
Roesler et al., "Immunize and disappear—safety-optimized mRNA vaccination with a panel of 29 allergens," *Journal of Allergy and Clinical Immunology*, 124(5):1070-1077, 2009.
Russell et al., "The stability of human beta-globin mRNA is dependent on structural determinants positioned within its 3' untranslated region," *Blood*, 87:5314-5323, 1996.
Sanchez et al., "Increased levels of polyadenylated histone H2B mRNA accumulate during *Entamoeba invadens* cyst formation," *Molecular and Biochemical Parasitology*, 67(1):137-146, 1994.
Sanchez et al., "The oligo(A) tail on histone mRNA plays an active role in translational silencing of histone mRNA during Xenopus oogenesis," *Mol Cell Biol.*, 24(6):2513-2525, 2004.
Shen et al., "Structures required for poly(A) tail-independent translation overlap with, but ar distinct from, cap-independent translation and RNA replication signals at the 3' end of *Tobacco necrosis* virus RNA," *Virology*, 358:448-458, 2007.
Sigmund, "Viewpoint: are studies in genetically altered mice out of control?" *Arteriosclerosis, Thrombosis, and Vascular Biology*, 20:1425-1429, 2000.
Smith, "Gene transfer in higher animals: theoretical considerations and key concepts," *Journal of Biotechnology*, 99:1-22, 2002.
Stauber et al., "A signal regulating mouse histone H4 mRNA levels in a mammalian cell cycle mutant and sequences controlling RNA 3' processing are both contained within the same 80-bp fragment," *EMBO J.*, 5(12):3297-3303, 1986.
Svoboda et al., "Hairpin RNA; a secondary structure of primary importance," *Cell Mol Life Sci.*, 63(7-8):901-908, 2006.
Thess et al., "Sequence-engineered mRNA without chemical nucleoside modifications enables an effective protein therapy in large animals," *Molecular Therapy*, pp. 1-9 and Supplementary Material, 2015.
Wagner et al., "A genome-wide RNA interference screen reveals that variant histones are necessary for replication-dependent histone pre-mRNA processing", *Molecular Cell*, 28(4):692-699, 2007.
Weiss et al., "Prophylactic mRNA vaccination against allergy," *Current Opinion in Allergy and Clinical Immunology*, 10(6):567-574, 2010.
Williams et al., "A simple, highly efficient method for heterologous expression in mammalian primary neurons using cationic lipid-mediated mRNA transfection," *Frontiers in Neuroscience*, 4:1-20, 2010.
Wooddell et al., "Sustained liver-specific transgene expression from the albumin promoter in mice following hydrodynamic plasmid DNA delivery," *The Journal of Gene Medicine*, 10:551-563, 2008.
Yamashita et al., "Comprehensive detection of human terminal oligo-pyrimidine (TOP) genes and analysis of their characteristics," *Nucleic Acids Res*, 36(11):3707-3715 and Supplementary Data (six pages), 2008.
Zhong et al., "A double-stranded RNA binding protein required for activation of repressed messages in mammalian germ cells," *Nat Genet.*, 22(2):171-174, 1999.
Zhu et al., "Binding of the La autoantigen to the 5' untranslated region of a chimeric human translation elongation factor 1A reporter mRNA inhibits translation in vitro," *Biochimica et Biophysica Acta*, 1521:19-29, 2001.
Attwood, "The babel of bioinformatics," *Science*, 290(5491):471-473, 2000.
Blumenthal et al., "Definition of an allergen (immunobiology)," *Allergens and Allergen Immunotherapy*, Ed. R. Lockey, S. Bukantz and J. Bousquet, pp. 37-50, 2004.
Cheung et al., "Specific interaction of HeLa cell proteins with coxsackievirus B3 3'UTR: La autoantigen binds the 3' and 5' UTR independently of the poly(A) tail," *Cell Microbiol.*, 9(7) :1705-1715, 2007.
Deml et al., "Multiple effects of codon usage optimization on expression and immunogenicity of DNA candidate vaccines encoding the human immunodeficiency virus type 1 Gag protein," Journal of Virology, 75(22):10991-11001, 2001.
Dollé et al., "Nerve growth factor overexpression and autocrine loop in breast cancer cells," *Oncogene*, 22(36):5592-5601, 2003.
Haines et al., "CL22—a novel cationic peptide for efficient transfection of mammalian cells," *Gene Ther.*, 8:99-110, 2001.
Henke et al., "Coxsackievirus B3 vaccines: use as an expression vector for prevention of myocarditis," *Expert Rev. Vaccines*, 7(10):1557-1567, 2008.
Kim et al., "Coxsackievirus B3 used as a gene therapy vector to express functional FGF2," *Gene Ther.*, 19(12):1159-1165, 2012.
Kim et al., "Systematic analysis of attenuated *Coxsackievirus* expressing a foreign gene as a viral vaccine vector," *Vaccine*, 28(5):1234-1240, 2010.
Kramarova et al., "A sequence predicted to form a stem-loop is proposed to be required for formation of an RNA-protein complex involving the 3'UTR of β-subunit $F_0F_1$-ATPase mRNA," *Biochim. Biophys. Acta.*, 1777(7-8):747-757, 2008.
Meier et al., "Fibroblast growth factor-2 but not Mel-CAM and/or β3 integrin promotes progression of melanocytes to melanoma," *Exp. Dermatol.*, 12(3):296-306, 2003.
Ngo et al., "Computational complexity, protein structure prediction, and the levinthal paradox," *The Protein Folding Problem and Tertiary Structure Prediction*, Ed. K. Merz and S. Le Grand, pp. 491-495, 1994.
Office Action issued in U.S. Appl. No. 14/378,572, dated Mar. 14, 2017.
Office Action issued in U.S. Appl. No. 14/378,591, dated Jan. 27, 2017.
Office Action issued in U.S. Appl. No. 14/945,349, dated Feb. 6, 2017.
Oliveira et al., "Inhibition of translational initiation in *Saccharomyces cerevisiae* by secondary structure: the roles of the stability and position of stem-loops in the mRNA leader," *Mol. Microbiol.*, 9(3):521-532, 1993.
Palmowski et al., "Intravenous injection of a lentiviral vector encoding NY-ESO-1 induces an effective CTL response," *J. Immunol.*, 172(3):1582-1587, 2004.
Sharma et al., "Functional role of the 5' terminal cloverleaf in Coxsackievirus RNA replication," *Virology*, 393 (2) :238-249, 2009.
Skolnick et al., "From genes to protein structure and function: novel applications of computational approaches in the genomic era," *Trends in Biotech.*, 18:34-39, 2000.
van Ooij et al., "Polyadenylation of genomic RNA and initiation of antigenomic RNA in a positive-strand RNA virus are controlled by the same cis-element," *Nucleic Acids Res.*, 34(10):2953-2965, 2006.

(56) References Cited

OTHER PUBLICATIONS

Dominski et al., "Stem-loop binding protein facilitates 3'-end formation by stabilizing U7 snRNP binding to histone pre-mRNA," *Mol Cell Biol.*, 19(5):3561-3570, 1999.
Eckner et al., "Mature mRNA 3' end formation stimulates RNA export from the nucleus," *The EMBO Journal*, 10(11):3513-3522, 1991.
Gorgoni et al., "The stem-loop binding protein stimulates histone translation at an early step in the initiation pathway," *RNA*, 11:1030-1042, 2005.
Office Action issued in U.S. Appl. No. 14/378,538, dated Jun. 21, 2016.
Office Action issued in U.S. Appl. No. 14/378,538, dated Oct. 11, 2016.
Office Action issued in U.S. Appl. No. 14/378,572, dated Aug. 12, 2016.
Office Action issued in U.S. Appl. No. 14/378,572, dated Mar. 3, 2016.
Office Action issued in U.S. Appl. No. 14/378,591, dated Aug. 22, 2016.
Office Action issued in U.S. Appl. No. 14/388,226, dated Jun. 21, 2016.
Shen and Higgins, "The 5' untranslated region-mediated enhancement of intracellular listeriolysin O production is required for *Listeria monocytogenes* pathogenicity," *Molecular Microbiology*, 57(5):1460-1473, 2005.

* cited by examiner

Nucleotide sequence of PpLuc(GC) – A64N64

GGGAGAAAGCTTGAGG*ATGGAGGACGCCAAGAACATCAAGAAGGGCCCGGCGCCCTTCTA*
*CCCGCTGGAGGACGGGACCGCCGGCGAGCAGCTCCACAAGGCCATGAAGCGGTACGCCCT*
*GGTGCCGGGCACGATCGCCTTCACCGACGCCCACATCGAGGTCGACATCACCTACGCGGA*
*GTACTTCGAGATGAGCGTGCGCCTGGCCGAGGCCATGAAGCGGTACGGCCTGAACACCAA*
*CCACCGGATCGTGGTGTGCTCGGAGAACAGCCTGCAGTTCTTCATGCCGGTGCTGGGCGC*
*CCTCTTCATCGGCGTGGCCGTCGCCCCGGCGAACGACATCTACAACGAGCGGGAGCTGCT*
*GAACAGCATGGGGATCAGCCAGCCGACCGTGGTGTTCGTGAGCAAGAAGGGCCTGCAGAA*
*GATCCTGAACGTGCAGAAGAAGCTGCCCATCATCCAGAAGATCATCATCATGGACAGCAA*
*GACCGACTACCAGGGCTTCCAGTCGATGTACACGTTCGTGACCAGCCACCTCCCGCCGGG*
*CTTCAACGAGTACGACTTCGTCCCGGAGAGCTTCGACCGGGACAAGACCATCGCCCTGAT*
*CATGAACAGCAGCGGCAGCACCGGCCTGCCGAAGGGGGTGGCCCTGCCGCACCGGACCGC*
*CTGCGTGCGCTTCTCGCACGCCCGGGACCCCATCTTCGGCAACCAGATCATCCCGGACAC*
*CGCCATCCTGAGCGTGGTGCCGTTCCACCACGGCTTCGGCATGTTCACGACCCTGGGCTA*
*CCTCATCTGCGGCTTCCGGGTGGTCCTGATGTACCGGTTCGAGGAGGAGCTGTTCCTGCG*
*GAGCCTGCAGGACTACAAGATCCAGAGCGCGCTGCTCGTGCCGACCCTGTTCAGCTTCTT*
*CGCCAAGAGCACCCTGATCGACAAGTACGACCTGTCGAACCTGCACGAGATCGCCAGCGG*
*GGGCGCCCCGCTGAGCAAGGAGGTGGGCGAGGCCGTGGCCAAGCGGTTCCACCTCCCGGG*
*CATCCGCCAGGGCTACGGCCTGACCGAGACCACGAGCGCGATCCTGATCACCCCCGAGGG*
*GGACGACAAGCCGGGCGCCGTGGGCAAGGTGGTCCCGTTCTTCGAGGCCAAGGTGGTGGA*
*CCTGGACACCGGCAAGACCCTGGGCGTGAACCAGCGGGGCGAGCTGTGCGTGCGGGGGCC*
*GATGATCATGAGCGGCTACGTGAACAACCCGGAGGCCACCAACGCCCTCATCGACAAGGA*
*CGGCTGGCTGCACAGCGGCGACATCGCCTACTGGGACGAGGACGAGCACTTCTTCATCGT*
*CGACCGGCTGAAGTCGCTGATCAAGTACAAGGGCTACCAGGTGGCGCCGGCCGAGCTGGA*
*GAGCATCCTGCTCCAGCACCCCAACATCTTCGACGCCGGCGTGGCCGGGCTGCCGGACGA*
*CGACGCCGGCGAGCTGCCGGCCGCGGTGGTGGTGCTGGAGCACGGCAAGACCATGACGGA*
*GAAGGAGATCGTCGACTACGTGGCCAGCCAGGTGACCACCGCCAAGAAGCTGCGGGGCGG*
*CGTGGTGTTCGTGGACGAGGTCCCGAAGGGCCTGACCGGGAAGCTCGACGCCCGGAAGAT*
*CCGCGAGATCCTGATCAAGGCCAAGAAGGGCGGCAAGATCGCCGTGTAA*GACTAGTAGAT
CTAAAAAAAAAAAAAAAAAAAAAAAAAAAAAAAAAAAAAAAAAAAAAAAAAAAAAAAAAA
AAAAAATGCATCCCCCCCCCCCCCCCCCCCCCCCCCCCCCCCAAAGGCTCTTTTCAGAGC
CACCAGAATT

Fig. 1

Nucleotide sequence of PpLuc(GC) – albumin7 – A64N64

GGGAGAAAGCTTGAGGATGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGTGCAT
CACATTTAAAAGCATCTCAGCCTACCATGAGAATAAGAGAAAGAAAATGAAGATCAATAG
CTTATTCATCTCTTTTTCTTTTTCGTTGGTGTAAAGCCAACACCCTGTCTAAAAAACATA
AATTTCTTTAATCATTTTGCCTCTTTTCTCTGTGCTTCAATTAATAAAAAATGGAAAGAA
CCTAGATCTAAAAAAAAAAAAAAAAAAAAAAAAAAAAAAAAAAAAAAAAAAAAAAAAAA
AAAAAAAAAAAAATGCATCCCCCCCCCCCCCCCCCCCCCCCCCCCCCCCAAAGGCTCTTT
TCAGAGCCACCAGAATT

Fig. 2

Nucleotide sequence of RPL32 – PpLuc(GC) – A64N64

GGGGCGCTGCCTACGGAGGTGGCAGCCATCTCCTTCTCGGCATCAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTAGATCTAAAAAAAAAAAAAAAAAAAA
AAAAAAAAAAAAAAAAAAAAAAAAAAAAAAAAAAAAAAAAAAAATGCATCCCCCCCCCCC
CCCCCCCCCCCCCCCCCCCCAAAGGCTCTTTTCAGAGCCACCAGAATT

Fig. 3

Nucleotide sequence of RPL32 – PpLuc(GC) – albumin7 – A64N64

GGGGCGCTGCCTACGGAGGTGGCAGCCATCTCCTTCTCGGCATCAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTGCATCACATTTAAAAGCATCTCAGCC
TACCATGAGAATAAGAGAAAGAAAATGAAGATCAATAGCTTATTCATCTCTTTTTCTTTT
TCGTTGGTGTAAAGCCAACACCCTGTCTAAAAAACATAAATTTCTTTAATCATTTTGCCT
CTTTTCTCTGTGCTTCAATTAATAAAAAATGGAAAGAACCTAGATCTAAAAAAAAAAAAA
AAAAAAAAAAAAAAAAAAAAAAAAAAAAAAAAAAAAAAAAAAAAAAAAAAAATGCATCCCC
CCCCCCCCCCCCCCCCCCCCCCCCCCAAAGGCTCTTTTCAGAGCCACCAGAATT

Fig. 4

Nucleotide sequence of RPL35 – PpLuc(GC) – albumin7 – A64N64

GGGGAGCGGGCGGCGGCGTTGGCGGCTTGTGCAGCAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTGCATCACATTTAAAAGCATCTCAGCCTACCATGA
GAATAAGAGAAAGAAAATGAAGATCAATAGCTTATTCATCTCTTTTTCTTTTTCGTTGGT
GTAAAGCCAACACCCTGTCTAAAAAACATAAATTTCTTTAATCATTTTGCCTCTTTTCTC
TGTGCTTCAATTAATAAAAAATGGAAAGAACCTAGATCTAAAAAAAAAAAAAAAAAAAAA
AAAAAAAAAAAAAAAAAAAAAAAAAAAAAAAAAAAAAAAAAAATGCATCCCCCCCCCCCC
CCCCCCCCCCCCCCCCCCCAAAGGCTCTTTTCAGAGCCACCAGAATT

Fig. 6

Nucleotide sequence of RPL21 – PpLuc(GC) – albumin7 – A64N64

GGGGCCGGAACCGCCATCTTCCAGTAATTCGCCAAAAAGCTTGAGG*ATGGAGGACGCCAA*
*GAACATCAAGAAGGGCCCGGCGCCCTTCTACCCGCTGGAGGACGGGACCGCCGGCGAGCA*
*GCTCCACAAGGCCATGAAGCGGTACGCCCTGGTGCCGGGCACGATCGCCTTCACCGACGC*
*CCACATCGAGGTCGACATCACCTACGCGGAGTACTTCGAGATGAGCGTGCGCCTGGCCGA*
*GGCCATGAAGCGGTACGGCCTGAACACCAACCACCGGATCGTGGTGTGCTCGGAGAACAG*
*CCTGCAGTTCTTCATGCCGGTGCTGGGCGCCCTCTTCATCGGCGTGGCCGTCGCCCCGGC*
*GAACGACATCTACAACGAGCGGGAGCTGCTGAACAGCATGGGGATCAGCCAGCCGACCGT*
*GGTGTTCGTGAGCAAGAAGGGCCTGCAGAAGATCCTGAACGTGCAGAAGAAGCTGCCCAT*
*CATCCAGAAGATCATCATCATGGACAGCAAGACCGACTACCAGGGCTTCCAGTCGATGTA*
*CACGTTCGTGACCAGCCACCTCCCGCCGGGCTTCAACGAGTACGACTTCGTCCCGGAGAG*
*CTTCGACCGGGACAAGACCATCGCCCTGATCATGAACAGCAGCGGCAGCACCGGCCTGCC*
*GAAGGGGGTGGCCCTGCCGCACCGGACCGCCTGCGTGCGCTTCTCGCACGCCCGGGACCC*
*CATCTTCGGCAACCAGATCATCCCGGACACCGCCATCCTGAGCGTGGTGCCGTTCCACCA*
*CGGCTTCGGCATGTTCACGACCCTGGGCTACCTCATCTGCGGCTTCCGGGTGGTCCTGAT*
*GTACCGGTTCGAGGAGGAGCTGTTCCTGCGGAGCCTGCAGGACTACAAGATCCAGAGCGC*
*GCTGCTCGTGCCGACCCTGTTCAGCTTCTTCGCCAAGAGCACCCTGATCGACAAGTACGA*
*CCTGTCGAACCTGCACGAGATCGCCAGCGGGGGCGCCCCGCTGAGCAAGGAGGTGGGCGA*
*GGCCGTGGCCAAGCGGTTCCACCTCCCGGGCATCCGCCAGGGCTACGGCCTGACCGAGAC*
*CACGAGCGCGATCCTGATCACCCCCGAGGGGGACGACAAGCCGGGCGCCGTGGGCAAGGT*
*GGTCCCGTTCTTCGAGGCCAAGGTGGTGGACCTGGACACCGGCAAGACCCTGGGCGTGAA*
*CCAGCGGGGCGAGCTGTGCGTGCGGGGGCCGATGATCATGAGCGGCTACGTGAACAACCC*
*GGAGGCCACCAACGCCCTCATCGACAAGGACGGCTGGCTGCACAGCGGCGACATCGCCTA*
*CTGGGACGAGGACGAGCACTTCTTCATCGTCGACCGGCTGAAGTCGCTGATCAAGTACAA*
*GGGCTACCAGGTGGCGCCGGCCGAGCTGGAGAGCATCCTGCTCCAGCACCCCAACATCTT*
*CGACGCCGGCGTGGCCGGGCTGCCGGACGACGACGCCGGCGAGCTGCCGGCCGCGGTGGT*
*GGTGCTGGAGCACGGCAAGACCATGACGGAGAAGGAGATCGTCGACTACGTGGCCAGCCA*
*GGTGACCACCGCCAAGAAGCTGCGGGGCGGCGTGGTGTTCGTGGACGAGGTCCCGAAGGG*
*CCTGACCGGGAAGCTCGACGCCCGGAAGATCCGCGAGATCCTGATCAAGGCCAAGAAGGG*
*CGGCAAGATCGCCGTGTAA*GACTAGTGCATCACATTTAAAAGCATCTCAGCCTACCATGA
GAATAAGAGAAAGAAAATGAAGATCAATAGCTTATTCATCTCTTTTTCTTTTTCGTTGGT
GTAAAGCCAACACCCTGTCTAAAAAACATAAATTTCTTTAATCATTTTGCCTCTTTTCTC
TGTGCTTCAATTAATAAAAAATGGAAAGAACCTAGATCTAAAAAAAAAAAAAAAAAAAAA
AAAAAAAAAAAAAAAAAAAAAAAAAAAAAAAAAAAAAAAAAAATGCATCCCCCCCCCCCCC
CCCCCCCCCCCCCCCCCAAAGGCTCTTTTCAGAGCCACCAGAATT

Fig. 7

Nucleotide sequence of atp5a1 – PpLuc(GC) – albumin7 – A64N64

GGGCGGCTCGGCCATTTTGTCCCAGTCAGTCCGGAGGCTGCGGCTGCAGAAGTACCGCCT
GCGGAGTAACTGCAAAGAAGCTTGAGGATGGAGGACGCCAAGAACATCAAGAAGGGCCCG
GCGCCCTTCTACCCGCTGGAGGACGGGACCGCCGGCGAGCAGCTCCACAAGGCCATGAAG
CGGTACGCCCTGGTGCCGGGCACGATCGCCTTCACCGACGCCCACATCGAGGTCGACATC
ACCTACGCGGAGTACTTCGAGATGAGCGTGCGCCTGGCCGAGGCCATGAAGCGGTACGGC
CTGAACACCAACCACCGGATCGTGGTGTGCTCGGAGAACAGCCTGCAGTTCTTCATGCCG
GTGCTGGGCGCCCTCTTCATCGGCGTGGCCGTCGCCCCGGCGAACGACATCTACAACGAG
CGGGAGCTGCTGAACAGCATGGGGATCAGCCAGCCGACCGTGGTGTTCGTGAGCAAGAAG
GGCCTGCAGAAGATCCTGAACGTGCAGAAGAAGCTGCCCATCATCCAGAAGATCATCATC
ATGGACAGCAAGACCGACTACCAGGGCTTCCAGTCGATGTACACGTTCGTGACCAGCCAC
CTCCCGCCGGGCTTCAACGAGTACGACTTCGTCCCGGAGAGCTTCGACCGGGACAAGACC
ATCGCCCTGATCATGAACAGCAGCGGCAGCACCGGCCTGCCGAAGGGGGTGGCCCTGCCG
CACCGGACCGCCTGCGTGCGCTTCTCGCACGCCCGGGACCCCATCTTCGGCAACCAGATC
ATCCCGGACACCGCCATCCTGAGCGTGGTGCCGTTCCACCACGGCTTCGGCATGTTCACG
ACCCTGGGCTACCTCATCTGCGGCTTCCGGGTGGTCCTGATGTACCGGTTCGAGGAGGAG
CTGTTCCTGCGGAGCCTGCAGGACTACAAGATCCAGAGCGCGCTGCTCGTGCCGACCCTG
TTCAGCTTCTTCGCCAAGAGCACCCTGATCGACAAGTACGACCTGTCGAACCTGCACGAG
ATCGCCAGCGGGGGCGCCCCGCTGAGCAAGGAGGTGGGCGAGGCCGTGGCCAAGCGGTTC
CACCTCCCGGGCATCCGCCAGGGCTACGGCCTGACCGAGACCACGAGCGCGATCCTGATC
ACCCCCGAGGGGGACGACAAGCCGGGCGCCGTGGGCAAGGTGGTCCCGTTCTTCGAGGCC
AAGGTGGTGGACCTGGACACCGGCAAGACCCTGGGCGTGAACCAGCGGGGCGAGCTGTGC
GTGCGGGGGCCGATGATCATGAGCGGCTACGTGAACAACCCGGAGGCCACCAACGCCCTC
ATCGACAAGGACGGCTGGCTGCACAGCGGCGACATCGCCTACTGGGACGAGGACGAGCAC
TTCTTCATCGTCGACCGGCTGAAGTCGCTGATCAAGTACAAGGGCTACCAGGTGGCGCCG
GCCGAGCTGGAGAGCATCCTGCTCCAGCACCCCAACATCTTCGACGCCGGCGTGGCCGGG
CTGCCGGACGACGACGCCGGCGAGCTGCCGGCCGCGGTGGTGGTGCTGGAGCACGGCAAG
ACCATGACGGAGAAGGAGATCGTCGACTACGTGGCCAGCCAGGTGACCACCGCCAAGAAG
CTGCGGGGCGGCGTGGTGTTCGTGGACGAGGTCCCGAAGGGCCTGACCGGGAAGCTCGAC
GCCCGGAAGATCCGCGAGATCCTGATCAAGGCCAAGAAGGGCGGCAAGATCGCCGTGTAA
GACTAGTGCATCACATTTAAAAGCATCTCAGCCTACCATGAGAATAAGAGAAAGAAAATG
AAGATCAATAGCTTATTCATCTCTTTTTCTTTTTCGTTGGTGTAAAGCCAACACCCTGTC
TAAAAAACATAAATTTCTTTAATCATTTTGCCTCTTTTCTCTGTGCTTCAATTAATAAAA
AATGGAAAGAACCTAGATCTAAAAAAAAAAAAAAAAAAAAAAAAAAAAAAAAAAAAAAAA
AAAAAAAAAAAAAAAAAAAAAAAATGCATCCCCCCCCCCCCCCCCCCCCCCCCCCCCCCC
AAAGGCTCTTTTCAGAGCCACCAGAATT

Fig. 8

Nucleotide sequence of HSD17B4 – PpLuc(GC) – albumin7 – A64N64

GGGTCCCGCAGTCGGCGTCCAGCGGCTCTGCTTGTTCGTGTGTGTGTCGTTGCAGGCCTT
ATTCAAGCTTGAGGATGGAGGACGCCAAGAACATCAAGAAGGGCCCGGCGCCCTTCTACC
CGCTGGAGGACGGGACCGCCGGCGAGCAGCTCCACAAGGCCATGAAGCGGTACGCCCTGG
TGCCGGGCACGATCGCCTTCACCGACGCCCACATCGAGGTCGACATCACCTACGCGGAGT
ACTTCGAGATGAGCGTGCGCCTGGCCGAGGCCATGAAGCGGTACGGCCTGAACACCAACC
ACCGGATCGTGGTGTGCTCGGAGAACAGCCTGCAGTTCTTCATGCCGGTGCTGGGCGCCC
TCTTCATCGGCGTGGCCGTCGCCCCGGCGAACGACATCTACAACGAGCGGGAGCTGCTGA
ACAGCATGGGGATCAGCCAGCCGACCGTGGTGTTCGTGAGCAAGAAGGGCCTGCAGAAGA
TCCTGAACGTGCAGAAGAAGCTGCCCATCATCCAGAAGATCATCATCATGGACAGCAAGA
CCGACTACCAGGGCTTCCAGTCGATGTACACGTTCGTGACCAGCCACCTCCCGCCGGGCT
TCAACGAGTACGACTTCGTCCCGGAGAGCTTCGACCGGGACAAGACCATCGCCCTGATCA
TGAACAGCAGCGGCAGCACCGGCCTGCCGAAGGGGGTGGCCCTGCCGCACCGGACCGCCT
GCGTGCGCTTCTCGCACGCCCGGGACCCCATCTTCGGCAACCAGATCATCCCGGACACCG
CCATCCTGAGCGTGGTGCCGTTCCACCACGGCTTCGGCATGTTCACGACCCTGGGCTACC
TCATCTGCGGCTTCCGGGTGGTCCTGATGTACCGGTTCGAGGAGGAGCTGTTCCTGCGGA
GCCTGCAGGACTACAAGATCCAGAGCGCGCTGCTCGTGCCGACCCTGTTCAGCTTCTTCG
CCAAGAGCACCCTGATCGACAAGTACGACCTGTCGAACCTGCACGAGATCGCCAGCGGGG
GCGCCCCGCTGAGCAAGGAGGTGGGCGAGGCCGTGGCCAAGCGGTTCCACCTCCCGGGCA
TCCGCCAGGGCTACGGCCTGACCGAGACCACGAGCGCGATCCTGATCACCCCCGAGGGGG
ACGACAAGCCGGGCGCCGTGGGCAAGGTGGTCCCGTTCTTCGAGGCCAAGGTGGTGGACC
TGGACACCGGCAAGACCCTGGGCGTGAACCAGCGGGGCGAGCTGTGCGTGCGGGGGCCGA
TGATCATGAGCGGCTACGTGAACAACCCGGAGGCCACCAACGCCCTCATCGACAAGGACG
GCTGGCTGCACAGCGGCGACATCGCCTACTGGGACGAGGACGAGCACTTCTTCATCGTCG
ACCGGCTGAAGTCGCTGATCAAGTACAAGGGCTACCAGGTGGCGCCGGCCGAGCTGGAGA
GCATCCTGCTCCAGCACCCCAACATCTTCGACGCCGGCGTGGCCGGGCTGCCGGACGACG
ACGCCGGCGAGCTGCCGGCCGCGGTGGTGGTGCTGGAGCACGGCAAGACCATGACGGAGA
AGGAGATCGTCGACTACGTGGCCAGCCAGGTGACCACCGCCAAGAAGCTGCGGGGCGGCG
TGGTGTTCGTGGACGAGGTCCCGAAGGGCCTGACCGGGAAGCTCGACGCCCGGAAGATCC
GCGAGATCCTGATCAAGGCCAAGAAGGGCGGCAAGATCGCCGTGTAAGACTAGTGCATCA
CATTTAAAAGCATCTCAGCCTACCATGAGAATAAGAGAAAGAAAATGAAGATCAATAGCT
TATTCATCTCTTTTTCTTTTTCGTTGGTGTAAAGCCAACACCCTGTCTAAAAAACATAAA
TTTCTTTAATCATTTTGCCTCTTTTCTCTGTGCTTCAATTAATAAAAAATGGAAAGAACC
TAGATCTAAAAAAAAAAAAAAAAAAAAAAAAAAAAAAAAAAAAAAAAAAAAAAAAAAAAA
AAAAAAAAAAATGCATCCCCCCCCCCCCCCCCCCCCCCCCCCCCCCAAAGGCTCTTTTC
AGAGCCACCAGAATT

Fig. 9

Nucleotide sequence of AIG1 – PpLuc(GC) – albumin7 – A64N64

GGGCCGCCCAGCCGGTCCAGGCCTCTGGCGAACAAGCTTGAGGATGGAGGACGCCAAGAA
CATCAAGAAGGGCCCGGCGCCCTTCTACCCGCTGGAGGACGGGACCGCCGGCGAGCAGCT
CCACAAGGCCATGAAGCGGTACGCCCTGGTGCCGGGCACGATCGCCTTCACCGACGCCCA
CATCGAGGTCGACATCACCTACGCGGAGTACTTCGAGATGAGCGTGCGCCTGGCCGAGGC
CATGAAGCGGTACGGCCTGAACACCAACCACCGGATCGTGGTGTGCTCGGAGAACAGCCT
GCAGTTCTTCATGCCGGTGCTGGGCGCCCTCTTCATCGGCGTGGCCGTCGCCCCGGCGAA
CGACATCTACAACGAGCGGGAGCTGCTGAACAGCATGGGGATCAGCCAGCCGACCGTGGT
GTTCGTGAGCAAGAAGGGCCTGCAGAAGATCCTGAACGTGCAGAAGAAGCTGCCCATCAT
CCAGAAGATCATCATCATGGACAGCAAGACCGACTACCAGGGCTTCCAGTCGATGTACAC
GTTCGTGACCAGCCACCTCCCGCCGGGCTTCAACGAGTACGACTTCGTCCCGGAGAGCTT
CGACCGGGACAAGACCATCGCCCTGATCATGAACAGCAGCGGCAGCACCGGCCTGCCGAA
GGGGGTGGCCCTGCCGCACCGGACCGCCTGCGTGCGCTTCTCGCACGCCCGGGACCCCAT
CTTCGGCAACCAGATCATCCCGGACACCGCCATCCTGAGCGTGGTGCCGTTCCACCACGG
CTTCGGCATGTTCACGACCCTGGGCTACCTCATCTGCGGCTTCCGGGTGGTCCTGATGTA
CCGGTTCGAGGAGGAGCTGTTCCTGCGGAGCCTGCAGGACTACAAGATCCAGAGCGCGCT
GCTCGTGCCGACCCTGTTCAGCTTCTTCGCCAAGAGCACCCTGATCGACAAGTACGACCT
GTCGAACCTGCACGAGATCGCCAGCGGGGGCGCCCCGCTGAGCAAGGAGGTGGGCGAGGC
CGTGGCCAAGCGGTTCCACCTCCCGGGCATCCGCCAGGGCTACGGCCTGACCGAGACCAC
GAGCGCGATCCTGATCACCCCCGAGGGGGACGACAAGCCGGGCGCCGTGGGCAAGGTGGT
CCCGTTCTTCGAGGCCAAGGTGGTGGACCTGGACACCGGCAAGACCCTGGGCGTGAACCA
GCGGGGCGAGCTGTGCGTGCGGGGGCCGATGATCATGAGCGGCTACGTGAACAACCCGGA
GGCCACCAACGCCCTCATCGACAAGGACGGCTGGCTGCACAGCGGCGACATCGCCTACTG
GGACGAGGACGAGCACTTCTTCATCGTCGACCGGCTGAAGTCGCTGATCAAGTACAAGGG
CTACCAGGTGGCGCCGGCCGAGCTGGAGAGCATCCTGCTCCAGCACCCCAACATCTTCGA
CGCCGGCGTGGCCGGGCTGCCGGACGACGACGCCGGCGAGCTGCCGGCCGCGGTGGTGGT
GCTGGAGCACGGCAAGACCATGACGGAGAAGGAGATCGTCGACTACGTGGCCAGCCAGGT
GACCACCGCCAAGAAGCTGCGGGGCGGCGTGGTGTTCGTGGACGAGGTCCCGAAGGGCCT
GACCGGGAAGCTCGACGCCCGGAAGATCCGCGAGATCCTGATCAAGGCCAAGAAGGGCGG
CAAGATCGCCGTGTAAGACTAGTGCATCACATTTAAAAGCATCTCAGCCTACCATGAGAA
TAAGAGAAAGAAAATGAAGATCAATAGCTTATTCATCTCTTTTTCTTTTTCGTTGGTGTA
AAGCCAACACCCTGTCTAAAAAACATAAATTTCTTTAATCATTTTGCCTCTTTTCTCTGT
GCTTCAATTAATAAAAAATGGAAAGAACCTAGATCTAAAAAAAAAAAAAAAAAAAAAAAA
AAAAAAAAAAAAAAAAAAAAAAAAAAAAAAAAAAAAAAAATGCATCCCCCCCCCCCCCCC
CCCCCCCCCCCCCCCAAAGGCTCTTTTCAGAGCCACCAGAATT

Fig. 10

Nucleotide sequence of COX6C – PpLuc(GC) – albumin7 – A64N64

GGAGTCAGGAAGGACGTTGGTGTTGAGGTTAGCATACGTATCAAGGACAGTAACTACCAA
GCTTGAGGATGGAGGACGCCAAGAACATCAAGAAGGGCCCGGCGCCCTTCTACCCGCTGG
AGGACGGGACCGCCGGCGAGCAGCTCCACAAGGCCATGAAGCGGTACGCCCTGGTGCCGG
GCACGATCGCCTTCACCGACGCCCACATCGAGGTCGACATCACCTACGCGGAGTACTTCG
AGATGAGCGTGCGCCTGGCCGAGGCCATGAAGCGGTACGGCCTGAACACCAACCACCGGA
TCGTGGTGTGCTCGGAGAACAGCCTGCAGTTCTTCATGCCGGTGCTGGGCGCCCTCTTCA
TCGGCGTGGCCGTCGCCCCGGCGAACGACATCTACAACGAGCGGGAGCTGCTGAACAGCA
TGGGGATCAGCCAGCCGACCGTGGTGTTCGTGAGCAAGAAGGGCCTGCAGAAGATCCTGA
ACGTGCAGAAGAAGCTGCCCATCATCCAGAAGATCATCATCATGGACAGCAAGACCGACT
ACCAGGGCTTCCAGTCGATGTACACGTTCGTGACCAGCCACCTCCCGCCGGGCTTCAACG
AGTACGACTTCGTCCCGGAGAGCTTCGACCGGGACAAGACCATCGCCCTGATCATGAACA
GCAGCGGCAGCACCGGCCTGCCGAAGGGGGTGGCCCTGCCGCACCGGACCGCCTGCGTGC
GCTTCTCGCACGCCCGGGACCCCATCTTCGGCAACCAGATCATCCCGGACACCGCCATCC
TGAGCGTGGTGCCGTTCCACCACGGCTTCGGCATGTTCACGACCCTGGGCTACCTCATCT
GCGGCTTCCGGGTGGTCCTGATGTACCGGTTCGAGGAGGAGCTGTTCCTGCGGAGCCTGC
AGGACTACAAGATCCAGAGCGCGCTGCTCGTGCCGACCCTGTTCAGCTTCTTCGCCAAGA
GCACCCTGATCGACAAGTACGACCTGTCGAACCTGCACGAGATCGCCAGCGGGGGCGCCC
CGCTGAGCAAGGAGGTGGGCGAGGCCGTGGCCAAGCGGTTCCACCTCCCGGGCATCCGCC
AGGGCTACGGCCTGACCGAGACCACGAGCGCGATCCTGATCACCCCCGAGGGGGACGACA
AGCCGGGCGCCGTGGGCAAGGTGGTCCCGTTCTTCGAGGCCAAGGTGGTGGACCTGGACA
CCGGCAAGACCCTGGGCGTGAACCAGCGGGGCGAGCTGTGCGTGCGGGGGCCGATGATCA
TGAGCGGCTACGTGAACAACCCGGAGGCCACCAACGCCCTCATCGACAAGGACGGCTGGC
TGCACAGCGGCGACATCGCCTACTGGGACGAGGACGAGCACTTCTTCATCGTCGACCGGC
TGAAGTCGCTGATCAAGTACAAGGGCTACCAGGTGGCGCCGGCCGAGCTGGAGAGCATCC
TGCTCCAGCACCCCAACATCTTCGACGCCGGCGTGGCCGGGCTGCCGGACGACGACGCCG
GCGAGCTGCCGGCCGCGGTGGTGGTGCTGGAGCACGGCAAGACCATGACGGAGAAGGAGA
TCGTCGACTACGTGGCCAGCCAGGTGACCACCGCCAAGAAGCTGCGGGGCGGCGTGGTGT
TCGTGGACGAGGTCCCGAAGGGCCTGACCGGGAAGCTCGACGCCCGGAAGATCCGCGAGA
TCCTGATCAAGGCCAAGAAGGGCGGCAAGATCGCCGTGTAAGACTAGTGCATCACATTTA
AAAGCATCTCAGCCTACCATGAGAATAAGAGAAAGAAAATGAAGATCAATAGCTTATTCA
TCTCTTTTTCTTTTTCGTTGGTGTAAAGCCAACACCCTGTCTAAAAAACATAAATTTCTT
TAATCATTTTGCCTCTTTTCTCTGTGCTTCAATTAATAAAAAATGGAAAGAACCTAGATC
TAAAAAAAAAAAAAAAAAAAAAAAAAAAAAAAAAAAAAAAAAAAAAAAAAAAAAAAAAAA
AAAAATGCATCCCCCCCCCCCCCCCCCCCCCCCCCCCCCCCAAAGGCTCTTTTCAGAGCC
ACCAGAATT

Fig. 11

Nucleotide sequence of ASAH1 – PpLuc(GC) – albumin7 – A64N64

GGGCCTCTGCTGGAGTCCGGGGAGTGGCGTTGGCTGCTAGAGCGAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTGCATCACATTTAAAAGCATCTCAGCC
TACCATGAGAATAAGAGAAAGAAAATGAAGATCAATAGCTTATTCATCTCTTTTTCTTTT
TCGTTGGTGTAAAGCCAACACCCTGTCTAAAAAACATAAATTTCTTTAATCATTTTGCCT
CTTTTCTCTGTGCTTCAATTAATAAAAAATGGAAAGAACCTAGATCTAAAAAAAAAAAAA
AAAAAAAAAAAAAAAAAAAAAAAAAAAAAAAAAAAAAAAAAAAAAAAAAAATGCATCCCC
CCCCCCCCCCCCCCCCCCCCCCCCCCCAAAGGCTCTTTTCAGAGCCACCAGAATT

Fig. 12

Nucleotide sequence of mRPL21 – PpLuc(GC) – albumin7 – A64N64

GGGGCCGCCGCAGCCATCTTCCAGTAACTCGCCAAAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTGCATCACATTTAAAAGCATCTCAGCCTACCATGA
GAATAAGAGAAAGAAAATGAAGATCAATAGCTTATTCATCTCTTTTTCTTTTTCGTTGGT
GTAAAGCCAACACCCTGTCTAAAAAACATAAATTTCTTTAATCATTTTGCCTCTTTTCTC
TGTGCTTCAATTAATAAAAAATGGAAAGAACCTAGATCTAAAAAAAAAAAAAAAAAAAAA
AAAAAAAAAAAAAAAAAAAAAAAAAAAAAAAAAAAAAAAAAAATGCATCCCCCCCCCCCC
CCCCCCCCCCCCCCCCCCCAAAGGCTCTTTTCAGAGCCACCAGAATT

Fig. 13

Nucleotide sequence of mRPL35A – PpLuc(GC) – albumin7 – A64N64

GGGCCATCTTGGCGCCTGTGGAGGCCTGCTGGGAACAGGACTTCTAACAGCAAGTAAGCT
TGAGGATGGAGGACGCCAAGAACATCAAGAAGGGCCCGGCGCCCTTCTACCCGCTGGAGG
ACGGGACCGCCGGCGAGCAGCTCCACAAGGCCATGAAGCGGTACGCCCTGGTGCCGGGCA
CGATCGCCTTCACCGACGCCCACATCGAGGTCGACATCACCTACGCGGAGTACTTCGAGA
TGAGCGTGCGCCTGGCCGAGGCCATGAAGCGGTACGGCCTGAACACCAACCACCGGATCG
TGGTGTGCTCGGAGAACAGCCTGCAGTTCTTCATGCCGGTGCTGGGCGCCCTCTTCATCG
GCGTGGCCGTCGCCCCGGCGAACGACATCTACAACGAGCGGGAGCTGCTGAACAGCATGG
GGATCAGCCAGCCGACCGTGGTGTTCGTGAGCAAGAAGGGCCTGCAGAAGATCCTGAACG
TGCAGAAGAAGCTGCCCATCATCCAGAAGATCATCATCATGGACAGCAAGACCGACTACC
AGGGCTTCCAGTCGATGTACACGTTCGTGACCAGCCACCTCCCGCCGGGCTTCAACGAGT
ACGACTTCGTCCCGGAGAGCTTCGACCGGGACAAGACCATCGCCCTGATCATGAACAGCA
GCGGCAGCACCGGCCTGCCGAAGGGGGTGGCCCTGCCGCACCGGACCGCCTGCGTGCGCT
TCTCGCACGCCCGGGACCCCATCTTCGGCAACCAGATCATCCCGGACACCGCCATCCTGA
GCGTGGTGCCGTTCCACCACGGCTTCGGCATGTTCACGACCCTGGGCTACCTCATCTGCG
GCTTCCGGGTGGTCCTGATGTACCGGTTCGAGGAGGAGCTGTTCCTGCGGAGCCTGCAGG
ACTACAAGATCCAGAGCGCGCTGCTCGTGCCGACCCTGTTCAGCTTCTTCGCCAAGAGCA
CCCTGATCGACAAGTACGACCTGTCGAACCTGCACGAGATCGCCAGCGGGGGCGCCCCGC
TGAGCAAGGAGGTGGGCGAGGCCGTGGCCAAGCGGTTCCACCTCCCGGGCATCCGCCAGG
GCTACGGCCTGACCGAGACCACGAGCGCGATCCTGATCACCCCCGAGGGGGACGACAAGC
CGGGCGCCGTGGGCAAGGTGGTCCCGTTCTTCGAGGCCAAGGTGGTGGACCTGGACACCG
GCAAGACCCTGGGCGTGAACCAGCGGGGCGAGCTGTGCGTGCGGGGGCCGATGATCATGA
GCGGCTACGTGAACAACCCGGAGGCCACCAACGCCCTCATCGACAAGGACGGCTGGCTGC
ACAGCGGCGACATCGCCTACTGGGACGAGGACGAGCACTTCTTCATCGTCGACCGGCTGA
AGTCGCTGATCAAGTACAAGGGCTACCAGGTGGCGCCGGCCGAGCTGGAGAGCATCCTGC
TCCAGCACCCCAACATCTTCGACGCCGGCGTGGCCGGGCTGCCGGACGACGACGCCGGCG
AGCTGCCGGCCGCGGTGGTGGTGCTGGAGCACGGCAAGACCATGACGGAGAAGGAGATCG
TCGACTACGTGGCCAGCCAGGTGACCACCGCCAAGAAGCTGCGGGGCGGCGTGGTGTTCG
TGGACGAGGTCCCGAAGGGCCTGACCGGGAAGCTCGACGCCCGGAAGATCCGCGAGATCC
TGATCAAGGCCAAGAAGGGCGGCAAGATCGCCGTGTAAGACTAGTGCATCACATTTAAAA
GCATCTCAGCCTACCATGAGAATAAGAGAAAGAAAATGAAGATCAATAGCTTATTCATCT
CTTTTTCTTTTTCGTTGGTGTAAAGCCAACACCCTGTCTAAAAAACATAAATTTCTTTAA
TCATTTTGCCTCTTTTCTCTGTGCTTCAATTAATAAAAAATGGAAAGAACCTAGATCTAA
AAAAAAAAAAAAAAAAAAAAAAAAAAAAAAAAAAAAAAAAAAAAAAAAAAAAAAAAAAAAAAAA
AATGCATCCCCCCCCCCCCCCCCCCCCCCCCCCCCCCCCCCCAAAGGCTCTTTTCAGAGCCACC
AGAATT

Fig. 14

Nucleotide sequence of RPL35 – PpLuc(GC) – A64N64

GG<u>GGAGCGGGCGGCGGCGTTGGCGGCTTGTGCAGCA</u>AAGCTTGAGG*ATGGAGGACGCCAA*
*GAACATCAAGAAGGGCCCGGCGCCCTTCTACCCGCTGGAGGACGGGACCGCCGGCGAGCA*
*GCTCCACAAGGCCATGAAGCGGTACGCCCTGGTGCCGGGCACGATCGCCTTCACCGACGC*
*CCACATCGAGGTCGACATCACCTACGCGGAGTACTTCGAGATGAGCGTGCGCCTGGCCGA*
*GGCCATGAAGCGGTACGGCCTGAACACCAACCACCGGATCGTGGTGTGCTCGGAGAACAG*
*CCTGCAGTTCTTCATGCCGGTGCTGGGCGCCCTCTTCATCGGCGTGGCCGTCGCCCCGGC*
*GAACGACATCTACAACGAGCGGGAGCTGCTGAACAGCATGGGGATCAGCCAGCCGACCGT*
*GGTGTTCGTGAGCAAGAAGGGCCTGCAGAAGATCCTGAACGTGCAGAAGAAGCTGCCCAT*
*CATCCAGAAGATCATCATCATGGACAGCAAGACCGACTACCAGGGCTTCCAGTCGATGTA*
*CACGTTCGTGACCAGCCACCTCCCGCCGGGCTTCAACGAGTACGACTTCGTCCCGGAGAG*
*CTTCGACCGGGACAAGACCATCGCCCTGATCATGAACAGCAGCGGCAGCACCGGCCTGCC*
*GAAGGGGGTGGCCCTGCCGCACCGGACCGCCTGCGTGCGCTTCTCGCACGCCCGGGACCC*
*CATCTTCGGCAACCAGATCATCCCGGACACCGCCATCCTGAGCGTGGTGCCGTTCCACCA*
*CGGCTTCGGCATGTTCACGACCCTGGGCTACCTCATCTGCGGCTTCCGGGTGGTCCTGAT*
*GTACCGGTTCGAGGAGGAGCTGTTCCTGCGGAGCCTGCAGGACTACAAGATCCAGAGCGC*
*GCTGCTCGTGCCGACCCTGTTCAGCTTCTTCGCCAAGAGCACCCTGATCGACAAGTACGA*
*CCTGTCGAACCTGCACGAGATCGCCAGCGGGGGCGCCCCGCTGAGCAAGGAGGTGGGCGA*
*GGCCGTGGCCAAGCGGTTCCACCTCCCGGGCATCCGCCAGGGCTACGGCCTGACCGAGAC*
*CACGAGCGCGATCCTGATCACCCCCGAGGGGGACGACAAGCCGGGCGCCGTGGGCAAGGT*
*GGTCCCGTTCTTCGAGGCCAAGGTGGTGGACCTGGACACCGGCAAGACCCTGGGCGTGAA*
*CCAGCGGGGCGAGCTGTGCGTGCGGGGGCCGATGATCATGAGCGGCTACGTGAACAACCC*
*GGAGGCCACCAACGCCCTCATCGACAAGGACGGCTGGCTGCACAGCGGCGACATCGCCTA*
*CTGGGACGAGGACGAGCACTTCTTCATCGTCGACCGGCTGAAGTCGCTGATCAAGTACAA*
*GGGCTACCAGGTGGCGCCGGCCGAGCTGGAGAGCATCCTGCTCCAGCACCCCAACATCTT*
*CGACGCCGGCGTGGCCGGGCTGCCGGACGACGACGCCGGCGAGCTGCCGGCCGCGGTGGT*
*GGTGCTGGAGCACGGCAAGACCATGACGGAGAAGGAGATCGTCGACTACGTGGCCAGCCA*
*GGTGACCACCGCCAAGAAGCTGCGGGGCGGCGTGGTGTTCGTGGACGAGGTCCCGAAGGG*
*CCTGACCGGGAAGCTCGACGCCCGGAAGATCCGCGAGATCCTGATCAAGGCCAAGAAGGG*
*CGGCAAGATCGCCGTGTAA*GACTAGTAGATCTAAAAAAAAAAAAAAAAAAAAAAAAAAAA
AAAAAAAAAAAAAAAAAAAAAAAAAAAAAAAAAAAATGCATCCCCCCCCCCCCCCCCCCC
CCCCCCCCCCCCAAAGGCTCTTTTCAGAGCCACCAGAATT

Fig. 15

Nucleotide sequence of RPL21 – PpLuc(GC) – A64N64

GGGGCCGGAACCGCCATCTTCCAGTAATTCGCCAAAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTAGATCTAAAAAAAAAAAAAAAAAAAAAAAAAAAA
AAAAAAAAAAAAAAAAAAAAAAAAAAAAAAAAAAAATGCATCCCCCCCCCCCCCCCCCCC
CCCCCCCCCCCCAAAGGCTCTTTTCAGAGCCACCAGAATT

Fig. 16

Nucleotide sequence of atp5a1 – PpLuc(GC) – A64N64

GGGCGGCTCGGCCATTTTGTCCCAGTCAGTCCGGAGGCTGCGGCTGCAGAAGTACCGCCT
GCGGAGTAACTGCAAAGAAGCTTGAGGATGGAGGACGCCAAGAACATCAAGAAGGGCCCG
GCGCCCTTCTACCCGCTGGAGGACGGGACCGCCGGCGAGCAGCTCCACAAGGCCATGAAG
CGGTACGCCCTGGTGCCGGGCACGATCGCCTTCACCGACGCCCACATCGAGGTCGACATC
ACCTACGCGGAGTACTTCGAGATGAGCGTGCGCCTGGCCGAGGCCATGAAGCGGTACGGC
CTGAACACCAACCACCGGATCGTGGTGTGCTCGGAGAACAGCCTGCAGTTCTTCATGCCG
GTGCTGGGCGCCCTCTTCATCGGCGTGGCCGTCGCCCCGGCGAACGACATCTACAACGAG
CGGGAGCTGCTGAACAGCATGGGGATCAGCCAGCCGACCGTGGTGTTCGTGAGCAAGAAG
GGCCTGCAGAAGATCCTGAACGTGCAGAAGAAGCTGCCCATCATCCAGAAGATCATCATC
ATGGACAGCAAGACCGACTACCAGGGCTTCCAGTCGATGTACACGTTCGTGACCAGCCAC
CTCCCGCCGGGCTTCAACGAGTACGACTTCGTCCCGGAGAGCTTCGACCGGGACAAGACC
ATCGCCCTGATCATGAACAGCAGCGGCAGCACCGGCCTGCCGAAGGGGGTGGCCCTGCCG
CACCGGACCGCCTGCGTGCGCTTCTCGCACGCCCGGGACCCCATCTTCGGCAACCAGATC
ATCCCGGACACCGCCATCCTGAGCGTGGTGCCGTTCCACCACGGCTTCGGCATGTTCACG
ACCCTGGGCTACCTCATCTGCGGCTTCCGGGTGGTCCTGATGTACCGGTTCGAGGAGGAG
CTGTTCCTGCGGAGCCTGCAGGACTACAAGATCCAGAGCGCGCTGCTCGTGCCGACCCTG
TTCAGCTTCTTCGCCAAGAGCACCCTGATCGACAAGTACGACCTGTCGAACCTGCACGAG
ATCGCCAGCGGGGGCGCCCCGCTGAGCAAGGAGGTGGGCGAGGCCGTGGCCAAGCGGTTC
CACCTCCCGGGCATCCGCCAGGGCTACGGCCTGACCGAGACCACGAGCGCGATCCTGATC
ACCCCCGAGGGGGACGACAAGCCGGGCGCCGTGGGCAAGGTGGTCCCGTTCTTCGAGGCC
AAGGTGGTGGACCTGGACACCGGCAAGACCCTGGGCGTGAACCAGCGGGGCGAGCTGTGC
GTGCGGGGGCCGATGATCATGAGCGGCTACGTGAACAACCCGGAGGCCACCAACGCCCTC
ATCGACAAGGACGGCTGGCTGCACAGCGGCGACATCGCCTACTGGGACGAGGACGAGCAC
TTCTTCATCGTCGACCGGCTGAAGTCGCTGATCAAGTACAAGGGCTACCAGGTGGCGCCG
GCCGAGCTGGAGAGCATCCTGCTCCAGCACCCCAACATCTTCGACGCCGGCGTGGCCGGG
CTGCCGGACGACGACGCCGGCGAGCTGCCGGCCGCGGTGGTGGTGCTGGAGCACGGCAAG
ACCATGACGGAGAAGGAGATCGTCGACTACGTGGCCAGCCAGGTGACCACCGCCAAGAAG
CTGCGGGGCGGCGTGGTGTTCGTGGACGAGGTCCCGAAGGGCCTGACCGGGAAGCTCGAC
GCCCGGAAGATCCGCGAGATCCTGATCAAGGCCAAGAAGGGCGGCAAGATCGCCGTGTAA
GACTAGTAGATCTAAAAAAAAAAAAAAAAAAAAAAAAAAAAAAAAAAAAAAAAAAAAAA
AAAAAAAAAAAAAAAAATGCATCCCCCCCCCCCCCCCCCCCCCCCCCCCCCCCAAAGGCT
CTTTTCAGAGCCACCAGAATT

Fig. 17

Nucleotide sequence of HSD17B4 – PpLuc(GC) – A64N64

GGGTCCCGCAGTCGGCGTCCAGCGGCTCTGCTTGTTCGTGTGTGTGTCGTTGCAGGCCTT
ATTCAAGCTTGAGG*ATGGAGGACGCCAAGAACATCAAGAAGGGCCCGGCGCCCTTCTACC*
*CGCTGGAGGACGGGACCGCCGGCGAGCAGCTCCACAAGGCCATGAAGCGGTACGCCCTGG*
*TGCCGGGCACGATCGCCTTCACCGACGCCCACATCGAGGTCGACATCACCTACGCGGAGT*
*ACTTCGAGATGAGCGTGCGCCTGGCCGAGGCCATGAAGCGGTACGGCCTGAACACCAACC*
*ACCGGATCGTGGTGTGCTCGGAGAACAGCCTGCAGTTCTTCATGCCGGTGCTGGGCGCCC*
*TCTTCATCGGCGTGGCCGTCGCCCCGGCGAACGACATCTACAACGAGCGGGAGCTGCTGA*
*ACAGCATGGGGATCAGCCAGCCGACCGTGGTGTTCGTGAGCAAGAAGGGCCTGCAGAAGA*
*TCCTGAACGTGCAGAAGAAGCTGCCCATCATCCAGAAGATCATCATCATGGACAGCAAGA*
*CCGACTACCAGGGCTTCCAGTCGATGTACACGTTCGTGACCAGCCACCTCCCGCCGGGCT*
*TCAACGAGTACGACTTCGTCCCGGAGAGCTTCGACCGGGACAAGACCATCGCCCTGATCA*
*TGAACAGCAGCGGCAGCACCGGCCTGCCGAAGGGGGTGGCCCTGCCGCACCGGACCGCCT*
*GCGTGCGCTTCTCGCACGCCCGGGACCCCATCTTCGGCAACCAGATCATCCCGGACACCG*
*CCATCCTGAGCGTGGTGCCGTTCCACCACGGCTTCGGCATGTTCACGACCCTGGGCTACC*
*TCATCTGCGGCTTCCGGGTGGTCCTGATGTACCGGTTCGAGGAGGAGCTGTTCCTGCGGA*
*GCCTGCAGGACTACAAGATCCAGAGCGCGCTGCTCGTGCCGACCCTGTTCAGCTTCTTCG*
*CCAAGAGCACCCTGATCGACAAGTACGACCTGTCGAACCTGCACGAGATCGCCAGCGGGG*
*GCGCCCCGCTGAGCAAGGAGGTGGGCGAGGCCGTGGCCAAGCGGTTCCACCTCCCGGGCA*
*TCCGCCAGGGCTACGGCCTGACCGAGACCACGAGCGCGATCCTGATCACCCCCGAGGGG*
*ACGACAAGCCGGGCGCCGTGGGCAAGGTGGTCCCGTTCTTCGAGGCCAAGGTGGTGGACC*
*TGGACACCGGCAAGACCCTGGGCGTGAACCAGCGGGGCGAGCTGTGCGTGCGGGGGCCGA*
*TGATCATGAGCGGCTACGTGAACAACCCGGAGGCCACCAACGCCCTCATCGACAAGGACG*
*GCTGGCTGCACAGCGGCGACATCGCCTACTGGGACGAGGACGAGCACTTCTTCATCGTCG*
*ACCGGCTGAAGTCGCTGATCAAGTACAAGGGCTACCAGGTGGCGCCGGCCGAGCTGGAGA*
*GCATCCTGCTCCAGCACCCCAACATCTTCGACGCCGGCGTGGCCGGGCTGCCGGACGACG*
*ACGCCGGCGAGCTGCCGGCCGCGGTGGTGGTGCTGGAGCACGGCAAGACCATGACGGAGA*
*AGGAGATCGTCGACTACGTGGCCAGCCAGGTGACCACCGCCAAGAAGCTGCGGGGCGGCG*
*TGGTGTTCGTGGACGAGGTCCCGAAGGGCCTGACCGGGAAGCTCGACGCCCGGAAGATCC*
*GCGAGATCCTGATCAAGGCCAAGAAGGGCGGCAAGATCGCCGTGTAA*GACTAGTAGATCT
AAAAAAAAAAAAAAAAAAAAAAAAAAAAAAAAAAAAAAAAAAAAAAAAAAAAAAAAAAAA
AAAATGCATCCCCCCCCCCCCCCCCCCCCCCCCCCCCCCCAAAGGCTCTTTTCAGAGCCA
CCAGAATT

Fig. 18

Nucleotide sequence of AIG1 – PpLuc(GC) – A64N64

GGGCCGCCCAGCCGGTCCAGGCCTCTGGCGAACAAGCTTGAGG*ATGGAGGACGCCAAGAA*
*CATCAAGAAGGGCCCGGCGCCCTTCTACCCGCTGGAGGACGGGACCGCCGGCGAGCAGCT*
*CCACAAGGCCATGAAGCGGTACGCCCTGGTGCCGGGCACGATCGCCTTCACCGACGCCCA*
*CATCGAGGTCGACATCACCTACGCGGAGTACTTCGAGATGAGCGTGCGCCTGGCCGAGGC*
*CATGAAGCGGTACGGCCTGAACACCAACCACCGGATCGTGGTGTGCTCGGAGAACAGCCT*
*GCAGTTCTTCATGCCGGTGCTGGGCGCCCTCTTCATCGGCGTGGCCGTCGCCCCGGCGAA*
*CGACATCTACAACGAGCGGGAGCTGCTGAACAGCATGGGGATCAGCCAGCCGACCGTGGT*
*GTTCGTGAGCAAGAAGGGCCTGCAGAAGATCCTGAACGTGCAGAAGAAGCTGCCCATCAT*
*CCAGAAGATCATCATCATGGACAGCAAGACCGACTACCAGGGCTTCCAGTCGATGTACAC*
*GTTCGTGACCAGCCACCTCCCGCCGGGCTTCAACGAGTACGACTTCGTCCCGGAGAGCTT*
*CGACCGGGACAAGACCATCGCCCTGATCATGAACAGCAGCGGCAGCACCGGCCTGCCGAA*
*GGGGGTGGCCCTGCCGCACCGGACCGCCTGCGTGCGCTTCTCGCACGCCCGGGACCCCAT*
*CTTCGGCAACCAGATCATCCCGGACACCGCCATCCTGAGCGTGGTGCCGTTCCACCACGG*
*CTTCGGCATGTTCACGACCCTGGGCTACCTCATCTGCGGCTTCCGGGTGGTCCTGATGTA*
*CCGGTTCGAGGAGGAGCTGTTCCTGCGGAGCCTGCAGGACTACAAGATCCAGAGCGCGCT*
*GCTCGTGCCGACCCTGTTCAGCTTCTTCGCCAAGAGCACCCTGATCGACAAGTACGACCT*
*GTCGAACCTGCACGAGATCGCCAGCGGGGGCGCCCCGCTGAGCAAGGAGGTGGGCGAGGC*
*CGTGGCCAAGCGGTTCCACCTCCCGGGCATCCGCCAGGGCTACGGCCTGACCGAGACCAC*
*GAGCGCGATCCTGATCACCCCCGAGGGGGACGACAAGCCGGGCGCCGTGGGCAAGGTGGT*
*CCCGTTCTTCGAGGCCAAGGTGGTGGACCTGGACACCGGCAAGACCCTGGGCGTGAACCA*
*GCGGGGCGAGCTGTGCGTGCGGGGGCCGATGATCATGAGCGGCTACGTGAACAACCCGGA*
*GGCCACCAACGCCCTCATCGACAAGGACGGCTGGCTGCACAGCGGCGACATCGCCTACTG*
*GGACGAGGACGAGCACTTCTTCATCGTCGACCGGCTGAAGTCGCTGATCAAGTACAAGGG*
*CTACCAGGTGGCGCCGGCCGAGCTGGAGAGCATCCTGCTCCAGCACCCCAACATCTTCGA*
*CGCCGGCGTGGCCGGGCTGCCGGACGACGACGCCGGCGAGCTGCCGGCCGCGGTGGTGGT*
*GCTGGAGCACGGCAAGACCATGACGGAGAAGGAGATCGTCGACTACGTGGCCAGCCAGGT*
*GACCACCGCCAAGAAGCTGCGGGGCGGCGTGGTGTTCGTGGACGAGGTCCCGAAGGGCCT*
*GACCGGGAAGCTCGACGCCCGGAAGATCCGCGAGATCCTGATCAAGGCCAAGAAGGGCGG*
*CAAGATCGCCGTGTAA*GACTAGTAGATCTAAAAAAAAAAAAAAAAAAAAAAAAAAAAAAA
AAAAAAAAAAAAAAAAAAAAAAAAAAAAAAAAATGCATCCCCCCCCCCCCCCCCCCCCCC
CCCCCCCCCAAAGGCTCTTTTCAGAGCCACCAGAATT

Fig. 19

Nucleotide sequence of COX6C – PpLuc(GC) – A64N64

GGAGTCAGGAAGGACGTTGGTGTTGAGGTTAGCATACGTATCAAGGACAGTAACTACCAA
GCTTGAGG*ATGGAGGACGCCAAGAACATCAAGAAGGGCCCGGCGCCCTTCTACCCGCTGG*
*AGGACGGGACCGCCGGCGAGCAGCTCCACAAGGCCATGAAGCGGTACGCCCTGGTGCCGG*
*GCACGATCGCCTTCACCGACGCCCACATCGAGGTCGACATCACCTACGCGGAGTACTTCG*
*AGATGAGCGTGCGCCTGGCCGAGGCCATGAAGCGGTACGGCCTGAACACCAACCACCGGA*
*TCGTGGTGTGCTCGGAGAACAGCCTGCAGTTCTTCATGCCGGTGCTGGGCGCCCTCTTCA*
*TCGGCGTGGCCGTCGCCCCGGCGAACGACATCTACAACGAGCGGGAGCTGCTGAACAGCA*
*TGGGGATCAGCCAGCCGACCGTGGTGTTCGTGAGCAAGAAGGGCCTGCAGAAGATCCTGA*
*ACGTGCAGAAGAAGCTGCCCATCATCCAGAAGATCATCATCATGGACAGCAAGACCGACT*
*ACCAGGGCTTCCAGTCGATGTACACGTTCGTGACCAGCCACCTCCCGCCGGGCTTCAACG*
*AGTACGACTTCGTCCCGGAGAGCTTCGACCGGGACAAGACCATCGCCCTGATCATGAACA*
*GCAGCGGCAGCACCGGCCTGCCGAAGGGGGTGGCCCTGCCGCACCGGACCGCCTGCGTGC*
*GCTTCTCGCACGCCCGGGACCCCATCTTCGGCAACCAGATCATCCCGGACACCGCCATCC*
*TGAGCGTGGTGCCGTTCCACCACGGCTTCGGCATGTTCACGACCCTGGGCTACCTCATCT*
*GCGGCTTCCGGGTGGTCCTGATGTACCGGTTCGAGGAGGAGCTGTTCCTGCGGAGCCTGC*
*AGGACTACAAGATCCAGAGCGCGCTGCTCGTGCCGACCCTGTTCAGCTTCTTCGCCAAGA*
*GCACCCTGATCGACAAGTACGACCTGTCGAACCTGCACGAGATCGCCAGCGGGGGCGCCC*
*CGCTGAGCAAGGAGGTGGGCGAGGCCGTGGCCAAGCGGTTCCACCTCCCGGGCATCCGCC*
*AGGGCTACGGCCTGACCGAGACCACGAGCGCGATCCTGATCACCCCCGAGGGGGACGACA*
*AGCCGGGCGCCGTGGGCAAGGTGGTCCCGTTCTTCGAGGCCAAGGTGGTGGACCTGGACA*
*CCGGCAAGACCCTGGGCGTGAACCAGCGGGGCGAGCTGTGCGTGCGGGGGCCGATGATCA*
*TGAGCGGCTACGTGAACAACCCGGAGGCCACCAACGCCCTCATCGACAAGGACGGCTGGC*
*TGCACAGCGGCGACATCGCCTACTGGGACGAGGACGAGCACTTCTTCATCGTCGACCGGC*
*TGAAGTCGCTGATCAAGTACAAGGGCTACCAGGTGGCGCCGGCCGAGCTGGAGAGCATCC*
*TGCTCCAGCACCCCAACATCTTCGACGCCGGCGTGGCCGGGCTGCCGGACGACGACGCCG*
*GCGAGCTGCCGGCCGCGGTGGTGGTGCTGGAGCACGGCAAGACCATGACGGAGAAGGAGA*
*TCGTCGACTACGTGGCCAGCCAGGTGACCACCGCCAAGAAGCTGCGGGGCGGCGTGGTGT*
*TCGTGGACGAGGTCCCGAAGGGCCTGACCGGGAAGCTCGACGCCCGGAAGATCCGCGAGA*
*TCCTGATCAAGGCCAAGAAGGGCGGCAAGATCGCCGTGTAA*GACTAGTAGATCTAAAAAA
AAAAAAAAAAAAAAAAAAAAAAAAAAAAAAAAAAAAAAAAAAAAAAAAAAAAAAAAAATG
CATCCCCCCCCCCCCCCCCCCCCCCCCCCCCCCCCAAAGGCTCTTTTCAGAGCCACCAGAA
TT

Fig. 20

Nucleotide sequence of ASAH1 – PpLuc(GC) – A64N64

GGGCCTCTGCTGGAGTCCGGGGAGTGGCGTTGGCTGCTAGAGCGAAGCTTGAGG*ATGGAG*
*GACGCCAAGAACATCAAGAAGGGCCCGGCGCCCTTCTACCCGCTGGAGGACGGGACCGCC*
*GGCGAGCAGCTCCACAAGGCCATGAAGCGGTACGCCCTGGTGCCGGGCACGATCGCCTTC*
*ACCGACGCCCACATCGAGGTCGACATCACCTACGCGGAGTACTTCGAGATGAGCGTGCGC*
*CTGGCCGAGGCCATGAAGCGGTACGGCCTGAACACCAACCACCGGATCGTGGTGTGCTCG*
*GAGAACAGCCTGCAGTTCTTCATGCCGGTGCTGGGCGCCCTCTTCATCGGCGTGGCCGTC*
*GCCCCGGCGAACGACATCTACAACGAGCGGGAGCTGCTGAACAGCATGGGGATCAGCCAG*
*CCGACCGTGGTGTTCGTGAGCAAGAAGGGCCTGCAGAAGATCCTGAACGTGCAGAAGAAG*
*CTGCCCATCATCCAGAAGATCATCATCATGGACAGCAAGACCGACTACCAGGGCTTCCAG*
*TCGATGTACACGTTCGTGACCAGCCACCTCCCGCCGGGCTTCAACGAGTACGACTTCGTC*
*CCGGAGAGCTTCGACCGGGACAAGACCATCGCCCTGATCATGAACAGCAGCGGCAGCACC*
*GGCCTGCCGAAGGGGGTGGCCCTGCCGCACCGGACCGCCTGCGTGCGCTTCTCGCACGCC*
*CGGGACCCCATCTTCGGCAACCAGATCATCCCGGACACCGCCATCCTGAGCGTGGTGCCG*
*TTCCACCACGGCTTCGGCATGTTCACGACCCTGGGCTACCTCATCTGCGGCTTCCGGGTG*
*GTCCTGATGTACCGGTTCGAGGAGGAGCTGTTCCTGCGGAGCCTGCAGGACTACAAGATC*
*CAGAGCGCGCTGCTCGTGCCGACCCTGTTCAGCTTCTTCGCCAAGAGCACCCTGATCGAC*
*AAGTACGACCTGTCGAACCTGCACGAGATCGCCAGCGGGGGCGCCCCGCTGAGCAAGGAG*
*GTGGGCGAGGCCGTGGCCAAGCGGTTCCACCTCCCGGGCATCCGCCAGGGCTACGGCCTG*
*ACCGAGACCACGAGCGCGATCCTGATCACCCCCGAGGGGGACGACAAGCCGGGCGCCGTG*
*GGCAAGGTGGTCCCGTTCTTCGAGGCCAAGGTGGTGGACCTGGACACCGGCAAGACCCTG*
*GGCGTGAACCAGCGGGGCGAGCTGTGCGTGCGGGGGCCGATGATCATGAGCGGCTACGTG*
*AACAACCCGGAGGCCACCAACGCCCTCATCGACAAGGACGGCTGGCTGCACAGCGGCGAC*
*ATCGCCTACTGGGACGAGGACGAGCACTTCTTCATCGTCGACCGGCTGAAGTCGCTGATC*
*AAGTACAAGGGCTACCAGGTGGCGCCGGCCGAGCTGGAGAGCATCCTGCTCCAGCACCCC*
*AACATCTTCGACGCCGGCGTGGCCGGGCTGCCGGACGACGACGCCGGCGAGCTGCCGGCC*
*GCGGTGGTGGTGCTGGAGCACGGCAAGACCATGACGGAGAAGGAGATCGTCGACTACGTG*
*GCCAGCCAGGTGACCACCGCCAAGAAGCTGCGGGGCGGCGTGGTGTTCGTGGACGAGGTC*
*CCGAAGGGCCTGACCGGGAAGCTCGACGCCCGGAAGATCCGCGAGATCCTGATCAAGGCC*
*AAGAAGGGCGGCAAGATCGCCGTGTAA*GACTAGTAGATCTAAAAAAAAAAAAAAAAAAAA
AAAAAAAAAAAAAAAAAAAAAAAAAAAAAAAAAAAAAAAAAAAATGCATCCCCCCCCCCC
CCCCCCCCCCCCCCCCCCCCAAAGGCTCTTTTCAGAGCCACCAGAATT

Fig. 21

ARTIFICIAL NUCLEIC ACID MOLECULES COMPRISING A 5'TOP UTR

This application is a national phase application under 35 U.S.C. § 371 of International Application No. PCT/EP2013/000938, filed Mar. 27, 2013, which claims priority to International Application No. PCT/EP2012/001334, filed Mar. 27, 2012, and International Application No. PCT/EP2012/002448, filed Jun. 8, 2012. The entire text of each of the above referenced disclosures is specifically incorporated herein by reference.

The invention relates to artificial nucleic acid molecules comprising a 5'UTR element derived from the 5'UTR of a TOP gene, an open reading frame, and optionally a 3'UTR element, a poly(A) sequence and/or a polyadenylation signal. The invention relates further to a vector comprising a 5'UTR element derived from the 5'UTR of a TOP gene, to a pharmaceutical composition comprising the artificial nucleic acid molecule or the vector, and to a kit comprising the artificial nucleic acid molecule, the vector and/or the pharmaceutical composition, preferably for use in the field of gene therapy and/or genetic vaccination.

Gene therapy and genetic vaccination belong to the most promising and quickly developing methods of modern medicine. They may provide highly specific and individual options for therapy of a large variety of diseases. Particularly, inherited genetic diseases but also autoimmune diseases, cancerous or tumour-related diseases as well as inflammatory diseases may be the subject of such treatment approaches. Also, it is envisaged to prevent (early) onset of such diseases by these approaches.

The main conceptual rational behind gene therapy is appropriate modulation of impaired gene expression associated with pathological conditions of specific diseases. Pathologically altered gene expression may result in lack or overproduction of essential gene products, for example, signalling factors such as hormones, housekeeping factors, metabolic enzymes, structural proteins or the like. Altered gene expression may not only be due to misregulation of transcription and/or translation, but also due to mutations within the ORF coding for a particular protein. Pathological mutations may be caused by e.g. chromosomal aberration, or by more specific mutations, such as point or frame-shift-mutations, all of them resulting in limited functionality and, potentially, total loss of function of the gene product. However, misregulation of transcription or translation may also occur, if mutations affect genes encoding proteins which are involved in the transcriptional or translational machinery of the cell. Such mutations may lead to pathological up- or down-regulation of genes which are—as such—functional. Genes encoding gene products which exert such regulating functions, may be, e.g., transcription factors, signal receptors, messenger proteins or the like. However, loss of function of such genes encoding regulatory proteins may, under certain circumstances, be reversed by artificial introduction of other factors acting further downstream of the impaired gene product. Such gene defects may also be compensated by gene therapy via substitution of the affected gene itself.

Genetic vaccination allows evoking a desired immune response to selected antigens, such as characteristic components of bacterial surfaces, viral particles, tumour antigens or the like. Generally, vaccination is one of the pivotal achievements of modern medicine. However, effective vaccines are currently available only for a smaller number of diseases. Accordingly, infections that are not preventable by vaccination still affect millions of people every year.

Commonly, vaccines may be subdivided into "first", "second" and "third" generation vaccines. "First generation" vaccines are, typically, whole-organism vaccines. They are based on either live and attenuated or killed pathogens, e.g. viruses, bacteria or the like. The major drawback of live and attenuated vaccines is the risk for a reversion to life-threatening variants. Thus, although attenuated, such pathogens may still intrinsically bear unpredictable risks. Killed pathogens may not be as effective as desired for generating a specific immune response. In order to minimize these risks, "second generation" vaccines were developed. These are, typically, subunit vaccines, consisting of defined antigens or recombinant protein components which are derived from pathogens.

Genetic vaccines, i.e. vaccines for genetic vaccination, are usually understood as "third generation" vaccines. They are typically composed of genetically engineered nucleic acid molecules which allow expression of peptide or protein (antigen) fragments characteristic for a pathogen or a tumor antigen in vivo. Genetic vaccines are expressed upon administration to a patient and uptake by competent cells. Expression of the administered nucleic acids results in production of the encoded proteins. In the event these proteins are recognized as foreign by the patient's immune system, an immune response is triggered.

As can be seen from the above, both methods, gene therapy and genetic vaccination, are essentially based on the administration of nucleic acid molecules to a patient and subsequent transcription and/or translation of the encoded genetic information.

Alternatively, genetic vaccination or gene therapy may also comprise methods which include isolation of specific body cells from a patient to be treated, subsequent in vitro transfection of such cells, and re-administration of the treated cells to the patient.

DNA as well as RNA may be used as nucleic acid molecules for administration in the context of gene therapy or genetic vaccination. DNA is known to be relatively stable and easy to handle. However, the use of DNA bears the risk of undesired insertion of the administered DNA-fragments into the patient's genome potentially resulting in loss of function of the impaired genes. As a further risk, the undesired generation of anti-DNA antibodies has emerged. Another drawback is the limited expression level of the encoded peptide or protein that is achievable upon DNA administration and its transcription/translation. Among other reasons, the expression level of the administered DNA will be dependent on the presence of specific transcription factors which regulate DNA transcription. In the absence of such factors, DNA transcription will not yield satisfying amounts of RNA. As a result, the level of translated peptide or protein obtained is limited.

By using RNA instead of DNA for gene therapy or genetic vaccination, the risk of undesired genomic integration and generation of anti-DNA antibodies is minimized or avoided. However, RNA is considered to be a rather unstable molecular species which may readily be degraded by ubiquitous RNAses.

In vivo, RNA-degradation contributes to the regulation of the RNA half-life time. That effect was considered and proven to fine tune the regulation of eukaryotic gene expression (Friedel et al., Conserved principles of mammalian transcriptional regulation revealed by RNA half-life, Nucleic Acid Research, 2009, 1-12). Accordingly, each naturally occurring mRNA has its individual half-life depending on the gene from which the mRNA is derived. It contributes to the regulation of the expression level of this gene. Unstable RNAs are important to realize transient gene expression at distinct points in time. However, long-lived RNAs may be associated with accumulation of distinct proteins or continuous expression of genes. In vivo, the half life of mRNAs may also be dependent on environmental factors, such as hormonal treatment, as has been shown, e.g., for insulin-like growth factor I, actin, and albumin mRNA (Johnson et al., Newly synthesized RNA: Simultaneous measurement in intact cells of transcription rates and RNA stability of insulin-like growth factor I, actin, and albumin in growth hormone-stimulated hepatocytes, Proc. Natl. Acad. Sci., Vol. 88, pp. 5287-5291, 1991).

For gene therapy and genetic vaccination, usually stable RNA is desired. This is, on the one hand, due to the fact that the product encoded by the RNA-sequence shall accumulate in vivo. On the other hand, the RNA has to maintain its structural and functional integrity when prepared for a suitable dosage form, in the course of its storage, and when administered. Thus, considerable attention was dedicated to provide stable RNA molecules for gene therapy or genetic vaccination in order to prevent them from being subject to early degradation or decay.

It has been reported that the G/C-content of nucleic acid molecules may influence their stability. Thus, nucleic acids comprising an increased amount of guanine (G) and/or cytosine (C) residues may be functionally more stable than nucleic acids containing a large amount of adenine (A) and thymine (T) or uracil (U) nucleotides. In this context, WO02/098443 provides a pharmaceutical composition containing an mRNA that is stabilised by sequence modifications in the translated region. Such a sequence modification takes advantage of the degeneracy of the genetic code. Accordingly, codons which contain a less favourable combination of nucleotides (less favourable in terms of RNA stability) may be substituted by alternative codons without altering the encoded amino acid sequence. This method of RNA stabilization is limited by the provisions of the specific nucleotide sequence of each single RNA molecule which is not allowed to leave the space of the desired amino acid sequence. Also, that approach is restricted to coding regions of the RNA.

As an alternative option for mRNA stabilisation, it has been found that naturally occurring eukaryotic mRNA molecules contain characteristic stabilising elements. For example, they may comprise so-called untranslated regions (UTR) at their 5'-end (5'UTR) and/or at their 3'-end (3'UTR) as well as other structural features, such as a 5'-cap structure or a 3'-poly(A) tail. Both, 5'UTR and 3'UTR are typically transcribed from the genomic DNA and are, thus, an element of the premature mRNA. Characteristic structural features of mature mRNA, such as the 5'-cap and the 3'-poly(A) tail (also called poly(A) tail or poly(A) sequence) are usually added to the transcribed (premature) mRNA during mRNA processing.

A 3'-poly(A) tail is typically a monotonous sequence stretch of adenine nucleotides added to the 3'-end of the transcribed mRNA. It may comprise up to about 400 adenine nucleotides. It was found that the length of such a 3'-poly(A) tail is a potentially critical element for the stability of the individual mRNA.

Also, it was shown that the 3'UTR of α-globin mRNA may be an important factor for the well-known stability of α-globin mRNA (Rodgers et al., Regulated α-globin mRNA decay is a cytoplasmic event proceeding through 3'-to-5' exosome-dependent decapping, RNA, 8, pp. 1526-1537, 2002). The 3'UTR of α-globin mRNA is obviously involved in the formation of a specific ribonucleoprotein-complex, the α-complex, whose presence correlates with mRNA stability in vitro (Wang et al., An mRNA stability complex functions with poly(A)-binding protein to stabilize mRNA in vitro, Molecular and Cellular biology, Vol 19, No. 7, July 1999, p. 4552-4560).

Irrespective of factors influencing mRNA stability, effective translation of the administered nucleic acid molecules by the target cells or tissue is crucial for any approach using nucleic acid molecules for gene therapy or genetic vaccination. Along with the regulation of stability, also translation of the majority of mRNAs is regulated by structural features like UTRs, 5'-cap and 3'-poly(A) tail. In this context, it has been reported that the length of the poly(A) tail may play an important role for translational efficiency as well. Stabilizing 3'-elements, however, may also have an attenuating effect on translation.

Further regulative elements, which may have an influence on expression levels, may be found in the 5'UTR. For example, it has been reported that synthesis of particular proteins, e.g. proteins belonging to the translational apparatus, may be regulated not only at the transcriptional but also at the translational level. For example, translation of proteins encoded by so called 'TOP-genes' may be down-regulated by translational repression. Therein, the term 'TOP-gene' relates to a gene corresponding to an mRNA that is characterized by the presence of a TOP sequence at the 5' end and in most cases by a growth-associated translation regulation (Iadevaia et al., All translation elongation factors and the e, f, and h subunits of translation initiation factor 3 are encoded by 5'-terminal oligopyrimidine (TOP) mRNAs; RNA, 2008, 14:1730-1736). In this context, a TOP sequence—also called the '5'-terminal oligopyrimidine tract'—typically consists of a C residue at the cap site, followed by an uninterrupted sequence of up to 13 or even more pyrimidines (Avni et al., Vertebrate mRNAs with a 5'-terminal pyrimidine tract are Candidates for translational repression in quiescent cells: characterization of the translational cis-regulatory element, Molecular and Cellular Biology, 1994, p. 3822-3833). These TOP sequences are reported to be present in many mRNAs encoding components of the translational machinery and to be responsible for selective repression of the translation of these TOP containing mRNAs due to growth arrest (Meyuhas, et al., Translational Control of Ribosomal Protein mRNAs in Eukaryotes, Translational Control. Cold Spring Harbor Monograph Archive. Cold Spring Harbor Laboratory Press, 1996, p. 363-388). These TOP sequences are thought to serve as a cis-regulatory element which inhibits the binding of translational regulatory proteins or the translational machinery itself. As a result, the translation of these genes is inhibited at the growth arrest of cells. More specifically, when a cell is faced with starvation or treated by some chemicals such as 12-Otetradecanoyl-1-phorbol-13-acetate (TPA), mRNAs of TOP genes, which are normally associated with polysomes, change their status into the translationally inactive 'sub-polysome' while most non-TOP mRNAs stay in the 'polysome' state (Yamashita et al., Comprehensive detection of human terminal oligo-pyrimidine (TOP) genes and analysis of their characteristics. Nucleic Acids Res. 2008 June; 36(11):3707-15. doi: 10.1093/nar/gkn248. Epub 2008 May 14). In this context, it was shown that the oligopyrimidine tract at the 5' end of the 5'UTR (TOP motif) was required for translational repression of TOP genes. The oligopyrimidine tract at the 5' end of mammalian ribosomal protein mRNAs is required for their translational control (Levy et al., Proc Natl Acad Sci USA. 1991 Apr. 15; 88(8):3319-23). Furthermore, it was shown that miRNA miR-10a positively controls the translation of ribosomal proteins by binding downstream of the TOP motif present in the 5'UTRs of TOP genes. Such an enhancement of translation was dependent on the presence of the TOP motif in the 5'UTR. Furthermore this translational regulation of ribosomal TOP genes was dependent on the presence of miR-10a or its human homolog miR-10b which is highly overexpressed in several tumor types and is reportedly involved in the progression of cancer (Ørom et al., MicroRNA-10a binds the 5'UTR of ribosomal protein mRNAs and enhances their translation. Mol. Cell. 2008 May 23; 30(4):460-71).

It is the object of the invention to provide nucleic acid molecules which may be suitable for application in gene therapy and/or genetic vaccination. Particularly, it is the object of the invention to provide artificial nucleic acid molecules, such as an mRNA species, which provide for increased protein production from said artificial nucleic acid molecules, preferably which exhibit increased translational efficiency. Another object of the present invention is to provide nucleic acid molecules coding for such a superior mRNA species which may be amenable for use in gene therapy and/or genetic vaccination. It is a further object of the present invention to provide a pharmaceutical composition for use in gene therapy and/or genetic vaccination. In summary, it is the object of the present invention to provide improved nucleic acid species which overcome the above discussed disadvantages of the prior art by a cost-effective and straight-forward approach.

The object underlying the present invention is solved by the claimed subject-matter.

For the sake of clarity and readability the following definitions are provided. Any technical feature mentioned for these definitions may be read on each and every embodiment of the invention. Additional definitions and explanations may be specifically provided in the context of these embodiments.

Adaptive immune response: The adaptive immune response is typically understood to be an antigen-specific response of the immune system. Antigen specificity allows for the generation of responses that are tailored to specific pathogens or pathogen-infected cells. The ability to mount these tailored responses is usually maintained in the body by "memory cells". Should a pathogen infect the body more than once, these specific memory cells are used to quickly eliminate it. In this context, the first step of an adaptive immune response is the activation of naïve antigen-specific T cells or different immune cells able to induce an antigen-specific immune response by antigen-presenting cells. This occurs in the lymphoid tissues and organs through which naïve T cells are constantly passing. The three cell types that may serve as antigen-presenting cells are dendritic cells, macrophages, and B cells. Each of these cells has a distinct function in eliciting immune responses. Dendritic cells may take up antigens by phagocytosis and macropinocytosis and may become stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. MHC-molecules are, typically, responsible for presentation of an antigen to T-cells. Therein, presenting the antigen on MHC molecules leads to activation of T cells which induces their proliferation and differentiation into armed effector T cells. The most important function of effector T cells is the killing of infected cells by CD8+ cytotoxic T cells and the activation of macrophages by Th1 cells which together make up cell-mediated immunity, and the activation of B cells by both Th2 and Th1 cells to produce different classes of antibody, thus driving the humoral immune response. T cells recognize an antigen by their T cell receptors which do not recognize and bind the antigen directly, but instead recognize short peptide fragments e.g. of pathogen-derived protein antigens, e.g. so-called epitopes, which are bound to MHC molecules on the surfaces of other cells.

Adaptive immune system: The adaptive immune system is essentially dedicated to eliminate or prevent pathogenic growth. It typically regulates the adaptive immune response by providing the vertebrate immune system with the ability to recognize and remember specific pathogens (to generate immunity), and to mount stronger attacks each time the pathogen is encountered. The system is highly adaptable because of somatic hypermutation (a process of accelerated somatic mutations), and V(D)J recombination (an irreversible genetic recombination of antigen receptor gene segments). This mechanism allows a small number of genes to generate a vast number of different antigen receptors, which are then uniquely expressed on each individual lymphocyte. Because the gene rearrangement leads to an irreversible change in the DNA of each cell, all of the progeny (offspring) of such a cell will then inherit genes encoding the same receptor specificity, including the Memory B cells and Memory T cells that are the keys to long-lived specific immunity.

Adjuvant/adjuvant component: An adjuvant or an adjuvant component in the broadest sense is typically a pharmacological and/or immunological agent that may modify, e.g. enhance, the effect of other agents, such as a drug or vaccine. It is to be interpreted in a broad sense and refers to a broad spectrum of substances. Typically, these substances are able to increase the immunogenicity of antigens. For example, adjuvants may be recognized by the innate immune systems and, e.g., may elicit an innate immune response. "Adjuvants" typically do not elicit an adaptive immune response. Insofar, "adjuvants" do not qualify as antigens. Their mode of action is distinct from the effects triggered by antigens resulting in an adaptive immune response.

Antigen: In the context of the present invention "antigen" refers typically to a substance which may be recognized by the immune system, preferably by the adaptive immune system, and is capable of triggering an antigen-specific immune response, e.g. by formation of antibodies and/or antigen-specific T cells as part of an adaptive immune response. Typically, an antigen may be or may comprise a peptide or protein which may be presented by the MHC to T-cells.

Artificial nucleic acid molecule: An artificial nucleic acid molecule may typically be understood to be a nucleic acid molecule, e.g. a DNA or an RNA, that does not occur naturally. In other words, an artificial nucleic acid molecule may be understood as a non-natural nucleic acid molecule. Such nucleic acid molecule may be non-natural due to its individual sequence (which does not occur naturally) and/or due to other modifications, e.g. structural modifications of nucleotides which do not occur naturally. An artificial nucleic acid molecule may be a DNA molecule, an RNA molecule or a hybrid-molecule comprising DNA and RNA portions. Typically, artificial nucleic acid molecules may be designed and/or generated by genetic engineering methods to correspond to a desired artificial sequence of nucleotides (heterologous sequence). In this context an artificial sequence is usually a sequence that may not occur naturally, i.e. it differs from the wild type sequence by at least one nucleotide. The term 'wild type' may be understood as a sequence occurring in nature. Further, the term 'artificial nucleic acid molecule' is not restricted to mean 'one single molecule' but is, typically, understood to comprise an ensemble of identical molecules. Accordingly, it may relate to a plurality of identical molecules contained in an aliquot.

Bicistronic RNA, multicistronic RNA: A bicistronic or multicistronic RNA is typically an RNA, preferably an mRNA, that typically may have two (bicistronic) or more (multicistronic) open reading frames (ORF). An open reading frame in this context is a sequence of codons that is translatable into a peptide or protein.

Carrier/polymeric carrier: A carrier in the context of the invention may typically be a compound that facilitates transport and/or complexation of another compound (cargo). A polymeric carrier is typically a carrier that is formed of a polymer. A carrier may be associated to its cargo by covalent or non-covalent interaction. A carrier may transport nucleic acids, e.g. RNA or DNA, to the target cells. The carrier may—for some embodiments—be a cationic component.

Cationic component: The term "cationic component" typically refers to a charged molecule, which is positively charged (cation) at a pH value typically from 1 to 9, preferably at a pH value of or below 9 (e.g. from 5 to 9), of or below 8 (e.g. from 5 to 8), of or below 7 (e.g. from 5 to 7), most preferably at a physiological pH, e.g. from 7.3 to 7.4. Accordingly, a cationic component may be any positively charged compound or polymer, preferably a cationic peptide or protein which is positively charged under physiological conditions, particularly under physiological conditions in vivo. A 'cationic peptide or protein' may contain at least one positively charged amino acid, or more than one positively charged amino acid, e.g. selected from Arg, His, Lys or Orn. Accordingly, 'polycationic' components are also within the scope exhibiting more than one positive charge under the conditions given.

5'-cap: A 5'-cap is an entity, typically a modified nucleotide entity, which generally 'caps' the 5'-end of a mature mRNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7 GpppN, wherein N is the terminal 5' nucleotide of the nucleic acid carrying the 5'-cap, typically the 5'-end of an RNA. Further examples of 5' cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3' phosphorothioate, phosphorodithioate, or bridging or non-bridging methylphosphonate moiety.

Cellular immunity/cellular immune response: Cellular immunity relates typically to the activation of macrophages, natural killer cells (NK), antigen-specific cytotoxic T-lymphocytes, and the release of various cytokines in response to an antigen. In more general terms, cellular immunity is not based on antibodies, but on the activation of cells of the immune system. Typically, a cellular immune response may be characterized e.g. by activating antigen-specific cytotoxic T-lymphocytes that are able to induce apoptosis in cells, e.g. specific immune cells like dendritic cells or other cells, displaying epitopes of foreign antigens on their surface. Such cells may be virus-infected or infected with intracellular bacteria, or cancer cells displaying tumor antigens. Further characteristics may be activation of macrophages and natural killer cells, enabling them to destroy pathogens and stimulation of cells to secrete a variety of cytokines that influence the function of other cells involved in adaptive immune responses and innate immune responses.

DNA: DNA is the usual abbreviation for deoxy-ribonucleic-acid. It is a nucleic acid molecule, i.e. a polymer consisting of nucleotides. These nucleotides are usually deoxy-adenosine-monophosphate, deoxy-thymidine-monophosphate, deoxy-guanosine-monophosphate and deoxy-cytidine-monophosphate monomers which are—by themselves—composed of a sugar moiety (deoxyribose), a base moiety and a phosphate moiety, and polymerize by a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA-sequence. DNA may be single stranded or double stranded. In the double stranded form, the nucleotides of the first strand typically hybridize with the nucleotides of the second strand, e.g. by A/T-base-pairing and G/C-base-pairing.

Epitope: Epitopes (also called 'antigen determinant') can be distinguished in T cell epitopes and B cell epitopes. T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule, i.e. the fragments are typically not recognized in their native form. B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

Fragment of a sequence: A fragment of a sequence may typically be a shorter portion of a full-length sequence of e.g. a nucleic acid molecule or an amino acid sequence. Accordingly, a fragment, typically, consists of a sequence that is identical to the corresponding stretch within the full-length sequence. A preferred fragment of a sequence in the context of the present invention, consists of a continuous stretch of entities, such as nucleotides or amino acids corresponding to a continuous stretch of entities in the molecule the fragment is derived from, which represents at least 20%, preferably at least 30%, more preferably at least 40%, more preferably at least 50%, even more preferably at least 60%, even more preferably at least 70%, and most preferably at least 80% of the total (i.e. full-length) molecule from which the fragment is derived.

G/C modified: A G/C-modified nucleic acid may typically be a nucleic acid, preferably an artificial nucleic acid molecule as defined herein, based on a modified wild-type sequence comprising a preferably increased number of guanosine and/or cytosine nucleotides as compared to the wild-type sequence. Such an increased number may be generated by substitution of codons containing adenosine or thymidine nucleotides by codons containing guanosine or cytosine nucleotides. If the enriched G/C content occurs in a coding region of DNA or RNA, it makes use of the degeneracy of the genetic code. Accordingly, the codon substitutions preferably do not alter the encoded amino acid residues, but exclusively increase the G/C content of the nucleic acid molecule.

Gene therapy: Gene therapy may typically be understood to mean a treatment of a patient's body or isolated elements of a patient's body, for example isolated tissues/cells, by nucleic acids encoding a peptide or protein. It typically may comprise at least one of the steps of a) administration of a nucleic acid, preferably an artificial nucleic acid molecule as defined herein, directly to the patient—by whatever administration route—or in vitro to isolated cells/tissues of the patient, which results in transfection of the patient's cells either in vivo/ex vivo or in vitro b) transcription and/or translation of the introduced nucleic acid molecule; and optionally c) re-administration of isolated, transfected cells to the patient, if the nucleic acid has not been administered directly to the patient.

Genetic vaccination: Genetic vaccination may typically be understood to be vaccination by administration of a nucleic acid molecule encoding an antigen or an immunogen or fragments thereof. The nucleic acid molecule may be administered to a subject's body or to isolated cells of a subject. Upon transfection of certain cells of the body or upon transfection of the isolated cells, the antigen or immunogen may be expressed by those cells and subsequently presented to the immune system, eliciting an adaptive, i.e. antigen-specific immune response. Accordingly, genetic vaccination typically comprises at least one of the steps of a) administration of a nucleic acid, preferably an artificial nucleic acid molecule as defined herein, to a subject, preferably a patient, or to isolated cells of a subject, preferably a patient, which usually results in transfection of the subject's cells either in vivo or in vitro b) transcription and/or translation of the introduced nucleic acid molecule; and optionally c) re-administration of isolated, transfected cells to the subject, preferably the patient, if the nucleic acid has not been administered directly to the patient.

Heterologous sequence: Two sequences are typically understood to be 'heterologous' if they are not derivable from the same gene. I.e., although heterologous sequences may be derivable from the same organism, they naturally (in nature) do not occur in the same nucleic acid molecule, such as in the same mRNA.

Humoral immunity/humoral immune response: Humoral immunity refers typically to antibody production and optionally to accessory processes accompanying antibody production. A humoral immune response may be typically characterized, e.g., by Th2 activation and cytokine production, germinal center formation and isotype switching, affinity maturation and memory cell generation. Humoral immunity also typically may refer to the effector functions of antibodies, which include pathogen and toxin neutralization, classical complement activation, and opsonin promotion of phagocytosis and pathogen elimination.

Immunogen: In the context of the present invention an immunogen may be typically understood to be a compound that is able to stimulate an immune response. Preferably, an immunogen is a peptide, polypeptide, or protein. In a particularly preferred embodiment, an immunogen in the sense of the present invention is the product of translation of a provided nucleic acid molecule, preferably an artificial nucleic acid molecule as defined herein. Typically, an immunogen elicits at least an adaptive immune response.

Immunostimulatory composition: In the context of the invention, an immunostimulatory composition may be typically understood to be a composition containing at least one component which is able to induce an immune response or from which a component which is able to induce an immune response is derivable. Such immune response may be preferably an innate immune response or a combination of an adaptive and an innate immune response. Preferably, an immunostimulatory composition in the context of the invention contains at least one artificial nucleic acid molecule, more preferably an RNA, for example an mRNA molecule. The immunostimulatory component, such as the mRNA may be complexed with a suitable carrier. Thus, the immunostimulatory composition may comprise an mRNA/carrier-complex. Furthermore, the immunostimulatory composition may comprise an adjuvant and/or a suitable vehicle for the immunostimulatory component, such as the mRNA.

Immune response: An immune response may typically be a specific reaction of the adaptive immune system to a particular antigen (so called specific or adaptive immune response) or an unspecific reaction of the innate immune system (so called unspecific or innate immune response), or a combination thereof.

Immune system: The immune system may protect organisms from infection. If a pathogen succeeds in passing a physical barrier of an organism and enters this organism, the innate immune system provides an immediate, but non-specific response. If pathogens evade this innate response, vertebrates possess a second layer of protection, the adaptive immune system. Here, the immune system adapts its response during an infection to improve its recognition of the pathogen. This improved response is then retained after the pathogen has been eliminated, in the form of an immunological memory, and allows the adaptive immune system to mount faster and stronger attacks each time this pathogen is encountered. According to this, the immune system comprises the innate and the adaptive immune system. Each of these two parts typically contains so called humoral and cellular components.

Immunostimulatory RNA: An immunostimulatory RNA (is RNA) in the context of the invention may typically be an RNA that is able to induce an innate immune response. It usually does not have an open reading frame and thus does not provide a peptide-antigen or immunogen but elicits an immune response e.g. by binding to a specific kind of Toll-like-receptor (TLR) or other suitable receptors. However, of course also mRNAs having an open reading frame and coding for a peptide/protein may induce an innate immune response and, thus, may be immunostimulatory RNAs.

Innate immune system: The innate immune system, also known as non-specific (or unspecific) immune system, typically comprises the cells and mechanisms that defend the host from infection by other organisms in a non-specific manner. This means that the cells of the innate system may recognize and respond to pathogens in a generic way, but unlike the adaptive immune system, it does not confer long-lasting or protective immunity to the host. The innate immune system may be, e.g., activated by ligands of Toll-like receptors (TLRs) or other auxiliary substances such as lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (is RNA), a CpG-DNA, an antibacterial agent, or an anti-viral agent. The pharmaceutical composition according to the present invention may comprise one or more such substances. Typically, a response of the innate immune system includes recruiting immune cells to sites of infection, through the production of chemical factors, including specialized chemical mediators, called cytokines; activation of the complement cascade; identification and removal of foreign substances present in organs, tissues, the blood and lymph, by specialized white blood cells; activation of the adaptive immune system; and/or acting as a physical and chemical barrier to infectious agents.

Cloning site: A cloning site is typically understood to be a segment of a nucleic acid molecule, which is suitable for insertion of a nucleic acid sequence, e.g., a nucleic acid sequence comprising an open reading frame. Insertion may be performed by any molecular biological method known to the one skilled in the art, e.g. by restriction and ligation. A cloning site typically comprises one or more restriction enzyme recognition sites (restriction sites). These one or more restrictions sites may be recognized by restriction enzymes which cleave the DNA at these sites. A cloning site which comprises more than one restriction site may also be termed a multiple cloning site (MCS) or a polylinker.

Nucleic acid molecule: A nucleic acid molecule is a molecule comprising, preferably consisting of nucleic acid components. The term nucleic acid molecule preferably refers to DNA or RNA molecules. It is preferably used synonymous with the term "polynucleotide". Preferably, a nucleic acid molecule is a polymer comprising or consisting of nucleotide monomers which are covalently linked to each other by phosphodiester-bonds of a sugar/phosphate-backbone. The term "nucleic acid molecule" also encompasses modified nucleic acid molecules, such as base-modified, sugar-modified or backbone-modified etc. DNA or RNA molecules.

Open reading frame: An open reading frame (ORF) in the context of the invention may typically be a sequence of several nucleotide triplets which may be translated into a peptide or protein. An open reading frame preferably contains a start codon, i.e. a combination of three subsequent nucleotides coding usually for the amino acid methionine (ATG or AUG), at its 5'-end and a subsequent region which usually exhibits a length which is a multiple of 3 nucleotides. An ORF is preferably terminated by a stop-codon (e.g., TAA, TAG, TGA). Typically, this is the only stop-codon of the open reading frame. Thus, an open reading frame in the context of the present invention is preferably a nucleotide sequence, consisting of a number of nucleotides that may be divided by three, which starts with a start codon (e.g. ATG or AUG) and which preferably terminates with a stop codon (e.g., TAA, TGA, or TAG or UAA, UAG, UGA, respectively). The open reading frame may be isolated or it may be incorporated in a longer nucleic acid sequence, for example in a vector or an mRNA. An open reading frame may also be termed 'protein coding region'.

Peptide: A peptide or polypeptide is typically a polymer of amino acid monomers, linked by peptide bonds. It typically contains less than 50 monomer units. Nevertheless, the term peptide is not a disclaimer for molecules having more than 50 monomer units. Long peptides are also called polypeptides, typically having between 50 and 600 monomeric units.

Pharmaceutically effective amount: A pharmaceutically effective amount in the context of the invention is typically understood to be an amount that is sufficient to induce a pharmaceutical effect, such as an immune response, altering a pathological level of an expressed peptide or protein, or substituting a lacking gene product, e.g., in case of a pathological situation.

Protein A protein typically comprises one or more peptides or polypeptides. A protein is typically folded into 3-dimensional form, which may be required for to protein to exert its biological function.

Poly(A) sequence: A poly(A) sequence, also called poly (A) tail or 3'-poly(A) tail, is typically understood to be a sequence of adenine nucleotides, e.g., of up to about 400 adenine nucleotides, e.g. from about 20 to about 400, preferably from about 50 to about 400, more preferably from about 50 to about 300, even more preferably from about 50 to about 250, most preferably from about 60 to about 250 adenine nucleotides. A poly(A) sequence is typically located at the 3' end of an mRNA. In the context of the present invention, a poly(A) sequence may be located within an mRNA or any other nucleic acid molecule, such as, e.g., in a vector, for example, in a vector serving as template for the generation of an RNA, preferably an mRNA, e.g., by transcription of the vector.

Polyadenylation: Polyadenylation is typically understood to be the addition of a poly(A) sequence to a nucleic acid molecule, such as an RNA molecule, e.g. to a premature mRNA. Polyadenylation may be induced by a so called polyadenylation signal. This signal is preferably located within a stretch of nucleotides at the 3'-end of a nucleic acid molecule, such as an RNA molecule, to be polyadenylated. A polyadenylation signal typically comprises a hexamer consisting of adenine and uracil/thymine nucleotides, preferably the hexamer sequence AAUAAA. Other sequences, preferably hexamer sequences, are also conceivable. Polyadenylation typically occurs during processing of a pre-mRNA (also called premature-mRNA). Typically, RNA maturation (from pre-mRNA to mature mRNA) comprises the step of polyadenylation.

Restriction site: A restriction site, also termed 'restriction enzyme recognition site', is a nucleotide sequence recognized by a restriction enzyme. A restriction site is typically a short, preferably palindromic nucleotide sequence, e.g. a sequence comprising 4 to 8 nucleotides. A restriction site is preferably specifically recognized by a restriction enzyme. The restriction enzyme typically cleaves a nucleotide sequence comprising a restriction site at this site. In a double-stranded nucleotide sequence, such as a double-stranded DNA sequence, the restriction enzyme typically cuts both strands of the nucleotide sequence.

RNA, mRNA: RNA is the usual abbreviation for ribonucleic-acid. It is a nucleic acid molecule, i.e. a polymer consisting of nucleotides. These nucleotides are usually adenosine-monophosphate, uridine-monophosphate, guanosine-monophosphate and cytidine-monophosphate monomers which are connected to each other along a so-called backbone. The backbone is formed by phosphodiester bonds between the sugar, i.e. ribose, of a first and a phosphate moiety of a second, adjacent monomer. The specific succession of the monomers is called the RNA-sequence. Usually RNA may be obtainable by transcription of a DNA-sequence, e.g., inside a cell. In eukaryotic cells, transcription is typically performed inside the nucleus or the mitochondria. In vivo, transcription of DNA usually results in the so-called premature RNA which has to be processed into so-called messenger-RNA, usually abbreviated as mRNA. Processing of the premature RNA, e.g. in eukaryotic organisms, comprises a variety of different posttranscriptional-modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino acid sequence of a particular peptide or protein. Typically, a mature mRNA comprises a 5'-cap, a 5'UTR, an open reading frame, a 3'UTR and a poly(A) sequence. Aside from messenger RNA, several non-coding types of RNA exist which may be involved in regulation of transcription and/or translation.

Sequence of a nucleic acid molecule: The sequence of a nucleic acid molecule is typically understood to be the particular and individual order, i.e. the succession of its nucleotides. The sequence of a protein or peptide is typically understood to be the order, i.e. the succession of its amino acids.

Sequence identity: Two or more sequences are identical if they exhibit the same length and order of nucleotides or amino acids. The percentage of identity typically describes the extent to which two sequences are identical, i.e. it typically describes the percentage of nucleotides that correspond in their sequence position with identical nucleotides of a reference-sequence. For determination of the degree of identity, the sequences to be compared are considered to exhibit the same length, i.e. the length of the longest sequence of the sequences to be compared. This means that a first sequence consisting of 8 nucleotides is 80% identical to a second sequence consisting of 10 nucleotides comprising the first sequence. In other words, in the context of the present invention, identity of sequences preferably relates to the percentage of nucleotides of a sequence which have the same position in two or more sequences having the same length. Gaps are usually regarded as non-identical positions, irrespective of their actual position in an alignment.

Stabilized nucleic acid molecule: A stabilized nucleic acid molecule is a nucleic acid molecule, preferably a DNA or RNA molecule that is modified such, that it is more stable to disintegration or degradation, e.g., by environmental factors or enzymatic digest, such as by an exo- or endonuclease degradation, than the nucleic acid molecule without the modification. Preferably, a stabilized nucleic acid molecule in the context of the present invention is stabilized in a cell, such as a prokaryotic or eukaryotic cell, preferably in a mammalian cell, such as a human cell. The stabilization effect may also be exerted outside of cells, e.g. in a buffer solution etc., for example, in a manufacturing process for a pharmaceutical composition comprising the stabilized nucleic acid molecule.

Transfection: The term 'transfection' refers to the introduction of nucleic acid molecules, such as DNA or RNA (e.g. mRNA) molecules, into cells, preferably into eukaryotic cells. In the context of the present invention, the term 'transfection' encompasses any method known to the skilled person for introducing nucleic acid molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc. Preferably, the introduction is non-viral.

Vaccine: A vaccine is typically understood to be a prophylactic or therapeutic material providing at least one antigen, preferably an immunogen. The antigen or immunogen may be derived from any material that is suitable for vaccination. For example, the antigen or immunogen may be derived from a pathogen, such as from bacteria or virus particles etc., or from a tumor or cancerous tissue. The antigen or immunogen stimulates the body's adaptive immune system to provide an adaptive immune response.

Vector: The term 'vector' refers to a nucleic acid molecule, preferably to an artificial nucleic acid molecule. A vector in the context of the present invention is suitable for incorporating or harboring a desired nucleic acid sequence, such as a nucleic acid sequence comprising an open reading frame. Such vectors may be storage vectors, expression vectors, cloning vectors, transfer vectors etc. A storage vector is a vector which allows the convenient storage of a nucleic acid molecule, for example, of an mRNA molecule. Thus, the vector may comprise a sequence corresponding, e.g., to a desired mRNA sequence or a part thereof, such as a sequence corresponding to the open reading frame and the 3'UTR of an mRNA. An expression vector may be used for production of expression products such as RNA, e.g. mRNA, or peptides, polypeptides or proteins. For example, an expression vector may comprise sequences needed for transcription of a sequence stretch of the vector, such as a promoter sequence, e.g. an RNA promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule. Preferably, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector.

Vehicle: A vehicle is typically understood to be a material that is suitable for storing, transporting, and/or administering a compound, such as a pharmaceutically active compound. For example, it may be a physiologically acceptable liquid which is suitable for storing, transporting, and/or administering a pharmaceutically active compound.

3'-untranslated region (3'UTR): A 3'UTR is typically the part of an mRNA which is located between the protein coding region (i.e. the open reading frame) and the poly(A) sequence of the mRNA. A 3'UTR of the mRNA is not translated into an amino acid sequence. The 3'UTR sequence is generally encoded by the gene which is transcribed into the respective mRNA during the gene expression process. The genomic sequence is first transcribed into pre-mature mRNA, which comprises optional introns. The pre-mature mRNA is then further processed into mature mRNA in a maturation process. This maturation process comprises the steps of 5' capping, splicing the pre-mature mRNA to excise optional introns and modifications of the 3'-end, such as polyadenylation of the 3'-end of the pre-mature mRNA and optional endo- or exonuclease cleavages etc. In the context of the present invention, a 3'UTR corresponds to the sequence of a mature mRNA which is located 3' to the stop codon of the protein coding region, preferably immediately 3' to the stop codon of the protein coding region, and which extends to the 5'-side of the poly(A) sequence, preferably to the nucleotide immediately 5' to the poly(A) sequence. The term "corresponds to" means that the 3'UTR sequence may be an RNA sequence, such as in the mRNA sequence used for defining the 3'UTR sequence, or a DNA sequence which corresponds to such RNA sequence. In the context of the present invention, the term "a 3'UTR of a gene", such as "a 3'UTR of an albumin gene", is the sequence which corresponds to the 3'UTR of the mature mRNA derived from this gene, i.e. the mRNA obtained by transcription of the gene and maturation of the pre-mature mRNA. The term "3'UTR of a gene" encompasses the DNA sequence and the RNA sequence of the 3'UTR.

5'-untranslated region (5'UTR): A 5'UTR is typically understood to be a particular section of messenger RNA (mRNA). It is located 5' of the open reading frame of the mRNA. Typically, the 5'UTR starts with the transcriptional start site and ends one nucleotide before the start codon of the open reading frame. The 5'UTR may comprise elements for controlling gene expression, also called regulatory elements. Such regulatory elements may be, for example, ribosomal binding sites or a 5'-Terminal Oligopyrimidine Tract. The 5'UTR may be posttranscriptionally modified, for example by addition of a 5'-cap. In the context of the present invention, a 5'UTR corresponds to the sequence of a mature mRNA which is located between the 5' cap and the start codon. Preferably, the 5'UTR corresponds to the sequence which extends from a nucleotide located 3' to the 5'-cap, preferably from the nucleotide located immediately 3' to the 5' cap, to a nucleotide located 5' to the start codon of the protein coding region, preferably to the nucleotide located immediately 5' to the start codon of the protein coding region. The nucleotide located immediately 3' to the 5' cap of a mature mRNA typically corresponds to the transcriptional start site. The term "corresponds to" means that the 5'UTR sequence may be an RNA sequence, such as in the mRNA sequence used for defining the 5'UTR sequence, or a DNA sequence which corresponds to such RNA sequence. In the context of the present invention, the term "a 5'UTR of a gene", such as "a 5'UTR of a TOP gene", is the sequence which corresponds to the 5'UTR of the mature mRNA derived from this gene, i.e. the mRNA obtained by transcription of the gene and maturation of the pre-mature mRNA. The term "5'UTR of a gene" encompasses the DNA sequence and the RNA sequence of the 5'UTR.

5'Terminal Oligopyrimidine Tract (TOP): The 5' terminal oligopyrimidine tract (TOP) is typically a stretch of pyrimidine nucleotides located at the 5' terminal region of a nucleic acid molecule, such as the 5' terminal region of certain mRNA molecules or the 5' terminal region of a functional entity, e.g. the transcribed region, of certain genes. The sequence starts with a cytidine, which usually corresponds to the transcriptional start site, and is followed by a stretch of usually about 3 to 30 pyrimidine nucleotides, more often 3 to 15 pyrimidine nucleotides. For example, the TOP may comprise 3, 4, 5, 6, 7, 8, 9, 10, 11, 12, 13, 14, 15, 16, 17, 18, 19, 20, 21, 22, 23, 24, 25, 26, 27, 28, 29, 30 or even more nucleotides. The pyrimidine stretch and thus the 5' TOP ends one nucleotide 5' to the first purine nucleotide located downstream of the TOP. Messenger RNA that contains a 5'-terminal oligopyrimidine tract is often referred to as TOP mRNA. Accordingly, genes that provide such messenger RNAs are referred to as TOP genes. TOP sequences have, for example, been found in genes and mRNAs encoding peptide elongation factors and ribosomal proteins.

TOP motif: In the context of the present invention, a TOP motif is a nucleic acid sequence which corresponds to a 5'TOP as defined above. Thus, a TOP motif in the context of the present invention is preferably a stretch of pyrimidine nucleotides having a length of 3-30 nucleotides. Preferably, the TOP-motif consists of at least 3 pyrimidine nucleotides, preferably at least 4 pyrimidine nucleotides, preferably at least 5 pyrimidine nucleotides, more preferably at least 6 nucleotides, more preferably at least 7 nucleotides, most preferably at least 8 pyrimidine nucleotides, wherein the stretch of pyrimidine nucleotides preferably starts at its 5' end with a cytosine nucleotide. In TOP genes and TOP mRNAs, the TOP-motif preferably starts at its 5' end with the transcriptional start site and ends one nucleotide 5' to the first purin residue in said gene or mRNA. A TOP motif in the sense of the present invention is preferably located at the 5' end of a sequence which represents a 5'UTR or at the 5' end of a sequence which codes for a 5'UTR. Thus, preferably, a stretch of 3 or more pyrimidine nucleotides is called "TOP motif" in the sense of the present invention if this stretch is located at the 5' end of a respective sequence, such as the artificial nucleic acid molecule according to the present invention, the 5'UTR element of the artificial nucleic acid molecule according to the present invention, or the nucleic acid sequence which is derived from the 5'UTR of a TOP gene as described herein. In other words, a stretch of 3 or more pyrimidine nucleotides which is not located at the 5'-end of a 5'UTR or a 5'UTR element but anywhere within a 5'UTR or a 5'UTR element is preferably not referred to as "TOP motif".

TOP gene: TOP genes are typically characterised by the presence of a 5' terminal oligopyrimidine tract. Furthermore, most TOP genes are characterized by a growth-associated translational regulation. However, also TOP genes with a tissue specific translational regulation are known. As defined above, the 5'UTR of a TOP gene corresponds to the sequence of a 5'UTR of a mature mRNA derived from a TOP gene, which preferably extends from the nucleotide located 3' to the 5' cap to the nucleotide located 5' to the start codon. A 5'UTR of a TOP gene typically does not comprise any start codons, preferably no upstream AUGs (uAUGs) or upstream open reading frames (uORFs). Therein, upstream AUGs and upstream open reading frames are typically understood to be AUGs and open reading frames that occur 5' of the start codon (AUG) of the open reading frame that should be translated. The 5'UTRs of TOP genes are generally rather short. The lengths of 5'UTRs of TOP genes may vary between 20 nucleotides up to 500 nucleotides, and are typically less than about 200 nucleotides, preferably less than about 150 nucleotides, more preferably less than about 100 nucleotides. Exemplary 5'UTRs of TOP genes in the sense of the present invention are the nucleic acid sequences extending from the nucleotide at position 5 to the nucleotide located immediately 5' to the start codon (e.g. the ATG) in the sequences according to SEQ ID NOs. 1-1363, SEQ ID NO. 1395, SEQ ID NO. 1421 and SEQ ID NO. 1422.

In a first aspect, the present invention relates to an artificial nucleic acid molecule comprising a. at least one 5'-untranslated region element (5'UTR element) which comprises or consists of a nucleic acid sequence which is derived from the 5'UTR of a TOP gene or which is derived from a variant of the 5'UTR of a TOP gene; and b. at least one open reading frame (ORF).

Such an artificial nucleic acid molecule may be DNA or RNA. In case the artificial nucleic acid molecule is DNA it may be used for providing RNA, preferably an mRNA with a corresponding sequence as is described further below. The inventive artificial nucleic acid molecule is particularly useful in gene therapy and genetic vaccination because it may provide increased and/or prolonged protein production of the protein encoded by the open reading frame. It is preferred, if the components (a) and (b) are heterologous, such that the inventive nucleic acid molecule does not occur naturally, but is an artificial chimeric recombinant nucleic acid molecule.

In this context, the term '5'UTR element' preferably refers to a nucleic acid sequence which represents a 5'UTR of an artificial nucleic acid sequence, such as an artificial mRNA, or which codes for a 5'UTR of an artificial nucleic acid molecule. Thus, preferably, a 5'UTR element may be the 5'UTR of an mRNA, preferably of an artificial mRNA, or it may be the transcription template for a 5'UTR of an mRNA. Thus, a 5'UTR element preferably is a nucleic acid sequence which corresponds to the 5'UTR of an mRNA, preferably to the 5'UTR of an artificial mRNA, such as an mRNA obtained by transcription of a genetically engineered vector construct. Preferably, a 5'UTR element in the sense of the present invention functions as a 5'UTR or codes for a nucleotide sequence that fulfils the function of a 5'UTR. The term '5'UTR element' may also refer to a fragment or part of a 5'UTR of an artificial nucleic acid sequence, such as an artificial mRNA, or which codes for a part or fragment of a 5'UTR of an artificial nucleic acid molecule. This means that the 5'UTR element in the sense of the present invention may be comprised in the 5'UTR of an artificial nucleic acid sequence, such as an artificial mRNA, or which codes for a 5'UTR of an artificial nucleic acid molecule.

According to the invention, the 5'UTR element comprises or consists of a nucleic acid sequence that is derived from the 5'UTR of a TOP gene or from a variant of the 5'UTR of a TOP gene.

The term 'a nucleic acid sequence which is derived from the 5'UTR of a TOP gene' preferably refers to a nucleic acid sequence which is based on the 5'UTR sequence of a TOP gene or on a fragment thereof. This term includes sequences corresponding to the entire 5'UTR sequence, i.e. the full length 5'UTR sequence of a TOP gene, and sequences corresponding to a fragment of the 5'UTR sequence of a TOP gene. Preferably, a fragment of a 5'UTR of a TOP gene consists of a continuous stretch of nucleotides corresponding to a continuous stretch of nucleotides in the full-length 5'UTR of a TOP gene, which represents at least 20%, preferably at least 30%, more preferably at least 40%, more preferably at least 50%, even more preferably at least 60%, even more preferably at least 70%, even more preferably at least 80%, and most preferably at least 90% of the full-length 5'UTR of a TOP gene. Such a fragment, in the sense of the present invention, is preferably a functional fragment as described herein. A particularly preferred fragment of a 5'UTR of a TOP gene is a 5'UTR of a TOP gene lacking the 5'TOP motif, which typically corresponds to a pyrimidine stretch of 3 to 30 pyrimidine nucleotides at the 5' terminus of the 5'UTR of a TOP gene. For the above preferred embodiment of the invention employing a 5'UTR of a TOP gene, the 5'UTR (comprised by the inventive nucleic acid molecule) starts with the first nucleotide following the most 3'-terminal nucleotide of the 5'TOP motif. In case the 5'TOP motif does not correspond to the 5' terminal part of the 5'UTR of the TOP gene, the 5' UTR (of the TOP gene) employed in the inventive nucleic acid may consist of the nucleotide sequence located upstream of the 5' terminus of the 5'TOP motif and/or of the nucleotide sequence located downstream of the 3' terminus of the 5'TOP motif. In an alternative embodiment, the 5' motif of a 5'UTR of a TOP gene may be rendered dysfunctional by e.g. introducing one or more purine nucleotides, which interrupt the monotonic pyrimidine nucleotide stretch of the 5'TOP motif such that the modified (interrupted) 5'TOP motif sequence cannot exert its regulatory function any longer, in particular cannot exert its function as an element for translational control. Another way of rendering the 5' TOP motif dysfunctional is the deletion of one or more pyrimidine nucleotides of the 5'TOP motif sequence (either at the termini and/or within the 5'TOP motif).

In one embodiment, the 5'UTR of a TOP gene will not be derived from the 5'UTR of ribosomal proteins (rp) mRNA (in particular not from mammalian 5'UTR of rp mRNA, more specifically not from rpP2 (e.g. rat rpP2), rpL32, rpL30, rpL13a (e.g. mouse transplantation antigen P198), rpS20, rpS6, rpL12 or rpS16 mRNA or not from an rpS19 mRNA (e.g. from *Xenopus*). In another embodiment, the 5'UTR of a TOP gene is not derived from the 5'UTR of a EF1alpha or (hamster) EF2 mRNA. The 5'UTRs of these afore-mentioned rp mRNAs are specifically not used, if they are linked to reporter genes in the ORF of the inventive nucleic acid. If e.g. the 5'UTR of rpS16 mRNA is used for the inventive nucleic acid, that 5'UTR will either not contain the 5'TOP motif sequence (composed of the oligonucleotide (CCTTTTCC or CCUUUUCC) or will contain a dysfunctional variant thereof by e.g. interruption of the oligopyrimidine sequence by purine nucleotides or by deletion of one or more pyrimidine nucleotides of that 5'TOP motif. Accordingly, the dysfunctional mutants may e.g. contain one or more purine nucleotides within the 5'TOP motif sequence thereby lacking the translational control function exerted by the 5'TOP motif, e.g. by abolishing its interaction with other regulatory compounds, e.g. miRNA or interaction with granule-associated proteins TIA-1 and TIAR.

The term '5'UTR of a TOP gene' preferably refers to the 5'UTR of a naturally occurring TOP gene.

The terms 'variant of the 5'UTR of a TOP gene' and 'variant thereof' in the context of a 5'UTR of a TOP gene refers to a variant of the 5'UTR of a naturally occurring TOP gene, preferably to a variant of the 5'UTR of a vertebrate TOP gene, preferably to a variant of the 5'UTR of a mammalian TOP gene, more preferably to a variant of the 5'UTR of a human TOP gene. Such variant may be a modified 5'UTR of a TOP gene. For example, a variant 5'UTR may exhibit one or more nucleotide deletions, insertions, additions and/or substitutions compared to the naturally occurring 5'UTR from which the variant is derived. Preferably, a variant of a 5'UTR of a TOP gene is at least 40%, preferably at least 50%, more preferably at least 60%, more preferably at least 70%, even more preferably at least 80%, even more preferably at least 90%, most preferably at least 95% identical to the naturally occurring 5'UTR the variant is derived from. Preferably, the variant is a functional variant as described herein.

The term "a nucleic acid sequence that is derived from a variant of the 5'UTR of a TOP gene" preferably refers to a nucleic acid sequence which is based on a variant of a 5'UTR sequence of a TOP gene or on a fragment thereof. This term includes sequences corresponding to the entire variant 5'UTR sequence, i.e. the full length variant 5'UTR sequence of a TOP gene, and sequences corresponding to a fragment of the variant 5'UTR sequence of a TOP gene. Preferably, a fragment of a variant of the 5'UTR of a TOP gene consists of a continuous stretch of nucleotides corresponding to a continuous stretch of nucleotides in the full-length variant 5'UTR of a TOP gene, which represents at least 20%, preferably at least 30%, more preferably at least 40%, more preferably at least 50%, even more preferably at least 60%, even more preferably at least 70%, even more preferably at least 80%, and most preferably at least 90% of the full-length variant 5'UTR of a TOP gene. Such a fragment of a variant, in the sense of the present invention, is preferably a functional fragment as described herein.

Thus, the 5'UTR element of the artificial nucleic acid molecule may comprise or consist of a fragment of the 5'UTR of a TOP gene or of a fragment of a variant of the 5'UTR of a TOP gene or may comprise or consist of the entire 5'UTR of a TOP gene or may comprise or consist of a variant of the 5'UTR of a TOP gene.

The 5'UTR element is preferably suitable for increasing protein production from the artificial nucleic acid molecule.

Preferably, the at least one 5'UTR element is functionally linked to the ORF. This means preferably that the 5'UTR element is associated with the ORF such that it may exert a function, such as a protein production increasing function for the protein encoded by the ORF or a stabilizing function on the artificial nucleic acid molecule. Preferably, the 5'UTR element and the ORF are associated in 5'→3' direction. Thus, preferably, the artificial nucleic acid molecule comprises the structure 5'-5'UTR element-(optional)linker-ORF-3', wherein the linker may be present or absent. For example, the linker may be one or more nucleotides, such as a stretch of 1-50 or 1-20 nucleotides, e.g., comprising or consisting of one or more restriction enzyme recognition sites (restriction sites).

Preferably, the 5'UTR element and the at least one open reading frame are heterologous. The term 'heterologous' in this context means that the open reading frame and the 5'UTR element are not occurring naturally (in nature) in this combination. Preferably, the 5'UTR element is derived from a different gene than the open reading frame. For example, the ORF may be derived from a different gene than the 5'UTR element, e.g. encoding a different protein or the same protein but of a different species etc. For example, the ORF does not encode the protein which is encoded by the gene from which the 5'UTR element is derived.

In a preferred embodiment, the 5'UTR element, preferably the artificial nucleic acid molecule, does not comprise a complete TOP-motif or 5'TOP sequence. Thus, preferably, the 5'UTR element, preferably the artificial nucleic acid molecule, does not comprise the complete TOP-motif of the TOP gene from which the nucleic acid sequence of the 5'UTR element is derived. For example, the 5'UTR element or the artificial nucleic acid molecule according to the present invention may comprise 1, 2, 3, 4, 5, 6, 7, 8, 9, 10 or more pyrimidine residues of the TOP-motif or 5'TOP, preferably 1, 2, 3, 4, 5, 6, 7, 8, 9, 10 or more pyrimidine residues of the TOP-motif located at the 3' side of the TOP-motif or 5'TOP. For example, the 5'UTR element may comprise or consist of a nucleic acid sequence which starts at its 5' end with a pyrimidine residue that corresponds to residue 2, 3, 4, 5, 6, 7, 8, 9, etc. of the TOP-motif or 5'TOP of the TOP gene from which the nucleic acid sequence of the 5'UTR element is derived.

It is particularly preferred that the 5'UTR element, preferably the artificial nucleic acid molecule according to the present invention, does not comprise a TOP-motif or a 5'TOP. For example, the nucleic acid sequence of the 5'UTR element which is derived from a 5'UTR of a TOP gene starts at its 5'-end with a nucleotide located at position 1, 2, 3, 4, 5, 6, 7, 8, 9 or 10 downstream of the 5' terminal oligopyrimidine tract (TOP) of the 5'UTR of a TOP gene. Position 1 downstream of the 5' terminal oligopyrimidine tract (TOP) is the first purine based nucleotide 3' of the TOP-motif or the 5'TOP. Accordingly, position 1 downstream of the 5' terminal oligopyrimidine tract is the first nucleotide following the 3'-end of the 5' terminal oligopyrimidine tract in 5'-3'-direction. Likewise, position 2 downstream of the 5'TOP is the second nucleotide following the end of the 5' terminal oligopyrimidine tract, position 3 the third nucleotide and so on.

Therefore, the 5'UTR element preferably starts 5, 10, 15, 20, 25, 30, 40 or 50 nucleotides downstream of the transcriptional start site of the 5'UTR of a TOP gene.

In some embodiments, the nucleic acid sequence of the 5'UTR element which is derived from a 5'UTR of a TOP gene terminates at its 3'-end with a nucleotide located at position 1, 2, 3, 4, 5, 6, 7, 8, 9 or 10 upstream of the start codon (e.g. A(U/T)G) of the gene or mRNA it is derived from. Thus, the 5'UTR element does not comprise any part of the protein coding region. Thus, preferably, the only protein coding part of the inventive artificial nucleic acid molecule is provided by the open reading frame. However, the open reading frame is preferably derived—as said above—from a gene that is different to the gene the 5'UTR element is derived from.

It is particularly preferred that the 5'UTR element does not comprise a start codon, such as the nucleotide sequence A(U/T)G. Thus, preferably, the artificial nucleic acid molecule will not comprise any upstream AUGs (or upstream ATGs in case it is a DNA molecule). In other words, in some embodiments, it may be preferred that the AUG or ATG, respectively, of the open reading frame is the only start codon of the artificial nucleic acid molecule.

Additionally, it is preferred that the 5'UTR element does not comprise an open reading frame. Thus, preferably, the artificial nucleic acid molecule will not comprise any upstream open reading frames.

The nucleic acid sequence which is derived from the 5'UTR of a TOP gene is derived from a eukaryotic TOP gene, preferably a plant or animal TOP gene, more preferably a chordate TOP gene, even more preferably a vertebrate TOP gene, most preferably a mammalian TOP gene, such as a human or mouse TOP gene.

Preferably, the artificial nucleic acid molecule according to the present invention comprises a 5'UTR element which comprises or consists of a nucleic acid sequence which is derived from the 5'UTR of a TOP gene or which is derived from a variant of the 5'UTR of a TOP gene, wherein the TOP gene is a plant or animal TOP gene, more preferably a chordate TOP gene, even more preferably a vertebrate TOP gene, most preferably a mammalian TOP gene, such as a human or mouse TOP gene and which optionally does not comprise the nucleotide sequence A(U/T)G and optionally does not comprise an open reading frame; at least one open reading frame (ORF); wherein optionally the 5'UTR element does not comprise a TOP motif and wherein optionally the 5'UTR element starts at its 5'-end with a nucleotide located at position 1, 2, 3, 4, 5, 6, 7, 8, 9 or 10 downstream of the 5' terminal oligopyrimidine tract (TOP) of the 5'UTR of a TOP gene and wherein further optionally the 5'UTR element which is derived from a 5'UTR of a TOP gene terminates at its 3'-end with a nucleotide located at position 1, 2, 3, 4, 5, 6, 7, 8, 9 or 10 upstream of the start codon (A(U/T)G) of the gene or mRNA it is derived from.

For example, the 5'UTR element comprises or consists of a nucleic acid sequence which is derived from a nucleic acid sequence selected from the group consisting of SEQ ID NOs. 1-1363, SEQ ID NO. 1395, SEQ ID NO. 1421 and SEQ ID NO. 1422, from the homologs of SEQ ID NOs. 1-1363, SEQ ID NO. 1395, SEQ ID NO. 1421 and SEQ ID NO. 1422, from a variant thereof, or a corresponding RNA sequence. The term "homologs of SEQ ID NOs. 1-1363, SEQ ID NO. 1395, SEQ ID NO. 1421 and SEQ ID NO. 1422" refers to sequences of other species, e.g. other species than *Homo sapiens* (human) or *Mus musculus* (mouse), which are homologous to the sequences according to SEQ ID NOs. 1-1363, SEQ ID NO. 1395, SEQ ID NO. 1421 or SEQ ID NO. 1422. For example, SEQ ID NO. 1 relates to a sequence comprising the 5'UTR of *Homo sapiens* alpha 2 macroglobulin (A2M). A homolog of SEQ ID NO. 1 in the context of the present invention is any such sequence derived from an alpha 2 macroglobulin (A2M) gene or mRNA of another species than *Homo sapiens*, such as any vertebrate, preferably any mammalian alpha 2 macroglobulin (A2M) gene other than the human alpha 2 macroglobulin (A2M) gene, such as a mouse, rat, rabbit, monkey etc. alpha 2 macroglobulin (A2M) gene.

In a preferred embodiment, the 5'UTR element comprises or consists of a nucleic acid sequence which is derived from a nucleic acid sequence extending from nucleotide position 5 (i.e. the nucleotide that is located at position 5 in the sequence) to the nucleotide position immediately 5' to the start codon (located at the 3' end of the sequences), e.g. the nucleotide position immediately 5' to the ATG sequence, of a nucleic acid sequence selected from SEQ ID NOs. 1-1363, SEQ ID NO. 1395, SEQ ID NO. 1421 or SEQ ID NO. 1422, from the homologs of SEQ ID NOs. 1-1363, SEQ ID NO. 1395, SEQ ID NO. 1421 or SEQ ID NO. 1422, from a variant thereof, or a corresponding RNA sequence. It is particularly preferred that the 5' UTR element is derived from a nucleic acid sequence extending from the nucleotide position immediately 3' to the 5'TOP to the nucleotide position immediately 5' to the start codon (located at the 3' end of the sequences), e.g. the nucleotide position immediately 5' to the ATG sequence, of a nucleic acid sequence selected from SEQ ID NOs. 1-1363, SEQ ID NO. 1395, SEQ ID NO. 1421 or SEQ ID NO. 1422, from the homologs of SEQ ID NOs. 1-1363, SEQ ID NO. 1395, SEQ ID NO. 1421 or SEQ ID NO. 1422, from a variant thereof, or a corresponding RNA sequence.

In a preferred embodiment, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to a nucleic acid sequence extending from nucleotide position 5 to the nucleotide position immediately 5' to the start codon (located at the 3' end of the sequences), e.g. the nucleotide position immediately 5' to the ATG sequence of a nucleic acid sequence selected from SEQ ID NOs. 1-1363, SEQ ID NO. 1395, SEQ ID NO. 1421 or SEQ ID NO. 1422, or a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to a nucleic acid sequence extending from nucleotide position 5 to the nucleotide position immediately 5' to the start codon (located at the 3' end of the sequences), e.g. the nucleotide position immediately 5' to the ATG sequence of a nucleic acid sequence, selected from SEQ ID NOs. 1-1363, SEQ ID NO. 1395, SEQ ID NO. 1421 or SEQ ID NO. 1422, or a corresponding RNA sequence, wherein, preferably, the fragment is as described above, i.e. being a continuous stretch of nucleotides representing at least 20% etc. of the full-length 5'UTR the fragment is derived from.

Preferably, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to a nucleic acid sequence extending from the nucleotide position immediately 3' to the 5'TOP to the nucleotide position immediately 5' to the start codon (located at the 3' end of the sequences), e.g. the nucleotide position immediately 5' to the ATG sequence, of a nucleic acid sequence selected from SEQ ID NOs. 1-1363, SEQ ID NO. 1395, SEQ ID NO. 1421 or SEQ ID NO. 1422, or a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to a nucleic acid sequence extending from the nucleotide position immediately 3' to the 5'TOP to the nucleotide position immediately 5' to the start codon (located at the 3' end of the sequences), e.g. the nucleotide position immediately 5' to the ATG sequence, of a nucleic acid sequence selected from SEQ ID NOs. 1-1363, SEQ ID NO. 1395, SEQ ID NO. 1421 or SEQ ID NO. 1422, or a corresponding RNA sequence, wherein, preferably, the fragment is as described above, i.e. being a continuous stretch of nucleotides representing at least 20% etc. of the full-length 5'UTR the fragment is derived from.

Preferably, the above defined fragments and variants (e.g. exhibiting at least 40% identity) of the sequences according to SEQ ID NOs. 1-1363, SEQ ID NO. 1395, SEQ ID NO. 1421 or SEQ ID NO. 1422, are functional fragments and variants as described herein.

Furthermore, the artificial nucleic acid molecule according to the present invention may comprise more than one 5'UTR elements as described above. For example, the artificial nucleic acid molecule according to the present invention may comprise one, two, three, four or more 5'UTR elements, wherein the individual 5'UTR elements may be the same or they may be different. For example, the artificial nucleic acid molecule according to the present invention may comprise two essentially identical 5'UTR elements as described above, e.g. two 5'UTR elements comprising or consisting of a nucleic acid sequence which is derived from a nucleic acid sequence selected from the group consisting of SEQ ID NOs. 1-1363, SEQ ID NO. 1395, SEQ ID NO. 1421 and SEQ ID NO. 1422, from the homologs of SEQ ID NOs. 1-1363, SEQ ID NO. 1395, SEQ ID NO. 1421 and SEQ ID NO. 1422, from a variant thereof, or a corresponding RNA sequence or from functional variants thereof, functional fragments thereof, or functional variant fragments thereof as described above.

In a particularly preferred embodiment, the 5'UTR element comprises or consists of a nucleic acid sequence which is derived from a 5'UTR of a TOP gene encoding a ribosomal protein or from a variant of a 5'UTR of a TOP gene encoding a ribosomal protein. Particularly preferred 5'UTR elements comprise or consist of a nucleic acid sequence which are derived from a 5' UTR of a TOP gene coding for a ribosomal protein selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, UBA52. Particularly preferred are nucleic acid sequences which are derived from a 5' UTR of TOP genes vertebrate coding for ribosomal proteins, such as mammalian ribosomal proteins e.g. human or mouse ribosomal proteins.

For example, the 5'UTR element comprises or consists of a nucleic acid sequence which is derived from a 5'UTR of a nucleic acid sequence according to any of SEQ ID NOs: 170, 232, 244, 259, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1346, 1347, 1348, 1349, 1350, 1351, 1352, 1353, 1354, 1355, 1356, 1357, 1358, 1359, or 1360; a corresponding RNA sequence, a homolog thereof, or a variant thereof as described herein, preferably lacking the 5'TOP motif. As described above, the sequence extending from position 5 to the nucleotide immediately 5' to the ATG (which is located at the 3' end of the sequences) corresponds to the 5'UTR of said sequences.

Preferably, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the 5'UTR of a nucleic acid sequence according to any of SEQ ID NOs.: 170, 232, 244, 259, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1346, 1347, 1348, 1349, 1350, 1351, 1352, 1353, 1354, 1355, 1356, 1357, 1358, 1359, or 1360; or a corresponding RNA sequence, preferably lacking the 5'TOP motif, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the 5'UTR of a nucleic acid sequence according to SEQ ID NOs: 170, 232, 244, 259, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1346, 1347, 1348, 1349, 1350, 1351, 1352, 1353, 1354, 1355, 1356, 1357, 1358, 1359, or 1360; or a corresponding RNA sequence, wherein, preferably, the fragment is as described above, i.e. being a continuous stretch of nucleotides representing at least 20% etc. of the full-length 5'UTR, preferably lacking the 5'TOP motif. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

Preferably, the 5'UTR element comprises or consists of a nucleic acid sequence which is derived from a 5'UTR of a TOP gene encoding a ribosomal Large protein (RPL) or from a variant of a 5'UTR of a TOP gene encoding a ribosomal Large protein (RPL). For example, the 5'UTR element comprises or consists of a nucleic acid sequence which is derived from a 5'UTR of a nucleic acid sequence according to any of SEQ ID NOs: 67, 259, 1284-1318, 1344, 1346, 1348-1354, 1357, 1358, 1421 and 1422, a corresponding RNA sequence, a homolog thereof, or a variant thereof as described herein, preferably lacking the 5'TOP motif.

Preferably, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the 5'UTR of a nucleic acid sequence according to any of SEQ ID NOs. 67, 259, 1284-1318, 1344, 1346, 1348-1354, 1357, 1358, 1421 and 1422 or a corresponding RNA sequence, preferably lacking the 5'TOP motif, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the 5'UTR of a nucleic acid sequence according to SEQ ID NOs: 67, 259, 1284-1318, 1344, 1346, 1348-1354, 1357, 1358, 1421 and 1422 or a corresponding RNA sequence, wherein, preferably, the fragment is as described above, i.e. being a continuous stretch of nucleotides representing at least 20% etc. of the full-length 5'UTR, preferably lacking the 5'TOP motif. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In a particularly preferred embodiment, the 5'UTR element comprises or consists of a nucleic acid sequence which is derived from the 5'UTR of a ribosomal protein Large 32 gene (RPL32), a ribosomal protein Large 35 gene (RPL35), a ribosomal protein Large 21 gene (RPL21), an ATP synthase, H+ transporting, mitochondrial F1 complex, alpha subunit 1, cardiac muscle (ATP5A1) gene, an hydroxysteroid (17-beta) dehydrogenase 4 gene (HSD17B4), an androgen-induced 1 gene (AIG1), cytochrome c oxidase subunit VIc gene (COX6C), or a N-acylsphingosine amidohydrolase (acid ceramidase) 1 gene (ASAH1) or from a variant thereof, preferably from a vertebrate ribosomal protein Large 32 gene (RPL32), a vertebrate ribosomal protein Large 35 gene (RPL35), a vertebrate ribosomal protein Large 21 gene (RPL21), a vertebrate ATP synthase, H+ transporting, mitochondrial F1 complex, alpha subunit 1, cardiac muscle (ATP5A1) gene, a vertebrate hydroxysteroid (17-beta) dehydrogenase 4 gene (HSD17B4), a vertebrate androgen-induced 1 gene (AIG1), a vertebrate cytochrome c oxidase subunit VIc gene (COX6C), or a vertebrate N-acylsphingosine amidohydrolase (acid ceramidase) 1 gene (ASAH1) or from a variant thereof, more preferably from a mammalian ribosomal protein Large 32 gene (RPL32), a ribosomal protein Large 35 gene (RPL35), a ribosomal protein Large 21 gene (RPL21), a mammalian ATP synthase, H+ transporting, mitochondrial F1 complex, alpha subunit 1, cardiac muscle (ATP5A1) gene, a mammalian hydroxysteroid (17-beta) dehydrogenase 4 gene (HSD17B4), a mammalian androgen-induced 1 gene (AIG1), a mammalian cytochrome c oxidase subunit VIc gene (COX6C), or a mammalian N-acylsphingosine amidohydrolase (acid ceramidase) 1 gene (ASAH1) or from a variant thereof, most preferably from a human ribosomal protein Large 32 gene (RPL32), a human ribosomal protein Large 35 gene (RPL35), a human ribosomal protein Large 21 gene (RPL21), a human ATP synthase, H+ transporting, mitochondrial F1 complex, alpha subunit 1, cardiac muscle (ATP5A1) gene, a human hydroxysteroid (17-beta) dehydrogenase 4 gene (HSD17B4), a human androgen-induced 1 gene (AIG1), a human cytochrome c oxidase subunit VIc gene (COX6C), or a human N-acylsphingosine amidohydrolase (acid ceramidase) 1 gene (ASAH1) or from a variant thereof, wherein preferably the 5'UTR element does not comprise the 5'TOP of said gene.

Accordingly, in a particularly preferred embodiment, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 1368, or SEQ ID NOs 1412-1420, or a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 1368, or SEQ ID NOs 1412-1420, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

Preferably, the at least one 5'UTR element exhibits a length of at least about 20 nucleotides or more, preferably of at least about 30 nucleotides or more, more preferably of at least about 40 nucleotides or more. However, it may be preferred if the 5'UTR element of the artificial nucleic acid molecule is rather short. Accordingly, it may have a length of less than about 200, preferably less than 150, more preferably less than 100 nucleotides. For example, the 5'UTR may have a length of less than about 25, 30, 35, 40, 45, 50, 55, 60, 65, 70, 80, 85, 90, 95, 100, 105, 110, 115, 120, 125, 130, 135, 140, 145, 150, 155, 160, 165, 170, 175, 180, 185, 190, 195, 200 nucleotides Preferably, the 5'UTR element may have a length of about 20-25, 26-30, 31-35, 36-40, 41-45, 46-50, 51-55, 56-60, 61-65, 66-70, 71-80, 81-85, 86-90, 91-95, 96-100, 101-105, 106-110, 111-115, 116-120, 121-125, 126-130, 131-135, 136-140, 141-145, 146-150, 151-155, 156-160, 161-165, 166-170, 171-175, 176-180, 181-185, 186-190, 191-195, 196-200 or more nucleotides. For example, the 5'UTR element may have a length of about 20, 26, 31, 36, 41, 46, 51, 56, 61, 66, 71, 81, 86, 91, 96, 101, 106, 111, 116, 121, 126, 131, 136, 141, 146, 151, 156, 161, 166, 171, 176, 181, 186, 191 or 196 nucleotides. Preferably, the 5'UTR element may have a length from about 20, 30, 40 or more to less than about 200 nucleotides, more preferably from about 20, 30, 40 or more to less than about 150 nucleotides, most preferably from about 20, 30, 40 or more to less than about 100 nucleotides.

Preferred 5'UTR elements are derived from a 5' UTR of a TOP gene selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, RPLP0, RPLP1, RPLP2, EEF1A1, EEF1B2, EEF1D, EEF1G, EEF2, EIF3E, EIF3F, EIF3H, EIF2S3, EIF3C, EIF3K, EIF3EIP, EIF4A2, PABPC1, HNRNPA1, TPT1, TUBB1, UBA52, NPM1, ATP5G2, GNB2L1, NME2, UQCRB or from a variant thereof.

In some embodiments, the artificial nucleic acid molecule comprises a 5'UTR element which comprises or consists of a nucleic acid sequence which is derived from the 5'UTR of a vertebrate TOP gene, such as a mammalian, e.g. a human TOP gene, selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, RPLP0, RPLP1, RPLP2, EEF1A1, EEF1B2, EEF1D, EEF1G, EEF2, EIF3E, EIF3F, EIF3H, EIF2S3, EIF3C, EIF3K, EIF3EIP, EIF4A2, PABPC1, HNRNPA1, TPT1, TUBB1, UBA52, NPM1, ATP5G2, GNB2L1, NME2, UQCRB, or from a variant thereof, wherein preferably the 5'UTR element does not comprise a TOP-motif or the 5'TOP of said genes, and wherein optionally the 5'UTR element starts at its 5'-end with a nucleotide located at position 1, 2, 3, 4, 5, 6, 7, 8, 9 or 10 downstream of the 5' terminal oligopyrimidine tract (TOP) and wherein further optionally the 5'UTR element which is derived from a 5'UTR of a TOP gene terminates at its 3'-end with a nucleotide located at position 1, 2, 3, 4, 5, 6, 7, 8, 9 or 10 upstream of the start codon (A(U/T)G) of the gene it is derived from.

In a preferred embodiment, the artificial nucleic acid molecule according to the present invention further comprises c. at least one 3'UTR element which comprises or consists of a nucleic acid sequence derived from the 3'UTR of a chordate gene, preferably a vertebrate gene, more preferably a mammalian gene, most preferably a human gene, or from a variant of the 3'UTR of a chordate gene, preferably a vertebrate gene, more preferably a mammalian gene, most preferably a human gene.

The term ‘3'UTR element’ refers to a nucleic acid sequence which comprises or consists of a nucleic acid sequence that is derived from a 3'UTR or from a variant of a 3'UTR. A 3'UTR element in the sense of the present invention may represent the 3'UTR of an mRNA, e.g., in the event that the artificial nucleic acid molecule is an mRNA, or it may represent a sequence in a nucleic acid construct, such as a vector construct, that when transcribed represents the 3'UTR of the transcription product, such as the mRNA. Thus, in the sense of the present invention, preferably, a 3'UTR element may be the 3'UTR of an mRNA, preferably of an artificial mRNA, or it may be the transcription template for a 3'UTR of an mRNA. Thus, a 3'UTR element preferably is a nucleic acid sequence which corresponds to the 3'UTR of an mRNA, preferably to the 3'UTR of an artificial mRNA, such as an mRNA obtained by transcription of a genetically engineered vector construct. Preferably, the 3'UTR element fulfils the function of a 3'UTR or encodes a sequence which fulfils the function of a 3'UTR. The term ‘3UTR element’ furthermore refers to a fragment or part of a 3'UTR of an artificial nucleic acid sequence, such as an artificial mRNA, or which codes for a part or fragment of a 3'UTR of an artificial nucleic acid molecule. This means that the 3'UTR element in the sense of the present invention may be comprised in the 3'UTR of an artificial nucleic acid sequence, such as an artificial mRNA, or which codes for a 3'UTR of an artificial nucleic acid molecule.

Preferably, the 3'UTR element and the at least one open reading frame are heterologous. For example, the artificial nucleic acid molecule may consist of at least two sequence parts that are derivable from two different genes, the 5'UTR element which is derivable from a TOP gene and the open reading frame and the 3'UTR which may be derivable from the gene encoding the desired protein product. More preferably, the artificial nucleic molecule consist of three sequence parts that are derivable from three different genes: the 5'UTR element which is derivable from a TOP gene, the open reading frame which is derivable from the gene encoding the desired gene product and the 3'UTR element which may be derivable from a gene that relates to an mRNA with an enhanced half-life, for example a 3'UTR element as defined and described below.

Preferably, the at least one 3'UTR element is functionally linked to the ORF. This means preferably that the 3'UTR element is associated with the ORF such that it may exert a function, such as a stabilizing function on the expression of the ORF or a stabilizing function on the artificial nucleic acid molecule. Preferably, the ORF and the 3'UTR element are associated in 5'→3' direction. Thus, preferably, the artificial nucleic acid molecule comprises the structure 5'-ORF-(optional)linker-3'UTR element-3', wherein the linker may be present or absent. For example, the linker may be one or more nucleotides, such as a stretch of 1-50 or 1-20 nucleotides, e.g., comprising or consisting of one or more restriction enzyme recognition sites (restriction sites).

Preferably, the at least one 5'UTR element and the at least one 3'UTR element are functionally linked to the ORF. This means preferably that the 5'UTR element and the 3'UTR element are associated with the ORF such that they may exert a function, preferably in an additive, more preferably in a synergistic manner, such as a stabilizing function on the expression of the ORF, a protein production increasing function for the protein encoded by the ORF, or a stabilizing function on the artificial nucleic acid molecule. Preferably, the 5'UTR element, the ORF, and the 3'UTR element are associated in 5'→3' direction. Thus, preferably, the artificial nucleic acid molecule comprises the structure 5'-5'UTR element-(optional)linker-ORF-(optional)linker-3'UTR element-3', wherein the linker may be present or absent. For example, the linker may be one or more nucleotides, such as a stretch of 1-50 or 1-20 nucleotides, e.g., comprising or consisting of one or more restriction enzyme recognition sites (restriction sites).

In a particularly preferred embodiment, the 5'UTR element and the 3'UTR element are heterologous, e.g. preferably the 5'UTR and the 3'UTR are derived from different genes of the same or of different species. Preferably, the 3'UTR is not derived from the TOP gene the 5'UTR is derived from.

In a preferred embodiment, the 3'UTR element is chosen such that it exerts at least an additive, preferably a synergistic function with the 5'UTR element on the protein production from the ORF of the artificial nucleic acid molecule. Preferably, the protein production is increased in at least an additive, preferably a synergistic way by the 3'UTR element and the 5'UTR element. Thus, the protein amount of the protein encoded by the ORF, such as a reporter protein, e.g. luciferase, at a certain time point after initiation of expression of the ORF, e.g. after transfection of a test cell or cell line, is preferably at least the same, preferably higher than what would be expected if the protein production increasing effects of the 3'UTR element and the 5'UTR element were purely additive. The additive, preferably the synergistic effect may, for example, be determined by the following assay. Four artificial nucleic acid molecules, e.g. mRNAs, comprising an ORF encoding, e.g. a reporter protein such as luciferase, are generated, i.e. (i) lacking UTR elements (E0), (ii) containing a 5'UTR element derived from a 5'UTR of a TOP gene or of a variant thereof (E1), (iii) containing a test 3'UTR element (E2), and (iv) containing both the 5'UTR element and the test 3'UTR element (E1E2). Expression of the ORF contained in the artificial nucleic acid molecules is initiated, for example, by transfecting a test cell line, such as a mammalian cell line, e.g. HELA cells, or primary cells, e.g. HDF cells. Samples are taken at specific time points after initiation of expression, for example, after 6 hours, 24 hours, 48 hours, and 72 hours and the amount of protein produced by expression of the ORF contained in the artificial nucleic acid molecules is measured, for example, by an ELISA assay or a luciferase test, depending on the type of protein encoded by the ORF. The predicted amount of protein at a certain time point after initiation of expression obtained by construct E1E2 if the effects of the 3'UTR element and the 5'UTR element were purely additive (PPA) may be calculated as follows:

$$PPA_x=(E1_x-E0_x)+(E2_x-E0_x)+E0_x,$$

E0 is the amount of protein obtained for the construct E0 (lacking UTRs), E1 is the amount of protein obtained for the construct E1, E2 is the protein amount obtained for the construct E2, and x is the time point after initiation of expression. The effect on increasing protein production is additive if $E1E2_x=PPA_x$ and synergistic in the sense of the present invention if $E1E2_x>PPA_x$, wherein $E1E2_x$ is the amount of protein obtained from construct E1E2 at time point x. Preferably, E1E2 is at least 1.0, preferably at least 1.1, more preferably at least 1.3, more preferably at least 1.5, even more preferably at least 1.75 times PPA at a given time point post initiation of expression, such as 24 hours, 48 hours or 72 hours post initiation of expression.

Thus, in a preferred embodiment, the present invention provides an artificial nucleic acid molecule comprising (a.) at least one 5'UTR element which comprises or consists of a nucleic acid sequence which is derived from the 5'UTR of a TOP gene or which is derived from a variant of the 5'UTR of a TOP gene; (b.) at least one open reading frame (ORF); and (c.) at least one 3'UTR element, wherein the 3'UTR element and the 5'UTR element act at least additively, preferably synergistically to increase protein production from the ORF, preferably wherein E1E2≥PPA, preferably E1E2 is at least 1.0 times PPA, preferably E1E2 is at least 1.1 times PPA, more preferably E1E2 is at least 1.3 times PPA, even more preferably E1E2 is at least 1.5 times PPA at a given time point post initiation of expression of the ORF, for example 24 hours, preferably 48 hours post initiation of expression, such as post transfection, wherein E1E2 and PPA are as described above.

Furthermore, it is preferred that the 3'UTR element and the 5'UTR element have at least an additive, preferably a synergistic effect on the total protein production from the artificial nucleic acid molecule in a certain time span, such as within 24 hours, 48 hours, or 72 hours post initiation of expression. The additive or the synergistic effect may be determined as described above, with the difference that the area under the curve (AUC) for the amount of protein over time predicted for E1E2 if the effects were purely additive is compared to the actual AUC measured for E1E2.

In a preferred embodiment, the 3'UTR element comprises or consists of a nucleic acid sequence which is derived from the 3'UTR of a stable mRNA or from a variant of the 3'UTR of a stable mRNA. Thus, in a preferred embodiment, the 3'UTR element comprises or consists of a sequence which is derived from a gene providing a stable mRNA or from a variant of a 3'UTR of a gene providing a stable mRNA. The term "stable mRNA", preferably refers to mRNAs which exhibit a longer half-life in mammalian cells than the average half-life of mRNA molecules in mammalian cells. Preferably, a stable mRNA in the sense of the present application refers to an mRNA which exhibits a half-life of more than 5 hours, preferably more than 8 hours, in a mammalian cell, such as in a mammalian cell line, e.g. in HELA cells, or in primary cells, e.g. in HDF cells, preferably determined by using a transcription inhibitor such as actinomycin D.

For example, the half-life of an mRNA in mammalian cells, such as HELA or HDF cells, may be determined by culturing the cells in presence of a transcription inhibitor, e.g. actinomycin D, 5,6-dichloro-1-β-D-ribofuranosylbenzimidazole (DRB), or α-amanitin, harvesting the cells at different time points after inhibition of transcription, and determining the amount of the mRNA present in the cell samples by methods well known to the person skilled in the art, e.g. by quantitative RT-PCR. The half-life of a particular mRNA may be calculated based on the amounts of the particular mRNA measured at the different time points post inhibition of transcription. Alternatively, pulse-chase methods, e.g. using radioactively labelled nucleotides, or constructs comprising inducible promoters may be used for determining the half-life of an mRNA in mammalian cells.

It is particularly preferred that the enhanced stability of a stable mRNA in the sense of the present invention is affected by its 3'UTR. Thus, preferably, the 3'UTR element comprises or consists of a nucleic acid sequence which is derived from the 3'UTR of a stable mRNA which exhibits a half-life of more than 5 hours, preferably more than 8 hours, in a mammalian cell, such as in a mammalian cell line, e.g. in HeLa cells, or in mammalian primary cells, e.g. in HDF cells, preferably determined by using a transcription inhibitor such as actinomycin D, wherein the enhanced stability of said stable mRNA is effected by its 3'UTR. The ability of a 3'UTR for enhancing stability may be tested as described herein, e.g. by using a reporter open reading frame such as a luciferase encoding open reading frame. Alternatively, an artificial construct encoding the test stable mRNA may be generated, wherein the 3'UTR of the stable mRNA is replaced with a reference 3'UTR, such as a 3'UTR of a short lived mRNA, e.g. a Myc 3'UTR. The stability of the wild type stable mRNA and the 3'UTR modified mRNA may be determined as described above. In the event the 3'UTR modified mRNA exhibits a shorter half-life than the wild type stable mRNA, it may be concluded that a stability enhancing effect is exerted by the 3'UTR of the stable mRNA.

In a particularly preferred embodiment, the 3'UTR element comprises or consists of a nucleic acid sequence which is derived from a 3'UTR of a gene selected from the group consisting of an albumin gene, an α-globin gene, a β-globin gene, a tyrosine hydroxylase gene, a lipoxygenase gene, and a collagen alpha gene, such as a collagen alpha 1(I) gene, or from a variant of a 3'UTR of a gene selected from the group consisting of an albumin gene, an α-globin gene, a β-globin gene, a tyrosine hydroxylase gene, a lipoxygenase gene, and a collagen alpha gene, such as a collagen alpha 1(I) gene. In a particularly preferred embodiment, the 3'UTR element comprises or consists of a nucleic acid sequence which is derived from a 3'UTR of an albumin gene, preferably a vertebrate albumin gene, more preferably a mammalian albumin gene, most preferably a human albumin gene. In another particularly preferred embodiment, the 3'UTR element comprises or consists of a nucleic acid sequence which is derived from a 3'UTR of an α-globin gene, preferably a vertebrate α-globin gene, more preferably a mammalian α-globin gene, most preferably a human α-globin gene. For example, the 3'UTR element may comprise or consist of the center, α-complex-binding portion of the 3'UTR of an α-globin gene, such as of a human α-globin gene.

Preferably, the at least one 3'UTR element comprises or consists of a nucleic acid sequence which is derived from the 3'UTR of a vertebrate albumin gene, a vertebrate α-globin gene, a vertebrate β-globin gene, a vertebrate tyrosine hydroxylase gene, a vertebrate lipoxygenase gene, and a vertebrate collagen alpha gene, such as a vertebrate collagen alpha 1(I) gene, or from a variant thereof, preferably from the 3'UTR of a mammalian albumin gene, a mammalian α-globin gene, a mammalian β-globin gene, a mammalian tyrosine hydroxylase gene, a mammalian lipoxygenase gene, and a mammalian collagen alpha gene, such as a mammalian collagen alpha 1(I) gene, or from a variant thereof, more preferably from the 3'UTR of a human albumin gene, a human α-globin gene, a human β-globin gene, a human tyrosine hydroxylase gene, a human lipoxygenase gene, and a human collagen alpha gene, such as a human collagen alpha 1(I) gene, or from a variant thereof, even more preferably from the 3'UTR of the human albumin gene according to GenBank Accession number NM_000477.5 or from a variant thereof. In a preferred embodiment, the 3'UTR element is not derived from the 3'UTR of a *Xenopus* albumin gene. Preferably, the 3'UTR element does not comprise a poly(A) limiting element B (PLEB) of a 3'UTR from a *Xenopus* albumin gene. Preferably, the 3'UTR element does not consist of a PLEB of a 3'UTR from a *Xenopus* albumin gene.

Preferably, the 3'UTR element and the at least one open reading frame are heterologous, e.g. preferably the 3'UTR element and the ORF are derived from different genes of the same or of different species. Preferably, the ORF does not encode an α-globin protein if the 3'UTR element is derived from an α-globin gene. Preferably, the ORF does not encode a β-globin protein if the 3'UTR element is derived from a β-globin gene. Preferably, the ORF does not encode an albumin protein if the 3'UTR element is derived from an albumin gene. Preferably, the ORF does not encode a tyrosine hydroxylase protein if the 3'UTR element is derived from a tyrosine hydroxylase gene. Preferably, the ORF does not encode a lipoxygenase protein if the 3'UTR element is derived from a lipoxygenase gene. Preferably, the ORF does not encode a collagen alpha protein if the 3'UTR element is derived from a collagen alpha gene. Preferably, the ORF does not code for a protein selected from the group consisting of albumin proteins, growth hormones, e.g. human growth hormone (hGH), α-globin proteins, β-globin proteins, tyrosine hydroxylase proteins, lipoxygenase proteins, and collagen alpha proteins. Furthermore, it is preferred that the open reading frame does not code for a reporter protein, e.g., selected from the group consisting of globin proteins, in particular beta-globin, luciferase protein, GFP proteins, e.g. EGFP, or variants thereof, for example, variants exhibiting at least 70% sequence identity to a globin protein, a luciferase protein, or a GFP protein.

The term 'a nucleic acid sequence which is derived from the 3'UTR of a [ . . . .] gene' preferably refers to a nucleic acid sequence which is based on the 3'UTR sequence of a [ . . . ] gene or on a part thereof, such as on the 3'UTR of an albumin gene, an α-globin gene, a β-globin gene, a tyrosine hydroxylase gene, a lipoxygenase gene, or a collagen alpha gene, such as a collagen alpha 1(I) gene, preferably of an albumin gene or on a part thereof. This term includes sequences corresponding to the entire 3'UTR sequence, i.e. the full length 3'UTR sequence of a gene, and sequences corresponding to a fragment of the 3'UTR sequence of a gene, such as an albumin gene, α-globin gene, β-globin gene, tyrosine hydroxylase gene, lipoxygenase gene, or collagen alpha gene, such as a collagen alpha 1(I) gene, preferably of an albumin gene. A fragment in this context preferably consists of a continuous stretch of nucleotides corresponding to a continuous stretch of nucleotides in the full-length 3'UTR, which represents at least 20%, preferably at least 30%, more preferably at least 40%, more preferably at least 50%, even more preferably at least 60%, even more preferably at least 70%, even more preferably at least 80%, and most preferably at least 90% of the full-length 3'UTR. Such a fragment, in the sense of the present invention, is preferably a functional fragment as described herein. The term '3'UTR of a [ . . . ] gene' preferably refers to the 3'UTR of a naturally occurring gene, such as of a naturally occurring albumin gene, α-globin gene, β-globin gene, tyrosine hydroxylase gene, lipoxygenase gene, or collagen alpha gene, such as a collagen alpha 1(I) gene, preferably of a naturally occurring albumin gene.

The terms 'variant of the 3'UTR of a [ . . . ] gene' and 'variant thereof' in the context of a 3'UTR refers to a variant of the 3'UTR of a naturally occurring gene, such as a naturally occurring albumin gene, a naturally occurring α-globin gene, a naturally occurring β-globin gene, a naturally occurring tyrosine hydroxylase gene, a naturally occurring lipoxygenase gene, or a naturally occurring collagen alpha gene, such as a naturally occurring collagen alpha 1(I) gene, preferably to a variant of the 3'UTR of a vertebrate albumin gene, a vertebrate α-globin gene, a vertebrate β-globin gene, a vertebrate tyrosine hydroxylase gene, a vertebrate lipoxygenase gene, and a vertebrate collagen alpha gene, such as a vertebrate collagen alpha 1(I) gene, preferably to a variant of the 3'UTR of a mammalian albumin gene, a mammalian α-globin gene, a mammalian β-globin gene, a mammalian tyrosine hydroxylase gene, a mammalian lipoxygenase gene, and a mammalian collagen alpha gene, such as a mammalian collagen alpha 1(I) gene, more preferably to a variant of the 3'UTR of a human albumin gene, a human α-globin gene, a human β-globin gene, a human tyrosine hydroxylase gene, a human lipoxygenase gene, and a human collagen alpha gene, such as a human collagen alpha 1(I) gene. Such variant may be a modified 3'UTR of a gene. For example, a variant 3'UTR may exhibit one or more nucleotide deletions, insertions, additions and/or substitutions compared to the naturally occurring 3'UTR from which the variant is derived. Preferably, a variant of a 3'UTR is at least 40%, preferably at least 50%, more preferably at least 60%, more preferably at least 70%, even more preferably at least 80%, even more preferably at least 90%, most preferably at least 95% identical to the naturally occurring 3'UTR the variant is derived from. Preferably, the variant is a functional variant as described herein.

The term 'a nucleic acid sequence which is derived from a variant of the 3'UTR of a [ . . . ] gene' preferably refers to a nucleic acid sequence which is based on a variant of the 3'UTR sequence of a gene, such as on a variant of the 3'UTR of an albumin gene, an α-globin gene, a β-globin gene, a tyrosine hydroxylase gene, a lipoxygenase gene, or a collagen alpha gene, such as a collagen alpha 1(I) gene, or on a part thereof as described above. This term includes sequences corresponding to the entire sequence of the variant of the 3'UTR of a gene, i.e. the full length variant 3'UTR sequence of a gene, and sequences corresponding to a fragment of the variant 3'UTR sequence of a gene. A fragment in this context preferably consists of a continuous stretch of nucleotides corresponding to a continuous stretch of nucleotides in the full-length variant 3'UTR, which represents at least 20%, preferably at least 30%, more preferably at least 40%, more preferably at least 50%, even more preferably at least 60%, even more preferably at least 70%, even more preferably at least 80%, and most preferably at least 90% of the full-length variant 3'UTR. Such a fragment of a variant, in the sense of the present invention, is preferably a functional fragment of a variant as described herein.

The terms 'functional variant', 'functional fragment', and 'functional fragment of a variant' (also termed 'functional variant fragment') in the context of the present invention, mean that the fragment of the 5'UTR or the 3'UTR, the variant of the 5'UTR or the 3'UTR, or the fragment of a variant of the 5'UTR or the 3'UTR of a gene fulfils at least one, preferably more than one, function of the naturally occurring 5'UTR or 3'UTR of the gene of which the variant, the fragment, or the fragment of a variant is derived. Such function may be, for example, stabilizing mRNA and/or stabilizing and/or prolonging protein production from an mRNA and/or increasing protein production from an mRNA, preferably in a mammalian cell, such as in a human cell. It is particularly preferred that the variant, the fragment, and the variant fragment in the context of the present invention fulfil the function of stabilizing an mRNA, preferably in a mammalian cell, such as a human cell, compared to an mRNA comprising a reference 5'UTR and/or a reference 3'UTR or lacking a 5'UTR and/or a 3'UTR, and/or the function of stabilizing and/or prolonging protein production from an mRNA, preferably in a mammalian cell, such as in a human cell, compared to an mRNA comprising a reference 5'UTR and/or a reference 3'UTR or lacking a 5'UTR and/or a 3'UTR, and/or the function of increasing protein production from an mRNA, preferably in a mammalian cell, such as in a human cell, compared to an mRNA comprising a reference 5'UTR and/or a reference 3'UTR or lacking a 5'UTR and/or a 3'UTR. A reference 3'UTR may be, for example, a 3'UTR naturally occurring in combination with the ORF. Furthermore, a functional variant, a functional fragment, or a functional variant fragment of a 5'UTR or of a 3'UTR of a gene preferably does not have a substantially diminishing effect on the efficiency of translation of the mRNA which comprises such variant of a 5'UTR and/or such variant of a 3'UTR compared to the wild type 5'UTR and/or 3'UTR from which the variant is derived. A particularly preferred function of a "functional fragment", a "functional variant" or a "functional fragment of a variant" of the 3'UTR of a gene, such as an albumin gene, α-globin gene, β-globin gene, tyrosine hydroxylase gene, lipoxygenase gene, or collagen alpha gene, such as a collagen alpha 1(I) gene, in the context of the present invention is the stabilization and/or prolongation of protein production by expression of an mRNA carrying the functional fragment, functional variant or functional fragment of a variant as described above. A particularly preferred function of a "functional fragment", a "functional variant" or a "functional fragment of a variant" of the 5'UTR in the context of the present invention is the protein production increasing function.

Preferably, the efficiency of the one or more functions exerted by the functional variant, the functional fragment, or the functional variant fragment, such as mRNA and/or protein production stabilizing efficiency and/or the protein production increasing efficiency, is at least 40%, more preferably at least 50%, more preferably at least 60%, even more preferably at least 70%, even more preferably at least 80%, most preferably at least 90% of the mRNA and/or protein production stabilizing efficiency and/or the protein production increasing efficiency exhibited by the naturally occurring 5'UTR and/or 3'UTR of which the variant, the fragment or the variant fragment is derived.

In the context of the present invention, a fragment or part of the 3'UTR of a gene, such as an albumin gene, α-globin gene, β-globin gene, tyrosine hydroxylase gene, lipoxygenase gene, or collagen alpha gene, such as a collagen alpha 1(I) gene, or of a variant thereof preferably exhibits a length of at least about 40 nucleotides, preferably of at least about 50 nucleotides, preferably of at least about 75 nucleotides, more preferably of at least about 100 nucleotides, even more preferably of at least about 125 nucleotides, most preferably of at least about 150 nucleotides. Preferably, such fragment of the 3'UTR of a gene or of a variant of the 3'UTR of a gene is a functional fragment as described above.

In the context of the present invention, a fragment or part of the 5'UTR of a TOP gene or of a variant thereof preferably exhibits a length of at least about 20 nucleotides, preferably of at least about 30 nucleotides, more preferably of at least about 50 nucleotides. Preferably, such fragment of the 5'UTR of a TOP gene or of a variant of the 5'UTR of a TOP gene is a functional fragment as described above.

In some embodiments, the at least one 3'UTR element of the artificial nucleic acid molecule according to the present invention comprises or consists of a "functional fragment", a "functional variant" or a "functional fragment of a variant" of the 3'UTR of a gene, such as of an albumin gene, α-globin gene, β-globin gene, tyrosine hydroxylase gene, lipoxygenase gene, or collagen alpha gene, such as a collagen alpha 1(I) gene, or of a variant thereof.

In some embodiments, the at least one 5'UTR element of the artificial nucleic acid molecule according to the present invention comprises or consists of a "functional fragment", a "functional variant" or a "functional fragment of a variant" of the 5'UTR of a TOP gene.

Preferably, the at least one 3'UTR element of the artificial nucleic acid molecule according to the present invention increases the stability of the artificial nucleic acid molecule, e.g. increases the stability of an mRNA according to the present invention, compared to a respective mRNA (reference mRNA) lacking a 3'UTR element or comprising a reference 3'UTR element, such as a 3'UTR naturally occurring in combination with the ORF. Preferably, the at least one 3'UTR element of the artificial nucleic acid molecule according to the present invention increases the stability of protein production from the artificial nucleic acid molecule according to the present invention, e.g. from an mRNA according to the present invention, compared to a respective mRNA lacking a 3'UTR element or comprising a reference 3'UTR element, such as a 3'UTR naturally occurring in combination with the ORF. Preferably, the at least one 3'UTR element of the artificial nucleic acid molecule according to the present invention prolongs protein production from the artificial nucleic acid molecule according to the present invention, e.g. from an mRNA according to the present invention, compared to a respective mRNA lacking a 3'UTR element or comprising a reference 3'UTR element, such as a 3'UTR naturally occurring in combination with the ORF. Preferably, the at least one 3'UTR element of the artificial nucleic acid molecule according to the present invention increases the protein production from the artificial nucleic acid molecule according to the present invention, e.g. from an mRNA according to the present invention, compared to a respective mRNA lacking a 3'UTR element or comprising a reference 3'UTR element, such as a 3'UTR naturally occurring in combination with the ORF. Preferably, the at least one 3'UTR element of the artificial nucleic acid molecule according to the present invention does not negatively influence translational efficiency of an mRNA compared to the translational efficiency of a respective mRNA lacking a 3'UTR element or comprising a reference 3'UTR element, such as a 3'UTR naturally occurring in combination with the ORF. The term 'respective mRNA' in this context means that—apart from the different 3'UTR—the reference mRNA is comparable, preferably identical, to the mRNA comprising the 3'UTR element.

Preferably, the at least one 5'UTR element of the artificial nucleic acid molecule according to the present invention increases the stability of the artificial nucleic acid molecule, e.g. increases the stability of an mRNA according to the present invention, compared to a respective mRNA (reference mRNA) lacking a 5'UTR element or comprising a reference 5'UTR element, such as a 5'UTR naturally occurring in combination with the ORF. Preferably, the at least one 5'UTR element of the artificial nucleic acid molecule according to the present invention increases protein production from the artificial nucleic acid molecule according to the present invention, e.g. from an mRNA according to the present invention, compared to a respective mRNA lacking a 5'UTR element or comprising a reference 5'UTR element, such as a 5'UTR naturally occurring in combination with the ORF. The term 'respective mRNA' in this context means that—apart from the different 5'UTR—the reference mRNA is comparable, preferably identical, to the mRNA comprising the inventive 5'UTR element.

Preferably, the at least one 5'UTR element and the at least one 3'UTR element act synergistically to increase protein production from the artificial nucleic acid molecule according to the present invention, e.g. from an mRNA according to the present invention, as described above.

The term 'stabilizing and/or prolonging protein production from an mRNA' preferably means that the protein production from the mRNA is stabilized and/or prolonged compared to the protein production from a reference mRNA, e.g. comprising a reference 3'UTR element or lacking a 3'UTR element.

'Stabilized protein expression' in this context preferably means that there is more uniform protein production from the artificial nucleic acid molecule according to the present invention over a predetermined period of time, such as over 24 hours, more preferably over 48 hours, even more preferably over 72 hours, when compared to a reference nucleic acid molecule, for example, an mRNA comprising a reference 3'UTR element or lacking a 3'UTR element. Thus, the level of protein production, e.g. in a mammalian system, from the artificial nucleic acid molecule comprising a 3'UTR element according to the present invention, e.g. from an mRNA according to the present invention, preferably does not drop to the extent observed for a reference nucleic acid molecule, such as a reference mRNA as described above. For example, the amount of a protein (encoded by the ORF) observed 6 hours after initiation of expression, e.g. 6 hours post transfection of the artificial nucleic acid molecule according to the present invention into a cell, such as a mammalian cell, may be comparable to the amount of protein observed 48 hours after initiation of expression, e.g. 48 hours post transfection. Thus, the ratio of the amount of protein encoded by the ORF, such as of a reporter protein, e.g., luciferase, observed at 48 hours post initiation of expression, e.g. 48 hours post transfection, to the amount of protein observed 6 hours after initiation of expression, e.g. 6 hours post transfection, is preferably above 0.4, preferably above 0.5, more preferably above 0.6, even more preferably above 0.7, e.g. between about 0.4 and about 4, preferably between about 0.65 and about 3, more preferably between about 0.7 and about 2 for a nucleic acid molecule according to the present invention. For a respective reference nucleic acid molecule, e.g. an mRNA comprising a reference 3'UTR element or lacking a 3'UTR element, said ratio may be, e.g. between about 0.05 and about 0.3. Thus, the present invention provides an artificial nucleic acid molecule comprising an ORF and a 3'UTR element as described above, wherein the ratio of the (reporter) protein amount observed 48 hours after initiation of expression to the (reporter) protein amount observed 6 hours after initiation of expression, preferably in a mammalian expression system, such as in mammalian cells, is preferably above 0.4, preferably above 0.5, more preferably above 0.6, even more preferably above 0.7, e.g. between about 0.4 and about 4, preferably between about 0.65 and about 3, more preferably between about 0.7 and about 2.

'Increased protein expression' in the context of the present invention may refer to increased protein expression at one time point after initiation of expression compared to a reference molecule or to an increased total protein production within a certain time period after initiation of expression. Thus, the protein level observed at a certain time point after initiation of expression, e.g. after transfection, of the artificial nucleic acid molecule according to the present invention, e.g. after transfection of an mRNA according to the present invention, for example, 24, 48, or 72 hours post transfection, or the total protein produced in a time span of, e.g. 24, 48 or 72 hours, is preferably higher than the protein level observed at the same time point after initiation of expression, e.g. after transfection, or the total protein produced within the same time span, for a reference nucleic acid molecule, such as a reference mRNA comprising a reference 5' and/or a reference 3'UTR or lacking a 5'UTR element and/or 3'UTR element. As set forth above, it is a particularly preferred function of the 5'UTR element to affect the increase in protein production from the artificial nucleic acid molecule. Preferably, the increase in protein production effected by the 5'UTR element compared to a reference nucleic acid molecule lacking such 5'UTR element at a given time point post initiation of expression is at least 1.5-fold, more preferably at least 2-fold, more preferably at least 3-fold, even more preferably at least 4-fold, most preferably at least 5-fold of the protein production observed for a reference nucleic acid molecule lacking the 5'UTR element. The same holds preferably for the total protein production in a given time period, for example in a time period of 24, 48 or 72 hours post initiation of expression.

Said increase in stability of the artificial nucleic acid molecule, said increase in stability of protein production, said prolongation of protein production and/or said increase in protein production is preferably determined by comparison with a respective reference nucleic acid molecule lacking a 5'UTR element and/or a 3'UTR element, e.g. an mRNA lacking a 5'UTR element and/or a 3'UTR element, or a reference nucleic acid molecule comprising a reference 5'UTR element and/or a reference 3'UTR element, such as a 3'UTR and/or a 5'UTR naturally occurring with the ORF or a 5'UTR and/or a 3'UTR of a reference gene.

The mRNA and/or protein production stabilizing effect and efficiency and/or the protein production increasing effect and efficiency of the variants, fragments and/or variant fragments of the 3'UTR of an albumin gene as well as the mRNA and/or protein production stabilizing effect and efficiency and/or the protein production increasing effect and efficiency of the at least one 3'UTR element, the at least one 5'UTR element, or the at least one 3'UTR element and the at least one 5'UTR element of the artificial nucleic acid molecule according to the present invention may be determined by any method suitable for this purpose known to the skilled person. For example, artificial mRNA molecules may be generated comprising a coding sequence for a reporter protein, such as luciferase, and no 3'UTR and/or no 5'UTR, a 5'UTR element derived from a TOP gene and/or a 3'UTR element derived from a gene as described above, a 5'UTR element derived from a reference gene and/or a 3'UTR derived from a reference gene (i.e., a reference 3'UTR element or a reference 5'UTR element, such as a 5'UTR or a 3'UTR naturally occurring with the ORF), as 3'UTR a variant of a 3'UTR of a gene as described above, as 3'UTR a fragment of a 3'UTR of a gene as described above, or as 3'UTR a fragment of a variant of a 3'UTR of a gene as described above, as 5'UTR a variant of a 5'UTR of a TOP gene, as 5'UTR a fragment of a 5'UTR of a TOP gene, or as 5'UTR a fragment of a variant of a 5'UTR of a TOP gene. Such mRNAs may be generated, for example, by in vitro transcription of respective vectors such as plasmid vectors, e.g. comprising a T7 promoter and a sequence encoding the respective mRNA sequences. The generated mRNA molecules may be transfected into cells by any transfection method suitable for transfecting mRNA, for example they may be electroporated into mammalian cells, such as HELA or HDF cells, and samples may be analyzed certain time points after transfection, for example, 6 hours, 24 hours, 48 hours, and 72 hours post transfection. Said samples may be analyzed for mRNA quantities and/or protein quantities by methods well known to the skilled person. For example, the quantities of reporter mRNA present in the cells at the sample time points may be determined by quantitative PCR methods. The quantities of reporter protein encoded by the respective mRNAs may be determined, e.g., by ELISA assays or reporter assays such as luciferase assays depending on the reporter protein used. The effect of stabilizing protein expression and/or prolonging protein expression may be, for example, analyzed by determining the ratio of the protein level observed 48 hours post transfection and the protein level observed 6 hours post transfection. The closer said value is to 1, the more stable the protein expression is within this time period. Said value may also be above 1 if the protein level is higher at the later time point. Such measurements may of course also be performed at 72 or more hours and the ratio of the protein level observed 72 hours post transfection and the protein level observed 6 hours post transfection may be determined to determine stability of protein expression.

Preferably, the at least one 3'UTR element of the artificial nucleic acid molecule according to the present invention comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to a nucleic acid sequence selected from SEQ ID No. 1369-1377, 1391, 1392, and 1393 and wherein the variants of the sequences according to SEQ ID No. 1369-1377, 1391, 1392 and 1393 are preferably functional variants as described above.

The at least one 3'UTR element of the artificial nucleic acid molecule according to the present invention may also comprise or consist of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the nucleic acid sequence according to SEQ ID No. 1369-1377, 1391, 1392, or 1393 wherein the fragment is preferably a functional fragment or a functional variant fragment as described above. Preferably, the fragment is as described above, i.e. being a continuous stretch of nucleotides representing at least 20% etc. of the full-length 3'UTR the fragment is derived from. Such fragment preferably exhibits a length of at least about 40 nucleotides, preferably of at least about 50 nucleotides, preferably of at least about 75 nucleotides, more preferably of at least about 100 nucleotides, even more preferably of at least about 125 nucleotides, most preferably of at least about 150 nucleotides.

For example, such fragment may exhibit a nucleic acid sequence according to SEQ ID Nos. 1378-1390, such as

```
                                        (SEQ ID No. 1378)
AAAAGCATCT CAGCCTACCA TGAGAATAAG AGAAAGAAAA
TGAAGATCAA AAGCTTATTC ATCTGTTTTT CTTTTTCGTT
GGTGTAAAGC CAACACCCTG TCTAAAAAAC ATAAATTTCT
TTAATCATTT TGCCTCTTTT CTCTGTGCTT CAATT

                                        (SEQ ID No. 1379)
CATCACATTT AAAAGCATCT CAGCCTACCA TGAGAATAAG
AGAAAGAAAA TGAAGATCAA AAGCTTATTC ATCTGTTTTT
CTTTTTCGTT GGTGTAAAGC CAACACCCTG

                                        (SEQ ID No. 1380)
AAAAGCATCT CAGCCTACCA TGAGAATAAG AGAAAGAAAA
TGAAGATCAA AAGCTTATTC ATCTGTTTTT CTTTTTCGTT
GGTGTAAAGC CAACACCCTG TCTAAAAAAC

                                        (SEQ ID No. 1381)
CAGCCTACCA TGAGAATAAG AGAAAGAAAA TGAAGATCAA
AAGCTTATTC ATCTGTTTTT CTTTTTCGTT GGTGTAAAGC
CAACACCCTG TCTAAAAAAC ATAAATTTCT

                                        (SEQ ID No. 1382)
TGAGAATAAG AGAAAGAAAA TGAAGATCAA AAGCTTATTC
ATCTGTTTTT CTTTTTCGTT GGTGTAAAGC CAACACCCTG
TCTAAAAAAC ATAAATTTCT TTAATCATTT

                                        (SEQ ID No. 1383)
AGAAAGAAAA TGAAGATCAA AAGCTTATTC ATCTGTTTTT
CTTTTTCGTT GGTGTAAAGC CAACACCCTG TCTAAAAAAC
ATAAATTTCT TTAATCATTT TGCCTCTTTT

                                        (SEQ ID No. 1384)
TGAAGATCAA AAGCTTATTC ATCTGTTTTT CTTTTTCGTT
GGTGTAAAGC CAACACCCTG TCTAAAAAAC ATAAATTTCT
TTAATCATTT TGCCTCTTTT CTCTGTGCTT

                                        (SEQ ID No. 1385)
AAGCTTATTC ATCTGTTTTT CTTTTTCGTT GGTGTAAAGC
CAACACCCTG TCTAAAAAAC ATAAATTTCT TTAATCATTT
TGCCTCTTTT CTCTGTGCTT CAATTAATAA

                                        (SEQ ID No. 1386)
ATCTGTTTTT CTTTTTCGTT GGTGTAAAGC CAACACCCTG
TCTAAAAAAC ATAAATTTCT TTAATCATTT TGCCTCTTTT
CTCTGTGCTT CAATTAATAA AAAATGGAAA

                                        (SEQ ID No. 1387)
CAGCCTACCA TGAGAATAAG AGAAAGAAAA TGAAGATCAA
AAGCTTATTC ATCTGTTTTT CTTTTTCGTT GGTGTAAAGC
CAACACCCTG TCTAAAAAAC ATAAATTTCT TTAATCATTT
TGCCTCTTTT CTCTGTGCTT CAATTAATAA A

                                        (SEQ ID No. 1388)
TGAAGATCAA AAGCTTATTC ATCTGTTTTT CTTTTTCGTT
GGTGTAAAGC CAACACCCTG TCTAAAAAAC ATAAATTTCT
TTAATCATTT TGCCTCTTTT CTCTGTGCTT CAATTAATAA
A

                                        (SEQ ID No. 1389)
CTTTTTCGTT GGTGTAAAGC CAACACCCTG TCTAAAAAAC
ATAAATTTCT TTAATCATTT TGCCTCTTTT CTCTGTGCTT
CAATTAATAA A

                                        (SEQ ID No. 1390)
AAGCTTATTC ATCTGTTTTT CTTTTTCGTT GGTGTAAAGC
CAACACCCTG TCTAAAAAAC
```

or the corresponding RNA sequence, or a nucleic acid sequence which is at least 40%, preferably at least about 50%, preferably at least about 60%, preferably at least about 70%, more preferably at least about 80%, more preferably at least about 90%, even more preferably at least about 95%, even more preferably at least about 99% identical to said nucleic acid sequences or the corresponding RNA sequence.

Thus, the at least one 3'UTR element of the artificial nucleic acid molecule according to the present invention may comprise or consist of a nucleic acid fragment as described above. Obviously, the thymidine nucleotides comprised in the fragments according to SEQ ID Nos. 1378-1390 may be replaced by uridine nucleotides.

Preferably, said variants, fragments or variant fragments are functional variants, functional fragments, or functional variant fragments as described above, exhibiting at least one function of the nucleic acid sequence according to SEQ ID Nos. 1369-1377, 1391, 1392, or 1393 such as stabilization of the artificial nucleic acid molecule according to the invention, stabilizing and/or prolonging protein expression from the artificial nucleic acid molecule according to the invention, and/or increasing protein production, preferably with an efficiency of at least 40%, more preferably of at least 50%, more preferably of at least 60%, even more preferably of at least 70%, even more preferably of at least 80%, most preferably of at least 90% of the stabilizing efficiency and/or protein production increasing efficiency exhibited by the nucleic acid sequence according to SEQ ID Nos. 1369-1377, 1391, 1392, or 1393. Preferably, variants, fragments or variant fragments are functional variants, functional fragments, or functional variant fragments exhibit the function of acting synergistically with the 5'UTR element to increase protein production from the artificial nucleic acid molecule.

Preferably, the at least one 3'UTR element of the artificial nucleic acid molecule according to the present invention exhibits a length of at least about 40 nucleotides, preferably of at least about 50 nucleotides, preferably of at least about 75 nucleotides, more preferably of at least about 100 nucleotides, even more preferably of at least about 125 nucleotides, most preferably of at least about 150 nucleotides. For example, the 3'UTR may exhibit a length of about 50 to about 300 nucleotides, preferably of about 100 to about 250 nucleotides, more preferably of about 150 to about 200 nucleotides.

Furthermore, the artificial nucleic acid molecule according to the present invention may comprise more than one 3'UTR elements as described above. For example, the artificial nucleic acid molecule according to the present invention may comprise one, two, three, four or more 3'UTR elements, wherein the individual 3'UTR elements may be the same or they may be different. For example, the artificial nucleic acid molecule according to the present invention may comprise two essentially identical 3'UTR elements as described above, e.g. two 3'UTR elements comprising or consisting of a nucleic acid sequence which is derived from the 3'UTR of an albumin gene or from a variant of the 3'UTR of an albumin gene, such as a nucleic acid sequence according to SEQ ID No. 1369 or 1376, functional variants thereof, functional fragments thereof, or functional variant fragments thereof as described above.

Surprisingly, the inventors found that an artificial nucleic acid molecule comprising a 5'UTR element comprising or consisting of a nucleic acid sequence derived from a TOP gene as described above may represent or may provide an mRNA molecule exhibiting strongly enhanced protein production from said artificial nucleic acid molecule.

The artificial nucleic acid molecule according to the present invention may be RNA, such as mRNA, DNA, such as a DNA vector, or may be a modified RNA or DNA molecule. It may be provided as a double-stranded molecule having a sense strand and an anti-sense strand, for example, as a DNA molecule having a sense strand and an anti-sense strand.

The artificial nucleic acid molecule according to the present invention may further comprise a 5'-cap. The optional 5'-cap is preferably attached to the 5'-side of the 5'UTR element.

In a preferred embodiment, the artificial nucleic acid sequence comprises a 5'UTR element which comprises or consists of a nucleic acid sequence which is derived from the 5'UTR of a TOP gene encoding a ribosomal protein as described above, for example, encoding a ribosomal Large protein, or from a variant thereof, and a 3'UTR element which comprises or consists of a nucleic acid sequence which is derived from the 3'UTR of an albumin gene or a variant thereof as described above.

In a particularly preferred embodiment, the artificial nucleic acid sequence comprises a 5'UTR element which comprises or consists of a nucleic acid sequence which is derived from the 5'UTR of a ribosomal protein Large 32 gene (RPL32), a ribosomal protein Large 35 gene (RPL35), a ribosomal protein Large 21 gene (RPL21), an ATP synthase, H+ transporting, mitochondrial F1 complex, alpha subunit 1, cardiac muscle (ATP5A1) gene, an hydroxysteroid (17-beta) dehydrogenase 4 gene (HSD17B4), an androgen-induced 1 gene (AIG1), cytochrome c oxidase subunit VIc gene (COX6C), or a N-acylsphingosine amidohydrolase (acid ceramidase) 1 gene (ASAH1) or from a variant thereof, preferably from a vertebrate ribosomal protein Large 32 gene (RPL32), a vertebrate ribosomal protein Large 35 gene (RPL35), a vertebrate ribosomal protein Large 21 gene (RPL21), a vertebrate ATP synthase, H+ transporting, mitochondrial F1 complex, alpha subunit 1, cardiac muscle (ATP5A1) gene, a vertebrate hydroxysteroid (17-beta) dehydrogenase 4 gene (HSD17B4), a vertebrate androgen-induced 1 gene (AIG1), a vertebrate cytochrome c oxidase subunit VIc gene (COX6C), or a vertebrate N-acylsphingosine amidohydrolase (acid ceramidase) 1 gene (ASAH1) or from a variant thereof, more preferably from a mammalian ribosomal protein Large 32 gene (RPL32), a ribosomal protein Large 35 gene (RPL35), a ribosomal protein Large 21 gene (RPL21), a mammalian ATP synthase, H+ transporting, mitochondrial F1 complex, alpha subunit 1, cardiac muscle (ATP5A1) gene, a mammalian hydroxysteroid (17-beta) dehydrogenase 4 gene (HSD17B4), a mammalian androgen-induced 1 gene (AIG1), a mammalian cytochrome c oxidase subunit VIc gene (COX6C), or a mammalian N-acylsphingosine amidohydrolase (acid ceramidase) 1 gene (ASAH1) or from a variant thereof, most preferably from a human ribosomal protein Large 32 gene (RPL32), a human ribosomal protein Large 35 gene (RPL35), a human ribosomal protein Large 21 gene (RPL21), a human ATP synthase, H+ transporting, mitochondrial F1 complex, alpha subunit 1, cardiac muscle (ATP5A1) gene, a human hydroxysteroid (17-beta) dehydrogenase 4 gene (HSD17B4), a human androgen-induced 1 gene (AIG1), a human cytochrome c oxidase subunit VIc gene (COX6C), or a human N-acylsphingosine amidohydrolase (acid ceramidase) 1 gene (ASAH1) or from a variant thereof, wherein preferably the 5'UTR element does not comprise the 5'TOP of said gene, and a 3'UTR element which comprises or consists of a nucleic acid sequence which is derived from an albumin gene as described above.

In a particularly preferred embodiment, the artificial nucleic acid molecule according to the present invention comprises a 5'UTR element which comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 1368 or SEQ ID NOs 1412-1420, or a corresponding RNA sequence, and a 3'UTR element which comprises or consist of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the nucleic acid sequence according to SEQ ID No. 1369, 1376, 1377, 1391, or 1392, e.g., a 5'UTR element which comprises or consists of a nucleic acid sequence which has an identity of at least about 90% to the nucleic acid sequence according to SEQ ID No. 1368 or a corresponding RNA sequence and a 3'UTR element which comprises or consist of a nucleic acid sequence which has an identity of at least about 90% to the nucleic acid sequence according to SEQ ID No. 1369, 1376, 1377, 1391, or 1392.

Preferably, the artificial nucleic acid molecule according to the present invention further comprises a poly(A) sequence and/or a polyadenylation signal. Preferably, the optional poly(A) sequence is located 3' to the ORF or the at least one 3'UTR element, preferably is connected to the 3'-end of the ORF or the 3'UTR element. The connection may be direct or indirect, for example, via a stretch of 2, 4, 6, 8, 10, 20 etc. nucleotides, such as via a linker of 1-50, preferably of 1-20 nucleotides, e.g. comprising or consisting of one or more restriction sites.

In one embodiment, the optional polyadenylation signal is located within the 3'UTR element. Preferably, the polyadenylation signal comprises the consensus sequence NN(U/T)ANA, with N=A or U, preferably AA(U/T)AAA or A(U/T)(U/T)AAA. Such consensus sequence may be recognised by most animal and bacterial cell-systems, for example by the polyadenylation-factors, such as cleavage/polyadenylation specificity factor (CPSF) cooperating with CstF, PAP, PAB2, CFI and/or CFII. Preferably, the polyadenylation signal, preferably the consensus sequence NNUANA, is located less than about 50 nucleotides, more preferably less than about 30 nucleotides, most preferably less than about 25 nucleotides, for example 21 nucleotides, upstream of the 3'-end of the 3'UTR element.

Using an appropriate transcription system will then lead to attachment of a poly(A) sequence to the premature-RNA. For example, the inventive artificial nucleic acid molecule may be a DNA molecule comprising a 3'UTR element as described above and a polyadenylation signal, which may result in polyadenylation of an RNA upon transcription of this DNA molecule. Accordingly, a resulting RNA may comprise a combination of the 3'UTR element followed by a poly(A) sequence.

Potential transcription systems are in vitro transcription systems or cellular transcription systems etc. Accordingly, transcription of an artificial nucleic acid molecule according to the invention, e.g. transcription of an artificial nucleic acid molecule comprising a 5'UTR element, an open reading frame, a 3'UTR element and a polyadenylation-signal, may result in an mRNA molecule comprising a 5'UTR element, an open reading frame, a 3'UTR element and a poly(A) sequence.

The invention also provides an artificial nucleic acid molecule which is an mRNA molecule comprising a, 5'UTR element, an open reading frame, an optional 3'UTR element as described above and a poly(A) sequence.

In one embodiment, the invention provides an artificial nucleic acid molecule which is an artificial DNA molecule comprising a 5'UTR element as described above, an open reading frame and optionally a nucleic acid sequence according to any one of SEQ ID Nos. 1369-1377, 1391, and 1392 or a sequence having an identity of at least about 40% or more to a nucleic acid sequence according to any one of SEQ ID Nos. 1369-1377, 1391, and 1392 or a fragment thereof. Furthermore, the invention provides an artificial nucleic acid molecule which is an artificial RNA molecule comprising a 5'UTR element as described above, an open reading frame and optionally an RNA sequence corresponding to a sequence according to any one of SEQ ID Nos. 1369-1377, 1391, and 1392 or a sequence having an identity of at least about 40% or more to any one of SEQ ID Nos. 1369-1377, 1391, and 1392, or a fragment thereof.

Accordingly, the invention provides an artificial nucleic acid molecule which may be a template for an RNA molecule, preferably for an mRNA molecule, which is stabilised and optimized with respect to translation efficiency. In other words, the artificial nucleic acid molecule may be a DNA or RNA which may be used for production of an mRNA. The obtainable mRNA, may, in turn, be translated for production of a desired peptide or protein encoded by the open reading frame. If the artificial nucleic acid molecule is a DNA, it may, for example, be used as a double-stranded storage form for continued and repetitive in vitro or in vivo production of mRNA.

In one embodiment, the artificial nucleic acid molecule according to the present invention further comprises a poly(A) sequence. The length of the poly(A) sequence may vary. For example, the poly(A) sequence may have a length of about 20 adenine nucleotides up to about 300 adenine nucleotides, preferably of about 40 to about 200 adenine nucleotides, more preferably from about 50 to about 100 adenine nucleotides, such as about 60, 70, 80, 90 or 100 adenine nucleotides.

For example, the artificial nucleic acid molecule according to the present invention may comprise a nucleic acid sequence corresponding to the DNA sequence

```
                                        (SEQ ID No. 1377)
CATCACATTT AAAAGCATCT CAGCCTACCA TGAGAATAAG

AGAAAGAAAA TGAAGATCAA AAGCTTATTC ATCTGTTTTT

CTTTTTCGTT GGTGTAAAGC CAACACCCTG TCTAAAAAAC

ATAAATTTCT TTAATCATTT TGCCTCTTTT CTCTGTGCTT

CAATTAATAA AAAATGGAAA GAATCTAGAT CTAAAAAAAA

AAAAAAAAAA AAAAAAAAAA AAAAAAAAAA AAAAAAAAAA

AAAAAAAAAA AAAAAA.
```

Transcription of such a sequence may result in an artificial nucleic acid molecule comprising a corresponding RNA sequence.

Such artificial RNA molecule may also be obtainable in vitro by common methods of chemical synthesis without being necessarily transcribed from a DNA progenitor.

In a particularly preferred embodiment, the artificial nucleic acid molecule according to the present invention is an RNA molecule, preferably an mRNA molecule comprising in 5'-to-3'-direction a 5'UTR element as described above, an open reading frame, a 3'UTR element as described above and a poly(A) sequence.

In a preferred embodiment, the open reading frame does not code for human albumin, provided that the 3'UTR element is identical to the 3'UTR of human albumin. In some further embodiments, it is preferred that the open reading frame does not code for human albumin according to GenBank Accession number NM_000477.5 provided that the 3'UTR element is identical to the 3'UTR of human albumin. In some further embodiments, it is preferred that the open reading frame does not code for human albumin or variants thereof provided that the 3'UTR element is a sequence which is identical to SEQ ID No. 1369. Furthermore, in some embodiments, it is preferred that the open reading frame does not code for a reporter protein, e.g., selected from the group consisting of globin proteins, luciferase proteins, GFP proteins or variants thereof, for example, variants exhibiting at least 70% sequence identity to a globin protein, a luciferase protein, or a GFP protein.

In some embodiments, it is preferred that the 3'UTR element does not consist of a histone stem-loop, preferably does not comprise a histone stem-loop. In one embodiment, the artificial nucleic acid molecule according to the present invention does not comprise a histone stem-loop. However, in some embodiments, the 3'UTR element of the artificial nucleic acid molecule or the artificial nucleic acid molecule according to the present invention may comprise a histone stem-loop in addition to the nucleic acid sequence derived form the 3'UTR of an albumin gene. Such artificial nucleic acid molecule according to the present invention, for example, may comprise in 5'-to-3'-direction a 5'UTR element, an ORF, a 3'UTR element, preferably comprising a polyadenylation signal, an optional histone stem-loop and an optional poly(A) sequence. It may also comprise in 5'-to-3'-direction a 5'UTR element as described above, an ORF, a 3'UTR element, e.g. comprising a polyadenylation signal, a poly(A) sequence and an optional histone stem-loop.

In the context of the present invention, such a histone stem-loop is typically derived from a histone gene and comprises an intramolecular base pairing of two neighbored entirely or partially reverse complementary sequences, thereby forming a stem-loop. A stem-loop can occur in single-stranded DNA or, more commonly, in RNA. The structure is also known as a hairpin or hairpin loop and usually consists of a stem and a (terminal) loop within a consecutive sequence, wherein the stem is formed by two neighbored entirely or partially reverse complementary sequences separated by a short sequence as sort of spacer, which builds the loop of the stem-loop structure. The two neighbored entirely or partially reverse complementary sequences may be defined as e.g. stem-loop elements stem1 and stem2. The stem loop is formed when these two neighbored entirely or partially reverse complementary sequences, e.g. stem-loop elements stem1 and stem2, form base-pairs with each other, leading to a double stranded nucleic acid sequence comprising an unpaired loop at its terminal ending formed by the short sequence located between stem-loop elements stem1 and stem2 on the consecutive sequence. The unpaired loop thereby typically represents a region of the nucleic acid which is not capable of base pairing with either of these stem-loop elements. The resulting lollipop-shaped structure is a key building block of many RNA secondary structures. The formation of a stem-loop structure is thus dependent on the stability of the resulting stem and loop regions, wherein the first prerequisite is typically the presence of a sequence that can fold back on itself to form a paired double strand. The stability of paired stem-loop elements is determined by the length, the number of mismatches or bulges it contains (a small number of mismatches is typically tolerable, especially in a long double strand), and the base composition of the paired region. In the context of the present invention, optimal loop length is 3-10 bases, more preferably 3 to 8, 3 to 7, 3 to 6 or even more preferably 4 to 5 bases, and most preferably 4 bases.

An example for a histone stem-loop sequence is the sequence according to SEQ ID NO: 1394 (CAAAGGCTCTTTTCAGAGCCACCA) or the corresponding RNA sequence.

Thus, in some embodiments, the artificial nucleic acid molecule according to the present invention comprises (a.) at least one 5'UTR element as described herein, (b.) at least one open reading frame, and at least one histone-stem loop which may, for example, comprise or consist of a sequence having a sequence identity of at least about 75%, preferably of at least about 80%, preferably at least about 85%, more preferably at least about 90%, even more preferably at least about 95% to the sequence according to SEQ ID NO. 1394 or the corresponding RNA sequence, wherein preferably positions 6, 13 and 20 of the sequence having a sequence identity of at least about 75%, preferably of at least about 80%, preferably at least about 85%, more preferably at least about 90%, even more preferably at least about 95% to the sequence according to SEQ ID NO. 1394 or the corresponding RNA sequence are conserved, i.e. are identical to the nucleotides at positions 6, 13 and 20 of SEQ ID NO. 1394.

In some embodiments, the artificial nucleic acid molecule comprises further elements such as a 5'-cap, a poly(C) sequence and/or an IRES-motif. A 5'-cap may be added posttranscriptionally to the 5' end of an RNA. Further, the inventive artificial nucleic acid molecule, particularly if the nucleic acid is in the form of an mRNA or codes for an mRNA, may be modified by a sequence of at least 10 cytidines, preferably at least 20 cytidines, more preferably at least 30 cytidines (so-called “poly(C) sequence”). Particularly, the inventive nucleic acid molecule may contain, especially if the nucleic acid is in the form of an (m)RNA or codes for an mRNA, a poly(C) sequence of typically about 10 to 200 cytidine nucleotides, preferably about 10 to 100 cytidine nucleotides, more preferably about 10 to 70 cytidine nucleotides or even more preferably about 20 to 50 or even 20 to 30 cytidine nucleotides.

An internal ribosome entry side (IRES) sequence or IRES-motif may separate several open reading frames, for example if the artificial nucleic acid molecule encodes for two or more peptides or proteins. An IRES-sequence may be particularly helpful if the mRNA is a bi- or multicistronic RNA.

Furthermore, the artificial nucleic acid molecule may comprise additional 5'-elements such as a promoter containing-sequence. The promoter may drive and or regulate transcription of the artificial nucleic acid molecule according to the present invention, for example of an artificial DNA-molecule according to the present invention.

In preferred embodiments, the invention provides artificial nucleic acid molecules, preferably mRNA molecules, comprising in 5'-to-3'-direction at least one of the following structures 5'-cap-5'UTR element-ORF-3'UTR element-histone stem-loop-poly(A) sequence 5'-cap-5'UTR element-ORF-3'UTR element-poly(A) sequence-histone stem-loop 5'-cap-5'UTR element-ORF-IRES-ORF-3'UTR element-histone stem-loop-poly(A) sequence 5'-cap-5'UTR element-ORF-IRES-ORF-3'UTR element-poly(A) sequence-histone stem-loop 5'-cap-5'UTR element-ORF-3'UTR element-poly(A) sequence-poly(C) sequence 5'-cap-5'UTR element-ORF-3'UTR element-poly(A) sequence-poly(C) sequence-histone stem-loop 5'-cap-5'UTR element-ORF-IRES-ORF-3'UTR element-histone stem-loop-poly(A) sequence-poly(C) sequence Preferably, the artificial nucleic acid molecule, preferably the open reading frame, is at least partially G/C modified. Thus, the inventive artificial nucleic acid molecule may be thermodynamically stabilized by modifying the G (guanosine)/C (cytidine) content of the molecule. The G/C content of the open reading frame of an artificial nucleic acid molecule according to the present invention may be increased compared to the G/C content of the open reading frame of a corresponding wild type sequence, preferably by using the degeneration of the genetic code. Thus, the encoded amino acid sequence of the nucleic acid molecule is preferably not modified by the G/C modification compared to the coded amino acid sequence of the particular wild type sequence. The codons of a coding sequence or a whole nucleic acid molecule, e.g. an mRNA, may therefore be varied compared to the wild type coding sequence, such that they include an increased amount of G/C nucleotides while the translated amino acid sequence is maintained. In respect to the fact that several codons code for one and the same amino acid (so-called degeneration of the genetic code), the most favourable codons for the stability can be determined (so-called alternative codon usage).

Depending on the amino acid to be encoded by the coding region of the inventive nucleic acid molecule as defined herein, there are various possibilities for modification of the nucleic acid sequence, e.g. the open reading frame, compared to its wild type coding region. In the case of amino acids which are encoded by codons which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U/T is present.

In contrast, codons which contain A and/or U/T nucleotides may be modified by substitution of other codons which code for the same amino acids but contain no A and/or U/T. For example the codons for Pro can be modified from CC(U/T) or CCA to CCC or CCG;

the codons for Arg can be modified from CA(U/T) or CGA or AGA or AGG to CGC or CGG;

the codons for Ala can be modified from GC(U/T) or GCA to GCC or GCG;

the codons for Gly can be modified from GG(U/T) or GGA to GGC or GGG.

In other cases, although A or (U/T) nucleotides cannot be eliminated from the codons, it is however possible to decrease the A and (U/T) content by using codons which contain a lower content of A and/or (U/T) nucleotides. Examples of these are:

The codons for Phe can be modified from (U/T)(U/T)(U/T) to (U/T) (U/T)C;

the codons for Leu can be modified from (U/T) (U/T)A, (U/T) (U/T)G, C(U/T) (U/T) or C(U/T)A to C(U/T)C or C(U/T)G;

the codons for Ser can be modified from (U/T)C(U/T) or (U/T)CA or AG(U/T) to (U/T)CC, (U/T)CG or AGC;

the codon for Tyr can be modified from (U/T)A(U/T) to (U/T)AC;

the codon for Cys can be modified from (U/T)G(U/T) to (U/T)GC;

the codon for His can be modified from CA(U/T) to CAC;

the codon for Gln can be modified from CAA to CAG;

the codons for Ile can be modified from A(U/T)(U/T) or A(V/T)A to A(U/T)C;

the codons for Thr can be modified from AC(U/T) or ACA to ACC or ACG;

the codon for Asn can be modified from AA(U/T) to AAC;

the codon for Lys can be modified from AAA to AAG;

the codons for Val can be modified from G(U/T)(U/T) or G(U/T)A to G(U/T)C or G(U/T)G;

the codon for Asp can be modified from GA(U/T) to GAC;

the codon for Glu can be modified from GAA to GAG;

the stop codon (U/T)AA can be modified to (U/T)AG or (U/T)GA.

In the case of the codons for Met (A(U/T)G) and Trp ((U/T)GG), on the other hand, there is no possibility of sequence modification without altering the encoded amino acid sequence.

The substitutions listed above can be used either individually or in all possible combinations to increase the G/C content of the open reading frame of the inventive nucleic acid sequence as defined herein, compared to its particular wild type open reading frame (i.e. the original sequence). Thus, for example, all codons for Thr occurring in the wild type sequence can be modified to ACC (or ACG).

Preferably, the G/C content of the open reading frame of the inventive artificial nucleic acid molecule as defined herein is increased by at least 7%, more preferably by at least 15%, particularly preferably by at least 20%, compared to the G/C content of the wild type coding region. According to a specific embodiment at least 5%, 10%, 20%, 30%, 40%, 50%, 60%, more preferably at least 70%, even more preferably at least 80% and most preferably at least 90%, 95% or even 100% of the substitutable codons in the open reading frame of the inventive artificial nucleic acid molecule or a fragment, variant or derivative thereof are substituted, thereby increasing the G/C content of said open reading frame.

In this context, it is particularly preferable to increase the G/C content of the open reading frame of the inventive nucleic acid sequence as defined herein, to the maximum (i.e. 100% of the substitutable codons), compared to the wild type open reading frame.

Furthermore, the open reading frame is preferably at least partially codon-optimized. Codon-optimization is based on the finding that the translation efficiency may be determined by a different frequency in the occurrence of transfer RNAs (tRNAs) in cells. Thus, if so-called "rare codons" are present in the coding region of the inventive artificial nucleic acid molecule as defined herein, to an increased extent, the translation of the corresponding modified nucleic acid sequence is less efficient than in the case where codons coding for relatively "frequent" tRNAs are present.

Thus, the open reading frame of the inventive nucleic acid sequence is preferably modified compared to the corresponding wild type coding region such that at least one codon of the wild type sequence which codes for a tRNA which is relatively rare in the cell is exchanged for a codon which codes for a tRNA which is comparably frequent in the cell and carries the same amino acid as the relatively rare tRNA. By this modification, the open reading frame of the inventive artificial nucleic acid molecule as defined herein, is modified such that codons for which frequently occurring tRNAs are available may replace codons which correspond to rare tRNAs. In other words, according to the invention, by such a modification all codons of the wild type open reading frame which code for a rare tRNA may be exchanged for a codon which codes for a tRNA which is more frequent in the cell and which carries the same amino acid as the rare tRNA. Which tRNAs occur relatively frequently in the cell and which, in contrast, occur relatively rarely is known to a person skilled in the art; cf. e.g. Akashi, Curr. Opin. Genet. Dev. 2001, 11(6): 660-666. Accordingly, preferably, the open reading frame is codon-optimized, preferably with respect to the system in which the nucleic acid molecule according to the present invention is to be expressed, preferably with respect to the system in which the nucleic acid molecule according to the present invention is to be translated. Preferably, the codon usage of the open reading frame is codon-optimized according to mammalian codon usage, more preferably according to human codon usage. Preferably, the open reading frame is codon-optimized and G/C-content modified.

For further improving degradation resistance, e.g. resistance to in vivo degradation by an exo- or endonuclease, and/or for further improving protein production from the artificial nucleic acid molecule according to the present invention, the artificial nucleic acid molecule may further comprise modifications, such as backbone modifications, sugar modifications and/or base modifications, e.g., lipid-modifications or the like. Preferably, the transcription and/or the translation of the artificial nucleic acid molecule according to the present invention is not significantly impaired by said modifications.

Nucleotide analogues/modifications that may be used in the context of the present invention may be selected, for example, from 2-amino-6-chloropurineriboside-5'-triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'-triphosphate, 5-methylcytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular prefer-ence is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

Further, lipid-modified artificial nucleic acid molecules may typically comprise at least one linker which is covalently linked with the artificial nucleic acid molecule, and at least one lipid which is covalently linked with this linker. Alternatively, a lipid-modified artificial nucleic acid molecule may comprise at least one artificial nucleic acid molecule as defined herein and at least one, preferably bifunctional lipid which is covalently linked, preferably without a linker, with that artificial nucleic acid molecule. According to a third alternative, a lipid-modified artificial nucleic acid molecule may comprise an artificial nucleic acid molecule as defined herein, at least one linker which is covalently linked with that artificial nucleic acid molecule, at least one lipid which is covalently linked with this linker, and additionally at least one, preferably bifunctional lipid which is covalently linked, preferably without a linker, with the artificial nucleic acid molecule.

In a further aspect, the present invention provides a vector comprising a. at least one 5'-untranslated region element (5'UTR element) which comprises or consists of a nucleic acid sequence which is derived from the 5'UTR of a TOP gene or which is derived from a variant of the 5'UTR of a TOP gene;
b. at least one open reading frame (ORF) and/or a cloning site; and
c. optionally, at least one 3'UTR element which comprises or consists of a nucleic acid sequence derived from the 3'UTR of a chordate gene, preferably a vertebrate gene, more preferably a mammalian gene, most preferably a human gene, or from a variant of the 3'UTR of a chordate gene, preferably a vertebrate gene, more preferably a mammalian gene, most preferably a human gene.

The at least one 5'UTR element, the optional at least one 3'UTR element and the at least one ORF are as described herein for the artificial nucleic acid molecule according to the present invention. The cloning site may be any sequence that is suitable for introducing an open reading frame or a sequence comprising an open reading frame, such as one or more restriction sites. The vector comprising a cloning site is preferably suitable for inserting an open reading frame into the vector 3' to the 5'UTR element, preferably directly 3' to the 5'UTR element. Thus, the vector comprising a cloning site is preferably suitable for inserting an open reading frame into the vector, preferably for inserting an open reading frame between the 5'UTR element and the optional 3'UTR element, preferably 5' to the optional 3'UTR element and 3' to the 5'UTR element. Preferably, the cloning site or the ORF is located 5' to the 3'UTR element, preferably in close proximity to the 5'-end of the 3'UTR element. For example, the cloning site or the ORF may be directly connected to the 5'-end of the 3'UTR element or they may be connected via a stretch of nucleotides, such as by a stretch of 2, 4, 6, 8, 10, 20 etc. nucleotides as described above for the artificial nucleic acid molecule according to the present invention. Preferably the cloning site or the ORF is located 3' to the 5'UTR element, preferably in close proximity to the 3'-end of the 5'UTR element. For example, the cloning site or the ORF may be directly connected to the 3'-end of the 5'UTR element or they may be connected via a stretch of nucleotides, such as by a stretch of 2, 4, 6, 8, 10, 20 etc. nucleotides as described above for the artificial nucleic acid molecule according to the present invention.

Preferably the vector according to the present invention is suitable for producing the artificial nucleic acid molecule according to the present invention, preferably for producing an artificial mRNA according to the present invention, for example, by optionally inserting an open reading frame or a sequence comprising an open reading frame into the vector and transcribing the vector. Thus, preferably, the vector comprises elements needed for transcription, such as a promoter, e.g. an RNA polymerase promoter. Preferably, the vector is suitable for transcription using eukaryotic, prokaryotic, viral or phage transcription systems, such as eukaryotic cells, prokaryotic cells, or eukaryotic, prokaryotic, viral or phage in vitro transcription systems. Thus, for example, the vector may comprise a promoter sequence, which is recognized by a polymerase, such as by an RNA polymerase, e.g. by a eukaryotic, prokaryotic, viral, or phage RNA polymerase. In a preferred embodiment, the vector comprises a phage RNA polymerase promoter such as an SP6 or T7, preferably a T7 promoter. Preferably, the vector is suitable for in vitro transcription using a phage based in vitro transcription system, such as a T7 RNA polymerase based in vitrotranscription system.

The vector may further comprise a poly(A) sequence and/or a polyadenylation signal as described above for the artificial nucleic acid molecule according to the present invention.

The vector may be an RNA vector or a DNA vector. Preferably, the vector is a DNA vector.

The vector may be any vector known to the skilled person, such as a viral vector or a plasmid vector. Preferably, the vector is a plasmid vector, preferably a DNA plasmid vector.

In a preferred embodiment, the vector according to the present invention comprises the artificial nucleic acid molecule according to the present invention.

Preferably, a vector according to the present invention comprises a sequence according to SEQ ID NOs. 1-1363, 1395, 1421, 1422, 1368, or 1412-1420, or a sequence having an identity of at least about 40%, preferably of at least about 50%, preferably of at least about 60%, preferably of at least about 70%, more preferably of at least about 80%, more preferably of at least about 90%, even more preferably of at least about 95%; even more preferably of at least about 99%; even more preferably of 100% sequence identity to a sequence according to any one of SEQ ID NOs. 1-1363, 1395, 1421, 1422, 1368, or 1412-1420, or a fragment thereof, preferably a functional fragment thereof, or a corresponding RNA sequence.

Preferably, a vector, such as a DNA vector, according to the present invention comprises a sequence according to SEQ ID NOs. 1368-1392 or 1412-1420, or a sequence having an identity of at least about 40%, preferably of at least about 50%, preferably of at least about 60%, preferably of at least about 70%, more preferably of at least about 80%, more preferably of at least about 90%, even more preferably of at least about 95%; even more preferably of at least about 99%; even more preferably of 100% sequence identity to a sequence according to any one of SEQ ID NOs. 1368-1392 or 1412-1420 or a fragment thereof, preferably a functional fragment thereof, or a corresponding RNA sequence.

Preferably, the vector is a circular molecule. Preferably, the vector is a double-stranded molecule, such as a double stranded DNA molecule. Such circular, preferably double stranded DNA molecule may be used conveniently as a storage form for the inventive artificial nucleic acid molecule. Furthermore, it may be used for transfection of cells, for example, cultured cells. Also it may be used for in vitro transcription for obtaining an artificial RNA molecule according to the invention.

Preferably, the vector, preferably the circular vector, is linearizable, for example, by restriction enzyme digestion. In a preferred embodiment, the vector comprises a cleavage site, such as a restriction site, preferably a unique cleavage site, located immediately 3' to the ORF, or—if present—immediately 3' to the 3'UTR element, or—if present—immediately 3' to the poly(A) sequence or polyadenylation signal, or—if present—located 3' to the poly(C) sequence, or—if present—located 3' to the histone stem-loop". Thus, preferably, the product obtained by linearizing the vector terminates at the 3' end with the stop codon, or—if present—the 3'-end of the 3'UTR element, or—if present—with the 3'-end of the poly(A) sequence or with the 3'-end of the polyadenylation signal, or—if present—with the 3'-end of the poly(C) sequence, or—if present—with the 3'-end of the histone stem-loop, plus optionally some nucleotides remaining from the restriction site after cleavage.

In a further aspect, the present invention relates to a cell comprising the artificial nucleic acid molecule according to the present invention or the vector according to present invention. The cell may be any cell, such as a bacterial cell, insect cell, plant cell, vertebrate cell, e.g. a mammalian cell. Such cell may be, e.g., used for replication of the vector of the present invention, for example, in a bacterial cell. Furthermore, the cell may be used for transcribing the artificial nucleic acid molecule or the vector according to the present invention and/or translating the open reading frame of the artificial nucleic acid molecule or the vector according to the present invention. For example, the cell may be used for recombinant protein production.

The cells according to the present invention are, for example, obtainable by standard nucleic acid transfer methods, such as standard transfection methods. For example, the artificial nucleic acid molecule or the vector according to the present invention may be transferred into the cell by electroporation, lipofection, e.g. based on cationic lipids and/or liposomes, calcium phosphate precipitation, nanoparticle based transfection, virus based transfection, or based on cationic polymers, such as DEAE-dextran or polyethylenimine etc.

Preferably, the cell is a mammalian cell, such as a cell of human subject, a domestic animal, a laboratory animal, such as a mouse or rat cell. Preferably the cell is a human cell. The cell may be a cell of an established cell line, such as a CHO, BHK, 293T, COS-7, HELA, HEK etc. cell, or the cell may be a primary cell, e.g. a HDF cell, preferably a cell isolated from an organism. In a preferred embodiment, the cell is an isolated cell of a mammalian subject, preferably of a human subject. For example, the cell may be an immune cell, such as a dendritic cell, a cancer or tumor cell, or any somatic cell etc., preferably of a mammalian subject, preferably of a human subject.

In a further aspect, the present invention provides a pharmaceutical composition comprising the artificial nucleic acid molecule according to the present invention, the vector according the present invention, or the cell according to the present invention. The pharmaceutical composition according to the invention may be used, e.g., as a vaccine, for example, for genetic vaccination. Thus, the ORF may, e.g., encode an antigen to be administered to a patient for vaccination. Thus, in a preferred embodiment, the pharmaceutical composition according to the present invention is a vaccine. Furthermore, the pharmaceutical composition according to the present invention may be used, e.g., for gene therapy.

Preferably, the pharmaceutical composition further comprises one or more pharmaceutically acceptable excipients, vehicles, fillers and/or diluents. In the context of the present invention, a pharmaceutically acceptable vehicle typically includes a liquid or non-liquid basis for the inventive pharmaceutical composition. In one embodiment, the pharmaceutical composition is provided in liquid form. In this context, preferably, the vehicle is based on water, such as pyrogen-free water, isotonic saline or buffered (aqueous) solutions, e.g. phosphate, citrate etc. buffered solutions. The buffer may be hypertonic, isotonic or hypo-tonic with reference to the specific reference medium, i.e. the buffer may have a higher, identical or lower salt content with reference to the specific reference medium, wherein preferably such concentrations of the afore mentioned salts may be used, which do not lead to damage of mammalian cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

One or more compatible solid or liquid fillers or diluents or encapsulating compounds suitable for administration to a patient may be used as well for the inventive pharmaceutical composition. The term "compatible" as used herein preferably means that these components of the inventive pharmaceutical composition are capable of being mixed with the inventive nucleic acid, vector or cells as defined herein in such a manner that no interaction occurs which would substantially reduce the pharmaceutical effectiveness of the inventive pharmaceutical composition under typical use conditions.

The pharmaceutical composition according to the present invention may optionally further comprise one or more additional pharmaceutically active components. A pharmaceutically active component in this context is a compound that exhibits a therapeutic effect to heal, ameliorate or prevent a particular indication or disease. Such compounds include, without implying any limitation, peptides or proteins, nucleic acids, (therapeutically active) low molecular weight organic or inorganic compounds (molecular weight less than 5000, preferably less than 1000), sugars, antigens or antibodies, therapeutic agents already known in the prior art, antigenic cells, antigenic cellular fragments, cellular fractions, cell wall components (e.g. polysaccharides), modified, attenuated or de-activated (e.g. chemically or by irradiation) pathogens (virus, bacteria etc.).

Furthermore, the inventive pharmaceutical composition may comprise a carrier for the artificial nucleic acid molecule or the vector. Such a carrier may be suitable for mediating dissolution in physiological acceptable liquids, transport and cellular uptake of the pharmaceutical active artificial nucleic acid molecule or the vector. Accordingly, such a carrier may be a component which may be suitable for depot and delivery of an artificial nucleic acid molecule or vector according to the invention. Such components may be, for example, cationic or polycationic carriers or compounds which may serve as transfection or complexation agent.

Particularly preferred transfection or complexation agents in this context are cationic or polycationic compounds, including protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (*Herpes* simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, pIsl, FGF, Lactoferrin, Transportan, Buforin-2, Bac715-24, SynB, SynB(1), pVEC, hCT-derived peptides, SAP, or histones.

Furthermore, such cationic or polycationic compounds or carriers may be cationic or polycationic peptides or proteins, which preferably comprise or are additionally modified to comprise at least one —SH moiety. Preferably, a cationic or polycationic carrier is selected from cationic peptides having the following sum formula (I):

$$\{(Arg)_l;(Lys)_m;(His)_n;(Orn)_o;(Xaa)_x\}; \qquad \text{formula (I)}$$

wherein l+m+n+o+x=3-100, and l, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Orn (Ornithine) represents at least 10% of all amino acids of the oligopeptide; and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide. Any of amino acids Arg, Lys, His, Orn and Xaa may be positioned at any place of the peptide. In this context cationic peptides or proteins in the range of 7-30 amino acids are particular preferred.

Further, the cationic or polycationic peptide or protein, when defined according to formula $\{(Arg)_l;(Lys)_m;(His)_n;(Orn)_o;(Xaa)_x\}$ (formula (I)) as shown above and which comprise or are additionally modified to comprise at least one —SH moeity, may be, without being restricted thereto, selected from subformula (Ia):

$$\{(Arg)_l;(Lys)_m;(His)_n;(Orn)_o;(Xaa')_x(Cys)_y\} \qquad \text{subformula (Ia)}$$

wherein $(Arg)_l;(Lys)_m;(His)_n;(Orn)_o$; and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide. Further, the cationic or polycationic peptide may be selected from subformula (Ib):

$$Cys_1\{(Arg)_l;(Lys)_m;(His)_n;(Orn)_o;(Xaa)_x\}Cys_2 \qquad \text{subformula (Ib)}$$

wherein empirical formula $\{(Arg)_l;(Lys)_m;(His)_n;(Orn)_o;(Xaa)_x\}$ (formula (III)) is as defined herein and forms a core of an amino acid sequence according to (semiempirical) formula (III) and wherein $Cys_l$ and $Cys_2$ are Cysteines proximal to, or terminal to $(Arg)_l;(Lys)_m;(His)_n;(Orn)_o;(Xaa)_x$.

Further preferred cationic or polycationic compounds, which can be used as transfection or complexation agent may include cationic polysaccharides, for example chitosan, poly-brene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphati-dylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O -ditetradecanoyl-N-(α-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl]trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole); etc.

In this context, it is particularly preferred that the inventive artificial nucleic acid molecule or the inventive vector is complexed at least partially with a cationic or polycationic compound, preferably cationic proteins or peptides. Partially means that only a part of the inventive artificial nucleic acid molecule or the inventive vector is complexed with a cationic or polycationic compound and that the rest of the inventive artificial nucleic acid molecule or the inventive vector is in uncomplexed form ("free"). Preferably the ratio of complexed nucleic acid to:free nucleic acid is selected from a range. of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of complexed nucleic acid to free nucleic acid is selected from a ratio of about 1:1 (w/w).

The pharmaceutical composition according to the present invention may optionally further comprise one or more adjuvants, for example, adjuvants for stimulating the innate immune system or for enhancing cellular uptake of the artificial nucleic acid molecule or vector. In this context, an adjuvant may be understood as any compound, which is suitable to initiate or increase an immune response of the innate immune system, i.e. a non-specific immune response. In other words, when administered, the inventive pharmaceutical composition preferably elicits an innate immune response due to the adjuvant, optionally contained therein. Preferably, such an adjuvant may be an adjuvant supporting the induction of an innate immune response in a mammal. Such an adjuvant may be, for example, an immunostimulatory nucleic acid, i.e. a nucleic acid that may bind to a Toll-like-receptor or the like, preferably an immunostimulatory RNA.

Such adjuvants, preferably such immunostimulatory nucleic acids, may induce an innate, i.e. unspecific, immune response which may support a specific, i.e. adaptive, immune response to the peptide or protein, i.e. the antigen, encoded by the artificial nucleic acid molecule of the pharmaceutical composition, preferably the vaccine.

The inventive pharmaceutical composition may also additionally comprise any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

Further additives which may be included in the inventive pharmaceutical composition are, e.g., emulsifiers, such as, for example, Tween®; wetting agents, such as, for example, so-dium lauryl sulfate; colouring agents; taste-imparting agents, pharmaceutical carriers; tablet-forming agents; stabilizers; antioxidants; preservatives etc.

The pharmaceutical composition according to the present invention preferably comprises a "safe and effective amount" of the components of the pharmaceutical composition, particularly of the inventive nucleic acid sequence, the vector and/or the cells as defined herein. As used herein, a "safe and effective amount" means an amount sufficient to significantly induce a positive modification of a disease or disorder as defined herein. At the same time, however, a "safe and effective amount" preferably avoids serious side-effects and permits a sensible relationship between advantage and risk. The determination of these limits typically lies within the scope of sensible medical judgment.

In a further aspect, the present invention provides the artificial nucleic acid molecule according to the present invention, the vector according to the present invention, the cell according to the present invention, or the pharmaceutical composition according to the present invention for use as a medicament, for example, as vaccine (in genetic vaccination) or in gene therapy.

The artificial nucleic acid molecule according to the present invention, the vector according to the present invention, the cell according to the present invention, or the pharmaceutical composition according to the present invention are particularly suitable for any medical application which makes use of the therapeutic action or effect of peptides, polypeptides or proteins, or where supplementation of a particular peptide or protein is needed. Thus, the present invention provides the artificial nucleic acid molecule according to the present invention, the vector according to the present invention, the cell according to the present invention, or the pharmaceutical composition according to the present invention for use in the treatment or prevention of diseases or disorders amenable to treatment by the therapeutic action or effect of peptides, polypeptides or proteins or amenable to treatment by supplementation of a particular peptide, polypeptide or protein. For example, the artificial nucleic acid molecule according to the present invention, the vector according to the present invention, the cell according to the present invention, or the pharmaceutical composition according to the present invention may be used for the treatment or prevention of genetic diseases, autoimmune diseases, cancerous or tumour-related diseases, infectious diseases, chronic diseases or the like, e.g., by genetic vaccination or gene therapy.

In particular, such therapeutic treatments which benefit from a stable, prolonged and/or increased presence of therapeutic peptides, polypeptides or proteins in a subject to be treated are especially suitable as medical application in the context of the present invention, since the 5'UTR element optionally in combination with the 3'UTR element provides for increased protein expression from the ORF and the 3'UTR element provides for a stable and prolonged expression of the ORF of the inventive nucleic acid molecule. Thus, a particularly suitable medical application for the artificial nucleic acid molecule according to the present invention, the vector according to the present invention, the cell according to the present invention, or the pharmaceutical composition according to the present invention is vaccination, for example against infections or tumours. Thus, the present invention provides the artificial nucleic acid molecule according to the present invention, the vector according to the present invention, the cell according to the present invention, or the pharmaceutical composition according to the present invention for vaccination of a subject, preferably a mammalian subject, more preferably a human subject. Preferred vaccination treatments are vaccination against infectious diseases, such as bacterial, protozoal or viral infections, and anti-tumour-vaccination. Such vaccination treatments may be prophylactic or therapeutic.

Depending on the disease to be treated or prevented, the ORF may be selected. For example, the open reading frame may code for a protein that has to be supplied to a patient suffering from total lack or at least partial loss of function of a protein, such as a patient suffering from a genetic disease. Additionally, the open reading frame may be chosen from an ORF coding for a peptide or protein which beneficially influences a disease or the condition of a subject. Furthermore, the open reading frame may code for a peptide or protein which effects down-regulation of a pathological overproduction of a natural peptide or protein or elimination of cells expressing pathologically a protein or peptide. Such lack, loss of function or overproduction may, e.g., occur in the context of tumour and neoplasia, autoimmune diseases, allergies, infections, chronic diseases or the like. Furthermore, the open reading frame may code for an antigen or immunogen, e.g. for an epitope of a pathogen or for a tumour antigen. Thus, in preferred embodiments, the artificial nucleic acid molecule or the vector according to the present invention comprises an ORF encoding an amino acid sequence comprising or consisting of an antigen or immunogen, e.g. an epitope of a pathogen or a tumour-associated antigen, a 5'UTR element as described above, and optional further components, such as a 3'UTR element and/or a poly(A) sequence etc. as described above.

In the context of medical application, in particular, in the context of vaccination, it is preferred that the artificial nucleic acid molecule according to the present invention is RNA, preferably mRNA, since DNA harbours the risk of eliciting an anti-DNA immune response and tends to insert into genomic DNA. However, in some embodiments, for example, if a viral delivery vehicle, such as an adenoviral delivery vehicle is used for delivery of the artificial nucleic acid molecule or the vector according to the present invention, e.g., in the context of gene therapeutic treatments, it may be desirable that the artificial nucleic acid molecule or the vector is a DNA molecule.

The artificial nucleic acid molecule according to the present invention, the vector according to the present invention, the cell according to the present invention, or the pharmaceutical composition according to the present invention may be administered orally, parenterally, by inhalation spray, topically, rectally, nasally, buccally, vaginally or via an implanted reser-voir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Preferably, the artificial nucleic acid molecule according to the present invention, the vector according to the present invention, the cell according to the present invention, or the pharmaceutical composition according to the present invention is administered parenterally, e.g. by parenteral injection, more preferably by subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, sublingual injection or via infusion techniques. Particularly preferred is intradermal and intramuscular injection. Sterile injectable forms of the inventive pharmaceutical composition may be aqueous or oleaginous suspension. These suspensions may be formulated according to techniques known in the art using suitable dispersing or wetting agents and suspending agents.

The artificial nucleic acid molecule according to the present invention, the vector according to the present invention, the cell according to the present invention, or the pharmaceutical composition according to the present invention may also be administered orally in any orally acceptable dosage form including, but not limited to, capsules, tablets, aqueous suspensions or solutions.

The artificial nucleic acid molecule according to the present invention, the vector according to the present invention, the cell according to the present invention, or the pharmaceutical composition according to the present invention may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the artificial nucleic acid molecule according to the present invention, the vector according to the present invention, the cell according to the present invention, or the pharmaceutical composition according to the present invention may be formulated in a suitable ointment suspended or dissolved in one or more carriers.

In one embodiment, the use as a medicament comprises the step of transfection of mammalian cells, preferably in vitro transfection of mammalian cells, more preferably in vitro transfection of isolated cells of a subject to be treated by the medicament. If the use comprises the in vitro transfection of isolated cells, the use as a medicament may further comprise the (re)administration of the transfected cells to the patient. The use of the inventive artificial nucleic acid molecules or the vector as a medicament may further comprise the step of selection of successfully transfected isolated cells. Thus, it may be beneficial if the vector further comprises a selection marker. Also, the use as a medicament may comprise in vitro transfection of isolated cells and purification of an expression-product, i.e. the encoded peptide or protein from these cells. This purified peptide or protein may subsequently be administered to a subject in need thereof.

The present invention also provides a method for treating or preventing a disease or disorder as described above comprising administering the artificial nucleic acid molecule according to the present invention, the vector according to the present invention, the cell according to the present invention, or the pharmaceutical composition according to the present invention to a subject in need thereof.

Furthermore, the present invention provides a method for treating or preventing a disease or disorder comprising transfection of a cell with an artificial nucleic acid molecule according to the present invention or with the vector according to the present invention. Said transfection may be performed in vitro or in vivo. In a preferred embodiment, transfection of a cell is performed in vitro and the transfected cell is administered to a subject in need thereof, preferably to a human patient. Preferably, the cell which is to be transfected in vitro is an isolated cell of the subject, preferably of the human patient. Thus, the present invention provides a method of treatment comprising the steps of isolating a cell from a subject, preferably from a human patient, transfecting the isolated cell with the artificial nucleic acid molecule according to the present invention or the vector according to the present invention, and administering the transfected cell to the subject, preferably the human patient.

The method of treating or preventing a disorder according to the present invention is preferably a vaccination method and/or a gene therapy method as described above.

As described above, the 5'UTR element and the optional 3'UTR element are capable of increasing protein production from an artificial nucleic acid molecule, such as an mRNA or vector, comprising the 5'UTR element and an ORF. Thus, in a further aspect, the present invention relates to a method for increasing protein production from an artificial nucleic acid molecule comprising the step of associating the artificial nucleic acid molecule, preferably the ORF contained within the artificial nucleic acid molecule, with (i) at least one 5'-untranslated region element (5'UTR element) which comprises or consists of a nucleic acid sequence which is derived from the 5'UTR of a TOP gene or which is derived from a variant of the 5'UTR of a TOP gene as described above and (ii) optionally at least one 3'UTR element which comprises or consists of a nucleic acid sequence derived from the 3'UTR of a chordate gene, preferably a vertebrate gene, more preferably a mammalian gene, most preferably a human gene, or from a variant of the 3'UTR of a chordate gene, preferably a vertebrate gene, more preferably a mammalian gene, most preferably a human gene as described above.

The term "associating the artificial nucleic acid molecule or the vector with a 5'UTR element and an optional 3'UTR element" in the context of the present invention preferably means functionally associating or functionally combining the artificial nucleic acid molecule, such as the mRNA or the vector, with the 5'UTR element and the optional 3'UTR element. This means that the artificial nucleic acid molecule, preferably the ORF contained within the artificial nucleic acid molecule, the 5'UTR element and the optional 3'UTR element as described above are associated or coupled such that the function of the 5'UTR element and the optional 3'UTR element, e.g., protein production increasing function, is exerted. Typically, this means that the 5'UTR element and the optional 3'UTR element are integrated into the artificial nucleic acid molecule, preferably into the mRNA molecule or the vector, such that the open reading frame is positioned 3' to the 5'UTR element, preferably between the 5'UTR element and the optional 3'UTR element.

In a further aspect, the present invention provides the use of at least one 5'-untranslated region element (5'UTR element) which comprises or consists of a nucleic acid sequence which is derived from the 5'UTR of a TOP gene or which is derived from a variant of the 5'UTR of a TOP gene as described above and optionally at least one 3'UTR element which comprises or consists of a nucleic acid sequence derived from the 3'UTR of a chordate gene, preferably a vertebrate gene, more preferably a mammalian gene, most preferably a human gene, or from a variant of the 3'UTR of a chordate gene, preferably a vertebrate gene, more preferably a mammalian gene, most preferably a human gene as described above for increasing protein production from an artificial nucleic acid molecule, such as an mRNA or a vector.

The use according to the present invention preferably comprises associating the artificial nucleic acid molecule with the 5'UTR element and the optional 3'UTR element as described above.

The method for increasing protein production from an artificial nucleic acid molecule and the above use may also comprise associating the artificial nucleic acid molecules with one or more further elements, such as a polyadenylation signal, a poly(A) sequence, a poly(C) sequence and/or a histone stem loop as described above.

The compounds and ingredients of the inventive pharmaceutical composition may also be manufactured and traded separately of each other. Thus, the invention relates further to a kit or kit of parts comprising an artificial nucleic acid molecule according to the invention, a vector according the invention, a cell according to the invention, and/or a pharmaceutical composition according to the invention. Preferably, such kit or kit of parts may, additionally, comprise instructions for use, cells for transfection, an adjuvant, a means for administration of the pharmaceutical composition, a pharmaceutically acceptable carrier and/or an pharmaceutically acceptable solution for dissolution or dilution of the artificial nucleic acid molecule, the vector, the cells or the pharmaceutical composition.

The following Figures, Sequences and Examples are intended to illustrate the invention further. They are not intended to limit the subject-matter of the invention thereto.

FIG. 1 shows the nucleotide sequence of a *Photinus pyralis* luciferase encoding nucleic acid molecule PpLuc (GC)-A64N64 (SEQ ID NO: 1364). This artificial construct does not comprise a 5'UTR element or a 3'UTR element in the sense of the present invention. The coding region for PpLuc(GC) is depicted in italics.

FIG. 2 shows the nucleotide sequence of PpLuc(GC)-albumin7-A64N64 (SEQ ID NO: 1365). The 3'UTR of human albumin, with a T7 termination signal as well as a HindIII and XbaI restriction site removed by three single point mutations, was inserted between the ORF and poly(A) of the construct shown in FIG. 1. The coding region for PpLuc(GC) is depicted in italics. The albumin 3'UTR is underlined.

FIG. 3 shows the nucleotide sequence of RPL32-PpLuc (GC)-A64N64 (SEQ ID NO: 1366). The 5'UTR of human ribosomal protein Large 32 gene lacking the 5' terminal oligopyrimidine tract (RPL32) according to SEQ ID NO. 1368 was inserted 5' of the ORF in the construct shown in FIG. 1. The coding region for PpLuc(GC) is depicted in italics. The RPL32 5'UTR is underlined.

FIG. 4 shows the nucleotide sequence of RPL32-PpLuc (GC)-albumin7-A64N64 (SEQ ID NO: 1367). The 5'UTR of human ribosomal protein Large 32 gene lacking the 5' terminal oligopyrimidine tract (RPL32) according to SEQ ID NO. 1368 and the albumin7 3'UTR element according to SEQ ID NO. 1376 were inserted 5' and 3' of the ORF in the construct shown in FIG. 1, respectively.

FIG. 5 is a graphical representation of the effect of the TOP 5'UTR element which is derived from the 5'UTR of the TOP gene RPL23 according to SEQ ID NO. 1368, the albumin 3' UTR element according to SEQ ID NO. 1376 and the combination of the TOP 5'UTR element and the albumin 3'UTR element on luciferase expression from mRNA. A variety of mRNAs were transfected into human dermal fibroblasts (HDF) by lipofection. Luciferase levels were measured at 24, 48, and 72 hours after transfection. The albumin 3'UTR element extends luciferase expression, while the TOP 5'UTR element increases luciferase levels compared to mRNA lacking 5'- and 3'UTR elements. Strikingly, the combination of TOP 5'UTR element and albumin 3'UTR element further strongly increases the luciferase level, much above the level observed with either of the individual elements, thus acting synergistically. Data are graphed as mean RLU±SD (relative light units±standard deviation) for triplicate transfections. RLU are summarized in Example 5.1.

FIG. 6 shows the nucleotide sequence of RPL35-PpLuc (GC)-albumin7-A64N64 SEQ ID NO: 1396). The 5'UTR of human ribosomal protein Large 35 gene lacking the 5' terminal oligopyrimidine tract (RPL35) according to SEQ ID NO. 1412 and the albumin7 3'UTR element according to SEQ ID NO. 1376 were inserted 5' and 3' of the ORF in the construct shown in FIG. 1, respectively.

FIG. 7 shows the nucleotide sequence of RPL21-PpLuc (GC)-albumin7-A64N64 (SEQ ID NO: 1397). The 5'UTR of human ribosomal protein Large 21 gene lacking the 5' terminal oligopyrimidine tract (RPL21) according to SEQ ID NO. 1413 and the albumin7 3'UTR element according to SEQ ID NO. 1376 were inserted 5' and 3' of the ORF in the construct shown in FIG. 1, respectively.

FIG. 8 shows the nucleotide sequence of atp5a1-PpLuc (GC)-albumin7-A64N64 (SEQ ID NO: 1398). The 5'UTR of human ATP synthase, H+ transporting, mitochondrial F1 complex, alpha subunit 1 gene lacking the 5' terminal oligopyrimidine tract (atp5a1) according to SEQ ID NO. 1414 and the albumin7 3'UTR element according to SEQ ID NO. 1376 were inserted 5' and 3' of the ORF in the construct shown in FIG. 1, respectively.

FIG. 9 shows the nucleotide sequence of HSD17B4-PpLuc(GC)-albumin7-A64N64 (SEQ ID NO: 1399). The 5'UTR of human hydroxysteroid (17-beta) dehydrogenase 4 gene lacking the 5' terminal oligopyrimidine tract (HSD17B4) according to SEQ ID NO. 1415 and the albumin7 3'UTR element according to SEQ ID NO. 1376 were inserted 5' and 3' of the ORF in the construct shown in FIG. 1, respectively.

FIG. 10 shows the nucleotide sequence of AIG1-PpLuc (GC)-albumin7-A64N64 (SEQ ID NO: 1400). The 5'UTR of human androgen-induced 1gene lacking the 5' terminal oligopyrimidine tract (AIG1) according to SEQ ID NO. 1416 and the albumin7 3'UTR element according to SEQ ID NO. 1376 were inserted 5' and 3' of the ORF in the construct shown in FIG. 1, respectively.

FIG. 11 shows the nucleotide sequence of COX6C-PpLuc (GC)-albumin7-A64N64 (SEQ ID NO: 1401). The 5'UTR of human cytochrome c oxidase subunit VIc gene lacking the 5' terminal oligopyrimidine tract (COX6C) according to SEQ ID NO. 1417 and the albumin7 3'UTR element according to SEQ ID NO. 1376 were inserted 5' and 3' of the ORF in the construct shown in FIG. 1, respectively.

FIG. 12 shows the nucleotide sequence of ASAH1-PpLuc (GC)-albumin7-A64N64 (SEQ ID NO: 1402). The 5'UTR of human N-acylsphingosine amidohydrolase (acid ceramidase) 1 lacking the 5' terminal oligopyrimidine tract (ASAH1) according to SEQ ID NO. 1418 and the albumin7 3'UTR according to SEQ ID NO. 1376 were inserted 5' and 3' of the ORF in the construct shown in FIG. 1, respectively.

FIG. 13 shows the nucleotide sequence of mRPL21-PpLuc(GC)-albumin7-A64N64 (SEQ ID NO: 1403). The 5'UTR of murine ribosomal protein Large 21 gene lacking the 5' terminal oligopyrimidine tract (mRPL21) according to SEQ ID NO. 1419 and the albumin7 3'UTR element according to SEQ ID NO. 1376 were inserted 5' and 3' of the ORF in the construct shown in FIG. 1, respectively.

FIG. 14 shows the nucleotide sequence of mRPL35A-PpLuc(GC)-albumin7-A64N64 (SEQ ID NO: 1404). The 5'UTR of murine ribosomal protein Large 35a gene lacking the 5' terminal oligopyrimidine tract (mRPL35A) according to SEQ ID NO. 1420 and the albumin7 3'UTR element according to SEQ ID NO. 1376 were inserted 5' and 3' of the ORF in the construct shown in FIG. 1, respectively.

FIG. 15 shows the nucleotide sequence of RPL35-PpLuc (GC)-A64N64 (SEQ ID NO: 1405). The 5'UTR of human ribosomal protein Large 35 gene lacking the 5' terminal oligopyrimidine tract (RPL35) according to SEQ ID NO. 1412 was inserted 5' of the ORF in the construct shown in FIG. 1.

FIG. 16 shows the nucleotide sequence of RPL21-PpLuc (GC)-A64N64 (SEQ ID NO: 1406). The 5'UTR of human ribosomal protein Large 21 gene lacking the 5' terminal oligopyrimidine tract (RPL21) according to SEQ ID NO. 1413 was inserted 5' of the ORF in the construct shown in FIG. 1.

FIG. 17 shows the nucleotide sequence of atp5a1-PpLuc (GC)-A64N64 (SEQ ID NO: 1407). The 5'UTR of human ATP synthase, H+ transporting, mitochondrial F1 complex, alpha subunit 1 gene lacking the 5' terminal oligopyrimidine tract (atp5a1) according to SEQ ID NO. 1414 was inserted 5' of the ORF in the construct shown in FIG. 1.

FIG. 18 shows the nucleotide sequence of HSD17B4-PpLuc(GC)-A64N64 (SEQ ID NO: 1408). The 5'UTR of human hydroxysteroid (17-beta) dehydrogenase 4 gene lacking the 5' terminal oligopyrimidine tract (HSD17B4) according to SEQ ID NO. 1415 was inserted 5' of the ORF in the construct shown in FIG. 1.

FIG. 19 shows the nucleotide sequence of AIG1-PpLuc (GC)-A64N64 (SEQ ID NO: 1409). The 5'UTR of human androgen-induced 1 gene lacking the 5' terminal oligopyrimidine tract (AIG1) according to SEQ ID NO. 1416 was inserted 5' of the ORF in the construct shown in FIG. 1.

FIG. 20 shows the nucleotide sequence of COX6C-PpLuc (GC)-A64N64 (SEQ ID NO: 1410). The 5'UTR of human cytochrome c oxidase subunit VIc gene lacking the 5' terminal oligopyrimidine tract (COX6C) according to SEQ ID NO. 1417 was inserted 5' of the ORF in the construct shown in FIG. 1.

FIG. 21 shows the nucleotide sequence of ASAH1-PpLuc (GC)-A64N64 (SEQ ID NO: 1411). The 5'UTR of human N-acylsphingosine amidohydrolase (acid ceramidase) 1 gene lacking the 5' terminal oligopyrimidine tract (ASAH1) according to SEQ ID NO. 1418 was inserted 5' of the ORF in the construct shown in FIG. 1.

Figure 22:
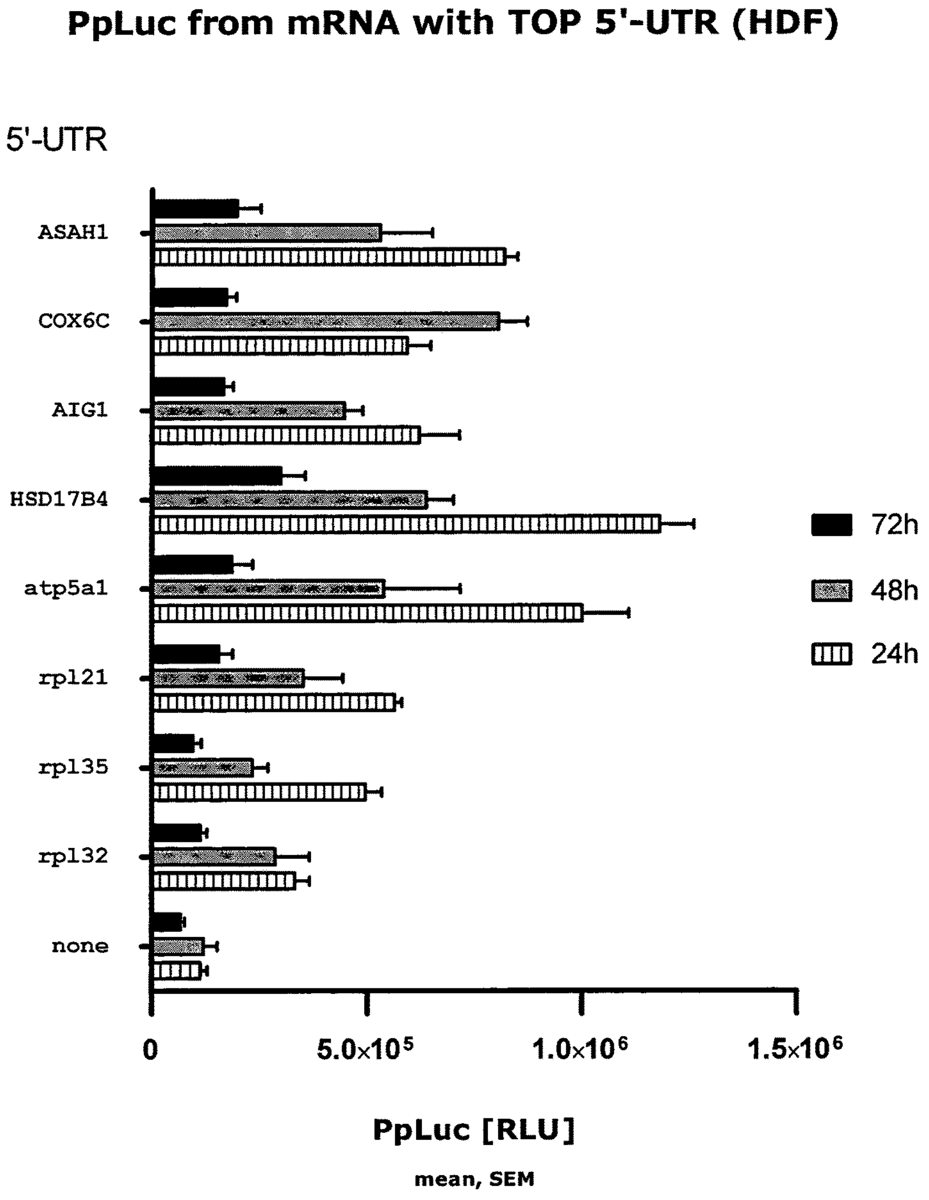

FIG. 22 is a graphical representation of the effect of different TOP 5'UTR elements on luciferase expression from mRNA. A variety of mRNAs were transfected into human dermal fibroblasts (HDF) by lipofection. Luciferase levels were measured at 24, 48, and 72 hours after transfection. TOP 5'UTR elements strongly increase luciferase levels compared to mRNA lacking a 5'UTR element. mRNAs comprising 5'UTR elements derived from the 5'UTRs of the TOP genes ASAH1, COX6C, AIG1, HSD17B4, atp5a1, RPL21, RPL35 and RPL32 were transfected into human dermal fibroblasts (HDF) by lipofection. Luciferase levels were measured at 24, 48, and 72 hours after transfection. The TOP 5'UTR elements increases luciferase levels compared to mRNA lacking a 5'UTR element. Data are graphed as mean RLU±SEM (relative light units±standard error) for triplicate transfections. RLU are summarized in Example 5.2.

Figure 23:
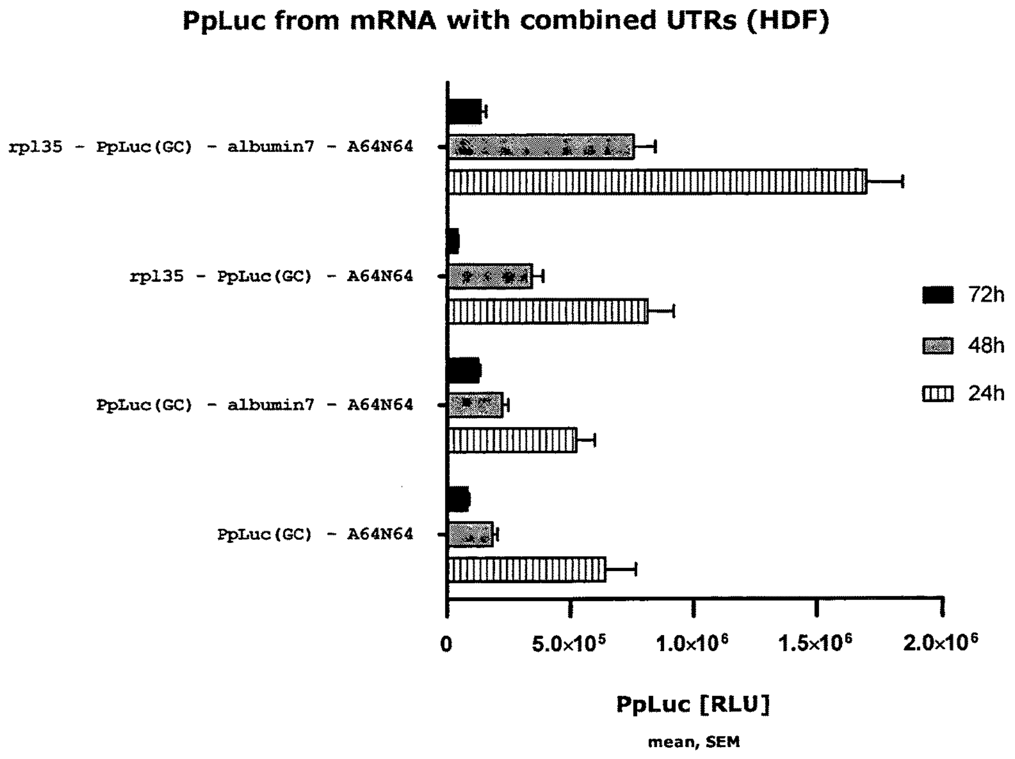

FIG. 23 is a graphical representation of the effect of the RPL35 TOP 5'UTR element, the albumin 3'UTR element and the combination of RPL35 TOP 5'UTR element and albumin 3'UTR element on luciferase expression from mRNA. A variety of mRNAs were transfected into human dermal fibroblasts (HDF) by lipofection. Luciferase levels were measured at 24, 48, and 72 hours after transfection. The albumin 3'UTR element extends luciferase expression, while the RPL35 TOP 5'UTR element increases luciferase levels compared to mRNA lacking 5'- and 3'UTR elements. Strikingly, the combination of RPL35 TOP 5'UTR element and albumin 3'UTR element further strongly increases the luciferase level, much above the level observed with either of the individual elements, thus acting synergistically. Data are graphed as mean RLU±SEM (relative light units±standard error) for triplicate transfections. Synergy is summarized in Example 5.3.

Figure 24:
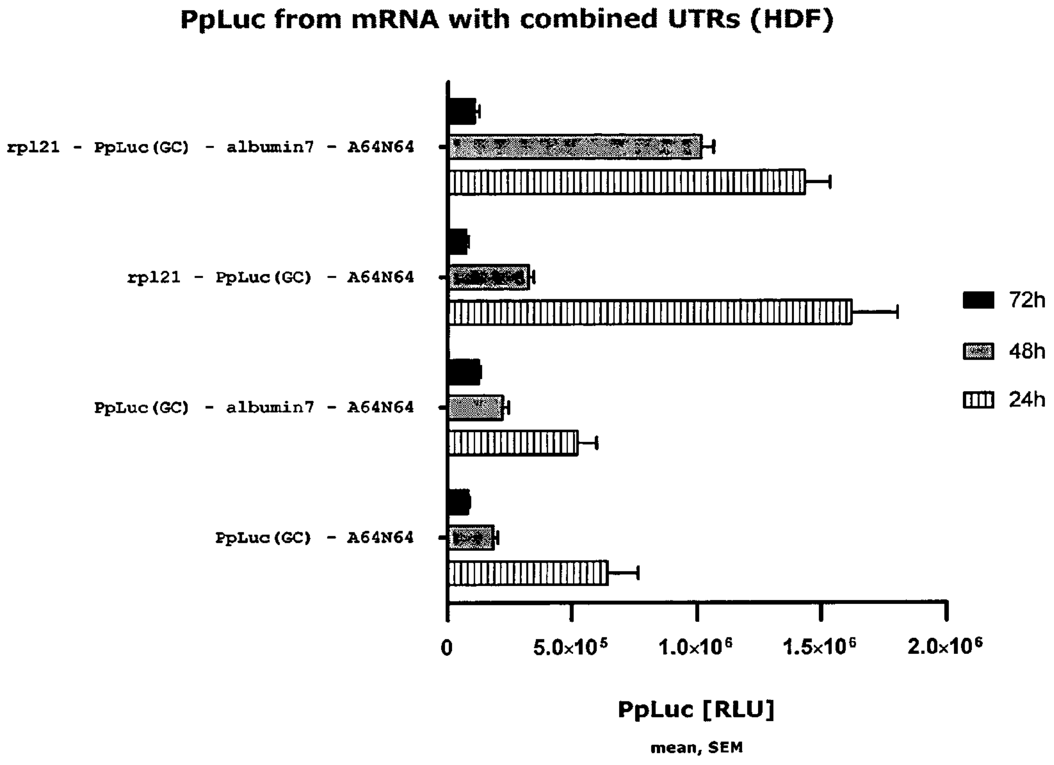

FIG. 24 is a graphical representation of the effect of the RPL21 TOP 5'UTR element, the albumin 3'UTR element and the combination of RPL21 TOP 5'UTR element and albumin 3'UTR element on luciferase expression from mRNA. A variety of mRNAs were transfected into human dermal fibroblasts (HDF) by lipofection. Luciferase levels were measured at 24, 48, and 72 hours after transfection. The albumin 3'UTR element extends luciferase expression, while the RPL21 TOP 5'UTR element increases luciferase levels compared to mRNA lacking 5'- and 3'UTR elements. Strikingly, the combination of RPL21 TOP 5'UTR element and albumin 3'UTR element further strongly increases the luciferase level, much above the level observed with either of the individual elements, thus acting synergistically. Data are graphed as mean RLU±SEM (relative light units±standard error) for triplicate transfections. Synergy is summarized in Example 5.3.

Figure 25:
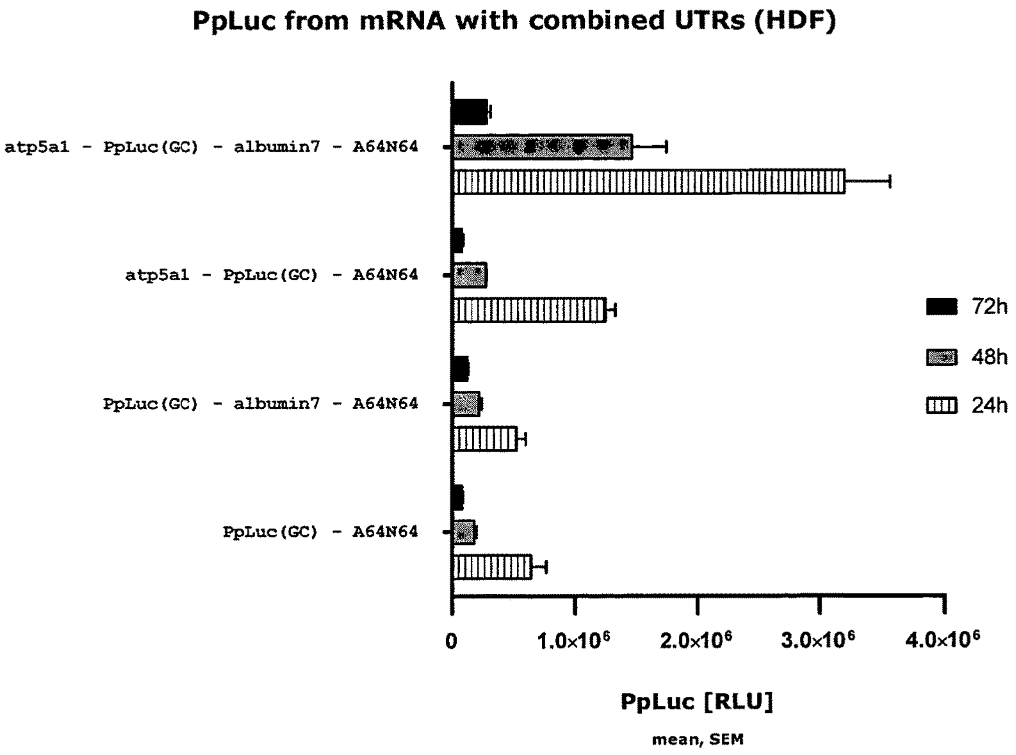

FIG. 25 is a graphical representation of the effect of the atp5a1 TOP 5'UTR element, the albumin 3'UTR element and the combination of atp5a1 TOP 5'UTR element and albumin 3'UTR element on luciferase expression from mRNA. A variety of mRNAs were transfected into human dermal fibroblasts (HDF) by lipofection. Luciferase levels were measured at 24, 48, and 72 hours after transfection. The albumin 3'UTR element extends luciferase expression, while the atp5a1 TOP 5'UTR element increases luciferase levels compared to mRNA lacking 5'- and 3'UTR elements. Strikingly, the combination of atp5a1 TOP 5'UTR element and albumin 3'UTR element further strongly increases the luciferase level, much above the level observed with either of the individual elements, thus acting synergistically. Data are graphed as mean RLU±SEM (relative light units±standard error) for triplicate transfections. Synergy is summarized in Example 5.3.

Figure 26:
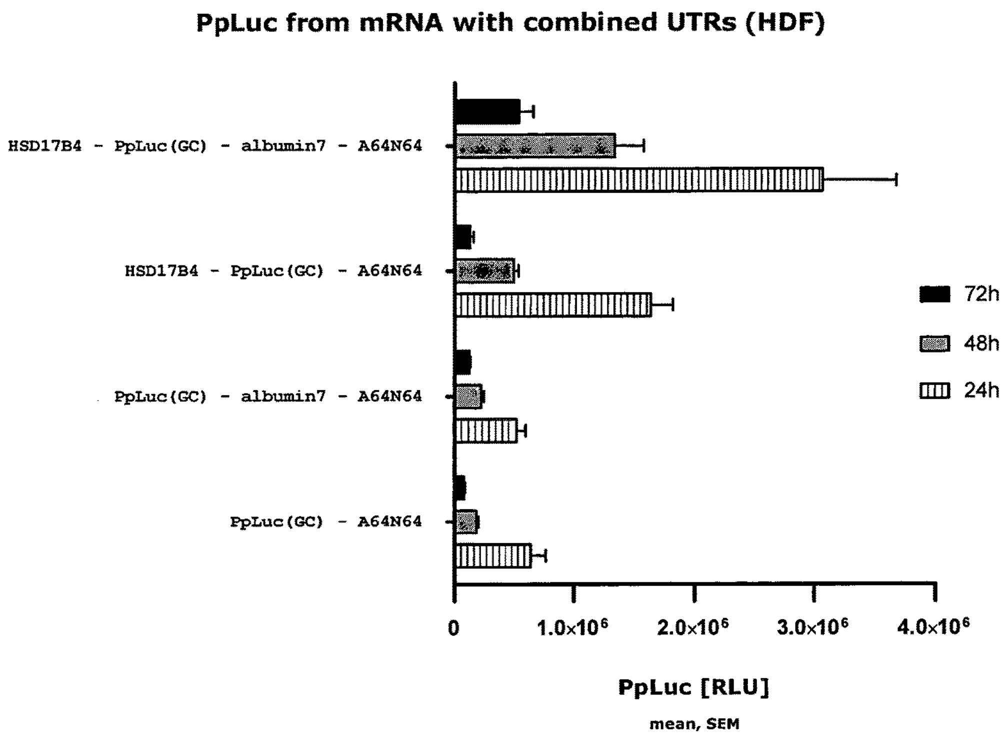

FIG. 26 is a graphical representation of the effect of the HSD17B4 TOP 5'UTR element, the albumin 3'UTR element and the combination of HSD17B4 TOP 5'UTR element and albumin 3'UTR element on luciferase expression from mRNA. A variety of mRNAs were transfected into human dermal fibroblasts (HDF) by lipofection. Luciferase levels were measured at 24, 48, and 72 hours after transfection. The albumin 3'UTR element extends luciferase expression, while the HSD17B4 TOP 5'UTR element increases luciferase levels compared to mRNA lacking 5'- and 3'UTR elements. Strikingly, the combination of HSD17B4 TOP 5'UTR element and albumin 3'UTR element further strongly increases the luciferase level, much above the level observed with either of the individual elements, thus acting synergistically. Data are graphed as mean RLU±SEM (relative light units±standard error) for triplicate transfections. Synergy is summarized in Example 5.3.

Figure 27:
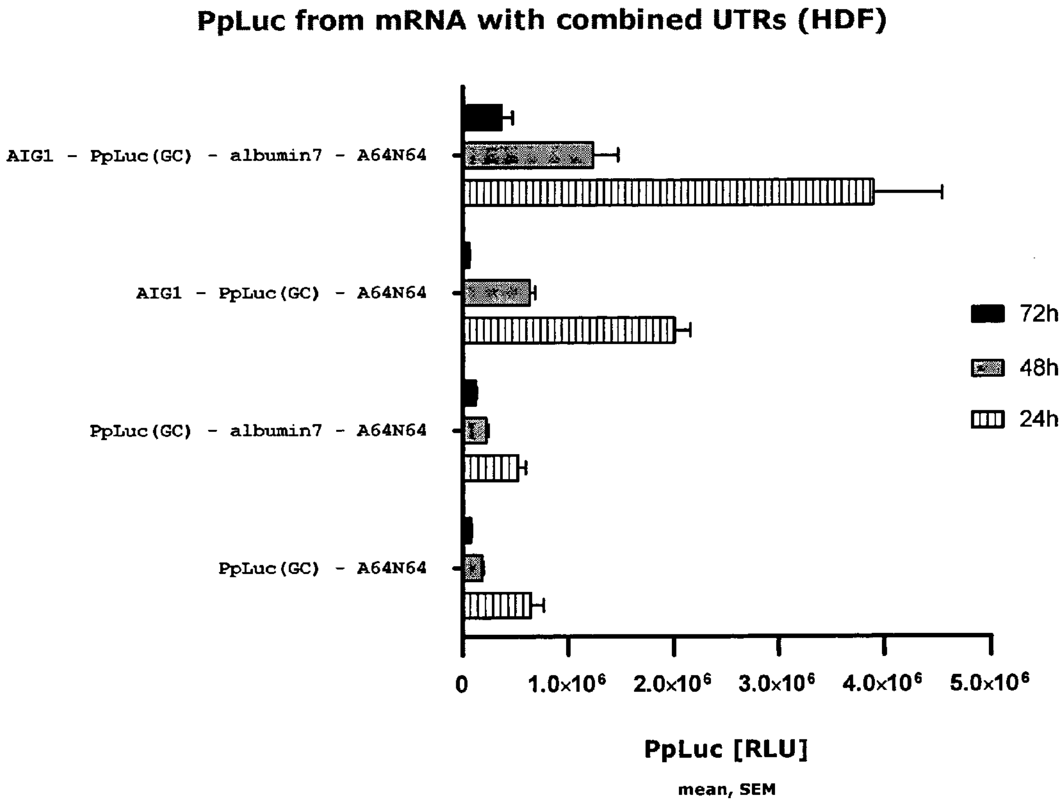

FIG. 27 is a graphical representation of the effect of the AIG1 TOP 5'UTR element, the albumin 3'UTR element and the combination of AIG1 TOP 5'UTR element and albumin 3'UTR element on luciferase expression from mRNA. A variety of mRNAs were transfected into human dermal fibroblasts (HDF) by lipofection. Luciferase levels were measured at 24, 48, and 72 hours after transfection. The albumin 3'UTR element extends luciferase expression, while the AIG1 TOP 5'UTR element increases luciferase levels compared to mRNA lacking 5'- and 3'UTR elements. Strikingly, the combination of AIG1 TOP 5'UTR element and albumin 3'UTR element further strongly increases the luciferase level, much above the level observed with either of the individual elements, thus acting synergistically. Data are graphed as mean RLU±SEM (relative light units±standard error) for triplicate transfections. Synergy is summarized in Example 5.3.

Figure 28:
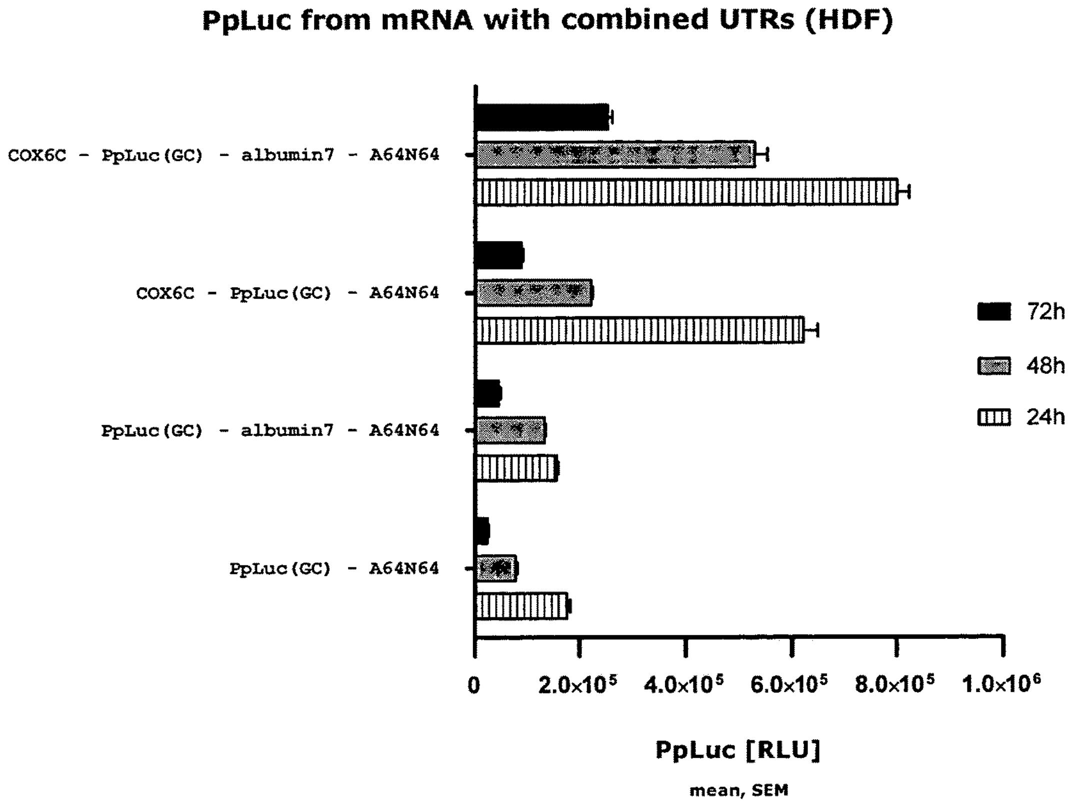

FIG. 28 is a graphical representation of the effect of the COX6C TOP 5'UTR element, the albumin 3'UTR element and the combination of COX6C TOP 5'UTR element and albumin 3'UTR element on luciferase expression from mRNA. A variety of mRNAs were transfected into human dermal fibroblasts (HDF) by lipofection. Luciferase levels were measured at 24, 48, and 72 hours after transfection. The albumin 3'UTR element extends luciferase expression, while the COX6C TOP 5'UTR element increases luciferase levels compared to mRNA lacking 5'- and 3'UTR elements. Strikingly, the combination of COX6C TOP 5'UTR element and albumin 3'UTR element further strongly increases the luciferase level, much above the level observed with either of the individual elements, thus acting synergistically. Data are graphed as mean RLU±SEM (relative light units±standard error) for triplicate transfections. Synergy is summarized in Example 5.3.

Figure 29:
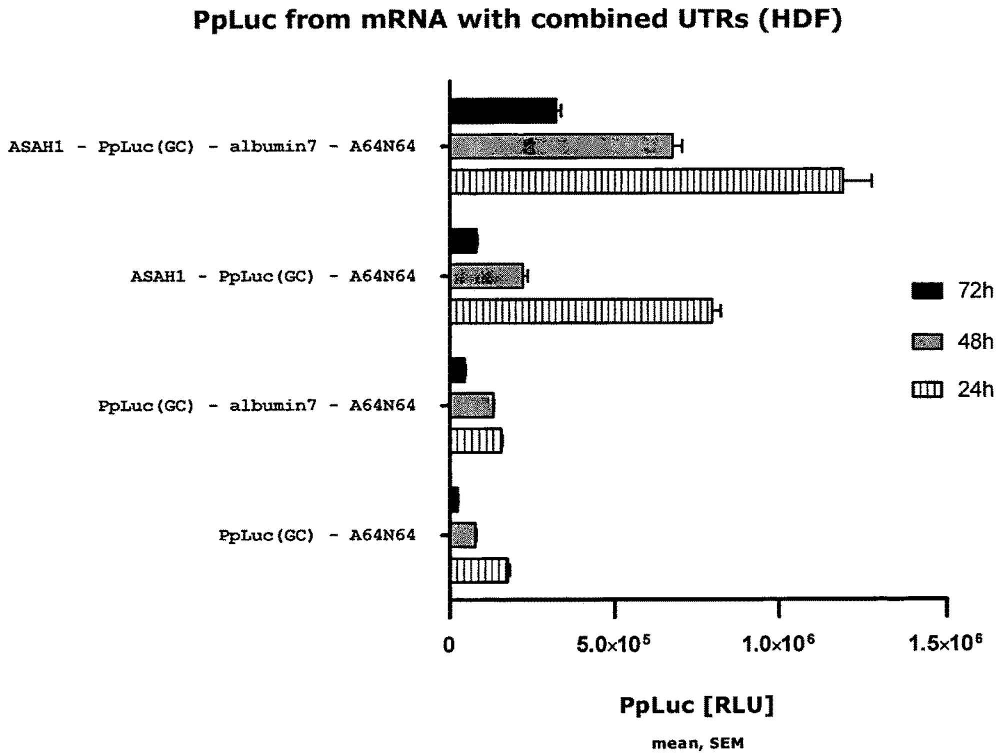

FIG. 29 is a graphical representation of the effect of the ASAH1 TOP 5'UTR element, the albumin 3'UTR element and the combination of ASAH1 TOP 5'UTR element and albumin 3'UTR element on luciferase expression from mRNA. A variety of mRNAs were transfected into human dermal fibroblasts (HDF) by lipofection. Luciferase levels were measured at 24, 48, and 72 hours after transfection. The albumin 3'UTR element extends luciferase expression, while the ASAH1 TOP 5'UTR element increases luciferase levels compared to mRNA lacking 5'- and 3'UTR elements. Strikingly, the combination of ASAH1 TOP 5'UTR element and albumin 3'UTR element further strongly increases the luciferase level, much above the level observed with either of the individual elements, thus acting synergistically. Data are graphed as mean RLU±SEM (relative light units±standard error) for triplicate transfections. Synergy is summarized in Example 5.3.

Figure 30:
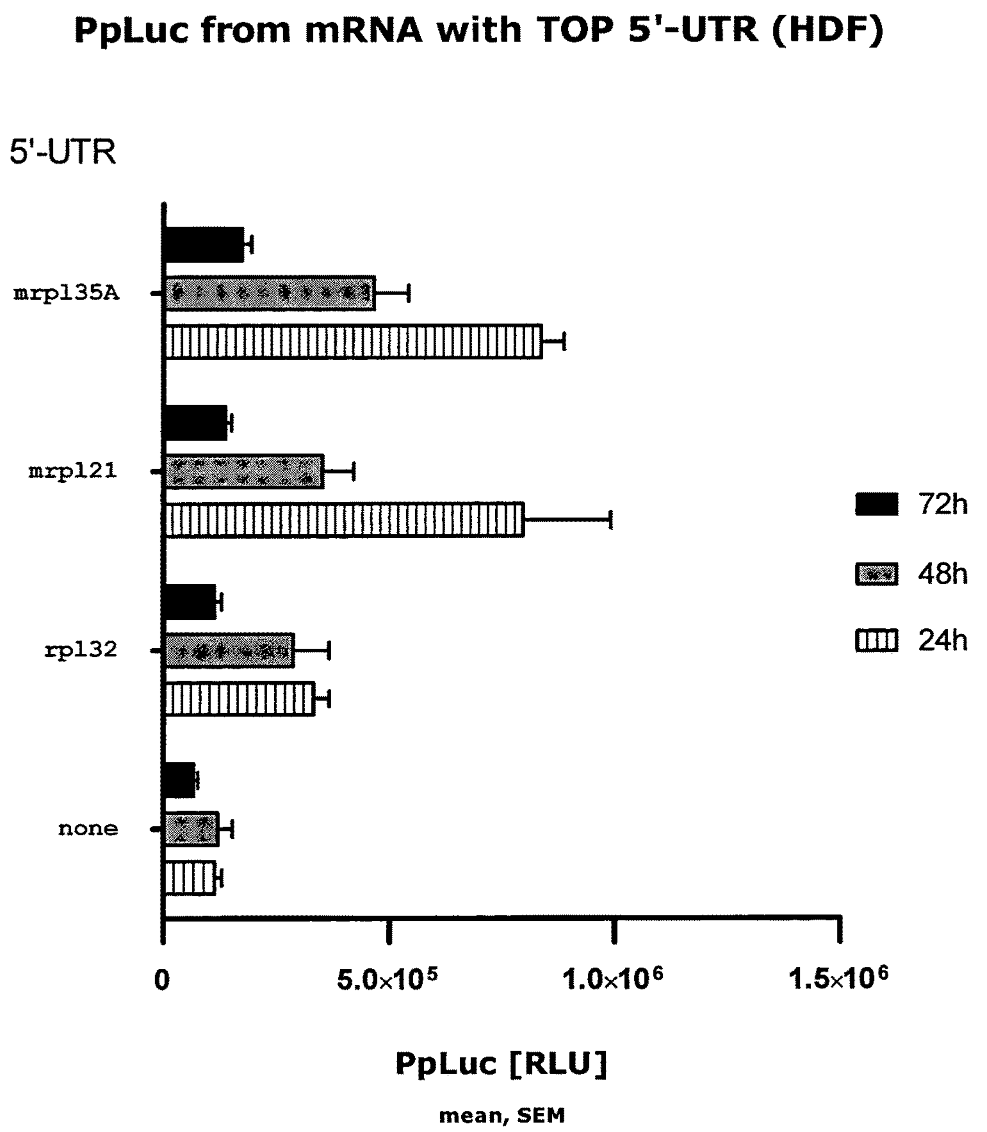

FIG. 30 is a graphical representation of the effect of the TOP 5'UTR element from mouse genes on luciferase expression from mRNA. mRNAs containing either a mouse or a human TOP 5'UTR element were transfected into human dermal fibroblasts (HDF) by lipofection. Luciferase levels were measured at 24, 48, and 72 hours after transfection. Mouse TOP 5'UTR elements strongly increase luciferase levels compared to mRNA lacking a 5'-element, similarly as the human TOP 5'UTR element. Data are graphed as mean RLU±SEM (relative light units±standard error) for triplicate transfections. RLU are summarized in Example 5.4.

SEQ ID No. 1-1363, 1395, 1421, and 1422 Sequences comprising 5'UTRs of TOP genes SEQ ID No. 1364 PpLuc(GC)-A64N64

SEQ ID No. 1365 PpLuc(GC)-albumin7-A64N64

SEQ ID No. 1366 RPL32-PpLuc(GC)-A64N64

SEQ ID No. 1367 RPL32-PpLuc(GC)-albumin7-A64N64

SEQ ID No. 1368 5'UTR of human ribosomal protein Large 32 lacking the 5' terminal oligopyrimidine tract SEQ ID No. 1369 Human albumin 3'UTR SEQ ID No. 1370 3'UTR of *Homo sapiens* hemoglobin, alpha 1 (HBA1)

SEQ ID No. 1371 3'UTR of *Homo sapiens* hemoglobin, alpha 2 (HBA2)

SEQ ID No. 1372 3'UTR of *Homo sapiens* hemoglobin, beta (HBB)

SEQ ID No. 1373 3'UTR of *Homo sapiens* tyrosine hydroxylase (TH)

SEQ ID No. 1374 3'UTR of *Homo sapiens* arachidonate 15-lipoxygenase (ALOX15)

SEQ ID No. 1375 3'UTR of *Homo sapiens* collagen, type I, alpha 1 (COL1A1)
SEQ ID No. 1376 albumin7 3'UTR
SEQ ID No. 1377 Human albumin 3'UTR+poly(A) sequence
SEQ ID No. 1378 Human albumin 3'UTR fragment 1
SEQ ID No. 1379 Human albumin 3'UTR fragment 2
SEQ ID No. 1380 Human albumin 3'UTR fragment 3
SEQ ID No. 1381 Human albumin 3'UTR fragment 4
SEQ ID No. 1382 Human albumin 3'UTR fragment 5
SEQ ID No. 1383 Human albumin 3'UTR fragment 6
SEQ ID No. 1384 Human albumin 3'UTR fragment 7
SEQ ID No. 1385 Human albumin 3'UTR fragment 8
SEQ ID No. 1386 Human albumin 3'UTR fragment 9
SEQ ID No. 1387 Human albumin 3'UTR fragment 10
SEQ ID No. 1388 Human albumin 3'UTR fragment 11
SEQ ID No. 1389 Human albumin 3'UTR fragment 12
SEQ ID No. 1390 Human albumin 3'UTR fragment 13
SEQ ID No. 1391 Albumin7 3'UTR-poly(A) sequence-poly (C) sequence-HL
SEQ ID No. 1392 Albumin7 3'UTR-poly(A) sequence-poly (C) sequence
SEQ ID No. 1393 Center, α-complex-binding portion of the 3'UTR of anα-globin gene
SEQ ID No. 1394 Histone stem-loop
SEQ ID NO. 1396 RPL35-PpLuc(GC)-albumin7-A64N64
SEQ ID NO. 1397 RPL21-PpLuc(GC)-albumin7-A64N64
SEQ ID NO. 1398 ATP5A1-PpLuc(GC)-albumin7-A64N64
SEQ ID NO. 1399 HSD17B4-PpLuc(GC)-albumin7-A64N64
SEQ ID NO. 1400 AIG1-PpLuc(GC)-albumin7-A64N64
SEQ ID NO. 1401 COX6C-PpLuc(GC)-albumin7-A64N64
SEQ ID NO. 1402 ASAH1-PpLuc(GC)-albumin7-A64N64
SEQ ID NO. 1403 mRPL21-PpLuc(GC)-albumin7-A64N64
SEQ ID NO. 1404 mRPL35A-PpLuc(GC)-albumin7-A64N64
SEQ ID NO. 1405 RPL35-PpLuc(GC)-A64N64
SEQ ID NO. 1406 RPL21-PpLuc(GC)-A64N64
SEQ ID NO. 1407 ATP5A1-PpLuc(GC)-A64N64
SEQ ID NO. 1408 HSD17B4-PpLuc(GC)-A64N64
SEQ ID NO. 1409 AIG1-PpLuc(GC)-A64N64
SEQ ID NO. 1410 COX6C-PpLuc(GC)-A64N64
SEQ ID NO. 1411 ASAH1-PpLuc(GC)-A64N64
SEQ ID NO. 1412 5'UTR of human ribosomal protein Large 35 (RPL35) lacking the 5' terminal oligopyrimidine tract
SEQ ID NO. 1413 5'UTR of human ribosomal protein Large 21 (RPL21) lacking the 5' terminal oligopyrimidine tract
SEQ ID NO. 1414 5'UTR of human ATP synthase, H+ transporting, mitochondrial F1 complex, alpha subunit 1, cardiac muscle (ATP5A1) lacking the 5' terminal oligopyrimidine tract
SEQ ID NO. 1415 5'UTR of human hydroxysteroid (17-beta) dehydrogenase 4 (HSD17B4) lacking the 5' terminal oligopyrimidine tract
SEQ ID NO. 1416 5'UTR of human androgen-induced 1 (AIG1) lacking the 5' terminal oligopyrimidine tract
SEQ ID NO. 1417 5'UTR of human cytochrome c oxidase subunit VIc (COX6C) lacking the 5' terminal oligopyrimidine tract
SEQ ID NO. 1418 5'UTR of human N-acylsphingosine amidohydrolase (acid ceramidase) 1 (ASAH1) lacking the 5' terminal oligopyrimidine tract
SEQ ID NO. 1419 5'UTR of mouse ribosomal protein Large 21 (mRPL21) lacking the 5' terminal oligopyrimidine tract
SEQ ID NO. 1420 5'UTR of mouse ribosomal protein large 35A (mRPL35A) lacking the 5' terminal oligopyrimidine tract

EXAMPLES

1. Preparation of DNA-Templates

A vector for in vitro transcription was constructed containing a T7 promoter followed by a GC-enriched sequence coding for *Photinus pyralis* luciferase (PpLuc(GC)) and an A64 poly(A) sequence. The poly(A) sequence was followed by a restriction site used for linearization of the vector before in vitro transcription. mRNA obtained from this vector accordingly by in vitro transcription is designated as "PpLuc (GC)-A64N64".

This vector was modified to include untranslated sequences 5' or 3' of the open reading frame (5'UTR or 3'UTR, respectively). In summary, vectors comprising the following mRNA encoding sequences have been generated (the mRNA coding sequences are depicted in FIGS. 1 to 4 and 6 to 21):

SEQ ID No. 1364 (FIG. 1): PpLuc(GC)-A64N64
SEQ ID No. 1365 (FIG. 2): PpLuc(GC)-albumin7-A64N64
SEQ ID No. 1366 (FIG. 3): RPL32-PpLuc(GC)-A64N64
SEQ ID No. 1367 (FIG. 4): RPL32-PpLuc(GC)-albumin7-A64N64
SEQ ID NO. 1396 (FIG. 6): RPL35-PpLuc(GC)-albumin7-A64N64
SEQ ID NO. 1397 (FIG. 7): RPL21-PpLuc(GC)-albumin7-A64N64
SEQ ID NO. 1398 (FIG. 8): ATP5A1-PpLuc(GC)-albumin7-A64N64
SEQ ID NO. 1399 (FIG. 9): HSD17B4-PpLuc(GC)-albumin7-A64N64
SEQ ID NO. 1400 (FIG. 10): AIG1-PpLuc(GC)-albumin7-A64N64
SEQ ID NO. 1401 (FIG. 11): COX6C-PpLuc(GC)-albumin7-A64N64
SEQ ID NO. 1402 (FIG. 12): ASAH1-PpLuc(GC)-albumin7-A64N64
SEQ ID NO. 1403 (FIG. 13): mRPL21-PpLuc(GC)-albumin7-A64N64
SEQ ID NO. 1404 (FIG. 14): mRPL35A-PpLuc(GC)-albumin7-A64N64
SEQ ID NO. 1405 (FIG. 15): RPL35-PpLuc(GC)-A64N64
SEQ ID NO. 1406 (FIG. 16): RPL21-PpLuc(GC)-A64N64
SEQ ID NO. 1407 (FIG. 17): ATP5A1-PpLuc(GC)-A64N64
SEQ ID NO. 1408 (FIG. 18): HSD17B4-PpLuc(GC)-A64N64
SEQ ID NO. 1409 (FIG. 19): AIG1-PpLuc(GC)-A64N64
SEQ ID NO. 1410 (FIG. 20): COX6C-PpLuc(GC)-A64N64
SEQ ID NO. 1411 (FIG. 21): ASAH1-PpLuc(GC)-A64N64

2. In Vitro Transcription

The DNA-template according to Example 1 was linearized and transcribed in vitro using T7-Polymerase. The DNA-template was then digested by DNase-treatment. mRNA transcripts contained a 5'-CAP structure obtained by adding an excess of N7-Methyl-Guanosine-5'-Triphosphate-5'-Guanosine to the transcription reaction. mRNA thus obtained was purified and resuspended in water.

3. Luciferase Expression by mRNA Lipofection

Human dermal fibroblasts (HDF) were seeded in 24 well plates at a density of $5\times10^4$ cells per well. The following day, cells were washed in opti-MEM and then transfected with 50 ng per well of Lipofectamine-2000-complexed PpLuc-encoding mRNA in opti-MEM. As a control, mRNA not coding for PpLuc was lipofected separately. mRNA coding for *Renilla reniformis* luciferase (RrLuc) was transfected together with PpLuc mRNA to control for transfection efficiency (20 ng of RrLuc mRNA per well). 90 minutes after start of transfection, opti-MEM was exchanged for medium. 24, 48, 72 hours after transfection, medium was aspirated and cells were lysed in 200 μl of lysis buffer (25 mM Tris, pH 7.5 (HCl), 2 mM EDTA, 10% glycerol, 1% Triton X-100, 2 mM DTT, 1 mM PMSF). Lysates were stored at −20° C. until luciferase activity was measured.

Alternatively, HDF were seeded in 96 well plates three days before transfection at a density of $10^4$ cells per well. Immediately before lipofection, cells were washed in opti-MEM. Cells were lipofected with 25 ng of PpLuc-encoding mRNA per well corn-plexed with Lipofectamine-2000. mRNA coding for *Renilla reniformis* luciferase (RrLuc) was transfected together with PpLuc mRNA to control for transfection efficiency (2.5 ng of RrLuc mRNA per well). 90 minutes after start of transfection, opti-MEM was exchanged for medium. 24, 48, 72 hours after transfection, medium was aspirated and cells were lysed in 100 μl of lysis buffer (Passive Lysis Buffer, Promega). Lysates were stored at −80° C. until luciferase activity was measured.

4. Luciferase Measurement

Luciferase activity was measured as relative light units (RLU) in a BioTek SynergyHT plate reader. PpLuc activity was measured at 15 seconds measuring time using 50 μl of lysate and 200 μl of luciferin buffer (75 μM luciferin, 25 mM Glycylglycin, pH 7.8 (NaOH), 15 mM MgSO4, 2 mM ATP). RrLuc activity was measured at 15 seconds measuring time using 50 μl of lysate and 200 μl of coelenterazin buffer (40 μM coelenterazin in phosphate buffered saline adjusted to 500 mM NaCl).

Alternatively, luciferase activity was measured as relative light units (RLU) in a Hidex Cha-meleon plate reader. PpLuc activity was measured at 2 seconds measuring time using 20 μl of lysate and 50 μl of luciferin buffer (Beetle-Juice, PJK GmbH). RrLuc activity was measured at 2 seconds measuring time using 20 μl of lysate and 50 μl of coelenterazin buffer (*Renilla*-Juice, PJK GmbH).

Results 5.1 The Combination of TOP 5'UTR Element and Albumin 3'UTR Element Increases Protein Expression from mRNA in a Synergistic Manner.

Figure 5:
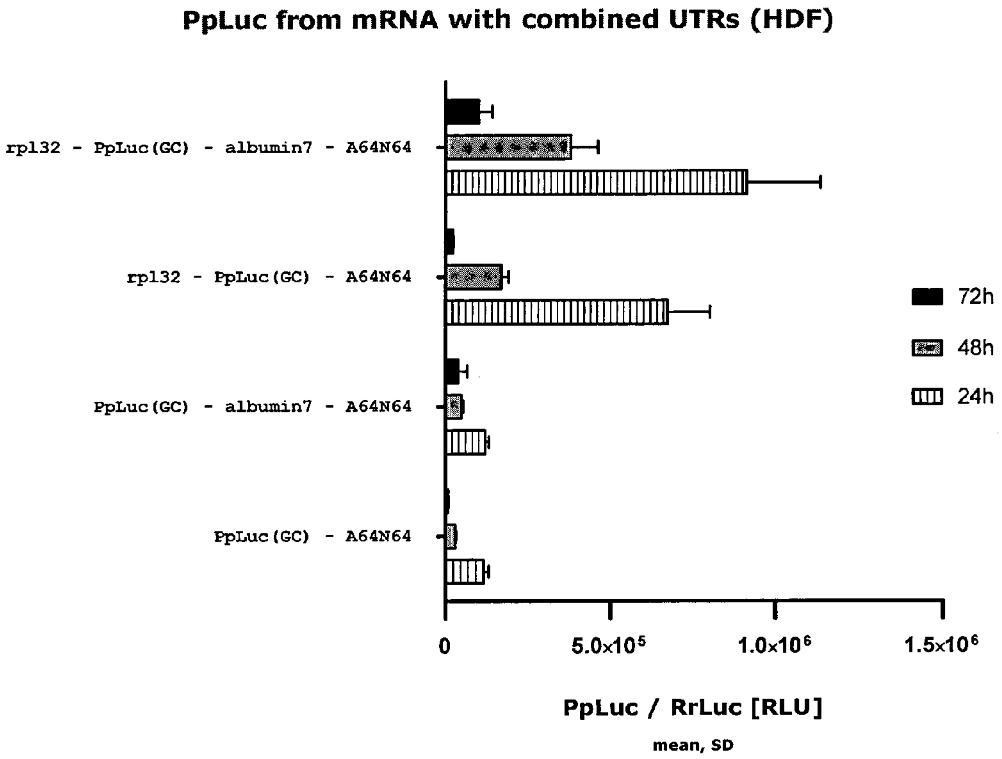

To investigate the effect of the combination of a TOP 5'UTR element and an albumin 3'UTR element on protein expression from mRNA, mRNAs with different UTRs were synthesized: mRNAs either lacked both TOP 5'UTR element and albumin 3'UTR element, or contained either a TOP 5'UTR element (RPL32) or an albumin 3'UTR element (albumin7), or both TOP 5'UTR element and albumin 3'UTR element. Luciferase encoding mRNAs or control mRNA were transfected into human dermal fibroblasts (HDF). Luciferase levels were measured at 24, 48, and 72 hours after transfection. The PpLuc signal was corrected for transfection efficiency by the signal of cotransfected RrLuc (see following Table 1 and FIG. 5).

TABLE 1

| mRNA | RLU at 24 hours | RLU at 48 hours | RLU at 72 hours |
|---|---|---|---|
| PpLuc(GC)-A64N64 | 115147 | 28973 | 8371 |
| PpLuc(GC)-albumin7-A64N64 | 120234 | 48546 | 38138 |
| RPL32-PpLuc(GC)-A64N64 | 671815 | 168741 | 21709 |
| RPL32-PpLuc(GC)-albumin7-A64N64 | 913310 | 381288 | 100890 |

Luciferase was clearly expressed from mRNA having neither TOP 5'UTR nor albumin 3'UTR (PpLuc(GC)-A64N64). The albumin 3'UTR element extended luciferase expression, while the TOP 5'UTR element increased luciferase levels compared to mRNA lacking 5'- and 3'UTR elements. Strikingly however, the combination of TOP 5'UTR element and albumin 3'UTR element further strongly increased the luciferase level, much above the level observed with either of the individual elements. The magnitude of the rise in luciferase level due to combining TOP 5'UTR element and albumin 3'UTR element in the same mRNA demonstrates that they are acting synergistically.

The synergy between TOP 5'UTR element and albumin 3'UTR element was quantified by dividing the signal from mRNA combining both elements by the sum of the signal from mRNA lacking both elements plus the rise in signal effected by the TOP 5'UTR element plus the rise in signal effected by the albumin 3'UTR element. This calculation was performed for the three time points individually and for total protein expressed from 0 to 72 hours calculated from the area under the curve (AUC) (see following Table 2).

TABLE 2

| RPL32 | albumin | RLU | Δ RLU | RLU predicted (additive) | synergy |
|---|---|---|---|---|---|
| | | 24 h | | | |
| − | − | 115147 | | | |
| − | + | 120234 | 5088 | | |
| + | − | 671815 | 556668 | | |
| + | + | 913310 | | 676903 | 1.35 |
| | | 48 h | | | |
| − | − | 28973 | | | |
| − | + | 48546 | 19573 | | |
| + | − | 168741 | 139768 | | |
| + | + | 381288 | | 188313 | 2.02 |
| | | 72 h | | | |
| − | − | 8371 | | | |
| − | + | 38138 | 29767 | | |
| + | − | 21709 | 13338 | | |
| + | + | 100890 | | 51476 | 1.96 |
| | | AUC 0-72 hours | | | |
| − | − | 3559000 | | | |
| − | + | 4508000 | 949000 | | |
| + | − | 20430000 | 16871000 | | |
| + | + | 32280000 | | 21379000 | 1.51 |

The synergy thus calculated specifies how much higher the luciferase level from mRNA combining TOP 5'UTR element and albumin 3'UTR element is than would be expected if the effects of TOP 5'UTR element and albumin 3'UTR element were purely additive. The luciferase level from mRNA combining TOP 5'UTR element and albumin 3'UTR element was up to two times higher than if their effects were purely additive. This result confirms that the combination of TOP 5'UTR element and albumin 3'UTR element effects a markedly synergistic increase in protein expression.

5.2 TOP 5'UTR Elements Increase Protein Expression from mRNA.

To investigate the effect of TOP 5'UTR elements on protein expression from mRNA, mRNAs comprising different TOP 5'UTR elements were synthesized. In addition, mRNAs contained the albumin7 3'UTR element. Luciferase encoding mRNAs were transfected into human dermal fibroblasts (HDF). Luciferase levels were measured at 24, 48, and 72 hours after transfection (see following Table 3 and FIG. 22).

TABLE 3

| 5'UTR | RLU at 24 hours | RLU at 48 hours | RLU at 72 hours |
|---|---|---|---|
| none | 114277 | 121852 | 68235 |
| RPL32 | 332236 | 286792 | 114148 |
| RPL35 | 495917 | 234070 | 96993 |
| RPL21 | 563314 | 352241 | 156605 |
| atp5a1 | 1000253 | 538287 | 187159 |
| HSD17B4 | 1179847 | 636877 | 299337 |
| AIG1 | 620315 | 446621 | 167846 |
| COX6C | 592190 | 806065 | 173743 |
| ASAH1 | 820413 | 529901 | 198429 |

Luciferase was clearly expressed from mRNA lacking a 5'UTR element. Strikingly however, all TOP 5'UTR elements strongly increased the luciferase level.

5.3 the Combination of TOP 5'UTR Elements and Albumin 3'UTR Element Increases Protein Expression from mRNA in a Synergistic Manner.

To investigate the effect of the combination of TOP 5'UTR elements and an albumin 3'UTR element on protein expression from mRNA, mRNAs comprising different UTR elements were synthesized: mRNAs either lacked both TOP 5'UTR element and albumin 3'UTR element, or contained an albumin 3'UTR element, or contained one of different TOP 5'UTR elements, or contained both one of different TOP 5'UTR elements and an albumin 3'UTR element. Luciferase encoding mRNAs were transfected into human dermal fibroblasts (HDF). Luciferase levels were measured at 24, 48, and 72 hours after transfection (see FIGS. 23 to 30). Luciferase was clearly expressed from mRNA having neither a TOP 5'UTR element nor an albumin 3'UTR element. The albumin 3'UTR element extended luciferase expression, while TOP 5'UTR elements increased luciferase levels compared to mRNA lacking 5' and 3'UTRs. Strikingly however, the combinations of TOP 5'UTR elements and albumin 3'UTR element further strongly increased the luciferase level, much above the level observed with either of the individual elements. The magnitude of the rise in luciferase level due to combining TOP 5'UTR element and albumin 3'UTR element in the same mRNA demonstrates that they are acting synergistically.

The synergy between TOP 5'UTR element and albumin 3'UTR element was quantified by dividing the signal from mRNA combining both elements by the sum of the signal from mRNA lacking both elements plus the rise in signal effected by the TOP 5'UTR element plus the rise in signal effected by the albumin 3'UTR element. This calculation was performed for total protein expressed from 0 to 72 hours calculated from the area under the curve (AUC) (see following Table 4).

TABLE 4

| TOP 5'UTR | Synergy with albumin 3'UTR |
|---|---|
| RPL35 | 2.25 |
| RPL21 | 1.30 |
| atp5a1 | 3.19 |
| HSD17B4 | 2.18 |
| AIG1 | 2.03 |
| COX6C | 1.56 |
| ASAH1 | 1.84 |

The synergy thus calculated specifies how much higher the luciferase level from mRNA combining TOP 5'UTR elements and albumin 3'UTR element is than would be expected if the effects of TOP 5'UTR element and albumin 3'UTR element were purely additive. The luciferase level from mRNA combining TOP 5'UTR element and albumin 3'UTR element was up to three times higher than if their effects were purely additive. This result confirms that the combination of TOP 5'UTR element and albumin 3'UTR element effects a markedly synergistic increase in protein expression.

5.4 TOP 5'UTR Elements from Mouse Genes Increase Protein Expression from mRNA.

To investigate the effect of TOP 5'UTR elements from mouse genes on protein expression from mRNA, mRNAs with two different mouse TOP 5'UTR elements were synthesized. In addition, mRNAs contained the albumin7 3'UTR element. Luciferase encoding mRNAs were transfected into human dermal fibroblasts (HDF). For comparison, mRNA containing the human RPL32 TOP 5'UTR element was transfected. Luciferase levels were measured at 24, 48, and 72 hours after transfection (see following Table 5 and FIG. 30).

TABLE 5

| 5'UTR | RLU at 24 hours | RLU at 48 hours | RLU at 72 hours |
|---|---|---|---|
| none | 114277 | 121852 | 68235 |
| 32L | 332236 | 286792 | 114148 |
| m21L | 798233 | 351894 | 139249 |
| m35AL | 838609 | 466236 | 174949 |

Luciferase was clearly expressed from mRNA lacking a 5'UTR element. Both mouse TOP 5'UTR elements strongly increased the luciferase level, similarly as the human TOP 5'UTR element.

SEQUENCES:

*Homo sapiens* alpha-2-macroglobulin (A2M): gctccttctttctgcaacatg (Seq ID No: 1)

Homo sapiens acyl-CoA dehydrogenase, C-4 to C-12 straight chain (ACADM):
ggctctctttccgcgctgcggtcagcctcggcgtcccacagagagggccagaggtggaaacgcaga
aaaccaaaccaggactatcagagattgcccggagaggggatg (Seq ID No: 2)

*Homo sapiens* arylsulfatase E (chondrodysplasia punctata 1) (ARSE):
cttcctcttcttgatcggggattcaggaaggagcccaggagcagaggaagtagagagagagacaac
atg (Seq ID No: 3)

*Homo sapiens* Bruton agammaglobulinemia tyrosine kinase (BTK):
tgtccttcctctctggactgtaagaatatgtctccagggccagtgtctgctgcgatcgagtcccac
cttccaagtcctggcatctcaatgcatctgggaagctacctgcattaagtcaggactgagcacaca
ggtgaactccagaaagaagaagctatg (Seq ID No: 4)

-continued

| SEQUENCES: |
|---|
| *Homo sapiens* complement component 2 (C2): tgaccttttccctcccgcggctctctacctctcgccgcccctagggaggacaccatg (Seq ID No: 5) |
| *Homo sapiens* cyclin-dependent kinase 4 (CDK4): gggcctctctagcttgcggcctgtgtctatggtcgggccctctgcgtccagctgctccggaccgag ctcgggtgtatggggccgtaggaaccggctccggggccccgataacgggccgcccccacagcaccc cgggctggcgtgagggtctcccttgatctgagaatg (Seq ID No: 6) |
| *Homo sapiens* cytochrome P450, family 17, subfamily A, polypeptide 1 (CYP17A1): agctcttctactccactgctgtctatcttgcctgccggcacccagccaccatg (Seq ID No: 7) |
| *Homo sapiens* endoglin (ENG): cttcctctacccggttggcaggcggcctggcccagccccttctctaaggaagcgcatttcctgcct ccctgggccggccgggctggatg (Seq ID No: 8) |
| *Homo sapiens* excision repair cross-complementing rodent repair deficiency, complementation group 3 (ERCC3): tcttctctctgctgctgtagctgccatg (Seq ID No: 9) |
| *Homo sapiens* excision repair cross-complementing rodent repair deficiency, complementation group 5 (ERCC5): ctgtctttcttccgggaggcggtgacagctgctgagacgtgttgcagccagagtctctccgcttta atgcgctcccattagtgccgtcccccactggaaaaccgtggcttctgtattatttgccatctttgt tgtgtaggagcagggagggcttcctcccggggtcctaggcggcggtgcagtccgtcgtagaagaat tagagtagaagttgtcggggtccgctcttaggacgcagccgcctcatg (Seq ID No: 10) |
| *Homo sapiens* ferritin, light polypeptide (FTL): cgtcccctcgcagttcggcggtcccgcgggtctgtctcttgcttcaacagtgtttggacggaacag atccggggactctcttccagcctccgaccgccctccgatttcctctccgcttgcaacctccgggac catcttctcggccatctcctgcttctgggacctgccagcaccgtttttgtggttagctccttcttg ccaaccaaccatg (Seq ID No: 11) |
| *Homo sapiens* galactosylceramidase (GALC): ccgcctccctgggcgccggagtcatgtgacccacacaatg (Seq ID No: 12) |
| *Homo sapiens* gap junction protein, alpha 1, 43 kDa (GJA1): ttttctttcattagggggaaggcgtgaggaaagtaccaaacagcagcggagttttaaactttaaat agacaggtctgagtgcctgaacttgccttttcattttacttcatcctccaaggagttcaatcactt ggcgtgacttcactacttttaagcaaaagagtggtgcccaggcaacatg (Seq ID No: 13) |
| *Homo sapiens* gap junction protein, beta 1, 32 kDa (GJB1): cattctctgggaaagggcagcagcagccaggtgtggcagtgacagggaggtgtgaatgaggcagga tg (Seq ID No: 14) |
| *Homo sapiens* glucose-6-phosphate isomerase (GPI): cgctccttcctcctcggctcgcgtctcactcagtgtaccttctagtcccgccatg (Seq ID No: 15) |
| *Homo sapiens* hydroxyacyl-CoA dehydrogenase/3-ketoacyl-CoA thiolase/ enoyl-CoA hydratase (trifunctional protein), alpha subunit (HADHA): ctgtcctcttcagctcaagatg (Seq ID No: 16) |
| *Homo sapiens* hydroxyacyl-CoA dehydrogenase/3-ketoacyl-CoA thiolase/ enoyl-CoA hydratase (trifunctional protein), beta subunit (HADHB): gggccctttctgggcaggacccgccccttggtcccgcagagccttggtacttggacctgaaccttg ctccgagagggagtcctcgcggacgtcagccaagattccagaatg (Seq ID No: 17) |
| *Homo sapiens* complement factor H (CFH): cttccttttgcagcaagttctttcctgcactaatcacaattcttggaagaggagaactggacgttg tgaacagagttagctggtaaatgtcctcttaaaagatccaaaaaatg (Seq ID No: 18) |
| *Homo sapiens* sarcoglycan, gamma (35 kDa dystrophin-associated glycoprotein) (SGCG): agccctttctccagggacagttgctgaagcttcatcctttgctctcattctgtaagtcatagaaaa gtttgaaacattctgtctgtggtagagctcgggccagctgtagttcattcgccagtgtgcttttct taatatctaagatg (Seq ID No: 19) |
| *Homo sapiens* lipase A, lysosomal acid, cholesterol esterase (LIPA): ggtcccctatccgcaccccggcccctgagagctggcactgcgactcgagacagcggcccggcagga cagctccagaatg (Seq ID No: 20) |

-continued

| SEQUENCES: |
|---|
| *Homo sapiens* lipoprotein lipase (LPL):<br>cccccctcttcctcctcctcaagggaaagctgcccacttctagctgccctgccatcccctttaaagg<br>gcgacttgctcagcgccaaaccgcggctccagccctctccagcctccggctcagccggctcatcag<br>tcggtccgcgccttgcagctcctccagagggacgcgccccgagatg (Seq ID No: 21) |
| *Homo sapiens* mutL homolog 1, colon cancer, nonpolyposis type 2<br>(*E. coli*) (MLH1): ggctcttctggcgccaaaatg (Seq ID No: 22) |
| *Homo sapiens* Niemann-Pick disease, type C1 (NPC1):<br>cttccttcctgaccggcgcgcgcagcctgctgccgcggtcagcgcctgctcctgctcctccgctcc<br>tcctgcgcggggtgctgaaacagcccggggaagtagagccgcctccggggagcccaaccagccgaa<br>cgccgccggcgtcagcagccttgcgcggccacagcatg (Seq ID No: 23) |
| *Homo sapiens* peroxisomal biogenesis factor 12 (PEX12):<br>gcgcctctcttccgccaggcatcccagaggtcctggtggtttcatttccgggtgcggcttctgtca<br>taaagcggagacctcccttcaaacgtggcgtcgtgggttgtttgcgcctcgcctggggtcagcgag<br>caaggacgggcgcgggcggggatactcaaagccaacagctggagtcagcccttgtgtcccgggctc<br>acagtggcacgactgaatcctcagagtcggctggcttttgagctctcacgattggggaggaggggg<br>cgtttctggttcgcagctccagaggattgcgttccttcccccatacctgtcccccacagtcacgct<br>ctgccctgacgtgcagcatttgacaagttacccccctcgccacatactacttccacccacgtccgag<br>ttaactttgttcttaaccttcttgagactaccctcggcctccaggtctttttttcccagttcattt<br>ttgcccataagattgagtttcgagtttcagatatcatgcagaaagtttacctttaagactgagcac<br>ccatctgatactcttcctcccgaaaaagttcatgctcacgagagagtttgtgggaaaagtgaaagc<br>cagtacacgcaggaaactatg (Seq ID No: 24) |
| *Homo sapiens* peroxisomal biogenesis factor 6 (PEX6):<br>cgctccttcaccctcctcgttggtgtcctgtcaccatg (Seq ID No: 25) |
| *Homo sapiens* phosphofructokinase, muscle (PFKM):<br>gagccttcttgtcagcatctgttagtggaggttgggaagcctctcctccttccccctccctctttg<br>cctccacctggctcctccccatgttcgtccatcaccccctccccccttttcccaaggacaatctgcaa<br>gaaagcagcggcggaggagagctaagactaaaagagtggatcatg (Seq ID No: 26) |
| *Homo sapiens* serpin peptidase inhibitor, clade A (alpha-<br>1 antiproteinase, antitrypsin), member 1 (SERPINA1):<br>ctgtctcctcagcttcaggcaccaccactgacctgggacagtgaatcgacaatg<br>(Seq ID No: 27) |
| *Homo sapiens* phosphatase and tensin homolog (PTEN):<br>agttctctcctctcggaagctgcagccatgatggaagtttgagagttgagccgctgtgaggcgagg<br>ccgggctcaggcgagggagatgagagacggcggcggccgcggcccggagcccctctcagcgcctgt<br>gagcagccgcgggggcagcgccctcggggagccggccggcctgcggcggcggcagcggcggcgttt<br>ctcgcctcctcttcgtcttttctaaccgtgcagcctcttcctcggcttctcctgaaagggaaggtg<br>gaagccgtgggctcgggcgggagccggctgaggcgcggcggcggcggcggcacctcccgctcctgg<br>agcgggggggagaagcggcggcggcggcggccgcggcggctgcagctccagggagggggtctgagt<br>cgcctgtcaccatttccagggctgggaacgccggagagttggtctctccccttctactgcctccaa<br>cacggcggcggcggcggcggcacatccagggacccgggccggttttaaacctcccgtccgccgccg<br>ccgcaccccccgtggcccgggctccggaggccgccggcggaggcagccgttcggaggattattcgt<br>cttctccccattccgctgccgccgctgccaggcctctggctgctgaggagaagcaggcccagtcgc<br>tgcaaccatccagcagccgccgcagcagccattacccggctgcggtccagagccaagcggcggcag<br>agcgaggggcatcagctaccgccaagtccagagccatttccatcctgcagaagaagccccgccacc<br>agcagcttctgccatctctctcctcctttttcttcagccacaggctcccagacatg<br>(Seq ID No: 28) |
| *Homo sapiens* solute carrier family 3<br>(cystine, dibasic and neutral amino acid transporters, activator of<br>cystine, dibasic and neutral amino acid transport), member 1<br>(SLC3A1): cctcccttactgcaggaaggcactccgaagacataagtcggtgagacatg<br>(Seq ID No: 29) |
| *Homo sapiens* aldehyde dehydrogenase 3 family, member A2 (ALDH3A2):<br>ccgcctcccactccccagcgcccccggaccgtgcagttctctgcaggaccaggccatg<br>(Seq ID No: 30) |
| *Homo sapiens* bleomycin hydrolase (BLMH):<br>gtttctcccagcctcagcctccccgccgccgccgccgccgccgccgagccggtttcctttttc<br>cggcgctccgggtgcgagagacaggtcgggccccctaggcagcgagccgcagcgcaatcccggcgc<br>tcgcccaaggaccctggaagctaccgttaccccgccgggcagcgtgggcgccatg<br>(Seq ID No: 31) |
| *Homo sapiens* cathepsin K (CTSK):<br>cctcctcctcttacccaaattttccagccgatcactggagctgacttccgcaatcccgatggaata<br>aatctagcacccctgatggtgtgcccacactttgctgccgaaacgaagccagacaacagatttcca<br>tcagcaggatg (Seq ID No: 32) |

-continued

| SEQUENCES: |
|---|

*Homo sapiens* GM2 ganglioside activator (GM2A):
gcttctttgcgtaaccaatactggaaggcatttaaaggcacctctgccgccacagaccttgcagtt
aactccgccctgacccacccttcccgatg (Seq ID No: 33)

*Homo sapiens* hydroxysteroid (17-beta) dehydrogenase 4 (HSD17B4):
ccgcctcctcctgtcccgcagtcggcgtccagcggctctgcttgttcgtgtgtgtgtcgttgcagg
ccttattcatg (Seq ID No: 34)

*Homo sapiens* neutrophil cytosolic factor 2 (NCF2):
ctctctctgcttctttcctttttctctctcatggtagggttatgagtcagttgccaaaaggtgggga
catttcctgatgcatttgcaacactgagaagttatcttaagggaggctgggccccattctactcat
ctggcccagaaagtgaacaccttgggggccactaaggcagccctgctaggggagacgctccaacct
gtcttctctctgtctcctggcagctctcttggcctcctagtttctacctaatcatg
(Seq ID No: 35)

*Homo sapiens* 3-oxoacid CoA transferase 1 (OXCT1):
cagcctcctcctgcctcaccgcccgaagatg (Seq ID No: 36)

*Homo sapiens* sulfite oxidase (SUOX):
ccgccccttctcgagaactcgcagagctgggctggtaaaattgcagtgctgaagacactggacccg
caaaaggctgtccctcccaaacctgggattctgggctcactgagttcacctgcgagtcagccctac
ctgcactgctctggtctagtacaaacaggctgctggcattgagggacggagtctccaactcctggc
ctctagcagtcctcctgtgtaggtctcccaaagtgctagtgtgtccggaattggtgggttcttggt
ctcactgacttcaagaatgaagccgcggaccctcgcagtctgctacaatg (Seq ID No: 37)

*Homo sapiens* albumin (ALB): ttttctcttctgtcaaccccacacgcctttggca-
caatg (Seq ID No: 38)

*Homo sapiens* arylsulfatase A (ARSA):
ctccctctagcgccttccccccggcccgactccgctggtcagcgccaagtgacttacgcccccgac
cctgagcccggaccgctaggcgaggaggatcagatctccgctcgagaatctgaaggtgccctggtc
ctggaggagttccgtcccagcccgcggtctcccggtactgtcgggccccggccctctggagcttca
ggaggcggccgtcagggtcggggagtatttgggtccggggtctcagggaagggcggcgcctgggtc
tgcggtatcggaaagagcctgctggagccaagtagccctccctctcttgggacagacccctcggtc
ccatg (Seq ID No: 39)

*Homo sapiens* elastin (ELN):
ctccctccctctttccctcacagccgacgaggcaacaattaggctttggggataaaacgaggtgcg
gagagcgggctggggcatttctccccgagatg (Seq ID No: 40)

*Homo sapiens* hemoglobin, alpha 2 (HBA2): cactcttctggtccccaca-
gactcagagagaacccaccatg (Seq ID No: 41)

*Homo sapiens* hexosaminidase B (beta polypeptide) (HEXB):
cttcctctgatccgggccgggcgggaagtcgggtcccgaggctccggctcggcagaccgggcggaa
agcagccgagcggccatg (Seq ID No: 42)

*Homo sapiens* mannosidase, alpha, class 2B, member 1 (MAN2B1):
cggcctttccagggccggggaaccccaggaggaagctgctgagccatg (Seq ID No: 43)

*Homo sapiens* recombination activating gene 2 (RAG2):
cactctctttacagtcagccttctgcttgccacagtcatagtgggcagtcagtgaatcttccccaa
gtgctgacaattaatacctggtttagcggcaaagattcagagaggcgtgagcagcccctctggcct
tcagacaaaaatctacgtaccatcagaaactatg (Seq ID No: 44)

*Homo sapiens* CD53 molecule (CD53):
tctccttttacacaaatagccccggatatctgtgttaccagccttgtctcggccacctcaaggata
atcactaaattctgccgaaaggactgaggaacggtgcctggaaaagggcaagaatatcacggcatg
(Seq ID No: 45)

*Homo sapiens* Fc fragment of IgG, low affinity IIIa, receptor
(CD16a) (FCGR3A): tggtccctttagggctccggatatctttggtgacttgtccactccag-
tgtggcatcatg (Seq ID No: 46)

*Homo sapiens* interleukin 1, beta (IL1B):
aaacctcttcgaggcacaaggcacaacaggctgctctgggattctcttcagccaatcttcattgct
caagtgtctgaagcagccatg (Seq ID No: 47)

*Homo sapiens* CD4 molecule (CD4):
ctgtctctcttcatttaagcacgactctgcagaaggaacaaagcaccctccccactgggctcctgg
ttgcagagctccaagtcctcacacagatacgcctgtttgagaagcagcgggcaagaaagacgcaag
cccagaggccctgccatttctgtgggctcaggtccctactggctcaggcccctgcctccctcggca
aggccacaatg (Seq ID No: 48)

-continued

| SEQUENCES: |
|---|

*Homo sapiens* serpin peptidase inhibitor, clade A (alpha-1 antiproteinase, antitrypsin), member 5 (SERPINA5):
agccctctgccctttctgagcccgagggactgccacctccactgtgtgcacactcagctacgggac
acatttcaggtatccaaggcagcagaggtgagtgggtcccccgagctctgtgaccttatgctccac
actaactctggcagagcctccgtttcctcatagaacaaagaacagccaccatg
(Seq ID No: 49)

*Homo sapiens* vitronectin (VTN):
tgccctccttccctgtctctgcctctccctcccttcctcaggcatcagagcggagacttcagggag
accagagcccagcttgccaggcactgagctagaagccctgccatg (Seq ID No: 50)

*Homo sapiens* aldehyde dehydrogenase 9 family, member A1 (ALDH9A1):
ccgcccctcccgcggccccgcccctcccgcggcccgtcagcctctgccgcggagctgcgtccgcca
ctcatg (Seq ID No: 51)

*Homo sapiens* annexin A1 (ANXA1):
cttcctttaaaatcctataaaatcagaagcccaagtctccactgccagtgtgaaatcttcagagaa
gaatttctctttagttctttgcaagaaggtagagataaagacactttttcaaaaatg
(Seq ID No: 52)

*Homo sapiens* ATPase, Na+/K+ transporting, alpha 1 polypeptide
(ATP1A1): ttttctctctgattctccagcgacaggacccggcgccgggcactgagcaccgc-
caccatg (Seq ID No: 53)

Homo sapiens ATPase, Na+/K+ transporting, alpha 2 polypeptide
(ATP1A2):
ctttctctgtctgccagggtctccgactgtcccagacgggctggtgtgggcttgggatcctcctgg
tgacctctcccgctaaggtccctcagccactctgccccaagatg (Seq ID No: 54)

*Homo sapiens* calcium channel, voltage-dependent, beta 3 subunit
(CACNB3):
ccctccttcgcgctctctcgctccctgccgccgcccgcagggctgcggggctcggtggcatctccc
gggcgcggcccgcagtccttgcccctgcctccgggccgctcccgcccccggcgccgctcgctcccc
cgacccggactcccccatg (Seq ID No: 55)

*Homo sapiens* cholinergic receptor, nicotinic, alpha 7 (neuronal)
(CHRNA7):
gtgcctctgtggccgcaggcgcaggcccgggcgacagccgagacgtggagcgcgccggctcgctgc
agctccgggactcaacatg (Seq ID No: 56)

*Homo sapiens* cytochrome P450, family 51, subfamily A, polypeptide
1 (CYP51A1):
gcttctctcgttccgtcgattgggaggagcggtggcgacctcggccttcagtgtttccgacggagt
gaatg (Seq ID No: 57)

*Homo sapiens* glutamate decarboxylase 1 (brain, 67 kDa) (GAD1):
atctctctcttctcctggcgctcgcgtgcgagagggaactagcgagaacgaggaagcagctggagg
tgacgccgggcagattacgcctgtcagggccgagccgagcggatcgctgggcgctgtgcagaggaa
aggcgggagtgcccggctcgctgtcgcagagccgagcctgtttctgcgccggaccagtcgaggact
ctggacagtagaggccccgggacgaccgagctgatg (Seq ID No: 58)

*Homo sapiens* gamma-glutamyl carboxylase (GGCX):
aattctcctggcggcctccgttcagacgcggcagctgtgacccacctgcctcctccgcagagcaat
g (Seq ID No: 59)

*Homo sapiens* glutamate receptor, metabotropic 3 (GRM3):
tcccctctttccccaacctcctccctctcttctactccacccctccgttttcccactccccactga
ctcggatgcctggatgttctgccaccgggcagtggtccagcgtgcagccgggagggggcaggggca
gggggcactgtgacaggaagctgcgcgcacaagttggccatttcgagggcaaaataagttctccct
tggatttggaaaggacaaagccagtaagctacctcttttgtgtcggatgaggaggaccaaccatga
gccagagcccgggtgcaggctcaccgccgccgctgccaccgcggtcagctccagttcctgccagga
gttgtcggtgcgaggaattttgtgacaggctctgttagtctgttcctcccttatttgaaggacagg
ccaaagatccagtttggaaatgagagaggactagcatgacacattggctccaccattgatatctcc
cagaggtacagaaacaggattcatgaagatg (Seq ID No: 60)

*Homo sapiens* guanylate cyclase 1, soluble, alpha 3 (GUCY1A3):
ggttcctttggggtgatcaaagagggagacacagacacagagagacaaaggcaaggaggactgtct
gggagccacgcgggcgatacagtttccgaggcacgccgcgtcccgcctagcctgttgaacaggtag
acatgagcgacccaagctgcggatttgcgaggcgcgccctggagctgctagagatccggaagcaca
gccccgaggtgtgcgaagccaccaagtcaagttcctaacgagtcttcagaggaggcagcaggaagc
tcagagagctgcaaagcaaccgtgcccatctgtcaagacattcctgagaagaacatacaagaaagt
cttcctcaaagaaaaaccagtcggagccgagtctatcttcacactttggcagagagtatttgcaaa
ctgattttcccagagtttgaacggctgaatgttgcacttcagagaacattggcaaagcacaaaata
aaagaaagcaggaaatctttggaaagagaagactttgaaaaaacaattgcagagcaagcagttgca
gcaggagttccagtggaggttatcaaagaatctcttggtgaagaggtttttaaaatatgttacgag
gaagatgaaaacatccttggggtggttggaggcaccccttaaagatttttaaacagcttcagtacc
cttctgaaacagagcagccattgccaagaagcaggaaaaaggggcaggcttgaggacgcctccatt -continued

SEQUENCES:

ctatgcctggataaggaggatgattttctacatgtttactacttcttccctaagagaaccacctcc
ctgattcttcccggcatcataaaggcagctgctcacgtattatatgaaacggaagtggaagtgtcg
ttaatg (Seq ID No: 61)

*Homo sapiens* 3-hydroxy-3-methylglutaryl-CoA reductase (HMGCR):
ggctccttccgctccgcgactgcgttaactggagccaggctgagcgtcggcgccggggttcggtgg
cctctagtgagatctggaggatccaaggattctgtagctacaatg (Seq ID No: 62)

*Homo sapiens* IMP (inosine 5'-monophosphate) dehydrogenase 2
(IMPDH2): aggtctctgcggcgcggtcctcggagacacgcggcggtgtcctgtgttggccatg
(Seq ID No: 63)

*Homo sapiens* leukotriene A4 hydrolase (LTA4H):
acttcctttcccggcgtgcaccgcgaatccctcctcctcttctttacctctctccctcctcctcag
gttctctatcgacgagtctggtagctgagcgttgggctgtaggtcgctgtgctgtgtgatccccca
gagccatg (Seq ID No: 64)

*Homo sapiens* neuropeptide Y receptor Y1 (NPY1R):
ccttctttaataagcaggagcgaaaaagacaaattccaaagaggattgttcagttcaagggaatga
agaattcagaataattttggtaaatggattccaatatggggaataagaataagctgaacagttgac
ctgctttgaagaaacatactgtccatttgtctaaaataatctataacaaccaaaccaatcaaaatg
(Seq ID No: 65)

*Homo sapiens* pyruvate dehydrogenase (lipoamide) beta (PDHB):
cggcccctctgttgtcgtttggcagcggatagaggacacgaccaagatg (Seq ID No: 66)

*Homo sapiens* ribosomal protein L36a-like (RPL36AL):
cttccctttcctgttaggcgagagctgcgaaaggcgagagctgcgaagggccaggtgtcgggcgct
gtttctcgttttcatcatatagacaaaacagccctgctgcaaagatg (Seq ID No: 67)

*Homo sapiens* ATPase, Ca++ transporting, type 2C, member 1
(ATP2C1):
gcttcttctcacgccgggagcaggctcccgcctcgcaccgctgccccgcgagcagctcctcttctc
ccgaggcgcgcggggcgcccccgcgagccccgcggctgagaccccgcagcctggaggagggctgtc
cggggctttggatgctgctgctaggggtggtgggagcagccgtgggacgcgtggccgggagcgggg
gtgacagcctgggattccgggggcttctcttccttgtcctcctcctctcctctctattcccagtgt
ggccgtggctgacactaaagactttgtagccatcaacccgagtgcagtttcgatggaaaatg
(Seq ID No: 68)

*Homo sapiens* UDP-glucose pyrophosphorylase 2 (UGP2):
ccgcctctttcattgaagaaatttaagttcgtgtggttttaccttttccgggagtctccagctggc
cctcatttgtgtccggagctcaggagttcccaaaccgactcagtcgcaccaagtttccgtcttttg
gaattggggaaggagtttctttctttcttttctttttcttgagccagttttaatcgctttgaata
aatactcccttaagtagttaaatataggaggagaaagaatacatcggttgttaaagcaggagagga
agagagacctgccctgtagcgtgactcctctagaaaaaaaaaaaaaaaagccggagtattttactaa
gcccctaaaatg (Seq ID No: 69)

*Homo sapiens* ATPase, Na+/K+ transporting, beta 1 polypeptide
(ATP1B1):
cctcctcctgctcctgccttggctcctccgccgcgcgtctcgcactccgagagccgcagcggcagc
ggcgcgtcctgcctgcagagagccaggccggagaagccgagcggcgcagaggacgccagggcgcgc
gccgcagccacccaccctccggaccgcggcagctgctgacccgccatcgccatg
(Seq ID No: 70)

*Homo sapiens* glycoprotein M6B (GPM6B):
ctgtctttatggaccagtaggcagagcgaaattgacgctgacaagacttttgcatcttggaaggga
ctgtaatctactgtagtgaagaacagagcctctcaatcagacgggtgtaaataagagacggagggg
agtccaaaagaaaaggaagaggaggaaaaacaagtgtgtgttgggggggaacaggggggaaaagcatt
tttggtggatggtatg (Seq ID No: 71)

*Homo sapiens* wntless homolog (*Drosophila*) (WLS):
gctcctttaagcgtccacaggcggcggagcggccacaatcacagctccgggcattgggggaacccg
agccggctgcgccgggggaatccgtgcgggcgccttccgtcccggtcccatcctcgccgcgctcca
gcacctctgaagttttgcagcgcccagaaaggaggcgaggaaggagggagtgtgtgagaggaggga
gcaaaaagctcaccctaaaacatttatttcaaggagaaaagaaaaaggggggggcgcaaaaatg
(Seq ID No: 72)

*Homo sapiens* flavin containing monooxygenase 3 (FM03):
ttttctctttcaaactgcccagacggttggacaggacgtagacacacagaagaaaagaagacaaag
aacgggtaggaaaattaaaaaggttaccatg (Seq ID No: 73)

*Homo sapiens* multiple C2 domains, transmembrane 1 (MCTP1):
cagcctcttttgccggtattcagtgaagaaagcaagtctaaatatgcagttctctcactggagtga
aagatgttttgttcatttctaatcaactatg (Seq ID No: 74)

-continued

SEQUENCES:

*Homo sapiens* structural maintenance of chromosomes 4 (SMC4):
ccgcctctcggcgagcccgccctcttctgaagaggcgtttctggaccactgagccccgcctcccac
tgtgagcggaaccctaccgttttaaaaaaatctttttcaaacttgccaggttgtctttccaaat
atttttaataatagtgctgctgctgtagaccacagagaaaagaatccctcgctcttccttttcact
tagtagaaacttctaccgcgtaggtcccgccaggagttcgcgcatgcgcaggagcgacaataagat
ggcggtgataatcgccgcactttttttcaaattagtggatcccagaaatcattgcgcgcatttgta
acgaatttccgttcgagtttgtattttaggcgccattttcgagtgaaggacccggagccgaaacac
cggtaggagcggggaggtgggtactacacaaccgtctccagccttggtctgagtggactgtcctgc
agcgaccatg (Seq ID No: 75)

*Homo sapiens* GLE1 RNA export mediator homolog (yeast) (GLE1):
tggccttcccggcggctgattcgagggcttgtttggtcagaagggggcgtcagagaagctgcccc
ttagccaaccatg (Seq ID No: 76)

*Homo sapiens* tripartite motif containing 6 (TRIM6):
gagtctttcggcctgggtggaggacgcggctgcttcaagtccttggctctgatccaggccacagat
tccaggattctacaggcaggaaacatcttagaaatcagggttgggcaggcaggagccaggagagta
gctacaatg (Seq ID No: 77)

*Homo sapiens* ecotropic viral integration site 2A (EVI2A):
tatcctttttttactgcagatttactttaaggctcatattctccaagtctattctgctttaaaaaga
agacaagaaaagaagtggtttatcaaaatcacgttataatcagattttgaccaagcattttgtaag
tatacaaatgtcagccaatgacatataacaaccatttcttataaaaccttgatgttcaaaagcctg
actagcagtggcatccatg (Seq ID No: 78)

*Homo sapiens* heterogeneous nuclear ribonucleoprotein L (HNRNPL):
tgctcttttcgatccgggacggccggtcaggctcgccgccgagctggagaactacgatgacccgca
caaaacccctgcctccccagttgtccacatcaggggcctgattgacggtgtggtggaagcagacct
tgtggaggccttgcaggagtttggacccatcagctatgtggtggtaatg (Seq ID No: 79)

*Homo sapiens* mitochondrial translational initiation factor 2
(MTIF2):
cattcttccgggtccagaaggtgatctccgcccgtgctcagaatccaggggcccggggctgtagat
tccttgacaaggatatcctagcggcgaaacaacaccgtactgggagtcagaacgtctgggttctag
tcttgactgccattaactagcggtatgacattggagaagctttttttgacccttctggatttccgtt
tcctttttctgtaaaatgaggagcttggaagatccggaaaatgaggcccataggaaacaagtgactt
gctgagtccagataacactgactgtcagagagaaacatg (Seq ID No: 80)

*Homo sapiens* nuclear factor of kappa light polypeptide gene enhancer
in B-cells inhibitor, zeta (NFKBIZ):
tggcctcctcttgccacgaggtcagacggcgagttcttagagaaaaaggctgcttagctgctgctt
atcatgtaacctcaaaaggaaactgatcgtctttctcatgctgtcacgtacttgggttattatcgc
tgattacagctggaaacaattgatttgctcttacgtatttgtgtgacttgactcttcaaacacaaa
ggttaacaggaagatctcgagggccctggctgaacttcaccttttggctttcttggcctgatgctg
aactctcgaggttgagccccatatg (Seq ID No: 81)

*Homo sapiens* v-erb-b2 erythroblastic leukemia viral oncogene homolog
3 (avian) (ERBB3):
atccctccccggactccggctccggctccgattgcaatttgcaacctccgctgccgtcgccgcagc
agccaccaattcgccagcggttcaggtggctcttgcctcgatgtcctagcctaggggcccccgggc
cggacttggctgggctcccttcaccctctgcggagtcatg (Seq ID No: 82)

*Homo sapiens* podoplanin (PDPN): ccgcctcctcgggagagataaatg
(Seq ID No: 83)

*Homo sapiens* ribonucleotide reductase M1 (RRM1):
gcgcccctttgtgcgtcacgggtggcgggcgcgggaaggggatttggattgttgcgcctctgctct
gaagaaagtgctgtctggctccaactccagttctttcccctgagcagcgcctggaacctaaccctt
cccactctgtcaccttctcgatcccgccggcgctttagagccgcagtccagtcttggatccttcag
agcctcagccactagctgcgatg (Seq ID No: 84)

*Homo sapiens* solute carrier family 2 (facilitated
glucose transporter), member 4 (SLC2A4):
gcgtcttttcccccagccccgctccaccagatccgcgggagccccactgctctccgggtccttggc
ttgtggctgtgggtcccatcgggcccgccctcgcacgtcactccgggacccccgcggcctccgcag
gttctgcgctccaggccggagtcagagactccaggatcggttctttcatcttcgccgcccctgcgc
gtccagctcttctaagacgagatg (Seq ID No: 85)

*Homo sapiens* steroid-5-alpha-reductase, alpha polypeptide 1
(3-oxo-5 alpha-steroid delta 4-dehydrogenase alpha 1) (SRD5A1):
aaccctttctgcagagtcccggcagtgcgggactccggtagccgcccctccggtagccgcccctcc
tgcccccgcgccgccgccctatatgttgcccgccgcggcctctggggcatggagcacgctgcccag
ccctggcgatg (Seq ID No: 86)

*Homo sapiens* thromboxane A synthase 1 (platelet) (TBXAS1):
gttccctttttctacctgcagagcacggttcccataagggcggcgagatcagcctcctgtctcatct
ggaagaccaccactctggggtctcagaggaatg (Seq ID No: 87)

-continued

SEQUENCES:

*Homo sapiens* transketolase (TKT):
ctatctctgtgtgtccgcgtgtgcgcccggtccccgcctgccgcaccatg (Seq ID No: 88)

*Homo sapiens* tumor necrosis factor receptor superfamily, member 1A (TNFRSF1A):
cctcctcctccagctcttcctgtcccgctgttgcaacactgcctcactcttcccctcccaccttct
ctcccctcctctctgctttaattttctcagaattctctggactgaggctccagttctggcctttgg
ggttcaagatcactgggaccaggccgtgatctctatgcccgagtctcaaccctcaactgtcacccc
aaggcacttgggacgtcctggacagaccgagtcccgggaagccccagcactgccgctgccacactg
ccctgagcccaaatgggggagtgagaggccatagctgtctggcatg (Seq ID No: 89)

*Homo sapiens* tubulin, beta 2A class IIa (TUBB2A):
aggtctctgcgcagcccagcccgccggtccacgccgcgcaccgctccgagggccagcgccacccgc
tccgcagccggcaccatg (Seq ID No: 90)

*Homo sapiens* actin, beta (ACTB): tcgcctttgccgatccgccgcccgtcca-
cacccgccgccagctcaccatg (Seq ID No: 91)

*Homo sapiens* adenylosuccinate synthase (ADSS):
ggctccttcttcctctgcatgtggctggcggccgcagagcagttcagttcgctcactcctcgccgg
ccgcctctccttcgggctctcctcgcgtcactggagccatg (Seq ID No: 92)

*Homo sapiens* alanyl (membrane) aminopeptidase (ANPEP):
cgttctctgcctggcctgaggctccctgagccgcctccccaccatcaccatg
(Seq ID No: 93)

*Homo sapiens* beaded filament structural protein 1, filensin (BFSP1):
gcctcctttctttctcagcccagacctggccctctggagagggttttggagtcctgggtaggcagg
gtacctcaggcagcaggcagcacaccttggatgtgagctgaatggattttcaaatttcacagaagg
agcctccatgctggagaaagtatgtatg (Seq ID No: 94)

*Homo sapiens* basic transcription factor 3 (BTF3):
cggcctccctttagctgccatcttgcgtccccgcgtgtgtgcgcctaatctcaggtggtccacccg
agaccccttgagcaccaaccctagtcccccgcgcggccccttattcgctccgacaagatg
(Seq ID No: 95)

*Homo sapiens* complement component 1, q subcomponent binding protein (C1QBP): ttgtcctttgcatctgcacgtgttcgcagtcgtttccgcgatg
(Seq ID No: 96)

*Homo sapiens* calsequestrin 1 (fast-twitch, skeletal muscle) (CASQ1):
tttcctttcttaatatggcgatgagctcttaggccagtgtggggaccggggctgaggtgccctgga
cactggaggagggggagggaaggagcccctgggagcctggggtagaagtgtaggaggtgggaggat
tccggcccgcatggagctgtcctggcctcagaaggttatccgtctctcctgccaaccatggagaca
tatttagacaggaccaggtggggactgaggggtgccaatttcagggggcagctccggttccctccc
cgccccctgctcctattcctccacctgacccttttttcccttggctctgtcggcagtttctccagga
cccagcagtgccctctgtccactgctctgggccattccccaatcccccctcccacttgagccccta
actcagaatctgggacccaggggcccctccctaccccagctaacctcttctggaccaggagagcca
acccagatcccactacctccatg (Seq ID No: 97)

*Homo sapiens* caveolin 3 (CAV3):
gtctctctgcccctctctgccccaagtattttcagccccagccggccacacagctcggatctcctc
ctgtggatccccccagctctgcgatg (Seq ID No: 98)

Homo sapiens serpin peptidase inhibitor, clade H (heat shock protein 47), member 1, (collagen binding protein 1) (SERPINH1):
aggtctttggcttttttggcggagctggggcgccctccggaagcgtttccaactttccagaagtt
tctcgggacgggcaggagggggtggggactgccatatatagatcccgggagcaggggagcgggcta
agagtagaatcgtgtcgcggctcgagagcgagagtcacgtcccggcgctagcccagcccgacccag
gcccaccgtggtgcacgcaaaccacttcctggccatg (Seq ID No: 99)

*Homo sapiens* CD68 molecule (CD68):
tttcctcctttccaagagagggctgagggagcagggttgagcaactggtgcagacagcctagctgg
actttgggtgaggcggttcagccatg (Seq ID No: 100)

*Homo sapiens* cell division cycle 20 homolog (*S. cerevisiae*) (CDC20):
gggtccctttctgtcccctgagcaccgtcgcctcctttcctccagggctccgtaggcaccaactgc
aaggacccctccccctgcgggcgctcccatg (Seq ID No: 101)

*Homo sapiens* cadherin 13, H-cadherin (heart) (CDH13):
gagcctctcctcaaagcctggctcccacggaaaatatgctcagtgcagccgcgtgcatgaatgaaa
acgccgccgggcgcttctagtcggacaaaatg (Seq ID No: 102)

-continued

SEQUENCES:

*Homo sapiens* regulator of chromosome condensation (RCC1) and BTB (POZ) domain containing protein 2 (RCBTB2):
cgctcccttcgtttccgtctcggccgggcacccgagcgcatcccgccgaggccgggccgtttcagg
gggaggcgccaactcatcgcggcgccgggcccctgaccgtgcagtaaccgctacccaggaggcgga
gcggacaaggctccggcctgcgaggagtcacattaactttgctctagaagacaactttacaaggat
ctaaaaggaacaggattaaagatgactgaatactgggttccagaaatttaaaacaatcagcttagc
aaatcatatattcttctgtggagctgagaattgatgtccgctcttccccgtgatttggaactttcc
aatcccagagaaaagttgacaaagggactgcccaggactgagtccatatg
(Seq ID No: 103)

*Homo sapiens* cold inducible RNA binding protein (CIRBP):
cccccctcactcgcgcgttaggaggctcgggtcgttgtggtgcgctgtcttcccgcttgcgtcag
ggacctgcccgactcagtggccgccatg (Seq ID No: 104)

*Homo sapiens* LIM domain binding 2 (LDB2):
cctcctctcctctccctctcctctcctgctatagagggctccgacagcagttcccagccagcgtgt
tcagcctgcctgcctgcctgcctctgtgtgtgtgtgagcgtgtgtgcgtgcgtctactttgtactg
ggaagaacacagcccatgtgctctgcatggacgttactgatactctgtttagcttgattttcgaaa
agcaggcaagatg (Seq ID No: 105)

*Homo sapiens* chloride channel, nucleotide-sensitive, 1A (CLNS1A):
ctgcctcttccagggcgggcggtgtggtgcacgcattgctgtgctccaactccctcagggcctgtg
ttgccgcactctgctgctatg (Seq ID No: 106)

*Homo sapiens* collapsin response mediator protein 1 (CRMP1):
cctcctccttctcccgccctcctcgccgatccgggcggtgctggcagccggagcggcggcgggcgg
gccgagcagccggggcagccgcgcgtgggcatccacgggcgccgagcctccgtccgtgtctctatc
cctcccgggcctttgtcagcgcgcccgctgggagcggggccgagagcgccggttccagtcagacag
ccccgcaggtcagcggccgggccgagggcgccagaggggggccatg (Seq ID No: 107)

*Homo sapiens* catenin (cadherin-associated protein), delta 1 (CTNND1):
ttgcctttggctgggtgcaacttccattttaggtgttggatctgagggggaaaaaaaagagagagg
gagagagagagaaagaagagcaggaaagatcccgaaaggaggaagaggtggcgaaaaatcaactgc
cctgctggatttgtctttctcagcaccttggcgaagccttgggtttctttcttaaaggactgattt
ttagaactccacatttgaggtgtgtggcttttgaagaaaatgtatgtactgacgggaaaaggagga
taagcaagtcgaatttttgtcttacgctctctccttcctgcttcctccttgctgtggtggctggga
tgcttcttccatgattttttgaatctagactgggctgttctctgtgttaaaccaatcagttgcgac
cttctcttaacagtgtgaagtgaggggggtctctccctccttctccttcctctgtgattcacctt
cctttttaccctgccctgcggcggctccgccccttaccttcatg (Seq ID No: 108)

*Homo sapiens* diacylglycerol kinase, alpha 80 kDa (DGKA):
ccgtcccctccagcccagctcgggctccagctccagcgccggcgcttcagctgcgaccgcgagccc
tctcaagcaagatataacttccccaagtcacacagtggtatcagagctaagaatgggacccagata
tgactgatctagttctgttccaaaaccgtgctgtattatattaacgcctaccctctgaagaggtcc
aagcaacggaagtactactacgaagctgcctttctggccatccttgagaaaaatagacagatgagt
tcctgccagtgagtccctaggcctccatctctctcccttgctgtaccaccttcaccaccatccatg
cgaccccaagagccttaatgactctagaagagactccaggcaggggaagctgaaaggacctttcac
tccctacttttggccagggccttctgtgccacctgccaagaccagcaggcctaccctctgaagagg
tccaagcaacggaagtactactacgaagctgcctttctggccatccttgagaaaaatagacagatg
(Seq ID No: 109)

*Homo sapiens* aspartyl-tRNA synthetase (DARS):
cgatctttctggagccgcacctccacgcggagtccgagcgcgtgtgctgagaccccagggtcggga
gggcggagactgggagggagggagaagcccctttggcctgccttacggaagcctgcgagggagggt
ggtgtccactgcccagttccgtgtcccgatg (Seq ID No: 110)

*Homo sapiens* dynein, cytoplasmic 1, intermediate chain 2 (DYNC1I2):
agttcttctcgatcgtgtcagtttgtaaggcgagggcggaagttggattcctggcctgagaatatt
aggcgtagttttccagttttggcaaagcggaaatacttaaggcccctgggttgactgggttcttt
gttttatctaccggcttctgctttacgacaggtcacaaacatg (Seq ID No: 111)

*Homo sapiens* dedicator of cytokinesis 1 (DOCK1):
tttcctccccatcctgtcgcggctcgaaaggaatggaaaatggcggcctagacgcggagtttcctg
cccgacccgcggcggctccggcggcgccatg (Seq ID No: 112)

*Homo sapiens* dihydropyrimidinase-like 2 (DPYSL2):
ctctctcttttttttccgccctagctggggctgtgttggaggagaggaagaaagagagacagagga
ttgcattcatccgttacgttcttgaaatttcctaatagcaagaccagcgaagcggttgcaccccttt
tcaatcttgcaaaggaaaaaaacaaaacaaaacaaaaaaaaacccaagtccccttcccggcagtttt
tgccttaaagctgccctcttgaaattaatttttcccaggagagagatg (Seq ID No: 113)

-continued

| SEQUENCES: |
| --- |

*Homo sapiens* developmentally regulated GTP binding protein 2 (DRG2):
tgttctctttggcttccgggcgcacgctactctgtcgccgccgtcagaccggaattgccggtgccg
ccgccaccgctgtctgtgcgcccacctctgctgctaccatg (Seq ID No: 114)

*Homo sapiens* eukaryotic translation elongation factor 1 alpha 1 (EEF1A1):
cgttcttttcgcaacgggtttgccgccagaacacaggtgtcgtgaaaactacccctaaaagccaa
aatg (Seq ID No: 115)

*Homo sapiens* eukaryotic translation elongation factor 1 gamma (EEF1G):
tctcctctttccccctcccttctctcccgggcggcttactttgcggcagcgccgagaaccccaccc
cctttctttgcggaatcaccatg (Seq ID No: 116)

*Homo sapiens* eukaryotic translation initiation factor 2, subunit 3 gamma, 52 kDa (EIF2S3): atttccttcctcttttggcaacatggcgggc
(Seq ID No: 117)

*Homo sapiens* eukaryotic translation initiation factor 4B (EIF4B):
gggtcttttgcgttctctttccctctcccaacatg (Seq ID No: 118)

*Homo sapiens* eukaryotic translation initiation factor 4 gamma, 2 (EIF4G2): tattcttttgaagattcttcgttgtcaagccgccaaagtg
(Seq ID No: 119)

*Homo sapiens* epithelial membrane protein 1 (EMP1):
cttcccctcagtgcggtcacatacttccagaagagcggaccagggctgctgccagcacctgccact
cagagcgcctctgtcgctgggacccttcagaactctctttgctcacaagttaccaaaaaaaaaaga
gccaacatg (Seq ID No: 120)

*Homo sapiens* fibrillarin (FBL):
cgctcttttccacgtgcgaaagccccggactcgtggagttgtgaacgccgcggactccggagccgc
acaaaccagggctcgccatg (Seq ID No: 121)

*Homo sapiens* exostoses (multiple)-like 2 (EXTL2):
ctgtcccttgctccaggcgctcactttgcgggcggcactttttccaggttgttaatccagctaatg
gagaaggatagatgcacgctacttggtttagaaaaaaaaacaaaaatgagcaaacgagacgcccct
tccgttttatgataactaagctgcagggaaataaatcggctggccctactgcaatctactgcactc
gagaaacatcacagaaaattctttgatttatcttaatagtgacaagtgagcctgcttctgtcaatt
actgaagctataaggagatttttaaaaattaaacttcaacacaatg (Seq ID No: 122)

*Homo sapiens* solute carrier family 37 (glucose-6-phosphate transporter), member 4 (SLC37A4):
ccgcctctgttcaggacactgggtccccttggagcctccccaggcttaatgattgtccagaaggcg
gctataaagggagcctgggaggctgggtggaggagggagcagaaaaaacccaactcagcagatctg
ggaactgtgagagcggcaagcaggaactgtggtcagaggctgtgcgtcttggctggtagggcctgc
tcttttctaccatg (Seq ID No: 123)

*Homo sapiens* GDP dissociation inhibitor 2 (GDI2):
agccctcccctcctcgctccctcccctcctctccccgcccagttcttctcttcccgtctgaggtgg
cggtcggtctcgccttgtcgccagctccattttcctctctttctcttccccttccttcgcgccca
agagcgcctcccagcctcgtagggtggtcacggagcccctgcgccttttccttgctcgggtcctgc
gtccgcgcctgccccgccatg (Seq ID No: 124)

*Homo sapiens* UDP-Gal: betaGlcNAc beta 1,4-galactosyltransferase, polypeptide 1 (B4GALT1): caccccttcttaaagcggcggcgggaagatg
(Seq ID No: 125)

*Homo sapiens* GDP-mannose 4,6-dehydratase (GMDS):
ggccctccctgcacggcctcccgtgcgcccctgtcagactgtggcggccggtcgcgcggtgcgctc
tccctccctgcccgcagcctggagaggcgcttcgtgctgcacaccccccgcgttcctgccggcaccg
cgcctgccctctgccgcgctccgccctgccgccgaccgcacgcccgccgcgggacatg
(Seq ID No: 126)

*Homo sapiens* histone deacetylase 2 (HDAC2):
ggccccctcctcgcgagttggtgccgctgccacctccgattccgagctttcggcacctctgccggg
tggtaccgagccttcccggcgccccctcctctcctcccaccggcctgcccttccccgcgggactat
cgcccccacgtttccctcagcccttttctctcccggccgagccgcggcggcagcagcagcagcagc
agcagcaggaggaggagcccggtggcggcggtggccggggagcccatg (Seq ID No: 127)

*Homo sapiens* protein arginine methyltransferase 2 (PRMT2):
gggccttcccggctgacggcctgcgtgcactgcgcttgcgcgggttgagggcggtggctcaggctc
ctggaaaggaccgtccacccctccgcgctggcggtgtggacgcggaactcagcggagaaacgcgat
tgagagcagtgtgtggattacactatcactggaaaaatacgaattgagaagaaggaaaagactgga
agatgcagaccttggttcctgttagtggaaacactgtaaggtcccagaaatggaaaagaaaatgaa
ataaatcagcagttatgaggcagagcctaagagaactatg (Seq ID No: 128)

-continued

SEQUENCES:

*Homo sapiens* immunoglobulin (CD79A) binding protein 1 (IGBP1): gttcctctctccccaagatg (Seq ID No: 129)

*Homo sapiens* eukaryotic translation initiation factor 3, subunit E (EIF3E): actccctttctttggcaagatg (Seq ID No: 130)

*Homo sapiens* activated leukocyte cell adhesion molecule (ALCAM):
gtccctctactcagagcagcccggagaccgctgccgccgctgccgctgctaccaccgctgccacct
gaggagacccgccgcccccccgtcgccgcctcctgcgagtccttcttagcacctggcgtttcatgc
acattgccactgccattattattatcattccaatacaaggaaaataaaagaagataccagcgaaaa
gaaccgcttacacctttccgaattactcaagtgtctcctggaaacagagggtcgttgtccccggag
gagcagccgaagggcccgtgggctggtgttgaccgggagggaggaggagttgggggcattgcgtgg
tggaaagttgcgtgcggcagagaaccgaaggtgcagcgccacagcccaggggacggtgtgtctggg
agaagacgctgcccctgcgtcgggacccgccagcgcgcgggcaccgcggggcccgggacgacgccc
cctcctgcggcgtggactccgtcagtggcccaccaagaaggaggaggaatatg
(Seq ID No: 131)

*Homo sapiens* acyloxyacyl hydrolase (neutrophil) (AOAH):
ttttctttatcctgcagtctttacctcagcagaaccgcacaccacagactccctccagctctttgt
gtgtggctctctcagggtccaacaagagcaagctgtgggtctgtgagtgtttatgtgtgcttttat
tcacttcacacttattgaaaagtgtgtatgtgagagggtggggtgtgtgtgtcaaagagagtgagg
aagagaaggagagagagagatcaattgattctgcagcctcagctccagcatccctcagttgggagctt
ccaaagccgggtgatcacttggggtgcatagctcggagatg (Seq ID No: 132)

*Homo sapiens* ADP-ribosylation factor 1 (ARF1):
ccgccccttacccggcgtgccccgcgcccggaggcgctgacgtggccgccgtcagagccgccatct
tgtgggagcaaaaccaacgcctggctcggagcagcagcctctgaggtgtccctggccagtgtcctt
ccacctgtccacaagcatg (Seq ID No: 133)

*Homo sapiens* ADP-ribosylation factor 6 (ARF6):
gcgccttttccggcagcggcggcggcagaactgggaggaggagttggaggccggagggagcccgcg
ctcggggcggcggctggaggcagcgcaccgagttcccgcgaggatccatgacctgacggggccccg
gagccgcgctgcctctcgggtgtcctgggtcggtggggagcccagtgctcgcaggccggcgggcgg
gccggagggctgcagtctccctcgcggtgagaggaaggcggaggagcgggaaccgcggcggcgctc
gcgcggcgcctgcggggggaagggcagttccgggccgggccgcgcctcagcagggcggcggctccc
agcgcagtctcagggcccgggtggcggcggcgactggagaaatcaagttgtgcggtcggtgatgcc
cgagtgagcggggggcctgggcctctgcccttaggaggcaactcccacgcaggccgcaaaggcgct
ctcgcggccgagaggcttcgtttcggtttcgcggcggcggcggcgttgttggctgaggggacccgg
gacacctgaatgcccccggccccggctcctccgacgcgatg (Seq ID No: 134)

*Homo sapiens* ras homolog family member A (RHOA):
cgccctcccgccgccgcccgccctcgctctctcgcgctacctcccgccgcccgcggtcctccgtc
ggttctctcgttagtccacggtctggtcttcagctacccgccttcgtctccgagtttgcgactcgc
ggaccggcgtccccggcgcgaagaggctggactcggattcgttgcctgagcaatg
(Seq ID No: 135)

*Homo sapiens* ras homolog family member G (RHOG):
cggcctcccgctctcacttccttctcgagcccggagccgctgccgccgcccccagctcccccgcct
cggggagggcaccaggtcactgcagccagaggggtccagaagagagagaggaggcactgcctccacta
cagcaactgcacccacgatg (Seq ID No: 136)

*Homo sapiens* ATP synthase, H+ transporting, mitochondrial F1 complex, O subunit (ATP50): ctctcttcccactcgggtttgacctacagccgcccgggagaa-gatg (Seq ID No: 137)

*Homo sapiens* B lymphoid tyrosine kinase (BLK):
ccacctctgtctgctgccggcagaaagccacaagccatgaaaactgattgagatgagaagaattca
tctgggactggcttttgcttaggatggtgttggaagttgctcgttgtcgctaggagcctgctcca
ctgtaagggtgtcaggatctgaagagctatggtgaaacaccactgaagcattgccaaggatg
(Seq ID No: 138)

*Homo sapiens* B-cell translocation gene 1, anti-proliferative (BTG1):
gcatctcttcgcctctcggagctggaaatgcagctattgagatcttcgaatgctgcggagctggag
gcggaggcagctggggaggtccgagcgatgtgaccaggccgccatcgctcgtctcttcctctctcc
tgccgcctcctgtctcgaaaataactttttttagtctaaagaaagaaagacaaaagtagtcgtccgc
ccctcacgccctctcttcctctcagccttccgcccggtgaggaagcccggggtggctgctccgccg
tcggggccgcgccgccgagccccagccgccccgggccgcccccgcacgccgcccccatg
(Seq ID No: 139)

*Homo sapiens* calcium modulating ligand (CAMLG):
cggcctctagtcatcgccctcgcagcggcggccaacatcaccgccactgccacccctcccagactg
tggacgggaggatg (Seq ID No: 140)

-continued

SEQUENCES:

*Homo sapiens* calnexin (CANX):
aggcctcttggttctgcggcacgtgacggtcgggccgcctccgcctctctctttactgcggcgcgg
ggcaaggtgtgcgggcgggaaggggcacgggcacccccgcggtccccgggaggctagagatcatg
(Seq ID No: 141)

*Homo sapiens* calpain 2, (m/II) large subunit (CAPN2):
cgacctttctctgcgcagtacggccgccgggaccgcagcatg (Seq ID No: 142)

*Homo sapiens* caveolin 1, caveolae protein, 22 kDa (CAV1):
gcgccttttttttcccccatacaatacaagatcttccttcctcagttcccttaaagcacagcccag
ggaaacctcctcacagttttcatccagccacgggccagcatg (Seq ID No: 143)

*Homo sapiens* CD1d molecule (CD1D):
cgacctctttgcagctcgcacagctaagggcgagggcgcccttcggcagaagcagcaaaccgccgg
caagcccagcgaggagggctgccggggtctgggcttgggaattggctggcacccagcggaaaggga
cgtgagctgagcggcgggggagaagagtgcgcaggtcagagggcggcgcgcagcggcgctccgcga
ggtccccacgccgggcgatatg (Seq ID No: 144)

*Homo sapiens* CD22 molecule (CD22):
tctccttttgctctcagatgctgccagggtccctgaagagggaagacacgcggaaacaggcttgca
cccagacacgacaccatg (Seq ID No: 145)

*Homo sapiens* CD37 molecule (CD37):
cttcctcttttggggttcttcctttctctctcagctctccgtctctctttctctctcagcctcttt
ctttctccctgtctcccccactgtcagcacctcttctgtgtggtgagtggaccgcttaccccacta
ggtgaagatg (Seq ID No: 146)

*Homo sapiens* CD38 molecule (CD38):
gcctctctcttgctgcctagcctcctgccggcctcatcttcgcccagccaaccccgcctggagccc
tatg (Seq ID No: 147)

*Homo sapiens* CD48 molecule (CD48):
cggccttttttctagccaggctctcaactgtctcctgcgttgctgggaagttctggaaggaagcatg
(Seq ID No: 148)

*Homo sapiens* chromogranin B (secretogranin 1) (CHGB):
cttcctttccgcacaggggccgccgagcggggccatg (Seq ID No: 149)

*Homo sapiens* chloride channel, voltage-sensitive 3 (CLCN3):
ttccccttccgtgggtcagggccggtccggtccggaacctgcagcccctttcccagtgttctagtt
cgcccgtgacccggaataatgagcaaggagggtgtggtgggttgaaagccatcctactttactccc
gagttagagcatggattcagttttagtcttaaggggggaagtgagattggagatttttatttttaat
tttgggcagaagcaggttgactctagggatctccagagcgagaggatttaacttcatgttgctccc
gtgtttgaaggaggacaataaaagtcccaccgggcaaaattttcgtaacctctgcggtagaaaacg
tcaggtatcttttaaatcgcgatagttttcgctgtgtcaggctttcttcggtggagctccgagggt
agctaggttctaggtttgaaacagatgcagaatccaaaggcagcgcaaaaaacagccaccgatttt
gctatgtctctgagctgcgagataatcagacagctaaatg (Seq ID No: 150)

*Homo sapiens* colipase, pancreatic (CLPS):
ttccccttccgtgggtcagggccggtccggtccggaacctgcagcccctttcccagtgttctagtt
cgcccgtgacccggaataatgagcaaggagggtgtggtgggttgaaagccatcctactttactccc
gagttagagcatggattcagttttagtcttaaggggggaagtgagattggagatttttatttttaat
tttgggcagaagcaggttgactctagggatctccagagcgagaggatttaacttcatgttgctccc
gtgtttgaaggaggacaataaaagtcccaccgggcaaaattttcgtaacctctgcggtagaaaacg
tcaggtatcttttaaatcgcgatagttttcgctgtgtcaggctttcttcggtggagctccgagggt
agctaggttctaggtttgaaacagatgcagaatccaaaggcagcgcaaaaaacagccaccgatttt
gctatgtctctgagctgcgagataatcagacagctaaatg (Seq ID No: 151)

*Homo sapiens* cytochrome c oxidase subunit IV isoform 1 (COX4I1):
ctacccttttccgctccacggtgacctccgtgcggccgggtgcgggcggagtcttcctcgatcccg
tggtgctccgcggcgcggccttgctctcttccggtcgcgggacaccgggtgtagagggcggtcgcg
gcgggcagtggcggcagaatg (Seq ID No: 152)

*Homo sapiens* cytochrome c oxidase subunit VIIc (COX7C):
ctttcttttcagtccttgcgcaccggggaacaaggtcgtgaaaaaaaaggtcttggtgaggtgccg
ccatttcatctgtcctcattctctgcgcctttcgcagagcttccagcagcggtatg
(Seq ID No: 153)

*Homo sapiens* activating transcription factor 2 (ATF2):
cagccttttcctccaggggtgctttgtaaacacggctgtgctcagggctcgcgggtgaccgaaagg
atcatgaactagtgacctggaaagggtactagatggaaacttgagaaaggactgcttattgataac
agctaaggtattcctggaagcagagtaaataaagctcatggcccaccagctagaaagtattcttgc
catgagaaaaagaatgtgataagttattcaacttatg (Seq ID No: 154)

*Homo sapiens* casein kinase 1, alpha 1 (CSNK1A1):
agatccctttcccagagtgctctgcgccgtgaagaagcggctcccggggactgggggcattttgtg
ttggctggagctggagtaacaagatggcgtcgtccgcggagtgacaggggtccctctgggccggag -continued

| SEQUENCES: |
|---|

ccggcggcagtggtggcagcggtatcgccgccctagctcaccgcgccccttttccagcccgcgacg
tcgccgcgcaagcgaggcagcggcggccgccgagaaacaagtggcccagcctggtaaccgccgaga
agcccttcacaaactgcggcctggcaaaaagaaacctgactgagcggcggtgatcaggttcccctc
tgctgattctgggccccgaaccccggtaaaggcctccgtgttccgtttcctgccgccctcctccgt
agccttgcctagtgtaggagccccgaggcctccgtcctcttcccagaggtgtcggggcttggcccc
agcctccatcttcgtctctcaggatg (Seq ID No: 155)

*Homo sapiens* catenin (cadherin-associated protein), beta 1, 88 kDa (CTNNB1):
aagcctctcggtctgtggcagcagcgttggcccggccccgggagcggagagcgaggggaggcggag
acggaggaaggtctgaggagcagcttcagtccccgccgagccgccaccgcaggtcgaggacggtcg
gactcccgcggcgggaggagcctgttcccctgagggtatttgaagtataccatacaactgttttga
aaatccagcgtggacaatg (Seq ID No: 156)

*Homo sapiens* dCMP deaminase (DCTD):
ccgcctcctcccccgacttccttccctgagcacggcggcggcggggacgagcaccggcctgcgcgc
ggagccggcaccggatgacccaacatg (Seq ID No: 157)

*Homo sapiens* damage-specific DNA binding protein 1, 127 kDa (DDB1):
ctgtcttttcgcttgtgtccctctttctagtgtcgcgctcgagtcccgacgggccgctccaagcct
cgacatg (Seq ID No: 158)

*Homo sapiens* desmin (DES):
ctgtctcccctcgccgcatccactctccggccggccgcctgcccgccgcctcctccgtgcgcccgc
cagcctcgcccgcgccgtcaccatg (Seq ID No: 159)

*Homo sapiens* deoxyhypusine synthase (DHPS):
cgttccctacttcctgtgctcttgcggagacgcgcgcgtcggggtttaacgcgtttctgggccgcc
gtaagcccggcctaggggcagctttgactcgagagccggctataggcgcatg
(Seq ID No: 160)

*Homo sapiens* dihydrolipoamide S-acetyltransferase (DLAT):
caccctttcggatgcctcccctagaaccctaccactttccaccccttttccgtctgttatttctccc
aaacttgcgcccgcacaggcccctctggaacactcctgccccgtagtgcccctcgtccccgctccg
tagagaaagagcgtgcgtgccgcgcatttctggcctggggagcgggtggagtaaacctgcgggaac
cattttacgacaacgtgcggctgtgcggtgtggctgacggcaacgccgctgctcttggagaggtca
ctccggagacggcgttggttttggggtgtggggggttggtggcactatg (Seq ID No: 161)

*Homo sapiens* down-regulator of transcription 1, TBP-binding (negative cofactor 2) (DR1):
ccttccctggcatctggagggaccaccgttgccgcgtcttcggcttccacgatctgcgttcgggct
acgcggccacggcggcagccactgcgactcccactgtgcctggctctgtccatattagttcccagg
cggccgtcgccgttccagcagcggcagcggcagcggcagcggcggacatgttgtgaggcggcggcg
cgggtgtctgaaggatggtttggccgaggcggcggcaacggctgctggcggcggcggcagcggcag
cggggcctcgggctctatagagccgagcccgctgggtacccgcccggtaccgcggcgaggccagtg
cccctggatcttgcctctgctccgacgccgttggggaccagttaggcgacagcgcccgcccctctg
aggagacacgaaggtggttccccagccgctcaaatttccggaccaccgcgctttcccctcctcagc
ctgggctgtgctctctctagaatcctcgggcccccactttcttcccaaactcatcctaaatctctc
acacacgcgagtgttcccagccctcaagccagctgctcctccgttcattttctgcaccctcttcgc
aaagcacccccgggatcactctccgagggcgactttttgagaaatctcggtggagtagtggacca
gagctggggagtttttaaaagccggggcgcgagaaacaggaaggtactatg
(Seq ID No: 162)

*Homo sapiens* endothelin receptor type A (EDNRA):
ttttctttttcgtgcgagccctcgcgcgcgtacagtcatcccgctggtctgacgattgtggaga
ggcggtggagaggcttcatccatcccacccggtcgtcgccggggattggggtcccagcgagacctc
cccgggagaagcagtgcccaggaggttttctgaagccggggaagctgtgcagccgaagccgccgcc
gcgccggagcccgggacaccggccaccctccgcgccacccaccctcgccggctccggcttcctctg
gcccaggcgccgcgcggacccggcagctgtctgcgcacgccgagctccacggtgaaaaaaaagtga
aggtgtaaaagcagcacaagtgcaataagagatatttcctcaaatttgcctcaagatg
(Seq ID No: 163)

*Homo sapiens* eukaryotic translation elongation factor 1 alpha 2 (EEF1A2):
cagtccctctggctgagacctcggctccggaatcactgcagcccccctcgccctgagccagagcac
cccgggtcccgccagcccctcacactcccagcaaaatg (Seq ID No: 164)

*Homo sapiens* eukaryotic translation elongation factor 2 (EEF2):
cgttctcttccgccgtcgtcgccgccatcctcggcgcgactcgcttctttcggttctacctgggag
aatccaccgccatccgccaccatg (Seq ID No: 165)

*Homo sapiens* eukaryotic translation initiation factor 4A2 (EIF4A2): ctgtcttttcagtcgggcgctgagtggtttttcggatcatg
(Seq ID No: 166)

-continued

| SEQUENCES: |
|---|

*Homo sapiens* egf-like module containing, mucin-like, hormone receptor-like 1 (EMR1): gtttcttttctttgaatgacagaactacagcataatg (Seq ID No: 167)

*Homo sapiens* enolase 2 (gamma, neuronal) (EN02):
gcgcctcctccgcccgccgcccgggagccgcagccgccgccgccactgccactcccgctctctcag
cgccgccgtcgccaccgccaccgccaccgccactaccaccgtctgagtctgcagtcccgagatccc
agccatcatg (Seq ID No: 168)

*Homo sapiens* esterase D (ESD):
ccgccttttacttcggcccgcttcttctggtcactccgccaccgtagaatcgcctaccatttggtg
caagcaaaaagcaatcagcaattggacaggaaaagaatg (Seq ID No: 169)

*Homo sapiens* Finkel-Biskis-Reilly murine sarcoma virus (FBR-MuSV) ubiquitously expressed (FAU):
cttcctctttctcgactccatcttcgcggtagctgggaccgccgttcagtcgccaatatg
(Seq ID No: 170)

*Homo sapiens* Friend leukemia virus integration 1 (FLI1):
ctgtctctttcgctccgctacaacaacaaacgtgcacaggggagtgagggcagggcgctcgcaggg
ggcacgcagggagggcccagggcgccagggaggccgcgccgggctaatccgaaggggctgcgaggt
caggctgtaaccgggtcaatgtgtggaatattggggggctcggctgcagacttggccaaatg
(Seq ID No: 171)

*Homo sapiens* fibromodulin (FMOD):
gccccttttcacaatatttgattaggaatttggggcgggaccctggtctggcacaggcacgcacac
tctcagtagactctttcactcctctctctcttcctctctcacacgttctccaacccaaggaggcca
gacagagggacgtggtcactctctgaaaagttcaacttgagagacaaaatg
(Seq ID No: 172)

*Homo sapiens* ferritin, heavy polypeptide 1 (FTH1):
cgttcttcgccgagagtcgtcggggtttcctgcttcaacagtgcttggacggaacccggcgctcgt
tccccaccccggccggccgcccatagccagccctccgtcacctcttcaccgcaccctcggactgcc
ccaaggcccccgccgccgctccagcgccgcgcagccaccgccgccgccgccgcctctccttagtcg
ccgccatg (Seq ID No: 173)

*Homo sapiens* glyceraldehyde-3-phosphate dehydrogenase (GAPDH):
cgctctctgctcctcctgttcgacagtcagccgcatcttcttttgcgtcgccagccgagccacatc
gctcagacaccatg (Seq ID No: 174)

*Homo sapiens* glycyl-tRNA synthetase (GARS):
caccctctctggacagcccagggccgcaggctcatg (Seq ID No: 175)

*Homo sapiens* glutamic-oxaloacetic transaminase 2, mitochondrial (aspartate aminotransferase 2) (GOT2):
ctgtccttaccttcagcaggagccggttccctgtgtgtgtgtccgctcgccctctgctccgtcctg
cggctgcccactgccctcctacggtccaccatg (Seq ID No: 176)

*Homo sapiens* general transcription factor IIF, polypeptide 1, 74 kDa (GTF2F1):
gcgcctcttccggttaccttttcccagcgccagaggcgcctagggttggggtcctcgctcaggcac
agagacccgacaccgagcggcggcttccccgggatcgagggagcgcgcacgccagaggagacgaaag
gaacccgggtcggaccagatcggaaccactgaccattgcccatg (Seq ID No: 177)

*Homo sapiens* glycogen synthase 1 (muscle) (GYS1):
cggcctccttctgcctaggtcccaacgcttcggggcaggggtgcggtcttgcaataggaagccgag
cgtcttgcaagcttcccgtcgggcaccagctactcggccccgcaccctacctggtgcattccctag
acacctccggggtccctacctggagatccccggagccccccttcctgcgccagccatg
(Seq ID No: 178)

*Homo sapiens* major histocompatibility complex, class I, C (HLA-C):
cattctccccagaggccgagatg (Seq ID No: 179)

*Homo sapiens* major histocompatibility complex, class II, DP beta 1 (HLA-DPB1):
gctccctttagcgagtccttcttttcctgactgcagctcttttcatttgccatccttttccagct
ccatg (Seq ID No: 180)

*Homo sapiens* 3-hydroxy-3-methylglutaryl-CoA synthase 1 (soluble) (HMGCS1):
ctgtcctttcgtggctcactccctttcctctgctgccgctcggtcacgcttgctctttcaccatg
(Seq ID No: 181)

*Homo sapiens* hippocalcin (HPCA):
ccgccttccctgcgcagtcggtgtctccgcgtcgctgggtgggacttggctcggcggccatg
(Seq ID No: 182)

-continued

| SEQUENCES: |
|---|

*Homo sapiens* hydroxysteroid (17-beta) dehydrogenase 2 (HSD17B2):
ctcccttcttgactctctgttcacagaactcaggctgcctccagccagcctttgcccgctagactc
actggccctgagcacttgaaggtgcagcaagtcactgagaatg (Seq ID No: 183)

*Homo sapiens* heat shock 60 kDa protein 1 (chaperonin) (HSPD1):
ctgtccctcactcgccgccgacgacctgtctcgccgagcgcacgccttgccgccgccccgcagaaa
tg (Seq ID No: 184)

*Homo sapiens* intercellular adhesion molecule 3 (ICAM3):
ccgccttttcccctgcctgcccttcgggcacctcaggaaggcaccttcctctgtcagaatg
(Seq ID No: 185)

*Homo sapiens* inositol polyphosphate-1-phosphatase (INPP1):
cgtcctctggccgcgcctgcggccgcacgcccagcgcccctcgcctaacctcgcgcccgggccgcg
cctcctcctcctcctgctccccgccgcttccgtttctcgagggaaaggctgctgcctcctgctctg
tcctcatccccggcttagctgacggcccagagggtgggtgccaattccaccagcagctgcaactga
aaagcaaggttcagaaatg (Seq ID No: 186)

*Homo sapiens* interferon regulatory factor 2 (IRF2):
gtttcctctccttgttttgctttcgatctggactgttctcaggcaagccggggagtaacttttagt
tttgctcctgcgattattcaactgacgggctttcatttccatttcacataccctagcaacacttat
accttgcggaattgtattggtagcgtgaaaaaagcacactgagagggcaccatg
(Seq ID No: 187)

*Homo sapiens* inter-alpha-trypsin inhibitor heavy chain 2 (ITIH2):
ttttcttcttttttcttctttcttaaagcgaactgtactcctctgctgttcctttgaacttggttc
agtaggaagaagtgatatcctccccagaccatctgctttggggagcttggcaaaactgtccagcaa
aatg (Seq ID No: 188)

*Homo sapiens* karyopherin (importin) beta 1 (KPNB1):
ccgccttcctccctccctcgctccctccctgcgcgccgcctctcactcacagcctcccttccttct
ttctccctccgcctcccgagcaccagcgcgctctgagctgcccccagggtccctcccccgccgcca
gcagcccatttggagggaggaagtaagggaagaggagaggaaggggagccggaccgactacccaga
cagagccggtgaatgggtttgtggtgaccccgcccccccacccccaccctcccttcccacccgaccc
ccaacccccatccccagttcgagccgccgcccgaaaggccgggccgtcgtcttaggaggagtcgcc
gccgccgccacctccgccatg (Seq ID No: 189)

*Homo sapiens* karyopherin alpha 3 (importin alpha 4) (KPNA3):
ctctccccctcctccccctcccgctccaagattcgccgccgccgccgccgcagccgcaggagtagc
cgccgccggagccgcgcgcagccatg (Seq ID No: 190)

*Homo sapiens* keratin 19 (KRT19):
gctcctcccgcgaatcgcagcttctgagaccagggttgctccgtccgtgctccgcctcgccatg
(Seq ID No: 191)

*Homo sapiens* laminin, beta 1 (LAMB1):
attcccttctttgggctcgggggctcccggagcagggcgagagctcgcgtcgccggaaaggaagac
gggaagaaagggcaggcggctcggcgggcgtcttctccactcctctgccgcgtccccgtggctgca
gggagccggcatg (Seq ID No: 192)

*Homo sapiens* ribosomal protein SA (RPSA):
ctgtcttttccgtgctacctgcagaggggtccatacggcgttgttctggattcccgtcgtaactta
aagggaaattttcacaatg (Seq ID No: 193)

*Homo sapiens* lymphocyte cytosolic protein 1 (L-plastin) (LCP1):
ttttctttcctggctgatgatttgtcattctagtcacttcctgccttgtgaccacacacccaggct
tgacaaagctgttctgcagatcagaaagaaggggttcctggtcatacaccagtactaccaaggaca
gctttttcctgcaagatctgttacctaaagcaataaaaaatg (Seq ID No: 194)

*Homo sapiens* lectin, galactoside-binding, soluble, 1 (LGALS1):
ccatctctctcgggtggagtcttctgacagctggtgcgcctgcccgggaacatcctcctggactca
atcatg (Seq ID No: 195)

*Homo sapiens* SH2 domain containing 1A (SH2D1A):
ttctctctttttgcacatctggctgaactgggagtcaggtggttgacttgtgcctggctgcagta
gcagcggcatctcccttgcacagttctcctcctcggcctgcccaagagtccaccaggccatg
(Seq ID No: 196)

*Homo sapiens* mannosidase, alpha, class 2A, member 1 (MAN2A1):
tgttcctttcccctccgcttctctgacctagctgcgcggccccggcccgggagctgccgaacccgc
gcctcccctgggtgaggaggacacgcctgccctcgtcgagaaaacttttcctgccgactcagttgg
ggcggcggtggcaggaagtgcgggcagcgacctctcctccgcctgccccgcgcgccctgccggagg
tcggcgctgagcttgcgatcaagtttgtgggggccccccttcccagttgccggcgagtctcgcctc
gagaggggcgcccgaccccggggagggcggcaggccagggcgaaggccaagggcgtgtggtggcgc
cggagactaggtgcggagcaaggcggggactcgcacccgcatccgagagcgcggaggtcgcgcagc
ccgggagaagggagcctccggcggctgcttcctagagtccacagtgcgctgtctcctttggctgag
gagagtgtcctggccccgagtctatcgaggaaaatg (Seq ID No: 197)

-continued

| SEQUENCES: |
| --- |

*Homo sapiens* myelin basic protein (MBP):
ccgcctcttttcccgagatgccccggggagggaggacaacaccttcaaagacaggccctctgagtc
cgacgagctccagaccatccaagaagacagtgcagccacctccgagagcctggatgtgatg
(Seq ID No: 198)

*Homo sapiens* melanocortin 1 receptor (alpha
melanocyte stimulating hormone receptor) (MC1R):
cattcttcccaggacctcagcgcagccctggcccaggaaggcaggagacagaggccaggacggtcc
agaggtgtcgaaatgtcctggggacctgagcagcagccaccagggaagaggcagggagggagctga
ggaccaggcttggttgtgagaatccctgagcccaggcggtagatgccaggaggtgtctggactggc
tgggccatgcctgggctgacctgtccagccagggagagggtgtgagggcagatctggggggtgccca
gatggaaggaggcaggcatgggggacacccaaggcccccctggcagcaccatgaactaagcaggaca
cctggaggggaagaactgtggggacctggaggcctccaacgactccttcctgcttcctggacagga
ctatg (Seq ID No: 199)

*Homo sapiens* malic enzyme 1, NADP(+)-dependent, cytosolic (ME1):
gggcctttcccagtgcggccgccgccgccacagctgcagtcagcaccgtcaccccagcagcatccg
ccgcctgcaccgcgcgtgcggcccgccccggcctgaccccgccgccgaacccggcgccagccatg
(Seq ID No: 200)

*Homo sapiens* myocyte enhancer factor 2C (MEF2C):
agctctctgctcgctctgctcgcagtcacagacacttgagcacacgcgtacacccagacatcttcg
ggctgctattggattgactttgaaggttctgtgtgggtcgccgtggctgcatgtttgaatcaggtg
gagaagcacttcaacgctggacgaagtaaagattattgttgttatttttttttctctctctctct
ctcttaagaaaggaaaatatcccaaggactaatctgatcgggtcttccttcatcaggaacgaatgc
aggaatttgggaactgagctgtgcaagtgctgaagaaggagatttgtttggaggaaacaggaaaga
gaaagaaaaggaaggaaaaaatacataatttcagggacgagagagagaagaaaaacggggactatg
(Seq ID No: 201)

*Homo sapiens* mannosyl (al-
pha-1,3-)-glycoprotein beta-1,2-N-acetylglucosaminyltransferase
(MGAT1):
agcccttcttggggaagtcagctacccagcagcctgtagtcctcggctacccaccctcaccgcctg
gggtcccatggtgagacagctgggtgggcatcaggcttctgcagagggccaggccggagggagctg
ggcgagggagtggggctggctcctggcttgcaccggcctcgtggaatccaggcctcagacctgatc
gctggcgaaactggctctgtgcgctggagcccctggtcttctgcgtctgtcctcctcccggccaga
ctttactcctggctcagcgacaggtatttgctatggaagagctgtccctccctcccctcggtgggc
ctgggtccacctccacctcctcttcaggtccgcaccttcctcccctttaaaacaccagccgggcgc
agacccgttctaggcttttccatggtgcttccgccaaagcttgtgaccgagtccttcccgcctagg
gctggtgggcctcccctgctggtaggtctctcttcgctttctttactcagaactgaagctctcatt
ccccacccaccaaggaaaaacaaaagggaagaagccacagctggccccggcttgctttggcacagg
tgtttcccccggccccccgtcgggcaccctggttcctgttctgtccctgccccacgcgaccctgg
ggctcccacccgggctcctcagcctcccctgggttggggtggggggactggctcccagcccttggc
ctagggtttggtgaacgcctttcctggactgcgggcccacttcaggcgcggctccaggctgggcag
ctgcgctggagggccgagggcaggggtggggtcggcgtccaccctcagggttgcgccagggagcc
ggaaagccgactcccgaagttggggtcctgggaaaacttgggtcctgggttgactgagaagcggcg
gggaaaggaggcgggccaggaggagggggcctggcggacgccggccgggggggcggggcgcggcggg
gctgtcggtcacgcccctcagtccgccccgccccgccccgcctgccggggaagggccacgttgccc
gcccggccgtccggccccggcgcgccgcagaaagggctggcgagtcgaaaggcgaggcggccgcgg
cagcgcttgggacgcgcctgggcaccgggctcgctccctgcgccccggagcaggccaagttcgggg
ccaggacgtcgggaggacctggtgcatggctgcctcctaatcccatagtccagaggaggcatccct
aggactgcgggcaagggagccgggcaagcccagggcagccttgaaccgtcccctggcctgccctcc
ccggtgggggccaggatg (Seq ID No: 202)

*Homo sapiens* mitogen-activated protein kinase kinase kinase 11
(MAP3K11):
ctgcctcccgcccccggggccaaagtacaaagggaggaggaagaagggagcggggtcggagccgtc
ggggccaaaggagacggggccaggaacaggcagtctcggcccaactgcggacgctccctccacccc
ctgcgcaaaaagacccaaccggagttgaggcgctgcccctgaaggccccaccttacacttggcggg
ggccggagccaggctcccaggactgctccagaaccgagggaagctcgggtccctccaagctagcca
tggtgaggcgccggaggccccggggccccacccccccggcctgaccacactgccctgggtgccctc
ctccagaagcccgagatgcggggggccgggagacaacactcctggctccccagagaggcgtgggtc
tggggctgagggccagggcccggatgcccaggttccgggactagggccttggcagccagcgggggt
ggggaccacgggcacccagagaaggtcctccacacatcccagcgccggctcccggccatg
(Seq ID No: 203)

*Homo sapiens* membrane protein, palmitoylated 1, 55 kDa (MPP1):
ccgccttctccgcagccccgcaggccccgggccctgtcattcccagcgctgccctgtcttgcgttc
cagtgttccagcttctgcgagatg (Seq ID No: 204)

*Homo sapiens* v-myc myelocytomatosis viral oncogene homolog (avian)
(MYC):
ggccctttataatgcgagggtctggacggctgaggacccccgagctgtgctgctcgcggccgccac
cgccgggccccggccgtccctggctcccctcctgcctcgagaagggcagggcttctcagaggcttg
gcgggaaaaagaacggagggagggatcgcgctgagtataaaagccggttttcggggctttatctaa
ctcgctgtagtaattccagcgagaggcagagggagcgagcgggcggccggctagggtggaagagcc -continued

SEQUENCES:

gggcgagcagagctgcgctgcgggcgtcctgggaagggagatccggagcgaatagggggcttcgcc
tctggcccagccctcccgctgatcccccagccagcggtccgcaacccttgccgcatccacgaaact
ttgcccatagcagcgggcgggcactttgcactggaacttacaacacccgagcaaggacgcgactct
cccgacgcggggaggctattctgcccatttggggacacttccccgccgctgccaggacccgcttct
ctgaaaggctctccttgcagctgcttagacgctg (Seq ID No: 205)

*Homo sapiens* nuclear cap binding protein subunit 1, 80 kDa (NCBP1):
tggcctctcggttccgcggcgcaccggagggcagcatg (Seq ID No: 206)

*Homo sapiens* necdin homolog (mouse) (NDN):
cttcctctccaggaatccgcggagggagcgcaggctcgaagagctcctggacgcagaggccctgcc
cttgccagacggcgcagacatg (Seq ID No: 207)

*Homo sapiens* NADH dehydrogenase
(ubiquinone) 1 beta subcomplex, 5, 16 kDa (NDUFB5):
ccttcttcctcctgcccgtagtagccatg (Seq ID No: 208)

*Homo sapiens* NADH dehydrogenase (ubiquinone) Fe—S protein 4, 18 kDa
(NADH-coenzyme Q reductase) (NDUFS4):
ccgtcctttcatcctggcgtttgcctgcagcaagatg (Seq ID No: 209)

*Homo sapiens* nuclear factor of kappa light polypeptide gene enhancer
in B-cells 2 (p49/p100) (NFKB2):
tgccccttccccggccaagcccaactccggatctcgctctccaccggatctcacccgccacacccg
gacaggcggctggaggaggcgggcgtctaaaattctgggaagcagaacctggccggagccactaga
cagagccgggcctagcccagagacatg (Seq ID No: 210)

*Homo sapiens* non-metastatic cells 2, protein (NM23B) expressed in
(NME2):
gcccctcctccgccgccggctcccgggtgtggtggtcgcaccagctctctgctctcccagcgcagc
gccgccgcccggcccctccagcttcccggaccatg (Seq ID No: 211)

*Homo sapiens* nucleophosmin (nucleolar
phosphoprotein B23, numatrin) (NPM1):
gcgtcctttccctggtgtgattccgtcctgcgcggttgttctctggagcagcgttcttttatctcc
gtccgccttctctcctacctaagtgcgtgccgccacccgatg (Seq ID No: 212)

*Homo sapiens* 5'-nucleotidase, ecto (CD73) (NT5E):
cattccttttgtagaaaaacccgtgcctcgaatgaggcgagactcagagaggacccaggcgcgggg
cggacccctccaattccttcctcgcgcccccgaaagagcggcgcaccagcagccgaactgccggcg
cccaggctccctggtccggccgggatgcggccggtacccgctccccgccgggaacaacctctccac
tcttcctgcagggagctggtgccagccgacagccgcgccagggccgctccgggtaccagggtcgga
tcgggtgacgtcgcgaacttgcgcctggccgccaagccggcctccaggctgaagaaggacccgccc
cggccttgacccgggccccgcccctccagccggggcaccgagccccggccctagctgctcgcccct
actcgccggcactcgcccggctcgcccgctttcgcacccagttcacgcgccacagctatg
(Seq ID No: 213)

*Homo sapiens* phosphatidylethanolamine binding protein 1 (PEBP1):
gcgtcttcccgagccagtgtgctgagctctccgcgtcgcctctgtcgcccgcgcctggcctaccgc
ggcactcccggctgcacgctctgcttggcctcgccatg (Seq ID No: 214)

*Homo sapiens* poly(A) binding protein, cytoplasmic 1 (PABPC1):
gcttccccttctccccggcggttagtgctgagagtgcggagtgtgtgctccgggctcggaacacac
atttattattaaaaaatccaaaaaaaatctaaaaaaatcttttaaaaaaccccaaaaaaatttaca
aaaaatccgcgtctcccccgccggagacttttatttttttcttcctcttttataaaataacccgg
tgaagcagccgagaccgacccgcccgcccgcggccccgcagcagctccaagaaggaaccaagagac
cgaggccttcccgctgcccggacccgacaccgccaccctcgctccccgccggcagccggcagccag
cggcagtggatcgaccccgttctgcggccgttgagtagttttcaattccggttgatttttgtccct
ctgcgcttgctccccgctcccctcccccggctccggcccccagccccggcactcgctctcctcct
ctcacggaaaggtcgcggcctgtggccctgcgggcagccgtgccgagatg
(Seq ID No: 215)

*Homo sapiens* proprotein convertase subtilisin/kexin type 2
(PCSK2):
cgctctttctctccggtacacacagctccccacattcgcacccctgcccgcgcgccgggccgcctg
actgcacggcttcccctccagccagatgctggagaacacacactgattcgctgctttccaagaccc
tgttcagtctctttctctatacaaagatttttttaaaaactatatataagaattctttatttgcac
cctccctccgagtcccctgctccgccagcctgcgcgcctcctagcaccacttttcactcccaaaga
aggatg (Seq ID No: 216)

*Homo sapiens* phosphogluconate dehydrogenase (PGD):
gggtctttccctcactcgtcctccgcgcgtcgccgctcttcggttctgctctgtccgccgccatg
(Seq ID No: 217)

*Homo sapiens* phosphoglucomutase 1 (PGM1):
cgctcccctttcccctcccgccggacctgccaggaggtgggctggcgcggagggagggccctgtcc
cctgtccctttaaggaggagggccaaacgccggcctagagtgcggcgtagcccccacccgccgtgc -continued

SEQUENCES:

cctcaccccagagcagctgcagcctcagccggccgcccctccgccagccaagtccgccgctctgac
ccccggcagcaagtcgccaccatg (Seq ID No: 218)

*Homo sapiens* solute carrier family 25 (mitochondrial
carrier; phosphate carrier), member 3 (SLC25A3):
cggcctctgtgagccgcaacctttccaagggagtggttgtgtgatcgccatcttagggagtgagtg
tggccgggccttctcctgtggcgggtgtggggagcggagcccagagctcctgtggggccgctgctt
tggcggtgggcccagccgggagcagcctctttcgaaggccgccgtgacctcttcaagggcgtggag
acgggaaggaaaaggccccggttggggttccagggcgccggtaacgttaaccggcgccttgcctgt
cctctaaccgtcgctccctcctcccctagaaagatg (Seq ID No: 219)

*Homo sapiens* pim-1 oncogene (PIM1):
cctcccctttactcctggctgcggggcgagccgggcgtctgctgcagcggccgcggtggctgagga
ggcccgagaggagtcggtggcagcggcggcggcgggaccggcagcagcagcagcagcagcagcagc
agcaaccactagcctcctgccccgcggcgctgccgcacgagccccacgagccgctcaccccgccgt
tctcagcgctgcccgaccccgctggcgcgccctcccgccgccagtcccggcagcgccctcagttgt
cctccgactcgccctcggccttccgcgccagccgcagccacagccgcaacgccacccgcagccaca
gccacagccacagccccaggcatagccttcggcacagccccggctccggctcctgcggcagctcct
ctgggcaccgtccctgcgccgacatcctggaggttgggatg (Seq ID No: 220)

*Homo sapiens* pyruvate kinase, muscle (PKM2):
ggatctcttcgtctttgcagcgtagcccgagtcggtcagcgccggaggtgagcggtgcaggaggct
acgccatcagtccccaccaagggccagtcgcccggctagtgcggaatcccggcgcgccggccggcc
ccgggcacgcaggcagggcggcgcaggatccagggcgtctgggatgcagtggagctcagagagagg
agaacggctcctcacgcctggggcctgctcttcagaagtccccagcgccgttccttccagatcagg
acctcagcagccatg (Seq ID No: 221)

*Homo sapiens* pleiomorphic adenoma gene-like 1 (PLAGL1):
cggcctcctcggcgcagccatcctcttggctgccgcgggcggcaaagcccacggcatctgccattt
gtcattcagcccgtcggtaccgccccgagccttgatttagacacggctggggcgtgctctggcctc
actctccgggcgggtgctggacggacggacggacggggcagccgtgctcacagctcagcagcgcgg
ggccttggcgcgcggggcgcttccccgggtcgccgtcatggccgcggaggtggcacgcccgagcgg
cctcgcctgagctccgggggtcgtcgccccgcagggattgctgtcacgtctaatgtggctgctgcc
tcgtgtcacatctgaaactcatctgtacctcacttagaaagtggttctgattagacaagactttc
gttgcagtcgacagaaacctaatgggaccattgaagaattccaaacaggtatttgcataggaatca
gaggagttaatcttgtctcttctcacaggtttgaatcttcagacaaacttctgggaggactcggtc
cctgcctcgcagcagatgttccctgtcactcagtaggcatatg (Seq ID No: 222)

*Homo sapiens* phospholipase D2 (PLD2):
tgctctcttggctccggaacccccgcgggcgctggctccgtctgccagggatg
(Seq ID No: 223)

*Homo sapiens* proteolipid protein 2 (colonic epithelium-enriched)
(PLP2):
ccccttcccggccagacggcgggcaagacagctgggtgtacagcgtcctcgaaaccacgagcaag
tgagcagatcctccgaggcaccagggactccagcccatgccatg (Seq ID No: 224)

*Homo sapiens* pinin, desmosome associated protein (PNN):
cagtcctttcgcgcctcggcggcgcggcatagcccggctcggcctgtaaagcagtctcaagcctgc
cgcagggagaagatg (Seq ID No: 225)

*Homo sapiens* phosphoribosyl pyrophosphate amidotransferase (PPAT):
ggtccttccacgtgctttcggcggcgacatg (Seq ID No: 226)

*Homo sapiens* protein phosphatase 1, catalytic subunit, gamma isozyme
(PPP1CC):
tgttcttctcgtggttccagtggggagagaaggaggaagtagggagcggggtggcaggggggggac
ccgccgcggctgctgccaccgccgccaccaccgcctctgctcgtggcgtgggaaaggaggtgtgag
tcccgggcgcgagccggcggcggcgccgctgcgggagggtcggcggtgggaaggcgatg
(Seq ID No: 227)

*Homo sapiens* protein phosphatase 1, regulatory subunit 8 (PPP1R8):
cggtcttccagtttcccggcgtgcttagggcgcgccaaatgggagggggagacgcaagatg
(Seq ID No: 228)

*Homo sapiens* protein phosphatase 6, catalytic subunit (PPP6C):
cggcctccgccgctgccgccgccgctgctacagccgccgccgccgctgttgccgcggcttgttatt
cttaaaatg (Seq ID No: 229)

*Homo sapiens* protein kinase C substrate 80K-H (PRKCSH):
ctttctttctgcagcaggaaccgcggctgctggacaagaggggtgcggtggatactgacctttgct
ccggcctcgtcgtgaagacacagcgcatctccccgctgtaggcttcctcccacagaacccgtttcg
ggcctcagagcgtctggtgagatg (Seq ID No: 230)

*Homo sapiens* mitogen-activated protein kinase 6 (MAPK6):
cgccccctcttcctcgccctctctcgcgggtcggggttacatggcggcgactgcggcaaagcgaga
gcctcggagacgccgctgccgccagcacagccggagacctgagccgacactgggggcagtccgcga -continued

| SEQUENCES: |
|---|

gccccgcactctctcgatgagtcggagaagtcccgttgtatcagagtaagatggacggtagctttg
attgtgattgtggtgagctggagccacctgatcactaacaaaagacatcttctgttaaccaacagc
cgccagggcttcctgttgaaataaatatatagcaacaaaggaaaaaaagaagcaaaacggaaatag
tgcttaccagcaccttagaatgatgctgctcaggaccagtccaacactgaatgtatctgcactgtg
aggagaatgttcatagaagcctgttgtgtgcatatttattcacattttttgttaaatgttaaatcgt
ttagcacggtaatctgagtgcacagtatgtcatttcattccgtttgagtttcttgttttcgttaaa
tgtctgcagagttgctgccccttttcttgaactatgagtactgcaatctttttaattctcaatatga
atagagctttttgagctttaaatctaaggggaactcgacaggcctgtttggcatatgcaatgaaca
tcaagaaaccatcttgctgtggaagcataattatttttcttctcccttttttgaaagatctttcctt
ttgatgccagttttcttccttgtttacacaagttcaatttgaaaggaaaaggcaatagtaagggtt
tcaaaatg (Seq ID No: 231)

*Homo sapiens* phosphoribosyl pyrophosphate synthetase 2 (PRPS2):
cctccccttccctacatctagccgccgcgctttcccgctcccgcagcagcagcctcccgcgtcgct
gtcgctgttgcctccgccacctcctccgccgccgcgcgcccctcggagttccgcgccccaccatg
(Seq ID No: 232)

*Homo sapiens* phosphoribosyl pyrophosphate synthetase-associated protein 1 (PRPSAP1):
ttgcctctggctctgaggcggcggcgccgggcgctgcgaaggctcggccgctgtagtcagtggtgt
ggggtgcgcaagggcacggacctcggagctctccccgcttgcgccgagtttctcagcgccttcccc
acccaaaccggggtctcgcagtcggaagcactcagagtgcagccccgcgcggggccggtcgtaacc
gcgccgcgggccggacgatg (Seq ID No: 233)

*Homo sapiens* proteasome (prosome, macropain) subunit, beta type, 5 (PSMB5): agttctttctgcccacactagacatg (Seq ID No: 234)

*Homo sapiens* proteasome (prosome, macropain) 26S subunit, non-ATPase, 13 (PSMD13):
tgttcttctgtgccgggggtcttcctgctgtcatg (Seq ID No: 235)

*Homo sapiens* protein tyrosine phosphatase, receptor type, N (PTPRN):
cagcccctctggcaggctcccgccagcgtcgctgcggctccggcccgggagcgagcgcccggagct
cggaaagatg (Seq ID No: 236)

*Homo sapiens* RAB3A, member RAS oncogene family (RAB3A):
ctccctttgcaggacgtcacggaggactgcaggggcctgagccgctgctgccgccgccgccgcgca
gccccacatcaacgcaccggggtcctgtcaccgccaccgccaaaaaagtcaccgccgctagggtcg
ccgttgcatcggtgcagggcaagatg (Seq ID No: 237)

*Homo sapiens* RNA binding motif, single stranded interacting protein 2 (RBMS2): ctctctctctctctctctcgctcgttccctaacattaaagagaaaatg
(Seq ID No: 238)

*Homo sapiens* reticulocalbin 1, EF-hand calcium binding domain (RCN1):
gcgcccctctgctccggctcggggcgggcactggcggagggactggccagtcccctcctccgcgcc
ggccccaaccctgtcgctgccgccgcgctccgagtccccattcccgagctgccgctgttgtcgctc
gctcagcgtctccctctcggccgccctctcctcgggacgatg (Seq ID No: 239)

*Homo sapiens* radixin (RDX):
ccgcctttcccgcggaggcgccgagcggccatattgcggagctgtctgcggtggcggcggcgcct
ctcgtctcccgcggcccagcgctcgcaccaccgcttctccctccctgtcgcagccgcgccgccgcg
cagcgccccagccacacgccggcgggcagaagccgcccgctctccggaaagtgataacagaattca
ttgaagtggagaatttttaaagaaggtaacaaaaagagaaagaaaatg (Seq ID No: 240)

*Homo sapiens* replication factor C (activator 1) 1, 145 kDa (RFC1):
tcgccttcttgcacttcgcgggagaagttgttggcgcgaatggatcctgagcctcgataacagatt
cctcaaccggcccacccgccagccagccagcgccttcatcctggggctgcgatg
(Seq ID No: 241)

*Homo sapiens* ring finger protein 4 (RNF4):
gcatctttctcgaggagctctcctgggcggctgaagaaggagcttcttctccggagtgcgccggcg
gtggcgcctgcggacctaactagctccaggttaggccgagctttgcgggaaagcagcggacttgaa
aatactggaaatctgtccggatccaaattattttgcaagccagatgagtaaccagagggcatgaaa
ggttgagaacatttgacttccctgcaaaccttggtatagatcacttccttttctgtaggaaaggaa
aggcaccaaagagcacaatg (Seq ID No: 242)

*Homo sapiens* ribophorin I (RPN1): tgctcttcccggtcatg
(Seq ID No: 243)

*Homo sapiens* ribosomal protein S27a (RPS27A):
cgttcttccttttcgatccgccatctgcggtggagccgccaccaaaatg (Seq ID No: 244)

-continued

| SEQUENCES: |
|---|

*Homo sapiens* secreted and transmembrane 1 (SECTM1):
cttcctttagcgtgaaccgcgggtgcggtgcctcccgtgaaaataataaattcaccgtcacgcttg
ttgtgaacgcgggtggttcccgaaacttggaggcttcccgtaaacccagctccttcctcatctggg
aggtgggtcccgcgcgggtccgccgcctcctccctggcccctccctctcgtgtctttcattttcct
ggggctccggggcgcggagaagctgcatcccagaggagcgcgtccaggagcggacccgggagtgtt
tcaagagccagtgacaaggaccaggggcccaagtcccaccagccatg (Seq ID No: 245)

*Homo sapiens* small glutamine-rich tetratricopeptide repeat
(TPR)-containing, alpha (SGTA):
ctttcttttgcgcaggcgtcgcgccctggggccggggccgggcggcaccgcggtgcgcaagcgcaa
ccgtcggtgggtcggggatcggtcgcctgagaggtatcacctcttctgggctcaagatg
(Seq ID No: 246)

*Homo sapiens* SH3 domain binding glutamic acid-rich protein like
(SH3BGRL):
agttctccttccaccttcccccacccttctctgccaaccgctgtttcagcccctagctggattcca
gccattgctgcagctgctccacagccccttttcaggacccaaacaaccgcagccgctgttcccagga
tg (Seq ID No: 247)

*Homo sapiens* solute carrier family 1 (gluta-
mate/neutral amino acid transporter), member 4 (SLC1A4):
cgccctcctacttccccgtctgcgtccgcgttcgcggctcccgtttgcatcatccccgtctgcgtc
cgcgttcgcggctcccgtttgcatcatctccagccggcggctgctccagggaggctgggcgcgatc
ctctccgcccgcggctccaacccgcactctgcgcctctcctcgcctttctcgcacctgctcctgcg
ccaggcccggagacccccggggcggcttcccagaacctgcggagcacaactggccgaccgacccat
tcattgggaaccccgtcttttgccagagcccacgtcccctgccacctctagctcggagcggcgtgt
agcgccatg (Seq ID No: 248)

*Homo sapiens* small nuclear RNA activating complex, polypeptide 2,
45 kDa (SNAPC2): ctgcctctttctgagcggcatg (Seq ID No: 249)

*Homo sapiens* sorting nexin 1 (SNX1): ctatctctcga-
taaagttgttgttgcggcttccgccgcgggtggaagaagatg (Seq ID No: 250)

*Homo sapiens* signal recognition particle 54 kDa (SRP54):
ctatctctcatctttccgctcttagctgggagtgctccgcctagtcacttttcttaaggtggctcg
tcgaggcctgacttcttccccgaaatcacgtccctagacagcctcctattttaccactaactttac
tcctgcagttattcagcggtaggaaactgaaaccaaaaaccagtgtaagcaagtaaacatctaaac
tgtttcaggagccgcgtagaaggaacgcggcggtgtgccccggaagcggaagtagattctcctata
gaaaggctggactacgcggagtggtgacgtttcctcattgggcggaaggttcgctggcactccgtt
ggtcttccagctggtgggagttgacgacgtggtgctgggcgttgggaccctactttatctagttcg
ggaagttgggttgtggggtcatacctgtctgtctgctcccagctttcttgggtttcttccgacggc
gtggggcctcgctaaggaattcccggcccctcagggccacggctttagcggtgtcttttgcgagtt
cttcgtaagtacatcttaaagctgtcaagatg (Seq ID No: 251)

*Homo sapiens* signal sequence receptor, beta (translocon-
associated protein beta) (SSR2):
cggtctttcggatgctgacgctctcttcctgtctttgtggctccggaaaggcgtttgggatgccaa
cgatg (Seq ID No: 252)

*Homo sapiens* signal transducer and activator of transcription 6, interleukin-
4 induced (STAT6):
ttttctttttggtggtggtggtggaagggggggaggtgctagcagggccagccttgaactcgctgga
cagagctacagacctatggggcctggaagtgcccgctgagaaagggagaagacagcagaggggttg
ccgaggcaacctccaagtcccagatcatg (Seq ID No: 253)

*Homo sapiens* suppressor of Ty 4 homolog 1 (*S. cerevisiae*)
(SUPT4H1): tgttcttcccatcggcgaagatg (Seq ID No: 254)

Homo sapiens transcription factor 7 (T-cell specific, HMG-box)
(TCF7):
ggtccttcccctaaaacttggcactgccgatactcccagcccgttccttcccaagtcaggaacttg
caggggaccccttggcaattctttttctctcaagagcagacagccttcagtcccagccgctgccag
ggctggtgtgtctgacccagctgtggtttttccaggcctgaaggccccggagtgcaccagcggcat
g (Seq ID No: 255)

*Homo sapiens* TEA domain family member 4 (TEAD4):
cagtctcctccccgaggtgccggtggccccgccgccactccctccggctccctccctcccgccgcg
gcgcgcatctcattccagccctcattccgcgcattccagcgtcctcctcgcacactcgaggccagg
gggcgggagggccgcagctccggcgccgccgcgtcccgccaggtgagaggcgcccgcgcccgccgc
acccgccggcgccctcacgggccgcgcgccccacgccgccgcagccgaccgctcgcgcccgcgtgct
cggctgctcttttctttccgccgcccgcgttcccgccttggacctctgcgctccgacgcgctccgt
cccgacctctggcttccctccgcgctccggcgctgctcgctgcccctctcccgcttccctcctgtc
cgcccccgcgctcccctcctcgctcccggttgactcactcctccaggaatagggatccccgtgtttt
cccgtcagtcccattctgggaaaactcctccctccgcgcgctccgctccgctccgctgggcgcacc
ggggccggtcggcgcggggtgggcttggccccgcggccccgccttcactgcgccgcccgtcggccc
cggccggagcccggctctgcgcgctgacgccctgtcgtccccgcagaacgatcgccgcggccggaa -continued

SEQUENCES:

gagttggcgctcggggcggactccttggaactggcttagcgcacccatcccaccttcccgcaccct
gggaccggtcggaacgagctgattgcccgctacatcaagctccggacagggaagacccgcaccagg
aagcaggtctccagccacatccaggtgctggctcgtcgcaaagctcgcgagatccaggccaagcta
aaggaccaggcagctaaggacaaggccctgcagagcatg (Seq ID No: 256)

*Homo sapiens* G protein-coupled receptor 137B (GPR137B):
ttttctttcctccagtctcggggctgcaggctgagcgcgatgcgcggagacccccgcgggggcggc
ggcggccgtgagccccgatg (Seq ID No: 257)

*Homo sapiens* tumor protein, translationally-controlled 1 (TPT1):
cggcctttttccgcccgctccccccctcccccgagcgccgctccggctgcaccgcgctcgctccgag
tttcaggctcgtgctaagctagcgccgtcgtcgtctcccttcagtcgccatcatg
(Seq ID No: 258)

*Homo sapiens* ubiquitin A-52 residue ribosomal protein fusion product
1 (UBA52): ctatcttctttttcttcagcgaggcggccgagctgacgcaaacatg
(Seq ID No: 259)

*Homo sapiens* ubiquinol-cytochrome c reductase core protein II
(UQCRC2):
cggcctccgccaccatcttgctttcctttaatccggcagtgaccgtgtgtcagaacaatcttgaat
catg (Seq ID No: 260)

*Homo sapiens* ubiquitin specific peptidase 1 (USP1):
ctgcctttcgtgtctctgcagcgtggagactggaaccggcaatttcaaaggacgccacgttcaatc
gcagcgctggcgcgggcggaggctaaaacacgggggtcctgagactgaggaaaacgcgccaagttc
ccctcggtggcggagtgctaaagaccctagcggttcaggcgttcggcgagcggggccgctgcttgt
tgcgctcctggctctcccggggcgggcgcagatgggcgccgctcccgggatgtagttggtgttggt
gcaagacgggagcgagcggcggtcggggttcccgctcttgggagcggatggtcactcccccgcggg
gagggcgagccgaccagattttcctggggccggggacccggcgggctcggggcagggactcacctg
tcgcacccacactcattcgggttggacttgccggcgtcaccgccgcggacttcgctttgggccatg
accagatataattggtgattacaactttcctctataaattaactcttgacactccttgggatttga
agaaaaaaatg (Seq ID No: 261)

*Homo sapiens* voltage-dependent anion channel 2 (VDAC2):
gtgtctccttcacttcgccctccagctgctggagctgcagcccgaccgcgagcgtgccaagcggct
tcagcagctagcggagcggtggcggcggccccccctcaggacaccaccagattcccctcttcccgcg
gcctcgccatg (Seq ID No: 262)

*Homo sapiens* vimentin (VIM):
gcctcttctccgggagccagtccgcgccaccgccgccgcccaggccatcgccaccctccgcagcca
tg (Seq ID No: 263)

*Homo sapiens* very low density lipoprotein receptor (VLDLR):
ccccctccccgctgctcaccccgctctccggccgccgccggtgcgggtgctccgctaccggctcct
ctccgttctgtgctctcttctgctctcggctccccacccccctctcccttccctcctctccccttgc
ctcccctcctctgcagcgcctgcattattttctgcccgcaggctcggcttgcactgctgctgcagc
ccggggaggtggctgggtgggtggggaggagactgtgcaagttgtaggggagggggtgccctcttc
ttccccgctcccttcccccgccaactccttcccctccttctccccctttcccctccccgcccccac
cttcttcctcctttcggaaggactggtaacttgtcgtgcggagcgaacggcggcggcggcggcggc
ggcggcaccatccaggcgggcaccatg (Seq ID No: 264)

*Homo sapiens* wingless-type MMTV integration site family, member 10
B (WNT10B):
agtcctttgctcgccggcttgctagctctctcgatcactccctcccttcctccctcccttcctccc
ggcggccgcggcggcgctggggaagcggtgaagaggagtggcccggccctggaagaatgcggctct
gacaaggggacagaacccagcgcagtctccccacggtttaagcagcactagtgaagcccaggcaac
ccaaccgtgcctgtctcggaccccgcacccaaaccactggaggtcctgatcgatctgcccaccgga
gcctccgggcttcgacatg (Seq ID No: 265)

*Homo sapiens* CCHC-type zinc finger, nucleic acid binding protein
(CNBP):
cagcctctaccttgcgagccgtcttccccaggcctgcgtccgagtctccgccgctgcgggcccgct
ccgacgcggaagatctgactgcagccatg (Seq ID No: 266)

*Homo sapiens* zinc finger protein 43 (ZNF43):
gggcctttgtctctggctgcagttggagctctgcgtctcgtcttcgttcttctgtgtcctctgctg
ctagaggtccagcctctgtggctctgtgacctgcgggtattgggggatccacagctaagacgccag
gacccccggaagcctagaaatg (Seq ID No: 267)

*Homo sapiens* zinc finger protein 74 (ZNF74):
cagtccttttgtgggagtccggtctgtccacttgccggtccctcagaccgtcggcggtctctgtcc
gcttcgggacctgtccgctggtcgctccgcgtccgatggctcctggccgcggaaccttaggcctgg
ccctggtctccgagcgcgggttcgccgggaggagcgtgtggcgggggtgtgccggggcgtgagtgc
gccgagcatggggctgagcctggtgtggggagtgggtatctgcggagccggcctgaaccccacctc -continued

| SEQUENCES: |
| --- |

agccgggcgcggggaggggggctccgtgcgtgtgatcgtgcagctgtgagcgcgtggccgccccgcg
gggctccgctgcaggcccctcagccccaggagcagtactcgctcttcagggcctgccctggatcct
ggaggctacacagctgcccactcctcctggggaggctgccgtggaggccatg
(Seq ID No: 268)

*Homo sapiens* zinc finger protein 85 (ZNF85):
gggcctttgtctctcgctgcagcctgagctctaggtcttgttttccctgctttgtgttttctgctc
gtggacgcccagcctctgtggccctgtggcctgcaggtattgggagatccacagctaagacgccgg
gaccccctggaagcctagaaatg (Seq ID No: 269)

*Homo sapiens* zinc finger protein 91 (ZNF91):
gggcctttgtctctcgctgccgccggagtttccaggtctcgacttcactgctctgtgtcctctgct
ccaggaggcccagcctgtgtggccctgtgacctgcaggtattggagagccacagctaagatg
(Seq ID No: 270)

*Homo sapiens* zinc finger protein 141 (ZNF141):
gggtctttgcgtctggctactaccagaccgcgggttaggggcttcatctctctgcgttctcagttg
tgggaggccttggtgattcggccacagcctcagcctccgtcgctctgtgacctgcgggtattggat
gattggtagctaagactcccgaatacttcagaagtggggaaatg (Seq ID No: 271)

*Homo sapiens* zinc finger protein 205 (ZNF205):
tgttctttctagctctgaaatagaaaatg (Seq ID No: 272)

*Homo sapiens* transmembrane protein 187 (TMEM187):
ctcccttttcggagatttgaatttcccccagcgaggcgagtgaggcgaaatacccgtatggtgata
gctggccttttcgcgccaatactgaaaaaggcagaacgttcctccgctggcgccagccaatcagca
ggactcctgccttccttcggggcaaggtcgcagcatctgcctcggaaatcacgaaatcacggggct
tctttctgctggctcagccgggaggcccagagtgttctgcagaggctgcgtattgaaggctgctct
ctgaagctccctgccccaggtcacgccgccggttccagatg (Seq ID No: 273)

*Homo sapiens* histone cluster 2, H2be (HIST2H2BE):
acttcttttcttggctaagccgcgtttgtactgtgtcttaccatg (Seq ID No: 274)

*Homo sapiens* solute carrier family 25 (mitochondrial
carrier; oxoglutarate carrier), member 11 (SLC25A11):
ccgcctttgcgctgcgcgcctgcgcccgcgccggcttccagcgggtgtcggacctgagagctggag
gggcgtgcgcgcgccctcgctctgttgcgcgcgcggtgtcaccttgggcgcgagcggggccgcgcg
cgcacgggacccggagccgagggccattgagtggcgatg (Seq ID No: 275)

*Homo sapiens* tyrosylprotein sulfotransferase 2 (TPST2):
cctccccctccccggctggggcggctggagagccgggagtcgctgggtgcgtggggctgcctcgc
cgcgtctcgccacgggctctgccagcagacagccttggcacacaggcacaagggctggagcccaga
gatgagagtgcccaagggagatgtgagcctggcgggctgcccgctaacctgtcgctgaagccccag
aagcgggccctcaggccaggcctaccctgcctccggcccagcatg (Seq ID No: 276)

*Homo sapiens* sorbin and SH3 domain containing 2 (SORBS2):
aagcctcttttatacatctcttcagggaagagagaagcaatgggcatgttagtatacaatgatcac
agccacgcaggcctgcaagctgccttttggacaggctgttgactgccgttccaattagctgattgg
agaatgtggaatgcagagtgataatgctgcatatctgctatcaggcagcagcaaaggtttttgtct
tgggaaggcaagctttccctgcaatattatctcagcagctccctagctgcttaccctgaaaacgag
ggatccaaacggagggtgttgcactctgctaacgctggtcctgtgcgtggctgtggcatatgagcg
gcaggtctgaaaaagcaggtgtgtgctgggacgggcactggactggaacgcaggcggacgctctcg
ggtttacctgcttcctgttaacagattgtgggctcccagggcatatgtctgcacgctgaggccgag
gcggagaaggggcttcctgagcgtcccagtacactgacagagacacttggattggacttaatctta
aacctctggagttcaagaccttttaaaaagggctaaataaacaatctctacatgtaaaaggccact
gactcctacttcctctgtatagagcaactgttgaactcagctgcctgtaggaaaactgaagacttt
aataacaaactctccaaggtgaaaatg (Seq ID No: 277)

*Homo sapiens* G protein-coupled receptor 65 (GPR65):
gtttctcttcttgacttgatgcaggcacagatttatcaagctcctcagtcaacaaacacatcaccg
gaagaaatatggaaggaaaggaattttaaaaggaaataccaatctctgtgcaaacaaagccttgta
tattcatgtttgcaccaatctactgtgagatttatgaagaaaaacaaattgcggacaactctctat
gtacacttacaaatgcctcagttgatgcttgtgggctgtttgtcagcgttctgtgataatgaacac
atggacttctgtttattaaattcagttgaccccttagccaattgccaggagcctggattttact
tccaactgctgatatctgtgtaaaaattgatctacatccacccctttaaaagcattgatgaattaat
tagaactttagacaacaaagaaaaattgaaaaagaattctcagtaaaagcgaattcgatgttcaaa
acaaactacaaagagacaagacttctctgtttactttctaagaactaatataattgctaccttaaa
aaggaaaaaaatg (Seq ID No: 278)

*Homo sapiens* nipsnap homolog 1 (*C. elegans*) (NIPSNAP1):
gggccttcctgcaacctttgcggctccaacatg (Seq ID No: 279)

*Homo sapiens* inhibitor of kappa light polypeptide gene enhancer in
B-cells, kinase complex-associated protein (IKBKAP):
gcttctttgcagcgcttcagcgttttcccctggagggcgcctccatccttggaggcctagtgccgt
cggagagagagcgggagccgcggacagagacgcgtgcgcaattcggagccgactctgggtgcggac -continued

SEQUENCES:

tgtgggagctgactctgggtagccggctgcgcgtggctggggaggcgaggccggacgcacctctgt
ttgggggtcctcagagattaatgattcatcaagggatagttgtacttgtctcgtgggaatcacttc
atcatg (Seq ID No: 280)

*Homo sapiens* COP9 constitutive photomorphogenic homolog subunit 3 (*Arabidopsis*) (COPS3): ctgccttcgccgctcgggccgcccgggggaaaacatg (Seq ID No: 281)

*Homo sapiens* pirin (iron-binding nuclear protein) (PIR):
ccgcctcctctaggccgccggccgcgaagcgctgagtcacggtgaggctactggacccacactctc
ttaacctgccctccctgcactcgctcccggcggctcttcgcgtcacccccgccgctaaggctccag
gtgccgctaccgcagcgtgagtacctggggctcctgcaggggtccactagccctccatcctctaca
gctcagcatcagaacactctcttttagactccgatatg (Seq ID No: 282)

*Homo sapiens* THO complex 5 (THOC5):
ccttccttacttccggttctctatggtgcgcgggcaagctttgctccgcctccggcagtggcttac
tcccggtgccaggttcttggagctgtgaggaggaacaaccatg (Seq ID No: 283)

*Homo sapiens* RuvB-like 1 (*E. coli*) (RUVBL1):
gggcctttgcaaaattgccctagtaacggccgcatggtaactcaggcgccgggcgcactgtcctag
ctgctggttttccacgctggttttagctcccggcgtctgcaaaatg (Seq ID No: 284)

*Homo sapiens* Kruppel-like factor 7 (ubiquitous) (KLF7):
tttccttttagttgactgaaacaaaacaaaacaaaagggccactggatgtctgccttcttggggg
gtgagccagacagactgacaaacaaacagccccaactgtgttcgggggagggtttcgcctcccgtt
ttgcccggcagcagcagcatg (Seq ID No: 285)

*Homo sapiens* USO1 vesicle docking protein homolog (yeast) (USO1):
gctcccctttgccttcaaccttcgagccgccacgtaatgccacgtccccgcgcatgcgcatcttg
gccgctgctggcggctgtttccgggcttagagggctggagtggccgccgagttggaggcggtggtg
gcagcagtaggagtgtgtagagtgcgggattgggggccaggccctgcggagggcgggggaagttgt
cttcttttttttccggaggggccggtaaacctggtggctgaacggcaagatg
(Seq ID No: 286)

*Homo sapiens* unc-5 homolog C (*C. elegans*) (UNC5C):
cccccttttggcccctgcctttggagaaagtggagtgtggcgcttggttgtcgttatttcttcgga
ctgcttcgcggtgcacggattcagcttctgcccagtggggctttcagctgtttgcgcgtctctctg
tccccctcccctcccccggcacacctctgtctacgatg (Seq ID No: 287)

*Homo sapiens* RNA terminal phosphate cyclase domain 1 (RTCD1):
gcttcttccgctttctcgtcaggctcctgcgccccaggcatgaaccaaggtttctgaactactggg
cgggagccaacgtctcttctttctcccgctctggcggaggctttgtcgctgcgggctgggccccag
ggtgtcccccatg (Seq ID No: 288)

*Homo sapiens* eukaryotic translation initiation factor 3, subunit A (EIF3A):
ggctccttcctttccgtctctggccggctgggcgcgggcgactgctggcgaggcgcgtgggacctt
acgctggttccccttcgtctcctctcccggcccgggccactagagagttcgctgacgccgggtgag
ctgagcctgccgccaagatg (Seq ID No: 289)

*Homo sapiens* eukaryotic translation initiation factor 3, subunit D (EIF3D):
gtttcctcttttcctggtttctcaagagtgctgctgctaacgcggtccccggcacgcaccatctgt
tgccatcccggccggccgaggccattgcagattttggaagatg (Seq ID No: 290)

*Homo sapiens* eukaryotic translation initiation factor 3, subunit F (EIF3F): ccgcctccttctttctcgacaagatg (Seq ID No: 291)

*Homo sapiens* eukaryotic translation initiation factor 3, subunit G (EIF3G): cgctctctggccgggcttgggctgcgtggagaatactttttgcgatg (Seq ID No: 292)

*Homo sapiens* eukaryotic translation initiation factor 3, subunit H (EIF3H): gtttctctttcttcctgtctgcttggaaagatg (Seq ID No: 293)

*Homo sapiens* eukaryotic translation initiation factor 3, subunit I (EIF3I): aaaccttttccggtcttactcacgttgcggccttcctcgcgtcacagccgggatg (Seq ID No: 294)

*Homo sapiens* eukaryotic translation initiation factor 3, subunit J (EIF3J): ctccctctcacacacgctcacacccggctcgagatg (Seq ID No: 295)

*Homo sapiens* poly(A) binding protein, cytoplasmic 4 (inducible form) (PABPC4):
ccgcctctctccgcccccgggtcgctgccgcctccgccgctttcgggcttcgcagcctgaggaaaaa
aagagaaaaagataaaaaaaatctgaaaacgcttcaaaatcctgaaaaaaaaaaggaaaagaaaa
aacgaatcctcggagaacccgcggggaagtcactttcgtacgcttccggcctgccccgcgcccgcc -continued

| SEQUENCES: |
|---|

gccgcagcgcttggcgtccgtcggtctccgtccgtcggtccgggggtgagccgcccgcccggcccg
ccgtgccctccccccgctcgggccccgagccccgcgccccgcgcctgccccggcgcaccacgtgtc
cgtgctgcccttcgccgcccgcccggggctcgccgagtcggcgcccacaaagatttggtttccctc
tgccccggcggttgtaatcttaaaccgccggagcccgaggcctatatttatagagaaacgcgtgtc
cccgaggccgccgtgggcagcgtccggtcgcctcttaaaggatttttacccttcggaaggggattc
cccgtttaatttttttcctactttgatttttttgaaatttggagcttcgcaccaggaccgcggagaa
gtgcaaagtcgcggggagggccgtattgtgcggagagccttttgtctgcggtgctgcggccgtggg
agccggcccccgcctcccgtttccgtcccgtctccaagcccgccgactccagctcgtcctcgccgc
gccggtgccacctgtgagccgcggcgcgggcccggggctccgaaggcgccccttttgtcctgcggcgg
gcccgataagaagtcctcctggcggggctcggggtggtggggggcggggagatg
(Seq ID No: 296)

*Homo sapiens* receptor-interacting serine-threonine kinase 2 (RIPK2):
agctctttcgcggcgctacggcgttggcaccagtctctagaaaagaagtcagctctggttcggaga
agcagcggctggcgtgggccatccggggaatgggcgccctcgtgacctagtgttgcggggcaaaaa
gggtcttgccggcctcgctcgtgcaggggcgtatctgggcgcctgagcgcggcgtgggagccttgg
gagccgccgcagcagggggcacacccggaaccggcctgagcgcccgggaccatg
(Seq ID No: 297)

*Homo sapiens* neuropilin 1 (NRP1):
ctttcttttctccaagacgggctgaggattgtacagctctaggcggagttggggctcttcggatcg
cttagattctcctctttgctgcatttccccccacgtcctcgttctcccgcgtctgcctgcggaccc
ggagaagggagaatg (Seq ID No: 298)

*Homo sapiens* guanine monphosphate synthetase (GMPS):
tggtcttctctcccgcggcgctggggcccgcgctccgctgctgttgctccattcggcgcttttctg
gcggctggctcctctccgctgccggctgctcctcgaccaggcctccttctcaacctcagcccgcgg
cgccgacccttccggcaccctcccgccccgtctcgtactgtcgccgtcaccgccgcggctccggcc
ctggccccgatg (Seq ID No: 299)

*Homo sapiens* far upstream element (FUSE) binding protein 1 (FUBP1):
ttttctttctttcttagctgttagctgagaggaagtctctgaacaggcggcagcggctcttatagt
gcaaccatg (Seq ID No: 300)

*Homo sapiens* eukaryotic translation initiation factor 2B, subunit 5 epsilon, 82 kDa (EIF2B5):
gatccttttttgtcccctactgcgtgcggtggcagcttccttgcggaagtggtgaccgtgagagaag
aagatg (Seq ID No: 301)

*Homo sapiens* eukaryotic translation initiation factor 2, subunit 2 beta, 38 kDa (EIF2S2):
gtttcctttcgctgatgcaagagcctagtgcggtggtgggagaggtatcggcaggggcagcgctgc
cgccggggcctggggctgacccgtctgacttcccgtccgtgccgagcccactcgagccgcagccat
g (Seq ID No: 302)

*Homo sapiens* adaptor-related protein complex 1, sigma 2 subunit (AP1S2):
cctcccctctccgcctaagcctgccctatgccagccgggtgtcctccccacagcaccacggcttct
cttcctcagcacggcgacaggggcttccccttcgccgccgccgccgccgccggccaagctccgccg
cgcccgcggcccgcggccgccatg (Seq ID No: 303)

*Homo sapiens* suppression of tumorigenicity 13 (colon carcinoma) (Hsp70 interacting protein) (ST13):
cgccccccttctgcgcggtcacgccgagccagcgcctgggcctggaaccgggccgtagccccccccag
tttcgcccaccacctccctaccatg (Seq ID No: 304)

*Homo sapiens* solute carrier family 7 (cationic amino acid transporter, y+ system), member 7 (SLC7A7):
ctccctttcttaaatgcttggggtgagagagaagagaggctagggtggggcatggaggacacagag
agagagagtgctgtgtattccttccccgctactgtcctgtcctcagctaacttgctctgggacagc
ttccccagggctacagatactgcactcagctgactgtcctttcttctgggcccctggtcccagagc
agagctgacaaaggagattcctgagagagcaccttcttatcacagaaagtgctgagccaagagctc
ctagctgccccttttgcagatgtgaagggccagtgaaccttggacccagatggttgcttaatactc
ctttccccctccctcactccttcctttgcgggctgcctcacctcctccacccttcttgcttaaatc
cataggcatttgtctggccttcccttttactgctggctgggaaggaggagcatcagaccacagatc
ctggaaggcacttctctccctgactgctgctcacactgccgtgagaacctgcttatatccaggacc
aaggaggcaatgccaggaagctggtgaagggtttcctctcctccaccatg
(Seq ID No: 305)

*Homo sapiens* paired box 2 (PAX2):
ctccctttttctcctcaagtcctgaagttgagtttgagaggcgacacggcggcggcggccgcgctgc
tcccgctcctctgcctccccatg (Seq ID No: 306)

-continued

SEQUENCES:

*Homo sapiens* 5-aminoimidazole-4-carboxamide ribonucleotide formyltransferase/IMP cyclohydrolase (ATIC):
agccctcctacctgcgcacgtggtgccgccgctgctgcctcccgctcgccctgaacccagtgcctg
cagccatg (Seq ID No: 307)

*Homo sapiens* ATP synthase, H+ transporting, mitochondrial F1 complex, alpha subunit 1, cardiac muscle (ATP5A1):
ccttctttgcggctcggccattttgtcccagtcagtccggaggctgcggctgcagaagtaccgcct
gcggagtaactgcaaagatg (Seq ID No: 308)

*Homo sapiens* cyclin G1 (CCNG1):
cggccccttcggctccgagctgaccctgatcagggccgagttgtctcggcggcgctgccgaggcct
ccacccaggacagtccccctccccgggcctctctcctcttgcctacgagtcccctctcctcgtagg
cctctcggatctgatatcgtggggtgaggtgagcaggcccggggagggtggttaccgctgaggagc
tgcagtctctgtcaagatg (Seq ID No: 309)

*Homo sapiens* cadherin 16, KSP-cadherin (CDH16):
agctctcttcttgcttggcagctggaccaagggagccagtcttgggcgctggagggcctgtcctga
ccatg (Seq ID No: 310)

*Homo sapiens* cyclin-dependent kinase inhibitor 1B (p27, Kipl) (CDKN1B):
ttttcttcttcgtcagcctcccttccaccgccatattgggccactaaaaaaagggggctcgtcttt
tcggggtgtttttctcccccctcccctgtccccgcttgctcacggctctgcgactccgacgccggca
aggtttggagagcggctgggttcgcgggacccgcgggcttgcacccgcccagactcggacgggctt
tgccaccctctccgcttgcctggtcccctctcctctccgccctcccgctcgccagtccatttgatc
agcggagactcggcggccgggccggggcttccccgcagcccctgcgcgctcctagagctcgggccg
tggctcgtcggggtctgtgtcttttggctccgagggcagtcgctgggcttccgagaggggttcggg
ctgcgtaggggcgctttgttttgttcggttttgtttttttgagagtgcgagagaggcggtcgtgca
gacccgggagaaagatg (Seq ID No: 311)

*Homo sapiens* chimerin (chimaerin) 2 (CHN2):
tctcctcttcttcctttgtgtgtgcgcgagcggagttggggcggagggagaaggggggaggtcgctc
tgtctgtccgtctcccgccgcctctgcccggtctactcgaagtgcggcgggagaggcgggagccca
ggagagggtgcgggagctggcggggcggctcggagctgccaggacgccctggtcccagccgcgcac
aggggagcgtggacggcagaggggctcggcgggagccgagatccgcccgtcccggctgcccctcgg
cctccctctgctcccacctacccccctgacacccatagaaaagcgtgcaaaggcgcggagcgggacg
gaaaccacaaataaatagcggcggcggcagcgcgtcatctggtggagcaggaagtgcaggcagagt
ccggaggctggtgctttctgcgcgtccccaggactttgccatgggctgggggccgcggaggctgcg
agcggccgggcgagggcagcggcggcggcgtccgcaccggggctgagcgagcagcgacgcgagggg
cgcgcggagatg (Seq ID No: 312)

*Homo sapiens* citrate synthase (CS):
gggcctccttgaggaccccgggctgggcgccgccgccggttcgtctactctttccttcagccgcct
cctttcaaccttgtcaacccgtcggcgcggcctctggtgcagcggcggcggctcctgttcctgccg
cagctctctccctttcttacctccccaccagatcccggagatcgcccgccatggctttacttactg
cggccgcccggctcttgggaaccaaggcacccagtggcaagtactagctgagcatttgggagatgc
ttgtcttacttggctgttgcttctcctgctgctggggaaaaggaatgcatcttgtcttgttcttgc
agcccggcatgccagtgcttcctccacgaatttgaaagacatattggctgacctgatacctaagga
gcaggccagaattaagactttcaggcagcaacatggcaagacggtggtgggccaaatcactgtgga
catg (Seq ID No: 313)

*Homo sapiens* cathepsin S (CTSS):
atttcttttcaagtcaattgaactgaaatctccttgttgctttgaaatcttagaagagagcccact
aattcaaggactcttactgtgggagcaactgctggttctatcacaatg (Seq ID No: 314)

*Homo sapiens* deoxynucleotidyltransferase, terminal (DNTT):
cagtctccctcccttctggagacaccaccagatgggccagccagaggcagcagcagcctcttccca
tg (Seq ID No: 315)

*Homo sapiens* dual specificity phosphatase 3 (DUSP3):
cgctctccgcctcgcttgctcctgccgggcgtgcagggccccgccgccgccatg
(Seq ID No: 316)

*Homo sapiens* coagulation factor II (thrombin) receptor-like 2 (F2RL2):
catcctttccctgcggaggaccagggcaagtttcctgcctgcacggcacaggagagcaaacttcta
cagacagaccaaggcttccatttgctgctgacacatggaactgaggtgaaattgtgctccatgatt
ttacagatttcataacgtttaagagacgggactcaggtcatcaaaatg (Seq ID No: 317)

*Homo sapiens* Fc fragment of IgG, receptor, transporter, alpha (FCGRT): cgtcctctcagcatg (Seq ID No: 318)

*Homo sapiens* guanylate binding protein 2, interferon-inducible (GBP2):
ttacctctttttcttgtctctcgtcaggtctctgacattgacagagcctggacgttggaggaagcc
ccaggacgttggaggggtaaagtaaaagtccacagttaccgtgagagaaaaaagagggagaaagca -continued

SEQUENCES:

gtgcagccaaactcggaagaaaagagaggaggaaaaggactcgactttcacattggaacaaccttc
tttccagtgctaaaggatctctgatctggggaacaacaccctggacatg (Seq ID No: 319)

*Homo sapiens* G protein pathway suppressor 1 (GPS1):
cgctctttctcccttcagcagccagccagctctgtgtcagggtcggggggtgcagaaagtcaggac
agaatg (Seq ID No: 320)

*Homo sapiens* general transcription factor IIF, polypeptide 2, 30 kDa
(GTF2F2):
gttcctcttttcctcggttcccagtgttctggcaggtaaggaacgccggctcttcgcctctcagcg
cggcttgtcctttgttccggacgcccgctcctcagccctgcggctcctggggtcgctgctgcatcc
cgcacgcctccaccggctgcagacccatg (Seq ID No: 321)

*Homo sapiens* glycogenin 1 (GYG1):
cgctccctcccggtgccggcttctctgagtcaccaacctgaggctgccccggccgcctgcgcaccc
ggcagcaccatg (Seq ID No: 322)

*Homo sapiens* heat shock 70 kDa protein 9 (mortalin) (HSPA9):
agctctttgccgtcggagcgcttgtttgctgcctcgtactcctccatttatccgccatg
(Seq ID No: 323)

*Homo sapiens* iron-responsive element binding protein 2 (IREB2):
cttccttctttcctcccttgccagtccgcctgtcttcctccccgtcttccctgcccggcctccccc
ttcttcccccgctggcccccctccccggagggataatatggtctccggcgatg
(Seq ID No: 324)

*Homo sapiens* origin recognition complex, subunit 1 (ORC1):
ccaccttcttttcatttctagtgagacacacgctttggtcctggctttcggcccgtagttgtagaa
ggagccctgctggtgcaggttagaggtgccgcatcccccggagctctcgaagtggaggcggtagga
aacggagggcttgcggctagccggaggaagctttggagccggaagccatg
(Seq ID No: 325)

*Homo sapiens* RAB1A, member RAS oncogene family (RAB1A):
cattcctttctttcgattacccgtggcgcggagagtcagggcggcggctgcggcagcaagggcggc
ggtggcggcggcggcagctgcagtgacatg (Seq ID No: 326)

*Homo sapiens* cytohesin 2 (CYTH2):
gagtcttttcagcgctgaggactggcgctgaggaggcggcggtggctcccggggcgtttgagcggg
ctcacccgagcccgcgggccaacgcggatccaggcccgactggcgggaccgccccggattccccgc
gggccttcctagccgccatg (Seq ID No: 327)

*Homo sapiens* COP9 constitutive photomorphogenic homolog subunit 2
(*Arabidopsis*) (COPS2): atttctcctcccccctcccggccaagatg
(Seq ID No: 328)

*Homo sapiens* solute carrier family 9 (sodium/
hydrogen exchanger), member 3 regulator 1 (SLC9A3R1):
ggtcctctctcggctcctcgcggctcgcggcggccgacggttcctgggacacctgcttgcttggcc
cgtccggcggctcagggcttctctgctgcgctcccggttcgctggacgggaagaagggctgggccg
tcccgtcccgtccccatcggaaccccaagtcgcgccgctgacccgtcgcagggcgagatg
(Seq ID No: 329)

*Homo sapiens* peptidase (mitochondrial processing) beta (PMPCB):
ctaccttccttctagcagaaatg (Seq ID No: 330)

*Homo sapiens* RAB3D, member RAS oncogene family (RAB3D):
cggcccttcctccgccttctgggcggagcccgcgcgggatccgggtggctgcaggctgctggcttc
tgcggctgcggggtcggggtcgcggccagggccaagccgcagcgagttcacaggcggaacccctgc
aggcggcgcccctacgcgaggtcaccctgggaaggagcgcagcccacccggcccctccgcatcc
gagcaggacgcccgtctcctctccctgaggatttcaggtctccctgtcccaggaggcttgtgccaa
gatg (Seq ID No: 331)

*Homo sapiens* ATP-binding cassette, sub-family B (MDR/TAP):
tcttctctcggttcctctttcctcgctcaagatg (Seq ID No: 332)

*Homo sapiens* N-acylsphingosine amidohydrolase (acid ceramidase) 1
(ASAH1): ggctcttctttgcctctgctggagtccggggagtggcgttggctgctagagcgatg
(Seq ID No: 333)

*Homo sapiens* cytochrome c oxidase subunit VIc (COX6C):
ttttcctttagtcaggaaggacgttggtgttgaggttagcatacgtatcaaggacagtaactacca
tg (Seq ID No: 334)

*Homo sapiens* COX15 homolog, cytochrome c oxidase assembly protein
(yeast) (COX15):
gcttctcttttccttggcggaggagggagaccacagagccctgggttgtggaagaggtggctgttc
cctgtcatcagtatg (Seq ID No: 335)

-continued

SEQUENCES:

*Homo sapiens* c-src tyrosine kinase (CSK):
cccccttcccccgcctttcttccctccgcgacccgggccgtgcgtccgtcccccctgcctctgcctg
gcggtccctcctcccctctccttgcacccatacctctttgtaccgcacccccctggggacccctgcg
cccctcccctccccccctgaccgcatggaccgtcccgcaggccgctgatgccgcccgcggcgaggtg
gcccggaccgcagtgccccaagagagctctaatggtaccaagtgacaggttggctttactgtgact
cggggacgccagagctcctgagaagatg (Seq ID No: 336)

*Homo sapiens* versican (VCAN):
gagcctttctggggaagaactccaggcgtgcggacgcaacagccgagaacattaggtgttgtggac
aggagctgggaccaagatcttcggccagccccgcatcctcccgcatcttccagcaccgtcccgcac
cctccgcatccttccccgggccaccacgcttcctatgtgacccgcctgggcaacgccgaacccagt
cgcgcagcgctgcagtgaattttccccccaaactgcaataagccgccttccaaggccaagatg
(Seq ID No: 337)

*Homo sapiens* dystroglycan 1 (dystrophin-associated glycoprotein 1)
(DAG1):
gcgcctcttaggcttggcggtggcggcggcggcagcttcgcgccgaatccccggggagcggcggtg
gcggcgtcctggggccaggaggagcgaacacctgccgcggtcctcccgccggcgctgggctctgtg
tgctccgggatggagcaggtgtgcagagggtgagaacccagctctgggaccaagtcacttgcttcc
ttacttagcaagactatcgacttgagcaaacttggacctgggatg (Seq ID No: 338)

*Homo sapiens* DEAD (Asp-Glu-Ala-Asp) box helicase 5 (DDX5):
cccccctcttttggttacagacgtgagggctctttggagacgtaaacatctccgagtggcgagggtg
ggcggggctgggcttgggaaagggcggggtggcttgcttgaggtgtggaaagaccagaagaaggtg
aggtcaagagagtgcagaatgaggcattccaatggtgggtgggccctgacctgagagagtggcgcg
gggaggggtgaaagcgcggcgatcctggaacgccagcgggcgttgcggcctatgcgcgaggggcgg
ggcgattaggtcatagagcggctcccagcgttccctgcggcgtaggaggcggtccagactataaaa
gcggctgccggaaagcggccggcacctcattcatttctaccggtctctagtagtgcagcttcggct
ggtgtcatcggtgtccttcctccgctgccgcccccgcaaggcttcgccgtcatcgaggccatttcc
agcgacttgtcgcacgcttttctatatacttcgttccccgccaaccgcaaccattgacgccatg
(Seq ID No: 339)

*Homo sapiens* desmoplakin (DSP):
gctcctctgcgcccttgccgccctccgagccacagctttcctcccgctcctgcccccggcccgtcg
ccgtctccgcgctcgcagcggcctcgggagggcccaggtagcgagcagcgacctcgcgagccttcc
gcactcccgcccggttccccggccgtccgcctatccttggcccccctccgctttctccgcgccggcc
cgcctcgcttatgcctcggcgctgagccgctctcccgattgcccgccgacatg
(Seq ID No: 340)

*Homo sapiens* glutamyl-prolyl-tRNA synthetase (EPRS):
cttcctttcgcggggtcctccgtagttctggcacgagccaggcgtactgacaggtggaccagcgga
ctggtggagatg (Seq ID No: 341)

*Homo sapiens* acyl-CoA synthetase long-chain family member 4
(ACSL4):
gctcctcctcgtcccagcgctagcgggcacgcggttcctttttgcgagctttccgagtgccaggcg
ccggccggctgcgaagacgcggtgggccgcccctccgattgaaatcacagaagatattcgtgttct
tcttaagagaaaaagaggacattttagctttctcagttgaaggcgtactttattgtcggcttccaa
agattactaacttttatctgtatcactaagattgaactgccttggctgtactgctattcttactgc
tgcttctattattgccttcttcagcacaataaggctttcaaaagccaaagaataacaagaaataag
caccattttagaagcctttccactatg (Seq ID No: 342)

*Homo sapiens* fibroblast activation protein, alpha (FAP):
tggtccttttcaacggttttcacagatccagtgacccacgctctgaagacagaattagctaacttt
caaaaacatctggaaaaatg (Seq ID No: 343)

*Homo sapiens* UDP-N-acetyl-alpha-D-galactosamine:
polypeptide N-acetylgalactosaminyltransferase 3 (GalNAc-T3) (GALNT3):
ctgcctctccaggcaacgcgggaggcccagcgggaaggcaggaggcggcggcggaggaggagctct
actgagccgcaactgtggcgacagcaaccggagtcgcagccgccgccacctgcacctggcgcctag
cccacgtccagcgcctgcccggccgccgcttcccgccaccctgccctgcccacccgccaggtacta
ccattaaagataccttcttctcagcaaatctatgataaaaaatataagtaacagaagaagaaataa
ctgttatttgtcaagtgacaagcttttaatgtcagaatg (Seq ID No: 344)

*Homo sapiens* glypican 3 (GPC3):
acgtctcttgctcctcagggccactgccaggcttgccgagtcctgggactgctctcgctccggctg
ccactctcccgcgctctcctagctccctgcgaagcaggatg (Seq ID No: 345)

*Homo sapiens* interleukin enhancer binding factor 2, 45 kDa (ILF2):
acgcctcttcagttgtctgctactcagaggaaggggcggttggtgcggcctccattgttcgtgttt
taaggcgccatg (Seq ID No: 346)

*Homo sapiens* nucleosome assembly protein 1-like 1 (NAP1L1):
gggtctttttagcgccatctgctcgcggcgccgcctcctgctcctcccgctgctgctgccgctgc
cgccctgagtcactgcctgcgcagctccggccgcctggctccccatactagtcgccgatatttgga
gttcttacaacatg (Seq ID No: 347)

-continued

| SEQUENCES: |
| --- |

*Homo sapiens* asparaginyl-tRNA synthetase (NARS):
cgctctctgatgcaacgccggaatcgcggaaaccgccggtgcacgttggagtcataagacggcgtc
ggtgttgcagtctgtgtccttggaggtgaccagggccactgcaggcatg (Seq ID No: 348)

*Homo sapiens* NADH dehydrogenase
(ubiquinone) 1 alpha subcomplex, 10, 42 kDa (NDUFA10):
cgtccccttgggtccttgatcctgagctgaccgggtagccatg (Seq ID No: 349)

*Homo sapiens* NADH dehydrogenase (ubiquinone) Fe—S protein 2, 49 kDa
(NADH-coenzyme Q reductase) (NDUFS2):
ttctccttcccgcagtctgcagccggagtaagatg (Seq ID No: 350)

*Homo sapiens* NADH dehydrogenase (ubiquinone) Fe—S protein 5, 15 kDa
(NADH-coenzyme Q reductase) (NDUFS5):
catcctttacggcaggcgtccgcgtcgctagctagtcgttctgaagcggcggccagagaagagtca
agggcacgagcatcgggtagccatg (Seq ID No: 351)

*Homo sapiens* phosphoenolpyruvate carboxykinase 2 (mitochondrial)
(PCK2):
ccctccttttaagcgcctcccgccagcctctgctgtggctcgcttcgccgcgctccctccttccc
cgccttccatacctccccggctccgctcggttcctggccaccccgcagcccctgcccaggtgccat
g (Seq ID No: 352)

*Homo sapiens* serpin peptidase inhibitor, clade B (ovalbumin),
member 6 (SERPINB6):
ctcccttcgcgctccggacgggcgacggtagctcgagacccgggactccgcccgcctccccgcgag
tatttgaggtccggggcggctccggcgcctctgcccgccgttctgctcgctcgctccccgctctgg
agtctgccatcatg (Seq ID No: 353)

*Homo sapiens* Rab geranylgeranyltransferase, alpha subunit
(RABGGTA):
ttctctcctcagacttcaagggctaccactggacccttcccctgtcttgaaccctgagccggcacc
atg (Seq ID No: 354)

*Homo sapiens* Rab geranylgeranyltransferase, beta subunit
(RABGGTB): ctctctcctttccctgttagacatg (Seq ID No: 355)

*Homo sapiens* small nuclear ribonucleoprotein polypeptide A
(SNRPA):
agttctctccgcacgcgggctggagaagcgggtcctacgcacgctttgttgtcgcgctttgcctcc
gtccttgcccctactcccgccttacctgacttccttttcggaggaagatccttgagcagccgacgt
tgggacaaaggatttggagaaacccagggctaaagtcacgtttttcctcctttaagacttacctca
acacttcactccatg (Seq ID No: 356)

*Homo sapiens* sterol regulatory element binding transcription factor
2 (SREBF2):
cgccctttctgtgcggcgcccgggcgcaacgcaaacatggcggcgggtggcacccgtcggtgaggc
ggtgccgggcgggggttgtcgggtgtcatgggcggtggcgacggcaccgcccccgcgtctccctga
gcgggacggcaggggggcttctgcgctgagccgggcgatg (Seq ID No: 357)

*Homo sapiens* translin (TSN):
ctgccctttggacgcgcgcctcggttccgaacgcagcggacggcgcctcaggcagcgcggcggaca
gcccgtcctccggcgcgccgcgagcctcggaggaccctagcgacggtcgtggcgtaagaccggggg
gacgcggcggtagcggcggccgttgcgattgattgcgctggttgcctgcggcgtccacttccttgg
ccgcccttgctacactggctgattgttgtgcagccggcgccatg (Seq ID No: 358)

*Homo sapiens* Fanconi anemia, complementation group G (FANCG):
ccaccctttctcgaggctgtggcctccgcgagagccgagcgggccgcaccgccggccgtgcgactg
ccccagtcagacacgaccccggcttctagcccgcctaagcctgtttggggttgctgactcgtttcc
tccccgagtttcccgcgggaactaactcttcaagaggaccaaccgcagcccagagcttcgcagacc
cggccaaccagaggcgaggttgagagcccggcgggccgcggggagagagcgtcccatctgtcctgg
aaagcctgggcgggtggattgggaccccgagagaagcaggggagctcggcggggtgcagaagtgcc
caggcccctccccgctggggttgggagcttgggcaggccagcttcacccttcctaagtccgcttct
ggtctccgggcccagcctcggccaccatg (Seq ID No: 359)

*Homo sapiens* DEAD (Asp-Glu-Ala-Asp) box polypeptide 39B (DDX39B):
ttccctccttcgtcgctgttgctgccgccatacgcgctctccctgtttagctcttctgttagaaat
agtatctttgttttcctttgctgttcctcaatcccctactcttcaccccttgttttcacctatttt
gcgagaacccatccagatccccccttcccttcttcccctgccggcccagttatg
(Seq ID No: 360)

*Homo sapiens* RAB11A, member RAS oncogene family (RAB11A):
ccgccctttcgctcctcggccgcgcaatg (Seq ID No: 361)

-continued

SEQUENCES:

*Homo sapiens* SPARC-like 1 (hevin) (SPARCL1):
agctctttccctttggtttgcaagcactgcctgtaaagccctcgcatgagaggccagcctgctag
ggaaatccaggaatctgcaacaaaaacgatgacagtctgaaatactctctggtgccaacctccaaa
ttctcgtctgtcacttcagaccccactagttgacagagcagcagaatttcaactccagtagactt
gaatatgcctctgggcaaagaagcagagctaacgaggaaagggatttaaagagtttttcttgggtg
tttgtcaaacttttattccctgtctgtgtgcagaggggattcaacttcaatttttctgcagtggct
ctgggtccagccccttacttaaagatctggaaagcatg (Seq ID No: 362)

*Homo sapiens* cyclin B2 (CCNB2):
ctcccttttcagtccgcgtccctccctgggccgggctggcactcttgccttccccgtccctcatg
(Seq ID No: 363)

*Homo sapiens* cytochrome c oxidase subunit VIIa polypeptide 2 like
(COX7A2L): ggtccttctctggggcggtcgcgttggcagcggatgcgggaagccggactctg-
ggcgtcatg (Seq ID No: 364)

*Homo sapiens* lysophosphatidic acid receptor 2 (LPAR2):
cgccctctcagcaacccgcacagggcgcacccggacgctctaccgctcccgccgcagtcgccgggc
catgggcctcgagcccgccccgaacccccgcgagcccgccttgtctgcggcgtgactggaggccca
gatg (Seq ID No: 365)

*Homo sapiens* adaptor-related protein complex 4, mu 1 subunit
(AP4M1):
cgttcttttgttccggggccgcagggcggggcaggcccgactttcgccgtcttcttgtctactctc
cagaacggccatg (Seq ID No: 366)

*Homo sapiens* budding uninhibited by benzimidazoles 3 homolog
(yeast) (BUB3):
cttcctctccgcctccttcgcctagcctgcgagtgttctgagggaagcaaggaggcggcggcggcc
gcagcgagtggcgagtagtggaaacgttgcttctgaggggagcccaagatg
(Seq ID No: 367)

*Homo sapiens* DEAD (Asp-Glu-Ala-Asp) box helicase 21 (DDX21):
ctacctcttcctctccacgcggttgagaagaccggtcggcctgggcaacctgcgctgaagatg
(Seq ID No: 368)

*Homo sapiens* solute carrier family 33 (acetyl-
CoA transporter), member 1 (SLC33A1):
tgctctctgccgcattgatagcagcgagagctggaggtgttgggtcgggagaccagccgttcgatc
ccgccgcaggtaggagctggtttccatcctggcaccacggcacacacctccagcctcgagcccggc
gctgctgcccggggtctccttcaggctctttgacgccgttccagggggcacctatccaggcatcc
tctgggcctctagccagaggactggctcccggcttcagcactccgggctgcagtaagaagtgccct
tatcgctctgagccctgccaccatcccgtgaaccaccgaaaccctggtccagcgcgacagccttgg
acctgggactggacggatccaaaacgctcagcctcggcccccacagacggggctctgcatcgtct
ctgatatg (Seq ID No: 369)

*Homo sapiens* G protein-coupled receptor 37 like 1 (GPR37L1):
tgctcttcctgggctggctgtctcctgctcatccagccatg (Seq ID No: 370)

*Homo sapiens* neuronal regeneration related protein homolog (rat)
(NREP):
ctgtctttctagcatgttgcccttttcaaccacatttgtgtttcaggtgtagagaggagagagag
tgaacagggagcggggcttttgtctgttggtctccctggactgaagagagggagaatagaagccca
agactaagattctcaaaatg (Seq ID No: 371)

*Homo sapiens* vesicle-associated membrane protein 3 (cellubrevin)
(VAMP3): gcttctctgctgaccctctctcgtcgccgctgccgccgccgcagctgccaaaatg
(Seq ID No: 372)

*Homo sapiens* synaptosomal-associated protein, 29 kDa (SNAP29):
cctccttctgtttcccagaccgagagccgcgccggcaccatg (Seq ID No: 373)

*Homo sapiens* Ion peptidase 1, mitochondrial (LONP1):
cccccctcttctccgcgtaggcccagctccctgaagcggctgtttcgagccacgcgcccatcgggta
ccgaggcacgcgccgggcgtcacgtgcgtttcgcggcgagcggaaatgacgcgagttgtgtgagcc
gccagtatggccgggctatg (Seq ID No: 374)

*Homo sapiens* kinesin family member 3B (KIF3B):
ctgtctctccccatccggggcagcggggaatggctgagccaggggttcgccgcccccgccgccgcc
gccgccgccgccgccgccgccgccgcccgctttcggctcggcctcaggaccgtagcatcctgaga
cattttgaattgacacttctcaagatttgactggatcagagttcatcatg
(Seq ID No: 375)

*Homo sapiens* transmembrane 9 superfamily member 2 (TM9SF2):
cttcctttatctctggcggccttgtagtcgtctccgagactccccacccctccttccctcttgacc
ccctaggtttgattgccctttccccgaaacaactatcatg (Seq ID No: 376)

-continued

| SEQUENCES: |
|---|

*Homo sapiens* cytosolic iron-sulfur protein assembly 1 (CIA01):
gagcctctgtcggccgcggaagcctggagtgggcggtacgcagacgcgcgcggtgagacccgctgt
ctgctcagcggactctgcccgcccccacctcccccctgcgtcgggccgacatg
(Seq ID No: 377)

*Homo sapiens* GRB2-related adaptor protein 2 (GRAP2):
caccctctttcagagtggtacatggaagacagcacaaagtggatccatactctgaaatgcagtaac
tctgatgcttgaatttgtctcccttcttgccagaaaggattctaataactcggtgtcaaagccaag
acataaactcaaccccttctcttccaaaagcttcacgttacagcatg (Seq ID No: 378)

*Homo sapiens* leupaxin (LPXN):
gtacctttctcggggtgtctgcgtaactgcccagacttgccttggtttggtcagatgacacctcct
ctgggactggctagccagcgttcatg (Seq ID No: 379)

*Homo sapiens* SH3-domain binding protein 5 (BTK-associated)
(SH3BP5):
tttcctctgctccgccgcggccggaggtatccgcatcggcgagctgcgtctcccgggtgtcggccc
cggcggctccccgaccgtgcccggctgtggcgaggcggctccagcccagcctgtggcagccgcgac
ccccggggcgctccggagcccactgcgcggcgcgcgtgccggctgcctgcatg
(Seq ID No: 380)

*Homo sapiens* phosphatidylinositolglycan anchor biosynthesis, class
B (PIGB): ctttcttccgccttaggaaggtggcggccagggatg (Seq ID No: 381)

*Homo sapiens* lipopolysaccharide-induced TNF factor (LITAF):
cggccctttttctcggggcgcccgagaggccagctcagacctcccggctcgacaggcggcgcgggcg
gcggtgagtgcggcgcggggacgccggggcgcggggaccagcgggagacagcggggggccggtggc
gccagcacctgctgggggccccgggcactgagcccttggctggggcctcctgggatgccagggggc
gcgggtcgggtcgcgggcatcgaggcgcggcggagggcgtgggggcccggccggggcggggtccgg
cctcccagcgctggtcccggccgcgtctccggttgggttcagctcctgcgtcccagagtggcccga
tcgcgcgtggcggggtcgtccggccccccacccgaacgagcgcccttcgcggcccgccgcgtccccc
tccccggagaggacggcccctgggctttttagaaaaaggcgcgattctctctagtgactcaggttg
agatttccagaaatatcccccggggttcagaaacaaaaccaaaacaaacaaaaaaacccccaacga
attcccaaatgctatttgccaaacatttgacttctaggggcgcgggtacccgcgtttctctccctg
cccccgcgacttcgcgcaagatccgggaaggacacccgaggcccctgggagaccctggggaggtga
aaatcagagagcgaagcgggccgtggccccctaggcctgacccctccccgcggggtaaggcgggcac
cccgcgagcgcaggggtcctcttactgctgatggcacccagctctgggcccagacgccgctcaccg
tccaccgccggtgctgggtaaaatg (Seq ID No: 382)

*Homo sapiens* etoposide induced 2.4 mRNA (EI24):
ccacccccttcggctctgggccccgcctcgtggtgccggctggttcttcgcgctcgcccgacttccc
agcggccccgtgcggcccgggcatgcccagtgcgggcgcagcggccccggccctggaagcgccccg
gcggagctggcctgcggtgggctaggggcagggccggagccgcggcggcggagctgtggatccttc
atgatgagagatttggggacacttctctctcctgtgtgtagttgatagtttggtggtgaagagatg
(Seq ID No: 383)

*Homo sapiens* chromosome 14 open reading frame 2 (C14orf2):
tgacctttccgagttggctgcagatttgtggtgcgttctgagccgtctgtcctgcgccaagatg
(Seq ID No: 384)

*Homo sapiens* peroxiredoxin 6 (PRDX6):
attcctccgcgcgctgggacaggctgcttcttcgccagaaccaaccggttgcttgctgtcccagcg
gcgccccctcatcaccgtcgccatg (Seq ID No: 385)

*Homo sapiens* solute carrier family 29 (nucleoside
transporters), member 1 (SLC29A1):
ctctcttccgcccggcggcccacaccggtcaggcccggcgcgggctgcgctctccagctgtggcta
tggccccagccccgagatgaggagggagagaactaggggcccgcaggcctgggaatttccgtcccc
caccaagtccggatgctcactccaaagtctcagcaggcccctgagggagggagctgtcagccaggg
aaaaccgagaacaccatcaccatg (Seq ID No: 386)

*Homo sapiens* heterogeneous nuclear ribonucleoprotein F (HNRNPF):
cgaccttcctgccgggccgggcggtccgaggctgctggagtgccgtgagcaggccgcgggaacgtc
gccgtcaccttgtctcggggcctcggcgctgcttcccgccaaaacacgtttaccgcgcgcccgggc
ctcccaccttgcggaagggaccccaccaccacttggatttctgttgcaggttgagaacaaaaacat
gcacctggagtttccccggagccctctgcgtggttgagcttcggtggaatttcggggctcttggct
gccagccgcgcttgcctggtagcaacagaaaccagtcctgctcgcctccgtggacatttcattacc
atccagaagtgtctcccactgaaggcatccgtggttgtttttaagccacaaaaaagccacacccaa
gatcacctgacacccaccctgacaagtgtccatg (Seq ID No: 387)

*Homo sapiens* islet cell autoantigen 1, 69 kDa (ICA1):
ccgccccttccctcgccttcggctgacgctgacgtcggatgagtgatccggagggacgctccgac
cgcggccgggaggctcctgggggccggggctccgaggttataatataacttatcctctcatgcttt
tttcctgccccttctccccaaatcatcaacaatagaagaagaagaaaacatg
(Seq ID No: 388)

-continued

| SEQUENCES: |
|---|
| *Homo sapiens* PWP2 periodic tryptophan protein homolog (yeast) (PWP2): gtgtctctgtgggcggccgccgggttgagctgcggcacacgtgcgacggccgtgatg (Seq ID No: 389) |
| *Homo sapiens* glutaminyl-tRNA synthetase (QARS): gtttcttttagtttccggtgtctctgcaatg (Seq ID No: 390) |
| *Homo sapiens* stearoyl-CoA desaturase (delta-9-desaturase) (SCD): cggcctctgtctcctcccctcccgcccttacctccacgcgggaccgcccgcgccagtcaactcct cgcactttgcccctgcttggcagcggataaaagggggctgaggaaataccggacacggtcacccgt tgccagctctagcctttaaattcccggctcggggacctccacgcaccgcggctagcgccgacaacc agctagcgtgcaaggcgccgcggctcagcgcgtaccggcgggcttcgaaaccgcagtcctccggcg accccgaactccgctccggagcctcagcccctggaaagtgatcccggcatccgagagccaagatg (Seq ID No: 391) |
| *Homo sapiens* fragile X mental retardation, autosomal homolog 1 (FXR1): cggcctttgcggttccaacatg (Seq ID No: 392) |
| *Homo sapiens* musculin (MSC): tagccttttcaaaaggcgcagcttaccgcggtgcgcgcggattctggacttgggcgccaactcgta gtccacgctccccggggtcagcagaggggcgctcacgctctcgccacccacctcgctttctcaccc cgcgcttcccggcctgggtttttagtcttccttggagcgctctctggcctccgcctccgccaggga gcggaaggcggagacagcgagactggccagggggaggaaagaggacgcgtgtgggcaagggggac aacgggatg (Seq ID No: 393) |
| *Homo sapiens* RNA binding motif protein 8A (RBM8A): cgacctttcccctctgcgacagtttcccgaggtacctagtgtctgagcggcacagacgagatctcg atcgaaggcgagatg (Seq ID No: 394) |
| *Homo sapiens* heparan sulfate (glucosamine) 3-O-sulfotransferase 1 (HS3ST1): ggtcctctgcgccctggcagccaggagtcgccgccacgaccgccgggtctcagtgggtgcctgcgc cttctccccgcccgcctgccccgggccatccagaaacttgctctacccgccgcgggtgctcggcag tgctgcccatggcccagcccaggagcctatttagggcgccggacgggctggacagaggcgcggctc agtaattgaaggcctgaaacgcccatgtgccactgactaggaggcttccctgctgcggcacttcat gacccagcggcgcgcggcccagtgaagccaccgtggtgtccagcatg (Seq ID No: 395) |
| *Homo sapiens* solute carrier family 12 (potassium/ chloride transporters), member 6 (SLC12A6): ctgtctcttgtaggcagggatcacagtctgaaacgacagcaaggaagaggtaggcagggaaaacta actggaaggaagtttaaatacagaaagagcaaagtattatctaactataacaatg (Seq ID No: 396) |
| *Homo sapiens* apelin receptor (APLNR): cttcctccagggtctggagaacccagaggcagctcctcctgagtgctgggaaggactctgggcatc ttcagcccttcttactctctgaggctcaagccagaaattcaggctgcttgcagagtgggtgacaga gccacggagctggtgtccctgggaccctctgcccgtcttctctccactccccagcatg (Seq ID No: 397) |
| *Homo sapiens* calpain 1, (mu/I) large subunit (CAPN1): cgctcttcctggttgggccctgccctgagctgccaccgggaagccagcctcagggactgcagcgac ccccaaacacccctcccccaggatg (Seq ID No: 398) |
| *Homo sapiens* cyclin C (CCNC): cttcctttcgccgtcgccgccgcggagcggagtcgagccgagctgatttgatcgaggagcgcggtt accggacgggctgggtctatggtcgctccgcgggccgctccgccggctggtgctttttttatcaggg caagctgtgttccatg (Seq ID No: 399) |
| *Homo sapiens* glutamate dehydrogenase 1 (GLUD1): cttcctccctagtcgcggggagtctgagaaagcgcgcctgtttcgcgaccatcacgcacctcccct ccgcttgtggccatg (Seq ID No: 400) |
| *Homo sapiens* guanine nucleotide binding protein-like 1 (GNL1): cctccttcctcgccgccggggcgccctctcggtgccactggctctcacgtgccagtagcccacccc gcatcatcctctcgcctcgctcctggagggaagtgactatatctcccccgtccgccttccatcgcc gccgcggcggtaattctgtcgggcccgcccgctgacgtcacctgctagccccgcctcctctagggt cccgggcccctgcggcgggggctgccccgggggcagtcagttgaggcggcgggagctcggcggag ggcgggccaggtgactggtccgggccatg (Seq ID No: 401) |
| *Homo sapiens* lysophosphatidic acid receptor 4 (LPAR4): aggccttttttgtgtcctgtttgctaaaggcatgcgggctacagcattcaagagagggagtcgttaa caaagggaaagagataaatgtaaataagctcacatttacagaatgagcggtttgcagtaaaaagct gcggcagcccagagtctgctactttaggctgggctaacctttccctgtaaaaaaaaaaaaaaaaa aaaaaaaaaaaaatggataaaaatatgcacttccaaagggcgagttgcccatttacatgtttatta gctaattatctacaggcatcagcacattctctcatctagcacactctttcttggggaggaaaatat ttcctaccggtccatagtgtcagagtggtgaacccctgcagccagcaggcctcctgaaaaaaaagt ccatg (Seq ID No: 402) |

-continued

SEQUENCES:

*Homo sapiens* G protein-coupled receptor kinase 5 (GRK5):
gctcctctttgcagaggggaaactcttgggctgagagcaggaataatgcggtaggcaaggcgggc
tgctggctcccccggctccggcagcagcggcggcagcccgagcagcggcagcagcagcggcagcac
cccaggcgctgacagccccgccggccggctccgttgctgaccgccgactgtcaatg
(Seq ID No: 403)

*Homo sapiens* glutamic-pyruvate transaminase
(alanine aminotransferase) (GPT):
agccctttctgtccctcccagtgaggccagctgcggtgaagagggtgctctcttgcctggagttcc
ctctgctacggctgccccctcccagccctggcccactaagccagacccagctgtcgccattcccac
ttctggtcctgccacctcctgagctgccttcccgcctggtctgggtagagtcatg
(Seq ID No: 404)

*Homo sapiens* hydroxyacyl-CoA dehydrogenase (HADH):
gggtctcctcgctgtcgccgccgctgccacaccatg (Seq ID No: 405)

*Homo sapiens* high density lipoprotein binding protein (HDLBP):
tcttctcctttaccaagatggcggcttgtccctgtttcgccacagttcctaccttatgagctcggt
tttcttatgcttataagagtggaacagcaaaagctggcaggctgacagaggcggcctcaggacgga
ccttctggctactgaccgttttgctgtggttttcccggattgtgtgtaggtgtgagatcaaccatg
(Seq ID No: 406)

*Homo sapiens* histidine triad nucleotide binding protein 1 (HINT1):
gttcctcccttcttccgagcctctcctctggccgccgcgcgggagagaggccgagatg
(Seq ID No: 407)

*Homo sapiens* heat shock 70 kDa protein 1A (HSPA1A):
ctaccttttcgagagtgactcccgttgtcccaaggcttcccagagcgaacctgtgcggctgcagg
caccggcgcgtcgagtttccggcgtccggaaggaccgagctcttctcgcggatccagtgttccgtt
tccagcccccaatctcagagcggagccgacagagagcagggaaccggcatg
(Seq ID No: 408)

*Homo sapiens* nucleolin (NCL):
cagtctttcgcctcagtctcgagctctcgctggccttcgggtgtacgtgctccgggatcttcagca
cccgcggccgccatcgccgtcgcttggcttcttctggactcatctgcgccacttgtccgcttcaca
ctccgccgccatcatg (Seq ID No: 409)

*Homo sapiens* nuclear factor, interleukin 3 regulated (NFIL3):
ccgcccctttctttctcctcgccggcccgagagcaggaacacgataacgaaggaggcccaacttca
ttcaataaggagcctgacggatttatcccagacggtagaacaaaaggaagaatattgatggatttt
aaaccagagtttttaaagagcttgagaatacggggaaattaatttgttctcctacacacatagata
gggtaaggttgtttctgatg (Seq ID No: 410)

*Homo sapiens* protein phosphatase 1, regulatory subunit 3C
(PPP1R3C):
cagtctctcccagcgaccgccgcgggggcaaggcctggagctgtggttcgaatttgtgcaggcagc
gggtgctggcttttagggtccgccgcctctctgcctaatg (Seq ID No: 411)

*Homo sapiens* protein tyrosine phosphatase, non-receptor type 14
(PTPN14):
agttctttccaactttttctcggcggagtgagcgcagcgggcgcagactcgggggcaggttgctgt
gcttctccgggctcagccgcctgctctcctggctcaggtcctcggggagccctagacagacatcaa
gtggccactggcgctccttcccctcccagctgagccatcctccccggcctcctcgggcgggacagc
cccgtgcttaggtttttctcctttttctcccccggtgcgcctctgctcggactctcgcgccgggatc
gcggcggaaacctccctcccctttcgcctcctgcggctccttcccttcgcccctcctccgccagtc
actggaatcaattccgtggggaatcggctccgccgccgcgaaggacagcctttccgcgcgggactc
cggggcgccacgggggccatgtaagcagctatcttccagagggccacactgggcatggacaccctt
ttccctgcctggaggagcacaggtgatagtgtaattttccagtcacgaaactgctaaggccatctc
aggggcgtgtgcgccaggataggcgggcggcgtccgaggaccacatagccatg
(Seq ID No: 412)

*Homo sapiens* selenoprotein P, plasma, 1 (SEPP1):
ctttcttttaagttgataacaatcagctcaggggtttgctctgcttgcaaggtcactgcaagaatg
aacattgaactttggactatacctgaggggtgaggtaaacaacaggactataaatatcagagtgtg
ctgctgtggctttgtggagctgccagagtaaagcaaagagaaaggaagcaggcccgttggaagtgg
ttgtgacaaccccagcaatg (Seq ID No: 413)

*Homo sapiens* serine hydroxymethyltransferase 2 (mitochondrial)
(SHMT2):
agctcttctcgcgcatgcgttctccgaacggtcttcttccgacagcttgctgccctagaccagagt
tggtggctggacctcctgcgacttccgagttgcgatg (Seq ID No: 414)

SEQUENCES:

*Homo sapiens* tyrosine kinase with immunoglobulin-like and EGF-like domains 1 (TIE1):
tttcctcttcctccccagcaccgacccacactgaccaacacaggctgagcagtcaggcccacagca
tctgaccccaggcccagctcgtcctggctggcctgggtcggcctctggagtatg
(Seq ID No: 415)

*Homo sapiens* coiled-coil domain containing 6 (CCDC6):
cctcctttccccagcccgccgcggccatg (Seq ID No: 416)

*Homo sapiens* nuclear receptor coactivator 4 (NCOA4):
ggacctttcgcactcgggtcaggggtaaagcagcctgtcgcttgccgggcagctggtgagtcggtg
acctggcctgtgaggagcagtgaggagaatg (Seq ID No: 417)

*Homo sapiens* chromatin assembly factor 1, subunit B (p60) (CHAF1B):
gtgcctctgactgtccgggtccctccagcattttgcagctttctcctgtcttgaagaagtagaacg
gtgcccgagaaacgtttttccccttcgagactcaggaggatgaaagtcatcacttgtgaaatagcc
tggcacaacaaggagcccgtgtacagcctggacttccagcatg (Seq ID No: 418)

*Homo sapiens* 3'-phosphoadenosine 5'-phosphosulfate synthase 1 (PAPSS1):
agccccgccccgctcgctggcctgccctcctcttgctaccctcccggcgcagagaaccccggctgc
tcagcgcgctccgcggtcatg (Seq ID No: 419)

*Homo sapiens* Fas apoptotic inhibitory molecule 3 (FAIM3):
tgccctcctcttgctaccctcccggcgcagagaaccccggctgctcagcgcgctccgcggtcatg
(Seq ID No: 420)

*Homo sapiens* N-acetylated alpha-linked acidic dipeptidase 2 (NAALAD2):
cagcctcctgccagcgcgctctctgtttctctgcagccccgaagctcgcgaatgtagcaggcgccc
caagctcggtcctcaagaagccatggcggaatccaggggccgtctgtacctttggatgtgcttggc
tgctgcgctggcatctttcctgatgggatttatggtgggtaagt (Seq ID No: 421)

*Homo sapiens* abl-interactor 1 (ABI1): ctgtctctttaacgcgagaggaag-
cgatgcagaggggtggaaaatg (Seq ID No: 422)

*Homo sapiens* potassium voltage-gated channel, Isk-related family, member 3 (KCNE3):
cttccttttctgccttctctcctgctttctagctctgggctttcccagctccgaagtcaatactga
gatcccagatgtgtccagagacatcctgaagaggctcgggggtggaggagccttagtgtgtccaca
aagggactcctgaaactgactgagagccagt (Seq ID No: 423)

*Homo sapiens* target of mybl (chicken)-like 1 (TOM1L1):
ggccctctggcgctaccatg (Seq ID No: 424)

*Homo sapiens* ubiquitin-like modifier activating enzyme 2 (UBA2):
cgccccttcccccacccgcttccggccgcggctcggttctcccgcctccgcctccgccgcggctcgt
ggttgtcccgccatg (Seq ID No: 425)

*Homo sapiens* scavenger receptor class B, member 2 (SCARB2):
ctccctccttgcagttggatccctggcgggtgcggcccggcccggcccgtgagcggcgcacagaat
g (Seq ID No: 426)

*Homo sapiens* insulin induced gene 1 (INSIG1):
actcctcctttcccccgccccgcctccgttcggagagccggcgggcgggcgcctctcggccaggaa
gcgcctcttggacgcgtgtgaccgatg (Seq ID No: 427)

*Homo sapiens* kinesin family member C3 (KIFC3):
aggcctcttctgaggctctaggtgccccagtagcagggccttctgcagcaaggccgggaactgctg
caccattggtgtgttttaccttaagggactccaggcagcttccttgctgggaagatattcatttgc
tggggtggggctgggggtgcagaggtaggaagtgctgtggctagaaggcggcctggccagcgagta
ggtggtggagcgagtgagagcgtgtgcgctgtaaacagtgtgagtgcatg
(Seq ID No: 428)

*Homo sapiens* LIM domain kinase 2 (LIMK2):
aggcctcttctgaggctctaggtgccccagtagcagggccttctgcagcaaggccgggaactgctg
caccattggtgtgttttaccttaagggactccaggcagcttccttgctgggaagatattcatttgc
tggggtggggctgggggtgcagaggtaggaagtgctgtggctagaaggcggcctggccagcgagta
ggtggtggagcgagtgagagcgtgtgcgctgtaaacagtgtgagtgcatgtgcgccagcgcgtgca
aggacacggtaagggatgtacatgtattgtctcgtgagtaagagcttgtgtgtgtgttgggatggg
aagacacgtactggtatgagagcccgcgtgagaagtgtatgtgtgagtactcgcgtggaagttttg
cactcgggtttgaggctgtgcaaaagtacgcatggctcaccaggtgtggggctgtgtgggctgcct
cgtgtgtgccagcccgtgtgcaggcctgttttgtgagagccttcagggaacgcatgagcacgtgtg
ccagtgcgagtgcgggacgcggggaggcgggagagaccgagtgggaggccccgcgaaggagtggga
gtgggagtgggagtgccggcgggagacctgcgggggcgcgcccgggctgacgcgtgcgcgccagtg
cgcgtgagtgcgggcgcgcgccgccgcccccccgccggggtcggagccggttgccatgggaacgcgc -continued

SEQUENCES:

cgcggcccgagttaatcatttcctgtggaaagtgtgcgggagggggcgcgagcgggctggccgagga
ggaggcggcggcgtggagctgcctcctgccggcgggccgggccgggccgagccccgggcgctgcgg
cgacgcctggatcctgcctccgccaggccggctgcctggtgccccgaggaggctgctgagccccag
gccatg (Seq ID No: 429)

*Homo sapiens* lectin, mannose-binding, 1 (LMAN1): cctcctccgcgttcca-
gaatccaagatg (Seq ID No: 430)

*Homo sapiens* MRE11 meiotic recombination 11 homolog A
(*S. cerevisiae*) (MRE11A):
cgttctctcccgcggaattcaggtttacggccctgcgggttctcagaggcaagttcagaccgtgtt
gttttcttttcacggatcctgccctttcttcccgaaaagaagacagccttgggtcgcgattgtggg
gcttcgaagagtccagcagtgggaatttctagaatttggaatcgagtgcattttctgacatttgag
tacagtacccaggggttcttggagaagaacctggtcccagaggagcttgactgaccataaaaatg
(Seq ID No: 431)

*Homo sapiens* nascent polypeptide-associated complex alpha subunit
(NACA):
cttccttctgcaacaggcgtgggtcacgctctcgctcggtctttctgccgccatcttggttccgcg
ttccctgcacagtaagtactttctgtgccgctactgtctatccgcagccatccgcctttctttcgg
gctaagccgccccggggactgagagttaaggagagttggaggctttactgggccacagggttccta
ctcgcccctgggcctccggacaaaatggggtctgcggttggtgtcctggcaaaagcagggtagaag
ggctgcggggcgggcccagaatccgagcctgcagagatgggagcagttgcagtgttgagggcggaa
gaggagtgcgtcttgttttgggaactgcttcacaggatccagaaaaggaaatg
(Seq ID No: 432)

*Homo sapiens* claudin 11 (CLDN11):
cgcccttcgccgctgagctcgcagcctccggcgcccacctccacctccagtgtcccgcctcgggcc
gtcgccctccagcggctcgcgagcgtgggagacgtacctgggcaggcactgtccagcccaggccca
ggcacagccgtgaggggcgaggcacggggacatcctggcggccaccatg (Seq ID No: 433)

*Homo sapiens* retinoblastoma binding protein 4 (RBBP4):
ccgcccctcccgcaacgctcgaccccaggattcccccggctcgcctgcccgccatg
(Seq ID No: 434)

*Homo sapiens* acyl-CoA synthetase medium-chain family member 3
(ACSM3):
ccctcttctttagactgccacgaggaaaaagcagatgtgagaactcaaggttcagggctgctcttc
taagaaacaagtctgccataatctccatctgtgttggaatctgttaactaatgaactggtctctgt
gcaaatcctgagtgctaaagcttccaacaagactgatg (Seq ID No: 435)

Homo sapiens syndecan binding protein (syntenin) (SDCBP):
cgctctcttacactcgggcctcagaagtccgtgccagtgaccggaggcggcggcggcgagcggttc
cttgtgggctagaagaatcctgcaaaaatg (Seq ID No: 436)

*Homo sapiens* serum/glucocorticoid regulated kinase 1 (SGK1):
agtccttctcattccttgcccccgcccaaggctctcttcaccttccccgcgggggtcctctcgttt
tctgtctcccaaatgctggcttcccgcctttcctcccccgcttatttacttaattaaggccctggg
gctgcaccccaccggcagctccttcgggggtgtggccgaagagctccgagggcggggctgaccgag
ccatattcgggcgtggccggtggtgattggtgagggcggggcctgccgcaggggggcggggcctgca
ggtttggccccccgcagggagcgcagctggcgccgctgggagctggtggcgcggcgcaggtcccggc
cgagtgtggcgcagcagtggcggcgcttcccattcgccatgcgccggggggtgggtgcccgaaggtt
gcatgatggaatttgaacattacttcaagaggttttgtattttggattagttaattgggtttgtcc
tctgctgactgtttcttcggatgcatttttttggtgtgctcttgagggattaaatg
(Seq ID No: 437)

*Homo sapiens* Wolf-Hirschhorn syndrome candidate 2 (WHSC2):
cgtccttccggctctcggctttgccacaaagcttcccgaagacgcggccgctacccggagacgcgg
tcgccacccagaagcgctctcccgggaagccccgctcgtgggaccgcgccacctgcgccgcctctg
cggcccgcagcccgacgggcgccgccatgttggggtcctagcgagggacgcgtaggtgtcttcata
agatg (Seq ID No: 438)

*Homo sapiens* nuclear receptor subfamily 1, group H, member 3
(NR1H3):
cagtccttttgcaagagctgctaagagcgctgggtaaggagaggaaggggagagacatggaacttg
gctggtctgcagggaaatgccactgttttggccgggagtagggggcgggagtggcgggagaggggg
tggccggctggggaggagccagcctggtggagaagctgccctgtgggcgggggtgaggaggggagg
gctgtggtcaccaggcaggaaggaggggtggcctgacccctcggcagtccctcccctcagcctttc
cccaaattgctacttctctggggctccaggtcctgcttgtgctcagctccagctcactggctggcc
accgagacttctggacaggaaactgcaccatcctcttctcccagcaaggggctccagagactgcc
cacccaggaagtctggtggcctggggatttggtgggtctgctccttag (Seq ID No: 439)

*Homo sapiens* glypican 6 (GPC6):
cctcctttctccttccctcttgcctccagtgactgtctccaggatttctctcttcctatttcagga
ggactctcacaggctcccacagcctgtgttaagctgaggtttcccctagatctcgtatatccccaa
cacatacctccacgcacacacatccccaagaacctcgagctcacaccaacagacacacgcgcgcat
acacactcgctctcgcttgtccatctccctcccgggggagccggcgcgcgctcccacctttgccgc -continued

SEQUENCES:

acactccggcgagccgagcccgcagcgctccaggattctgcggctcggaactcggattgcagctct
gaacccccatggtggtttttaaacacttcttttccttctcttcctcgttttgattgcaccgtttc
catctggggggctagaggagcaaggcagcagccttcccagccagcccttgttggcttgccatcgtcc
atctggcttataaaagtttgctgagcgcagtccagagggctgcgctgctcgtcccctcggctggca
gaagggggtgacgctgggcagcggcgaggagcgcgccgctgcctctggcgggctttcggcttgagg
ggcaaggtgaagagcgcaccggccgtggggtttaccgagctggatttgtatgttgcaccatg
(Seq ID No: 440)

*Homo sapiens* peptidylprolyl isomerase F (PPIF):
cggccttctgggcgcgcgcgacgtcagtttgagttctgtgttctccccgcccgtgtcccgcccgac
ccgcgcccgcgatg (Seq ID No: 441)

*Homo sapiens* ARP1 actin-related protein 1 homolog A, centractin alpha
(yeast) (ACTR1A): agttccttccccagaaggagagattcctctgccatg
(Seq ID No: 442)

*Homo sapiens* tripartite motif containing 28 (TRIM28):
ggctctttctgcgagcgggcgcgcgggcgagcggttgtgcttgtgcttgtggcgcgtggtgcgggt
ttcggcggcggctgaggaagaagcgcgggcggcgccttcgggaggcgagcaggcagcagttggccg
tgccgtagcagcgtcccgcgcgcggcgggcagcggcccaggaggcgcgtggcggcgctcggcctcg
cggcggcggcggcagcggcccagcagttggcggcgagcgcgtctgcgcctgcgcggcgggccc
cgcgcccctcctcccccctgggcgcccccggcggcgtgtgaatg (Seq ID No: 443)

*Homo sapiens* aminoadipate-semialdehyde synthase (AASS):
cggccttccatcccagtttcttctaggaattcggagcctcccctgcagcgactcggaagattcgag
gcggcgggggacaagtcggcgccccagagcggacgagtcaccaggtgtcaagatg
(Seq ID No: 444)

*Homo sapiens* cornichon homolog (*Drosophila*) (CNIH):
ccgcctttctccgctggcaacggcgccgctccccgctcctcctccccagccatg
(Seq ID No: 445)

*Homo sapiens* M-phase phosphoprotein 10
(U3 small nucleolar ribonucleoprotein) (MPHOSPH10):
ctcccttcccttgcatgctgcattgtgtcgggagttgctgacagccatg (Seq ID No: 446)

*Homo sapiens* ubiquitin specific peptidase like 1 (USPL1):
ccgccttcctagtggagacgcgagtgggggaggagcagtccgaggggaacgtgggttgaacgttgc
aactagggtggagatcaagctggaacaggagttccgatcgacccggtaccaagaaggggagtgccc
gcggcagggttcattgaaaaaatccttagtgatattgacatgtctcaagtgacataaattagccaa
tgactcggaatg (Seq ID No: 447)

*Homo sapiens* solute carrier family 23 (nucleo-
base transporters), member 1 (SLC23A1):
tggcctttgtcaagtcatcccctcttctcctcaggaactgctcaaacctgtgccccaaagatg
(Seq ID No: 448)

*Homo sapiens* splicing factor 3b, subunit 4, 49 kDa (SF3B4):
ggatctctttcgccatg (Seq ID No: 449)

*Homo sapiens* DnaJ (Hsp40) homolog, subfamily A, member 2 (DNAJA2):
ctgtctccctcggcctgtgccgccgccgacgccgcttgtgggcccgactccgctctgtctgcttcg
ccaccttctccccgagcactgcccggccggccgccatg (Seq ID No: 450)

*Homo sapiens* calicin (CCIN):
catcctctcttccaccctctcttctccctggtcaaccgctctgcaaacaaccatcaatctgatccc
acaggcctgagaaagtctgctctccagtacctgctgctgatctgtttcagccgacaagaggcacca
tg (Seq ID No: 451)

*Homo sapiens* mannosidase, beta A, lysosomal (MANBA):
ctgcctttcgatctctccacatctcggtggcgcgggatctcaagatg (Seq ID No: 452)

*Homo sapiens* microtubule-associated protein 1B (MAP1B):
aatcctttctcctgccgcagtggagaggagcggccggagcgagacacttcgccgaggcacagcagc
cggcaggatg (Seq ID No: 453)

*Homo sapiens* malate dehydrogenase 1, NAD (soluble) (MDH1):
gagccttttctcgctaacaccgctcgccctctccgagtcagttccgcggtagaggtgacctgactc
tctgaggctcatttgcagttgttgaaattgtccccgcagttttcaatcatg
(Seq ID No: 454)

*Homo sapiens* microfibrillar-associated protein 1 (MFAP1):
gtttctctatcagtcgcgcagctgtgttcgcggactcaggtggaaggaatttcttctcttcgttga
cgttgctggtgttcactgtttggaattagtcaagtttcgggaatcaccgtcgctgccatcaacatg
(Seq ID No: 455)

-continued

SEQUENCES:

*Homo sapiens* chaperonin containing TCP1, subunit 3 (gamma) (CCT3): ggttctctctctccagaaggttctgccggttcccccagctctgggtacccggctctgcatcgcgtc gccatg (Seq ID No: 456)

*Homo sapiens* tubulin, alpha 1a (TUBA1A): caacctctcctcttcgtctccgccatcagctcggcagtcgcgaagcagcaaccatg (Seq ID No: 457)

*Homo sapiens* CD164 molecule, sialomucin (CD164): ctttctcccgaacgccagcgctgaggacacgatg (Seq ID No: 458)

*Homo sapiens* cysteine-rich secretory protein 3 (CRISP3): ctctctctgcaccttccttctgtcaatagatg (Seq ID No: 459)

*Homo sapiens* SMYD family member 5 (SMYD5): cggcctccatgtgcgacgtgttctccttctgcgtgggcgtggcgggccgcgcgcgggtctccgtgg aagtccgtttcgtgagcagcgccaaggtgaggtcggggcgggtcctgccgggagcctctccccagt ccggccatg (Seq ID No: 460)

Homo sapiens kelch repeat and BTB (POZ) domain containing 10 (KBTBD10): ctgccttttacagctagacctgtgtgctgcaaggagctaaggccttcagtgtccccttccttacc caggtttctcacagaatg (Seq ID No: 461)

*Homo sapiens* aldo-keto reductase family 1, member A1 (aldehyde reductase) (AKR1A1): ccgccccttgcaccgcccacgtggccagcgccacctgcctcattgtgcccaggagttctccaaacc cgcgctgcggagtgagtgaccaagttccggccagttcgacctcgaggatccagaggtggagacggt actacctcccagctctgttttccatccccttcaggtccttcctcgggaggcggcgaaggcggtcca ccctgcgcgtgatcctttatgcccggcccctgcccctccctccgggtggaacttccccctcaccgc cagacttaagctgaggatcgttggatctctggcggggtgcagaactgagcccaggccacagtaccc tattcacgctctgtgcttgtgccaaggtttcaagtgatcctcccgcctcagcctgcccaggtgctg agattacatgtatgagccactgcacctggaaaggagccagaaatgtgaagtgctagctgaaggatg agcagcagctagccaggcaaagggggcaatg (Seq ID No: 462)

*Homo sapiens* TRK-fused gene (TFG): tgttcttcccccacctgccacgtacagagcccaagttctcgctaggcttgttgggtcagcgcgatt ggccggggcccgcgcgagcctgcgagcgaggtgcggcggtcgcgaagggcaaccgagggggcgtg accaccgcctccccgcgacgccccagtccagtggcctcgcgtccgcccattcagcggagacctgcg gagaggcggcggccgcggcctccgcaagccgtctttctctagagttgtatatatagaacatcctgg agtccaccatg (Seq ID No: 463)

*Homo sapiens* 3'(2'), 5'-bisphosphate nucleotidase 1 (BPNT1): catccttctcaaaagacttattgacagtgccaaagctcggtactggacacaacgagggacctgggt ctacgataacgcgcttttgctcctcctgaagtgtctttggtccaacgttgttccagagtgtaccat g (Seq ID No: 464)

*Homo sapiens* guanine nucleotide binding protein (G protein): ttttctctctctctttcactgcaaggcggcggcaggagaggttgtggtgctagtttctctaagcca tccagtgccatcctcgtcgctgcagcgacacacgctctcgccgccgccatg (Seq ID No: 465)

*Homo sapiens* major histocompatibility complex, class II, DM alpha (HLA-DMA): caccctctcggggagggagttggggaagctgggttggctgggttggtagctcctacctactgtgtg gcaagaaggtatg (Seq ID No: 466)

*Homo sapiens* transmembrane protein 50B (TMEM50B): tctccttcctgcgcgcgcgcctgaagtcggcgtgggcgtttgaggaagctgggatacagcatttaa tgaaaaatttatgcttaagaagtaaaaatg (Seq ID No: 467)

*Homo sapiens* lactoperoxidase (LPO): cagtctttcctgctaagcctcagcgtctcctccaagccacatcaaaatctttccttctgggccttt cccagaagtgaattcttgctggaaggtataaaagaccagctcctccaagcagagcaactccctggc tgccgtgaaaagacaaggcactgggcagtgatg (Seq ID No: 468)

*Homo sapiens* NEL-like 2 (chicken) (NELL2): ctgcctttacaacagaggga-gacgatggactgagctgatccgcaccatg (Seq ID No: 469)

*Homo sapiens* nucleobindin 1 (NUCB1): cgccctctgcggtgaaggagagacca-cactgccatg (Seq ID No: 470)

*Homo sapiens* paired box 9 (PAX9): aagcctctttcatcggggcacagacttccttttacttcttccttttgccctctcgcctcctcctcc tgggaagaagcggaggcgccggcggtcggccgggatagcaacaggccgggccactgaggcggtgcg gaaagtttctgtctgggagtgcggaactggggccgggttggtgtactgctcggagcaatg (Seq ID No: 471)

-continued

SEQUENCES:

*Homo sapiens* cyclin-dependent kinase 16 (CDK16):
cgccctttattcttgctcggcctcgccacagagagcaaatcagattggctgggcgacaacctcaaa
gggcggggctgcacacgttcactacgggaatgaggtagcggtggagggggcagttgggcggggata
ggccgtcctagctaaggtggtaaaggccaataactcttcaggctgcctctcctcgaaaagtcatct
tctcgcgaacctttaaaatgccttcctccccaagcacctcaagggactagaactgagtgcttcatt
tgtctttttttcctccttgcaaaagtcccgtttgccaccatggggatgtaccaagtgagaccgagta
gggggaacgagtggtgattgacgcgccaggttactggccactgctcacctaggcgctagcaaactt
ctgccaagatcggaactgagtactaaacagcctccacagttctccctggtgccgtctccggcttgg
cgccgcatcctcctctgggctcgcgatggccgcgtcccctcccgctgcggacgggtcctttggtac
atg (Seq ID No: 472)

*Homo sapiens* serpin peptidase inhibitor, clade E
(nexin, plasminogen activator inhibitor type 1), member 2 (SERPINE2):
ctgcctctttccggctgtgaccctcctcgccgccgccgcttggctgcgtcctccgactccccgcgc
cgccgagaccaggctcccgctccggttgcggccgcaccgccctccgcggccgccccctggggatcc
agcgagcgcggtcgtccttggtggaaggaaccatg (Seq ID No: 473)

*Homo sapiens* pancreatic lipase-related protein 1 (PNLIPRP1):
aactcctttccccctgctgtgacgtacaggtgaggtaaacagtactgaagtccagggcgtcggtgc
tcactgctctggcaatgcccggtgagactgaattatgtttaaatttattgtagatg
(Seq ID No: 474)

*Homo sapiens* peripherin (PRPH):
ggctccttcccagcccccggcctagctctgcgaacggtgactgcccatccttggccgcaatg
(Seq ID No: 475)

*Homo sapiens* RAD21 homolog (*S. pombe*) (RAD21):
gacccttttcccctccccgggccacccagcccgcccaactcccagcggagagcaaggttttcttct
gttttcatagccagccagaacaatg (Seq ID No: 476)

*Homo sapiens* signal sequence receptor, delta (SSR4):
ttttcttttcctctaggcagagaagaggcgatg (Seq ID No: 477)

*Homo sapiens* tissue factor pathway inhibitor (lipoprotein-
associated coagulation inhibitor) (TFPI):
ctccctctttgctctaacagacagcagcgactttaggctggataatagtcaaattcttacctcgct
ctttcactgctagtaagatcagattgcgtttctttcagttactcttcaatcgccagtttcttgatc
tgcttctaaaagaagaagtagagaagataaatcctgtcttcaatacctggaaggaaaaacaaaata
acctcaactccgttttgaaaaaaacattccaagaactttcatcagagattttacttagatg
(Seq ID No: 478)

*Homo sapiens* ubiquinol-cytochrome c reductase binding protein
(UQCRB): gcttctctttctggtcaaaatg (Seq ID No: 479)

*Homo sapiens* mitogen-activated protein kinase kinase kinase 12
(MAP3K12):
ccgccttttgtgctgcggccgcggagcccccgagggcccagtgttcaccatcataccaggggccag
aggcgatg (Seq ID No: 480)

*Homo sapiens* sushi-repeat containing protein, X-linked (SRPX):
tggtctcttcggtctcctgccgcccccgggaagcgcgctgcgctgccgaggcgagctaagcgcccg
ctcgccatg (Seq ID No: 481)

*Homo sapiens* aminopeptidase puromycin sensitive (NPEPPS):
cccccctctccctcctccttgcgggccctcctccccttccctcccctccgccccttccccgtagg
cagcccgcccgccagtccgcccgcaccgcctccttcccagcccctagcgctccggctgggtctctc
ccccgcccccaggctcccccggtcgctctcctccggcggtcgcccgcgctcggtggatg
(Seq ID No: 482)

*Homo sapiens* fibulin 5 (FBLN5):
tcgccttctgcccgggcgctcgcagccgagcgcggccggggaagggctctcctcccagcgccgagc
actgggccctggcagacgccccaagattgttgtgaggagtctagccagttggtgagcgctgtaatc
tgaaccagctgtgtccagactgaggccccatttgcattgtttaacatacttagaaaatgaagtgtt
catttttaacattcctcctccaattggtttaatgctgaattactgaagagggctaagcaaaaccag
gtgcttgcgctgagggctctgcagtggctgggaggaccccggcgctctccccgtgtcctctccacg
actcgctcggcccctctggaataaaacacccgcgagccccgagggcccagaggaggccgacgtgcc
cgagctcctccggggggtcccgcccgcgagctttcttctcgccttcgcatctcctcctcgcgcgtct
tggacatg (Seq ID No: 483)

*Homo sapiens* lysophospholipase I (LYPLA1):
cgctcttccttccgcttgcgctgtgagctgaggcggtgtatg (Seq ID No: 484)

-continued

SEQUENCES:

Homo sapiens high mobility group nucleosomal binding domain 4 (HMGN4):
tcgtcttctctgtcttagggctggtgctggccctgcccacgcctagggctccggcgcgtcacgggc
ctcagctgggattcccgcgcccctcggacggccacgagactcggacatctttccaggaacagcgtg
aggaggacagaagcacccaacaggactgctcaagccacctgcgaacactgctgctaccatg
(Seq ID No: 485)

*Homo sapiens* eukaryotic translation initiation factor 3, subunit M (EIF3M):
agttccccttttccggtcggcgtggtcttgcgagtggagtgtccgctgtgcccgggcctgcaccatg
(Seq ID No: 486)

*Homo sapiens* Sec23 homolog A (*S. cerevisiae*) (SEC23A):
cctcctcttgacgtggcagaggcggcgccagccatg (Seq ID No: 487)

*Homo sapiens* cartilage associated protein (CRTAP):
cgtcctctttcctttccttctccctccccttttcccttccttcgtcccttccttccttcctttcgc
cgggcgcgatg (Seq ID No: 488)

*Homo sapiens* vesicle amine transport protein 1 homolog (*T. californica*) (VAT1):
ccgcccctcccgctggatcccgcagccgcggctcttcccgacgcgttccgccttccccagctgtgc
actctccatccagctgtgcgctctcgtcgggagtcccagccatg (Seq ID No: 489)

*Homo sapiens* importin 7 (IPO7):
gcttctctttcctttcgcgccggttgccgctgcggagcgcggcgggtccatgtgcgcagtgagtgg
cgctattcctggcccagtagcacccgagccccgggtttgaccgagtccgcgctgcgatg
(Seq ID No: 490)

*Homo sapiens* ATG7 autophagy related 7 homolog (*S. cerevisiae*) (ATG7):
gctcctttgcgcacgcgcgccgcttcccagtggcaagcgcgggcaggaccgcgttgcgtcatcggg
gcgcgcgcctcagagagagctgtggttgccggaagttgagcggcggtaagtgagccgcggcgggcg
agggtgtagtggggtcttgctgggccggttttggaggcctggagtcaaggggcgagctcgccaggg
agggcgagggtcacagcaagtctcaggatcctcctctgccagtttctgggtggtccttcctcctcc
agggactcactgattccggctggcgcccttcgtctgtagccgcgtcccctcagactggttcagtcc
ggggtcttctgacttggaagctcgtgctgatttcctaagtcagcccctcctgtcctcttggtaggc
agtgctcagaatcttcagtgttggaacacgggagatgggacatttggattcccagcctggctgtgt
ctggatttgctgtctctggcacgttccttccccatctaagctgcttttccatctgcaaaatgggaa
tgataatccgccatttgtttaagtgaggaggttaaataagtttactttctgagaaagaagattctc
gattccttggttacagggttagaaactaatg (Seq ID No: 491)

*Homo sapiens* dynactin 2 (p50) (DCTN2):
cgctcccctttgccgccgccttagcccgggacccgaacccagcctctcccctacccgaacaccggcc
ccggctccaccgaggcccgggtcccccagcccgtctcgccgccgccatg (Seq ID No: 492)

*Homo sapiens* acidic (leucine-rich) nuclear phosphoprotein 32 family, member B (ANP32B):
agccccccttttccctccatggtttctctccgctcccgtgagtaacttggctccgggggctccgctc
gcctgcccgcacgccgcccgccacccaggaccgcgccgccggcctccgccgctagcaaacccttcc
gacggccctcgctgcgcaagccgggacgcctctcccccctccgcccccgccgcggaaagttaagtt
tgaagaggggggaagaggggaacatg (Seq ID No: 493)

*Homo sapiens* protein C receptor, endothelial (PROCR):
acttctcttttccctagactgcagccagcggagcccgcagccggcccgagccaggaacccaggtcc
ggagcctcaacttcaggatg (Seq ID No: 494)

*Homo sapiens* actin related protein 2/3 complex, subunit 1A, 41 kDa (ARPC1A):
cgctccctctgggcttccgtcctccgcccgcgcccgacggagcctgttcgcgtcgactgcccagag
tccgcgaatcctccgctccgagcccgtccggactcccccgatcccagctttctctcctttgaaaac
actaagaataatg (Seq ID No: 495)

*Homo sapiens* chaperonin containing TCP1, subunit 4 (delta) (CCT4):
aggcccccttctccgcctccgcctcctcccgacgccggcgccgctttctggaaggttcgtgaaggc
agtgagggcttaccgttattacactgcggccggccagaatccgggtccatccgtccttcccgagcc
aacccagacacagcggagtttgccatg (Seq ID No: 496)

*Homo sapiens* Niemann-Pick disease, type C2 (NPC2):
gcttctttcccgagcttggaacttcgttatccgcgatg (Seq ID No: 497)

*Homo sapiens* phosphoribosylaminoimidazole carboxylase, phosphoribosylaminoimidazole succinocarboxamide synthetase (PAICS):
acccctcttttctagagttctgcctcgcttcccggcgcggtcgcagccctcagcccacttaggata
atg (Seq ID No: 498)

-continued

| SEQUENCES: |
|---|

*Homo sapiens* ST6 (alpha-N-acetyl-neuraminyl-2,3-beta-galactosyl-1,3)-N-acetylgalactosaminide alpha-2,6-sialyltransferase 2 (ST6GALNAC2):
ctcccttctgcctgggacgtcagcggacggggcgctcgcgggccggggctgtatg
(Seq ID No: 499)

*Homo sapiens* polymerase (RNA) III (DNA directed) polypeptide C (62kD) (POLR3C):
aagccctttccgaggatggcaaaggatctgggaatgcttctccaaagatatgtggatggacgaaat
aggtctctggtgatactgaggcggggtggggacggggaggcaaagacttggcttcttaggaattgg
aagaaataagtaaacaatgtttggtagcaatttgtaataaggaagtaatcataaaattaactacgt
ccgtttctgattgtgtcaactttgtcaaggagtagaagtttaagaattgaatactgtcctgcaaac
aacgtaacctcatctcctgtttgacacaccctgttgagaagcagtcctttacctcctaaatttctt
tttcgaaattatcatttcctttatggactgagaataacactgcctgttcactcccaccgagctgtg
aacagtgaccttaattcttccaagcagggaagtgtagaaactaaggtctgtgacagaccgcaaaat
catctcccaatctttaaggaaaatcagaatcacgcataatcccatagagataaatttgatgcatag
tcttttcctatgcatacattttcctttttttttacaataattgaatttttatattttttcagctt
gcttctgtcacttaatatattatgagtaatttttttttggtttttttttgttttggagacagaatctc
gcactgtcgcccgggttggagtgcagtggcgcgatctcggctcactgcaacctctgcctcccggct
tcaagcgattctcctgtctcagcctccctagtagctgggattacaggcacccgccaccacgcccag
ctaatttttttgtgtgtttttagtagagaaggggtttcactatattggccaggctggtctcaaact
cctgacctcatgatacgcccacctcggtctcccaaagtgctaggattacaggcctgagccaccgcg
ccagcctattatgaataatttctacatgaatacgcatcgtactaaataactttaaatgttggtgt
agtatgccattgtatgggtatggcatcatttattgttagacgttagattgtttccactaagtcggt
attataaagagaactaatgacttcattattattagctttttctttctttggacacaatatccaaaa
agaaattgttgtttcaaagatatgcaagatttttaaggctttttgatatgtattgtcaaattgccc
tccagaaagaatacatgaatttacactcagcagctctgcttccagcgtgaaagactttctattgta
ccatttggtgttttttccctagctctcagactccccagtacaatg (Seq ID No: 500)

*Homo sapiens* influenza virus NS1A binding protein (IVNS1ABP):
gtgtctcccggtcgcgcgtggaggtcggtcgctcagagctgctgggcgcagtttctccgcctgctg
cttcggcgcggctgtatcggcgagcgagcgagttcccgcgagttctcggtggcgctccccccttcct
ttcagtctccacggactggcccctcgtccttctacttgaccgctcccgtcttccgccgccttctgg
cgctttccgttgggccgattcccgcccgcttcctcctgcttcccatcgaagctctagaaatgaatg
tttccatctcttcagagatgaaccagattatgatgcatcattatcacagaagaaattcgtgtctat
agcttttaaggacttgattacatcattttcaagcctgatagttttggaatcaccattagagcttaa
gacacacctgccttcatttcaaccacctgtcttcataccctgacgaagtgcaccttttaacactcc
tttgtccttggattacttaagagttcccagaaatacatttgccaccaacagagtagccaaatttat
aaggaaaaatg (Seq ID No: 501)

*Homo sapiens* thioredoxin interacting protein (TXNIP):
acccctctttttctccaaaggagtgcttgtggagatcggatcttttctccagcaattgggggaaag
aaggctttttctctgaattcgcttagtgtaaccagcggcgtatattttttaggcgccttttcgaaa
acctagtagttaatattcatttgtttaaatcttattttattttttaagctcaaactgcttaagaata
ccttaattccttaaagtgaaataatttttgcaaaggggtttcctcgatttggagcttttttttttc
ttccaccgtcatttctaactcttaaaaccaactcagttccatcatg (Seq ID No: 502)

*Homo sapiens* ecotropic viral integration site 2B (EVI2B):
ttttcctttcttagccaaatcaccaaaatgtccagttagaacaagaatttagcattctgcaaaaga
agttaacagctgagataacgaggaaatattctgaaatg (Seq ID No: 503)

*Homo sapiens* guanine nucleotide binding protein (G protein), alpha inhibiting activity polypeptide 3 (GNAI3):
ggttcttctgggcgctaagggagctgacggagagggccaccgcccagcaatagacggtgcctcagc
ctgccgagccgcagtttccgtggtgtgagtgagtccgggcccgtgtcccctctcccgccgccgcca
tg (Seq ID No: 504)

*Homo sapiens* polymerase (DNA directed), eta (POLH):
cggcccttcgcagcgggcgcgctgtcagacctcagtctggcggctgcattgctgggcgcgccgctc
tcgtctgatccctgctggggacggttgcccgggcaggatcctttacgatcccttctcggtttctcc
gtcgtcacagggaataaatctcgctcgaaactcactggaccgctcctagaaaggcgaaaagatatt
caggagcccttccattttccttccagtaggcaccgaacccagcatttcggcaaccgctgctggca
gttttgccaggtgtttgttaccttgaaaaatg (Seq ID No: 505)

*Homo sapiens* solute carrier family 2 (facilitated glucose transporter), member 1 (SLC2A1):
cgctctctggcaagaggcaagaggtagcaacagcgagcgtgccggtcgctagtcgcgggtccccga
gtgagcacgccagggagcaggagaccaaacgacgggggtcggagtcagagtcgcagtgggagtccc
cggaccggagcacgagcctgagcgggagagcgccgctcgcacgcccgtcgccacccgcgtacccgg
cgcagccagagccaccagcgcagcgctgccatg (Seq ID No: 506)

*Homo sapiens* zinc finger protein 138 (ZNF138):
gggtctttgtctcgctgcagcgggtgctgcaggtctggccttcacttttctgcgtcctcttactcc
tagaggcccagcctctgtggcgctgtgatctggttattgggagattcacagctaagacgccaggat
cccccggaagcctagaaatg (Seq ID No: 507)

-continued

SEQUENCES:

*Homo sapiens* ubiquitin specific peptidase 3 (USP3):
ctttctttgacgcaagggctcgagacgcagccgccgtcggccgagcgcccggctagaagcgacacc
agacggagcctccggagttcctccgcccccacctcgccgggtcctggagccgcagtcctcccagct
gccctcctcgtggccatg (Seq ID No: 508)

*Homo sapiens* calcium channel, voltage-dependent, gamma subunit 3
(CACNG3):
ctgtcttttctccagtttgagcgggggtgtcgggagcaggcggagagctttcctgcgaggctgtgg
aagcagtgaacactcttctcagcggctcgcctcccagcagtgctatttttttgccatccgccctcac
ccccagcacacgcgctcgcacacacacgcacgcacgcacacacacacacacacactcacacaga
gacctctctgggtttctttgccttgagtctcccggggctgtgagaagccaggcgcatctcaaaccg
agctggcagctccaggctccggagccatgccctgcacggaccctcgtctttaccacgctcctgagg
aatgaaaggaacccagggaccctcagaaggcagcagtgatgcggaccaaccccccggagcctgcac
ccttccgagggccataggcgacccagggaactggagagagctccagaaaggaaatcccagctttcc
caaagtccctgtggatgctgacaaaaggagacctgaattttggaagagcctgtactaggttaccc
ggctgcagagtgattttcccctccggcactgactctccccctccaacccccagccgtccagagtac
catgaagaattatg (Seq ID No: 509)

*Homo sapiens* guanine nucleotide binding protein
(G protein), beta 5 (GNB5): ttccctctccgctgcgtccccgcgcgaagatg
(Seq ID No: 510)

*Homo sapiens* chaperonin containing TCP1, subunit 8 (theta) (CCT8):
cttcctccgcggtcttccgagcggtcgcgtgaactgcttcctgcaggctggccatg
(Seq ID No: 511)

*Homo sapiens* prostaglandin E synthase 3 (cytosolic) (PTGES3):
cgctctttccgcgcggtgcattctggggcccgaggtcgagcccgccgctgccgccgtcgcctgagg
gaagcgagaagaggccgcgaccggagagaaaaagcggagtcgccaccggagagaagtcgactccct
agcagcagccgccgccagagaggcccgcccaccagttcgcccgtcccccctgccccgttcacaatg
(Seq ID No: 512)

*Homo sapiens* zinc finger protein 266 (ZNF266):
ttttcttcctggtggcgtttgggcttaatacagctttggcgaggtcggatgacgggtgggagccag
cggtggaaggggtggcgaaagtaccggtttgccccaggccgccgaggggcctccttagagagacct
tgcctgctccgctcgcgtccgccggggccgcgcgggtcctcctggcgccgccaggttcaaaaagcc
actcgagttgtcactgcgacggccctgggccaggagccgtttcgggatctgtcaaacaacgagttt
tcgtcgttcgaatcaggttgactggtccttcatcccccccaatctcccgtacctggcgagtccagct
cgtcgcggcaatgctaagaaaagagtgatatgcaagctgagaccaaaaatatggtatgatttagcc
atactgaaggggaaggaaataagagctgggcaaagcattctgtgaattggctgactccacttctat
ggtgagagagaggagtgcatcaaagattactcccagtagagatggtttcagcatgttggccagtct
ggtctcagactcctgacctcaagtgatccacccacctcggcctcccaaaatgctgggattacaggt
ataagccactgtgcctggccaaagataccgttaaccctggataaagagaatggaggttacctctgt
ccgtgtagattcctaagctgtcctggagtgatccttggagtaaaggaaaggtgctttgaagcacat
tcagccatcagccctgtgggatggcagccactgatttgtcctatggtctttacagggacccagtct
gccttcaagaaaagacagaagtagaaagggtggtggctgactgtctgacaaattgttatcaggtat
gcaggaagtatatccttctccaaaatatcatacttgcatcaccaggtagacacatttccttctaca
cagaattatcttcagagcttcttaaagcaaataaagcctgcttcaaggactgagtccctagtcgaa
ttcccggaaggagtggagcctgtcatattgtgtttatctagcatctgctcaagagtgtgctgcagt
ggagggaaatcagatgacctcccagtctggttgtgttacatacaatcatgtgtaagaagtgccatt
caagccgtgtcactggaggggactgacagtgagattcagtgacttttgatgatctggctgtggact
tcaccccagaagaatggactttactggacccaactcagagaaacctctacagagatgtgatg
(Seq ID No: 513)

*Homo sapiens* methylenetetrahydrofolate dehydrogenase
(NADP+ dependent) 2, methenyltetrahydrofolate cyclohydrolase
(MTHFD2): gcttccctcccggcgcagtcaccggcgcggtctatg (Seq ID No: 514)

*Homo sapiens* chemokine (C-C motif) receptor 9 (CCR9):
cttcctttctcgtgttgttatcgggtagctgcctgctcagaacccacaaagcctgcccctcatccc
aggcagagagcaacccagctctttccccagacactgagagctggtggtgcctgctgtcccagggag
agttgcatcgccctccacagagcaggcttgcatctgactgacccaccatg
(Seq ID No: 515)

*Homo sapiens* heat shock 105 kDa/110 kDa protein 1 (HSPH1):
cctccccttttgggtcggtagttcagcgccggcgccggtgtgcgagccgcggcagagtgaggcagg
caacccgaggtgcggagcgacctgcggaggctgagccccgctttctcccagggtttcttatcagcc
agccgccgctgtcccgggggagtaggaggctcctgacaggccgcggctgtctgtgtgtccttctg
agtgtcagaggaacggccagaccccgcgggccggagcagaacgcggccagggcagaaagcggcggc
aggagaagcaggcagggggccggaggacgcagaccgagacccgaggcggaggcggaccgcgagccg
gccatg (Seq ID No: 516)

*Homo sapiens* StAR-related lipid transfer
(START) domain containing 10 (STARD10):
tggtcctttcttttatgattcacaaggaatgaccctcttcatcgcctctcctaattcagtcctcac
aacagtccttttacaaatgggacaacaggttagaggaagtcaggcagatttccagcatcatagaga
gtaaaggaccagggaaggatcaggattcaaggactgcacccaggctctgcttccagcttgctgtgt -continued

| SEQUENCES: |
|---|

gactttgggtaattttgttcccttagggaactgagctttctcatttgtaaatgcaaacaggctgtt
gggaggatcaaatgagatccaggggtgaaaacagcttagtttactttcaggaatttaccccacgcgg
tatataaaggcaaaatattattatagtcaggtgattgtagattgaggaacccatttcctcattctg
caaattgcaaacctgagggcccaaagagggacaggggcttgccccaggtctcagcaggctgtgagc
aagagctaaagcctaatcctcctgcctttgggcctggagcccttccttgtaccccaggggtcagtg
tctttgttggatacaggcttagattgactgactgtaccctgagaacctaggggagtccctgttccc
aattcttctcctacccccaccttggcctgatggaggaagaccctgctgtgttgagatgagcaccag
agccaagaagctgaggaggatctggagaattctggaggaagaggagagtgttgctggagctgtaca
gaccctgcttctcaggtcccaggaaggtggcgtcagcatctgcagccgcgtcgacgttgtcggagc
ctccgcggaggacccaggagagccggactaggaccagggccctgggcctccccacactccccatg
(Seq ID No: 517)

*Homo sapiens* UTP14, U3 small nucleolar ribonucleoprotein, homolog A (yeast) (UTP14A): ctttccttcggcttccgttcttggtccatgtgagagaagctggct-gctgaaatg (Seq ID No: 518)

*Homo sapiens* SUB1 homolog (*S. cerevisiae*) (SUB1):
ggttctctgtcagtcgcgagcgaacgaccaagagggtgttcgactgctagagccgagcgaagcgat
g (Seq ID No: 519)

*Homo sapiens* minichromosome maintenance complex component 5 (MCM5):
ccgcctcttgtttttcccgcgaaactcggcggctgagcgtggaggttcttgtctcccctggtttgt
gaagtgcggaaaaccagaggcgcagtcatg (Seq ID No: 520)

*Homo sapiens* RNA binding motif (RNP1, RRM) protein 3 (RBM3):
tactctttatcaatcgtcttccggcgcagccccgtccctgtttttttgtgctcctccgagctcgctg
ttcgtccgggtttttttacgttttaatttccaggacttgaactgccatg (Seq ID No: 521)

*Homo sapiens* KDEL (Lys-Asp-Glu-Leu) endoplasmic reticulum protein retention receptor 1 (KDELR1):
ctccccctctcgctctcctccctcttcccggctccagctccgccgccagctccagcctttgctccc
cctcccaaagtcccctccccggagcggagcgcacctagggtccctcttccgtccccccagcccagc
tacccgttcagaccagcagcctcggggggcacccccccgccagcctgcctccctcccgctcagccc
tgccagggttccccagccatg (Seq ID No: 522)

*Homo sapiens* StAR-related lipid transfer (START) domain containing 3 (STARD3):
agatcttcttccgctctgaggcgctactgaggccgcggagccggactgcggttggggcgggaagag
ccggggccgtggctgacatggagcagccctgctgctgaggccgcgccctccccgccctgaggtggg
ggcccaccaggatg (Seq ID No: 523)

*Homo sapiens* heterogeneous nuclear ribonucleoprotein A0 (HNRNPA0):
cggcctctttgtgtggtgcccagataggggagcggaggtggcggcggcggcggtagcggtggcctt
ggttgtcttccagtctcctcggctcgccctttagccggcaccgctccccttccctccccccttcctc
tcttccttccttccctccccttcccttttttcccttccccgtcggtgagcggcgggggtggctccag
caacggctgggcccaagctgtgtagaggccttaaccaacgataacggcggcgacggcgaaacctcg
gagctcgcagggcgggggcaaggcccgggccttggagatg (Seq ID No: 524)

*Homo sapiens* chromobox homolog 1 (CBX1):
ggctcttttgttcggctgaggggagggccgttggccggggcctgcggtacgccgcttcagtgaggg
acgccactgcggccacccggcttgctgccttcctgggcgccactcccccaggcgacccgacgcgac
gcgccagcagcgcagcaccgattcctctcgggctcttgggcgctgctctgaggtgaggagcccgct
ggaggcgggagagctgggggaggggggcgcggcggcggcggcggcggcgggagccctgcgtgagggaacg
cgctttcgaggcggaggttaggagcggggagcgcgcccgggtccagcgtcctgcttctccgcttcc
cgcgctgagctcttcgcctgtcgctgaggcgtcggtgccagctgcgtgaaggatggagagggcggg
gcgcgaatcctgagccagagactgagtgcttgggggtgggccgagcacttgggggccgctcttcgg
ggcccgggtggtctggaacaatgttgcttggctgggcggctgcgggatagggcggaaggggacagg
cttgaggcttggataggcgtgaggaggcgcatacgaccgcacaacccgaggtttgtaactgtattc
ggaagacgccgggtccggctgggactgccagaggaacctggctttgcaggactacggaggagtaac
gtcgagtgaattggaagagggcccagggccgcacaagcagcgtcaccctttacaccagaaagctgg
cgggcactatg (Seq ID No: 525)

*Homo sapiens* myeloid/lymphoid or mixed-lineage leukemia (trithorax homolog, *Drosophila*); translocated to, 11 (MLLT11):
cgccccttcttaggaggggctgcattgcaggggggagagtgaactgacagactcagtcactgaagagg
gaaaaggagtgagaagacaaagccgtcaaagccccaacagctttgtatttctccagcccggcgcag
accccggagctcccgaggcactccctccatctttggaacacgccagtaattgattgataacaggaa
gctatg (Seq ID No: 526)

*Homo sapiens* interferon-induced protein 44-like (IFI44L):
ttttctttctttcctagagtctctgaagccacagatctcttaagaactttctgtctccaaaccgtg
gctgctcgataaatcagacagaacagttaatcctcaatttaagcctgatctaacccctagaaacag
atatagaacaatg (Seq ID No: 527)

-continued

SEQUENCES:

*Homo sapiens* cyclin I (CCNI):
acttcttcctcccttcccctctcttcccctccctccccagccttccccgcgagcggacgcggcagc
gcctctgtctcgcttttcttatttttcccccttttcccctttctttttttttttttcttttcttt
tctcccctcccccccttttcaccatttcccctcggaggcgctttccccgggcaggggcagagccggt
ctcaccccccgcctctccccggcccccgccgccctatggcgagagggagccccctcccaacccggg
ctcgagcggcggcggcctcaggccgggggtcatcatggaactaattcgctgaccgacccagcggcc
gcagccgtgcgtcccgctcgagcgccagcgcccgcgcccgcgccccccgatccgcttcccctttct
ccctcctcagttggccgagtcgtcccgcgcgcaccgcctccgcgcgcctatgagaatgaggtggta
acgggcccccggatgaccccgcgtcaccactgtgaggcctacagctctgccggggaggaggaggag
gaggaagaggaggagaaggtagctacagcaagctgggtagcaggcagatccaaaggatatcatg
(Seq ID No: 528)

*Homo sapiens* methionyl aminopeptidase 2 (METAP2):
cattccctcgcgctctctcgggcaacatg (Seq ID No: 529)

*Homo sapiens* leukocyte immunoglobulin-like receptor, subfamily B
(with TM and ITIM domains), member 4 (LILRB4):
gtctctttgtcctgccggcactgaggactcatccatctgcacagctggggcccctgggaggagacg
ccatg (Seq ID No: 530)

*Homo sapiens* destrin (actin depolymerizing factor) (DSTN):
gggtctctcggtcccgcagccgtgaggaggacggtctgcatactcgctgcccgccggctccctccc
ccgcgtccctgcgaccgccgcggcgaagatg (Seq ID No: 531)

*Homo sapiens* eukaryotic translation initiation factor 2D (EIF2D):
gggccctttttcgcggccgggccccagcatggctgcccccacggctgagggcctggcagctgctgcg
ccctcgctttcttgacattccctggcttctgtgctctcttccccaggccaccccagcagacatg
(Seq ID No: 532)

*Homo sapiens* histamine N-methyltransferase (HNMT): ctgtctttctca-
gaaaaccaaatatg (Seq ID No: 533)

*Homo sapiens* ras-related C3 botulinum toxin substrate 1
(rho family, small GTP binding protein Rac1) (RAC1):
gtttctctgcagttttcctcagctttgggtggtggccgctgccgggcatcggcttccagtccgcgg
agggcgaggcggcgtggacagcggccccggcacccagcgccccgccgcccgcaagccgcgcgcccg
tccgccgcgccccgagcccgccgcttcctatctcagcgccctgccgccgccgccgcggcccagcga
gcggccctgatgcaggccatcaagtgtgtggtggtgggagacggaaacaagaatctcagtgtaacc
cgagcaaaatcgcgcgtctcagcgttgcttgtatagagctgtaggtaaaacttgcctactgatcag
ttacacaaccaatgcatttcctggagaatatatccctactgtctttgacaattattctgccaatgt
tatg (Seq ID No: 534)

*Homo sapiens* signal recognition particle 72 kDa (SRP72):
tcgtctcctccaagatg (Seq ID No: 535)

*Homo sapiens* zinc finger protein 33B (ZNF33B):
ccgcctttccttttgtttgtctcacgttttgcgtgggaggcggtcccgggatttcaggggtctacc
ggctctcttatggcgaatgcaacccgaagagagagtgagctgtatcttcagagttgtctccgtctt
tccaagaacagaacaaaatg (Seq ID No: 536)

*Homo sapiens* zinc finger protein 16 (ZNF16):
gcctcctttccaagcgcgacccgttgaggtccttgtcatg (Seq ID No: 537)

*Homo sapiens* zinc finger protein 33A (ZNF33A):
ccgcctttccttttgtttttctcaggttttgcgtgggaggcggtcccgggatttcaagggtctacg
cgcttttctatggcgaatgcaacccgacgagggagtgggctgtatcttcagagttgtctccgtctt
tccaagaacagaacaaaatg (Seq ID No: 538)

*Homo sapiens* butyrophilin, subfamily 3, member A3 (BTN3A3):
ctttctttttcctttcttcggaatgagagactcaaccataatagaaagaatggagaactattaacc
accattcttcagtgggctgtgattttcagaggggaatactaagaaatggttttccatactggaacc
caaaggtaaagacactcaaggacagacattttggcagagctgctcactccttgctcagctcagtt
ttctgtgcttggaccctctgggcccatcctggccatg (Seq ID No: 539)

*Homo sapiens* butyrophilin, subfamily 2, member A2 (BTN2A2):
ctctttgggatgctttgttgtctggtggtgactgtgcccatgggtgagttgtatcggaaaatcgtc
atgtgaggatcagaggggaaaagaaaacagaggcctctggtctctgcctgccctgggtgctcatg
(Seq ID No: 540)

*Homo sapiens* nudix (nucleoside
diphosphate linked moiety X)-type motif 21 (NUDT21):
acgcctcctcttgcgctgtcctgttaatggcgggcagtagccgctgaggggattgcagataaccgc
ttcccgcacggggaaagtctaccctgcctgccactttctgctcgccgtcagcgccggagctcgcca
gcatg (Seq ID No: 541)

-continued

SEQUENCES:

*Homo sapiens* stathmin-like 2 (STMN2):
tgctctttctctagcacggtcccactctgcagactcagtgccttattcagtcttctctctcgctct
ctccgctgctgtagccggaccctttgccttcgccactgctcagcgtctgcacatccctacaatg
(Seq ID No: 542)

*Homo sapiens* katanin p60 (ATPase containing) subunit A 1 (KATNA1):
caccctcttccgccgctcccgcccagcgacctcgctcccggggcgacgccccgcgtgcgccagagt
cgccgaggtcgtccccggcaccggaagtgaccctggcgggtttgtcttcaaattctcggcgagcag
gagccgcgccggcaggtggtgttgacgattgaactgggcagtactggggccgtgagcggagagcaa
agtgggctggactgggtcaggccctccttcctcgctgccgggatctccactccgccaatcccctgt
gcctggcgttgggcggtttcccgaggagcttgggccgccgcagcttacagttgaacatg
(Seq ID No: 543)

Homo sapiens butyrophilin, subfamily 3, member A2 (BTN3A2):
ctttctcttttcctttcttccggatgagaggctaagccataatagaaagaatggagaattattga
ttgaccgtctttattctgtgggctctgattctccaatgggaataccaagggatggttttccatact
ggaacccaaaggtaaagacactcaaggacagacatttttggcagagcatagatg
(Seq ID No: 544)

*Homo sapiens* CLK4-associating serine/arginine rich protein
(CLASRP):
cggcctttcatttccgcttccggtgcgggccgcgcgcgagcgcagcggtgggaggcggcgaccagc
cggttgaggccccaggcttggcctcaccacaatg (Seq ID No: 545)

*Homo sapiens* clathrin, light chain A (CLTA):
ctccctcctggcgcttgtcctcctctcccagtcggcaccacagcggtggctgccgggcgtggtgtc
ggtgggtcggttggtttttgtctcaccgttggtgtccgtgccgttcagttgcccgccatg
(Seq ID No: 546)

*Homo sapiens* NADH dehydrogenase (ubiquinone) flavoprotein 1, 51 kDa
(NDUFV1):
gcgtctctatcgcgccagttcctcagcctcagtgctatgaaggtgacagcgtgaggtgacccatct
ggcccgccgcgatg (Seq ID No: 547)

*Homo sapiens* signal sequence receptor, gamma (translocon-
associated protein gamma) (SSR3):
gggcctttgcccgccttggcggccggctctacgttccctgttctcgcctgcagctccgccatg
(Seq ID No: 548)

*Homo sapiens* valosin containing protein (VCP):
gcttcccttccgatgattcggctcttctcggctcagtctcagcgaagcgtctgcgaccgtcgtttg
agtcgtcgctgccgctgccgctgccactgccactgccacctcgcggatcaggagccagcgttgttc
gcccgacgcctcgctgccggtgggaggaagcgagagggaagccgcttgcgggtttgtcgccgctgc
tcgcccaccgcctggaagagccgagccccggcccagtcggtcgcttgccaccgctcgtagccgtta
cccgcgggccgccacagccgccggccgggagaggcgcgcgccatg (Seq ID No: 549)

*Homo sapiens* zinc finger protein 195 (ZNF195):
gggcctttgtcccgacagagctccacttcctgtccccgcggctctgtgtcccctgctagccgtagg
tcgtgtgacccgcaggcaccgggagatccagaagtgaaacgccaggctctctggaggccaggagat
g (Seq ID No: 550)

*Homo sapiens* testis-specific kinase 2 (TESK2):
cagtctttcgcggcccgggagctcagcagagctaccagctgccctgttggcttcgctggtcggatc
gtcctcctggccccgccaaacaggcgggggggagcggccccgactgtggggccatggcagtagtctc
ctcgttcgccgccgccgctagcctagctgagtcgccggcttctgcgctaggggctcccaccgcctc
cgcaggctaaggagccgctgccaccaacgagctgtgagggttactatgctccctctttgccgccgt
ctcctcctcttgcccgcgcaggcacccctctggctgctcagtcctgcctcagtgtcaaaccagaag
agaagtaaaattcaacaaaaatttatgtgtggagttccttcttaaaagaagaaaaaagtgattatt
tagactatg (Seq ID No: 551)

*Homo sapiens* family with sequence similarity 107, member A
(FAM107A):
agccctccttgctagtctgggacttcccggtggagtgaggaacccagcaacacgctcctgacttcc
cttcccaaggactcgacctgagaaggacacagcagtctctgaatttcatgctctcctctttgatgt
gaagaaaatgaaaagctgaacagttgtggaactgtggatagagttagacaataaggccgccatg
(Seq ID No: 552)

*Homo sapiens* serine/threonine kinase receptor associated protein
(STRAP):
ccctccctccctttccctccctcgtcgactgttgcttgctggtcgcagactccctgacccctccct
cacccctccctaacctcggtgccaccggattgcccttcttttcctgttgcccagcccagccctagt
gtcagggcgggggcctggagcagcccgaggcactgcagcagaagagagaaaagacaacgacgaccc
tcagctcgccagtccggtcgctggcttcgccgccgccatg (Seq ID No: 553)

-continued

SEQUENCES:

*Homo sapiens* mitochondrial ribosomal protein L3 (MRPL3):
ctttctttccgtcgcagagagcatcggccggcgaccgttccggcggccattgcgaaaacttcccca
cggctactgcgtccacgtggcggtggcgtggggactccctgaaagcagagcggcagggcgcccgga
agtcgtgagtcgagtcttcccgggctaatccatg (Seq ID No: 554)

*Homo sapiens* zinc fingers and homeoboxes 1 (ZHX1):
ctcccttcccctccgcccccggacggccgctggggcgcgcgcctctcctcgcacccccaccctga
gtccccacactccgcggggccaccgagctgctgaggcccctttgcgggcccgccgagcggttccgg
gtttagggttcacaggtcagagttgactccctgaaaagtgcagccggtttgaaatgcaagatggcg
gcggcgtggcgctgagaggcgcggcggcccctgcaggagaagacagactgctgctttggacctgtt
ggtaatgatggcctgagctaaacatctaactagaagggatacccttccatttcaaagaacagaatg
ctaaggaagctgtggcaagtgattggagttgtgcttcaaaaatttcagaaattcagcagtatttta
tctgccaacaataagctctttacttgattgcaccatgagaaagctgctaatgagacttgttgagca
caaaaatggacttgaagaaccaaaagccattgttttcaaatgaagaacactgaacagttttaagcc
tcgatgctttttaatcaccactgagcttttcctcataacatcagaatg (Seq ID No: 555)

*Homo sapiens* calcium binding protein P22 (CHP):
ccttccttccctccctccttccctcctgtcgccgtctcttctggcgccgctgctcccggaggagct
cccggcacggcgatg (Seq ID No: 556)

*Homo sapiens* ecdysoneless homolog (*Drosophila*) (ECD):
ctttctctcaggatttccgctggcttcaggttccggtcaggcgtcgggacagagcctgatccaggc
ttcggcggccggtggcagctctcgatcagctctcgcagtcggagaggcggctaaggaaaggtgcca
cagcagagacgcgaaggagaggccctagaaccttttcaaagaagaatg (Seq ID No: 557)

*Homo sapiens* V-set and immunoglobulin domain containing 4 (VSIG4):
gagcctctttggtagcaggaggctggaagaaaggacagaagtagctctggctgtgatg
(Seq ID No: 558)

*Homo sapiens* prohibitin 2 (PHB2):
tgccctttctttcgccagccttacgggcccgaaccctcgtgtgaagggtgcagtacctaagccgga
gcggggtagaggcgggccggcaccccttctgacctccagtgccgccggcctcaagatcagacatg
(Seq ID No: 559)

*Homo sapiens* signal transducer and activator of transcription 1, 9 kDa
(STAT1):
ctgccttttctcctgccgggtagtttcgctttcctgcgcagagtctgcggaggggctcggctgcac
cggggggatcgcgcctggcagaccccagaccgagcagaggcgacccagcgcgctcgggagaggctg
caccgccgcgcccccgcctagcccttccggatcctgcgcgcagaaaagtttcatttgctgtatgcc
atcctcgagagctgtctaggttaacgttcgcactctgtgtatataacctcgacagtcttggcacct
aacgtgctgtgcgtagctgctcctttggttgaatccccaggcccttgttggggcacaaggtggcag
gatg (Seq ID No: 560)

*Homo sapiens* heat shock protein 90 kDa alpha (cytosolic),
class B member 1 (HSP90AB1):
agctctctcgagtcactccggcgcagtgttgggactgtctgggtatcggaaagcaagcctacgttg
ctcactattacgtataatccttttcttttcaagatg (Seq ID No: 561)

*Homo sapiens* cancer susceptibility candidate 3 (CASC3):
cgttctccgtaagatg (Seq ID No: 562)

*Homo sapiens* nuclear cap binding protein subunit 2, 20 kDa (NCBP2):
gcttctctgcactatg (Seq ID No: 563)

*Homo sapiens* non-POU domain containing, octamer-binding (NONO):
cgctcttttctcgggacgggagaggccgtgtagcgtcgccgttactccgaggagataccagtcggt
agaggagaagtcgaggttagagggaactgggaggcactttgctgtctgcaatcgaagttgagggtg
caaaaatg (Seq ID No: 564)

*Homo sapiens* lectin, galactoside-binding, soluble, 9 (LGALS9):
atttctttgttaagtcgttccctctacaaaggacttcctagtgggtgtgaaaggcagcggtggcca
cagaggcggcggagagatg (Seq ID No: 565)

*Homo sapiens* chaperonin containing TCP1, subunit 5 (epsilon)
(CCT5): cggtctccgccggttggggggaagtaattccggttgttgcaccatg
(Seq ID No: 566)

*Homo sapiens* haloacid dehalogenase-like hydrolase domain containing
1 (HDHD1): cttcctcctcgcccccacccagacccagaaggcgccaccatg
(Seq ID No: 567)

-continued

| SEQUENCES: |
| --- |

*Homo sapiens* glutamate dehydrogenase 2 (GLUD2):
cttccttcctagtcgcggggagtctgagaaagcgcacctgttccgcgaccgtcacgcacccctcct
ccgcctgccgcgatg (Seq ID No: 568)

*Homo sapiens* general transcription factor IIIC, polypeptide 3, 102 kDa
(GTF3C3): ggttctctgtcccggttcctggggttgcacagacagaccctgtaaacatg
(Seq ID No: 569)

*Homo sapiens* general transcription factor IIIC, polypeptide 5, 63 kDa
(GTF3C5):
gggtccctcgctggctagtaggagagactggtgcttgccccgcccggtggactaactcgcttaatt
ttaaataaaaagtcgaggacacggcggtcgttttcccgaagacatgggccctcccatgggccattt
gctccctggaggccctcgcgtcttgctgagcccggggagttaggatgacgcgagcggtgagggagc
ccggaacgattccttcgcggaacaattgaggcgaggcctttgggagtactttgtgggacggaccct
ggcgggccctgccagacgcacagggatg (Seq ID No: 570)

*Homo sapiens* ancient ubiquitous protein 1 (AUP1):
ccgccttcccaagagcccctgcggccgggcgcgaaaatggcggcggcggcgacggccgggcgctcc
tgaagcagcagttatg (Seq ID No: 571)

*Homo sapiens* coatomer protein complex, subunit gamma 2 (COPG2):
cggccttcctgcagcctcttccgctcgccggctgcggcgcctgggacggttgcggtgggtctgggc
gctgggaagtcgtccaagatg (Seq ID No: 572)

*Homo sapiens* apoptosis antagonizing transcription factor (AATF):
cggtctctggcggagtcggggaatcggatcaaggcgagaggatccggcagggaaggagcttcgggg
ccgggggttgggccgcacatttacgtgcgcgaagcggagtggaccgggagctggtgacgatg
(Seq ID No: 573)

*Homo sapiens* integrator complex subunit 6 (INTS6):
tctcctctttctccaccacctcgggccccggtgtccccggccagcactatg
(Seq ID No: 574)

*Homo sapiens* F-box and leucine-rich repeat protein 4 (FBXL4):
tcttccttccgggtcgcgctaggccgggcttgcggcggttgtgccgcatctagagagtcggggagc
cgcccccgcacccaggccttctcgcgctgcctggtcgctggtgaagcccgcggcgcgcgcctctcc
cggaccctgcagggtaaaagaatgtcacatgtcagcatttgtacctgaagtcagcatgcaaagttc
agggtacctggatgaatgccaacttttgcatttcccatgtgtatcctgtgaccattctatctggga
acatccttcaaagagttcatgcatcttactgaggacacctgaccttttgaagcttcataattcaca
tctagatg (Seq ID No: 575)

*Homo sapiens* guanine nucleotide binding protein
(G protein), gamma 3 (GNG3):
gctccttctagcatccttcatccttcaggtaccagccatccagacagtgcttgagctgcagaaact
gagaccagacctctggcctggccctccccaggggcctcctttcgtatagtcactgcttctgcatca
gatactttcagctgcaactccctactgggtggggcacccatttcaggcagaaggttttggtaccct
ccactgaccctacacccagggctgctactgccgcttgtggcttcaggatg
(Seq ID No: 576)

*Homo sapiens* histidyl-tRNA synthetase 2, mitochondrial (putative)
(HARS2): aggccttttgttcctgtcccggaaagccggcgtcctgccgcgcgatg
(Seq ID No: 577)

*Homo sapiens* interleukin enhancer binding factor 3, 90 kDa (ILF3):
cctcctcctcctcttctcgccattgcagttggacccagcagcccggcgcgcaccgcgtggcttttg
ggggcagaccccggcgggctgtggcaggagggcggcggcggcggctgcggtcgaagaaggggacgc
cgacaagagttgaagtattgataacaccaaggaactctatcacaatttgaaaagataagcaaaagt
ttgatttccagacactacagaagaagtaaaaatg (Seq ID No: 578)

*Homo sapiens* polymerase I and transcript release factor (PTRF):
gtttcctctgctctccgctctcgcccgctagctctcctcccttccgctcctgcttctctccgggtc
tcccgctccagctccagccccacccggccggtcccgcacggctccgggtagccatg
(Seq ID No: 579)

*Homo sapiens* 5'-3' exoribonuclease 2 (XRN2):
tgccctctgccgctgctcccgtctctttggttacgctcgtcagccggtcggccgccgcctccagcc
gtgtgccgctatg (Seq ID No: 580)

*Homo sapiens* 2-hydroxyacyl-CoA lyase 1 (HACL1):
ccgcctcttccttcccgttgtttaaggcagttggttgccctcctgtccgtcagaggtgcagtacca
gaggtggcgtgctgccgatttcgcgtttgccttgctggatgattccgcttgtttgccggctgcgtg
agtgcttagagcttttcggtggaagatg (Seq ID No: 581)

-continued

SEQUENCES:

*Homo sapiens* zinc finger protein 346 (ZNF346):
ggctctctaccggtgagggtttgcggggaagatg (Seq ID No: 582)

*Homo sapiens* microtubule-associated protein, RP/EB family, member 3 (MAPRE3):
cagtctctgtgcgttgaagccggagaccgcggcggcctcagcgaggaccctccgccccggagccgc
cggccggagccgcagcctctgccgcagcgcccccgccacctgtcccctcccccctccgcctccgccg
gagccgcctcgtgcactctggggtatg (Seq ID No: 583)

*Homo sapiens* splicing factor 3b, subunit 3, 130 kDa (SF3B3):
gtgccttttccgccgcgcgccaccagaatgtccctgtcttgaggtctaatggcggacgccagtat
gttggagttggtggtggcttaagttttgaagggaggtagcatccgttggatatccacaccatcctt
ctcgctgcaggctttcttggactccgtactgttggtgtaaccaaggcctggaggtctgggtggctc
aggtttcctgcagccatg (Seq ID No: 584)

*Homo sapiens* spondin 2, extracellular matrix protein (SPON2):
ctgcctctcgctggaggccaggccgtgcagcatcgaagacaggaggaactggagcctcattggccg
gcccggggcgccggcctcgggcttaaataggagctccgggctctggctgggacccgaccgctgccg
gccgcgctcccgctgctcctgccgggtgatg (Seq ID No: 585)

*Homo sapiens* solute carrier family 13 (sodium/sulfate symporters), member 4 (SLC13A4):
ttttcttttctgctttgcaggcccaggctcaaggcaaattataagtagggaaccaatttgagggaa
agacatgtgaacagagttaaggtaccacgtcctgggagcgaccagcagccccacctgaagtccgca
tgcaactctgacaagctcaggtgcttgttttaaggaaaggggctactagagtcttaccaacagcga
gcccaggtgggagatgaaacaggtactccccaaaataggtcatccgagggaggaaaactgatggag
agcacaatgtgctctgagcgtttttaatgtttttaagcttttaaatgatttcttcaaggccgagca
gcagcagcaaaggtgtggcttaaaggattaaggggggtttctgctgacacctagaatgaagttactc
tattactaatcaagccgagaggaggcccactatgccccgtttatcatcctttcccagttcctttt
tgctggtcacaaaacgatgctcatcaatcccacctaaagcaggaggccaggagcccagcctcttgt
agaaacagcgagggtataactgccctcccgttctgcccccaagacgaaggaggactctcggaagcc
aagaaaggtttaagaagtctttctggatagagagcagtgcccaggcaggaagcctttcgccggcag
agcggggtccaaggacgagctggagaggacagaggcgcgatg (Seq ID No: 586)

*Homo sapiens* PRP6 pre-mRNA processing factor 6 homolog (*S. cerevisiae*) (PRPF6): attcctttccttcctagccttggtcgtcgccgccaccatg (Seq ID No: 587)

*Homo sapiens* eukaryotic translation initiation factor 3, subunit K (EIF3K):
ccacctcttcctgttcccgtccttgaggacgccgtgccgggtcagtgttagcctccagccctggtt
gtggaaggcgacagaagtcatg (Seq ID No: 588)

*Homo sapiens* ataxin 10 (ATXN10):
ccccctcccccgcggcgccgtctcctcctcccgcctgaggcgagtctgggctcagcctagagctct
ccggcggcggcgcagcttcagggcagcgcgggctgcagcggcggcggcggttagggctgtgtaggg
cgaggcctccccccttcctcctcgccatcctactcctccctcctcgtcatcctccccccttcgtcctc
ctcgccttcctcctcctcgtcaggctcgacccagctgtgagcggcaagatg
(Seq ID No: 589)

*Homo sapiens* secretogranin III (SCG3):
cttccttcctcacttcctctgcaggagggagcgagagtaaagctacgccctggcgcgcagtctccg
cgtcacaggaacttcagcacccacagggcggacagcgctcccctctacctggagacttgactcccg
cgcgccccaaccctgcttatcccttgaccgtcgagtgtcagagatcctgcagccgcccagtcccgg
cccctctcccgccccacacccaccctcctggctcttcctgtttttactcctccttttcattcataa
caaaagctacagctccaggagcccagcgccgggctgtgacccaagccgagcgtggaagaatg
(Seq ID No: 590)

*Homo sapiens* polymerase (DNA directed), mu (POLM):
cttccttccgtctcgctcggagtttccctctgcgttcgctccgcgctgctggaggctgtcgtccca
atg (Seq ID No: 591)

*Homo sapiens* epsin 1 (EPN1):
cctccttctgttgcttcccgtctcctcggcggctcccctcccccgcccggctctccgcgccccttc
tgggcggcggggcggcggagccgtcggcgtgcggccctccttgcgttcgtgcgtgcgcccgtggcc
cggcgcacgtcccgcgacaccgaggccgagcggggcagggggctgaccgccatgaccccccagagc
ccggcgtgagggggccgagatgcggtgacctgccagcacctgccgcagccttcgtccgggagtcgc
cccatctctccacgcatcggggccctgtgccccttgctgctgcagccgggcaccatg
(Seq ID No: 592)

*Homo sapiens* Sec61 alpha 1 subunit (*S. cerevisiae*) (SEC61A1):
gtgtctctcggcggagctgctgtgcagtggaacgcgctgggccgcgggcagcgtcgcctcacgcgg
agcagagctgagctgaagcgggacccggagcccgagcagccgccgccatg
(Seq ID No: 593)

-continued

SEQUENCES:

*Homo sapiens* Obg-like ATPase 1 (OLA1):
cgttctctcctccttcctccccgcctccagctgccggcaggacctttctctcgctgccgctgggac
cccgtgtcatcgcccaggccgagcacgatg (Seq ID No: 594)

*Homo sapiens* sorting nexin 12 (SNX12):
aggcctctgtcccccaccccctttccccggtcccaggctctccttcggaaagatg
(Seq ID No: 595)

*Homo sapiens* LAG1 longevity assurance homolog 2 (*S. cerevisiae*)
(LASS2):
cggcctttttttcccggctgggctcgggctcagctcgactgggctcggcgggcggcggcggcggcg
ccggcggctggcggaggagggagggcgagggcgggcgcgggccggcgggcgggcggaagagggagg
agaggcgcggggagccaggcctcggggcctcggagcaaccacccgagcagacggagtacacggagc
agcggccccggccccgccaacgctgccgccggctactccctcttgatgccctccccttttgcccctc
actcaggatg (Seq ID No: 596)

*Homo sapiens* cytohesin 4 (CYTH4): tcatcttttccccagaggcgtcggaatg
(Seq ID No: 597)

*Homo sapiens* transportin 2 (TNP02):
aattctctctctttggctccctccttccgcgcgagtctctggagaagccgcagcgcgagttgccgc
cgctgctgcccggggccgggtaagtgggcctcactcagagcccgaccctcttggccccggcttgcg
tcgacccccgccgggcaccgagcctgcgccgcgcgcggcccgggcgtcggggccgcgcccgaccgg
gaaaggccgggaagccggttgggcccgatcctcctggcagctagaacgggccgggcgggggagggg
ggaaccgagcagagcttaggggggtggggcctcggagccaggccatgtcggggctcctcaagaagag
ggccagtgggactgctggggtcgggctggaggggatctgattggggaagcgtctggggactgctt
ggggcctgattggggacgtcgcgaggatcggcttgccttgcgccatg (Seq ID No: 598)

*Homo sapiens* makorin ring finger protein 1 (MKRN1):
gggcctttgctgtgtgggataaacagtaatg (Seq ID No: 599)

*Homo sapiens* vinculin (VCL):
ctgtctcttcgccggttcccggccccgtggatcctacttctctgtcgcccgcggttcgccgccccg
ctcgccgccgcgatg (Seq ID No: 600)

*Homo sapiens* DEAH (Asp-Glu-Ala-His) box polypeptide 38 (DHX38):
cctccttttcctgcccccagactagaggcgggatgtagtctcttaggctaagagtgattggtcaca
aggagactcggaagtgtctgatcagagccccagaggaggccttgagagcctgttggcgtaccgttc
cacacttggatccaggaatcgggcgtgttccaggctgctctctatggtagctttgggcggatagag
ggggcgcgcaaagtattaagggacaataatggccgctttcaaggtgtggattttggctccttgagc
ctgtctgagcgaggggtggcagcgccggcgccccagaatccgggacagaagggtcccaagagtcgc
gcttggtgagagaaatcccagatcctgtgatg (Seq ID No: 601)

*Homo sapiens* osteoglycin (OGN):
catcctctaagcttttaaatattgcttcgatggtctgaattttatttccagggaaaaagagagtt
ttgtcccacagtcagcaggccactagtttattaacttccagtcaccttgatttttgctaaaatg
(Seq ID No: 602)

*Homo sapiens* NIN1/RPN12 binding protein 1 homolog (*S. cerevisiae*)
(NOB1): gctcccctctcacgcagccaacatg (Seq ID No: 603)

*Homo sapiens* nudix (nucleoside
diphosphate linked moiety X)-type motif 5 (NUDT5):
catccttttagcaccgcgagaggcgccggtgtttcgagccgtggcaccggcatcggctgacactgc
tgcctccagctagttatttcgtcctcttccgttcttcacccctacaccttggaggtgaacttctca
cctgagggctgtaaagactcgtttgaaaatg (Seq ID No: 604)

*Homo sapiens* WD repeat domain 91 (WDR91): cgtccctcaccgcac-
cacccctaaagacgctagcgctgcgatg (Seq ID No: 605)

*Homo sapiens* nuclear transcription factor Y, gamma (NFYC):
gggcctctgcattgcccgactccgtaggagcgcgggggcggctcctgctcttcctggactcctgag
cagagttgtcgagatg (Seq ID No: 606)

*Homo sapiens* protein phosphatase 2, regulatory subunit A, alpha
(PPP2R1A):
ccgcccttccttcttctcccagcattgccccccccacgtttcagcacagcgctggccgcagtctga
caggaaagggacggagccaagatg (Seq ID No: 607)

*Homo sapiens* vesicle-associated membrane protein 2 (synapto-
brevin 2) (VAMP2):
ccatctttccgtcccgggcagccagcgccagtcggagccagcgcgagccgccgccgccatcactgc
cgctgccaagtcctccacccgctgcccccgccatg (Seq ID No: 608)

*Homo sapiens* transmembrane protein 5 (TMEM5):
gattctctttccgcccgctccatggcggtggatgcctgactggaagcccgagtgggatg
(Seq ID No: 609)

-continued

SEQUENCES:

*Homo sapiens* UDP-GlcNAc: betaGal beta-1,3-N-acetylglucosaminyltransferase 3 (B3GNT3):
aactctttcttcggctcgcgagctgagaggagcaggtagaggggcagaggcgggactgtcgtctgg
gggagccgcccaggaggctcctcaggccgaccccagaccctggctggccaggatg
(Seq ID No: 610)

*Homo sapiens* SEC11 homolog A (*S. cerevisiae*) (SEC11A):
gcgccctttccccctgccggtgtcctgctcgccgtccccgccatg (Seq ID No: 611)

*Homo sapiens* RUN and SH3 domain containing 1 (RUSC1):
ctccctccccgcgccccgtcctctcccgccctacaggccctagcagggcaggcgggaggtgagcgc
ggccatcccgctcccggagttccgggatcctggagtccgtagttcgtggtccttcgccggtgtccc
cggagcccagcggctgtggatg (Seq ID No: 612)

*Homo sapiens* aryl hydrocarbon receptor interacting protein-like 1
(AIPL1): cctccctttctcctgcagccatg (Seq ID No: 613)

*Homo sapiens* tumor necrosis factor, alpha-induced protein 8
(TNFAIP8):
cctccttttctcccgccggctctaacccgcgcttggctaaggtccgcgggaacccgtgagccaccg
agagagcagagaactcggcgccgccaaacagcccagctcgcgcttcagcgtcccggcgccgtcgcg
ccactcctccgatg (Seq ID No: 614)

*Homo sapiens* staphylococcal nuclease and tudor domain containing 1
(SND1):
gcgtctctttcgctccgtgtcccgctgctgctcctgtgagcgcccggcgagtccgtcccgtccacc
gtccgcagctggtagccagcctgcccctcgcctcgactccctttcaccaacaccgacacccacatt
gacacctccagtccggccagccgctccactcgttgcctttgcatctccacacatg
(Seq ID No: 615)

*Homo sapiens* DNA segment on chromosome 4
(unique) 234 expressed sequence (D4S234E):
cgccctcttttggtcgccccctccccaacccagcactaaggagcaccctgctctggtctccgccac
cacccagcgcctcctggacccatccccccaaacccttgaacgtcctcaggaccccccaggtgagcgc
ggcgcgctgcgggcggggaccctctctgcacctccccgcacccctgggggtcgctctgtccctacg
gtccccgcctcccctttctcctttctaagcgcctcgcgcccaggccgccgcccggggtggcgcagc
ccgcagccctcccgctccgggcgccctccgccgctccgagaccccctgggggcgcgtcctctcccg
ctcccctgttccctcccccggctcagggcgggcgcgtggtcccaggggaggctcccgcccagcccc
gcactcctttgtgcggccgggcgggcgctgcgtcaaggtggaggcgcggccacacgcgcgcaccca
cccgcgcgcacccagcccccgggagaggcaggaagggaggcggcggcgcgaggaggagggagcggc
cgtggagcccaatcgttcgctccccttcccgggtccgcgcgcggcgccgcctccgccattgctgcg
agcaggagcaggagacgcggagctcggagcgctcagctgacctgccggagccgggcgtgggctgca
gcctcggagctcccggaacgatg (Seq ID No: 616)

*Homo sapiens* growth hormone inducible transmembrane protein
(GHITM):
acgtcctttcgatgttgcgtcatgcagtgcgccggaggaactgtgctctttgaggccgacgctagg
ggcccggaagggaaactgcgaggcgaaggtgaccggggaccgagcatttcagatctgctcggtaga
cctggtgcaccaccaccatg (Seq ID No: 617)

*Homo sapiens* stress-associated endoplasmic reticulum protein 1
(SERP1):
tttccttcctctttcactccgcgctcacggcggcggccaaagcggcggcgacggcggcgcgagaac
gacccggcggccagttctcttcctcctgcgcacctgccccgctcggtcagtcagtcggcggccggc
gcccggcttgtgctcagacctcgcgcttgcggcgcccaggcccagcggccgtagctagcgtctggc
ctgagaacctcggcgctccggcggcgcgggcaccacgagccgagcctcgcagcggctccagaggag
gcaggcgagtgagcgagtccgaggggtggccggggcaggtggtggcgccgcgaagatg
(Seq ID No: 618)

*Homo sapiens* ADP-ribosylation factor interacting protein 1 (AR-FIP1):
cggtctcctcacttccggcttcgctgctcttggttctggttctggaggctgggttgagaggtcgcc
ggtccgactgtcctcggcggttggtcagtgtgaatttgtgacagctgcagttgctccccgcccccg
agcagccgaggagtctaccatg (Seq ID No: 619)

*Homo sapiens* tumor necrosis factor receptor superfamily, member 21
(TNFRSF21):
ccgccccttcggcgccaccacgtgtgtccctgcgcccggtggccaccgactcagtccctcgccgac
cagtctgggcagcggaggagggtggttggcagtggctggaagcttcgctatgggaagttgttcctt
tgctctctcgcgcccagtcctcctccctggttctcctcagccgctgtcggaggagagcacccggag
acgcgggctgcagtcgcggcggcttctccccgcctgggcggccgcgccgctgggcaggtgctgagc
gcccctagagcctcccttgccgcctccctcctctgcccggccgcagcagtgcacatggggtgttgg
aggtagatgggctcccggcccgggaggcggcggtggatgcggcgctgggcagaagcagccgccgat
tccagctgccccgcgcgccccgggcgcccctgcgagtccccggttcagccatg
(Seq ID No: 620)

-continued

| SEQUENCES: |
|---|

*Homo sapiens* sushi-repeat containing protein, X-linked 2 (SRPX2):
cccccctcttctgcagcagacggactgagttcctctaatccctgtgttccttctcccccatctttct
aaaacccttctctgagagaggaataactatagcttcagggataatatagctttaaggaaacttttg
gcagatgtggacgtcgtaacatctgggcagtgttaacagaatcccggaggccgggacagaccagga
gccactcgttctaggaatgttaaagtagaaggtttttttccaattgatgagaggagcagagaggaag
gagaaagaggaggagagagaaaaagggcacaaaataccataaaacagatcccatatttctgcttcc
cctcacttttagaagttaattgatggctgacttctgaaagtcactttcctttgccctggtacttca
ggccatatacatcttttcttgtctccataatcctccctttcaaggatg (Seq ID No: 621)

*Homo sapiens* HIV-1 Tat specific factor 1 (HTATSF1):
acctccctttctctgctcagctccagcgtcatttcggcctcttagttcttctgaaccctgctcctg
agctaggtaggaaacatg (Seq ID No: 622)

*Homo sapiens* trafficking protein particle complex 2 (TRAPPC2):
gggtctcttccgcggaaactgacattgcgtttccgttgtcggcctcccactgcaggagccatatat
tgaagaccatg (Seq ID No: 623)

*Homo sapiens* UDP-N-acetyl-alpha-D-galactosamine:
polypeptide N-acetylgalactosaminyltransferase 5 (GalNAc-T5) (GALNT5):
ccacctttcttgggcttgtaggaaggtggacatgggctcccggagacaagacaagtgatatgttg
aactgttcggtggctggaatcaactgctcctggagtgacctaaggccagtgtttatcagaacttag
ccagggccagccaagcaggcacagatgctctgctatgaaatgccacgcaggcagagactgacaagc
ggtaggaactgagctttccccttggactgctgcttcctgctgtgttcaggggagggggtcactttc
tggcaactctgctgctgctgctgctgctgctgctacttcagcttcctctccactcaaggtaagcag
gctaagggagggcaggctgctagggaaagctttgtaccatg (Seq ID No: 624)

*Homo sapiens* transmembrane protein 97 (TMEM97): tggcccctcttctca-
catcagcgggtccaggcccaaccgacagactatg (Seq ID No: 625)

*Homo sapiens* EH-domain containing 2 (EHD2):
cgtcctccccgctccgggccccacccggctcagacggctccggacgggaccgcgagcacaggccgc
tccgcgggcgcttcggatcctcgcgggaccccaccctctcccagcctgcccagcccgctgcagccg
ccagcgcgccccgtcggcagctctccatctgcacgtctctccgtgaaccccgtgagcggtgtgcag
ccaccatg (Seq ID No: 626)

*Homo sapiens* tubulin tyrosine ligase-like family, member 4
(TTLL4):
cgccctcttcttccagactctcggtctgtccgctgggggcgcgcgcggtgtgtggcaggcggcagc
ggcgctggcggccgagtgcgcttgtcacgcgtggcggtgcgtggttgctaggggcgcctgaggctg
ccgggtagcccagcaggccgagggaggaagtagcgtggagccggtgccgagccggggcgaagctgg
atcccctagatagactgtcttcaagctcactgatattttcctctgcttgatccattgtgctgttga
gagcctctagtaaatttttcagactgacagacttcaaggatgcagctgctactaccggaggtgtgt
ggcaccttacctcagcaaggccatgagaccgtgtggccatgatgtgggcccctcatg
(Seq ID No: 627)

*Homo sapiens* basic leucine zipper and W2 domains 1 (BZW1):
acctctccctcctcctggcgttagttccggtcgcagaggagacaccgccgcagttgccggtacatc
ggggatttctggctctttcctcttcgccttaaattcgggtgtcttttatg
(Seq ID No: 628)

*Homo sapiens* centrosomal protein 57 kDa (CEP57):
ttgccctttctgtgtaagctgtgagcgtaggcggccctgagggggtgtgttgcaggggtttccaag
cccagcaccagcacccttgcccttttccatcaggggttcagcctagggtccccgctggtgggcggc
tcccgagtcttggagaagagcacgagaacctagaccgcccccgaagtgcggagaccccctgggcag
gctgaaagatg (Seq ID No: 629)

*Homo sapiens* family with sequence similarity 115, member A
(FAM115A):
ctgccctttgcctcctgggcggagaagctgcttcctcctgggaacaaccgcctcccgctcctagca
ggttgctactgccccgaacccgcgctgcagggaacagcggggcaaacagtgagtggggttcagcgt
agactctggaccaggagaggcccgcggtgaccgaggcctgggccccggaaaccaatagagccatg
(Seq ID No: 630)

*Homo sapiens* ATG13 autophagy related 13 homolog (*S. cerevisiae*)
(ATG13):
agccctctttcaccccccccccccggccattaccgaagcggatgaaaacaaacactaacgatggcg
gcgccgggaagcgaccggctgctgggcttaaggcgggagtgaccgcttaaccagtgagggaagcac
tgaagagcgccagtcgacgtgggtgcgacaactcgcggagtcttaggagcaaaacgtctggggcct
gcgagccaggacccttctgaagccttaggtgtctatcggcgacgtgtacggtcactgcagctccgg
agcgcggaaccctcagccaggaggcgcggctggtcggtcccaggtcccggcctccgtaatgagagc
ccggaaccactctttgtgccgcagcttcgcagcatcttggactcaagtgattctcctgcctcagcc
tcctgagtagctgggactacagattcctataggcaatg (Seq ID No: 631)

*Homo sapiens* sorting nexin 17 (SNX17):
ccgccttcccacatcggatcgcagggctcccaaaatggcgagtgaggctgcggggactcgctgagc
agcggaggggggagcgtgcagagccgctgcggccctcacagtccggagcccggccgtgccgtgccgt
agggaacatg (Seq ID No: 632)

-continued

SEQUENCES:

*Homo sapiens* phytanoyl-CoA 2-hydroxylase interacting protein (PHY-HIP):
cgttctttctcccttctctgcctctctctcctccacgctgctttgatttcgctcttgcctctcttc
ttgcgctgctcagctgggaacatcgtctcaccaggggcagcagcgacgcgctgcacagccagacag
gagctggctgcggggcatggaagcagcctccttggcagccgggagaggagcaagcgcacgccactg
cccgtgacccaggcgtccggctgctgtcccctgccggggagctcatccacgcagaggtctctccct
gtcctccctgcgagcttttcctctgcagagcccagtggagccagtccccacaggagacaaccctga
cgggagcatg (Seq ID No: 633)

*Homo sapiens* translocase of outer mitochondrial membrane 20 homolog (yeast) (TOMM20):
cggcctttctgtgttcctggcccgcggccgtcgggtgtgagctgcgccgaccgctctgagggttcg
tggcccaccgctccttcgcggtccctgccgccaccgtccacgctcagcgttgtagagaagatg
(Seq ID No: 634)

*Homo sapiens* KIAA0141 (KIAA0141):
cggcctttctagccgctgtcccaagggttggtctcgcgctttcggctgcgagctctctgtggtgct
ggcagcgacatg (Seq ID No: 635)

*Homo sapiens* janus kinase and microtubule interacting protein 2 (JAKMIP2):
ctccctcctttaaacagcttctccgggtctcagcatgggcttccagggcagcgattgaggagacct
taccaaggagcaccacacagtagatgctgagacatcgtactccaggataagaaacagtaacatggc
agcacctgcttgaaagaaattaaaaaccaacagactccatttagaaaggaacaatg
(Seq ID No: 636)

*Homo sapiens* EPM2A (laforin) interacting protein 1 (EPM2AIP1):
cctcctctccccttgcggcctttctaacgttggccctgctcttgtggcctcccgcagaatg
(Seq ID No: 637)

*Homo sapiens* centrosomal protein 170 kDa (CEP170):
cggtctttgccgttaccgctatgtgtggggcgtgtgtggaataacgttattgcccagcggagctga
gggccccggagctcgaccgcagcggcagcgacgacaacagcggcgacgacgacgacgacgaggtgg
ggggaggacggcgtgcgagagactcacgggacgcgacgcgccccgcctcccccgtccggtccctct
ctccacggtaaggggatgacgtagctttgccaaagacttagaagctaagcagaaaatg
(Seq ID No: 638)

*Homo sapiens* suppressor of Ty 7 (*S. cerevisiae*)-like (SUPT7L):
aggcctctcgaggtccagacagccgcccagcccgctctgcgacgcagcagtgaatagtgtggtacc
tccttgtctcggttcaggtccagacctccccgtcttccggctgccctgaacgtcaggcgacctcag
gaccctgtgattggcgcctgcgccggcggaccgtgaccgaggaaacccctggagggacttgggcat
tccttgggctccgtgcctgttcttcgtgctcctttcgggcaaggatctcacattatcagtctttga
ccgacacagaatgcctggcatttgataaatgtttgttgaacttgaagagacatatggacaatg
(Seq ID No: 639)

*Homo sapiens* non-SMC condensin I complex, subunit D2 (NCAPD2):
ttttccttttcatttcagcctgactgccggaatcagagccgcgggtgagatccccagccctgtgag
cctgtaggagtagaatg (Seq ID No: 640)

*Homo sapiens* ring finger protein 10 (RNF10):
ggttctttgagatgctgtttggcgactcgtcgccattcccggagcaggtcggcctcggcccagggg
cgagtatccgttgctgtgtcggagacactagtccccgacaccgagacagccagccctctcccctgc
ctcgcggcgggagagcgtgtccggccggccggccggcggggctcgcgcaacctccctcgcctcccc
ttcccccgcagcctccgccccgccaggcccggcccggactcccgagccccggcctcctcgtcctcg
gtcgccgctgccgccgggcttaacagccccgtccgccgcttctcttcctagtttgagaagccaagg
aaggaaacagggaaaaatgtcgccatgaaggccgagaaccgctgccgccgccgacccccgccggcc
ctgaacgccatgagcctgggtccccgccgcgcccgctccgctccgactgccgtcgccgccgaggcc
cccgttgatg (Seq ID No: 641)

*Homo sapiens* PAN2 poly(A) specific ribonuclease subunit homolog (*S. cerevisiae*) (PAN2):
agcccttcttgattggaagaagcgcctcggaccccggtccttggcgccgtagtggttaggttgagc
cctaggcgtgggggagaactggggaaactggaatttcccgcggagctgacagcgcttgcgctcccc
ctactcgttctaattccacgcgctccaaaatatccgccatggagaaatcttggccaggatgtccat
tctaggcccatcggtgctgtcttgctgaaggttgggtcaggcatctaaagggactgtggtaaggga
gggtgtgacacaggtgtaagctgccatcgtcatcatg (Seq ID No: 642)

*Homo sapiens* CD302 molecule (CD302):
gctcctctccggccgcgcagccgctgccgcccacccgcacccgccgtcatg
(Seq ID No: 643)

*Homo sapiens* NSA2 ribosome biogenesis homolog (*S. cerevisiae*) (NSA2):
gactctttcctgtcccggcctgcgtggtgtgggcttgtgggtctttgagacccgaaaattgagagc
gttttcgcactccagcggctgctcctggcggctctgcggccgtcaccatg
(Seq ID No: 644)

-continued

| SEQUENCES: |
|---|

*Homo sapiens* DIS3 mitotic control homolog (*S. cerevisiae*) (DIS3):
acgccttttgctggaagagcgctgctggggttaggattctgcgcggcgaggcaagatg
(Seq ID No: 645)

*Homo sapiens* caspase recruitment domain family, member 8 (CARD8):
cctcctctgcgagcgttatttcaaaagaagttgagaaccagagaaaccgacctaaggggattctcc
catttggcccgtcctaccctaaagtcaccacctgctgcttttctggagcgcttaccagtgaccaag
aggaacagaacacagagcagcctggcagtgtccaagcaacaagcctccgctcctccttcctgcacc
ctggggctcctgaaactcacatgggtaaaaaagatacagtaaagacataaataccacatttgacaa
atg (Seq ID No: 646)

*Homo sapiens* epsin 2 (EPN2):
ccgcctctcgagcgctgccggtggccgcagcggcgcacccacgccggcccggaggagcagagtgtt
catttctgtgtcgggcacagtgctaagtgctgggtgctcactggtgatgaggcagatgaaggttac
caaacttgtggacaggagcctcatatcagagacgtggacctcactgtagcctggtcatggcttcca
gcttttcgaatctgaggctccaaaggaggaaatgaccattcagggatcttactccagcttgattac
ggagactgaaccttcatagggtgcgcacttaccaaggacaggaaggtttctctgtttgaagggctt
taaacttataacaaagaaaataaaaatg (Seq ID No: 647)

*Homo sapiens* pyridoxal-dependent decarboxylase domain containing 1
(PDXDC1):
ccgcctctcaaccatcaggttcggcagcccgcggcgccgcctggcagctcctcctcttctccgccc
cgccggccgcgggcgcgggggacgtcagcgctgccagcgtggaaggagctgcggggcgcgggagga
ggaagtagagcccgggaccgccaggccaccaccggccgcctcagccatg (Seq ID No: 648)

*Homo sapiens* nicotinamide nucleotide adenylyltransferase 2
(NMNAT2):
ccttcctttctccctctgcagacacaacgagacacaaaaagagaggcaacccctagaccaccgcga
aggacccatctgcaccatg (Seq ID No: 649)

*Homo sapiens* mitochondrial ribosomal protein S27 (MRPS27):
tgttccttttggtacgctccaagatg (Seq ID No: 650)

*Homo sapiens* leucine-rich repeats and calponin homology
(CH) domain containing 1 (LRCH1):
tcccctccttccagcgcctttcggtggagcactgcggcactcagcccgagctgccgttttcccctc
gcggggaacgctgtgaccccccgcaggagcggcggggcggggtgggggggcccgggagaagatg
(Seq ID No: 651)

*Homo sapiens* PAS domain containing serine/threonine kinase (PASK):
gctcctttccgtggtgtgtagccggcttggcgtgaccctcgcctgatccagttgttagagttggaa
gcttggcagttggcctcccttcttcccatg (Seq ID No: 652)

*Homo sapiens* megalencephalic leukoencephalopathy with subcortical
cysts 1 (MLC1):
cttcctttcctagttgggttctgacagctccgaggcagtggtttacacaaccaacacgaaacattt
ctacgatccacccgattcctcccctcattgatattcaggaagcagctctccttcccctgccttcag
ctcaagtttgctgagcttttgtttcatttgtgaatacttcttgctggaagtccctcacccagagac
cagtgctcccaacggcagagcagcgggggagataaagaactggtgacacgtggctgtacattcagc
acagctgtggtgtccccaagtgccatg (Seq ID No: 653)

*Homo sapiens* RRS1 ribosome biogenesis regulator homolog
(*S. cerevisiae*) (RRS1):
ctttcttttccggattgggcatcccggcatctgcacgtggttatgctgccggagtttgggccgcca
ctgtaggaaaagtaacttcagctgcagccccaaagcgagtgagccgagccggagccatg
(Seq ID No: 654)

*Homo sapiens* formin binding protein 4 (FNBP4):
cgctctctgctcgcgcttgggctcgcgatg (Seq ID No: 655)

*Homo sapiens* peptidylprolyl isomerase domain and WD repeat containing
1 (PPWD1): gcgccttttctgacgatgcgaacaacatg (Seq ID No: 656)

*Homo sapiens* sorting and assembly machinery component 50 homolog
(*S. cerevisiae*) (SAMM50):
ccgccttctgccctcagcagcagacgctctgtcccgcccgggcagctctgcgaggcagcggctgga
gagggaaccatg (Seq ID No: 657)

*Homo sapiens* Yipl domain family, member 3 (YIPF3):
gcttctccttttgtgttccggccgatcccacctctcctcgaccctggacgtctaccttccggagg
cccacatcttgcccactccgcgcgcggggctagcgcgggtttcagcgacgggagccctcaagggac
atg (Seq ID No: 658)

*Homo sapiens* tectonin beta-propeller repeat containing 1 (TECPR1):
caccctcttgcccggtccccgggagggccggtccgctcctcccggacgccgaggacctaccaccgc
gacttcgccccgcccggcgcgggcccaggaccctgatgtcgcttttgaacagcccctgcacctggc

SEQUENCES:

agccagcgagctactgtagtaggcattgccgactgtttgcataccggatgggagtgacagtgtaat
agaaaaacaagcaagaaacctttaggtaggactcctaaggctcagaggaagttacctccagccgc
tgccatg (Seq ID No: 659)

*Homo sapiens* DDB1 and CUL4 associated factor 12 (DCAF12):
ccttccctttcccggctcaagtccttcctctctctttcctttctttccgcctatctttttctgct
gccgctccgggtccgggccattttccgggccgggcgcactaaggtgcgcggccccggggcccagta
tatgacccgccgtcctgctatccttcgcttccccgccccatgtggctgcggggccgcggcggcgc
tgcccactatg (Seq ID No: 660)

*Homo sapiens* chromosome 3 open reading frame 17 (C3orf17):
ccgcctttcgtaagtccccccgcctcgcatg (Seq ID No: 661)

*Homo sapiens* LETM1 domain containing 1 (LETMD1):
caacctcttctctcccgcttctctcgctgtgaagatg (Seq ID No: 662)

*Homo sapiens* chordin-like 2 (CHRDL2):
ctcccttctgctggaccttccttcgtctctccatctctccctcctttccccgcgttctctttccac
ctttctcttcttcccaccttagacctcccttcctgccctcctttcctgcccaccgctgcttcctgg
cccttctccgaccccgctctagcagcagacctcctggggtctgtgggttgatctgtggcccctgtg
cctccgtgtccttttcgtctcccttcctcccgactccgctcccggaccagcggcctgaccctgggg
aaaggatg (Seq ID No: 663)

*Homo sapiens* CCR4-NOT transcription complex, subunit 10 (CNOT10):
actcctctagccggaacctgggggcccggagccggggtaggcacagagttgtcctcggaggtccag
gacagcggccagcccggcggcgggagtcagggccacgccacctgcagggaagaacccgagtcgaag
cgggaagatg (Seq ID No: 664)

*Homo sapiens* THUMP domain containing 3 (THUMPD3):
cttcctcttgcagttgaggccggcgccgagccggacttcaggcggatctcgtggcggagcccatct
tgctccctctcccaggcctttacccgctccctaggattcccgggccctgtaggtgggagttgggag
acgacagtactgcttttaaagagacagtgttagggatcttggaagcacagccaacatg
(Seq ID No: 665)

*Homo sapiens* nipsnap homolog 3A (*C. elegans*) (NIPSNAP3A):
gctcctttccactcgggaaaccttcagaggagtctcagaaaggacacggctggctgcttttctcag
cgccgaagccgcgccatg (Seq ID No: 666)

*Homo sapiens* CAP-GLY domain containing linker protein 3 (CLIP3):
gcccctccctctccgcccccacccccctgtcggcgtctgggcctcgtccccttctctctgtctccct
tgcctcccccatcacgtcccctgacaccgacaccccattgctcccacagtctccccagtctccact
ttggtccccagcgctgtctgcccgaggatttgcctgaaggctgcccccaactctgcacccgccccc
cgagggccaccgaggaccatg (Seq ID No: 667)

*Homo sapiens* ring finger protein 167 (RNF167):
cacccttcccgaagtttttctgtcacctgtgttaggctccgtcccctttccgcgttttatccccgt
accagaaaaggatacatttagtgcctcccacccagctccactaaacgggttggatatctcattctt
tgagttggtgttccttccccggcgcccccatgtagctgggaagtgggacctgggggtggttggacc
cctgggatcctaaaggaggggcagggagggcgcagaactccgcttctgctccttgctaccaggacg
cgcggcctcctcagcctctttcctcccgctgccatg (Seq ID No: 668)

*Homo sapiens* polymerase (RNA) II (DNA directed) polypeptide M
(POLR2M):
cgttcttccgggaaaatggcgactcccgctcgtgccccggagtcaccgccgtccgcggatccggcg
ctagtagcggggcctgccgaggaagccgagtgcccgccgccgcgccagcctcagcccgcgcagaat
g (Seq ID No: 669)

*Homo sapiens* dihydroxyacetone kinase 2 homolog (*S. cerevisiae*)
(DAK):
tcgcctctttccgccagcgcccgcaggacccggatgagagcgcacgcttcggggtctccgggaagt
cgcggcgccttcggatgtggcggatgcggccgtgagccggcgggggaggtgctgctgctgcctcca
ctgtactcagacccaggtagcacaggattgtccatcctccagcagctcagtgcaacggtgtgaact
cagcctgtttcagagcctccacaccatg (Seq ID No: 670)

*Homo sapiens* RNA polymerase II associated protein 1 (RPAP1):
cgatctctgcggggcaagatggcggcgcccagacaggcctggagcacggatgaataagagggaacc
cccacacggagacactgctggagagagtcgtactggggaggcagctggagcagcaagatg
(Seq ID No: 671)

*Homo sapiens* torsin A interacting protein 1 (TOR1AIP1):
cctcctctttggtgcctccagccaggaggcgggagcgatccacagcagctgacccagctcaggcac
tgcctctctcacagccctcaagacacaccatgggcccagaggcaggtttgctacacagcagcgacg
acgcaggcggcggccccagcgactcgcaactgcctccctgaccacagcggccaccgcccaacaccc
ccgagaagccatcgccaccaccggcaggagaacctagggtccataaagccatcttcgcgatcgact
aaagctacgtcaacaactatg (Seq ID No: 672)

-continued

| SEQUENCES: |
|---|

*Homo sapiens* SERPINE1 mRNA binding protein 1 (SERBP1):
ccccctctctcggcccggccatcttgtgggaagagctgaagcaggcgctcttggctcggcgcggcc
cgctgcaatccgtggaggaacgcgccgccgagccaccatcatg (Seq ID No: 673)

*Homo sapiens* N-acetyltransferase 9 (GCN5-related, putative)
(NAT9): caccctttctgcgggggacgatttcgtcggtggtaggctgctaccatg
(Seq ID No: 674)

*Homo sapiens* ribosomal LI domain containing 1 (RSL1D1):
gcgcctcttcacgaggtggaaacaagatg (Seq ID No: 675)

*Homo sapiens* SH3 domain containing, Ysc84-like 1 (*S. cerevisiae*)
(SH3YL1): cttcctcttcctgggcagcctcgggacggggcgccgcggccgggcgggcagcatg
(Seq ID No: 676)

*Homo sapiens* methylmalonic aciduria (cobalamin
deficiency) cblD type, with homocystinuria (MMADHC):
acttcctttgcctgctcaccgccagcgtaggtgctaccaccgctgccgtcgccgccgccattttga
tggcaggaagagtccggttctgggacagctggagacagtggtggtgactgaaataactttaccaaa
ggaaagctattttgcgaactatcttctccagcggagatg (Seq ID No: 677)

*Homo sapiens* glioma tumor suppressor candidate region gene 2
(GLTSCR2): agttcttcctttgacaagatg (Seq ID No: 678)

*Homo sapiens* DDB1 and CUL4 associated factor 8 (DCAF8):
cagtcttctcgagcacatcgtcgcaaacggggccggaaagcgtggcagcgcaggcgcaagcgcaga
gagcggaggcggtggtggtggcggccgctggccagttccttcagtgaatctacagacctattttct
caggagctcagcctggccttacttcagtgataaaaggaggaaaggctggctacagcaaacatcatt
caagatg (Seq ID No: 679)

*Homo sapiens* UBX domain protein 1 (UBXN1):
ctttcttctcgtcggtgttcccggctgctatagagccgggtgagagagcgagcgcccgtcggcggg
tgtcgagggcgggttgcctcgcgctgacccttcccgccctccttctcgtcacacaccaggtccccg
cggaagccgcggtgtcggcgccatg (Seq ID No: 680)

*Homo sapiens* antizyme inhibitor 1 (AZIN1):
ccgccttctcacactttcaggctctgatcgcggccgcagttttcctttttcttctgccgtcgcc
ttctctgcctcttctcatcctttctcgctctgctgctctgcagtgtgacgagtccgaatcctcttc
ccacccagcccgcgcctttcttcttttgcctgcgctgttctatttctccttcggccgccgccgcca
ctgctgcacacagctggtgtcggtgccgcgcttttacccccaagtcgttcccgcagcctatggccc
aggccgccttgggtatttctgctcaaggtaaccacatccctctttaaaaattccgccgaaaaagag
aagacgctttacccgactctttgggccgttatctcacggcgaactttctgaccaagtatacaacta
cccagagggcctaggagaagtgctgtatagagagcagttcgacttcaacgctgagccaccttggga
acctagctgatgatagggggggttccatctcccaacttgtccatggaggtcttcacttcagaaatcc
aagactcatattcatccagcttggtgtcaagtgggctgttgctgccagaattatcttgtgattatt
tgagagatgtatcagtttcttctgaagtacaatcaactgtagaagcctttgtagcagtttgttgca
tattctaaggacccagacataggcttggtggcccgtctcttgtctttcctggtttatgactttcgg
ctttgtggaatacggctgagatg (Seq ID No: 681)

*Homo sapiens* cell division cycle 40 homolog (*S. cerevisiae*)
(CDC40): gcctcttcttcttccgccctggcagggtctccgcagaagatttgttgccgtcatg
(Seq ID No: 682)

*Homo sapiens* stathmin-like 3 (STMN3):
gcgcctctccagcctccgcaggcccaaccgccgccagcaccatg (Seq ID No: 683)

*Homo sapiens* nudix (nucleoside
diphosphate linked moiety X)-type motif 13 (NUDT13):
tttcctcttttgtgctgattcctgaggactaggaaggtgccccgaaaagaattcagagacctgaca
atg (Seq ID No: 684)

*Homo sapiens* calcium homeostasis modulator 2 (CALHM2):
ctctcttttctggagttagattagtctgaagccgccaccagccccaggcccccgtgcagaagaaaa
gcgggagggaacggcggaggccgccgctgccctgcaccgccctcctggaggccacttggagagtcc
ggccccgaggaggccatggccacaagtgcccacagctggccccaggttgccagcgtcgctacagcc
cagaccaaggcagaataatctccggatgagctggtggcaccgctgagcctttggtctcaccagggc
ttcctgttgctggcaggcggggtggagcggagctgctgggaggctgctggataggagaggggtcac
ggctgcggaagaggaggttcttcgggacacccgtggatggacacggcaaggaaacaccaggccaac
cacagctggggataaaatagcacaaccacaccctgccgtccagcgcctcccagcctgtgcccttc
ctagtaccaccagcaaccatcaatcccgtctcctcctgcctcctctcctgcaatccaccccgccac
gactatcgccatg (Seq ID No: 685)

*Homo sapiens* NMD3 homolog (*S. cerevisiae*) (NMD3):
tcttctctgtggcggagacagccaggttggcagctgacgggacagccggggtctattttgttgcgg
gttttcagcaaatccagggctggtctggaggcgcgaaaacttaaggcatacagaacgatg
(Seq ID No: 686)

-continued

SEQUENCES:

*Homo sapiens* ATPase, H+ transporting, lysosomal 50/57 kDa, V1 subunit H (ATP6V1H):
gcgcctctgtcattctactgcggccgccctggcttccttctacctgtgcggccctcaacgtctcct
tggtgcgggacccgcttcactttcggctcccggagtctccctccactgctcagacctctggacctg
acaggagacgcctacttggctctgacgcggcgccccagcccggctgtgtccccggcgccccggacc
accctccctgccggctttgggtgcgttgtggggtcccgaggattcgcgagatttgttgaaagacat
tcaagattacgaagtttagatg (Seq ID No: 687)

*Homo sapiens* DPH5 homolog (*S. cerevisiae*) (DPH5):
gggccttttctctgcacggagccggcgcttttgcagttgcttctgcggaaaggtggtagttaagaa
tttgtaaaggccagagaactacctacgattctctcagcggtctctcttctcctcaagtttgaaatg
(Seq ID No: 688)

*Homo sapiens* polymerase (RNA) I polypeptide D, 16 kDa (POLR1D):
cctcctccctccttccgtcctccgcgccttccgtcggtcggtccttgcttcctgcttcgcctccgc
gcctcgcgctatgggacagagcccccgatccgccagcaccacctgaggatccagaaaccgccccag
cgatg (Seq ID No: 689)

*Homo sapiens* HMP19 protein (HMP19):
ctgtcctttcagcaccacaagctcgggctgaggagggaggactcctggccgtcctcctcctcttca
aattggcttgaatcttctctgaccccccacgagtgcagcacagtctgggaagaaaggcgtaaggat
g (Seq ID No: 690)

*Homo sapiens* adiponectin receptor 1 (ADIPOR1):
gcgccccttccggcgcggggagggcgctgaagatcggggccgctcggccgcaggccgcctccagcg
ccgcgggatgtagcgcgggggaccgcggcccccagcagagcccgcctgcccggcttgtctaccatc
agagggagatctctgccccctggggctgagagaccccaacctttccccaagctgaagctgcagggt
attgaggtaccagccagatg (Seq ID No: 691)

*Homo sapiens* SH3-domain GRB2-like endophilin B1 (SH3GLB1):
ttttcccttgggacccgggtccacacggcggggtcgcccgtccatctccggctcgcccgcggggcc
catcgtcgacgttagcggccgttctccgagccgactgacccatccttggcgctgccgccgcgcgct
tgttctcctccctcgccccgccttcatcctccccgttcacggaaacgacagctgcggctgcggggc
tggcgccgcctccctccacctaccacgtctgccctcgccgctctagccctgcgccccagcccggcc
gcggcacctccgcctcgccgccgctaggtcggccggctccgcccggctgccgcctaggatg
(Seq ID No: 692)

*Homo sapiens* anterior pharynx defective 1 homolog A (*C. elegans*)
(APH1A):
gtcccctcttcggcttccgtagaggaagtggcgcggaccttcatttggggtttcggttccccccct
tccccttccccggggtctgggggtgacattgcaccgcgcccctcgtggggtcgcgttgccacccca
cgcggactccccagctggcgcgcccctcccatttgcctgtcctggtcaggccccccaccccccttcc
cacctgaccagccatg (Seq ID No: 693)

*Homo sapiens* RNA binding motif protein, X-linked 2 (RBMX2):
ctgcctttcccgggcgctgattcctgagtgctgagcgcgaacccgaggagatg
(Seq ID No: 694)

*Homo sapiens* family with sequence similarity 82, member B
(FAM82B):
atctcctttagccccgcccgcctccgtagctgcctgaagtagtgcagggtcagcccgcaagttgca
ggtcatg (Seq ID No: 695)

*Homo sapiens* UTP11-like, U3 small nucleolar ribonucleoprotein,
(yeast) (UTP11L): tgatcttttccaaggctgtacagacatg (Seq ID No: 696)

*Homo sapiens* chromosome 14 open reading frame 166 (C14orf166):
cgccctctcgccgcgtcgccggtgcctgcgcctcccgctccacctcgcttcttctctcccggccga
ggcccgggggaccagagcgagaagcggggaccatg (Seq ID No: 697)

*Homo sapiens* transmembrane emp24 protein transport domain containing
5 (TMED5):
gcttctctttcggagggagtgttcgccgccgccgcggccgccacctggagtttcttcagactccag
atttccctgtcaaccacgaggagtccagagaggaaacgcggagcggagacaacagtacctgacgcc
tctttcagcccgggatcgccccagcagggatg (Seq ID No: 698)

*Homo sapiens* coatomer protein complex, subunit zeta 1 (COPZ1):
gtttcttttgcggctccacgtcggcaccagctgcggggcaagat (Seq ID No: 699)

*Homo sapiens* mitochondrial ribosomal protein S16 (MRPS16):
ggttctttctgtgtttgttctctgccctgccaaggccgtagagctggtgcgtgcgggtagcggggc
tctccgaggagccgcacgccggcggcaccatg (Seq ID No: 700)

-continued

| SEQUENCES: |
| --- |

*Homo sapiens* charged multivesicular body protein 3 (CHMP3):
ctacctccttttccgcgggccccgcccaggcggctgcccgtgacctgcctgggcgcggggaactga
aagccggaaggggcaagacgggttcagttcgtcatggggctgtttggaaagacccaggagaagccg
cccaaagaactgatatccaaagagaagaagaaaaagtgaaacgatctgtgaaagatgctgccaaga
agggccagaaggatgtctgcatagttctggccaaggagatg (Seq ID No: 701)

*Homo sapiens* RNA binding motif protein 7 (RBM7):
cgaccttttggccaggttagggaggggcgacgctgagatg (Seq ID No: 702)

*Homo sapiens* eukaryotic translation initiation factor 3, subunit L (EIF3L): cgctctttccggcggtgctcgcaagcgaggcagccatg (Seq ID No: 703)

*Homo sapiens* zinc finger protein 706 (ZNF706):
ccttcctttccctccggcgtcctctcccggccctctcgcgctgcactgtctctccgacgcaagact
gtcccggcccggatatg (Seq ID No: 704)

*Homo sapiens* androgen-induced 1 (AIG1):
cgccctccttgccgcccagccggtccaggcctctggcgaacatg (Seq ID No: 705)

*Homo sapiens* interleukin-1 receptor-associated kinase 4 (IRAK4):
cgccccttcgcggcgcttcctagttcggctggttcttctgtcgccggcttcagcagcccgcgcccg
ggcaggaatagaagatg (Seq ID No: 706)

*Homo sapiens* transmembrane protein 66 (TMEM66):
cgttccttcgccgccgccaggggtagcggtgtagctgcgcagcgtcgcgcgcgctaccgcacccag
gttcggcccgtaggcgtctggcagcccggcgccatcttcatcgagcgccatg
(Seq ID No: 707)

*Homo sapiens* carboxypeptidase Q (CPQ):
ccgcctctcggccccgcggcctggccggcaagcagggctgcagtcacggggcggcgcggagggccc
cagcccagtcaggggtgtggccgccgccaccgtaaggctaggccgcgagcttagtcctgggagccg
cctccgtcgccgccgtcagagccgccctatcagattatcttaacaagaaaaccaactggaaaaaaa
aatg (Seq ID No: 708)

*Homo sapiens* hydroxysteroid (17-beta) dehydrogenase 12 (HSD17B12):
cgctcttttcattcacgaaggtagtgaggcctagtggaaagccatg (Seq ID No: 709)

*Homo sapiens* protein phosphatase methylesterase 1 (PPME1):
cctcccctcgatg (Seq ID No: 710)

*Homo sapiens* HemK methyltransferase family member 1 (HEMK1):
cccccttccggcaggctactgggctccgcccacacacctcccggcctggttcctaaacgccagct
cggagcaatccccttgggctggagccaaatccctgctgtgattttaaggaagaccggcaggtccgg
gcccccaagggtcaaccccacacacatccccgcactttcctgtatgcaggcctgcgagcgtagagg
gagtggaattcacagcctccccacccatccgcaggggtctcctgggaggaacccaccagcgatagg
aacactgaagctgggctacggcgtccgcccgagccttttcttaaaggcgccgaccccggaagcggg
gcgtccgagggagcgcgcgacgggccacgcacgtccgggcgtccagttcggggcagcttctccggc
tggtgggtgggtggggcagcctttcaggcagggtggcaaccaactatatctgaggaccagagccat
tttggggcaccagagcttgtgacctctccatctccacccagctgggtccaggggccactctcagca
ctcacctcagcagctgacatcataaagcagacttgggaacctggaagcactctggagaacctttcc
ctgagacatg (Seq ID No: 711)

*Homo sapiens* N(alpha)-acetyltransferase 38, NatC auxiliary subunit (NAA38):
cgcccttcagttctgcttgctgtcggcaccgctgcgttacccggaaccgccgggccgaacagcat
g (Seq ID No: 712)

*Homo sapiens* cleavage and polyadenylation specific factor 3, 73 kDa (CPSF3):
ggttcttcctttttatttaccggtggctgtgcttccaatttaggaagaccccggcgacctgttcc
tcacccccgcttcgccctcacactttcgggatg (Seq ID No: 713)

*Homo sapiens* dynactin 4 (p62) (DCTN4): tcgcctcctccctccccaagatg
(Seq ID No: 714)

*Homo sapiens* hydroxysteroid (17-beta) dehydrogenase 11 (HSD17B11):
gttcctccttgctctcgcccctactctttctggtgttagatcgagctaccctctaaaagcagttta
gagtggtaaaaaaaaaaaaaacacaccaaacgctcgcagccacaaaagggatg
(Seq ID No: 715)

*Homo sapiens* YTH domain family, member 2 (YTHDF2):
tagtctttccaggtgttagtcgaaacctcgtggtgcgaccctggtcgtcccaaaccccctaggcct
taatcctggggcggtgggggcggggaggccgtgagcacggcttccgctcctccaatccgccagagg
gcgcagcggccggcctctcccttcccggggttcttcgcgccgggcccccttccgcgtgggtgagtga
atgtgagagtcagcgctcgcgccgcgcgcgccgcccgcctccgctgttcggcgctctgctttaggc
ggtggggggcgggcgcgcgcgtaaaagcatagagacgggcattgagctcttgggctagagcgtcgc
cgagtcggagccggagcctgagccgcgcgctgtgtctccgctgcgtccgccgaggcccccgagtgt -continued

SEQUENCES:

cagggacaaaagcctccgcctgctcccgcagccggggctcatctgccgccgccgccgcgctgagga gagttcgccgccgtcgccgcccgtgaggatctgagagccatg (Seq ID No: 716)

*Homo sapiens* tubulin, epsilon 1 (TUBE1):
agctctctagcagagcgccgttgctgggggaatgcagaagcggccgcgggctagcaagctcccgga gccggcggcgcaccaccatg (Seq ID No: 717)

*Homo sapiens* ubiquitin interaction motif containing 1 (UIMC1):
cctccttttcttcctcagcgggtccgcggcccgctactctccgggaggggcgcttcccgacgccaa ggtaggcctctcccgacgccggggcggcccttcctgatgccggggtgtgtctctcgcgacgcgggg gtgggctccggacgccggggctggccttgccgaagtcgggggtgggtccctccggacgccgaagtg ggctcgggatgcggggctgggaccctcccgattccggggcggattccggacgccgggaccggccat tactggtgccgggttgggcttctccagatgccggggctgggtccttcccaaggttgagacaaaagg atg (Seq ID No: 718)

*Homo sapiens* TNF receptor-associated protein 1 (TRAP1):
ccgccccttcccatcgtgtacggtcccgcgtggctgcgcgcggcgctctgggagtacgacatg (Seq ID No: 719)

*Homo sapiens* cereblon (CRBN): cagcctcctttgcgggtaaacagacatg (Seq ID No: 720)

*Homo sapiens* ribosomal L24 domain containing 1 (RSL24D1):
cttcctctcaagcttggcgtttgtttggtggggttacacgcgggttcaacatg (Seq ID No: 721)

*Homo sapiens* leucine carboxyl methyltransferase 1 (LCMT1):
taccctcttctgttgctttctccctgtggctcgcgccgtcccccgccgcccgtcgaccccgcttcc atgtccctggcggacacagctcccaggaacctccacgcccatggccactaggcagagggaatcctc tatcacctcctgctgttccacctcgagctgcgacgcagacgacgagggcgtgcgcggcacctgcga agatg (Seq ID No: 722)

*Homo sapiens* RAB14, member RAS oncogene family (RAB14):
ccccccttcttttgtggtccggcccattgcgagggtgacaggaaaccctgtgcagggagcgccgcca tcttggaccagcccgaggaagatactgagggagcacaggagcagtcaccgctgccactgctactgc cgctactgctgccggcgcgtctgcacctctcggcctgccagtgtacctgccggcgcctcggtcgac cgcccccgcccccctctcccgctgcgtccgcactcctgttcctggtcctgacgccccctcccgccc ggaaagctgcccagccaccagcaaccccccagtgccaccatg (Seq ID No: 723)

*Homo sapiens* Enah/Vasp-like (EVL):
cttccttttcctgtttggttttaagtaggctataaaaatcaagttgctgtcttcagagggtctgtg gtcctctgatcaacataggctggtgggagtacaggactcgcctcctcagggttccctgtgctgcca cttttcagccatg (Seq ID No: 724)

*Homo sapiens* LIM domain and actin binding 1 (LIMA1):
ctctcttcccctctccctctccctctgccgggtggatgctttctccatgtggcaaggctgtaactg ttcacagctgtctgaaacagcagtggaccaggagcagcttggagttttaactttcattttacaaag aacaacatgtttgaatgtttcagcaggcaagttataactggcatctacttcttgttcttctagaac accgaaaatctctcccagcactttagaaaggggaccctgactgtgttaaagaagaagtgggagaac ccagggctgggagcagagtctcacacagactctctacggaacagcagcactgagattaggcacaga gcagaccatcctcctgctgaagtgacaagccacgctgcttctggagccaaagctgaccaagaagaa caaatccaccccagatctagactcaggtcacctcctgaagccctcgttcagggtcgatatccccac atcaaggacggtgaggatcttaaagaccactcaacagaaagtaaaaaaatg (Seq ID No: 725)

*Homo sapiens* ubiquitin-fold modifier conjugating enzyme 1 (UFC1):
gtttctcttgcgccctggtccaagatg (Seq ID No: 726)

*Homo sapiens* coatomer protein complex, subunit beta 1 (COPB1):
caccccccttccacgtcagccaaggactctggagccgccgccgccgctgctgcggttcatagccgga gtagacggagccgcagtagacggatccgcggctgcaccaaaccactgcccctcggagcctggtagt gggccacaagcccccagtcccagaggcgtggtgggtcgggcagagtcggaagaactggctttctag ctggaagatgcggaaggggagcgactaggccgcttgcgtctgggcctggcagaagggaccggattt tctggcatccttaaatcttgtgtcaaggattggttataatataaccagaaaccatg (Seq ID No: 727)

*Homo sapiens* transmembrane protein 9 (TMEM9):
gggtcttttgcggctgcagcgggcttgtaggtgtccggctttgctggcccagcaagcctgataagc atg (Seq ID No: 728)

*Homo sapiens* shisa homolog 5 (*Xenopus laevis*) (SHISA5):
ctttctttttctccaaaaggggaggaaattgaaactgagtggcccacgatgggaagaggggaagcc caggggtacaggaggcctctgggtgaaggcagaggctaacatg (Seq ID No: 729)

-continued

| SEQUENCES: |
|---|

*Homo sapiens* transmembrane protein 69 (TMEM69):
gtgcctttccagtggacctgggctgttgttgcggttgttttccttctctccgtgcaacgctggcaa
gtctcaaagtcgccacagaaacatgcccctgattcagtgcctctgcttagctgtaacatgttaatc
agaactacctggcatcttcctgaacaagactttcaataggggccagtatg
(Seq ID No: 730)

Homo sapiens kelch repeat and BTB (POZ) domain containing 4
(KBTBD4): agatcttcttccgggcggacgtggagccggaagcggaggttccgggctccgggatg
(Seq ID No: 731)

*Homo sapiens* pipecolic acid oxidase (PIPOX):
cgtcctttagccgggagcctgtctttgcttgcctttgcctttgaggctctgtggctgtggggctga
gtggcatcatg (Seq ID No: 732)

*Homo sapiens* blocked early in transport 1 homolog
(*S. cerevisiae*)-like (BET1L):
agctctttccccgcgactgcgccacgtctgaggcggctgtggccgcgtcggtgtccgcgtcgagga
gccggggcagggcacgatg (Seq ID No: 733)

*Homo sapiens* zinc finger protein 581 (ZNF581):
ttctctctttcggccggcgccgccagttcctggggcacacccagaggtccccttctcgccgccgcc
tgcaactgcgagggtagcccggggccgcttggagtcgcccggacctgagaggctgctgcactgggc
ctcagccagccctccggatg (Seq ID No: 734)

*Homo sapiens* armadillo repeat containing, X-linked 1 (ARMCX1):
cgtccttctaatcctagtcttcgtttggtccggttgcactcttcctatagcccagagggcgagagg
gcctgtggcctggggaaggaggacgaggttctgcctggatcccagcagtaggacgctgtgccatt
tgggaacaaaggaatagtctgcctggaatccctgcagatcttggggccggaggccagtccaaccct
tggagcaggaagaaacgcaaagttgtcaagaaccaagtcgagctgcctcagagccggcccgcagta
gctgcagactccgcccgcgacgtgtgcgcgcttctctgggccagagcgagcctgttttgtgctcgg
gttaagagatttgtcccagctataccatg (Seq ID No: 735)

*Homo sapiens* spastic paraplegia 21 (autosomal
recessive, Mast syndrome) (SPG21):
cggcctcccgcacgcaccgcgcagcctgctgtgcccgtgggtcccgagtgctccgccgcccgcccc
gacccgggcccagccgcctccacggcccgcgctcgtactggagcgaagagcggcctcctgaaggag
gggaagggacgtgggggcggccacggcaggattaacctccatttcagctaatcatg
(Seq ID No: 736)

Homo sapiens.staufen, RNA binding protein, homolog 1 (*Drosophila*)
(STAU1):
tctccctttttccttcttccttcccctcctcgccgccaccgcccaggaccgccggccgggggacg
agctcggagcagcagccagagtttattaaccacttaacctctcagaactgaacaaagacaacattg
ttcctggaacgccctctttttaaaaaagaaagcataacccctactgtagaactaaatgcactgtgc
atg (Seq ID No: 737)

*Homo sapiens* adducin 2 (beta) (ADD2):
cggccttttgtcagcgcgcagggccaggagagctctcatttcctcccagcctcgtgcgggaaatgg
ctttaattctgacggcagggctgtgagggactagcgggaacccgagccttttgtcaaggaactgcg
gcgtcggtggccagtcatccccgccgccgcggagccgctgcactgctgggggatctcccagcagct
ctgacgagcgcgggctgcagcatgggcagaaaacgctgccctgcagattagctgggtggattttt
aagcgcaccccaccccccaaacccataaaataacaaaaccaacccgcagtggccgaccggagatag
ctaagatgccgcgcaggagtttccacctggatgtttgaggttgtgtagatgtggccggcaccccttg
agagtggagctaggggtgcagactgagcagtgaacagaaggagccttggacagggctgggccagc
ctcccgagttccaggagcgaattgcaaacccaccgggaaaatg (Seq ID No: 738)

*Homo sapiens* WD repeat domain 1 (WDR1):
ccgccttccggctccagtccccgggctcggcctcggcgaggtgtaattcgcagcgcgggccggccc
cggaggctctcggcgagcgcggcgcggtaacaagtgggcgaggatg (Seq ID No: 739)

*Homo sapiens* family with sequence similarity 20, member A
(FAM20A):
cgacctctacttccacctctggccccaagtacagcgccagctgcggcctcgggagcgcccgcgggg
gtgcccgtgcaccggccgcgcctcctccctggcgcgggactcggccgcagctgcctcggaccccgg
cacgatcgtgcacaacttttcccgaaccgagccccggactgaaccggctggcggcagccacagcgg
gtcgagctccaagttgcaggccctcttcgcccacccgctgtacaacgtcccggaggagccgcctct
cctgggagccgaggactcgctcctggccagccaggaggcgctgcggtattaccggaggaaggtggc
ccgctggaacaggcctcagttcctgcttttgaaaggaagaggggggagtctgtgacccctgaggcct
ccttgcaactctgttttccaagctttgcacatcttccgaatttcttcttcaaagtctaccctaatg
aaatatcagacaattttccaagtgtgcttcatgaacttctgggaggtgcttcacagtttctgcaaa
tgattgattgaattttcactttgaaaaaatatactttaaggcgacacaagatg
(Seq ID No: 740)

-continued

| SEQUENCES: |
|---|

*Homo sapiens* kelch domain containing 4 (KLHDC4):
ttttctttcctggtgtcccgtcgcggcttgggacccggcaagatg (Seq ID No: 741)

*Homo sapiens* calcium channel flower domain containing 1 (CACFD1):
tgctccctctcccacaaggcagcgcgccggctcggacgcggccggctaccgagccctttgtgaggg
ctgtgagctgcgcctgacggtggcaccatg (Seq ID No: 742)

*Homo sapiens* zinc finger, CCHC domain containing 8 (ZCCHC8):
gaatcttttccacagcccaaaatg (Seq ID No: 743)

*Homo sapiens* ketch-like 24 (*Drosophila*) (KLHL24):
gtttcctttgttgtgagctgcggcagagactggtggctggaggagacgccggcgctggagagtgcg
ctgcgccgcccgccgctgagggaccgcggggttagccactgctggctgcttccagtgttcgccgag
aggtaccgggggtgacagctccgggaccggccgaaaggcgaggaaccggtgtggaaattaaaagaa
cacacatattttgactggggctttgatcaaccaaatgctaaaaagccacataaagaagatccctaa
tagtcatttctcaacaattatatagtcaactgatgtaacaatg (Seq ID No: 744)

*Homo sapiens* FtsJ homolog 3 (*E. coli*) (FTSJ3): ctcccccctttccaccatg
(Seq ID No: 745)

*Homo sapiens* dymeclin (DYM):
gcttccctcttctctcgccgcctcctggcctccgcaccgacgcggcccgggctggagccgagccgg
ggccgagctgcaggccggaccggagccggatctgtacccgctgagacgtggaaacatggaggcctg
agccggtgtgcgccacctgggctgcggcggcgacagcgacttctcctgacccctctgccaccctcc
catccgtccgcgggtccgtggagctggagcagatcccccagccggctgagacaggttgtcttttgg
aaatgcaggtttaaggacaaattatctgcttaagctagaagatg (Seq ID No: 746)

*Homo sapiens* zinc finger protein 280D (ZNF280D):
cctcctctttctcctcctcctcagggctccagtcaggccgatccgctccgctcacggaaggaaaac
agaaataacttgctggcttgtctggagtcacatgtacttaggtgacaatttacagaaagtcatctc
tgcagcttgatg (Seq ID No: 747)

*Homo sapiens* ankyrin repeat domain 10 (ANKRD10):
cgttcctttgtgctgcggcggcggcttctcgagtcctccccgacgcgtcctctaggccagcgagcc
ccgcgctctccggtgacggaccatg (Seq ID No: 748)

*Homo sapiens* SWT1 RNA endoribonuclease homolog (*S. cerevisiae*)
(SWT1):
ctctcctttggcttggggctccggagttgccactgccgccggcgctggtaagcttttcaggatg
(Seq ID No: 749)

*Homo sapiens* leucine rich repeat containing 49 (LRRC49):
tgacctctttcgggtctctttgaatctccgctgtagcgtcacctggaaggcagatctaacagagaa
cctggactgtctcctatcatg (Seq ID No: 750)

*Homo sapiens* F-box and leucine-rich repeat protein 12 (FBXL12):
ccgccttctggacttggtcttagttcccagtcgcggccaaatcacgcctcagccacctcccgcaag
cctctcactgcctcagccacgctttccaggctggtttctggtccccatccgcggctggtccggccc
tgggaccgaatcacttcccagcgagaggaaggtcaaatttctcgaccggctacgggaaggtcgcgg
ccgccgccctgtcagccgcctcggcgcccccaggacccctcgggtctctttaaccggaagcggaag
tgcgtgtcggcgggatcatg (Seq ID No: 751)

*Homo sapiens* WD repeat domain 55 (WDR55): cagtccttctcagcatg
(Seq ID No: 752)

*Homo sapiens* zinc finger protein 3 (ZNF3):
cgttctttgttctgtccccggtgtgtgggtctgtgacagggtccaacagggcctggtccgtgtccg
gtcccccaaatctgtcgtccctgcccccaggcattggcatcaacaaaagtcagaattcccgggaac
ttgaacagaggctgctaaattcccagtaattgctcctttggccttctagggactgacttcaaagaa
ggaaggaaagaatcaggcagtgcttcctcattctcttttaaaacccgcttcccgctgagtctgcac
ccaggagaccagagagcaccttgcccttccatg (Seq ID No: 753)

*Homo sapiens* tetratricopeptide repeat domain 27 (TTC27):
ggttcttctcctaggcggaagccagaccagagagcgtgcgtgtttttcccagggtgccccgcgctg
ctgttatggccgcctccttgaggtagtatccgcacatggaattctagggccgcaggtgtatttacg
gtaactgtcgccactagatttcagcgcctttggactctcctgttttcactttcttttgttgactcc
cgtgtggccctcgtgggagcctgttttggctgcagcggtgtctggggtgatg
(Seq ID No: 754)

*Homo sapiens* THUMP domain containing 1 (THUMPD1):
gtttctctttcctctcagtttgcgcacaccatg (Seq ID No: 755)

*Homo sapiens* ankyrin repeat and KH domain containing 1 (ANKHD1):
tgctcttctcgttcccgagatcagcggcggcggtgaccgcgagtgggtcggcaccgtctccggctc
cgggtgcgaacaatg (Seq ID No: 756)

-continued

| SEQUENCES: |
|---|

*Homo sapiens* syntabulin (syntaxin-interacting) (SYBU):
cctcctcctggacggcggcagcggcggcgcgaggagccggcgggcagcggcgcgatg
(Seq ID No: 757)

*Homo sapiens* coiled-coil-helix-coiled-coil-helix domain containing 3 (CHCHD3):
gcgccttctccttgcttctgggggtcgtggccttgctcccgctgtgcgggaaaagaatccaggccc
ttccacgcgcgtgtgggtgcgggggccccgaagtgctcgtggttccccgctaggtctccgctgggg
caggaaccggaatcatg (Seq ID No: 758)

*Homo sapiens* HAUS augmin-like complex, subunit 4 (HAUS4):
cctccttcgtcgcggcctctagtgcactttcggctccttccccttcccgggcctttcagcttggtc
tttccgggcctcgcttcccccagcccctgcgcccggcccgaacgagaggttccggagccccggcgc
gggcgggttctggggtgtagacgctgctggccagcccgccccagccgaggttctcggcaccgcctt
gagagcttcagctgccccaggattagaatcccaagaaaatcaaatg (Seq ID No: 759)

*Homo sapiens* solute carrier family 41, member 3 (SLC41A3):
ccgcctctttcccgccgccgcctgggaggggacccgggctgccaggcgcccagctgtgcccagatg
(Seq ID No: 760)

*Homo sapiens* phosphatidylinositol glycan anchor biosynthesis, class V (PIGV):
cttcctttccagcctcccgccctcgtctgcttccggccctgtggcctggtggggctctgcaggctc
cctcgggagtggtccttgggccgtggcccctctgggaggcctgagggagctcaatcctggtagcaa
cacccctgaattcctggtggtgaaaggatg (Seq ID No: 761)

*Homo sapiens* poly (ADP-ribose) polymerase family, member 16 (PARP16):
agttcctttatccctgggcccaacctccccgccgacccgcggtccaggcctcggtctctctcttcg
gcggcgagccgcggcccagaccccggcagaggacacttgtcggcacgttctcacccctgtcatctc
agcccccctgcctagctccaccccaggcttgggaacccggcccctgacggcccattgtccgcgggcc
cagcccccgcgctgaacgcacgctcgcccttgcccctaaccagcgcgtctaccccggcaacgcgca
gtgacctgggatg (Seq ID No: 762)

*Homo sapiens* thioredoxin-like 4B (TXNL4B):
gtttcttttctgcgcttgtgcgttttctgttcggtttccttcccgctagcggggccacgagggttg
ctaggcaacagcccctgggtgacttggtcttagggtcctgtccggcttggggctgatgaaaggagc
tgtccgcgcccgggctcttccgagaagtggttgctgacagccacaaagtgaaagggagtgaggcgg
cgtggacgagtaaggagtgacagtgaggattcacatttgggttatttcaagatg
(Seq ID No: 763)

*Homo sapiens* slingshot homolog 3 (*Drosophila*) (SSH3):
cgtccttcctggtcctgcgggtccaggactgtccgcggggttgagggaaggggccgtgcccggtgc
cagcccaggtgctcgcggcctggctccatg (Seq ID No: 764)

*Homo sapiens* zinc finger protein 692 (ZNF692):
ctccctctggggcgcgggcctcagttccgggctacagcagccgacgccgagaggcaccgtttcttc
ttaaaagagaaacgctgcgcgcgcgaggtgggcccctgtcttccagcagctccgggcctgctcgct
aggcccgggaggcgcaggcgcaggcgcagtgggggtgagggcgcgtgggggcgcacagcctctggt
gcacatg (Seq ID No: 765)

*Homo sapiens* tRNA-histidine guanylyltransferase 1-like (*S. cerevisiae*) (THG1L): tggccctttcctttccgcgtgtagaatg
(Seq ID No: 766)

*Homo sapiens* solute carrier family 25, member 38 (SLC25A38):
tctccccttctacagagttcctccggcgcttcctccaccccgggatacacagaacctcatctccta
cggtgctgaagcctgcagcagggcaggatgggcaggagagcagagccgcggagtctgcggcgcggg
tgaagagcggcgcgtaattcccgcagcaagattgttccgcgcccgcagcccctggactagcaggat
ccgaaccccggcggctgcgtgcttataggcgcagacgtcagagagcccgcggcttaaagcgcgtcg
cctggctagcgccaccccctagccttcttcaaggcctccagggctgggcccaagcgcccgtcgacg
gcaccctgggcccagaggactcgcgggcctcatctccaatg (Seq ID No: 767)

*Homo sapiens* WD repeat domain 13 (WDR13):
agttctttctgatagcaggcagccatcttgcctggagcctgagaaagggaggagagacagaaggaa
ccggcgacagtggtctcagggccgctccggggggcctcaagaaccggaggcagccccggaggtggt
ccccgatcccgggctatgctcttggatctgagaagggaaggcggagggcggcggggacaagatggg
tggagaatgtcaagcaaggaatgctaggcgggggagggggcgttgctatggcgactggggaggggcg
gtgtctgttctgaatcgctgtgtgtcacccgggcgctgcccaggaagggcagggctggggtgatga
ccatggtaacacccggggggggagttcgtgacatctccggcgcggagggactcgatgtctatggcaa
tggtcgcctggtggaagggacggaactagatcccttcgctcgggacgctcacattccaggcccttg
tcctgcaggctgccgcgggcggacacgccagaggaggaggccggggaatg
(Seq ID No: 768)

*Homo sapiens* chromosome 1 open reading frame 123 (Clorf123):
ccgccttttacgacgcgccggaaagcaacggcaagggcggcagccagcaccgggcggagagggcta
ccatg (Seq ID No: 769)

SEQUENCES:

*Homo sapiens* chromosome 20 open reading frame 11 (C20orf11):
ctgcctccttctactcgggcgccccggcggccgccacctctccccagcccaggagaggctgcggag
ccgcagccgcccagaccgcgcagcgcgggaggcaggttccgcacgaaataaatcagaatg
(Seq ID No: 770)

*Homo sapiens* zinc finger protein 446 (ZNF446):
ttccccttttggggacagatcccgaagttcgagcatccctcggataggccgggtgtcaggcctggt
ctctcaggcccgtccaggcccatcttgacgattccaagaccacccccttgagcaagaatg
(Seq ID No: 771)

*Homo sapiens* mitofusin 1 (MFN1):
ccgccctttgccactcccccctgcctcctctccgcctttaacttctcgggaagatgaggcagtttgg
catctgtggccgagttgctgttgccgggtgatagttggagcggagacttagcataatg
(Seq ID No: 772)

*Homo sapiens* phosphotyrosine interaction domain containing 1
(PID1):
agtcctctcgcagctgcgccaggacagccggcgcgcggccgtgcccacaagttgccggcagctgag
cgccgcgcctcctcctgctcgcagccccctacgcccacccggcggcggtggccagcgccaggacgc
acatcccgcggacaccgaccccagatgtaaagcgggaccccagcccctcgccccccggcgcgatcg
acagtctcgccagcgtctcctctgccaaaacccagggctggaagatgtggcagccggccacggagc
gcctgcaggagagatttgcagacacagaagcggcacagagaaggccattgtgaagatcaaggcaga
aaccggagttatggcatcataagccaaggaatg (Seq ID No: 773)

*Homo sapiens* pleckstrin homology domain interacting protein
(PHIP):
tttcctcctcctcctcctccgcctccgccgccgttgcttgaatggtggagccgaagctcggctcgt
gaacacacactgacagctatagggcaggcggcggcaccgtccccgcttcccctcggcggcggggtg
tcccgtcggcggccctgaagtgacccataaacatg (Seq ID No: 774)

*Homo sapiens* LIM and senescent cell antigen-like domains 2
(LIMS2):
tggcctttttgggcgtctccctgctccgcggcccgggctggcgggcgggcgctcggctggcggct
gcagcagcagagggagacccgcggcaaccccggcaacccagggctcggcgtcgctgccaccatg
(Seq ID No: 775)

*Homo sapiens* SCY1-like 2 (*S. cerevisiae*) (SCYL2):
aggtcttttagtctttttcccccctcccttactcttcgtccccggtccctcccctccccaccccttt
ccttctagctccgacgtttgcggccgcgggggcggcggaggatatggagtaaagccagagtcagtg
gccaggcacgaaggcagagcaggaacagccaggaggcgtttattaggggggcgggggaaagagcc
ccagcaccgcccctcctggaagaaggaagaggtaagtgaccggccgccggcaccgaccgacctccc
tcaccggcggctctctcgcctgggctcccggagccggcgaggagggaatggaggactcgcgcccgg
gttaggcctcccagggccgctcaggctggtgggtgttgcctggtgacgggcctgccggcggccggc
cgggcgatcggcggtcggcgcccgcgcaaagcggggctggacgagcagcgagctccggggagcgga
tccgagagggccgagtcctcgaaagaggccttgaggcgacgggagacccgggatcgaagtcagctg
ccggagggagagccccccatgccggctcgagagctcgggtttcggtggtggagaacgtagtacctt
tcggggacattggacactactctaggaccgggtaactataactacccaatattgcagccatg
(Seq ID No: 776)

*Homo sapiens* ring finger protein 31 (RNF31):
caccctctctcctagtacttcctgttctcggctaaccctggcgctgggccgggggctggagagtga
ccgtggtctgagtgacctggggcggctgcgtgggccggggtgggcctcaaagccgggcaccagacg
ggaggggcggcgctcgggccgcgcgctgcccgcgccgggtcctggcgggcggcgaggctggggctg
actcctgcctcaggatg (Seq ID No: 777)

*Homo sapiens* mediator complex subunit 9 (MED9): cgacctctggctaacc-
tacccccggagccatg (Seq ID No: 778)

*Homo sapiens* ATP5S-like (ATP5SL): cggccccttccggttacgaaaccttagcaa-
gatg (Seq ID No: 779)

*Homo sapiens* GPN-loop GTPase 2 (GPN2):
tctccttttgcgcgacacggtctcagctgttccgcctgaggcgagtgacgctggccgccaacgagg
tatacgtactgggaccctcgccctcagtctcgtctccggcgcggctacctgccccgttttccctgt
gagttgacctgctccgggccgcgggccgccaatg (Seq ID No: 780)

*Homo sapiens* transmembrane protein 48 (TMEM48):
cggtctcctgtacgccctagactaggggccgccatctccatg (Seq ID No: 781)

*Homo sapiens* ankyrin repeat and zinc finger domain containing 1
(ANKZF1):
ttgtcctcttcgctgctccgtagtgacggggattgttgtgttgcagaaatccggcaatcgacctga
ggacttgcgagccgctcagctcccgggacgtttggagctgctgctaaataatttctgctcagccat
g (Seq ID No: 782)

| SEQUENCES: |
| --- |

*Homo sapiens* notchless homolog 1 (*Drosophila*) (NLE1):
ggctctttctcctccacgtggggacgcaggatg (Seq ID No: 783)

*Homo sapiens* cell division cycle associated 8 (CDCA8):
cgctctctctcactggcacagcgaggttttgctcagcccttgtctcgggaccgcagcctccgccga
gcgccatg (Seq ID No: 784)

*Homo sapiens* polymerase (RNA) III (DNA directed) polypeptide E
(80 kD) (POLR3E):
cgctccccccacgtgtccgccggagtttctccaccagcaacatggccgccgcctgagaggagagc
cgggccgccgccgtctctgcagcccgcgggtaactgggccgttgccgccgtccgcgctcggccccc
gcggagagatcgagctgaaggactgcgcggctggctctcctctagtatg (Seq ID No: 785)

*Homo sapiens* armadillo repeat containing 1 (ARMC1):
gagcctttgcccgccagcgccttcgctctttggctccctgagttagtccggttgcttgcgatcgcc
gcggccggggctgcgaaccgaagggctcgctccgcgccgcctgggtctctacctcatccgtaggtg
tggccctgatggtgtggcaggctctggactcctaaagctctggagcgaatttaagattttattcat
gtgcatggcatagaagatg (Seq ID No: 786)

*Homo sapiens* transmembrane protein 33 (TMEM33):
ccgtctttctggaaacaccgctttgatctcggcggtgcgggacaggtacctcccggctgctgcggg
tgccctggatccagtcggctgcaccaggcgagcgagacccttccctggtggaggctcagagttccg
gcagggtgcatccggcctgtgtgtggcgcgaggcagggaagccggtacccgggtcctggccccagc
gctgacgttttctctccccttcttctctcttcgcggttgcggcgtcgcagacgctagtgtgagcc
cccatg (Seq ID No: 787)

*Homo sapiens* pyridoxamine 5'-phosphate oxidase (PNPO):
ccttccttccccggggtagaagtccagggtgagaaattggttccgaactcaaaggaacccagtgcc
gggccacagccgggtcacgtggccggcggccccccatg (Seq ID No: 788)

*Homo sapiens* golgi phosphoprotein 3-like (GOLPH3L):
attccttctctgcatcgaaggatcaggaagtttgtgctctctgcgtggctaagtttttcacctact
aggacgggggtggggtggggagaacaggtgtccttctaaaatacagcacaagctacagcctgcgtc
cagccataacccaggagtaacatcagaaacaggtgagaatg (Seq ID No: 789)

*Homo sapiens* regulator of chromosome condensation (RCC1) and BTB
(POZ) domain containing protein 1 (RCBTB1):
cgctcctcctcttcgctgccggtgggcaccgccgctcgctcgcacttctgcgcccattggagcttc
ggagatccctgcggtcccgcgggacggcgcggcagcagctgacctcgcagacaggatcttgctctc
ttgcccagactggaatacagtggtgtgaacacggctcactgcagcctcaacctcctggactcagag
atgtcggcttatttataggaattgcttgaagccagagtcatg (Seq ID No: 790)

*Homo sapiens* leprecan-like 1 (LEPREL1):
cgtccctttaagagcggctggccaggcacggcctccgcctctcagtacgcggagcgccggcggtca
cctggggctcgcggagcggccagatcgcggcggagtcggcgcgcttccccgaggaaggtgggaga
ggggacccggacgcgaggtgccccgaagccctctcgagcgtaaccgtcccgcgcctctctgaggcg
gaggatg (Seq ID No: 791)

*Homo sapiens* hedgehog acyltransferase (HHAT):
ctgtctcttggctcaggcttggaggcctccgagcagcaacatcgtcccaattataccccgttggag
catcttcagatcttccactcttttcacaacgcaatcaaaatcttcgtacccattttgcagtagtga
tctctgtaagttgctttacaattcataaagtttattctatttgatcttcactctaatttacaaaga
aaagcagggaagtctatttctgttttacagaggtgtacagggaggctcacaggggctaagttcaca
cagtaagccctcgaagctgccagggctgcaaagcccaccctctttccaccgcaccgaactacctcc
tttcgcctacaaaacgtaggtggggaccactggtgttggaatgacggcccacctcgagtttcaggt
gacttccactctgcaattaacttgcaggcagccccagacctgcaatgaacacacgggtgggggaga
gatatgcacgccagggtcagtgggaaccaacagccgagggggtgagcggggctaggggccccgggcc
gccggcggggcaaacgcggttcagaaacgcaggccgcgctctggcccgccccctgcagcagcacgg
cctgctcgccatcgcccggagagcgccgcgggttcccgagtccgggcgcggagggcgcgcgggcac
ggcggcaggggcgtgctcggaggacgcgcgctgcgctgctcctccaaagggcagctccgggggaaa
gagggtggcgtcccggggaagcccgcagccgccgccgatgtcgctgggactcggaagtgccgaaag
aggggtgttgggaactcgcggcgcgcgtgaacgttgccgtcgccgccgcccgggacagcccggaga
aactctcagcgtaggcatcgggaaccttcgtgccaaggagccatg (Seq ID No: 792)

*Homo sapiens* chromosome 11 open reading frame 57 (C11orf57):
cctccttttctcccaaaccacttcttccccccctacccccgccacgcgaggctgcggcgcacggt
atgggtgtgtttgtgtgtatttgtgtggggagggcgtttggagggaaggttaccgggagctccgag
gccgctggggaacagggatcccggtgacaaagatggggatatttcctctgtcttccacttggaaac
ctcaacccccgcttcaggctccctagatactttctggggcccaaccgaaggccgtagccatccaaa
gcgttcccagcctttctggggagtgaaacttacccccggggttcgtcctagaggagcgtgagcggg
gaatgcccaggtcaaccgggctgtccgaattccgccccggctcagcctccggcctcagtccgggag
agagatctgcctgtcggtctgggctgggggaaacgcggcagtggcctgggccacaggtgagggcag
agtaaccagtgggaaggctgcgttttcacgaaggactcgggtgaagctgcagagctgcctttgagc
cctgactccttggcttcctgggtcggaggagatcttgtaatggagtggttcttcgtctcactagca
agatgcctgatttcctcaggatcaagggattgaagaatg (Seq ID No: 793)

-continued

| SEQUENCES: |
|---|
| *Homo sapiens* high mobility group 20A (HMG20A):<br>agtccttcgccgcattggggcaaaataatcccttcatttttgtgaaggtaccgtggaaaatatttc<br>atttttcttctcaccggagcaattgtaaatgctatgcggtaagaggagttacctgtggaaaggtgg<br>ttaagagattaggtaaagaaaaggaaaggacaccaaaataaagtgctgcggaagaatttttgtcca<br>gctgtgagacgacgagtgcgtgaagtgaaggcgattgagaggggctgagggaattgtcctctgtgg<br>aagggactttcttttggccctaggccccttcctgcccctgtcgtcagcagagtctctacaaggaag<br>ataacggactgtaaaattctataaagcaaagctacacatcacttgacaccatacaccatcttggtt<br>acataatgaagagagatg (Seq ID No: 794) |
| *Homo sapiens* checkpoint with forkhead and ring finger domains, E3<br>ubiquitin protein ligase (CHFR):<br>atgtctcttgacagcggcggcggcgcagccggttccgggttcggcgcggggcggggatgtgaatcc<br>cgatg (Seq ID No: 795) |
| *Homo sapiens* nucleoporin 133 kDa (NUP133):<br>ccatctcttcccttaggtgtttaagttccgcgcgcaggccaggctgcaacctgacggccagatccc<br>tcgctgtcctagtcgctgctccttggagtcatg (Seq ID No: 796) |
| *Homo sapiens* CNDP dipeptidase 2 (metallopeptidase M20 family)<br>(CNDP2): cttccttccaagaaccttcgagatctgcggtctggggtctggttgaaagatg<br>(Seq ID No: 797) |
| *Homo sapiens* oxoglutarate dehydrogenase-like (OGDHL):<br>gcaccccttccgcgcagcccccctgacctgcagcctccggacctcgctgcagcgcggacccggcccg<br>cccgcccgaatg (Seq ID No: 798) |
| *Homo sapiens* transmembrane protein 30A (TMEM30A):<br>ccgcctcttccgctctacagcggaggtggctgtggcggtggcgctggtggctgcggcggcggcggc<br>ggcagcggcgctcgagcggttcctgtcagggtcagccggcgggcccccctgggtggtccacctgcaa<br>atcgcggagcggcgccccagggatcgatg (Seq ID No: 799) |
| *Homo sapiens* elongation protein 2 homolog (*S. cerevisiae*) (ELP2):<br>gcgtctcttgtttgtgcggctgaccagttggcgacatg (Seq ID No: 800) |
| *Homo sapiens* WD repeat domain 12 (WDR12):<br>cgttcttttctttgtatttccgcctctcgcctctctctaaaagccgcagttagaggcgagatttag<br>gaaaaacctctgccgagtgagcctctggttgggaatatgtatgagaaaaaaaaactggcaaggcgt<br>tagtcaagcaaagctgaaggcagaggaaatttgatatctggctggagtctagaggatttaatgcaa<br>ataagatactctgagggcagcgtggcaaaaaaagactacaattcccggtggtcacagcgtttgaga<br>agcgatgctttctgagacttgtagtaactaggagctgtgtttgaactatccaggctcaggacagcc<br>tcttgaaaaaaaatttttattaataaagcggatttgagtgggatctttttcctaatcgattacgg<br>gcccacacgtatgggaagaattctaacaatgattaaagggacatgctacctttacgactatccttt<br>tctaatcgatgactcctaaatctaggagtaggtagtcgatgtttgtggtctgggcgtctgtagaag<br>ggcaacctcgtgctttctgcagaggagaccggagggcagaaggcagagtccaggcttagactgcag<br>ttcctcgcttacctgtgcagtctaattttgagctgcctctttgtagtcttaaaaggcaggagcttc<br>gtgttgtgggtctgctaacccgtacgtttccgtgggcaagtcgtgtgtactcctcgccatg<br>(Seq ID No: 801) |
| *Homo sapiens* tetratricopeptide repeat domain 17 (TTC17):<br>cgacctcttcaagatggcgggcgccggagactagcttccgcttccggtgtgagcggcccggccggg<br>ggggcaagatg (Seq ID No: 802) |
| *Homo sapiens* proline rich 11 (PRR11):<br>ttttctttatggcgtgggagaggccacagcccggactccatcgactcccccggctcttagactaaa<br>atcatg (Seq ID No: 803) |
| *Homo sapiens* TBC1 domain family, member 23 (TBC1D23):<br>ctccctctttcttcccctctggggaagctcagtgctggacttccgaagaccttttacgacattgag<br>tctcggagttggtctcagcgccggatccacttttcggcaaagtgacgtggacgtcaacagcaatg<br>(Seq ID No: 804) |
| *Homo sapiens* leucine rich repeat neuronal 3 (LRRN3):<br>gctcctctctggggagtggagggtgttcagttattaatgaccgctgagcaggcagcaccatgtcag<br>tgtgacaactgatcgggtgaacgatgcaccactaaccaccatggaaacaaggaaaaataaagccag<br>ctcacaggatctctcttcactggattgagagcctcagcctgccgactgagaaaaagagttccagga<br>aaaagaaggaatcccggctgcagcctcctgccttcctttatattttaaaatagagagataagattg<br>cgtgcatgtgtgcatatctatagtatatattttgtacactttgttacacagacacacaaatgcacc<br>tatttataccgggcaagaacacaaccatgtgattatctcaaccaaggaactgaggaatccagcacg<br>caaggacatcggaggtgggctagcactgaaactgcttttcaagcatcatgctgctattcctgcaaa<br>tactgaagaagcatgggatttaaatattttacttctaaataaatgaattactcaatctcctatgac<br>catctatacatactccaccttcaaaaagtacatcaatattatatcattaaggaaatagtaaccttc<br>tcttctccaatatgcatgacattttggacaatgcaattgtggcactggcacttatttcagtgaag<br>aaaaactttgtggttctatggcattcatcatttgacaaatgcaagcatcttccttatcaatcagct<br>cctattgaacttactagcactgactgtggaatccttaagggcccattacatttctgaagaagaaag<br>ctaagatg (Seq ID No: 805) |

-continued

SEQUENCES:

*Homo sapiens* MIS18 binding protein 1 (MIS18BP1):
ggccctctctccgcgcggagccgagccggaactgcggcagtctctccctgccaggctcttcatcca
aggtttctgtggatcccttctgaagttctatctgaaaattgcgcttaagtgaattttctgttagaa
gaacttggttgctactttcttgtcaagatg (Seq ID No: 806)

*Homo sapiens* LMBR1 domain containing 1 (LMBRD1):
ccgcccctttaacctttagggtgcgcgggtgcagtatatctcgcgctctctcccctttccccctcc
cctttccccaccccgggcgctcaggttggtctggaccggaagcgaagatg
(Seq ID No: 807)

*Homo sapiens* ST6 (al-
pha-N-acetyl-neuraminyl-2,3-beta-galactosyl-1,3)-N-acetylgalactosaminide
alpha-2,6-sialyltransferase 1 (ST6GALNAC1): cttcctcta-
gaacccgacccaccaccatg (Seq ID No: 808)

*Homo sapiens* spermatogenesis associated 7 (SPATA7):
gctcctcttttccagtcctccactgccggggctgggcccggccgcgggaaggaccgaaggggatac
agcgtgtccctgcggcggctgcaagaggactaagcatg (Seq ID No: 809)

*Homo sapiens* docking protein 5 (DOK5):
cctcctccttcctcctcctcctcctccttcttctcctccttctcggccgggaggaggcagggctgg
atccctcagccgccgccgctcctcctcctggcaggccggccgcggagtcagctgacgccggcgctc
cagcctcgcctccccgcgccgcgctctgcgctccccgaaagtggctgcaagccggccgcccactgt
cagggttggggggacagagaaagtgatgtgcgccttctaaagcctcgcccagcgccgccgaagcag
cttcacctctccaactttctcccaccgactgcttgtcttgaccctgccctccaccctccccagagc
cacttcgggtgcgcgctcttgggtaaaggggggggtcaccggctgtctgggatg
(Seq ID No: 810)

*Homo sapiens* glycosyltransferase 8 domain containing 1 (GLT8D1):
tctcctccatcgcctgcagtaagggcggccgcggcgagcctttgaggggaacgacttgtcggagcc
ctaaccaggggtatctctgagcctggtgggatccccggagcgtcacatcactttccgatcacttca
aagtggttaaaaactaatatttatatgacagaagaaaaagatg (Seq ID No: 811)

*Homo sapiens* cullin-associated and neddylation-dissociated 1
(CAND1):
tggccttttgccctagggagcgagtgcggagcgagtgggagcgagacggccctgagtggaagtgtc
tggctccccgtagaggcccttctgtacgccccgccgcccatgagctcgttctcacgcgaacagcgc
cgtcgttaggctggctctgtagcctcggcttaccccgggacaggcccacgcctcgccagggagggg
gcagcccgtcgaggcgcctccctagtcagcgtcggcgtcgcgctgcgaccctggaagcgggagccg
ccgcgagcgagaggaggagctccagtggcggcggcggcggcggcggcagcggcagcgggcagcagctcc
agcagcgccagcaggcgggatcgaggccgtcaacatg (Seq ID No: 812)

*Homo sapiens* BRICK1, SCAR/WAVE actin-nucleating complex subunit
(BRK1): cgctcttcctcaggcggcggccatg (Seq ID No: 813)

*Homo sapiens* zinc finger CCCH-type containing 15 (ZC3H15):
cggtcttcctcctcgtcctgccgcagggccagaacccctgacggtattcagctgcgcgtaagtctg
gccggtgccatctgtctccgcaatg (Seq ID No: 814)

*Homo sapiens* polo-like kinase 1 substrate 1 (PLK1S1):
cggtctccttcggcaaccccggccgaacggccacccagaggctgtgctgagctggcgcagcggcag
cagcatg (Seq ID No: 815)

*Homo sapiens* dysbindin (dystro-
brevin binding protein 1) domain containing 2 (DBNDD2):
gtttctttcctacgcagccgctcctgccgccgtggtcgctggagctttgcctctctaggccggcag
cgcctctcctccatggtcctgtctgtcagcgctgttttgggagcccgccggtgaggccgggccacg
ctcagacacttcgatcgtcgagtctgtcactgggcatg (Seq ID No: 816)

*Homo sapiens* KIAA1704 (KIAA1704):
gattctttttggatagggttgacgttcgtggatagactcatatctgtgaccagtgtccgccaccgc
ggatg (Seq ID No: 817)

*Homo sapiens* solute carrier family 25, member 37 (SLC25A37):
ccccctccctgcccacctcctgcagcctcctgcgccccgccgagctggcggatg
(Seq ID No: 818)

*Homo sapiens* myoneurin (MYNN):
cgtcctcccaagatggcggagacagagtgaagaaactgtgttccccccttgggttgctatcgatca
agggtaaaattccattctgatatcaaaatg (Seq ID No: 819)

*Homo sapiens* vacuolar protein sorting 33 homolog B (yeast)
(VPS33B):
gcttctttttctggtagaaggcggggttctcctcgtacgctgcggagtctctgcggggtgtagacc
ggaatcctgctgacgggcagagtggatcagggagggagggtcgagacacggtggctgcaggtctga
gacaaggctgctccgaggtagtagctctcttgcctggaggtggccattcattcctggagtgctgct
gaggagcgagggcccatctggggtctctggaagtcggtgcccaggcctgaaggatagcccccccttg -continued

SEQUENCES:

cgcttccctgggctgcggccggccttctcagaacgaagggcgtccttccaccccgcggcgcaggtg
accgctgccatg (Seq ID No: 820)

*Homo sapiens* zinc finger, C4H2 domain containing (ZC4H2):
aggcctctccaagcccctaccgcacaggctcatagccccaagcccggaggaggtggctacattgtg
tctattgtatcccttggctggtgtatttgtacatctctcgggacgtgaaattgacagtgaaaagta
tg (Seq ID No: 821)

*Homo sapiens* BAI1-associated protein 2-like 1 (BAIAP2L1):
cttcctctggcggcgtccggcgcttctcctctgctcctcgaagaaggccagggcggcgctgccgc
aagttttgacattttcgcagcggagacgcgcgcgggcactctcgggccgacggctgcggcggcggc
cgaccctccagagccccttagtcgcgccccggccctcccgctgcccggagtccggcggccacgagg
cccagccgcgtcctcccgcgcttgctcgcccggcggccgcagccatg (Seq ID No: 822)

*Homo sapiens* solute carrier family 25, member 40 (SLC25A40):
cgtccttctcgcgcctcgctctggccctgcaggttgtgtttccgcctctaccccgcctccattccg
ttgctctctcagtctcagacccgggctctcggtccgccgcttcaggtcttggcgcagcctcagaga
gttggcgcggctctgtgttgaccaaacctagtggatgcagttagcgccggagcccggccccgcccg
tcaccagggttattcccgccttctaggtttgccaggactgccggccctgcagctgccttctgcccc
aggtttttggctactgatgttacaaacaataaaatattggagcatagagttgaagaacagactcaa
accaggtttttatttaattagttaaaaatatg (Seq ID No: 823)

*Homo sapiens* protocadherin alpha subfamily C, 2 (PCDHAC2):
tttccttttccctcccccctggagctgtagcggcagcagcagcaggaagccgagccgggttgagcga
ctcggaggcgagcggaggagctggaatatggggagtcagcgaggacggtggggccaggagcccttg
ggagggcctacggagggagcggccccaggcgctttctagagcgtgagcggtgggggagcaggcgca
gggtggcacgagcggaggcggggcccgggcgtggggcacggctggggaagctgccgcctccggccc
tgcccggctgcctccgccgcggccagtggctatg (Seq ID No: 824)

*Homo sapiens* chondroitin polymerizing factor 2 (CHPF2):
gttccttttttgggttagctttggcagtattgagttttacttcctcctctttttagtggaagacaga
ccataatcccagtgtgagtgaaattgattgtttcatttattaccgttttggctgggggttagttcc
gacaccttcacagttgaagagcaggcagaaggagttgtgaagacaggacaatcttcttggggatgc
tggtcctggaagccagcgggcctcgctctgtctttggcctcattgaccccaggttctctggttaaa
actgaaagcctactactggcctggtgcccatcaatccattgatccttgaggctgtgcccctggggc
acccacctggcagggcctaccaccatg (Seq ID No: 825)

*Homo sapiens* thioredoxin-related transmembrane protein 3 (TMX3):
gcttctcttccgctccgggtcggctccgtttccctttccgggcgggcaggcggcggaccccagtgt
ctttatccctcttttgcacagtcagcttctgcagctctcccgggctagcatg
(Seq ID No: 826)

*Homo sapiens* ras homolog family member F (in filopodia) (RHOF):
cgacctcttggctccgctagtgcccggcgcgccgccgccagtgctgcgggctccgggcaatg
(Seq ID No: 827)

*Homo sapiens* amyloid beta
(A4) precursor protein-binding, family B, member 1 interacting protein
(APBB1IP):
ctttctctcaggaaactccactcccaactgacaggtgctatttccagccagtcctatgctgttgca
aatagtgagtccatgaatgccctctgccgtgtgcattacttattttcatcagcagatcttcgtaac
acactcctggaagtgggatgacggggtcaaaaggcgaatccatacataagttaaatagatattgct
caattctcttccacggggttcagaccattttggatttctacgagcaatgaagacagtgctattcct
ctacaccctggccggccaactgagcgtggttaaacgtggggagggaggagggtgaggttaccaacc
tgatggttgagaaagggcctccgcccagcgcgcccttcctccacccccacccgagagacagctgaa
ctccggccgggacgcgcgtgttgccagtccagccctgcaccgcgtcccctgagggcgggctgcagg
cggccgggaagccttgcacaaccggcccaaaagaggaagcccagaaagtgctgaagtaaacacttt
gggagaccgttgcaacataaagcggcctctcagtctttggtggaaccatcactaggccccaatccc
ttagtccctcttgcgtcgaggctgcaaaatggttccattcgccaggagacgctcctgagagaaggg
cgcgcgcggcacaggggccttccttgcacctcggagcaaagcagctcggatagcgccacacgtctg
cgcgctgcgtgggaagggcagggctgacagcacttcctccccggggcagcgacctggagcccgggt
gcggcagtctgcaccgcgcgtcgctttcccggccggagtctcgccgccttcccgcgccccgcagcg
ccccgcagagcagtcgagatg (Seq ID No: 828)

*Homo sapiens* roundabout, axon guidance receptor, homolog 4 (*Drosophila*)
(ROBO4):
ccttccctcttcactgtgagctcagagcagcaggacaaagtgctcgggacaaggacatagggctga
gagtagccatg (Seq ID No: 829)

*Homo sapiens* translocase of outer mitochondrial membrane 7 homolog
(yeast) (TOMM7):
acctcctttccctttcggattcccgacgctgtggttgctgtaaggggtcctccctgcgccacacgg
ccgtcgccatg (Seq ID No: 830)

-continued

| SEQUENCES: |
| --- |

*Homo sapiens* major histocompatibility complex, class II, DR alpha (HLA-DRA):
ttttcttttattcttgtctgttctgcctcactcccgagctctactgactcccaacagagcgcccaa
gaagaaaatg (Seq ID No: 831)

*Homo sapiens* protein arginine methyltransferase 8 (PRMT8):
cctcctctactatctcggtatcaccaaacccttgccggctcttatg (Seq ID No: 832)

*Homo sapiens* adducin 3 (gamma) (ADD3):
ctgcctcttatgaagcaatactagagaggaaaaacaaaacccattcctttaagaaagattccgcct
cctctcataagcaagcgcctaatggtaattgtagagtttactaagtcaaacacttactactcagca
ttgagagaagctgctgctgctaatgctgctgctgctgctgccgccgccgccgctgctgctgctgct
gttggtctgaggctgcagtaggtttctgtgcagcattgcagaatccacacctagagaacagaagac
acagacacgtacgtctactacccttgttagaaggaagctttggatcttcggtggataacaagagta
atccacagacttaaaacatg (Seq ID No: 833)

*Homo sapiens* BarH-like homeobox 1 (BARHL1):
agccccttttggatctaatgcgcagaggaggttggcccagagctcccgggctcccccaaggctgaac
tccgtccaaggtgcccgcaggctccctgcccgccttccccatgccagcccgcagctaggggcaggg
gcagcggcggctggggttgggggtgggtggggagcttttggggaggacaggtcgcagcttggctat
g (Seq ID No: 834)

*Homo sapiens* intraflagellar transport 46 homolog (*Chlamydomonas*) (IFT46):
ttatctttttgcctagcgactgacaacaggctggttgcttggcgtggaatcctaaagtggcctggc
tttgagactggagtgagaccccagccctaggctggggttctttccattatagaggagacggattca
gaagggctacagaccaaggttgttgaaaaccagacatatgatgagcgtctagagattaacgactcc
gaagaggttgcaagtatttatactccaaccccaagacaccaaggacttcctcgttctgcccatctt
cctaacaaggctatg (Seq ID No: 835)

*Homo sapiens* carbonic anhydrase X (CA10):
cccccttttcgggaggagggaggcagggacttgcaggcaagagttgcacctggtctaggaacctgc
agagaaaagaactctggggtaagtagtgttctggcactggcacggaaaggggtaaagggtgggggg
catgagagggacgaaatggagagggcagggaatgaattatgcaaaaaaatctccaatatttcgcag
cggagggagagcacagcacagcactcccaggatgagtcctgcctgggtctcccgcgccgaacccgc
agcacgaagttctttttaagaagagaaactcgaaaatcctggagggtaacagaggcagccagggcg
gggcggagtgcggaggcggctgccagggactggggccgaggcggcggccaaggtggcctgaagctg
tgacacccagcctcctcctcctcctcctcatggccgcgctcagcctcacctccccgcccgggcctc
ctgcctccgcccccgggtgccgggctgcggagctgacgctgggacgcccggcggcggcgaggacgc
tcacctggccaagcctccttctcctcctccccctcccgcccccacctgtcctcctcctctctgagt
tgggaagcgtagggatccgtaggcgaggaaataacgacccctgcagttgtattgcggaaaatctcg
acagcggcgctagttgcgggcgatggaagccaggcaactgggggttctggggagttcaggaaaata
gcagaggagcaggaagggcgcgcgcgacctggagagtctgtgtgcccccaccgcgccccagtcccc
ggggcccagcccttcccctcggcgccctggacgcactgccggaacccggctgagaggctgcaggct
gcgcgcggacctggggagcagggagggtcggcggaggctgccggcggctggcggtttcgggcaata
atccctgcctctctttctctgtgtgtctgctgtgtctgctccttccccgccccccggaagcaggag
aagaactgccccggagcgcagcagccaccctccgaccatgccccggtgaggggggcggacttcgag
ggcaacttgccgcggactgcctgggcttagccagcgagctacgcgctcccgggagcccggaattgc
acggcgcagcccggcggggggctatcgtctatgtcttcttggggcgccagacgaatcggggtctcg
tttttgctggaagagcccagtgttggtggcttcaggtggctgctgccgccgccgccgccgccgccg
ctgctagtgcggtttccgccgctggtgcgaagagaagagacacgcgagcggggagacctccaaggc
agcgaggcatcggacatgtgtcagcacatctggggcgcacatccgtcgagcccgaggggagatttg
ccggaacaattcaaactgcgatattgatcttggggtgactgtccctggccggctgtcgggtggga
gtgcgagtgtgcactcgctcggaagtgtgtgcgagtgtgtatgtgtgtgtgccgtgtcgggctccc
cccttccccccgttttcccgtcgagtgatgcacttggaatgagaatcagaggatg
(Seq ID No: 836)

*Homo sapiens* dual specificity phosphatase 22 (DUSP22):
cctcctccctgtaacatgccatagtgcgcctgcgaccacacggccggggcgctagcgttcgccttc
agccaccatg (Seq ID No: 837)

*Homo sapiens* olfactomedin-like 3 (OLFML3): gttccttctactctggcac-
cactctccaggctgccatg (Seq ID No: 838)

*Homo sapiens* phosphoribosyl transferase domain containing 1 (PRTFDC1): ccgtcttcccttcccgcgttccccgggagaaacatg (Seq ID No: 839)

*Homo sapiens* translocase of outer mitochondrial membrane 22 homolog (yeast) (TOMM22): cctcctttccgcttccggtgtcccctacagtcatg
(Seq ID No: 840)

*Homo sapiens* arrestin, beta 1 (ARRB1):
gctcctcctgctggctggggattttccagcctgggcgctgacgccgcggacctccctgcgaccgtc
gcggaccatg (Seq ID No: 841)

SEQUENCES:

*Homo sapiens* cytokine induced apoptosis inhibitor 1 (CIAPIN1):
cctcctctcgcgagaggcgcaaggcgtggagtcgacggctggagagaagccgggagcgagcccagg
cggcagtcttgattccctttggccagcagtttttaggtctgtcagtactgcactgcaagaatg
(Seq ID No: 842)

*Homo sapiens* leucine zipper transcription factor-like 1 (LZTFL1):
taccctccttccccatttctgtggtccaactaccctcggcgatcccaggcttggcggggcaccgc
ctggcctctcccgttcctttaggctgccgccgctgcctgccgccatg (Seq ID No: 843)

*Homo sapiens* phospholipid scramblase 4 (PLSCR4):
agccctcccttccgcgcgcttactttgtttataacttgaaaaatcctctccgtctcccttccctgc
ctcctttcctttccctttcctctgccagtacaactagacccggcgtctggcgtccccggtgcccag
cattctgcggggcaggcggattaattggaattcttcaaaatg (Seq ID No: 844)

*Homo sapiens* ectonucleoside triphosphate diphosphohydrolase 7
(ENTPD7):
cctccttccggctgggcaaggggccgcggggagcagctcgggactgaaccgagaggtgccgaagga
accggcgggccgcttgatcccgctgcagacgtaggagatgcctgggacaaggaggccaccttctca
gggcaaaagaaaaagaaggtgacaggcgttgagaccaccgaagggaacccatg
(Seq ID No: 845)

*Homo sapiens* fascin homolog 3, actin-bundling protein, testicular
(*Strongylocentrotus purpuratus*) (FSCN3):
agttctctctgggaacatctggtgggtactacaggccctattccaggccctatggcctgtggaacc
tcaccacgggggggagggctgggccagacggagacatcacctgtggtgtcagccccatg
(Seq ID No: 846)

*Homo sapiens* X-prolyl aminopeptidase (aminopeptidase P) 1, soluble
(XPNPEP1):
cctccttcgcgccggcccttccgcgggtgatcagctggtctgcgctcccctgacgtgggctggggc
acgtcaccgccgaatg (Seq ID No: 847)

*Homo sapiens* REX4, RNA exonuclease 4 homolog (*S. cerevisiae*)
(REX04):
gggtctcttccggagtcttttcctggacggggtccctgcggtgggtgtgtttcggcctggcctggg
caggcgcttgtgctgccagggcgccgggcccggggaggccggggtctcgggtggccgccggcccag
gcgctggacggcagcaggatg (Seq ID No: 848)

*Homo sapiens* LYR motif containing 4 (LYRM4): ttttctttccaaaatg
(Seq ID No: 849)

*Homo sapiens* DEAD (Asp-Glu-Ala-Asp) box polypeptide 24 (DDX24):
ggttcttcactcgcgactgacggagctgcggtggcgtctccacacgcaaccatg
(Seq ID No: 850)

*Homo sapiens* transmembrane protein 159 (TMEM159):
ccttcttcctcttgttcctcctcctgcctctcttcgcttcgcctgcaaacgcggtgggggctgctc
ggcggtcaggagcaggttaccctccgtctgcatgcccaccatcaaggtatgaggatggtagaagct
ctcgtcgaaccagatggatgaagaccactaacggcttttgtttcctctggtaacagcaagagacag
agcgacatgagagattggaccgcgggctgcactggagaatttactggtaggataattcatccctaa
agagattgaagtgagcttcagaatg (Seq ID No: 851)

*Homo sapiens* NDRG family member 4 (NDRG4):
cggcctccgcccctgcagccgcgggcacgcggaggggctcctggctgcccgcacctgcacccgcgc
gtcggcggcgccgaagccccgctccccgcctgcgcgtctgtctcgtccgcatctccgcggcctcct
gctccacgacgtgaccatg (Seq ID No: 852)

*Homo sapiens* pre-B-cell leukemia homeobox interacting protein 1
(PBXIP1):
ttttcttctcgggctgcaaacaaagggaagcctgcaacaagttaagctgaagaccgaagcaagagc
tggttcaggtggcagccacagcagcctcagggacctcagcaactatg (Seq ID No: 853)

*Homo sapiens* twisted gastrulation homolog 1 (*Drosophila*) (TWSG1):
ctgtctctttaaggtgcccgaggctcgcgggcgctgcgctgaggggacggcgggaggcgcggcctg
gcctcgcactcaaagccgccgcagcgcgccccgggctcggccgacccggcggggatctaggggtgg
gcgacttcgcgggaccgtggcgcatgtttcctgggagttactgatcatcttctttgaagaaacatg
(Seq ID No: 854)

*Homo sapiens* zinc finger protein 286A (ZNF286A):
gtcccctttgtgaggcccgggatgggaggtgcccggttcccccagggacagcttcaagcggtaggg
acagacatctgaggacccagcctcagggatgctgtccccgggcttccaggctccagcgccgtagga
ctgaggcagactccacggtgagaaagagacccgatctaacccaggcctttcatcagagcccaggag
ggaaggcaggaagtgggaccacgaggcccgggggcttctaactcgtctggccagggagatctgaa
ttggggtgaagagcagaatctccagaacaaggaggaggtggtgatcatg (Seq ID No: 855)

-continued

| SEQUENCES: |
|---|

*Homo sapiens* S100 calcium binding protein A14 (S100A14):
gctcctcctgtcttgtctcagcggctgccaacagatcatgagccatcagctcctctggggccagct
ataggacaacagaactctcaccaaaggaccagacacagtgggcaccatg (Seq ID No: 856)

*Homo sapiens* ANKHD1-EIF4EBP3 readthrough (ANKHD1-EIF4EBP3):
tgctcttctcgttcccgagatcagcggcggcggtgaccgcgagtgggtcggcaccgtctccggctc
cgggtgcgaacaatg (Seq ID No: 857)

*Homo sapiens* KIAA1143 (KIAA1143): ctgtctttacccagagctaccatg
(Seq ID No: 858)

*Homo sapiens* neuroligin 4, X-linked (NLGN4X):
ctctcttttcttgcagaaccgtctctctcccttctctgtctcttagcacagagctcttattcagc
cactagcttggcccttcctgcttcaattgtaatgcttgttctgcccgtccacagactattggcggc
agaaacaacgaatttcctccaaactaggcggtgttggtggctcttgcattcctctggatgaggaaa
tctagttggggggttccagaaggggaaggctcctgggctttcaatacatcctcctgaatcatacct
cgtttcgggttccctagaaaaatctggacgtgtaaaaagaactcttaacggccgatgcagctcttc
caaagctaaggctgccttggagttttcataagaaattgtccctggaggtgttggatgatcacagct
tccttggagcattgcagttgctggaatccagtttcaggattaagggagggctgcctccttgcaatg
ggctgccaagaaaacggctgtgcttgttcttaacctcaggctctgtctgtgatcagtctgagagtc
tctcccaggtctactgctccctggaaagccctatctctctgcaggctcgcctctgggctttgtctc
cttggagccacatcactgggacagctgtggatgtggatgcagatttgaaccatg
(Seq ID No: 859)

*Homo sapiens* mitochondrial antiviral signaling protein (MAVS):
ccgcctcctcgctgcgggaagggtcctgggcccgggcggcggtcgccaggtctcagggccggggg
tacccgagtctcgtttcctctcagtccatccacccttcatggggccagagccctctctccagaatc
tgagcagcaatg (Seq ID No: 860)

*Homo sapiens* serine incorporator 1 (SERINC1):
ctgtctccatcttgtctgtatccgctgctcttgtgacgttgtggagatg (Seq ID No: 861)

*Homo sapiens* KIAA1324 (KIAA1324):
cctccccttttttccgccttctgccagcagaagcagcagccgcagcacctgagccgctactgccg
ctcactcaggacaacgctatg (Seq ID No: 862)

*Homo sapiens* synaptotagmin IV (SYT4):
ggacctccctctttgcctcctccctgttccaggagctggtgccctgggctctgcgctgttgtttc
agcgctccgaaagccggcgcttgagatccaggcaagtgaatccagccaggcagttttcccttcagc
acctcggacagaacacgcagtaaaaaatg (Seq ID No: 863)

*Homo sapiens* pyruvate dehyrogenase phosphatase catalytic subunit 2
(PDP2):
cttccttctggagctgggtcctgactagggaccgcctgggtgaggtgaggacctggtggccgcagt
tgtggcactgtgcgcaggcgctgaactgaccggacggagcgggcggctgtggcctcgccagctggt
ttaaaaatatcctttttttgctgaaggaacacatttgctggtatagtttcagaatg
(Seq ID No: 864)

*Homo sapiens* gephyrin (GPHN):
ctatcctttcctctcagtcctgccatctagctgccttgggtctcgcgctccgcagagcgttccgac
actctccggcctcgttctgccgcctccgcgcgctctccccgtgcggccaccgcgccccccaagctt
gcctccttcttgccggacttggggccgcgcgccctgactccttcccctcccgcggacccgcgcact
cccggcgcggcctctcccccacgcaggccaccgtgcactctgtggcctcccccctccttccccgctc
tcctcgcgcttctctggctccctagctgtcgcgctctcctcggcgagcgcgctcccggcccgcgcg
ctccgggctccggtttctcccggctcctgtcagtgcggtgactgcgctgggaaacatg
(Seq ID No: 865)

*Homo sapiens* deltex homolog 2 (*Drosophila*) (DTX2):
ccttctcctgagagtcggagccacagccagagccctgcccaggccgagccggagctgcagcccgag
cgcggtggtgccctcagccccgtcctcttgtcctcctcagcctcggtgccttggaatttgtgtcgc
tgagtcagcaagcctttcagatttgcccggtttttgttgtttgtggtttgtatcaagatgggaact
caaacaagtcattcctcctaaggagctggtgtcttcatccagaagggacagtttgtgccagctctc
cagagagaaaaggatctggtactgttctggagtggcctgtagcagacactgaaccaccagccagct
gcatttgttgtcctggaagtcattgccaactctgccagtcacactggggtccccagagaagtcaag
atctgccggaggcgctgggcaatgaccccgggactccaggccagaggggtctgaagctgtttggga
aagcagcgggactccttgggaagatg (Seq ID No: 866)

*Homo sapiens* melanoma antigen family E, 1 (MAGEE1):
ctgccttttttcaccacctctaatttcagcttcagcagttgcttggaactttggttctggcagcagc
agcaacatcattaccgctagcggcagttttgtgccgaggcacctacacacctcccgtcctctctgc
cagatcgcgggcctgtcggtgtctgctcctacacgccaacgccggtgggcaggaccatg
(Seq ID No: 867)

*Homo sapiens* G protein-coupled receptor 107 (GPR107):
cgcccctttcaccccggacgtgggcgggagaggaagcggctggtgatgctggaacaaacatg
(Seq ID No: 868)

-continued

SEQUENCES:

*Homo sapiens* PDZ and LIM domain 1 (PDLIM1):
cgctctttctccgacagctgccggggggtgccctgcaagctgttccgcgcgtcctgcccgtctgtcc
ccgcgggtcgtcgcccgccacagccgcgccatg (Seq ID No: 869)

*Homo sapiens* thymosin beta 10 (TMSB10):
cgctcttttgtttcttgctgcagcaacgcgagtgggagcaccaggatctcgggctcggaacgagac
tgcacggattgttttaagaaaatg (Seq ID No: 870)

*Homo sapiens* phospholipid scramblase 1 (PLSCR1):
agaccctttcagacccttttccggctgacttctgagaaggttgcgcagcagctgtgcccggcagt
ctagaggcgcagaagaggaagccatcgcctggccccggctctctggaccttgtctcgctcgggagc
ggaaacagcggcagccagagaactgttttaatcatg (Seq ID No: 871)

*Homo sapiens* eukaryotic translation elongation factor 1 beta 2
(EEF1B2):
gggtccttttttcctctcttcagcgtggggcgcccacaatttgcgcgctctctttctgctgctcccc
agctctcggatacagccgacaccatg (Seq ID No: 872)

*Homo sapiens* pyrophosphatase (inorganic) 1 (PPA1):
ggctctctccttgtcagtcggcgccgcgtgcgggctggtggctctgtggcagcggcggcggcagga
ctccggcactatg (Seq ID No: 873)

*Homo sapiens* X-ray repair complementing defective repair in Chinese
hamster cells 5 (double-strand-break rejoining) (XRCC5):
ggctctttccgctatctgccgcttgtccaccggaagcgagttgcgacacggcaggttcccgcccgg
aagaagcgaccaaagcgcctgaggaccggcaacatg (Seq ID No: 874)

*Homo sapiens* GATA zinc finger domain containing 1 (GATAD1):
gatccctttcccagtcctgcttcccagtgcctcgggccagggaatcctggcctccgcctgcggagc
cggcggaacccgcttcccgcctccacggggcagcgccagcggcctggtcctttcaccggcagctcc
gtgccgacgctctcaccgctcttcctatcgccgggagtggcgggccgaccagggggcggccgggct
accgtccgccattcccgtgtctctgcgcccgcgggggccgcccgagccggccaccatg
(Seq ID No: 875)

*Homo sapiens* enolase-phosphatase 1 (ENOPH1):
ccgccttttccagttccaggtgtgcagaagtgtcctctccccacgcgcggcgggctgcacttggtc
gctggctccgagatcgcgcggggccgccggaagcccaagacggtaccgggggccgcagccgcagcc
ggcgccgccctccgccctccccaacagcaggccgagtcccgtagcatccggtagggaaatg
(Seq ID No: 876)

*Homo sapiens* regulation of nuclear pre-mRNA domain containing 1B
(RPRD1B):
agctctttccgggggcccggggaactactctccttgcctcgctctgtctccttcgaagtgctctgc
gcgaggttcagagcggccgccgcctccaaagggacggttttctagagctccgacgcctctcggtgc
ccctctgctccggcccttgccctttgacctcgctctcgcggcagggtgagaggtcgggtggccatc
ttgtggcggcggcgcgggcggctgttactgcggagacccatcccctccccttctcgcacccctgg
cagtctgtcagtcggtaaaaagtcccgcagcctgtcaggtgaggccccggcctcgtgccgtcgctc
ttcccgccgcactgggcggcccaggccgctccctgccgggcctcactgccgccaccatg
(Seq ID No: 877)

*Homo sapiens* family with sequence similarity 60, member A
(FAM60A):
ctatctttctagacaaggcagttgaggaggagggagcgcttgagggggactggcctggcgtgcact
ccgcacctcggggacattattgcgcgtggaacggctgcttttggaaggcacaacttcctgaatgga
ccatgactcccaccaaagatccctgtctctgattcaccaaacagcttcaaccctgaaaccaggacg
agaagttgacaacatctgagtggacagctaattgacctaagacttcagaccagactattgcccaga
agaaaagatg (Seq ID No: 878)

*Homo sapiens* MIDI interacting protein 1 (MID1IP1):
gggccttttatctcggtgctgccggggaggcgggaggaggagacaccaggggtggccctgagcgc
cggcgacacctttcctggactataaattgagcacctgggatgggtagggggccaacgcagtcaccg
ccgtccgcagtcacagtccagccactgaccgcagcagcgcccttgcgtagcagccgcttgcagcga
gaacactgaattgccaacgagcaggagagtctcaaggcgcaagaggaggccagggctcgacccaca
gagcaccctcagccatcgcgagtttccgggcgccaaagccaggagaagccgcccatcccgcagggc
cggtctgccagcgagacgagagttggcgagggcggaggagtgccgggaatcccgccacaccggcta
tagccaggcccccagcgcgggccttggagagcgcgtgaaggcgggcatccccttgacccggccgac
catccccgtgcccctgcgtccctgcgctccaacgtccgcgcggccaccatg
(Seq ID No: 879)

*Homo sapiens* transmembrane protein 35 (TMEM35):
ctctccctttgtcattctagctgcctgctgcctccgcagcgtcccccagctctccctgtgctaac
tgcctgcaccttggacagagcgggtgcgcaaatcagaaggattagttgggacctgccttggcgacc
ccatg (Seq ID No: 880)

*Homo sapiens* Fc fragment of IgG, low affinity IIa, receptor (CD32)
(FCGR2A): cttcctcttttctaagcttgtctcttaaaacccactggacgttggcacagtgctg-
ggatg (Seq ID No: 881)

SEQUENCES:

*Homo sapiens* tribbles homolog 2 (*Drosophila*) (TRIB2):
ctttctctttttgtttggcttctaacgcgttgggactgagtcgccgccgtgagctccccgaagact
gcacaaactaccgcgggctcctccgccccgtctgcgattcggaagccggcctgggggtcgcgtcgg
gagccctggcgctgcagctccgcaccttagcagcccgggtactcatccagatccacgccggggaca
cacacacagagtaactaaaagtgcggcgattctgcacatcgccgactgctttggggtaacaaaaag
acccgagttgcctgccgaccgaggacccccgggagccgggctcggagcagacgaggtatccggcgg
cgcccatttggggggcttctaactctttctccacgcagcccctcttctgtcccctcccctctcgctc
ccttttaaaatcagtggcaccgaggcgcctgcagccgcactcgccagcgactcatctctccagcgg
gtttttttttgtttgtcgtgtgcgatcctcacactcatg (Seq ID No: 882)

*Homo sapiens* family with sequence similarity 3, member A (FAM3A):
cgtcctctccggggggcggagcgggtcggcgggcctgacagggaacctccctgaccgagcccacgtc
tccccacggccagagagaaatctccggcccggcccgcatcgccagcccccaggcccggaggaacggcc
cgagcccaggagaaccacatcttcgtcccagccccggaggctcctgtgggcaagatcgtgagccaa
cgggttcctgaggcccctcctggccaggcagggtttccccgcgcgtttccgaggagccctgcctgg
ccgggcggctggacaaacaggtcgtagcaccgatcgcgcccgcccccagcaggggtcccgcacagg
cttgcccctgacccccacccaaacctgtccttccgctttgcccccaaacagtgcacttgccggcgg
tcccaacccagcaggagaagtggacatg (Seq ID No: 883)

*Homo sapiens* exocyst complex component 4 (EXOC4):
ggctctccccgcgtccaagatg (Seq ID No: 884)

*Homo sapiens* ELOVL fatty acid elongase 5 (ELOVL5):
gcgccttcctcttcccatcgcgcgggtcctagccaccggtgtctccttctacatccgcctctgcgc
cggctgccacccgcgctccctccgccgccgccgccttgctgctgctcaaagctgctgccgcccctt
gggctaaaaggttttcaaatg (Seq ID No: 885)

*Homo sapiens* apolipoprotein B mRNA editing enzyme, catalytic polypeptide-like 3G (APOBEC3G):
ctttctctttccctttgcaattgccttgggtcctgccgcacagagcggcctgtctttatcagaggt
ccctctgccagggggagggccccagagaaaaccagaaagagggtgagagactgaggaagataaagc
gtcccagggcctcctacaccagcgcctgagcaggaagcgggaggggccatgactacgaggccctgg
gaggtcactttagggagggctgtcctaaaaccagaagcttggagcagaaagtgaaaccctggtgct
ccagacaaagatcttagtcgggactagccggccaaggatg (Seq ID No: 886)

*Homo sapiens* gamma-aminobutyric acid (GABA) B receptor, 1 (GABBR1):
gctcctcctcctcccctccgtcggtcagtcagtccgcgaggagagtccgcggtggcggcgacggtg
gcgagagccgcgggggccgtaggaagccaaccttccctgcttctccggggccctcgccccctcctc
cccacaaaatcagggatggaggcgcctccccggcaccctcttagcagccctccccaggaaaagtgt
cccccctgagctcctaacgctccccaacagctacccctgccccccacgccatg
(Seq ID No: 887)

*Homo sapiens* cofilin 2 (muscle) (CFL2):
cctccttctcctcccagtgccacagagccgaagcccgagctgccgccgcagccacagccgagggca
ctatg (Seq ID No: 888)

*Homo sapiens* DEAH (Asp-Glu-Ala-His) box polypeptide 35 (DHX35):
tgaccttttaccccaacatg (Seq ID No: 889)

*Homo sapiens* resistance to inhibitors of cholinesterase 8 homolog A (*C. elegans*) (RIC8A): ccgccttccccggcgcgccatg (Seq ID No: 890)

*Homo sapiens* FK506 binding protein 10, 65 kDa (FKBP10):
agttctttgtagtgcctccctcagactctaacacactcagcctggccccctcctcctattgcaacc
ccctcccccgctcctcccggccaggccagctcagtcttcccagcccccattccacgtggaccagcc
agggcgggggtagggaaagaggacaggaagagggggagccagttctgggaggcggggggaaggagg
ttggtggcgactccctcgctcgccctcactgccggcggtcccaactccaggcaccatg
(Seq ID No: 891)

*Homo sapiens* small ArfGAP 1 (SMAP1):
cctcctcccgttccagctgccgctgccgcttcctgggctgagtccgcccgcggtcccggcggcgcc
aggtgcgttcactctgcccggctccagccagcgtccgccgccgccgtagctgccccaggctccccg
ccccgctgccgagatg (Seq ID No: 892)

*Homo sapiens* chromosome 14 open reading frame 93 (C14orf93):
cctccttttgcacacacacgaatacaaagagccatacgaccttcggatgccggaaggtccttctg
aatcccttccctgttccttaggttgcactagtcgggggttccatgctggggggcagaaggaatgct
ctctaccgtctgaaaccgttcatcaggaaggccttgatttgtgatgtgctaggagagcacaggatc
tgcaaatagaaggcacctgtctcccttctgcaggccgaggagaggccgccatggactgtgtgcttc
ttcatggcttgtttactcttctttcacagaccctacagcttggggcctgggctcctctgaccatcc
tcattgagaaaggaaagtgagtccagagaagttgatgcttcctacctgttggagcggcccagcagt
gtaagcgtggttgttactgccccatccgccatg (Seq ID No: 893)

-continued

SEQUENCES:

*Homo sapiens* brevican (BCAN):
cgccctcttccgaatgtcctgcggccccagcctctcctcacgctcgcgcagtctccgccgcagtct
cagctgcagctgcaggactgagccgtgcacccggaggagacccccggaggaggcgacaaacttcgc
agtgccgcgacccaaccccagccctgggtagcctgcagcatg (Seq ID No: 894)

*Homo sapiens* H2.0-like homeobox (HLX):
cggcctctcttcctcagtgcgggcggagaagcgaaagcggatcgtcctcggctgccgccgccttct
ccgggactcgcgcgcccctccccgcgcgcccacccacccagtccggctggactgcggcagccgcgc
ggctcaccccggcaggatg (Seq ID No: 895)

*Homo sapiens* v-rel reticuloendotheliosis viral oncogene homolog A (avian) (RELA):
ccgcctctggcgaatggctcgtctgtagtgcacgccgcgggcccagctgcgaccccggccccgccc
ccgggaccccggccatg (Seq ID No: 896)

*Homo sapiens* zinc finger protein 277 (ZNF277):
cctccctttttcttttctgccgggtaatg (Seq ID No: 897)

*Homo sapiens* globoside alpha-1,3-N-acetylgalactosaminyltransferase 1 (GBGT1):
cttcctcttttctgtctggcccgcggccccgctgcctgccctgctccaggctccacctgcgccgcc
gatcgcccgggtatcgcgggggcccaggccagctgagtccgttttccgcgccggggtggcgcccct
ccaaccgtcctaacgccgggccggcagcaaggagtgttcctgggacctcagagaccaggctcagag
cctgacatccctgcgaggggacagcctcatccgcccaggccagtgggggtctctacaagtgcccag
gctcaggtgcagcccccagcaatg (Seq ID No: 898)

*Homo sapiens* FXYD domain containing ion transport regulator 6 (FXYD6): ggtcctcctgggagtctcggaggggaccggctgtgcagacgccatg
(Seq ID No: 899)

*Homo sapiens* nuclear RNA export factor 3 (NXF3):
tcctctctatgcttggggaaggaacttcctgtaagcaaggcttgaggcttgctctcgccttcgtca
gcagccctcctcaatcttctccaaactcccgtccccaggccacacagattctcctcaagagagccc
tataaggacattggtaaaatg (Seq ID No: 900)

*Homo sapiens* chromosome 14 open reading frame 133 (C14orf133):
attcccttccgccccccttctctaagctgcacagcctgaatagaagggctggtccagcggcggcgga
ggctggcgctgtcctgagagggagggctctgtgcggaagagtcagggcgacccttgggcgctggag
tacgcttgggactggggctgcgagtgagcaccagcgattggttcggaagcggacatttggttcaga
acgagcatttaactctgccagggatccgctgggctctgacgactgcggtagatccatggcttcctg
gacgttcacccgtagagtcatcctagcttaactcttgttccctggtctcagttcacaagcctcacc
tgtatcttcctggctcggaagataattgaaaccaagtctgacttctcaatg
(Seq ID No: 901)

*Homo sapiens* X-prolyl aminopeptidase (aminopeptidase P) 3, putative (XPNPEP3): ctttctcttcccgacgcgtgagttaggccgtaatg
(Seq ID No: 902)

*Homo sapiens* death inducer-obliterator 1 (DIDO1):
ggccctctggcaagatggctgctgcggaggcgttggagcgcggaaatctggaaccgggatggcgac
gtctacactgagtcggaggcgaaggagcttactccacgggaacagcctctagataatctgagttgt
tgaaaatacgaagcctgttactcgtgaacagtggctgacaacagtgttgttgtgagcctggctgtc
tgcttggacccagaggtttcgtctgccagggtttttggttgtatttaggatttcagggaaaagtgt
ccaagctttcagtgttggagcaggtatg (Seq ID No: 903)

*Homo sapiens* PERP, TP53 apoptosis effector (PERP):
cggcctcttcgcttttgtggcggcgcccgcgctcgcaggccactctctgctgtcgcccgtcccgcg
cgctcctccgacccgctccgctccgctccgctcggccccgcgccgcccgtcaacatg
(Seq ID No: 904)

*Homo sapiens* tubulointerstitial nephritis antigen-like 1 (TINAGL1):
tcctctcttgactttgagcgtccggcggtcgcagagccaggaggcggaggcgcgcgggccagcctg
ggccccagcccacaccttcaccagggcccaggagccaccatg (Seq ID No: 905)

*Homo sapiens* eukaryotic translation initiation factor 4H (EIF4H):
ggttcctctcggagcggagacggcaaatg (Seq ID No: 906)

*Homo sapiens* non-SMC condensin I complex, subunit G (NCAPG):
ccccctctcgcgggaattatttgaacgttcgagcggtaaatactccctggggctgtcatagaagac
tactcggagagcgctgcctctgggttggcgggctggcaggctgtagccgagcgcgggcaggactcg
tcccggcagggttccagagccatg (Seq ID No: 907)

*Homo sapiens* MMS19 nucleotide excision repair homolog (*S. cerevisiae*) (MMS19): tatcccctcccacggtctctagttcgcgttatg
(Seq ID No: 908)

-continued

| SEQUENCES: |
|---|

*Homo sapiens* DnaJ (Hsp40) homolog, subfamily C, member 1 (DNAJC1):
ctgcctctacagctgtgtgtaggcctgggggcgagggtcttcggaacgtagcgctggctgcggccc
cgcccgcctacccacccgcccgtccggcagccggctcccgccgcctccgcgctctgtctggggcca
gccacctggcgggccgctccggtgcgcctgcccgcgcttttcactgacaggcgctgttccccacag
ccagcgccgcccgccacgtcccagctctcggccaacggagctgcgcggcgggtgacctttccgagc
ccagcgcgatg (Seq ID No: 909)

*Homo sapiens* stimulated by retinoic acid gene 6 homolog (mouse)
(STRA6):
ctaccctttcatctctgcaactccttcctccctgggcctcccttctggtgtgtctgtgggtctgtc
taggtgggcttgggaaaggggaaggaaggggcgtctctttaggcagctcagactggacaagccttc
tttgaaaatggtcctttgaacacacgcctgctggtggttggtcagacagatgcgccagcgggagcc
ccggggccccaaggggacagctatctctgcaggaccagtgcgatg (Seq ID No: 910)

*Homo sapiens* 5-azacytidine induced 2 (AZI2):
cagccccttttccggctgagagctcatccacacttccaatcactttccggagtgcttcccctccct
ccggcccgtgctggtcccgacggcgggcctgggtctcgcgcgcgtattgctgggtaacgggccttc
tctcgcgtcggcccggcccctcctgcctcggctcgtccctccttccagaacgtcccgggctcctgc
cgagtcagaagaaatgggactccctccgcgacgtgcccggagcagctcccttcgctgtggaagcgg
cggtgtcttcgaagaaaccggaagcccgtggtgaccccctggcgacccggtttgttttcggtccgtt
tccaaacactaaggaatcgaaactcggcggccttgggggcggccctacgtagcctggcttctggtt
gtcatg (Seq ID No: 911)

*Homo sapiens* polymerase (RNA) I polypeptide E, 53 kDa (POLR1E):
acgccttttccggcccgcagcgcggcctgggctcccgcgtgtttaaaagtgcgcttgtggctgctg
ctgtcttaactcctgtgcttggcggacagacaggcgagatg (Seq ID No: 912)

*Homo sapiens* mitochondrial ribosomal protein S25 (MRPS25):
agtcctttctcgtcgctgctcggctcgcggcccgtggggtcggccccgccaccgttgccgccatg
(Seq ID No: 913)

*Homo sapiens* TRM2 tRNA methyltransferase 2 homolog A
(*S. cerevisiae*) (TRMT2A):
cggcctccgccgcacgcgctggcggactaagagtggctggcgaagcgagcggccggcgcgggcccc
tggcgggcgggcggtacagccccaagcctgagacccggacctgagcatcgcaggttcgagtcccgc
cccgcctggggcgaagccgggggtggcggcgacctcgcggcgttgcaccggctctgtgagcacctc
ccctctgagcacttcccttgtgacaggccacttcccttgtgacaggcccaggacgaggtggccagg
cggcccccatggcgtccctggtctaggcggagaaccgcctgggcgatg (Seq ID No: 914)

*Homo sapiens* lipid phosphate phosphatase-related protein type 2
(LPPR2):
ccctccctccacctcggagtctgcgcggcgcggccaggcccggccgaccgcgtctcggtcttcgcg
tctgccagcctggctggcagtccgtctgtccatcccgccgcgcgccggggcagtctaggcggagcggg
ggctcaggcggcggcggcctcgacgcgagtgagtgtcgtggttggggtgctggacccagagtgcct
accctcgcctgcctgggcctcagtttccacatctgcacaatgggggtgaccatccctgccctgctg
gctgccaggagcggctgtgagtcttcaggcgtggatgcagcctgggggaagccatagggcgctttc
acaggcctggccttcaccatg (Seq ID No: 915)

*Homo sapiens* chromosome 11 open reading frame 1 (C11orf1):
gaacctttttcacctcgtctgaaatg (Seq ID No: 916)

*Homo sapiens* microtubule associated monoxygenase, calponin and LIM
domain containing 1 (MICAL1):
cgccctcccacccgctcagacctggttgccagcccaacaggaagcggcccctcccggcttcggagc
cgccgccactcatctctgcccagctgctgccctccccaggaggcctccatg
(Seq ID No: 917)

*Homo sapiens* kinesin light chain 2 (KLC2):
gctcctttaaggcagcgaacgggccaagagaagcgtgtttcgcccctccgacgccaccgaggtag
cggcttcacctttaaggcggcgcgggggctgctgggaaggccggcgggatggaggcggcgggaccg
gctcgcgggtgcgggtccgggtgaagcgggaggcagccagagtcggagccgggcccgagcaccagg
cgcaggcccggcgcccgcctgcccgcaccctcgtcctcacagacgccacagccatg
(Seq ID No: 918)

*Homo sapiens* DNA cross-link repair 1B (DCLRE1B):
acttccttttctgcccactctggtaacttattgctctgctgggctctttcccttagggtctctgg
ccctgttcttgccccagcatgacttttatcgggacgccgttgtggaagcctcacgcaggagccctg
cccccgtggagaagatcccactggtgactccaaccctaccaccatg (Seq ID No: 919)

*Homo sapiens* armadillo repeat containing, X-linked 5 (ARMCX5):
gctcctcccactgccgttgtgggtaacgcggacgtggaagaacctcgtctgcggaggaaaaggtag
atgttaaatggtaactacgcgcgaggttctgaggagccctgggaacaggaaggagaaaagaatacc
aaaagtgacaacagtttgccaatcgcagtctttaatctgataaagcggttatctcgtcttgagtcc
caggtgccgagtcaatccccatacacagccgccgccattgcctcgagtccttgtgtctgactgtct
gttcctgctgctgtatgacacagcacctcgaggcaaggaaataagaaaactgcctctgatccaagc
agagaaggtctgcctgtagatctgctgtagggcttgtcaccattggaagcaaggtcctacttcagt
ggcagatctggtggccttggagtggctgaagaccaccaccctccacagggctgggcccatgcacag -continued

SEQUENCES:

ccatccttccctaccttgagtgagcttcctctgcatgttttctatatcactggcagagcctgtagt
tggaaaggggacagagtgactactggactttgtgtgaaaacaccaacccgggacaaaacttcagtca
aggctgagacgggtgggggtatataacttgtccttacgttaaacttggaacatg
(Seq ID No: 920)

*Homo sapiens* chromosome 12 open reading frame 43 (C12orf43):
aatcctttgcggtggttcaagatg (Seq ID No: 921)

*Homo sapiens* vacuolar protein sorting 33 homolog A (*S. cerevisiae*)
(VPS33A):
ggtcctcccgtaggaaccggcggactcggttggcgttgtggggcaggggggtggtggagcaagatg
(Seq ID No: 922)

*Homo sapiens* arginine/serine-rich coiled-coil 2 (RSRC2):
gggcctcctcgcctttgtgccatccgggtctctcgcgcgagcgatttagtctgaggcgaagcttcg
gagcggccggtactgttgaaagcgacaagtggaggcgccgctctagcggccgggactctgaactat
ggcggctagtgatacagagcgagatggactagccccagaaaagacatcaccagatagagataagaa
aaaagagcagtcagaagtatctgtttctcctagagcttcaaaacatcattattcaagatcacgatc
aaggtcaagagaaagaaaacgaaagtcagataatgaaggaagaaaacacaggagccggagcagaag
caaagagcgtgcttatgcgcgaagagactgaactgaagacgctgcagactcagatagcaaaataat
aagcctacttcatgataagggaagaagacatgaatccaaagataaatcctctaagaaacataagtc
tgaggaacataatgacaaagaacattcttctgataaaggaagagagcgactaaattcatctgaaaa
tggtgaggacaggcacaaacgcaaagaaagaaagtcatcaagaggcagaagtcactcaagatctag
gtctcgtgaaagacgccatcgtagtagaagcagggagcggaagaagtctcgatccaggagtaggga
gcggaagaaatcgagatccagaagcagagagaggaagaaatcgagatccagaagcagggaaagaaa
acggcggatcaggtctcgttcccgctcaagatcaagacacaggcataggactagaagcaggagtag
gacaaggagtaggagtcgagatagaaagaagagagaattgaaaagccgagaagatttagcagaagttt
aagccggactccaagtccacctcccttcagaggcagaaacacagcaatg (Seq ID No: 923)

*Homo sapiens* integrator complex subunit 3 (INTS3):
ccgccttcccacccccgcccttccactatggccgcttctgtgtggtgtggggagacgctggtcct
ccccgtcctcccatagcgcttattgcctcaccctcacccccctaggggccggatccaaaggcgctgc
actccccaagccttggggcatcagccaggaaggtttcctacctcctaattcaggggcaggactcct
cttttcccccccacggggaaaagaggcagaaacttaggggtttccctcctttcttagggtcagacgc
tcttagggtccacttcttcaggggcggaagcctctcctacccttcccataggggcacaggccttta
ccccactgtacttcggagccaacgcctttccctcagcactgccaccccagagtcaggacccagagg
actgtgccttcgcccccaacgcaggcgcggccttttggagaggagggaggagtggagaggacaggg
gcccttgctctcccctccccaacttgttcctcttgccccccagtccctggcaatccagagatcccg
atatctaggactgtccatccatccactccctgaccttttcccggctcctggctgcagccatg
(Seq ID No: 924)

*Homo sapiens* spermatogenesis associated, serine-rich 2 (SPATS2):
tctcctttcctcttctcagacccgggagcgtccgggacgcggagcccggagctggggcgacgaggc
gattgcgggggcctgggctagctgctggctaccaatattctactttctgtctctatgaatgtgact
accctggttacctcatataatctccctggaaaaggagacatgaatgtctgcaatgatacttcctga
caagaagttgatacaagaaaaggaaaggagattaacagctagtgagcagaatttcgaacagcagga
tttcgtatttttttgcttccaactgcacacttccgttgcccactttttaaatcagagatacctacact
caaaacccagacaaggcaaaaggatacttttcttgtatattttttgagatcgaagaaacgacaatg
(Seq ID No: 925)

*Homo sapiens* fibroblast growth factor receptor 1 (FGFR1):
ccgcccctttcacctcctggctccctcccgggcgatccgcgcccccttgggtctcccctcccttccc
tccgtccgcgtctcctgcgcccccctccctgcgctcgtcccgccgctcttcccgccgcccaacttttt
cctccaactcgcgctcgggagctggcgaggcggcggcggctcctcaggtcagtttgaaaaggagga
tcgagctcactgtggagtatccatggagatgtggagccttgtcaccaacctctaactgcagaactg
ggatg (Seq ID No: 926)

*Homo sapiens* FUN14 domain containing 2 (FUNDC2):
ctccctcttccgctgccgccgtgggaatg (Seq ID No: 927)

*Homo sapiens* ganglioside induced differentiation associated protein
1-like 1 (GDAP1L1): cctccttctttcctgcctctgattccgggctgtcatg
(Seq ID No: 928)

*Homo sapiens* chromosome 19 open reading frame 43 (C19orf43):
agtcctttgcgcggcacctggcgacaaaatg (Seq ID No: 929)

*Homo sapiens* MIS12, MIND kinetochore complex component, homolog
(S. pombe) (MIS12):
ccctctcttctccaccagccaacgtccgggaaaaacgagtaagtacaggttccttctgccaatccc
cgccggccacagctaactttcccgcccggcccctttctgtcataattgaggtgtccacaaccagcc
aatcaggaacgcgagagtatcccgcgtttgctttcgctcgccgaggcgcgtatcagtcggaatttt
ggggagccaaccgcgccgtctgtccctggcaagccagcggcggtttaaaggaggtggcgggaagcc
tgtgtgtgcttcaaatcgtcaccctcatggtcgctccggtaagtgctgcggggcagcattttctct
gaggaggagcggggacgggcgagactggcataagcgtcttcgcgagggagcaaggcggcctgtggg
tcggcctcaccccggcctccgacctgaagatcccagcatgcagcgcgggcgcggggcccgacggaa
gccgggagccggccggaagcagttcctgcgctctggcttctgggtcctgtcctgcgcgatcgcggg -continued

SEQUENCES:

gtcttagacagctcaactcgccgagatgacctgggcacctctgcgttgaatcggcaaatactgatc
aagccgcatttattctgctctcaggaactctaagtctagcagagaagatgaggcggtagaagttca
tcaatggcttggctggaggacaagcaaattgaggacattggcaacggagtgatcaaaatgatagat
catgaggcctaaaatgaataaggaaagaagagaagtggcagaggctgagaacagaaagagagggtg
gaggggctgtaaatcttgaagattagggtataatatgagtatatgggtaagaattggaagaattgt
gtaggaggcagtagtcaaaaagtagaagcagtttggaagagtagttacaaatatcaagagccaggt
ggctaaaaggtggagctataggtcattgaagctcaagaaactgagtctctagggcattggttaagt
catctgtctagacttcaaagttgtctaggatgataattcagaagactgatctgtgccaaagtcaca
ggtttttcacgactgaaaacaacatagcaaaataagccaagatg (Seq ID No: 930)

*Homo sapiens* DEAD (Asp-Glu-Ala-Asp) box polypeptide 50 (DDX50):
cttcctttcacgctgtcgctgcccgtaggtggttgtggccactgtgcccggagggaggcggcggtg
gccagtaatg (Seq ID No: 931)

*Homo sapiens* chromosome 7 open reading frame 25 (C7orf25):
cggcctctgcgtgcacgcgcctgcgtgctcgcgctcgcggttctggcgctgccggaataatgctga
cagcatg (Seq ID No: 932)

*Homo sapiens* KxDL motif containing 1 (KXD1):
ccgccctttcctgtcgtgacttaacgcacgcaagcggctccagggtacgtccccgccacgcgcgct
cgcaggatcggtgcgtggtgacgtttcgccggcgcgggcgccatcccggaagcgcgagcaaggccg
ccagatgtgcaggcagcggaggaggagaaagagatg (Seq ID No: 933)

*Homo sapiens* defective in sister chromatid cohesion 1 homolog
(*S. cerevisiae*) (DSCC1):
acttctttcttgcccgccaagcccgcagccacccgggcgcggcgggactcctagacccggcgctgc
gatg (Seq ID No: 934)

*Homo sapiens* zinc finger protein 426 (ZNF426):
cgttccttttgtgacgccggctgtgagcgcctgagagtctttttgcctttcagagttaaggcctca
ctggcctgggaaaataattgctgccttttgcatccgcgttggctccgtccccaggatcttcccggt
tcagggacctggcgatttctgagtgttccggaatcccaataaccctgtttaaagaggaatggagat
tgccactgtccatttagattaatgaggtgtcctgaagtgatggtgacatcaatgaaaggagggttc
tgacacgttctcacctcgcgggatg (Seq ID No: 935)

*Homo sapiens* TATA box binding protein
(TBP)-associated factor, RNA polymerase I, D, 41 kDa (TAF1D):
caaccctttcttccgcacggttggaggaggtcggctggttatcgggagttggagggctgaggtcg
ggagggtggtgtgtacagagctctaggacaccaggccagtcgcgggttttgggccgaggcctgggt
tacaagcagcaagtgcgcggttggggccactgcgaggccgttttagaaaactgtttaaaacaaaga
gcaattgatg (Seq ID No: 936)

*Homo sapiens* PHD finger protein 1 (PHF1):
ccgcctcctcctcctgccgctgccgctgctttggctgctgcgtcatacgccccagagccgccggga
cggaggggctgggcctggggaccccccggcctccgcctgcacgcccccccacgcccggacgtgccc
tctccgcgcgggggactcgcctaggtctcctacgtctgcccctgcccggctcccggcggcccccagc
tgtcaccggcccccccaggatgcaatg (Seq ID No: 937)

*Homo sapiens* family with sequence similarity 134, member A
(FAM134A):
ccccccttccgcctgacgcgcccccggcggcggccgcgcagccctggctcctcgcgggctcgggcgg
cggctgcggcggggctatg (Seq ID No: 938)

*Homo sapiens* membrane bound O-acyltransferase domain containing 7
(MBOAT7):
ccgcctcctttccggagcccgtctgttccccttcgggtccaaagcttttggctcctccttgttccg
agcccgaaggcccgccccttcacgtactcggagctcggatcccagtgtggacctggactcgaatcc
cgttgccgactcgcgctctcggcttctgctccggggcttcttccctgcccgcccggggccctgacc
gtggcttcttccccggcctgatctgcgcagcccggcgggcgcccagaaggagcaggcggcgcgggg
gcgcgctgggcgggggaggcgtggccggagctgcggcggcaagcgggctgggactgctcggccgcc
tcctgcccggcgagcagctcagaccatg (Seq ID No: 939)

*Homo sapiens* major facilitator superfamily domain containing 11
(MFSD11):
acgcccctttttgctcagccgtcagccccgtctccgtctgaagagtgcttctgccctcatttgcc
tctccctgtgaccccggccccctcagactccgctgcgtcgtctctcggccccgtccagccgttcct
gactgctcttcgccggagtccgcttcccaaccccctttcgccagagcccgagagctccgtcggctc
tgcgtcctggcggattgtcagtggcttcgccccgaggagagctgactgccctgggctgctgcctcc
ggcagagctgagccaaaatg (Seq ID No: 940)

*Homo sapiens* thiamine triphosphatase (THTPA):
ctcccttccccctctgtgggtcccgcgaggagactctcgggctttgaggtgagacctgaagttccg
ctggccggtagtgtagcaggaaagggcaggtcctcccgggtcgtgagccagtagcctcctggggtg
gcaaggtgtagagaggggggcgttgaaaggacacccgctacccggcctgctttctaggggtctctt
tggattgaggacatcagcagcagtggaagggattttactggagacctgtcactgtcagagccttaa -continued

| SEQUENCES: |
| --- |

aatatcaccgacggggccttaatgtcaccgaggtagagagaaaagggcagtagccctagagactat
tgcgacacagtgtgcccctcataagtttttccagggaggggttctgtactgagttgacgccccagg
agctgagcaccaggctttgcatccttgggaactcagcaaacgtttgttcagccaattgcaggtagc
atg (Seq ID No: 941)

*Homo sapiens* acyl-CoA synthetase short-chain family member 3
(ACSS3):
tactcccttccctcaggccccaggaagttgcaagagtaccatttgtcgcacactcggggaccgcgg
gtggccggaggagatg (Seq ID No: 942)

*Homo sapiens* chromosome 6 open reading frame 211 (C6orf211):
gctcctccttcgcggcggtaccgcctctgtttctgcggcgattgaacagccgagctttgcggccgg
gatcgcggaaagtgatg (Seq ID No: 943)

*Homo sapiens* transmembrane protein 204 (TMEM204):
atttcctctctgctgagagccagggaaggcgagctctgcgcacacgggcgtccctgcagcagccac
tctgctttccaggaccggccaactgccctggaggcatccacacaggggcccaggcagcacagagga
gctgtgaacccgctccacaccggccaccctgcccggagcctggcactcacagcaggccggtgctaa
ggagtgtggcgcgggctcgactcccactgctgccggcctcccgagtgactctgttttccactgctg
caggcgagaagaggcacgcgcggcacaggccggcctccgcttcccgggaagacggcgcactcctgg
ccctgggttcttgctgctgcccaccctctgctccctgggatgggccccgaggcgagcagcttcagc
acaggcctggccctgctccaggtgcaggaaggaggataaggccgggccgagaggcggcacacctgg
accatcccatgggcctccgcccgcgccgccccgaggatgagtggtgatgtcctctagccacccta
gcagcgtcggctctccctggacgtgcggccgcggactgggacttggctttctccggataagcggcg
gcaccggcgtcagcgatg (Seq ID No: 944)

Homo sapiens DEAH (Asp-Glu-Ala-His) box polypeptide 40 (DHX40):
tcgtctttcccctcccatctcctcagatcggtggacgtgctcgcctccactcggggccaggtctat
g (Seq ID No: 945)

*Homo sapiens* importin 4 (IP04): cctcccctttcggcccagtagcggcggctcag-
ttgctgccatg (Seq ID No: 946)

*Homo sapiens* N-acetyltransferase 10 (GCN5-related) (NAT10):
ccttctctttcggagttgttccgtgctcccacgtgcttccccttctccactggctgggatcccccg
ggctcggggcgcagtaataatttttcaccatg (Seq ID No: 947)

*Homo sapiens* lin-28 homolog A (*C. elegans*) (LIN28A):
aaccctttgccttcggacttctccggggccagcagccgcccgaccaggggcccggggccacgggct
cagccgacgaccatg (Seq ID No: 948)

*Homo sapiens* CAP-GLY domain containing linker protein family, member
4 (CLIP4):
cggcctttcctccgcgcccccgcgtccccagccggccgctccgagaggacccggaggaggcaggtg
gctttctagaagatg (Seq ID No: 949)

*Homo sapiens* zinc finger, AN1-type domain 1 (ZFAND1):
ccgcccccttacggcgccggagagatg (Seq ID No: 950)

*Homo sapiens* GTPase, IMAP family member 6 (GIMAP6):
cctcccttttctacttccgaggctgcaaagtgcaacagcagactcttctgactcaggaaggccgg
tgctcctacccacttcctgttcctccatctccagcggacactgctctttcaagggcaggtctccag
cccagctctctgaaaacatttgctgaaaatataagcaaacatcggccttgtcctccttgtgttca
tacactgtggaagcttttctctgcctcctccgtgagagtgcgtggccgggagaccagaaacgtggt
cctttctcttgcctgtgagctggtgcagagatg (Seq ID No: 951)

*Homo sapiens* thioredoxin domain containing 15 (TXNDC15):
cttcctccggctggcagcacgactcgcgtagccgtgcgccgattgcctctcggcctgggcaatg
(Seq ID No: 952)

*Homo sapiens* asparagine-linked glycosylation 9, alpha-1,2-mannosyl
transferase homolog (*S. cerevisiae*) (ALG9):
aattctttttccccaggcttgccatg (Seq ID No: 953)

*Homo sapiens* glutathione S-transferase, C-terminal domain containing
(GSTCD):
acttcccttttttccggtccgccggattatgaatgacggccggcgcgagtattttccacataaggtg
gctgtcgtttttctcctggcgtctgtggaggcgagtggtctgcgggcagcagctcccagaggcagc
cttggaattccagctcggactgggcgggaaggcgcaggcggcccaggtcgccgacacgctcacgca
ccctccctgcctggccgcgcctctgcgaccaggtgacccaatgaaagaagaaaatg
(Seq ID No: 954)

-continued

SEQUENCES:

*Homo sapiens* CXADR-like membrane protein (CLMP):
actccttttttctttccaaacagggaaaagtgttccacgaagcggtagcgcctttccgcctcgcgtt
ttcctccctgaccctggtcccggctcccgtccgggcgccagctggtggggcgagcgccgggagccc
atctgcccccaggggcacggggcgcggggccggctcccgcccggcacatggctgcagccacctcgc
gcgcaccccgaggcgccgcgcccagctcgcccgaggtccgtcggaggcgcccggccgccccggagc
caagcagcagctgagcggggaagcgcccgcgtccggggatcgggatg (Seq ID No: 955)

*Homo sapiens* nonhomologous end-joining factor 1 (NHEJ1):
cctcctcttgcggtggggggaaagcggcctcttactctaggcctttcggtttgcgcgagcgggcag
gaaagcgtgcgtgcggctaagagagtgggcgctctcgcggccgctgacgatg
(Seq ID No: 956)

*Homo sapiens* gametogenetin binding protein 2 (GGNBP2):
cctccttcttccactccccgcggcgcgagcggctgactgcccgtagaggaaacgacattcggagct
gcgctcccgcccaggccggccctgacgcgggcctcgtcagccagtaacagggagcagaggtgggag
ttagcgaggcgaccacgaaaacggtgaaggtcggaaccgacagcctcctccgagaagggcaggagc
tgggaggaggcggcagcggcggcggcagaaacagcagcggcggcggcggcggcagctgggaggagg
tggtgacggtggcaacggcagcgtcggggacgatg (Seq ID No: 957)

*Homo sapiens* zinc finger protein 672 (ZNF672):
ctttctcttttagccccgcctgcttcccggctccagctggggccggagaggctgagtggttggtac
gctgctcgctggcctcccagtcttcccagcaaccggtgacactgcccgcgccagactgaccactag
ccgacgcgggcgagagggacaggagcgtgacctccccatcccgagggggccggacgctcgggcgcct
ccccgctcccccactcggaggccgcgcgcgccgttagccccttcctcgctcccccgccccagtcc
cgcagtccgggaggcgggggtcggcagccggctgagtgggaaccgcgcggtgtctgaggaggcagt
cggcgaccggtttccacttcaagcgtgacccttttgcctgtgggatgagctccagcatggggtgag
gtacagaagagagagacttgaagagcgtgccttgggactcaagcgccaaacctgtaccctagcgagtg
tcctactccgcatccgtaatggaaggaaatgcacatcttactccagaggcacaagaggaggacatc
ccatgcggctactcctgcccagcgtggtggggcagcagaagctccagagcccagacttgcaggctc
acggtgcagggtgaacctggccacagctcaccctggaacagccacaatgtctgccccttagagaag
aaccctgaaatcagaccagtttttgcggcctcccccttcctctctgttacagtgccctttccagg
ccttaagagaagtaaaacttagctgcagcgccaggaggtggaccccagagtgtgagtggcacgctt
ccctgtgaacccgtcctcaccatg (Seq ID No: 958)

*Homo sapiens* N(alpha)-acetyltransferase 60, NatF catalytic subunit (NAA60):
ccgcctccgtcccggctgcggcccctgccggttacataactcgttgcgggctccgcgcggtcccac
ttcccggctcccttcgcctccaggatgcgctgagccctacaacaccccccagcggccgccggctccc
ccacgaggtgtgaatg (Seq ID No: 959)

*Homo sapiens* transcription elongation factor A (SII)-like 4 (TCEAL4):
tgccctctgtccccgcggctgggtctcgtctgctccggttcctgggctcctaattcttggtccagc
ttcttccaggtcagtgtgcgggccttccacgctgccagcggaacactggaatggcggaaggggaac
gggtctgcgcgtctgttgttcccagcgctctgcgaagcctgaaaaggaggagcaacctgtccagaa
tccccgcaggacaggaaaaggagggga aatctcgacatg (Seq ID No: 960)

*Homo sapiens* progestin and adipoQ receptor family member VI (PAQR6):
tccccttgtctccccactccccgcccaggcctggcccgcctgcctggccactcttcctccatcag
cctggctggcagcagccttggactccgcccgtggagccctgggcctgttgacccaccagcttagga
gcacccaccaagctctgggtaaggaagctcaccttctggggctcttctgggaaaatagaggtcaac
gtggaggtaccaggccaccatgctcagtctcaagctgccccaacttcttcaagtccaccaggtccc
ccgggtgttctgggaagatggcatcatgtctggctaccgccgccccaccagctcggctttggactg
tgtcctcagctccttccagatgaccaacgagacggtcaacatctggactcacttcctgcccacctg
gtgaggggaggctctgccccaggccgcggccttgagctcagaggggtacccaggcgggcagggac
cgtccaggcccacgggctgcagcggcagtcgcggggggtccgcggcggcctgagcacgcgcccgccg
caggtacttcctgtggcggctcctggcgctggcgggcggccccggcttccgtgcggagccgtacca
ctggccgctgctggtcttcctgctgcccgcctgcctctaccccttcgcgtcgtgctgcgcgcacac
cttcagctccatg (Seq ID No: 961)

*Homo sapiens* DENN/MADD domain containing 2D (DENND2D):
catccttcttgctcaaccactgggtgcacaggatggaaacttctattccctctctggaagacagcg
cgtggcttggcttcacagagttgtggctggagaccgaagcagcccctttctcaggcttactgtcac
cagtctgtctgtgttaggggagaggggagtccgctctgtcctgaaggcccagagatg
(Seq ID No: 962)

*Homo sapiens* family with sequence similarity 188, member A (FAM188A):
ccttcttctttcctgcctcaccttccaattcgtttgccgccgccgtcccgcagctgctgtttccgg
agttgccccttccccatgttccggggcaggagtccgcaaagcgaagatccgcccgccggttcctca
tcatg (Seq ID No: 963)

*Homo sapiens* neurensin 2 (NRSN2):
ccgcctttgctcggcggagacagcaggcagagagatgaggaaactgagacccagaaaggtggaagc
acttgtctaaggtcacgcctccaggaagcagtgtgtccacgactccagtccaagtggtcaggctcc
agagcccacagtcccaggggtccatg (Seq ID No: 964)

-continued

SEQUENCES:

*Homo sapiens* tripartite motif containing 46 (TRIM46):
agccctcctcacacccccactgggctcctgcattaagcccggggttcgcagccgcagccgggatcg
ggcacccaggggcgggcgggcacggtagggccatg (Seq ID No: 965)

*Homo sapiens* target of EGR1, member 1 (nuclear) (TOE1):
catcctctctgggaatttaccgatgcccagaacgcccttctttcccccacacgaccctctcctagt
ctaactcctgggcgtgctttaagctcagctcaggcagcgtcaccttctctggaaagcccaaaccca
gccaccccactacccgctacccgcggcccacgctgatgaagacagcagaacacggaggccccgcgt
tcccgccgcgagagcaggagagaaagattacctcccgcgagctctagcgcgcccggctttccggcg
cactccaggggggcgtggctcgggtccacccgggctgcgagccggcagcacaggccaataggcaatt
agcgcgcgccaggctgccttccccgcgccggacccgggacgtctgaacggaagttcgacccatcgg
cgacccgacggcgagaccccgccccatccccgactgcctgaaccgcgccaggagacggaccgcaag
tccagcgtacccacagacgactcaggcgggagacgagcggtgtcatg (Seq ID No: 966)

*Homo sapiens* DBF4 homolog B (*S. cerevisiae*) (DBF4B):
cgttcttttaggggtggagccggcaggaaatttaaactgaagccgcggccgaaaacgccaagagat
tgatgctgtagctgccctgagataaccaggactgtggaatcgggaagagctcatggagctcgcgaa
tgtaatacggaggcctctgaggaaggagtacggaggccgagaaggagccggcatttgatg
(Seq ID No: 967)

*Homo sapiens* myc target 1 (MYCT1): atttccttttatg (Seq ID No: 968)

*Homo sapiens* myosin XIX (MY019):
ggttcctttcctcactgcacgctcttgcccctcctcttttctctcctgcccgtgttcttcccgccg
cctgacctggcccgcccgcctttccagtctggccgggcgggggcctgaagcacggcggctcgggcc
gtgggaccgtgttcacaccctttccagaaattcttggctggtaaccgcgaaaccgactggagcagg
agctgggagaactggagaaaactgctctaatctcacttgactccagctaggagctgatgctgcatc
gtaataacatttgcagagcgctttcacaggcgctggagtgacttgtctgagattcctccagaactg
agccctttgttggaaccataccccagcccatggtcccatgactaggtggatagtactccttgtacc
tcctgcaacccagaaccctggctgaccactttgaaggaggatg (Seq ID No: 969)

*Homo sapiens* KIAA0226-like (KIAA0226L):
cctccccttctgctgttaccgggagcgcggtggccacggaacgctgcccggagccgcgcgaggga
ggacccgacgcgcggcgtttacccagcgcagcgttccaccgctcgggtttggctggataaaataaa
aaatggggatattgacctcctgtcactactgcatggactttgatggtttccaatcattactttctc
ctctgtgtcaatctgcctcttcgagaaattcatactcctgaatagctctccagacccccagctggc
catgtggtgagttcagggcccaaatcaagtagtaccagcaatcagggaactcctatctgttttgaa
tggattcacaccagccacaagcctggaaagatg (Seq ID No: 970)

*Homo sapiens* MUS81 endonuclease homolog (*S. cerevisiae*) (MUS81):
ctccctcttcccccgccccgccctgggccaggtgttcgaatcccgactccagaactggcggcgtcc
cagtcccgcgggcgtggagcgccggaggacccgccctcggctcatg (Seq ID No: 971)

*Homo sapiens* zinc finger protein 430 (ZNF430):
gggcctttgtccctcgctgtggcctgagctccaggtctcgtcttcagcgctctgtgtcctctgctc
ctagaggtccaggctctgtggccctgtgacccgcaggtattgggagatctacagctaagacgccag
gaacccctggaagcctagaaatg (Seq ID No: 972)

*Homo sapiens* mutS homolog 5 (*E. coli*) (MSH5):
gctccttttgcaggctcgtggcggtcggtcagcggggcgttctcccacctgtagcgactcaggtta
ctgaaaaggcgggaaaacgctgcgatggcggcagctgggggaggaggaagataagcgcgtgaggct
ggggtcctggcgcgtggttggcagaggcagagacataagacgtgcacgactcgccccacagggccc
tcagacccctccttccaaaggagcctccaagctcatg (Seq ID No: 973)

*Homo sapiens* proline rich 3 (PRR3): gcccccttcctcac-
taccctccaaatcccgctgcagccattgccgcagacacgatg (Seq ID No: 974)

*Homo sapiens* sirtuin 2 (SIRT2):
cgcccctttaccaacatggctgctgacgccacgccttctgggactcgtagtccggtcctcgcgcgct
ttcttacctaactggggcgctctgggtgttgtacgaaagcgcgtctgcggccgcaatgtctgctga
gagttgtagttctgtgccctatcacggccactcccatttctggtgccgtcacgggacagagcagtc
ggtgacaggacagagcagtcggtgacgggacacagtggttggtgacgggacagagcggtcggtgac
agcctcaagggcttcagcaccgcgcccatggcagagccagaccgactcagattcagactctgaggg
aggagccgctggtggagaagcagacatg (Seq ID No: 975)

*Homo sapiens* KIAA1715 (KIAA1715):
ttgtctctctgtcagtggcggctgctgcctgctctggaggcaggctgggcggtggcggccgagact
ggcgggggtggacgcccgggccgggctgcgcccgcttcttgcagctgtgaattcctttggacaatt
gatgatatttatcattgtgcccagtttctacaaataaaagatg (Seq ID No: 976)

*Homo sapiens* proline-rich transmembrane protein 1 (PRRT1):
ctgccttcatctctccatctctgcgctgctgccggctgcgccatccagcacccagactccagcacc
ggccgaggacccccactccggctgcagggaccctgtcccagcgagaccgcaggcatg
(Seq ID No: 977)

-continued

SEQUENCES:

*Homo sapiens* t-complex 1 (TCP1):
ccgccccttccccggagcctcacttccgtcacagtcctgtttctctccctgttgtccctgcctctt
tttccttcccgccgtgccccgcggccgggccggggcagccgggaagcgggtggggtggtgtgttac
ccagtagctcctgggacatcgctcgggtacgctccacgccgtcgcagccactgctgtggtcgccgg
tcggccgaggggccgcgatactggttgcccgcggtgtaagcagaattcgacgtgtatcgctgccgt
caagatg (Seq ID No: 978)

*Homo sapiens* Yipl domain family, member 5 (YIPF5):
cgttctttggccctgtgacacgtagcaacggggctggttcagggtctgaaacagagtttgggggtt
gtttgggattagtgaagctactgcctttgccgccagcgcagcctcagagtttgattatttgcaatg
(Seq ID No: 979)

*Homo sapiens* glucose-fructose oxidoreductase domain containing 2
(GFOD2):
cctccctttccagagcccccagttccttagaaaccaggcggcgcgttcccggtggcggcgccctgg
actcccgggcccgcgcatccccgccagccttccttaaggcggatgggtggcccccgagaccccgtc
ggacccatggtttccagtgcagcgcggagtgggcgatgccagcgtgccaggagccatgtctgacca
ggacgtttggaagatcatatccatgccagaggctcttgtgaggagatgagttggtaaagagagagg
ctgggatg (Seq ID No: 980)

*Homo sapiens* apolipoprotein L, 2 (APOL2):
ttccctttcgaattccagggtatatctgggaggccggaggacgtgtctggttattacacagatgca
cagctggacgtgggatccacacagctcagaacagttggatcttgctcagtctctgtcagaggaaga
tcccttggacaagaggaccctgccttggtgtgagagtgagggaagaggaagctggaacgagggtta
aggaaaaccttccagtctggacagtgactggagagctccaaggaaagcccctcggtaacccagccg
ctggcaccatg (Seq ID No: 981)

*Homo sapiens* microtubule-associated protein 4 (MAP4):
ccgcctccctgcgccccgcccctccggctagctcgctggctcccggctcctcccgacgtctcctac
ctcctcacggctcttcccggcgctctcctggctcccttctgccccagctccgtctcggcggcggcg
ggcagttgcagtggtgcagaatg (Seq ID No: 982)

*Homo sapiens* exonuclease NEF-sp (LOC81691): cttccttctttgccaggca-
gacgcccgttgtagccgttggggaaccgttgagaatccgccatg (Seq ID No: 983)

*Homo sapiens* ST6 (al-
pha-N-acetyl-neuraminyl-2,3-beta-galactosyl-1,3)-N-acetylgalactosaminide
alpha-2,6-sialyltransferase 5 (ST6GALNAC5):
ctgtctctaatctctgcaacagccgcgcttcccgggtcccgcggctcccgcgcgcgatctgccgcg
gccggctgctgggcaaaaatcagagccgcctccgccccattacccatcatggaaaccctccaggaa
aaagtggccccggacgcgcgagcctgaggattctgcacaaaagaggtgcccaaaatg
(Seq ID No: 984)

*Homo sapiens* heterogeneous nuclear ribonucleoprotein A1 (HNRNPA1):
tgctcctttctgcccgtggacgccgccgaagaagcatcgttaaagtctctcttcaccctgccgtca
tg (Seq ID No: 985)

*Homo sapiens* zinc finger protein 93 (ZNF93):
gggtcctttgtctctcggtgcagccggagctccaggtctcctcttcactactctgtgtcctgtgct
cctacaggcccagcctctgtggccctgtgacctgcaggtattgggagatccacagctaagacacca
ggacccctggaagcctagaaatg (Seq ID No: 986)

*Homo sapiens* N-terminal EF-hand calcium binding protein 3 (NE-
CAB3):
cggcctctagccacaccgagtccgccgcggcgtccagggtcggcagcaaccgcagccgagcccgag
cgggtggcggcgccatg (Seq ID No: 987)

*Homo sapiens* splicing factor 3b, subunit 5, 10 kDa (SF3B5):
cattcttctgcgacggcgcggacctggagcttccgcgcggtggcttcactctcctgtaaaacgcta
gagcggcgagttgttacctgcgtcctctgacctgagagcgaaggggaaagcggcgagatg
(Seq ID No: 988)

*Homo sapiens* INO80 complex subunit B (INO80B): gtcccctttcctcgcag-
gacctcatg (Seq ID No: 989)

*Homo sapiens* polyamine modulated factor 1 binding protein 1
(PMFBP1):
ctttcttcctcttggcttatattagggataggggatgtggtttgttacaaaggatgagtattttga
tagcttctcattccttgaactattctgcaggtttataacaaagctcagaaaatactaaaggttaaa
ggagaattgagagctgccaaggaaatg (Seq ID No: 990)

*Homo sapiens* pseudouridylate synthase 3 (PUS3):
cttcctttctcggaaacgcggcgcggccggctgccggaaaacagggcagacctgtatggttcgttt
attcctggggttgtcatatcatg (Seq ID No: 991)

-continued

SEQUENCES:

*Homo sapiens* heterogeneous nuclear ribonucleoprotein D (AU-rich element RNA binding protein 1, 37 kDa) (HNRNPD):
tattctttttagtgcagcgggagagagcgggagtgtgcgccgcgcgagagtgggaggcgaaggggg
gcaggccagggagaggcgcaggagcctttgcagccacgcgcgcgccttccctgtcttgtgtgcttc
gcgaggtagagcgggcgcgcggcagcggcggggattactttgctgctagtttcggttcgcggcagc
ggcgggtgtagtctcggcggcagcggcggagacactagcactatg (Seq ID No: 992)

*Homo sapiens* GABA(A) receptor-associated protein like 1 (GABARAPL1):
atttctccatctggctctcctctacctccaggcaggctcacccgagatccccgccccgaaccccccc
ctgcacactcggcccagcgctgttgcccccggagcggacgtttctgcagctattctgagcacacct
tgacgtcggctgagggagcgggacagggtcagcggcgaaggaggcaggccccgcgcggggatctcg
gaagccctgcggtgcatcatg (Seq ID No: 993)

*Homo sapiens* chromosome 22 open reading frame 13 (C22orf13):
ccttcctttccccagtgttgagcgcggtctcgcctccgcttcctcctcactccgcctgccggctgg
gaaactagggcaccagtacgatagttccggcaccggaaaagagggctgatgactgggcccgggggc
cgccgcaacgacccttggggccggcaaagagccagagagggtgctcacacttccaagcaccccaca
ccaaggacaggctggacggcaaggcggagacgcggggcttgggccctcagaccggggacagcagga
ggttgggccaagggccaggacttcccgtcacaatttcatttgttgatcccggcaccgccaggtaag
gggggccctgagtgaggctaggtatctggtacggataaagttaggtatagagtagagcggctgccc
gctcagggttatccctaaagacagttggaggagagttgcttggggcctcggggatgcactgggcgg
gatcagggcttacacctaggactggcaaaagagcgggacccggcagaggcggggcttgccgaaggg
acgagcctctattcaggaaatgcacgagctttggggcggggctcaaagaaaggggcggggcttccg
gggcccgcgtcctggtgagctgcgcgtctgcgcgaggattgggcgagagggtggggccactcaacg
ctgaggcggcgaatggccggagcagacttaaatcaagaggctggggacctctaagatcaaagtttg
gggcggggcctaaggagggggcggggcctccagattcgagacctggaagggctggggcggcgcttg
gggcggccctgccgccgcctcccgttctcccctccgcagcggcggcggtggcggagaaggaactcg
acacgcaccgaccgccctcccgccccagccgaagcggaagctgtagcccgctctgggccggggcca
tgggcgccccgcgccgcccgggtcatg (Seq ID No: 994)

*Homo sapiens* Ion peptidase 2, peroxisomal (LONP2):
ggctctttttgacagcccccagtgcgaaaggctgccagcatg (Seq ID No: 995)

*Homo sapiens* RNA binding motif protein 4B (RBM4B):
ggttctctctgacgtgggagccgccgtcgctgccgccacccggaggctcttgtcaggatg
(Seq ID No: 996)

*Homo sapiens* protocadherin alpha 3 (PCDHA3):
aggtctttctccacaaaagaaataacagcgtgcattacgtattcagatactgctttgcttcatcct
ctctaaaatttaacaccgaggagtttaagaaatgaagataaggaactcgaattatttttaaacttt
ggatcaatgtaaaggcaatctaatatttggaaaatacttgcaatg (Seq ID No: 997)

*Homo sapiens* RAB34, member RAS oncogene family (RAB34):
gcctctccttgggcccccttctctccccctttcccctccctgctggttcctggcatcgccagatgct
gcgcagcagtctccgattccccatcaccaattcggctggcgtctccgagaccgcggactcccgtag
ggtccccgtggccccgagttgtagtcgggacacccggccgcgggtgatcgtcgggtctccacgcg
cccgggtcgctgacgcggatccggcctcggcgccttctcagggcgccctgcaaggccgcaggcagg
atg (Seq ID No: 998)

*Homo sapiens* cell division cycle associated 7 (CDCA7):
gctcctcctgctgtgggaccgctgaccgcgcggctgctccgctctccccgctccaagcgccgatct
gggcacccgccaccagcatg (Seq ID No: 999)

*Homo sapiens* ArfGAP with GTPase domain, ankyrin repeat and PH domain 3 (AGAP3):
gggtcttttaggagagcactgctgcagccggcagtggagagcctgggcagggagacagggagaaaa
ctccggcagcagggtggtctctagggctgacctcggagcctggggacaggggagcctatgccgcac
tgaaggcgggacgctgtaagcgaggagcagctgggcctgggcggactcctcggccaatcagcctcg
gtcagcagcaccctcaggcgcagggcactgtttgggcattgcctagagatccgacaccccgcccag
atcagcgcagggaggcgaaagcgacagccgggcgcgggaggagaccagggcagctgtcccctccgc
gagggtggccctcgaggcaatgcgggtgggggctggtgaggaggcggaagggccgaggctgagtgg
gaggggccggggcgccagggctggagcgcgcggctcgggggtggaggctgcagagccagcgagcga
gcgaggggcgggggcgcccgggccggcgcgcaggaggggcgggggcggcggggagggggctcggg
ctgcgtgtgccggagccggcgggggcggcggtgcgtgcgcatgacgcgggggagggcctgggccg
cgcgctcccggtcccgttgttgttgccgctggaggctgctccgaggcagcgggatcacggcgctgg
gaagcgctcggcagcggcggccacagcgtgcgcggcggcgcctcctggcctcggcctccggccccc
ggcccccggctccatgcgctagccccgcgccgccagcccagtagtcccggccccgccagccccgcg
ctcccgctcgccgctgccgccgccgccgccgccgccgcctccgccgcgccgccccgggcccgcctc
gggccccacggctccgaagccatg (Seq ID No: 1000)

*Homo sapiens* potassium channel tetramerisation domain containing 10 (KCTD10): ctgcctctctcagtccgggtttggagactcctgcgtcctccgacttttcatg
(Seq ID No: 1001)

-continued

| SEQUENCES: |
| --- |

*Homo sapiens* cyclin B1 (CCNB1):
cattctctgcgaccggcagccgccaatgggaagggagtgagtgccacgaacaggccaataaggagg
gagcagtgcggggtttaaatctgaggctaggctggctcttctcggcgtgctgcggcggaacggctg
ttggtttctgctgggtgtaggtccttggctggtcgggcctccggtgttctgcttctccccgctgag
ctgctgcctggtgaagaggaagccatg (Seq ID No: 1002)

*Homo sapiens* eukaryotic translation initiation factor 2A, 65 kDa
(EIF2A): gtttctctttccgggacaacatg (Seq ID No: 1003)

*Homo sapiens* protocadherin gamma subfamily B, 7 (PCDHGB7):
cagcctctagcctgggattccctgcgcagccaacaacagaaaagaaaaccagctcccacacagagg
ctcccggctgcgcagaccttgcccagcacaccagattgccagctccgagacccgggactcctcctg
tcctgggccgaatgctcttttagcgcggtagagtgcactttctccaactggaaaagcggggaccca
gcgagaacccgagcgaacgatg (Seq ID No: 1004)

*Homo sapiens* acyl-CoA dehydrogenase family, member 11 (ACAD11):
ggctctttcggcttccttcctcgctgggccggctaaacccggccgcagcagcaccggggtgataag
tgtccagggcaggaggccagcgatgttgccttgctaaccgggtatctaagagaaacagggtctttt
tattcttaggctcgacagtctgacggcccttttctgaacgggaccctgcaggtcttccgcctgct
gttgcattaaatttgggggtggaagaggcttctgcgttgttccttacccgcaacgatgaccatggc
tttgccttctttaaaattgaggcctccaactctgacgctgactggagaattgaaacccgaacacac
attgggctcttttggcacttgactagagctaaaacctcgggattcagcgggcaagcgttgctcagc
aacggcgcgtaggctgtgtgcggttggctggagccagaccccaccccggcctcggcccatgctcta
gaggggacgttgccccaatcctgaaggacttcggcactcgagacctgtggatgccgcgttgctgtg
gcctgcgggggtgatcatg (Seq ID No: 1005)

*Homo sapiens* zinc finger, CCHC domain containing 7 (ZCCHC7):
ccgtccctctacgcgttttggttcccggttggtgcttcctgttcgcagctgcggcacttcaaggtt
actgactttttatg (Seq ID No: 1006)

*Homo sapiens* zinc finger, MYND-type containing 12 (ZMYND12):
gggcctttctggacttggactccttgggagtcgtttctcggccatttgacccgtgggacttgtggg
ttttgtgctgcttttcttcttcttccccttttccaacttcagcaatacacccagatgttagtc
gagtcacgtcccgccgccctctgcccttgaaatgctggcaagtacgcagccccgcgatcgtcacgt
gacgccggggttcagcgtatccttgctgggcaaccgtcttagagaccagcactgctggctgcacca
tg (Seq ID No: 1007)

*Homo sapiens* forty-two-three domain containing 1 (FYTTD1):
cgctccctcggtgcggcgggctgcgtgcgcgagtgggaggtggcaggcctgcgactccggccttgt
ccgcgcccgctctcggcgcgacgtctccagccatg (Seq ID No: 1008)

*Homo sapiens* SH3-domain GRB2-like (endo-
philin) interacting protein 1 (SGIP1):
ctccctttctctcagcatcttcttggtagcctgcctgtaggtgaagaagcaccagcagcatccatg
gcctgtcttttggcttaacacttatctcctttggctttgacagcggacggaatagacctcagcagc
ggcgtggtgaggacttagctgggacctggaatcgtatcctcctgtgttttttcagactccttggaa
attaaggaatgcaattctgccaccatg (Seq ID No: 1009)

*Homo sapiens* GTPase activating Rap/RanGAP domain-like 3 (GARNL3):
cagccctttttgcaaatg (Seq ID No: 1010)

*Homo sapiens* DCN1, defective in cullin neddylation 1, domain containing
5 (*S. cerevisiae*) (DCUN1D5):
gagcctcttgcttgctgtgactggtggagctgccgcgctgtccgcgttatctcctcccggtgagaa
cgaaccgcagtgtccaccggcgaggagccagccctgtcccggtcagagaaagacgacgaggatacc
tgggagcgggcggcggccgggctgggccgcgccggtgcgggctggcgactctgctcctccgcttgc
tgctgtctctgggaactgggtgccagcgctgaggggcttccagcggacagggacccccttccccgg
ctcccctgcccaccctgccggggagggcggaagatg (Seq ID No: 1011)

*Homo sapiens* alkB, alkylation repair homolog 7 (*E. coli*) (ALKBH7):
tgccctctctcatgaccccgctccgggattatg (Seq ID No: 1012)

*Homo sapiens* nitric oxide associated 1 (NOA1):
ccgcccctttggagctacttcctcatg (Seq ID No: 1013)

*Homo sapiens* BTB (POZ) domain containing 10 (BTBD10):
tcgcctcttcgcattgtgagctctcgcggtaagaggctgaggagccggcctgcaacctgccggggc
ggctccgctacgcgcagccgcctcagtggcttcctccacagccacctccggagggatctggctgag
gaggaagtggaggtgtcactggccccggcctttgccccaatcttgtgtgggcactgaagggggact
acaggttcgagagttatgggtgctacatgtgtgctttcagagcagtagtgtgaggaagcttggagt
gggatg (Seq ID No: 1014)

*Homo sapiens* zinc finger protein 397 (ZNF397):
cggtctttgtggcttgcagctcggggtgggtggctcatttcctggccgctcctgggcttcgcggaa
agaagagattactcacactccttcgcaagcacagaaccagttgtactgagctttttgctaagctgt
ttcagccaagaatg (Seq ID No: 1015)

-continued

SEQUENCES:

*Homo sapiens* mitochondrial ribosomal protein L45 (MRPL45):
gctcccttcccggcggcctttgcgggaacaagatg (Seq ID No: 1016)

*Homo sapiens* AKT1 substrate 1 (proline-rich) (AKT1S1):
cttccttctccatattgtatactggaattgaagccaaggaggtaccattttgctcgagggcatggc
ctaagccggtcagctaaggccatgttaatacggggctgtcccatctctctgcggggcgcgacagct
ggaagagccgaacggataagagaagaggaggtgagaggagctgtacaccacaagaggcactgaggg
actcaggataacgggatgaagccgtcagtgcccccagaaacgaagcggccccggacgaatttctga
gtcaccgtcgcgagaaagcgggctgagccgccattttgaagcctggcaaaccgaagcaagaaatgc
tgccgtgttggatctttgccagccttcgtgccgaatgggagcaggttggagggagggagagccaat
atacactatgggctgattaagcccggttggctgccatgttgttaacgagcaccgatttcctctact
tttgtcgaagaagtttattgtgggtcagggacgtcaggtcgcttgccttcgtttactgtggtcatg
attgagcatatgaggacggccattattgttggggggcaaatggaaatgctctaggcggggccatttt
tcttaggggcaagctgtcgtcacccttgtcaactggttcggatgaagcccctgtggccgccatctt
gatctcgggcggccccgataagggaggcggagtgtgcggagaggaggcggggcaactgcgcggacg
tgacgcaaggcgccgccatgtcttttgagggcggtgacggcgccgggccggccatgctggctacgg
gcacggcgcggatg (Seq ID No: 1017)

*Homo sapiens* transmembrane protein 101 (TMEM101): ctgccctttcccaa-
gatg (Seq ID No: 1018)

*Homo sapiens* eukaryotic translation elongation factor 1 delta
(guanine nucleotide exchange protein) (EEF1D):
ggccctccctttcatcagtcttcccgcgtccgccgattcctcctccttggtcgccgcgtccttggc
tggcgttagagacagggtttcaacgtgttagccaggatggtctcagtctccagaccctgtgatccg
cccgcctcggcctcccaaagtgttgggattacaggtgtgagccaccgtgcctggccgaggctcctt
cttttatg (Seq ID No: 1019)

*Homo sapiens* ADP-ribosylation factor GTPase activating protein 2
(ARFGAP2):
cgccctccccgccgtggattggcccgcggcgggacccgtcagccgcggttgtgtctgggaaggaga
gaaaatg (Seq ID No: 1020)

*Homo sapiens* junctophilin 4 (JPH4):
atttctctcctccctggggggtctcagtgcatctccttctcctctctgcctgcctcctccctcaccg
aagggttagcggacacccatccttttctgcttggggaccccaccaccacccgcaacactgccgctg
tctcttcttcaccgtatccttctctacccaccctcttctctcttctcttctccctgccccttttaaa
tctgcctggcccagcctcccccgtgatgctgggatggagcaaacattgatttgtgctgggatggaa
tcggaattttgatttatttttcctctcccaaccataagaagaaaaaaataataaaaacaccccctc
ttgagagccccctccccctttgcatccagctcccagctcttcttccctatctccatccaaggcaga
ttttttcccctacactattctcatcttcccccacccttgccactacctcgcccccccacccagcct
gctcctccagctggggagagaggggactctccggactcccccacctttcctctctgggttggagca
gtctctccggaaggggagggggcttggcttgtccgggcgaggtgggagtggaggtatcctgccatg
gatgctgtgccggggaggcagcctgagccccagcccacatgagacgccgaagaaccggggcagagg
ggtcctgacagcagccagggaaacgggtgccctacgattctgcccagcccccctctcaggaccccca
aactgccatccacactcgacacttcggggttctagccactcaggatgagggtccggccctgcctgc
cctcgctggggccccccgcccggccccggtctaactgcccccgccccgaggcctcgcccggctcc
aaggcccccagcaggctctccagtcccaggatgcgctgagccgccggggggctgaggccgcgccaa
ctacatgcatg (Seq ID No: 1021)

*Homo sapiens* embryonal Fyn-associated substrate (EFS):
tttctttctcctcctccaaccttggcggaggccacgactcaggcgccacagctgggggctagagg
ccgcggaccatggtgcggggcagccaccgctgaagtcagcaaaaccgagcctggcctgaggcaggc
tgcgcgggaggccaaagccatg (Seq ID No: 1022)

*Homo sapiens* GH3 domain containing (GHDC):
cgctccttctttctggccggatgtgtgctgagacccagagtcacccaggggtctccgtcacgtgcc
aggagtaggcagaagtgggctgtgacagatcaggaaacagagctcagtgcagcccactaaattgct
cagggccctacagctaacaagcggcagaggcaggatctgcactcaggagctgcttggagatg
(Seq ID No: 1023)

*Homo sapiens* acrosin binding protein (ACRBP):
ggctctctctgcggcttggcccgttagaggcggcttgtgtccacgggacgcgggcggatcttctcc
ggccatg (Seq ID No: 1024)

*Homo sapiens* jagunal homolog 1 (*Drosophila*) (JAGN1):
agttctcttcacggagccgcgcggctgcgggggcgcaaatagggtcagtgggccgcttggcggtgt
cgttgcggtaccaggtccgcgtgaggggttcgggggttctgggcaggcacaatg
(Seq ID No: 1025)

*Homo sapiens* ligand of numb-protein XI, E3 ubiquitin protein ligase
(LNX1):
gttcctttcctgggcatcagcttgcctgctctcagcctaagctctctcgccaaccgtggtggctcc
ttgcgttcctacatcctctcatctgagaatcagagagcataatcttcttacgggcccgtgatttat
taacgtggcttaatctgaaggttctcagtcaaattctttgtgatctactgattgtgggggcatggc
aaggtttgcttaaaggagcttggctggtttgggcccttgtagctgacagaaggtggccagggagaa
ggcagcacactgctcggagaatg (Seq ID No: 1026)

-continued

SEQUENCES:

*Homo sapiens* cyclin-dependent kinase 2 interacting protein (CINP): tctccttctacggatatctgtggaccttatg (Seq ID No: 1027)

*Homo sapiens* splA/ryanodine receptor domain and SOCS box containing 2 (SPSB2): gcttctttccgcccggctccttcagaggcccggcgacctccagggctgggaagtcaaccgagctcc cttccaggtcaatccaaactggagctcaactttcagaagagaaagacgccccagcaagcctctttc ggggagtcctctagctcctcacctccatg (Seq ID No: 1028)

*Homo sapiens* Berardinelli-Seip congenital lipodystrophy 2 (seipin) (BSCL2): cctcctcctttcctccctctactctgacacagcacttagcacctgaatcttcgtttctctcccagg gaccctccatttccatatccaggaaaatgtgatgcgccacaggtatcagcgtctggatcgccact tcacgttttagccacaagtgactcagtggaagatccagagtcaacagaggctcgtcaggaagatg (Seq ID No: 1029)

*Homo sapiens* tubulin, alpha 1c (TUBA1C): cacccttcactacttctcccccggactccttggtagtctgttagtgggagatccttgttgccgtc ccttcgcctccttcaccgccgcagaccccttcaagttctagtcatg (Seq ID No: 1030)

Homo sapiens 1-acylglycerol-3-phosphate O-acyltransferase 9 (AG-PAT9): tttccttcctctcttcccttcgcagaggtgagtgccgggctcggcgctctgctcctggagctcccg cgggactgcctggggacagggactgctgtggcgctcggccctccactgcggacctctcctgagtgg gtgcgccgagtcatg (Seq ID No: 1031)

*Homo sapiens* 1-acylglycerol-3-phosphate O-acyltransferase 1 (lyso-phosphatidic acid acyltransferase, alpha) (AGPAT1): gcccctttctttccttcgcttcctcttttagagaatgtccggattgctattggactttggagcgta tggctccaaatcaactcattggctaaaacttgacggaaaatggtggttaggtggccagaatg (Seq ID No: 1032)

*Homo sapiens* abhydrolase domain containing 14B (ABHD14B): cggcctcttcccagcgttcctcctccggccccaggtcaccgccagcacgcgcctgcttcccgtctg cgcgagtccacgcagctccccagatcaagaagctgaggccccaggttacacactaaagtaaatggc agaggcagaaataacacctatgtcctcctgaccccaaggcatgttcttaaagttctggaaacctcc tggaggcttccttgctgctcctctgggactgccaccctgggcagggtgttctgtggcccctcatca tcgtggttttgaaccacaggcccttcaccagcacagcagcagcaggcatg (Seq ID No: 1033)

*Homo sapiens* protein tyrosine phosphatase, non-receptor type 5 (striatum-enriched) (PTPN5): catcctcccgccagcctgcccgcctgctcgccggcgcccggagcccgctctggccgcttgcttttt gctgagaaagcttcctgccctggaagatggcacccttccccatccagacaccttgggaatg (Seq ID No: 1034)

*Homo sapiens* carbonyl reductase 4 (CBR4): cttcctccttttcacggcgtcttgcattactattgtgcggctgcaggaggtgtcgagcggcgttat tttttttgcggtttgcctttttttttctttttttttttttggaaccgcggttgtttaaaagcct gagggaacctggagaggggctcccactccctaccctctttcctccgagtttgtgactccgagatg (Seq ID No: 1035)

*Homo sapiens* zinc finger CCCH-type containing 10 (ZC3H10): ggctctttgtcgaagctagaggaccggcaggcggcagcagcaactacggcggcggcggcagaaccc agcagcgatgtggaggtggagacccacaggagccccggacttcacctgagctacctcagtggtcac caagagtggcaagataaagaaaaccctgagttgggcgggaccaggatg (Seq ID No: 1036)

*Homo sapiens* poly (ADP-ribose) polymerase family, member 10 (PARP10): ccgtctttcagtttcacttttgttttcctgctcccagcagggttaggcttgctgaggggcaggcac aggagtcctggctgagctcatggcctgaggctgcctagcggccacggggaatg (Seq ID No: 1037)

*Homo sapiens* RNA pseudouridylate synthase domain containing 4 (RPUSD4): ccgcccttccttgtaagatg (Seq ID No: 1038)

*Homo sapiens* family with sequence similarity 73, member B (FAM73B): ctgcccttccgcagcgatggcatcccgggtgagtatcggccccggccgagcccccaaggcgggcgg gcagcgcggcagggccgggacttgagcggaggaccgagtaggcgcaggtgtccgggcccaacagga ccaggaaggtgtcggggttggaatgagtgggtacccgggccggggacggtgcgagagggtgccttg cttgggagcggaacgagaaggtacttgggtcagggaggtgatgcccgggcctggaacgtggcgggg attggagcaggcgcgcaggtacccgatccgaggcggggagagcacccgggatggaaggagcaggcg tgcgggccgtgagcggcgccagagggtacctggctctgtggaggggccctctggtatgtgtgtccc tgtccttctggggcgtggatggtgcctgggacccagctggcaaccagttgaagacgttctccttgg aagctcttggccctgaggactttgcctggggcattggccctgccatg (Seq ID No: 1039)

-continued

SEQUENCES:

*Homo sapiens* protein phosphatase 1, regulatory subunit 15B (PPP1R15B):
gcgtctcttccggcgtctagggggtgtcctgccggcgcgcgggccctgcggccattttgggcttc
gcttccaccgcaccagccggcctacccagtccttccggtatcgcgttgctcaggggcttttcaacc
ctctgtcagtcggaaaaccatcgccgaggccgtgggggactcctatccatggtgttgaagcgtcg
agccgactagggaacctccttccccgccaggatggaagtcgcatcagtcgccgcctattgcgcggg
ctgttcttccctgtgttctgccgcccgctgccgcattcgctgccctctgtggcttttctgctggct
cgaagatcggcctggagcagcgacgccaccgctgggcaaggccgagactctgtaggcttcctccga
atcccgtcgacctccagccgctgagcgccgcggccctacctgagagactgtcaagaaaaaggagat
g (Seq ID No: 1040)

*Homo sapiens* family with sequence similarity 104, member A (FAM104A): ccctctcttcgcggagcggcgccgcgtagcttccatccgccagctgccatg
(Seq ID No: 1041)

*Homo sapiens* PRP38 pre-mRNA processing factor 38 (yeast) domain containing A (PRPF38A):
agccctttacactacggtgtttccggcttcaagatggtcgcctaagctgtttagtgaaacttcttc
cacctttctccattcctctaggtgctttttctgaacctggatgtgaggcattaaaggatccgacgg
aaatagaattgaaggcattctaaaatg (Seq ID No: 1042)

*Homo sapiens* synaptotagmin-like 1 (SYTL1):
cctcctccgtgtggggcagctgctggctgggctgcctgttgagtcagccttcttccctcacggctc
ttctcccggtccctgaaactcggctgccaggggagctggagccacctgcgaaggtgtcctcccata
ctggacccctacaggaagctccgtgtgcccagctggggcacagccccagctgatg
(Seq ID No: 1043)

*Homo sapiens* ubiquitin associated and SH3 domain containing B (UB-ASH3B):
gctccttttccttttgatccattcaaaaattactcattgcaaattcccggactgctaggcgagga
gagggaagggggcggaggagacagggctactgcaggcgcagagctgggggcagccgggggcccgag
tggctgaggctggtcccgcagcggccgcttgccggcgttctggctcctgtggcctcaccaggaagc
gtcagagtcccgacactggggaagctcggagcgccgcctccgctgccgccgcctcctgcctggctc
tgggtccccgagcccccctcccctggcccagcccgactccctcctccttcccgaaccatccggctcg
ggctccttccctggcgatggctggccgctgagccatg (Seq ID No: 1044)

*Homo sapiens* transmembrane protein 241 (TMEM241):
ccgtctctgggcggctgctgccgctgccgctgctgctgctgcgggggtcgggcggcggccagggga
tttgggcaggcaccgtggatccccgagaaggggacgagttgacagatg (Seq ID No: 1045)

*Homo sapiens* ataxia, cerebellar, Cayman type (ATCAY):
gagcctctgccagccctgagctgggaagaagcagctacctcggaggcagggcgcgcaggcgggcgg
cgatgagaggggggcgcagccgcagccccgcgctggggagcccaccgctaaccctgcaccccaccca
cccctgcacaaaagagctggcgggcgctggccacgtcgccctgggtgaccttcctcggatgcagaa
tccgcccctgcgagcatcctcttcctcctaggctctgaaggcccggggagcgtgagcgatgcccag
ctgcacccgggcagggctcgcctttgtttgccagtaaggaggagaggctgtctcagctgcagaggg
gtcatccctgcttcaagccagtgcctcttcccagctcccatg (Seq ID No: 1046)

*Homo sapiens* ELL associated factor 1 (EAF1):
attcctctctcacccccacgcagaggagagaacttgcttctggacccgggtgggtgccggctcggc
tctccttgtcttccagagcggtggcccggaagcacagtcctcccagacgccagcgccagaagctcg
gatcgcggctgcaccgggagagcgccgatctgggtgcgaggcaggtgcggggccatg
(Seq ID No: 1047)

*Homo sapiens* tripartite motif containing 5 (TRIM5):
gttcctctaggaaaattcctttgtgcagatcaggcccgtggattggtgagtgaatcctaaccacgt
cttccctggcctgtcttcactcttctccccagaatcaccacttctgcactggtgtctgaaggtgta
ttgagtgattttgtggagggcagaagtaggaagtctttgggacaaaactgtatttaccttgggatc
tgtgaacaagaggaacctcagcagccaggacaggcaggagcagtggaatagctactatg
(Seq ID No: 1048)

*Homo sapiens* wingless-type MMTV integration site family, member 3A (WNT3A): cgccctctcgcgcggcgatg (Seq ID No: 1049)

*Homo sapiens* chromosome 16 open reading frame 45 (C16orf45):
ctccctccctgcagcccgcaacgggaatggagtaaagggagacccgtcgacctggccacggggatc
agcgatg (Seq ID No: 1050)

*Homo sapiens* zinc finger protein 502 (ZNF502):
cattcttccggtttcagaagttaaggctggtgtcctggccccagtccacctctgggagcgcctgcg
ccgctccgcggagagtccgtggatctcacagtgaaaaatgtttgctgacccttgacattgacaaac
tgctgacagctcagatgatccatgattggaaggatgtggtcatcaccaagatgtctttctttctcc
ggttcccagttttccagacctgaagtgttttccaatcaaagcgaagagacgatctgtggatg
(Seq ID No: 1051)

-continued

| SEQUENCES: |
| --- |

*Homo sapiens* armadillo repeat containing 6 (ARMC6):
ggctctcttgcgcaagcgcgctgtccgcttcttctgggcggacgctctggaggcaaaacatttccc
tgctgggggcggcgaccaccgtgagcgtcccggaaggggcggcaaagacgcctccgtcgcgcacga
ggtggcctcgttggctttaccttggttcgcggtcgtccttggttatcgtgagcgtccgcgagtctc
tgggaggccaagcctaggggcgccacagcgcctgcgcgcgtacggcggccggaaggggctagaggc
ggctccctgggtgacaaccgcgcgccccacctttccccacgtggccgcgaagaccggctcaggagc
atctatcggctgcacgccaacatcaacacaggcgaagatg (Seq ID No: 1052)

*Homo sapiens* post-GPI attachment to proteins 3 (PGAP3):
gctcctcccccggcggcgagccagggagaaaggatg (Seq ID No: 1053)

*Homo sapiens* histone cluster 3, H2a (HIST3H2A):
tgccctcttgtttttagtctcgcttttcggttgccgttgtctttttttccttgactcggaaatg
(Seq ID No: 1054)

*Homo sapiens* ethanolaminephosphotransferase 1
(CDP-ethanolamine-specific) (EPT1):
ggctctcctaccttctcgggcagcccagtctttgccatccttgcccagccggtgtggtgcttgtgt
gtcacagccttgtagccgggagtcgctgccgagtgggcgctcagttttcgggtcgtcatg
(Seq ID No: 1055)

*Homo sapiens* F-box and leucine-rich repeat protein 5 (FBXL5):
ccgcctctgccccgcggcgagggtgtctatggagaggcggcggccgcggctgctgaggcggaggct
gaggcagtggcgatggcgcccttcctgaagaagtggacgtcttcaccgccccacactggcggatg
aagcagctggtggggctctactgcgacaagctttctaaaaccaatttttccaacaacaacgatttc
cgtgctcttctgcagtctttgtatgctactttcaaggagttcaaaatgcatgagcagattgaaaat
gaatacattattggtttgcttcaacaacgcagccagaccatttataatgtacattctgacaataaa
ctctccgagatgcttagcctctttgaaaagggactgaagaatgttaagcctactactgttgactgg
aagccttaccaataacataaaacaatcgaataacaattatttcatgtattatatgtaaaatatata
tactggattcttacagtaagaatgaatatgaacagttaaattatgcaaaacaactgaaagagagat
tggaggcttttacaagagatttcttcctcacatg (Seq ID No: 1056)

*Homo sapiens* major histocompatibility complex, class II, DP alpha
1 (HLA-DPA1):
ctgcctccactcggcctcagttcctcatcactgttcctgtgctcacagtcatcaattatagacccc
acaacatg (Seq ID No: 1057)

*Homo sapiens* secretory carrier membrane protein 1 (SCAMPI):
tcgtctctctctctgcgcctgggtcgggtgggtgacgccgagagccagagagatg
(Seq ID No: 1058)

*Homo sapiens* chromosome 15 open reading frame 57 (C15orf57):
ccgcccctcccgatttcctccgggctacaggcgacagagctgagccaagcgtttactgggcagctg
ttacggtaagtgaggaggggctggggtgcccagcgttttggatctcccactctggcccggccccgg
aataccacatagaggccttgggacctgattcatcccgtccagacagccctagagacctgagcgact
gaggcctgggatctggacgccggaatttcctgcgtggttctggacgccctgccctgggctcagatt
ccaaatg (Seq ID No: 1059)

*Homo sapiens* WD repeat and FYVE domain containing 2 (WDFY2):
cctcctcttgtagtggcgccggcttgcatcccaggtcgtggcggttttggtgcctgaagcagggag
cgcggagtcgttcccgagagaggcggccaggctatgctcgccggtttccggcgttccgctccggcc
agccagagtctctgtctcaacctgtgtccgtgctccagcagtctcctcagcccggccccgcggcgc
ggttggcggcggcgccccaggcgcgccccctcctccgatg (Seq ID No: 1060)

*Homo sapiens* topoisomerase (DNA) I, mitochondrial (TOP1MT):
cgctctttcccggaggctggcagatg (Seq ID No: 1061)

*Homo sapiens* intraflagellar transport 122 homolog (*Chlamydomonas*)
(IFT122):
ctttccctttcggacatgcgcgctcggagcaaggcgccctcgcactcagcttaccgcgcatgtacg
ttgccaggggtaacgcaggtagccaaagtggcttgtggagtggcgaccgttagtgaggcggttgct
gagacagacgctgaggcgggtaggaggagcccgagccgtaagggaagccgtgatg
(Seq ID No: 1062)

*Homo sapiens* mitochondrial ribosomal protein L53 (MRPL53):
agttcttccggggcggaggtcaccatg (Seq ID No: 1063)

*Homo sapiens* T-cell activation RhoGTPase activating protein (TA-
GAP):
ccgccccttcgcttataatgcagagcatgtgaagggagaccggctcggtctctctctctcccagtg
gactagaaggagcagagagttatgctgtttctcccattctttacagctcaccggatgtaaaagaac
tctggctagagaccctccaaggacagaggcacagccacacgggagtgaaatccacccctggacagt
cagccgcaatactgatgaagctgagaagcagccacaatgcttcaaaaacactaaacgccaataata
tggagacactaatcgaatgtcaatcagagggtgatatcaaggaacatcccctgttggcatcatgtg -continued

SEQUENCES:

agagtgaagacagtatttgccagctcattggacattctcactattctatgccttaaaggcccttca
acggaagggatattcaggagagcagccaacgagaaagcccgtaaggagctgaaggaggagctcaac
tctggggatgcggtggatctggagaggctccccgtgcacctcctcgctgtggtctttaaggacttc
ctcagaagtatcccccggaagctactttcaagcgacctctttgaggagtggatg
(Seq ID No: 1064)

*Homo sapiens* phosphoserine aminotransferase 1 (PSAT1):
ggtcctccttggctgactcaccgccctggccgccgcaccatg (Seq ID No: 1065)

*Homo sapiens* CD97 molecule (CD97):
ccccctccttcataaagtcctggcctcgggacagcctgcacagctgcctagcctgtggagacggga
cagccctgtcccactcactctttcccctgccgctcctgccggcagctccaaccatg
(Seq ID No: 1066)

*Homo sapiens* protein tyrosine phosphatase, non-receptor type 2 (PTPN2):
cgctctccccggatcgtgcggggcctgagcctctccgccggcgcaggctctgctcgcgccagctcg
ctcccgcagccatg (Seq ID No: 1067)

*Homo sapiens* chromosome 20 open reading frame 112 (C20orf112):
gcccctctccccgggcagccgcggcggcagcagcagcagcagcagctggagctgtggggctgtcac
cgccgcccgccccgctcactcgcggatcccgaccgcccatctccgcctcgcttccagcccaggatg
agacttctgtgagcagcgaggattttgatatg (Seq ID No: 1068)

*Homo sapiens* APEX nuclease (multifunctional DNA repair enzyme) 1 (APEX1):
cacccttctttgtgctcgggttaggaggagctaggctgccatcgggccggtgcagatacggggttg
ctcttttgctcataagaggggcttcgctggcagtctgaacggcaagcttgagtcaggacccttaat
taagatcctcaattggctggagggcagatctcgcgagtagggcaacgcggtaaaaatattgcttcg
gtgggtgacgcggtacagctgcccaagggcgttcgtaacgggaatg (Seq ID No: 1069)

*Homo sapiens* intermediate filament family orphan 1 (IFF01):
tttcctcttgagccatcatgcacatctgactgcagccccagcgagcccttccttccttgtctgact
gctcttcttctcgatttcttcttgttctgccttctcggtttgcagccctgacccccgctgtgtgtc
tggcccttggtgactgtccgtgtttctgttcctgtcattgtaactgtgacttttctctctgtctgc
ccccccttcctactggttcatgcttctcccccattcccacccctctgcccggcctcccgctcccg
ccctttctcctcatgcacccggcctcgtctctgtagtctctgcacttgtctcccattaaggtccca
tccatg (Seq ID No: 1070)

*Homo sapiens* neuralized homolog 2 (*Drosophila*) (NEURL2):
cagtcttcctcccgccccttctttggtccctacggacctgggggggcggtggcggtcaatgccgggt
caaggtccgcgggcctcgcagatcgtagcccgggcgcacgcgatcagatgatcctgttgtggacgg
ctaagttgtaggcgggatggctgagaaagcggcgctaggacccccgggcagaggctcggggaaggg
agtcaggggggaaatgccttacaaggtcgccttgcggtcaccatcattgcccgccgcccaaaatag
cccccggcgccagctggcctgccctatggccgagagatg (Seq ID No: 1071)

*Homo sapiens* drebrin 1 (DBN1):
ctccctctttccctccctcctcctccgtccgcccgtccgtccgcgcgtctgtccgttcggcccggt
ccggcccgaagcatg (Seq ID No: 1072)

*Homo sapiens* WW domain containing adaptor with coiled-coil (WAC):
cagcctcccttatttagtccgcgatggcttccctcgcgccccaccgtcctcttccggaaggcggct
ccctccctgcgcagcccggagcccctgagatcagcctcgagcaggcgcccgagcgagactatccct
aaacgggaacggcggtggccgactcgcgagtgaggaaaagaaggaaagggcagactggtcgcgaag
agaagatccaggcctcagaggaggagaaaggccggagccagccgaggtttgccgagggcggtgttc
cggacccgcgcggtgcggggaggaaggccgagggtgggagaggaggggcccggcggaaactgccga
ggtttcccgaaggcggcagcgtccgagttgcccggatgtagttggtggagcggcagcggcggcacc
agcggcggcggcggcggcgggaggaggaggaggagaagaaggaccaggcggcggcagcagcggcgg
cggcggggggaggaggggaggaggcggcggagcaggaggaggagaaggcggaggaggcagtcgctc
tccgcggggctgagccggacgcgtcgtcttgccccccctcccccggttcgcggtgccgccgtgtag
ttggcgccgctgccccggctgagagtgagcgtggtgtcgacggagggagatggcccgggagcgccg
gcgccagtaactgggagctgatgagagtcgccgagggcgcgccgggcccaggtgccggggctgccc
gccgcccgccgccgccgccgcctgcgcgcccgcccgcctttcgcggccgctctccccccctccccga
cacacactcacaggccgggcattgatg (Seq ID No: 1073)

*Homo sapiens* kelch-like 6 (*Drosophila*) (KLHL6):
cgctccttcagtctcgatg (Seq ID No: 1074)

*Homo sapiens* GTPase, IMAP family member 1 (GIMAP1):
cagccttctgcactcacagccgaagggaaagcagcaggttggggcttcttgtggccaacttcagag
cctgtcaccaggaaaggtaagcatg (Seq ID No: 1075)

*Homo sapiens* RAB24, member RAS oncogene family (RAB24):
cgccctctagccccctcccgcgggagtcgcggcgctgcgggtaggagccgggttgcgggagacccc
aggttcggttgggattcccagccagaacggagcttaagccgggcaggcgagcgaatgacggagtag
cgagctgcacggcggcgtgctgcgctgttgaggacgctgtcccgcgcgctcccaggccgccccgag
gcttggggtcttcgaaggataatcggcgcccggggccgaacagcgggggcacacggggcgctgccg -continued

| SEQUENCES: |
|---|

aagtgcaaggccacggccagagctcgagcccgacgcgctgtctggagtcgtaggaccctgacgtgg
ctgaagcggccccgggagcatg (Seq ID No: 1076)

*Homo sapiens* adaptor-related protein complex 2, alpha 1 subunit
(AP2A1):
agccctccccgcggccggctcggctccttggcgctgcctggggtcctttccgcccggtccccgctt
gccagccccgctgctctgtgccctgtccggccaggcctggagccgacaccaccgccatcatg
(Seq ID No: 1077)

*Homo sapiens* copine IV (CPNE4):
ctccctcttttctcagtaccctcctctttactctccgagttaactgagagccgacctgacatctcc
aacattttcaccctcttccccacccccatcaccgagaatggagtcagggtttccggagagaccga
actctgctctcagcacctttcccagccgctgttgctaaactgacctcggaggacgagaggggaagg
aggtgcgacgccccttacatcagtacataactaccacaccaaccacctccacttcaaagccggatt
ttgcatcctgggggcgggacagacctcgtcccgggctgaattctctctccactcttcgagattggc
acacccagaatg (Seq ID No: 1078)

*Homo sapiens* synaptosomal-associated protein, 25 kDa (SNAP25):
ctgtctttccttccctccctgctcggcggctccaccacagttgcaacctgcagaggcccggagaac
acaaccctcccgagaagcccaggtccagagccaaacccgtcactgacccccagcccaggcgccca
gccactccccaccgctaccatg (Seq ID No: 1079)

*Homo sapiens* cAMP responsive element binding protein 3-like 4
(CREB3L4):
aggtctcttgactctttccgcctttgtttacaaccctgccatgatctccctcttgcaaaagcgagg
gctacagaacaggcattcaggagtcctgtgctccagtcacagccttttctgttcttcagctaggag
acaccaaaccctcaggaagatttactatagctaagagaaaactgcagcagaaagggcgcggctacc
tacttcttaaattccgtttgtggaccctcagactcttagtcccctactcccagatacagcggccct
accgtggctcctggcaaggtggcatccacttttgtagtaagcatg (Seq ID No: 1080)

*Homo sapiens* leucine-rich pentatricopeptide repeat containing
(LRPPRC): ctgtccttctggcggagcgtgcttcccgctgcggggacgttcgagcaatg
(Seq ID No: 1081)

*Homo sapiens* zinc finger protein 418 (ZNF418):
cgttctctggtagcgaccattttggttaatgttgggtgtgtttctgcggtttgtgaggtgagaggc
gctggagctatgggtccgaaccgcggtgtctgaacccagaaggtgaagagtccttcttgctgcaca
gaggcagatcttaggccccgtaacggcgcccgccgctcccggcagtgctttccccgcgtactcggg
atggcggcggccgcgctgaggctcccggctcaggcatcatctggctgcaaagaagagaacacactg
tgtttgagggaggaggaaggaggatcagagtttaaactcctgccataatg
(Seq ID No: 1082)

*Homo sapiens* tetratricopeptide repeat domain 14 (TTC14):
gtttcttccgcttcctgtaccacccggctcaagtagcggacacggaacagggaactatcagcccgt
cggcctccgggccctgcattctctagccatg (Seq ID No: 1083)

*Homo sapiens* BMP binding endothelial regulator (BMPER):
agccctttcgactgtgagctgcggcagctgagcagaggcggcggcgcgggacctgcagtcgccag
ggattccctccaggtgacgatg (Seq ID No: 1084)

*Homo sapiens* zinc finger protein 384 (ZNF384):
ccccctttcgtttccggcgctcccgccttctctccgcagagctcttctctgagcctgttgggggg
agggagggggggcgtggaggaactggggttcgcgggagcacgagctgcagcaccacttccgggtgag
tgcaaggggagggcagcaaggagggggggccacccactacctcgcgcccccgccctgcgggtgtct
cgcgcgcgttccgtgcgtgtgagtgtgtgggtctgtctcgctccagaagtgcgtgcccgcgcgctg
cgccttgcgctttttcccctccctcgccccttcctggtcctcccaccctcctcggctccctccttt
cccagcaaacgccgcccctcccgcgccctggctcaggctctggcgccgcgccgcagccgtcgccgccc
gaaagttcaggagccctggaaaggagaaggaataagacggcaggaggaagagagagagagagggtaga
atg (Seq ID No: 1085)

*Homo sapiens* RAD51-like 3 (*S. cerevisiae*) (RAD51L3):
ctctcctttctcctccggcagccagcgcgcctgtgtcctctctaggaaggggtaggggaggggcgt
ctggagaggacccccccgcgaatgcccacgtgacgtgcagtccccctggggctgttccggcctgcgg
ggaacatg (Seq ID No: 1086)

*Homo sapiens* CD99 molecule-like 2 (CD99L2):
gctcctcctcccgctcctcctcggcctccccttcgggcgctctcgcgctaactgtgctcctccggg
gccctccgcctgctcccagccatg (Seq ID No: 1087)

*Homo sapiens* glucosamine-6-phosphate deaminase 2 (GNPDA2):
gcgcctttatctgcatccgggtccgtgggattcgcgctccactggtcagctggggtcgctctcggg
tggttgggtgttgcttgttcccgctgttccagcgtcgaagaaccattgggtctgccggtttgaact
tgttctggaagctgtgcgtcaccgtaatg (Seq ID No: 1088)

*Homo sapiens* methionyl-tRNA synthetase 2, mitochondrial (MARS2):
ccgcctcctccgcttgcggccggtctgcaccatg (Seq ID No: 1089)

-continued

SEQUENCES:

*Homo sapiens* chromosome 12 open reading frame 57 (C12orf57):
tttcctttccgctcccaggggcgttgggaacggttgtaggacgtggctctttattcgtgagttttc
catttacctccgctgaacctagagcttcagacgccctatg (Seq ID No: 1090)

*Homo sapiens* tRNA-yW synthesizing protein 3 homolog
(*S. cerevisiae*) (TYW3):
ggaccttttcggccaccgctcgcttcaatatggctgcccccagggagagacgaggctaccatgaag
gagccgagcgcagaccctgagtccgtcacccatg (Seq ID No: 1091)

*Homo sapiens* Spl transcription factor (SP1):
ctccctcctccttacccccccctccctgtccggtccgggttcgcttgcctcgtcagcgtccgcgtt
tttcccggcccccccaacccccccggacaggacccccttgagcttgtccctcagctgccaccatg
(Seq ID No: 1092)

*Homo sapiens* histidine triad nucleotide binding protein 3 (HINT3):
cgccctctagtggcagccggttttgaggccggcctccggctttgaagttcctcaccgcgtctcctt
ccctctccccaaagcctggatcaccgcccagcgtcaggcgaggggcgacgtctcgaggtaaaacgg
aggaggtgcgggacgcggagactgcgcgggcccggtagccctggagaggccgaggctctaggccgc
gaggggcgggtgcaatg (Seq ID No: 1093)

*Homo sapiens* M-phase specific PLK1 interacting protein (MPLKIP):
agttctctgcggagggccggttgatacagttccggtgggagaacgcggctgcgaggttttcggctt
tggctcctgatatg (Seq ID No: 1094)

*Homo sapiens* palmitoyl-protein thioesterase 2 (PPT2):
cacccttcccccgccaccgtgggttccagacttgggataagtaaacagcgggtggagcgaggcct
acggacccaggccaggtgggagtctgcactcttcaaggggcctgggctgctgctcacgggtattaa
agaactccgcgttgttcatggctgaggcgatgcattaggaagatcctggacctagagaacaagtcc
cccgaacgctgagttggaggcgggacttcgggtgcgcgttggcgggagcatg
(Seq ID No: 1095)

*Homo sapiens* BCL2-like 14 (apoptosis facilitator) (BCL2L14):
aagcctcttttcaggctgagtcctaaacctgaagaaagtttagagcctggggctctaaactacctg
agtctttccaaacgacaagccaagaagacctgttgaaagttcctcttaagtttcgtggagagaga
ctcaggtatagaaatatccttactgccacctgacctgaagcagaagaaatcacagacagcttccag
accaggcccaacatg (Seq ID No: 1096)

*Homo sapiens* galactose mutarotase (aldose 1-epimerase) (GALM):
acgccccttctcctgtaaacttgggtcgcctctagcttagcgagcgctggagtttgaagagcgggc
agtggctgcacacgccaaactttccctatg (Seq ID No: 1097)

*Homo sapiens* carboxymethylenebutenolidase homolog (*Pseudomonas*)
(CMBL):
cttccttcccttccccgactttgcagatttctcttcccccaggcctccctcctccacctctccgcc
ccctccgggcttggctctcccaggaggctacgactggagccactggtcccgcaggatccccgcgtc
ctcggtcgccgcgtccacgtccctctcgcgtccccgcccggcgccacgccgcctcctctgggttcg
gcctccgcgcggtgcagcgcagtctcaggccgcgggacaagcccgacttaaatctctgcaatg
(Seq ID No: 1098)

*Homo sapiens* chromosome 7 open reading frame 31 (C7orf31):
cgtccttctcccgcccccgcccctgcctgccagctccaccgggccgtaggtgcggacgacctcaaa
attcctcggcccgcgaaggccgccagctgcggggagggggagggggaggcgcggtcccgcagcgcccc
caggctcatgtcccaggtatgtccagacccccgaggcaccgcttgcagggcagtgacagcccgtga
ggctcggcctcgacccctggcacccttggtcccagctacgccggctcctggccttcccccaagtcc
gagagagaggtgggattctccccgacgcagttggaaaccgggaatccccttttagggtcccgttcgt
gctgcactactgactccaccatctgcaaagggattcttgtccagaatccccgaaggctttaggaca
gcgcttattttgttgaatgaagagtctctaattttcggaaagaccacaggctaaaagtcaagttgt
gccttttttagccaagaagcatg (Seq ID No: 1099)

*Homo sapiens* secretory carrier membrane protein 5 (SCAMP5):
cggcctttcggcagccgaacggccgcggcagttcaggacaaagaggtgtgggcaggccactgggcc
agctggtaacatcatg (Seq ID No: 1100)

*Homo sapiens* mitogen-activated protein kinase 10 (MAPK10):
tgctcctttcggttgccatagcaaccccattccccaagccctctgtccgtctcctctggtaggttc
cacaatggtacaggcagcatcacgctgcacaatggtttccaggcagtgaaagagggtgattcagca
agccactcttcttctatttcttttaacctccccttcactttttattttttatggggggtgggtggtgc
ttgctatatgcttaccttttttcttttctttttttcattttttacaaatttcctttttttgtcctcaccc
ctcaattcctaggggcttgagtgagtttaagattgggttttcttggaaatcacctgtccatcgtta
attttaaacaatctccatatctccaaagaatctcttccatgttagtctggaatgtggttaatgaaa
aacaagtagggaggatttctggggcaaacactgccggatcaggatcgtagttctcaggcacggaat
ggctagtgtgagaaacaccaacagcaggcccatctcagatcttcactatggcaacttatgcaagaa
actgttgaattagacccgtttcctatagatgagaaaccatacaagctgtggtatttatgagcctcc
atttcttatactactgcagtgaaccaacattggatgtgaaaattgccttttgtcaggtgtgtgttc
cttacaggtaaaacaaggggattcgataaacaagtggatgtgtcatatattgccaaacattacaaca
tg (Seq ID No: 1101)

-continued

| SEQUENCES: |
|---|

*Homo sapiens* beta-site APP-cleaving enzyme 2 (BACE2):
cgtcctccccgccgccgccggtcccggtgcgcgcccatccctgcccgcagccccgcgcgccggccg
agtcgctgagccgcggctgccggacgggacgggaccggctaggctgggcgcgcccccgggccccg
ccgtgggcatg (Seq ID No: 1102)

*Homo sapiens* SWI/SNF related, matrix associated, actin dependent regulator of chromatin, subfamily d, member 1 (SMARCD1):
acgccttttccgctagtcgccccgctctatcccatagtctcgctgccctgagcctcccgtgccggc
cggccggccgggggaacaggcgggcgctcggggggcgctcggggggcgggggagttccggttccg
gttctttgtgcggctgcatcggcggctccgggaagatg (Seq ID No: 1103)

*Homo sapiens* family with sequence similarity 175, member A (FAM175A): cgtcctcttgtgtagcctgaggcggcggtagcatg (Seq ID No: 1104)

*Homo sapiens* adenosine deaminase domain containing 1 (testis-specific) (ADAD1):
aggcctcttttgaaagatgcggccctgaccctgtgaacctcgcgcagagcggcctgaagcgagagg
ttgaggctgggaggtgagaaaatg (Seq ID No: 1105)

*Homo sapiens* acyl-CoA synthetase short-chain family member 2 (ACSS2):
gcccctctacggaggccccgcctctagttcggcctgttttctcagtcccggcacccgccgcgaccg
caaaggcggccgcggttctaggaacttgacgtgatg (Seq ID No: 1106)

*Homo sapiens* multiple coagulation factor deficiency 2 (MCFD2):
cttcccttactcaccggtgtccggaaaggtgaacgctgcgctcgggctgcctcgcctgttacctcc
gccgccgggcatg (Seq ID No: 1107)

*Homo sapiens* SPOC domain containing 1 (SPOCD1):
gctccttttcagctagtgggtggaaccccaggagggaaaactcagggaagcccagggcccgtgttg
tgcttttggcccaggtaggtggacagacatg (Seq ID No: 1108)

*Homo sapiens* LY6/PLAUR domain containing 1 (LYPD1):
agttccttcagtctcagccgccaactccggaggcgcggtgctcggcccgggagcgcgagcgggagg
agcagagacccgcagccgggagcccgagcgcgggcgatgcaggctccgcgagcggcacctgcggct
cctctaagctacgaccgtcgtctccgcggcagcagcgcgggccccagcagcctcggcagccacagc
cgctgcagccggggcagcctccgctgctgtcgcctcctctgatgcgcttgccctctcccggccccg
ggactccgggagaatg (Seq ID No: 1109)

*Homo sapiens* cytochrome b5 domain containing 1 (CYB5D1):
cattctttcatactgcctcctcccttgtttttctgtctcagagagatagtctgtcctaaatatccc
atgtagcccaggccactgaattaaaacggagcgtattcgttctctgccccaccccgcaactcctga
aagcggcgcaactcaattacttgatccttatatgccccacgcgggactcatactacgtttcccgtg
aacacgtgcagtccaaaccccgcccctgatatttatctcagtggacggtggccggaaaaggacaat
ggtttccatgtcagcggataaacgctctcccctcggctcccggacgcgacggaggtcgtagtagta
gtgagtacgtgctgaggagcaaaggagtaaccaagagatccagtgaccgacagagcaagagccatg
(Seq ID No: 1110)

*Homo sapiens* synaptoporin (SYNPR):
tctcctcctttgcttcataaaaagagggacaagtggctggtgctgtggacagagaagctttatttt
tagtatgagacaacctctattttctttcaggagagggaagttggattatcaattcttttgtaaatg
(Seq ID No: 1111)

*Homo sapiens* heterogeneous nuclear ribonucleoprotein U-like 1 (HNRPUL1):
cccccccctttccccccttcgcctcctgacaggaaaggtttaagggggacagagccctgggaggccgg
gccgggctcgggggccaccccgggggcccgggccatg (Seq ID No: 1112)

*Homo sapiens* schlafen family member 5 (SLFN5):
ggttctctgctctggacttgggaggctccgttgcctgctcccggagggagacgcgctgccgaggag
aacccagcgggagaacatttcaggataggaataggccaagtgctgagaagatg
(Seq ID No: 1113)

*Homo sapiens* MAS-related GPR, member F (MRGPRF):
ccatctcttccagcaggagagggctctactctgagctcctattttccaaggctccgggccgcgctc
ggcgctggcctgctgccccggcgggtccgccggccggaggcgggagtcacaggaagagccctccac
aaaaggaggcctcggcggatcaggacagctgcaggtgggtgtgcagactggtgagctgccagcagg
ggcccagacgcgccaggcctggagatg (Seq ID No: 1114)

*Homo sapiens* ubiquitin-like domain containing CTD phosphatase 1 (UBLCP1):
cggtctctcagcggccggtttctgcgtccgctgccgcaggttccaccgcgctccaggtattttttt
ttctgaaggaaagctgcttcctcatatgtttcaagaatg (Seq ID No: 1115)

*Homo sapiens* Rab interacting lysosomal protein-like 2 (RILPL2):
cctccttttccgttgtcccttcgcgccccaaaccacatcctggagcgcactctccagcgtggctgg
cagcggggacggtgcgccggggcgcaggcccaagagtcgcgtgcgcggccccttgcaccatccccc

SEQUENCES:

cgggcccacccccgggccgcgctgattgggcaggtagggactctgcccagcggaaagttttgggtg
ccgggaggaagtctaacctttgggagactccaagacagcagctccgaggtcggcgggggtctgggt
ggccatg (Seq ID No: 1116)

*Homo sapiens* zinc finger with UFM1-specific peptidase domain
(ZUFSP):
acttcttttccgtgggagtaaggaagtgcttttgaatgaggtactgagggccaaggtgttggaagt
tcctaattctttcctcggttaactgtgaaactctgcgtattgggaaggcctggcctcagtcatcag
gccaggagaggtactggacgccgcgcacgcactcgtctgccagcgaggcccaaaggggaagcctag
cggagctcagtgtggcagctgctggcctctgggccgctacttgtcaataccatg
(Seq ID No: 1117)

*Homo sapiens* mitogen-activated protein kinase kinase 5 (MAP2K5):
ccgccttcctcctcctcctctcgccgctaccgccgtcgccgccgccgcagccgccgccggtccgcg
cggcctcgggtggccggagctcagcctgcgcgcgccgcgccctgtgtctccgggtggggcagaaga
ctcgccccttgaacctcccgcggggactctccgtggtgtggcggccctggggctctttcttaatag
ccccggactgagtcccctccagtcgaggaccctctcctagtccactgacgagcggtggacacctgc
cgctgtatctcccccaaaccgagtccttgccctgctgcctcctcatacccacacggcggcagagac
cttcaccatagcgttcgctcaactccagaaccttccgacctccgctagttcctgcgggcctttgcc
cgcttcccggtgcaccctccccgggagacacctcagacccccgacagcctgggcaggctcggtgcc
tgcgggtgcgttcctgatcacccctcccctcttccctcccccctcatcctccattcccttgttttca
ccctctgtcctctgcccgtcactccccttgtcacctcttggagcccccctcctaaccagcggccagt
gggtttcccataccccaggatgtgagcctctttaacctgtaatg (Seq ID No: 1118)

*Homo sapiens* solute carrier family 2 (facilitated
glucose transporter), member 12 (SLC2A12):
cactcttctttagcatgctattatggggaaagtgaccactcctgggagcgggggtggtcggggcgg
tttggtggcggggaagcggctgtaacttctacgtgaccatg (Seq ID No: 1119)

*Homo sapiens* mitochondrial ribosomal protein L30 (MRPL30):
cttcctctgctctgcttcccttcggaggaaaatttcaggctgaaggtttagcgggtgccgcctcta
aagagagcaatcactacacttatg (Seq ID No: 1120)

*Homo sapiens* tripartite motif containing 11 (TRIM11):
gctcctcttcctgccggcatccgggatccctacgtcccgcgtcccccgagcgctcggagcctacgc
gcccagcgctaccgaaacccagagtcctgcgccctggagtccccgcgccccggagcccgagcaccc
gggagtcccgagcctcgcgccccggagtgcccgagcctgcgccgccgcacccggatacccgcgtc
cccgcgagctgccgaggccgcccgccgccgcccccgcggacagtaccgccttcctcccctctgtccg
cgccatg (Seq ID No: 1121)

*Homo sapiens* proline-rich transmembrane protein 2 (PRRT2):
ctccctccctagctgacttgctccctcccgggctgcggctgctgcaaaagccagcagcggcagcgg
gagctgtccggaggccggcgtcgagggtttgccgctgtctctgctattccatcctccccatagggg
ctctctcccctctcccatctcaagatg (Seq ID No: 1122)

*Homo sapiens* zinc finger protein 626 (ZNF626):
cggcctttgtctctcgctgcagtcagagctccaggtctggttcttctcctaaaggcccaggctgtg
tggccccgtgtcctgcaggtattgggagatccacagctaagacaccgggacctcctggaagccaaa
aatg (Seq ID No: 1123)

*Homo sapiens* solute carrier family 25, member 43 (SLC25A43):
cggtcttccgggcccgggtcggggctcgatg (Seq ID No: 1124)

*Homo sapiens* crystallin, zeta (quinone reductase)-like 1 (CRYZL1):
ggctctctgacgaaggactggaaggtggcggtggtgaaggtgcaggccgttggggcggctcagagg
caggtgactatg (Seq ID No: 1125)

*Homo sapiens* mitogen-activated protein kinase kinase kinase 7
(MAP3K7):
ctgcctctacccccgccacggatcgccgggtagtaggactgcgcggctccaggctgagggtcggtc
cggaggcgggtgggcgcgggtctcacccggattgtccgggtggcaccgttcccggccccaccgggc
gccgcgagggatcatg (Seq ID No: 1126)

*Homo sapiens* septin 6 (SEPT6):
ctttctctttgtcggaggagctcctctgtttcctgtgcagtagctcccgttgcggcggcacccgtg
gcagccctggcggacgcaggagcgatg (Seq ID No: 1127)

*Homo sapiens* myotrophin (MTPN):
ctgcctctcctcggccaggcggaacctctctgctgggcccggtggccgcaaaagaactttctttct
cccgcccgaacggtcgccgcggccaactgcctcgcccgcctggcagcctaaccctccttctcttct
tctcctctccggcttcgcgcggccctgcctccctctcgcccggcggcatccgcttgctgctgccac
cgcctcctcatcttctgcccggccaaccggcctgccccgctgcagtgatg
(Seq ID No: 1128)

*Homo sapiens* annexin A11 (ANXA11):
ccctcccttgcactgcctctggcacctggggcagccgcgcccgcggagttttccgcccggcgctga
cggctgctgcgcccgcggctccccagtgccccgagtgccccgcgggccccgcgagcgggagtggga -continued

SEQUENCES:

cccagcccctaggcagaacccaggcgccgcgcccgggacgcccgcggagagagccactcccgccca
cgtcccatttcgcccctcgcgtccggagtccccgtggccagggattattggacctgcctggtttaa
actattgtcttagttaattttgtgctgctctaacaaaatatcacagactgagtaatttataagcaa
tagtagcttatttggctcacagttctggaggctgagaagatcgtgaggctgcatctggcaagggcc
ttcttgctgcttcataacatggcagaagacatcatgcgggtgtgtgtctggggaagagacttacag
aagtggagttgctgagtcaaagatctaaccatg (Seq ID No: 1129)

*Homo sapiens* RNA binding protein, fox-1 homolog (*C. elegans*) 1
(RBFOX1):
ttttctttctttcctctcccggcgttgatgagtgcttggctcctgacagaagggatttggctccca
gctttgtagttcggaagaagttgggtctatagatttcccctaactctccattgatgtgttgagct
tcagagggaataataactctacgtaaagcatg (Seq ID No: 1130)

*Homo sapiens* prefoldin subunit 5 (PFDN5):
cttcctcttcgttaagtcggccttcccaacatg (Seq ID No: 1131)

*Homo sapiens* high mobility group AT-hook 1 (HMGA1):
cgctctttttaagctcccctgagccggtgctgcgctcctctaattgggactccgagccggggctat
ttctggcgctggcgcggctccaagaaggcatccgcatttgctaccagcggcggccgcggcggagcc
aggccggtcctcagcgcccagcaccgccgctcccggcaacccggagcgcgcaccgcaggccggcgg
ccgagctcgcgcatcccagccatcactcttccacctgctccttagagaagggaagatg
(Seq ID No: 1132)

*Homo sapiens* zinc finger protein 323 (ZNF323):
cggcctttgcggttgatcggtcattggggtgctgcagccccgccacctgttccgtagcttgccggt
gccccgaaggtgtcttctcctaaggaagattaaatcagaaaattttaaatcacagttatcccttta
cttaaagccagagtaagccttccaaattaaccccaggaatg (Seq ID No: 1133)

*Homo sapiens* tumor protein p53 inducible protein 3 (TP53I3):
ctttctcttctcttagcagcacccagcttgcccacccatgctcaagatgggcgggatgccagcctg
ttacataaatgtgccaaaagcctggccatgcctggaaaatggaccaatccgcccgccaagaggttg
ggtctcgttccctagagagaaggaagtttcctctccttgaagtgagagctagaatcgcactttctg
tcaagctgagagaaagactcttttccagaggctaaaaggacaagaaaatctgatttgcttgcttct
aactttgcgttttaaaggggggaaggaggaaaggaaagagggggagggtggttctgcttagccccac
ccctccggctaccccaggtccagccgtccattccggtggaggcagaggcagtcctggggctctggg
gctcgggctttgtcaccgggacccgcaggagccagaaccactcggcgccgcctggtgcatgggagg
ggagccgggccaggaacaatatg (Seq ID No: 1134)

*Homo sapiens* ceramide synthase 5 (CERS5):
ccgcctccccgcgggttccgttggctgtggcggcagctgacgcttgtggcggcggtggcttcgggg
tgggcgtaagatg (Seq ID No: 1135)

*Homo sapiens* TRAF3 interacting protein 2 (TRAF3IP2):
tgttcttctacttacctgggcccggagaaggtggagggagacgagaagccgccgagagccgactac
cctccgggcccagtctgtctgtccgtggtggatctaagaaactagaatg
(Seq ID No: 1136)

*Homo sapiens* Smith-Magenis syndrome chromosome region, candidate 7
(SMCR7):
ggtccttcacgttccattcccaggctggtctgagctccggggccgtggtcccgctgcctcctccgg
tcgtcgtgcggaagctgcgacgcaggcagaccatg (Seq ID No: 1137)

*Homo sapiens* mitochondrial ribosomal protein L10 (MRPL10):
cattcttccggtggagatggctgcggccgtggcggggatgctgcgagggggtctcctgccccaggc
gggctagagtgcagtggcatg (Seq ID No: 1138)

*Homo sapiens* proteasome (prosome,
macropain) subunit, alpha type, 1 (PSMA1):
acttctctgtagatcgctgagcgatactttcggcagcacctccttgattctcagttttgctggagg
ccgcaaccaggcccgcgccgccaccatg (Seq ID No: 1139)

*Homo sapiens* sorting nexin 5 (SNX5):
cggtctttctctagacgcgtcttgctgggagagtgtccgttgcttcccgtccgtgtcgcggccctg
cggttggcggcctcctcgtggagcggagcaaggccaggcggcccctgctcgagtcccgcgtcgcca
tg (Seq ID No: 1140)

*Homo sapiens* zinc finger protein 276 (ZNF276):
gggccccctccgcgcgtactgcgggccccacgggtgttagtggcgggggcggcagagtccgggtgg
gttgtcgcgacggagccgggcctcttcgccgtcttgagacggggctggcgagaagggcccctcacg
gagttgccatgggcgtctaaccgcggcagccaggcccctctctacgtgagaccccggccccctcc
cctttctgcagcccgcccgccacctgcgcgccgcgtggcctccgccggcgcctgcccgccccgcgc
ctccgtctcccacggagcaggccgggctctcgccatg (Seq ID No: 1141)

-continued

SEQUENCES:

*Homo sapiens* zinc finger protein 561 (ZNF561):
ccatcttttccggcgctggctcctctccgtcagtgcggtttcgcctttatggtggtggagtctgcc
caggctgtggaccgcaaataaccctgtacaaagaggaatggagattgcctctatccacctagattc
ataagctggcctgaggtgatcttggcatcaaggaagggatgcacatcatcacaccatcagcttcag
agaatg (Seq ID No: 1142)

*Homo sapiens* mucin 7, secreted (MUC7):
ctttctcttcttttgcttctagttaccatcctcaaaggattggctaaaagcaagcaactggattga
acaccctaagaagaaagattcacactgcaccaggagacatcagaaagaatg
(Seq ID No: 1143)

*Homo sapiens* threonyl-tRNA synthetase (TARS):
gcgcctttcgattgcatcagctggtccagccgaggccaagtcccgggcgctagcccacctcccacc
cgcctcttggctcctctcctctaggccgtcgctttcgggttctctcatcgcttcgtcgttcgccaa
tg (Seq ID No: 1144)

*Homo sapiens* ATPase, Na+/K+ transporting, alpha 3 polypeptide
(ATP1A3):
cagcctctgtgcggtgggaccaacggacggacggacggacgcgcgcacctaccgaggcgcgggcgc
tgcagaggctcccagcccaagcctgagcctgagcccgccccgaggtccccgccccgcccgcctggc
tctctcgccgcggagccgccaagatg (Seq ID No: 1145)

*Homo sapiens* chromosome 11 open reading frame 46 (C11orf46):
cgtcctctcagtggtagcgcggggactggctgggaagcggtcggtcgagtgtggcctgtgtggact
cgcatcttgcccgaagccgggcggaggagagctcaagctaagggtgatcagcccatgacctaaacc
tccagacaaaataaaacggaaaatttgctagaatcaagaatg (Seq ID No: 1146)

*Homo sapiens* chromosome 17 open reading frame 45 (C17orf45):
tgacctttcattcccgttgttatggaggtaggctctctaggaatctgggagtagtagctgggggg
caagagcaaataaagagctcgagcttctgtggtctctggggagatg (Seq ID No: 1147)

*Homo sapiens* AHA1, activator of heat shock 90 kDa protein ATPase homolog
2 (yeast) (AHSA2):
gggccttctggcagtttctgggagctgcgaacgcgccgccccggggctcggcggccggaaacgctg
gcttcggagccttaggcgccgcggcctttccttgttttccgcccagtccacgccgccatggccaag
tggggccaggggaaccccccactggatcgtggaggagcgggaggacgggaccaacgtgaacaactgg
cgctggcgcggctggcggcggcctccttccgggatctggggagggccgggccgcgggagccggggc
tgccctggggtctgtgcggggccgcggggccagggggtcaggggccgccccccctcagctgctgg
acgcagggctcggccttcgcctctcggctcgggagagtccttgagtacggagaccggctaggaggg
ttgcagctgcctctttttgaaagttgggttgggccccaagagtgacttccgacagacctttccact
cccaccgtctgtggcctgagggccttcccttctcctcccgcccacccctctggatgtttcggggag
ttagaagggagctggattgagagactgtgttaggggcgggggtatggaacgtagtggaaagggcag
aaatttggatctcagttcgcgcccaccccgcaggcgcctcccgcgagccgggccctctgtgagtga
gacaagctccccttcctttacgcgcctcacctggcgcgtggggagaggtcggcagccctccgccgc
agaacctccggaagggatgtcctctgccctgcgcctctggccggggctgtggtccctccaggccgt
cgaggggatgctgaggccggtccccagaggagcatgacttggctggtccggaggagctctgagggc
atgggcaatcttggctcgctgcaacctcagcttccagagttcaagcgagtctcctgcttcagcctc
atgagtagctgggactacagatgcgtgccactacgtccgtctgatgtttgtatttttagtagagac
agggtttcaccatgttggtcaggctgctctcgaactccagatctcgtgatccgcccgcctgggcct
actaaagtgctgggattacaggcgtgagctagatctgactttctagtgtcctagccttggcccgat
ggacatgtcatttctctcagctcgtttctgtcccctaaagtgagaatattgcctgggaagattaca
ttagacgatgtatatgcgaagacacttgatagctggtattgtcatgattctgattagttcactact
gctactttccctgtggcctaggctttgcctatttccagtgggcgagctagctagatcctcctccct
taaataagccagtgtttttaagacagaatactacttgcatagtggacaataatatcttaaagaact
gagcaggatgaaaagaatttgatagaaagcaggtttgaggagcacattggaggttggcaggtttcg
aggctgcttgagaggacttgggccgatctgggctgggcttggacgtgaccctggcacccaggcagg
tggatcccagctggggcttccattcacgactttctggtccctggcaggacagagcgggatgccacc
agcttgtccaaagggaagttccaggagctcctggtgggcatcgttgtggagaatgacgctggccgc
ggcgagatcaacgagttgaagcaggtggaaggggaggcttcgtgcagcagccgcaaaggaaagctg
atttcttctatgagtggaacatcaaactgggctggaaaggcatcgttaaagaatctggagtgaag
cacaagggattgattgaaatacccaatctttctgaggaaaatgaagtagatgacactgagaattta
caacgggaatg (Seq ID No: 1148)

*Homo sapiens* GrpE-like 2, mitochondrial (*E. coli*) (GRPEL2):
ctgcctctcagcccaaattggaaacatg (Seq ID No: 1149)

*Homo sapiens* xyloside xylosyltransferase 1 (XXYLT1):
ccgcccctttcatggccgccgcctggcgccggggctaagtggccgccggcgtccgggtacccgagg
gctctcccgcgttgctggcaccgctggcgccgcggtctcgtagcgcatg
(Seq ID No: 1150)

*Homo sapiens* chromosome 7 open reading frame 60 (C7orf60):
cctcctctggctgctgcctccgcagctccctcctcctaccccacctcctccatctggggagcgtct
gcgggggcctgaggggcggcggcggcggcggcggctgcgatatg (Seq ID No: 1151)

-continued

| SEQUENCES: |
|---|

*Homo sapiens* tetratricopeptide repeat domain 39B (TTC39B):
ccctcctttgcgctgggctgagcccagagccgagagcaggggtcggctctgagttccctgcttggt
ttttgggtggcagcagccagaggaggaatatg (Seq ID No: 1152)

*Homo sapiens* motile sperm domain containing 2 (MOSPD2):
caccccttctctgtctacctctgggcgggactgccgggtgatgagatactcggtcggcgacggtaga
acgggcgacggcgacaaccgcaatcacatccacgacggtgatcatg (Seq ID No: 1153)

*Homo sapiens* major facilitator superfamily domain containing 6-like
(MFSD6L):
ggccccctttcggtccaacggcaggacctgggggctgtggccgggggcggccgttgacctggtgacc
gcggcgccgccccagaccgggggcgcagtcccactcgctccgagccccggtcccccaagcctccct
cccgggtacctggggccgcgcccgccctgcgcccagctccgccctccgtcggcccaggcctgacag
agcccggcagccatg (Seq ID No: 1154)

*Homo sapiens* consortin, connexin sorting protein (CNST):
cttcctctctagccgccagtgctctatgctccgcggtcgcgggccgccagcctccagccggccagc
cgcgaggggtgcgcagagggaggcggggcggaaaggcgagaggtgtctcctccaccggagccaggg
gagacccgagcaagctccgtgacagcacgtcggccgccatgtcgccgagtggggctggaaacagac
ccggcgcccagcggtagccctccttgcgcctccgattcccagacatggaaggtctttaatgtaact
ttaaatggttcaccaaaggatgctctaatg (Seq ID No: 1155)

*Homo sapiens* zinc finger protein 92 (ZNF92):
gggcctttgtctctcgctgcagccggcgctccacgtctagtcttcactgctctgcgtcctgtgctg
ataaaggctcgccgctgtgaccctgttacctgcaagaacttggaggttcacagctaagacgccagg
accccctggaagcctagaaatg (Seq ID No: 1156)

*Homo sapiens* DnaJ (Hsp40) homolog, subfamily C, member 18
(DNAJC18):
cccccttctctttcagcctcgggcacgggggaggctcggcggacctgctgattgggaaccgatatg
(Seq ID No: 1157)

*Homo sapiens* polymerase (RNA) I polypeptide D, 16 kDa (POLR1D):
cctcctccctccttccgtcctccgcgccttccgtcggtcggtccttgcttcctgcttcgcctccgc
gcctcgcgctatgggacagagcccccgatccgccagcaccacctgaggatccagaaaccgccccag
cgatg (Seq ID No: 1158)

*Homo sapiens* ring finger protein 182 (RNF182):
acctccctcccctcccaggcgccgccgcagccggagcggctcccgggccctgggccgccgccggcc
aggaagaaatacttgtgttggctgcatttccagggatgctaccagagctcaaggctgtcacctggt
cttgcccagaagagccgttcttagaggcaggacttgatgaaggctttcctgctgatggaataggtt
tgctagagctggccttggaattagaaccccttcatgtggcctttataaatatgcgtttgagacagag
ttatatgcagaagttgaaaatgcctggaagatttctggtttctttcactacttatcctgccttttt
gcatcgctgccagatttggatgatatgatattcagaggggcaccttaatcaaagccattcttcaac
aagacccacctggcataagattgcacacataattcaagatg (Seq ID No: 1159)

*Homo sapiens* transmembrane protein 18 (TMEM18):
cctcctctgtggattctggccaggccgggttcggcggttgctgtgagagcgggcttcccaacacca
tg (Seq ID No: 1160)

*Homo sapiens* Hermansky-Pudlak syndrome 4 (HPS4):
aggcctctctgccgcgcgcgcaggtacggggcagaagtcgcaggtacccagctgctgcccacattt
ctggtccagagtcccgaaccccgagcactgggatgcctggctactccgagccaaggcactgatgtt
tgaactggaaacttcaaaacgtttaataagagtcttcaggatgggtttgaactagacaagctagaa
atttctttagaacaccagctctagcatgcatctcccacttttggctttcctggagaggagcttgaa
gaggtggttctgcagacagccacagtgatacttaggaaaccagaggaatggatttgacttttctgc
taggattctctgttatagtttctccctgagttgtaagaggcatggaaatatacatgaaactgaaga
acctgcaaggaagggaagtggaactttccatgctgagtgaaaactaaccaagtggcagttgtgact
gaaaacactgaaacctaccacgtccagattcactggattggggatagaggaacggtcacagctag
ggagaaagaagtgataccggaaaagaaaacctaaatgaagagaatgaggatgactgcacagtagat
g (Seq ID No: 1161)

*Homo sapiens* PTK7 protein tyrosine kinase 7 (PTK7):
agctccttttcctgagcccgccgcgatg (Seq ID No: 1162)

*Homo sapiens* kelch repeat and BTB (POZ) domain containing 6
(KBTBD6):
agttctcctgggcgcctagcattgtcgcccacgctgcagtagcggcttctgcggctccaagccagc
gggtcctgtgaaggcgagcagacgcggagaaaggacgcgggagtgagagagggtgagtcagccact
gtctaaacgataacgggaggcggctctgcggggtagggttgaattcagtaaatgggctcgtgctgc
tgtctcttcggagacgctgctatcttagcgtcagcgagggaaggttgaggaggagccagagccggg
tcctgcagcgtttctcgccatcagcgcccgtcgccatctccaccatg (Seq ID No: 1163)

-continued

SEQUENCES:

*Homo sapiens* sperm antigen with calponin homology and coiled-coil domains 1 (SPECC1):
ctttctttgactggagcggacccgccggacgcaaccgcctcgccagccggagccagcgcgagctcg
gcacggtggacacccggtccgaggccggcaagccggctggtgcccgagtcggccaagcatg
(Seq ID No: 1164)

*Homo sapiens* ST6 (alpha-N-acetyl-neuraminyl-2,3-beta-galactosyl-1,3)-N-acetylgalactosaminide alpha-2,6-sialyltransferase 3 (ST6GALNAC3):
ggtccccttatttggatctgcgggaatgtgggctggagaggtcctgccgtggtaccagcctccagc
ctgcccccaggactgcccctgacccaggcgcgcccgctgctcggtggcaggagggccggcggagcg
ccatg (Seq ID No: 1165)

*Homo sapiens* transportin 1 (TNPO1):
gattctctttgttccgcagccatttcaggccccggacaggaggcagtgccgcttcggccgaaggcc
cgagcgcccgaggcgtctgggatg (Seq ID No: 1166)

*Homo sapiens* heat shock 70 kDa protein 8 (HSPA8):
cttccttcgttattggagccaggcctacaccccagcaaccatg (Seq ID No: 1167)

*Homo sapiens* hyaluronoglucosaminidase 1 (HYAL1):
ggctccttcctccaggagtctctggtgcagctggggtggaatctggccaggccctgcttaggcccc
catcctggggtcaggaaatttggaggataaggcccttcagccccaaggacatcctggctgccatac
ctgctcctgacttctcagggctggcagtcatcgactgggaggcatggcgcccacgctgggccttca
actgggacaccaaggacatttaccggcagcgctcacgggcactggtacaggcacagcaccctgatt
ggccagctcctcaggtggaggcagtagcccaggaccagttccagggagctgcacgggcctggatg
(Seq ID No: 1168)

*Homo sapiens* STE20-related kinase adaptor alpha (STRADA):
agtcctcccggtcgccccactgcgcatggcacgttgcgtactcccctcccagcaaccggtctggcg
gcggcgcggcagtaaaactgaggaggcggagccaagacggtcggggctgcttgctaactccaggaa
caggtttaagtttttgaaactgaagtaggcctacacagtaggaactcatg
(Seq ID No: 1169)

*Homo sapiens* transmembrane protein 161B (TMEM161B):
ccctctctttcgctgtttgagagtctctcggctcaaggaccgggaggtaagaggtttgggactgcc
ccggcaactccagggtgtctggtccacgacctatcctaggcgccatg (Seq ID No: 1170)

*Homo sapiens* Usher syndrome 1C (autosomal recessive, severe) (USH1C):
ggctctttccagctcctggcagccgggcacccgaaggaacgggtcgtgcaacgacgcagctggacc
tggcccagccatg (Seq ID No: 1171)

*Homo sapiens* interleukin 12 receptor, beta 1 (IL12RB1):
cagtcttttctccttgctcagcttcaatgtgttccggagtggggacggggtggctgaacctcgcag
gtggcagagaggctcccctggggctgtggggctctacgtggatccgatg
(Seq ID No: 1172)

*Homo sapiens* Meis homeobox 2 (MEIS2):
atcccttcctctcttttctgttcgccctcttctccctgctctttttccctttccacccccctcctc
tgttctccctcacctcctgcgccccctccccccttcccgggttctgacagtacgatgagctgcccca
ttacggcgggatg (Seq ID No: 1173)

*Homo sapiens* G elongation factor, mitochondrial 2 (GFM2):
ttttcttttcgtttagatacattgccttttgcctaggctggcgtcgagacttgaggccgttgcaga
ctttggcgcggctcgcgcctcctgcttcaagagcccagcggtgagagctggcctgcggcacgcggc
ctaatgccagacagtaacagtttggaggatcaagatg (Seq ID No: 1174)

*Homo sapiens* lamin A/C (LMNA):
gagcctttgccccggcgtcggtgactcagtgttcgcgggagcgccgcacctacaccagccaaccca
gatcccgaggtccgacagcgcccggcccagatccccacgcctgccaggagcaagccgagagccagc
cggccggcgcactccgactccgagcagtctctgtccttcgacccgagccccgcgccctttccggga
cccctgccccgcgggcagcgctgccaacctgccggccatg (Seq ID No: 1175)

*Homo sapiens* calcium/calmodulin-dependent protein kinase II delta (CAMK2D):
cgctctttctctcgccgcgccgtcttgaagccgcgcgggctcgtgagcagcgcgaggccgccaagg
tgcctcgcttcgccggagccgctgccgcccgccggagggaagccggcctcgggcgcgcacgctcgt
cggagccccggcgcgccccgcgcctgagcctgctgacagcggccgctgggctcaggctgtccgctc
tgggctccgcggcctcggccccgctgcactccacctccgcccccctcggactccctcccctctgctt
ctactcctcctgctccagtgcggatcgtttcgcaactgcttgccactcgtcccgtgcctggctgtt
tttccatttcccggccccctcttcttgagtactttacccccctgcatttggggacagggactggaaa
aggggcgggtggagcgtccagtggagaagaaggaagcgaggcccgcaggaggaggaggatcggcgg
actgtggggaggagaccccacgccacccttctggtcatctcccctcccgccccgcccctgcgcac
actccctcgcgggcgagctactttcggaccaggaaagtaagagcggccctgggtgacagcgccgcg
gggccagtcccggggttagccgcgcgtctgctcgcttctggtccgtcgcgctcccagccagggcac
agcccggaccgaggatg (Seq ID No: 1176)

-continued

| SEQUENCES: |
|---|

*Homo sapiens* calcium/calmodulin-dependent protein kinase II gamma (CAMK2G):
ccgtctcctcctcttgctccctcggccgggcggcggtgactgtgcaccgacgtcggcgcgggctgc
accgccgcgtccgcccgcccgccagcatg (Seq ID No: 1177)

*Homo sapiens* interleukin 15 (IL15):
ttttcttttcgccaggggttgggactccgggtggcaggcgcccgggggaatcccagctgactcgct
cactgccttcgaagtccggcgcccccccgggagggaactgggtggccgcaccctcccggctgcggtg
gctgtcgcccccaccctgcagccaggactcgatggagaatccattccaatatatggccatgtggc
tctttggagcaatgttccatcatgttccatgctgctgacgtcacatggagcacagaaatcaatgtt
agcagatagccagcccatacaagatcgttttcaactagtggccccactgtgtccggaattgatggg
ttcttggtctcactgacttcaagaatgaagccgcggaccctcgcggtgagtgttacagctcttaag
gtggcgcatctggagtttgttccttctgatgttcggatgtgttcggagtttcttccttctggtggg
ttcgtggtctcgctggctcaggagtgaagctacagaccttcgcggaggcattgtggatggatggct
gctggaaaccccttgccatagccagctcttcttcaatacttaaggatttaccgtggctttgagtaa
tgagaatttcgaaaccacatttgagaagtatttccatccagtgctacttgtgtttacttctaaaca
gtcattttctaactgaagctggcattcatgtcttcattttgggatgcagctaatatacccagttgg
cccaaagcacctaacctatagttatataatctgactctcagttcagttttactctactaatgcctt
catg (Seq ID No: 1178)

*Homo sapiens* protein O-fucosyltransferase 1 (POFUT1):
gtccctccttccctccccgactgtgcgccgcggctggctcgggttcccgggccgacatg
(Seq ID No: 1179)

*Homo sapiens* calpain 3, (p94) (CAPN3):
cactctctttctctctccctctggcatgcatgctgctggtaggagacccccaagtcaacattgctt
cagaaatcctttagcactcatttctcaggagaacttatggcttcagaatcacagctcggtttttaa
gatggacataacctgtacgaccttctgatgggctttcaactttgaactggatgtggacacttttct
ctcagatgacagaattactccaacttcccctttgcagttgcttcctttccttgaaggtagctgtat
cttatttctttaaaaagctttttcttccaaagccacttgccatg (Seq ID No: 1180)

*Homo sapiens* PTK2B protein tyrosine kinase 2 beta (PTK2B):
agccctttttactcagccacagcctccggagccgttgcacacctacctgcccggccgacttacctgt
acttgccgccgtcccggctcacctggcggtgcccgaggagtagtcgctggagtccgcgcctccctg
ggactgcaatgtgccgatcttagctgctgcctgagaggatg (Seq ID No: 1181)

*Homo sapiens* ST6 beta-galactosamide alpha-2,6-sialyltranferase 1 (ST6GAL1):
cttccttccttctccagtcccttccactgtgcgtcttctgtccccccgttcttccccagcggacccc
tctttcgagactccctagtggggtccccagctcccgggcgatcctgcccttgccgagcgcgttttc
tggagtcacctgggggaggggagtcctgggcagggccgggctggggaagacgcctggggcactgcc
cggcgttaacaaagggagccgataccgaccggcgtgggcgcggagcgggcggccgccaccgagcgt
gctgagcaaccgcagcctccgcggccgagagtgcagcgagcaaggggagagccagttgcgcagagc
cctgcaaccagcagtccagggagaagtggtgaatgtcatggagcccagctgaaatggactggcccc
cttgagcctgtcccaagccctggtgccaggtgtccatccccgtgctgagatgagttttgatcatcc
tgagaaaaatgggccttggcctgcagacccaataaaccttccctcccatggataatagtgctaatt
cctgaggacctgaagggcctgccgcccctgggggattagccagaagcagatgatcatgacgcagtc
ctgaggtttaatggggcacccacagccaacttccaacaagatgtgggcacaaaaactaccattcgc
ctgatg (Seq ID No: 1182)

*Homo sapiens* ubiquitin-conjugating enzyme E2Q family member 2 (UBE2Q2): ctccccttccgcgcccggctccccttccgcgcccctcccgccggagatgaggg-
gaagatg (Seq ID No: 1183)

*Homo sapiens* membrane magnesium transporter 1 (MMGT1):
gcttcttttgctgggctgctgctccttcggcatcatg (Seq ID No: 1184)

*Homo sapiens* PAP associated domain containing 4 (PAPD4):
cggtcttccgggtgtctttgacagggttttctacgccgctttttcggcgactttttgctcttccgc
tttttgccaccgcccccaaccttctatatccttgcagcccctacctttttcttgtgttgctcctccc
ctggcagccgtgaggggggttagatctcagccggagccggagctgggcctagctgtcccacgggcc
accactacctcctttggttcgggagaaagctacgaccaagtacgcccagctcggccttagaactt
ctgaacgggcagtgcgggtaggccctgcttagcccttcccggaggacacctgaccaaaagaggaag
atagtcttgggacccttgcatggtgtttcaaagggtggtgaagaactaaggtagaagaatacatgt
tcacttccagtgaacaagagcatg (Seq ID No: 1185)

*Homo sapiens* chromosome 3 open reading frame 23 (C3orf23):
ctccccttctggtgtactgggtgggaggtggaactagtcggacaaagccctcgcgtcggacccttgc
cagaactcaattaatggatgcctcgaagttgacgtacatatatattcagaaatg
(Seq ID No: 1186)

-continued

| SEQUENCES: |
|---|

*Homo sapiens* mucosa associated lymphoid tissue lymphoma translocation gene 1 (MALT1):
cgcccctttgcgcggctggcgcggccagccggccaggctcccctcggcaaacctgtctaattgggg
cggggagcggagcttcctcctctgagggccgtgccgcgctgccagatttgttcttccgcccctgcc
tccgcggctcggaggcgagcggaaggtgccccggggccgaggcccgtgacggggcgggcgggagcc
ccggcagtccggggtcgccggcgagggccatg (Seq ID No: 1187)

*Homo sapiens* UDP glycosyltransferase 3 family, polypeptide A2 (UGT3A2):
ctacctctacccacagccagtgcctttggcgcactgaggtgcacagggtcccttagccgggcgcag
ggcgcgcagcccaggctgagatccgcggcttccgtagaagtgagcatg (Seq ID No: 1188)

*Homo sapiens* sodium channel, voltage gated, type IV, beta subunit (SCN4B):
cctcctctcgctctctgcccgctaactttcccgagccccgaccggcggcgcagagctccggggtag
ctttgtggccgaacgccgacctcgggcggagagcgcggctgtgcccagtatcccatccccgcgacc
cccgcgcgctccggagagaacaggactatg (Seq ID No: 1189)

*Homo sapiens* JAZF zinc finger 1 (JAZF1):
tcccctctgcctcccggtggctcctcgctctccttccatctctctcgccccctctccctccgtccc
gtcctcgccgctcccctcaccccgcctctctcccccctcccccagcccctcctctcctcaccccacc
cggcctccctccctccctcgcccgcccggcgctcgcagagccgacaccagggggggctctcgatgta
gcaccatg (Seq ID No: 1190)

*Homo sapiens* chromosome 15 open reading frame 55 (C15orf55):
ttcccttccttggatccctgtgcacctactggagccaggttactctgggtcctggacctgactgcc
tcattctggaggcttccagacagccacagttagtgcccaaacctgagaggatg
(Seq ID No: 1191)

*Homo sapiens* ras homolog family member C (RHOC):
cgccctctcttcctgcagcctgggaacttcagccggctggagccccaccatg
(Seq ID No: 1192)

*Homo sapiens* CTP synthase II (CTPS2):
cattctctttccttttccttctctcctgagcgctcctgcagttcctggggcgtagtaggggatcca
caagcgtttgtgaccagtgaagttctttacaagggtgagatctgcacgggaggacccgagcgaggg
tctcggcttgccaggaagccggggttccccgggaagcgtggagttcacccgcgcactcgaagtgcc
tttgcaaaattatatctgggtgttggcacccagccactattctgccaatg
(Seq ID No: 1193)

*Homo sapiens* PRP4 pre-mRNA processing factor 4 homolog B (yeast) (PRPF4B):
agctcttttccttcttcctccacttcccctaccctccaccgtccgggagccgccgccaccgccgcc
gaggagtcaggaagttcaagatg (Seq ID No: 1194)

*Homo sapiens* molybdenum cofactor synthesis 2 (MOCS2):
gcgcctttgcggccgtgattcggtcccgctgtcctaggcgggatggtgccgctgtgccaggtaagg
gtggcgggtgtgcgtgcgggcctgggtgcggagccctcctcgacgtgtctctcccgccctttccct
ccacatacccagccttggtcagtcggacctccccactagcccccaacctggccggcgtcttgggtt
cgggggcgcccccgcccccgcccccgggcccttcctgtctccgggctttactgcgactgccccagc
agaagtcgggtcctctccgagaactcttgtcagctcacggcagcaaggacggactcgttctgaagg
cgcctccaccttttatgaccacctctttcccagattattcgttttgatgaagctaaaattttaatc
taaaaagaaatgcacctcatggagaattcttgtgaagaactgtgcttcatctgtggatttctacac
ccttgatcatttgcaaacctgtaattatttcgtaaagagttgtttgcacggagtgacaggttgaag
tattgtattttgcaaaaagtgctgaaataacaggagttcgttcagagaccatttctgtgcctcaag
aaataaaagcgttgcagctgtggaaggagatagaaactcgacatcctggattggctgatgttagaa
atcagataatatttgctgttcgtcaagaatatg (Seq ID No: 1195)

*Homo sapiens* cat eye syndrome chromosome region, candidate 1 (CECR1): tttcctttttccggaggggagatg (Seq ID No: 1196)

*Homo sapiens* solute carrier family 13 (sodium-dependent citrate transporter), member 5 (SLC13A5):
ctgcccctcactcgtctcgcccgccagtctccctcccgcgcgatg (Seq ID No: 1197)

*Homo sapiens* armadillo repeat containing, X-linked 3 (ARMCX3):
agtccttcttgtcctggtcgttgttcccgtctgagtaccagctccccactgccctgagggcgggcc
ggcctgcggcggagggaaaaaggaagaggagaaggaaattgtcccgaatccctgcagtgggtccaa
gcctctcccgggtggccagtctttctgtaggttgcggcacaacgccaggcaaaagaagaggaagga
atttaatcctaatcggtggaggtcgatttgagggtctgctgtagcaggtggctccgcttgaagcga
gggaggaagtttcctccgatcagtagagattggaaagattgttgggagtggcacaccactagggaa
aagaagaaggggcgaactgcttgtcttgaggaggtcaacccccagaatcagctcttgtggccttga
agtggctgaagacgatcaccctccacaggcttgagcccagtcccacagccttcctcccccagcctg
agtgactactctattccttggtccctgctattgtcggggacgattgcatg
(Seq ID No: 1198)

SEQUENCES:

*Homo sapiens* armadillo repeat containing, X-linked 2 (ARMCX2):
cgtcctcctctgggtaccaactctattgcgcagctcgctgccgtgcgtttaacccaggcgaggagg
aggaggagaaaattcccccagattcgggcaggcccgcaccccacattccgtcctgttttgagagga
ggagggaagagaaataaacgtggcagcgcatagaaggccagcagggagactgctttccagacacct
ccggcccacacagccgttcaccccccgtcttttcagtcctggaaaaggaattcggtctgtccttag
gatgaagctctaactgaactgaagtaaggagaaacagccttgaatctttggagggtctgtcttcct
tttgggctctgtgcaactgcagctacagtggaaaaaagcaaactgctcttgatcccaggccctgcc
taagcctcagcagaacttgtaagcctaaactgaagagcctcacccggacgagcaggcatcccttaa
ccttaagcaatccagttccacgccctggatcagtgaataaccccagctgcaccatg
(Seq ID No: 1199)

Homo sapiens UBA domain containing 2 (UBAC2):
cgccctctggggctccgagcccggcgggaccatgttcaccagcaccggctccagtgggctctgtga
gtaccggcctccgccatcctggctgcccccctacacgccaccctaggcacctctttgaggaggctgg
ggcagcggggaccctcgggtttgccggaggtggtggggccgaccctccagacccgcgtccgaaccc
tgctagttcccggtcttgggggtcagcggaaaccgcccccatttcggcctggaggggcgaatgggg
acaaagccccgccgcccgccccgaccccacctggtatccccaggtgctctgcccaggagtctcttg
gggccgctgcaagtgggcaggtgccctggtgttctcgtgggccggccccaggccctttgcggagcg
tgtgccgcgctgaaggaagggggccgtccccccttaccatgccccattcttttaggcttgggggaccg
aactaactccccccgcccccacttgcaaagttcagcctccgctttagaagctgacctctcagtttc
acttggatg (Seq ID No: 1200)

*Homo sapiens* cancer susceptibility candidate 4 (CASC4):
cctcctccctcggccggccctggggccgtgtccgccgggcaactccagccgaggcctgggcttctg
cctgcaggtgtctgcggcgaggcccctagggtacagcccgatttggccccatg
(Seq ID No: 1201)

*Homo sapiens* protein phosphatase, Mg2+/Mn2+ dependent, 1G (PPM1G):
cgctccctcacagctcccgtcccgttaccgcctcctggccggcctcgcgcctttcaccggcacctt
gcgtcggtcgcgccgcggggcctgctcctgccgcgcgcaccccggggcttcggctccggcacggg
tcgcgcccagctttcctgcacctgaggccgccggccagccgccgccatg
(Seq ID No: 1202)

*Homo sapiens* StAR-related lipid transfer
(START) domain containing 13 (STARD13):
ctttctttttaaaaatcgctgggtctgttgagctgtcctgggctgggtgccttgctctttgactga
gactggagacagacggcaacagccacaggcagactgaggtggcaataggaaatctgccgagatg
(Seq ID No: 1203)

*Homo sapiens* tubulin, beta class I (TUBB):
gattctcccgcctcccagccccggcgcacgcgcgccccgcccagcctgctttccctccgcgccctc
ccctctcctttctccctctcagaaccttcctgccgtcgcgtttgcacctcgctgctccagcctctg
gggcgcattccaaccttccagcctgcgacctgcggagaaaaaaaaattacttatttcttgccccat
acataccttgaggcgagcaaaaaaattaaattttaaccatg (Seq ID No: 1204)

*Homo sapiens* cytochrome P450, family 4, subfamily X, polypeptide 1
(CYP4X1):
tttccttcttcccgcgagtcagaagcttcgcgagggcccagagaggcggtggggtgggcgacccta
cgccagctccgggcgggagaaagcccaccctctcccgcgccccaggaaaccgccggcgttcggcgc
tgcgcagagccatg (Seq ID No: 1205)

*Homo sapiens* doublecortin (DCX):
ttttctttctctcagcatctccacccaaccagcagaaaaccggtgagtggggcttttaagtgattt
tcaagaagaatgtaacagatgtcaaacgggaaaagcacaaggcaaagcctgctctctctgtctctc
tgtctcctcttctcctttttttgccttattctatccgatttttttccctaagcttctacctgggattt
tcctttggaaaagtctctgaggttccaccaaaatatg (Seq ID No: 1206)

*Homo sapiens* protein phosphatase 2, regulatory subunit B', gamma
(PPP2R5C):
ttgtcttttttttttttaaactaaaatggaggctggtttcttgccttaaggagcccattgcctttcc
cgctgaagtctagatg (Seq ID No: 1207)

*Homo sapiens* solute carrier family 9, subfamily B
(cation proton antiporter 2), member 2 (SLC9B2):
ccacctttccgggggaagccacgcgcaccaggcatcgcacgcggctctgcacccgcgccgccggac
ctgaaacccggcggagggcacacggggctgccgctgcgggccccggaccaacccatgcttactccg
gagcctgtaccggcgccgacgggtcggacctccctgcgcggtgtcgcccagcgggttcgtgcgaaa
ggcggggccgactacacgcggtgccgcgccctgagaccgtttatctgcagtcaacgcagcctcccg
gctcagcctgggaagatgcgcgaatcgggaaccccagagcgcggtggctagaccgggctccgccgc
ctcccccacagcccctttcctaatcgttcagacggagcctggtcgacttcgccggagactgccaga
tctcgttcctcttccctgtgtcatcttcttaattataaataatg (Seq ID No: 1208)

SEQUENCES:

*Homo sapiens* hypoxia inducible factor 1, alpha subunit (basic helix-loop-helix transcription factor) (HIF1A):
caccctcttcgtcgcttcggccagtgtgtcgggctgggccctgacaagccacctgaggagaggctc
ggagccgggcccggaccccggcgattgccgcccgcttctctctagtctcacgaggggtttcccgcc
tcgcaccccccacctctggacttgcctttccttctcttctccgcgtgtggagggagccagcgcttag
gccggagcgagcctgggggccgcccgccgtgaagacatcgcggggaccgattcaccatg
(Seq ID No: 1209)

*Homo sapiens* interleukin 21 receptor (IL21R):
cctcctcttcctccccactctgcacatgcggctgggtggcagccagcggcctcagacagacccact
ggcgtctctctgctgagtgaccgtaagctcggcgtctggccctctgcctgcctctccctgagtgtg
gctgacagccacgcagctgtgtctgtctgtctgcggcccgtgcatccctgctgcggccgcctggta
ccttccttgccgtctctttcctctgtctgctgctctgtgggacacctgcctggaggcccagctgcc
cgtcatcagagtgacaggtcttatgacagcctgattggtgactcgggctgggtgtggattctcacc
ccaggcctctgcctgctttctcagaccctcatctgtcacccccacgctgaacccagctgccacccc
cagaagcccatcagactgcccccagcacacggaatggatttctgagaaagaagccgaaacagaaga
tgaggcaatgaggctgcgagaggtagagtgattttccctcggtgactcaactgggacgtagcaggt
cgggcagtcaagccaggtgaccccatg (Seq ID No: 1210)

*Homo sapiens* DDB1 and CUL4 associated factor 4 (DCAF4):
tggtctttccgggtccttgcacgcttcgctccaactcctgcagagctgagccggaggggaatccgg
aagggacacgctgaacaggtctgactcccgggcagcacagcccgctcacgattccggccacggtga
tgacgagtctccgtcaacctcgtctggcacagctgggacctcctctgtgccagagctacctgggtt
ttactttgaccctgaaaagaaacgctacttccgcttgctccctggacataacaactgcaaccccct
gacgaaagagagcatccggcagaaggagatg (Seq ID No: 1211)

*Homo sapiens* oxidation resistance 1 (OXR1):
ccgcctcttgtgaggcgcgcggagccgcctcccctgggtcaggtctgatgggccggtgggcgcgct
agtggtggccgccaccgccgaaaccgtcgacctcctgggccccagttccgcgtccagccccgcggc
agcatg (Seq ID No: 1212)

*Homo sapiens* cut-like homeobox 1 (CUX1): ccccctctctat-
cagccgctcactccgtctcaatatgtctcaagatg (Seq ID No: 1213)

*Homo sapiens* atlastin GTPase 1 (ATL1):
ctccctttcctccccactccttcccaccagcgccacagcaacatcctcagagtctgagcgaactg
cgcccagcgcgggcacggagcctcccaccgccagcaacctgcggccccggagaaggcagcgagcgc
agtgacagcgcctcaccgccaccagctcctggaccaccatg (Seq ID No: 1214)

*Homo sapiens* chemokine-like factor superfamily 5 (CKLFSF5):
ctgccttctctcccggggccctgtgggcaagcctcctgcttcactttcaggtttctcgaagtgcct
tcttgctcctgtctgtttccccatcctgccagatttctgtttctcttgctgggcttttggcagtag
ggggctgtgttggtgggccctacgaagatg (Seq ID No: 1215)

*Homo sapiens* transmembrane emp24 protein transport domain containing 7 (TMED7):
aggccttttccgcttctcttttacctccccaggtccgcccgtctgcgcccctcacaggaagccgga
gggtcgctctgatcccgaatctcccacaggcgtgaacctgctctgctgtgtatctttgcggggtgg
cctgcgctgaggcctgccgcgcgcggtgagtccgcgcagacctgaccctgcgtctcgcagctcggt
tgaggccgccgccgccttctcgggatg (Seq ID No: 1216)

*Homo sapiens* ubiquitin-conjugating enzyme E2D 3 (UBE2D3):
cttcctttaccttcctcccatggtctccttccggttctcgatgcttctctgagcctaagggtttcc
gccactcgttcaccctccccccagctcatgatcctcctccctcccccgccctcctggtccaatctc
cgatctgtttagtaagaaggtgctgttccgagaagaaggaaaagggcttgacacgtattcactcgg
ccccggacgtgggaagcaagccgtctggcttcggcctcacatcggtcttgtgctcgggacggcggc
gttggcggactgatccgcggcggtgaagagaggccgggaagttaaacttgtagccaccacctccgc
tcttcccgtcaccctcgcccccacttcgggccgaaagcacggtacagaggctgttggtggctttgc
cacgccaccccacccaccccggatcgcggctgtcttaagggacctggattcatcaggggctcttcg
gggcctgtgcgagtgctgatctgctccgtttttgcaaaaggcgcctgtgtctggcagagctggtgt
gagacgagacaatcctgccccgccgccgggataatcaagagttttggccggacctttgagcataca
ccgagagagtgaggagccagacgacaagcacacactatg (Seq ID No: 1217)

*Homo sapiens* zinc finger protein 595 (ZNF595):
tttcctctggctcctgcgagggcttggtttagggcttcagctctctgcgttctcggctccgggagg
cctcggtgattcagccacagcctctgcctcccgttgctctgtgacctgagggtattggacaatttg
tagctaagactcccggataccctgaagtcgggaaatg (Seq ID No: 1218)

*Homo sapiens* acyl-CoA synthetase medium-chain family member 2B (ACSM2B):
tgctctcttccaaggctgtaggagttctggagctgctggctggagaggagggtggacgaagctctc
tccagaaagacatcctgagaggacttggcagcctgcagatggcctattgtgggaccttgtgatcat
gcctgaacatg (Seq ID No: 1219)

-continued

SEQUENCES:

*Homo sapiens* SRSF protein kinase 2 (SRPK2):
tttccctttatagcaccattgaatcccagtcctaacagaagtactgcgaatcttgtggcctcattc
tgaacaaaagggattagagaagaaaaatctcttgatataaggcttgaaagcaagggcaggcaatct
tggttgtgaatattttctgatttttccagaaatcaagcagaagattgagctgctgatg
(Seq ID No: 1220)

*Homo sapiens* synaptophysin-like 1 (SYPL1):
tgcccttcctcgccaccgggctgctctggtctcgtcggtcccctcctccgccccgtcgtcctgact
ctctctccctcctttcctcagaggatg (Seq ID No: 1221)

*Homo sapiens* thioredoxin reductase 1 (TXNRD1):
aaccctttcacctcagttttcttcactccggcatttgcagcagagcgaaaggtggtcgagtcctga
aggagggcctgatgtcttcatcattctcaaattcttgtaagctctgcgtcgggtgaaaccagacaa
agccgcgagcccagggatgggagcacgcgggggacggcctgccggcggggacgacagcattgcgcc
tgggtgcagcagtgtgcgtctcggggaagggaagatattttaaggcgtgtctgagcagacggggag
gcttttccaaacccaggcagcttcgtggcgtgtgcggtttcgacccggtcacacaaagcttcagca
tgtcatgtggcttatcaggaggggcagacttcaaaagctactaaaaatg (Seq ID No: 1222)

*Homo sapiens* minichromosome maintenance complex component 7
(MCM7):
tgtccttccgcgcggcggccgcggagagagctgcggcccgggggggcgtgcctgggatccggagct
tcgctcgggcccgggaaaggcggcagtgggctgggatcgcggtgtctctgggtgtgatggccaatg
gctggactggctcccgccctgggcggaggaatcccgagctgtgaagcggctggaatccgggcccat
gtgcttctttgtttactaagagcggaagcgatggcgggagcgggggtggggtgcggtggcggggtg
cggtggcggaggtcccggtgaaatcaggggctaaggggacccaaagaaggcgggggatcatagggg
tggaaagaaagctgagaaccttgagaccggagtgtgaggggccaacggggaagggcgctagaattt
taaactaaagtagggaccggaattcccctggggagatgttggatggccctgtgcactgccacgggc
tctttattcttcgctggttagaaacagacttgtgaaaaagagttatgcccactttggggagacttc
gaaaaggttaagaagttcttacaagagttctaccaggatgatgaactcgggaagaagcagttcaag
tatgggaaccagttggttcggctggctcatcgggaacaggtggctctgtatgtggacctggacgac
gtagccgaggatgaccccgagttggtggactcaatttgtgagaatgccaggcgctacgcgaagctc
tttgctgatgccgtacaagagctgctgcctcagtacaaggagagggaagtggtaaataaagatgtc
ctggacgtttacattgagcatcggctaatgatggagcagcggagtcgggaccctgggatggtccga
agcccccagaaccagtaccctgctgaactcatgcgcagattgtgagtggtctctgtcgggaaagat
gtagggattggttctccaggatcttgtttgtgactgttttctccccttagtgagctgtattttcaa
ggccctagcagcaacaagcctcgtgtgatccgggaagtgcggctgactctgtggggaagttggta
actgtgcgtggaatcgtcactcgtgtctctgaagtcaaacccaagatg (Seq ID No: 1223)

*Homo sapiens* pre-B-cell colony enhancing factor 1 (PBEF1):
tttcccctctcccctcctccgccgaccgagcagtgacttaagcaacggagcgcggtgaagctca
tttttctccttcctcgcagccgcgccagggagctcgcggcgcgcggcccctgtcctccggcccgag
atg (Seq ID No: 1224)

*Homo sapiens* cyclin B1 interacting protein 1,. E3 ubiquitin protein
ligase (CCNB1IP1):
ctttctttccctctccgttttggtgggctggttgaagatgaaatccactgaggagggaagtccagc
accctgtgtgccagtccagaactggcccatctgtagaccccctgaaaatcatatgggcttggattt
ggatattctcaacagaaagggttaaaggctgatggtacctaaagcctggtacttgaattttgatca
agataagctgccttaagttctcttcattacacaaatgatcctagataattgatagatcctgtggtt
caactggatttctagatagaagctggattcatgtgatgccagaggagtaaaatttcaagagactga
aaccagatctgagtttcgctgttccagtctggacctctttggtgctgtaaatcctggatatactgt
agatgagtactgcgtttttcttttatggcctctcttcagcttctggagacctcactatcctattat
g (Seq ID No: 1225)

*Homo sapiens* STEAP family member 3, metalloreductase (STEAP3):
ccgccttcgccgcggaccttcagctgccgcggtcgctccgagcggcgggccgcagagatgacattt
attcattttatgcatcctgggttctactggtcgtcccacctcagttcctgtagcaaagagacttga
gtctgagccactaattatcacccgtgaggtttcctccccgagcaggaagcagcaggccagagctgc
gctctctcagtgcactctccaaccaagcatcagtcaccactcccggtccagcccctgtggccaaga
gctggcgtgcaggctgcgggaggcagctggctgtgcaagaccctggcagggccctcgcctcctgag
aaaccgagagtcagaaccaaagccaggctgtcctggttggagactgagccagaaagggtggctcac
ctcacggtgaggctgtcgagtgacctgagagcctcagaccctcacgtcagccggatg
(Seq ID No: 1226)

*Homo sapiens* nicotinamide nucleotide transhydrogenase (NNT):
tgttcttccgggttggaggcgcagcgccgcggggcccaagcccgggtctgccagcgcgacgtcctc
tcgcggccctcagggcacagcccaaggctgtcagcctcccggcccagtgatttgccttcaaggaaa
ctggggagtcagaaaattgggaactcatatcaacatg (Seq ID No: 1227)

*Homo sapiens* SHC
(Src homology 2 domain containing) transforming protein 1 (SHC1):
gtccctctccctccccaggacttctgtgactcctgggccacagaggtccaaccaggctaagggcct
ggggataccccctgcctggccccttgcccaaactggcaggggggccaggctgggcagcagcccct
ctttcacctcaactatg (Seq ID No: 1228)

*Homo sapiens* bromodomain containing 8 (BRD8): cggcccttcca-
gaccgtctctcctcagggttggagacttcggggccaagatg (Seq ID No: 1229)

-continued

| SEQUENCES: |
| --- |

*Homo sapiens* ring finger protein 13 (RNF13):
tcgcctctttagtaggtcgggtgagtgtagtgtgcagggaagagacgcgtcagcgccagggccagg
cccgcccgggggcagcccggcagccgaatcttgggctactctgtcccaacagccggagcagatcag
accgaccggccctgcccgctcggtcccgcgccctccagaccctacggtctccgtttctaggggcac
atggttagcggcaggcgcccacagccaatccactttgccagcctgccccttcctctgccaagagca
gcttcttcagccgcgctccagttccgcagacgcctgccccaccctgctcttcccttccagggaaga
cggatcacgcggccaagaacgagactcgcaaactgggcatttctccgagccgggctagagcaagta
gcgagactccgcgtgagagtgggaaagagccttaacaggcaaccatgttgcccagtgggttttctg
tgcctttgggtgcggaccaatgaggcgcgtggggcgggacttccgcttcgcctaggtgttgtcgtc
cctgctagtactccgggctgtgggggtcggtgcggatattcagtcatgaaatcagggtagggactt
ctcccgcagcgacgcggctggcaagactgtttgtgttgcgggggccggacttcaagagagaaagag
agagtgggcagacatcgaagccaaacagcagtatcccggaagcactcatgcaactttggtggcggc
cactcagttttctctgccagtgtctggtgattttacaacgagatg (Seq ID No: 1230)

*Homo sapiens* aldolase A, fructose-bisphosphate (ALDOA):
ccgcctcctgcgccgccccttccgaggctaaatcggctgcgttcctctcggaacgcgccgcagaag
gggtcctggtgacgagtcccgcgttctctccttgaatccactcgccagcccgccgccctctgccgc
cgcaccctgcacacccgcccctctcctgtgccaggaacttgctactaccagcaccatg
(Seq ID No: 1231)

*Homo sapiens* LY6/PLAUR domain containing 6 (LYPD6):
cgctccttccctgagctcccgggctccggcagcgcgctggcggggcgccgcattgcacactctggg
ggcgccgcagtgttcgtgggatggggcagcgggctgcagctggcggccggaatccgcgcgcagccc
gggtgcaagttctctcctgttgccctgagtgcccactcccaggccctctgtatgagtgacacttca
gtctgccatg (Seq ID No: 1232)

*Homo sapiens* butyrophilin, subfamily 3, member A1 (BTN3A1):
cagtctctgctttctttttcctttcttccagaaggagatttaaccatagtagaaagaatggagaac
tattaactgcctttcttctgtgggctgtgattttcagaggggaatgctaagaggtgattttcaatg
ttgggactcaaaggtgaagacactgaaggacagaatttttggcagaggaaagatcttcttcggtca
ccatacttgagttagctctagggaagtggaggtttccatttggaattctatagcttcttccaggtc
atagtgtctgccccccaccttccagtatctcctgatatgcagcatgaatg
(Seq ID No: 1233)

*Homo sapiens* lipoic acid synthetase (LIAS):
ctgtcctttcccgggagttagcgatccctcaacccctgcactgcgctagtcctaaagaggaaatg
(Seq ID No: 1234)

*Homo sapiens* C-type lectin domain family 7, member A (CLEC7A):
gattctcttttgtccacagacagtcatctcaggagcagaaagaaaagagctcccaaatgctatatc
tattcaggggctctcaagaacaatg (Seq ID No: 1235)

*Homo sapiens* CD247 molecule (CD247):
actccttttctcctaaccgtcccggccaccgctgcctcagcctctgcctcccagcctctttctgag
ggaaaggacaagatg (Seq ID No: 1236)

*Homo sapiens* myeloid zinc finger 1 (MZF1):
aagcctttctccattttgcggtctaggaagtagcagaggccccttcctgtagggagttgccatgga
gacgcggtggggcaccgacggagttctaatgacggccgtgattggtgcaggatcctgctaatctca
ggaaggcccgtagagaagtgaggaaaacgtggtgggggcatgcgcgatctggtaggcggtgctgc
cgtctgttgtacctgagaggcttgcgcatgccgacgcacggattcgaggcggggagcatgggaaga
agcggccaggagtatgacctgatcattgcgaccaccgctaggggaagggaggagagggtgtagaaa
cggggacgagggtgggggaagggcaaggaggcgctcgagctggtgcgcggagcatcctgggagacg
tagtccagcgggagggggaagtcgaagactgcgcgtgctcaggagcgcggagcggcccgctgagcg
cagaggggcagacactggcctcagatacctgacctggtaccctctatg (Seq ID No: 1237)

*Homo sapiens* E2F transcription factor 6 (E2F6):
cctcctcttttccgtctgcgtcgggagctcccgggcacgtgaggccgtgccgcgtttactggcgg
gcgggacggcctagccgggcggcgcctcggaggaagccgcggaccccttaggtgctgggcccttgg
aaatcggcgcgtgggggcggtgctcgagctgagcgcgagagggcgggagagctcgtggggtgcga
ggggagcaggacgcccggccgggcagcatg (Seq ID No: 1238)

*Homo sapiens* purinergic receptor P2Y, G-protein coupled, 10
(P2RY10):
cttcctctttcaacaacaaatgtgtcagttatcagcaggatccatgccgccagagtaaagctttct
accctttactccctgcaaagaaacaagagtgcttatcccagctaagctccagggtaatgttatcat
gacagcttcaacttttagaccacaggcaaatgctttgttaaaactctatgctggtcattcccttca
ggatttggcactcaccaacatacccttctttcaagtgaaaaggcatctcttttaatggtcctgacc
tttggaataggaagcatgtaccctggacagagcacttcaaactagaggaaccataaatccatg
(Seq ID No: 1239)

*Homo sapiens* chromosome 9 open reading frame 85 (C9orf85):
catccttttgcctgctcccggcgaggggtggctttgatttcggcgatg (Seq ID No: 1240)

*Homo sapiens* ERGIC and golgi 3 (ERGIC3):
cgtccccttccggccggtccccatg (Seq ID No: 1241)

-continued

SEQUENCES:

*Homo sapiens* ankyrin repeat domain 46 (ANKRD46):
ccctcccctccgcccgtcaccgcctccttgaagctgccgctgtcgctgctgctcgttcgagtcgca
gatccttgccagcacattacagaatatttttgttgaaccttcttgagaattcagagaaactgctga
gtgaccactgaacgaaaagatctaatcttaaggcttacgcctcactttgatgcccaggctggagtg
ctgtggctcaatcacagctcatcgcaacctcgacctcccgggctcaagtgatcctctcacctcagc
gtcccgaacaggcgtgttccatccaccacatcagaacaatg (Seq ID No: 1242)

*Homo sapiens* Ras and Rab interactor-like (RINL):
tcctctctccacttcctgctactgcaggcctctcctccgagaacagaggccaggtcatgactcact
ggcttcctgcaacctgacgatggcccagccagaagacaaggcacctgaagtccccacagagggggt
gaggtgaacaaagcagacaggacccctctaggggtcctcagcaccctagagccacttactcgcctg
cagaggacatggggggtgtggcatgtgccagagctggatacccaggatgcggaggcccttgtgggg
ctgtggccactagggagtttcttggtcacaggacgtgaccccagccaggccctggtgttgaggtca
ggacctttaccaggagaagtcaatacctaccagatccagaagattcccagaggtgtgtccctggaa
tcctccaacctctgcatg (Seq ID No: 1243)

*Homo sapiens* embigin (EMB):
ccgccttttcttcagcgtcctacccgcggcactggctgcgagcgccgggccacctgcgagtgtgcg
cagggactctggacacccgcggcggcgagctgagggagcagtctccacgaggacccaggcggaccc
tctggcgccatg (Seq ID No: 1244)

*Homo sapiens* MMS22-like, DNA repair protein (MMS22L):
ccgcctttccggagcgcgggcgcgcggtggcgggaatttcgcctgtttgcggtttagaccccaaag
attcctgttggtggtctgggtcacaggaggcaggtttcgggagctggaaatgtgagcgggtacgac
aggcaccgcgggtaaccgacgccccgggtccttgctgcagccgggtacgcgggataccggcacccc
gccttctccgcccgagtgctgccaggcgtgggcctggaatctcttcacaccttctctttggagccc
ttaatgatacgacgaaccccaagtgtttcagaacatgaagtaaacaatg
(Seq ID No: 1245)

*Homo sapiens* chromosome 19 open reading frame 54 (C19orf54):
actcctttccttttttccagtggttatcgcggcgcccaccggcctctgatctctgagtcttctccaa
cccacagacgttttttgttgctctggttccaggaccttctccacaactaggccattttccctgcca
ggtgtccttttttgacctcttgacctctgactcaaagggcctgctccccctcatgtcttcggcctgg
agaagagccagctcctgaaggaggcctttgataaggccggcccggtccccaagggcagagaagatg
tgaagaggcttctgaaactacacaaggaccggttccgaggtgacctgcggtggatcctcttctgtg
cagacctgccgtccctcatccaagaaggccctcaatg (Seq ID No: 1246)

*Homo sapiens* zinc finger protein 621 (ZNF621):
cgcccttccggctcggcctttagttagtgaccagctcctcggcgttctgcagagcgtgggtttcag
cgagttctacgtgccaggtccgcccggtgccggcttcctcgctgcccctggcggctcgtcagcccc
cactacccctgaacttggtcccaatggcggcccgcccctccttcacccggaccgtgggcatctggg
cctcgccgaagccgtcaaggtggctgctcgggcttctagagcccgtgtccagccctttgccaccga
ggcctgatcctcttttctgccctaaagaacttgccctgacagcctctggctcccgctcttgaggat
cttgcttgtccaaacccagaagacagtgcatgaagccaggggacatccgccatg
(Seq ID No: 1247)

*Homo sapiens* family with sequence similarity 73, member A
(FAM73A): ccgccttctccatg (Seq ID No: 1248)

*Homo sapiens* RNA binding motif protein 43 (RBM43):
ccgcccttttcttcgtagcctccaagggagctggaacaaaaaacgaaaccaaaacctgcctgctcg
ctcctctccccatcgcctgcgttccgctggttgtgggctttctgcggccgctgagggcgcgtctcc
cctccgccatg (Seq ID No: 1249)

*Homo sapiens* spermatogenesis and centriole associated 1 (SPATC1):
caccctccttcagcccaggcaaggcctggggccctgggcagcctccaggtgcagtgccctcccgtg
ggccgcacccttgccactgccccagggcatg (Seq ID No: 1250)

*Homo sapiens* carbonic anhydrase XIII (CA13):
ctttctcttccttccaccccgagggaccatg (Seq ID No: 1251)

*Homo sapiens* transglutaminase 2
(C polypeptide, protein-glutamine-gamma-glutamyltransferase)
(TGM2):
cgctctccgcctcggcagtgccagccgccagtggtcgcacttggagggtctcgccgccagtggaag
gagccaccgcccccgcccgaccatg (Seq ID No: 1252)

*Homo sapiens* NOP2/Sun domain family, member 4 (NSUN4):
atttcctttccctttttcgctcgtgtcccgccgggtggcgctcaccacctccccggaacacgcga
gtctcctgtcgcggttccggtcggaattaccccgtggagcacgccgatatg
(Seq ID No: 1253)

*Homo sapiens* mitochondrial ribosome recycling factor (MRRF):
gagtctttccttagtaacctgggcgatagctgtggatgtttccaaggattgtcttcagtcatg
(Seq ID No: 1254)

-continued

| SEQUENCES: |
| --- |

*Homo sapiens* PHD finger protein 17 (PHF17):
cttcctccataacaagccaaacgccagaccgagagtgcctccgtgcgcgagtgcccggtgtgtgcg
cgccggcgagagcaggggcccgcccggctccccgcccgccgcggcccgaactcatgcagctccgag
cgagcgagcggcgcccagcccagcgcctcggccgaacccctccgcagcaggctgcctgctgtttcc
cggggagatcatg (Seq ID No: 1255)

*Homo sapiens* prolylcarboxypeptidase (angiotensinase C) (PROP):
cctccttttcgccctcccacccgcactgcagtctccagcctgagccatg
(Seq ID No: 1256)

*Homo sapiens* proteolipid protein 1 (PLP1):
aagcccttttcattgcaggagaagaggacaaagatactcagagagaaaaagtaaaagaccgaagaa
ggaggctggagagaccaggatccttccagctgaacaaagtcagccacaaagcagactagccagccg
gctacaattggagtcagagtcccaaagacatg (Seq ID No: 1257)

*Homo sapiens* coiled-coil domain containing 80 (CCDC80):
cagccttctcactcctcactgagtccactctgaacgtgctaaaatgggaaggaggcggtgttttgc
tgatctgttaaattcttagtgaagtttccttgatttccagtggctgctgttgtttgagtttggttt
ggagcaaaactgaggtagtcctaacatttctgggactgaatccaggcaagagaaagaagaaaaaga
agaagaaaaagaggaggaaaaaggtagggagaaataaagggaggagagagaagcacagtgaaagaaaa
aaaaagtcccttttcgacatcacattcctgtgttttccctcagcctggaaaacatattaatcccag
tgcttttacgcccggaaacaaagagactaagccagactatggggaaagggagataagaaggatcc
tggaactttaaagagggaaagagtgagattcagaaatcgccaggactggactttaagggacgtcct
gtgtcagcacaagggactggcacacacagacacacgagaccgaggagaaactgcagacaaatggag
atacaaagacttagaaggacagctcctttcacctcatcctacttgtccagaaggtaaaaagacaca
gccagaaagaaaaggcatcggctcagctctcagatcaggacaggctgtggatctgtggcggtactc
tgaaagctggagctgcagcacaccccttttgtattgctcaccctcggtaaagagagagagggctgg
gaggaaaagtagttcatctaggaaactgtcctgggaaccaaacttctgatttcttttgcaaccctc
tgcattccatctctatgagccaccattggattacacaatg (Seq ID No: 1258)

*Homo sapiens* chromosome 20 open reading frame 44 (C20orf44):
cgacctctttgcgcctgcgccccccttgccagtctttcgccggcaaaaggaggacgtagaaaaggg
gacaccggaaactcactcttcacccggaaatggttattgaggaacatg (Seq ID No: 1259)

*Homo sapiens* tryptophanyl tRNA synthetase 2, mitochondrial
(WARS2): cgcccttctcaagatg (Seq ID No: 1260)

*Homo sapiens* myotubularin related protein 2 (MTMR2):
ctttccctgtgctgcccctgccgcgcgatggagaagagctcgagctgcgagagtcttggctcccag
ccggcggcggctcggccgcccagcgtggactccttgtccagttaatgtgttaagagccattgacat
ttgaagatcatcagaagtgaagataaaacatctcaaaaattataattgcctccacttctcattcag
agaattcagtgcatacaaaatcagcttctgttgtatcatcagattccatttcaacttctgccgaca
acttttctcctgatttgaggagggagtctcgctctatcccctaggctggagtgcattggcgccatc
tcggctcatttgcaacctctgtctcccgggttcaagcgattctcctgcctcagcttcccgaggagc
tgggattacaggtcctgagggagtctaacaagttagcagaaatg (Seq ID No: 1261)

*Homo sapiens* reticulon 3 (RTN3):
cgccctctagctgcgctcggctgagtcagtcagtctgtcggagtctgtcctcggagcaggcggagt
aaagggacttgagcgagccagttgccggattattctatttcccctccctctctcccgccccgtatc
tcttttcacccttctcccaccctcgctcgcgtagccatg (Seq ID No: 1262)

*Homo sapiens* G protein-coupled receptor 56 (GPR56):
gtccctccctctccgcactagctgtctgccctgccctgccgtaggagatgggctgggagcctccca
cgctctccagctcactcggcaggcagcggggaccagggctggcaggttaagcctctgggggtggat
cctgaaaggtggtccagccgcctggccctgcgtgggaccctccacctggcagcagacagggtctcg
ctctgtcacacaggctggagtgcagtggtgtgatcttggctcatcgtaacctccacctcccgggtt
caagtgattctcatgcctcagcctcccgagtagctgggattacaggtggtgacttccaagagtgac
tccgtcggaggaaaatg (Seq ID No: 1263)

*Homo sapiens* immunoglobulin superfamily containing leucine-rich repeat
(ISLR):
gctcctccctgccgcctcctctcagtggatggttccaggcaccctgtctggggcagggagggcaca
ggcctgcacatcgaaggtggggtgggaccaggctgcccctcgccccagcatccaagtcctcccttg
ggcgcccgtggccctgcagactctcagggctaaggtcctctgttgctttttggttccaccttagaa
gaggctccgcttgactaagagtagcttgaaggaggcaccatg (Seq ID No: 1264)

*Homo sapiens* glycoprotein M6A (GPM6A):
atttcttttccccattttaaatgcaaagcaagacttgtgaatcatagtgtctctgctcctgggatt
cagaccaaatttcccccaaaattctcaggctatttgtttgaatacctgcttacagtggtacacaa
tgggcagctttgagaagaaaaattgataatcttcacggaagagtaatttgaatgaaattacacttg
acagcctgtctccaagcaaacaagaggaacgagggagcctgagctaagctctgaggacttgcccaa
gccactgctgttggagcttcccaggaaaaaaaaaaaaaaaaaaaaaaaaaaaaaaaaaaaaaaaac
accagtttttccaacatctaattgagcttttgattaattccgtgtaccagattctactgaagaaag
gtagccatg (Seq ID No: 1265)

-continued

SEQUENCES:

*Homo sapiens* splicing factor 1 (SF1):
ctccctctttgtgcgtctcgcgccgccgccgcccgccgcgtgagaggacgggctccgcgcgctccg
gcagcgcattcgggtcccctcccccgggaggcttgcgaaggagaagccgccgcagaggaaaagca
ggtgccggtgcctgtccccgggggcgccatg (Seq ID No: 1266)

*Homo sapiens* cell cycle associated protein 1 (CAPRIN1):
ccgcccctcgcgacccagagggctgctggctggctaagtccctcccgctcccggctctcgcctcac
taggagcggctctcggtgcagcgggacagggcgaagcggcctgcgcccacggagcgcgcgacactg
cccggaagggaccgccacccttgccccctcagctgcccactcgtgatttccagcggcctccgcgcg
cgcacgatg (Seq ID No: 1267)

*Homo sapiens* hypothetical protein FLJ90297 (LOC388152):
ctgccctcttgcgtgccccggccacccccgggcggcttgtagccggtgcgcggggtggctggggct
acgtgcagagctgtcgcggagccggaacagcagcggtgaagcccctcggctcggccgagaccgccg
tgcccattgctcgcctcggttgccgccgctttagccgcagccgctgctgccgccgccgggggagag
gcagcctattgtctttctccgcggcgaaggtgaggagctgtctcggctcggcccgcgggggagccc
cgggagccgcacggagatggaggaggacatctggacagtgagcaggaggcgcctcggcccatg
(Seq ID No: 1268)

*Homo sapiens* kelch-like ECH-associated protein 1 (KEAP1):
cgccctctccccgcctcctttcgggcgtcccgaggccgctccccaaccgacaaccaagaccccgc
aggccacgcagccctggagccgaggccccccgacggcggaggcgcccgcgggtcccctacagccaa
ggtccctgagtgccagaggtggtggtgttgcttatcttctggaaccccatg
(Seq ID No: 1269)

*Homo sapiens* F-box protein 38 (FBX038):
ctccctctcaaccacaataacaggcggagggtcggcgtaggtactttgaactcaagtaaacaaaag
ggaagatttctcgttgatactggagactgcacaacaatg (Seq ID No: 1270)

*Homo sapiens* musculoskeletal, embryonic nuclear protein 1
(MUSTN1):
agatcttttccagcagctgctgcctgccagagaggcgccttcagagacccagcgcttacacaatac
ccaccatg (Seq ID No: 1271)

*Homo sapiens* QKI, KH domain containing, RNA binding (QKI):
cctcctctccggcggcggcggcggcggcggcgggcggagtgagctgcggagcctggaatatg
(Seq ID No: 1272)

*Homo sapiens* protein phosphatase 1, catalytic subunit, beta isoform
(PPP1CB):
gggcctctcttgtttatttatttattttccgtgggtgcctccgagtgtgcgcgcgctctcgctacc
cggcggggaggggggtgggggggagggcccgggaaaaggggggagttggagccggggtcgaaacgccgc
gtgacttgtaggtgagagaacgccgagccgtcgccgcagcctccgccgccgagaagcccttgttcc
cgctgctgggaaggagagtctgtgccgacaagatg (Seq ID No: 1273)

*Homo sapiens* methyltransferase like 21B (METTL21B):
cagcctctaccccgctccggatccgggatctgagcgccggccgcggtgcccaggcactcccttggc
gggccggatg (Seq ID No: 1274)

*Homo sapiens* adaptor-related protein complex 3, mu 1 subunit
(AP3M1):
cggccttctcggcttctccagcttcggtaggagaggatccggcgccgaatcactgactggcacagg
tgttgggatagtgtctcacttggtcacccaggctggagtgcagtggcgcaatcttagctctctaca
gcgtcgatcttcctcctgggctcaagcaattctcctgcttcatcctcctgagtacctaggactaca
gaaaatg (Seq ID No: 1275)

*Homo sapiens* muscleblind-like splicing regulator 1 (MBNL1):
cagtcttttcactgcagctgaatgagttgtggcgcccacaatgctcccatgacaaggagctgacaa
gttccattttccgtcgcgggcatcttggaatcatgactcccacaatgccttgggcacttggtcgac
agtggggccgcctctgaaaaaaaaatgtgagaggttggtactaagaagtgcctttcctgacgtctc
tgctgcttggaaccgcttctagagcagtctctgcttttgccttgcttgctgccagctagactgtga
cgacagcacatccaccctccacctctagcccagacacccccatttctacttataatcaagagaaaa
gctctaagtatctggcattgccctaggctgctttagtgttaaaagaaaagtttgctgaaaaagtaa
gatatcttctgccaggaaatcaaggaggaaaaaaaaaatcattttctcgattttgctctaaactgc
tgcatctgtctatgccaaactaatcaataccgattgcaccaccaaactccattgcaaattcagctg
tgaggagattccctttcagacaactttgctgaaagcagcttggaaattcggtgtcgaagggtctgc
cacgttttcatgcttgcattttgggctccaaattggcactgggaaggggttactgagagcacaagg
ctgataccaggccctacttttaaacgttcatctacttacaatcctagtatttctctaaaaaccaaa
acctctttgaattaacagtttcatgctgtgaatttctagtgggagatcttttccttgatattgacg
acacaattttccatgtacttttaaagcagggagtggggaaaagtattttgaggggacattttcatc
atcagttcagcttttttttttggttgttgctctttttggggggggttgggtttgttggtttcact
gaaacatttaactacctgtaaaatctaaacatg (Seq ID No: 1276)

*Homo sapiens* lipid phosphate phosphatase-related protein type 1
(LPPR1):
cagccttttgctctttcctttcattaaacaaacaggagatcctgaaacctggaccctgtgcaagct
gcagcgccaggaggaggcagcggaggaagcagagcgcgggatgggcgcccagcggcatctgtgatc -continued

SEQUENCES:

ccgcgcacctccgccccacgggcgcgcgcacaaacacggacacacacatacacacactcgcgcaca
cactcgcacaaacacacactcgtacacgcccgcgccgctcgctcgccggcttgctctcccacgcaa
gcggaatgcagcagcgcctggagagcgtgtctcggaccgccgcctgaatgtacctcgctcccggga
gccggacggcccagtagggcgcactggaggacgctccgctgcgggagcctggacagtttttgacgg
tgcagtcttgctatatggtgtgagaaatg (Seq ID No: 1277)

Homo sapiens muscleblind-like splicing regulator 2 (MBNL2):
ctgtctttgcttcatcatctgaaggtaaaattttccagatacggcagacggctttcagagtacaat
aaacagggaatgagaactatttacatggaagtttctttctcatgatgcggtggagaagcctcggcc
acttggttctgccagatgttcctggggttactgtaaatgggaaggacaggcagagctaaacaaggt
ttatcatttaaaagtgcctgtgtgaagtcacttttgctggaaaactgcagcttgggagctttcttt
gtattcacatcccactcttctgtcaagtacactttaccctgaccttatgagtggatgaagatacct
cagttgtctgactttgccaattgcttaatttcagaatttaaaaaggggaaagaaaaacatcctgct
aaaatatgaacatctgagtgtcttattttccaacatcgtcaatagctgtgagcgtcagcattaaat
attctcccaaggagtgccatgatattgaagtcactttattaataacagctgtatctgcaaaacagt
caagagactcggacgttgaaagccagagatgacactgagcatgcttttattgcggcctaccatctt
taagtgggacatattgattgatgagtgattgcctgtccatacactctctcatcatcctgttccttg
gattggacttcactaagcaatttatcactcaccttcagacttacatgtgggagttttcacaacagt
agttttggaatcattagaacttggattgatttcatcatttaacagaaacaaacagcccaaattact
ttatcaccatg (Seq ID No: 1278)

*Homo sapiens* chromosome 3 open reading frame 25 (C3orf25):
gcgcctttcgcacgacttggagttacggtttatctgataccgcggtacccctacgcaagcaagccc
acatcgacacacattcacacacgcccttcagcacccccctcccagcaccacgaccatg
(Seq ID No: 1279)

*Homo sapiens* testis expressed 19 (TEX19):
cctcctcctttccctgggtgcccacatgaacagagacaccaggatgctctcctgagaccacagcaa
ctgcagaagctgaagacatttccagaagttcaagcttccaccctctgcaggtccccactgagctgg
gacccaggtcatccaccccaccccaaatccctggataggaaacccctttctcctcctgctccttgt
ccccttcatccctgccgcccagcatcctactggcctcagcacctgtggccagaccgtccaagatcc
tctgaaggcccagctcttgctgtccaccccggcagtaggcaggcagcctggccatg
(Seq ID No: 1280)

*Homo sapiens* protein kinase C, beta (PRKCB):
gcctccctcccccgcagctggggccagcggtgccaagcgcagctggacgagcggcagcagctgggc
gagtgacagccccggctccgcgcgccgcggccgccagagccggcgcaggggaagcgcccgcggccc
cgggtgcagcagcggccgccgcctcccgcgcctccccggcccgcagcccgcggtcccgcggccccg
gggccggcacctctcgggctccggctccccgcgcgcaagatg (Seq ID No: 1281)

*Homo sapiens* protein kinase N1 (PKN1):
ccctccctccgcgcggggacccctggcgggcggcaggaggacatg (Seq ID No: 1282)

*Homo sapiens* hemochromatosis type 2 (juvenile) (HFE2):
ccttctctggttccctgacctcagtgagacagcagccggcctggggacctggggggagacacggagg
acccccctggctggagctgacccacagagtagggaatcatggctggagaattggatagcagagtaat
gtttgacctctggaaacatcacttacagggcttccggtcaaaattcactaggtaggagggtcatca
gctgggaagaaccggcgcctgggaaacctggctggataggtatg (Seq ID No: 1283)

*Homo sapiens* ribosomal protein L9 (RPL9):
cgttctttctttgctgcgtctactgcgagaatg (Seq ID No: 1284)

*Homo sapiens* ribosomal protein L3 (RPL3):
cggcctctaccggcgggatttgatggcgtgatg (Seq ID No: 1285)

*Homo sapiens* ribosomal protein. L4 (RPL4):
acttcctttcctgtggcagcagccgggctgagaggagcgtggctgtctcctctctccgccatg
(Seq ID No: 1286)

*Homo sapiens* ribosomal protein L5 (RPL5):
tggccctttcccaccccctagcgccgctgggcctgcaggtctctgtcgagcagcggacgccggtc
tctgttccgcaggatg (Seq ID No: 1287)

*Homo sapiens* ribosomal protein L6 (RPL6): aattctctttcccatcttgcaa-
gatg (Seq ID No: 1288)

*Homo sapiens* ribosomal protein L7 (RPL7): cttcctctttttccggctggaac-
catg (Seq ID No: 1289)

*Homo sapiens* ribosomal protein L7a (RPL7A):
ctttcctttctctctcctcccgccgcccaagatg (Seq ID No: 1290)

*Homo sapiens* ribosomal protein L11 (RPL11): ctttctcttcctgctctccat-
catg (Seq ID No: 1291)

-continued

| SEQUENCES: |
|---|

*Homo sapiens* ribosomal protein L12 (RPL12):
cggcctctcggctttcggctcggaggaggccaaggtgcaacttccttcggtcgtcccgaatccggg
ttcatccgacaccagccgcctccaccatg (Seq ID No: 1292)

*Homo sapiens* ribosomal protein L13 (RPL13):
gcttcctttccgctcggctgttttcctgcgcaggagccgcagggccgtaggcagccatg
(Seq ID No: 1293)

*Homo sapiens* ribosomal protein L23 (RPL23):
acttcctttttttctttttttccggcgttcaagatg (Seq ID No: 1294)

*Homo sapiens* ribosomal protein L18 (RPL18):
cgttctctctttccggacctggccgagcaggaggcgccatcatg (Seq ID No: 1295)

*Homo sapiens* ribosomal protein L18a (RPL18A):
acttccttttgcgggtggcggcgaacgcggagagcacgccatg (Seq ID No: 1296)

*Homo sapiens* ribosomal protein L19 (RPL19):
agctctttcctttcgctgctgcggccgcagccatg (Seq ID No: 1297)

*Homo sapiens* ribosomal protein L21 (RPL21):
gcctctttcctttcggccggaaccgccatcttccagtaattcgccaaaatg
(Seq ID No: 1298)

*Homo sapiens* ribosomal protein L22 (RPL22):
acctccctttctaactccgctgccgccatg (Seq ID No: 1299)

*Homo sapiens* ribosomal protein L23a (RPL23A): agacccttttcacaagatg
(Seq ID No: 1300)

*Homo sapiens* ribosomal protein L17 (RPL17):
cgctcttcctctttccctaagcagcctgagggttgactggattggtgaggcccgtgtggctacttc
tgtggaagcagtgctgtagttactggaagataaaagggaaagcaagcccttggtgggggaaagtat
ggctgcgatgatggcatttcttaggacacctttggattaataatgaaaacaactactctctgagca
gctgttcgaatcatctgatatttatactgaatgagttactgtaagtacgtattgacagaattacac
tgtactttcctctaggtgatctgtgaaaatg (Seq ID No: 1301)

*Homo sapiens* ribosomal protein L24 (RPL24):
ttctctctttcttttcgccatcttttgtctttccgtggagctgtcgccatg
(Seq ID No: 1302)

*Homo sapiens* ribosomal protein L26 (RPL26):
agttctcttcccttttgcggccatcaccgaagcgggagcggccaaaatg
(Seq ID No: 1303)

*Homo sapiens* ribosomal protein L27 (RPL27):
ctttcctttttgctggtagggccgggtggttgctgccgaaatg (Seq ID No: 1304)

*Homo sapiens* ribosomal protein L30 (RPL30):
aagtctttcctttctcgttccccggccatcttagcggctgctgttggttgggggccgtcccgctcc
taaggcaggaagatg (Seq ID No: 1305)

*Homo sapiens* ribosomal protein L27a (RPL27A):
ccttcctttttcgtctgggctgccaacatg (Seq ID No: 1306)

*Homo sapiens* ribosomal protein L28 (RPL28):
cttcctctttccgtctcaggtcgccgctgcgaagggagccgccgccatg
(Seq ID No: 1307)

*Homo sapiens* ribosomal protein L29 (RPL29):
cagccccttcctcttccggttctaggcgcttcgggagccgcggcttatggtgcagacatg
(Seq ID No: 1308)

*Homo sapiens* ribosomal protein L31 (RPL31):
cgctcttcctttccaacttggacgctgcagaatg (Seq ID No: 1309)

*Homo sapiens* ribosomal protein L32 (RPL32):
ccgtcccttctctcttcctcggcgctgcctacggaggtggcagccatctccttctcggcatcatg
(Seq ID No: 1310)

*Homo sapiens* ribosomal protein L35a (RPL35A):
cgtccttctcttaccgccatcttggctcctgtggaggcctgctgggaacgggacttctaaaaggaa
ctatg (Seq ID No: 1311)

*Homo sapiens* ribosomal protein L37 (RPL37):
ccttctcttccggtctttctggtctcggccgcagaagcgagatg (Seq ID No: 1312)

-continued

| SEQUENCES: |
|---|
| *Homo sapiens* ribosomal protein L37a (RPL37A):<br>gcgtctcttcctttctgggctcggacctaggtcgcggcgacatg (Seq ID No: 1313) |
| *Homo sapiens* ribosomal protein L38 (RPL38):<br>cgttctttttcgtccttttccccggttgctgcttgctgtgagtgtctctagggtgatacgtgggtg<br>agaaaggtcctggtccgcgccagagcccagcgcgcctcgtcgccatg (Seq ID No: 1314) |
| *Homo sapiens* ribosomal protein L39 (RPL39):<br>ccctcctcttcctttctccgccatcgtggtgtgttcttgactccgctgctcgccatg<br>(Seq ID No: 1315) |
| *Homo sapiens* ribosomal protein, large, P0 (RPLP0):<br>aggcccttctctcgccaggcgtcctcgtggaagtgacatcgtctttaaaccctgcgtggcaatccc<br>tgacgcaccgccgtgatg (Seq ID No: 1316) |
| *Homo sapiens* ribosomal protein, large, P1 (RPLP1):<br>cggtccttccgaggaagctaaggctgcgttggggtgaggccctcacttcatccggcgactagcacc<br>gcgtccggcagcgccagccctacactcgcccgcgccatg (Seq ID No: 1317) |
| *Homo sapiens* ribosomal protein, large, P2 (RPLP2):<br>ccttcctttcctccctgtcgccaccgaggtcgcacgcgtgagacttctccgccgcctccgccgca<br>gacgccgccgcgatg (Seq ID No: 1318) |
| *Homo sapiens* ribosomal protein S3 (RPS3):<br>acttcctttcctttcagcggagcgcggcggcaagatg (Seq ID No: 1319) |
| *Homo sapiens* ribosomal protein S3A (RPS3A):<br>ccgccctttggctctctgaccagcaccatg (Seq ID No: 1320) |
| *Homo sapiens* ribosomal protein S4, X-linked (RPS4X):<br>ggtcctctttccttgcctaacgcagccatg (Seq ID No: 1321) |
| *Homo sapiens* ribosomal protein S4, Y-linked 1 (RPS4Y1):<br>gattctcttccgtcgcagagtttcgccatg (Seq ID No: 1322) |
| *Homo sapiens* ribosomal protein S5 (RPS5):<br>ttttcttcccagttaaaagtgttggcccgcggcgcgcggcctcttcctgtctgtaccagggcggcg<br>cgtggtctacgccgagtgacagagacgctcaggctgtgttctcaggatg<br>(Seq ID No: 1323) |
| *Homo sapiens* ribosomal protein S6 (RPS6):<br>ggccctcttttccgtggcgcctcggaggcgttcagctgcttcaagatg (Seq ID No: 1324) |
| *Homo sapiens* ribosomal protein S7 (RPS7):<br>gggtctcttcctaagccggcgctcggcaagttctcccaggagaaagccatg<br>(Seq ID No: 1325) |
| *Homo sapiens* ribosomal protein S8 (RPS8):<br>gtttctctttccagccagcgccgagcgatg (Seq ID No: 1326) |
| *Homo sapiens* ribosomal protein S9 (RPS9):<br>gcgcctctttctcagtgaccgggtggtttgcttaggcgcagacggggaagcggagccaacatg<br>(Seq ID No: 1327) |
| *Homo sapiens* ribosomal protein S10 (RPS10):<br>gctccttcctttccagccccggtaccggaccctgcagccgcagagatg (Seq ID No: 1328) |
| *Homo sapiens* ribosomal protein S11 (RPS11):<br>ctgccccttttcttttttcaggcggccgggaagatg (Seq ID No: 1329) |
| *Homo sapiens* ribosomal protein S12 (RPS12):<br>aggcctctttccctgccgccgccgagtcgcgcggaggcggaggcttgggtgcgttcaagattcaac<br>ttcacccgtaacccaccgccatg (Seq ID No: 1330) |
| *Homo sapiens* ribosomal protein S13 (RPS13):<br>cgctctcctttcgttgcctgatcgccgccatcatg (Seq ID No: 1331) |
| *Homo sapiens* ribosomal protein S15 (RPS15):<br>cgatctcttctgaggatccggcaagatg (Seq ID No: 1332) |
| *Homo sapiens* ribosomal protein S15a (RPS15A):<br>cgtcctctttccgccatctttccgcgccggtgagtagcactctctgagagctccaatttcatccgt<br>ctgccatcggcgccatcctgcaatctaagccacaatg (Seq ID No: 1333) |
| *Homo sapiens* ribosomal protein S16 (RPS16):<br>ctttcctttttccggttgcggcgccgcgcggtgaggttgtctagtccacgctcggagccatg<br>(Seq ID No: 1334) |

-continued

SEQUENCES:

*Homo sapiens* ribosomal protein S19 (RPS19):
cgttccctttcccctggctggcagcgcggaggccgcacgatg (Seq ID No: 1335)

*Homo sapiens* ribosomal protein S20 (RPS20):
ccacccctttctttttgaggaagacgcggtcgtaagggctgaggatttttggtccgcacgctcctg
ctcctgactcaccgctgttcgctctcgccgaggaacaagtcggtcaggaagcccgcgcgcaacagc
catg (Seq ID No: 1336)

*Homo sapiens* ribosomal protein S21 (RPS21):
gcttcctttctctctcgcgcgcggtgtggtggcagcaggcgcagcccagcctcgaaatg
(Seq ID No: 1337)

*Homo sapiens* ribosomal protein S23 (RPS23):
gcttctctctttcgctcaggcccgtggcgccgacaggatg (Seq ID No: 1338)

*Homo sapiens* ribosomal protein S25 (RPS25):
gcttccttttgtccgacatcttgacgaggctgcggtgtctgctgctattctccgagcttcgcaat
g (Seq ID No: 1339)

*Homo sapiens* ribosomal protein S26 (RPS26):
ccgtctcctctctccggtccgtgcctccaagatg (Seq ID No: 1340)

*Homo sapiens* ribosomal protein S27 (RPS27):
cgctcctttccggcggtgacgacctacgcacacgagaacatg (Seq ID No: 1341)

*Homo sapiens* ribosomal protein S28 (RPS28):
actcctctccgccagaccgccgccgcgccgccatcatg (Seq ID No: 1342)

*Homo sapiens* ribosomal protein S29 (RPS29):
gcttcttcctttttacctcgttgcactgctgagagcaagatg (Seq ID No: 1343)

*Homo sapiens* ribosomal protein L15 (RPL15):
agctctttcctttccgtctggcggcagccatcaggtaagccaagatg (Seq ID No: 1344)

*Homo sapiens* ribosomal protein S2 (RPS2):
cgttcttcttttccgacaaaacaccaaatg (Seq ID No: 1345)

*Homo sapiens* ribosomal protein L14 (RPL14):
gggtcttcttccttctcgcctaacgccgccaacatg (Seq ID No: 1346)

*Homo sapiens* ribosomal protein S14 (RPS14):
ctctctttccggtgtggagtctggagacgacgtgcagaaatg (Seq ID No: 1347)

*Homo sapiens* ribosomal protein L10 (RPL10):
gcgcctctttcccttcggtgtgccactgaagatcctggtgtcgccatg (Seq ID No: 1348)

*Homo sapiens* ribosomal protein L10a (RPL10A):
tagtctcttttccggttagcgcggcgtgagaagccatg (Seq ID No: 1349)

*Homo sapiens* ribosomal protein L35 (RPL35):
tcctctttccctcggagcgggcggcggcgttggcggcttgtgcagcaatg
(Seq ID No: 1350)

*Homo sapiens* ribosomal protein L13a (RPL13A):
cctcctccttttccaagcggctgccgaagatg (Seq ID No: 1351)

*Homo sapiens* ribosomal protein L36 (RPL36):
cagcccttccgccacggccgtctctggagagcagcagccatg (Seq ID No: 1352)

*Homo sapiens* ribosomal protein L36a (RPL36A):
gtttctttctttccgcgccgatagcgctcacgcaagcatg (Seq ID No: 1353)

*Homo sapiens* ribosomal protein L41 (RPL41):
tcgcc tttctctcggccttagcgccatttttttggaaacctctgcgccatg
(Seq ID No: 1354)

*Homo sapiens* ribosomal protein S18 (RPS18):
cgctctctcttccacaggaggcctacacgccgccgcttgtgctgcagccatg
(Seq ID No: 1355)

*Homo sapiens* ribosomal protein S24 (RPS24):
ggttctcttttcctccttggctgtctgaagatagatcgccatcatg (Seq ID No: 1356)

*Homo sapiens* ribosomal protein L8 (RPL8):
tttcctctttcggccgcgctggtgaacaggtaggtcatccttgcggccttgcggcatg
(Seq ID No: 1357)

-continued

SEQUENCES:

*Homo sapiens* ribosomal protein L34 (RPL34):
cttcctcttccggggacgttgtctgcaggtatg (Seq ID No: 1358)

*Homo sapiens* ribosomal protein S17 (RPS17):
gtttcctcttttaccaaggacccgccaacatg (Seq ID No: 1359)

*Homo sapiens* ribosomal protein SA (RPSA):
ctgtcttttccgtgctacctgcagaggggtccatacggcgttgttctggattcccgtcgtaactta
aagggaaattttcacaatg (Seq ID No: 1360)

*Homo sapiens* eukaryotic translation initiation factor 3, subunit C (EIF3C):
cttctctctcggcgtttccgctgtcagggccctgcggtgtgactcgcgggctcagctggtccggcc
gtagcacctccgcgccgtcgccatg (Seq ID No: 1361)

*Homo sapiens* poly(A) binding protein, cytoplasmic 1 (PABPC1):
cgctctcctcctctcacggaaaggtcgcggcctgtggccctgcgggcagccgtgccgagatg
(Seq ID No: 1362)

*Homo sapiens* tubulin, beta 1 class VI (TUBB1):
cactcccttccaaaagcatgacaggcagaaagcagagaagggccaggactggctgagggcggggag
ctgggcctctggggtggacacacccttggtcacattgtgagggtagcttggttggccagtcccacc
actgcagtgaccacagttgtgttgggctcacaccagtgaaccgaagctctggattctgagagtctg
aggattccgtgaagatctcagacttgggctcagagcaaggatg (Seq ID No: 1363)

PpLuc(GC) - A64N64
GGGAGAAAGCTTGAGGATGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGTAGAT
CTAAAAAAAAAAAAAAAAAAAAAAAAAAAAAAAAAAAAAAAAAAAAAAAAAAAAAAAAAA
AAAAAATGCATCCCCCCCCCCCCCCCCCCCCCCCCCCCCCCCCCAAAGGCTCTTTTCAGAGC
CACCAGAATT (SEQ ID No: 1364)

PpLuc(GC) - albumin7 - A64N64
GGGAGAAAGCTTGAGGATGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG -continued

SEQUENCES:

CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGTGCAT
CACATTTAAAAGCATCTCAGCCTACCATGAGAATAAGAGAAAGAAAATGAAGATCAATAG
CTTATTCATCTCTTTTTCTTTTTCGTTGGTGTAAAGCCAACACCCTGTCTAAAAAACATA
AATTTCTTTAATCATTTTGCCTCTTTTCTCTGTGCTTCAATTAATAAAAAATGGAAAGAA
CCTAGATCTAAAAAAAAAAAAAAAAAAAAAAAAAAAAAAAAAAAAAAAAAAAAAAAAAAA
AAAAAAAAAAAAATGCATCCCCCCCCCCCCCCCCCCCCCCCCCCCCCCCCCAAAGGCTCTTT
TCAGAGCCACCAGAATT (SEQ ID No: 1365)

RPL32RPL32 - PpLuc(GC) - A64N64
GGGGCGCTGCCTACGGAGGTGGCAGCCATCTCCTTCTCGGCATCAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTAGATCTAAAAAAAAAAAAAAAAAAAA
AAAAAAAAAAAAAAAAAAAAAAAAAAAAAAAAAAAAAAAAAAAAATGCATCCCCCCCCCCC
CCCCCCCCCCCCCCCCCCCCCAAAGGCTCTTTTCAGAGCCACCAGAATT (SEQ ID No: 1366)

RPL32 - PpLuc(GC) - albumin7 - A64N64
GGGGCGCTGCCTACGGAGGTGGCAGCCATCTCCTTCTCGGCATCAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC -continued

SEQUENCES:

GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTGCATCACATTTAAAAGCATCTCAGCC
TACCATGAGAATAAGAGAAAGAAAATGAAGATCAATAGCTTATTCATCTCTTTTTCTTTT
TCGTTGGTGTAAAGCCAACACCCTGTCTAAAAAACATAAATTTCTTTAATCATTTTGCCT
CTTTTCTCTGTGCTTCAATTAATAAAAAATGGAAAGAACCTAGATCTAAAAAAAAAAAAA
AAAAAAAAAAAAAAAAAAAAAAAAAAAAAAAAAAAAAAAAAAAAAAAAAAATGCATCCCC
CCCCCCCCCCCCCCCCCCCCCCCCCCCAAAGGCTCTTTTCAGAGCCACCAGAATT (SEQ ID No: 1367)

5'UTR of human ribosomal protein Large 32 (RPL32) lacking the 5' terminal oligopyrimidine tract
GGCGCTGCCTACGGAGGTGGCAGCCATCTCCTTCTCGGCATC (SEQ ID No: 1368)

Human albumin 3'UTR
CATCACATTT AAAAGCATCT CAGCCTACCA TGAGAATAAG AGAAAGAAAA TGAAGATCAA
AAGCTTATTC ATCTGTTTTT CTTTTTCGTT GGTGTAAAGC CAACACCCTG TCTAAAAAAC
ATAAATTTCT TTAATCATTT TGCCTCTTTT CTCTGTGCTT CAATTAATAA AAAATGGAAA
GAATCT (SEQ ID No: 1369)

3'UTR of *Homo sapiens* hemoglobin, alpha 1 (HBA1)
gctggagcctcggtggccatgcttcttgccccttgggcctccccccagcccctcctccccttcctg
cacccgtacccccgtggtctttgaataaagtctgagtgggcggc (SEQ ID No: 1370)

3'UTR of *Homo sapiens* hemoglobin, alpha 2 (HBA2)
gctggagcctcggtagccgttcctcctgcccgctgggcctcccaacgggccctcctcccctccttg
caccggcccttcctggtctttgaataaagtctgagtgggcag (SEQ ID No: 1371)

3'UTR of *Homo sapiens* hemoglobin, beta (HBB)
Gctcgctttcttgctgtccaatttctattaaaggttcctttgttccctaagtccaactactaaact
gggggatattatgaagggccttgagcatctggattctgcctaataaaaaacatttattttcattgc
(SEQ ID No: 1372)

3'UTR of *Homo sapiens* tyrosine hydroxylase (TH)
gtgcacggcgtccctgagggcccttcccaacctcccctggtcctgcactgtcccggagctcaggcc
ctggtgaggggctgggtcccgggtgcccccatgccctccctgctgccaggctcccactgcccctg
cacctgcttctcagcgcaacagctgtgtgtgcccgtggtgaggttgtgctgcctgtggtgaggtcc
tgtcctggctcccagggtcctgggggctgctgcactgccctccgcccttccctgacactgtctgct
gccccaatcaccgtcacaataaaagaaactgtggtctcta (SEQ ID No: 1373)

3'UTR of *Homo sapiens* arachidonate 15-lipoxygenase (ALOX15)
gcgtcgccaccctttggttatttcagccccccatcacccaagccacaagctgaccccttcgtggtta
tagccctgccctcccaagtcccaccctcttcccatgtcccaccctccctagaggggcaccttttca
tggtctctgcacccagtgaacacattttactctagaggcatcacctgggaccttactcctctttcc
ttccttcctcctttcctatcttccttcctctctctcttcctctttcttcattcagatctatatggc
aaatagccacaattatataaatcatttcaagactagaatagggggatataatacatattactccac
acctttttatgaatcaaatatgatttttttgttgttgttaagacagagtctcactttgacacccagg
ctggagtgcagtggtgccatcaccacggctcactgcagcctcagcgtcctgggctcaaatgatcct
cccacctcagcctcctgagtagctgggactacaggctcatgccatcatgcccagctaatattttt
tattttcgtggagacggggcctcactatgttgcctaggctggaaataggattttgaacccaaattg
agtttaacaataataaaaagttgttttacgctaaagatggaaaagaactaggactgaactattta
aataaaatattggc (SEQ ID No: 1374)

3'UTR of *Homo sapiens* collagen, type I, alpha 1 (COL1A1)
actccctccatcccaacctggctccctcccacccaaccaactttccccccaacccggaaacagaca
agcaacccaaactgaaccccctcaaaagccaaaaaatgggagacaatttcacatggactttggaaa
atatttttttcctttgcattcatctctcaaacttagttttatctttgaccaaccgaacatgacca
aaaaccaaaagtgcattcaaccttaccaaaaaaaaaaaaaaaaaagaataaataaataacttttt
aaaaaaggaagcttggtccacttgcttgaagacccatgcgggggtaagtccctttctgcccgttgg
gcttatgaaaccccaatgctgccctttctgctcctttctccacaccccccttggggcctcccctcc
actccttcccaaatctgtctccccagaagacacaggaaacaatgtattgtctgcccagcaatcaaa
ggcaatgctcaaacacccaagtggcccccaccctcagcccgctcctgcccgcccagcacccccagg
ccctgggggacctggggttctcagactgccaaagaagccttgccatctggcgctcccatggctctt
gcaacatctccccttcgtttttgaggggtcatgccgggggagccaccagcccctcactgggttcg
gaggagagtcaggaagggccacgacaaagcagaaacatcggatttggggaacgcgtgtcaatccct
tgtgccgcagggctgggcgggagagactgttctgttccttgtgtaactgtgttgctgaaagactac
ctcgttcttgtcttgatgtgtcaccggggcaactgcctgggggcggggatgggggcagggtggaag
cggctccccatttataccaaaggtgctacatctatgtgatgggtggggtggggagggaatcactg
gtgctatagaaattgagatgcccccccaggccagcaaatgttccttttttgttcaaagtctatttt
attccttgatattttcttttttttttttttttttttgtggatggggacttgtgaattttctaaag
gtgctatttaacatgggaggagagcgtgtgcggctccagcccagcccgctgctcactttccaccct
ctctccacctgcctctggcttctcaggcctctgctctccgacctctctcctctgaaaccctcctcc
acagctgcagcccatcctcccggctccctcctagtctgtcctgcgtcctctgtccccgggtttcag
agacaacttcccaaagcacaaagcagtttttccccctaggggtgggaggaagcaaaagactctgta
cctattttgtatgtgtataataatttgagatgttttaattattttgattgctggaataaagcatg
tggaaatgacccaaacataa (SEQ ID No: 1375)

-continued

SEQUENCES:

albumin7 3'UTR
CATCACATTTAAAAGCATCTCAGCCTACCATGAGAATAAGAGAAAGAAAATGAAGATCAATAGCTT
ATTCATCTCTTTTTCTTTTTCGTTGGTGTAAAGCCAACACCCTGTCTAAAAAACATAAATTTCTTT
AATCATTTTGCCTCTTTTCTCTGTGCTTCAATTAATAAAAAATGGAAAGAACCT (SEQ ID No: 1376)

Human albumin 3'UTR + poly(A) sequence
CATCACATTT AAAAGCATCT CAGCCTACCA TGAGAATAAG AGAAAGAAAA TGAAGATCAA
AAGCTTATTC ATCTGTTTTT CTTTTTCGTT GGTGTAAAGC CAACACCCTG TCTAAAAAAC
ATAAATTTCT TTAATCATTT TGCCTCTTTT CTCTGTGCTT CAATTAATAA AAAATGGAAA
GAATCTAGAT CTAAAAAAAA AAAAAAAAAA AAAAAAAAAA AAAAAAAAAA AAAAAAAAAA
AAAAAAAAAA AAAAAA (SEQ ID No: 1377)

Human albumin 3'UTR fragment 1
AAAAGCATCT CAGCCTACCA TGAGAATAAG AGAAAGAAAA TGAAGATCAA AAGCTTATTC
ATCTGTTTTT CTTTTTCGTT GGTGTAAAGC CAACACCCTG TCTAAAAAAC ATAAATTTCT
TTAATCATTT TGCCTCTTTT CTCTGTGCTT CAATT (SEQ ID No: 1378)

Human albumin 3'UTR fragment 2
CATCACATTT AAAAGCATCT CAGCCTACCA TGAGAATAAG AGAAAGAAAA TGAAGATCAA
AAGCTTATTC ATCTGTTTTT CTTTTTCGTT GGTGTAAAGC CAACACCCTG (SEQ ID No: 1379)

Human albumin 3'UTR fragment 3
AAAAGCATCT CAGCCTACCA TGAGAATAAG AGAAAGAAAA TGAAGATCAA AAGCTTATTC
ATCTGTTTTT CTTTTTCGTT GGTGTAAAGC CAACACCCTG TCTAAAAAAC (SEQ ID No: 1380)

Human albumin 3'UTR fragment 4
CAGCCTACCA TGAGAATAAG AGAAAGAAAA TGAAGATCAA AAGCTTATTC ATCTGTTTTT
CTTTTTCGTT GGTGTAAAGC CAACACCCTG TCTAAAAAAC ATAAATTTCT (SEQ ID No: 1381)

Human albumin 3'UTR fragment 5
TGAGAATAAG AGAAAGAAAA TGAAGATCAA AAGCTTATTC ATCTGTTTTT CTTTTTCGTT
GGTGTAAAGC CAACACCCTG TCTAAAAAAC ATAAATTTCT TTAATCATTT (SEQ ID No: 1382)

Human albumin 3'UTR fragment 6
AGAAAGAAAA TGAAGATCAA AAGCTTATTC ATCTGTTTTT CTTTTTCGTT GGTGTAAAGC
CAACACCCTG TCTAAAAAAC ATAAATTTCT TTAATCATTT TGCCTCTTTT (SEQ ID No: 1383)

Human albumin 3'UTR fragment 7
TGAAGATCAA AAGCTTATTC ATCTGTTTTT CTTTTTCGTT GGTGTAAAGC CAACACCCTG
TCTAAAAAAC ATAAATTTCT TTAATCATTT TGCCTCTTTT CTCTGTGCTT (SEQ ID No: 1384)

Human albumin 3'UTR fragment 8
AAGCTTATTC ATCTGTTTTT CTTTTTCGTT GGTGTAAAGC CAACACCCTG TCTAAAAAAC
ATAAATTTCT TTAATCATTT TGCCTCTTTT CTCTGTGCTT CAATTAATAA (SEQ ID No: 1385)

Human albumin 3'UTR fragment 9
ATCTGTTTTT CTTTTTCGTT GGTGTAAAGC CAACACCCTG TCTAAAAAAC ATAAATTTCT
TTAATCATTT TGCCTCTTTT CTCTGTGCTT CAATTAATAA AAAATGGAAA (SEQ ID No: 1386)

Human albumin 3'UTR fragment 10
CAGCCTACCA TGAGAATAAG AGAAAGAAAA TGAAGATCAA AAGCTTATTC ATCTGTTTTT
CTTTTTCGTT GGTGTAAAGC CAACACCCTG TCTAAAAAAC ATAAATTTCT TTAATCATTT
TGCCTCTTTT CTCTGTGCTT CAATTAATAA A (SEQ ID No: 1387)

Human albumin 3'UTR fragment 11
TGAAGATCAA AAGCTTATTC ATCTGTTTTT CTTTTTCGTT GGTGTAAAGC CAACACCCTG
TCTAAAAAAC ATAAATTTCT TTAATCATTT TGCCTCTTTT CTCTGTGCTT CAATTAATAA
A (SEQ ID No: 1388)

Human albumin 3'UTR fragment 12
CTTTTTCGTT GGTGTAAAGC CAACACCCTG TCTAAAAAAC ATAAATTTCT TTAATCATTT
TGCCTCTTTT CTCTGTGCTT CAATTAATAA A (SEQ ID No: 1389)

Human albumin 3'UTR fragment 13
AAGCTTATTC ATCTGTTTTT CTTTTTCGTT GGTGTAAAGC CAACACCCTG TCTAAAAAAC
(SEQ ID No: 1390)

-continued

SEQUENCES:

Albumin7 3'UTR - poly(A) sequence - poly(C) sequence - HL
CATCACATTTAAAAGCATCTCAGCCTACCATGAGAATAAGAGAAAGAAAATGAAGATCAATAGCTT
ATTCATCTCTTTTTCTTTTTCGTTGGTGTAAAGCCAACACCCTGTCTAAAAAACATAAATTTCTTT
AATCATTTTGCCTCTTTTCTCTGTGCTTCAATTAATAAAAAATGGAAAGAACCTAGATCTAAAAAA
AAAAAAAAAAAAAAAAAAAAAAAAAAAAAAAAAAAAAAAAAAAAAAAAAAAAAAAAAAATGCATCCC
CCCCCCCCCCCCCCCCCCCCCCCCCCCCAAAGGCTCTTTTCAGAGCCACCAGAATT (SEQ ID
No: 1391)

Albumin7 3'UTR - poly(A) sequence - poly(C) sequence
CATCACATTTAAAAGCATCTCAGCCTACCATGAGAATAAGAGAAAGAAAATGAAGATCAATAGCTT
ATTCATCTCTTTTTCTTTTTCGTTGGTGTAAAGCCAACACCCTGTCTAAAAAACATAAATTTCTTT
AATCATTTTGCCTCTTTTCTCTGTGCTTCAATTAATAAAAAATGGAAAGAACCTAGATCTAAAAAA
AAAAAAAAAAAAAAAAAAAAAAAAAAAAAAAAAAAAAAAAAAAAAAAAAAAAAAAAAAATGCATCCC
CCCCCCCCCCCCCCCCCCCCCCCCCCCC (SEQ ID No: 1392)

Center, α-complex-binding portion of the 3'UTR of an a-globin gene
GCCCGATGGGCCTCCCAACGGGCCCTCCTCCCCTCCTTGCACCG (SEQ ID NO: 1393)

Histone stem-loop
CAAAGGCTCTTTTCAGAGCCACCA (SEQ ID NO: 1394)

ATP synthase lipid-binding protein, mitochondrial (atp5g2)
tagttt ctcctctcga acgccaggtg gagcaaccgg ccggataccg ccacagccct
ggcaggcggc gctgtgatg (SEQ ID NO: 1395)

RPL35 - PpLuc(GC) - albumin7 - A64N64
GGGGAGCGGGCGGCGGCGTTGGCGGCTTGTGCAGCAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGGCCGATGATCATGAGCGGCTACGTGAACAACCC
GGAGGCCACCAACGCCCTCATCGACAAGGACGGCTGGCTGCACAGCGGCGACATCGCCTA
CTGGGAGGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTGCATCACATTTAAAAGCATCTCAGCCTACCATGA
GAATAAGAGAAAGAAAATGAAGATCAATAGCTTATTCATCTCTTTTTCTTTTTCGTTGGT
GTAAAGCCAACACCCTGTCTAAAAAACATAAATTTCTTTAATCATTTTGCCTCTTTTCTC
TGTGCTTCAATTAATAAAAAATGGAAAGAACCTAGATCTAAAAAAAAAAAAAAAAAAAAA
AAAAAAAAAAAAAAAAAAAAAAAAAAAAAAAAAAAAAAAAAATGCATCCCCCCCCCCCC
CCCCCCCCCCCCCCCCCCCAAAGGCTCTTTTCAGAGCCACCAGAATT (SEQ ID NO: 1396)

RPL21 - PpLuc(GC) - albumin7 - A64N64
GGGGCCGGAACCGCCATCTTCCAGTAATTCGCCAAAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC -continued

SEQUENCES:

GCTGCTCGTGCCGACCCTGTTCAGCTTCTTCGCCAAGAGCACCCTGATCGACAAGTACGA
CCTGTCGAACCTGCACGAGATCGCCAGCGGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTGCATCACATTTAAAAGCATCTCAGCCTACCATGA
GAATAAGAGAAAGAAAATGAAGATCAATAGCTTATTCATCTCTTTTTCTTTTTCGTTGGT
GTAAAGCCAACACCCTGTCTAAAAAACATAAATTTCTTTAATCATTTTGCCTCTTTTCTC
TGTGCTTCAATTAATAAAAAATGGAAAGAACCTAGATCTAAAAAAAAAAAAAAAAAAAAA
AAAAAAAAAAAAAAAAAAAAAAAAAAAAAAAAAAAAAAAAAAATGCATCCCCCCCCCCCC
CCCCCCCCCCCCCCCCCCCCAAAGGCTCTTTTCAGAGCCACCAGAATT (SEQ ID NO: 1397)

ATP5A1 - PpLuc(GC) - albumin7 - A64N64
GGGCGGCTCGGCCATTTTGTCCCAGTCAGTCCGGAGGCTGCGGCTGCAGAAGTACCGCCT
GCGGAGTAACTGCAAAGAAGCTTGAGGATGGAGGACGCCAAGAACATCAAGAAGGGCCCG
GCGCCCTTCTACCCGCTGGAGGACGGGACCGCCGGCGAGCAGCTCCACAAGGCCATGAAG
CGGTACGCCCTGGTGCCGGGCACGATCGCCTTCACCGACGCCCACATCGAGGTCGACATC
ACCTACGCGGAGTACTTCGAGATGAGCGTGCGCCTGGCCGAGGCCATGAAGCGGTACGGC
CTGAACACCAACCACCGGATCGTGGTGTGCTCGGAGAACAGCCTGCAGTTCTTCATGCCG
GTGCTGGGCGCCCTCTTCATCGGCGTGGCCGTCGCCCCGGCGAACGACATCTACAACGAG
CGGGAGCTGCTGAACAGCATGGGGATCAGCCAGCCGACCGTGGTGTTCGTGAGCAAGAAG
GGCCTGCAGAAGATCCTGAACGTGCAGAAGAAGCTGCCCATCATCCAGAAGATCATCATC
ATGGACAGCAAGACCGACTACCAGGGCTTCCAGTCGATGTACACGTTCGTGACCAGCCAC
CTCCCGCCGGGCTTCAACGAGTACGACTTCGTCCCGGAGAGCTTCGACCGGGACAAGACC
ATCGCCCTGATCATGAACAGCAGCGGCAGCACCGGCCTGCCGAAGGGGGTGGCCCTGCCG
CACCGGACCGCCTGCGTGCGCTTCTCGCACGCCCGGGACCCCATCTTCGGCAACCAGATC
ATCCCGGACACCGCCATCCTGAGCGTGGTGCCGTTCCACCACGGCTTCGGCATGTTCACG
ACCCTGGGCTACCTCATCTGCGGCTTCCGGGTGGTCCTGATGTACCGGTTCGAGGAGGAG
CTGTTCCTGCGGAGCCTGCAGGACTACAAGATCCAGAGCGCGCTGCTCGTGCCGACCCTG
TTCAGCTTCTTCGCCAAGAGCACCCTGATCGACAAGTACGACCTGTCGAACCTGCACGAG
ATCGCCAGCGGGGGCGCCCCGCTGAGCAAGGAGGTGGGCGAGGCCGTGGCCAAGCGGTTC
CACCTCCCGGGCATCCGCCAGGGCTACGGCCTGACCGAGACCACGAGCGCGATCCTGATC
ACCCCCGAGGGGGACGACAAGCCGGGCGCCGTGGGCAAGGTGGTCCCGTTCTTCGAGGCC
AAGGTGGTGGACCTGGACACCGGCAAGACCCTGGGCGTGAACCAGCGGGGCGAGCTGTGC
GTGCGGGGGCCGATGATCATGAGCGGCTACGTGAACAACCCGGAGGCCACCAACGCCCTC
ATCGACAAGGACGGCTGGCTGCACAGCGGCGACATCGCCTACTGGGACGAGGACGAGCAC
TTCTTCATCGTCGACCGGCTGAAGTCGCTGATCAAGTACAAGGGCTACCAGGTGGCGCCG
GCCGAGCTGGAGAGCATCCTGCTCCAGCACCCCAACATCTTCGACGCCGGCGTGGCCGGG
CTGCCGGACGACGACGCCGGCGAGCTGCCGGCCGCGGTGGTGGTGCTGGAGCACGGCAAG
ACCATGACGGAGAAGGAGATCGTCGACTACGTGGCCAGCCAGGTGACCACCGCCAAGAAG
CTGCGGGGCGGCGTGGTGTTCGTGGACGAGGTCCCGAAGGGCCTGACCGGGAAGCTCGAC
GCCCGGAAGATCCGCGAGATCCTGATCAAGGCCAAGAAGGGCGGCAAGATCGCCGTGTAA
GACTAGTGCATCACATTTAAAAGCATCTCAGCCTACCATGAGAATAAGAGAAAGAAAATG
AAGATCAATAGCTTATTCATCTCTTTTTCTTTTTCGTTGGTGTAAAGCCAACACCCTGTC
TAAAAAACATAAATTTCTTTAATCATTTTGCCTCTTTTCTCTGTGCTTCAATTAATAAAA
AATGGAAAGAACCTAGATCTAAAAAAAAAAAAAAAAAAAAAAAAAAAAAAAAAAAAAAAA
AAAAAAAAAAAAAAAAAAAAAAAATGCATCCCCCCCCCCCCCCCCCCCCCCCCCCCCCCC
AAAGGCTCTTTTCAGAGCCACCAGAATT (SEQ ID NO: 1398)

HSD17B4 - PpLuc(GC) - albumin7 - A64N64
GGGTCCCGCAGTCGGCGTCCAGCGGCTCTGCTTGTTCGTGTGTGTGTCGTTGCAGGCCTT
ATTCAAGCTTGAGGATGGAGGACGCCAAGAACATCAAGAAGGGCCCGGCGCCCTTCTACC
CGCTGGAGGACGGGACCGCCGGCGAGCAGCTCCACAAGGCCATGAAGCGGTACGCCCTGG
TGCCGGGCACGATCGCCTTCACCGACGCCCACATCGAGGTCGACATCACCTACGCGGAGT
ACTTGGAGATGAGCGTGCGCCTGGCCGAGGCCATGAAGCGGTACGGCCTGAACACCAACC
ACCGGATCGTGGTGTGCTCGGAGAACAGCCTGCAGTTCTTCATGCCGGTGCTGGGCGCCC
TCTTCATCGGCGTGGCCGTCGCCCCGGCGAACGACATCTACAACGAGCGGGAGCTGCTGA
ACAGCATGGGGATGAGCCAGCCGACCGTGGTGTTCGTGAGCAAGAAGGGCCTGCAGAAGA
TCCTGAACGTGCAGAAGAAGCTGCCCATCATCCAGAAGATCATCATCATGGACAGCAAGA
CCGACTACCAGGGCTTCCAGTCGATGTACACGTTCGTGACCAGCCACCTCCCGCCGGGCT
TCAACGAGTACGACTTCGTCCCGGAGAGCTTCGACCGGGACAAGACCATCGCCCTGATCA
TGAACAGCAGCGGCAGCACCGGCCTGCCGAAGGGGGTGGCCCTGCCGCACCGGACCGCCT
GCGTGCGCTTCTCGCACGCCCGGGACCCCATCTTCGGCAACCAGATCATCCCGGACACCG
CCATCCTGAGCGTGGTGCCGTTCCACCACGGCTTCGGCATGTTCACGACCCTGGGCTACC
TCATCTGCGGCTTCCGGGTGGTCCTGATGTACCGGTTCGAGGAGGAGCTGTTCCTGCGGA
GCCTGCAGGACTACAAGATCCAGAGCGCGCTGCTCGTGCCGACCCTGTTCAGCTTCTTCG
CCAAGAGCACCCTGATCGACAAGTACGACCTGTCGAACCTGCACGAGATCGCCAGCGGGG
GCGCCCCGCTGAGCAAGGAGGTGGGCGAGGCCGTGGCCAAGCGGTTCCACCTCCCGGGCA
TCCGCCAGGGCTACGGCCTGACCGAGACCACGAGCGCGATCCTGATCACCCCCGAGGGGG -continued

SEQUENCES:

ACGACAAGCCGGGCGCCGTGGGCAAGGTGGTCCCGTTCTTCGAGGCCAAGGTGGTGGACC
TGGACACCGGCAAGACCCTGGGCGTGAACCAGCGGGGCGAGCTGTGCGTGCGGGGGCCGA
TGATCATGAGCGGCTACGTGAACAACCCGGAGGCCACCAACGCCCTCATCGACAAGGACG
GCTGGCTGCACAGCGGCGACATCGCCTACTGGGACGAGGACGAGCACTTCTTCATCGTCG
ACCGGCTGAAGTCGCTGATCAAGTACAAGGGCTACCAGGTGGCGCCGGCCGAGCTGGAGA
GCATCCTGCTCCAGCAGCCCAAGATCTTCGACGCCGGCGTGGCCGGGCTGCCGGACGACG
ACGCCGGCGAGCTGCCGGCCGCGGTGGTGGTGCTGGAGCACGGCAAGACCATGACGGAGA
AGGAGATCGTCGACTACGTGGCCAGCCAGGTGACCACCGCCAAGAAGCTGCGGGGCGGCG
TGGTGTTCGTGGACGAGGTCCCGAAGGGCCTGACCGGGAAGCTCGACGCCCGGAAGATCC
GCGAGATCCTGATCAAGGCCAAGAAGGGCGGCAAGATCGCCGTGTAAGACTAGTGCATCA
CATTTAAAAGCATCTCAGCCTACCATGAGAATAAGAGAAAGAAAATGAAGATCAATAGCT
TATTCATCTCTTTTTCTTTTTCGTTGGTGTAAAGCCAACACCCTGTCTAAAAAACATAAA
TTTCTTTAATCATTTTGCCTCTTTTCTCTGTGCTTCAATTAATAAAAAATGGAAAGAACC
TAGATCTAAAAAAAAAAAAAAAAAAAAAAAAAAAAAAAAAAAAAAAAAAAAAAAAAAAAA
AAAAAAAAAAATGCATCCGCCCCCCCCCCCCCCCCCCCCCCCCCCCCCCAAAGGCTCTTTTC
AGAGCCACCAGAATT (SEQ ID NO: 1399)

AIG1 - PpLuc(GC) - albumin7 - A64N64
GGGCCGCCCAGCCGGTCCAGGCCTCTGGCGAACAAGCTTGAGGATGGAGGACGCCAAGAA
CATCAAGAAGGGCCCGGCGCCCTTCTACCCGCTGGAGGACGGGACCGCCGGCGAGCAGCT
CCACAAGGCCATGAAGCGGTACGCCCTGGTGCCGGGCACGATCGCCTTCACCGACGCCCA
CATCGAGGTCGACATCACCTACGCGGAGTACTTCGAGATGAGCGTGCGCCTGGCCGAGGC
CATGAAGCGGTACGGCCTGAACACCAACCACCGGATCGTGGTGTGCTCGGAGAACAGCCT
GCAGTTCTTCATGCCGGTGCTGGGCGCCCTCTTCATCGGCGTGGCCGTCGCCCCGGCGAA
CGACATCTACAACGAGCGGGAGCTGCTGAACAGCATGGGGATCAGCCAGCCGACCGTGGT
GTTCGTGAGCAAGAAGGGCCTGCAGAAGATCCTGAACGTGCAGAAGAAGCTGCCCATCAT
CCAGAAGATCATCATCATGGACAGCAAGACCGACTACCAGGGCTTCCAGTCGATGTACAC
GTTCGTGACCAGCCACCTCCCGCCGGGCTTCAACGAGTACGACTTCGTCCCGGAGAGCTT
CGACCGGGACAAGACCATCGCCCTGATCATGAACAGCAGCGGCAGCACCGGCCTGCCGAA
GGGGGTGGCCCTGCCGCACCGGACCGCCTGCGTGCGCTTCTCGCACGCCCGGGACCCCAT
CTTCGGCAACCAGATCATCCCGGACACCGCCATCCTGAGCGTGGTGCCGTTCCACCACGG
CTTCGGCATGTTCACGACCCTGGGCTACCTCATCTGCGGCTTCCGGGTGGTCCTGATGTA
CCGGTTCGAGGAGGAGCTGTTCCTGCGGAGCCTGCAGGACTACAAGATCCAGAGCGCGCT
GCTCGTGCCGACCCTGTTCAGCTTCTTCGCCAAGAGCACCCTGATCGACAAGTACGACCT
GTCGAACCTGCACGAGATCGCCAGCGGGGGCGCCCCGCTGAGCAAGGAGGTGGGCGAGGC
CGTGGCCAAGCGGTTCCACCTCCCGGGCATCCGCCAGGGCTACGGCCTGACCGAGACCAC
GAGCGCGATCCTGATCACCCCCGAGGGGGACGACAAGCCGGGCGCCGTGGGCAAGGTGGT
CCCGTTCTTCGAGGCCAAGGTGGTGGACCTGGACACCGGCAAGACCCTGGGCGTGAACCA
GCGGGGCGAGCTGTGCGTGCGGGGGCCGATGATCATGAGCGGCTACGTGAACAACCCGGA
GGCCACCAACGCCCTCATCGACAAGGACGGCTGGCTGCACAGCGGCGACATCGCCTACTG
GGACGAGGACGAGCACTTCTTCATCGTCGACCGGCTGAAGTCGCTGATCAAGTACAAGGG
CTACCAGGTGGCGCCGGCCGAGCTGGAGAGCATCCTGCTCCAGCACCCCAACATCTTCGA
CGCCGGCGTGGCCGGGCTGCCGGACGACGACGCCGGCGAGCTGCCGGCCGCGGTGGTGGT
GCTGGAGCACGGCAAGACCATGACGGAGAAGGAGATCGTCGACTACGTGGCCAGCCAGGT
GACCACCGCCAAGAAGCTGCGGGGCGGCGTGGTGTTCGTGGACGAGGTCCCGAAGGGCCT
GACCGGGAAGCTCGACGCCCGGAAGATCCGCGAGATCCTGATCAAGGCCAAGAAGGGCGG
CAAGATCGCCGTGTAAGACTAGTGCATCACATTTAAAAGCATCTCAGCCTACCATGAGAA
TAAGAGAAAGAAAATGAAGATCAATAGCTTATTCATCTCTTTTTCTTTTTCGTTGGTGTA
AAGCCAACACCCTGTCTAAAAAACATAAATTTCTTTAATCATTTTGCCTCTTTTCTCTGT
GCTTCAATTAATAAAAAATGGAAAGAACCTAGATCTAAAAAAAAAAAAAAAAAAAAAAAA
AAAAAAAAAAAAAAAAAAAAAAAAAAAAAAAAAAAAAAAATGCATCCCCCCCCCCCCCCC
CCCCCCCCCCCCCCCCCAAAGGCTCTTTTCAGAGCCACCAGAATT (SEQ ID NO: 1400)

COX6C - PpLuc(GC) - albumin7 - A64N64
GGAGTCAGGAAGGACGTTGGTGTTGAGGTTAGCATACGTATCAAGGACAGTAACTACCAA
GCTTGAGGATGGAGGACGCCAAGAACATCAAGAAGGGCCCGGCGCCCTTCTACCCGCTGG
AGGACGGGACCGCCGGCGAGCAGCTCCACAAGGCCATGAAGCGGTACGCCCTGGTGCCGG
GCACGATCGCCTTCACCGACGCCCACATCGAGGTCGACATCACCTACGCGGAGTACTTCG
AGATGAGCGTGCGCCTGGCCGAGGCCATGAAGCGGTACGGCCTGAACACCAACCACCGGA
TCGTGGTGTGCTCGGAGAACAGCCTGCAGTTCTTCATGCCGGTGCTGGGCGCCCTCTTCA
TCGGCGTGGCCGTCGCCCCGGCGAACGACATCTACAACGAGCGGGAGCTGCTGAACAGCA
TGGGGATCAGCCAGCCGACCGTGGTGTTCGTGAGCAAGAAGGGCCTGCAGAAGATCCTGA
ACGTGCAGAAGAAGCTGCCCATCATCCAGAAGATCATCATCATGGACAGCAAGACCGACT
ACCAGGGCTTCCAGTCGATGTACACGTTCGTGACCAGCCACCTCCCGCCGGGCTTCAACG
AGTACGACTTCGTCCCGGAGAGCTTCGACCGGGACAAGACCATCGCCCTGATCATGAACA
GCAGCGGCAGCACCGGCCTGCCGAAGGGGGTGGCCCTGCCGCACCGGACCGCCTGCGTGC
GCTTCTCGCACGCCCGGGACCCCATCTTCGGCAACCAGATCATCCCGGACACCGCCATCC
TGAGCGTGGTGCCGTTCCACCACGGCTTCGGCATGTTCACGACCCTGGGCTACCTCATCT
GCGGCTTCCGGGTGGTCCTGATGTACCGGTTCGAGGAGGAGCTGTTCCTGCGGAGCCTGC
AGGACTACAAGATCCAGAGCGCGCTGCTCGTGCCGACCCTGTTCAGCTTCTTCGCCAAGA
GCACCCTGATCGACAAGTACGACCTGTCGAACCTGCACGAGATCGCCAGCGGGGGCGCCC
CGCTGAGCAAGGAGGTGGGCGAGGCCGTGGCCAAGCGGTTCCACCTCCCGGGCATCCGCC
AGGGCTACGGCCTGACCGAGACCACGAGCGCGATCCTGATCACCCCCGAGGGGGACGACA
AGCCGGGCGCCGTGGGCAAGGTGGTCCCGTTCTTCGAGGCCAAGGTGGTGGACCTGGACA
CCGGCAAGACCCTGGGCGTGAACCAGCGGGGCGAGCTGTGCGTGCGGGGGCCGATGATCA
TGAGCGGCTACGTGAACAACCCGGAGGCCACCAACGCCCTCATCGACAAGGACGGCTGGC
TGCACAGCGGCGACATCGCCTACTGGGACGAGGACGAGCACTTCTTCATCGTCGACCGGC -continued

| SEQUENCES: |
|---|

TGAAGTCGCTGATCAAGTACAAGGGCTACCAGGTGGCGCCGGCCGAGCTGGAGAGCATCC
TGCTCCAGCACCCCAACATCTTCGACGCCGGCGTGGCCGGGCTGCCGGACGACGACGCCG
GCGAGCTGCCGGCCGCGGTGGTGGTGCTGGAGCACGGCAAGACCATGACGGAGAAGGAGA
TCGTCGACTACGTGGCCAGCCAGGTGACCACCGCCAAGAAGCTGCGGGGCGGCGTGGTGT
TCGTGGACGAGGTCCCGAAGGGCCTGACCGGGAAGCTCGACGCCCGGAAGATCCGCGAGA
TCCTGATCAAGGCCAAGAAGGGCGGCAAGATCGCCGTGTAAGACTAGTGCATCACATTTA
AAAGCATCTCAGCCTACCATGAGAATAAGAGAAAGAAAATGAAGATCAATAGCTTATTCA
TCTCTTTTTCTTTTTCGTTGGTGTAAAGCCAACACCCTGTCTAAAAAACATAAATTTCTT
TAATCATTTTGCCTCTTTTCTCTGTGCTTCAATTAATAAAAAATGGAAAGAACCTAGATC
TAAAAAAAAAAAAAAAAAAAAAAAAAAAAAAAAAAAAAAAAAAAAAAAAAAAAAAAAAAA
AAAAATGCATCCCCCCCCCCCCCCCCCCCCCCCCCCCCCCCCCCCAAAGGCTCTTTTCAGAGCC
ACCAGAATT (SEQ ID NO: 1401)

ASAH1 - PpLuc(GC) - albumin7 - A64N64
GGGCCTCTGCTGGAGTCCGGGGAGTGGCGTTGGCTGCTAGAGCGAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTGCATCACATTTAAAAGCATCTCAGCC
TACCATGAGAATAAGAGAAAGAAAATGAAGATCAATAGCTTATTCATCTCTTTTTCTTTT
TCGTTGGTGTAAAGCCAACACCCTGTCTAAAAAACATAAATTTCTTTAATCATTTTGCCT
CTTTTCTCTGTGCTTCAATTAATAAAAAATGGAAAGAACCTAGATCTAAAAAAAAAAAAA
AAAAAAAAAAAAAAAAAAAAAAAAAAAAAAAAAAAAAAAAAAAAAAAAATGCATCCCC
CCCCCCCCCCCCCCCCCCCCCCCCCCCCAAAGGCTCTTTTCAGAGCCACCAGAATT (SEQ ID
NO: 1402)

mRPL21 - PpLuc(GC) - albumin7 - A64N64
GGGGCCGCCGCAGCCATCTTCCAGTAACTCGCCAAAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA

SEQUENCES:

GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTGCATCACATTTAAAAGCATCTCAGCCTACCATGA
GAATAAGAGAAAGAAAATGAAGATCAATAGCTTATTCATCTCTTTTTCTTTTTCGTTGGT
GTAAAGCCAACACCCTGTCTAAAAAACATAAATTTCTTTAATCATTTTGCCTCTTTTCTC
TGTGCTTCAATTAATAAAAAATGGAAAGAACCTAGATCTAAAAAAAAAAAAAAAAAAAAA
AAAAAAAAAAAAAAAAAAAAAAAAAAAAAAAAAAAAAAAAAAAATGCATCCCCCCCCCCC
CCCCCCCCCCCCCCCCCCCAAAGGCTCTTTTCAGAGCCACCAGAATT (SEQ ID NO: 1403)

mRPL35A - PpLuc(GC) - albumin7 - A64N64
GGGCCATCTTGGCGCCTGTGGAGGCCTGCTGGGAACAGGACTTCTAACAGCAAGTAAGCT
TGAGGATGGAGGACGCCAAGAACATCAAGAAGGGCCCGGCGCCCTTCTACCCGCTGGAGG
ACGGGACCGCCGGCGAGCAGCTCCACAAGGCCATGAAGCGGTACGCCCTGGTGCCGGGCA
CGATCGCCTTCACCGACGCCCACATCGAGGTCGACATCACCTACGCGGAGTACTTCGAGA
TGAGCGTGCGCCTGGCCGAGGCCATGAAGCGGTACGGCCTGAACACCAACCACCGGATCG
TGGTGTGCTCGGAGAACAGCCTGCAGTTCTTCATGCCGGTGCTGGGCGCCCTCTTCATCG
GCGTGGCCGTCGCCCCGGCGAACGACATCTACAACGAGCGGGAGCTGCTGAACAGCATGG
GGATCAGCCAGCCGACCGTGGTGTTCGTGAGCAAGAAGGGCCTGCAGAAGATCCTGAACG
TGCAGAAGAAGCTGCCCATCATCCAGAAGATCATCATCATGGACAGCAAGACCGACTACC
AGGGCTTCCAGTCGATGTACACGTTCGTGACCAGCCACCTCCCGCCGGGCTTCAACGAGT
ACGACTTCGTCCCGGAGAGCTTCGACCGGGACAAGACCATCGCCCTGATCATGAACAGCA
GCGGCAGCACCGGCCTGCCGAAGGGGGTGGCCCTGCCGCACCGGACCGCCTGCGTGCGCT
TCTCGCACGCCCGGGACCCCATCTTCGGCAACCAGATCATCCCGGACACCGCCATCCTGA
GCGTGGTGCCGTTCCACCACGGCTTCGGCATGTTCACGACCCTGGGCTACCTCATCTGCG
GCTTCCGGGTGGTCCTGATGTACCGGTTCGAGGAGGAGCTGTTCCTGCGGAGCCTGCAGG
ACTACAAGATCCAGAGCGCGCTGCTCGTGCCGACCCTGTTCAGCTTCTTCGCCAAGAGCA
CCCTGATCGACAAGTACGACCTGTCGAACCTGCACGAGATCGCCAGCGGGGGCGCCCCGC
TGAGCAAGGAGGTGGGCGAGGCCGTGGCCAAGCGGTTCCACCTCCCGGGCATCCGCCAGG
GCTACGGCCTGACCGAGACCACGAGCGCGATCCTGATCACCCCCGAGGGGGACGACAAGC
CGGGCGCCGTGGGCAAGGTGGTCCCGTTCTTCGAGGCCAAGGTGGTGGACCTGGACACCG
GCAAGACCCTGGGCGTGAACCAGCGGGGCGAGCTGTGCGTGCGGGGGCCGATGATCATGA
GCGGCTACGTGAACAACCCGGAGGCCACCAACGCCCTCATCGACAAGGACGGCTGGCTGC
ACAGCGGCGACATCGCCTACTGGGACGAGGACGAGCACTTCTTCATCGTCGACCGGCTGA
AGTCGCTGATCAAGTACAAGGGCTACCAGGTGGCGCCGGCCGAGCTGGAGAGCATCCTGC
TCCAGCACCCCAACATCTTCGACGCCGGCGTGGCCGGGCTGCCGGACGACGACGCCGGCG
AGCTGCCGGCCGCGGTGGTGGTGCTGGAGCACGGCAAGACCATGACGGAGAAGGAGATCG
TCGACTACGTGGCCAGCCAGGTGACCACCGCCAAGAAGCTGCGGGGCGGCGTGGTGTTCG
TGGACGAGGTCCCGAAGGGCCTGACCGGGAAGCTCGACGCCCGGAAGATCCGCGAGATCC
TGATCAAGGCCAAGAAGGGCGGCAAGATCGCCGTGTAAGACTAGTGCATCACATTTAAAA
GCATCTCAGCCTACCATGAGAATAAGAGAAAGAAAATGAAGATCAATAGCTTATTCATCT
CTTTTTCTTTTTCGTTGGTGTAAAGCCAACACCCTGTCTAAAAAACATAAATTTCTTTAA
TCATTTTGCCTCTTTTCTCTGTGCTTCAATTAATAAAAAATGGAAAGAACCTAGATCTAA
AAAAAAAAAAAAAAAAAAAAAAAAAAAAAAAAAAAAAAAAAAAAAAAAAAAAAAAAAAAA
AATGCATCCCCCCCCCCCCCCCCCCCCCCCCCCCCCCAAAGGCTCTTTTCAGAGCCACC
AGAATT (SEQ ID NO: 1404)

RPL35 - PpLuc(GC) - A64N64
GGGGAGCGGGCGGCGGCGTTGGCGGCTTGTGCAGCAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA

-continued

| SEQUENCES: |
| --- |

GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTAGATCTAAAAAAAAAAAAAAAAAAAAAAAAAAAA
AAAAAAAAAAAAAAAAAAAAAAAAAAAAAAAAAAAAATGCATCCCCCCCCCCCCCCCCCC
CCCCCCCCCCCCAAAGGCTCTTTTCAGAGCCACCAGAATT (SEQ ID NO: 1405)

RPL21 - PpLuc(GC) - A64N64
GGGGCCGGAACCGCCATCTTCCAGTAATTCGCCAAAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTAGATCTAAAAAAAAAAAAAAAAAAAAAAAAAAAA
AAAAAAAAAAAAAAAAAAAAAAAAAAAAAAAAAAAAATGCATCCCCCCCCCCCCCCCCCC
CCCCCCCCCCCCAAAGGCTCTTTTCAGAGCCACCAGAATT (SEQ ID NO: 1406)

ATP5A1 - PpLuc(GC) - A64N64
GGGCGGCTCGGCCATTTTGTCCCAGTCAGTCCGGAGGCTGCGGCTGCAGAAGTACCGCCT
GCGGAGTAACTGCAAAGAAGCTTGAGGATGGAGGACGCCAAGAACATCAAGAAGGGCCCG
GCGCCCTTCTACCCGCTGGAGGACGGGACCGCCGGCGAGCAGCTCCACAAGGCCATGAAG
CGGTACGCCCTGGTGCCGGGCACGATCGCCTTCACCGACGCCCACATCGAGGTCGACATC
ACCTACGCGGAGTACTTCGAGATGAGCGTGCGCCTGGCCGAGGCCATGAAGCGGTACGGC
CTGAACACCAACCACCGGATCGTGGTGTGCTCGGAGAACAGCCTGCAGTTCTTCATGCCG
GTGCTGGGCGCCCTCTTCATCGGCGTGGCCGTCGCCCCGGCGAACGACATCTACAACGAG
CGGGAGCTGCTGAACAGCATGGGGATCAGCCAGCCGACCGTGGTGTTCGTGAGCAAGAAG
GGCCTGCAGAAGATCCTGAACGTGCAGAAGAAGCTGCCCATCATCCAGAAGATCATCATC
ATGGACAGCAAGACCGACTACCAGGGCTTCCAGTCGATGTACACGTTCGTGACCAGCCAC
CTCCCGCCGGGCTTCAACGAGTACGACTTCGTCCCGGAGAGCTTCGACCGGGACAAGACC
ATCGCCCTGATCATGAACAGCAGCGGCAGCACCGGCCTGCCGAAGGGGGTGGCCCTGCCG
CACCGGACCGCCTGCGTGCGCTTCTCGCACGCCCGGGACCCCATCTTCGGCAACCAGATC
ATCCCGGACACCGCCATCCTGAGCGTGGTGCCGTTCCACCACGGCTTCGGCATGTTCACG
ACCCTGGGCTACCTCATCTGCGGCTTCCGGGTGGTCCTGATGTACCGGTTCGAGGAGGAG
CTGTTCCTGCGGAGCCTGCAGGACTACAAGATCCAGAGCGCGCTGCTCGTGCCGACCCTG
TTCAGCTTCTTCGCCAAGAGCACCCTGATCGACAAGTACGACCTGTCGAACCTGCACGAG
ATCGCCAGCGGGGGCGCCCCGCTGAGCAAGGAGGTGGGCGAGGCCGTGGCCAAGCGGTTC
CACCTCCCGGGCATCCGCCAGGGCTACGGCCTGACCGAGACCACGAGCGCGATCCTGATC
ACCCCCGAGGGGGACGACAAGCCGGGCGCCGTGGGCAAGGTGGTCCCGTTCTTCGAGGCC
AAGGTGGTGGACCTGGACACCGGCAAGACCCTGGGCGTGAACCAGCGGGGCGAGCTGTGC
GTGCGGGGGCCGATGATCATGAGCGGCTACGTGAACAACCCGGAGGCCACCAACGCCCTC
ATCGACAAGGACGGCTGGCTGCACAGCGGCGACATCGCCTACTGGGACGAGGACGAGCAC
TTCTTCATCGTCGACCGGCTGAAGTCGCTGATCAAGTACAAGGGCTACCAGGTGGCGCCG
GCCGAGCTGGAGAGCATCCTGCTCCAGCACCCCAACATCTTCGACGCCGGCGTGGCCGGG
CTGCCGGACGACGACGCCGGCGAGCTGCCGGCCGCGGTGGTGGTGCTGGAGCACGGCAAG
ACCATGACGGAGAAGGAGATCGTCGACTACGTGGCCAGCCAGGTGACCACCGCCAAGAAG
CTGCGGGGCGGCGTGGTGTTCGTGGACGAGGTCCCGAAGGGCCTGACCGGGAAGCTCGAC
GCCCGGAAGATCCGCGAGATCCTGATCAAGGCCAAGAAGGGCGGCAAGATCGCCGTGTAA
GACTAGTAGATCTAAAAAAAAAAAAAAAAAAAAAAAAAAAAAAAAAAAAAAAAAAAAAAA
AAAAAAAAAAAAAAAATGCATCCCCCCCCCCCCCCCCCCCCCCCCCCCCCCCCCAAAGGCT
CTTTTCAGAGCCACCAGAATT (SEQ ID NO: 1407)

HSD17B4 - PpLuc(GC) - A64N64
GGGTCCCGCAGTCGGCGTCCAGCGGCTCTGCTTGTTCGTGTGTGTGTCGTTGCAGGCCTT
ATTCAAGCTTGAGGATGGAGGACGCCAAGAACATCAAGAAGGGCCCGGCGCCCTTCTACC
CGCTGGAGGACGGGACCGCCGGCGAGCAGCTCCACAAGGCCATGAAGCGGTACGCCCTGG

-continued

SEQUENCES:

TGCCGGGCACGATCGCCTTCACCGACGCCCACATCGAGGTCGACATCACCTACGCGGAGT
ACTTCGAGATGAGCGTGCGCCTGGCCGAGGCCATGAAGCGGTACGGCCTGAACACCAACC
ACCGGATCGTGGTGTGCTCGGAGAACAGCCTGCAGTTCTTCATGCCGGTGCTGGGCGCCC
TCTTCATCGGCGTGGCCGTCGCCCCGGCGAACGACATCTACAACGAGCGGGAGCTGCTGA
ACAGCATGGGGATCAGCCAGCCGACCGTGGTGTTCGTGAGCAAGAAGGGCCTGCAGAAGA
TCCTGAACGTGCAGAAGAAGCTGCCCATCATCCAGAAGATCATCATCATGGACAGCAAGA
CCGACTACCAGGGCTTCCAGTCGATGTACACGTTCGTGACCAGCCACCTCCCGCCGGGCT
TCAACGAGTACGACTTCGTCCCGGAGAGCTTCGACCGGGACAAGACCATCGCCCTGATCA
TGAACAGCAGCGGCAGCACCGGCCTGCCGAAGGGGGTGGCCCTGCCGCACCGGACCGCCT
GCGTGCGCTTCTCGCACGCCCGGGACCCCATCTTCGGCAACCAGATCATCCCGGACACCG
CCATCCTGAGCGTGGTGCCGTTCCACCACGGCTTCGGCATGTTCACGACCCTGGGCTACC
TCATCTGCGGCTTCCGGGTGGTCCTGATGTACCGGTTCGAGGAGGAGCTGTTCCTGCGGA
GCCTGCAGGACTACAAGATCCAGAGCGCGCTGCTCGTGCCGACCCTGTTCAGCTTCTTCG
CCAAGAGCACCCTGATCGACAAGTACGACCTGTCGAACCTGCACGAGATCGCCAGCGGGG
GCGCCCCGCTGAGCAAGGAGGTGGGCGAGGCCGTGGCCAAGCGGTTCCACCTCCCGGGCA
TCCGCCAGGGCTACGGCCTGACCGAGACCACGAGCGCGATCCTGATCACCCCCGAGGGGG
ACGACAAGCCGGGCGCCGTGGGCAAGGTGGTCCCGTTCTTCGAGGCCAAGGTGGTGGACC
TGGACACCGGCAAGACCCTGGGCGTGAACCAGCGGGGCGAGCTGTGCGTGCGGGGGCCGA
TGATCATGAGCGGCTACGTGAACAACCCGGAGGCCACCAACGCCCTCATCGACAAGGACG
GCTGGCTGCACAGCGGCGACATCGCCTACTGGGACGAGGACGAGCACTTCTTCATCGTCG
ACCGGCTGAAGTCGCTGATCAAGTACAAGGGCTACCAGGTGGCGCCGGCCGAGCTGGAGA
GCATCCTGCTCCAGCACCCCAACATCTTCGACGCCGGCGTGGCCGGGCTGCCGGACGACG
ACGCCGGCGAGCTGCCGGCCGCGGTGGTGGTGCTGGAGCACGGCAAGACCATGACGGAGA
AGGAGATCGTCGACTACGTGGCCAGCCAGGTGACCACCGCCAAGAAGCTGCGGGGCGGCG
TGGTGTTCGTGGACGAGGTCCCGAAGGGCCTGACCGGGAAGCTCGACGCCCGGAAGATCC
GCGAGATCCTGATCAAGGCCAAGAAGGGCGGCAAGATCGCCGTGTAAGACTAGTAGATCT
AAAAAAAAAAAAAAAAAAAAAAAAAAAAAAAAAAAAAAAAAAAAAAAAAAAAAAAAAAAA
AAAATGCATCCCCCCCCCCCCCCCCCCCCCCCCCCCCCCCCCAAAGGCTCTTTTCAGAGCCA
CCAGAATT (SEQ ID NO: 1408)

AIG1 - PpLuc(GC) - A64N64
GGGCCGCCCAGCCGGTCCAGGCCTCTGGCGAACAAGCTTGAGGATGGAGGACGCCAAGAA
CATCAAGAAGGGCCCGGCGCCCTTCTACCCGCTGGAGGACGGGACCGCCGGCGAGCAGCT
CCACAAGGCCATGAAGCGGTACGCCCTGGTGCCGGGCACGATCGCCTTCACCGACGCCCA
CATCGAGGTCGACATCACCTACGCGGAGTACTTCGAGATGAGCGTGCGCCTGGCCGAGGC
CATGAAGCGGTACGGCCTGAACACCAACCACCGGATCGTGGTGTGCTCGGAGAACAGCCT
GCAGTTCTTCATGCCGGTGCTGGGCGCCCTCTTCATCGGCGTGGCCGTCGCCCCGGCGAA
CGACATCTACAACGAGCGGGAGCTGCTGAACAGCATGGGGATCAGCCAGCCGACCGTGGT
GTTCGTGAGCAAGAAGGGCCTGCAGAAGATCCTGAACGTGCAGAAGAAGCTGCCCATCAT
CCAGAAGATCATCATCATGGACAGCAAGACCGACTACCAGGGCTTCCAGTCGATGTACAC
GTTCGTGACCAGCCACCTCCCGCCGGGCTTCAACGAGTACGACTTCGTCCCGGAGAGCTT
CGACCGGGACAAGACCATCGCCCTGATCATGAACAGCAGCGGCAGCACCGGCCTGCCGAA
GGGGGTGGCCCTGCCGCACCGGACCGCCTGCGTGCGCTTCTCGCACGCCCGGGACCCCAT
CTTCGGCAACCAGATCATCCCGGACACCGCCATCCTGAGCGTGGTGCCGTTCCACCACGG
CTTCGGCATGTTCACGACCCTGGGCTACCTCATCTGCGGCTTCCGGGTGGTCCTGATGTA
CCGGTTCGAGGAGGAGCTGTTCCTGCGGAGCCTGCAGGACTACAAGATCCAGAGCGCGCT
GCTCGTGCCGACCCTGTTCAGCTTCTTCGCCAAGAGCACCCTGATCGACAAGTACGACCT
GTCGAACCTGCACGAGATCGCCAGCGGGGGCGCCCCGCTGAGCAAGGAGGTGGGCGAGGC
CGTGGCCAAGCGGTTCCACCTCCCGGGCATCCGCCAGGGCTACGGCCTGACCGAGACCAC
GAGCGCGATCCTGATCACCCCCGAGGGGGACGACAAGCCGGGCGCCGTGGGCAAGGTGGT
CCCGTTCTTCGAGGCCAAGGTGGTGGACCTGGACACCGGCAAGACCCTGGGCGTGAACCA
GCGGGGCGAGCTGTGCGTGCGGGGGCCGATGATCATGAGCGGCTACGTGAACAACCCGGA
GGCCACCAACGCCCTCATCGACAAGGACGGCTGGCTGCACAGCGGCGACATCGCCTACTG
GGACGAGGACGAGCACTTCTTCATCGTCGACCGGCTGAAGTCGCTGATCAAGTACAAGGG
CTACCAGGTGGCGCCGGCCGAGCTGGAGAGCATCCTGCTCCAGCACCCCAACATCTTCGA
CGCCGGCGTGGCCGGGCTGCCGGACGACGACGCCGGCGAGCTGCCGGCCGCGGTGGTGGT
GCTGGAGCACGGCAAGACCATGACGGAGAAGGAGATCGTCGACTACGTGGCCAGCCAGGT
GACCACCGCCAAGAAGCTGCGGGGCGGCGTGGTGTTCGTGGACGAGGTCCCGAAGGGCCT
GACCGGGAAGCTCGACGCCCGGAAGATCCGCGAGATCCTGATCAAGGCCAAGAAGGGCGG
CAAGATCGCCGTGTAAGACTAGTAGATCTAAAAAAAAAAAAAAAAAAAAAAAAAAAAAAA
AAAAAAAAAAAAAAAAAAAAAAAAAAAAAAAAAATGCATCCCCCCCCCCCCCCCCCCCCC
CCCCCCCCCAAAGGCTCTTTTCAGAGCCACCAGAATT (SEQ ID NO: 1409)

COX6C - PpLuc(GC) - A64N64
GGAGTCAGGAAGGACGTTGGTGTTGAGGTTAGCATACGTATCAAGGACAGTAACTACCAA
GCTTGAGGATGGAGGACGCCAAGAACATCAAGAAGGGCCCGGCGCCCTTCTACCCGCTGG
AGGACGGGACCGCCGGCGAGCAGCTCCACAAGGCCATGAAGCGGTACGCCCTGGTGCCGG
GCACGATCGCCTTCACCGACGCCCACATCGAGGTCGACATCACCTACGCGGAGTACTTCG
AGATGAGCGTGCGCCTGGCCGAGGCCATGAAGCGGTACGGCCTGAACACCAACCACCGGA
TCGTGGTGTGCTCGGAGAACAGCCTGCAGTTCTTCATGCCGGTGCTGGGCGCCCTCTTCA
TCGGCGTGGCCGTCGCCCCGGCGAACGACATCTACAACGAGCGGGAGCTGCTGAACAGCA
TGGGGATCAGCCAGCCGACCGTGGTGTTCGTGAGCAAGAAGGGCCTGCAGAAGATCCTGA
ACGTGCAGAAGAAGCTGCCCATCATCCAGAAGATCATCATCATGGACAGCAAGACCGACT
ACCAGGGCTTCCAGTCGATGTACACGTTCGTGACCAGCCACCTCCCGCCGGGCTTCAACG
AGTACGACTTCGTCCCGGAGAGCTTCGACCGGGACAAGACCATCGCCCTGATCATGAACA
GCAGCGGCAGCACCGGCCTGCCGAAGGGGGTGGCCCTGCCGCACCGGACCGCCTGCGTGC
GCTTCTCGCACGCCCGGGACCCCATCTTCGGCAACCAGATCATCCCGGACACCGCCATCC

-continued

| SEQUENCES: |
| --- |

TGAGCGTGGTGCCGTTCCACCACGGCTTCGGCATGTTCACGACCCTGGGCTACCTCATCT
GCGGCTTCCGGGTGGTCCTGATGTACCGGTTCGAGGAGGAGCTGTTCCTGCGGAGCCTGC
AGGACTACAAGATCCAGAGCGCGCTGCTCGTGCCGACCCTGTTCAGCTTCTTCGCCAAGA
GCACCCTGATCGACAAGTACGACCTGTCGAACCTGCACGAGATCGCCAGCGGGGGCGCCC
CGCTGAGCAAGGAGGTGGGCGAGGCCGTGGCCAAGCGGTTCCACCTCCCGGGCATCCGCC
AGGGCTACGGCCTGACCGAGACCACGAGCGCGATCCTGATCACCCCCGAGGGGGACGACA
AGCCGGGCGCCGTGGGCAAGGTGGTCCCGTTCTTCGAGGCCAAGGTGGTGGACCTGGACA
CCGGCAAGACCCTGGGCGTGAACCAGCGGGGCGAGCTGTGCGTGCGGGGGCCGATGATCA
TGAGCGGCTACGTGAACAACCCGGAGGCCACCAACGCCCTCATCGACAAGGACGGCTGGC
TGCACAGCGGCGACATCGCCTACTGGGACGAGGACGAGCACTTCTTCATCGTCGACCGGC
TGAAGTCGCTGATCAAGTACAAGGGCTACCAGGTGGCGCCGGCCGAGCTGGAGAGCATCC
TGCTCCAGCACCCCAACATCTTCGACGCCGGCGTGGCCGGGCTGCCGGACGACGACGCCG
GCGAGCTGCCGGCCGCGGTGGTGGTGCTGGAGCACGGCAAGACCATGACGGAGAAGGAGA
TCGTCGACTACGTGGCCAGCCAGGTGACCACCGCCAAGAAGCTGCGGGGCGGCGTGGTGT
TCGTGGACGAGGTCCCGAAGGGCCTGACCGGGAAGCTCGACGCCCGGAAGATCCGCGAGA
TCCTGATCAAGGCCAAGAAGGGCGGCAAGATCGCCGTGTAAGACTAGTAGATCTAAAAAA
AAAAAAAAAAAAAAAAAAAAAAAAAAAAAAAAAAAAAAAAAAAAAAAAAAAAAAAAAATG
CATCCCCCCCCCCCCCCCCCCCCCCCCCCCCCCCCAAAGGCTCTTTTCAGAGCCACCAGAA
TT (SEQ ID NO: 1410)

ASAH1 - PpLuc(GC) - A64N64
GGGCCTCTGCTGGAGTCCGGGGAGTGGCGTTGGCTGCTAGAGCGAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTAGATCTAAAAAAAAAAAAAAAAAAAA
AAAAAAAAAAAAAAAAAAAAAAAAAAAAAAAAAAAAAAAAAAAATGCATCCCCCCCCCCC
CCCCCCCCCCCCCCCCCCCCCAAAGGCTCTTTTCAGAGCCACCAGAATT (SEQ ID NO: 1411)

5'UTR of human ribosomal protein Large 35 (RPL35) lacking the 5'
terminal oligopyrimidine tract
GGAGCGGGCGGCGGCGTTGGCGGCTTGTGCAGCA (SEQ ID NO: 1412)

5'UTR of human
ribosomal protein Large 21 (RPL21) lacking the 5' terminal oligopyrimidine
tract
GGCCGGAACCGCCATCTTCCAGTAATTCGCCAAA (SEQ ID NO: 1413)

5'UTR of human ATP synthase, H+ transporting, mitochondrial F1
complex, alpha subunit 1, cardiac muscle (ATP5A1) lacking the 5'
terminal oligopyrimidine tract
GCGGCTCGGCCATTTTGTCCCAGTCAGTCCGGAGGCTGCGGCTGCAGAAGTACCGCCTGCGGAGTA
ACTGCAAAG (SEQ ID NO: 1414)

5'UTR of human hydroxysteroid (17-beta) dehydrogenase 4 (HSD17B4)
lacking the 5' terminal oligopyrimidine tract
GTCCCGCAGTCGGCGTCCAGCGGCTCTGCTTGTTCGTGTGTGTGTCGTTGCAGGCCTTATTC
(SEQ ID NO: 1415)

-continued

| SEQUENCES: |
|---|
| 5'UTR of human androgen-induced 1 (AIG1) lacking the 5' terminal oligopyrimidine tract<br>GCCGCCCAGCCGGTCCAGGCCTCTGGCGAAC (SEQ ID NO: 1416) |
| 5'UTR of human cytochrome c oxidase subunit VIc (COX6C) lacking the 5' terminal oligopyrimidine tract<br>AGTCAGGAAGGACGTTGGTGTTGAGGTTAGCATACGTATCAAGGACAGTAACTACC (SEQ ID NO: 1417) |
| 5'UTR of human N-acylsphingosine amidohydrolase (acid ceramidase) 1 (ASAH1) lacking the 5' terminal oligopyrimidine tract<br>GCCTCTGCTGGAGTCCGGGGAGTGGCGTTGGCTGCTAGAGCG (SEQ ID NO: 1418) |
| 5'UTR of mouse ribosomal protein Large 21 (mRPL21) lacking the 5' terminal oligopyrimidine tract<br>GGCCGCCGCAGCCATCTTCCAGTAACTCGCCAAA (SEQ ID NO: 1419) |
| 5'UTR of mouse ribosomal protein large 35A (mRPL35A) lacking the 5' terminal oligopyrimidine tract<br>GCCATCTTGGCGCCTGTGGAGGCCTGCTGGGAACAGGACTTCTAACAGCAAGT (SEQ ID NO: 1420) |
| Mouse ribosomal protein Large 21 (mRPL21)<br>TCCTCCTTTCGGCCGCCGCAGCCATCTTCCAGTAACTCGCCAAAATGCCATCTTCCAGTAACTCGCCAAAATG (SEQ ID NO: 1421) |
| mouse ribosomal protein large 35A (mRPL35A)<br>CTTCCTCTTTCCGCCATCTTGGCGCCTGTGGAGGCCTGCTGGGAACAGGACTTCTAACAGCAAGTATG (SEQ ID NO: 1422) |

The inventions claimed is:

1. An artificial nucleic acid molecule comprising, from 5' to 3':

(a) a 5'-untranslated region element (5'UTR element) of a mammalian TOP gene selected from the group consisting of AIG1, ASAH1, ATP5A1, COX6C, HSD17B4, RPL21, RPL32, and RPL35; and (b) at least one heterologous open reading frame (ORF); and (c) at least one 3'UTR element of a human albumin gene with greater than 90% identity to the gene encoded by SEQ ID NO: 1376.

2. The artificial nucleic acid molecule according to claim 1, further comprising (d) a poly(A) sequence and/or a polyadenylation signal.

3. The artificial nucleic acid molecule according to claim 1, further comprising a polyadenylation signal wherein the polyadenylation signal is located within the 3'UTR element.

4. The artificial nucleic acid molecule according to claim 2, wherein the poly(A) sequence has a length of about 20 to about 300 adenine nucleotides.

5. The artificial nucleic acid molecule according to claim 1, wherein the open reading frame does not code for a GFP protein, a luciferase protein, a globin protein, human growth hormone, or human albumin.

6. The artificial nucleic acid molecule according to claim 1, further comprising a poly(C) sequence positioned 3' relative to the ORF.

7. The artificial nucleic acid molecule according to claim 1, wherein the molecule is a DNA and further comprises a promoter containing-sequence operably linked to the ORF.

8. The artificial nucleic acid molecule according to claim 1, wherein the molecule is a RNA.

9. The artificial nucleic acid molecule according to claim 8, wherein the RNA is a mRNA and comprises a 5' cap.

10. The artificial nucleic acid molecule according to claim 8, wherein the RNA comprises at least one nucleotide position that is substituted with an analogue of the nucleotide selected from the group consisting of 2-amino-6-chloropurineriboside-5'-triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'-triphosphate, 5-methylcytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, puromycin-5'-triphosphate and xanthosine-5'-triphosphate.

11. The artificial nucleic acid molecule according to claim 1, wherein the G/C content of the open reading frame is increased compared to the wild type version of the open reading frame.

12. The artificial nucleic acid molecule according to claim 1, wherein the ORF encodes a human polypeptide, a tumour antigen or an infectious disease antigen.

13. The artificial nucleic acid molecule according to claim 1, wherein the ORF encodes an antibody or a portion thereof.

14. A pharmaceutical composition comprising a RNA molecule in accordance with claim 8 in a pharmaceutically acceptable carrier.

15. A method of expressing a polypeptide in a subject comprising administering an artificial nucleic acid molecule according to claim 1 to the subject, wherein the polypeptide is encoded by the ORF of said artificial nucleic acid molecule.

16. The artificial nucleic acid molecule according to claim 1, further comprising a histone stem-loop sequence.

17. The artificial nucleic acid molecule according to claim 1, wherein the 5' UTRS element is from RPL32.

* * * * *

SEQUENCE LISTING

<160> NUMBER OF SEQ ID NOS: 1422

<210> SEQ ID NO 1
<211> LENGTH: 21
<212> TYPE: DNA
<213> ORGANISM: Homo sapiens

<400> SEQUENCE: 1
gctccttctt tctgcaacat g 21

<210> SEQ ID NO 2
<211> LENGTH: 108
<212> TYPE: DNA
<213> ORGANISM: Homo sapiens

<400> SEQUENCE: 2
ggctctcttt ccgcgctgcg gtcagcctcg gcgtcccaca gagagggcca gaggtggaaa 60
cgcagaaaac caaaccagga ctatcagaga ttgcccggag aggggatg 108

<210> SEQ ID NO 3
<211> LENGTH: 69
<212> TYPE: DNA
<213> ORGANISM: Homo sapiens

<400> SEQUENCE: 3
cttcctcttc ttgatcgggg attcaggaag gagcccagga gcagaggaag tagagagaga 60
gacaacatg 69

<210> SEQ ID NO 4
<211> LENGTH: 159
<212> TYPE: DNA
<213> ORGANISM: Homo sapiens

<400> SEQUENCE: 4
tgtccttcct ctctggactg taagaatatg tctccagggc cagtgtctgc tgcgatcgag 60
tcccaccttc caagtcctgg catctcaatg catctgggaa gctacctgca ttaagtcagg 120
actgagcaca caggtgaact ccagaaagaa gaagctatg 159

<210> SEQ ID NO 5
<211> LENGTH: 57
<212> TYPE: DNA
<213> ORGANISM: Homo sapiens

<400> SEQUENCE: 5 tgacctttc cctcccgcgg ctctctacct ctcgccgccc ctagggagga caccatg 57

<210> SEQ ID NO 6
<211> LENGTH: 168
<212> TYPE: DNA
<213> ORGANISM: Homo sapiens

<400> SEQUENCE: 6
gggcctctct agcttgcggc ctgtgtctat ggtcgggccc tctgcgtcca gctgctccgg 60
accgagctcg ggtgtatggg gccgtaggaa ccggctccgg ggccccgata acgggccgcc 120
cccacagcac cccgggctgg cgtgagggtc tcccttgatc tgagaatg 168

<210> SEQ ID NO 7
<211> LENGTH: 53
<212> TYPE: DNA
<213> ORGANISM: Homo sapiens

<400> SEQUENCE: 7
agctcttcta ctccactgct gtctatcttg cctgccggca cccagccacc atg 53

<210> SEQ ID NO 8
<211> LENGTH: 89
<212> TYPE: DNA
<213> ORGANISM: Homo sapiens

<400> SEQUENCE: 8
cttcctctac ccggttggca ggcggcctgg cccagcccct tctctaagga agcgcatttc 60
ctgcctccct gggccggccg ggctggatg 89

<210> SEQ ID NO 9
<211> LENGTH: 28
<212> TYPE: DNA
<213> ORGANISM: Homo sapiens

<400> SEQUENCE: 9
tcttctctct gctgctgtag ctgccatg 28

<210> SEQ ID NO 10
<211> LENGTH: 246
<212> TYPE: DNA
<213> ORGANISM: Homo sapiens

<400> SEQUENCE: 10
ctgtctttct tccgggaggc ggtgacagct gctgagacgt gttgcagcca gagtctctcc 60
gctttaatgc gctcccatta gtgccgtccc ccactggaaa accgtggctt ctgtattatt 120
tgccatcttt gttgtgtagg agcagggagg gcttcctccc ggggtcctag gcggcggtgc 180
agtccgtcgt agaagaatta gagtagaagt tgtcggggtc cgctcttagg acgcagccgc 240
ctcatg 246

<210> SEQ ID NO 11
<211> LENGTH: 211
<212> TYPE: DNA
<213> ORGANISM: Homo sapiens

<400> SEQUENCE: 11
cgtcccctcg cagttcggcg gtcccgcggg tctgtctctt gcttcaacag tgtttggacg 60
gaacagatcc ggggactctc ttccagcctc cgaccgccct ccgatttcct ctccgcttgc 120
aacctccggg accatcttct cggccatctc ctgcttctgg gacctgccag caccgttttt 180
gtggttagct ccttcttgcc aaccaaccat g 211

<210> SEQ ID NO 12
<211> LENGTH: 40
<212> TYPE: DNA
<213> ORGANISM: Homo sapiens

<400> SEQUENCE: 12
ccgcctccct gggcgccgga gtcatgtgac ccacacaatg 40

<210> SEQ ID NO 13
<211> LENGTH: 181
<212> TYPE: DNA
<213> ORGANISM: Homo sapiens

<400> SEQUENCE: 13
ttttctttca ttagggggaa ggcgtgagga aagtaccaaa cagcagcgga gttttaaact 60
ttaaatagac aggtctgagt gcctgaactt gccttttcat tttacttcat cctccaagga 120
gttcaatcac ttggcgtgac ttcactactt ttaagcaaaa gagtggtgcc caggcaacat 180
g 181

<210> SEQ ID NO 14
<211> LENGTH: 68
<212> TYPE: DNA
<213> ORGANISM: Homo sapiens

<400> SEQUENCE: 14
cattctctgg gaaagggcag cagcagccag gtgtggcagt gacagggagg tgtgaatgag 60
gcaggatg 68

<210> SEQ ID NO 15
<211> LENGTH: 55
<212> TYPE: DNA
<213> ORGANISM: Homo sapiens

<400> SEQUENCE: 15
cgctccttcc tcctcggctc gcgtctcact cagtgtacct tctagtcccg ccatg 55

<210> SEQ ID NO 16
<211> LENGTH: 22
<212> TYPE: DNA
<213> ORGANISM: Homo sapiens

<400> SEQUENCE: 16
ctgtcctctt cagctcaaga tg 22

<210> SEQ ID NO 17

<211> LENGTH: 111
<212> TYPE: DNA
<213> ORGANISM: Homo sapiens

<400> SEQUENCE: 17
gggccctttc tgggcaggac ccgccccttg gtcccgcaga gccttggtac ttggacctga 60
accttgctcc gagagggagt cctcgcggac gtcagccaag attccagaat g 111

<210> SEQ ID NO 18
<211> LENGTH: 113
<212> TYPE: DNA
<213> ORGANISM: Homo sapiens

<400> SEQUENCE: 18
cttccttttg cagcaagttc tttcctgcac taatcacaat tcttggaaga ggagaactgg 60
acgttgtgaa cagagttagc tggtaaatgt cctcttaaaa gatccaaaaa atg 113

<210> SEQ ID NO 19
<211> LENGTH: 146
<212> TYPE: DNA
<213> ORGANISM: Homo sapiens

<400> SEQUENCE: 19
agccctttct ccagggacag ttgctgaagc ttcatccttt gctctcattc tgtaagtcat 60
agaaaagttt gaaacattct gtctgtggta gagctcgggc cagctgtagt tcattcgcca 120
gtgtgctttt cttaatatct aagatg 146

<210> SEQ ID NO 20
<211> LENGTH: 79
<212> TYPE: DNA
<213> ORGANISM: Homo sapiens

<400> SEQUENCE: 20
ggtcccctat ccgcaccccg gcccctgaga gctggcactg cgactcgaga cagcggcccg 60
gcaggacagc tccagaatg 79

<210> SEQ ID NO 21
<211> LENGTH: 178
<212> TYPE: DNA
<213> ORGANISM: Homo sapiens

<400> SEQUENCE: 21
ccccctcttc ctcctcctca agggaaagct gcccacttct agctgccctg ccatcccctt 60
taaagggcga cttgctcagc gccaaaccgc ggctccagcc ctctccagcc tccggctcag 120
ccggctcatc agtcggtccg cgccttgcag ctcctccaga gggacgcgcc ccgagatg 178

<210> SEQ ID NO 22
<211> LENGTH: 21
<212> TYPE: DNA
<213> ORGANISM: Homo sapiens

<400> SEQUENCE: 22
ggctcttctg gcgccaaaat g 21

<210> SEQ ID NO 23
<211> LENGTH: 170
<212> TYPE: DNA
<213> ORGANISM: Homo sapiens

<400> SEQUENCE: 23
cttccttcct gaccggcgcg cgcagcctgc tgccgcggtc agcgcctgct cctgctcctc 60
cgctcctcct gcgcggggtg ctgaaacagc ccggggaagt agagccgcct ccggggagcc 120
caaccagccg aacgccgccg gcgtcagcag ccttgcgcgg ccacagcatg 170

<210> SEQ ID NO 24
<211> LENGTH: 615
<212> TYPE: DNA
<213> ORGANISM: Homo sapiens

<400> SEQUENCE: 24
gcgcctctct tccgccaggc atcccagagg tcctggtggt ttcatttccg ggtgcggctt 60
ctgtcataaa gcggagacct cccttcaaac gtggcgtcgt gggttgtttg cgcctcgcct 120
ggggtcagcg agcaaggacg ggcgcgggcg gggatactca aagccaacag ctggagtcag 180
cccttgtgtc ccgggctcac agtggcacga ctgaatcctc agagtcggct ggcttttgag 240
ctctcacgat tggggaggag ggggcgtttc tggttcgcag ctccagagga ttgcgttcct 300
tcccccatac ctgtccccca cagtcacgct ctgccctgac gtgcagcatt tgacaagtta 360
ccccctcgcc acatactact tccacccacg tccgagttaa ctttgttctt aaccttcttg 420
agactaccct cggcctccag gtcttttttt cccagttcat ttttgcccat aagattgagt 480
ttcgagtttc agatatcatg cagaaagttt acctttaaga ctgagcaccc atctgatact 540
cttcctcccg aaaaagttca tgctcacgag agagtttgtg ggaaaagtga aagccagtac 600
acgcaggaaa ctatg 615

<210> SEQ ID NO 25
<211> LENGTH: 38
<212> TYPE: DNA
<213> ORGANISM: Homo sapiens

<400> SEQUENCE: 25
cgctccttca ccctcctcgt tggtgtcctg tcaccatg 38

<210> SEQ ID NO 26
<211> LENGTH: 177
<212> TYPE: DNA
<213> ORGANISM: Homo sapiens

<400> SEQUENCE: 26
gagccttctt gtcagcatct gttagtggag gttgggaagc ctctcctcct tccccctccc 60
tctttgcctc cacctggctc ctccccatgt tcgtccatca cccctccccc ctttcccaag 120
gacaatctgc aagaaagcag cggcggagga gagctaagac taaaagagtg gatcatg 177

<210> SEQ ID NO 27
<211> LENGTH: 54
<212> TYPE: DNA
<213> ORGANISM: Homo sapiens

<400> SEQUENCE: 27
ctgtctcctc agcttcaggc accaccactg acctgggaca gtgaatcgac aatg 54

<210> SEQ ID NO 28
<211> LENGTH: 848
<212> TYPE: DNA
<213> ORGANISM: Homo sapiens

<400> SEQUENCE: 28

-continued

```
agttctctcc tctcggaagc tgcagccatg atggaagttt gagagttgag ccgctgtgag      60

gcgaggccgg gctcaggcga gggagatgag agacggcggc ggccgcggcc cggagcccct     120

ctcagcgcct gtgagcagcc gcgggggcag cgccctcggg gagccggccg gcctgcggcg     180

gcggcagcgg cggcgtttct cgcctcctct tcgtcttttc taaccgtgca gcctcttcct     240

cggcttctcc tgaaagggaa ggtggaagcc gtgggctcgg gcgggagccg gctgaggcgc     300

ggcggcggcg gcggcacctc ccgctcctgg agcggggggg agaagcggcg gcggcggcgg     360

ccgcggcggc tgcagctcca gggagggggt ctgagtcgcc tgtcaccatt tccagggctg     420

ggaacgccgg agagttggtc tctccccttc tactgcctcc aacacggcgg cggcggcggc     480

ggcacatcca gggacccggg ccggttttaa acctcccgtc cgccgccgcc gcaccccccg     540

tggcccgggc tccggaggcc gccggcggag gcagccgttc ggaggattat tcgtcttctc     600

cccattccgc tgccgccgct gccaggcctc tggctgctga ggagaagcag gcccagtcgc     660

tgcaaccatc cagcagccgc cgcagcagcc attacccggc tgcggtccag agccaagcgg     720

cggcagagcg aggggcatca gctaccgcca agtccagagc catttccatc ctgcagaaga     780

agccccgcca ccagcagctt ctgccatctc tctcctcctt tttcttcagc cacaggctcc     840

cagacatg                                                              848
```

<210> SEQ ID NO 29
<211> LENGTH: 50
<212> TYPE: DNA
<213> ORGANISM: Homo sapiens

<400> SEQUENCE: 29

```
cctcccttac tgcaggaagg cactccgaag acataagtcg gtgagacatg                 50
```

<210> SEQ ID NO 30
<211> LENGTH: 58
<212> TYPE: DNA
<213> ORGANISM: Homo sapiens

<400> SEQUENCE: 30

```
ccgcctccca ctccccagcg cccccggacc gtgcagttct ctgcaggacc aggccatg        58
```

<210> SEQ ID NO 31
<211> LENGTH: 187
<212> TYPE: DNA
<213> ORGANISM: Homo sapiens

<400> SEQUENCE: 31

```
gtttctccca gcctcagcct ccccgccgcc gccgccgccg ccgccgccga gccggtttcc      60

tttttccggc gctccgggtg cgagagacag gtcgggcccc ctaggcagcg agccgcagcg     120

caatcccggc gctcgcccaa ggaccctgga agctaccgtt accccgccgg gcagcgtggg     180

cgccatg                                                               187
```

<210> SEQ ID NO 32
<211> LENGTH: 143
<212> TYPE: DNA
<213> ORGANISM: Homo sapiens

<400> SEQUENCE: 32

```
cctcctcctc ttacccaaat tttccagccg atcactggag ctgacttccg caatcccgat      60

ggaataaatc tagcacccct gatggtgtgc ccacactttg ctgccgaaac gaagccagac     120

aacagatttc catcagcagg atg                                             143
```

<210> SEQ ID NO 33
<211> LENGTH: 95
<212> TYPE: DNA
<213> ORGANISM: Homo sapiens

<400> SEQUENCE: 33
gcttctttgc gtaaccaata ctggaaggca tttaaaggca cctctgccgc cacagacctt 60
gcagttaact ccgccctgac ccacccttcc cgatg 95

<210> SEQ ID NO 34
<211> LENGTH: 77
<212> TYPE: DNA
<213> ORGANISM: Homo sapiens

<400> SEQUENCE: 34
ccgcctcctc ctgtcccgca gtcggcgtcc agcggctctg cttgttcgtg tgtgtgtcgt 60
tgcaggcctt attcatg 77

<210> SEQ ID NO 35
<211> LENGTH: 254
<212> TYPE: DNA
<213> ORGANISM: Homo sapiens

<400> SEQUENCE: 35
ctctctctgc ttctttcctt ttctctctca tggtagggtt atgagtcagt tgccaaaagg 60
tggggacatt tcctgatgca tttgcaacac tgagaagtta tcttaaggga ggctgggccc 120
cattctactc atctggccca gaaagtgaac accttggggg ccactaaggc agccctgcta 180
ggggagacgc tccaacctgt cttctctctg tctcctggca gctctcttgg cctcctagtt 240
tctacctaat catg 254

<210> SEQ ID NO 36
<211> LENGTH: 31
<212> TYPE: DNA
<213> ORGANISM: Homo sapiens

<400> SEQUENCE: 36
cagcctcctc ctgcctcacc gcccgaagat g 31

<210> SEQ ID NO 37
<211> LENGTH: 314
<212> TYPE: DNA
<213> ORGANISM: Homo sapiens

<400> SEQUENCE: 37
ccgccccttc tcgagaactc gcagagctgg gctggtaaaa ttgcagtgct gaagacactg 60
gacccgcaaa aggctgtccc tcccaaacct gggattctgg gctcactgag ttcacctgcg 120
agtcagccct acctgcactg ctctggtcta gtacaaacag gctgctggca ttgagggacg 180
gagtctccaa ctcctggcct ctagcagtcc tcctgtgtag gtctcccaaa gtgctagtgt 240
gtccggaatt ggtgggttct tggtctcact gacttcaaga atgaagccgc ggaccctcgc 300
agtctgctac aatg 314

<210> SEQ ID NO 38
<211> LENGTH: 39
<212> TYPE: DNA
<213> ORGANISM: Homo sapiens

<400> SEQUENCE: 38
ttttctcttc tgtcaacccc acacgccttt ggcacaatg 39

<210> SEQ ID NO 39
<211> LENGTH: 335
<212> TYPE: DNA
<213> ORGANISM: Homo sapiens

<400> SEQUENCE: 39
ctccctctag cgccttcccc ccggcccgac tccgctggtc agcgccaagt gacttacgcc 60
cccgaccctg agcccggacc gctaggcgag gaggatcaga tctccgctcg agaatctgaa 120
ggtgccctgg tcctggagga gttccgtccc agcccgcggt ctcccggtac tgtcgggccc 180
cggccctctg gagcttcagg aggcggccgt cagggtcggg gagtatttgg gtccggggtc 240
tcagggaagg gcggcgcctg ggtctgcggt atcggaaaga gcctgctgga gccaagtagc 300
cctccctctc ttgggacaga cccctcggtc ccatg 335

<210> SEQ ID NO 40
<211> LENGTH: 98
<212> TYPE: DNA
<213> ORGANISM: Homo sapiens

<400> SEQUENCE: 40
ctccctccct ctttccctca cagccgacga ggcaacaatt aggctttggg gataaaacga 60
ggtgcggaga gcgggctggg gcatttctcc ccgagatg 98

<210> SEQ ID NO 41
<211> LENGTH: 41
<212> TYPE: DNA
<213> ORGANISM: Homo sapiens

<400> SEQUENCE: 41
cactcttctg gtccccacag actcagagag aacccaccat g 41

<210> SEQ ID NO 42
<211> LENGTH: 84
<212> TYPE: DNA
<213> ORGANISM: Homo sapiens

<400> SEQUENCE: 42
cttcctctga tccgggccgg gcgggaagtc gggtcccgag gctccggctc ggcagaccgg 60
gcggaaagca gccgagcggc catg 84

<210> SEQ ID NO 43
<211> LENGTH: 48
<212> TYPE: DNA
<213> ORGANISM: Homo sapiens

<400> SEQUENCE: 43
cggcctttcc agggccgggg aaccccagga ggaagctgct gagccatg 48

<210> SEQ ID NO 44
<211> LENGTH: 166
<212> TYPE: DNA
<213> ORGANISM: Homo sapiens

<400> SEQUENCE: 44
cactctcttt acagtcagcc ttctgcttgc cacagtcata gtgggcagtc agtgaatctt 60
ccccaagtgc tgacaattaa tacctggttt agcggcaaag attcagagag gcgtgagcag 120
cccctctggc cttcagacaa aaatctacgt accatcagaa actatg 166

<210> SEQ ID NO 45
<211> LENGTH: 132
<212> TYPE: DNA
<213> ORGANISM: Homo sapiens

<400> SEQUENCE: 45
tctcctttta cacaaatagc cccggatatc tgtgttacca gccttgtctc ggccacctca 60
aggataatca ctaaattctg ccgaaaggac tgaggaacgg tgcctggaaa agggcaagaa 120
tatcacggca tg 132

<210> SEQ ID NO 46
<211> LENGTH: 59
<212> TYPE: DNA
<213> ORGANISM: Homo sapiens

<400> SEQUENCE: 46
tggtcccttt agggctccgg atatctttgg tgacttgtcc actccagtgt ggcatcatg 59

<210> SEQ ID NO 47
<211> LENGTH: 87
<212> TYPE: DNA
<213> ORGANISM: Homo sapiens

<400> SEQUENCE: 47
aaacctcttc gaggcacaag gcacaacagg ctgctctggg attctcttca gccaatcttc 60
attgctcaag tgtctgaagc agccatg 87

<210> SEQ ID NO 48
<211> LENGTH: 209
<212> TYPE: DNA
<213> ORGANISM: Homo sapiens

<400> SEQUENCE: 48
ctgtctctct tcatttaagc acgactctgc agaaggaaca aagcaccctc cccactgggc 60
tcctggttgc agagctccaa gtcctcacac agatacgcct gtttgagaag cagcgggcaa 120
gaaagacgca agcccagagg ccctgccatt tctgtgggct caggtcccta ctggctcagg 180
cccctgcctc cctcggcaag gccacaatg 209

<210> SEQ ID NO 49
<211> LENGTH: 185
<212> TYPE: DNA
<213> ORGANISM: Homo sapiens

<400> SEQUENCE: 49
agccctctgc cctttctgag cccgagggac tgccacctcc actgtgtgca cactcagcta 60
cgggacacat ttcaggtatc caaggcagca gaggtgagtg ggtcccccga gctctgtgac 120
cttatgctcc acactaactc tggcagagcc tccgtttcct catagaacaa agaacagcca 180
ccatg 185

<210> SEQ ID NO 50
<211> LENGTH: 111
<212> TYPE: DNA
<213> ORGANISM: Homo sapiens

<400> SEQUENCE: 50

-continued tgccctcctt ccctgtctct gcctctccct cccttcctca ggcatcagag cggagacttc 60
agggagacca gagcccagct tgccaggcac tgagctagaa gccctgccat g 111

<210> SEQ ID NO 51
<211> LENGTH: 72
<212> TYPE: DNA
<213> ORGANISM: Homo sapiens

<400> SEQUENCE: 51
ccgcccctcc cgcggccccg cccctcccgc ggcccgtcag cctctgccgc ggagctgcgt 60
ccgccactca tg 72

<210> SEQ ID NO 52
<211> LENGTH: 123
<212> TYPE: DNA
<213> ORGANISM: Homo sapiens

<400> SEQUENCE: 52
cttcctttaa aatcctataa aatcagaagc ccaagtctcc actgccagtg tgaaatcttc 60
agagaagaat ttctctttag ttctttgcaa gaaggtagag ataaagacac tttttcaaaa 120
atg 123

<210> SEQ ID NO 53
<211> LENGTH: 60
<212> TYPE: DNA
<213> ORGANISM: Homo sapiens

<400> SEQUENCE: 53
ttttctctct gattctccag cgacaggacc cggcgccggg cactgagcac cgccaccatg 60

<210> SEQ ID NO 54
<211> LENGTH: 110
<212> TYPE: DNA
<213> ORGANISM: Homo sapiens

<400> SEQUENCE: 54
ctttctctgt ctgccagggt ctccgactgt cccagacggg ctggtgtggg cttgggatcc 60
tcctggtgac ctctcccgct aaggtccctc agccactctg ccccaagatg 110

<210> SEQ ID NO 55
<211> LENGTH: 151
<212> TYPE: DNA
<213> ORGANISM: Homo sapiens

<400> SEQUENCE: 55
ccctccttcg cgctctctcg ctccctgccg ccgcccgcag ggctgcgggg ctcggtggca 60
tctcccgggc gcggcccgca gtccttgccc ctgcctccgg gccgctcccg cccccggcgc 120
cgctcgctcc cccgacccgg actcccccat g 151

<210> SEQ ID NO 56
<211> LENGTH: 85
<212> TYPE: DNA
<213> ORGANISM: Homo sapiens

<400> SEQUENCE: 56
gtgcctctgt ggccgcaggc gcaggcccgg gcgacagccg agacgtggag cgcgccggct 60
cgctgcagct ccgggactca acatg 85

<210> SEQ ID NO 57
<211> LENGTH: 71
<212> TYPE: DNA
<213> ORGANISM: Homo sapiens

<400> SEQUENCE: 57
gcttctctcg ttccgtcgat tgggaggagc ggtggcgacc tcggccttca gtgtttccga 60
cggagtgaat g 71

<210> SEQ ID NO 58
<211> LENGTH: 234
<212> TYPE: DNA
<213> ORGANISM: Homo sapiens

<400> SEQUENCE: 58
atctctctct tctcctggcg ctcgcgtgcg agagggaact agcgagaacg aggaagcagc 60
tggaggtgac gccgggcaga ttacgcctgt cagggccgag ccgagcggat cgctgggcgc 120
tgtgcagagg aaaggcggga gtgcccggct cgctgtcgca gagccgagcc tgtttctgcg 180
ccggaccagt cgaggactct ggacagtaga ggccccggga cgaccgagct gatg 234

<210> SEQ ID NO 59
<211> LENGTH: 67
<212> TYPE: DNA
<213> ORGANISM: Homo sapiens

<400> SEQUENCE: 59
aattctcctg gcggcctccg ttcagacgcg gcagctgtga cccacctgcc tcctccgcag 60
agcaatg 67

<210> SEQ ID NO 60
<211> LENGTH: 493
<212> TYPE: DNA
<213> ORGANISM: Homo sapiens

<400> SEQUENCE: 60
tcccctcttt ccccaacctc ctccctctct tctactccac ccctccgttt tcccactccc 60
cactgactcg gatgcctgga tgttctgcca ccgggcagtg gtccagcgtg cagccgggag 120
ggggcagggg cagggggcac tgtgacagga agctgcgcgc acaagttggc catttcgagg 180
gcaaaataag ttctcccttg gatttggaaa ggacaaagcc agtaagctac ctcttttgtg 240
tcggatgagg aggaccaacc atgagccaga gcccgggtgc aggctcaccg ccgccgctgc 300
caccgcggtc agctccagtt cctgccagga gttgtcggtg cgaggaattt tgtgacaggc 360
tctgttagtc tgttcctccc ttatttgaag gacaggccaa agatccagtt tggaaatgag 420
agaggactag catgacacat tggctccacc attgatatct cccagaggta cagaaacagg 480
attcatgaag atg 493

<210> SEQ ID NO 61
<211> LENGTH: 864
<212> TYPE: DNA
<213> ORGANISM: Homo sapiens

<400> SEQUENCE: 61
ggttcctttg gggtgatcaa agagggagac acagacacag agagacaaag gcaaggagga 60
ctgtctggga gccacgcggg cgatacagtt tccgaggcac gccgcgtccc gcctagcctg 120
ttgaacaggt agacatgagc gacccaagct gcggatttgc gaggcgcgcc ctggagctgc 180
tagagatccg gaagcacagc cccgaggtgt gcgaagccac caagtcaagt tcctaacgag 240
tcttcagagg aggcagcagg aagctcagag agctgcaaag caaccgtgcc catctgtcaa 300
gacattcctg agaagaacat acaagaaagt cttcctcaaa gaaaaaccag tcggagccga 360
gtctatcttc acactttggc agagagtatt tgcaaactga ttttcccaga gtttgaacgg 420
ctgaatgttg cacttcagag aacattggca aagcacaaaa taaaagaaag caggaaatct 480
ttggaaagag aagactttga aaaaacaatt gcagagcaag cagttgcagc aggagttcca 540
gtggaggtta tcaaagaatc tcttggtgaa gaggtttta aaatatgtta cgaggaagat 600
gaaaacatcc ttggggtggt tggaggcacc cttaaagatt ttttaaacag cttcagtacc 660
cttctgaaac agagcagcca ttgccaagaa gcaggaaaaa ggggcaggct tgaggacgcc 720
tccattctat gcctggataa ggaggatgat tttctacatg tttactactt cttccctaag 780
agaaccacct ccctgattct tcccggcatc ataaaggcag ctgctcacgt attatatgaa 840
acggaagtgg aagtgtcgtt aatg 864

<210> SEQ ID NO 62
<211> LENGTH: 111
<212> TYPE: DNA
<213> ORGANISM: Homo sapiens

<400> SEQUENCE: 62
ggctccttcc gctccgcgac tgcgttaact ggagccaggc tgagcgtcgg cgccggggtt 60
cggtggcctc tagtgagatc tggaggatcc aaggattctg tagctacaat g 111

<210> SEQ ID NO 63
<211> LENGTH: 55
<212> TYPE: DNA
<213> ORGANISM: Homo sapiens

<400> SEQUENCE: 63
aggtctctgc ggcgcggtcc tcggagacac gcggcggtgt cctgtgttgg ccatg 55

<210> SEQ ID NO 64
<211> LENGTH: 140
<212> TYPE: DNA
<213> ORGANISM: Homo sapiens

<400> SEQUENCE: 64
acttcctttc ccggcgtgca ccgcgaatcc ctcctcctct tctttacctc tctccctcct 60
cctcaggttc tctatcgacg agtctggtag ctgagcgttg ggctgtaggt cgctgtgctg 120
tgtgatcccc cagagccatg 140

<210> SEQ ID NO 65
<211> LENGTH: 198
<212> TYPE: DNA
<213> ORGANISM: Homo sapiens

<400> SEQUENCE: 65
ccttctttaa taagcaggag cgaaaaagac aaattccaaa gaggattgtt cagttcaagg 60
gaatgaagaa ttcagaataa ttttggtaaa tggattccaa tatggggaat aagaataagc 120
tgaacagttg acctgctttg aagaaacata ctgtccattt gtctaaaata atctataaca 180
accaaaccaa tcaaaatg 198

<210> SEQ ID NO 66
<211> LENGTH: 49

<212> TYPE: DNA
<213> ORGANISM: Homo sapiens

<400> SEQUENCE: 66
cggcccctct gttgtcgttt ggcagcggat agaggacacg accaagatg 49

<210> SEQ ID NO 67
<211> LENGTH: 113
<212> TYPE: DNA
<213> ORGANISM: Homo sapiens

<400> SEQUENCE: 67
cttccctttc ctgttaggcg agagctgcga aaggcgagag ctgcgaaggg ccaggtgtcg 60
ggcgctgttt ctcgttttca tcatatagac aaaacagccc tgctgcaaag atg 113

<210> SEQ ID NO 68
<211> LENGTH: 326
<212> TYPE: DNA
<213> ORGANISM: Homo sapiens

<400> SEQUENCE: 68
gcttcttctc acgccgggag caggctcccg cctcgcaccg ctgccccgcg agcagctcct 60
cttctcccga ggcgcgcggg gcgcccccgc gagccccgcg gctgagaccc cgcagcctgg 120
aggagggctg tccggggctt tggatgctgc tgctaggggt ggtgggagca gccgtgggac 180
gcgtggccgg gagcgggggt gacagcctgg gattccgggg gcttctcttc cttgtcctcc 240
tcctctcctc tctattccca gtgtggccgt ggctgacact aaagactttg tagccatcaa 300
cccgagtgca gtttcgatgg aaaatg 326

<210> SEQ ID NO 69
<211> LENGTH: 342
<212> TYPE: DNA
<213> ORGANISM: Homo sapiens

<400> SEQUENCE: 69
ccgcctcttt cattgaagaa atttaagttc gtgtggtttt accttttccg ggagtctcca 60
gctggccctc atttgtgtcc ggagctcagg agttcccaaa ccgactcagt cgcaccaagt 120
ttccgtcttt tggaattggg gaaggagttt ctttctttct tttctttttt cttgagccag 180
ttttaatcgc tttgaataaa tactccctta agtagttaaa tataggagga gaaagaatac 240
atcggttgtt aaagcaggag aggaagagag acctgccctg tagcgtgact cctctagaaa 300
aaaaaaaaaa aagccggagt attttactaa gcccctaaaa tg 342

<210> SEQ ID NO 70
<211> LENGTH: 186
<212> TYPE: DNA
<213> ORGANISM: Homo sapiens

<400> SEQUENCE: 70
cctcctcctg ctcctgcctt ggctcctccg ccgcgcgtct cgcactccga gagccgcagc 60
ggcagcggcg cgtcctgcct gcagagagcc aggccggaga agccgagcgg cgcagaggac 120
gccagggcgc gcgccgcagc cacccaccct ccggaccgcg gcagctgctg acccgccatc 180
gccatg 186

<210> SEQ ID NO 71
<211> LENGTH: 214
<212> TYPE: DNA

<213> ORGANISM: Homo sapiens

<400> SEQUENCE: 71
ctgtctttat ggaccagtag gcagagcgaa attgacgctg acaagacttt tgcatcttgg 60
aagggactgt aatctactgt agtgaagaac agagcctctc aatcagacgg gtgtaaataa 120
gagacggagg ggagtccaaa agaaaaggaa gaggaggaaa aacaagtgtg tgttgggggg 180
aacaggggga aaagcatttt tggtggatgg tatg 214

<210> SEQ ID NO 72
<211> LENGTH: 261
<212> TYPE: DNA
<213> ORGANISM: Homo sapiens

<400> SEQUENCE: 72
gctcctttaa gcgtccacag gcggcggagc ggccacaatc acagctccgg gcattggggg 60
aacccgagcc ggctgcgccg ggggaatccg tgcgggcgcc ttccgtcccg gtcccatcct 120
cgccgcgctc cagcacctct gaagttttgc agcgcccaga aaggaggcga ggaaggaggg 180
agtgtgtgag aggagggagc aaaaagctca ccctaaaaca tttatttcaa ggagaaaaga 240
aaaagggggg gcgcaaaaat g 261

<210> SEQ ID NO 73
<211> LENGTH: 97
<212> TYPE: DNA
<213> ORGANISM: Homo sapiens

<400> SEQUENCE: 73
ttttctcttt caaactgccc agacggttgg acaggacgta gacacacaga agaaaagaag 60
acaaagaacg ggtaggaaaa ttaaaaaggt taccatg 97

<210> SEQ ID NO 74
<211> LENGTH: 97
<212> TYPE: DNA
<213> ORGANISM: Homo sapiens

<400> SEQUENCE: 74
cagcctcttt tgccggtatt cagtgaagaa agcaagtcta aatatgcagt tctctcactg 60
gagtgaaaga tgttttgttc atttctaatc aactatg 97

<210> SEQ ID NO 75
<211> LENGTH: 472
<212> TYPE: DNA
<213> ORGANISM: Homo sapiens

<400> SEQUENCE: 75
ccgcctctcg gcgagcccgc cctcttctga agaggcgttt ctggaccact gagccccgcc 60
tcccactgtg agcggaaccc taccgttttt aaaaaaatct ttttcaaaac ttgccaggtt 120
gtctttccaa atatttttaa taatagtgct gctgctgtag accacagaga aaagaatccc 180
tcgctcttcc ttttcactta gtagaaactt ctaccgcgta ggtcccgcca ggagttcgcg 240
catgcgcagg agcgacaata agatggcggt gataatcgcc gcactttttt tcaaattagt 300
ggatcccaga aatcattgcg cgcatttgta acgaatttcc gttcgagttt gtattttagg 360
cgccattttc gagtgaagga cccggagccg aaacaccggt aggagcgggg aggtgggtac 420
tacacaaccg tctccagcct tggtctgagt ggactgtcct gcagcgacca tg 472

```
<210> SEQ ID NO 76
<211> LENGTH: 79
<212> TYPE: DNA
<213> ORGANISM: Homo sapiens

<400> SEQUENCE: 76

tggccttccc ggcggctgat tcgagggctt gtttggtcag aaggggggcg tcagagaagc      60

tgccccttag ccaaccatg                                                   79

<210> SEQ ID NO 77
<211> LENGTH: 141
<212> TYPE: DNA
<213> ORGANISM: Homo sapiens

<400> SEQUENCE: 77

gagtctttcg gcctgggtgg aggacgcggc tgcttcaagt ccttggctct gatccaggcc      60

acagattcca ggattctaca ggcaggaaac atcttagaaa tcagggttgg gcaggcagga     120

gccaggagag tagctacaat g                                               141

<210> SEQ ID NO 78
<211> LENGTH: 217
<212> TYPE: DNA
<213> ORGANISM: Homo sapiens

<400> SEQUENCE: 78

tatccttttt tactgcagat ttactttaag gctcatattc tccaagtcta ttctgcttta      60

aaaagaagac aagaaaagaa gtggtttatc aaaatcacgt tataatcaga ttttgaccaa     120

gcattttgta agtatacaaa tgtcagccaa tgacatataa caaccatttc ttataaaacc     180

ttgatgttca aaagcctgac tagcagtggc atccatg                              217

<210> SEQ ID NO 79
<211> LENGTH: 181
<212> TYPE: DNA
<213> ORGANISM: Homo sapiens

<400> SEQUENCE: 79

tgctcttttc gatccgggac ggccggtcag gctcgccgcc gagctggaga actacgatga      60

cccgcacaaa acccctgcct ccccagttgt ccacatcagg ggcctgattg acggtgtggt     120

ggaagcagac cttgtggagg ccttgcagga gtttggaccc atcagctatg tggtggtaat     180

g                                                                    181

<210> SEQ ID NO 80
<211> LENGTH: 303
<212> TYPE: DNA
<213> ORGANISM: Homo sapiens

<400> SEQUENCE: 80

cattcttccg ggtccagaag gtgatctccg cccgtgctca gaatccaggg gcccggggct      60

gtagattcct tgacaaggat atcctagcgg cgaaacaaca ccgtactggg agtcagaacg     120

tctgggttct agtcttgact gccattaact agcggtatga cattggagaa gctttttga     180

cccttctgga tttccgtttc cttttctgta aaatgaggag cttggaagat ccggaaaatg     240

aggcccatag gaaacaagtg acttgctgag tccagataac actgactgtc agagagaaac     300

atg                                                                  303

<210> SEQ ID NO 81
```

<211> LENGTH: 289
<212> TYPE: DNA
<213> ORGANISM: Homo sapiens

<400> SEQUENCE: 81
tggcctcctc ttgccacgag gtcagacggc gagttcttag agaaaaaggc tgcttagctg 60
ctgcttatca tgtaacctca aaaggaaact gatcgtcttt ctcatgctgt cacgtacttg 120
ggttattatc gctgattaca gctggaaaca attgatttgc tcttacgtat ttgtgtgact 180
tgactcttca aacacaaagg ttaacaggaa gatctcgagg gccctggctg aacttcacct 240
tttggctttc ttggcctgat gctgaactct cgaggttgag ccccatatg 289

<210> SEQ ID NO 82
<211> LENGTH: 172
<212> TYPE: DNA
<213> ORGANISM: Homo sapiens

<400> SEQUENCE: 82
atccctcccc ggactccggc tccggctccg attgcaattt gcaacctccg ctgccgtcgc 60
cgcagcagcc accaattcgc cagcggttca ggtggctctt gcctcgatgt cctagcctag 120
gggcccccgg gccggacttg gctgggctcc cttcaccctc tgcggagtca tg 172

<210> SEQ ID NO 83
<211> LENGTH: 24
<212> TYPE: DNA
<213> ORGANISM: Homo sapiens

<400> SEQUENCE: 83
ccgcctcctc gggagagata aatg 24

<210> SEQ ID NO 84
<211> LENGTH: 221
<212> TYPE: DNA
<213> ORGANISM: Homo sapiens

<400> SEQUENCE: 84
gcgccccttt gtgcgtcacg ggtggcgggc gcgggaaggg gatttggatt gttgcgcctc 60
tgctctgaag aaagtgctgt ctggctccaa ctccagttct ttcccctgag cagcgcctgg 120
aacctaaccc ttcccactct gtcaccttct cgatcccgcc ggcgctttag agccgcagtc 180
cagtcttgga tccttcagag cctcagccac tagctgcgat g 221

<210> SEQ ID NO 85
<211> LENGTH: 222
<212> TYPE: DNA
<213> ORGANISM: Homo sapiens

<400> SEQUENCE: 85
gcgtcttttc ccccagcccc gctccaccag atccgcggga gccccactgc tctccgggtc 60
cttggcttgt ggctgtgggt cccatcgggc ccgccctcgc acgtcactcc gggacccccg 120
cggcctccgc aggttctgcg ctccaggccg gagtcagaga ctccaggatc ggttctttca 180
tcttcgccgc ccctgcgcgt ccagctcttc taagacgaga tg 222

<210> SEQ ID NO 86
<211> LENGTH: 143
<212> TYPE: DNA
<213> ORGANISM: Homo sapiens

<400> SEQUENCE: 86 aacccttttct gcagagtccc ggcagtgcgg gactccggta gccgcccctc cggtagccgc 60
ccctcctgcc cccgcgccgc cgccctatat gttgcccgcc gcggcctctg gggcatggag 120
cacgctgccc agccctggcg atg 143

<210> SEQ ID NO 87
<211> LENGTH: 99
<212> TYPE: DNA
<213> ORGANISM: Homo sapiens

<400> SEQUENCE: 87
gttccctttt ctacctgcag agcacggttc ccataagggc ggcgagatca gcctcctgtc 60
tcatctggaa gaccaccact ctggggtctc agaggaatg 99

<210> SEQ ID NO 88
<211> LENGTH: 50
<212> TYPE: DNA
<213> ORGANISM: Homo sapiens

<400> SEQUENCE: 88
ctatctctgt gtgtccgcgt gtgcgcccgg tccccgcctg ccgcaccatg 50

<210> SEQ ID NO 89
<211> LENGTH: 310
<212> TYPE: DNA
<213> ORGANISM: Homo sapiens

<400> SEQUENCE: 89
cctcctcctc cagctcttcc tgtcccgctg ttgcaacact gcctcactct tcccctccca 60
ccttctctcc cctcctctct gctttaattt tctcagaatt ctctggactg aggctccagt 120
tctggccttt ggggttcaag atcactggga ccaggccgtg atctctatgc ccgagtctca 180
accctcaact gtcaccccaa ggcacttggg acgtcctgga cagaccgagt cccgggaagc 240
cccagcactg ccgctgccac actgccctga gcccaaatgg gggagtgaga ggccatagct 300
gtctggcatg 310

<210> SEQ ID NO 90
<211> LENGTH: 84
<212> TYPE: DNA
<213> ORGANISM: Homo sapiens

<400> SEQUENCE: 90
aggtctctgc gcagcccagc ccgccggtcc acgccgcgca ccgctccgag ggccagcgcc 60
acccgctccg cagccggcac catg 84

<210> SEQ ID NO 91
<211> LENGTH: 50
<212> TYPE: DNA
<213> ORGANISM: Homo sapiens

<400> SEQUENCE: 91
tcgcctttgc cgatccgccg cccgtccaca cccgccgcca gctcaccatg 50

<210> SEQ ID NO 92
<211> LENGTH: 107
<212> TYPE: DNA
<213> ORGANISM: Homo sapiens

<400> SEQUENCE: 92
ggctccttct tcctctgcat gtggctggcg gccgcagagc agttcagttc gctcactcct 60
cgccggccgc ctctccttcg ggctctcctc gcgtcactgg agccatg 107

<210> SEQ ID NO 93
<211> LENGTH: 52
<212> TYPE: DNA
<213> ORGANISM: Homo sapiens

<400> SEQUENCE: 93
cgttctctgc ctggcctgag gctccctgag ccgcctcccc accatcacca tg 52

<210> SEQ ID NO 94
<211> LENGTH: 160
<212> TYPE: DNA
<213> ORGANISM: Homo sapiens

<400> SEQUENCE: 94
gcctcctttc tttctcagcc cagacctggc cctctggaga gggttttgga gtcctgggta 60
ggcagggtac ctcaggcagc aggcagcaca ccttggatgt gagctgaatg gattttcaaa 120
tttcacagaa ggagcctcca tgctggagaa agtatgtatg 160

<210> SEQ ID NO 95
<211> LENGTH: 126
<212> TYPE: DNA
<213> ORGANISM: Homo sapiens

<400> SEQUENCE: 95
cggcctccct ttagctgcca tcttgcgtcc ccgcgtgtgt gcgcctaatc tcaggtggtc 60
cacccgagac cccttgagca ccaaccctag tccccgcgc ggccccttat tcgctccgac 120
aagatg 126

<210> SEQ ID NO 96
<211> LENGTH: 43
<212> TYPE: DNA
<213> ORGANISM: Homo sapiens

<400> SEQUENCE: 96
ttgtcctttg catctgcacg tgttcgcagt cgtttccgcg atg 43

<210> SEQ ID NO 97
<211> LENGTH: 485
<212> TYPE: DNA
<213> ORGANISM: Homo sapiens

<400> SEQUENCE: 97
tttcctttct taatatggcg atgagctctt aggccagtgt ggggaccggg gctgaggtgc 60
cctggacact ggaggagggg gagggaagga gcccctggga gcctggggta gaagtgtagg 120
aggtgggagg attccggccc gcatggagct gtcctggcct cagaaggtta tccgtctctc 180
ctgccaacca tggagacata tttagacagg accaggtggg gactgagggg tgccaatttc 240
agggggcagc tccggttccc tccccgcccc ctgctcctat tcctccacct gacccttttt 300
cccttggctc tgtcggcagt ttctccagga cccagcagtg ccctctgtcc actgctctgg 360
gccattcccc aatcccccct cccacttgag cccctaactc agaatctggg acccaggggc 420
ccctccctac cccagctaac ctcttctgga ccaggagagc caacccagat cccactacct 480
ccatg 485

<210> SEQ ID NO 98
<211> LENGTH: 92
<212> TYPE: DNA
<213> ORGANISM: Homo sapiens

<400> SEQUENCE: 98
gtctctctgc ccctctctgc cccaagtatt ttcagcccca gccggccaca cagctcggat 60
ctcctcctgt ggatcccccc agctctgcga tg 92

<210> SEQ ID NO 99
<211> LENGTH: 235
<212> TYPE: DNA
<213> ORGANISM: Homo sapiens

<400> SEQUENCE: 99
aggtctttgg cttttttttgg cggagctggg gcgccctccg gaagcgtttc caactttcca 60
gaagtttctc gggacgggca ggagggggtg gggactgcca tatatagatc ccgggagcag 120
gggagcgggc taagagtaga atcgtgtcgc ggctcgagag cgagagtcac gtcccggcgc 180
tagcccagcc cgacccaggc ccaccgtggt gcacgcaaac cacttcctgg ccatg 235

<210> SEQ ID NO 100
<211> LENGTH: 92
<212> TYPE: DNA
<213> ORGANISM: Homo sapiens

<400> SEQUENCE: 100
tttcctcctt tccaagagag ggctgaggga gcagggttga gcaactggtg cagacagcct 60
agctggactt tgggtgaggc ggttcagcca tg 92

<210> SEQ ID NO 101
<211> LENGTH: 97
<212> TYPE: DNA
<213> ORGANISM: Homo sapiens

<400> SEQUENCE: 101
gggtcccttt ctgtcccctg agcaccgtcg cctcctttcc tccagggctc cgtaggcacc 60
aactgcaagg acccctcccc ctgcgggcgc tcccatg 97

<210> SEQ ID NO 102
<211> LENGTH: 98
<212> TYPE: DNA
<213> ORGANISM: Homo sapiens

<400> SEQUENCE: 102
gagcctctcc tcaaagcctg gctcccacgg aaaatatgct cagtgcagcc gcgtgcatga 60
atgaaaacgc cgccgggcgc ttctagtcgg acaaaatg 98

<210> SEQ ID NO 103
<211> LENGTH: 380
<212> TYPE: DNA
<213> ORGANISM: Homo sapiens

<400> SEQUENCE: 103
cgctcccttc gtttccgtct cggccgggca cccgagcgca tcccgccgag gccgggccgt 60
ttcaggggga ggcgccaact catcgcggcg ccgggcccct gaccgtgcag taaccgctac 120
ccaggaggcg gagcggacaa ggctccggcc tgcgaggagt cacattaact ttgctctaga 180
agacaacttt acaaggatct aaaaggaaca ggattaaaga tgactgaata ctgggttcca 240

-continued

```
gaaatttaaa acaatcagct tagcaaatca tatattcttc tgtggagctg agaattgatg    300

tccgctcttc cccgtgattt ggaactttcc aatcccagag aaaagttgac aaagggactg    360

cccaggactg agtccatatg                                                380


<210> SEQ ID NO 104
<211> LENGTH: 94
<212> TYPE: DNA
<213> ORGANISM: Homo sapiens

<400> SEQUENCE: 104

ccccccctca ctcgcgcgtt aggaggctcg ggtcgttgtg gtgcgctgtc ttcccgcttg     60

cgtcagggac ctgcccgact cagtggccgc catg                                 94


<210> SEQ ID NO 105
<211> LENGTH: 211
<212> TYPE: DNA
<213> ORGANISM: Homo sapiens

<400> SEQUENCE: 105

cctcctctcc tctccctctc ctctcctgct atagagggct ccgacagcag ttcccagcca     60

gcgtgttcag cctgcctgcc tgcctgcctc tgtgtgtgtg tgagcgtgtg tgcgtgcgtc    120

tactttgtac tgggaagaac acagcccatg tgctctgcat ggacgttact gatactctgt    180

ttagcttgat tttcgaaaag caggcaagat g                                   211


<210> SEQ ID NO 106
<211> LENGTH: 87
<212> TYPE: DNA
<213> ORGANISM: Homo sapiens

<400> SEQUENCE: 106

ctgcctcttc cagggcgggc ggtgtggtgc acgcattgct gtgctccaac tccctcaggg     60

cctgtgttgc cgcactctgc tgctatg                                         87


<210> SEQ ID NO 107
<211> LENGTH: 243
<212> TYPE: DNA
<213> ORGANISM: Homo sapiens

<400> SEQUENCE: 107

cctcctcctt ctcccgccct cctcgccgat ccgggcggtg ctggcagccg gagcggcggc     60

gggcgggccg agcagccggg gcagccgcgc gtgggcatcc acgggcgccg agcctccgtc    120

cgtgtctcta tccctcccgg gcctttgtca gcgcgcccgc tgggagcggg gccgagagcg    180

ccggttccag tcagacagcc ccgcaggtca gcggccgggc cgagggcgcc agagggggcc    240

atg                                                                  243


<210> SEQ ID NO 108
<211> LENGTH: 506
<212> TYPE: DNA
<213> ORGANISM: Homo sapiens

<400> SEQUENCE: 108

ttgcctttgg ctgggtgcaa cttccatttt aggtgttgga tctgaggggg aaaaaaaaga     60

gagagggaga gagagagaaa gaagagcagg aaagatcccg aaaggaggaa gaggtggcga    120

aaaatcaact gccctgctgg atttgtcttt ctcagcacct tggcgaagcc ttgggtttct    180

ttcttaaagg actgattttt agaactccac atttgaggtg tgtggctttt gaagaaaatg    240
```

tatgtactga cgggaaaagg aggataagca agtcgaattt ttgtcttacg ctctctcctt 300
cctgcttcct ccttgctgtg gtggctggga tgcttcttcc atgatttttt gaatctagac 360
tgggctgttc tctgtgttaa accaatcagt tgcgaccttc tcttaacagt gtgaagtgag 420
ggggtctctc tccctccttc tccttcctct gtgattcacc ttcctttttta ccctgccctg 480 cggcggctcc gcccccttacc ttcatg 506

<210> SEQ ID NO 109
<211> LENGTH: 528
<212> TYPE: DNA
<213> ORGANISM: Homo sapiens

<400> SEQUENCE: 109
ccgtcccctc cagcccagct cgggctccag ctccagcgcc ggcgcttcag ctgcgaccgc 60
gagccctctc aagcaagata taacttcccc aagtcacaca gtggtatcag agctaagaat 120
gggacccaga tatgactgat ctagttctgt tccaaaaccg tgctgtatta tattaacgcc 180
taccctctga agaggtccaa gcaacggaag tactactacg aagctgcctt tctggccatc 240
cttgagaaaa atagacagat gagttcctgc cagtgagtcc ctaggcctcc atctctctcc 300
cttgctgtac caccttcacc accatccatg cgaccccaag agccttaatg actctagaag 360
agactccagg caggggaagc tgaaaggacc tttcactccc tacttttggc cagggccttc 420
tgtgccacct gccaagacca gcaggcctac cctctgaaga ggtccaagca acggaagtac 480
tactacgaag ctgcctttct ggccatcctt gagaaaaata gacagatg 528

<210> SEQ ID NO 110
<211> LENGTH: 163
<212> TYPE: DNA
<213> ORGANISM: Homo sapiens

<400> SEQUENCE: 110
cgatctttct ggagccgcac ctccacgcgg agtccgagcg cgtgtgctga gaccccaggg 60
tcgggagggc ggagactggg agggagggag aagccccttt ggcctgcctt acggaagcct 120
gcgagggagg gtggtgtcca ctgcccagtt ccgtgtcccg atg 163

<210> SEQ ID NO 111
<211> LENGTH: 175
<212> TYPE: DNA
<213> ORGANISM: Homo sapiens

<400> SEQUENCE: 111
agttcttctc gatcgtgtca gtttgtaagg cgagggcgga agttggattc ctggcctgag 60
aatattaggc gtagttttcc agtttttggc aaagcggaaa tacttaaggc ccctgggttg 120
actgggttct ttgttttatc taccggcttc tgctttacga caggtcacaa acatg 175

<210> SEQ ID NO 112
<211> LENGTH: 97
<212> TYPE: DNA
<213> ORGANISM: Homo sapiens

<400> SEQUENCE: 112
tttcctcccc atcctgtcgc ggctcgaaag gaatggaaaa tggcggccta gacgcggagt 60
ttcctgcccg acccgcggcg gctccggcgg cgccatg 97

<210> SEQ ID NO 113

<211> LENGTH: 247
<212> TYPE: DNA
<213> ORGANISM: Homo sapiens

<400> SEQUENCE: 113
ctctctcttt tttttccgcc ctagctgggg ctgtgttgga ggagaggaag aaagagagac 60
agaggattgc attcatccgt tacgttcttg aaatttccta atagcaagac cagcgaagcg 120
gttgcaccct tttcaatctt gcaaaggaaa aaaacaaaac aaaacaaaaa aaacccaagt 180
ccccttcccg gcagtttttg ccttaaagct gccctcttga aattaatttt ttcccaggag 240
agagatg 247

<210> SEQ ID NO 114
<211> LENGTH: 107
<212> TYPE: DNA
<213> ORGANISM: Homo sapiens

<400> SEQUENCE: 114
tgttctcttt ggcttccggg cgcacgctac tctgtcgccg ccgtcagacc ggaattgccg 60
gtgccgccgc caccgctgtc tgtgcgccca cctctgctgc taccatg 107

<210> SEQ ID NO 115
<211> LENGTH: 70
<212> TYPE: DNA
<213> ORGANISM: Homo sapiens

<400> SEQUENCE: 115
cgttcttttt cgcaacgggt ttgccgccag aacacaggtg tcgtgaaaac tacccctaaa 60
agccaaaatg 70

<210> SEQ ID NO 116
<211> LENGTH: 89
<212> TYPE: DNA
<213> ORGANISM: Homo sapiens

<400> SEQUENCE: 116
tctcctcttt ccccctccct tctctcccgg gcggcttact ttgcggcagc gccgagaacc 60
ccaccccctt tctttgcgga atcaccatg 89

<210> SEQ ID NO 117
<211> LENGTH: 31
<212> TYPE: DNA
<213> ORGANISM: Homo sapiens

<400> SEQUENCE: 117
atttccttcc tcttttggca acatggcggg c 31

<210> SEQ ID NO 118
<211> LENGTH: 35
<212> TYPE: DNA
<213> ORGANISM: Homo sapiens

<400> SEQUENCE: 118
gggtcttttg cgttctcttt ccctctccca acatg 35

<210> SEQ ID NO 119
<211> LENGTH: 40
<212> TYPE: DNA
<213> ORGANISM: Homo sapiens

<400> SEQUENCE: 119
tattcttttg aagattcttc gttgtcaagc cgccaaagtg 40

<210> SEQ ID NO 120
<211> LENGTH: 141
<212> TYPE: DNA
<213> ORGANISM: Homo sapiens

<400> SEQUENCE: 120
cttcccctca gtgcggtcac atacttccag aagagcggac cagggctgct gccagcacct 60
gccactcaga gcgcctctgt cgctgggacc cttcagaact ctctttgctc acaagttacc 120
aaaaaaaaaa gagccaacat g 141

<210> SEQ ID NO 121
<211> LENGTH: 86
<212> TYPE: DNA
<213> ORGANISM: Homo sapiens

<400> SEQUENCE: 121
cgctcttttc cacgtgcgaa agccccggac tcgtggagtt gtgaacgccg cggactccgg 60
agccgcacaa accagggctc gccatg 86

<210> SEQ ID NO 122
<211> LENGTH: 311
<212> TYPE: DNA
<213> ORGANISM: Homo sapiens

<400> SEQUENCE: 122
ctgtcccttg ctccaggcgc tcactttgcg ggcggcactt tttccaggtt gttaatccag 60
ctaatggaga aggatagatg cacgctactt ggtttagaaa aaaaaacaaa aatgagcaaa 120
cgagacgccc cttccgtttt atgataacta agctgcaggg aaataaatcg gctggcccta 180
ctgcaatcta ctgcactcga gaaacatcac agaaaattct ttgatttatc ttaatagtga 240
caagtgagcc tgcttctgtc aattactgaa gctataagga gatttttttaa aaattaaact 300 tcaacacaat g 311

<210> SEQ ID NO 123
<211> LENGTH: 212
<212> TYPE: DNA
<213> ORGANISM: Homo sapiens

<400> SEQUENCE: 123
ccgcctctgt tcaggacact gggtcccctt ggagcctccc caggcttaat gattgtccag 60
aaggcggcta taaagggagc ctgggaggct gggtggagga gggagcagaa aaaacccaac 120
tcagcagatc tgggaactgt gagagcggca agcaggaact gtggtcagag gctgtgcgtc 180
ttggctggta gggcctgctc ttttctacca tg 212

<210> SEQ ID NO 124
<211> LENGTH: 219
<212> TYPE: DNA
<213> ORGANISM: Homo sapiens

<400> SEQUENCE: 124
agccctcccc tcctcgctcc ctcccctcct ctccccgccc agttcttctc ttcccgtctg 60
aggtggcggt cggtctcgcc ttgtcgccag ctccattttc ctctctttct cttcccccttt 120 ccttcgcgcc caagagcgcc tcccagcctc gtagggtggt cacggagccc ctgcgccttt 180
tccttgctcg ggtcctgcgt ccgcgcctgc cccgccatg 219

<210> SEQ ID NO 125
<211> LENGTH: 30
<212> TYPE: DNA
<213> ORGANISM: Homo sapiens

<400> SEQUENCE: 125
cacccttctt aaagcggcgg cgggaagatg 30

<210> SEQ ID NO 126
<211> LENGTH: 190
<212> TYPE: DNA
<213> ORGANISM: Homo sapiens

<400> SEQUENCE: 126
ggccctccct gcacggcctc ccgtgcgccc ctgtcagact gtggcggccg gtcgcgcggt 60
gcgctctccc tccctgcccg cagcctggag aggcgcttcg tgctgcacac ccccgcgttc 120
ctgccggcac cgcgcctgcc ctctgccgcg ctccgccctg ccgccgaccg cacgcccgcc 180
gcgggacatg 190

<210> SEQ ID NO 127
<211> LENGTH: 246
<212> TYPE: DNA
<213> ORGANISM: Homo sapiens

<400> SEQUENCE: 127
ggccccctcc tcgcgagttg gtgccgctgc cacctccgat tccgagcttt cggcacctct 60
gccgggtggt accgagcctt cccggcgccc cctcctctcc tcccaccggc ctgcccttcc 120
ccgcgggact atcgccccca cgtttccctc agcccttttc tctcccggcc gagccgcggc 180
ggcagcagca gcagcagcag cagcaggagg aggagcccgg tggcggcggt ggccggggag 240
cccatg 246

<210> SEQ ID NO 128
<211> LENGTH: 304
<212> TYPE: DNA
<213> ORGANISM: Homo sapiens

<400> SEQUENCE: 128
gggccttccc ggctgacggc ctgcgtgcac tgcgcttgcg cgggttgagg gcggtggctc 60
aggctcctgg aaaggaccgt ccacccctcc gcgctggcgg tgtggacgcg gaactcagcg 120
gagaaacgcg attgagagca gtgtgtggat tacactatca ctggaaaaat acgaattgag 180
aagaaggaaa agactggaag atgcagacct tggttcctgt tagtggaaac actgtaaggt 240
cccagaaatg gaaaagaaaa tgaaataaat cagcagttat gaggcagagc ctaagagaac 300
tatg 304

<210> SEQ ID NO 129
<211> LENGTH: 20
<212> TYPE: DNA
<213> ORGANISM: Homo sapiens

<400> SEQUENCE: 129
gttcctctct ccccaagatg 20

<210> SEQ ID NO 130
<211> LENGTH: 23

<212> TYPE: DNA
<213> ORGANISM: Homo sapiens

<400> SEQUENCE: 130
actccctttt ctttggcaag atg 23

<210> SEQ ID NO 131
<211> LENGTH: 515
<212> TYPE: DNA
<213> ORGANISM: Homo sapiens

<400> SEQUENCE: 131
gtccctctac tcagagcagc ccggagaccg ctgccgccgc tgccgctgct accaccgctg 60
ccacctgagg agacccgccg cccccccgtc gccgcctcct gcgagtcctt cttagcacct 120
ggcgtttcat gcacattgcc actgccatta ttattatcat tccaatacaa ggaaaataaa 180
agaagatacc agcgaaaaga accgcttaca cctttccgaa ttactcaagt gtctcctgga 240
aacagagggt cgttgtcccc ggaggagcag ccgaagggcc cgtgggctgg tgttgaccgg 300
gagggaggag gagttggggg cattgcgtgg tggaaagttg cgtgcggcag agaaccgaag 360
gtgcagcgcc acagcccagg ggacggtgtg tctgggagaa gacgctgccc ctgcgtcggg 420
acccgccagc gcgcgggcac cgcggggccc gggacgacgc cccctcctgc ggcgtggact 480
ccgtcagtgg cccaccaaga aggaggagga atatg 515

<210> SEQ ID NO 132
<211> LENGTH: 305
<212> TYPE: DNA
<213> ORGANISM: Homo sapiens

<400> SEQUENCE: 132
ttttctttat cctgcagtct ttacctcagc agaaccgcac accacagact ccctccagct 60
ctttgtgtgt ggctctctca gggtccaaca agagcaagct gtgggtctgt gagtgtttat 120
gtgtgctttt attcacttca cacttattga aaagtgtgta tgtgagaggg tggggtgtgt 180
gtgtcaaaga gagtgaggaa gagaaggaga gagagatcaa ttgattctgc agcctcagct 240
ccagcatccc tcagttggga gcttccaaag ccgggtgatc acttggggtg catagctcgg 300
agatg 305

<210> SEQ ID NO 133
<211> LENGTH: 151
<212> TYPE: DNA
<213> ORGANISM: Homo sapiens

<400> SEQUENCE: 133
ccgcccctta cccggcgtgc cccgcgcccg gaggcgctga cgtggccgcc gtcagagccg 60
ccatcttgtg ggagcaaaac caacgcctgg ctcggagcag cagcctctga ggtgtccctg 120
gccagtgtcc ttccacctgt ccacaagcat g 151

<210> SEQ ID NO 134
<211> LENGTH: 569
<212> TYPE: DNA
<213> ORGANISM: Homo sapiens

<400> SEQUENCE: 134
gcgccttttc cggcagcggc ggcggcagaa ctgggaggag gagttggagg ccggagggag 60
cccgcgctcg gggcggcggc tggaggcagc gcaccgagtt cccgcgagga tccatgacct 120
gacggggccc cggagccgcg ctgcctctcg ggtgtcctgg gtcggtgggg agcccagtgc 180
tcgcaggccg gcgggcgggc cggagggctg cagtctccct cgcggtgaga ggaaggcgga 240
ggagcgggaa ccgcggcggc gctcgcgcgg cgcctgcggg gggaagggca gttccgggcc 300
gggccgcgcc tcagcagggc ggcggctccc agcgcagtct cagggcccgg gtggcggcgg 360
cgactggaga aatcaagttg tgcggtcggt gatgcccgag tgagcggggg gcctgggcct 420
ctgcccttag gaggcaactc ccacgcaggc cgcaaaggcg ctctcgcggc cgagaggctt 480
cgtttcggtt tcgcggcggc ggcggcgttg ttggctgagg ggacccggga cacctgaatg 540
cccccggccc cggctcctcc gacgcgatg 569

<210> SEQ ID NO 135
<211> LENGTH: 187
<212> TYPE: DNA
<213> ORGANISM: Homo sapiens

<400> SEQUENCE: 135
cgccctcccg ccgccgcccg ccctcgctct ctcgcgctac cctcccgccg cccgcggtcc 60
tccgtcggtt ctctcgttag tccacggtct ggtcttcagc tacccgcctt cgtctccgag 120
tttgcgactc gcggaccggc gtccccggcg cgaagaggct ggactcggat tcgttgcctg 180
agcaatg 187

<210> SEQ ID NO 136
<211> LENGTH: 152
<212> TYPE: DNA
<213> ORGANISM: Homo sapiens

<400> SEQUENCE: 136
cggcctcccg ctctcacttc cttctcgagc ccggagccgc tgccgccgcc cccagctccc 60
ccgcctcggg gagggcacca ggtcactgca gccagagggg tccagaagag agaggaggca 120
ctgcctccac tacagcaact gcacccacga tg 152

<210> SEQ ID NO 137
<211> LENGTH: 46
<212> TYPE: DNA
<213> ORGANISM: Homo sapiens

<400> SEQUENCE: 137
ctctcttccc actcgggttt gacctacagc cgcccgggag aagatg 46

<210> SEQ ID NO 138
<211> LENGTH: 194
<212> TYPE: DNA
<213> ORGANISM: Homo sapiens

<400> SEQUENCE: 138
ccacctctgt ctgctgccgg cagaaagcca caagccatga aaactgattg agatgagaag 60
aattcatctg ggactggctt ttgctttagg atggtgttgg aagttgctcg ttgtcgctag 120
gagcctgctc cactgtaagg gtgtcaggat ctgaagagct atggtgaaac accactgaag 180
cattgccaag gatg 194

<210> SEQ ID NO 139
<211> LENGTH: 323
<212> TYPE: DNA
<213> ORGANISM: Homo sapiens

<400> SEQUENCE: 139
gcatctcttc gcctctcgga gctggaaatg cagctattga gatcttcgaa tgctgcggag 60
ctggaggcgg aggcagctgg ggaggtccga gcgatgtgac caggccgcca tcgctcgtct 120
cttcctctct cctgccgcct cctgtctcga aaataacttt tttagtctaa agaaagaaag 180
acaaaagtag tcgtccgccc ctcacgccct ctcttcctct cagccttccg cccggtgagg 240
aagcccgggg tggctgctcc gccgtcgggg ccgcgccgcc gagccccagc cgccccgggc 300
cgcccccgca cgccgccccc atg 323

<210> SEQ ID NO 140
<211> LENGTH: 80
<212> TYPE: DNA
<213> ORGANISM: Homo sapiens

<400> SEQUENCE: 140
cggcctctag tcatcgccct cgcagcggcg gccaacatca ccgccactgc cacccctccc 60
agactgtgga cgggaggatg 80

<210> SEQ ID NO 141
<211> LENGTH: 131
<212> TYPE: DNA
<213> ORGANISM: Homo sapiens

<400> SEQUENCE: 141
aggcctcttg gttctgcggc acgtgacggt cgggccgcct ccgcctctct ctttactgcg 60
gcgcggggca aggtgtgcgg gcgggaaggg gcacgggcac ccccgcggtc cccgggaggc 120
tagagatcat g 131

<210> SEQ ID NO 142
<211> LENGTH: 42
<212> TYPE: DNA
<213> ORGANISM: Homo sapiens

<400> SEQUENCE: 142
cgacctttct ctgcgcagta cggccgccgg gaccgcagca tg 42

<210> SEQ ID NO 143
<211> LENGTH: 108
<212> TYPE: DNA
<213> ORGANISM: Homo sapiens

<400> SEQUENCE: 143
gcgccttttt ttccccccat acaatacaag atcttccttc ctcagttccc ttaaagcaca 60
gcccagggaa acctcctcac agttttcatc cagccacggg ccagcatg 108

<210> SEQ ID NO 144
<211> LENGTH: 220
<212> TYPE: DNA
<213> ORGANISM: Homo sapiens

<400> SEQUENCE: 144
cgacctcttt gcagctcgca cagctaaggg cgagggcgcc cttcggcaga agcagcaaac 60
cgccggcaag cccagcgagg agggctgccg gggtctgggc ttgggaattg gctggcaccc 120
agcggaaagg gacgtgagct gagcggcggg ggagaagagt gcgcaggtca gagggcggcg 180
cgcagcggcg ctccgcgagg tccccacgcc gggcgatatg 220

<210> SEQ ID NO 145

<211> LENGTH: 84
<212> TYPE: DNA
<213> ORGANISM: Homo sapiens

<400> SEQUENCE: 145
tctccttttg ctctcagatg ctgccagggt ccctgaagag ggaagacacg cggaaacagg 60
cttgcaccca gacacgacac catg 84

<210> SEQ ID NO 146
<211> LENGTH: 142
<212> TYPE: DNA
<213> ORGANISM: Homo sapiens

<400> SEQUENCE: 146
cttcctcttt tggggttctt cctttctctc tcagctctcc gtctctcttt ctctctcagc 60
ctctttcttt ctccctgtct cccccactgt cagcacctct tctgtgtggt gagtggaccg 120
cttaccccac taggtgaaga tg 142

<210> SEQ ID NO 147
<211> LENGTH: 70
<212> TYPE: DNA
<213> ORGANISM: Homo sapiens

<400> SEQUENCE: 147
gcctctctct tgctgcctag cctcctgccg gcctcatctt cgcccagcca accccgcctg 60
gagccctatg 70

<210> SEQ ID NO 148
<211> LENGTH: 66
<212> TYPE: DNA
<213> ORGANISM: Homo sapiens

<400> SEQUENCE: 148
cggccttttt ctagccaggc tctcaactgt ctcctgcgtt gctgggaagt tctggaagga 60
agcatg 66

<210> SEQ ID NO 149
<211> LENGTH: 37
<212> TYPE: DNA
<213> ORGANISM: Homo sapiens

<400> SEQUENCE: 149
cttcctttcc gcacaggggc cgccgagcgg ggccatg 37

<210> SEQ ID NO 150
<211> LENGTH: 502
<212> TYPE: DNA
<213> ORGANISM: Homo sapiens

<400> SEQUENCE: 150
ttccccttcc gtgggtcagg gccggtccgg tccggaacct gcagcccctt tcccagtgtt 60
ctagttcgcc cgtgacccgg aataatgagc aaggagggtg tggtgggttg aaagccatcc 120
tactttactc ccgagttaga gcatggattc agttttagtc ttaaggggga agtgagattg 180
gagattttta tttttaattt tgggcagaag caggttgact ctagggatct ccagagcgag 240
aggatttaac ttcatgttgc tcccgtgttt gaaggaggac aataaaagtc ccaccgggca 300
aaattttcgt aacctctgcg gtagaaaacg tcaggtatct tttaaatcgc gatagttttc 360
gctgtgtcag gctttcttcg gtggagctcc gagggtagct aggttctagg tttgaaacag 420
atgcagaatc caaaggcagc gcaaaaaaca gccaccgatt ttgctatgtc tctgagctgc 480
gagataatca gacagctaaa tg 502

<210> SEQ ID NO 151
<211> LENGTH: 502
<212> TYPE: DNA
<213> ORGANISM: Homo sapiens

<400> SEQUENCE: 151
ttccccttcc gtgggtcagg gccggtccgg tccggaacct gcagcccctt tcccagtgtt 60
ctagttcgcc cgtgacccgg aataatgagc aaggagggtg tggtgggttg aaagccatcc 120
tactttactc ccgagttaga gcatggattc agttttagtc ttaaggggga agtgagattg 180
gagattttta tttttaattt tgggcagaag caggttgact ctagggatct ccagagcgag 240
aggatttaac ttcatgttgc tcccgtgttt gaaggaggac aataaaagtc ccaccgggca 300
aaattttcgt aacctctgcg gtagaaaacg tcaggtatct tttaaatcgc gatagttttc 360
gctgtgtcag gctttcttcg gtggagctcc gagggtagct aggttctagg tttgaaacag 420
atgcagaatc caaaggcagc gcaaaaaaca gccaccgatt ttgctatgtc tctgagctgc 480
gagataatca gacagctaaa tg 502

<210> SEQ ID NO 152
<211> LENGTH: 153
<212> TYPE: DNA
<213> ORGANISM: Homo sapiens

<400> SEQUENCE: 152
ctaccctttt ccgctccacg gtgacctccg tgcggccggg tgcgggcgga gtcttcctcg 60
atcccgtggt gctccgcggc gcggccttgc tctcttccgg tcgcgggaca ccgggtgtag 120
agggcggtcg cggcgggcag tggcggcaga atg 153

<210> SEQ ID NO 153
<211> LENGTH: 122
<212> TYPE: DNA
<213> ORGANISM: Homo sapiens

<400> SEQUENCE: 153
ctttcttttc agtccttgcg caccggggaa caaggtcgtg aaaaaaaagg tcttggtgag 60
gtgccgccat ttcatctgtc ctcattctct gcgcctttcg cagagcttcc agcagcggta 120
tg 122

<210> SEQ ID NO 154
<211> LENGTH: 235
<212> TYPE: DNA
<213> ORGANISM: Homo sapiens

<400> SEQUENCE: 154
cagccttttc ctccaggggt gctttgtaaa cacggctgtg ctcagggctc gcgggtgacc 60
gaaaggatca tgaactagtg acctggaaag ggtactagat ggaaacttga gaaaggactg 120
cttattgata acagctaagg tattcctgga agcagagtaa ataaagctca tggcccacca 180
gctagaaagt attcttgcca tgagaaaaag aatgtgataa gttattcaac ttatg 235

<210> SEQ ID NO 155
<211> LENGTH: 488
<212> TYPE: DNA

<213> ORGANISM: Homo sapiens

<400> SEQUENCE: 155
agatcccttt cccagagtgc tctgcgccgt gaagaagcgg ctcccgggga ctgggggcat 60
tttgtgttgg ctggagctgg agtaacaaga tggcgtcgtc cgcggagtga caggggtccc 120
tctgggccgg agccggcggc agtggtggca gcggtatcgc cgccctagct caccgcgccc 180
cttttccagc ccgcgacgtc gccgcgcaag cgaggcagcg gcggccgccg agaaacaagt 240
ggcccagcct ggtaaccgcc gagaagccct tcacaaactg cggcctggca aaaagaaacc 300
tgactgagcg gcggtgatca ggttcccctc tgctgattct gggccccgaa ccccggtaaa 360
ggcctccgtg ttccgtttcc tgccgccctc ctccgtagcc ttgcctagtg taggagcccc 420
gaggcctccg tcctcttccc agaggtgtcg gggcttggcc ccagcctcca tcttcgtctc 480
tcaggatg 488

<210> SEQ ID NO 156
<211> LENGTH: 217
<212> TYPE: DNA
<213> ORGANISM: Homo sapiens

<400> SEQUENCE: 156
aagcctctcg gtctgtggca gcagcgttgg cccggccccg ggagcggaga gcgaggggag 60
gcggagacgg aggaaggtct gaggagcagc ttcagtcccc gccgagccgc caccgcaggt 120
cgaggacggt cggactcccg cggcgggagg agcctgttcc cctgagggta tttgaagtat 180
accatacaac tgttttgaaa atccagcgtg gacaatg 217

<210> SEQ ID NO 157
<211> LENGTH: 93
<212> TYPE: DNA
<213> ORGANISM: Homo sapiens

<400> SEQUENCE: 157
ccgcctcctc ccccgacttc cttccctgag cacggcggcg gcggggacga gcaccggcct 60
gcgcgcggag ccggcaccgg atgacccaac atg 93

<210> SEQ ID NO 158
<211> LENGTH: 73
<212> TYPE: DNA
<213> ORGANISM: Homo sapiens

<400> SEQUENCE: 158
ctgtcttttc gcttgtgtcc ctctttctag tgtcgcgctc gagtcccgac gggccgctcc 60
aagcctcgac atg 73

<210> SEQ ID NO 159
<211> LENGTH: 91
<212> TYPE: DNA
<213> ORGANISM: Homo sapiens

<400> SEQUENCE: 159
ctgtctcccc tcgccgcatc cactctccgg ccggccgcct gcccgccgcc tcctccgtgc 60
gcccgccagc ctcgcccgcg ccgtcaccat g 91

<210> SEQ ID NO 160
<211> LENGTH: 118
<212> TYPE: DNA
<213> ORGANISM: Homo sapiens

<400> SEQUENCE: 160
cgttccctac ttcctgtgct cttgcggaga cgcgcgcgtc ggggtttaac gcgtttctgg 60
gccgccgtaa gcccggccta ggggcagctt tgactcgaga gccggctata ggcgcatg 118

<210> SEQ ID NO 161
<211> LENGTH: 313
<212> TYPE: DNA
<213> ORGANISM: Homo sapiens

<400> SEQUENCE: 161
caccctttcg gatgcctccc ctagaaccct accactttcc accccttttcc gtctgttatt 60 tctcccaaac ttgcgcccgc acaggcccct ctggaacact cctgccccgt agtgcccctc 120
gtccccgctc cgtagagaaa gagcgtgcgt gccgcgcatt tctggcctgg ggagcgggtg 180
gagtaaacct gcgggaacca ttttacgaca acgtgcggct gtgcggtgtg gctgacggca 240
acgccgctgc tcttggagag gtcactccgg agacggcgtt ggttttgggg tgtgggggt 300 tggtggcact atg 313

<210> SEQ ID NO 162
<211> LENGTH: 711
<212> TYPE: DNA
<213> ORGANISM: Homo sapiens

<400> SEQUENCE: 162
ccttccctgg catctggagg gaccaccgtt gccgcgtctt cggcttccac gatctgcgtt 60
cgggctacgc ggccacggcg gcagccactg cgactcccac tgtgcctggc tctgtccata 120
ttagttccca ggcggccgtc gccgttccag cagcggcagc ggcagcggca gcggcggaca 180
tgttgtgagg cggcggcgcg ggtgtctgaa ggatggtttg gccgaggcgg cggcaacggc 240
tgctggcggc ggcggcagcg gcagcggggc ctcgggctct atagagccga gcccgctggg 300
tacccgcccg gtaccgcggc gaggccagtg cccctggatc ttgcctctgc tccgacgccg 360
ttggggacca gttaggcgac agcgcccgcc cctctgagga gacacgaagg tggttcccca 420
gccgctcaaa tttccggacc accgcgcttt cccctcctca gcctgggctg tgctctctct 480
agaatcctcg ggcccccact ttcttcccaa actcatccta aatctctcac acacgcgagt 540
gttcccagcc ctcaagccag ctgctcctcc gttcattttc tgcaccctct tcgcaaagca 600
ccccccggga tcactctccg agggcgactt tttgagaaat ctcggtggag tagtggacca 660
gagctgggga gtttttaaaa gccggggcgc gagaaacagg aaggtactat g 711

<210> SEQ ID NO 163
<211> LENGTH: 388
<212> TYPE: DNA
<213> ORGANISM: Homo sapiens

<400> SEQUENCE: 163
ttttcttttt cgtgcgagcc ctcgcgcgcg cgtacagtca tcccgctggt ctgacgattg 60
tggagaggcg gtggagaggc ttcatccatc ccacccggtc gtcgccgggg attggggtcc 120
cagcgagacc tccccgggag aagcagtgcc caggaggttt tctgaagccg gggaagctgt 180
gcagccgaag ccgccgccgc gccggagccc gggacaccgg ccaccctccg cgccacccac 240
cctcgccggc tccggcttcc tctggcccag gcgccgcgcg gacccggcag ctgtctgcgc 300
acgccgagct ccacggtgaa aaaaaagtga aggtgtaaaa gcagcacaag tgcaataaga 360
gatatttcct caaatttgcc tcaagatg 388

<210> SEQ ID NO 164
<211> LENGTH: 104
<212> TYPE: DNA
<213> ORGANISM: Homo sapiens

<400> SEQUENCE: 164
cagtccctct ggctgagacc tcggctccgg aatcactgca gcccccctcg ccctgagcca 60
gagcaccccg ggtcccgcca gcccctcaca ctcccagcaa aatg 104

<210> SEQ ID NO 165
<211> LENGTH: 90
<212> TYPE: DNA
<213> ORGANISM: Homo sapiens

<400> SEQUENCE: 165
cgttctcttc cgccgtcgtc gccgccatcc tcggcgcgac tcgcttcttt cggttctacc 60
tgggagaatc caccgccatc cgccaccatg 90

<210> SEQ ID NO 166
<211> LENGTH: 41
<212> TYPE: DNA
<213> ORGANISM: Homo sapiens

<400> SEQUENCE: 166
ctgtcttttc agtcgggcgc tgagtggttt ttcggatcat g 41

<210> SEQ ID NO 167
<211> LENGTH: 37
<212> TYPE: DNA
<213> ORGANISM: Homo sapiens

<400> SEQUENCE: 167
gtttcttttc tttgaatgac agaactacag cataatg 37

<210> SEQ ID NO 168
<211> LENGTH: 142
<212> TYPE: DNA
<213> ORGANISM: Homo sapiens

<400> SEQUENCE: 168
gcgcctcctc cgcccgccgc ccgggagccg cagccgccgc cgccactgcc actcccgctc 60
tctcagcgcc gccgtcgcca ccgccaccgc caccgccact accaccgtct gagtctgcag 120
tcccgagatc ccagccatca tg 142

<210> SEQ ID NO 169
<211> LENGTH: 105
<212> TYPE: DNA
<213> ORGANISM: Homo sapiens

<400> SEQUENCE: 169
ccgcctttta cttcggcccg cttcttctgg tcactccgcc accgtagaat cgcctaccat 60
ttggtgcaag caaaaagcaa tcagcaattg gacaggaaaa gaatg 105

<210> SEQ ID NO 170
<211> LENGTH: 60
<212> TYPE: DNA
<213> ORGANISM: Homo sapiens

<400> SEQUENCE: 170
cttcctcttt ctcgactcca tcttcgcggt agctgggacc gccgttcagt cgccaatatg 60

<210> SEQ ID NO 171
<211> LENGTH: 194
<212> TYPE: DNA
<213> ORGANISM: Homo sapiens

<400> SEQUENCE: 171
ctgtctcttt cgctccgcta caacaacaaa cgtgcacagg ggagtgaggg cagggcgctc 60
gcagggggca cgcagggagg gcccagggcg ccagggaggc cgcgccgggc taatccgaag 120
gggctgcgag gtcaggctgt aaccgggtca atgtgtggaa tattgggggg ctcggctgca 180
gacttggcca aatg 194

<210> SEQ ID NO 172
<211> LENGTH: 183
<212> TYPE: DNA
<213> ORGANISM: Homo sapiens

<400> SEQUENCE: 172
gccccttttc acaatatttg attaggaatt tggggcggga ccctggtctg gcacaggcac 60
gcacactctc agtagactct ttcactcctc tctctcttcc tctctcacac gttctccaac 120
ccaaggaggc cagacagagg gacgtggtca ctctctgaaa agttcaactt gagagacaaa 180
atg 183

<210> SEQ ID NO 173
<211> LENGTH: 206
<212> TYPE: DNA
<213> ORGANISM: Homo sapiens

<400> SEQUENCE: 173
cgttcttcgc cgagagtcgt cggggtttcc tgcttcaaca gtgcttggac ggaacccggc 60
gctcgttccc caccccggcc ggccgcccat agccagccct ccgtcacctc ttcaccgcac 120
cctcggactg ccccaaggcc cccgccgccg ctccagcgcc gcgcagccac cgccgccgcc 180
gccgcctctc cttagtcgcc gccatg 206

<210> SEQ ID NO 174
<211> LENGTH: 80
<212> TYPE: DNA
<213> ORGANISM: Homo sapiens

<400> SEQUENCE: 174
cgctctctgc tcctcctgtt cgacagtcag ccgcatcttc ttttgcgtcg ccagccgagc 60
cacatcgctc agacaccatg 80

<210> SEQ ID NO 175
<211> LENGTH: 36
<212> TYPE: DNA
<213> ORGANISM: Homo sapiens

<400> SEQUENCE: 175
caccctctct ggacagccca gggccgcagg ctcatg 36

<210> SEQ ID NO 176
<211> LENGTH: 99
<212> TYPE: DNA
<213> ORGANISM: Homo sapiens

<400> SEQUENCE: 176
ctgtccttac cttcagcagg agccggttcc ctgtgtgtgt gtccgctcgc cctctgctcc 60
gtcctgcggc tgcccactgc cctcctacgg tccaccatg 99

<210> SEQ ID NO 177
<211> LENGTH: 176
<212> TYPE: DNA
<213> ORGANISM: Homo sapiens

<400> SEQUENCE: 177
gcgcctcttc cggttacctt ttcccagcgc cagaggcgcc tagggttggg gtcctcgctc 60
aggcacagag acccgacacc gagcggcggc ttccccggga tcgagggacg cgcacgccag 120
aggagacgaa aggaacccgg gtcggaccag atcggaacca ctgaccattg cccatg 176

<210> SEQ ID NO 178
<211> LENGTH: 190
<212> TYPE: DNA
<213> ORGANISM: Homo sapiens

<400> SEQUENCE: 178
cggcctcctt ctgcctaggt cccaacgctt cggggcaggg gtgcggtctt gcaataggaa 60
gccgagcgtc ttgcaagctt cccgtcgggc accagctact cggccccgca ccctacctgg 120
tgcattccct agacacctcc ggggtcccta cctggagatc cccggagccc cccttcctgc 180
gccagccatg 190

<210> SEQ ID NO 179
<211> LENGTH: 23
<212> TYPE: DNA
<213> ORGANISM: Homo sapiens

<400> SEQUENCE: 179
cattctcccc agaggccgag atg 23

<210> SEQ ID NO 180
<211> LENGTH: 71
<212> TYPE: DNA
<213> ORGANISM: Homo sapiens

<400> SEQUENCE: 180
gctcccttta gcgagtcctt cttttcctga ctgcagctct tttcattttg ccatcctttt 60
ccagctccat g 71

<210> SEQ ID NO 181
<211> LENGTH: 65
<212> TYPE: DNA
<213> ORGANISM: Homo sapiens

<400> SEQUENCE: 181
ctgtcctttc gtggctcact ccctttcctc tgctgccgct cggtcacgct tgctctttca 60
ccatg 65

<210> SEQ ID NO 182
<211> LENGTH: 62
<212> TYPE: DNA
<213> ORGANISM: Homo sapiens

<400> SEQUENCE: 182
ccgccttccc tgcgcagtcg gtgtctccgc gtcgctgggt gggacttggc tcggcggcca 60
tg 62

<210> SEQ ID NO 183
<211> LENGTH: 109
<212> TYPE: DNA
<213> ORGANISM: Homo sapiens

<400> SEQUENCE: 183
ctcccttctt gactctctgt tcacagaact caggctgcct ccagccagcc tttgcccgct 60
agactcactg gccctgagca cttgaaggtg cagcaagtca ctgagaatg 109

<210> SEQ ID NO 184
<211> LENGTH: 68
<212> TYPE: DNA
<213> ORGANISM: Homo sapiens

<400> SEQUENCE: 184
ctgtccctca ctcgccgccg acgacctgtc tcgccgagcg cacgccttgc cgccgccccg 60
cagaaatg 68

<210> SEQ ID NO 185
<211> LENGTH: 61
<212> TYPE: DNA
<213> ORGANISM: Homo sapiens

<400> SEQUENCE: 185
ccgccttttc ccctgcctgc ccttcgggca cctcaggaag gcaccttcct ctgtcagaat 60
g 61

<210> SEQ ID NO 186
<211> LENGTH: 217
<212> TYPE: DNA
<213> ORGANISM: Homo sapiens

<400> SEQUENCE: 186
cgtcctctgg ccgcgcctgc ggccgcacgc ccagcgcccc tcgcctaacc tcgcgcccgg 60
gccgcgcctc ctcctcctcc tgctccccgc cgcttccgtt tctcgaggga aaggctgctg 120
cctcctgctc tgtcctcatc cccggcttag ctgacggccc agagggtggg tgccaattcc 180
accagcagct gcaactgaaa agcaaggttc agaaatg 217

<210> SEQ ID NO 187
<211> LENGTH: 186
<212> TYPE: DNA
<213> ORGANISM: Homo sapiens

<400> SEQUENCE: 187
gtttcctctc cttgttttgc tttcgatctg gactgttctc aggcaagccg gggagtaact 60
tttagttttg ctcctgcgat tattcaactg acgggctttc atttccattt cacataccct 120
agcaacactt ataccttgcg gaattgtatt ggtagcgtga aaaaagcaca ctgagagggc 180
accatg 186

<210> SEQ ID NO 188
<211> LENGTH: 136
<212> TYPE: DNA
<213> ORGANISM: Homo sapiens

<400> SEQUENCE: 188
ttttcttctt ttttcttctt tcttaaagcg aactgtactc ctctgctgtt cctttgaact 60
tggttcagta ggaagaagtg atatcctccc cagaccatct gctttgggga gcttggcaaa 120
actgtccagc aaaatg 136

<210> SEQ ID NO 189
<211> LENGTH: 351
<212> TYPE: DNA
<213> ORGANISM: Homo sapiens

<400> SEQUENCE: 189
ccgccttcct ccctccctcg ctccctccct gcgcgccgcc tctcactcac agcctccctt 60
ccttctttct ccctccgcct cccgagcacc agcgcgctct gagctgcccc cagggtccct 120
cccccgccgc cagcagccca tttggaggga ggaagtaagg gaagaggaga ggaaggggag 180
ccggaccgac tacccagaca gagccggtga atgggtttgt ggtgaccccc gccccccacc 240
ccaccctccc ttcccacccg acccccaacc cccatcccca gttcgagccg ccgcccgaaa 300
ggccgggccg tcgtcttagg aggagtcgcc gccgccgcca cctccgccat g 351

<210> SEQ ID NO 190
<211> LENGTH: 92
<212> TYPE: DNA
<213> ORGANISM: Homo sapiens

<400> SEQUENCE: 190
ctctccccct cctccccctc ccgctccaag attcgccgcc gccgccgccg cagccgcagg 60
agtagccgcc gccggagccg cgcgcagcca tg 92

<210> SEQ ID NO 191
<211> LENGTH: 64
<212> TYPE: DNA
<213> ORGANISM: Homo sapiens

<400> SEQUENCE: 191
gctcctcccg cgaatcgcag cttctgagac cagggttgct ccgtccgtgc tccgcctcgc 60
catg 64

<210> SEQ ID NO 192
<211> LENGTH: 145
<212> TYPE: DNA
<213> ORGANISM: Homo sapiens

<400> SEQUENCE: 192
attcccttct ttgggctcgg gggctcccgg agcagggcga gagctcgcgt cgccggaaag 60
gaagacggga agaaagggca ggcggctcgg cgggcgtctt ctccactcct ctgccgcgtc 120
cccgtggctg cagggagccg gcatg 145

<210> SEQ ID NO 193
<211> LENGTH: 85
<212> TYPE: DNA
<213> ORGANISM: Homo sapiens

<400> SEQUENCE: 193
ctgtcttttc cgtgctacct gcagaggggt ccatacggcg ttgttctgga ttcccgtcgt 60
aacttaaagg gaaattttca caatg 85

<210> SEQ ID NO 194
<211> LENGTH: 175

<212> TYPE: DNA
<213> ORGANISM: Homo sapiens

<400> SEQUENCE: 194
ttttctttcc tggctgatga tttgtcattc tagtcacttc ctgccttgtg accacacacc 60
caggcttgac aaagctgttc tgcagatcag aaagaagggg ttcctggtca tacaccagta 120
ctaccaagga cagctttttt cctgcaagat ctgttaccta aagcaataaa aaatg 175

<210> SEQ ID NO 195
<211> LENGTH: 72
<212> TYPE: DNA
<213> ORGANISM: Homo sapiens

<400> SEQUENCE: 195
ccatctctct cgggtggagt cttctgacag ctggtgcgcc tgcccgggaa catcctcctg 60
gactcaatca tg 72

<210> SEQ ID NO 196
<211> LENGTH: 128
<212> TYPE: DNA
<213> ORGANISM: Homo sapiens

<400> SEQUENCE: 196
ttctctcttt tttgcacatc tggctgaact gggagtcagg tggttgactt gtgcctggct 60
gcagtagcag cggcatctcc cttgcacagt tctcctcctc ggcctgccca agagtccacc 120
aggccatg 128

<210> SEQ ID NO 197
<211> LENGTH: 498
<212> TYPE: DNA
<213> ORGANISM: Homo sapiens

<400> SEQUENCE: 197
tgttcctttc ccctccgctt ctctgaccta gctgcgcggc cccggcccgg gagctgccga 60
acccgcgcct cccctgggtg aggaggacac gcctgccctc gtcgagaaaa cttttcctgc 120
cgactcagtt ggggcggcgg tggcaggaag tgcgggcagc gacctctcct ccgcctgccc 180
cgcgcgccct gccggaggtc ggcgctgagc ttgcgatcaa gtttgtgggg gcccccccttc 240 ccagttgccg gcgagtctcg cctcgagagg ggcgcccgac cccggggagg gcggcaggcc 300
agggcgaagg ccaagggcgt gtggtggcgc cggagactag gtgcggagca aggcggggac 360
tcgcacccgc atccgagagc gcggaggtcg cgcagcccgg gagaagggag cctccggcgg 420
ctgcttccta gagtccacag tgcgctgtct cctttggctg aggagagtgt cctggccccg 480
agtctatcga ggaaaatg 498

<210> SEQ ID NO 198
<211> LENGTH: 127
<212> TYPE: DNA
<213> ORGANISM: Homo sapiens

<400> SEQUENCE: 198
ccgcctcttt tcccgagatg ccccggggag ggaggacaac accttcaaag acaggccctc 60
tgagtccgac gagctccaga ccatccaaga agacagtgca gccacctccg agagcctgga 120
tgtgatg 127

<210> SEQ ID NO 199

<211> LENGTH: 401
<212> TYPE: DNA
<213> ORGANISM: Homo sapiens

<400> SEQUENCE: 199
cattcttccc aggacctcag cgcagccctg gcccaggaag gcaggagaca gaggccagga 60
cggtccagag gtgtcgaaat gtcctgggga cctgagcagc agccaccagg gaagaggcag 120
ggagggagct gaggaccagg cttggttgtg agaatccctg agcccaggcg gtagatgcca 180
ggaggtgtct ggactggctg ggccatgcct gggctgacct gtccagccag ggagagggtg 240
tgagggcaga tctgggggtg cccagatgga aggaggcagg catgggggac acccaaggcc 300
ccctggcagc accatgaact aagcaggaca cctggagggg aagaactgtg gggacctgga 360
ggcctccaac gactccttcc tgcttcctgg acaggactat g 401

<210> SEQ ID NO 200
<211> LENGTH: 131
<212> TYPE: DNA
<213> ORGANISM: Homo sapiens

<400> SEQUENCE: 200
gggcctttcc cagtgcggcc gccgccgcca cagctgcagt cagcaccgtc accccagcag 60
catccgccgc ctgcaccgcg cgtgcggccc gccccggcct gaccccgccg ccgaacccgg 120
cgccagccat g 131

<210> SEQ ID NO 201
<211> LENGTH: 396
<212> TYPE: DNA
<213> ORGANISM: Homo sapiens

<400> SEQUENCE: 201
agctctctgc tcgctctgct cgcagtcaca gacacttgag cacacgcgta cacccagaca 60
tcttcgggct gctattggat tgactttgaa ggttctgtgt gggtcgccgt ggctgcatgt 120
ttgaatcagg tggagaagca cttcaacgct ggacgaagta aagattattg ttgttatttt 180
tttttctctc ctctctctct cttaagaaag gaaaatatcc caaggactaa tctgatcggg 240
tcttccttca tcaggaacga atgcaggaat ttgggaactg agctgtgcaa gtgctgaaga 300
aggagatttg tttggaggaa acaggaaaga gaaagaaaag gaaggaaaaa atacataatt 360
tcagggacga gagagagaag aaaaacgggg actatg 396

<210> SEQ ID NO 202
<211> LENGTH: 1338
<212> TYPE: DNA
<213> ORGANISM: Homo sapiens

<400> SEQUENCE: 202
agcccttctt ggggaagtca gctacccagc agcctgtagt cctcggctac ccaccctcac 60
cgcctggggt cccatggtga gacagctggg tgggcatcag gcttctgcag agggccaggc 120
cggagggagc tgggcgaggg agtggggctg gctcctggct tgcaccggcc tcgtggaatc 180
caggcctcag acctgatcgc tggcgaaact ggctctgtgc gctggagccc ctggtcttct 240
gcgtctgtcc tcctcccggc cagactttac tcctggctca gcgacaggta tttgctatgg 300
aagagctgtc cctccctccc ctcggtgggc ctgggtccac ctccacctcc tcttcaggtc 360
cgcaccttcc tcccctttaa aacaccagcc gggcgcagac ccgttctagg cttttccatg 420
gtgcttccgc caaagcttgt gaccgagtcc ttcccgccta gggctggtgg gcctcccctg 480
ctggtaggtc tctcttcgct ttctttactc agaactgaag ctctcattcc ccacccacca 540
aggaaaaaca aaagggaaga agccacagct ggccccggct tgctttggca caggtgtttc 600
cccccggccc cccgtcgggc accctggttc ctgttctgtc cctgccccac gcgaccctgg 660
ggctcccacc cgggctcctc agcctcccct gggttggggt ggggggactg gctcccagcc 720
cttggcctag ggtttggtga acgcctttcc tggactgcgg gcccacttca ggcgcggctc 780
caggctgggc agctgcgctg gagggccgag ggcaggggtg gggtcgggcg tccaccctca 840
gggttgcgcc agggagccgg aaagccgact cccgaagttg gggtcctggg aaaacttggg 900
tcctgggttg actgagaagc ggcggggaaa ggaggcgggc caggaggagg gggcctggcg 960
gacgccggcc ggggggcggg gcgcggcggg gctgtcggtc acgcccctca gtccgccccg 1020
ccccgccccg cctgccgggg aagggccacg ttgcccgccc ggccgtccgg ccccggcgcg 1080
ccgcagaaag ggctggcgag tcgaaaggcg aggcggccgc ggcagcgctt gggacgcgcc 1140
tgggcaccgg gctcgctccc tgcgccccgg agcaggccaa gttcggggcc aggacgtcgg 1200
gaggacctgg tgcatggctg cctcctaatc ccatagtcca gaggaggcat ccctaggact 1260
gcgggcaagg gagccgggca agcccagggc agccttgaac cgtcccctgg cctgccctcc 1320
ccggtggggg ccaggatg 1338

<210> SEQ ID NO 203
<211> LENGTH: 522
<212> TYPE: DNA
<213> ORGANISM: Homo sapiens

<400> SEQUENCE: 203
ctgcctcccg cccccggggc caaagtacaa agggaggagg aagaagggag cggggtcgga 60
gccgtcgggg ccaaaggaga cggggccagg aacaggcagt ctcggcccaa ctgcggacgc 120
tccctccacc ccctgcgcaa aaagacccaa ccggagttga ggcgctgccc ctgaaggccc 180
caccttacac ttggcggggg ccggagccag gctcccagga ctgctccaga accgagggaa 240
gctcgggtcc ctccaagcta gccatggtga ggcgccggag gccccggggc cccaccccc 300 cggcctgacc acactgccct gggtgccctc ctccagaagc ccgagatgcg gggggccggg 360
agacaacact cctggctccc cagagaggcg tgggtctggg gctgagggcc agggcccgga 420
tgcccaggtt ccgggactag ggccttggca gccagcgggg gtggggacca cgggcaccca 480
gagaaggtcc tccacacatc ccagcgccgg ctcccggcca tg 522

<210> SEQ ID NO 204
<211> LENGTH: 90
<212> TYPE: DNA
<213> ORGANISM: Homo sapiens

<400> SEQUENCE: 204
ccgccttctc cgcagccccg caggccccgg gccctgtcat tcccagcgct gccctgtctt 60
gcgttccagt gttccagctt ctgcgagatg 90

<210> SEQ ID NO 205
<211> LENGTH: 562
<212> TYPE: DNA
<213> ORGANISM: Homo sapiens

<400> SEQUENCE: 205
ggccctttat aatgcgaggg tctggacggc tgaggacccc cgagctgtgc tgctcgcggc 60
cgccaccgcc gggccccggc cgtccctggc tcccctcctg cctcgagaag ggcagggctt 120
ctcagaggct tggcgggaaa aagaacggag ggagggatcg cgctgagtat aaaagccggt 180
tttcggggct ttatctaact cgctgtagta attccagcga gaggcagagg gagcgagcgg 240
gcggccggct agggtggaag agccgggcga gcagagctgc gctgcgggcg tcctgggaag 300
ggagatccgg agcgaatagg gggcttcgcc tctggcccag ccctcccgct gatcccccag 360
ccagcggtcc gcaacccttg ccgcatccac gaaactttgc ccatagcagc gggcgggcac 420
tttgcactgg aacttacaac acccgagcaa ggacgcgact ctcccgacgc ggggaggcta 480
ttctgcccat ttggggacac ttccccgccg ctgccaggac ccgcttctct gaaaggctct 540
ccttgcagct gcttagacgc tg 562

<210> SEQ ID NO 206
<211> LENGTH: 38
<212> TYPE: DNA
<213> ORGANISM: Homo sapiens

<400> SEQUENCE: 206
tggcctctcg gttccgcggc gcaccggagg gcagcatg 38

<210> SEQ ID NO 207
<211> LENGTH: 88
<212> TYPE: DNA
<213> ORGANISM: Homo sapiens

<400> SEQUENCE: 207
cttcctctcc aggaatccgc ggagggagcg caggctcgaa gagctcctgg acgcagaggc 60
cctgcccttg ccagacggcg cagacatg 88

<210> SEQ ID NO 208
<211> LENGTH: 29
<212> TYPE: DNA
<213> ORGANISM: Homo sapiens

<400> SEQUENCE: 208
ccttcttcct cctgcccgta gtagccatg 29

<210> SEQ ID NO 209
<211> LENGTH: 37
<212> TYPE: DNA
<213> ORGANISM: Homo sapiens

<400> SEQUENCE: 209
ccgtcctttc atcctggcgt ttgcctgcag caagatg 37

<210> SEQ ID NO 210
<211> LENGTH: 159
<212> TYPE: DNA
<213> ORGANISM: Homo sapiens

<400> SEQUENCE: 210
tgccccttcc ccggccaagc ccaactccgg atctcgctct ccaccggatc tcacccgcca 60
cacccggaca ggcggctgga ggaggcgggc gtctaaaatt ctgggaagca gaacctggcc 120
ggagccacta gacagagccg ggcctagccc agagacatg 159

<210> SEQ ID NO 211
<211> LENGTH: 101
<212> TYPE: DNA
<213> ORGANISM: Homo sapiens

<400> SEQUENCE: 211
gcccctcctc cgccgccggc tcccgggtgt ggtggtcgca ccagctctct gctctcccag 60
cgcagcgccg ccgcccggcc cctccagctt cccggaccat g 101

<210> SEQ ID NO 212
<211> LENGTH: 108
<212> TYPE: DNA
<213> ORGANISM: Homo sapiens

<400> SEQUENCE: 212
gcgtcctttc cctggtgtga ttccgtcctg cgcggttgtt ctctggagca gcgttctttt 60
atctccgtcc gccttctctc ctacctaagt gcgtgccgcc acccgatg 108

<210> SEQ ID NO 213
<211> LENGTH: 456
<212> TYPE: DNA
<213> ORGANISM: Homo sapiens

<400> SEQUENCE: 213
cattcctttt gtagaaaaac ccgtgcctcg aatgaggcga gactcagaga ggacccaggc 60
gcggggcgga cccctccaat tccttcctcg cgccccccgaa agagcggcgc accagcagcc 120
gaactgccgg cgcccaggct ccctggtccg gccgggatgc ggccggtacc cgctccccgc 180
cgggaacaac ctctccactc ttcctgcagg gagctggtgc cagccgacag ccgcgccagg 240
gccgctccgg gtaccagggt cggatcgggt gacgtcgcga acttgcgcct ggccgccaag 300
ccggcctcca ggctgaagaa ggacccgccc cggccttgac ccgggccccg cccctccagc 360
cggggcaccg agccccggcc ctagctgctc gcccctactc gccggcactc gcccggctcg 420
cccgctttcg cacccagttc acgcgccaca gctatg 456

<210> SEQ ID NO 214
<211> LENGTH: 104
<212> TYPE: DNA
<213> ORGANISM: Homo sapiens

<400> SEQUENCE: 214
gcgtcttccc gagccagtgt gctgagctct ccgcgtcgcc tctgtcgccc gcgcctggcc 60
taccgcggca ctcccggctg cacgctctgc ttggcctcgc catg 104

<210> SEQ ID NO 215
<211> LENGTH: 512
<212> TYPE: DNA
<213> ORGANISM: Homo sapiens

<400> SEQUENCE: 215
gcttcccctt ctccccggcg gttagtgctg agagtgcgga gtgtgtgctc cgggctcgga 60
acacacattt attattaaaa aatccaaaaa aaatctaaaa aaatctttta aaaaaccccca 120 aaaaaattta caaaaaatcc gcgtctcccc cgccggagac ttttattttt tttcttcctc 180
ttttataaaa taacccggtg aagcagccga gaccgacccg cccgcccgcg gccccgcagc 240
agctccaaga aggaaccaag agaccgaggc cttcccgctg cccggacccg acaccgccac 300
cctcgctccc cgccggcagc cggcagccag cggcagtgga tcgaccccgt tctgcggccg 360
ttgagtagtt ttcaattccg gttgattttt gtccctctgc gcttgctccc cgctcccctc 420
cccccggctc cggcccccag ccccggcact cgctctcctc ctctcacgga aaggtcgcgg 480
cctgtggccc tgcgggcagc cgtgccgaga tg 512

<210> SEQ ID NO 216
<211> LENGTH: 270
<212> TYPE: DNA
<213> ORGANISM: Homo sapiens

<400> SEQUENCE: 216
cgctctttct ctccggtaca cacagctccc cacattcgca cccctgcccg cgcgccgggc 60
cgcctgactg cacggcttcc cctccagcca gatgctggag aacacacact gattcgctgc 120
tttccaagac cctgttcagt ctctttctct atacaaagat ttttttaaaa actatatata 180
agaattcttt atttgcaccc tccctccgag tcccctgctc cgccagcctg cgcgcctcct 240
agcaccactt ttcactccca aagaaggatg 270

<210> SEQ ID NO 217
<211> LENGTH: 65
<212> TYPE: DNA
<213> ORGANISM: Homo sapiens

<400> SEQUENCE: 217
gggtctttcc ctcactcgtc ctccgcgcgt cgccgctctt cggttctgct ctgtccgccg 60
ccatg 65

<210> SEQ ID NO 218
<211> LENGTH: 222
<212> TYPE: DNA
<213> ORGANISM: Homo sapiens

<400> SEQUENCE: 218
cgctcccctt tcccctcccg ccggacctgc caggaggtgg gctggcgcgg agggagggcc 60
ctgtcccctg tccctttaag gaggagggcc aaacgccggc ctagagtgcg gcgtagcccc 120
cacccgccgt gccctcaccc cagagcagct gcagcctcag ccggccgccc ctccgccagc 180
caagtccgcc gctctgaccc ccggcagcaa gtcgccacca tg 222

<210> SEQ ID NO 219
<211> LENGTH: 300
<212> TYPE: DNA
<213> ORGANISM: Homo sapiens

<400> SEQUENCE: 219
cggcctctgt gagccgcaac ctttccaagg gagtggttgt gtgatcgcca tcttagggag 60
tgagtgtggc cgggccttct cctgtggcgg gtgtggggag cggagcccag agctcctgtg 120
gggccgctgc tttggcggtg ggcccagccg ggagcagcct ctttcgaagg ccgccgtgac 180
ctcttcaagg gcgtggagac gggaaggaaa aggccccggt tggggttcca gggcgccggt 240
aacgttaacc ggcgccttgc ctgtcctcta accgtcgctc cctcctcccc tagaaagatg 300

<210> SEQ ID NO 220
<211> LENGTH: 437
<212> TYPE: DNA
<213> ORGANISM: Homo sapiens

<400> SEQUENCE: 220 cctcccctttt actcctggct gcggggcgag ccgggcgtct gctgcagcgg ccgcggtggc 60
tgaggaggcc cgagaggagt cggtggcagc ggcggcggcg ggaccggcag cagcagcagc 120
agcagcagca gcagcaacca ctagcctcct gccccgcggc gctgccgcac gagccccacg 180
agccgctcac cccgccgttc tcagcgctgc ccgaccccgc tggcgcgccc tcccgccgcc 240
agtcccggca gcgccctcag ttgtcctccg actcgccctc ggccttccgc gccagccgca 300
gccacagccg caacgccacc cgcagccaca gccacagcca cagccccagg catagccttc 360
ggcacagccc cggctccggc tcctgcggca gctcctctgg gcaccgtccc tgcgccgaca 420
tcctggaggt tgggatg 437

<210> SEQ ID NO 221
<211> LENGTH: 279
<212> TYPE: DNA
<213> ORGANISM: Homo sapiens

<400> SEQUENCE: 221
ggatctcttc gtctttgcag cgtagcccga gtcggtcagc gccggaggtg agcggtgcag 60
gaggctacgc catcagtccc caccaagggc cagtcgcccg gctagtgcgg aatcccggcg 120
cgccggccgg ccccgggcac gcaggcaggg cggcgcagga tccagggcgt ctgggatgca 180
gtggagctca gagagaggag aacggctcct cacgcctggg gcctgctctt cagaagtccc 240
cagcgccgtt ccttccagat caggacctca gcagccatg 279

<210> SEQ ID NO 222
<211> LENGTH: 571
<212> TYPE: DNA
<213> ORGANISM: Homo sapiens

<400> SEQUENCE: 222
cggcctcctc ggcgcagcca tcctcttggc tgccgcgggc ggcaaagccc acggcatctg 60
ccatttgtca ttcagcccgt cggtaccgcc ccgagccttg atttagacac ggctggggcg 120
tgctctggcc tcactctccg ggcgggtgct ggacggacgg acggacgggg cagccgtgct 180
cacagctcag cagcgcgggg ccttggcgcg cggggcgctt ccccgggtcg ccgtcatggc 240
cgcggaggtg gcacgcccga gcggcctcgc ctgagctccg gggtcgtcg ccccgcaggg 300 attgctgtca cgtctaatgt ggctgctgcc tcgtgtcaca tctgaaactc atctgtacct 360
cacttagaaa gtggttctga ttagacaaga cttttcgttg cagtcgacag aaacctaatg 420
ggaccattga agaattccaa acaggtattt gcataggaat cagaggagtt aatcttgtct 480
cttctcacag gtttgaatct tcagacaaac ttctgggagg actcggtccc tgcctcgcag 540
cagatgttcc ctgtcactca gtaggcatat g 571

<210> SEQ ID NO 223
<211> LENGTH: 53
<212> TYPE: DNA
<213> ORGANISM: Homo sapiens

<400> SEQUENCE: 223
tgctctcttg gctccggaac ccccgcgggc gctggctccg tctgccaggg atg 53

<210> SEQ ID NO 224
<211> LENGTH: 110
<212> TYPE: DNA
<213> ORGANISM: Homo sapiens

<400> SEQUENCE: 224
ccccctcccc ggccagacgg cgggcaagac agctgggtgt acagcgtcct cgaaaccacg 60
agcaagtgag cagatcctcc gaggcaccag ggactccagc ccatgccatg 110

<210> SEQ ID NO 225
<211> LENGTH: 81
<212> TYPE: DNA
<213> ORGANISM: Homo sapiens

<400> SEQUENCE: 225
cagtcctttc gcgcctcggc ggcgcggcat agcccggctc ggcctgtaaa gcagtctcaa 60
gcctgccgca gggagaagat g 81

<210> SEQ ID NO 226
<211> LENGTH: 31
<212> TYPE: DNA
<213> ORGANISM: Homo sapiens

<400> SEQUENCE: 226
ggtccttcca cgtgctttcg gcggcgacat g 31

<210> SEQ ID NO 227
<211> LENGTH: 191
<212> TYPE: DNA
<213> ORGANISM: Homo sapiens

<400> SEQUENCE: 227
tgttcttctc gtggttccag tggggagaga aggaggaagt agggagcggg gtggcagggg 60
ggggacccgc cgcggctgct gccaccgccg ccaccaccgc ctctgctcgt ggcgtgggaa 120
aggaggtgtg agtcccgggc gcgagccggc ggcggcgccg ctgcgggagg gtcggcggtg 180
ggaaggcgat g 191

<210> SEQ ID NO 228
<211> LENGTH: 61
<212> TYPE: DNA
<213> ORGANISM: Homo sapiens

<400> SEQUENCE: 228
cggtcttcca gtttcccggc gtgcttaggg cgcgccaaat gggaggggga gacgcaagat 60
g 61

<210> SEQ ID NO 229
<211> LENGTH: 75
<212> TYPE: DNA
<213> ORGANISM: Homo sapiens

<400> SEQUENCE: 229
cggcctccgc cgctgccgcc gccgctgcta cagccgccgc cgccgctgtt gccgcggctt 60
gttattctta aaatg 75

<210> SEQ ID NO 230
<211> LENGTH: 156
<212> TYPE: DNA
<213> ORGANISM: Homo sapiens

<400> SEQUENCE: 230
ctttctttct gcagcaggaa ccgcggctgc tggacaagag gggtgcggtg gatactgacc 60
tttgctccgg cctcgtcgtg aagacacagc gcatctcccc gctgtaggct tcctcccaca 120
gaacccgttt cgggcctcag agcgtctggt gagatg 156

<210> SEQ ID NO 231
<211> LENGTH: 800

-continued

<212> TYPE: DNA
<213> ORGANISM: Homo sapiens

<400> SEQUENCE: 231
cgccccctct tcctcgccct ctctcgcggg tcggggttac atggcggcga ctgcggcaaa 60
gcgagagcct cggagacgcc gctgccgcca gcacagccgg agacctgagc cgacactggg 120
ggcagtccgc gagccccgca ctctctcgat gagtcggaga agtcccgttg tatcagagta 180
agatggacgg tagctttgat tgtgattgtg gtgagctgga gccacctgat cactaacaaa 240
agacatcttc tgttaaccaa cagccgccag ggcttcctgt tgaaataaat atatagcaac 300
aaaggaaaaa aagaagcaaa acggaaatag tgcttaccag caccttagaa tgatgctgct 360
caggaccagt ccaacactga atgtatctgc actgtgagga gaatgttcat agaagcctgt 420
tgtgtgcata tttattcaca tttttgttaa atgttaaatc gtttagcacg gtaatctgag 480
tgcacagtat gtcatttcat tccgtttgag tttcttgttt tcgttaaatg tctgcagagt 540
tgctgcccct ttcttgaact atgagtactg caatcttttt aattctcaat atgaatagag 600
ctttttgagc tttaaatcta aggggaactc gacaggcctg tttggcatat gcaatgaaca 660
tcaagaaacc atcttgctgt ggaagcataa ttatttttct tctccctttt tgaaagatct 720
ttccttttga tgccagtttt cttccttgtt tacacaagtt caatttgaaa ggaaaaggca 780
atagtaaggg tttcaaaatg 800

<210> SEQ ID NO 232
<211> LENGTH: 131
<212> TYPE: DNA
<213> ORGANISM: Homo sapiens

<400> SEQUENCE: 232
cctccccttc cctacatcta gccgccgcgc tttcccgctc ccgcagcagc agcctcccgc 60
gtcgctgtcg ctgttgcctc cgccacctcc tccgccgccg cgcgcccctc ggagttccgc 120
gccccaccat g 131

<210> SEQ ID NO 233
<211> LENGTH: 218
<212> TYPE: DNA
<213> ORGANISM: Homo sapiens

<400> SEQUENCE: 233
ttgcctctgg ctctgaggcg gcggcgccgg gcgctgcgaa ggctcggccg ctgtagtcag 60
tggtgtgggg tgcgcaaggg cacggacctc ggagctctcc ccgcttgcgc cgagtttctc 120
agcgccttcc ccacccaaac cggggtctcg cagtcggaag cactcagagt gcagccccgc 180
gcggggccgg tcgtaaccgc gccgcgggcc ggacgatg 218

<210> SEQ ID NO 234
<211> LENGTH: 26
<212> TYPE: DNA
<213> ORGANISM: Homo sapiens

<400> SEQUENCE: 234
agttctttct gcccacacta gacatg 26

<210> SEQ ID NO 235
<211> LENGTH: 35
<212> TYPE: DNA
<213> ORGANISM: Homo sapiens

<400> SEQUENCE: 235
tgttcttctg tgccgggggt cttcctgctg tcatg 35

<210> SEQ ID NO 236
<211> LENGTH: 76
<212> TYPE: DNA
<213> ORGANISM: Homo sapiens

<400> SEQUENCE: 236
cagcccctct ggcaggctcc cgccagcgtc gctgcggctc cggcccggga gcgagcgccc 60
ggagctcgga aagatg 76

<210> SEQ ID NO 237
<211> LENGTH: 158
<212> TYPE: DNA
<213> ORGANISM: Homo sapiens

<400> SEQUENCE: 237
ctccctttgc aggacgtcac ggaggactgc aggggcctga gccgctgctg ccgccgccgc 60
cgcgcagccc cacatcaacg caccggggtc ctgtcaccgc caccgccaaa aaagtcaccg 120
ccgctagggt cgccgttgca tcggtgcagg gcaagatg 158

<210> SEQ ID NO 238
<211> LENGTH: 48
<212> TYPE: DNA
<213> ORGANISM: Homo sapiens

<400> SEQUENCE: 238
ctctctctct ctctctctcg ctcgttccct aacattaaag agaaaatg 48

<210> SEQ ID NO 239
<211> LENGTH: 174
<212> TYPE: DNA
<213> ORGANISM: Homo sapiens

<400> SEQUENCE: 239
gcgcccctct gctccggctc ggggcgggca ctggcggagg gactggccag tcccctcctc 60
cgcgccggcc ccaaccctgt cgctgccgcc gcgctccgag tccccattcc cgagctgccg 120
ctgttgtcgc tcgctcagcg tctccctctc ggccgccctc tcctcgggac gatg 174

<210> SEQ ID NO 240
<211> LENGTH: 246
<212> TYPE: DNA
<213> ORGANISM: Homo sapiens

<400> SEQUENCE: 240
ccgccttttc ccgcggaggc gccgagcggc catattgcgg agctgtctgc ggtggcggcg 60
gcgcctctcg tctcccgcgg cccagcgctc gcaccaccgc ttctccctcc ctgtcgcagc 120
cgcgccgccg cgcagcgccc cagccacacg ccggcgggca gaagccgccc gctctccgga 180
aagtgataac agaattcatt gaagtggaga atttttaaag aaggtaacaa aaagagaaag 240
aaaatg 246

<210> SEQ ID NO 241
<211> LENGTH: 120
<212> TYPE: DNA
<213> ORGANISM: Homo sapiens

<400> SEQUENCE: 241
tcgccttctt gcacttcgcg ggagaagttg ttggcgcgaa tggatcctga gcctcgataa 60
cagattcctc aaccggccca cccgccagcc agccagcgcc ttcatcctgg ggctgcgatg 120

<210> SEQ ID NO 242
<211> LENGTH: 284
<212> TYPE: DNA
<213> ORGANISM: Homo sapiens

<400> SEQUENCE: 242
gcatctttct cgaggagctc tcctgggcgg ctgaagaagg agcttcttct ccggagtgcg 60
ccggcggtgg cgcctgcgga cctaactagc tccaggttag gccgagcttt gcgggaaagc 120
agcggacttg aaaatactgg aaatctgtcc ggatccaaat tattttgcaa gccagatgag 180
taaccagagg gcatgaaagg ttgagaacat ttgacttccc tgcaaacctt ggtatagatc 240
acttcctttt ctgtaggaaa ggaaaggcac caaagagcac aatg 284

<210> SEQ ID NO 243
<211> LENGTH: 17
<212> TYPE: DNA
<213> ORGANISM: Homo sapiens

<400> SEQUENCE: 243
tgctcttccc ggtcatg 17

<210> SEQ ID NO 244
<211> LENGTH: 49
<212> TYPE: DNA
<213> ORGANISM: Homo sapiens

<400> SEQUENCE: 244
cgttcttcct tttcgatccg ccatctgcgg tggagccgcc accaaaatg 49

<210> SEQ ID NO 245
<211> LENGTH: 311
<212> TYPE: DNA
<213> ORGANISM: Homo sapiens

<400> SEQUENCE: 245
cttcctttag cgtgaaccgc gggtgcggtg cctcccgtga aaataataaa ttcaccgtca 60
cgcttgttgt gaacgcgggt ggttcccgaa acttggaggc ttcccgtaaa cccagctcct 120
tcctcatctg ggaggtgggt cccgcgcggg tccgccgcct cctccctggc ccctccctct 180
cgtgtctttc attttcctgg ggctccgggg cgcggagaag ctgcatccca gaggagcgcg 240
tccaggagcg gacccgggag tgtttcaaga gccagtgaca aggaccaggg gcccaagtcc 300
caccagccat g 311

<210> SEQ ID NO 246
<211> LENGTH: 125
<212> TYPE: DNA
<213> ORGANISM: Homo sapiens

<400> SEQUENCE: 246
ctttcttttg cgcaggcgtc gcgccctggg gccggggccg ggcggcaccg cggtgcgcaa 60
gcgcaaccgt cggtgggtcg gggatcggtc gcctgagagg tatcacctct tctgggctca 120
agatg 125

<210> SEQ ID NO 247

<211> LENGTH: 134
<212> TYPE: DNA
<213> ORGANISM: Homo sapiens

<400> SEQUENCE: 247
agttctcctt ccaccttccc ccacccttct ctgccaaccg ctgtttcagc ccctagctgg 60
attccagcca ttgctgcagc tgctccacag ccccttttcag gacccaaaca accgcagccg 120
ctgttcccag gatg 134

<210> SEQ ID NO 248
<211> LENGTH: 339
<212> TYPE: DNA
<213> ORGANISM: Homo sapiens

<400> SEQUENCE: 248
cgccctccta cttccccgtc tgcgtccgcg ttcgcggctc ccgtttgcat catccccgtc 60
tgcgtccgcg ttcgcggctc ccgtttgcat catctccagc cggcggctgc tccagggagg 120
ctgggcgcga tcctctccgc ccgcggctcc aacccgcact ctgcgcctct cctcgccttt 180
ctcgcacctg ctcctgcgcc aggcccggag acccccgggg cggcttccca gaacctgcgg 240
agcacaactg gccgaccgac ccattcattg ggaaccccgt cttttgccag agcccacgtc 300
ccctgccacc tctagctcgg agcggcgtgt agcgccatg 339

<210> SEQ ID NO 249
<211> LENGTH: 22
<212> TYPE: DNA
<213> ORGANISM: Homo sapiens

<400> SEQUENCE: 249
ctgcctcttt ctgagcggca tg 22

<210> SEQ ID NO 250
<211> LENGTH: 53
<212> TYPE: DNA
<213> ORGANISM: Homo sapiens

<400> SEQUENCE: 250
ctatctctcg ataaagttgt tgttgcggct tccgccgcgg gtggaagaag atg 53

<210> SEQ ID NO 251
<211> LENGTH: 560
<212> TYPE: DNA
<213> ORGANISM: Homo sapiens

<400> SEQUENCE: 251
ctatctctca tctttccgct cttagctggg agtgctccgc ctagtcactt ttcttaaggt 60
ggctcgtcga ggcctgactt cttccccgaa atcacgtccc tagacagcct cctattttac 120
cactaacttt actcctgcag ttattcagcg gtaggaaact gaaaccaaaa accagtgtaa 180
gcaagtaaac atctaaactg tttcaggagc cgcgtagaag gaacgcggcg gtgtgccccg 240
gaagcggaag tagattctcc tatagaaagg ctggactacg cggagtggtg acgtttcctc 300
attgggcgga aggttcgctg gcactccgtt ggtcttccag ctggtgggag ttgacgacgt 360
ggtgctgggc gttgggaccc tactttatct agttcgggaa gttgggttgt ggggtcatac 420
ctgtctgtct gctcccagct ttcttgggtt tcttccgacg gcgtggggcc tcgctaagga 480
attcccggcc cctcagggcc acggctttag cggtgtcttt tgcgagttct tcgtaagtac 540
atcttaaagc tgtcaagatg 560

<210> SEQ ID NO 252
<211> LENGTH: 71
<212> TYPE: DNA
<213> ORGANISM: Homo sapiens

<400> SEQUENCE: 252
cggtctttcg gatgctgacg ctctcttcct gtctttgtgg ctccggaaag gcgtttggga 60
tgccaacgat g 71

<210> SEQ ID NO 253
<211> LENGTH: 161
<212> TYPE: DNA
<213> ORGANISM: Homo sapiens

<400> SEQUENCE: 253
ttttcttttt ggtggtggtg gtggaagggg ggaggtgcta gcagggccag ccttgaactc 60
gctggacaga gctacagacc tatggggcct ggaagtgccc gctgagaaag ggagaagaca 120
gcagaggggt tgccgaggca acctccaagt cccagatcat g 161

<210> SEQ ID NO 254
<211> LENGTH: 23
<212> TYPE: DNA
<213> ORGANISM: Homo sapiens

<400> SEQUENCE: 254
tgttcttccc atcggcgaag atg 23

<210> SEQ ID NO 255
<211> LENGTH: 199
<212> TYPE: DNA
<213> ORGANISM: Homo sapiens

<400> SEQUENCE: 255
ggtccttccc ctaaaacttg gcactgccga tactcccagc ccgttccttc ccaagtcagg 60
aacttgcagg ggaccccttg gcaattcttt ttctctcaag agcagacagc cttcagtccc 120
agccgctgcc agggctggtg tgtctgaccc agctgtggtt tttccaggcc tgaaggcccc 180
ggagtgcacc agcggcatg 199

<210> SEQ ID NO 256
<211> LENGTH: 897
<212> TYPE: DNA
<213> ORGANISM: Homo sapiens

<400> SEQUENCE: 256
cagtctcctc cccgaggtgc cggtggcccc gccgccactc cctccggctc cctccctccc 60
gccgcggcgc gcatctcatt ccagccctca ttccgcgcat tccagcgtcc tcctcgcaca 120
ctcgaggcca gggggcggga gggccgcagc tccggcgccg ccgcgtcccg ccaggtgaga 180
ggcgcccgcg cccgccgcac ccgccggcgc cctcacgggc cgcgcgcccc acgccgccgc 240
agccgaccgc tcgcgccgcg tgctcggctg ctcttttctt tccgccgccc gcgttcccgc 300
cttggacctc tgcgctccga cgcgctccgt cccgacctct ggcttccctc cgcgctccgg 360
cgctgctcgc tgcccctctc ccgcttccct cctgtccgcc ccgcgctccc ctcctcgctc 420
ccggttgact cactcctcca ggaataggga tccccgtgtt ttcccgtcag tcccattctg 480
ggaaaactcc tccctccgcg cgctccgctc cgctccgctg ggcgcaccgg ggccggtcgg 540
cgcggggtgg gcttggcccc gcggccccgc cttcactgcg ccgcccgtcg gccccggccg 600
gagcccggct ctgcgcgctg acgccctgtc gtccccgcag aacgatcgcc gcggccggaa 660
gagttggcgc tcggggcgga ctccttggaa ctggcttagc gcacccatcc caccttcccg 720
caccctggga ccggtcggaa cgagctgatt gcccgctaca tcaagctccg gacagggaag 780
acccgcacca ggaagcaggt ctccagccac atccaggtgc tggctcgtcg caaagctcgc 840
gagatccagg ccaagctaaa ggaccaggca gctaaggaca aggccctgca gagcatg 897

<210> SEQ ID NO 257
<211> LENGTH: 86
<212> TYPE: DNA
<213> ORGANISM: Homo sapiens

<400> SEQUENCE: 257
ttttctttcc tccagtctcg gggctgcagg ctgagcgcga tgcgcggaga cccccgcggg 60
ggcggcggcg gccgtgagcc ccgatg 86

<210> SEQ ID NO 258
<211> LENGTH: 121
<212> TYPE: DNA
<213> ORGANISM: Homo sapiens

<400> SEQUENCE: 258
cggccttttc cgcccgctcc cccctccccc cgagcgccgc tccggctgca ccgcgctcgc 60
tccgagtttc aggctcgtgc taagctagcg ccgtcgtcgt ctcccttcag tcgccatcat 120
g 121

<210> SEQ ID NO 259
<211> LENGTH: 46
<212> TYPE: DNA
<213> ORGANISM: Homo sapiens

<400> SEQUENCE: 259
ctatcttctt tttcttcagc gaggcggccg agctgacgca aacatg 46

<210> SEQ ID NO 260
<211> LENGTH: 70
<212> TYPE: DNA
<213> ORGANISM: Homo sapiens

<400> SEQUENCE: 260
cggcctccgc caccatcttg ctttccttta atccggcagt gaccgtgtgt cagaacaatc 60
ttgaatcatg 70

<210> SEQ ID NO 261
<211> LENGTH: 539
<212> TYPE: DNA
<213> ORGANISM: Homo sapiens

<400> SEQUENCE: 261
ctgcctttcg tgtctctgca gcgtggagac tggaaccggc aatttcaaag gacgccacgt 60
tcaatcgcag cgctggcgcg ggcggaggct aaaacacggg ggtcctgaga ctgaggaaaa 120
cgcgccaagt tcccctcggt ggcggagtgc taaagaccct agcggttcag gcgttcggcg 180
agcggggccg ctgcttgttg cgctcctggc tctcccgggg cgggcgcaga tgggcgccgc 240
tcccgggatg tagttggtgt tggtgcaaga cgggagcgag cggcggtcgg ggttcccgct 300
cttgggagcg gatggtcact cccccgcggg gagggcgagc cgaccagatt ttcctggggc 360
cggggacccg gcgggctcgg ggcagggact cacctgtcgc acccacactc attcgggttg 420
gacttgccgg cgtcaccgcc gcggacttcg ctttgggcca tgaccagata taattggtga 480
ttacaacttt cctctataaa ttaactcttg acactccttg ggatttgaag aaaaaaatg 539

<210> SEQ ID NO 262
<211> LENGTH: 143
<212> TYPE: DNA
<213> ORGANISM: Homo sapiens

<400> SEQUENCE: 262
gtgtctcctt cacttcgccc tccagctgct ggagctgcag cccgaccgcg agcgtgccaa 60
gcggcttcag cagctagcgg agcggtggcg gcggcccccc tcaggacacc accagattcc 120
cctcttcccg cggcctcgcc atg 143

<210> SEQ ID NO 263
<211> LENGTH: 68
<212> TYPE: DNA
<213> ORGANISM: Homo sapiens

<400> SEQUENCE: 263
gcctcttctc cgggagccag tccgcgccac cgccgccgcc caggccatcg ccaccctccg 60
cagccatg 68

<210> SEQ ID NO 264
<211> LENGTH: 423
<212> TYPE: DNA
<213> ORGANISM: Homo sapiens

<400> SEQUENCE: 264
ccccctcccc gctgctcacc ccgctctccg gccgccgccg gtgcgggtgc tccgctaccg 60
gctcctctcc gttctgtgct ctcttctgct ctcggctccc cacccccctct cccttccctc 120 ctctcccctt gcctcccctc ctctgcagcg cctgcattat tttctgcccg caggctcggc 180
ttgcactgct gctgcagccc ggggaggtgg ctgggtgggt ggggaggaga ctgtgcaagt 240
tgtaggggag ggggtgccct cttcttcccc gctcccttcc cccgccaact ccttcccctc 300
cttctccccc tttcccctcc ccgcccccac cttcttcctc ctttcggaag gactggtaac 360
ttgtcgtgcg gagcgaacgg cggcggcggc ggcggcggcg gcaccatcca ggcgggcacc 420
atg 423

<210> SEQ ID NO 265
<211> LENGTH: 283
<212> TYPE: DNA
<213> ORGANISM: Homo sapiens

<400> SEQUENCE: 265
agtcctttgc tcgccggctt gctagctctc tcgatcactc cctcccttcc tccctccctt 60
cctcccggcg gccgcggcgg cgctggggaa gcggtgaaga ggagtggccc ggccctggaa 120
gaatgcggct ctgacaaggg gacagaaccc agcgcagtct ccccacggtt taagcagcac 180
tagtgaagcc caggcaaccc aaccgtgcct gtctcggacc ccgcacccaa accactggag 240
gtcctgatcg atctgcccac cggagcctcc gggcttcgac atg 283

<210> SEQ ID NO 266
<211> LENGTH: 95
<212> TYPE: DNA

<213> ORGANISM: Homo sapiens

<400> SEQUENCE: 266
cagcctctac cttgcgagcc gtcttcccca ggcctgcgtc cgagtctccg ccgctgcggg 60
cccgctccga cgcggaagat ctgactgcag ccatg 95

<210> SEQ ID NO 267
<211> LENGTH: 155
<212> TYPE: DNA
<213> ORGANISM: Homo sapiens

<400> SEQUENCE: 267
gggcctttgt ctctggctgc agttggagct ctgcgtctcg tcttcgttct tctgtgtcct 60
ctgctgctag aggtccagcc tctgtggctc tgtgacctgc gggtattggg ggatccacag 120
ctaagacgcc aggacccccc ggaagcctag aaatg 155

<210> SEQ ID NO 268
<211> LENGTH: 448
<212> TYPE: DNA
<213> ORGANISM: Homo sapiens

<400> SEQUENCE: 268
cagtcctttt gtgggagtcc ggtctgtcca cttgccggtc cctcagaccg tcggcggtct 60
ctgtccgctt cgggacctgt ccgctggtcg ctccgcgtcc gatggctcct ggccgcggaa 120
ccttaggcct ggccctggtc tccgagcgcg ggttcgccgg gaggagcgtg tggcgggggt 180
gtgccggggc gtgagtgcgc cgagcatggg gctgagcctg gtgtggggag tgggtatctg 240
cggagccggc ctgaacccca cctcagccgg gcgcggggag ggggctccgt gcgtgtgatc 300
gtgcagctgt gagcgcgtgg ccgccccgcg gggctccgct gcaggcccct cagccccagg 360
agcagtactc gctcttcagg gcctgccctg gatcctggag gctacacagc tgcccactcc 420
tcctggggag gctgccgtgg aggccatg 448

<210> SEQ ID NO 269
<211> LENGTH: 155
<212> TYPE: DNA
<213> ORGANISM: Homo sapiens

<400> SEQUENCE: 269
gggcctttgt ctctcgctgc agcctgagct ctaggtcttg ttttccctgc tttgtgtttt 60
ctgctcgtgg acgcccagcc tctgtggccc tgtggcctgc aggtattggg agatccacag 120
ctaagacgcc gggacccccct ggaagcctag aaatg 155

<210> SEQ ID NO 270
<211> LENGTH: 128
<212> TYPE: DNA
<213> ORGANISM: Homo sapiens

<400> SEQUENCE: 270
gggcctttgt ctctcgctgc cgccggagtt tccaggtctc gacttcactg ctctgtgtcc 60
tctgctccag gaggcccagc ctgtgtggcc ctgtgacctg caggtattgg agagccacag 120
ctaagatg 128

<210> SEQ ID NO 271
<211> LENGTH: 176
<212> TYPE: DNA
<213> ORGANISM: Homo sapiens

<400> SEQUENCE: 271
gggtctttgc gtctggctac taccagaccg cgggttaggg gcttcatctc tctgcgttct 60
cagttgtggg aggccttggt gattcggcca cagcctcagc ctccgtcgct ctgtgacctg 120
cgggtattgg atgattggta gctaagactc ccgaatactt cagaagtggg gaaatg 176

<210> SEQ ID NO 272
<211> LENGTH: 29
<212> TYPE: DNA
<213> ORGANISM: Homo sapiens

<400> SEQUENCE: 272
tgttctttct agctctgaaa tagaaaatg 29

<210> SEQ ID NO 273
<211> LENGTH: 305
<212> TYPE: DNA
<213> ORGANISM: Homo sapiens

<400> SEQUENCE: 273 ctccctttc ggagatttga atttccccca gcgaggcgag tgaggcgaaa tacccgtatg 60
gtgatagctg gccttttcgc gccaatactg aaaaaggcag aacgttcctc cgctggcgcc 120
agccaatcag caggactcct gccttccttc ggggcaaggt cgcagcatct gcctcggaaa 180
tcacgaaatc acggggcttc tttctgctgg ctcagccggg aggcccagag tgttctgcag 240
aggctgcgta ttgaaggctg ctctctgaag ctccctgccc caggtcacgc cgccggttcc 300
agatg 305

<210> SEQ ID NO 274
<211> LENGTH: 45
<212> TYPE: DNA
<213> ORGANISM: Homo sapiens

<400> SEQUENCE: 274
acttcttttc ttggctaagc cgcgtttgta ctgtgtctta ccatg 45

<210> SEQ ID NO 275
<211> LENGTH: 171
<212> TYPE: DNA
<213> ORGANISM: Homo sapiens

<400> SEQUENCE: 275
ccgcctttgc gctgcgcgcc tgcgcccgcg ccggcttcca gcgggtgtcg gacctgagag 60
ctggaggggc gtgcgcgcgc cctcgctctg ttgcgcgcgc ggtgtcacct tgggcgcgag 120
cggggccgcg cgcgcacggg acccggagcc gagggccatt gagtggcgat g 171

<210> SEQ ID NO 276
<211> LENGTH: 243
<212> TYPE: DNA
<213> ORGANISM: Homo sapiens

<400> SEQUENCE: 276 cctcccccctt ccccggctgg ggcggctgga gagccgggag tcgctgggtg cgtggggctg 60
cctcgccgcg tctcgccacg ggctctgcca gcagacagcc ttggcacaca ggcacaaggg 120
ctggagccca gagatgagag tgcccaaggg agatgtgagc ctggcgggct gcccgctaac 180
ctgtcgctga agccccagaa gcgggccctc aggccaggcc taccctgcct ccggcccagc 240
atg 243

<210> SEQ ID NO 277
<211> LENGTH: 687
<212> TYPE: DNA
<213> ORGANISM: Homo sapiens

<400> SEQUENCE: 277
aagcctcttt tatacatctc ttcagggaag agagaagcaa tgggcatgtt agtatacaat 60
gatcacagcc acgcaggcct gcaagctgcc ttttggacag gctgttgact gccgttccaa 120
ttagctgatt ggagaatgtg gaatgcagag tgataatgct gcatatctgc tatcaggcag 180
cagcaaaggt ttttgtcttg ggaaggcaag ctttccctgc aatattatct cagcagctcc 240
ctagctgctt accctgaaaa cgagggatcc aaacggaggg tgttgcactc tgctaacgct 300
ggtcctgtgc gtggctgtgg catatgagcg gcaggtctga aaaagcaggt gtgtgctggg 360
acgggcactg gactggaacg caggcggacg ctctcgggtt tacctgcttc ctgttaacag 420
attgtgggct cccagggcat atgtctgcac gctgaggccg aggcggagaa ggggcttcct 480
gagcgtccca gtacactgac agagacactt ggattggact taatcttaaa cctctggagt 540
tcaagacctt ttaaaaaggg ctaaataaac aatctctaca tgtaaaaggc cactgactcc 600
tacttcctct gtatagagca actgttgaac tcagctgcct gtaggaaaac tgaagacttt 660
aataacaaac tctccaaggt gaaaatg 687

<210> SEQ ID NO 278
<211> LENGTH: 540
<212> TYPE: DNA
<213> ORGANISM: Homo sapiens

<400> SEQUENCE: 278
gtttctcttc ttgacttgat gcaggcacag atttatcaag ctcctcagtc aacaaacaca 60
tcaccggaag aaatatggaa ggaaaggaat tttaaaagga aataccaatc tctgtgcaaa 120
caaagccttg tatattcatg tttgcaccaa tctactgtga gatttatgaa gaaaaacaaa 180
ttgcggacaa ctctctatgt acacttacaa atgcctcagt tgatgcttgt gggctgtttg 240
tcagcgttct gtgataatga acacatggac ttctgtttat taaattcagt tgacccctt 300 agccaattgc caggagcctg gatttttact tccaactgct gatatctgtg taaaaattga 360
tctacatcca ccctttaaaa gcattgatga attaattaga actttagaca acaaagaaaa 420
attgaaaaag aattctcagt aaaagcgaat tcgatgttca aaacaaacta caaagagaca 480
agacttctct gtttactttc taagaactaa tataattgct accttaaaaa ggaaaaaatg 540

<210> SEQ ID NO 279
<211> LENGTH: 33
<212> TYPE: DNA
<213> ORGANISM: Homo sapiens

<400> SEQUENCE: 279
gggccttcct gcaacctttg cggctccaac atg 33

<210> SEQ ID NO 280
<211> LENGTH: 270
<212> TYPE: DNA
<213> ORGANISM: Homo sapiens

<400> SEQUENCE: 280
gcttctttgc agcgcttcag cgttttcccc tggagggcgc ctccatcctt ggaggcctag 60
tgccgtcgga gagagagcgg gagccgcgga cagagacgcg tgcgcaattc ggagccgact 120
ctgggtgcgg actgtgggag ctgactctgg gtagccggct gcgcgtggct ggggaggcga 180
ggccggacgc acctctgttt gggggtcctc agagattaat gattcatcaa gggatagttg 240
tacttgtctc gtgggaatca cttcatcatg 270

<210> SEQ ID NO 281
<211> LENGTH: 37
<212> TYPE: DNA
<213> ORGANISM: Homo sapiens

<400> SEQUENCE: 281
ctgccttcgc cgctcgggcc gcccggggga aaacatg 37

<210> SEQ ID NO 282
<211> LENGTH: 237
<212> TYPE: DNA
<213> ORGANISM: Homo sapiens

<400> SEQUENCE: 282
ccgcctcctc taggccgccg gccgcgaagc gctgagtcac ggtgaggcta ctggacccac 60
actctcttaa cctgccctcc ctgcactcgc tcccggcggc tcttcgcgtc acccccgccg 120
ctaaggctcc aggtgccgct accgcagcgt gagtacctgg ggctcctgca ggggtccact 180
agccctccat cctctacagc tcagcatcag aacactctct ttttagactc cgatatg 237

<210> SEQ ID NO 283
<211> LENGTH: 109
<212> TYPE: DNA
<213> ORGANISM: Homo sapiens

<400> SEQUENCE: 283
ccttccttac ttccggttct ctatggtgcg cgggcaagct ttgctccgcc tccggcagtg 60
gcttactccc ggtgccaggt tcttggagct gtgaggagga acaaccatg 109

<210> SEQ ID NO 284
<211> LENGTH: 112
<212> TYPE: DNA
<213> ORGANISM: Homo sapiens

<400> SEQUENCE: 284
gggcctttgc aaaattgccc tagtaacggc cgcatggtaa ctcaggcgcc gggcgcactg 60
tcctagctgc tggttttcca cgctggtttt agctcccggc gtctgcaaaa tg 112

<210> SEQ ID NO 285
<211> LENGTH: 153
<212> TYPE: DNA
<213> ORGANISM: Homo sapiens

<400> SEQUENCE: 285
tttccttttt agttgactga aacaaaacaa aacaaaaggg ccactggatg tctgccttct 60
tggggggtga gccagacaga ctgacaaaca aacagcccca actgtgttcg ggggagggtt 120
tcgcctcccg ttttgcccgg cagcagcagc atg 153

<210> SEQ ID NO 286
<211> LENGTH: 250
<212> TYPE: DNA
<213> ORGANISM: Homo sapiens

<400> SEQUENCE: 286 gctcccctttt tgccttcaac cttcgagccg ccacgtaatg ccacgtcccc gcgcatgcgc 60
atcttggccg ctgctggcgg ctgtttccgg gcttagaggg ctggagtggc cgccgagttg 120
gaggcggtgg tggcagcagt aggagtgtgt agagtgcggg attgggggcc aggccctgcg 180
gagggcgggg gaagttgtct tcttttttt ccggaggggc cggtaaacct ggtggctgaa 240
cggcaagatg 250

<210> SEQ ID NO 287
<211> LENGTH: 171
<212> TYPE: DNA
<213> ORGANISM: Homo sapiens

<400> SEQUENCE: 287 ccccctttg gcccctgcct ttggagaaag tggagtgtgg cgcttggttg tcgttatttc 60
ttcggactgc ttcgcggtgc acggattcag cttctgccca gtggggcttt cagctgtttg 120
cgcgtctctc tgtccccctc ccctcccccc ggcacacctc tgtctacgat g 171

<210> SEQ ID NO 288
<211> LENGTH: 145
<212> TYPE: DNA
<213> ORGANISM: Homo sapiens

<400> SEQUENCE: 288
gcttcttccg ctttctcgtc aggctcctgc gccccaggca tgaaccaagg tttctgaact 60
actgggcggg agccaacgtc tcttctttct cccgctctgg cggaggcttt gtcgctgcgg 120
gctgggcccc agggtgtccc ccatg 145

<210> SEQ ID NO 289
<211> LENGTH: 152
<212> TYPE: DNA
<213> ORGANISM: Homo sapiens

<400> SEQUENCE: 289
ggctccttcc tttccgtctc tggccggctg ggcgcgggcg actgctggcg aggcgcgtgg 60
gaccttacgc tggttcccct tcgtctcctc tcccggcccg ggccactaga gagttcgctg 120
acgccgggtg agctgagcct gccgccaaga tg 152

<210> SEQ ID NO 290
<211> LENGTH: 109
<212> TYPE: DNA
<213> ORGANISM: Homo sapiens

<400> SEQUENCE: 290
gtttcctctt ttcctggttt ctcaagagtg ctgctgctaa cgcggtcccc ggcacgcacc 60
atctgttgcc atcccggccg gccgaggcca ttgcagattt tggaagatg 109

<210> SEQ ID NO 291
<211> LENGTH: 26
<212> TYPE: DNA
<213> ORGANISM: Homo sapiens

<400> SEQUENCE: 291
ccgcctcctt ctttctcgac aagatg 26

<210> SEQ ID NO 292
<211> LENGTH: 47

<212> TYPE: DNA
<213> ORGANISM: Homo sapiens

<400> SEQUENCE: 292
cgctctctgg ccgggcttgg gctgcgtgga gaatactttt tgcgatg 47

<210> SEQ ID NO 293
<211> LENGTH: 33
<212> TYPE: DNA
<213> ORGANISM: Homo sapiens

<400> SEQUENCE: 293
gtttctcttt cttcctgtct gcttggaaag atg 33

<210> SEQ ID NO 294
<211> LENGTH: 55
<212> TYPE: DNA
<213> ORGANISM: Homo sapiens

<400> SEQUENCE: 294 aaacctttc cggtcttact cacgttgcgg ccttcctcgc gtcacagccg ggatg 55

<210> SEQ ID NO 295
<211> LENGTH: 36
<212> TYPE: DNA
<213> ORGANISM: Homo sapiens

<400> SEQUENCE: 295
ctccctctca cacacgctca cacccggctc gagatg 36

<210> SEQ ID NO 296
<211> LENGTH: 846
<212> TYPE: DNA
<213> ORGANISM: Homo sapiens

<400> SEQUENCE: 296
ccgcctctct ccgccccggg tcgctgccgc ctccgccgct ttcgggcttc gcagcctgag 60
gaaaaaaaga gaaaaagata aaaaaaatct gaaaacgctt caaaatcctg aaaaaaaaaa 120
aggaaaagaa aaaacgaatc ctcggagaac ccgcggggaa gtcactttcg tacgcttccg 180
gcctgccccg cgcccgccgc cgcagcgctt ggcgtccgtc ggtctccgtc cgtcggtccg 240
ggggtgagcc gcccgcccgg cccgccgtgc cctccccccg ctcgggcccc gagccccgcg 300
ccccgcgcct gccccggcgc accacgtgtc cgtgctgccc ttcgccgccc gcccggggct 360
cgccgagtcg gcgcccacaa agatttggtt tccctctgcc ccggcggttg taatcttaaa 420
ccgccggagc ccgaggccta tatttataga gaaacgcgtg tccccgaggc cgccgtgggc 480
agcgtccggt cgcctcttaa aggattttta cccttcggaa ggggattccc cgtttaattt 540
ttttcctact ttgatttttt gaaatttgga gcttcgcacc aggaccgcgg agaagtgcaa 600
agtcgcgggg agggccgtat tgtgcggaga gccttttgtc tgcggtgctg cggccgtggg 660
agccggcccc cgcctcccgt ttccgtcccg tctccaagcc cgccgactcc agctcgtcct 720
cgccgcgccg gtgccacctg tgagccgcgg cgcgggcccg ggctccgaag gcgcccccttt 780 gtcctgcggc gggcccgata agaagtcctc ctggcggggc tcggggtggt ggggggcggg 840
gagatg 846

<210> SEQ ID NO 297
<211> LENGTH: 252
<212> TYPE: DNA

<213> ORGANISM: Homo sapiens

<400> SEQUENCE: 297
agctctttcg cggcgctacg gcgttggcac cagtctctag aaaagaagtc agctctggtt 60
cggagaagca gcggctggcg tgggccatcc ggggaatggg cgccctcgtg acctagtgtt 120
gcggggcaaa aagggtcttg ccggcctcgc tcgtgcaggg gcgtatctgg gcgcctgagc 180
gcggcgtggg agccttggga gccgccgcag cagggggcac acccggaacc ggcctgagcg 240
cccgggacca tg 252

<210> SEQ ID NO 298
<211> LENGTH: 147
<212> TYPE: DNA
<213> ORGANISM: Homo sapiens

<400> SEQUENCE: 298
ctttcttttc tccaagacgg gctgaggatt gtacagctct aggcggagtt ggggctcttc 60
ggatcgctta gattctcctc tttgctgcat ttccccccac gtcctcgttc tcccgcgtct 120
gcctgcggac ccggagaagg gagaatg 147

<210> SEQ ID NO 299
<211> LENGTH: 210
<212> TYPE: DNA
<213> ORGANISM: Homo sapiens

<400> SEQUENCE: 299
tggtcttctc tcccgcggcg ctggggcccg cgctccgctg ctgttgctcc attcggcgct 60
tttctggcgg ctggctcctc tccgctgccg gctgctcctc gaccaggcct ccttctcaac 120
ctcagcccgc ggcgccgacc cttccggcac cctcccgccc cgtctcgtac tgtcgccgtc 180
accgccgcgg ctccggccct ggccccgatg 210

<210> SEQ ID NO 300
<211> LENGTH: 75
<212> TYPE: DNA
<213> ORGANISM: Homo sapiens

<400> SEQUENCE: 300
ttttcttctt ttcttagctg ttagctgaga ggaagtctct gaacaggcgg cagcggctct 60
tatagtgcaa ccatg 75

<210> SEQ ID NO 301
<211> LENGTH: 72
<212> TYPE: DNA
<213> ORGANISM: Homo sapiens

<400> SEQUENCE: 301
gatccttttt gtcccctact gcgtgcggtg gcagcttcct tgcggaagtg gtgaccgtga 60
gagaagaaga tg 72

<210> SEQ ID NO 302
<211> LENGTH: 133
<212> TYPE: DNA
<213> ORGANISM: Homo sapiens

<400> SEQUENCE: 302
gtttcctttc gctgatgcaa gagcctagtg cggtggtggg agaggtatcg gcaggggcag 60
cgctgccgcc ggggcctggg gctgacccgt ctgacttccc gtccgtgccg agcccactcg 120
agccgcagcc atg 133

<210> SEQ ID NO 303
<211> LENGTH: 156
<212> TYPE: DNA
<213> ORGANISM: Homo sapiens

<400> SEQUENCE: 303
cctcccctct ccgcctaagc ctgccctatg ccagccgggt gtcctcccca cagcaccacg 60
gcttctcttc ctcagcacgg cgacaggggc ttccccttcg ccgccgccgc cgccgccggc 120
caagctccgc cgcgcccgcg gcccgcggcc gccatg 156

<210> SEQ ID NO 304
<211> LENGTH: 91
<212> TYPE: DNA
<213> ORGANISM: Homo sapiens

<400> SEQUENCE: 304 cgccccccttc tgcgcggtca cgccgagcca gcgcctgggc ctggaaccgg gccgtagccc 60
ccccagtttc gcccaccacc tccctaccat g 91

<210> SEQ ID NO 305
<211> LENGTH: 578
<212> TYPE: DNA
<213> ORGANISM: Homo sapiens

<400> SEQUENCE: 305
ctccctttct taaatgcttg gggtgagaga gaagagaggc tagggtgggg catggaggac 60
acagagagag agagtgctgt gtattccttc cccgctactg tcctgtcctc agctaacttg 120
ctctgggaca gcttccccag ggctacagat actgcactca gctgactgtc ctttcttctg 180
ggcccctggt cccagagcag agctgacaaa ggagattcct gagagagcac cttcttatca 240
cagaaagtgc tgagccaaga gctcctagct gccccttttg cagatgtgaa gggccagtga 300
accttggacc cagatggttg cttaatactc ctttcccccct ccctcactcc ttcctttgcg 360
ggctgcctca cctcctccac ccttcttgct taaatccata ggcatttgtc tggccttccc 420
ttttactgct ggctgggaag gaggagcatc agaccacaga tcctggaagg cacttctctc 480
cctgactgct gctcacactg ccgtgagaac ctgcttatat ccaggaccaa ggaggcaatg 540
ccaggaagct ggtgaagggt ttcctctcct ccaccatg 578

<210> SEQ ID NO 306
<211> LENGTH: 89
<212> TYPE: DNA
<213> ORGANISM: Homo sapiens

<400> SEQUENCE: 306
ctcccttttc tcctcaagtc ctgaagttga gtttgagagg cgacacggcg gcggcggccg 60
cgctgctccc gctcctctgc ctccccatg 89

<210> SEQ ID NO 307
<211> LENGTH: 74
<212> TYPE: DNA
<213> ORGANISM: Homo sapiens

<400> SEQUENCE: 307
agccctccta cctgcgcacg tggtgccgcc gctgctgcct cccgctcgcc ctgaacccag 60
tgcctgcagc catg 74

<210> SEQ ID NO 308
<211> LENGTH: 86
<212> TYPE: DNA
<213> ORGANISM: Homo sapiens

<400> SEQUENCE: 308
ccttctttgc ggctcggcca ttttgtccca gtcagtccgg aggctgcggc tgcagaagta 60
ccgcctgcgg agtaactgca aagatg 86

<210> SEQ ID NO 309
<211> LENGTH: 217
<212> TYPE: DNA
<213> ORGANISM: Homo sapiens

<400> SEQUENCE: 309
cggccccttc ggctccgagc tgaccctgat cagggccgag ttgtctcggc ggcgctgccg 60
aggcctccac ccaggacagt ccccctcccc gggcctctct cctcttgcct acgagtcccc 120
tctcctcgta ggcctctcgg atctgatatc gtggggtgag gtgagcaggc ccggggaggg 180
tggttaccgc tgaggagctg cagtctctgt caagatg 217

<210> SEQ ID NO 310
<211> LENGTH: 71
<212> TYPE: DNA
<213> ORGANISM: Homo sapiens

<400> SEQUENCE: 310
agctctcttc ttgcttggca gctggaccaa gggagccagt cttgggcgct ggagggcctg 60
tcctgaccat g 71

<210> SEQ ID NO 311
<211> LENGTH: 479
<212> TYPE: DNA
<213> ORGANISM: Homo sapiens

<400> SEQUENCE: 311
ttttcttctt cgtcagcctc ccttccaccg ccatattggg ccactaaaaa aagggggctc 60
gtcttttcgg ggtgtttttc tccccctccc ctgtccccgc ttgctcacgg ctctgcgact 120
ccgacgccgg caaggtttgg agagcggctg ggttcgcggg acccgcgggc ttgcacccgc 180
ccagactcgg acgggctttg ccaccctctc cgcttgcctg gtcccctctc ctctccgccc 240
tcccgctcgc cagtccattt gatcagcgga gactcggcgg ccgggccggg gcttccccgc 300
agcccctgcg cgctcctaga gctcgggccg tggctcgtcg gggtctgtgt cttttggctc 360
cgagggcagt cgctgggctt ccgagagggg ttcgggctgc gtaggggcgc tttgttttgt 420
tcggttttgt ttttttgaga gtgcgagaga ggcggtcgtg cagacccggg agaaagatg 479

<210> SEQ ID NO 312
<211> LENGTH: 540
<212> TYPE: DNA
<213> ORGANISM: Homo sapiens

<400> SEQUENCE: 312
tctcctcttc ttcctttgtg tgtgcgcgag cggagttggg gcggagggag aagggggagg 60
tcgctctgtc tgtccgtctc ccgccgcctc tgcccggtct actcgaagtg cggcgggaga 120
ggcgggagcc caggagaggg tgcgggagct ggcggggcgg ctcggagctg ccaggacgcc 180

```
ctggtcccag ccgcgcacag gggagcgtgg acggcagagg ggctcggcgg gagccgagat    240

ccgcccgtcc cggctgcccc tcggcctccc tctgctccca cctaccccct gacacccata    300

gaaaagcgtg caaaggcgcg gagcgggacg gaaaccacaa ataaatagcg gcggcggcag    360

cgcgtcatct ggtggagcag gaagtgcagg cagagtccgg aggctggtgc tttctgcgcg    420

tccccaggac tttgccatgg gctgggggcc gcggaggctg cgagcggccg ggcgagggca    480

gcggcggcgg cgtccgcacc ggggctgagc gagcagcgac gcgaggggcg cgcggagatg    540
```

```
<210> SEQ ID NO 313
<211> LENGTH: 466
<212> TYPE: DNA
<213> ORGANISM: Homo sapiens

<400> SEQUENCE: 313

gggcctcctt gaggaccccg ggctgggcgc cgccgccggt tcgtctactc tttccttcag     60

ccgcctcctt tcaaccttgt caacccgtcg gcgcggcctc tggtgcagcg gcggcggctc    120

ctgttcctgc cgcagctctc tccctttctt acctccccac cagatcccgg agatcgcccg    180

ccatggcttt acttactgcg gccgcccggc tcttgggaac caaggcaccc agtggcaagt    240

actagctgag catttgggag atgcttgtct tacttggctg ttgcttctcc tgctgctggg    300

gaaaaggaat gcatcttgtc ttgttcttgc agcccggcat gccagtgctt cctccacgaa    360

tttgaaagac atattggctg acctgatacc taaggagcag gccagaatta agactttcag    420

gcagcaacat ggcaagacgg tggtgggcca aatcactgtg gacatg                   466
```

```
<210> SEQ ID NO 314
<211> LENGTH: 114
<212> TYPE: DNA
<213> ORGANISM: Homo sapiens

<400> SEQUENCE: 314

atttcttttc aagtcaattg aactgaaatc tccttgttgc tttgaaatct tagaagagag     60

cccactaatt caaggactct tactgtggga gcaactgctg gttctatcac aatg          114
```

```
<210> SEQ ID NO 315
<211> LENGTH: 68
<212> TYPE: DNA
<213> ORGANISM: Homo sapiens

<400> SEQUENCE: 315

cagtctccct cccttctgga gacaccacca gatgggccag ccagaggcag cagcagcctc     60

ttcccatg                                                              68
```

```
<210> SEQ ID NO 316
<211> LENGTH: 54
<212> TYPE: DNA
<213> ORGANISM: Homo sapiens

<400> SEQUENCE: 316

cgctctccgc ctcgcttgct cctgccgggc gtgcagggcc ccgccgccgc catg           54
```

```
<210> SEQ ID NO 317
<211> LENGTH: 180
<212> TYPE: DNA
<213> ORGANISM: Homo sapiens

<400> SEQUENCE: 317
```

catcctttcc ctgcggagga ccagggcaag tttcctgcct gcacggcaca ggagagcaaa 60
cttctacaga cagaccaagg cttccatttg ctgctgacac atggaactga ggtgaaattg 120
tgctccatga ttttacagat ttcataacgt ttaagagacg ggactcaggt catcaaaatg 180

<210> SEQ ID NO 318
<211> LENGTH: 15
<212> TYPE: DNA
<213> ORGANISM: Homo sapiens

<400> SEQUENCE: 318
cgtcctctca gcatg 15

<210> SEQ ID NO 319
<211> LENGTH: 247
<212> TYPE: DNA
<213> ORGANISM: Homo sapiens

<400> SEQUENCE: 319
ttacctcttt ttcttgtctc tcgtcaggtc tctgacattg acagagcctg gacgttggag 60
gaagccccag gacgttggag gggtaaagta aaagtccaca gttaccgtga gagaaaaaag 120
agggagaaag cagtgcagcc aaactcggaa gaaaagagag gaggaaaagg actcgacttt 180
cacattggaa caaccttctt tccagtgcta aaggatctct gatctgggga acaacaccct 240
ggacatg 247

<210> SEQ ID NO 320
<211> LENGTH: 72
<212> TYPE: DNA
<213> ORGANISM: Homo sapiens

<400> SEQUENCE: 320
cgctctttct cccttcagca gccagccagc tctgtgtcag ggtcgggggg tgcagaaagt 60
caggacagaa tg 72

<210> SEQ ID NO 321
<211> LENGTH: 161
<212> TYPE: DNA
<213> ORGANISM: Homo sapiens

<400> SEQUENCE: 321
gttcctcttt tcctcggttc ccagtgttct ggcaggtaag gaacgccggc tcttcgcctc 60
tcagcgcggc ttgtcctttg ttccggacgc ccgctcctca gccctgcggc tcctggggtc 120
gctgctgcat cccgcacgcc tccaccggct gcagacccat g 161

<210> SEQ ID NO 322
<211> LENGTH: 78
<212> TYPE: DNA
<213> ORGANISM: Homo sapiens

<400> SEQUENCE: 322
cgctccctcc cggtgccggc ttctctgagt caccaacctg aggctgcccc ggccgcctgc 60
gcacccggca gcaccatg 78

<210> SEQ ID NO 323
<211> LENGTH: 59
<212> TYPE: DNA
<213> ORGANISM: Homo sapiens

<400> SEQUENCE: 323
agctctttgc cgtcggagcg cttgtttgct gcctcgtact cctccattta tccgccatg 59

<210> SEQ ID NO 324
<211> LENGTH: 118
<212> TYPE: DNA
<213> ORGANISM: Homo sapiens

<400> SEQUENCE: 324
cttccttctt tcctcccttg ccagtccgcc tgtcttcctc cccgtcttcc ctgcccggcc 60
tcccccttct tcccccgctg gccccctccc cggagggata atatggtctc cggcgatg 118

<210> SEQ ID NO 325
<211> LENGTH: 182
<212> TYPE: DNA
<213> ORGANISM: Homo sapiens

<400> SEQUENCE: 325
ccaccttctt ttcatttcta gtgagacaca cgctttggtc ctggctttcg gcccgtagtt 60
gtagaaggag ccctgctggt gcaggttaga ggtgccgcat cccccggagc tctcgaagtg 120
gaggcggtag gaaacggagg gcttgcggct agccggagga agctttggag ccggaagcca 180
tg 182

<210> SEQ ID NO 326
<211> LENGTH: 96
<212> TYPE: DNA
<213> ORGANISM: Homo sapiens

<400> SEQUENCE: 326
cattcctttc tttcgattac ccgtggcgcg gagagtcagg gcggcggctg cggcagcaag 60
ggcggcggtg gcggcggcgg cagctgcagt gacatg 96

<210> SEQ ID NO 327
<211> LENGTH: 152
<212> TYPE: DNA
<213> ORGANISM: Homo sapiens

<400> SEQUENCE: 327
gagtcttttc agcgctgagg actggcgctg aggaggcggc ggtggctccc ggggcgtttg 60
agcgggctca cccgagcccg cgggccaacg cggatccagg cccgactggc gggaccgccc 120
cggattcccc gcgggccttc ctagccgcca tg 152

<210> SEQ ID NO 328
<211> LENGTH: 28
<212> TYPE: DNA
<213> ORGANISM: Homo sapiens

<400> SEQUENCE: 328
atttctcctc cccctcccgg ccaagatg 28

<210> SEQ ID NO 329
<211> LENGTH: 192
<212> TYPE: DNA
<213> ORGANISM: Homo sapiens

<400> SEQUENCE: 329
ggtcctctct cggctcctcg cggctcgcgg cggccgacgg ttcctgggac acctgcttgc 60
ttggcccgtc cggcggctca gggcttctct gctgcgctcc cggttcgctg gacgggaaga 120
agggctgggc cgtcccgtcc cgtccccatc ggaaccccaa gtcgcgccgc tgacccgtcg 180
cagggcgaga tg 192

<210> SEQ ID NO 330
<211> LENGTH: 23
<212> TYPE: DNA
<213> ORGANISM: Homo sapiens

<400> SEQUENCE: 330
ctaccttcct tctagcagaa atg 23

<210> SEQ ID NO 331
<211> LENGTH: 268
<212> TYPE: DNA
<213> ORGANISM: Homo sapiens

<400> SEQUENCE: 331
cggcccttcc tccgccttct gggcggagcc cgcgcgggat ccgggtggct gcaggctgct 60
ggcttctgcg gctgcggggt cggggtcgcg gccagggcca agccgcagcg agttcacagg 120
cggaacccct gcaggcggcg ccccctacgc gaggtcaccc ctgggaagga gcgcagccca 180
cccggcccct ccgcatccga gcaggacgcc cgtctcctct ccctgaggat ttcaggtctc 240
cctgtcccag gaggcttgtg ccaagatg 268

<210> SEQ ID NO 332
<211> LENGTH: 34
<212> TYPE: DNA
<213> ORGANISM: Homo sapiens

<400> SEQUENCE: 332
tcttctctcg gttcctcttt cctcgctcaa gatg 34

<210> SEQ ID NO 333
<211> LENGTH: 56
<212> TYPE: DNA
<213> ORGANISM: Homo sapiens

<400> SEQUENCE: 333
ggctcttctt tgcctctgct ggagtccggg gagtggcgtt ggctgctaga gcgatg 56

<210> SEQ ID NO 334
<211> LENGTH: 68
<212> TYPE: DNA
<213> ORGANISM: Homo sapiens

<400> SEQUENCE: 334
ttttccttta gtcaggaagg acgttggtgt tgaggttagc atacgtatca aggacagtaa 60
ctaccatg 68

<210> SEQ ID NO 335
<211> LENGTH: 81
<212> TYPE: DNA
<213> ORGANISM: Homo sapiens

<400> SEQUENCE: 335
gcttctcttt tccttggcgg aggagggaga ccacagagcc ctgggttgtg gaagaggtgg 60
ctgttccctg tcatcagtat g 81

<210> SEQ ID NO 336
<211> LENGTH: 292

<212> TYPE: DNA
<213> ORGANISM: Homo sapiens

<400> SEQUENCE: 336 ccccttccc ccgcctttct tccctccgcg acccgggccg tgcgtccgtc cccctgcctc 60
tgcctggcgg tccctcctcc cctctccttg cacccatacc tctttgtacc gcaccccctg 120 gggaccccctg cgcccctccc ctcccccctg accgcatgga ccgtcccgca ggccgctgat 180
gccgcccgcg gcgaggtggc ccggaccgca gtgccccaag agagctctaa tggtaccaag 240
tgacaggttg gctttactgt gactcgggga cgccagagct cctgagaaga tg 292

<210> SEQ ID NO 337
<211> LENGTH: 261
<212> TYPE: DNA
<213> ORGANISM: Homo sapiens

<400> SEQUENCE: 337
gagcctttct ggggaagaac tccaggcgtg cggacgcaac agccgagaac attaggtgtt 60
gtggacagga gctgggacca agatcttcgg ccagccccgc atcctcccgc atcttccagc 120
accgtcccgc accctccgca tccttccccg ggccaccacg cttcctatgt gacccgcctg 180
ggcaacgccg aacccagtcg cgcagcgctg cagtgaattt tccccccaaa ctgcaataag 240
ccgccttcca aggccaagat g 261

<210> SEQ ID NO 338
<211> LENGTH: 243
<212> TYPE: DNA
<213> ORGANISM: Homo sapiens

<400> SEQUENCE: 338
gcgcctctta ggcttggcgg tggcggcggc ggcagcttcg cgccgaatcc ccggggagcg 60
gcggtggcgg cgtcctgggg ccaggaggag cgaacacctg ccgcggtcct cccgccggcg 120
ctgggctctg tgtgctccgg gatggagcag gtgtgcagag ggtgagaacc cagctctggg 180
accaagtcac ttgcttcctt acttagcaag actatcgact tgagcaaact tggacctggg 240
atg 243

<210> SEQ ID NO 339
<211> LENGTH: 526
<212> TYPE: DNA
<213> ORGANISM: Homo sapiens

<400> SEQUENCE: 339
ccccctcttt tggttacaga cgtgagggct ctttggagac gtaaacatct ccgagtggcg 60
agggtgggcg gggctgggct tgggaaaggg cggggtggct tgcttgaggt gtggaaagac 120
cagaagaagg tgaggtcaag agagtgcaga atgaggcatt ccaatggtgg gtgggccctg 180
acctgagaga gtggcgcggg gaggggtgaa agcgcggcga tcctggaacg ccagcgggcg 240
ttgcggccta tgcgcgaggg gcggggcgat taggtcatag agcggctccc agcgttccct 300
gcggcgtagg aggcggtcca gactataaaa gcggctgccg gaaagcggcc ggcacctcat 360
tcatttctac cggtctctag tagtgcagct tcggctggtg tcatcggtgt ccttcctccg 420
ctgccgcccc cgcaaggctt cgccgtcatc gaggccattt ccagcgactt gtcgcacgct 480
tttctatata cttcgttccc cgccaaccgc aaccattgac gccatg 526

<210> SEQ ID NO 340

<211> LENGTH: 251
<212> TYPE: DNA
<213> ORGANISM: Homo sapiens

<400> SEQUENCE: 340
gctcctctgc gcccttgccg ccctccgagc cacagctttc ctcccgctcc tgcccccggc 60
ccgtcgccgt ctccgcgctc gcagcggcct cgggagggcc caggtagcga gcagcgacct 120
cgcgagcctt ccgcactccc gcccggttcc ccggccgtcc gcctatcctt ggccccctcc 180
gctttctccg cgccggcccg cctcgcttat gcctcggcgc tgagccgctc tcccgattgc 240
ccgccgacat g 251

<210> SEQ ID NO 341
<211> LENGTH: 78
<212> TYPE: DNA
<213> ORGANISM: Homo sapiens

<400> SEQUENCE: 341
cttcctttcg cggggtcctc cgtagttctg gcacgagcca ggcgtactga caggtggacc 60
agcggactgg tggagatg 78

<210> SEQ ID NO 342
<211> LENGTH: 357
<212> TYPE: DNA
<213> ORGANISM: Homo sapiens

<400> SEQUENCE: 342
gctcctcctc gtcccagcgc tagcgggcac gcggttcctt tttgcgagct ttccgagtgc 60
caggcgccgg ccggctgcga agacgcggtg ggccgcccct ccgattgaaa tcacagaaga 120
tattcgtgtt cttcttaaga gaaaaagagg acattttagc tttctcagtt gaaggcgtac 180
tttattgtcg gcttccaaag attactaact tttatctgta tcactaagat tgaactgcct 240
tggctgtact gctattctta ctgctgcttc tattattgcc ttcttcagca caataaggct 300
ttcaaaagcc aaagaataac aagaaataag caccatttta gaagcctttc cactatg 357

<210> SEQ ID NO 343
<211> LENGTH: 86
<212> TYPE: DNA
<213> ORGANISM: Homo sapiens

<400> SEQUENCE: 343
tggtcctttt caacggtttt cacagatcca gtgacccacg ctctgaagac agaattagct 60
aactttcaaa aacatctgga aaaatg 86

<210> SEQ ID NO 344
<211> LENGTH: 303
<212> TYPE: DNA
<213> ORGANISM: Homo sapiens

<400> SEQUENCE: 344
ctgcctctcc aggcaacgcg ggaggcccag cgggaaggca ggaggcggcg gcggaggagg 60
agctctactg agccgcaact gtggcgacag caaccggagt cgcagccgcc gccacctgca 120
cctggcgcct agcccacgtc cagcgcctgc ccggccgccg cttcccgcca ccctgccctg 180
cccacccgcc aggtactacc attaaagata ccttcttctc agcaaatcta tgataaaaaa 240
tataagtaac agaagaagaa ataactgtta tttgtcaagt gacaagcttt taatgtcaga 300
atg 303

<210> SEQ ID NO 345
<211> LENGTH: 107
<212> TYPE: DNA
<213> ORGANISM: Homo sapiens

<400> SEQUENCE: 345
acgtctcttg ctcctcaggg ccactgccag gcttgccgag tcctgggact gctctcgctc 60
cggctgccac tctcccgcgc tctcctagct ccctgcgaag caggatg 107

<210> SEQ ID NO 346
<211> LENGTH: 78
<212> TYPE: DNA
<213> ORGANISM: Homo sapiens

<400> SEQUENCE: 346
acgcctcttc agttgtctgc tactcagagg aaggggcggt tggtgcggcc tccattgttc 60
gtgttttaag gcgccatg 78

<210> SEQ ID NO 347
<211> LENGTH: 146
<212> TYPE: DNA
<213> ORGANISM: Homo sapiens

<400> SEQUENCE: 347
gggtcttttt tagcgccatc tgctcgcggc gccgcctcct gctcctcccg ctgctgctgc 60
cgctgccgcc ctgagtcact gcctgcgcag ctccggccgc ctggctcccc atactagtcg 120
ccgatatttg gagttcttac aacatg 146

<210> SEQ ID NO 348
<211> LENGTH: 115
<212> TYPE: DNA
<213> ORGANISM: Homo sapiens

<400> SEQUENCE: 348
cgctctctga tgcaacgccg gaatcgcgga aaccgccggt gcacgttgga gtcataagac 60
ggcgtcggtg ttgcagtctg tgtccttgga ggtgaccagg gccactgcag gcatg 115

<210> SEQ ID NO 349
<211> LENGTH: 43
<212> TYPE: DNA
<213> ORGANISM: Homo sapiens

<400> SEQUENCE: 349
cgtccccttg ggtccttgat cctgagctga ccgggtagcc atg 43

<210> SEQ ID NO 350
<211> LENGTH: 35
<212> TYPE: DNA
<213> ORGANISM: Homo sapiens

<400> SEQUENCE: 350
ttctccttcc cgcagtctgc agccggagta agatg 35

<210> SEQ ID NO 351
<211> LENGTH: 91
<212> TYPE: DNA
<213> ORGANISM: Homo sapiens

<400> SEQUENCE: 351
catcctttac ggcaggcgtc cgcgtcgcta gctagtcgtt ctgaagcggc ggccagagaa 60
gagtcaaggg cacgagcatc gggtagccat g 91

<210> SEQ ID NO 352
<211> LENGTH: 133
<212> TYPE: DNA
<213> ORGANISM: Homo sapiens

<400> SEQUENCE: 352
ccctcctttt taagcgcctc ccgccagcct ctgctgtggc tcgcttcgcc gcgctccctc 60
cttccccgcc ttccatacct ccccggctcc gctcggttcc tggccacccc gcagcccctg 120
cccaggtgcc atg 133

<210> SEQ ID NO 353
<211> LENGTH: 146
<212> TYPE: DNA
<213> ORGANISM: Homo sapiens

<400> SEQUENCE: 353
ctcccttcgc gctccggacg ggcgacggta gctcgagacc cgggactccg cccgcctccc 60
cgcgagtatt tgaggtccgg ggcggctccg gcgcctctgc ccgccgttct gctcgctcgc 120
tccccgctct ggagtctgcc atcatg 146

<210> SEQ ID NO 354
<211> LENGTH: 69
<212> TYPE: DNA
<213> ORGANISM: Homo sapiens

<400> SEQUENCE: 354
ttctctcctc agacttcaag ggctaccact ggacccttcc cctgtcttga accctgagcc 60
ggcaccatg 69

<210> SEQ ID NO 355
<211> LENGTH: 25
<212> TYPE: DNA
<213> ORGANISM: Homo sapiens

<400> SEQUENCE: 355
ctctctcctt tccctgttag acatg 25

<210> SEQ ID NO 356
<211> LENGTH: 213
<212> TYPE: DNA
<213> ORGANISM: Homo sapiens

<400> SEQUENCE: 356
agttctctcc gcacgcgggc tggagaagcg ggtcctacgc acgctttgtt gtcgcgcttt 60
gcctccgtcc ttgcccctac tcccgcctta cctgacttcc ttttcggagg aagatccttg 120
agcagccgac gttgggacaa aggatttgga gaaacccagg gctaaagtca cgtttttcct 180
cctttaagac ttacctcaac acttcactcc atg 213

<210> SEQ ID NO 357
<211> LENGTH: 173
<212> TYPE: DNA
<213> ORGANISM: Homo sapiens

<400> SEQUENCE: 357
cgccctttct gtgcggcgcc cgggcgcaac gcaaacatgg cggcgggtgg cacccgtcgg 60
tgaggcggtg ccgggcgggg gttgtcgggt gtcatgggcg gtggcgacgg caccgccccc 120
gcgtctccct gagcgggacg gcaggggggg cttctgcgct gagccgggcg atg 173

<210> SEQ ID NO 358
<211> LENGTH: 242
<212> TYPE: DNA
<213> ORGANISM: Homo sapiens

<400> SEQUENCE: 358
ctgccctttg gacgcgcgcc tcggttccga acgcagcgga cggcgcctca ggcagcgcgg 60
cggacagccc gtcctccggc gcgccgcgag cctcggagga ccctagcgac ggtcgtggcg 120
taagaccggg gggacgcggc ggtagcggcg gccgttgcga ttgattgcgc tggttgcctg 180
cggcgtccac ttccttggcc gcccttgcta cactggctga ttgttgtgca gccggcgcca 240
tg 242

<210> SEQ ID NO 359
<211> LENGTH: 425
<212> TYPE: DNA
<213> ORGANISM: Homo sapiens

<400> SEQUENCE: 359
ccaccctttc tcgaggctgt ggcctccgcg agagccgagc gggccgcacc gccggccgtg 60
cgactgcccc agtcagacac gaccccggct tctagcccgc ctaagcctgt ttggggttgc 120
tgactcgttt cctccccgag tttcccgcgg gaactaactc ttcaagagga ccaaccgcag 180
cccagagctt cgcagacccg gccaaccaga ggcgaggttg agagcccggc gggccgcggg 240
gagagagcgt cccatctgtc ctggaaagcc tgggcgggtg gattgggacc ccgagagaag 300
caggggagct cggcggggtg cagaagtgcc caggcccctc cccgctgggg ttgggagctt 360
gggcaggcca gcttcaccct tcctaagtcc gcttctggtc tccgggccca gcctcggcca 420
ccatg 425

<210> SEQ ID NO 360
<211> LENGTH: 185
<212> TYPE: DNA
<213> ORGANISM: Homo sapiens

<400> SEQUENCE: 360
ttccctcctt cgtcgctgtt gctgccgcca tacgcgctct ccctgtttag ctcttctgtt 60
agaaatagta tctttgtttt cctttgctgt tcctcaatcc cctactcttc accccttgtt 120
ttcacctatt ttgcgagaac ccatccagat ccccccttccc ttcttcccct gccggcccag 180
ttatg 185

<210> SEQ ID NO 361
<211> LENGTH: 29
<212> TYPE: DNA
<213> ORGANISM: Homo sapiens

<400> SEQUENCE: 361
ccgccctttc gctcctcggc cgcgcaatg 29

<210> SEQ ID NO 362
<211> LENGTH: 368
<212> TYPE: DNA
<213> ORGANISM: Homo sapiens

<400> SEQUENCE: 362
agctctttcc cttttggttt gcaagcactg cctgtaaagc cctcgcatga gaggccagcc 60
tgctagggaa atccaggaat ctgcaacaaa aacgatgaca gtctgaaata ctctctggtg 120
ccaacctcca aattctcgtc tgtcacttca gacccccact agttgacaga gcagcagaat 180
ttcaactcca gtagacttga atatgcctct gggcaaagaa gcagagctaa cgaggaaagg 240
gatttaaaga gtttttcttg ggtgtttgtc aaacttttat tccctgtctg tgtgcagagg 300
ggattcaact tcaatttttc tgcagtggct ctgggtccag ccccttactt aaagatctgg 360
aaagcatg 368

<210> SEQ ID NO 363
<211> LENGTH: 65
<212> TYPE: DNA
<213> ORGANISM: Homo sapiens

<400> SEQUENCE: 363 ctccctttc agtccgcgtc cctccctggg ccgggctggc actcttgcct tccccgtccc 60
tcatg 65

<210> SEQ ID NO 364
<211> LENGTH: 62
<212> TYPE: DNA
<213> ORGANISM: Homo sapiens

<400> SEQUENCE: 364
ggtccttctc tggggcggtc gcgttggcag cggatgcggg aagccggact ctgggcgtca 60
tg 62

<210> SEQ ID NO 365
<211> LENGTH: 136
<212> TYPE: DNA
<213> ORGANISM: Homo sapiens

<400> SEQUENCE: 365
cgccctctca gcaacccgca cagggcgcac ccggacgctc taccgctccc gccgcagtcg 60
ccgggccatg ggcctcgagc ccgccccgaa cccccgcgag cccgccttgt ctgcggcgtg 120
actggaggcc cagatg 136

<210> SEQ ID NO 366
<211> LENGTH: 79
<212> TYPE: DNA
<213> ORGANISM: Homo sapiens

<400> SEQUENCE: 366
cgttcttttg ttccggggcc gcagggcggg gcaggcccga ctttcgccgt cttcttgtct 60
actctccaga acggccatg 79

<210> SEQ ID NO 367
<211> LENGTH: 117
<212> TYPE: DNA
<213> ORGANISM: Homo sapiens

<400> SEQUENCE: 367
cttcctctcc gcctccttcg cctagcctgc gagtgttctg agggaagcaa ggaggcggcg 60
gcggccgcag cgagtggcga gtagtggaaa cgttgcttct gaggggagcc caagatg 117

<210> SEQ ID NO 368
<211> LENGTH: 63
<212> TYPE: DNA
<213> ORGANISM: Homo sapiens

<400> SEQUENCE: 368
ctacctcttc ctctccacgc ggttgagaag accggtcggc ctgggcaacc tgcgctgaag 60
atg 63

<210> SEQ ID NO 369
<211> LENGTH: 404
<212> TYPE: DNA
<213> ORGANISM: Homo sapiens

<400> SEQUENCE: 369
tgctctctgc cgcattgata gcagcgagag ctggaggtgt tgggtcggga gaccagccgt 60
tcgatcccgc cgcaggtagg agctggtttc catcctggca ccacggcaca cacctccagc 120
ctcgagcccg gcgctgctgc ccgggggtct ccttcaggct ctttgacgcc gttccagggg 180
gcacctatcc aggcatcctc tgggcctcta gccagaggac tggctcccgg cttcagcact 240
ccgggctgca gtaagaagtg cccttatcgc tctgagccct gccaccatcc cgtgaaccac 300
cgaaaccctg gtccagcgcg acagccttgg acctgggact ggacggatcc aaaacgctca 360
gcctcggccc cccacagacg gggctctgca tcgtctctga tatg 404

<210> SEQ ID NO 370
<211> LENGTH: 41
<212> TYPE: DNA
<213> ORGANISM: Homo sapiens

<400> SEQUENCE: 370
tgctcttcct gggctggctg tctcctgctc atccagccat g 41

<210> SEQ ID NO 371
<211> LENGTH: 152
<212> TYPE: DNA
<213> ORGANISM: Homo sapiens

<400> SEQUENCE: 371
ctgtctttct agcatgttgc ccttttttcaa ccacatttgt gtttcaggtg tagagaggag 60
agagagtgaa cagggagcgg ggcttttgtc tgttggtctc cctggactga agagagggag 120
aatagaagcc caagactaag attctcaaaa tg 152

<210> SEQ ID NO 372
<211> LENGTH: 55
<212> TYPE: DNA
<213> ORGANISM: Homo sapiens

<400> SEQUENCE: 372
gcttctctgc tgaccctctc tcgtcgccgc tgccgccgcc gcagctgcca aaatg 55

<210> SEQ ID NO 373
<211> LENGTH: 42
<212> TYPE: DNA
<213> ORGANISM: Homo sapiens

<400> SEQUENCE: 373
cctccttctg tttcccagac cgagagccgc gccggcacca tg 42

<210> SEQ ID NO 374

<211> LENGTH: 152
<212> TYPE: DNA
<213> ORGANISM: Homo sapiens

<400> SEQUENCE: 374
ccccctcttc tccgcgtagg cccagctccc tgaagcggct gtttcgagcc acgcgcccat 60
cgggtaccga ggcacgcgcc gggcgtcacg tgcgtttcgc ggcgagcgga aatgacgcga 120
gttgtgtgag ccgccagtat ggccgggcta tg 152

<210> SEQ ID NO 375
<211> LENGTH: 182
<212> TYPE: DNA
<213> ORGANISM: Homo sapiens

<400> SEQUENCE: 375
ctgtctctcc ccatccgggg cagcggggaa tggctgagcc aggggttcgc cgcccccgcc 60
gccgccgccg ccgccgccgc cgccgccgcc gcccgctttc ggctcgggcc tcaggaccgt 120
agcatcctga gacattttga attgacactt ctcaagattt gactggatca gagttcatca 180
tg 182

<210> SEQ ID NO 376
<211> LENGTH: 106
<212> TYPE: DNA
<213> ORGANISM: Homo sapiens

<400> SEQUENCE: 376
cttcctttat ctctggcggc cttgtagtcg tctccgagac tccccacccc tccttccctc 60 ttgacccccct aggtttgatt gccctttccc cgaaacaact atcatg 106

<210> SEQ ID NO 377
<211> LENGTH: 118
<212> TYPE: DNA
<213> ORGANISM: Homo sapiens

<400> SEQUENCE: 377
gagcctctgt cggccgcgga agcctggagt gggcggtacg cagacgcgcg cggtgagacc 60
cgctgtctgc tcagcggact ctgcccgccc ccacctcccc ctgcgtcggg ccgacatg 118

<210> SEQ ID NO 378
<211> LENGTH: 179
<212> TYPE: DNA
<213> ORGANISM: Homo sapiens

<400> SEQUENCE: 378
caccctcttt cagagtggta catggaagac agcacaaagt ggatccatac tctgaaatgc 60
agtaactctg atgcttgaat ttgtctccct tcttgccaga aaggattcta ataactcggt 120
gtcaaagcca agacataaac tcaacccctt ctcttccaaa agcttcacgt tacagcatg 179

<210> SEQ ID NO 379
<211> LENGTH: 92
<212> TYPE: DNA
<213> ORGANISM: Homo sapiens

<400> SEQUENCE: 379
gtacctttct cggggtgtct gcgtaactgc ccagacttgc cttggtttgg tcagatgaca 60
cctcctctgg gactggctag ccagcgttca tg 92

<210> SEQ ID NO 380
<211> LENGTH: 185
<212> TYPE: DNA
<213> ORGANISM: Homo sapiens

<400> SEQUENCE: 380
tttcctctgc tccgccgcgg ccggaggtat ccgcatcggc gagctgcgtc tcccgggtgt 60
cggccccggc ggctccccga ccgtgcccgg ctgtggcgag gcggctccag cccagcctgt 120
ggcagccgcg acccccgggg cgctccggag cccactgcgc ggcgcgcgtg ccggctgcct 180
gcatg 185

<210> SEQ ID NO 381
<211> LENGTH: 36
<212> TYPE: DNA
<213> ORGANISM: Homo sapiens

<400> SEQUENCE: 381
ctttcttccg ccttaggaag gtggcggcca gggatg 36

<210> SEQ ID NO 382
<211> LENGTH: 817
<212> TYPE: DNA
<213> ORGANISM: Homo sapiens

<400> SEQUENCE: 382
cggccctttt ctcggggcgc ccgagaggcc agctcagacc tcccggctcg acaggcggcg 60
cgggcggcgg tgagtgcggc gcggggacgc cggggcgcgg ggaccagcgg gagacagcgg 120
ggggccggtg gcgccagcac ctgctggggg ccccgggcac tgagcccttg gctggggcct 180
cctgggatgc cagggggcgc gggtcgggtc gcgggcatcg aggcgcggcg gagggcgtgg 240
gggcccggcc ggggcggggt ccggcctccc agcgctggtc ccggccgcgt ctccggttgg 300
gttcagctcc tgcgtcccag agtggcccga tcgcgcgtgg cggggtcgtc cggccccccac 360 ccgaacgagc gcccttcgcg gcccgccgcg tccccctccc cggagaggac ggcccctggg 420
ctttttagaa aaaggcgcga ttctctctag tgactcaggt tgagatttcc agaaatatcc 480
cccgggggtt cagaaacaaa accaaaacaa acaaaaaaac cccaacgaat tcccaaatgc 540
tatttgccaa acatttgact tctaggggcg cgggtacccg cgtttctctc cctgcccccg 600
cgacttcgcg caagatccgg gaaggacacc cgaggcccct gggagaccct ggggaggtga 660
aaatcagaga gcgaagcggg ccgtggcccc taggcctgac ccctccccgc ggggtaaggc 720
gggcaccccg cgagcgcagg ggtcctctta ctgctgatgg cacccagctc tgggcccaga 780
cgccgctcac cgtccaccgc cggtgctggg taaaatg 817

<210> SEQ ID NO 383
<211> LENGTH: 264
<212> TYPE: DNA
<213> ORGANISM: Homo sapiens

<400> SEQUENCE: 383
ccaccccttc ggctctgggc cccgcctcgt ggtgccggct ggttcttcgc gctcgcccga 60
cttcccagcg gccccgtgcg gcccgggcat gcccagtgcg ggcgcagcgg ccccggccct 120
ggaagcgccc cggcggagct ggcctgcggt gggctagggg cagggccgga gccgcggcgg 180
cggagctgtg gatccttcat gatgagagat ttggggacac ttctctctcc tgtgtgtagt 240
tgatagtttg gtggtgaaga gatg 264

<210> SEQ ID NO 384
<211> LENGTH: 64
<212> TYPE: DNA
<213> ORGANISM: Homo sapiens

<400> SEQUENCE: 384
tgacctttcc gagttggctg cagatttgtg gtgcgttctg agccgtctgt cctgcgccaa 60
gatg 64

<210> SEQ ID NO 385
<211> LENGTH: 91
<212> TYPE: DNA
<213> ORGANISM: Homo sapiens

<400> SEQUENCE: 385
attcctccgc gcgctgggac aggctgcttc ttcgccagaa ccaaccggtt gcttgctgtc 60
ccagcggcgc cccctcatca ccgtcgccat g 91

<210> SEQ ID NO 386
<211> LENGTH: 222
<212> TYPE: DNA
<213> ORGANISM: Homo sapiens

<400> SEQUENCE: 386
ctctcttccg cccggcggcc cacaccggtc aggcccggcg cgggctgcgc tctccagctg 60
tggctatggc cccagccccg agatgaggag ggagagaact aggggcccgc aggcctggga 120
atttccgtcc cccaccaagt ccggatgctc actccaaagt ctcagcaggc ccctgaggga 180
gggagctgtc agccagggaa aaccgagaac accatcacca tg 222

<210> SEQ ID NO 387
<211> LENGTH: 430
<212> TYPE: DNA
<213> ORGANISM: Homo sapiens

<400> SEQUENCE: 387
cgaccttcct gccgggccgg gcggtccgag gctgctggag tgccgtgagc aggccgcggg 60
aacgtcgccg tcaccttgtc tcggggcctc ggcgctgctt cccgccaaaa cacgtttacc 120
gcgcgcccgg gcctcccacc ttgcggaagg gaccccacca ccacttggat ttctgttgca 180
ggttgagaac aaaaacatgc acctggagtt tccccggagc cctctgcgtg gttgagcttc 240
ggtggaattt cggggctctt ggctgccagc cgcgcttgcc tggtagcaac agaaaccagt 300
cctgctcgcc tccgtggaca tttcattacc atccagaagt gtctcccact gaaggcatcc 360
gtggttgttt ttaagccaca aaaaagccac acccaagatc acctgacacc caccctgaca 420
agtgtccatg 430

<210> SEQ ID NO 388
<211> LENGTH: 184
<212> TYPE: DNA
<213> ORGANISM: Homo sapiens

<400> SEQUENCE: 388 ccgcccctt ccctcgcctt cggctgacgc tgacgtcgga tgagtgatcc ggagggacgc 60
tccgaccgcg gccgggaggc tcctgggggc cggggctccg aggttataat ataacttatc 120
ctctcatgct tttttcctgc cccttctccc caaatcatca acaatagaag aagaagaaaa 180
catg 184

<210> SEQ ID NO 389
<211> LENGTH: 57
<212> TYPE: DNA
<213> ORGANISM: Homo sapiens

<400> SEQUENCE: 389
gtgtctctgt gggcggccgc cgggttgagc tgcggcacac gtgcgacggc cgtgatg 57

<210> SEQ ID NO 390
<211> LENGTH: 31
<212> TYPE: DNA
<213> ORGANISM: Homo sapiens

<400> SEQUENCE: 390
gtttctttta gtttccggtg tctctgcaat g 31

<210> SEQ ID NO 391
<211> LENGTH: 330
<212> TYPE: DNA
<213> ORGANISM: Homo sapiens

<400> SEQUENCE: 391
cggcctctgt ctcctccccc tcccgccctt acctccacgc gggaccgccc gcgccagtca 60
actcctcgca ctttgcccct gcttggcagc ggataaaagg gggctgagga aataccggac 120
acggtcaccc gttgccagct ctagccttta aattcccggc tcggggacct ccacgcaccg 180
cggctagcgc cgacaaccag ctagcgtgca aggcgccgcg gctcagcgcg taccggcggg 240
cttcgaaacc gcagtcctcc ggcgaccccg aactccgctc cggagcctca gccccctgga 300
aagtgatccc ggcatccgag agccaagatg 330

<210> SEQ ID NO 392
<211> LENGTH: 22
<212> TYPE: DNA
<213> ORGANISM: Homo sapiens

<400> SEQUENCE: 392
cggcctttgc ggttccaaca tg 22

<210> SEQ ID NO 393
<211> LENGTH: 273
<212> TYPE: DNA
<213> ORGANISM: Homo sapiens

<400> SEQUENCE: 393
tagccttttc aaaaggcgca gcttaccgcg gtgcgcgcgg attctggact tgggcgccaa 60
ctcgtagtcc acgctccccg gggtcagcag aggggcgctc acgctctcgc cacccacctc 120
gctttctcac cccgcgcttc ccggcctggg tttttagtct tccttggagc gctctctggc 180
ctccgcctcc gccagggagc ggaaggcgga gacagcgaga ctggccaggg gggaggaaag 240
aggacgcgtg tgggcaaggg ggacaacggg atg 273

<210> SEQ ID NO 394
<211> LENGTH: 81
<212> TYPE: DNA
<213> ORGANISM: Homo sapiens

<400> SEQUENCE: 394
cgacctttcc cctctgcgac agtttcccga ggtacctagt gtctgagcgg cacagacgag 60
atctcgatcg aaggcgagat g 81

<210> SEQ ID NO 395
<211> LENGTH: 311
<212> TYPE: DNA
<213> ORGANISM: Homo sapiens

<400> SEQUENCE: 395
ggtcctctgc gccctggcag ccaggagtcg ccgccacgac cgccgggtct cagtgggtgc 60
ctgcgccttc tccccgcccg cctgccccgg gccatccaga aacttgctct acccgccgcg 120
ggtgctcggc agtgctgccc atggcccagc ccaggagcct atttagggcg ccggacgggc 180
tggacagagg cgcggctcag taattgaagg cctgaaacgc ccatgtgcca ctgactagga 240
ggcttccctg ctgcggcact tcatgaccca gcggcgcgcg gcccagtgaa gccaccgtgg 300
tgtccagcat g 311

<210> SEQ ID NO 396
<211> LENGTH: 121
<212> TYPE: DNA
<213> ORGANISM: Homo sapiens

<400> SEQUENCE: 396
ctgtctcttg taggcaggga tcacagtctg aaacgacagc aaggaagagg taggcaggga 60
aaactaactg gaaggaagtt taaatacaga aagagcaaag tattatctaa ctataacaat 120
g 121

<210> SEQ ID NO 397
<211> LENGTH: 190
<212> TYPE: DNA
<213> ORGANISM: Homo sapiens

<400> SEQUENCE: 397
cttcctccag ggtctggaga acccagaggc agctcctcct gagtgctggg aaggactctg 60
ggcatcttca gcccttctta ctctctgagg ctcaagccag aaattcaggc tgcttgcaga 120
gtgggtgaca gagccacgga gctggtgtcc ctgggaccct ctgcccgtct tctctccact 180
ccccagcatg 190

<210> SEQ ID NO 398
<211> LENGTH: 91
<212> TYPE: DNA
<213> ORGANISM: Homo sapiens

<400> SEQUENCE: 398
cgctcttcct ggttgggccc tgccctgagc tgccaccggg aagccagcct cagggactgc 60
agcgaccccc aaacacccct cccccaggat g 91

<210> SEQ ID NO 399
<211> LENGTH: 148
<212> TYPE: DNA
<213> ORGANISM: Homo sapiens

<400> SEQUENCE: 399
cttcctttcg ccgtcgccgc cgcggagcgg agtcgagccg agctgatttg atcgaggagc 60
gcggttaccg gacgggctgg gtctatggtc gctccgcggg ccgctccgcc ggctggtgct 120
tttttatcag ggcaagctgt gttccatg 148

<210> SEQ ID NO 400
<211> LENGTH: 81
<212> TYPE: DNA
<213> ORGANISM: Homo sapiens

<400> SEQUENCE: 400
cttcctccct agtcgcgggg agtctgagaa agcgcgcctg tttcgcgacc atcacgcacc 60
tcccctccgc ttgtggccat g 81

<210> SEQ ID NO 401
<211> LENGTH: 293
<212> TYPE: DNA
<213> ORGANISM: Homo sapiens

<400> SEQUENCE: 401
cctccttcct cgccgccggg gcgccctctc ggtgccactg gctctcacgt gccagtagcc 60
caccccgcat catcctctcg cctcgctcct ggagggaagt gactatatct cccccgtccg 120
ccttccatcg ccgccgcggc ggtaattctg tcgggcccgc ccgctgacgt cacctgctag 180
ccccgcctcc tctagggtcc cgggcccctg cggcgggggc tgccccgggg ggcagtcagt 240
tgaggcggcg ggagctcggc ggagggcggg ccaggtgact ggtccgggcc atg 293

<210> SEQ ID NO 402
<211> LENGTH: 401
<212> TYPE: DNA
<213> ORGANISM: Homo sapiens

<400> SEQUENCE: 402
aggccttttt gtgtcctgtt tgctaaaggc atgcgggcta cagcattcaa gagagggagt 60
cgttaacaaa gggaaagaga taaatgtaaa taagctcaca tttacagaat gagcggtttg 120
cagtaaaaag ctgcggcagc ccagagtctg ctactttagg ctgggctaac ctttccctgt 180
aaaaaaaaaa aaaaaaaaaa aaaaaaaaaa atggataaaa atatgcactt ccaaagggcg 240
agttgcccat ttacatgttt attagctaat tatctacagg catcagcaca ttctctcatc 300
tagcacactc tttcttgggg aggaaaatat ttcctaccgg tccatagtgt cagagtggtg 360
aacccctgca gccagcaggc ctcctgaaaa aaaagtccat g 401

<210> SEQ ID NO 403
<211> LENGTH: 188
<212> TYPE: DNA
<213> ORGANISM: Homo sapiens

<400> SEQUENCE: 403
gctcctcttt gcagaggggg aaactcttgg gctgagagca ggaataatgc ggtaggcaag 60
gcgggctgct ggctcccccg gctccggcag cagcggcggc agcccgagca gcggcagcag 120
cagcggcagc accccaggcg ctgacagccc cgccggccgg ctccgttgct gaccgccgac 180
tgtcaatg 188

<210> SEQ ID NO 404
<211> LENGTH: 187
<212> TYPE: DNA
<213> ORGANISM: Homo sapiens

<400> SEQUENCE: 404
agccctttct gtccctccca gtgaggccag ctgcggtgaa gagggtgctc tcttgcctgg 60
agttccctct gctacggctg ccccctccca gccctggccc actaagccag acccagctgt 120
cgccattccc acttctggtc ctgccacctc ctgagctgcc ttcccgcctg gtctgggtag 180
agtcatg 187

<210> SEQ ID NO 405
<211> LENGTH: 36
<212> TYPE: DNA
<213> ORGANISM: Homo sapiens

<400> SEQUENCE: 405
gggtctcctc gctgtcgccg ccgctgccac accatg 36

<210> SEQ ID NO 406
<211> LENGTH: 198
<212> TYPE: DNA
<213> ORGANISM: Homo sapiens

<400> SEQUENCE: 406
tcttctcctt taccaagatg gcggcttgtc cctgtttcgc cacagttcct accttatgag 60
ctcggttttc ttatgcttat aagagtggaa cagcaaaagc tggcaggctg acagaggcgg 120
cctcaggacg gaccttctgg ctactgaccg ttttgctgtg gttttcccgg attgtgtgta 180
ggtgtgagat caaccatg 198

<210> SEQ ID NO 407
<211> LENGTH: 58
<212> TYPE: DNA
<213> ORGANISM: Homo sapiens

<400> SEQUENCE: 407
gttcctccct tcttccgagc ctctcctctg gccgccgcgc gggagagagg ccgagatg 58

<210> SEQ ID NO 408
<211> LENGTH: 183
<212> TYPE: DNA
<213> ORGANISM: Homo sapiens

<400> SEQUENCE: 408
ctaccttttt cgagagtgac tcccgttgtc ccaaggcttc ccagagcgaa cctgtgcggc 60
tgcaggcacc ggcgcgtcga gtttccggcg tccggaagga ccgagctctt ctcgcggatc 120
cagtgttccg tttccagccc ccaatctcag agcggagccg acagagagca gggaaccggc 180
atg 183

<210> SEQ ID NO 409
<211> LENGTH: 148
<212> TYPE: DNA
<213> ORGANISM: Homo sapiens

<400> SEQUENCE: 409
cagtctttcg cctcagtctc gagctctcgc tggccttcgg gtgtacgtgc tccgggatct 60
tcagcacccg cggccgccat cgccgtcgct tggcttcttc tggactcatc tgcgccactt 120
gtccgcttca cactccgccg ccatcatg 148

<210> SEQ ID NO 410
<211> LENGTH: 218
<212> TYPE: DNA
<213> ORGANISM: Homo sapiens

<400> SEQUENCE: 410
ccgccccttt ctttctcctc gccggcccga gagcaggaac acgataacga aggaggccca 60
acttcattca ataaggagcc tgacggattt atcccagacg gtagaacaaa aggaagaata 120
ttgatggatt ttaaaccaga gtttttaaag agcttgagaa tacggggaaa ttaatttgtt 180
ctcctacaca catagatagg gtaaggttgt ttctgatg 218

<210> SEQ ID NO 411
<211> LENGTH: 106
<212> TYPE: DNA
<213> ORGANISM: Homo sapiens

<400> SEQUENCE: 411
cagtctctcc cagcgaccgc cgcgggggca aggcctggag ctgtggttcg aatttgtgca 60
ggcagcgggt gctggctttt agggtccgcc gcctctctgc ctaatg 106

<210> SEQ ID NO 412
<211> LENGTH: 581
<212> TYPE: DNA
<213> ORGANISM: Homo sapiens

<400> SEQUENCE: 412
agttctttcc aactttttct cggcggagtg agcgcagcgg gcgcagactc gggggcaggt 60
tgctgtgctt ctccgggctc agccgcctgc tctcctggct caggtcctcg gggagcccta 120
gacagacatc aagtggccac tggcgctcct tcccctccca gctgagccat cctccccggc 180
ctcctcgggc gggacagccc cgtgcttagg tttttctcct tttctccccc ggtgcgcctc 240
tgctcggact ctcgcgccgg gatcgcggcg gaaacctccc tcccctttcg cctcctgcgg 300
ctccttccct tcgcccctcc tccgccagtc actggaatca attccgtggg gaatcggctc 360
cgccgccgcg aaggacagcc tttccgcgcg ggactccggg gcgccacggg ggccatgtaa 420
gcagctatct tccagagggc cacactgggc atggacaccc ttttccctgc ctggaggagc 480
acaggtgata gtgtaatttt ccagtcacga aactgctaag gccatctcag ggcgtgtgc 540 gccaggatag gcgggcggcg tccgaggacc acatagccat g 581

<210> SEQ ID NO 413
<211> LENGTH: 218
<212> TYPE: DNA
<213> ORGANISM: Homo sapiens

<400> SEQUENCE: 413
ctttctttta agttgataac aatcagctca ggggtttgct ctgcttgcaa ggtcactgca 60
agaatgaaca ttgaactttg gactatacct gaggggtgag gtaaacaaca ggactataaa 120
tatcagagtg tgctgctgtg gctttgtgga gctgccagag taaagcaaag agaaaggaag 180
caggcccgtt ggaagtggtt gtgacaaccc cagcaatg 218

<210> SEQ ID NO 414
<211> LENGTH: 103
<212> TYPE: DNA
<213> ORGANISM: Homo sapiens

<400> SEQUENCE: 414
agctcttctc gcgcatgcgt tctccgaacg gtcttcttcc gacagcttgc tgccctagac 60
cagagttggt ggctggacct cctgcgactt ccgagttgcg atg 103

<210> SEQ ID NO 415
<211> LENGTH: 120
<212> TYPE: DNA

<213> ORGANISM: Homo sapiens

<400> SEQUENCE: 415
tttcctcttc ctccccagca ccgacccaca ctgaccaaca caggctgagc agtcaggccc 60
acagcatctg accccaggcc cagctcgtcc tggctggcct gggtcggcct ctggagtatg 120

<210> SEQ ID NO 416
<211> LENGTH: 29
<212> TYPE: DNA
<213> ORGANISM: Homo sapiens

<400> SEQUENCE: 416
cctcctttcc ccagcccgcc gcggccatg 29

<210> SEQ ID NO 417
<211> LENGTH: 97
<212> TYPE: DNA
<213> ORGANISM: Homo sapiens

<400> SEQUENCE: 417
ggacctttcg cactcgggtc aggggtaaag cagcctgtcg cttgccgggc agctggtgag 60
tcggtgacct ggcctgtgag gagcagtgag gagaatg 97

<210> SEQ ID NO 418
<211> LENGTH: 175
<212> TYPE: DNA
<213> ORGANISM: Homo sapiens

<400> SEQUENCE: 418
gtgcctctga ctgtccgggt ccctccagca ttttgcagct ttctcctgtc ttgaagaagt 60
agaacggtgc ccgagaaacg tttttcccct tcgagactca ggaggatgaa agtcatcact 120
tgtgaaatag cctggcacaa caaggagccc gtgtacagcc tggacttcca gcatg 175

<210> SEQ ID NO 419
<211> LENGTH: 87
<212> TYPE: DNA
<213> ORGANISM: Homo sapiens

<400> SEQUENCE: 419
agccccgccc cgctcgctgg cctgccctcc tcttgctacc ctcccggcgc agagaacccc 60
ggctgctcag cgcgctccgc ggtcatg 87

<210> SEQ ID NO 420
<211> LENGTH: 65
<212> TYPE: DNA
<213> ORGANISM: Homo sapiens

<400> SEQUENCE: 420
tgccctcctc ttgctaccct cccggcgcag agaaccccgg ctgctcagcg cgctccgcgg 60
tcatg 65

<210> SEQ ID NO 421
<211> LENGTH: 176
<212> TYPE: DNA
<213> ORGANISM: Homo sapiens

<400> SEQUENCE: 421
cagcctcctg ccagcgcgct ctctgtttct ctgcagcccc gaagctcgcg aatgtagcag 60
gcgccccaag ctcggtcctc aagaagccat ggcggaatcc aggggccgtc tgtacctttg 120
gatgtgcttg gctgctgcgc tggcatcttt cctgatggga tttatggtgg gtaagt 176

<210> SEQ ID NO 422
<211> LENGTH: 46
<212> TYPE: DNA
<213> ORGANISM: Homo sapiens

<400> SEQUENCE: 422
ctgtctcttt aacgcgagag gaagcgatgc agaggggtgg aaaatg 46

<210> SEQ ID NO 423
<211> LENGTH: 163
<212> TYPE: DNA
<213> ORGANISM: Homo sapiens

<400> SEQUENCE: 423
cttccttttc tgccttctct cctgctttct agctctgggc tttcccagct ccgaagtcaa 60
tactgagatc ccagatgtgt ccagagacat cctgaagagg ctcgggggtg gaggagcctt 120
agtgtgtcca caaagggact cctgaaactg actgagagcc agt 163

<210> SEQ ID NO 424
<211> LENGTH: 20
<212> TYPE: DNA
<213> ORGANISM: Homo sapiens

<400> SEQUENCE: 424
ggccctctgg cgctaccatg 20

<210> SEQ ID NO 425
<211> LENGTH: 81
<212> TYPE: DNA
<213> ORGANISM: Homo sapiens

<400> SEQUENCE: 425
cgcccttccc ccacccgctt ccggccgcgg ctcggttctc ccgcctccgc ctccgccgcg 60
gctcgtggtt gtcccgccat g 81

<210> SEQ ID NO 426
<211> LENGTH: 67
<212> TYPE: DNA
<213> ORGANISM: Homo sapiens

<400> SEQUENCE: 426
ctccctcctt gcagttggat ccctggcggg tgcggcccgg cccggcccgt gagcggcgca 60
cagaatg 67

<210> SEQ ID NO 427
<211> LENGTH: 93
<212> TYPE: DNA
<213> ORGANISM: Homo sapiens

<400> SEQUENCE: 427
actcctcctt tcccccgccc cgcctccgtt cggagagccg gcgggcgggc gcctctcggc 60
caggaagcgc ctcttggacg cgtgtgaccg atg 93

<210> SEQ ID NO 428
<211> LENGTH: 248
<212> TYPE: DNA
<213> ORGANISM: Homo sapiens

<400> SEQUENCE: 428
aggcctcttc tgaggctcta ggtgccccag tagcagggcc ttctgcagca aggccgggaa 60
ctgctgcacc attggtgtgt tttaccttaa gggactccag gcagcttcct tgctgggaag 120
atattcattt gctggggtgg ggctgggggt gcagaggtag gaagtgctgt ggctagaagg 180
cggcctggcc agcgagtagg tggtggagcg agtgagagcg tgtgcgctgt aaacagtgtg 240
agtgcatg 248

<210> SEQ ID NO 429
<211> LENGTH: 930
<212> TYPE: DNA
<213> ORGANISM: Homo sapiens

<400> SEQUENCE: 429
aggcctcttc tgaggctcta ggtgccccag tagcagggcc ttctgcagca aggccgggaa 60
ctgctgcacc attggtgtgt tttaccttaa gggactccag gcagcttcct tgctgggaag 120
atattcattt gctggggtgg ggctgggggt gcagaggtag gaagtgctgt ggctagaagg 180
cggcctggcc agcgagtagg tggtggagcg agtgagagcg tgtgcgctgt aaacagtgtg 240
agtgcatgtg cgccagcgcg tgcaaggaca cggtaaggga tgtacatgta ttgtctcgtg 300
agtaagagct tgtgtgtgtg ttgggatggg aagacacgta ctggtatgag agcccgcgtg 360
agaagtgtat gtgtgagtac tcgcgtggaa gttttgcact cgggtttgag gctgtgcaaa 420
agtacgcatg gctcaccagg tgtggggctg tgtgggctgc ctcgtgtgtg ccagcccgtg 480
tgcaggcctg ttttgtgaga gccttcaggg aacgcatgag cacgtgtgcc agtgcgagtg 540
cgggacgcgg ggaggcggga gagaccgagt gggaggcccc gcgaaggagt gggagtggga 600
gtgggagtgc cggcgggaga cctgcggggg cgcgcccggg ctgacgcgtg cgcgccagtg 660
cgcgtgagtg cgggcgcgcg ccgccgcccc ccgccggggt cggagccggt tgccatggga 720
acgcgccgcg gcccgagtta atcatttcct gtggaaagtg tgcgggaggg gcgcgagcgg 780
gctggccgag gaggaggcgg cggcgtggag ctgcctcctg ccggcgggcc gggccgggcc 840
gagccccggg cgctgcggcg acgcctggat cctgcctccg ccaggccggc tgcctggtgc 900
cccgaggagg ctgctgagcc ccaggccatg 930

<210> SEQ ID NO 430
<211> LENGTH: 28
<212> TYPE: DNA
<213> ORGANISM: Homo sapiens

<400> SEQUENCE: 430
cctcctccgc gttccagaat ccaagatg 28

<210> SEQ ID NO 431
<211> LENGTH: 263
<212> TYPE: DNA
<213> ORGANISM: Homo sapiens

<400> SEQUENCE: 431
cgttctctcc cgcggaattc aggtttacgg ccctgcgggt tctcagaggc aagttcagac 60
cgtgttgttt tcttttcacg gatcctgccc tttcttcccg aaaagaagac agccttgggt 120
cgcgattgtg gggcttcgaa gagtccagca gtgggaattt ctagaatttg gaatcgagtg 180
cattttctga catttgagta cagtacccag gggttcttgg agaagaacct ggtcccagag 240
gagcttgact gaccataaaa atg 263

<210> SEQ ID NO 432
<211> LENGTH: 383
<212> TYPE: DNA
<213> ORGANISM: Homo sapiens

<400> SEQUENCE: 432
cttccttctg caacaggcgt gggtcacgct ctcgctcggt ctttctgccg ccatcttggt 60
tccgcgttcc ctgcacagta agtactttct gtgccgctac tgtctatccg cagccatccg 120
cctttctttc gggctaagcc gccccgggga ctgagagtta aggagagttg gaggctttac 180
tgggccacag ggttcctact cgcccctggg cctccggaca aaatggggtc tgcggttggt 240
gtcctggcaa aagcagggta gaagggctgc ggggcgggcc cagaatccga gcctgcagag 300
atgggagcag ttgcagtgtt gagggcggaa gaggagtgcg tcttgttttg ggaactgctt 360
cacaggatcc agaaaaggaa atg 383

<210> SEQ ID NO 433
<211> LENGTH: 181
<212> TYPE: DNA
<213> ORGANISM: Homo sapiens

<400> SEQUENCE: 433
cgcccttcgc cgctgagctc gcagcctccg gcgcccacct ccacctccag tgtcccgcct 60
cgggccgtcg ccctccagcg gctcgcgagc gtgggagacg tacctgggca ggcactgtcc 120
agcccaggcc caggcacagc cgtgaggggc gaggcacggg gacatcctgg cggccaccat 180
g 181

<210> SEQ ID NO 434
<211> LENGTH: 56
<212> TYPE: DNA
<213> ORGANISM: Homo sapiens

<400> SEQUENCE: 434
ccgcccctcc cgcaacgctc gaccccagga ttcccccggc tcgcctgccc gccatg 56

<210> SEQ ID NO 435
<211> LENGTH: 170
<212> TYPE: DNA
<213> ORGANISM: Homo sapiens

<400> SEQUENCE: 435
ccctcttctt tagactgcca cgaggaaaaa gcagatgtga gaactcaagg ttcagggctg 60
ctcttctaag aaacaagtct gccataatct ccatctgtgt tggaatctgt taactaatga 120
actggtctct gtgcaaatcc tgagtgctaa agcttccaac aagactgatg 170

<210> SEQ ID NO 436
<211> LENGTH: 96
<212> TYPE: DNA
<213> ORGANISM: Homo sapiens

<400> SEQUENCE: 436
cgctctctta cactcgggcc tcagaagtcc gtgccagtga ccggaggcgg cggcggcgag 60
cggttccttg tgggctagaa gaatcctgca aaaatg 96

<210> SEQ ID NO 437
<211> LENGTH: 517
<212> TYPE: DNA

<213> ORGANISM: Homo sapiens

<400> SEQUENCE: 437
agtccttctc attccttgcc cccgcccaag gctctcttca ccttccccgc gggggtcctc 60
tcgttttctg tctcccaaat gctggcttcc cgcctttcct cccccgctta tttacttaat 120
taaggccctg gggctgcacc ccaccggcag ctccttcggg ggtgtggccg aagagctccg 180
agggcggggc tgaccgagcc atattcgggc gtggccggtg gtgattggtg agggcggggc 240
ctgccgcagg gggcggggcc tgcaggtttg gcccccgcag ggagcgcagc tggcgccgct 300
gggagctggt ggcgcggcgc aggtcccggc cgagtgtggc gcagcagtgg cggcgcttcc 360
cattcgccat gcgccggggg tgggtgcccg aaggttgcat gatggaattt gaacattact 420
tcaagaggtt ttgtattttg gattagttaa ttgggtttgt cctctgctga ctgtttcttc 480
ggatgcattt tttggtgtgc tcttgaggga ttaaatg 517

<210> SEQ ID NO 438
<211> LENGTH: 203
<212> TYPE: DNA
<213> ORGANISM: Homo sapiens

<400> SEQUENCE: 438
cgtccttccg gctctcggct ttgccacaaa gcttcccgaa gacgcggccg ctacccggag 60
acgcggtcgc cacccagaag cgctctcccg ggaagccccg ctcgtgggac cgcgccacct 120
gcgccgcctc tgcggcccgc agcccgacgg gcgccgccat gttggggtcc tagcgaggga 180
cgcgtaggtg tcttcataag atg 203

<210> SEQ ID NO 439
<211> LENGTH: 444
<212> TYPE: DNA
<213> ORGANISM: Homo sapiens

<400> SEQUENCE: 439
cagtcctttt gcaagagctg ctaagagcgc tgggtaagga gaggaagggg agagacatgg 60
aacttggctg gtctgcaggg aaatgccact gttttggccg ggagtagggg gcgggagtgg 120
cgggagaggg ggtggccggc tggggaggag ccagcctggt ggagaagctg ccctgtgggc 180
gggggtgagg aggggagggc tgtggtcacc aggcaggaag gaggggtggc ctgacccctc 240
ggcagtccct cccctcagcc tttccccaaa ttgctacttc tctggggctc caggtcctgc 300
ttgtgctcag ctccagctca ctggctggcc accgagactt ctggacagga aactgcacca 360
tcctcttctc ccagcaaggg ggctccagag actgcccacc caggaagtct ggtggcctgg 420
ggatttggtg ggtctgctcc ttag 444

<210> SEQ ID NO 440
<211> LENGTH: 656
<212> TYPE: DNA
<213> ORGANISM: Homo sapiens

<400> SEQUENCE: 440
cctcctttct ccttccctct tgcctccagt gactgtctcc aggatttctc tcttcctatt 60
tcaggaggac tctcacaggc tcccacagcc tgtgttaagc tgaggtttcc cctagatctc 120
gtatatcccc aacacatacc tccacgcaca cacatcccca agaacctcga gctcacacca 180
acagacacac gcgcgcatac acactcgctc tcgcttgtcc atctccctcc cgggggagcc 240
ggcgcgcgct cccacctttg ccgcacactc cggcgagccg agcccgcagc gctccaggat 300
tctgcggctc ggaactcgga ttgcagctct gaacccccat ggtggttttt taaacacttc 360
ttttccttct cttcctcgtt ttgattgcac cgtttccatc tgggggctag aggagcaagg 420
cagcagcctt cccagccagc ccttgttggc ttgccatcgt ccatctggct tataaaagtt 480
tgctgagcgc agtccagagg gctgcgctgc tcgtcccctc ggctggcaga agggggtgac 540
gctgggcagc ggcgaggagc gcgccgctgc ctctggcggg ctttcggctt gaggggcaag 600
gtgaagagcg caccggccgt ggggtttacc gagctggatt tgtatgttgc accatg 656

<210> SEQ ID NO 441
<211> LENGTH: 80
<212> TYPE: DNA
<213> ORGANISM: Homo sapiens

<400> SEQUENCE: 441
cggccttctg ggcgcgcgcg acgtcagttt gagttctgtg ttctccccgc ccgtgtcccg 60
cccgacccgc gcccgcgatg 80

<210> SEQ ID NO 442
<211> LENGTH: 36
<212> TYPE: DNA
<213> ORGANISM: Homo sapiens

<400> SEQUENCE: 442
agttccttcc ccagaaggag agattcctct gccatg 36

<210> SEQ ID NO 443
<211> LENGTH: 309
<212> TYPE: DNA
<213> ORGANISM: Homo sapiens

<400> SEQUENCE: 443
ggctctttct gcgagcgggc gcgcgggcga gcggttgtgc ttgtgcttgt ggcgcgtggt 60
gcgggtttcg gcggcggctg aggaagaagc gcgggcggcg ccttcgggag gcgagcaggc 120
agcagttggc cgtgccgtag cagcgtcccg cgcgcggcgg gcagcggccc aggaggcgcg 180
tggcggcgct cggcctcgcg gcggcggcgg cggcagcggc ccagcagttg gcggcgagcg 240
cgtctgcgcc tgcgcggcgg gccccgcgcc cctcctcccc ccctgggcgc ccccggcggc 300
gtgtgaatg 309

<210> SEQ ID NO 444
<211> LENGTH: 121
<212> TYPE: DNA
<213> ORGANISM: Homo sapiens

<400> SEQUENCE: 444
cggccttcca tcccagtttc ttctaggaat tcggagcctc ccctgcagcg actcggaaga 60
ttcgaggcgg cgggggacaa gtcggcgccc cagagcggac gagtcaccag gtgtcaagat 120
g 121

<210> SEQ ID NO 445
<211> LENGTH: 54
<212> TYPE: DNA
<213> ORGANISM: Homo sapiens

<400> SEQUENCE: 445
ccgcctttct ccgctggcaa cggcgccgct ccccgctcct cctccccagc catg 54

<210> SEQ ID NO 446
<211> LENGTH: 49
<212> TYPE: DNA
<213> ORGANISM: Homo sapiens

<400> SEQUENCE: 446
ctcccttccc ttgcatgctg cattgtgtcg ggagttgctg acagccatg 49

<210> SEQ ID NO 447
<211> LENGTH: 210
<212> TYPE: DNA
<213> ORGANISM: Homo sapiens

<400> SEQUENCE: 447
ccgccttcct agtggagacg cgagtggggg aggagcagtc cgaggggaac gtgggttgaa 60
cgttgcaact agggtggaga tcaagctgga acaggagttc cgatcgaccc ggtaccaaga 120
aggggagtgc ccgcggcagg gttcattgaa aaaatcctta gtgatattga catgtctcaa 180
gtgacataaa ttagccaatg actcggaatg 210

<210> SEQ ID NO 448
<211> LENGTH: 63
<212> TYPE: DNA
<213> ORGANISM: Homo sapiens

<400> SEQUENCE: 448
tggcctttgt caagtcatcc cctcttctcc tcaggaactg ctcaaacctg tgccccaaag 60
atg 63

<210> SEQ ID NO 449
<211> LENGTH: 17
<212> TYPE: DNA
<213> ORGANISM: Homo sapiens

<400> SEQUENCE: 449
ggatctcttt cgccatg 17

<210> SEQ ID NO 450
<211> LENGTH: 104
<212> TYPE: DNA
<213> ORGANISM: Homo sapiens

<400> SEQUENCE: 450
ctgtctccct cggcctgtgc cgccgccgac gccgcttgtg ggcccgactc cgctctgtct 60
gcttcgccac cttctccccg agcactgccc ggccggccgc catg 104

<210> SEQ ID NO 451
<211> LENGTH: 134
<212> TYPE: DNA
<213> ORGANISM: Homo sapiens

<400> SEQUENCE: 451
catcctctct tccaccctct cttctccctg gtcaaccgct ctgcaaacaa ccatcaatct 60
gatcccacag gcctgagaaa gtctgctctc cagtacctgc tgctgatctg tttcagccga 120
caagaggcac catg 134

<210> SEQ ID NO 452
<211> LENGTH: 47
<212> TYPE: DNA
<213> ORGANISM: Homo sapiens

<400> SEQUENCE: 452
ctgcctttcg atctctccac atctcggtgg cgcgggatct caagatg 47

<210> SEQ ID NO 453
<211> LENGTH: 76
<212> TYPE: DNA
<213> ORGANISM: Homo sapiens

<400> SEQUENCE: 453
aatcctttct cctgccgcag tggagaggag cggccggagc gagacacttc gccgaggcac 60
agcagccggc aggatg 76

<210> SEQ ID NO 454
<211> LENGTH: 118
<212> TYPE: DNA
<213> ORGANISM: Homo sapiens

<400> SEQUENCE: 454 gagcctttc tcgctaacac cgctcgccct ctccgagtca gttccgcggt agaggtgacc 60
tgactctctg aggctcattt tgcagttgtt gaaattgtcc ccgcagtttt caatcatg 118

<210> SEQ ID NO 455
<211> LENGTH: 132
<212> TYPE: DNA
<213> ORGANISM: Homo sapiens

<400> SEQUENCE: 455
gtttctctat cagtcgcgca gctgtgttcg cggactcagg tggaaggaat ttcttctctt 60
cgttgacgtt gctggtgttc actgtttgga attagtcaag tttcgggaat caccgtcgct 120
gccatcaaca tg 132

<210> SEQ ID NO 456
<211> LENGTH: 72
<212> TYPE: DNA
<213> ORGANISM: Homo sapiens

<400> SEQUENCE: 456
ggttctctct ctccagaagg ttctgccggt tcccccagct ctgggtaccc ggctctgcat 60
cgcgtcgcca tg 72

<210> SEQ ID NO 457
<211> LENGTH: 56
<212> TYPE: DNA
<213> ORGANISM: Homo sapiens

<400> SEQUENCE: 457
caacctctcc tcttcgtctc cgccatcagc tcggcagtcg cgaagcagca accatg 56

<210> SEQ ID NO 458
<211> LENGTH: 34
<212> TYPE: DNA
<213> ORGANISM: Homo sapiens

<400> SEQUENCE: 458
ctttctcccg aacgccagcg ctgaggacac gatg 34

<210> SEQ ID NO 459
<211> LENGTH: 32
<212> TYPE: DNA

<213> ORGANISM: Homo sapiens

<400> SEQUENCE: 459
ctctctctgc accttccttc tgtcaataga tg 32

<210> SEQ ID NO 460
<211> LENGTH: 141
<212> TYPE: DNA
<213> ORGANISM: Homo sapiens

<400> SEQUENCE: 460
cggcctccat gtgcgacgtg ttctccttct gcgtgggcgt ggcgggccgc gcgcgggtct 60
ccgtggaagt ccgtttcgtg agcagcgcca aggtgaggtc ggggcgggtc ctgccgggag 120
cctctcccca gtccggccat g 141

<210> SEQ ID NO 461
<211> LENGTH: 84
<212> TYPE: DNA
<213> ORGANISM: Homo sapiens

<400> SEQUENCE: 461
ctgccttttt acagctagac ctgtgtgctg caaggagcta aggccttcag tgtccccttc 60
cttacccagg tttctcacag aatg 84

<210> SEQ ID NO 462
<211> LENGTH: 493
<212> TYPE: DNA
<213> ORGANISM: Homo sapiens

<400> SEQUENCE: 462
ccgccccttg caccgcccac gtggccagcg ccacctgcct cattgtgccc aggagttctc 60
caaacccgcg ctgcggagtg agtgaccaag ttccggccag ttcgacctcg aggatccaga 120
ggtggagacg gtactacctc ccagctctgt tttccatccc cttcaggtcc ttcctcggga 180
ggcggcgaag gcggtccacc ctgcgcgtga tcctttatgc ccggcccctg cccctccctc 240
cgggtggaac ttccccctca ccgccagact taagctgagg atcgttggat ctctggcggg 300
gtgcagaact gagcccaggc cacagtaccc tattcacgct ctgtgcttgt gccaaggttt 360
caagtgatcc tcccgcctca gcctgcccag gtgctgagat tacatgtatg agccactgca 420
cctggaaagg agccagaaat gtgaagtgct agctgaagga tgagcagcag ctagccaggc 480
aaagggggca atg 493

<210> SEQ ID NO 463
<211> LENGTH: 275
<212> TYPE: DNA
<213> ORGANISM: Homo sapiens

<400> SEQUENCE: 463
tgttcttccc ccacctgcca cgtacagagc ccaagttctc gctaggcttg ttgggtcagc 60
gcgattggcc ggggcccgcg cgagcctgcg agcgaggtgc ggcggtcgcg aagggcaacc 120
gagggggccg tgaccaccgc ctccccgcga cgccccagtc cagtggcctc gcgtccgccc 180
attcagcgga gacctgcgga gaggcggcgg ccgcggcctc cgcaagccgt ctttctctag 240
agttgtatat atagaacatc ctggagtcca ccatg 275

<210> SEQ ID NO 464
<211> LENGTH: 133

<212> TYPE: DNA
<213> ORGANISM: Homo sapiens

<400> SEQUENCE: 464
catccttctc aaaagactta ttgacagtgc caaagctcgg tactggacac aacgagggac 60
ctgggtctac gataacgcgc ttttgctcct cctgaagtgt ctttggtcca acgttgttcc 120
agagtgtacc atg 133

<210> SEQ ID NO 465
<211> LENGTH: 117
<212> TYPE: DNA
<213> ORGANISM: Homo sapiens

<400> SEQUENCE: 465
ttttctctct ctctttcact gcaaggcggc ggcaggagag gttgtggtgc tagtttctct 60
aagccatcca gtgccatcct cgtcgctgca gcgacacacg ctctcgccgc cgccatg 117

<210> SEQ ID NO 466
<211> LENGTH: 79
<212> TYPE: DNA
<213> ORGANISM: Homo sapiens

<400> SEQUENCE: 466
caccctctcg gggagggagt tggggaagct gggttggctg ggttggtagc tcctacctac 60
tgtgtggcaa gaaggtatg 79

<210> SEQ ID NO 467
<211> LENGTH: 96
<212> TYPE: DNA
<213> ORGANISM: Homo sapiens

<400> SEQUENCE: 467
tctccttcct gcgcgcgcgc ctgaagtcgg cgtgggcgtt tgaggaagct gggatacagc 60
atttaatgaa aaatttatgc ttaagaagta aaaatg 96

<210> SEQ ID NO 468
<211> LENGTH: 165
<212> TYPE: DNA
<213> ORGANISM: Homo sapiens

<400> SEQUENCE: 468
cagtctttcc tgctaagcct cagcgtctcc tccaagccac atcaaaatct ttccttctgg 60
gcctttccca gaagtgaatt cttgctggaa ggtataaaag accagctcct ccaagcagag 120
caactccctg gctgccgtga aaagacaagg cactgggcag tgatg 165

<210> SEQ ID NO 469
<211> LENGTH: 49
<212> TYPE: DNA
<213> ORGANISM: Homo sapiens

<400> SEQUENCE: 469
ctgcctttac aacagaggga gacgatggac tgagctgatc cgcaccatg 49

<210> SEQ ID NO 470
<211> LENGTH: 36
<212> TYPE: DNA
<213> ORGANISM: Homo sapiens

<400> SEQUENCE: 470
cgccctctgc ggtgaaggag agaccacact gccatg 36

<210> SEQ ID NO 471
<211> LENGTH: 192
<212> TYPE: DNA
<213> ORGANISM: Homo sapiens

<400> SEQUENCE: 471
aagcctcttt catcggggca cagacttcct tttacttctt ccttttgccc tctcgcctcc 60
tcctcctggg aagaagcgga ggcgccggcg gtcggccggg atagcaacag gccgggccac 120
tgaggcggtg cggaaagttt ctgtctggga gtgcggaact ggggccgggt tggtgtactg 180
ctcggagcaa tg 192

<210> SEQ ID NO 472
<211> LENGTH: 531
<212> TYPE: DNA
<213> ORGANISM: Homo sapiens

<400> SEQUENCE: 472
cgccctttat tcttgctcgg cctcgccaca gagagcaaat cagattggct gggcgacaac 60
ctcaaagggc ggggctgcac acgttcacta cgggaatgag gtagcggtgg agggggcagt 120
tgggcgggga taggccgtcc tagctaaggt ggtaaaggcc aataactctt caggctgcct 180
ctcctcgaaa agtcatcttc tcgcgaacct ttaaaatgcc ttcctcccca agcacctcaa 240
gggactagaa ctgagtgctt catttgtctt ttttcctcct tgcaaaagtc ccgtttgcca 300
ccatggggat gtaccaagtg agaccgagta gggggaacga gtggtgattg acgcgccagg 360
ttactggcca ctgctcacct aggcgctagc aaacttctgc caagatcgga actgagtact 420
aaacagcctc cacagttctc cctggtgccg tctccggctt ggcgccgcat cctcctctgg 480
gctcgcgatg gccgcgtccc ctcccgctgc ggacgggtcc tttggtacat g 531

<210> SEQ ID NO 473
<211> LENGTH: 167
<212> TYPE: DNA
<213> ORGANISM: Homo sapiens

<400> SEQUENCE: 473
ctgcctcttt ccggctgtga ccctcctcgc cgccgccgct tggctgcgtc ctccgactcc 60
ccgcgccgcc gagaccaggc tcccgctccg gttgcggccg caccgccctc cgcggccgcc 120
ccctggggat ccagcgagcg cggtcgtcct tggtggaagg aaccatg 167

<210> SEQ ID NO 474
<211> LENGTH: 122
<212> TYPE: DNA
<213> ORGANISM: Homo sapiens

<400> SEQUENCE: 474
aactcctttc cccctgctgt gacgtacagg tgaggtaaac agtactgaag tccagggcgt 60
cggtgctcac tgctctggca atgcccggtg agactgaatt atgtttaaat ttattgtaga 120
tg 122

<210> SEQ ID NO 475
<211> LENGTH: 62
<212> TYPE: DNA
<213> ORGANISM: Homo sapiens

<400> SEQUENCE: 475
ggctccttcc cagcccccgg cctagctctg cgaacggtga ctgcccatcc ttggccgcaa 60
tg 62

<210> SEQ ID NO 476
<211> LENGTH: 91
<212> TYPE: DNA
<213> ORGANISM: Homo sapiens

<400> SEQUENCE: 476 gaccctttc ccctccccgg gccacccagc ccgcccaact cccagcggag agcaaggttt 60
tcttctgttt tcatagccag ccagaacaat g 91

<210> SEQ ID NO 477
<211> LENGTH: 33
<212> TYPE: DNA
<213> ORGANISM: Homo sapiens

<400> SEQUENCE: 477
ttttcttttc ctctaggcag agaagaggcg atg 33

<210> SEQ ID NO 478
<211> LENGTH: 259
<212> TYPE: DNA
<213> ORGANISM: Homo sapiens

<400> SEQUENCE: 478
ctccctcttt gctctaacag acagcagcga ctttaggctg gataatagtc aaattcttac 60
ctcgctcttt cactgctagt aagatcagat tgcgtttctt tcagttactc ttcaatcgcc 120
agtttcttga tctgcttcta aaagaagaag tagagaagat aaatcctgtc ttcaatacct 180
ggaaggaaaa acaaaataac ctcaactccg ttttgaaaaa aacattccaa gaactttcat 240
cagagatttt acttagatg 259

<210> SEQ ID NO 479
<211> LENGTH: 22
<212> TYPE: DNA
<213> ORGANISM: Homo sapiens

<400> SEQUENCE: 479
gcttctcttt ctggtcaaaa tg 22

<210> SEQ ID NO 480
<211> LENGTH: 74
<212> TYPE: DNA
<213> ORGANISM: Homo sapiens

<400> SEQUENCE: 480
ccgccttttg tgctgcggcc gcggagcccc cgagggccca gtgttcacca tcataccagg 60
ggccagaggc gatg 74

<210> SEQ ID NO 481
<211> LENGTH: 75
<212> TYPE: DNA
<213> ORGANISM: Homo sapiens

<400> SEQUENCE: 481
tggtctcttc ggtctcctgc cgcccccggg aagcgcgctg cgctgccgag gcgagctaag 60
cgcccgctcg ccatg 75

<210> SEQ ID NO 482
<211> LENGTH: 192
<212> TYPE: DNA
<213> ORGANISM: Homo sapiens

<400> SEQUENCE: 482 cccccctctcc ctccctcctt gcgggccctc ctccccttcc ctcccctccg cccccttccc 60
cgtaggcagc ccgcccgcca gtccgcccgc accgcctcct tcccagcccc tagcgctccg 120
gctgggtctc tcccccgccc cccaggctcc cccggtcgct ctcctccggc ggtcgcccgc 180
gctcggtgga tg 192

<210> SEQ ID NO 483
<211> LENGTH: 470
<212> TYPE: DNA
<213> ORGANISM: Homo sapiens

<400> SEQUENCE: 483
tcgccttctg cccgggcgct cgcagccgag cgcggccggg gaagggctct cctcccagcg 60
ccgagcactg ggccctggca gacgccccaa gattgttgtg aggagtctag ccagttggtg 120
agcgctgtaa tctgaaccag ctgtgtccag actgaggccc catttgcatt gtttaacata 180
cttagaaaat gaagtgttca tttttaacat tcctcctcca attggtttaa tgctgaatta 240
ctgaagaggg ctaagcaaaa ccaggtgctt gcgctgaggg ctctgcagtg gctgggagga 300
ccccggcgct ctccccgtgt cctctccacg actcgctcgg cccctctgga ataaaacacc 360
cgcgagcccc gagggcccag aggaggccga cgtgcccgag ctcctccggg ggtcccgccc 420
gcgagctttc ttctcgcctt cgcatctcct cctcgcgcgt cttggacatg 470

<210> SEQ ID NO 484
<211> LENGTH: 42
<212> TYPE: DNA
<213> ORGANISM: Homo sapiens

<400> SEQUENCE: 484
cgctcttcct tccgcttgcg ctgtgagctg aggcggtgta tg 42

<210> SEQ ID NO 485
<211> LENGTH: 193
<212> TYPE: DNA
<213> ORGANISM: Homo sapiens

<400> SEQUENCE: 485
tcgtcttctc tgtcttaggg ctggtgctgg ccctgcccac gcctagggct ccggcgcgtc 60
acgggcctca gctgggattc ccgcgcccct cggacggcca cgagactcgg acatctttcc 120
aggaacagcg tgaggaggac agaagcaccc aacaggactg ctcaagccac ctgcgaacac 180
tgctgctacc atg 193

<210> SEQ ID NO 486
<211> LENGTH: 66
<212> TYPE: DNA
<213> ORGANISM: Homo sapiens

<400> SEQUENCE: 486
agttcccttt tccggtcggc gtggtcttgc gagtggagtg tccgctgtgc ccgggcctgc 60
accatg 66

<210> SEQ ID NO 487
<211> LENGTH: 36
<212> TYPE: DNA
<213> ORGANISM: Homo sapiens

<400> SEQUENCE: 487
cctcctcttg acgtggcaga ggcggcgcca gccatg 36

<210> SEQ ID NO 488
<211> LENGTH: 77
<212> TYPE: DNA
<213> ORGANISM: Homo sapiens

<400> SEQUENCE: 488
cgtcctcttt cctttccttc tccctcccct tttcccttcc ttcgtccctt ccttccttcc 60
tttcgccggg cgcgatg 77

<210> SEQ ID NO 489
<211> LENGTH: 110
<212> TYPE: DNA
<213> ORGANISM: Homo sapiens

<400> SEQUENCE: 489
ccgcccctcc cgctggatcc cgcagccgcg gctcttcccg acgcgttccg ccttccccag 60
ctgtgcactc tccatccagc tgtgcgctct cgtcgggagt cccagccatg 110

<210> SEQ ID NO 490
<211> LENGTH: 125
<212> TYPE: DNA
<213> ORGANISM: Homo sapiens

<400> SEQUENCE: 490
gcttctcttt cctttcgcgc cggttgccgc tgcggagcgc ggcgggtcca tgtgcgcagt 60
gagtggcgct attcctggcc cagtagcacc cgagccccgg gtttgaccga gtccgcgctg 120
cgatg 125

<210> SEQ ID NO 491
<211> LENGTH: 625
<212> TYPE: DNA
<213> ORGANISM: Homo sapiens

<400> SEQUENCE: 491
gctcctttgc gcacgcgcgc cgcttcccag tggcaagcgc gggcaggacc gcgttgcgtc 60
atcggggcgc gcgcctcaga gagagctgtg gttgccggaa gttgagcggc ggtaagtgag 120
ccgcggcggg cgagggtgta gtggggtctt gctgggccgg ttttggaggc ctggagtcaa 180
ggggcgagct cgccagggag ggcgagggtc acagcaagtc tcaggatcct cctctgccag 240
tttctgggtg gtccttcctc ctccagggac tcactgattc cggctggcgc ccttcgtctg 300
tagccgcgtc ccctcagact ggttcagtcc ggggtcttct gacttggaag ctcgtgctga 360
tttcctaagt cagcccctcc tgtcctcttg gtaggcagtg ctcagaatct tcagtgttgg 420
aacacgggag atgggacatt tggattccca gcctggctgt gtctggattt gctgtctctg 480
gcacgttcct tccccatcta agctgctttt ccatctgcaa aatgggaatg ataatccgcc 540
atttgtttaa gtgaggaggt taaataagtt tactttctga gaaagaagat tctcgattcc 600
ttggttacag ggttagaaac taatg 625

<210> SEQ ID NO 492

<211> LENGTH: 115
<212> TYPE: DNA
<213> ORGANISM: Homo sapiens

<400> SEQUENCE: 492
cgctcccttt gccgccgcct tagcccggga cccgaaccca gcctctcccc tacccgaaca 60
ccggccccgg ctccaccgag gcccgggtcc cccagcccgt ctcgccgccg ccatg 115

<210> SEQ ID NO 493
<211> LENGTH: 224
<212> TYPE: DNA
<213> ORGANISM: Homo sapiens

<400> SEQUENCE: 493 agccccctttt tccctccatg gtttctctcc gctcccgtga gtaacttggc tccgggggct 60
ccgctcgcct gcccgcacgc cgcccgccac ccaggaccgc gccgccggcc tccgccgcta 120
gcaaaccctt ccgacggccc tcgctgcgca agccgggacg cctctccccc ctccgccccc 180
gccgcggaaa gttaagtttg aagagggggg aagaggggaa catg 224

<210> SEQ ID NO 494
<211> LENGTH: 86
<212> TYPE: DNA
<213> ORGANISM: Homo sapiens

<400> SEQUENCE: 494
acttctcttt tccctagact gcagccagcg gagcccgcag ccggcccgag ccaggaaccc 60
aggtccggag cctcaacttc aggatg 86

<210> SEQ ID NO 495
<211> LENGTH: 145
<212> TYPE: DNA
<213> ORGANISM: Homo sapiens

<400> SEQUENCE: 495
cgctccctct gggcttccgt cctccgcccg cgcccgacgg agcctgttcg cgtcgactgc 60
ccagagtccg cgaatcctcc gctccgagcc cgtccggact cccccgatcc cagctttctc 120
tcctttgaaa acactaagaa taatg 145

<210> SEQ ID NO 496
<211> LENGTH: 159
<212> TYPE: DNA
<213> ORGANISM: Homo sapiens

<400> SEQUENCE: 496
aggccccctt ctccgcctcc gcctcctccc gacgccggcg ccgctttctg gaaggttcgt 60
gaaggcagtg agggcttacc gttattacac tgcggccggc cagaatccgg gtccatccgt 120
ccttcccgag ccaacccaga cacagcggag tttgccatg 159

<210> SEQ ID NO 497
<211> LENGTH: 38
<212> TYPE: DNA
<213> ORGANISM: Homo sapiens

<400> SEQUENCE: 497
gcttctttcc cgagcttgga acttcgttat ccgcgatg 38

<210> SEQ ID NO 498
<211> LENGTH: 69

<212> TYPE: DNA
<213> ORGANISM: Homo sapiens

<400> SEQUENCE: 498
acccctcttt tctagagttc tgcctcgctt cccggcgcgg tcgcagccct cagcccactt 60
aggataatg 69

<210> SEQ ID NO 499
<211> LENGTH: 55
<212> TYPE: DNA
<213> ORGANISM: Homo sapiens

<400> SEQUENCE: 499
ctcccttctg cctgggacgt cagcggacgg ggcgctcgcg ggccggggct gtatg 55

<210> SEQ ID NO 500
<211> LENGTH: 1300
<212> TYPE: DNA
<213> ORGANISM: Homo sapiens

<400> SEQUENCE: 500
aagccctttc cgaggatggc aaaggatctg ggaatgcttc tccaaagata tgtggatgga 60
cgaaataggt ctctggtgat actgaggcgg ggtggggacg gggaggcaaa gacttggctt 120
cttaggaatt ggaagaaata agtaaacaat gtttggtagc aatttgtaat aaggaagtaa 180
tcataaaatt aactacgtcc gtttctgatt gtgtcaactt tgtcaaggag tagaagttta 240
agaattgaat actgtcctgc aaacaacgta acctcatctc ctgtttgaca caccctgttg 300
agaagcagtc ctttacctcc taaatttctt tttcgaaatt atcatttcct ttatggactg 360
agaataacac tgcctgttca ctcccaccga gctgtgaaca gtgaccttaa ttcttccaag 420
cagggaagtg tagaaactaa ggtctgtgac agaccgcaaa atcatctccc aatctttaag 480
gaaaatcaga atcacgcata atcccataga gataaatttg atgcatagtc ttttcctatg 540
catacatttt tcctttttt ttacaataat tgaattttta tattttttca gcttgcttct 600
gtcacttaat atattatgag taattttttt tggttttttt tgttttggag acagaatctc 660
gcactgtcgc ccgggttgga gtgcagtggc gcgatctcgg ctcactgcaa cctctgcctc 720
ccggcttcaa gcgattctcc tgtctcagcc tccctagtag ctgggattac aggcacccgc 780
caccacgccc agctaatttt tttgtgtgtt tttagtagag aaggggtttc actatattgg 840
ccaggctggt ctcaaactcc tgacctcatg atacgcccac ctcggtctcc caaagtgcta 900
ggattacagg cctgagccac cgcgccagcc tattatgaat aattttctac atgaatacgc 960
atcgtactaa ataactttaa atgttggtgt agtatgccat tgtatgggta tggcatcatt 1020
tattgttaga cgttagattg tttccactaa gtcggtatta taaagagaac taatgacttc 1080
attattatta gctttttctt tctttggaca caatatccaa aaagaaattg ttgtttcaaa 1140
gatatgcaag atttttaagg ctttttgata tgtattgtca aattgccctc cagaaagaat 1200
acatgaattt acactcagca gctctgcttc cagcgtgaaa gactttctat tgtaccattt 1260
tggtgttttt tccctagctc tcagactccc cagtacaatg 1300

<210> SEQ ID NO 501
<211> LENGTH: 539
<212> TYPE: DNA
<213> ORGANISM: Homo sapiens

<400> SEQUENCE: 501
gtgtctcccg gtcgcgcgtg gaggtcggtc gctcagagct gctgggcgca gtttctccgc 60
ctgctgcttc ggcgcggctg tatcggcgag cgagcgagtt cccgcgagtt ctcggtggcg 120 ctccccccttc ctttcagtct ccacggactg gcccctcgtc cttctacttg accgctcccg 180
tcttccgccg ccttctggcg ctttccgttg ggccgattcc cgcccgcttc ctcctgcttc 240
ccatcgaagc tctagaaatg aatgtttcca tctcttcaga gatgaaccag attatgatgc 300
atcattatca cagaagaaat tcgtgtctat agcttttaag gacttgatta catcattttc 360
aagcctgata gttttggaat caccattaga gcttaagaca cacctgcctt catttcaacc 420
acctgtcttc ataccctgac gaagtgcacc ttttaacact cctttgtcct tggattactt 480
aagagttccc agaaatacat ttgccaccaa cagagtagcc aaatttataa ggaaaaatg 539

<210> SEQ ID NO 502
<211> LENGTH: 310
<212> TYPE: DNA
<213> ORGANISM: Homo sapiens

<400> SEQUENCE: 502
acccctcttt ttctccaaag gagtgcttgt ggagatcgga tcttttctcc agcaattggg 60
ggaaagaagg ctttttctct gaattcgctt agtgtaacca gcggcgtata ttttttaggc 120
gccttttcga aaacctagta gttaatattc atttgtttaa atcttatttt atttttaagc 180
tcaaactgct taagaatacc ttaattcctt aaagtgaaat aattttttgc aaaggggttt 240
cctcgatttg gagctttttt tttcttccac cgtcatttct aactcttaaa accaactcag 300
ttccatcatg 310

<210> SEQ ID NO 503
<211> LENGTH: 104
<212> TYPE: DNA
<213> ORGANISM: Homo sapiens

<400> SEQUENCE: 503
ttttcctttc ttagccaaat caccaaaatg tccagttaga acaagaattt agcattctgc 60
aaaagaagtt aacagctgag ataacgagga aatattctga aatg 104

<210> SEQ ID NO 504
<211> LENGTH: 134
<212> TYPE: DNA
<213> ORGANISM: Homo sapiens

<400> SEQUENCE: 504
ggttcttctg ggcgctaagg gagctgacgg agagggccac cgcccagcaa tagacggtgc 60
ctcagcctgc cgagccgcag tttccgtggt gtgagtgagt ccgggcccgt gtcccctctc 120
ccgccgccgc catg 134

<210> SEQ ID NO 505
<211> LENGTH: 296
<212> TYPE: DNA
<213> ORGANISM: Homo sapiens

<400> SEQUENCE: 505
cggcccttcg cagcgggcgc gctgtcagac ctcagtctgg cggctgcatt gctgggcgcg 60
ccgctctcgt ctgatccctg ctggggacgg ttgcccgggc aggatccttt acgatccctt 120
ctcggtttct ccgtcgtcac agggaataaa tctcgctcga aactcactgg accgctccta 180
gaaaggcgaa aagatattca ggagcccttc cattttcctt ccagtaggca ccgaacccag 240
cattttcggc aaccgctgct ggcagttttg ccaggtgttt gttaccttga aaaatg 296

<210> SEQ ID NO 506
<211> LENGTH: 231
<212> TYPE: DNA
<213> ORGANISM: Homo sapiens

<400> SEQUENCE: 506
cgctctctgg caagaggcaa gaggtagcaa cagcgagcgt gccggtcgct agtcgcgggt 60
ccccgagtga gcacgccagg gagcaggaga ccaaacgacg ggggtcggag tcagagtcgc 120
agtgggagtc cccggaccgg agcacgagcc tgagcgggag agcgccgctc gcacgcccgt 180
cgccacccgc gtacccggcg cagccagagc caccagcgca gcgctgccat g 231

<210> SEQ ID NO 507
<211> LENGTH: 152
<212> TYPE: DNA
<213> ORGANISM: Homo sapiens

<400> SEQUENCE: 507
gggtctttgt ctcgctgcag cgggtgctgc aggtctggcc ttcacttttc tgcgtcctct 60
tactcctaga ggcccagcct ctgtggcgct gtgatctggt tattgggaga ttcacagcta 120
agacgccagg atcccccgga agcctagaaa tg 152

<210> SEQ ID NO 508
<211> LENGTH: 150
<212> TYPE: DNA
<213> ORGANISM: Homo sapiens

<400> SEQUENCE: 508
ctttctttga cgcaagggct cgagacgcag ccgccgtcgg ccgagcgccc ggctagaagc 60
gacaccagac ggagcctccg gagttcctcc gcccccacct cgccgggtcc tggagccgca 120
gtcctcccag ctgccctcct cgtggccatg 150

<210> SEQ ID NO 509
<211> LENGTH: 608
<212> TYPE: DNA
<213> ORGANISM: Homo sapiens

<400> SEQUENCE: 509
ctgtcttttc tccagtttga gcgggggtgt cgggagcagg cggagagctt tcctgcgagg 60
ctgtggaagc agtgaacact cttctcagcg gctcgcctcc cagcagtgct attttttgcc 120
atccgccctc acccccagca cacgcgctcg cacacacacg cacgcacgca cacacacaca 180
cacacacact cacacagaga cctctctggg tttctttgcc ttgagtctcc cggggctgtg 240
agaagccagg cgcatctcaa accgagctgg cagctccagg ctccggagcc atgccctgca 300
cggaccctcg tctttaccac gctcctgagg aatgaaagga acccagggac cctcagaagg 360
cagcagtgat gcggaccaac cccccggagc ctgcaccctt ccgagggcca taggcgaccc 420
agggaactgg agagagctcc agaaaggaaa tcccagcttt cccaaagtcc ctgtggatgc 480
tgacaaaagg agacctgaat ttttggaaga gcctgtacta ggttacccgg ctgcagagtg 540
attttcccct ccggcactga ctctccccct ccaaccccca gccgtccaga gtaccatgaa 600
gaattatg 608

<210> SEQ ID NO 510

<211> LENGTH: 32
<212> TYPE: DNA
<213> ORGANISM: Homo sapiens

<400> SEQUENCE: 510
ttccctctcc gctgcgtccc cgcgcgaaga tg 32

<210> SEQ ID NO 511
<211> LENGTH: 56
<212> TYPE: DNA
<213> ORGANISM: Homo sapiens

<400> SEQUENCE: 511
cttcctccgc ggtcttccga gcggtcgcgt gaactgcttc ctgcaggctg gccatg 56

<210> SEQ ID NO 512
<211> LENGTH: 197
<212> TYPE: DNA
<213> ORGANISM: Homo sapiens

<400> SEQUENCE: 512
cgctctttcc gcgcggtgca ttctggggcc cgaggtcgag cccgccgctg ccgccgtcgc 60
ctgagggaag cgagaagagg ccgcgaccgg agagaaaaag cggagtcgcc accggagaga 120
agtcgactcc ctagcagcag ccgccgccag agaggcccgc ccaccagttc gcccgtcccc 180
ctgccccgtt cacaatg 197

<210> SEQ ID NO 513
<211> LENGTH: 1250
<212> TYPE: DNA
<213> ORGANISM: Homo sapiens

<400> SEQUENCE: 513
ttttcttcct ggtggcgttt gggcttaata cagctttggc gaggtcggat gacgggtggg 60
agccagcggt ggaaggggtg gcgaaagtac cggtttgccc caggccgccg aggggcctcc 120
ttagagagac cttgcctgct ccgctcgcgt ccgccggggc cgcgcgggtc ctcctggcgc 180
cgccaggttc aaaaagccac tcgagttgtc actgcgacgg ccctgggcca ggagccgttt 240
cgggatctgt caaacaacga gttttcgtcg ttcgaatcag gttgactggt ccttcatccc 300
cccaatctcc cgtacctggc gagtccagct cgtcgcggca atgctaagaa aagagtgata 360
tgcaagctga gaccaaaaat atggtatgat ttagccatac tgaaggggaa ggaaataaga 420
gctgggcaaa gcattctgtg aattggctga ctccacttct atggtgagag agaggagtgc 480
atcaaagatt actcccagta gagatggttt cagcatgttg gccagtctgg tctcagactc 540
ctgacctcaa gtgatccacc cacctcggcc tcccaaaatg ctgggattac aggtataagc 600
cactgtgcct ggccaaagat accgttaacc ctggataaag agaatggagg ttacctctgt 660
ccgtgtagat tcctaagctg tcctggagtg atccttggag taaaggaaag gtgctttgaa 720
gcacattcag ccatcagccc tgtgggatgg cagccactga tttgtcctat ggtctttaca 780
gggacccagt ctgccttcaa gaaaagacag aagtagaaag ggtggtggct gactgtctga 840
caaattgtta tcaggtatgc aggaagtata tccttctcca aaatatcata cttgcatcac 900
caggtagaca catttccttc tacacagaat tatcttcaga gcttcttaaa gcaaataaag 960
cctgcttcaa ggactgagtc cctagtcgaa ttcccggaag gagtggagcc tgtcatattg 1020
tgtttatcta gcatctgctc aagagtgtgc tgcagtggag ggaaatcaga tgacctccca 1080
gtctggttgt gttacataca atcatgtgta agaagtgcca ttcaagccgt gtcactggag 1140
gggactgaca gtgagattca gtgacttttg atgatctggc tgtggacttc accccagaag 1200
aatggacttt actggaccca actcagagaa acctctacag agatgtgatg 1250

<210> SEQ ID NO 514
<211> LENGTH: 36
<212> TYPE: DNA
<213> ORGANISM: Homo sapiens

<400> SEQUENCE: 514
gcttccctcc cggcgcagtc accggcgcgg tctatg 36

<210> SEQ ID NO 515
<211> LENGTH: 182
<212> TYPE: DNA
<213> ORGANISM: Homo sapiens

<400> SEQUENCE: 515
cttcctttct cgtgttgtta tcgggtagct gcctgctcag aacccacaaa gcctgcccct 60
catcccaggc agagagcaac ccagctcttt ccccagacac tgagagctgg tggtgcctgc 120
tgtcccaggg agagttgcat cgccctccac agagcaggct tgcatctgac tgacccacca 180
tg 182

<210> SEQ ID NO 516
<211> LENGTH: 336
<212> TYPE: DNA
<213> ORGANISM: Homo sapiens

<400> SEQUENCE: 516 cctcccccttt tgggtcggta gttcagcgcc ggcgccggtg tgcgagccgc ggcagagtga 60
ggcaggcaac ccgaggtgcg gagcgacctg cggaggctga gccccgcttt ctcccagggt 120
ttcttatcag ccagccgccg ctgtccccgg gggagtagga ggctcctgac aggccgcggc 180
tgtctgtgtg tccttctgag tgtcagagga acggccagac cccgcgggcc ggagcagaac 240
gcggccaggg cagaaagcgg cggcaggaga agcaggcagg gggccggagg acgcagaccg 300
agacccgagg cggaggcgga ccgcgagccg gccatg 336

<210> SEQ ID NO 517
<211> LENGTH: 857
<212> TYPE: DNA
<213> ORGANISM: Homo sapiens

<400> SEQUENCE: 517
tggtcctttc ttttatgatt cacaaggaat gaccctcttc atcgcctctc ctaattcagt 60
cctcacaaca gtcctttttac aaatgggaca acaggttaga ggaagtcagg cagatttcca 120
gcatcataga gagtaaagga ccagggaagg atcaggattc aaggactgca cccaggctct 180
gcttccagct tgctgtgtga ctttgggtaa ttttgttccc ttagggaact gagctttctc 240
atttgtaaat gcaaacaggc tgttgggagg atcaaatgag atccaggggt gaaaacagct 300
tagtttactt tcaggaattt acccacgcgg tatataaagg caaaatatta ttatagtcag 360
gtgattgtag attgaggaac ccatttcctc attctgcaaa ttgcaaacct gagggcccaa 420
agagggacag gggcttgccc caggtctcag caggctgtga gcaagagcta aagcctaatc 480
ctcctgcctt tgggcctgga gcccttcctt gtaccccagg ggtcagtgtc tttgttggat 540
acaggcttag attgactgac tgtaccctga gaacctaggg gagtccctgt tcccaattct 600
tctcctaccc ccaccttggc ctgatggagg aagaccctgc tgtgttgaga tgagcaccag 660
agccaagaag ctgaggagga tctggagaat tctggaggaa gaggagagtg ttgctggagc 720
tgtacagacc ctgcttctca ggtcccagga aggtggcgtc agcatctgca gccgcgtcga 780
cgttgtcgga gcctccgcgg aggacccagg agagccggac taggaccagg gccctgggcc 840
tccccacact ccccatg 857

<210> SEQ ID NO 518
<211> LENGTH: 54
<212> TYPE: DNA
<213> ORGANISM: Homo sapiens

<400> SEQUENCE: 518
ctttccttcg gcttccgttc ttggtccatg tgagagaagc tggctgctga aatg 54

<210> SEQ ID NO 519
<211> LENGTH: 67
<212> TYPE: DNA
<213> ORGANISM: Homo sapiens

<400> SEQUENCE: 519
ggttctctgt cagtcgcgag cgaacgacca agagggtgtt cgactgctag agccgagcga 60
agcgatg 67

<210> SEQ ID NO 520
<211> LENGTH: 96
<212> TYPE: DNA
<213> ORGANISM: Homo sapiens

<400> SEQUENCE: 520
ccgcctcttg tttttcccgc gaaactcggc ggctgagcgt ggaggttctt gtctcccctg 60
gtttgtgaag tgcggaaaac cagaggcgca gtcatg 96

<210> SEQ ID NO 521
<211> LENGTH: 114
<212> TYPE: DNA
<213> ORGANISM: Homo sapiens

<400> SEQUENCE: 521
tactctttat caatcgtctt ccggcgcagc cccgtccctg ttttttgtgc tcctccgagc 60
tcgctgttcg tccgggtttt ttacgtttta atttccagga cttgaactgc catg 114

<210> SEQ ID NO 522
<211> LENGTH: 219
<212> TYPE: DNA
<213> ORGANISM: Homo sapiens

<400> SEQUENCE: 522
ctccccctct cgctctcctc cctcttcccg gctccagctc cgccgccagc tccagccttt 60
gctccccctc ccaaagtccc ctccccggag cggagcgcac ctagggtccc tcttccgtcc 120
ccccagccca gctacccgtt cagaccagca gcctcggggg gcaccccccc gccagcctgc 180
ctccctcccg ctcagccctg ccagggttcc ccagccatg 219

<210> SEQ ID NO 523
<211> LENGTH: 146
<212> TYPE: DNA
<213> ORGANISM: Homo sapiens

<400> SEQUENCE: 523
agatcttctt ccgctctgag gcgctactga ggccgcggag ccggactgcg gttggggcgg 60
gaagagccgg ggccgtggct gacatggagc agccctgctg ctgaggccgc gccctccccg 120
ccctgaggtg ggggcccacc aggatg 146

<210> SEQ ID NO 524
<211> LENGTH: 304
<212> TYPE: DNA
<213> ORGANISM: Homo sapiens

<400> SEQUENCE: 524
cggcctcttt gtgtggtgcc cagataggg agcggaggtg gcggcggcgg cggtagcggt 60
ggccttggtt gtcttccagt ctcctcggct cgccctttag ccggcaccgc tccccttccc 120 tccccttcc tctcttcctt ccttccctcc ccttcccttt ttcccttccc cgtcggtgag 180
cggcgggggt ggctccagca acggctgggc ccaagctgtg tagaggcctt aaccaacgat 240
aacggcggcg acggcgaaac ctcggagctc gcagggcggg ggcaaggccc gggccttgga 300
gatg 304

<210> SEQ ID NO 525
<211> LENGTH: 737
<212> TYPE: DNA
<213> ORGANISM: Homo sapiens

<400> SEQUENCE: 525
ggctcttttg ttcggctgag gggagggccg ttggccgggg cctgcggtac gccgcttcag 60
tgagggacgc cactgcggcc acccggcttg ctgccttcct gggcgccact cccccaggcg 120
acccgacgcg acgcgccagc agcgcagcac cgattcctct cgggctcttg ggcgctgctc 180
tgaggtgagg agcccgctgg aggcgggaga gctgggggag ggggcgcggc ggcggcggcg 240
gcgggagccc tgcgtgaggg aacgcgcttt cgaggcggag gttaggagcg gggagcgcgc 300
ccgggtccag cgtcctgctt ctccgcttcc cgcgctgagc tcttcgcctg tcgctgaggc 360
gtcggtgcca gctgcgtgaa ggatggagag ggcggggcgc gaatcctgag ccagagactg 420
agtgcttggg ggtgggccga gcacttgggg gccgctcttc ggggcccggg tggtctggaa 480
caatgttgct tggctgggcg gctgcgggat agggcggaag gggacaggct tgaggcttgg 540
ataggcgtga ggaggcgcat acgaccgcac aacccgaggt ttgtaactgt attcggaaga 600
cgccgggtcc ggctgggact gccagaggaa cctggctttg caggactacg gaggagtaac 660
gtcgagtgaa ttggaagagg gcccagggcc gcacaagcag cgtcaccctt tacaccagaa 720
agctggcggg cactatg 737

<210> SEQ ID NO 526
<211> LENGTH: 204
<212> TYPE: DNA
<213> ORGANISM: Homo sapiens

<400> SEQUENCE: 526
cgcccttctt aggaggggct gcattgcagg gggagagtga actgacagac tcagtcactg 60
aagagggaaa aggagtgaga agacaaagcc gtcaaagccc caacagcttt gtatttctcc 120
agcccggcgc agaccccgga gctcccgagg cactccctcc atctttggaa cacgccagta 180
attgattgat aacaggaagc tatg 204

<210> SEQ ID NO 527

<211> LENGTH: 145
<212> TYPE: DNA
<213> ORGANISM: Homo sapiens

<400> SEQUENCE: 527
ttttctttct ttcctagagt ctctgaagcc acagatctct taagaacttt ctgtctccaa 60
accgtggctg ctcgataaat cagacagaac agttaatcct caatttaagc ctgatctaac 120
ccctagaaac agatatagaa caatg 145

<210> SEQ ID NO 528
<211> LENGTH: 592
<212> TYPE: DNA
<213> ORGANISM: Homo sapiens

<400> SEQUENCE: 528
acttcttcct cccttcccct ctcttcccct ccctccccag ccttccccgc gagcggacgc 60
ggcagcgcct ctgtctcgct ttttcttatt tttccccccct ttccccctttc ttttttttt 120 tttcttttct tttctcccct ccccccccttt caccatttcc cctcggaggc gctttccccg 180
ggcaggggca gagccggtct caccccccgc ctctccccgg cccccgccgc cctatggcga 240
gagggagccc cctcccaacc cgggctcgag cggcggcggc ctcaggccgg gggtcatcat 300
ggaactaatt cgctgaccga cccagcggcc gcagccgtgc gtcccgctcg agcgccagcg 360
cccgcgcccg cgccccccga tccgcttccc ctttctccct cctcagttgg ccgagtcgtc 420
ccgcgcgcac cgcctccgcg cgcctatgag aatgaggtgg taacgggccc ccggatgacc 480
ccgcgtcacc actgtgaggc ctacagctct gccggggagg aggaggagga ggaagaggag 540
gagaaggtag ctacagcaag ctgggtagca ggcagatcca aaggatatca tg 592

<210> SEQ ID NO 529
<211> LENGTH: 29
<212> TYPE: DNA
<213> ORGANISM: Homo sapiens

<400> SEQUENCE: 529
cattccctcg cgctctctcg ggcaacatg 29

<210> SEQ ID NO 530
<211> LENGTH: 71
<212> TYPE: DNA
<213> ORGANISM: Homo sapiens

<400> SEQUENCE: 530
gtctctttgt cctgccggca ctgaggactc atccatctgc acagctgggg cccctgggag 60
gagacgccat g 71

<210> SEQ ID NO 531
<211> LENGTH: 97
<212> TYPE: DNA
<213> ORGANISM: Homo sapiens

<400> SEQUENCE: 531
gggtctctcg gtcccgcagc cgtgaggagg acggtctgca tactcgctgc ccgccggctc 60
cctcccccgc gtccctgcga ccgccgcggc gaagatg 97

<210> SEQ ID NO 532
<211> LENGTH: 130
<212> TYPE: DNA
<213> ORGANISM: Homo sapiens

```
<400> SEQUENCE: 532

gggccctttt cgcggccggg ccccagcatg gctgccccca cggctgaggg cctggcagct    60

gctgcgccct cgctttcttg acattccctg gcttctgtgc tctcttcccc aggccacccc   120

agcagacatg                                                          130

<210> SEQ ID NO 533
<211> LENGTH: 26
<212> TYPE: DNA
<213> ORGANISM: Homo sapiens

<400> SEQUENCE: 533

ctgtctttct cagaaaacca aatatg                                         26

<210> SEQ ID NO 534
<211> LENGTH: 400
<212> TYPE: DNA
<213> ORGANISM: Homo sapiens

<400> SEQUENCE: 534

gtttctctgc agttttcctc agctttgggt ggtggccgct gccgggcatc ggcttccagt    60

ccgcggaggg cgaggcggcg tggacagcgg ccccggcacc cagcgccccg ccgcccgcaa   120

gccgcgcgcc cgtccgccgc gccccgagcc cgccgcttcc tatctcagcg ccctgccgcc   180

gccgccgcgg cccagcgagc ggccctgatg caggccatca agtgtgtggt ggtgggagac   240

ggaaacaaga atctcagtgt aacccgagca aaatcgcgcg tctcagcgtt gcttgtatag   300

agctgtaggt aaaacttgcc tactgatcag ttacacaacc aatgcatttc ctggagaata   360

tatccctact gtctttgaca attattctgc caatgttatg                         400

<210> SEQ ID NO 535
<211> LENGTH: 17
<212> TYPE: DNA
<213> ORGANISM: Homo sapiens

<400> SEQUENCE: 535

tcgtctcctc caagatg                                                   17

<210> SEQ ID NO 536
<211> LENGTH: 152
<212> TYPE: DNA
<213> ORGANISM: Homo sapiens

<400> SEQUENCE: 536

ccgcctttcc ttttgtttgt ctcacgtttt gcgtgggagg cggtcccggg atttcagggg    60

tctaccggct ctcttatggc gaatgcaacc cgaagagaga gtgagctgta tcttcagagt   120

tgtctccgtc tttccaagaa cagaacaaaa tg                                 152

<210> SEQ ID NO 537
<211> LENGTH: 40
<212> TYPE: DNA
<213> ORGANISM: Homo sapiens

<400> SEQUENCE: 537

gcctcctttc caagcgcgac ccgttgaggt ccttgtcatg                          40

<210> SEQ ID NO 538
<211> LENGTH: 152
<212> TYPE: DNA
```

<213> ORGANISM: Homo sapiens

<400> SEQUENCE: 538
ccgcctttcc ttttgttttt ctcaggtttt gcgtgggagg cggtcccggg atttcaaggg 60
tctacgcgct tttctatggc gaatgcaacc cgacgaggga gtgggctgta tcttcagagt 120
tgtctccgtc tttccaagaa cagaacaaaa tg 152

<210> SEQ ID NO 539
<211> LENGTH: 235
<212> TYPE: DNA
<213> ORGANISM: Homo sapiens

<400> SEQUENCE: 539
ctttcttttt cctttcttcg gaatgagaga ctcaaccata atagaaagaa tggagaacta 60
ttaaccacca ttcttcagtg ggctgtgatt ttcagagggg aatactaaga aatggttttc 120
catactggaa cccaaaggta aagacactca aggacagaca tttttggcag agctgctcac 180
tccttgctca gctcagtttt ctgtgcttgg accctctggg cccatcctgg ccatg 235

<210> SEQ ID NO 540
<211> LENGTH: 131
<212> TYPE: DNA
<213> ORGANISM: Homo sapiens

<400> SEQUENCE: 540
ctctttggga tgctttgttg tctggtggtg actgtgccca tgggtgagtt gtatcggaaa 60
atcgtcatgt gaggatcaga ggggaaaaga aaacagaggc ctctggtctc tgcctgccct 120
gggtgctcat g 131

<210> SEQ ID NO 541
<211> LENGTH: 137
<212> TYPE: DNA
<213> ORGANISM: Homo sapiens

<400> SEQUENCE: 541
acgcctcctc ttgcgctgtc ctgttaatgg cgggcagtag ccgctgaggg gattgcagat 60
aaccgcttcc cgcacgggga aagtctaccc tgcctgccac tttctgctcg ccgtcagcgc 120
cggagctcgc cagcatg 137

<210> SEQ ID NO 542
<211> LENGTH: 130
<212> TYPE: DNA
<213> ORGANISM: Homo sapiens

<400> SEQUENCE: 542
tgctctttct ctagcacggt cccactctgc agactcagtg ccttattcag tcttctctct 60
cgctctctcc gctgctgtag ccggaccctt tgccttcgcc actgctcagc gtctgcacat 120
ccctacaatg 130

<210> SEQ ID NO 543
<211> LENGTH: 323
<212> TYPE: DNA
<213> ORGANISM: Homo sapiens

<400> SEQUENCE: 543
caccctcttc cgccgctccc gcccagcgac ctcgctcccg gggcgacgcc ccgcgtgcgc 60
cagagtcgcc gaggtcgtcc ccggcaccgg aagtgaccct ggcgggtttg tcttcaaatt 120
ctcggcgagc aggagccgcg ccggcaggtg gtgttgacga ttgaactggg cagtactggg 180
gccgtgagcg gagagcaaag tgggctggac tgggtcaggc cctccttcct cgctgccggg 240
atctccactc cgccaatccc ctgtgcctgg cgttgggcgg tttcccgagg agcttgggcc 300
gccgcagctt acagttgaac atg 323

<210> SEQ ID NO 544
<211> LENGTH: 186
<212> TYPE: DNA
<213> ORGANISM: Homo sapiens

<400> SEQUENCE: 544
ctttctcttt ttcctttctt ccggatgaga ggctaagcca taatagaaag aatggagaat 60
tattgattga ccgtctttat tctgtgggct ctgattctcc aatgggaata ccaagggatg 120
gttttccata ctggaaccca aaggtaaaga cactcaagga cagacatttt tggcagagca 180
tagatg 186

<210> SEQ ID NO 545
<211> LENGTH: 100
<212> TYPE: DNA
<213> ORGANISM: Homo sapiens

<400> SEQUENCE: 545
cggcctttca tttccgcttc cggtgcgggc cgcgcgcgag cgcagcggtg ggaggcggcg 60
accagccggt tgaggcccca ggcttggcct caccacaatg 100

<210> SEQ ID NO 546
<211> LENGTH: 126
<212> TYPE: DNA
<213> ORGANISM: Homo sapiens

<400> SEQUENCE: 546
ctccctcctg gcgcttgtcc tcctctccca gtcggcacca cagcggtggc tgccgggcgt 60
ggtgtcggtg ggtcggttgg tttttgtctc accgttggtg tccgtgccgt tcagttgccc 120
gccatg 126

<210> SEQ ID NO 547
<211> LENGTH: 80
<212> TYPE: DNA
<213> ORGANISM: Homo sapiens

<400> SEQUENCE: 547
gcgtctctat cgcgccagtt cctcagcctc agtgctatga aggtgacagc gtgaggtgac 60
ccatctggcc cgccgcgatg 80

<210> SEQ ID NO 548
<211> LENGTH: 63
<212> TYPE: DNA
<213> ORGANISM: Homo sapiens

<400> SEQUENCE: 548
gggcctttgc ccgccttggc ggccggctct acgttccctg ttctcgcctg cagctccgcc 60
atg 63

<210> SEQ ID NO 549
<211> LENGTH: 309
<212> TYPE: DNA

<213> ORGANISM: Homo sapiens

<400> SEQUENCE: 549
gcttcccttc cgatgattcg gctcttctcg gctcagtctc agcgaagcgt ctgcgaccgt 60
cgtttgagtc gtcgctgccg ctgccgctgc cactgccact gccacctcgc ggatcaggag 120
ccagcgttgt tcgcccgacg cctcgctgcc ggtgggagga agcgagaggg aagccgcttg 180
cgggtttgtc gccgctgctc gcccaccgcc tggaagagcc gagccccggc ccagtcggtc 240
gcttgccacc gctcgtagcc gttacccgcg ggccgccaca gccgccggcc gggagaggcg 300
cgcgccatg 309

<210> SEQ ID NO 550
<211> LENGTH: 133
<212> TYPE: DNA
<213> ORGANISM: Homo sapiens

<400> SEQUENCE: 550
gggcctttgt cccgacagag ctccacttcc tgtccccgcg gctctgtgtc ccctgctagc 60
cgtaggtcgt gtgacccgca ggcaccggga gatccagaag tgaaacgcca ggctctctgg 120
aggccaggag atg 133

<210> SEQ ID NO 551
<211> LENGTH: 405
<212> TYPE: DNA
<213> ORGANISM: Homo sapiens

<400> SEQUENCE: 551
cagtctttcg cggcccggga gctcagcaga gctaccagct gccctgttgg cttcgctggt 60
cggatcgtcc tcctggcccc gccaaacagg cggggggagc ggccccgact gtggggccat 120
ggcagtagtc tcctcgttcg ccgccgccgc tagcctagct gagtcgccgg cttctgcgct 180
aggggctccc accgcctccg caggctaagg agccgctgcc accaacgagc tgtgagggtt 240
actatgctcc ctctttgccg ccgtctcctc ctcttgcccg cgcaggcacc cctctggctg 300
ctcagtcctg cctcagtgtc aaaccagaag agaagtaaaa ttcaacaaaa atttatgtgt 360
ggagttcctt cttaaaagaa gaaaaaagtg attatttaga ctatg 405

<210> SEQ ID NO 552
<211> LENGTH: 196
<212> TYPE: DNA
<213> ORGANISM: Homo sapiens

<400> SEQUENCE: 552
agccctcctt gctagtctgg gacttcccgg tggagtgagg aacccagcaa cacgctcctg 60
acttcccttc ccaaggactc gacctgagaa ggacacagca gtctctgaat ttcatgctct 120
cctctttgat gtgaagaaaa tgaaaagctg aacagttgtg gaactgtgga tagagttaga 180
caataaggcc gccatg 196

<210> SEQ ID NO 553
<211> LENGTH: 238
<212> TYPE: DNA
<213> ORGANISM: Homo sapiens

<400> SEQUENCE: 553
ccctccctcc ctttccctcc ctcgtcgact gttgcttgct ggtcgcagac tccctgaccc 60
ctccctcacc cctccctaac ctcggtgcca ccggattgcc cttcttttcc tgttgcccag 120
cccagcccta gtgtcagggc gggggcctgg agcagcccga ggcactgcag cagaagagag 180
aaaagacaac gacgaccctc agctcgccag tccggtcgct ggcttcgccg ccgccatg 238

<210> SEQ ID NO 554
<211> LENGTH: 166
<212> TYPE: DNA
<213> ORGANISM: Homo sapiens

<400> SEQUENCE: 554
ctttctttcc gtcgcagaga gcatcggccg gcgaccgttc cggcggccat tgcgaaaact 60
tccccacggc tactgcgtcc acgtggcggt ggcgtgggga ctccctgaaa gcagagcggc 120
agggcgcccg gaagtcgtga gtcgagtctt cccgggctaa tccatg 166

<210> SEQ ID NO 555
<211> LENGTH: 576
<212> TYPE: DNA
<213> ORGANISM: Homo sapiens

<400> SEQUENCE: 555
ctcccttccc cctccgcccc cggacggccg ctggggcgcg cgcctctcct cgcaccccca 60
ccctgagtcc ccacactccg cggggccacc gagctgctga ggcccctttg cgggcccgcc 120
gagcggttcc gggtttaggg ttcacaggtc agagttgact ccctgaaaag tgcagccggt 180
ttgaaatgca agatggcggc ggcgtggcgc tgagaggcgc ggcggcccct gcaggagaag 240
acagactgct gctttggacc tgttggtaat gatggcctga gctaaacatc taactagaag 300
ggataccctt ccatttcaaa gaacagaatg ctaaggaagc tgtggcaagt gattggagtt 360
gtgcttcaaa aatttcagaa attcagcagt attttatctg ccaacaataa gctctttact 420
tgattgcacc atgagaaagc tgctaatgag acttgttgag cacaaaaatg gacttgaaga 480
accaaaagcc attgttttca aatgaagaac actgaacagt tttaagcctc gatgcttttt 540
aatcaccact gagcttttcc tcataacatc agaatg 576

<210> SEQ ID NO 556
<211> LENGTH: 81
<212> TYPE: DNA
<213> ORGANISM: Homo sapiens

<400> SEQUENCE: 556
ccttccttcc ctccctcctt ccctcctgtc gccgtctctt ctggcgccgc tgctcccgga 60
ggagctcccg gcacggcgat g 81

<210> SEQ ID NO 557
<211> LENGTH: 180
<212> TYPE: DNA
<213> ORGANISM: Homo sapiens

<400> SEQUENCE: 557
ctttctctca ggatttccgc tggcttcagg ttccggtcag gcgtcgggac agagcctgat 60
ccaggcttcg gcggccggtg gcagctctcg atcagctctc gcagtcggag aggcggctaa 120
ggaaaggtgc cacagcagag acgcgaagga gaggccctag aaccttttca aagaagaatg 180

<210> SEQ ID NO 558
<211> LENGTH: 58
<212> TYPE: DNA
<213> ORGANISM: Homo sapiens

<400> SEQUENCE: 558
gagcctcttt ggtagcagga ggctggaaga aaggacagaa gtagctctgg ctgtgatg 58

<210> SEQ ID NO 559
<211> LENGTH: 132
<212> TYPE: DNA
<213> ORGANISM: Homo sapiens

<400> SEQUENCE: 559
tgccctttct ttcgccagcc ttacgggccc gaaccctcgt gtgaagggtg cagtacctaa 60
gccggagcgg ggtagaggcg ggccggcacc cccttctgac ctccagtgcc gccggcctca 120
agatcagaca tg 132

<210> SEQ ID NO 560
<211> LENGTH: 334
<212> TYPE: DNA
<213> ORGANISM: Homo sapiens

<400> SEQUENCE: 560
ctgccttttc tcctgccggg tagtttcgct ttcctgcgca gagtctgcgg aggggctcgg 60
ctgcaccggg gggatcgcgc ctggcagacc ccagaccgag cagaggcgac ccagcgcgct 120
cgggagaggc tgcaccgccg cgcccccgcc tagcccttcc ggatcctgcg cgcagaaaag 180
tttcatttgc tgtatgccat cctcgagagc tgtctaggtt aacgttcgca ctctgtgtat 240
ataacctcga cagtcttggc acctaacgtg ctgtgcgtag ctgctccttt ggttgaatcc 300
ccaggccctt gttggggcac aaggtggcag gatg 334

<210> SEQ ID NO 561
<211> LENGTH: 102
<212> TYPE: DNA
<213> ORGANISM: Homo sapiens

<400> SEQUENCE: 561
agctctctcg agtcactccg gcgcagtgtt gggactgtct gggtatcgga aagcaagcct 60
acgttgctca ctattacgta taatcctttt cttttcaaga tg 102

<210> SEQ ID NO 562
<211> LENGTH: 16
<212> TYPE: DNA
<213> ORGANISM: Homo sapiens

<400> SEQUENCE: 562
cgttctccgt aagatg 16

<210> SEQ ID NO 563
<211> LENGTH: 16
<212> TYPE: DNA
<213> ORGANISM: Homo sapiens

<400> SEQUENCE: 563
gcttctctgc actatg 16

<210> SEQ ID NO 564
<211> LENGTH: 140
<212> TYPE: DNA
<213> ORGANISM: Homo sapiens

<400> SEQUENCE: 564
cgctcttttc tcgggacggg agaggccgtg tagcgtcgcc gttactccga ggagatacca 60
gtcggtagag gagaagtcga ggttagaggg aactgggagg cactttgctg tctgcaatcg 120
aagttgaggg tgcaaaaatg 140

<210> SEQ ID NO 565
<211> LENGTH: 85
<212> TYPE: DNA
<213> ORGANISM: Homo sapiens

<400> SEQUENCE: 565
atttctttgt taagtcgttc cctctacaaa ggacttccta gtgggtgtga aaggcagcgg 60
tggccacaga ggcggcggag agatg 85

<210> SEQ ID NO 566
<211> LENGTH: 46
<212> TYPE: DNA
<213> ORGANISM: Homo sapiens

<400> SEQUENCE: 566
cggtctccgc cggttggggg gaagtaattc cggttgttgc accatg 46

<210> SEQ ID NO 567
<211> LENGTH: 42
<212> TYPE: DNA
<213> ORGANISM: Homo sapiens

<400> SEQUENCE: 567
cttcctcctc gcccccaccc agacccagaa ggcgccacca tg 42

<210> SEQ ID NO 568
<211> LENGTH: 81
<212> TYPE: DNA
<213> ORGANISM: Homo sapiens

<400> SEQUENCE: 568
cttccttcct agtcgcgggg agtctgagaa agcgcacctg ttccgcgacc gtcacgcacc 60
cctcctccgc ctgccgcgat g 81

<210> SEQ ID NO 569
<211> LENGTH: 50
<212> TYPE: DNA
<213> ORGANISM: Homo sapiens

<400> SEQUENCE: 569
ggttctctgt cccggttcct ggggttgcac agacagaccc tgtaaacatg 50

<210> SEQ ID NO 570
<211> LENGTH: 292
<212> TYPE: DNA
<213> ORGANISM: Homo sapiens

<400> SEQUENCE: 570
gggtccctcg ctggctagta ggagagactg gtgcttgccc cgcccggtgg actaactcgc 60
ttaattttaa ataaaaagtc gaggacacgg cggtcgtttt cccgaagaca tgggccctcc 120
catgggccat ttgctccctg gaggccctcg cgtcttgctg agcccgggga gttaggatga 180
cgcgagcggt gagggagccc ggaacgattc cttcgcggaa caattgaggc gaggcctttg 240
ggagtacttt gtgggacgga ccctggcggg ccctgccaga cgcacaggga tg 292

<210> SEQ ID NO 571

<211> LENGTH: 82
<212> TYPE: DNA
<213> ORGANISM: Homo sapiens

<400> SEQUENCE: 571
ccgccttccc aagagcccct gcggccgggc gcgaaaatgg cggcggcggc gacggccggg 60
cgctcctgaa gcagcagtta tg 82

<210> SEQ ID NO 572
<211> LENGTH: 87
<212> TYPE: DNA
<213> ORGANISM: Homo sapiens

<400> SEQUENCE: 572
cggccttcct gcagcctctt ccgctcgccg gctgcggcgc ctgggacggt tgcggtgggt 60
ctgggcgctg ggaagtcgtc caagatg 87

<210> SEQ ID NO 573
<211> LENGTH: 128
<212> TYPE: DNA
<213> ORGANISM: Homo sapiens

<400> SEQUENCE: 573
cggtctctgg cggagtcggg gaatcggatc aaggcgagag gatccggcag ggaaggagct 60
tcggggccgg gggttgggcc gcacatttac gtgcgcgaag cggagtggac cgggagctgg 120
tgacgatg 128

<210> SEQ ID NO 574
<211> LENGTH: 51
<212> TYPE: DNA
<213> ORGANISM: Homo sapiens

<400> SEQUENCE: 574
tctcctcttt ctccaccacc tcgggccccg gtgtccccgg ccagcactat g 51

<210> SEQ ID NO 575
<211> LENGTH: 338
<212> TYPE: DNA
<213> ORGANISM: Homo sapiens

<400> SEQUENCE: 575
tcttccttcc gggtcgcgct aggccgggct tgcggcggtt gtgccgcatc tagagagtcg 60
gggagccgcc cccgcaccca ggccttctcg cgctgcctgg tcgctggtga agcccgcggc 120
gcgcgcctct cccggaccct gcagggtaaa agaatgtcac atgtcagcat ttgtacctga 180
agtcagcatg caaagttcag ggtacctgga tgaatgccaa cttttgcatt tcccatgtgt 240
atcctgtgac cattctatct gggaacatcc ttcaaagagt tcatgcatct tactgaggac 300
acctgacctt ttgaagcttc ataattcaca tctagatg 338

<210> SEQ ID NO 576
<211> LENGTH: 248
<212> TYPE: DNA
<213> ORGANISM: Homo sapiens

<400> SEQUENCE: 576
gctccttcta gcatccttca tccttcaggt accagccatc cagacagtgc ttgagctgca 60
gaaactgaga ccagacctct ggcctggccc tccccagggg cctcctttcg tatagtcact 120
gcttctgcat cagatacttt cagctgcaac tccctactgg gtggggcacc catttcaggc 180
agaaggtttt ggtaccctcc actgacccta cacccagggc tgctactgcc gcttgtggct 240
tcaggatg 248

<210> SEQ ID NO 577
<211> LENGTH: 47
<212> TYPE: DNA
<213> ORGANISM: Homo sapiens

<400> SEQUENCE: 577
aggccttttg ttcctgtccc ggaaagccgg cgtcctgccg cgcgatg 47

<210> SEQ ID NO 578
<211> LENGTH: 232
<212> TYPE: DNA
<213> ORGANISM: Homo sapiens

<400> SEQUENCE: 578
cctcctcctc ctcttctcgc cattgcagtt ggacccagca gcccggcgcg caccgcgtgg 60
cttttggggg cagaccccgg cgggctgtgg caggagggcg gcggcggcgg ctgcggtcga 120
agaaggggac gccgacaaga gttgaagtat tgataacacc aaggaactct atcacaattt 180
gaaaagataa gcaaaagttt gatttccaga cactacagaa gaagtaaaaa tg 232

<210> SEQ ID NO 579
<211> LENGTH: 122
<212> TYPE: DNA
<213> ORGANISM: Homo sapiens

<400> SEQUENCE: 579
gtttcctctg ctctccgctc tcgcccgcta gctctcctcc cttccgctcc tgcttctctc 60
cgggtctccc gctccagctc cagccccacc cggccggtcc cgcacggctc cgggtagcca 120
tg 122

<210> SEQ ID NO 580
<211> LENGTH: 79
<212> TYPE: DNA
<213> ORGANISM: Homo sapiens

<400> SEQUENCE: 580
tgccctctgc cgctgctccc gtctctttgg ttacgctcgt cagccggtcg gccgccgcct 60
ccagccgtgt gccgctatg 79

<210> SEQ ID NO 581
<211> LENGTH: 160
<212> TYPE: DNA
<213> ORGANISM: Homo sapiens

<400> SEQUENCE: 581
ccgcctcttc cttcccgttg tttaaggcag ttggttgccc tcctgtccgt cagaggtgca 60
gtaccagagg tggcgtgctg ccgatttcgc gtttgccttg ctggatgatt ccgcttgttt 120
gccggctgcg tgagtgctta gagcttttcg gtggaagatg 160

<210> SEQ ID NO 582
<211> LENGTH: 34
<212> TYPE: DNA
<213> ORGANISM: Homo sapiens

<400> SEQUENCE: 582
ggctctctac cggtgagggt ttgcggggaa gatg 34

<210> SEQ ID NO 583
<211> LENGTH: 159
<212> TYPE: DNA
<213> ORGANISM: Homo sapiens

<400> SEQUENCE: 583
cagtctctgt gcgttgaagc cggagaccgc ggcggcctca gcgaggaccc tccgccccgg 60
agccgccggc cggagccgca gcctctgccg cagcgccccc gccacctgtc ccctccccct 120
ccgcctccgc cggagccgcc tcgtgcactc tggggtatg 159

<210> SEQ ID NO 584
<211> LENGTH: 216
<212> TYPE: DNA
<213> ORGANISM: Homo sapiens

<400> SEQUENCE: 584
gtgccttttt ccgccgcgcg ccaccagaat gtccctgtct tgaggtctaa tggcggacgc 60
cagtatgttg gagttggtgg tggcttaagt tttgaaggga ggtagcatcc gttggatatc 120
cacaccatcc ttctcgctgc aggctttctt ggactccgta ctgttggtgt aaccaaggcc 180
tggaggtctg ggtggctcag gtttcctgca gccatg 216

<210> SEQ ID NO 585
<211> LENGTH: 163
<212> TYPE: DNA
<213> ORGANISM: Homo sapiens

<400> SEQUENCE: 585
ctgcctctcg ctggaggcca ggccgtgcag catcgaagac aggaggaact ggagcctcat 60
tggccggccc ggggcgccgg cctcgggctt aaataggagc tccgggctct ggctgggacc 120
cgaccgctgc cggccgcgct cccgctgctc ctgccgggtg atg 163

<210> SEQ ID NO 586
<211> LENGTH: 702
<212> TYPE: DNA
<213> ORGANISM: Homo sapiens

<400> SEQUENCE: 586
ttttcttttc tgctttgcag gcccaggctc aaggcaaatt ataagtaggg aaccaatttg 60
agggaaagac atgtgaacag agttaaggta ccacgtcctg ggagcgacca gcagccccac 120
ctgaagtccg catgcaactc tgacaagctc aggtgcttgt tttaaggaaa ggggctacta 180
gagtcttacc aacagcgagc ccaggtggga gatgaaacag gtactcccca aaataggtca 240
tccgagggag gaaaactgat ggagagcaca atgtgctctg agcgttttta atgtttttaa 300
gcttttaaat gatttcttca aggccgagca gcagcagcaa aggtgtggct taaaggatta 360
agggggtttc tgctgacacc tagaatgaag ttactctatt actaatcaag ccgagaggag 420
gcccactatg cccccgttta tcatcctttc ccagttcctt tttgctggtc acaaaacgat 480
gctcatcaat cccacctaaa gcaggaggcc aggagcccag cctcttgtag aaacagcgag 540
ggtataactg ccctcccgtt ctgcccccaa gacgaaggag gactctcgga agccaagaaa 600
ggtttaagaa gtctttctgg atagagagca gtgcccaggc aggaagcctt tcgccggcag 660
agcggggtcc aaggacgagc tggagaggac agaggcgcga tg 702

<210> SEQ ID NO 587
<211> LENGTH: 40
<212> TYPE: DNA
<213> ORGANISM: Homo sapiens

<400> SEQUENCE: 587
attcctttcc ttcctagcct tggtcgtcgc cgccaccatg 40

<210> SEQ ID NO 588
<211> LENGTH: 88
<212> TYPE: DNA
<213> ORGANISM: Homo sapiens

<400> SEQUENCE: 588
ccacctcttc ctgttcccgt ccttgaggac gccgtgccgg gtcagtgtta gcctccagcc 60
ctggttgtgg aaggcgacag aagtcatg 88

<210> SEQ ID NO 589
<211> LENGTH: 249
<212> TYPE: DNA
<213> ORGANISM: Homo sapiens

<400> SEQUENCE: 589
ccccctcccc cgcggcgccg tctcctcctc ccgcctgagg cgagtctggg ctcagcctag 60
agctctccgg cggcggcgca gcttcagggc agcgcgggct gcagcggcgg cggcggttag 120
ggctgtgtag ggcgaggcct ccccccttcct cctcgccatc ctactcctcc ctcctcgtca 180
tcctccccct tcgtcctcct cgccttcctc ctcctcgtca ggctcgaccc agctgtgagc 240
ggcaagatg 249

<210> SEQ ID NO 590
<211> LENGTH: 326
<212> TYPE: DNA
<213> ORGANISM: Homo sapiens

<400> SEQUENCE: 590
cttccttcct cacttcctct gcaggaggga gcgagagtaa agctacgccc tggcgcgcag 60
tctccgcgtc acaggaactt cagcacccac agggcggaca gcgctcccct ctacctggag 120
acttgactcc cgcgcgcccc aaccctgctt atcccttgac cgtcgagtgt cagagatcct 180
gcagccgccc agtcccggcc cctctcccgc ccccacaccca ccctcctggc tcttcctgtt 240
tttactcctc cttttcattc ataacaaaag ctacagctcc aggagcccag cgccgggctg 300
tgacccaagc cgagcgtgga agaatg 326

<210> SEQ ID NO 591
<211> LENGTH: 69
<212> TYPE: DNA
<213> ORGANISM: Homo sapiens

<400> SEQUENCE: 591
cttccttccg tctcgctcgg agtttccctc tgcgttcgct ccgcgctgct ggaggctgtc 60
gtcccaatg 69

<210> SEQ ID NO 592
<211> LENGTH: 321
<212> TYPE: DNA
<213> ORGANISM: Homo sapiens

<400> SEQUENCE: 592
cctccttctg ttgcttcccg tctcctcggc ggctcccctc ccccgcccgg ctctccgcgc 60
cccttctggg cggcggggcg gcggagccgt cggcgtgcgg ccctccttgc gttcgtgcgt 120
gcgcccgtgg cccggcgcac gtcccgcgac accgaggccg agcggggcag ggggctgacc 180
gccatgaccc cccagagccc ggcgtgaggg ggccgagatg cggtgacctg ccagcacctg 240
ccgcagcctt cgtccgggag tcgccccatc tctccacgca tcggggccct gtgccccttg 300
ctgctgcagc cgggcaccat g 321

<210> SEQ ID NO 593
<211> LENGTH: 116
<212> TYPE: DNA
<213> ORGANISM: Homo sapiens

<400> SEQUENCE: 593
gtgtctctcg gcggagctgc tgtgcagtgg aacgcgctgg gccgcgggca gcgtcgcctc 60
acgcggagca gagctgagct gaagcgggac ccggagcccg agcagccgcc gccatg 116

<210> SEQ ID NO 594
<211> LENGTH: 96
<212> TYPE: DNA
<213> ORGANISM: Homo sapiens

<400> SEQUENCE: 594
cgttctctcc tccttcctcc ccgcctccag ctgccggcag gacctttctc tcgctgccgc 60
tgggaccccg tgtcatcgcc caggccgagc acgatg 96

<210> SEQ ID NO 595
<211> LENGTH: 55
<212> TYPE: DNA
<213> ORGANISM: Homo sapiens

<400> SEQUENCE: 595
aggcctctgt cccccacccc ctttccccgg tcccaggctc tccttcggaa agatg 55

<210> SEQ ID NO 596
<211> LENGTH: 274
<212> TYPE: DNA
<213> ORGANISM: Homo sapiens

<400> SEQUENCE: 596
cggccttttt ttcccggctg ggctcgggct cagctcgact gggctcggcg ggcggcggcg 60
gcggcgccgg cggctggcgg aggagggagg gcgagggcgg gcgcgggccg gcgggcgggc 120
ggaagaggga ggagaggcgc ggggagccag gcctcggggc ctcggagcaa ccacccgagc 180
agacggagta cacggagcag cggccccggc cccgccaacg ctgccgccgg ctactccctc 240
ttgatgccct cccctttgcc cctcactcag gatg 274

<210> SEQ ID NO 597
<211> LENGTH: 28
<212> TYPE: DNA
<213> ORGANISM: Homo sapiens

<400> SEQUENCE: 597
tcatcttttc cccagaggcg tcggaatg 28

<210> SEQ ID NO 598
<211> LENGTH: 444
<212> TYPE: DNA
<213> ORGANISM: Homo sapiens

<400> SEQUENCE: 598
aattctctct ctttggctcc ctccttccgc gcgagtctct ggagaagccg cagcgcgagt 60
tgccgccgct gctgcccggg gccgggtaag tgggcctcac tcagagcccg accctcttgg 120
ccccggcttg cgtcgacccc cgccgggcac cgagcctgcg ccgcgcgcgg cccgggcgtc 180
ggggccgcgc ccgaccggga aaggccggga agccggttgg gcccgatcct cctggcagct 240
agaacgggcc gggcggggga ggggggaacc gagcagagct tagggggtgg ggcctcggag 300
ccaggccatg tcggggctcc tcaagaagag ggccagtggg actgctgggg tcgggctgga 360
ggggatctga ttgggggaag cgtctgggga ctgcttgggg cctgattggg ggacgtcgcg 420
aggatcggct tgccttgcgc catg 444

<210> SEQ ID NO 599
<211> LENGTH: 31
<212> TYPE: DNA
<213> ORGANISM: Homo sapiens

<400> SEQUENCE: 599
gggcctttgc tgtgtgggat aaacagtaat g 31

<210> SEQ ID NO 600
<211> LENGTH: 81
<212> TYPE: DNA
<213> ORGANISM: Homo sapiens

<400> SEQUENCE: 600
ctgtctcttc gccggttccc ggccccgtgg atcctacttc tctgtcgccc gcggttcgcc 60
gccccgctcg ccgccgcgat g 81

<210> SEQ ID NO 601
<211> LENGTH: 362
<212> TYPE: DNA
<213> ORGANISM: Homo sapiens

<400> SEQUENCE: 601
cctccttttc ctgcccccag actagaggcg ggatgtagtc tcttaggcta agagtgattg 60
gtcacaagga gactcggaag tgtctgatca gagccccaga ggaggccttg agagcctgtt 120
ggcgtaccgt tccacacttg gatccaggaa tcgggcgtgt tccaggctgc tctctatggt 180
agctttgggc ggatagaggg ggcgcgcaaa gtattaaggg acaataatgg ccgctttcaa 240
ggtgtggatt ttggctcctt gagcctgtct gagcgagggg tggcagcgcc ggcgccccag 300
aatccgggac agaagggtcc caagagtcgc gcttggtgag agaaatccca gatcctgtga 360
tg 362

<210> SEQ ID NO 602
<211> LENGTH: 130
<212> TYPE: DNA
<213> ORGANISM: Homo sapiens

<400> SEQUENCE: 602
catcctctaa gcttttaaat attgcttcga tggtctgaat ttttatttcc agggaaaaag 60
agagttttgt cccacagtca gcaggccact agtttattaa cttccagtca ccttgatttt 120
tgctaaaatg 130

<210> SEQ ID NO 603

<211> LENGTH: 25
<212> TYPE: DNA
<213> ORGANISM: Homo sapiens

<400> SEQUENCE: 603
gctcccctct cacgcagcca acatg 25

<210> SEQ ID NO 604
<211> LENGTH: 163
<212> TYPE: DNA
<213> ORGANISM: Homo sapiens

<400> SEQUENCE: 604
catcctttta gcaccgcgag aggcgccggt gtttcgagcc gtggcaccgg catcggctga 60
cactgctgcc tccagctagt tatttcgtcc tcttccgttc ttcaccccta caccttggag 120
gtgaacttct cacctgaggg ctgtaaagac tcgtttgaaa atg 163

<210> SEQ ID NO 605
<211> LENGTH: 43
<212> TYPE: DNA
<213> ORGANISM: Homo sapiens

<400> SEQUENCE: 605
cgtccctcac cgcaccaccc ctaaagacgc tagcgctgcg atg 43

<210> SEQ ID NO 606
<211> LENGTH: 82
<212> TYPE: DNA
<213> ORGANISM: Homo sapiens

<400> SEQUENCE: 606
gggcctctgc attgcccgac tccgtaggag cgcgggggcg gctcctgctc ttcctggact 60
cctgagcaga gttgtcgaga tg 82

<210> SEQ ID NO 607
<211> LENGTH: 90
<212> TYPE: DNA
<213> ORGANISM: Homo sapiens

<400> SEQUENCE: 607
ccgcccttcc ttcttctccc agcattgccc cccccacgtt tcagcacagc gctggccgca 60
gtctgacagg aaagggacgg agccaagatg 90

<210> SEQ ID NO 608
<211> LENGTH: 101
<212> TYPE: DNA
<213> ORGANISM: Homo sapiens

<400> SEQUENCE: 608
ccatctttcc gtcccgggca gccagcgcca gtcggagcca gcgcgagccg ccgccgccat 60
cactgccgct gccaagtcct ccacccgctg cccccgccat g 101

<210> SEQ ID NO 609
<211> LENGTH: 59
<212> TYPE: DNA
<213> ORGANISM: Homo sapiens

<400> SEQUENCE: 609
gattctcttt ccgcccgctc catggcggtg gatgcctgac tggaagcccg agtgggatg 59

<210> SEQ ID NO 610
<211> LENGTH: 121
<212> TYPE: DNA
<213> ORGANISM: Homo sapiens

<400> SEQUENCE: 610
aactctttct tcggctcgcg agctgagagg agcaggtaga ggggcagagg cgggactgtc 60
gtctggggga gccgcccagg aggctcctca ggccgacccc agaccctggc tggccaggat 120
g 121

<210> SEQ ID NO 611
<211> LENGTH: 44
<212> TYPE: DNA
<213> ORGANISM: Homo sapiens

<400> SEQUENCE: 611
gcgccctttc ccctgccggt gtcctgctcg ccgtccccgc catg 44

<210> SEQ ID NO 612
<211> LENGTH: 154
<212> TYPE: DNA
<213> ORGANISM: Homo sapiens

<400> SEQUENCE: 612
ctccctcccc gcgccccgtc ctctcccgcc ctacaggccc tagcagggca ggcgggaggt 60
gagcgcggcc atcccgctcc cggagttccg ggatcctgga gtccgtagtt cgtggtcctt 120
cgccggtgtc cccggagccc agcggctgtg gatg 154

<210> SEQ ID NO 613
<211> LENGTH: 23
<212> TYPE: DNA
<213> ORGANISM: Homo sapiens

<400> SEQUENCE: 613
cctccctttc tcctgcagcc atg 23

<210> SEQ ID NO 614
<211> LENGTH: 146
<212> TYPE: DNA
<213> ORGANISM: Homo sapiens

<400> SEQUENCE: 614 cctcctttc tcccgccggc tctaacccgc gcttggctaa ggtccgcggg aacccgtgag 60
ccaccgagag agcagagaac tcggcgccgc caaacagccc agctcgcgct tcagcgtccc 120
ggcgccgtcg cgccactcct ccgatg 146

<210> SEQ ID NO 615
<211> LENGTH: 187
<212> TYPE: DNA
<213> ORGANISM: Homo sapiens

<400> SEQUENCE: 615
gcgtctcttt cgctccgtgt cccgctgctg ctcctgtgag cgcccggcga gtccgtcccg 60
tccaccgtcc gcagctggta gccagcctgc ccctcgcctc gactcccttt caccaacacc 120
gacacccaca ttgacacctc cagtccggcc agccgctcca ctcgttgcct ttgcatctcc 180
acacatg 187

<210> SEQ ID NO 616

<211> LENGTH: 683
<212> TYPE: DNA
<213> ORGANISM: Homo sapiens

<400> SEQUENCE: 616
cgccctcttt tggtcgcccc ctccccaacc cagcactaag gagcaccctg ctctggtctc 60
cgccaccacc cagcgcctcc tggacccatc cccccaaacc cttgaacgtc ctcaggaccc 120
ccaggtgagc gcggcgcgct gcgggcgggg accctctctg cacctccccg cacccctggg 180
ggtcgctctg tccctacggt ccccgcctcc cctttctcct ttctaagcgc ctcgcgccca 240
ggccgccgcc cggggtggcg cagcccgcag ccctcccgct ccgggcgccc tccgccgctc 300
cgagaccccc tgggggcgcg tcctctcccg ctcccctgtt ccctcccccg gctcagggcg 360
ggcgcgtggt cccaggggag gctcccgccc agccccgcac tcctttgtgc ggccgggcgg 420
gcgctgcgtc aaggtggagg cgcggccaca cgcgcgcacc cacccgcgcg cacccagccc 480
ccgggagagg caggaaggga ggcggcggcg cgaggaggag ggagcggccg tggagcccaa 540
tcgttcgctc cccttcccgg gtccgcgcgc ggcgccgcct ccgccattgc tgcgagcagg 600
agcaggagac gcggagctcg gagcgctcag ctgacctgcc ggagccgggc gtgggctgca 660
gcctcggagc tcccggaacg atg 683

<210> SEQ ID NO 617
<211> LENGTH: 152
<212> TYPE: DNA
<213> ORGANISM: Homo sapiens

<400> SEQUENCE: 617
acgtcctttc gatgttgcgt catgcagtgc gccggaggaa ctgtgctctt tgaggccgac 60
gctaggggcc cggaagggaa actgcgaggc gaaggtgacc ggggaccgag catttcagat 120
ctgctcggta gacctggtgc accaccacca tg 152

<210> SEQ ID NO 618
<211> LENGTH: 322
<212> TYPE: DNA
<213> ORGANISM: Homo sapiens

<400> SEQUENCE: 618
tttccttcct ctttcactcc gcgctcacgg cggcggccaa agcggcggcg acggcggcgc 60
gagaacgacc cggcggccag ttctcttcct cctgcgcacc tgccccgctc ggtcagtcag 120
tcggcggccg gcgcccggct tgtgctcaga cctcgcgctt gcggcgccca ggcccagcgg 180
ccgtagctag cgtctggcct gagaacctcg gcgctccggc ggcgcgggca ccacgagccg 240
agcctcgcag cggctccaga ggaggcaggc gagtgagcga gtccgagggg tggccggggc 300
aggtggtggc gccgcgaaga tg 322

<210> SEQ ID NO 619
<211> LENGTH: 154
<212> TYPE: DNA
<213> ORGANISM: Homo sapiens

<400> SEQUENCE: 619
cggtctcctc acttccggct tcgctgctct tggttctggt tctggaggct gggttgagag 60
gtcgccggtc cgactgtcct cggcggttgg tcagtgtgaa tttgtgacag ctgcagttgc 120
tccccgcccc cgagcagccg aggagtctac catg 154

<210> SEQ ID NO 620
<211> LENGTH: 449
<212> TYPE: DNA
<213> ORGANISM: Homo sapiens

<400> SEQUENCE: 620 ccgcccccttc ggcgccacca cgtgtgtccc tgcgcccggt ggccaccgac tcagtccctc 60
gccgaccagt ctgggcagcg gaggagggtg gttggcagtg gctggaagct tcgctatggg 120
aagttgttcc tttgctctct cgcgcccagt cctcctccct ggttctcctc agccgctgtc 180
ggaggagagc acccggagac gcgggctgca gtcgcggcgg cttctccccg cctgggcggc 240
cgcgccgctg ggcaggtgct gagcgcccct agagcctccc ttgccgcctc cctcctctgc 300
ccggccgcag cagtgcacat ggggtgttgg aggtagatgg gctcccggcc cgggaggcgg 360
cggtggatgc ggcgctgggc agaagcagcc gccgattcca gctgccccgc gcgccccggg 420
cgcccctgcg agtccccggt tcagccatg 449

<210> SEQ ID NO 621
<211> LENGTH: 444
<212> TYPE: DNA
<213> ORGANISM: Homo sapiens

<400> SEQUENCE: 621 cccccctcttc tgcagcagac ggactgagtt cctctaatcc ctgtgttcct tctcccccat 60
ctttctaaaa cccttctctg agagaggaat aactatagct tcagggataa tatagcttta 120
aggaaacttt tggcagatgt ggacgtcgta acatctgggc agtgttaaca gaatcccgga 180
ggccgggaca gaccaggagc cactcgttct aggaatgtta aagtagaagg ttttttccaa 240
ttgatgagag gagcagagag gaaggagaaa gaggaggaga gagaaaaagg gcacaaaata 300
ccataaaaca gatcccatat ttctgcttcc cctcactttt agaagttaat tgatggctga 360
cttctgaaag tcactttcct ttgccctggt acttcaggcc atatacatct tttcttgtct 420
ccataatcct ccctttcaag gatg 444

<210> SEQ ID NO 622
<211> LENGTH: 84
<212> TYPE: DNA
<213> ORGANISM: Homo sapiens

<400> SEQUENCE: 622
acctcccttt ctctgctcag ctccagcgtc atttcggcct cttagttctt ctgaaccctg 60
ctcctgagct aggtaggaaa catg 84

<210> SEQ ID NO 623
<211> LENGTH: 77
<212> TYPE: DNA
<213> ORGANISM: Homo sapiens

<400> SEQUENCE: 623
gggtctcttc cgcggaaact gacattgcgt ttccgttgtc ggcctcccac tgcaggagcc 60
atatattgaa gaccatg 77

<210> SEQ ID NO 624
<211> LENGTH: 371
<212> TYPE: DNA
<213> ORGANISM: Homo sapiens

<400> SEQUENCE: 624 ccacctttc ttgggcttgt aggaaggtgg acatgggctc ccggagacaa gacaagtgat 60
atgttgaact gttcggtggc tggaatcaac tgctcctgga gtgacctaag gccagtgttt 120
atcagaactt agccagggcc agccaagcag gcacagatgc tctgctatga aatgccacgc 180
aggcagagac tgacaagcgg taggaactga gctttcccct tggactgctg cttcctgctg 240
tgttcagggg agggggtcac tttctggcaa ctctgctgct gctgctgctg ctgctgctac 300
ttcagcttcc tctccactca aggtaagcag gctaagggag ggcaggctgc tagggaaagc 360
tttgtaccat g 371

<210> SEQ ID NO 625
<211> LENGTH: 49
<212> TYPE: DNA
<213> ORGANISM: Homo sapiens

<400> SEQUENCE: 625
tggcccctct tctcacatca gcgggtccag gcccaaccga cagactatg 49

<210> SEQ ID NO 626
<211> LENGTH: 206
<212> TYPE: DNA
<213> ORGANISM: Homo sapiens

<400> SEQUENCE: 626
cgtcctcccc gctccgggcc ccacccggct cagacggctc cggacgggac cgcgagcaca 60
ggccgctccg cgggcgcttc ggatcctcgc gggaccccac cctctcccag cctgcccagc 120
ccgctgcagc cgccagcgcg ccccgtcggc agctctccat ctgcacgtct ctccgtgaac 180
cccgtgagcg gtgtgcagcc accatg 206

<210> SEQ ID NO 627
<211> LENGTH: 387
<212> TYPE: DNA
<213> ORGANISM: Homo sapiens

<400> SEQUENCE: 627
cgccctcttc ttccagactc tcggtctgtc cgctgggggc gcgcgcggtg tgtggcaggc 60
ggcagcggcg ctggcggccg agtgcgcttg tcacgcgtgg cggtgcgtgg ttgctagggg 120
cgcctgaggc tgccgggtag cccagcaggc cgagggagga agtagcgtgg agccggtgcc 180
gagccggggc gaagctggat cccctagata gactgtcttc aagctcactg atattttcct 240
ctgcttgatc cattgtgctg ttgagagcct ctagtaaatt tttcagactg acagacttca 300
aggatgcagc tgctactacc ggaggtgtgt ggcaccttac ctcagcaagg ccatgagacc 360
gtgtggccat gatgtgggcc cctcatg 387

<210> SEQ ID NO 628
<211> LENGTH: 116
<212> TYPE: DNA
<213> ORGANISM: Homo sapiens

<400> SEQUENCE: 628
acctctccct cctcctggcg ttagttccgg tcgcagagga gacaccgccg cagttgccgg 60
tacatcgggg atttctggct ctttcctctt cgccttaaat tcgggtgtct tttatg 116

<210> SEQ ID NO 629
<211> LENGTH: 209
<212> TYPE: DNA
<213> ORGANISM: Homo sapiens

<400> SEQUENCE: 629
ttgccctttc tgtgtaagct gtgagcgtag gcggccctga gggggtgtgt tgcaggggtt 60
tccaagccca gcaccagcac ccttgccctt ttccatcagg ggttcagcct agggtccccg 120
ctggtgggcg gctcccgagt cttggagaag agcacgagaa cctagaccgc ccccgaagtg 180
cggagacccc ctgggcaggc tgaaagatg 209

<210> SEQ ID NO 630
<211> LENGTH: 197
<212> TYPE: DNA
<213> ORGANISM: Homo sapiens

<400> SEQUENCE: 630
ctgccctttg cctcctgggc ggagaagctg cttcctcctg ggaacaaccg cctcccgctc 60
ctagcaggtt gctactgccc cgaacccgcg ctgcagggaa cagcggggca aacagtgagt 120
ggggttcagc gtagactctg gaccaggaga ggcccgcggt gaccgaggcc tgggccccgg 180
aaaccaatag agccatg 197

<210> SEQ ID NO 631
<211> LENGTH: 434
<212> TYPE: DNA
<213> ORGANISM: Homo sapiens

<400> SEQUENCE: 631
agccctcttt caccccccc ccccggccat taccgaagcg gatgaaaaca aacactaacg 60
atggcggcgc cgggaagcga ccggctgctg ggcttaaggc gggagtgacc gcttaaccag 120
tgagggaagc actgaagagc gccagtcgac gtgggtgcga caactcgcgg agtcttagga 180
gcaaaacgtc tggggcctgc gagccaggac ccttctgaag ccttaggtgt ctatcggcga 240
cgtgtacggt cactgcagct ccggagcgcg gaaccctcag ccaggaggcg cggctggtcg 300
gtcccaggtc ccggcctccg taatgagagc ccggaaccac tctttgtgcc gcagcttcgc 360
agcatcttgg actcaagtga ttctcctgcc tcagcctcct gagtagctgg gactacagat 420
tcctataggc aatg 434

<210> SEQ ID NO 632
<211> LENGTH: 142
<212> TYPE: DNA
<213> ORGANISM: Homo sapiens

<400> SEQUENCE: 632
ccgccttccc acatcggatc gcagggctcc caaaatggcg agtgaggctg cggggactcg 60
ctgagcagcg gagggggagc gtgcagagcc gctgcggccc tcacagtccg gagcccggcc 120
gtgccgtgcc gtagggaaca tg 142

<210> SEQ ID NO 633
<211> LENGTH: 340
<212> TYPE: DNA
<213> ORGANISM: Homo sapiens

<400> SEQUENCE: 633
cgttctttct cccttctctg cctctctctc ctccacgctg ctttgatttc gctcttgcct 60
ctcttcttgc gctgctcagc tgggaacatc gtctcaccag gggcagcagc gacgcgctgc 120
acagccagac aggagctggc tgcggggcat ggaagcagcc tccttggcag ccgggagagg 180
agcaagcgca cgccactgcc cgtgacccag gcgtccggct gctgtcccct gccggggagc 240
tcatccacgc agaggtctct ccctgtcctc cctgcgagct tttcctctgc agagcccagt 300
ggagccagtc cccacaggag acaaccctga cgggagcatg 340

<210> SEQ ID NO 634
<211> LENGTH: 129
<212> TYPE: DNA
<213> ORGANISM: Homo sapiens

<400> SEQUENCE: 634
cggcctttct gtgttcctgg cccgcggccg tcgggtgtga gctgcgccga ccgctctgag 60
ggttcgtggc ccaccgctcc ttcgcggtcc ctgccgccac cgtccacgct cagcgttgta 120
gagaagatg 129

<210> SEQ ID NO 635
<211> LENGTH: 78
<212> TYPE: DNA
<213> ORGANISM: Homo sapiens

<400> SEQUENCE: 635
cggcctttct agccgctgtc ccaagggttg gtctcgcgct ttcggctgcg agctctctgt 60
ggtgctggca gcgacatg 78

<210> SEQ ID NO 636
<211> LENGTH: 188
<212> TYPE: DNA
<213> ORGANISM: Homo sapiens

<400> SEQUENCE: 636
ctccctcctt taaacagctt ctccgggtct cagcatgggc ttccagggca gcgattgagg 60
agaccttacc aaggagcacc acacagtaga tgctgagaca tcgtactcca ggataagaaa 120
cagtaacatg gcagcacctg cttgaaagaa attaaaaacc aacagactcc atttagaaag 180
gaacaatg 188

<210> SEQ ID NO 637
<211> LENGTH: 61
<212> TYPE: DNA
<213> ORGANISM: Homo sapiens

<400> SEQUENCE: 637
cctcctctcc ccttgcggcc tttctaacgt tggccctgct cttgtggcct cccgcagaat 60
g 61

<210> SEQ ID NO 638
<211> LENGTH: 256
<212> TYPE: DNA
<213> ORGANISM: Homo sapiens

<400> SEQUENCE: 638
cggtctttgc cgttaccgct atgtgtgggg cgtgtgtgga ataacgttat tgcccagcgg 60
agctgagggc cccggagctc gaccgcagcg gcagcgacga caacagcggc gacgacgacg 120
acgacgaggt ggggggagga cggcgtgcga gagactcacg ggacgcgacg cgccccgcct 180
cccccgtccg gtccctctct ccacggtaag gggatgacgt agctttgcca aagacttaga 240
agctaagcag aaaatg 256

<210> SEQ ID NO 639
<211> LENGTH: 327
<212> TYPE: DNA
<213> ORGANISM: Homo sapiens

<400> SEQUENCE: 639
aggcctctcg aggtccagac agccgcccag cccgctctgc gacgcagcag tgaatagtgt 60
ggtacctcct tgtctcggtt caggtccaga cctccccgtc ttccggctgc cctgaacgtc 120
aggcgacctc aggaccctgt gattggcgcc tgcgccggcg gaccgtgacc gaggaaaccc 180
ctggagggac ttgggcattc cttgggctcc gtgcctgttc ttcgtgctcc tttcgggcaa 240
ggatctcaca ttatcagtct ttgaccgaca cagaatgcct ggcatttgat aaatgtttgt 300
tgaacttgaa gagacatatg gacaatg 327

<210> SEQ ID NO 640
<211> LENGTH: 83
<212> TYPE: DNA
<213> ORGANISM: Homo sapiens

<400> SEQUENCE: 640
ttttcctttt catttcagcc tgactgccgg aatcagagcc gcgggtgaga tccccagccc 60
tgtgagcctg taggagtaga atg 83

<210> SEQ ID NO 641
<211> LENGTH: 472
<212> TYPE: DNA
<213> ORGANISM: Homo sapiens

<400> SEQUENCE: 641
ggttctttga gatgctgttt ggcgactcgt cgccattccc ggagcaggtc ggcctcggcc 60
caggggcgag tatccgttgc tgtgtcggag acactagtcc ccgacaccga gacagccagc 120
cctctcccct gcctcgcggc gggagagcgt gtccggccgg ccggccggcg gggctcgcgc 180
aacctccctc gcctcccctt cccccgcagc ctccgccccg ccaggcccgg cccggactcc 240
cgagccccgg cctcctcgtc ctcggtcgcc gctgccgccg ggcttaacag ccccgtccgc 300
cgcttctctt cctagtttga gaagccaagg aaggaaacag ggaaaaatgt cgccatgaag 360
gccgagaacc gctgccgccg ccgacccccg ccggccctga acgccatgag cctgggtccc 420
cgccgcgccc gctccgctcc gactgccgtc gccgccgagg cccccgttga tg 472

<210> SEQ ID NO 642
<211> LENGTH: 301
<212> TYPE: DNA
<213> ORGANISM: Homo sapiens

<400> SEQUENCE: 642
agcccttctt gattggaaga agcgcctcgg accccggtcc ttggcgccgt agtggttagg 60
ttgagcccta ggcgtggggg agaactgggg aaactggaat ttcccgcgga gctgacagcg 120
cttgcgctcc ccctactcgt tctaattcca cgcgctccaa aatatccgcc atggagaaat 180
cttggccagg atgtccattc taggcccatc ggtgctgtct tgctgaaggt tgggtcaggc 240
atctaaaggg actgtggtaa gggagggtgt gacacaggtg taagctgcca tcgtcatcat 300
g 301

<210> SEQ ID NO 643
<211> LENGTH: 51
<212> TYPE: DNA

<213> ORGANISM: Homo sapiens

<400> SEQUENCE: 643
gctcctctcc ggccgcgcag ccgctgccgc ccacccgcac ccgccgtcat g 51

<210> SEQ ID NO 644
<211> LENGTH: 116
<212> TYPE: DNA
<213> ORGANISM: Homo sapiens

<400> SEQUENCE: 644
gactctttcc tgtcccggcc tgcgtggtgt gggcttgtgg gtctttgaga cccgaaaatt 60
gagagcgttt tcgcactcca gcggctgctc ctggcggctc tgcggccgtc accatg 116

<210> SEQ ID NO 645
<211> LENGTH: 58
<212> TYPE: DNA
<213> ORGANISM: Homo sapiens

<400> SEQUENCE: 645
acgccttttg ctggaagagc gctgctgggg ttaggattct gcgcggcgag gcaagatg 58

<210> SEQ ID NO 646
<211> LENGTH: 267
<212> TYPE: DNA
<213> ORGANISM: Homo sapiens

<400> SEQUENCE: 646
cctcctctgc gagcgttatt tcaaaagaag ttgagaacca gagaaaccga cctaagggga 60
ttctcccatt tggcccgtcc taccctaaag tcaccacctg ctgcttttct ggagcgctta 120
ccagtgacca agaggaacag aacacagagc agcctggcag tgtccaagca acaagcctcc 180
gctcctcctt cctgcaccct ggggctcctg aaactcacat gggtaaaaaa gatacagtaa 240
agacataaat accacatttg acaaatg 267

<210> SEQ ID NO 647
<211> LENGTH: 358
<212> TYPE: DNA
<213> ORGANISM: Homo sapiens

<400> SEQUENCE: 647
ccgcctctcg agcgctgccg gtggccgcag cggcgcaccc acgccggccc ggaggagcag 60
agtgttcatt tctgtgtcgg gcacagtgct aagtgctggg tgctcactgg tgatgaggca 120
gatgaaggtt accaaacttg tggacaggag cctcatatca gagacgtgga cctcactgta 180
gcctggtcat ggcttccagc ttttcgaatc tgaggctcca aaggaggaaa tgaccattca 240
gggatcttac tccagcttga ttacggagac tgaaccttca tagggtgcgc acttaccaag 300
gacaggaagg tttctctgtt tgaagggctt taaacttata acaaagaaaa taaaaatg 358

<210> SEQ ID NO 648
<211> LENGTH: 181
<212> TYPE: DNA
<213> ORGANISM: Homo sapiens

<400> SEQUENCE: 648
ccgcctctca accatcaggt tcggcagccc gcggcgccgc ctggcagctc ctcctcttct 60
ccgccccgcc ggccgcgggc gcgggggacg tcagcgctgc cagcgtggaa ggagctgcgg 120
ggcgcgggag gaggaagtag agcccgggac cgccaggcca ccaccggccg cctcagccat 180
g 181

<210> SEQ ID NO 649
<211> LENGTH: 85
<212> TYPE: DNA
<213> ORGANISM: Homo sapiens

<400> SEQUENCE: 649
ccttcctttc tccctctgca gacacaacga gacacaaaaa gagaggcaac ccctagacca 60
ccgcgaagga cccatctgca ccatg 85

<210> SEQ ID NO 650
<211> LENGTH: 26
<212> TYPE: DNA
<213> ORGANISM: Homo sapiens

<400> SEQUENCE: 650
tgttcctttt ggtacgctcc aagatg 26

<210> SEQ ID NO 651
<211> LENGTH: 131
<212> TYPE: DNA
<213> ORGANISM: Homo sapiens

<400> SEQUENCE: 651
tcccctcctt ccagcgcctt tcggtggagc actgcggcac tcagcccgag ctgccgtttt 60
cccctcgcgg ggaacgctgt gacccccccg caggagcggc ggggcggggt ggggggcccc 120
gggagaagat g 131

<210> SEQ ID NO 652
<211> LENGTH: 96
<212> TYPE: DNA
<213> ORGANISM: Homo sapiens

<400> SEQUENCE: 652
gctcctttcc gtggtgtgta gccggcttgg cgtgaccctc gcctgatcca gttgttagag 60
ttggaagctt ggcagttggc ctcccttctt cccatg 96

<210> SEQ ID NO 653
<211> LENGTH: 291
<212> TYPE: DNA
<213> ORGANISM: Homo sapiens

<400> SEQUENCE: 653
cttcctttcc tagttgggtt ctgacagctc cgaggcagtg gtttacacaa ccaacacgaa 60
acatttctac gatccacccg attcctcccc tcattgatat tcaggaagca gctctccttc 120
ccctgccttc agctcaagtt tgctgagctt ttgtttcatt tgtgaatact tcttgctgga 180
agtccctcac ccagagacca gtgctcccaa cggcagagca gcgggggaga taaagaactg 240
gtgacacgtg gctgtacatt cagcacagct gtggtgtccc caagtgccat g 291

<210> SEQ ID NO 654
<211> LENGTH: 125
<212> TYPE: DNA
<213> ORGANISM: Homo sapiens

<400> SEQUENCE: 654
ctttcttttc cggattgggc atcccggcat ctgcacgtgg ttatgctgcc ggagtttggg 60

-continued ccgccactgt aggaaaagta acttcagctg cagccccaaa gcgagtgagc cgagccggag 120
ccatg 125

<210> SEQ ID NO 655
<211> LENGTH: 30
<212> TYPE: DNA
<213> ORGANISM: Homo sapiens

<400> SEQUENCE: 655
cgctctctgc tcgcgcttgg gctcgcgatg 30

<210> SEQ ID NO 656
<211> LENGTH: 29
<212> TYPE: DNA
<213> ORGANISM: Homo sapiens

<400> SEQUENCE: 656
gcgccttttc tgacgatgcg aacaacatg 29

<210> SEQ ID NO 657
<211> LENGTH: 78
<212> TYPE: DNA
<213> ORGANISM: Homo sapiens

<400> SEQUENCE: 657
ccgccttctg ccctcagcag cagacgctct gtcccgcccg ggcagctctg cgaggcagcg 60
gctggagagg gaaccatg 78

<210> SEQ ID NO 658
<211> LENGTH: 135
<212> TYPE: DNA
<213> ORGANISM: Homo sapiens

<400> SEQUENCE: 658
gcttctcctt tttgtgttcc ggccgatccc acctctcctc gaccctggac gtctaccttc 60
cggaggccca catcttgccc actccgcgcg cggggctagc gcgggtttca gcgacgggag 120
ccctcaaggg acatg 135

<210> SEQ ID NO 659
<211> LENGTH: 271
<212> TYPE: DNA
<213> ORGANISM: Homo sapiens

<400> SEQUENCE: 659
caccctcttg cccggtcccc gggagggccg gtccgctcct cccggacgcc gaggacctac 60
caccgcgact tcgccccgcc cggcgcgggc ccaggaccct gatgtcgctt ttgaacagcc 120
cctgcacctg gcagccagcg agctactgta gtaggcattg ccgactgttt gcataccgga 180
tgggagtgac agtgtaatag aaaaacaagc aagaaacctt ttaggtagga ctcctaaggc 240
tcagaggaag ttacctccag ccgctgccat g 271

<210> SEQ ID NO 660
<211> LENGTH: 209
<212> TYPE: DNA
<213> ORGANISM: Homo sapiens

<400> SEQUENCE: 660
ccttcccttt cccggctcaa gtccttcctc tctctttcct ttctttccgc ctatcttttt 60
tctgctgccg ctccgggtcc gggccatttt ccgggccggg cgcactaagg tgcgcggccc 120
cggggcccag tatatgaccc gccgtcctgc tatccttcgc ttcccccgcc ccatgtggct 180
gcggggccgc ggcggcgctg cccactatg 209

<210> SEQ ID NO 661
<211> LENGTH: 31
<212> TYPE: DNA
<213> ORGANISM: Homo sapiens

<400> SEQUENCE: 661
ccgcctttcg taagtccccc cgcctcgcat g 31

<210> SEQ ID NO 662
<211> LENGTH: 37
<212> TYPE: DNA
<213> ORGANISM: Homo sapiens

<400> SEQUENCE: 662
caacctcttc tctcccgctt ctctcgctgt gaagatg 37

<210> SEQ ID NO 663
<211> LENGTH: 272
<212> TYPE: DNA
<213> ORGANISM: Homo sapiens

<400> SEQUENCE: 663
ctcccttctg ctggaccttc cttcgtctct ccatctctcc ctcctttccc cgcgttctct 60
ttccaccttt ctcttcttcc caccttagac ctcccttcct gccctccttt cctgcccacc 120
gctgcttcct ggcccttctc cgaccccgct ctagcagcag acctcctggg gtctgtgggt 180
tgatctgtgg cccctgtgcc tccgtgtcct tttcgtctcc cttcctcccg actccgctcc 240
cggaccagcg gcctgaccct ggggaaagga tg 272

<210> SEQ ID NO 664
<211> LENGTH: 142
<212> TYPE: DNA
<213> ORGANISM: Homo sapiens

<400> SEQUENCE: 664
actcctctag ccggaacctg gggcccgga gccggggtag gcacagagtt gtcctcggag 60
gtccaggaca gcggccagcc cggcggcggg agtcagggcc acgccacctg cagggaagaa 120
cccgagtcga agcgggaaga tg 142

<210> SEQ ID NO 665
<211> LENGTH: 190
<212> TYPE: DNA
<213> ORGANISM: Homo sapiens

<400> SEQUENCE: 665
cttcctcttg cagttgaggc cggcgccgag ccggacttca ggcggatctc gtggcggagc 60
ccatcttgct ccctctccca ggcctttacc cgctccctag gattcccggg ccctgtaggt 120
gggagttggg agacgacagt actgctttta aagagacagt gttagggatc ttggaagcac 180
agccaacatg 190

<210> SEQ ID NO 666
<211> LENGTH: 84
<212> TYPE: DNA
<213> ORGANISM: Homo sapiens

<400> SEQUENCE: 666
gctcctttcc actcgggaaa ccttcagagg agtctcagaa aggacacggc tggctgcttt 60
tctcagcgcc gaagccgcgc catg 84

<210> SEQ ID NO 667
<211> LENGTH: 219
<212> TYPE: DNA
<213> ORGANISM: Homo sapiens

<400> SEQUENCE: 667
gcccctccct ctccgccccc accccctgtc ggcgtctggg cctcgtcccc ttctctctgt 60
ctcccttgcc tcccccatca cgtcccctga caccgacacc ccattgctcc cacagtctcc 120
ccagtctcca ctttggtccc cagcgctgtc tgcccgagga tttgcctgaa ggctgccccc 180
aactctgcac ccgcccccg agggccaccg aggaccatg 219

<210> SEQ ID NO 668
<211> LENGTH: 300
<212> TYPE: DNA
<213> ORGANISM: Homo sapiens

<400> SEQUENCE: 668
cacccttccc gaagtttttc tgtcacctgt gttaggctcc gtcccctttc cgcgttttat 60
ccccgtacca gaaaaggata catttagtgc ctcccaccca gctccactaa acgggttgga 120
tatctcattc tttgagttgg tgttccttcc ccggcgcccc catgtagctg ggaagtggga 180
cctgggggtg gttggacccc tgggatccta aaggaggggc agggagggcg cagaactccg 240
cttctgctcc ttgctaccag gacgcgcggc ctcctcagcc tctttcctcc cgctgccatg 300

<210> SEQ ID NO 669
<211> LENGTH: 133
<212> TYPE: DNA
<213> ORGANISM: Homo sapiens

<400> SEQUENCE: 669
cgttcttccg ggaaaatggc gactcccgct cgtgccccgg agtcaccgcc gtccgcggat 60
ccggcgctag tagcggggcc tgccgaggaa gccgagtgcc cgccgccgcg ccagcctcag 120
cccgcgcaga atg 133

<210> SEQ ID NO 670
<211> LENGTH: 226
<212> TYPE: DNA
<213> ORGANISM: Homo sapiens

<400> SEQUENCE: 670
tcgcctcttt ccgccagcgc ccgcaggacc cggatgagag cgcacgcttc ggggtctccg 60
ggaagtcgcg gcgccttcgg atgtggcgga tgcggccgtg agccggcggg ggaggtgctg 120
ctgctgcctc cactgtactc agacccaggt agcacaggat tgtccatcct ccagcagctc 180
agtgcaacgg tgtgaactca gcctgtttca gagcctccac accatg 226

<210> SEQ ID NO 671
<211> LENGTH: 126
<212> TYPE: DNA
<213> ORGANISM: Homo sapiens

<400> SEQUENCE: 671
cgatctctgc ggggcaagat ggcggcgccc agacaggcct ggagcacgga tgaataagag 60
ggaaccccca cacggagaca ctgctggaga gagtcgtact ggggaggcag ctggagcagc 120
aagatg 126

<210> SEQ ID NO 672
<211> LENGTH: 285
<212> TYPE: DNA
<213> ORGANISM: Homo sapiens

<400> SEQUENCE: 672
cctcctcttt ggtgcctcca gccaggaggc gggagcgatc cacagcagct gacccagctc 60
aggcactgcc tctctcacag ccctcaagac acaccatggg cccagaggca ggtttgctac 120
acagcagcga cgacgcaggc ggcggcccca gcgactcgca actgcctccc tgaccacagc 180
ggccaccgcc caacaccccc gagaagccat cgccaccacc ggcaggagaa cctagggtcc 240
ataaagccat cttcgcgatc gactaaagct acgtcaacaa ctatg 285

<210> SEQ ID NO 673
<211> LENGTH: 109
<212> TYPE: DNA
<213> ORGANISM: Homo sapiens

<400> SEQUENCE: 673
ccccctctct cggcccggcc atcttgtggg aagagctgaa gcaggcgctc ttggctcggc 60
gcggcccgct gcaatccgtg gaggaacgcg ccgccgagcc accatcatg 109

<210> SEQ ID NO 674
<211> LENGTH: 48
<212> TYPE: DNA
<213> ORGANISM: Homo sapiens

<400> SEQUENCE: 674 cacccttct gcgggggacg atttcgtcgg tggtaggctg ctaccatg 48

<210> SEQ ID NO 675
<211> LENGTH: 29
<212> TYPE: DNA
<213> ORGANISM: Homo sapiens

<400> SEQUENCE: 675
gcgcctcttc acgaggtgga aacaagatg 29

<210> SEQ ID NO 676
<211> LENGTH: 55
<212> TYPE: DNA
<213> ORGANISM: Homo sapiens

<400> SEQUENCE: 676
cttcctcttc ctgggcagcc tcgggacggg gcgccgcggc cgggcgggca gcatg 55

<210> SEQ ID NO 677
<211> LENGTH: 171
<212> TYPE: DNA
<213> ORGANISM: Homo sapiens

<400> SEQUENCE: 677
acttcctttg cctgctcacc gccagcgtag gtgctaccac cgctgccgtc gccgccgcca 60
ttttgatggc aggaagagtc cggttctggg acagctggag acagtggtgg tgactgaaat 120
aactttacca aaggaaagct attttgcgaa ctatcttctc cagcggagat g 171

<210> SEQ ID NO 678
<211> LENGTH: 21
<212> TYPE: DNA
<213> ORGANISM: Homo sapiens

<400> SEQUENCE: 678
agttcttcct ttgacaagat g 21

<210> SEQ ID NO 679
<211> LENGTH: 205
<212> TYPE: DNA
<213> ORGANISM: Homo sapiens

<400> SEQUENCE: 679
cagtcttctc gagcacatcg tcgcaaacgg ggccggaaag cgtggcagcg caggcgcaag 60
cgcagagagc ggaggcggtg gtggtggcgg ccgctggcca gttccttcag tgaatctaca 120
gacctatttt ctcaggagct cagcctggcc ttacttcagt gataaaagga ggaaaggctg 180
gctacagcaa acatcattca agatg 205

<210> SEQ ID NO 680
<211> LENGTH: 157
<212> TYPE: DNA
<213> ORGANISM: Homo sapiens

<400> SEQUENCE: 680
ctttcttctc gtcggtgttc ccggctgcta tagagccggg tgagagagcg agcgcccgtc 60
ggcgggtgtc gagggcgggt tgcctcgcgc tgacccttcc cgccctcctt ctcgtcacac 120
accaggtccc cgcggaagcc gcggtgtcgg cgccatg 157

<210> SEQ ID NO 681
<211> LENGTH: 749
<212> TYPE: DNA
<213> ORGANISM: Homo sapiens

<400> SEQUENCE: 681
ccgccttctc acactttcag gctctgatcg cggccgcagt ttttcctttt ttcttctgcc 60
gtcgccttct ctgcctcttc tcatcctttc tcgctctgct gctctgcagt gtgacgagtc 120
cgaatcctct tcccacccag cccgcgcctt tcttcttttg cctgcgctgt tctatttctc 180
cttcggccgc cgccgccact gctgcacaca gctggtgtcg gtgccgcgct tttacccccca 240 agtcgttccc gcagcctatg gcccaggccg ccttgggtat ttctgctcaa ggtaaccaca 300
tccctcttta aaaattccgc cgaaaaagag aagacgcttt acccgactct ttgggccgtt 360
atctcacggc gaactttctg accaagtata caactaccca gagggcctag gagaagtgct 420
gtatagagag cagttcgact tcaacgctga gccaccttgg gaacctagct gatgataggg 480
gggttccatc tcccaacttg tccatggagg tcttcacttc agaaatccaa gactcatatt 540
catccagctt ggtgtcaagt gggctgttgc tgccagaatt atcttgtgat tatttgagag 600
atgtatcagt ttcttctgaa gtacaatcaa ctgtagaagc ctttgtagca gtttgttgca 660
tattctaagg acccagacat aggcttggtg gcccgtctct tgtctttcct ggtttatgac 720
tttcggcttt gtggaatacg gctgagatg 749

<210> SEQ ID NO 682
<211> LENGTH: 55
<212> TYPE: DNA
<213> ORGANISM: Homo sapiens

<400> SEQUENCE: 682
gcctcttctt cttccgccct ggcagggtct ccgcagaaga tttgttgccg tcatg 55

<210> SEQ ID NO 683
<211> LENGTH: 44
<212> TYPE: DNA
<213> ORGANISM: Homo sapiens

<400> SEQUENCE: 683
gcgcctctcc agcctccgca ggcccaaccg ccgccagcac catg 44

<210> SEQ ID NO 684
<211> LENGTH: 69
<212> TYPE: DNA
<213> ORGANISM: Homo sapiens

<400> SEQUENCE: 684
tttcctcttt tgtgctgatt cctgaggact aggaaggtgc cccgaaaaga attcagagac 60
ctgacaatg 69

<210> SEQ ID NO 685
<211> LENGTH: 541
<212> TYPE: DNA
<213> ORGANISM: Homo sapiens

<400> SEQUENCE: 685
ctctcttttc tggagttaga ttagtctgaa gccgccacca gccccaggcc cccgtgcaga 60
agaaaagcgg gagggaacgg cggaggccgc cgctgccctg caccgccctc ctggaggcca 120
cttggagagt ccggccccga ggaggccatg gccacaagtg cccacagctg gccccaggtt 180
gccagcgtcg ctacagccca gaccaaggca gaataatctc cggatgagct ggtggcaccg 240
ctgagccttt ggtctcacca gggcttcctg ttgctggcag gcggggtgga gcggagctgc 300
tgggaggctg ctggatagga gaggggtcac ggctgcggaa gaggaggttc ttcgggacac 360
ccgtggatgg acacggcaag gaaacaccag gccaaccaca gctggggata aaatagcaca 420
accacaccct gccgtccagc gcctcccagc ctgtgcccct tcctagtacc accagcaacc 480
atcaatcccg tctcctcctg cctcctctcc tgcaatccac cccgccacga ctatcgccat 540
g 541

<210> SEQ ID NO 686
<211> LENGTH: 126
<212> TYPE: DNA
<213> ORGANISM: Homo sapiens

<400> SEQUENCE: 686
tcttctctgt ggcggagaca gccaggttgg cagctgacgg gacagccggg gtctattttg 60
ttgcgggttt tcagcaaatc cagggctggt ctggaggcgc gaaaacttaa ggcatacaga 120
acgatg 126

<210> SEQ ID NO 687
<211> LENGTH: 286
<212> TYPE: DNA
<213> ORGANISM: Homo sapiens

<400> SEQUENCE: 687
gcgcctctgt cattctactg cggccgccct ggcttccttc tacctgtgcg gccctcaacg 60
tctccttggt gcgggacccg cttcactttc ggctcccgga gtctccctcc actgctcaga 120
cctctggacc tgacaggaga cgcctacttg gctctgacgc ggcgccccag cccggctgtg 180
tccccggcgc cccggaccac cctccctgcc ggctttgggt gcgttgtggg gtcccgagga 240
ttcgcgagat ttgttgaaag acattcaaga ttacgaagtt tagatg 286

<210> SEQ ID NO 688
<211> LENGTH: 132
<212> TYPE: DNA
<213> ORGANISM: Homo sapiens

<400> SEQUENCE: 688
gggccttttc tctgcacgga gccggcgctt ttgcagttgc ttctgcggaa aggtggtagt 60
taagaatttg taaaggccag agaactacct acgattctct cagcggtctc tcttctcctc 120
aagtttgaaa tg 132

<210> SEQ ID NO 689
<211> LENGTH: 137
<212> TYPE: DNA
<213> ORGANISM: Homo sapiens

<400> SEQUENCE: 689
cctcctccct ccttccgtcc tccgcgcctt ccgtcggtcg gtccttgctt cctgcttcgc 60
ctccgcgcct cgcgctatgg gacagagccc ccgatccgcc agcaccacct gaggatccag 120
aaaccgcccc agcgatg 137

<210> SEQ ID NO 690
<211> LENGTH: 133
<212> TYPE: DNA
<213> ORGANISM: Homo sapiens

<400> SEQUENCE: 690
ctgtcctttc agcaccacaa gctcgggctg aggagggagg actcctggcc gtcctcctcc 60
tcttcaaatt ggcttgaatc ttctctgacc ccccacgagt gcagcacagt ctgggaagaa 120
aggcgtaagg atg 133

<210> SEQ ID NO 691
<211> LENGTH: 218
<212> TYPE: DNA
<213> ORGANISM: Homo sapiens

<400> SEQUENCE: 691
gcgccccttc cggcgcgggg agggcgctga agatcggggc cgctcggccg caggccgcct 60
ccagcgccgc gggatgtagc gcgggggacc gcggccccca gcagagcccg cctgcccggc 120
ttgtctacca tcagagggag atctctgccc cctggggctg agagacccca acctttcccc 180
aagctgaagc tgcagggtat tgaggtacca gccagatg 218

<210> SEQ ID NO 692
<211> LENGTH: 325
<212> TYPE: DNA
<213> ORGANISM: Homo sapiens

<400> SEQUENCE: 692
ttttcccttg ggacccgggt ccacacggcg gggtcgcccg tccatctccg gctcgcccgc 60
ggggcccatc gtcgacgtta gcggccgttc tccgagccga ctgacccatc cttggcgctg 120
ccgccgcgcg cttgttctcc tccctcgccc cgccttcatc ctccccgttc acggaaacga 180
cagctgcggc tgcggggctg gcgccgcctc cctccaccta ccacgtctgc cctcgccgct 240
ctagccctgc gccccagccc ggccgcggca cctccgcctc gccgccgcta ggtcggccgg 300
ctccgcccgg ctgccgccta ggatg 325

<210> SEQ ID NO 693
<211> LENGTH: 214
<212> TYPE: DNA
<213> ORGANISM: Homo sapiens

<400> SEQUENCE: 693
gtcccctctt cggcttccgt agaggaagtg gcgcggacct tcatttgggg tttcggttcc 60 ccccttccc cttccccggg gtctgggggt gacattgcac cgcgcccctc gtggggtcgc 120
gttgccaccc cacgcggact ccccagctgg cgcgcccctc ccatttgcct gtcctggtca 180 ggccccacc ccccttccca cctgaccagc catg 214

<210> SEQ ID NO 694
<211> LENGTH: 53
<212> TYPE: DNA
<213> ORGANISM: Homo sapiens

<400> SEQUENCE: 694
ctgcctttcc cgggcgctga ttcctgagtg ctgagcgcga acccgaggag atg 53

<210> SEQ ID NO 695
<211> LENGTH: 73
<212> TYPE: DNA
<213> ORGANISM: Homo sapiens

<400> SEQUENCE: 695
atctccttta gccccgcccg cctccgtagc tgcctgaagt agtgcagggt cagcccgcaa 60
gttgcaggtc atg 73

<210> SEQ ID NO 696
<211> LENGTH: 28
<212> TYPE: DNA
<213> ORGANISM: Homo sapiens

<400> SEQUENCE: 696
tgatcttttc caaggctgta cagacatg 28

<210> SEQ ID NO 697
<211> LENGTH: 101
<212> TYPE: DNA
<213> ORGANISM: Homo sapiens

<400> SEQUENCE: 697
cgccctctcg ccgcgtcgcc ggtgcctgcg cctcccgctc cacctcgctt cttctctccc 60
ggccgaggcc cgggggacca gagcgagaag cggggaccat g 101

<210> SEQ ID NO 698
<211> LENGTH: 164
<212> TYPE: DNA
<213> ORGANISM: Homo sapiens

<400> SEQUENCE: 698
gcttctcttt cggagggagt gttcgccgcc gccgcggccg ccacctggag tttcttcaga 60
ctccagattt ccctgtcaac cacgaggagt ccagagagga aacgcggagc ggagacaaca 120
gtacctgacg cctctttcag cccgggatcg ccccagcagg gatg 164

<210> SEQ ID NO 699
<211> LENGTH: 44
<212> TYPE: DNA
<213> ORGANISM: Homo sapiens

<400> SEQUENCE: 699
gtttcttttg cggctccacg tcggcaccag ctgcggggca agat 44

<210> SEQ ID NO 700
<211> LENGTH: 98
<212> TYPE: DNA
<213> ORGANISM: Homo sapiens

<400> SEQUENCE: 700
ggttctttct gtgtttgttc tctgccctgc caaggccgta gagctggtgc gtgcgggtag 60
cggggctctc cgaggagccg cacgccggcg gcaccatg 98

<210> SEQ ID NO 701
<211> LENGTH: 239
<212> TYPE: DNA
<213> ORGANISM: Homo sapiens

<400> SEQUENCE: 701
ctacctcctt ttccgcgggc cccgcccagg cggctgcccg tgacctgcct gggcgcgggg 60
aactgaaagc cggaaggggc aagacgggtt cagttcgtca tggggctgtt tggaaagacc 120
caggagaagc cgcccaaaga actgatatcc aaagagaaga agaaaaagtg aaacgatctg 180
tgaaagatgc tgccaagaag ggccagaagg atgtctgcat agttctggcc aaggagatg 239

<210> SEQ ID NO 702
<211> LENGTH: 41
<212> TYPE: DNA
<213> ORGANISM: Homo sapiens

<400> SEQUENCE: 702
cgaccttttg gccaggttag ggagggggcg acgctgagat g 41

<210> SEQ ID NO 703
<211> LENGTH: 38
<212> TYPE: DNA
<213> ORGANISM: Homo sapiens

<400> SEQUENCE: 703
cgctctttcc ggcggtgctc gcaagcgagg cagccatg 38

<210> SEQ ID NO 704
<211> LENGTH: 83
<212> TYPE: DNA
<213> ORGANISM: Homo sapiens

<400> SEQUENCE: 704
ccttcctttc cctccggcgt cctctcccgg ccctctcgcg ctgcactgtc tctccgacgc 60
aagactgtcc cggcccggat atg 83

<210> SEQ ID NO 705
<211> LENGTH: 44
<212> TYPE: DNA
<213> ORGANISM: Homo sapiens

<400> SEQUENCE: 705
cgccctcctt gccgcccagc cggtccaggc ctctggcgaa catg 44

<210> SEQ ID NO 706
<211> LENGTH: 83
<212> TYPE: DNA
<213> ORGANISM: Homo sapiens

<400> SEQUENCE: 706
cgccccttcg cggcgcttcc tagttcggct ggttcttctg tcgccggctt cagcagcccg 60
cgcccgggca ggaatagaag atg 83

<210> SEQ ID NO 707
<211> LENGTH: 118
<212> TYPE: DNA
<213> ORGANISM: Homo sapiens

<400> SEQUENCE: 707
cgttccttcg ccgccgccag ggtagcggt gtagctgcgc agcgtcgcgc gcgctaccgc 60
acccaggttc ggcccgtagg cgtctggcag cccggcgcca tcttcatcga gcgccatg 118

<210> SEQ ID NO 708
<211> LENGTH: 202
<212> TYPE: DNA
<213> ORGANISM: Homo sapiens

<400> SEQUENCE: 708
ccgcctctcg gccccgcggc ctggccggca agcagggctg cagtcacggg gcggcgcgga 60
gggccccagc ccagtcaggg gtgtggccgc cgccaccgta aggctaggcc gcgagcttag 120
tcctgggagc cgcctccgtc gccgccgtca gagccgccct atcagattat cttaacaaga 180
aaaccaactg gaaaaaaaaa tg 202

<210> SEQ ID NO 709
<211> LENGTH: 46
<212> TYPE: DNA
<213> ORGANISM: Homo sapiens

<400> SEQUENCE: 709
cgctcttttc attcacgaag gtagtgaggc ctagtggaaa gccatg 46

<210> SEQ ID NO 710
<211> LENGTH: 13
<212> TYPE: DNA
<213> ORGANISM: Homo sapiens

<400> SEQUENCE: 710
cctcccctcg atg 13

<210> SEQ ID NO 711
<211> LENGTH: 604
<212> TYPE: DNA
<213> ORGANISM: Homo sapiens

<400> SEQUENCE: 711
ccccctttcc ggcaggctac tgggctccgc ccacacacct cccggcctgg ttcctaaacg 60
ccagctcgga gcaatcccct tgggctggag ccaaatccct gctgtgattt taaggaagac 120
cggcaggtcc gggcccccaa gggtcaaccc cacacacatc cccgcacttt cctgtatgca 180
ggcctgcgag cgtagaggga gtggaattca cagcctcccc acccatccgc aggggtctcc 240

-continued tgggaggaac ccaccagcga taggaacact gaagctgggc tacggcgtcc gcccgagcct 300
tttcttaaag gcgccgaccc cggaagcggg gcgtccgagg gagcgcgcga cgggccacgc 360
acgtccgggc gtccagttcg gggcagcttc tccggctggt gggtgggtgg ggcagccttt 420
caggcagggt ggcaaccaac tatatctgag gaccagagcc attttggggc accagagctt 480
gtgacctctc catctccacc cagctgggtc caggggccac tctcagcact cacctcagca 540
gctgacatca taaagcagac ttgggaacct ggaagcactc tggagaacct ttccctgaga 600
catg 604

<210> SEQ ID NO 712
<211> LENGTH: 67
<212> TYPE: DNA
<213> ORGANISM: Homo sapiens

<400> SEQUENCE: 712
cgccctttca gttctgcttg ctgtcggcac cgctgcgtta cccggaaccg ccgggccgaa 60
cagcatg 67

<210> SEQ ID NO 713
<211> LENGTH: 99
<212> TYPE: DNA
<213> ORGANISM: Homo sapiens

<400> SEQUENCE: 713
ggttcttcct tttttattta ccggtggctg tgcttccaat ttaggaagac cccggcgacc 60
tgttcctcac ccccgcttcg ccctcacact ttcgggatg 99

<210> SEQ ID NO 714
<211> LENGTH: 23
<212> TYPE: DNA
<213> ORGANISM: Homo sapiens

<400> SEQUENCE: 714
tcgcctcctc cctccccaag atg 23

<210> SEQ ID NO 715
<211> LENGTH: 120
<212> TYPE: DNA
<213> ORGANISM: Homo sapiens

<400> SEQUENCE: 715
gttcctcctt gctctcgccc ctactctttc tggtgttaga tcgagctacc ctctaaaagc 60
agtttagagt ggtaaaaaaa aaaaaaaaca caccaaacgc tcgcagccac aaaagggatg 120

<210> SEQ ID NO 716
<211> LENGTH: 504
<212> TYPE: DNA
<213> ORGANISM: Homo sapiens

<400> SEQUENCE: 716
tagtctttcc aggtgttagt cgaaacctcg tggtgcgacc ctggtcgtcc caaaccccct 60
aggccttaat cctggggcgg tgggggcggg gaggccgtga gcacggcttc cgctcctcca 120
atccgccaga gggcgcagcg gccggcctct cccttcccgg ggttcttcgc gccgggcccc 180
ttccgcgtgg gtgagtgaat gtgagagtca gcgctcgcgc cgcgcgcgcc gcccgcctcc 240
gctgttcggc gctctgcttt aggcggtggg gggcgggcgc gcgcgtaaaa gcatagagac 300
gggcattgag ctcttgggct agagcgtcgc cgagtcggag ccggagcctg agccgcgcgc 360
tgtgtctccg ctgcgtccgc cgaggccccc gagtgtcagg gacaaaagcc tccgcctgct 420
cccgcagccg gggctcatct gccgccgccg ccgcgctgag gagagttcgc cgccgtcgcc 480
gcccgtgagg atctgagagc catg 504

<210> SEQ ID NO 717
<211> LENGTH: 86
<212> TYPE: DNA
<213> ORGANISM: Homo sapiens

<400> SEQUENCE: 717
agctctctag cagagcgccg ttgctggggg aatgcagaag cggccgcggg ctagcaagct 60
cccggagccg gcggcgcacc accatg 86

<210> SEQ ID NO 718
<211> LENGTH: 333
<212> TYPE: DNA
<213> ORGANISM: Homo sapiens

<400> SEQUENCE: 718
cctccttttc ttcctcagcg ggtccgcggc ccgctactct ccgggagggg cgcttcccga 60
cgccaaggta ggcctctccc gacgccgggg cggcccttcc tgatgccggg gtgtgtctct 120
cgcgacgcgg gggtgggctc cggacgccgg ggctggcctt gccgaagtcg ggggtgggtc 180
cctccggacg ccgaagtggg ctcgggatgc ggggctggga ccctcccgat tccggggcgg 240
attccggacg ccgggaccgg ccattactgg tgccgggttg ggcttctcca gatgccgggg 300
ctgggtcctt cccaaggttg agacaaaagg atg 333

<210> SEQ ID NO 719
<211> LENGTH: 63
<212> TYPE: DNA
<213> ORGANISM: Homo sapiens

<400> SEQUENCE: 719
ccgccccttc ccatcgtgta cggtcccgcg tggctgcgcg cggcgctctg ggagtacgac 60
atg 63

<210> SEQ ID NO 720
<211> LENGTH: 28
<212> TYPE: DNA
<213> ORGANISM: Homo sapiens

<400> SEQUENCE: 720
cagcctcctt tgcgggtaaa cagacatg 28

<210> SEQ ID NO 721
<211> LENGTH: 53
<212> TYPE: DNA
<213> ORGANISM: Homo sapiens

<400> SEQUENCE: 721
cttcctctca agcttggcgt ttgtttggtg gggttacacg cgggttcaac atg 53

<210> SEQ ID NO 722
<211> LENGTH: 203
<212> TYPE: DNA
<213> ORGANISM: Homo sapiens

<400> SEQUENCE: 722

-continued

```
taccctcttc tgttgctttc tccctgtggc tcgcgccgtc ccccgccgcc cgtcgacccc     60

gcttccatgt ccctggcgga cacagctccc aggaacctcc acgcccatgg ccactaggca    120

gagggaatcc tctatcacct cctgctgttc cacctcgagc tgcgacgcag acgacgaggg    180

cgtgcgcggc acctgcgaag atg                                            203
```

<210> SEQ ID NO 723
<211> LENGTH: 306
<212> TYPE: DNA
<213> ORGANISM: Homo sapiens

<400> SEQUENCE: 723

```
ccccttctt ttgtggtccg gcccattgcg agggtgacag gaaaccctgt gcagggagcg      60

ccgccatctt ggaccagccc gaggaagata ctgagggagc acaggagcag tcaccgctgc    120

cactgctact gccgctactg ctgccggcgc gtctgcacct ctcggcctgc cagtgtacct    180

gccggcgcct cggtcgaccg cccccgcccc ctctcccgct gcgtccgcac tcctgttcct    240

ggtcctgacg cccccctccc gcccggaaag ctgcccagcc accagcaacc ccccagtgcc    300

accatg                                                               306
```

<210> SEQ ID NO 724
<211> LENGTH: 145
<212> TYPE: DNA
<213> ORGANISM: Homo sapiens

<400> SEQUENCE: 724

```
cttccttttc ctgtttggtt ttaagtaggc tataaaaatc aagttgctgt cttcagaggg     60

tctgtggtcc tctgatcaac ataggctggt gggagtacag gactcgcctc ctcagggttc    120

cctgtgctgc cactttttcag ccatg                                         145
```

<210> SEQ ID NO 725
<211> LENGTH: 513
<212> TYPE: DNA
<213> ORGANISM: Homo sapiens

<400> SEQUENCE: 725

```
ctctcttccc ctctccctct ccctctgccg ggtggatgct ttctccatgt ggcaaggctg     60

taactgttca cagctgtctg aaacagcagt ggaccaggag cagcttggag ttttaacttt    120

cattttacaa agaacaacat gtttgaatgt ttcagcaggc aagttataac tggcatctac    180

ttcttgttct tctagaacac cgaaaatctc tcccagcact ttagaaaggg gaccctgact    240

gtgttaaaga agaagtggga gaacccaggg ctgggagcag agtctcacac agactctcta    300

cggaacagca gcactgagat taggcacaga gcagaccatc ctcctgctga agtgacaagc    360

cacgctgctt ctggagccaa agctgaccaa gaagaacaaa tccaccccag atctagactc    420

aggtcacctc ctgaagccct cgttcagggt cgatatcccc acatcaagga cggtgaggat    480

cttaaagacc actcaacaga aagtaaaaaa atg                                 513
```

<210> SEQ ID NO 726
<211> LENGTH: 27
<212> TYPE: DNA
<213> ORGANISM: Homo sapiens

<400> SEQUENCE: 726

```
gtttctcttg cgccctggtc caagatg                                         27
```

<210> SEQ ID NO 727
<211> LENGTH: 320
<212> TYPE: DNA
<213> ORGANISM: Homo sapiens

<400> SEQUENCE: 727 caccccccttc cacgtcagcc aaggactctg gagccgccgc cgccgctgct gcggttcata 60
gccggagtag acggagccgc agtagacgga tccgcggctg caccaaacca ctgcccctcg 120
gagcctggta gtgggccaca agcccccagt cccagaggcg tggtgggtcg ggcagagtcg 180
gaagaactgg ctttctagct ggaagatgcg gaaggggagc gactaggccg cttgcgtctg 240
ggcctggcag aagggaccgg attttctggc atccttaaat cttgtgtcaa ggattggtta 300
taatataacc agaaaccatg 320

<210> SEQ ID NO 728
<211> LENGTH: 69
<212> TYPE: DNA
<213> ORGANISM: Homo sapiens

<400> SEQUENCE: 728
gggtcttttg cggctgcagc gggcttgtag gtgtccggct ttgctggccc agcaagcctg 60
ataagcatg 69

<210> SEQ ID NO 729
<211> LENGTH: 109
<212> TYPE: DNA
<213> ORGANISM: Homo sapiens

<400> SEQUENCE: 729
ctttcttttt ctccaaaagg ggaggaaatt gaaactgagt ggcccacgat gggaagaggg 60
gaagcccagg ggtacaggag gcctctgggt gaaggcagag gctaacatg 109

<210> SEQ ID NO 730
<211> LENGTH: 182
<212> TYPE: DNA
<213> ORGANISM: Homo sapiens

<400> SEQUENCE: 730
gtgcctttcc agtggacctg ggctgttgtt gcggttgttt tccttctctc cgtgcaacgc 60
tggcaagtct caaagtcgcc acagaaacat gcccctgatt cagtgcctct gcttagctgt 120
aacatgttaa tcagaactac ctggcatctt cctgaacaag actttcaata ggggccagta 180
tg 182

<210> SEQ ID NO 731
<211> LENGTH: 56
<212> TYPE: DNA
<213> ORGANISM: Homo sapiens

<400> SEQUENCE: 731
agatcttctt ccgggcggac gtggagccgg aagcggaggt tccgggctcc gggatg 56

<210> SEQ ID NO 732
<211> LENGTH: 77
<212> TYPE: DNA
<213> ORGANISM: Homo sapiens

<400> SEQUENCE: 732
cgtcctttag ccgggagcct gtctttgctt gcctttgcct ttgaggctct gtggctgtgg 60
ggctgagtgg catcatg 77

<210> SEQ ID NO 733
<211> LENGTH: 85
<212> TYPE: DNA
<213> ORGANISM: Homo sapiens

<400> SEQUENCE: 733
agctctttcc ccgcgactgc gccacgtctg aggcggctgt ggccgcgtcg gtgtccgcgt 60
cgaggagccg gggcagggca cgatg 85

<210> SEQ ID NO 734
<211> LENGTH: 152
<212> TYPE: DNA
<213> ORGANISM: Homo sapiens

<400> SEQUENCE: 734
ttctctcttt cggccggcgc cgccagttcc tggggcacac ccagaggtcc ccttctcgcc 60
gccgcctgca actgcgaggg tagcccgggg ccgcttggag tcgcccggac ctgagaggct 120
gctgcactgg gcctcagcca gccctccgga tg 152

<210> SEQ ID NO 735
<211> LENGTH: 359
<212> TYPE: DNA
<213> ORGANISM: Homo sapiens

<400> SEQUENCE: 735
cgtccttcta atcctagtct tcgtttggtc cggttgcact cttcctatag cccagagggc 60
gagagggcct gtggcctggg ggaaggagga cgaggttctg cctggatccc agcagtagga 120
cgctgtgcca tttgggaaca aaggaatagt ctgcctggaa tccctgcaga tcttggggcc 180
ggaggccagt ccaacccttg gagcaggaag aaacgcaaag ttgtcaagaa ccaagtcgag 240
ctgcctcaga gccggcccgc agtagctgca gactccgccc gcgacgtgtg cgcgcttctc 300
tgggccagag cgagcctgtt ttgtgctcgg gttaagagat ttgtcccagc tataccatg 359

<210> SEQ ID NO 736
<211> LENGTH: 188
<212> TYPE: DNA
<213> ORGANISM: Homo sapiens

<400> SEQUENCE: 736
cggcctcccg cacgcaccgc gcagcctgct gtgcccgtgg gtcccgagtg ctccgccgcc 60
cgccccgacc cgggcccagc cgcctccacg gcccgcgctc gtactggagc gaagagcggc 120
ctcctgaagg aggggaaggg acgtgggggc ggccacggca ggattaacct ccatttcagc 180
taatcatg 188

<210> SEQ ID NO 737
<211> LENGTH: 201
<212> TYPE: DNA
<213> ORGANISM: Homo sapiens

<400> SEQUENCE: 737
tctccctttt ttccttcttc cttcccctcc tcgccgccac cgcccaggac cgccggccgg 60
gggacgagct cggagcagca gccagagttt attaaccact taacctctca gaactgaaca 120
aagacaacat tgttcctgga acgccctctt tttaaaaaag aaagcataac ccctactgta 180
gaactaaatg cactgtgcat g 201

<210> SEQ ID NO 738
<211> LENGTH: 505
<212> TYPE: DNA
<213> ORGANISM: Homo sapiens

<400> SEQUENCE: 738
cggccttttg tcagcgcgca gggccaggag agctctcatt tcctcccagc ctcgtgcggg 60
aaatggcttt aattctgacg gcagggctgt gagggactag cgggaacccg agccttttgt 120
caaggaactg cggcgtcggt ggccagtcat ccccgccgcc gcggagccgc tgcactgctg 180
ggggatctcc cagcagctct gacgagcgcg ggctgcagca tgggcagaaa acgctgccct 240
gcagattagc tgggtggatt ttttaagcgc accccacccc ccaaacccat aaaataacaa 300
aaccaacccg cagtggccga ccggagatag ctaagatgcc gcgcaggagt ttccacctgg 360
atgtttgagg ttgtgtagat gtggccggca cccttgagag tggagctagg gggtgcagac 420
tgagcagtga acagaaggag ccttggacag ggctgggcca gcctcccgag ttccaggagc 480
gaattgcaaa cccaccggga aaatg 505

<210> SEQ ID NO 739
<211> LENGTH: 112
<212> TYPE: DNA
<213> ORGANISM: Homo sapiens

<400> SEQUENCE: 739
ccgccttccg gctccagtcc ccgggctcgg cctcggcgag gtgtaattcg cagcgcgggc 60
cggccccgga ggctctcggc gagcgcggcg cggtaacaag tgggcgagga tg 112

<210> SEQ ID NO 740
<211> LENGTH: 581
<212> TYPE: DNA
<213> ORGANISM: Homo sapiens

<400> SEQUENCE: 740
cgacctctac ttccacctct ggccccaagt acagcgccag ctgcggcctc gggagcgccc 60
gcgggggtgc ccgtgcaccg gccgcgcctc ctccctggcg cgggactcgg ccgcagctgc 120
ctcggacccc ggcacgatcg tgcacaactt ttcccgaacc gagccccgga ctgaaccggc 180
tggcggcagc cacagcgggt cgagctccaa gttgcaggcc ctcttcgccc acccgctgta 240
caacgtcccg gaggagccgc ctctcctggg agccgaggac tcgctcctgg ccagccagga 300
ggcgctgcgg tattaccgga ggaaggtggc ccgctggaac aggcctcagt tcctgctttt 360
gaaaggaaga gggggagtct gtgacccctg aggcctcctt gcaactctgt tttccaagct 420
ttgcacatct tccgaatttc ttcttcaaag tctaccctaa tgaaatatca gacaattttc 480
caagtgtgct tcatgaactt ctgggaggtg cttcacagtt tctgcaaatg attgattgaa 540
ttttcacttt gaaaaaatat actttaaggc gacacaagat g 581

<210> SEQ ID NO 741
<211> LENGTH: 45
<212> TYPE: DNA
<213> ORGANISM: Homo sapiens

<400> SEQUENCE: 741
ttttctttcc tggtgtcccg tcgcggcttg ggacccggca agatg 45

<210> SEQ ID NO 742

<211> LENGTH: 96
<212> TYPE: DNA
<213> ORGANISM: Homo sapiens

<400> SEQUENCE: 742
tgctccctct cccacaaggc agcgcgccgg ctcggacgcg gccggctacc gagccctttg 60
tgagggctgt gagctgcgcc tgacggtggc accatg 96

<210> SEQ ID NO 743
<211> LENGTH: 24
<212> TYPE: DNA
<213> ORGANISM: Homo sapiens

<400> SEQUENCE: 743
gaatcttttc cacagcccaa aatg 24

<210> SEQ ID NO 744
<211> LENGTH: 307
<212> TYPE: DNA
<213> ORGANISM: Homo sapiens

<400> SEQUENCE: 744
gtttcctttg ttgtgagctg cggcagagac tggtggctgg aggagacgcc ggcgctggag 60
agtgcgctgc gccgcccgcc gctgagggac cgcggggtta gccactgctg gctgcttcca 120
gtgttcgccg agaggtaccg ggggtgacag ctccgggacc ggccgaaagg cgaggaaccg 180
gtgtggaaat taaaagaaca cacatatttt gactggggct ttgatcaacc aaatgctaaa 240
aagccacata aagaagatcc ctaatagtca tttctcaaca attatatagt caactgatgt 300
aacaatg 307

<210> SEQ ID NO 745
<211> LENGTH: 18
<212> TYPE: DNA
<213> ORGANISM: Homo sapiens

<400> SEQUENCE: 745 ctccccccttt ccaccatg 18

<210> SEQ ID NO 746
<211> LENGTH: 308
<212> TYPE: DNA
<213> ORGANISM: Homo sapiens

<400> SEQUENCE: 746
gcttccctct tctctcgccg cctcctggcc tccgcaccga cgcggcccgg gctggagccg 60
agccggggcc gagctgcagg ccggaccgga gccggatctg tacccgctga gacgtggaaa 120
catggaggcc tgagccggtg tgcgccacct gggctgcggc ggcgacagcg acttctcctg 180
acccctctgc caccctccca tccgtccgcg ggtccgtgga gctggagcag atcccccagc 240
cggctgagac aggttgtctt ttggaaatgc aggtttaagg acaaattatc tgcttaagct 300
agaagatg 308

<210> SEQ ID NO 747
<211> LENGTH: 144
<212> TYPE: DNA
<213> ORGANISM: Homo sapiens

<400> SEQUENCE: 747
cctcctcttt ctcctcctcc tcagggctcc agtcaggccg atccgctccg ctcacggaag 60
gaaaacagaa ataacttgct ggcttgtctg gagtcacatg tacttaggtg acaatttaca 120
gaaagtcatc tctgcagctt gatg 144

<210> SEQ ID NO 748
<211> LENGTH: 91
<212> TYPE: DNA
<213> ORGANISM: Homo sapiens

<400> SEQUENCE: 748
cgttcctttg tgctgcggcg gcggcttctc gagtcctccc cgacgcgtcc tctaggccag 60
cgagccccgc gctctccggt gacggaccat g 91

<210> SEQ ID NO 749
<211> LENGTH: 64
<212> TYPE: DNA
<213> ORGANISM: Homo sapiens

<400> SEQUENCE: 749
ctctcctttg gcttggggct ccggagttgc cactgccgcc ggcgctggta agcttttcag 60
gatg 64

<210> SEQ ID NO 750
<211> LENGTH: 87
<212> TYPE: DNA
<213> ORGANISM: Homo sapiens

<400> SEQUENCE: 750
tgacctcttt cgggtctctt tgaatctccg ctgtagcgtc acctggaagg cagatctaac 60
agagaacctg gactgtctcc tatcatg 87

<210> SEQ ID NO 751
<211> LENGTH: 284
<212> TYPE: DNA
<213> ORGANISM: Homo sapiens

<400> SEQUENCE: 751
ccgccttctg gacttggtct tagttcccag tcgcggccaa atcacgcctc agccacctcc 60
cgcaagcctc tcactgcctc agccacgctt tccaggctgg tttctggtcc ccatccgcgg 120
ctggtccggc cctgggaccg aatcacttcc cagcgagagg aaggtcaaat ttctcgaccg 180
gctacgggaa ggtcgcggcc gccgccctgt cagccgcctc ggcgccccca ggacccctcg 240
ggtctcttta accggaagcg gaagtgcgtg tcggcgggat catg 284

<210> SEQ ID NO 752
<211> LENGTH: 17
<212> TYPE: DNA
<213> ORGANISM: Homo sapiens

<400> SEQUENCE: 752
cagtccttct cagcatg 17

<210> SEQ ID NO 753
<211> LENGTH: 297
<212> TYPE: DNA
<213> ORGANISM: Homo sapiens

<400> SEQUENCE: 753
cgttctttgt tctgtccccg gtgtgtgggt ctgtgacagg gtccaacagg gcctggtccg 60
tgtccggtcc cccaaatctg tcgtccctgc ccccaggcat tggcatcaac aaaagtcaga 120
attcccggga acttgaacag aggctgctaa attcccagta attgctcctt tggccttcta 180
gggactgact tcaaagaagg aaggaaagaa tcaggcagtg cttcctcatt ctcttttaaa 240
acccgcttcc cgctgagtct gcacccagga gaccagagag caccttgccc ttccatg 297

<210> SEQ ID NO 754
<211> LENGTH: 250
<212> TYPE: DNA
<213> ORGANISM: Homo sapiens

<400> SEQUENCE: 754
ggttcttctc ctaggcggaa gccagaccag agagcgtgcg tgtttttccc agggtgcccc 60
gcgctgctgt tatggccgcc tccttgaggt agtatccgca catggaattc tagggccgca 120
ggtgtattta cggtaactgt cgccactaga tttcagcgcc tttggactct cctgttttca 180
ctttcttttg ttgactcccg tgtggccctc gtgggagcct gttttggctg cagcggtgtc 240
tggggtgatg 250

<210> SEQ ID NO 755
<211> LENGTH: 33
<212> TYPE: DNA
<213> ORGANISM: Homo sapiens

<400> SEQUENCE: 755
gtttctcttt cctctcagtt tgcgcacacc atg 33

<210> SEQ ID NO 756
<211> LENGTH: 81
<212> TYPE: DNA
<213> ORGANISM: Homo sapiens

<400> SEQUENCE: 756
tgctcttctc gttcccgaga tcagcggcgg cggtgaccgc gagtgggtcg gcaccgtctc 60
cggctccggg tgcgaacaat g 81

<210> SEQ ID NO 757
<211> LENGTH: 57
<212> TYPE: DNA
<213> ORGANISM: Homo sapiens

<400> SEQUENCE: 757
cctcctcctg gacggcggca gcggcggcgc gaggagccgg cgggcagcgg cgcgatg 57

<210> SEQ ID NO 758
<211> LENGTH: 149
<212> TYPE: DNA
<213> ORGANISM: Homo sapiens

<400> SEQUENCE: 758
gcgccttctc cttgcttctg ggggtcgtgg ccttgctccc gctgtgcggg aaaagaatcc 60
aggcccttcc acgcgcgtgt gggtgcgggg gccccgaagt gctcgtggtt ccccgctagg 120
tctccgctgg ggcaggaacc ggaatcatg 149

<210> SEQ ID NO 759
<211> LENGTH: 244
<212> TYPE: DNA
<213> ORGANISM: Homo sapiens

<400> SEQUENCE: 759
cctccttcgt cgcggcctct agtgcacttt cggctccttc cccttcccgg gcctttcagc 60
ttggtctttc cgggcctcgc ttcccccagc ccctgcgccc ggcccgaacg agaggttccg 120
gagccccggc gcgggcgggt tctggggtgt agacgctgct ggccagcccg ccccagccga 180
ggttctcggc accgccttga gagcttcagc tgccccagga ttagaatccc aagaaaatca 240
aatg 244

<210> SEQ ID NO 760
<211> LENGTH: 66
<212> TYPE: DNA
<213> ORGANISM: Homo sapiens

<400> SEQUENCE: 760
ccgcctcttt cccgccgccg cctgggaggg gacccgggct gccaggcgcc cagctgtgcc 60
cagatg 66

<210> SEQ ID NO 761
<211> LENGTH: 162
<212> TYPE: DNA
<213> ORGANISM: Homo sapiens

<400> SEQUENCE: 761
cttcctttcc agcctcccgc cctcgtctgc ttccggccct gtggcctggt ggggctctgc 60
aggctccctc gggagtggtc cttgggccgt ggcccctctg ggaggcctga gggagctcaa 120
tcctggtagc aacacccctg aattcctggt ggtgaaagga tg 162

<210> SEQ ID NO 762
<211> LENGTH: 277
<212> TYPE: DNA
<213> ORGANISM: Homo sapiens

<400> SEQUENCE: 762
agttccttta tccctgggcc caacctcccc gccgacccgc ggtccaggcc tcggtctctc 60
tcttcggcgg cgagccgcgg cccagacccc ggcagaggac acttgtcggc acgttctcac 120
ccctgtcatc tcagccccct gcctagctcc accccaggct tgggaacccg gcccctgacg 180
gcccattgtc cgcgggccca gcccccgcgc tgaacgcacg ctcgcccttg cccctaacca 240
gcgcgtctac cccggcaacg cgcagtgacc tgggatg 277

<210> SEQ ID NO 763
<211> LENGTH: 252
<212> TYPE: DNA
<213> ORGANISM: Homo sapiens

<400> SEQUENCE: 763
gtttcttttc tgcgcttgtg cgttttctgt tcggtttcct tcccgctagc ggggccacga 60
gggttgctag gcaacagccc ctgggtgact tggtcttagg gtcctgtccg gcttggggct 120
gatgaaagga gctgtccgcg cccgggctct tccgagaagt ggttgctgac agccacaaag 180
tgaaagggag tgaggcggcg tggacgagta aggagtgaca gtgaggattc acatttgggt 240
tatttcaaga tg 252

<210> SEQ ID NO 764
<211> LENGTH: 96
<212> TYPE: DNA
<213> ORGANISM: Homo sapiens

<400> SEQUENCE: 764
cgtccttcct ggtcctgcgg gtccaggact gtccgcgggg ttgagggaag gggccgtgcc 60
cggtgccagc ccaggtgctc gcggcctggc tccatg 96

<210> SEQ ID NO 765
<211> LENGTH: 205
<212> TYPE: DNA
<213> ORGANISM: Homo sapiens

<400> SEQUENCE: 765
ctccctctgg ggcgcgggcc tcagttccgg gctacagcag ccgacgccga gaggcaccgt 60
ttcttcttaa aagagaaacg ctgcgcgcgc gaggtgggcc cctgtcttcc agcagctccg 120
ggcctgctcg ctaggcccgg gaggcgcagg cgcaggcgca gtgggggtga gggcgcgtgg 180
gggcgcacag cctctggtgc acatg 205

<210> SEQ ID NO 766
<211> LENGTH: 28
<212> TYPE: DNA
<213> ORGANISM: Homo sapiens

<400> SEQUENCE: 766
tggccctttc ctttccgcgt gtagaatg 28

<210> SEQ ID NO 767
<211> LENGTH: 371
<212> TYPE: DNA
<213> ORGANISM: Homo sapiens

<400> SEQUENCE: 767
tctccccttc tacagagttc ctccggcgct tcctccaccc cgggatacac agaacctcat 60
ctcctacggt gctgaagcct gcagcagggc aggatgggca ggagagcaga gccgcggagt 120
ctgcggcgcg ggtgaagagc ggcgcgtaat tcccgcagca agattgttcc gcgcccgcag 180
cccctggact agcaggatcc gaaccccggc ggctgcgtgc ttataggcgc agacgtcaga 240
gagcccgcgg cttaaagcgc gtcgcctggc tagcgccacc ccctagcctt cttcaaggcc 300
tccagggctg ggcccaagcg cccgtcgacg gcaccctggg cccagaggac tcgcgggcct 360
catctccaat g 371

<210> SEQ ID NO 768
<211> LENGTH: 512
<212> TYPE: DNA
<213> ORGANISM: Homo sapiens

<400> SEQUENCE: 768
agttctttct gatagcaggc agccatcttg cctggagcct gagaaaggga ggagagacag 60
aaggaaccgg cgacagtggt ctcagggccg ctccgggggg cctcaagaac cggaggcagc 120
cccggaggtg gtccccgatc ccgggctatg ctcttggatc tgagaaggga aggcggaggg 180
cggcggggac aagatgggtg gagaatgtca agcaaggaat gctaggcggg ggaggggcgt 240
tgctatggcg actggggagg ggcggtgtct gttctgaatc gctgtgtgtc acccgggcgc 300
tgcccaggaa gggcagggct ggggtgatga ccatggtaac acccgggggg gagttcgtga 360
catctccggc gcggagggac tcgatgtcta tggcaatggt cgcctggtgg aagggacgga 420
actagatccc ttcgctcggg acgctcacat tccaggccct tgtcctgcag gctgccgcgg 480
gcggacacgc cagaggagga ggccggggaa tg 512

<210> SEQ ID NO 769
<211> LENGTH: 71
<212> TYPE: DNA
<213> ORGANISM: Homo sapiens

<400> SEQUENCE: 769
ccgcctttta cgacgcgccg gaaagcaacg gcaagggcgg cagccagcac cgggcggaga 60
gggctaccat g 71

<210> SEQ ID NO 770
<211> LENGTH: 126
<212> TYPE: DNA
<213> ORGANISM: Homo sapiens

<400> SEQUENCE: 770
ctgcctcctt ctactcgggc gccccggcgg ccgccacctc tccccagccc aggagaggct 60
gcggagccgc agccgcccag accgcgcagc gcgggaggca ggttccgcac gaaataaatc 120
agaatg 126

<210> SEQ ID NO 771
<211> LENGTH: 126
<212> TYPE: DNA
<213> ORGANISM: Homo sapiens

<400> SEQUENCE: 771 ttccccttt ggggacagat cccgaagttc gagcatccct cggataggcc gggtgtcagg 60
cctggtctct caggcccgtc caggcccatc ttgacgattc caagaccacc cccttgagca 120
agaatg 126

<210> SEQ ID NO 772
<211> LENGTH: 124
<212> TYPE: DNA
<213> ORGANISM: Homo sapiens

<400> SEQUENCE: 772
ccgccctttg ccactccccc tgcctcctct ccgcctttaa cttctcggga agatgaggca 60
gtttggcatc tgtggccgag ttgctgttgc cgggtgatag ttggagcgga gacttagcat 120
aatg 124

<210> SEQ ID NO 773
<211> LENGTH: 363
<212> TYPE: DNA
<213> ORGANISM: Homo sapiens

<400> SEQUENCE: 773
agtcctctcg cagctgcgcc aggacagccg gcgcgcggcc gtgcccacaa gttgccggca 60
gctgagcgcc gcgcctcctc ctgctcgcag ccccctacgc ccacccggcg gcggtggcca 120
gcgccaggac gcacatcccg cggacaccga ccccagatgt aaagcgggac cccagcccct 180
cgccccccgg cgcgatcgac agtctcgcca gcgtctcctc tgccaaaacc cagggctgga 240
agatgtggca gccggccacg gagcgcctgc aggagagatt tgcagacaca gaagcggcac 300
agagaaggcc attgtgaaga tcaaggcaga aaccggagtt atggcatcat aagccaagga 360
atg 363

<210> SEQ ID NO 774

<211> LENGTH: 167
<212> TYPE: DNA
<213> ORGANISM: Homo sapiens

<400> SEQUENCE: 774
tttcctcctc ctcctcctcc gcctccgccg ccgttgcttg aatggtggag ccgaagctcg 60
gctcgtgaac acacactgac agctataggg caggcggcgg caccgtcccc gcttcccctc 120
ggcggcgggg tgtcccgtcg gcggccctga agtgacccat aaacatg 167

<210> SEQ ID NO 775
<211> LENGTH: 130
<212> TYPE: DNA
<213> ORGANISM: Homo sapiens

<400> SEQUENCE: 775
tggccttttt tgggcgtctc cctgctccgc ggcccgggct ggcgggcggg cgctcggctg 60
gcggctgcag cagcagaggg agacccgcgg caaccccggc aacccagggc tcggcgtcgc 120
tgccaccatg 130

<210> SEQ ID NO 776
<211> LENGTH: 656
<212> TYPE: DNA
<213> ORGANISM: Homo sapiens

<400> SEQUENCE: 776
aggtctttta gtctttttcc ccctccctta ctcttcgtcc ccggtccctc ccctccccac 60
ccctttcctt ctagctccga cgtttgcggc cgcgggggcg gcggaggata tggagtaaag 120
ccagagtcag tggccaggca cgaaggcaga gcaggaacag ccaggaggcg tttattaggg 180
gggcgggggg aaagagcccc agcaccgccc ctcctggaag aaggaagagg taagtgaccg 240
gccgccggca ccgaccgacc tccctcaccg gcggctctct cgcctgggct cccggagccg 300
gcgaggaggg aatggaggac tcgcgcccgg gttaggcctc ccagggccgc tcaggctggt 360
gggtgttgcc tggtgacggg cctgccggcg gccggccggg cgatcggcgg tcggcgcccg 420
cgcaaagcgg ggctggacga gcagcgagct ccggggagcg gatccgagag ggccgagtcc 480
tcgaaagagg ccttgaggcg acgggagacc cgggatcgaa gtcagctgcc ggagggagag 540
ccccccatgc cggctcgaga gctcgggttt cggtggtgga gaacgtagta cctttcgggg 600
acattggaca ctactctagg accgggtaac tataactacc caatattgca gccatg 656

<210> SEQ ID NO 777
<211> LENGTH: 215
<212> TYPE: DNA
<213> ORGANISM: Homo sapiens

<400> SEQUENCE: 777
caccctctct cctagtactt cctgttctcg gctaaccctg gcgctgggcc gggggctgga 60
gagtgaccgt ggtctgagtg acctggggcg gctgcgtggg ccggggtggg cctcaaagcc 120
gggcaccaga cgggaggggc ggcgctcggg ccgcgcgctg cccgcgccgg gtcctggcgg 180
gcggcgaggc tggggctgac tcctgcctca ggatg 215

<210> SEQ ID NO 778
<211> LENGTH: 32
<212> TYPE: DNA
<213> ORGANISM: Homo sapiens

<400> SEQUENCE: 778
cgacctctgg ctaacctacc cccggagcca tg                                    32

<210> SEQ ID NO 779
<211> LENGTH: 34
<212> TYPE: DNA
<213> ORGANISM: Homo sapiens

<400> SEQUENCE: 779
cggccccttc cggttacgaa accttagcaa gatg                                  34

<210> SEQ ID NO 780
<211> LENGTH: 166
<212> TYPE: DNA
<213> ORGANISM: Homo sapiens

<400> SEQUENCE: 780
tctccttttg cgcgacacgg tctcagctgt tccgcctgag gcgagtgacg ctggccgcca      60
acgaggtata cgtactggga ccctcgccct cagtctcgtc tccggcgcgg ctacctgccc    120
cgttttccct gtgagttgac ctgctccggg ccgcgggccg ccaatg                    166

<210> SEQ ID NO 781
<211> LENGTH: 42
<212> TYPE: DNA
<213> ORGANISM: Homo sapiens

<400> SEQUENCE: 781
cggtctcctg tacgccctag actaggggcc gccatctcca tg                         42

<210> SEQ ID NO 782
<211> LENGTH: 133
<212> TYPE: DNA
<213> ORGANISM: Homo sapiens

<400> SEQUENCE: 782
ttgtcctctt cgctgctccg tagtgacggg gattgttgtg ttgcagaaat ccggcaatcg     60
acctgaggac ttgcgagccg ctcagctccc gggacgtttg gagctgctgc taaataattt   120
ctgctcagcc atg                                                         133

<210> SEQ ID NO 783
<211> LENGTH: 33
<212> TYPE: DNA
<213> ORGANISM: Homo sapiens

<400> SEQUENCE: 783
ggctctttct cctccacgtg gggacgcagg atg                                  33

<210> SEQ ID NO 784
<211> LENGTH: 74
<212> TYPE: DNA
<213> ORGANISM: Homo sapiens

<400> SEQUENCE: 784
cgctctctct cactggcaca gcgaggtttt gctcagccct tgtctcggga ccgcagcctc     60
cgccgagcgc catg                                                        74

<210> SEQ ID NO 785
<211> LENGTH: 181
<212> TYPE: DNA
<213> ORGANISM: Homo sapiens

<400> SEQUENCE: 785
cgctcccccc cacgtgtccg ccggagtttc tccaccagca acatggccgc cgcctgagag 60
gagagccggg ccgccgccgt ctctgcagcc cgcgggtaac tgggccgttg ccgccgtccg 120
cgctcggccc ccgcggagag atcgagctga aggactgcgc ggctggctct cctctagtat 180
g 181

<210> SEQ ID NO 786
<211> LENGTH: 217
<212> TYPE: DNA
<213> ORGANISM: Homo sapiens

<400> SEQUENCE: 786
gagcctttgc ccgccagcgc cttcgctctt tggctccctg agttagtccg gttgcttgcg 60
atcgccgcgg ccggggctgc gaaccgaagg gctcgctccg cgccgcctgg gtctctacct 120
catccgtagg tgtggccctg atggtgtggc aggctctgga ctcctaaagc tctggagcga 180
atttaagatt ttattcatgt gcatggcata gaagatg 217

<210> SEQ ID NO 787
<211> LENGTH: 270
<212> TYPE: DNA
<213> ORGANISM: Homo sapiens

<400> SEQUENCE: 787
ccgtctttct ggaaacaccg ctttgatctc ggcggtgcgg gacaggtacc tcccggctgc 60
tgcgggtgcc ctggatccag tcggctgcac caggcgagcg agacccttcc ctggtggagg 120
ctcagagttc cggcagggtg catccggcct gtgtgtggcg cgaggcaggg aagccggtac 180
ccgggtcctg gccccagcgc tgacgttttc tctcccttt cttctctctt cgcggttgcg 240
gcgtcgcaga cgctagtgtg agccccccatg 270

<210> SEQ ID NO 788
<211> LENGTH: 104
<212> TYPE: DNA
<213> ORGANISM: Homo sapiens

<400> SEQUENCE: 788
ccttccttcc ccggggtaga agtccagggt gagaaattgg ttccgaactc aaaggaaccc 60
agtgccgggc cacagccggg tcacgtggcc ggcggccccc catg 104

<210> SEQ ID NO 789
<211> LENGTH: 173
<212> TYPE: DNA
<213> ORGANISM: Homo sapiens

<400> SEQUENCE: 789
attccttctc tgcatcgaag gatcaggaag tttgtgctct ctgcgtggct aagtttttca 60
cctactagga cgggggtggg gtggggagaa caggtgtcct tctaaaatac agcacaagct 120
acagcctgcg tccagccata acccaggagt aacatcagaa acaggtgaga atg 173

<210> SEQ ID NO 790
<211> LENGTH: 240
<212> TYPE: DNA
<213> ORGANISM: Homo sapiens

<400> SEQUENCE: 790
cgctcctcct cttcgctgcc ggtgggcacc gccgctcgct cgcacttctg cgcccattgg 60
agcttcggag atccctgcgg tcccgcggga cggcgcggca gcagctgacc tcgcagacag 120
gatcttgctc tcttgcccag actggaatac agtggtgtga acacggctca ctgcagcctc 180
aacctcctgg actcagagat gtcggcttat ttataggaat tgcttgaagc cagagtcatg 240

<210> SEQ ID NO 791
<211> LENGTH: 205
<212> TYPE: DNA
<213> ORGANISM: Homo sapiens

<400> SEQUENCE: 791 cgtccctta agagcggctg gccaggcacg gcctccgcct ctcagtacgc ggagcgccgg 60
cggtcacctg gggctcgcgg agcggccaga tcgcggcgga gtcggcgcgc ttccccgagg 120
gaaggtggga gaggggaccc ggacgcgagg tgccccgaag ccctctcgag cgtaaccgtc 180
ccgcgcctct ctgaggcgga ggatg 205

<210> SEQ ID NO 792
<211> LENGTH: 903
<212> TYPE: DNA
<213> ORGANISM: Homo sapiens

<400> SEQUENCE: 792
ctgtctcttg gctcaggctt ggaggcctcc gagcagcaac atcgtcccaa ttataccccg 60
ttggagcatc ttcagatctt ccactctttt cacaacgcaa tcaaaatctt cgtacccatt 120
ttgcagtagt gatctctgta agttgcttta caattcataa agtttattct atttgatctt 180
cactctaatt tacaaagaaa agcagggaag tctatttctg ttttacagag gtgtacaggg 240
aggctcacag gggctaagtt cacacagtaa gccctcgaag ctgccagggc tgcaaagccc 300
accctctttc caccgcaccg aactacctcc tttcgcctac aaaacgtagg tggggaccac 360
tggtgttgga atgacggccc acctcgagtt tcaggtgact tccactctgc aattaacttg 420
caggcagccc cagacctgca atgaacacac gggtggggga gagatatgca cgccagggtc 480
agtgggaacc aacagccgag gggtgagcgg ggctaggggc cccgggccgc cggcggggca 540
aacgcggttc agaaacgcag gccgcgctct ggcccgcccc ctgcagcagc acggcctgct 600
cgccatcgcc cggagagcgc cgcgggttcc cgagtccggg cgcggagggc gcgcgggcac 660
ggcggcaggg gcgtgctcgg aggacgcgcg ctgcgctgct cctccaaagg gcagctccgg 720
gggaaagagg gtggcgtccc ggggaagccc gcagccgccg ccgatgtcgc tgggactcgg 780
aagtgccgaa agaggggtgt tgggaactcg cggcgcgcgt gaacgttgcc gtcgccgccg 840
cccgggacag cccggagaaa ctctcagcgt aggcatcggg aaccttcgtg ccaaggagcc 900
atg 903

<210> SEQ ID NO 793
<211> LENGTH: 633
<212> TYPE: DNA
<213> ORGANISM: Homo sapiens

<400> SEQUENCE: 793 cctcctttt ctcccaaacc acttcttccc ccctaccccc cgccacgcga ggctgcggcg 60
cacggtatgg gtgtgtttgt gtgtatttgt gtggggaggg cgtttggagg gaaggttacc 120
gggagctccg aggccgctgg ggaacaggga tcccggtgac aaagatgggg atatttcctc 180
tgtcttccac ttggaaacct caaccccgc ttcaggctcc ctagatactt tctggggccc 240
aaccgaaggc cgtagccatc caaagcgttc ccagcctttc tggggagtga aacttacccc 300
cggggttcgt cctagaggag cgtgagcggg gaatgcccag gtcaaccggg ctgtccgaat 360
tccgccccgg ctcagcctcc ggcctcagtc cgggagagag atctgcctgt cggtctgggc 420
tgggggaaac gcggcagtgg cctgggccac aggtgagggc agagtaacca gtgggaaggc 480
tgcgttttca cgaaggactc gggtgaagct gcagagctgc ctttgagccc tgactccttg 540
gcttcctggg tcggaggaga tcttgtaatg gagtggttct tcgtctcact agcaagatgc 600
ctgatttcct caggatcaag ggattgaaga atg 633

<210> SEQ ID NO 794
<211> LENGTH: 414
<212> TYPE: DNA
<213> ORGANISM: Homo sapiens

<400> SEQUENCE: 794
agtccttcgc cgcattgggg caaaataatc ccttcatttt tgtgaaggta ccgtggaaaa 60
tatttcattt ttcttctcac cggagcaatt gtaaatgcta tgcggtaaga ggagttacct 120
gtggaaaggt ggttaagaga ttaggtaaag aaaaggaaag gacaccaaaa taaagtgctg 180
cggaagaatt tttgtccagc tgtgagacga cgagtgcgtg aagtgaaggc gattgagagg 240
ggctgaggga attgtcctct gtggaaggga ctttcttttg gccctaggcc ccttcctgcc 300
cctgtcgtca gcagagtctc tacaaggaag ataacggact gtaaaattct ataaagcaaa 360
gctacacatc acttgacacc atacaccatc ttggttacat aatgaagaga gatg 414

<210> SEQ ID NO 795
<211> LENGTH: 71
<212> TYPE: DNA
<213> ORGANISM: Homo sapiens

<400> SEQUENCE: 795
atgtctcttg acagcggcgg cggcgcagcc ggttccgggt tcggcgcggg gcggggatgt 60
gaatcccgat g 71

<210> SEQ ID NO 796
<211> LENGTH: 99
<212> TYPE: DNA
<213> ORGANISM: Homo sapiens

<400> SEQUENCE: 796
ccatctcttc ccttaggtgt ttaagttccg cgcgcaggcc aggctgcaac ctgacggcca 60
gatccctcgc tgtcctagtc gctgctcctt ggagtcatg 99

<210> SEQ ID NO 797
<211> LENGTH: 52
<212> TYPE: DNA
<213> ORGANISM: Homo sapiens

<400> SEQUENCE: 797
cttccttcca agaaccttcg agatctgcgg tctggggtct ggttgaaaga tg 52

<210> SEQ ID NO 798
<211> LENGTH: 78
<212> TYPE: DNA
<213> ORGANISM: Homo sapiens

<400> SEQUENCE: 798
gcaccccttc cgcgcagccc cctgacctgc agcctccgga cctcgctgca gcgcggaccc 60
ggcccgcccg cccgaatg 78

<210> SEQ ID NO 799
<211> LENGTH: 161
<212> TYPE: DNA
<213> ORGANISM: Homo sapiens

<400> SEQUENCE: 799
ccgcctcttc cgctctacag cggaggtggc tgtggcggtg gcgctggtgg ctgcggcggc 60
ggcggcggca gcggcgctcg agcggttcct gtcagggtca gccggcgggc cccctgggtg 120
gtccacctgc aaatcgcgga gcggcgcccc agggatcgat g 161

<210> SEQ ID NO 800
<211> LENGTH: 38
<212> TYPE: DNA
<213> ORGANISM: Homo sapiens

<400> SEQUENCE: 800
gcgtctcttg tttgtgcggc tgaccagttg gcgacatg 38

<210> SEQ ID NO 801
<211> LENGTH: 721
<212> TYPE: DNA
<213> ORGANISM: Homo sapiens

<400> SEQUENCE: 801
cgttcttttc tttgtatttc cgcctctcgc ctctctctaa aagccgcagt tagaggcgag 60
atttaggaaa aacctctgcc gagtgagcct ctggttggga atatgtatga gaaaaaaaaa 120
ctggcaaggc gttagtcaag caaagctgaa ggcagaggaa atttgatatc tggctggagt 180
ctagaggatt taatgcaaat aagatactct gagggcagcg tggcaaaaaa agactacaat 240
tcccggtggt cacagcgttt gagaagcgat gctttctgag acttgtagta actaggagct 300
gtgtttgaac tatccaggct caggacagcc tcttgaaaaa aaatttttta ttaataaagc 360
ggatttgagt gggatctttt tcctaatcga ttacgggccc acacgtatgg gaagaattct 420
aacaatgatt aaagggacat gctaccttta cgactatcct tttctaatcg atgactccta 480
aatctaggag taggtagtcg atgtttgtgg tctgggcgtc tgtagaaggg caacctcgtg 540
ctttctgcag aggagaccgg agggcagaag gcagagtcca ggcttagact gcagttcctc 600
gcttacctgt gcagtctaat tttgagctgc ctctttgtag tcttaaaagg caggagcttc 660
gtgttgtggg tctgctaacc cgtacgtttc cgtgggcaag tcgtgtgtac tcctcgccat 720
g 721

<210> SEQ ID NO 802
<211> LENGTH: 77
<212> TYPE: DNA
<213> ORGANISM: Homo sapiens

<400> SEQUENCE: 802
cgacctcttc aagatggcgg gcgccggaga ctagcttccg cttccggtgt gagcggcccg 60
gccggggggg caagatg 77

<210> SEQ ID NO 803
<211> LENGTH: 72
<212> TYPE: DNA
<213> ORGANISM: Homo sapiens

<400> SEQUENCE: 803
ttttctttat ggcgtgggag aggccacagc ccggactcca tcgactcccc cggctcttag 60
actaaaatca tg 72

<210> SEQ ID NO 804
<211> LENGTH: 131
<212> TYPE: DNA
<213> ORGANISM: Homo sapiens

<400> SEQUENCE: 804
ctccctcttt cttcccctct ggggaagctc agtgctggac ttccgaagac cttttacgac 60
attgagtctc ggagttggtc tcagcgccgg atccactttt cggcaaagtg acgtggacgt 120
caacagcaat g 131

<210> SEQ ID NO 805
<211> LENGTH: 800
<212> TYPE: DNA
<213> ORGANISM: Homo sapiens

<400> SEQUENCE: 805
gctcctctct ggggagtgga gggtgttcag ttattaatga ccgctgagca ggcagcacca 60
tgtcagtgtg acaactgatc gggtgaacga tgcaccacta accaccatgg aaacaaggaa 120
aaataaagcc agctcacagg atctctcttc actggattga gagcctcagc ctgccgactg 180
agaaaaagag ttccaggaaa aagaaggaat cccggctgca gcctcctgcc ttcctttata 240
ttttaaaata gagagataag attgcgtgca tgtgtgcata tctatagtat atattttgta 300
cactttgtta cacagacaca caaatgcacc tatttatacc gggcaagaac acaaccatgt 360
gattatctca accaaggaac tgaggaatcc agcacgcaag gacatcggag gtgggctagc 420
actgaaactg cttttcaagc atcatgctgc tattcctgca aatactgaag aagcatggga 480
tttaaatatt ttacttctaa ataaatgaat tactcaatct cctatgacca tctatacata 540
ctccaccttc aaaaagtaca tcaatattat atcattaagg aaatagtaac cttctcttct 600
ccaatatgca tgacattttt ggacaatgca attgtggcac tggcacttat ttcagtgaag 660
aaaaactttg tggttctatg gcattcatca tttgacaaat gcaagcatct tccttatcaa 720
tcagctccta ttgaacttac tagcactgac tgtggaatcc ttaagggccc attacatttc 780
tgaagaagaa agctaagatg 800

<210> SEQ ID NO 806
<211> LENGTH: 162
<212> TYPE: DNA
<213> ORGANISM: Homo sapiens

<400> SEQUENCE: 806
ggccctctct ccgcgcggag ccgagccgga actgcggcag tctctccctg ccaggctctt 60
catccaaggt ttctgtggat cccttctgaa gttctatctg aaaattgcgc ttaagtgaat 120
tttctgttag aagaacttgg ttgctacttt cttgtcaaga tg 162

<210> SEQ ID NO 807
<211> LENGTH: 116
<212> TYPE: DNA
<213> ORGANISM: Homo sapiens

<400> SEQUENCE: 807
ccgccccttt aacctttagg gtgcgcgggt gcagtatatc tcgcgctctc tcccctttcc 60
ccctcccctt tccccacccc gggcgctcag gttggtctgg accggaagcg aagatg 116

<210> SEQ ID NO 808
<211> LENGTH: 29
<212> TYPE: DNA
<213> ORGANISM: Homo sapiens

<400> SEQUENCE: 808
cttcctctag aacccgaccc accaccatg 29

<210> SEQ ID NO 809
<211> LENGTH: 104
<212> TYPE: DNA
<213> ORGANISM: Homo sapiens

<400> SEQUENCE: 809
gctcctcttt tccagtcctc cactgccggg gctgggcccg gccgcgggaa ggaccgaagg 60
ggatacagcg tgtccctgcg gcggctgcaa gaggactaag catg 104

<210> SEQ ID NO 810
<211> LENGTH: 383
<212> TYPE: DNA
<213> ORGANISM: Homo sapiens

<400> SEQUENCE: 810
cctcctcctt cctcctcctc ctcctccttc ttctcctcct tctcggccgg gaggaggcag 60
ggctggatcc ctcagccgcc gccgctcctc ctcctggcag gccggccgcg gagtcagctg 120
acgccggcgc tccagcctcg cctccccgcg ccgcgctctg cgctccccga aagtggctgc 180
aagccggccg cccactgtca gggttggggg gacagagaaa gtgatgtgcg ccttctaaag 240
cctcgcccag cgccgccgaa gcagcttcac ctctccaact ttctcccacc gactgcttgt 300
cttgaccctg ccctccaccc tccccagagc cacttcgggt gcgcgctctt gggtaaaggg 360
ggggtcaccg gctgtctggg atg 383

<210> SEQ ID NO 811
<211> LENGTH: 175
<212> TYPE: DNA
<213> ORGANISM: Homo sapiens

<400> SEQUENCE: 811
tctcctccat cgcctgcagt aagggcggcc gcggcgagcc tttgagggga acgacttgtc 60
ggagccctaa ccaggggtat ctctgagcct ggtgggatcc ccggagcgtc acatcacttt 120
ccgatcactt caaagtggtt aaaaactaat atttatatga cagaagaaaa agatg 175

<210> SEQ ID NO 812
<211> LENGTH: 367
<212> TYPE: DNA
<213> ORGANISM: Homo sapiens

<400> SEQUENCE: 812
tggccttttg ccctagggag cgagtgcgga gcgagtggga gcgagacggc cctgagtgga 60
agtgtctggc tccccgtaga ggcccttctg tacgccccgc cgcccatgag ctcgttctca 120
cgcgaacagc gccgtcgtta ggctggctct gtagcctcgg cttaccccgg gacaggccca 180
cgcctcgcca gggagggggc agcccgtcga ggcgcctccc tagtcagcgt cggcgtcgcg 240
ctgcgaccct ggaagcggga gccgccgcga gcgagaggag gagctccagt ggcggcggcg 300
gcggcggcag cggcagcggg cagcagctcc agcagcgcca gcaggcggga tcgaggccgt 360
caacatg 367

<210> SEQ ID NO 813
<211> LENGTH: 25
<212> TYPE: DNA
<213> ORGANISM: Homo sapiens

<400> SEQUENCE: 813
cgctcttcct caggcggcgg ccatg 25

<210> SEQ ID NO 814
<211> LENGTH: 91
<212> TYPE: DNA
<213> ORGANISM: Homo sapiens

<400> SEQUENCE: 814
cggtcttcct cctcgtcctg ccgcagggcc agaacccctg acggtattca gctgcgcgta 60
agtctggccg gtgccatctg tctccgcaat g 91

<210> SEQ ID NO 815
<211> LENGTH: 73
<212> TYPE: DNA
<213> ORGANISM: Homo sapiens

<400> SEQUENCE: 815
cggtctcctt cggcaacccc ggccgaacgg ccacccagag gctgtgctga gctggcgcag 60
cggcagcagc atg 73

<210> SEQ ID NO 816
<211> LENGTH: 170
<212> TYPE: DNA
<213> ORGANISM: Homo sapiens

<400> SEQUENCE: 816
gtttctttcc tacgcagccg ctcctgccgc cgtggtcgct ggagctttgc ctctctaggc 60
cggcagcgcc tctcctccat ggtcctgtct gtcagcgctg ttttgggagc ccgccggtga 120
ggccgggcca cgctcagaca cttcgatcgt cgagtctgtc actgggcatg 170

<210> SEQ ID NO 817
<211> LENGTH: 71
<212> TYPE: DNA
<213> ORGANISM: Homo sapiens

<400> SEQUENCE: 817
gattcttttt ggatagggtt gacgttcgtg gatagactca tatctgtgac cagtgtccgc 60
caccgcggat g 71

<210> SEQ ID NO 818
<211> LENGTH: 54
<212> TYPE: DNA
<213> ORGANISM: Homo sapiens

<400> SEQUENCE: 818
ccccctccct gcccacctcc tgcagcctcc tgcgccccgc cgagctggcg gatg 54

<210> SEQ ID NO 819
<211> LENGTH: 96
<212> TYPE: DNA
<213> ORGANISM: Homo sapiens

<400> SEQUENCE: 819
cgtcctccca agatggcgga gacagagtga agaaactgtg ttcccccctt gggttgctat 60
cgatcaaggg taaaattcca ttctgatatc aaaatg 96

<210> SEQ ID NO 820
<211> LENGTH: 342
<212> TYPE: DNA
<213> ORGANISM: Homo sapiens

<400> SEQUENCE: 820
gcttcttttt ctggtagaag gcggggttct cctcgtacgc tgcggagtct ctgcggggtg 60
tagaccggaa tcctgctgac gggcagagtg gatcagggag ggagggtcga gacacggtgg 120
ctgcaggtct gagacaaggc tgctccgagg tagtagctct cttgcctgga ggtggccatt 180
cattcctgga gtgctgctga ggagcgaggg cccatctggg gtctctggaa gtcggtgccc 240
aggcctgaag gatagccccc cttgcgcttc cctgggctgc ggccggcctt ctcagaacga 300
agggcgtcct tccaccccgc ggcgcaggtg accgctgcca tg 342

<210> SEQ ID NO 821
<211> LENGTH: 134
<212> TYPE: DNA
<213> ORGANISM: Homo sapiens

<400> SEQUENCE: 821
aggcctctcc aagcccctac cgcacaggct catagcccca agcccggagg aggtggctac 60
attgtgtcta ttgtatccct tggctggtgt atttgtacat ctctcgggac gtgaaattga 120
cagtgaaaag tatg 134

<210> SEQ ID NO 822
<211> LENGTH: 245
<212> TYPE: DNA
<213> ORGANISM: Homo sapiens

<400> SEQUENCE: 822
cttcctctgg cggcgtccgg ccgcttctcc tctgctcctc gaagaaggcc agggcggcgc 60
tgccgcaagt tttgacattt tcgcagcgga gacgcgcgcg ggcactctcg ggccgacggc 120
tgcggcggcg gccgaccctc cagagcccct tagtcgcgcc ccggccctcc cgctgcccgg 180
agtccggcgg ccacgaggcc cagccgcgtc ctcccgcgct tgctcgcccg gcggccgcag 240
ccatg 245

<210> SEQ ID NO 823
<211> LENGTH: 362
<212> TYPE: DNA
<213> ORGANISM: Homo sapiens

<400> SEQUENCE: 823
cgtccttctc gcgcctcgct ctggccctgc aggttgtgtt tccgcctcta ccccgcctcc 60
attccgttgc tctctcagtc tcagacccgg gctctcggtc cgccgcttca ggtcttggcg 120
cagcctcaga gagttggcgc ggctctgtgt tgaccaaacc tagtggatgc agttagcgcc 180
ggagcccggc cccgcccgtc accagggtta ttcccgcctt ctaggtttgc caggactgcc 240
ggccctgcag ctgccttctg ccccaggttt ttggctactg atgttacaaa caataaaata 300
ttggagcata gagttgaaga acagactcaa accaggtttt tatttaatta gttaaaaata 360
tg 362

<210> SEQ ID NO 824
<211> LENGTH: 298
<212> TYPE: DNA
<213> ORGANISM: Homo sapiens

<400> SEQUENCE: 824 tttcctttc cctccccctg gagctgtagc ggcagcagca gcaggaagcc gagccgggtt 60
gagcgactcg gaggcgagcg gaggagctgg aatatgggga gtcagcgagg acggtggggc 120
caggagccct tgggagggcc tacggaggga gcggccccag gcgctttcta gagcgtgagc 180
ggtgggggag caggcgcagg gtggcacgag cggaggcggg gcccgggcgt ggggcacggc 240
tggggaagct gccgcctccg gccctgcccg gctgcctccg ccgcggccag tggctatg 298

<210> SEQ ID NO 825
<211> LENGTH: 357
<212> TYPE: DNA
<213> ORGANISM: Homo sapiens

<400> SEQUENCE: 825 gttcctttt gggttagctt tggcagtatt gagttttact tcctcctctt tttagtggaa 60
gacagaccat aatcccagtg tgagtgaaat tgattgtttc atttattacc gttttggctg 120
ggggttagtt ccgacacctt cacagttgaa gagcaggcag aaggagttgt gaagacagga 180
caatcttctt ggggatgctg gtcctggaag ccagcgggcc tcgctctgtc tttggcctca 240
ttgaccccag gttctctggt taaaactgaa agcctactac tggcctggtg cccatcaatc 300
cattgatcct tgaggctgtg cccctggggc acccacctgg cagggcctac caccatg 357

<210> SEQ ID NO 826
<211> LENGTH: 118
<212> TYPE: DNA
<213> ORGANISM: Homo sapiens

<400> SEQUENCE: 826
gcttctcttc cgctccgggt cggctccgtt tccctttccg ggcgggcagg cggcggaccc 60
cagtgtcttt atccctcttt tgcacagtca gcttctgcag ctctcccggg ctagcatg 118

<210> SEQ ID NO 827
<211> LENGTH: 62
<212> TYPE: DNA
<213> ORGANISM: Homo sapiens

<400> SEQUENCE: 827
cgacctcttg gctccgctag tgcccggcgc gccgccgcca gtgctgcggg ctccgggcaa 60
tg 62

<210> SEQ ID NO 828
<211> LENGTH: 879
<212> TYPE: DNA
<213> ORGANISM: Homo sapiens

<400> SEQUENCE: 828
ctttctctca ggaaactcca ctcccaactg acaggtgcta tttccagcca gtcctatgct 60
gttgcaaata gtgagtccat gaatgccctc tgccgtgtgc attacttatt ttcatcagca 120
gatcttcgta acacactcct ggaagtggga tgacggggtc aaaaggcgaa tccatacata 180
agttaaatag atattgctca attctcttcc acggggttca gaccattttg gatttctacg 240
agcaatgaag acagtgctat tcctctacac cctggccggc caactgagcg tggttaaacg 300
tggggaggga ggagggtgag gttaccaacc tgatggttga gaaagggcct ccgcccagcg 360
cgcccttcct ccaccccac ccgagagaca gctgaactcc ggccgggacg cgcgtgttgc 420
cagtccagcc ctgcaccgcg tcccctgagg gcgggctgca ggcggccggg aagccttgca 480
caaccggccc aaaagaggaa gcccagaaag tgctgaagta aacactttgg gagaccgttg 540
caacataaag cggcctctca gtctttggtg gaaccatcac taggccccaa tcccttagtc 600
cctcttgcgt cgaggctgca aaatggttcc attcgccagg agacgctcct gagagaaggg 660
cgcgcgcggc acaggggcct tccttgcacc tcggagcaaa gcagctcgga tagcgccaca 720
cgtctgcgcg ctgcgtggga agggcagggc tgacagcact tcctccccgg ggcagcgacc 780
tggagcccgg gtgcggcagt ctgcaccgcg cgtcgctttc ccggccggag tctcgccgcc 840
ttcccgcgcc ccgcagcgcc ccgcagagca gtcgagatg 879

<210> SEQ ID NO 829
<211> LENGTH: 77
<212> TYPE: DNA
<213> ORGANISM: Homo sapiens

<400> SEQUENCE: 829
ccttccctct tcactgtgag ctcagagcag caggacaaag tgctcgggac aaggacatag 60
ggctgagagt agccatg 77

<210> SEQ ID NO 830
<211> LENGTH: 77
<212> TYPE: DNA
<213> ORGANISM: Homo sapiens

<400> SEQUENCE: 830
acctcctttc cctttcggat tcccgacgct gtggttgctg taaggggtcc tccctgcgcc 60
acacggccgt cgccatg 77

<210> SEQ ID NO 831
<211> LENGTH: 76
<212> TYPE: DNA
<213> ORGANISM: Homo sapiens

<400> SEQUENCE: 831
ttttctttta ttcttgtctg ttctgcctca ctcccgagct ctactgactc ccaacagagc 60
gcccaagaag aaaatg 76

<210> SEQ ID NO 832
<211> LENGTH: 46
<212> TYPE: DNA
<213> ORGANISM: Homo sapiens

<400> SEQUENCE: 832
cctcctctac tatctcggta tcaccaaacc cttgccggct cttatg 46

<210> SEQ ID NO 833
<211> LENGTH: 350
<212> TYPE: DNA
<213> ORGANISM: Homo sapiens

<400> SEQUENCE: 833
ctgcctctta tgaagcaata ctagagagga aaaacaaaac ccattccttt aagaaagatt 60
ccgcctcctc tcataagcaa gcgcctaatg gtaattgtag agtttactaa gtcaaacact 120
tactactcag cattgagaga agctgctgct gctaatgctg ctgctgctgc tgccgccgcc 180
gccgctgctg ctgctgctgt tggtctgagg ctgcagtagg tttctgtgca gcattgcaga 240
atccacacct agagaacaga agacacagac acgtacgtct actacccttg ttagaaggaa 300
gctttggatc ttcggtggat aacaagagta atccacagac ttaaaacatg 350

<210> SEQ ID NO 834
<211> LENGTH: 199
<212> TYPE: DNA
<213> ORGANISM: Homo sapiens

<400> SEQUENCE: 834 agccctttg gatctaatgc gcagaggagg ttggcccaga gctcccgggc tcccccaagg 60
ctgaactccg tccaaggtgc ccgcaggctc cctgcccgcc ttccccatgc cagcccgcag 120
ctaggggcag gggcagcggc ggctggggtt gggggtgggt ggggagcttt tggggaggac 180
aggtcgcagc ttggctatg 199

<210> SEQ ID NO 835
<211> LENGTH: 279
<212> TYPE: DNA
<213> ORGANISM: Homo sapiens

<400> SEQUENCE: 835
ttatcttttt gcctagcgac tgacaacagg ctggttgctt ggcgtggaat cctaaagtgg 60
cctggctttg agactggagt gagaccccag ccctaggctg ggttctttc cattatagag 120 gagacggatt cagaagggct acagaccaag gttgttgaaa accagacata tgatgagcgt 180
ctagagatta acgactccga agaggttgca agtatttata ctccaacccc aagacaccaa 240
ggacttcctc gttctgccca tcttcctaac aaggctatg 279

<210> SEQ ID NO 836
<211> LENGTH: 1573
<212> TYPE: DNA
<213> ORGANISM: Homo sapiens

<400> SEQUENCE: 836 ccccctttc gggaggaggg aggcagggac ttgcaggcaa gagttgcacc tggtctagga 60
acctgcagag aaaagaactc tggggtaagt agtgttctgg cactggcacg gaaaggggta 120
aagggtgggg ggcatgagag ggacgaaatg gagagggcag ggaatgaatt atgcaaaaaa 180
atctccaata tttcgcagcg gagggagagc acagcacagc actcccagga tgagtcctgc 240
ctgggtctcc cgcgccgaac ccgcagcacg aagttctttt taagaagaga aactcgaaaa 300
tcctggaggg taacagaggc agccagggcg gggcggagtg cggaggcggc tgccagggac 360
tggggccgag gcggcggcca aggtggcctg aagctgtgac acccagcctc ctcctcctcc 420
tcctcatggc cgcgctcagc ctcacctccc cgcccgggcc tcctgcctcc gcccccgggt 480
gccgggctgc ggagctgacg ctgggacgcc cggcggcggc gaggacgctc acctggccaa 540
gcctccttct cctcctcccc ctcccgcccc cacctgtcct cctcctctct gagttgggaa 600
gcgtagggat ccgtaggcga ggaaataacg accccctgcag ttgtattgcg gaaaatctcg 660
acagcggcgc tagttgcggg cgatggaagc caggcaactg gggttctgg ggagttcagg 720 aaaatagcag aggagcagga agggcgcgcg cgacctggag agtctgtgtg cccccaccgc 780
gccccagtcc ccggggccca gcccttcccc tcggcgccct ggacgcactg ccggaacccg 840
gctgagaggc tgcaggctgc gcgcggacct ggggagcagg gagggtcggc ggaggctgcc 900
ggcggctggc ggtttcgggc aataatccct gcctctcttt ctctgtgtgt ctgctgtgtc 960
tgctccttcc ccgcccccg gaagcaggag aagaactgcc ccggagcgca gcagccaccc 1020
tccgaccatg ccccggtgag gggggcggac ttcgagggca acttgccgcg gactgcctgg 1080
gcttagccag cgagctacgc gctcccggga gcccggaatt gcacggcgca gcccggcggg 1140
gggctatcgt ctatgtcttc ttggggcgcc agacgaatcg gggtctcgtt tttgctggaa 1200
gagcccagtg ttggtggctt caggtggctg ctgccgccgc cgccgccgcc gccgctgcta 1260
gtgcggtttc cgccgctggt gcgaagagaa gagacacgcg agcggggaga cctccaaggc 1320
agcgaggcat cggacatgtg tcagcacatc tggggcgcac atccgtcgag cccgagggga 1380
gatttgccgg aacaattcaa actgcgatat tgatcttggg ggtgactgtc cctggccggc 1440
tgtcgggtgg gagtgcgagt gtgcactcgc tcggaagtgt gtgcgagtgt gtatgtgtgt 1500
gtgccgtgtc gggctccccc cttccccccg ttttcccgtc gagtgatgca cttggaatga 1560
gaatcagagg atg 1573

<210> SEQ ID NO 837
<211> LENGTH: 76
<212> TYPE: DNA
<213> ORGANISM: Homo sapiens

<400> SEQUENCE: 837
cctcctccct gtaacatgcc atagtgcgcc tgcgaccaca cggccggggc gctagcgttc 60
gccttcagcc accatg 76

<210> SEQ ID NO 838
<211> LENGTH: 38
<212> TYPE: DNA
<213> ORGANISM: Homo sapiens

<400> SEQUENCE: 838
gttccttcta ctctggcacc actctccagg ctgccatg 38

<210> SEQ ID NO 839
<211> LENGTH: 36
<212> TYPE: DNA
<213> ORGANISM: Homo sapiens

<400> SEQUENCE: 839
ccgtcttccc ttcccgcgtt ccccgggaga aacatg 36

<210> SEQ ID NO 840
<211> LENGTH: 35
<212> TYPE: DNA
<213> ORGANISM: Homo sapiens

<400> SEQUENCE: 840
cctcctttcc gcttccggtg tcccctacag tcatg 35

<210> SEQ ID NO 841
<211> LENGTH: 76
<212> TYPE: DNA
<213> ORGANISM: Homo sapiens

<400> SEQUENCE: 841
gctcctcctg ctggctgggg attttccagc ctgggcgctg acgccgcgga cctccctgcg 60
accgtcgcgg accatg 76

<210> SEQ ID NO 842
<211> LENGTH: 130
<212> TYPE: DNA
<213> ORGANISM: Homo sapiens

<400> SEQUENCE: 842
cctcctctcg cgagaggcgc aaggcgtgga gtcgacggct ggagagaagc cgggagcgag 60
cccaggcggc agtcttgatt cccttttggc cagcagtttt taggtctgtc agtactgcac 120
tgcaagaatg 130

<210> SEQ ID NO 843
<211> LENGTH: 113
<212> TYPE: DNA
<213> ORGANISM: Homo sapiens

<400> SEQUENCE: 843
taccctcctt ccccattttc tgtggtccaa ctaccctcgg cgatcccagg cttggcgggg 60
caccgcctgg cctctcccgt tcctttaggc tgccgccgct gcctgccgcc atg 113

<210> SEQ ID NO 844
<211> LENGTH: 174
<212> TYPE: DNA
<213> ORGANISM: Homo sapiens

<400> SEQUENCE: 844
agccctccct tccgcgcgct tactttgttt ataacttgaa aaatcctctc cgtctccctt 60
ccctgcctcc tttcctttcc ctttcctctg ccagtacaac tagacccggc gtctggcgtc 120
cccggtgccc agcattctgc ggggcaggcg gattaattgg aattcttcaa aatg 174

<210> SEQ ID NO 845
<211> LENGTH: 185
<212> TYPE: DNA
<213> ORGANISM: Homo sapiens

<400> SEQUENCE: 845
cctccttccg gctgggcaag gggccgcggg gagcagctcg ggactgaacc gagaggtgcc 60
gaaggaaccg gcgggccgct tgatcccgct gcagacgtag gagatgcctg ggacaaggag 120
gccaccttct cagggcaaaa gaaaaagaag gtgacaggcg ttgagaccac cgaagggaac 180
ccatg 185

<210> SEQ ID NO 846
<211> LENGTH: 125
<212> TYPE: DNA
<213> ORGANISM: Homo sapiens

<400> SEQUENCE: 846
agttctctct gggaacatct ggtgggtact acaggcccta ttccaggccc tatggcctgt 60
ggaacctcac cacggggggg agggctgggc cagacggaga catcacctgt ggtgtcagcc 120
ccatg 125

<210> SEQ ID NO 847
<211> LENGTH: 82
<212> TYPE: DNA
<213> ORGANISM: Homo sapiens

<400> SEQUENCE: 847
cctccttcgc gccggccctt ccgcgggtga tcagctggtc tgcgctcccc tgacgtgggc 60
tggggcacgt caccgccgaa tg 82

<210> SEQ ID NO 848
<211> LENGTH: 153
<212> TYPE: DNA
<213> ORGANISM: Homo sapiens

<400> SEQUENCE: 848
gggtctcttc cggagtcttt tcctggacgg ggtccctgcg gtgggtgtgt ttcggcctgg 60
cctgggcagg cgcttgtgct gccagggcgc cgggcccggg gaggccgggg tctcgggtgg 120
ccgccggccc aggcgctgga cggcagcagg atg 153

<210> SEQ ID NO 849
<211> LENGTH: 16
<212> TYPE: DNA
<213> ORGANISM: Homo sapiens

<400> SEQUENCE: 849
ttttctttcc aaaatg 16

<210> SEQ ID NO 850
<211> LENGTH: 54
<212> TYPE: DNA
<213> ORGANISM: Homo sapiens

<400> SEQUENCE: 850
ggttcttcac tcgcgactga cggagctgcg gtggcgtctc cacacgcaac catg 54

<210> SEQ ID NO 851
<211> LENGTH: 289
<212> TYPE: DNA
<213> ORGANISM: Homo sapiens

<400> SEQUENCE: 851
ccttcttcct cttgttcctc ctcctgcctc tcttcgcttc gcctgcaaac gcggtggggg 60
ctgctcggcg gtcaggagca ggttaccctc cgtctgcatg cccaccatca aggtatgagg 120
atggtagaag ctctcgtcga accagatgga tgaagaccac taacggcttt tgtttcctct 180
ggtaacagca agagacagag cgacatgaga gattggaccg cgggctgcac tggagaattt 240
actggtagga taattcatcc ctaaagagat tgaagtgagc ttcagaatg 289

<210> SEQ ID NO 852
<211> LENGTH: 151
<212> TYPE: DNA
<213> ORGANISM: Homo sapiens

<400> SEQUENCE: 852
cggcctccgc ccctgcagcc gcgggcacgc ggaggggctc ctggctgccc gcacctgcac 60
ccgcgcgtcg gcggcgccga agccccgctc cccgcctgcg cgtctgtctc gtccgcatct 120
ccgcggcctc ctgctccacg acgtgaccat g 151

<210> SEQ ID NO 853
<211> LENGTH: 113
<212> TYPE: DNA
<213> ORGANISM: Homo sapiens

<400> SEQUENCE: 853
ttttcttctc gggctgcaaa caaagggaag cctgcaacaa gttaagctga agaccgaagc 60
aagagctggt tcaggtggca gccacagcag cctcagggac ctcagcaact atg 113

<210> SEQ ID NO 854
<211> LENGTH: 198
<212> TYPE: DNA
<213> ORGANISM: Homo sapiens

<400> SEQUENCE: 854
ctgtctcttt aaggtgcccg aggctcgcgg gcgctgcgct gaggggacgg cgggaggcgc 60
ggcctggcct cgcactcaaa gccgccgcag cgcgccccgg gctcggccga cccggcgggg 120
atctaggggt gggcgacttc gcgggaccgt ggcgcatgtt tcctgggagt tactgatcat 180
cttctttgaa gaaacatg 198

<210> SEQ ID NO 855
<211> LENGTH: 313
<212> TYPE: DNA
<213> ORGANISM: Homo sapiens

<400> SEQUENCE: 855
gtcccctttg tgaggcccgg gatgggaggt gcccggttcc cccagggaca gcttcaagcg 60
gtagggacag acatctgagg acccagcctc agggatgctg tccccgggct tccaggctcc 120
agcgccgtag gactgaggca gactccacgg tgagaaagag acccgatcta acccaggcct 180
ttcatcagag cccaggaggg aaggcaggaa gtgggaccac gaggcccggg gggcttctaa 240
ctcgtctggc cagggagatc tgaattgggg tgaagagcag aatctccaga acaaggagga 300
ggtggtgatc atg 313

<210> SEQ ID NO 856
<211> LENGTH: 115
<212> TYPE: DNA
<213> ORGANISM: Homo sapiens

<400> SEQUENCE: 856
gctcctcctg tcttgtctca gcggctgcca acagatcatg agccatcagc tcctctgggg 60
ccagctatag gacaacagaa ctctcaccaa aggaccagac acagtgggca ccatg 115

<210> SEQ ID NO 857
<211> LENGTH: 81
<212> TYPE: DNA
<213> ORGANISM: Homo sapiens

<400> SEQUENCE: 857
tgctcttctc gttcccgaga tcagcggcgg cggtgaccgc gagtgggtcg gcaccgtctc 60
cggctccggg tgcgaacaat g 81

<210> SEQ ID NO 858
<211> LENGTH: 24
<212> TYPE: DNA
<213> ORGANISM: Homo sapiens

<400> SEQUENCE: 858
ctgtctttac ccagagctac catg 24

<210> SEQ ID NO 859
<211> LENGTH: 648
<212> TYPE: DNA
<213> ORGANISM: Homo sapiens

<400> SEQUENCE: 859
ctctcttttt cttgcagaac cgtctctctc ccttctctgt ctcttagcac agagctctta 60
ttcagccact agcttggccc ttcctgcttc aattgtaatg cttgttctgc ccgtccacag 120
actattggcg gcagaaacaa cgaatttcct ccaaactagg cggtgttggt ggctcttgca 180
ttcctctgga tgaggaaatc tagttggggg gttccagaag gggaaggctc ctgggctttc 240
aatacatcct cctgaatcat acctcgtttc gggttcccta gaaaaatctg gacgtgtaaa 300
aagaactctt aacggccgat gcagctcttc caaagctaag gctgccttgg agttttcata 360
agaaattgtc cctggaggtg ttggatgatc acagcttcct tggagcattg cagttgctgg 420
aatccagttt caggattaag ggagggctgc ctccttgcaa tgggctgcca agaaaacggc 480
tgtgcttgtt cttaacctca ggctctgtct gtgatcagtc tgagagtctc tcccaggtct 540
actgctccct ggaaagccct atctctctgc aggctcgcct ctgggctttg tctccttgga 600
gccacatcac tgggacagct gtggatgtgg atgcagattt gaaccatg 648

<210> SEQ ID NO 860
<211> LENGTH: 144
<212> TYPE: DNA
<213> ORGANISM: Homo sapiens

<400> SEQUENCE: 860
ccgcctcctc gctgcgggaa gggtcctggg ccccgggcgg cggtcgccag gtctcagggc 60
cgggggtacc cgagtctcgt ttcctctcag tccatccacc cttcatgggg ccagagccct 120
ctctccagaa tctgagcagc aatg 144

<210> SEQ ID NO 861
<211> LENGTH: 49
<212> TYPE: DNA
<213> ORGANISM: Homo sapiens

<400> SEQUENCE: 861
ctgtctccat cttgtctgta tccgctgctc ttgtgacgtt gtggagatg 49

<210> SEQ ID NO 862
<211> LENGTH: 87
<212> TYPE: DNA
<213> ORGANISM: Homo sapiens

<400> SEQUENCE: 862
cctcccnttt ttttccgcct tctgccagca gaagcagcag ccgcagcacc tgagccgcta 60
ctgccgctca ctcaggacaa cgctatg 87

<210> SEQ ID NO 863
<211> LENGTH: 161
<212> TYPE: DNA
<213> ORGANISM: Homo sapiens

<400> SEQUENCE: 863
ggacctccct ctttgcctcc tccctgttcc aggagctggt gccctgggct ctgcgctgtt 60
gttttcagcg ctccgaaagc cggcgcttga gatccaggca agtgaatcca gccaggcagt 120
tttcccttca gcacctcgga cagaacacgc agtaaaaaat g 161

<210> SEQ ID NO 864
<211> LENGTH: 187
<212> TYPE: DNA

<213> ORGANISM: Homo sapiens

<400> SEQUENCE: 864
cttccttctg gagctgggtc ctgactaggg accgcctggg tgaggtgagg acctggtggc 60
cgcagttgtg gcactgtgcg caggcgctga actgaccgga cggagcgggc ggctgtggcc 120
tcgccagctg gtttaaaaat atcctttttt gctgaaggaa cacatttgct ggtatagttt 180
cagaatg 187

<210> SEQ ID NO 865
<211> LENGTH: 388
<212> TYPE: DNA
<213> ORGANISM: Homo sapiens

<400> SEQUENCE: 865
ctatcctttc ctctcagtcc tgccatctag ctgccttggg tctcgcgctc cgcagagcgt 60
tccgacactc tccggcctcg ttctgccgcc tccgcgcgct ctccccgtgc ggccaccgcg 120
ccccccaagc ttgcctcctt cttgccggac ttggggccgc gcgccctgac tccttcccct 180
cccgcggacc cgcgcactcc cggcgcggcc tctcccccac gcaggccacc gtgcactctg 240
tggcctcccc ctccttcccc gctctcctcg cgcttctctg gctccctagc tgtcgcgctc 300
tcctcggcga gcgcgctccc ggcccgcgcg ctccgggctc cggtttctcc cggctcctgt 360
cagtgcggtg actgcgctgg gaaacatg 388

<210> SEQ ID NO 866
<211> LENGTH: 488
<212> TYPE: DNA
<213> ORGANISM: Homo sapiens

<400> SEQUENCE: 866
ccttctcctg agagtcggag ccacagccag agccctgccc aggccgagcc ggagctgcag 60
cccgagcgcg gtggtgccct cagccccgtc ctcttgtcct cctcagcctc ggtgccttgg 120
aatttgtgtc gctgagtcag caagcctttc agatttgccc ggtttttgtt gtttgtggtt 180
tgtatcaaga tgggaactca aacaagtcat tcctcctaag gagctggtgt cttcatccag 240
aagggacagt ttgtgccagc tctccagaga gaaaaggatc tggtactgtt ctggagtggc 300
ctgtagcaga cactgaacca ccagccagct gcatttgttg tcctggaagt cattgccaac 360
tctgccagtc acactggggt ccccagagaa gtcaagatct gccggaggcg ctgggcaatg 420
accccgggac tccaggccag aggggtctga agctgtttgg gaaagcagcg ggactccttg 480
ggaagatg 488

<210> SEQ ID NO 867
<211> LENGTH: 191
<212> TYPE: DNA
<213> ORGANISM: Homo sapiens

<400> SEQUENCE: 867
ctgccttttt caccacctct aatttcagct tcagcagttg cttggaactt tggttctggc 60
agcagcagca acatcattac cgctagcggc agttttgtgc cgaggcacct acacacctcc 120
cgtcctctct gccagatcgc gggcctgtcg gtgtctgctc ctacacgcca acgccggtgg 180
gcaggaccat g 191

<210> SEQ ID NO 868
<211> LENGTH: 61

<212> TYPE: DNA
<213> ORGANISM: Homo sapiens

<400> SEQUENCE: 868
cgccctttca ccccggacgt gggcgggaga ggaagcggct ggtgatgctg gaacaaacat 60
g 61

<210> SEQ ID NO 869
<211> LENGTH: 99
<212> TYPE: DNA
<213> ORGANISM: Homo sapiens

<400> SEQUENCE: 869
cgctctttct ccgacagctg ccgggggtgc cctgcaagct gttccgcgcg tcctgcccgt 60
ctgtccccgc gggtcgtcgc ccgccacagc cgcgccatg 99

<210> SEQ ID NO 870
<211> LENGTH: 90
<212> TYPE: DNA
<213> ORGANISM: Homo sapiens

<400> SEQUENCE: 870
cgctcttttg tttcttgctg cagcaacgcg agtgggagca ccaggatctc gggctcggaa 60
cgagactgca cggattgttt taagaaaatg 90

<210> SEQ ID NO 871
<211> LENGTH: 168
<212> TYPE: DNA
<213> ORGANISM: Homo sapiens

<400> SEQUENCE: 871 agacccttttt cagacccttt tccggctgac ttctgagaag gttgcgcagc agctgtgccc 60
ggcagtctag aggcgcagaa gaggaagcca tcgcctggcc ccggctctct ggaccttgtc 120
tcgctcggga gcggaaacag cggcagccag agaactgttt taatcatg 168

<210> SEQ ID NO 872
<211> LENGTH: 92
<212> TYPE: DNA
<213> ORGANISM: Homo sapiens

<400> SEQUENCE: 872
gggtcctttt tcctctcttc agcgtggggc gcccacaatt tgcgcgctct ctttctgctg 60
ctccccagct ctcggataca gccgacacca tg 92

<210> SEQ ID NO 873
<211> LENGTH: 79
<212> TYPE: DNA
<213> ORGANISM: Homo sapiens

<400> SEQUENCE: 873
ggctctctcc ttgtcagtcg gcgccgcgtg cgggctggtg gctctgtggc agcggcggcg 60
gcaggactcc ggcactatg 79

<210> SEQ ID NO 874
<211> LENGTH: 102
<212> TYPE: DNA
<213> ORGANISM: Homo sapiens

<400> SEQUENCE: 874
ggctctttcc gctatctgcc gcttgtccac cggaagcgag ttgcgacacg gcaggttccc 60
gcccggaaga agcgaccaaa gcgcctgagg accggcaaca tg 102

<210> SEQ ID NO 875
<211> LENGTH: 256
<212> TYPE: DNA
<213> ORGANISM: Homo sapiens

<400> SEQUENCE: 875
gatccctttc ccagtcctgc ttcccagtgc ctcgggccag ggaatcctgg cctccgcctg 60
cggagccggc ggaacccgct tcccgcctcc acggggcagc gccagcggcc tggtcctttc 120
accggcagct ccgtgccgac gctctcaccg ctcttcctat cgccgggagt ggcgggccga 180
ccagggggcg gccgggctac cgtccgccat tcccgtgtct ctgcgcccgc gggggccgcc 240
cgagccggcc accatg 256

<210> SEQ ID NO 876
<211> LENGTH: 193
<212> TYPE: DNA
<213> ORGANISM: Homo sapiens

<400> SEQUENCE: 876
ccgccttttc cagttccagg tgtgcagaag tgtcctctcc ccacgcgcgg cgggctgcac 60
ttggtcgctg gctccgagat cgcgcggggc cgccggaagc ccaagacggt accgggggcc 120
gcagccgcag ccggcgccgc cctccgccct ccccaacagc aggccgagtc ccgtagcatc 180
cggtagggaa atg 193

<210> SEQ ID NO 877
<211> LENGTH: 389
<212> TYPE: DNA
<213> ORGANISM: Homo sapiens

<400> SEQUENCE: 877
agctctttcc gggggcccgg ggaactactc tccttgcctc gctctgtctc cttcgaagtg 60
ctctgcgcga ggttcagagc ggccgccgcc tccaaaggga cggttttcta gagctccgac 120
gcctctcggt gcccctctgc tccggccctt gccctttgac ctcgctctcg cggcagggtg 180
agaggtcggg tggccatctt gtggcggcgg cgcgggcggc tgttactgcg gagacccatc 240
ccctccccct tctcgcaccc ctggcagtct gtcagtcggt aaaaagtccc gcagcctgtc 300
aggtgaggcc ccggcctcgt gccgtcgctc ttcccgccgc actgggcggc ccaggccgct 360
ccctgccggg cctcactgcc gccaccatg 389

<210> SEQ ID NO 878
<211> LENGTH: 274
<212> TYPE: DNA
<213> ORGANISM: Homo sapiens

<400> SEQUENCE: 878
ctatctttct agacaaggca gttgaggagg agggagcgct tgagggggac tggcctggcg 60
tgcactccgc acctcgggga cattattgcg cgtggaacgg ctgcttttgg aaggcacaac 120
ttcctgaatg gaccatgact cccaccaaag atccctgtct ctgattcacc aaacagcttc 180
aaccctgaaa ccaggacgag aagttgacaa catctgagtg gacagctaat tgacctaaga 240
cttcagacca gactattgcc cagaagaaaa gatg 274

<210> SEQ ID NO 879
<211> LENGTH: 513
<212> TYPE: DNA
<213> ORGANISM: Homo sapiens

<400> SEQUENCE: 879
gggcctttta tctcggtgct gccgggggag gcgggaggag gagacaccag gggtggccct 60
gagcgccggc gacacctttc ctggactata aattgagcac ctgggatggg tagggggcca 120
acgcagtcac cgccgtccgc agtcacagtc cagccactga ccgcagcagc gcccttgcgt 180
agcagccgct tgcagcgaga acactgaatt gccaacgagc aggagagtct caaggcgcaa 240
gaggaggcca gggctcgacc cacagagcac cctcagccat cgcgagtttc cgggcgccaa 300
agccaggaga agccgcccat cccgcagggc cggtctgcca gcgagacgag agttggcgag 360
ggcggaggag tgccgggaat cccgccacac cggctatagc caggccccca gcgcgggcct 420
tggagagcgc gtgaaggcgg gcatcccctt gacccggccg accatccccg tgcccctgcg 480
tccctgcgct ccaacgtccg cgcggccacc atg 513

<210> SEQ ID NO 880
<211> LENGTH: 137
<212> TYPE: DNA
<213> ORGANISM: Homo sapiens

<400> SEQUENCE: 880
ctctcccttt gtcattctag ctgcctgctg cctccgcagc gtccccccag ctctccctgt 60
gctaactgcc tgcaccttgg acagagcggg tgcgcaaatc agaaggatta gttgggacct 120
gccttggcga ccccatg 137

<210> SEQ ID NO 881
<211> LENGTH: 60
<212> TYPE: DNA
<213> ORGANISM: Homo sapiens

<400> SEQUENCE: 881
cttcctcttt tctaagcttg tctcttaaaa cccactggac gttggcacag tgctgggatg 60

<210> SEQ ID NO 882
<211> LENGTH: 501
<212> TYPE: DNA
<213> ORGANISM: Homo sapiens

<400> SEQUENCE: 882
ctttctcttt ttgtttggct tctaacgcgt tgggactgag tcgccgccgt gagctccccg 60
aagactgcac aaactaccgc gggctcctcc gccccgtctg cgattcggaa gccggcctgg 120
gggtcgcgtc gggagccctg gcgctgcagc tccgcacctt agcagcccgg gtactcatcc 180
agatccacgc cggggacaca cacacagagt aactaaaagt gcggcgattc tgcacatcgc 240
cgactgcttt ggggtaacaa aaagacccga gttgcctgcc gaccgaggac ccccgggagc 300
cgggctcgga gcagacgagg tatccggcgg cgcccatttg gggcttcta actctttctc 360 cacgcagccc ctcttctgtc ccctcccctc tcgctccctt ttaaaatcag tggcaccgag 420
gcgcctgcag ccgcactcgc cagcgactca tctctccagc gggttttttt ttgtttgtcg 480
tgtgcgatcc tcacactcat g 501

<210> SEQ ID NO 883
<211> LENGTH: 424
<212> TYPE: DNA

<213> ORGANISM: Homo sapiens

<400> SEQUENCE: 883
cgtcctctcc gggggcggag cgggtcggcg ggcctgacag ggaacctccc tgaccgagcc 60
cacgtctccc cacggccaga gaaatctccg gcccggcccg catcgccagc cccccaggccc 120 ggaggaacgg cccgagccca ggagaaccac atcttcgtcc cagccccgga ggctcctgtg 180
ggcaagatcg tgagccaacg ggttcctgag gcccctcctg gccaggcagg gtttccccgc 240
gcgtttccga ggagccctgc ctggccgggc ggctggacaa acaggtcgta gcaccgatcg 300
cgcccgcccc cagcaggggt cccgcacagg cttgcccctg acccccaccc aaacctgtcc 360
ttccgctttg cccccaaaca gtgcacttgc cggcggtccc aacccagcag gagaagtgga 420
catg 424

<210> SEQ ID NO 884
<211> LENGTH: 22
<212> TYPE: DNA
<213> ORGANISM: Homo sapiens

<400> SEQUENCE: 884
ggctctcccc gcgtccaaga tg 22

<210> SEQ ID NO 885
<211> LENGTH: 153
<212> TYPE: DNA
<213> ORGANISM: Homo sapiens

<400> SEQUENCE: 885
gcgccttcct cttcccatcg cgcgggtcct agccaccggt gtctccttct acatccgcct 60
ctgcgccggc tgccacccgc gctccctccg ccgccgccgc cttgctgctg ctcaaagctg 120
ctgccgcccc ttgggctaaa aggttttcaa atg 153

<210> SEQ ID NO 886
<211> LENGTH: 304
<212> TYPE: DNA
<213> ORGANISM: Homo sapiens

<400> SEQUENCE: 886
ctttctcttt ccctttgcaa ttgccttggg tcctgccgca cagagcggcc tgtctttatc 60
agaggtccct ctgccagggg gagggcccca gagaaaacca gaaagagggt gagagactga 120
ggaagataaa gcgtcccagg gcctcctaca ccagcgcctg agcaggaagc gggaggggcc 180
atgactacga ggccctggga ggtcacttta gggagggctg tcctaaaacc agaagcttgg 240
agcagaaagt gaaaccctgg tgctccagac aaagatctta gtcgggacta gccggccaag 300
gatg 304

<210> SEQ ID NO 887
<211> LENGTH: 251
<212> TYPE: DNA
<213> ORGANISM: Homo sapiens

<400> SEQUENCE: 887
gctcctcctc ctcccctccg tcggtcagtc agtccgcgag gagagtccgc ggtggcggcg 60
acggtggcga gagccgcggg ggccgtagga agccaacctt ccctgcttct ccggggccct 120
cgccccctcc tccccacaaa atcagggatg gaggcgcctc cccggcaccc tcttagcagc 180
cctccccagg aaaagtgtcc cccctgagct cctaacgctc cccaacagct acccctgccc 240
cccacgccat g 251

<210> SEQ ID NO 888
<211> LENGTH: 71
<212> TYPE: DNA
<213> ORGANISM: Homo sapiens

<400> SEQUENCE: 888
cctccttctc ctcccagtgc cacagagccg aagcccgagc tgccgccgca gccacagccg 60
agggcactat g 71

<210> SEQ ID NO 889
<211> LENGTH: 20
<212> TYPE: DNA
<213> ORGANISM: Homo sapiens

<400> SEQUENCE: 889
tgacctttta ccccaacatg 20

<210> SEQ ID NO 890
<211> LENGTH: 22
<212> TYPE: DNA
<213> ORGANISM: Homo sapiens

<400> SEQUENCE: 890
ccgccttccc cggcgcgcca tg 22

<210> SEQ ID NO 891
<211> LENGTH: 256
<212> TYPE: DNA
<213> ORGANISM: Homo sapiens

<400> SEQUENCE: 891
agttctttgt agtgcctccc tcagactcta acacactcag cctggccccc tcctcctatt 60
gcaaccccct cccccgctcc tcccggccag gccagctcag tcttcccagc ccccattcca 120
cgtggaccag ccagggcggg ggtagggaaa gaggacagga agagggggag ccagttctgg 180
gaggcggggg gaaggaggtt ggtggcgact ccctcgctcg ccctcactgc cggcggtccc 240
aactccaggc accatg 256

<210> SEQ ID NO 892
<211> LENGTH: 148
<212> TYPE: DNA
<213> ORGANISM: Homo sapiens

<400> SEQUENCE: 892
cctcctcccg ttccagctgc cgctgccgct tcctgggctg agtccgcccg cggtcccggc 60
ggcgccaggt gcgttcactc tgcccggctc cagccagcgt ccgccgccgc cgtagctgcc 120
ccaggctccc cgccccgctg ccgagatg 148

<210> SEQ ID NO 893
<211> LENGTH: 429
<212> TYPE: DNA
<213> ORGANISM: Homo sapiens

<400> SEQUENCE: 893
cctccttttt gcacacacac gaatacaaag agccatacga ccttcggatg ccggaaggtc 60
cttctgaatc ccttccctgt tccttaggtt gcactagtcg gggttccat gctgggggc 120

```
agaaggaatg ctctctaccg tctgaaaccg ttcatcagga aggccttgat ttgtgatgtg    180

ctaggagagc acaggatctg caaatagaag gcacctgtct cccttctgca ggccgaggag    240

aggccgccat ggactgtgtg cttcttcatg gcttgtttac tcttctttca cagaccctac    300

agcttggggc ctgggctcct ctgaccatcc tcattgagaa aggaaagtga gtccagagaa    360

gttgatgctt cctacctgtt ggagcggccc agcagtgtaa gcgtggttgt tactgcccca    420

tccgccatg                                                            429
```

```
<210> SEQ ID NO 894
<211> LENGTH: 174
<212> TYPE: DNA
<213> ORGANISM: Homo sapiens

<400> SEQUENCE: 894

cgccctcttc cgaatgtcct gcggccccag cctctcctca cgctcgcgca gtctccgccg     60

cagtctcagc tgcagctgca ggactgagcc gtgcacccgg aggagacccc cggaggaggc    120

gacaaacttc gcagtgccgc gacccaaccc cagccctggg tagcctgcag catg          174
```

```
<210> SEQ ID NO 895
<211> LENGTH: 151
<212> TYPE: DNA
<213> ORGANISM: Homo sapiens

<400> SEQUENCE: 895

cggcctctct tcctcagtgc gggcggagaa gcgaaagcgg atcgtcctcg gctgccgccg     60

ccttctccgg gactcgcgcg cccctccccg cgcgcccacc cacccagtcc ggctggactg    120

cggcagccgc gcggctcacc ccggcaggat g                                   151
```

```
<210> SEQ ID NO 896
<211> LENGTH: 83
<212> TYPE: DNA
<213> ORGANISM: Homo sapiens

<400> SEQUENCE: 896

ccgcctctgg cgaatggctc gtctgtagtg cacgccgcgg gcccagctgc gaccccggcc     60

ccgcccccgg gaccccggcc atg                                             83
```

```
<210> SEQ ID NO 897
<211> LENGTH: 28
<212> TYPE: DNA
<213> ORGANISM: Homo sapiens

<400> SEQUENCE: 897

cctccctttt cttttctgcc gggtaatg                                        28
```

```
<210> SEQ ID NO 898
<211> LENGTH: 288
<212> TYPE: DNA
<213> ORGANISM: Homo sapiens

<400> SEQUENCE: 898

cttcctcttt tctgtctggc ccgcggcccc gctgcctgcc ctgctccagg ctccacctgc     60

gccgccgatc gcccgggtat cgcgggggcc caggccagct gagtccgttt tccgcgccgg    120

ggtggcgccc ctccaaccgt cctaacgccg ggccggcagc aaggagtgtt cctgggacct    180

cagagaccag gctcagagcc tgacatccct gcgaggggac agcctcatcc gcccaggcca    240

gtgggggtct ctacaagtgc ccaggctcag gtgcagcccc cagcaatg                 288
```

<210> SEQ ID NO 899
<211> LENGTH: 46
<212> TYPE: DNA
<213> ORGANISM: Homo sapiens

<400> SEQUENCE: 899
ggtcctcctg ggagtctcgg aggggaccgg ctgtgcagac gccatg 46

<210> SEQ ID NO 900
<211> LENGTH: 153
<212> TYPE: DNA
<213> ORGANISM: Homo sapiens

<400> SEQUENCE: 900
tcctctctat gcttggggaa ggaacttcct gtaagcaagg cttgaggctt gctctcgcct 60
tcgtcagcag ccctcctcaa tcttctccaa actcccgtcc ccaggccaca cagattctcc 120
tcaagagagc cctataagga cattggtaaa atg 153

<210> SEQ ID NO 901
<211> LENGTH: 381
<212> TYPE: DNA
<213> ORGANISM: Homo sapiens

<400> SEQUENCE: 901
attcccttcc gccccccttct ctaagctgca cagcctgaat agaagggctg gtccagcggc 60
ggcggaggct ggcgctgtcc tgagagggag ggctctgtgc ggaagagtca gggcgaccct 120
tgggcgctgg agtacgcttg ggactggggc tgcgagtgag caccagcgat tggttcggaa 180
gcggacattt ggttcagaac gagcatttaa ctctgccagg gatccgctgg gctctgacga 240
ctgcggtaga tccatggctt cctggacgtt cacccgtaga gtcatcctag cttaactctt 300
gttccctggt ctcagttcac aagcctcacc tgtatcttcc tggctcggaa gataattgaa 360
accaagtctg acttctcaat g 381

<210> SEQ ID NO 902
<211> LENGTH: 35
<212> TYPE: DNA
<213> ORGANISM: Homo sapiens

<400> SEQUENCE: 902
ctttctcttc ccgacgcgtg agttaggccg taatg 35

<210> SEQ ID NO 903
<211> LENGTH: 292
<212> TYPE: DNA
<213> ORGANISM: Homo sapiens

<400> SEQUENCE: 903
ggccctctgg caagatggct gctgcggagg cgttggagcg cggaaatctg gaaccgggat 60
ggcgacgtct acactgagtc ggaggcgaag gagcttactc cacgggaaca gcctctagat 120
aatctgagtt gttgaaaata cgaagcctgt tactcgtgaa cagtggctga caacagtgtt 180
gttgtgagcc tggctgtctg cttggaccca gaggtttcgt ctgccagggt ttttggttgt 240
atttaggatt tcagggaaaa gtgtccaagc tttcagtgtt ggagcaggta tg 292

<210> SEQ ID NO 904
<211> LENGTH: 123
<212> TYPE: DNA

<213> ORGANISM: Homo sapiens

<400> SEQUENCE: 904
cggcctcttc gcttttgtgg cggcgcccgc gctcgcaggc cactctctgc tgtcgcccgt 60
cccgcgcgct cctccgaccc gctccgctcc gctccgctcg gccccgcgcc gcccgtcaac 120
atg 123

<210> SEQ ID NO 905
<211> LENGTH: 108
<212> TYPE: DNA
<213> ORGANISM: Homo sapiens

<400> SEQUENCE: 905
tcctctcttg actttgagcg tccggcggtc gcagagccag gaggcggagg cgcgcgggcc 60
agcctgggcc ccagcccaca ccttcaccag ggcccaggag ccaccatg 108

<210> SEQ ID NO 906
<211> LENGTH: 29
<212> TYPE: DNA
<213> ORGANISM: Homo sapiens

<400> SEQUENCE: 906
ggttcctctc ggagcggaga cggcaaatg 29

<210> SEQ ID NO 907
<211> LENGTH: 156
<212> TYPE: DNA
<213> ORGANISM: Homo sapiens

<400> SEQUENCE: 907
ccccctctcg cgggaattat ttgaacgttc gagcggtaaa tactccctgg ggctgtcata 60
gaagactact cggagagcgc tgcctctggg ttggcgggct ggcaggctgt agccgagcgc 120
gggcaggact cgtcccggca gggttccaga gccatg 156

<210> SEQ ID NO 908
<211> LENGTH: 33
<212> TYPE: DNA
<213> ORGANISM: Homo sapiens

<400> SEQUENCE: 908
tatcccctcc cacggtctct agttcgcgtt atg 33

<210> SEQ ID NO 909
<211> LENGTH: 275
<212> TYPE: DNA
<213> ORGANISM: Homo sapiens

<400> SEQUENCE: 909
ctgcctctac agctgtgtgt aggcctgggg gcgagggtct tcggaacgta gcgctggctg 60
cggccccgcc cgcctaccca cccgcccgtc cggcagccgg ctcccgccgc ctccgcgctc 120
tgtctggggc cagccacctg gcgggccgct ccggtgcgcc tgcccgcgct tttcactgac 180
aggcgctgtt ccccacagcc agcgccgccc gccacgtccc agctctcggc caacggagct 240
gcgcggcggg tgacctttcc gagcccagcg cgatg 275

<210> SEQ ID NO 910
<211> LENGTH: 243
<212> TYPE: DNA
<213> ORGANISM: Homo sapiens

<400> SEQUENCE: 910 ctacccttc atctctgcaa ctccttcctc cctgggcctc ccttctggtg tgtctgtggg 60
tctgtctagg tgggcttggg aaaggggaag gaaggggcgt ctctttaggc agctcagact 120
ggacaagcct tctttgaaaa tggtcctttg aacacacgcc tgctggtggt tggtcagaca 180
gatgcgccag cgggagcccc ggggccccaa ggggacagct atctctgcag gaccagtgcg 240
atg 243

<210> SEQ ID NO 911
<211> LENGTH: 402
<212> TYPE: DNA
<213> ORGANISM: Homo sapiens

<400> SEQUENCE: 911
cagccccttt tccggctgag agctcatcca cacttccaat cactttccgg agtgcttccc 60
ctccctccgg cccgtgctgg tcccgacggc gggcctgggt ctcgcgcgcg tattgctggg 120
taacgggcct tctctcgcgt cggcccggcc cctcctgcct cggctcgtcc ctccttccag 180
aacgtcccgg gctcctgccg agtcagaaga aatgggactc cctccgcgac gtgcccggag 240
cagctccctt cgctgtggaa gcggcggtgt cttcgaagaa accggaagcc cgtggtgacc 300
cctggcgacc cggtttgttt tcggtccgtt tccaaacact aaggaatcga aactcggcgg 360
ccttgggggc ggccctacgt agcctggctt ctggttgtca tg 402

<210> SEQ ID NO 912
<211> LENGTH: 107
<212> TYPE: DNA
<213> ORGANISM: Homo sapiens

<400> SEQUENCE: 912
acgccttttc cggcccgcag cgcggcctgg gctcccgcgt gtttaaaagt gcgcttgtgg 60
ctgctgctgt cttaactcct gtgcttggcg gacagacagg cgagatg 107

<210> SEQ ID NO 913
<211> LENGTH: 65
<212> TYPE: DNA
<213> ORGANISM: Homo sapiens

<400> SEQUENCE: 913
agtcctttct cgtcgctgct cggctcgcgg cccgtggggt cggccccgcc accgttgccg 60
ccatg 65

<210> SEQ ID NO 914
<211> LENGTH: 312
<212> TYPE: DNA
<213> ORGANISM: Homo sapiens

<400> SEQUENCE: 914
cggcctccgc cgcacgcgct ggcggactaa gagtggctgg cgaagcgagc ggccggcgcg 60
ggcccctggc gggcgggcgg tacagcccca agcctgagac ccggacctga gcatcgcagg 120
ttcgagtccc gccccgcctg gggcgaagcc gggggtggcg gcgacctcgc ggcgttgcac 180
cggctctgtg agcacctccc ctctgagcac ttcccttgtg acaggccact tcccttgtga 240
caggcccagg acgaggtggc caggcggccc ccatggcgtc cctggtctag gcggagaacc 300
gcctgggcga tg 312

<210> SEQ ID NO 915
<211> LENGTH: 351
<212> TYPE: DNA
<213> ORGANISM: Homo sapiens

<400> SEQUENCE: 915
ccctccctcc acctcggagt ctgcgcggcg cggccaggcc cggccgaccg cgtctcggtc 60
ttcgcgtctg ccagcctggc tggcagtccg tctgtccatc ccgccgcgcc ggggcagtct 120
aggcggagcg ggggctcagg cggcggcggc ctcgacgcga gtgagtgtcg tggttggggt 180
gctggaccca gagtgcctac cctcgcctgc ctgggcctca gtttccacat ctgcacaatg 240
ggggtgacca tccctgccct gctggctgcc aggagcggct gtgagtcttc aggcgtggat 300
gcagcctggg ggaagccata gggcgctttc acaggcctgg ccttcaccat g 351

<210> SEQ ID NO 916
<211> LENGTH: 27
<212> TYPE: DNA
<213> ORGANISM: Homo sapiens

<400> SEQUENCE: 916
gaaccttttt tcacctcgtc tgaaatg 27

<210> SEQ ID NO 917
<211> LENGTH: 117
<212> TYPE: DNA
<213> ORGANISM: Homo sapiens

<400> SEQUENCE: 917
cgccctccca cccgctcaga cctggttgcc agcccaacag gaagcggccc ctcccggctt 60
cggagccgcc gccactcatc tctgcccagc tgctgccctc cccaggaggc ctccatg 117

<210> SEQ ID NO 918
<211> LENGTH: 254
<212> TYPE: DNA
<213> ORGANISM: Homo sapiens

<400> SEQUENCE: 918
gctcctttaa ggcagcgaac gggccaagag aagcgtgttt cgccccctcc gacgccaccg 60
aggtagcggc ttcaccttta aggcggcgcg ggggctgctg ggaaggccgg cgggatggag 120
gcggcgggac cggctcgcgg gtgcgggtcc gggtgaagcg ggaggcagcc agagtcggag 180
ccgggcccga gcaccaggcg caggcccggc gcccgcctgc ccgcaccctc gtcctcacag 240
acgccacagc catg 254

<210> SEQ ID NO 919
<211> LENGTH: 178
<212> TYPE: DNA
<213> ORGANISM: Homo sapiens

<400> SEQUENCE: 919
acttcctttt tctgcccact ctggtaactt attgctctgc tgggctcttt cccttagggt 60
ctctggccct gttcttgccc cagcatgact tttatcggga cgccgttgtg gaagcctcac 120
gcaggagccc tgcccccgtg gagaagatcc cactggtgac tccaacccta ccaccatg 178

<210> SEQ ID NO 920
<211> LENGTH: 648
<212> TYPE: DNA
<213> ORGANISM: Homo sapiens

<400> SEQUENCE: 920
gctcctccca ctgccgttgt gggtaacgcg gacgtggaag aacctcgtct gcggaggaaa 60
aggtagatgt taaatggtaa ctacgcgcga ggttctgagg agccctggga acaggaagga 120
gaaaagaata ccaaaagtga caacagtttg ccaatcgcag tctttaatct gataaagcgg 180
ttatctcgtc ttgagtccca ggtgccgagt caatccccat acacagccgc cgccattgcc 240
tcgagtcctt gtgtctgact gtctgttcct gctgctgtat gacacagcac ctcgaggcaa 300
ggaaataaga aaactgcctc tgatccaagc agagaaggtc tgcctgtaga tctgctgtag 360
ggcttgtcac cattggaagc aaggtcctac ttcagtggca gatctggtgg ccttggagtg 420
gctgaagacc accaccctcc acagggctgg gcccatgcac agccatcctt ccctaccttg 480
agtgagcttc ctctgcatgt tttctatatc actggcagag cctgtagttg gaaaggggac 540
agagtgacta ctggactttg tgtgaaaaca ccaaccggga caaaacttca gtcaaggctg 600
agacgggtgg gggtatataa cttgtcctta cgttaaactt ggaacatg 648

<210> SEQ ID NO 921
<211> LENGTH: 24
<212> TYPE: DNA
<213> ORGANISM: Homo sapiens

<400> SEQUENCE: 921
aatcctttgc ggtggttcaa gatg 24

<210> SEQ ID NO 922
<211> LENGTH: 65
<212> TYPE: DNA
<213> ORGANISM: Homo sapiens

<400> SEQUENCE: 922
ggtcctcccg taggaaccgg cggactcggt tggcgttgtg gggcaggggg tggtggagca 60
agatg 65

<210> SEQ ID NO 923
<211> LENGTH: 907
<212> TYPE: DNA
<213> ORGANISM: Homo sapiens

<400> SEQUENCE: 923
gggcctcctc gcctttgtgc catccgggtc tctcgcgcga gcgatttagt ctgaggcgaa 60
gcttcggagc ggccggtact gttgaaagcg acaagtggag gcgccgctct agcggccggg 120
actctgaact atggcggcta gtgatacaga gcgagatgga ctagccccag aaaagacatc 180
accagataga gataagaaaa aagagcagtc agaagtatct gtttctccta gagcttcaaa 240
acatcattat tcaagatcac gatcaaggtc aagagaaaga aaacgaaagt cagataatga 300
aggaagaaaa cacaggagcc ggagcagaag caaagagcgt gcttatgcgc gaagagactg 360
aactgaagac gctgcagact cagatagcaa aataataagc ctacttcatg ataagggaag 420
aagacatgaa tccaaagata aatcctctaa gaaacataag tctgaggaac ataatgacaa 480
agaacattct tctgataaag gaagagagcg actaaattca tctgaaaatg gtgaggacag 540
gcacaaacgc aaagaaagaa agtcatcaag aggcagaagt cactcaagat ctaggtctcg 600
tgaaagacgc catcgtagta gaagcaggga gcggaagaag tctcgatcca ggagtaggga 660
gcggaagaaa tcgagatcca gaagcagaga gaggaagaaa tcgagatcca gaagcaggga 720

```
aagaaaacgg cggatcaggt ctcgttcccg ctcaagatca agacacaggc ataggactag    780

aagcaggagt aggacaagga gtaggagtcg agatagaaag aagagaattg aaaagccgag    840

aagatttagc agaagtttaa gccggactcc aagtccacct cccttcagag gcagaaacac    900

agcaatg                                                              907
```

<210> SEQ ID NO 924
<211> LENGTH: 590
<212> TYPE: DNA
<213> ORGANISM: Homo sapiens

<400> SEQUENCE: 924

```
ccgccttccc accccccgcc cttccactat ggccgcttct gtgtggtgtg gggagacgct     60

ggtcctcccc gtcctcccat agcgcttatt gcctcacct cacccccctag gggccggatc    120

caaaggcgct gcactcccca agccttgggg catcagccag gaaggtttcc tacctcctaa    180

ttcaggggca ggactcctct tttcccccca cggggaaaag aggcagaaac ttaggggttt    240

ccctcctttc ttagggtcag acgctcttag ggtccacttc ttcaggggcg gaagcctctc    300

ctacccttcc cataggggca caggccttta ccccactgta cttcggagcc aacgcctttc    360

cctcagcact gccaccccag agtcaggacc cagaggactg tgccttcgcc cccaacgcag    420

gcgcggcctt ttggagagga gggaggagtg gagaggacag gggcccttgc tctcccctcc    480

ccaacttgtt cctcttgccc cccagtccct ggcaatccag agatcccgat atctaggact    540

gtccatccat ccactccctg accttttccc ggctcctggc tgcagccatg               590
```

<210> SEQ ID NO 925
<211> LENGTH: 396
<212> TYPE: DNA
<213> ORGANISM: Homo sapiens

<400> SEQUENCE: 925

```
tctcctttcc tcttctcaga cccgggagcg tccgggacgc ggagcccgga gctggggcga     60

cgaggcgatt gcgggggcct gggctagctg ctggctacca atattctact ttctgtctct    120

atgaatgtga ctaccctggt tacctcatat aatctccctg gaaaaggaga catgaatgtc    180

tgcaatgata cttcctgaca agaagttgat acaagaaaag gaaaggagat taacagctag    240

tgagcagaat ttcgaacagc aggatttcgt attttttgct tccaactgca cacttccgtt    300

gcccactttt aaatcagaga tacctacact caaaacccag acaaggcaaa aggatacttt    360

tcttgtatat tttttgagat cgaagaaacg acaatg                              396
```

<210> SEQ ID NO 926
<211> LENGTH: 269
<212> TYPE: DNA
<213> ORGANISM: Homo sapiens

<400> SEQUENCE: 926

```
ccgccccttt cacctcctgg ctccctcccg ggcgatccgc gcccccttggg tctcccctcc     60

cttccctccg tccgcgtctc ctgcgccccc tccctgcgct cgtcccgccg ctcttcccgc    120

cgcccaactt ttcctccaac tcgcgctcgg gagctggcga ggcggcggcg gctcctcagg    180

tcagtttgaa aaggaggatc gagctcactg tggagtatcc atggagatgt ggagccttgt    240

caccaacctc taactgcaga actgggatg                                      269
```

<210> SEQ ID NO 927
<211> LENGTH: 29

<212> TYPE: DNA
<213> ORGANISM: Homo sapiens

<400> SEQUENCE: 927
ctccctcttc cgctgccgcc gtgggaatg 29

<210> SEQ ID NO 928
<211> LENGTH: 37
<212> TYPE: DNA
<213> ORGANISM: Homo sapiens

<400> SEQUENCE: 928
cctccttctt tcctgcctct gattccgggc tgtcatg 37

<210> SEQ ID NO 929
<211> LENGTH: 31
<212> TYPE: DNA
<213> ORGANISM: Homo sapiens

<400> SEQUENCE: 929
agtcctttgc gcggcacctg gcgacaaaat g 31

<210> SEQ ID NO 930
<211> LENGTH: 1100
<212> TYPE: DNA
<213> ORGANISM: Homo sapiens

<400> SEQUENCE: 930
ccctctcttc tccaccagcc aacgtccggg aaaaacgagt aagtacaggt tccttctgcc 60
aatccccgcc ggccacagct aactttcccg cccggcccct ttctgtcata attgaggtgt 120
ccacaaccag ccaatcagga acgcgagagt atcccgcgtt tgctttcgct cgccgaggcg 180
cgtatcagtc ggaattttgg ggagccaacc gcgccgtctg tccctggcaa gccagcggcg 240
gtttaaagga ggtggcggga agcctgtgtg tgcttcaaat cgtcaccctc atggtcgctc 300
cggtaagtgc tgcggggcag cattttctct gaggaggagc ggggacgggc gagactggca 360
taagcgtctt cgcgagggag caaggcggcc tgtgggtcgg cctcaccccg gcctccgacc 420
tgaagatccc agcatgcagc gcgggcgcgg ggcccgacgg aagccgggag ccggccggaa 480
gcagttcctg cgctctggct tctgggtcct gtcctgcgcg atcgcggggt cttagacagc 540
tcaactcgcc gagatgacct gggcacctct gcgttgaatc ggcaaatact gatcaagccg 600
catttattct gctctcagga actctaagtc tagcagagaa gatgaggcgg tagaagttca 660
tcaatggctt ggctggagga caagcaaatt gaggacattg gcaacggagt gatcaaaatg 720
atagatcatg aggcctaaaa tgaataagga aagaagagaa gtggcagagg ctgagaacag 780
aaagagaggg tggaggggct gtaaatcttg aagattaggg tataatatga gtatatgggt 840
aagaattgga agaattgtgt aggaggcagt agtcaaaaag tagaagcagt ttggaagagt 900
agttacaaat atcaagagcc aggtggctaa aaggtggagc tataggtcat tgaagctcaa 960
gaaactgagt ctctagggca ttggttaagt catctgtcta gacttcaaag ttgtctagga 1020
tgataattca gaagactgat ctgtgccaaa gtcacaggtt tttcacgact gaaaacaaca 1080
tagcaaaata agccaagatg 1100

<210> SEQ ID NO 931
<211> LENGTH: 76
<212> TYPE: DNA
<213> ORGANISM: Homo sapiens

<400> SEQUENCE: 931
cttcctttca cgctgtcgct gcccgtaggt ggttgtggcc actgtgcccg gagggaggcg 60
gcggtggcca gtaatg 76

<210> SEQ ID NO 932
<211> LENGTH: 73
<212> TYPE: DNA
<213> ORGANISM: Homo sapiens

<400> SEQUENCE: 932
cggcctctgc gtgcacgcgc ctgcgtgctc gcgctcgcgg ttctggcgct gccggaataa 60
tgctgacagc atg 73

<210> SEQ ID NO 933
<211> LENGTH: 168
<212> TYPE: DNA
<213> ORGANISM: Homo sapiens

<400> SEQUENCE: 933
ccgccctttc ctgtcgtgac ttaacgcacg caagcggctc cagggtacgt ccccgccacg 60
cgcgctcgca ggatcggtgc gtggtgacgt ttcgccggcg cgggcgccat cccggaagcg 120
cgagcaaggc cgccagatgt gcaggcagcg gaggaggaga aagagatg 168

<210> SEQ ID NO 934
<211> LENGTH: 70
<212> TYPE: DNA
<213> ORGANISM: Homo sapiens

<400> SEQUENCE: 934
acttctttct tgcccgccaa gcccgcagcc acccgggcgc ggcgggactc ctagacccgg 60
cgctgcgatg 70

<210> SEQ ID NO 935
<211> LENGTH: 289
<212> TYPE: DNA
<213> ORGANISM: Homo sapiens

<400> SEQUENCE: 935
cgttcctttt gtgacgccgg ctgtgagcgc ctgagagtct ttttgccttt cagagttaag 60
gcctcactgg cctgggaaaa taattgctgc cttttgcatc cgcgttggct ccgtccccag 120
gatcttcccg gttcagggac ctggcgattt ctgagtgttc cggaatccca ataaccctgt 180
ttaaagagga atggagattg ccactgtcca tttagattaa tgaggtgtcc tgaagtgatg 240
gtgacatcaa tgaaaggagg gttctgacac gttctcacct cgcgggatg 289

<210> SEQ ID NO 936
<211> LENGTH: 208
<212> TYPE: DNA
<213> ORGANISM: Homo sapiens

<400> SEQUENCE: 936
caaccctttt cttccgcacg gttggaggag gtcggctggt tatcgggagt tggagggctg 60
aggtcgggag ggtggtgtgt acagagctct aggacaccag gccagtcgcg ggttttgggc 120
cgaggcctgg gttacaagca gcaagtgcgc ggttggggcc actgcgaggc cgttttagaa 180
aactgtttaa aacaaagagc aattgatg 208

<210> SEQ ID NO 937
<211> LENGTH: 225
<212> TYPE: DNA
<213> ORGANISM: Homo sapiens

<400> SEQUENCE: 937
ccgcctcctc ctcctgccgc tgccgctgct ttggctgctg cgtcatacgc cccagagccg 60
ccgggacgga ggggctgggc ctggggaccc cccggcctcc gcctgcacgc ccccccacgc 120
ccggacgtgc cctctccgcg cgggggactc gcctaggtct cctacgtctg cccctgcccg 180
gctcccggcg gccccagctg tcaccggccc ccccaggatg caatg 225

<210> SEQ ID NO 938
<211> LENGTH: 85
<212> TYPE: DNA
<213> ORGANISM: Homo sapiens

<400> SEQUENCE: 938 ccccccttccg cctgacgcgc ccccggcggc ggccgcgcag ccctggctcc tcgcgggctc 60
gggcggcggc tgcggcgggg ctatg 85

<210> SEQ ID NO 939
<211> LENGTH: 358
<212> TYPE: DNA
<213> ORGANISM: Homo sapiens

<400> SEQUENCE: 939
ccgcctcctt tccggagccc gtctgttccc cttcgggtcc aaagcttttg gctcctcctt 60
gttccgagcc cgaaggcccg ccccttcacg tactcggagc tcggatccca gtgtggacct 120
ggactcgaat cccgttgccg actcgcgctc tcggcttctg ctccggggct tcttccctgc 180
ccgcccgggg ccctgaccgt ggcttcttcc ccggcctgat ctgcgcagcc cggcgggcgc 240
ccagaaggag caggcggcgc gggggcgcgc tgggcggggg aggcgtggcc ggagctgcgg 300
cggcaagcgg gctgggactg ctcggccgcc tcctgcccgg cgagcagctc agaccatg 358

<210> SEQ ID NO 940
<211> LENGTH: 284
<212> TYPE: DNA
<213> ORGANISM: Homo sapiens

<400> SEQUENCE: 940 acgcccettt tttgctcagc cgtcagcccc gtctccgtct gaagagtgct tctgccctca 60
tttgcctctc cctgtgaccc cggccccctc agactccgct gcgtcgtctc tcggccccgt 120
ccagccgttc ctgactgctc ttcgccggag tccgcttccc aaccccccttt cgccagagcc 180 cgagagctcc gtcggctctg cgtcctggcg gattgtcagt ggcttcgccc cgaggagagc 240
tgactgccct gggctgctgc ctccggcaga gctgagccaa aatg 284

<210> SEQ ID NO 941
<211> LENGTH: 465
<212> TYPE: DNA
<213> ORGANISM: Homo sapiens

<400> SEQUENCE: 941
ctcccttccc cctctgtggg tcccgcgagg agactctcgg gctttgaggt gagacctgaa 60
gttccgctgg ccggtagtgt agcaggaaag ggcaggtcct cccgggtcgt gagccagtag 120
cctcctgggg tggcaaggtg tagagagggg ggcgttgaaa ggacacccgc tacccggcct 180
gctttctagg ggtctctttg gattgaggac atcagcagca gtggaaggga ttttactgga 240
gacctgtcac tgtcagagcc ttaaaatatc accgacgggg ccttaatgtc accgaggtag 300
agagaaaagg gcagtagccc tagagactat tgcgacacag tgtgcccctc ataagttttt 360
ccagggaggg gttctgtact gagttgacgc cccaggagct gagcaccagg ctttgcatcc 420
ttgggaactc agcaaacgtt tgttcagcca attgcaggta gcatg 465

<210> SEQ ID NO 942
<211> LENGTH: 82
<212> TYPE: DNA
<213> ORGANISM: Homo sapiens

<400> SEQUENCE: 942
tactcccttc cctcaggccc caggaagttg caagagtacc atttgtcgca cactcgggga 60
ccgcgggtgg ccggaggaga tg 82

<210> SEQ ID NO 943
<211> LENGTH: 83
<212> TYPE: DNA
<213> ORGANISM: Homo sapiens

<400> SEQUENCE: 943
gctcctcctt cgcggcggta ccgcctctgt ttctgcggcg attgaacagc cgagctttgc 60
ggccgggatc gcggaaagtg atg 83

<210> SEQ ID NO 944
<211> LENGTH: 612
<212> TYPE: DNA
<213> ORGANISM: Homo sapiens

<400> SEQUENCE: 944
atttcctctc tgctgagagc cagggaaggc gagctctgcg cacacgggcg tccctgcagc 60
agccactctg ctttccagga ccggccaact gccctggagg catccacaca ggggcccagg 120
cagcacagag gagctgtgaa cccgctccac accggccacc ctgcccggag cctggcactc 180
acagcaggcc ggtgctaagg agtgtggcgc gggctcgact cccactgctg ccggcctccc 240
gagtgactct gttttccact gctgcaggcg agaagaggca cgcgcggcac aggccggcct 300
ccgcttcccg ggaagacggc gcactcctgg ccctgggttc ttgctgctgc ccaccctctg 360
ctccctggga tgggccccga ggcgagcagc ttcagcacag gcctggccct gctccaggtg 420
caggaaggag gataaggccg ggccgagagg cggcacacct ggaccatccc atgggcctcc 480
gcccgcgccg ccccgaggat gagtggtgat gtcctctagc cacccctagc agcgtcggct 540
ctccctggac gtgcggccgc ggactgggac ttggctttct ccggataagc ggcggcaccg 600
gcgtcagcga tg 612

<210> SEQ ID NO 945
<211> LENGTH: 67
<212> TYPE: DNA
<213> ORGANISM: Homo sapiens

<400> SEQUENCE: 945
tcgtctttcc cctcccatct cctcagatcg gtggacgtgc tcgcctccac tcggggccag 60
gtctatg 67

<210> SEQ ID NO 946
<211> LENGTH: 44

<212> TYPE: DNA
<213> ORGANISM: Homo sapiens

<400> SEQUENCE: 946 cctcccctt tcggcccagt agcggcggct cagttgctgc catg 44

<210> SEQ ID NO 947
<211> LENGTH: 98
<212> TYPE: DNA
<213> ORGANISM: Homo sapiens

<400> SEQUENCE: 947
ccttctcttt cggagttgtt ccgtgctccc acgtgcttcc ccttctccac tggctgggat 60
cccccgggct cggggcgcag taataatttt tcaccatg 98

<210> SEQ ID NO 948
<211> LENGTH: 81
<212> TYPE: DNA
<213> ORGANISM: Homo sapiens

<400> SEQUENCE: 948
aaccctttgc cttcggactt ctccggggcc agcagccgcc cgaccagggg cccggggcca 60
cgggctcagc cgacgaccat g 81

<210> SEQ ID NO 949
<211> LENGTH: 81
<212> TYPE: DNA
<213> ORGANISM: Homo sapiens

<400> SEQUENCE: 949
cggcctttcc tccgcgcccc cgcgtcccca gccggccgct ccgagaggac ccggaggagg 60
caggtggctt tctagaagat g 81

<210> SEQ ID NO 950
<211> LENGTH: 26
<212> TYPE: DNA
<213> ORGANISM: Homo sapiens

<400> SEQUENCE: 950
ccgcccctta cggcgccgga gagatg 26

<210> SEQ ID NO 951
<211> LENGTH: 297
<212> TYPE: DNA
<213> ORGANISM: Homo sapiens

<400> SEQUENCE: 951
cctccctttt tctacttccg aggctgcaaa gtgcaacagc agactcttct gactcaggaa 60
ggccggtgct cctacccact tcctgttcct ccatctccag cggacactgc tctttcaagg 120
gcaggtctcc agcccagctc tctgaaaaca ttttgctgaa aatataagca aacatcggcc 180
ttgtcctcct tgtgttcata cactgtggaa gcttttctct gcctcctccg tgagagtgcg 240
tggccgggag accagaaacg tggtcctttc tcttgcctgt gagctggtgc agagatg 297

<210> SEQ ID NO 952
<211> LENGTH: 64
<212> TYPE: DNA
<213> ORGANISM: Homo sapiens

<400> SEQUENCE: 952

-continued cttcctccgg ctggcagcac gactcgcgta gccgtgcgcc gattgcctct cggcctgggc 60
aatg 64

<210> SEQ ID NO 953
<211> LENGTH: 27
<212> TYPE: DNA
<213> ORGANISM: Homo sapiens

<400> SEQUENCE: 953
aattcttttt tccccaggct tgccatg 27

<210> SEQ ID NO 954
<211> LENGTH: 254
<212> TYPE: DNA
<213> ORGANISM: Homo sapiens

<400> SEQUENCE: 954
acttcccttt ttccggtccg ccggattatg aatgacggcc ggcgcgagta ttttccacat 60
aaggtggctg tcgtttttct cctggcgtct gtggaggcga gtggtctgcg ggcagcagct 120
cccagaggca gccttggaat tccagctcgg actgggcggg aaggcgcagg cggcccaggt 180
cgccgacacg ctcacgcacc ctccctgcct ggccgcgcct ctgcgaccag gtgacccaat 240
gaaagaagaa aatg 254

<210> SEQ ID NO 955
<211> LENGTH: 311
<212> TYPE: DNA
<213> ORGANISM: Homo sapiens

<400> SEQUENCE: 955
actccttttt ctttccaaac agggaaaagt gttccacgaa gcggtagcgc ctttccgcct 60
cgcgttttcc tccctgaccc tggtcccggc tcccgtccgg gcgccagctg gtggggcgag 120
cgccgggagc ccatctgccc ccaggggcac ggggcgcggg gccggctccc gcccggcaca 180
tggctgcagc cacctcgcgc gcaccccgag gcgccgcgcc cagctcgccc gaggtccgtc 240
ggaggcgccc ggccgccccg gagccaagca gcagctgagc ggggaagcgc ccgcgtccgg 300
ggatcgggat g 311

<210> SEQ ID NO 956
<211> LENGTH: 118
<212> TYPE: DNA
<213> ORGANISM: Homo sapiens

<400> SEQUENCE: 956
cctcctcttg cggtgggggg aaagcggcct cttactctag gcctttcggt ttgcgcgagc 60
gggcaggaaa gcgtgcgtgc ggctaagaga gtgggcgctc tcgcggccgc tgacgatg 118

<210> SEQ ID NO 957
<211> LENGTH: 299
<212> TYPE: DNA
<213> ORGANISM: Homo sapiens

<400> SEQUENCE: 957
cctccttctt ccactccccg cggcgcgagc ggctgactgc ccgtagagga aacgacattc 60
ggagctgcgc tcccgcccag gccggccctg acgcgggcct cgtcagccag taacagggag 120
cagaggtggg agttagcgag gcgaccacga aaacggtgaa ggtcggaacc gacagcctcc 180
tccgagaagg gcaggagctg ggaggaggcg gcagcggcgg cggcagaaac agcagcggcg 240
gcggcggcgg cagctgggag gaggtggtga cggtggcaac ggcagcgtcg gggacgatg 299

<210> SEQ ID NO 958
<211> LENGTH: 816
<212> TYPE: DNA
<213> ORGANISM: Homo sapiens

<400> SEQUENCE: 958
ctttctcttt tagccccgcc tgcttcccgg ctccagctgg ggccggagag gctgagtggt 60
tggtacgctg ctcgctggcc tcccagtctt cccagcaacc ggtgacactg cccgcgccag 120
actgaccact agccgacgcg ggcgagaggg acaggagcgt gacctcccca tcccgagggg 180
ccggacgctc gggcgcctcc ccgctccccc cactcggagg ccgcgcgcgc cgttagcccc 240
ttcctcgctc ccccgcccca gtcccgcagt ccgggaggcg ggggtcggca gccggctgag 300
tgggaaccgc gcggtgtctg aggaggcagt cggcgaccgg tttccacttc aagcgtgacc 360
cttttgcctg tgggatgagc tccagcatgg ggtgaggtac agaagagaga cttgaagagc 420
gtgccttggg actcaagcgc caaacctgta ccctagcgag tgtcctactc cgcatccgta 480
atggaaggaa atgcacatct tactccagag gcacaagagg aggacatccc atgcggctac 540
tcctgcccag cgtggtgggg cagcagaagc tccagagccc agacttgcag gctcacggtg 600
cagggtgaac ctggccacag ctcaccctgg aacagccaca atgtctgccc cttagagaag 660
aaccctgaaa tcagaccagt ttttgcggcc tccccctttc ctctctgtta cagtgccctt 720
tccaggcctt aagagaagta aaacttagct gcagcgccag gaggtggacc ccagagtgtg 780
agtggcacgc ttccctgtga acccgtcctc accatg 816

<210> SEQ ID NO 959
<211> LENGTH: 148
<212> TYPE: DNA
<213> ORGANISM: Homo sapiens

<400> SEQUENCE: 959
ccgcctccgt cccggctgcg gcccctgccg gttacataac tcgttgcggg ctccgcgcgg 60
tcccacttcc cggctccctt cgcctccagg atgcgctgag ccctacaaca cccccagcgg 120
ccgccggctc ccccacgagg tgtgaatg 148

<210> SEQ ID NO 960
<211> LENGTH: 237
<212> TYPE: DNA
<213> ORGANISM: Homo sapiens

<400> SEQUENCE: 960
tgccctctgt ccccgcggct gggtctcgtc tgctccggtt cctgggctcc taattcttgg 60
tccagcttct tccaggtcag tgtgcgggcc ttccacgctg ccagcggaac actggaatgg 120
cggaagggga acgggtctgc gcgtctgttg ttcccagcgc tctgcgaagc ctgaaaagga 180
ggagcaacct gtccagaatc cccgcaggac aggaaaagga ggggaaatct cgacatg 237

<210> SEQ ID NO 961
<211> LENGTH: 673
<212> TYPE: DNA
<213> ORGANISM: Homo sapiens

<400> SEQUENCE: 961 tccccttttgt ctccccactc cccgcccagg cctggcccgc ctgcctggcc actcttcctc 60

```
catcagcctg gctggcagca gccttggact ccgcccgtgg agccctgggc ctgttgaccc      120

accagcttag gagcacccac caagctctgg gtaaggaagc tcaccttctg gggctcttct      180

gggaaaatag aggtcaacgt ggaggtacca ggccaccatg ctcagtctca agctgcccca      240

acttcttcaa gtccaccagg tcccccgggt gttctgggaa gatggcatca tgtctggcta      300

ccgccgcccc accagctcgg ctttggactg tgtcctcagc tccttccaga tgaccaacga      360

gacggtcaac atctggactc acttcctgcc cacctggtga ggggaggctc tgccccaggc      420

cgcggccttg agctcagagg gggtacccag gcgggcaggg accgtccagg cccacgggct      480

gcagcggcag tcgcgggggt ccgcggcggc ctgagcacgc gccgccgca ggtacttcct       540

gtggcggctc ctggcgctgg cgggcggccc cggcttccgt gcggagccgt accactggcc      600

gctgctggtc ttcctgctgc ccgcctgcct ctaccccttc gcgtcgtgct gcgcgcacac      660

cttcagctcc atg                                                        673

<210> SEQ ID NO 962
<211> LENGTH: 189
<212> TYPE: DNA
<213> ORGANISM: Homo sapiens

<400> SEQUENCE: 962

catccttctt gctcaaccac tgggtgcaca ggatggaaac ttctattccc tctctggaag       60

acagcgcgtg gcttggcttc acagagttgt ggctggagac cgaagcagcc cctttctcag      120

gcttactgtc accagtctgt ctgtgttagg ggagagggga gtccgctctg tcctgaaggc      180

ccagagatg                                                             189

<210> SEQ ID NO 963
<211> LENGTH: 137
<212> TYPE: DNA
<213> ORGANISM: Homo sapiens

<400> SEQUENCE: 963

ccttcttctt tcctgcctca ccttccaatt cgtttgccgc cgccgtcccg cagctgctgt       60

ttccggagtt gccccttccc catgttccgg ggcaggagtc cgcaaagcga agatccgccc      120

gccggttcct catcatg                                                    137

<210> SEQ ID NO 964
<211> LENGTH: 158
<212> TYPE: DNA
<213> ORGANISM: Homo sapiens

<400> SEQUENCE: 964

ccgcctttgc tcggcggaga cagcaggcag agagatgagg aaactgagac ccagaaaggt       60

ggaagcactt gtctaaggtc acgcctccag gaagcagtgt gtccacgact ccagtccaag      120

tggtcaggct ccagagccca cagtcccagg ggtccatg                              158

<210> SEQ ID NO 965
<211> LENGTH: 101
<212> TYPE: DNA
<213> ORGANISM: Homo sapiens

<400> SEQUENCE: 965

agccctcctc acacccccac tgggctcctg cattaagccc ggggttcgca gccgcagccg       60

ggatcgggca cccaggggcg ggcgggcacg gtagggccat g                         101
```

-continued

<210> SEQ ID NO 966
<211> LENGTH: 509
<212> TYPE: DNA
<213> ORGANISM: Homo sapiens

<400> SEQUENCE: 966
catcctctct gggaatttac cgatgcccag aacgcccttc tttcccccac acgaccctct 60
cctagtctaa ctcctgggcg tgctttaagc tcagctcagg cagcgtcacc ttctctggaa 120
agcccaaacc cagccacccc actacccgct acccgcggcc cacgctgatg aagacagcag 180
aacacggagg ccccgcgttc ccgccgcgag agcaggagag aaagattacc tcccgcgagc 240
tctagcgcgc ccggctttcc ggcgcactcc agggggcgtg gctcgggtcc acccgggctg 300
cgagccggca gcacaggcca ataggcaatt agcgcgcgcc aggctgcctt ccccgcgccg 360
gacccgggac gtctgaacgg aagttcgacc catcggcgac ccgacggcga gaccccgccc 420
catccccgac tgcctgaacc gcgccaggag acggaccgca agtccagcgt acccacagac 480
gactcaggcg ggagacgagc ggtgtcatg 509

<210> SEQ ID NO 967
<211> LENGTH: 192
<212> TYPE: DNA
<213> ORGANISM: Homo sapiens

<400> SEQUENCE: 967
cgttctttta ggggtggagc cggcaggaaa tttaaactga agccgcggcc gaaaacgcca 60
agagattgat gctgtagctg ccctgagata accaggactg tggaatcggg aagagctcat 120
ggagctcgcg aatgtaatac ggaggcctct gaggaaggag tacggaggcc gagaaggagc 180
cggcatttga tg 192

<210> SEQ ID NO 968
<211> LENGTH: 13
<212> TYPE: DNA
<213> ORGANISM: Homo sapiens

<400> SEQUENCE: 968
atttcctttt atg 13

<210> SEQ ID NO 969
<211> LENGTH: 439
<212> TYPE: DNA
<213> ORGANISM: Homo sapiens

<400> SEQUENCE: 969
ggttcctttc ctcactgcac gctcttgccc ctcctctttt ctctcctgcc cgtgttcttc 60
ccgccgcctg acctggcccg cccgcctttc cagtctggcc gggcgggggc ctgaagcacg 120
gcggctcggg ccgtgggacc gtgttcacac cctttccaga aattcttggc tggtaaccgc 180
gaaaccgact ggagcaggag ctgggagaac tggagaaaac tgctctaatc tcacttgact 240
ccagctagga gctgatgctg catcgtaata acatttgcag agcgctttca caggcgctgg 300
agtgacttgt ctgagattcc tccagaactg agccctttgt tggaaccata ccccagccca 360
tggtcccatg actaggtgga tagtactcct tgtacctcct gcaacccaga accctggctg 420
accactttga aggaggatg 439

<210> SEQ ID NO 970
<211> LENGTH: 363
<212> TYPE: DNA

<213> ORGANISM: Homo sapiens

<400> SEQUENCE: 970 cctcccccttt ctgctgttac cgggagcgcg gtggccacgg aacgctgccc ggagccgcgc 60
gagggaggac ccgacgcgcg gcgtttaccc agcgcagcgt tccaccgctc gggtttggct 120
ggataaaata aaaaatgggg atattgacct cctgtcacta ctgcatggac tttgatggtt 180
tccaatcatt actttctcct ctgtgtcaat ctgcctcttc gagaaattca tactcctgaa 240
tagctctcca gacccccagc tggccatgtg gtgagttcag ggcccaaatc aagtagtacc 300
agcaatcagg gaactcctat ctgttttgaa tggattcaca ccagccacaa gcctggaaag 360
atg 363

<210> SEQ ID NO 971
<211> LENGTH: 113
<212> TYPE: DNA
<213> ORGANISM: Homo sapiens

<400> SEQUENCE: 971
ctccctcttc ccccgccccg ccctgggcca ggtgttcgaa tcccgactcc agaactggcg 60
gcgtcccagt cccgcgggcg tggagcgccg gaggacccgc cctcgggctc atg 113

<210> SEQ ID NO 972
<211> LENGTH: 155
<212> TYPE: DNA
<213> ORGANISM: Homo sapiens

<400> SEQUENCE: 972
gggcctttgt ccctcgctgt ggcctgagct ccaggtctcg tcttcagcgc tctgtgtcct 60
ctgctcctag aggtccaggc tctgtggccc tgtgacccgc aggtattggg agatctacag 120
ctaagacgcc aggaacccct ggaagcctag aaatg 155

<210> SEQ ID NO 973
<211> LENGTH: 236
<212> TYPE: DNA
<213> ORGANISM: Homo sapiens

<400> SEQUENCE: 973
gctccttttg caggctcgtg gcggtcggtc agcggggcgt tctcccacct gtagcgactc 60
aggttactga aaaggcggga aaacgctgcg atggcggcag ctgggggagg aggaagataa 120
gcgcgtgagg ctggggtcct ggcgcgtggt tggcagaggc agagacataa gacgtgcacg 180
actcgcccca cagggccctc agacccccttc cttccaaagg agcctccaag ctcatg 236

<210> SEQ ID NO 974
<211> LENGTH: 55
<212> TYPE: DNA
<213> ORGANISM: Homo sapiens

<400> SEQUENCE: 974
gccccttcct cactaccctc caaatcccgc tgcagccatt gccgcagaca cgatg 55

<210> SEQ ID NO 975
<211> LENGTH: 358
<212> TYPE: DNA
<213> ORGANISM: Homo sapiens

<400> SEQUENCE: 975
cgccctttac caacatggct gctgacgcca cgccttctgg gactcgtagt ccggtcctcg 60
cgcgctttct tacctaactg gggcgctctg ggtgttgtac gaaagcgcgt ctgcggccgc 120
aatgtctgct gagagttgta gttctgtgcc ctatcacggc cactcccatt tctggtgccg 180
tcacgggaca gagcagtcgg tgacaggaca gagcagtcgg tgacgggaca cagtggttgg 240
tgacgggaca gagcggtcgg tgacagcctc aagggcttca gcaccgcgcc catggcagag 300
ccagaccgac tcagattcag actctgaggg aggagccgct ggtggagaag cagacatg 358

<210> SEQ ID NO 976
<211> LENGTH: 175
<212> TYPE: DNA
<213> ORGANISM: Homo sapiens

<400> SEQUENCE: 976
ttgtctctct gtcagtggcg gctgctgcct gctctggagg caggctgggc ggtggcggcc 60
gagactggcg ggggtggacg cccgggccgg gctgcgcccg cttcttgcag ctgtgaattc 120
ctttggacaa ttgatgatat ttatcattgt gcccagtttc tacaaataaa agatg 175

<210> SEQ ID NO 977
<211> LENGTH: 123
<212> TYPE: DNA
<213> ORGANISM: Homo sapiens

<400> SEQUENCE: 977
ctgccttcat ctctccatct ctgcgctgct gccggctgcg ccatccagca cccagactcc 60
agcaccggcc gaggaccccc actccggctg cagggaccct gtcccagcga gaccgcaggc 120
atg 123

<210> SEQ ID NO 978
<211> LENGTH: 271
<212> TYPE: DNA
<213> ORGANISM: Homo sapiens

<400> SEQUENCE: 978
ccgccccttc cccggagcct cacttccgtc acagtcctgt ttctctccct gttgtccctg 60
cctctttttc cttcccgccg tgccccgcgg ccgggccggg gcagccggga agcgggtggg 120
gtggtgtgtt acccagtagc tcctgggaca tcgctcgggt acgctccacg ccgtcgcagc 180
cactgctgtg gtcgccggtc ggccgagggg ccgcgatact ggttgcccgc ggtgtaagca 240
gaattcgacg tgtatcgctg ccgtcaagat g 271

<210> SEQ ID NO 979
<211> LENGTH: 132
<212> TYPE: DNA
<213> ORGANISM: Homo sapiens

<400> SEQUENCE: 979
cgttctttgg ccctgtgaca cgtagcaacg gggctggttc agggtctgaa acagagtttg 60
ggggttgttt gggattagtg aagctactgc ctttgccgcc agcgcagcct cagagtttga 120
ttatttgcaa tg 132

<210> SEQ ID NO 980
<211> LENGTH: 272
<212> TYPE: DNA
<213> ORGANISM: Homo sapiens

<400> SEQUENCE: 980
cctccctttc cagagccccc agttccttag aaaccaggcg gcgcgttccc ggtggcggcg 60
ccctggactc ccgggcccgc gcatccccgc cagccttcct taaggcggat gggtggcccc 120
cgagaccccg tcggacccat ggtttccagt gcagcgcgga gtgggcgatg ccagcgtgcc 180
aggagccatg tctgaccagg acgtttggaa gatcatatcc atgccagagg ctcttgtgag 240
gagatgagtt ggtaaagaga gaggctggga tg 272

<210> SEQ ID NO 981
<211> LENGTH: 275
<212> TYPE: DNA
<213> ORGANISM: Homo sapiens

<400> SEQUENCE: 981
ttccctttcg aattccaggg tatatctggg aggccggagg acgtgtctgg ttattacaca 60
gatgcacagc tggacgtggg atccacacag ctcagaacag ttggatcttg ctcagtctct 120
gtcagaggaa gatcccttgg acaagaggac cctgccttgg tgtgagagtg agggaagagg 180
aagctggaac gagggttaag gaaaaccttc cagtctggac agtgactgga gagctccaag 240
gaaagcccct cggtaaccca gccgctggca ccatg 275

<210> SEQ ID NO 982
<211> LENGTH: 155
<212> TYPE: DNA
<213> ORGANISM: Homo sapiens

<400> SEQUENCE: 982
ccgcctccct gcgccccgcc cctccggcta gctcgctggc tcccggctcc tcccgacgtc 60
tcctacctcc tcacggctct tcccggcgct ctcctggctc ccttctgccc cagctccgtc 120
tcggcggcgg cgggcagttg cagtggtgca gaatg 155

<210> SEQ ID NO 983
<211> LENGTH: 63
<212> TYPE: DNA
<213> ORGANISM: Homo sapiens

<400> SEQUENCE: 983
cttccttctt tgccaggcag acgcccgttg tagccgttgg ggaaccgttg agaatccgcc 60
atg 63

<210> SEQ ID NO 984
<211> LENGTH: 189
<212> TYPE: DNA
<213> ORGANISM: Homo sapiens

<400> SEQUENCE: 984
ctgtctctaa tctctgcaac agccgcgctt cccgggtccc gcggctcccg cgcgcgatct 60
gccgcggccg gctgctgggc aaaaatcaga gccgcctccg ccccattacc catcatggaa 120
accctccagg aaaaagtggc cccggacgcg cgagcctgag gattctgcac aaaagaggtg 180
cccaaaatg 189

<210> SEQ ID NO 985
<211> LENGTH: 68
<212> TYPE: DNA
<213> ORGANISM: Homo sapiens

<400> SEQUENCE: 985
tgctcctttc tgcccgtgga cgccgccgaa gaagcatcgt taaagtctct cttcaccctg 60
ccgtcatg 68

<210> SEQ ID NO 986
<211> LENGTH: 155
<212> TYPE: DNA
<213> ORGANISM: Homo sapiens

<400> SEQUENCE: 986
gggtcctttg tctctcggtg cagccggagc tccaggtctc ctcttcacta ctctgtgtcc 60
tgtgctccta caggcccagc ctctgtggcc ctgtgacctg caggtattgg gagatccaca 120
gctaagacac caggacccct ggaagcctag aaatg 155

<210> SEQ ID NO 987
<211> LENGTH: 83
<212> TYPE: DNA
<213> ORGANISM: Homo sapiens

<400> SEQUENCE: 987
cggcctctag ccacaccgag tccgccgcgg cgtccagggt cggcagcaac cgcagccgag 60
cccgagcggg tggcggcgcc atg 83

<210> SEQ ID NO 988
<211> LENGTH: 126
<212> TYPE: DNA
<213> ORGANISM: Homo sapiens

<400> SEQUENCE: 988
cattcttctg cgacggcgcg gacctggagc ttccgcgcgg tggcttcact ctcctgtaaa 60
acgctagagc ggcgagttgt tacctgcgtc ctctgacctg agagcgaagg ggaaagcggc 120
gagatg 126

<210> SEQ ID NO 989
<211> LENGTH: 26
<212> TYPE: DNA
<213> ORGANISM: Homo sapiens

<400> SEQUENCE: 989
gtcccctttc ctcgcaggac ctcatg 26

<210> SEQ ID NO 990
<211> LENGTH: 159
<212> TYPE: DNA
<213> ORGANISM: Homo sapiens

<400> SEQUENCE: 990
ctttcttcct cttggcttat attagggata ggggatgtgg tttgttacaa aggatgagta 60
ttttgatagc ttctcattcc ttgaactatt ctgcaggttt ataacaaagc tcagaaaata 120
ctaaaggtta aaggagaatt gagagctgcc aaggaaatg 159

<210> SEQ ID NO 991
<211> LENGTH: 89
<212> TYPE: DNA
<213> ORGANISM: Homo sapiens

<400> SEQUENCE: 991
cttcctttct cggaaacgcg gcgcggccgg ctgccggaaa acagggcaga cctgtatggt 60
tcgtttattc ctggggttgt catatcatg 89

<210> SEQ ID NO 992
<211> LENGTH: 243
<212> TYPE: DNA
<213> ORGANISM: Homo sapiens

<400> SEQUENCE: 992
tattcttttt tagtgcagcg ggagagagcg ggagtgtgcg ccgcgcgaga gtgggaggcg 60
aagggggcag gccagggaga ggcgcaggag cctttgcagc cacgcgcgcg ccttccctgt 120
cttgtgtgct tcgcgaggta gagcgggcgc gcggcagcgg cggggattac tttgctgcta 180
gtttcggttc gcggcagcgg cgggtgtagt ctcggcggca gcggcggaga cactagcact 240
atg 243

<210> SEQ ID NO 993
<211> LENGTH: 219
<212> TYPE: DNA
<213> ORGANISM: Homo sapiens

<400> SEQUENCE: 993
atttctccat ctggctctcc tctacctcca ggcaggctca cccgagatcc ccgccccgaa 60 cccccctgc acactcggcc cagcgctgtt gccccccggag cggacgtttc tgcagctatt 120
ctgagcacac cttgacgtcg gctgagggag cgggacaggg tcagcggcga aggaggcagg 180
ccccgcgcgg ggatctcgga agccctgcgg tgcatcatg 219

<210> SEQ ID NO 994
<211> LENGTH: 951
<212> TYPE: DNA
<213> ORGANISM: Homo sapiens

<400> SEQUENCE: 994
ccttcctttc cccagtgttg agcgcggtct cgcctccgct tcctcctcac tccgcctgcc 60
ggctgggaaa ctagggcacc agtacgatag ttccggcacc ggaaaagagg gctgatgact 120
gggcccgggg gccgccgcaa cgacccttgg ggccggcaaa gagccagaga gggtgctcac 180
acttccaagc accccacacc aaggacaggc tggacggcaa ggcggagacg cggggcttgg 240
gccctcagac cggggacagc aggaggttgg gccaagggcc aggacttccc gtcacaattt 300
catttgttga tcccggcacc gccaggtaag gggggccctg agtgaggcta ggtatctggt 360
acggataaag ttaggtatag agtagagcgg ctgcccgctc agggttatcc ctaaagacag 420
ttggaggaga gttgcttggg gcctcgggga tgcactgggc gggatcaggg cttacaccta 480
ggactggcaa aagagcggga cccggcagag gcggggcttg ccgaagggac gagcctctat 540
tcaggaaatg cacgagcttt ggggcggggc tcaaagaaag gggcggggct tccggggccc 600
gcgtcctggt gagctgcgcg tctgcgcgag gattgggcga gagggtgggg ccactcaacg 660
ctgaggcggc gaatggccgg agcagactta aatcaagagg ctggggacct ctaagatcaa 720
agtttggggc ggggcctaag gagggggcgg ggcctccaga ttcgagacct ggaagggctg 780
gggcggcgct tggggcggcc ctgccgccgc ctcccgttct cccctccgca gcggcggcgg 840
tggcggagaa ggaactcgac acgcaccgac cgccctcccg ccccagccga agcggaagct 900
gtagcccgct ctgggccggg gccatgggcg ccccgcgccg cccgggtcat g 951

<210> SEQ ID NO 995
<211> LENGTH: 42
<212> TYPE: DNA
<213> ORGANISM: Homo sapiens

<400> SEQUENCE: 995
ggctcttttt gacagccccc agtgcgaaag gctgccagca tg 42

<210> SEQ ID NO 996
<211> LENGTH: 60
<212> TYPE: DNA
<213> ORGANISM: Homo sapiens

<400> SEQUENCE: 996
ggttctctct gacgtgggag ccgccgtcgc tgccgccacc cggaggctct tgtcaggatg 60

<210> SEQ ID NO 997
<211> LENGTH: 177
<212> TYPE: DNA
<213> ORGANISM: Homo sapiens

<400> SEQUENCE: 997
aggtctttct ccacaaaaga aataacagcg tgcattacgt attcagatac tgctttgctt 60
catcctctct aaaatttaac accgaggagt ttaagaaatg aagataagga actcgaatta 120
tttttaaact ttggatcaat gtaaaggcaa tctaatattt ggaaaatact tgcaatg 177

<210> SEQ ID NO 998
<211> LENGTH: 267
<212> TYPE: DNA
<213> ORGANISM: Homo sapiens

<400> SEQUENCE: 998
gcctctcctt gggccccttc tctccccctt tcccctccct gctggttcct ggcatcgcca 60
gatgctgcgc agcagtctcc gattccccat caccaattcg gctggcgtct ccgagaccgc 120
ggactcccgt agggtccccg tggccccgag ttgtagtcgg gacaccccgg ccgcgggtga 180
tcgtcgggtc tccacgcgcc cgggtcgctg acgcggatcc ggcctcggcg ccttctcagg 240
gcgccctgca aggccgcagg caggatg 267

<210> SEQ ID NO 999
<211> LENGTH: 86
<212> TYPE: DNA
<213> ORGANISM: Homo sapiens

<400> SEQUENCE: 999
gctcctcctg ctgtgggacc gctgaccgcg cggctgctcc gctctccccg ctccaagcgc 60
cgatctgggc acccgccacc agcatg 86

<210> SEQ ID NO 1000
<211> LENGTH: 882
<212> TYPE: DNA
<213> ORGANISM: Homo sapiens

<400> SEQUENCE: 1000
gggtctttta ggagagcact gctgcagccg gcagtggaga gcctgggcag ggagacaggg 60
agaaaactcc ggcagcaggg tggtctctag ggctgacctc ggagcctggg gacaggggag 120
cctatgccgc actgaaggcg ggacgctgta agcgaggagc agctgggcct gggcggactc 180
ctcggccaat cagcctcggt cagcagcacc ctcaggcgca gggcactgtt tgggcattgc 240
ctagagatcc gacaccccgc ccagatcagc gcagggaggc gaaagcgaca gccgggcgcg 300
ggaggagacc agggcagctg tcccctccgc gagggtggcc ctcgaggcaa tgcgggtggg 360

-continued ggctggtgag gaggcggaag ggccgaggct gagtgggagg ggccggggcg ccagggctgg 420
agcgcgcggc tcgggggtgg aggctgcaga gccagcgagc gagcgagggg cgggggcgcc 480
cgggccggcg cgcaggaggg gcgggggcgg cggggagggg ggctcgggct gcgtgtgccg 540
gagccggcgg gggcggcggt gcgtgcgcat gacgcggggg gagggcctgg gccgcgcgct 600
cccggtcccg ttgttgttgc cgctggaggc tgctccgagg cagcgggatc acggcgctgg 660
gaagcgctcg gcagcggcgg ccacagcgtg cgcggcggcg cctcctggcc tcggcctccg 720
gcccccggcc cccggctcca tgcgctagcc ccgcgccgcc agcccagtag tcccggcccc 780
gccagccccg cgctcccgct cgccgctgcc gccgccgccg ccgccgccgc ctccgccgcg 840
ccgccccggg cccgcctcgg gccccacggc tccgaagcca tg 882

<210> SEQ ID NO 1001
<211> LENGTH: 52
<212> TYPE: DNA
<213> ORGANISM: Homo sapiens

<400> SEQUENCE: 1001
ctgcctctct cagtccgggt ttggagactc ctgcgtcctc cgacttttca tg 52

<210> SEQ ID NO 1002
<211> LENGTH: 225
<212> TYPE: DNA
<213> ORGANISM: Homo sapiens

<400> SEQUENCE: 1002
cattctctgc gaccggcagc cgccaatggg aagggagtga gtgccacgaa caggccaata 60
aggagggagc agtgcggggt ttaaatctga ggctaggctg gctcttctcg gcgtgctgcg 120
gcggaacggc tgttggtttc tgctgggtgt aggtccttgg ctggtcgggc ctccggtgtt 180
ctgcttctcc ccgctgagct gctgcctggt gaagaggaag ccatg 225

<210> SEQ ID NO 1003
<211> LENGTH: 23
<212> TYPE: DNA
<213> ORGANISM: Homo sapiens

<400> SEQUENCE: 1003
gtttctcttt ccgggacaac atg 23

<210> SEQ ID NO 1004
<211> LENGTH: 220
<212> TYPE: DNA
<213> ORGANISM: Homo sapiens

<400> SEQUENCE: 1004
cagcctctag cctgggattc cctgcgcagc caacaacaga aaagaaaacc agctcccaca 60
cagaggctcc cggctgcgca gaccttgccc agcacaccag attgccagct ccgagacccg 120
ggactcctcc tgtcctgggc cgaatgctct tttagcgcgg tagagtgcac tttctccaac 180
tggaaaagcg gggacccagc gagaacccga gcgaacgatg 220

<210> SEQ ID NO 1005
<211> LENGTH: 547
<212> TYPE: DNA
<213> ORGANISM: Homo sapiens

<400> SEQUENCE: 1005
ggctctttcg gcttccttcc tcgctgggcc ggctaaaccc ggccgcagca gcaccggggt 60
gataagtgtc cagggcagga ggccagcgat gttgccttgc taaccgggta tctaagagaa 120
acagggtctt tttattctta ggctcgacag tctgacggcc ctttttctga acgggaccct 180
gcaggtcttc cgcctgctgt tgcattaaat ttgggggtgg aagaggcttc tgcgttgttc 240
cttacccgca acgatgacca tggctttgcc ttctttaaaa ttgaggcctc caactctgac 300
gctgactgga gaattgaaac ccgaacacac attgggctct tttggcactt gactagagct 360
aaaacctcgg gattcagcgg gcaagcgttg ctcagcaacg gcgcgtaggc tgtgtgcggt 420
tggctggagc cagaccccac cccggcctcg gcccatgctc tagaggggac gttgccccaa 480
tcctgaagga cttcggcact cgagacctgt ggatgccgcg ttgctgtggc ctgcgggggt 540
gatcatg 547

<210> SEQ ID NO 1006
<211> LENGTH: 80
<212> TYPE: DNA
<213> ORGANISM: Homo sapiens

<400> SEQUENCE: 1006
ccgtccctct acgcgttttg gttcccggtt ggtgcttcct gttcgcagct gcggcacttc 60
aaggttactg actttttatg 80

<210> SEQ ID NO 1007
<211> LENGTH: 266
<212> TYPE: DNA
<213> ORGANISM: Homo sapiens

<400> SEQUENCE: 1007
gggcctttct ggacttggac tccttgggag tcgtttctcg gccatttgac ccgtgggact 60
tgtgggtttt gtgctgcttt ttctttcttt cttccccttt tccaacttca gcaatacacc 120
cagatgttag tcgagtcacg tcccgccgcc ctctgccctt gaaatgctgg caagtacgca 180
gccccgcgat cgtcacgtga cgccggggtt cagcgtatcc ttgctgggca accgtcttag 240
agaccagcac tgctggctgc accatg 266

<210> SEQ ID NO 1008
<211> LENGTH: 101
<212> TYPE: DNA
<213> ORGANISM: Homo sapiens

<400> SEQUENCE: 1008
cgctccctcg gtgcggcggg ctgcgtgcgc gagtgggagg tggcaggcct gcgactccgg 60
ccttgtccgc gcccgctctc ggcgcgacgt ctccagccat g 101

<210> SEQ ID NO 1009
<211> LENGTH: 225
<212> TYPE: DNA
<213> ORGANISM: Homo sapiens

<400> SEQUENCE: 1009
ctccctttct ctcagcatct tcttggtagc ctgcctgtag gtgaagaagc accagcagca 60
tccatggcct gtcttttggc ttaacactta tctcctttgg ctttgacagc ggacggaata 120
gacctcagca gcggcgtggt gaggacttag ctgggacctg gaatcgtatc ctcctgtgtt 180
ttttcagact ccttggaaat taaggaatgc aattctgcca ccatg 225

<210> SEQ ID NO 1010

<211> LENGTH: 18
<212> TYPE: DNA
<213> ORGANISM: Homo sapiens

<400> SEQUENCE: 1010
cagccctttt tgcaaatg 18

<210> SEQ ID NO 1011
<211> LENGTH: 300
<212> TYPE: DNA
<213> ORGANISM: Homo sapiens

<400> SEQUENCE: 1011
gagcctcttg cttgctgtga ctggtggagc tgccgcgctg tccgcgttat ctcctcccgg 60
tgagaacgaa ccgcagtgtc caccggcgag gagccagccc tgtcccggtc agagaaagac 120
gacgaggata cctgggagcg ggcggcggcc gggctgggcc gcgccggtgc gggctggcga 180
ctctgctcct ccgcttgctg ctgtctctgg gaactgggtg ccagcgctga ggggcttcca 240
gcggacaggg acccccttcc ccggctcccc tgcccaccct gccggggagg gcggaagatg 300

<210> SEQ ID NO 1012
<211> LENGTH: 33
<212> TYPE: DNA
<213> ORGANISM: Homo sapiens

<400> SEQUENCE: 1012
tgccctctct catgaccccg ctccgggatt atg 33

<210> SEQ ID NO 1013
<211> LENGTH: 27
<212> TYPE: DNA
<213> ORGANISM: Homo sapiens

<400> SEQUENCE: 1013
ccgccccttt ggagctactt cctcatg 27

<210> SEQ ID NO 1014
<211> LENGTH: 270
<212> TYPE: DNA
<213> ORGANISM: Homo sapiens

<400> SEQUENCE: 1014
tcgcctcttc gcattgtgag ctctcgcggt aagaggctga ggagccggcc tgcaacctgc 60
cggggcggct ccgctacgcg cagccgcctc agtggcttcc tccacagcca cctccggagg 120
gatctggctg aggaggaagt ggaggtgtca ctggccccgg cctttgcccc aatcttgtgt 180
gggcactgaa gggggactac aggttcgaga gttatgggtg ctacatgtgt gctttcagag 240
cagtagtgtg aggaagcttg gagtgggatg 270

<210> SEQ ID NO 1015
<211> LENGTH: 146
<212> TYPE: DNA
<213> ORGANISM: Homo sapiens

<400> SEQUENCE: 1015
cggtctttgt ggcttgcagc tcggggtggg tggctcattt cctggccgct cctgggcttc 60
gcggaaagaa gagattactc acactccttc gcaagcacag aaccagttgt actgagcttt 120
ttgctaagct gtttcagcca agaatg 146

<210> SEQ ID NO 1016
<211> LENGTH: 35
<212> TYPE: DNA
<213> ORGANISM: Homo sapiens

<400> SEQUENCE: 1016
gctcccttcc cggcggcctt tgcgggaaca agatg 35

<210> SEQ ID NO 1017
<211> LENGTH: 806
<212> TYPE: DNA
<213> ORGANISM: Homo sapiens

<400> SEQUENCE: 1017
cttccttctc catattgtat actggaattg aagccaagga ggtaccattt tgctcgaggg 60
catggcctaa gccggtcagc taaggccatg ttaatacggg gctgtcccat ctctctgcgg 120
ggcgcgacag ctggaagagc cgaacggata agagaagagg aggtgagagg agctgtacac 180
cacaagaggc actgagggac tcaggataac gggatgaagc cgtcagtgcc cccagaaacg 240
aagcggcccc ggacgaattt ctgagtcacc gtcgcgagaa agcgggctga gccgccattt 300
tgaagcctgg caaaccgaag caagaaatgc tgccgtgttg gatctttgcc agccttcgtg 360
ccgaatggga gcaggttgga gggagggaga gccaatatac actatgggct gattaagccc 420
ggttggctgc catgttgtta acgagcaccg atttcctcta cttttgtcga agaagtttat 480
tgtgggtcag ggacgtcagg tcgcttgcct tcgtttactg tggtcatgat tgagcatatg 540
aggacggcca ttattgttgg gggcaaatgg aaatgctcta ggcggggcca tttttcttag 600
gggcaagctg tcgtcaccct tgtcaactgg ttcggatgaa gcccctgtgg ccgccatctt 660
gatctcgggc ggccccgata agggaggcgg agtgtgcgga gaggaggcgg ggcaactgcg 720
cggacgtgac gcaaggcgcc gccatgtctt ttgagggcgg tgacggcgcc gggccggcca 780
tgctggctac gggcacggcg cggatg 806

<210> SEQ ID NO 1018
<211> LENGTH: 18
<212> TYPE: DNA
<213> ORGANISM: Homo sapiens

<400> SEQUENCE: 1018
ctgccctttc ccaagatg 18

<210> SEQ ID NO 1019
<211> LENGTH: 206
<212> TYPE: DNA
<213> ORGANISM: Homo sapiens

<400> SEQUENCE: 1019
ggccctccct ttcatcagtc ttcccgcgtc cgccgattcc tcctccttgg tcgccgcgtc 60
cttggctggc gttagagaca gggtttcaac gtgttagcca ggatggtctc agtctccaga 120
ccctgtgatc cgcccgcctc ggcctcccaa agtgttggga ttacaggtgt gagccaccgt 180
gcctggccga ggctccttct tttatg 206

<210> SEQ ID NO 1020
<211> LENGTH: 73
<212> TYPE: DNA
<213> ORGANISM: Homo sapiens

<400> SEQUENCE: 1020
cgccctcccc gccgtggatt ggcccgcggc gggacccgtc agccgcggtt gtgtctggga 60
aggagagaaa atg 73

<210> SEQ ID NO 1021
<211> LENGTH: 935
<212> TYPE: DNA
<213> ORGANISM: Homo sapiens

<400> SEQUENCE: 1021
atttctctcc tccctggggg tctcagtgca tctccttctc ctctctgcct gcctcctccc 60
tcaccgaagg gttagcggac acccatcctt ttctgcttgg ggaccccacc accacccgca 120
acactgccgc tgtctcttct tcaccgtatc cttctctacc caccctcttc tctcttctct 180
tctccctgcc cctttaaatc tgcctggccc agcctccccc gtgatgctgg gatggagcaa 240
acattgattt gtgctgggat ggaatcggaa ttttgattta tttttcctct cccaaccata 300
agaagaaaaa aataataaaa acaccccctc ttgagagccc cctccccctt tgcatccagc 360
tcccagctct tcttccctat ctccatccaa ggcagatttt ttcccctaca ctattctcat 420
cttcccccac ccttgccact acctcgcccc cccacccagc ctgctcctcc agctggggag 480
agaggggact ctccggactc ccccaccttt cctctctggg ttggagcagt ctctccggaa 540
ggggaggggg cttggcttgt ccgggcgagg tgggagtgga ggtatcctgc catggatgct 600
gtgccgggga ggcagcctga gccccagccc acatgagacg ccgaagaacc ggggcagagg 660
ggtcctgaca gcagccaggg aaacgggtgc cctacgattc tgcccagccc cctctcagga 720
cccccaaact gccatccaca ctcgacactt cggggttcta gccactcagg atgagggtcc 780
ggccctgcct gccctcgctg gggccccccc gcccggcccc ggtctaactg cccccgcccc 840
gaggcctcgc ccggctccaa ggcccccagc aggctctcca gtcccaggat gcgctgagcc 900 gccgggggc tgaggccgcg ccaactacat gcatg 935

<210> SEQ ID NO 1022
<211> LENGTH: 154
<212> TYPE: DNA
<213> ORGANISM: Homo sapiens

<400> SEQUENCE: 1022
ttttctttct cctcctccaa ccttggcgga ggccacgact caggcgccac agctgggggc 60
tagaggccgc ggaccatggt gcggggcagc caccgctgaa gtcagcaaaa ccgagcctgg 120
cctgaggcag gctgcgcggg aggccaaagc catg 154

<210> SEQ ID NO 1023
<211> LENGTH: 194
<212> TYPE: DNA
<213> ORGANISM: Homo sapiens

<400> SEQUENCE: 1023
cgctccttct ttctggccgg atgtgtgctg agacccagag tcacccaggg gtctccgtca 60
cgtgccagga gtaggcagaa gtgggctgtg acagatcagg aaacagagct cagtgcagcc 120
cactaaattg ctcagggccc tacagctaac aagcggcaga ggcaggatct gcactcagga 180
gctgcttgga gatg 194

<210> SEQ ID NO 1024
<211> LENGTH: 73
<212> TYPE: DNA
<213> ORGANISM: Homo sapiens

<400> SEQUENCE: 1024
ggctctctct gcggcttggc ccgttagagg cggcttgtgt ccacgggacg cgggcggatc 60
ttctccggcc atg 73

<210> SEQ ID NO 1025
<211> LENGTH: 120
<212> TYPE: DNA
<213> ORGANISM: Homo sapiens

<400> SEQUENCE: 1025
agttctcttc acggagccgc gcggctgcgg gggcgcaaat agggtcagtg ggccgcttgg 60
cggtgtcgtt gcggtaccag gtccgcgtga ggggttcggg ggttctgggc aggcacaatg 120

<210> SEQ ID NO 1026
<211> LENGTH: 287
<212> TYPE: DNA
<213> ORGANISM: Homo sapiens

<400> SEQUENCE: 1026
gttcctttcc tgggcatcag cttgcctgct ctcagcctaa gctctctcgc caaccgtggt 60
ggctccttgc gttcctacat cctctcatct gagaatcaga gagcataatc ttcttacggg 120
cccgtgattt attaacgtgg cttaatctga aggttctcag tcaaattctt tgtgatctac 180
tgattgtggg ggcatggcaa ggtttgctta aaggagcttg gctggtttgg gcccttgtag 240
ctgacagaag gtggccaggg agaaggcagc acactgctcg gagaatg 287

<210> SEQ ID NO 1027
<211> LENGTH: 31
<212> TYPE: DNA
<213> ORGANISM: Homo sapiens

<400> SEQUENCE: 1027
tctccttcta cggatatctg tggaccttat g 31

<210> SEQ ID NO 1028
<211> LENGTH: 161
<212> TYPE: DNA
<213> ORGANISM: Homo sapiens

<400> SEQUENCE: 1028
gcttctttcc gcccggctcc ttcagaggcc cggcgacctc cagggctggg aagtcaaccg 60
agctcccttc caggtcaatc caaactggag ctcaactttc agaagagaaa gacgccccag 120
caagcctctt tcggggagtc ctctagctcc tcacctccat g 161

<210> SEQ ID NO 1029
<211> LENGTH: 197
<212> TYPE: DNA
<213> ORGANISM: Homo sapiens

<400> SEQUENCE: 1029
cctcctcctt tcctccctct actctgacac agcacttagc acctgaatct tcgtttctct 60
cccagggacc ctccattttc catatccagg aaaatgtgat gcgccacagg tatcagcgtc 120
tggatcgcca cttcacgttt tagccacaag tgactcagtg gaagatccag agtcaacaga 180
ggctcgtcag gaagatg 197

<210> SEQ ID NO 1030

<211> LENGTH: 112
<212> TYPE: DNA
<213> ORGANISM: Homo sapiens

<400> SEQUENCE: 1030
caccctttca ctacttctcc cccggactcc ttggtagtct gttagtggga gatccttgtt 60
gccgtccctt cgcctccttc accgccgcag accccttcaa gttctagtca tg 112

<210> SEQ ID NO 1031
<211> LENGTH: 147
<212> TYPE: DNA
<213> ORGANISM: Homo sapiens

<400> SEQUENCE: 1031
tttccttcct ctcttccctt cgcagaggtg agtgccgggc tcggcgctct gctcctggag 60
ctcccgcggg actgcctggg gacagggact gctgtggcgc tcggccctcc actgcggacc 120
tctcctgagt gggtgcgccg agtcatg 147

<210> SEQ ID NO 1032
<211> LENGTH: 128
<212> TYPE: DNA
<213> ORGANISM: Homo sapiens

<400> SEQUENCE: 1032
gcccctttct ttccttcgct tcctctttta gagaatgtcc ggattgctat tggactttgg 60
agcgtatggc tccaaatcaa ctcattggct aaaacttgac ggaaaatggt ggttaggtgg 120
ccagaatg 128

<210> SEQ ID NO 1033
<211> LENGTH: 314
<212> TYPE: DNA
<213> ORGANISM: Homo sapiens

<400> SEQUENCE: 1033
cggcctcttc ccagcgttcc tcctccggcc ccaggtcacc gccagcacgc gcctgcttcc 60
cgtctgcgcg agtccacgca gctccccaga tcaagaagct gaggccccag gttacacact 120
aaagtaaatg gcagaggcag aaataacacc tatgtcctcc tgaccccaag gcatgttctt 180
aaagttctgg aaacctcctg gaggcttcct tgctgctcct ctgggactgc caccctgggc 240
agggtgttct gtggcccctc atcatcgtgg ttttgaacca caggcccttc accagcacag 300
cagcagcagg catg 314

<210> SEQ ID NO 1034
<211> LENGTH: 127
<212> TYPE: DNA
<213> ORGANISM: Homo sapiens

<400> SEQUENCE: 1034
catcctcccg ccagcctgcc cgcctgctcg ccggcgcccg gagcccgctc tggccgcttg 60
ctttttgctg agaaagcttc ctgccctgga agatggcacc cttccccatc cagacacctt 120
gggaatg 127

<210> SEQ ID NO 1035
<211> LENGTH: 197
<212> TYPE: DNA
<213> ORGANISM: Homo sapiens

<400> SEQUENCE: 1035
cttcctcctt ttcacggcgt cttgcattac tattgtgcgg ctgcaggagg tgtcgagcgg 60
cgttattttt ttttgcggtt tgcctttttt tttctttttt tttttttgg aaccgcggtt 120 gtttaaaagc ctgagggaac ctggagaggg gctcccactc cctaccctct ttcctccgag 180
tttgtgactc cgagatg 197

<210> SEQ ID NO 1036
<211> LENGTH: 180
<212> TYPE: DNA
<213> ORGANISM: Homo sapiens

<400> SEQUENCE: 1036
ggctctttgt cgaagctaga ggaccggcag gcggcagcag caactacggc ggcggcggca 60
gaacccagca gcgatgtgga ggtggagacc cacaggagcc ccggacttca cctgagctac 120
ctcagtggtc accaagagtg gcaagataaa gaaaaccctg agttgggcgg gaccaggatg 180

<210> SEQ ID NO 1037
<211> LENGTH: 119
<212> TYPE: DNA
<213> ORGANISM: Homo sapiens

<400> SEQUENCE: 1037
ccgtctttca gtttcacttt tgttttcctg ctcccagcag ggttaggctt gctgaggggc 60
aggcacagga gtcctggctg agctcatggc ctgaggctgc ctagcggcca cggggaatg 119

<210> SEQ ID NO 1038
<211> LENGTH: 20
<212> TYPE: DNA
<213> ORGANISM: Homo sapiens

<400> SEQUENCE: 1038
ccgcccttcc ttgtaagatg 20

<210> SEQ ID NO 1039
<211> LENGTH: 509
<212> TYPE: DNA
<213> ORGANISM: Homo sapiens

<400> SEQUENCE: 1039
ctgcccttcc gcagcgatgg catcccgggt gagtatcggc cccggccgag cccccaaggc 60
gggcgggcag cgcggcaggg ccgggacttg agcggaggac cgagtaggcg caggtgtccg 120
ggcccaacag gaccaggaag gtgtcggggt tggaatgagt gggtacccgg gccggggacg 180
gtgcgagagg gtgccttgct tgggagcgga acgagaaggt acttgggtca gggaggtgat 240
gcccgggcct ggaacgtggc ggggattgga gcaggcgcgc aggtacccga tccgaggcgg 300
ggagagcacc cgggatggaa ggagcaggcg tgcgggccgt gagcggcgcc agagggtacc 360
tggctctgtg gaggggccct ctggtatgtg tgtccctgtc cttctggggc gtggatggtg 420
cctgggaccc agctggcaac cagttgaaga cgttctcctt ggaagctctt ggccctgagg 480
actttgcctg gggcattggc cctgccatg 509

<210> SEQ ID NO 1040
<211> LENGTH: 463
<212> TYPE: DNA
<213> ORGANISM: Homo sapiens

<400> SEQUENCE: 1040
gcgtctcttc cggcgtctag gggggtgtcc tgccggcgcg cgggccctgc ggccattttg 60
ggcttcgctt ccaccgcacc agccggccta cccagtcctt ccggtatcgc gttgctcagg 120
ggcttttcaa ccctctgtca gtcggaaaac catcgccgag gccgtggggg gactcctatc 180
catggtgttg aagcgtcgag ccgactaggg aacctccttc cccgccagga tggaagtcgc 240
atcagtcgcc gcctattgcg cggctgttc ttccctgtgt tctgccgccc gctgccgcat 300
tcgctgccct ctgtggcttt tctgctggct cgaagatcgg cctggagcag cgacgccacc 360
gctgggcaag gccgagactc tgtaggcttc ctccgaatcc cgtcgacctc cagccgctga 420
gcgccgcggc cctacctgag agactgtcaa gaaaaaggag atg 463

<210> SEQ ID NO 1041
<211> LENGTH: 51
<212> TYPE: DNA
<213> ORGANISM: Homo sapiens

<400> SEQUENCE: 1041
ccctctcttc gcggagcggc gccgcgtagc ttccatccgc cagctgccat g 51

<210> SEQ ID NO 1042
<211> LENGTH: 159
<212> TYPE: DNA
<213> ORGANISM: Homo sapiens

<400> SEQUENCE: 1042
agccctttac actacggtgt ttccggcttc aagatggtcg cctaagctgt ttagtgaaac 60
ttcttccacc tttctccatt cctctaggtg ctttttctga acctggatgt gaggcattaa 120
aggatccgac ggaaatagaa ttgaaggcat tctaaaatg 159

<210> SEQ ID NO 1043
<211> LENGTH: 187
<212> TYPE: DNA
<213> ORGANISM: Homo sapiens

<400> SEQUENCE: 1043
cctcctccgt gtggggcagc tgctggctgg gctgcctgtt gagtcagcct tcttccctca 60
cggctcttct cccggtccct gaaactcggc tgccagggga gctggagcca cctgcgaagg 120
tgtcctccca tactggaccc ctacaggaag ctccgtgtgc ccagctgggg cacagcccca 180
gctgatg 187

<210> SEQ ID NO 1044
<211> LENGTH: 367
<212> TYPE: DNA
<213> ORGANISM: Homo sapiens

<400> SEQUENCE: 1044
gctccttttc ctttttgatc cattcaaaaa ttactcattg caaattcccg gactgctagg 60
cgaggagagg gaagggggcg gaggagacag ggctactgca ggcgcagagc tgggggcagc 120
cgggggcccg agtggctgag gctggtcccg cagcggccgc ttgccggcgt tctggctcct 180
gtggcctcac caggaagcgt cagagtcccg acactgggga agctcggagc gccgcctccg 240
ctgccgccgc ctcctgcctg gctctgggtc cccgagcccc ctcccctggc ccagcccgac 300
tccctcctcc ttcccgaacc atccggctcg ggctccttcc ctggcgatgg ctggccgctg 360
agccatg 367

<210> SEQ ID NO 1045
<211> LENGTH: 114
<212> TYPE: DNA
<213> ORGANISM: Homo sapiens

<400> SEQUENCE: 1045
ccgtctctgg gcggctgctg ccgctgccgc tgctgctgct gcgggggtcg ggcggcggcc 60
aggggatttg ggcaggcacc gtggatcccc gagaagggga cgagttgaca gatg 114

<210> SEQ ID NO 1046
<211> LENGTH: 372
<212> TYPE: DNA
<213> ORGANISM: Homo sapiens

<400> SEQUENCE: 1046
gagcctctgc cagccctgag ctgggaagaa gcagctacct cggaggcagg gcgcgcaggc 60
gggcggcgat gagagggggc gcagccgcag ccccgcgctg gggagcccac cgctaaccct 120
gcaccccacc cacccctgca caaaagagct ggcgggcgct ggccacgtcg ccctgggtga 180
ccttcctcgg atgcagaatc cgcccctgcg agcatcctct tcctcctagg ctctgaaggc 240
ccggggagcg tgagcgatgc ccagctgcac ccgggcaggg ctcgcctttg tttgccagta 300
aggaggagag gctgtctcag ctgcagaggg gtcatccctg cttcaagcca gtgcctcttc 360
ccagctccca tg 372

<210> SEQ ID NO 1047
<211> LENGTH: 189
<212> TYPE: DNA
<213> ORGANISM: Homo sapiens

<400> SEQUENCE: 1047
attcctctct cacccccacg cagaggagag aacttgcttc tggacccggg tgggtgccgg 60
ctcggctctc cttgtcttcc agagcggtgg cccggaagca cagtcctccc agacgccagc 120
gccagaagct cggatcgcgg ctgcaccggg agagcgccga tctgggtgcg aggcaggtgc 180
ggggccatg 189

<210> SEQ ID NO 1048
<211> LENGTH: 257
<212> TYPE: DNA
<213> ORGANISM: Homo sapiens

<400> SEQUENCE: 1048
gttcctctag gaaaattcct ttgtgcagat caggcccgtg gattggtgag tgaatcctaa 60
ccacgtcttc cctggcctgt cttcactctt ctccccagaa tcaccacttc tgcactggtg 120
tctgaaggtg tattgagtga ttttgtggag ggcagaagta ggaagtcttt gggacaaaac 180
tgtatttacc ttgggatctg tgaacaagag gaacctcagc agccaggaca ggcaggagca 240
gtggaatagc tactatg 257

<210> SEQ ID NO 1049
<211> LENGTH: 20
<212> TYPE: DNA
<213> ORGANISM: Homo sapiens

<400> SEQUENCE: 1049
cgccctctcg cgcggcgatg 20

<210> SEQ ID NO 1050

<211> LENGTH: 73
<212> TYPE: DNA
<213> ORGANISM: Homo sapiens

<400> SEQUENCE: 1050
ctccctccct gcagcccgca acgggaatgg agtaaaggga gacccgtcga cctggccacg 60
gggatcagcg atg 73

<210> SEQ ID NO 1051
<211> LENGTH: 260
<212> TYPE: DNA
<213> ORGANISM: Homo sapiens

<400> SEQUENCE: 1051
cattcttccg gtttcagaag ttaaggctgg tgtcctggcc ccagtccacc tctgggagcg 60
cctgcgccgc tccgcggaga gtccgtggat ctcacagtga aaaatgtttg ctgacccttg 120
acattgacaa actgctgaca gctcagatga tccatgattg gaaggatgtg gtcatcacca 180
agatgtcttt ctttctccgg ttcccagttt tccagacctg aagtgttttc caatcaaagc 240
gaagagacga tctgtggatg 260

<210> SEQ ID NO 1052
<211> LENGTH: 370
<212> TYPE: DNA
<213> ORGANISM: Homo sapiens

<400> SEQUENCE: 1052
ggctctcttg cgcaagcgcg ctgtccgctt cttctgggcg gacgctctgg aggcaaaaca 60
tttccctgct gggggcggcg accaccgtga gcgtcccgga aggggcggca aagacgcctc 120
cgtcgcgcac gaggtggcct cgttggcttt accttggttc gcggtcgtcc ttggttatcg 180
tgagcgtccg cgagtctctg ggaggccaag cctaggggcg ccacagcgcc tgcgcgcgta 240
cggcggccgg aaggggctag aggcggctcc ctgggtgaca accgcgcgcc ccacctttcc 300
ccacgtggcc gcgaagaccg gctcaggagc atctatcggc tgcacgccaa catcaacaca 360
ggcgaagatg 370

<210> SEQ ID NO 1053
<211> LENGTH: 36
<212> TYPE: DNA
<213> ORGANISM: Homo sapiens

<400> SEQUENCE: 1053
gctcctcccc cggcggcgag ccagggagaa aggatg 36

<210> SEQ ID NO 1054
<211> LENGTH: 63
<212> TYPE: DNA
<213> ORGANISM: Homo sapiens

<400> SEQUENCE: 1054
tgccctcttg tttttagtct cgcttttcgg ttgccgttgt cttttttcct tgactcggaa 60
atg 63

<210> SEQ ID NO 1055
<211> LENGTH: 126
<212> TYPE: DNA
<213> ORGANISM: Homo sapiens

<400> SEQUENCE: 1055
ggctctccta ccttctcggg cagcccagtc tttgccatcc ttgcccagcc ggtgtggtgc 60
ttgtgtgtca cagccttgta gccgggagtc gctgccgagt gggcgctcag ttttcgggtc 120
gtcatg 126

<210> SEQ ID NO 1056
<211> LENGTH: 563
<212> TYPE: DNA
<213> ORGANISM: Homo sapiens

<400> SEQUENCE: 1056
ccgcctctgc cccgcggcga gggtgtctat ggagaggcgg cggccgcggc tgctgaggcg 60
gaggctgagg cagtggcgat ggcgcccttt cctgaagaag tggacgtctt caccgcccca 120
cactggcgga tgaagcagct ggtggggctc tactgcgaca agctttctaa aaccaatttt 180
tccaacaaca acgatttccg tgctcttctg cagtctttgt atgctacttt caaggagttc 240
aaaatgcatg agcagattga aaatgaatac attattggtt tgcttcaaca acgcagccag 300
accatttata atgtacattc tgacaataaa ctctccgaga tgcttagcct ctttgaaaag 360
ggactgaaga atgttaagcc tactactgtt gactggaagc cttaccaata acataaaaca 420
atcgaataac aattatttca tgtattatat gtaaaatata tatactggat tcttacagta 480
agaatgaata tgaacagtta aattatgcaa aacaactgaa agagagattg gaggctttta 540
caagagattt tcttcctcac atg 563

<210> SEQ ID NO 1057
<211> LENGTH: 74
<212> TYPE: DNA
<213> ORGANISM: Homo sapiens

<400> SEQUENCE: 1057
ctgcctccac tcggcctcag ttcctcatca ctgttcctgt gctcacagtc atcaattata 60
gaccccacaa catg 74

<210> SEQ ID NO 1058
<211> LENGTH: 55
<212> TYPE: DNA
<213> ORGANISM: Homo sapiens

<400> SEQUENCE: 1058
tcgtctctct ctctgcgcct gggtcgggtg ggtgacgccg agagccagag agatg 55

<210> SEQ ID NO 1059
<211> LENGTH: 271
<212> TYPE: DNA
<213> ORGANISM: Homo sapiens

<400> SEQUENCE: 1059
ccgcccctcc cgatttcctc cgggctacag gcgacagagc tgagccaagc gtttactggg 60
cagctgttac ggtaagtgag gaggggctgg ggtgcccagc gttttggatc tcccactctg 120
gcccggcccc ggaataccac atagaggcct tgggacctga ttcatcccgt ccagacagcc 180
ctagagacct gagcgactga ggcctgggat ctggacgccg gaatttcctg cgtggttctg 240
gacgccctgc cctgggctca gattccaaat g 271

<210> SEQ ID NO 1060
<211> LENGTH: 238
<212> TYPE: DNA

<213> ORGANISM: Homo sapiens

<400> SEQUENCE: 1060
cctcctcttg tagtggcgcc ggcttgcatc ccaggtcgtg gcggttttgg tgcctgaagc 60
agggagcgcg gagtcgttcc cgagagaggc ggccaggcta tgctcgccgg tttccggcgt 120
tccgctccgg ccagccagag tctctgtctc aacctgtgtc cgtgctccag cagtctcctc 180
agcccggccc cgcggcgcgg ttggcggcgg cgccccaggc gcgccccctc ctccgatg 238

<210> SEQ ID NO 1061
<211> LENGTH: 26
<212> TYPE: DNA
<213> ORGANISM: Homo sapiens

<400> SEQUENCE: 1061
cgctctttcc cggaggctgg cagatg 26

<210> SEQ ID NO 1062
<211> LENGTH: 187
<212> TYPE: DNA
<213> ORGANISM: Homo sapiens

<400> SEQUENCE: 1062
ctttcccttt cggacatgcg cgctcggagc aaggcgccct cgcactcagc ttaccgcgca 60
tgtacgttgc caggggtaac gcaggtagcc aaagtggctt gtggagtggc gaccgttagt 120
gaggcggttg ctgagacaga cgctgaggcg ggtaggagga gcccgagccg taagggaagc 180
cgtgatg 187

<210> SEQ ID NO 1063
<211> LENGTH: 27
<212> TYPE: DNA
<213> ORGANISM: Homo sapiens

<400> SEQUENCE: 1063
agttcttccg gggcggaggt caccatg 27

<210> SEQ ID NO 1064
<211> LENGTH: 582
<212> TYPE: DNA
<213> ORGANISM: Homo sapiens

<400> SEQUENCE: 1064
ccgccccttc gcttataatg cagagcatgt gaagggagac cggctcggtc tctctctctc 60
ccagtggact agaaggagca gagagttatg ctgtttctcc cattctttac agctcaccgg 120
atgtaaaaga actctggcta gagaccctcc aaggacagag gcacagccac acgggagtga 180
aatccacccc tggacagtca gccgcaatac tgatgaagct gagaagcagc cacaatgctt 240
caaaaacact aaacgccaat aatatggaga cactaatcga atgtcaatca gagggtgata 300
tcaaggaaca tcccctgttg gcatcatgtg agagtgaaga cagtatttgc cagctcattg 360
gacattctca ctattctatg ccttaaaggc ccttcaacgg aagggatatt caggagagca 420
gccaacgaga aagcccgtaa ggagctgaag gaggagctca actctgggga tgcggtggat 480
ctggagaggc tccccgtgca cctcctcgct gtggtcttta aggacttcct cagaagtatc 540
ccccggaagc tactttcaag cgacctcttt gaggagtgga tg 582

<210> SEQ ID NO 1065
<211> LENGTH: 42

<212> TYPE: DNA
<213> ORGANISM: Homo sapiens

<400> SEQUENCE: 1065
ggtcctcctt ggctgactca ccgccctggc cgccgcacca tg 42

<210> SEQ ID NO 1066
<211> LENGTH: 122
<212> TYPE: DNA
<213> ORGANISM: Homo sapiens

<400> SEQUENCE: 1066
ccccctcctt cataaagtcc tggcctcggg acagcctgca cagctgccta gcctgtggag 60
acgggacagc cctgtcccac tcactctttc ccctgccgct cctgccggca gctccaacca 120
tg 122

<210> SEQ ID NO 1067
<211> LENGTH: 80
<212> TYPE: DNA
<213> ORGANISM: Homo sapiens

<400> SEQUENCE: 1067
cgctctcccc ggatcgtgcg gggcctgagc ctctccgccg gcgcaggctc tgctcgcgcc 60
agctcgctcc cgcagccatg 80

<210> SEQ ID NO 1068
<211> LENGTH: 164
<212> TYPE: DNA
<213> ORGANISM: Homo sapiens

<400> SEQUENCE: 1068
gcccctctcc ccgggcagcc gcggcggcag cagcagcagc agcagctgga gctgtggggc 60
tgtcaccgcc gcccgccccg ctcactcgcg gatcccgacc gcccatctcc gcctcgcttc 120
cagcccagga tgagacttct gtgagcagcg aggattttga tatg 164

<210> SEQ ID NO 1069
<211> LENGTH: 244
<212> TYPE: DNA
<213> ORGANISM: Homo sapiens

<400> SEQUENCE: 1069 caccccttctt tgtgctcggg ttaggaggag ctaggctgcc atcgggccgg tgcagatacg 60
gggttgctct tttgctcata agaggggctt cgctggcagt ctgaacggca agcttgagtc 120
aggaccctta attaagatcc tcaattggct ggagggcaga tctcgcgagt agggcaacgc 180
ggtaaaaata ttgcttcggt gggtgacgcg gtacagctgc ccaagggcgt tcgtaacggg 240
aatg 244

<210> SEQ ID NO 1070
<211> LENGTH: 336
<212> TYPE: DNA
<213> ORGANISM: Homo sapiens

<400> SEQUENCE: 1070
tttcctcttg agccatcatg cacatctgac tgcagcccca gcgagccctt ccttccttgt 60
ctgactgctc ttcttctcga tttcttcttg ttctgccttc tcggtttgca gccctgaccc 120
ccgctgtgtg tctggccctt ggtgactgtc cgtgtttctg ttcctgtcat tgtaactgtg 180
acttttctct ctgtctgccc cccccttccta ctggttcatg cttctccccc attcccaccc 240
tctctgcccg gcctcccgct cccgcccttt ctcctcatgc acccggcctc gtctctgtag 300
tctctgcact tgtctcccat taaggtccca tccatg 336

<210> SEQ ID NO 1071
<211> LENGTH: 303
<212> TYPE: DNA
<213> ORGANISM: Homo sapiens

<400> SEQUENCE: 1071
cagtcttcct cccgcccctt ctttggtccc tacggacctg gggggcggtg gcggtcaatg 60
ccgggtcaag gtccgcgggc ctcgcagatc gtagcccggg cgcacgcgat cagatgatcc 120
tgttgtggac ggctaagttg taggcgggat ggctgagaaa gcggcgctag gaccccccggg 180 cagaggctcg gggaagggag tcagggggga aatgccttac aaggtcgcct tgcggtcacc 240
atcattgccc gccgcccaaa atagccccccg gcgccagctg gcctgcccta tggccgagag 300
atg 303

<210> SEQ ID NO 1072
<211> LENGTH: 81
<212> TYPE: DNA
<213> ORGANISM: Homo sapiens

<400> SEQUENCE: 1072
ctccctcttt ccctccctcc tcctccgtcc gcccgtccgt ccgcgcgtct gtccgttcgg 60
cccggtccgg cccgaagcat g 81

<210> SEQ ID NO 1073
<211> LENGTH: 819
<212> TYPE: DNA
<213> ORGANISM: Homo sapiens

<400> SEQUENCE: 1073
cagcctccct tatttagtcc gcgatggctt ccctcgcgcc ccaccgtcct cttccggaag 60
gcggctccct ccctgcgcag cccggagccc ctgagatcag cctcgagcag gcgcccgagc 120
gagactatcc ctaaacggga acggcggtgg ccgactcgcg agtgaggaaa agaaggaaag 180
ggcagactgg tcgcgaagag aagatccagg cctcagagga ggagaaaggc cggagccagc 240
cgaggtttgc cgagggcggt gttccggacc cgcgcggtgc ggggaggaag gccgagggtg 300
ggagaggagg ggcccggcgg aaactgccga ggtttcccga aggcggcagc gtccgagttg 360
cccggatgta gttggtggag cggcagcggc ggcaccagcg gcggcggcgg cggcgggagg 420
aggaggagga gaagaaggac caggcggcgg cagcagcggc ggcggcgggg ggaggagggg 480
aggaggcggc ggagcaggag gaggagaagg cggaggaggc agtcgctctc cgcggggctg 540
agccggacgc gtcgtcttgc ccccctcccc ccggttcgcg gtgccgccgt gtagttggcg 600
ccgctgcccc ggctgagagt gagcgtggtg tcgacggagg gagatggccc gggagcgccg 660
gcgccagtaa ctgggagctg atgagagtcg ccgagggcgc gccgggccca ggtgccgggg 720
ctgcccgccg cccgccgccg ccgccgcctg cgcgcccgcc cgcctttcgc ggccgctctc 780
ccccctcccc gacacacact cacaggccgg gcattgatg 819

<210> SEQ ID NO 1074
<211> LENGTH: 19
<212> TYPE: DNA
<213> ORGANISM: Homo sapiens

<400> SEQUENCE: 1074
cgctccttca gtctcgatg 19

<210> SEQ ID NO 1075
<211> LENGTH: 91
<212> TYPE: DNA
<213> ORGANISM: Homo sapiens

<400> SEQUENCE: 1075
cagccttctg cactcacagc cgaagggaaa gcagcaggtt ggggcttctt gtggccaact 60
tcagagcctg tcaccaggaa aggtaagcat g 91

<210> SEQ ID NO 1076
<211> LENGTH: 352
<212> TYPE: DNA
<213> ORGANISM: Homo sapiens

<400> SEQUENCE: 1076
cgccctctag ccccctcccg cgggagtcgc ggcgctgcgg gtaggagccg ggttgcggga 60
gaccccaggt tcggttggga ttcccagcca gaacggagct taagccgggc aggcgagcga 120
atgacggagt agcgagctgc acggcggcgt gctgcgctgt tgaggacgct gtcccgcgcg 180
ctcccaggcc gccccgaggc ttggggtctt cgaaggataa tcggcgcccg gggccgaaca 240
gcgggggcac acggggcgct gccgaagtgc aaggccacgg ccagagctcg agcccgacgc 300
gctgtctgga gtcgtaggac cctgacgtgg ctgaagcggc cccgggagca tg 352

<210> SEQ ID NO 1077
<211> LENGTH: 129
<212> TYPE: DNA
<213> ORGANISM: Homo sapiens

<400> SEQUENCE: 1077
agccctcccc gcggccggct cggctccttg gcgctgcctg gggtcctttc cgcccggtcc 60
ccgcttgcca gcccccgctg ctctgtgccc tgtccggcca ggcctggagc cgacaccacc 120
gccatcatg 129

<210> SEQ ID NO 1078
<211> LENGTH: 342
<212> TYPE: DNA
<213> ORGANISM: Homo sapiens

<400> SEQUENCE: 1078
ctccctcttt tctcagtacc ctcctcttta ctctccgagt taactgagag ccgacctgac 60
atctccaaca ttttcaccct cttcccccac ccccatcacc gagaatggag tcagggtttc 120
cggagagacc gaactctgct ctcagcacct ttcccagccg ctgttgctaa actgacctcg 180
gaggacgaga ggggaaggag gtgcgacgcc ccttacatca gtacataact accacaccaa 240
ccacctccac ttcaaagccg gattttgcat cctgggggcg ggacagacct cgtcccgggc 300
tgaattctct ctccactctt cgagattggc acacccagaa tg 342

<210> SEQ ID NO 1079
<211> LENGTH: 154
<212> TYPE: DNA
<213> ORGANISM: Homo sapiens

<400> SEQUENCE: 1079

-continued

```
ctgtctttcc ttccctccct gctcggcggc tccaccacag ttgcaacctg cagaggcccg     60

gagaacacaa ccctcccgag aagcccaggt ccagagccaa acccgtcact gaccccccag    120

cccaggcgcc cagccactcc ccaccgctac catg                                154


<210> SEQ ID NO 1080
<211> LENGTH: 309
<212> TYPE: DNA
<213> ORGANISM: Homo sapiens

<400> SEQUENCE: 1080

aggtctcttg actctttccg cctttgttta caaccctgcc atgatctccc tcttgcaaaa     60

gcgagggcta cagaacaggc attcaggagt cctgtgctcc agtcacagcc ttttctgttc    120

ttcagctagg agacaccaaa ccctcaggaa gatttactat agctaagaga aaactgcagc    180

agaaagggcg cggctaccta cttcttaaat tccgtttgtg gaccctcaga ctcttagtcc    240

cctactccca gatacagcgg ccctaccgtg gctcctggca aggtggcatc cacttttgta    300

gtaagcatg                                                            309


<210> SEQ ID NO 1081
<211> LENGTH: 50
<212> TYPE: DNA
<213> ORGANISM: Homo sapiens

<400> SEQUENCE: 1081

ctgtccttct ggcggagcgt gcttcccgct gcggggacgt tcgagcaatg                50


<210> SEQ ID NO 1082
<211> LENGTH: 314
<212> TYPE: DNA
<213> ORGANISM: Homo sapiens

<400> SEQUENCE: 1082

cgttctctgg tagcgaccat tttggttaat gttgggtgtg tttctgcggt ttgtgaggtg     60

agaggcgctg gagctatggg tccgaaccgc ggtgtctgaa cccagaaggt gaagagtcct    120

tcttgctgca cagaggcaga tcttaggccc cgtaacggcg cccgccgctc ccggcagtgc    180

tttccccgcg tactcgggat ggcggcggcc gcgctgaggc tcccggctca ggcatcatct    240

ggctgcaaag aagagaacac actgtgtttg agggaggagg aaggaggatc agagtttaaa    300

ctcctgccat aatg                                                      314


<210> SEQ ID NO 1083
<211> LENGTH: 97
<212> TYPE: DNA
<213> ORGANISM: Homo sapiens

<400> SEQUENCE: 1083

gtttcttccg cttcctgtac cacccggctc aagtagcgga cacggaacag ggaactatca     60

gcccgtcggc ctccgggccc tgcattctct agccatg                              97


<210> SEQ ID NO 1084
<211> LENGTH: 88
<212> TYPE: DNA
<213> ORGANISM: Homo sapiens

<400> SEQUENCE: 1084

agcccttttc gactgtgagc tgcggcagct gagcagaggc ggcggcgcgg gacctgcagt     60

cgccagggat tccctccagg tgacgatg                                        88
```

<210> SEQ ID NO 1085
<211> LENGTH: 465
<212> TYPE: DNA
<213> ORGANISM: Homo sapiens

<400> SEQUENCE: 1085 ccccctttc gtttccggcg ctcccgcctt ctctccgcag agctcttctc tgagcctgtt 60 gggggaggg aggggggcgt ggaggaactg gggttcgcgg gagcacgagc tgcagcacca 120
cttccgggtg agtgcaaggg gagggcagca aggagggggg gccacccact acctcgcgcc 180
cccgccctgc gggtgtctcg cgcgcgttcc gtgcgtgtga gtgtgtgggt ctgtctcgct 240
ccagaagtgc gtgcccgcgc gctgcgcctt gcgctttttc ccctccctcg cccottcctg 300 gtcctcccac cctcctcggc tccctccttt cccagcaaac gccgcccctc ccgcgccctg 360
gctcaggctc tggcgccgcc gcagccgtcg ccgcccgaaa gttcaggagc cctggaaagg 420
agaaggaata agacggcagg aggaagagag agagagggta gaatg 465

<210> SEQ ID NO 1086
<211> LENGTH: 140
<212> TYPE: DNA
<213> ORGANISM: Homo sapiens

<400> SEQUENCE: 1086
ctctcctttc tcctccggca gccagcgcgc ctgtgtcctc tctaggaagg ggtaggggag 60
gggcgtctgg agaggacccc ccgcgaatgc ccacgtgacg tgcagtcccc ctggggctgt 120
tccggcctgc ggggaacatg 140

<210> SEQ ID NO 1087
<211> LENGTH: 90
<212> TYPE: DNA
<213> ORGANISM: Homo sapiens

<400> SEQUENCE: 1087
gctcctcctc ccgctcctcc tcggcctccc cttcgggcgc tctcgcgcta actgtgctcc 60
tccggggccc tccgcctgct cccagccatg 90

<210> SEQ ID NO 1088
<211> LENGTH: 161
<212> TYPE: DNA
<213> ORGANISM: Homo sapiens

<400> SEQUENCE: 1088
gcgcctttat ctgcatccgg gtccgtggga ttcgcgctcc actggtcagc tggggtcgct 60
ctcgggtggt tgggtgttgc ttgttcccgc tgttccagcg tcgaagaacc attgggtctg 120
ccggtttgaa cttgttctgg aagctgtgcg tcaccgtaat g 161

<210> SEQ ID NO 1089
<211> LENGTH: 34
<212> TYPE: DNA
<213> ORGANISM: Homo sapiens

<400> SEQUENCE: 1089
ccgcctcctc cgcttgcggc cggtctgcac catg 34

<210> SEQ ID NO 1090
<211> LENGTH: 106
<212> TYPE: DNA

<213> ORGANISM: Homo sapiens

<400> SEQUENCE: 1090
tttcctttcc gctcccaggg gcgttgggaa cggttgtagg acgtggctct ttattcgtga 60
gttttccatt tacctccgct gaacctagag cttcagacgc cctatg 106

<210> SEQ ID NO 1091
<211> LENGTH: 100
<212> TYPE: DNA
<213> ORGANISM: Homo sapiens

<400> SEQUENCE: 1091 ggacctttc ggccaccgct cgcttcaata tggctgcccc cagggagaga cgaggctacc 60
atgaaggagc cgagcgcaga ccctgagtcc gtcacccatg 100

<210> SEQ ID NO 1092
<211> LENGTH: 132
<212> TYPE: DNA
<213> ORGANISM: Homo sapiens

<400> SEQUENCE: 1092
ctccctcctc cttacccccc cctccctgtc cggtccgggt tcgcttgcct cgtcagcgtc 60
cgcgtttttc ccggcccccc ccaacccccc cggacaggac ccccttgagc ttgtccctca 120
gctgccacca tg 132

<210> SEQ ID NO 1093
<211> LENGTH: 215
<212> TYPE: DNA
<213> ORGANISM: Homo sapiens

<400> SEQUENCE: 1093
cgccctctag tggcagccgg ttttgaggcc ggcctccggc tttgaagttc ctcaccgcgt 60
ctccttccct ctccccaaag cctggatcac cgcccagcgt caggcgaggg gcgacgtctc 120
gaggtaaaac ggaggaggtg cgggacgcgg agactgcgcg ggcccggtag ccctggagag 180
gccgaggctc taggccgcga ggggcgggtg caatg 215

<210> SEQ ID NO 1094
<211> LENGTH: 80
<212> TYPE: DNA
<213> ORGANISM: Homo sapiens

<400> SEQUENCE: 1094
agttctctgc ggagggccgg ttgatacagt tccggtggga gaacgcggct gcgaggtttt 60
cggctttggc tcctgatatg 80

<210> SEQ ID NO 1095
<211> LENGTH: 250
<212> TYPE: DNA
<213> ORGANISM: Homo sapiens

<400> SEQUENCE: 1095 caccccttccc cccgccaccg tgggttccag acttgggata agtaaacagc gggtggagcg 60
aggcctacgg acccaggcca ggtgggagtc tgcactcttc aaggggcctg ggctgctgct 120
cacgggtatt aaagaactcc gcgttgttca tggctgaggc gatgcattag gaagatcctg 180
gacctagaga acaagtcccc cgaacgctga gttggaggcg ggacttcggg tgcgcgttgg 240
cgggagcatg 250

<210> SEQ ID NO 1096
<211> LENGTH: 213
<212> TYPE: DNA
<213> ORGANISM: Homo sapiens

<400> SEQUENCE: 1096
aagcctcttt tcaggctgag tcctaaacct gaagaaagtt tagagcctgg ggctctaaac 60
tacctgagtc tttccaaacg acaagccaag aagacctgtt gaaagtttcc tcttaagttt 120
cgtggagaga gactcaggta tagaaatatc cttactgcca cctgacctga agcagaagaa 180
atcacagaca gcttccagac caggcccaac atg 213

<210> SEQ ID NO 1097
<211> LENGTH: 96
<212> TYPE: DNA
<213> ORGANISM: Homo sapiens

<400> SEQUENCE: 1097
acgccccttc tcctgtaaac ttgggtcgcc tctagcttag cgagcgctgg agtttgaaga 60
gcgggcagtg gctgcacacg ccaaactttc cctatg 96

<210> SEQ ID NO 1098
<211> LENGTH: 261
<212> TYPE: DNA
<213> ORGANISM: Homo sapiens

<400> SEQUENCE: 1098
cttccttccc ttccccgact ttgcagattt ctcttccccc aggcctccct cctccacctc 60
tccgccccct ccgggcttgg ctctcccagg aggctacgac tggagccact ggtcccgcag 120
gatccccgcg tcctcggtcg ccgcgtccac gtccctctcg cgtccccgcc cggcgccacg 180
ccgcctcctc tgggttcggc ctccgcgcgg tgcagcgcag tctcaggccg cgggacaagc 240
ccgacttaaa tctctgcaat g 261

<210> SEQ ID NO 1099
<211> LENGTH: 484
<212> TYPE: DNA
<213> ORGANISM: Homo sapiens

<400> SEQUENCE: 1099
cgtccttctc ccgcccccgc ccctgcctgc cagctccacc gggccgtagg tgcggacgac 60
ctcaaaattc ctcggcccgc gaaggccgcc agctgcgggg aggggagggg aggcgcggtc 120
ccgcagcgcc cccaggctca tgtcccaggt atgtccagac ccccgaggca ccgcttgcag 180
ggcagtgaca gcccgtgagg ctcggcctcg acccctggca cccttggtcc cagctacgcc 240
ggctcctggc cttcccccaa gtccgagaga gaggtgggat tctccccgac gcagttggaa 300
accgggaatc ccctttaggg tcccgttcgt gctgcactac tgactccacc atctgcaaag 360
ggattcttgt ccagaatccc cgaaggcttt aggacagcgc ttattttgtt gaatgaagag 420
tctctaattt tcggaaagac cacaggctaa aagtcaagtt gtgccttttt agccaagaag 480
catg 484

<210> SEQ ID NO 1100
<211> LENGTH: 82
<212> TYPE: DNA
<213> ORGANISM: Homo sapiens

<400> SEQUENCE: 1100
cggcctttcg gcagccgaac ggccgcggca gttcaggaca aagaggtgtg ggcaggccac 60
tgggccagct ggtaacatca tg 82

<210> SEQ ID NO 1101
<211> LENGTH: 728
<212> TYPE: DNA
<213> ORGANISM: Homo sapiens

<400> SEQUENCE: 1101
tgctcctttc ggttgccata gcaaccccat tccccaagcc ctctgtccgt ctcctctggt 60
aggttccaca atggtacagg cagcatcacg ctgcacaatg gtttccaggc agtgaaagag 120
ggtgattcag caagccactc ttcttctatt ttctttaacc tccccttcac tttttatttt 180
tatgggggtg ggtggtgctt gctatatgct tacctttttc ttttcttttt tcatttttac 240
aaatttcctt ttttgtcctc acccctcaat tcctaggggc ttgagtgagt ttaagattgg 300
gttttcttgg aaatcacctg tccatcgtta attttaaaca atctccatat ctccaaagaa 360
tctcttccat gttagtctgg aatgtggtta atgaaaaaca agtagggagg atttctgggg 420
caaacactgc cggatcagga tcgtagttct caggcacgga atggctagtg tgagaaacac 480
caacagcagg cccatctcag atcttcacta tggcaactta tgcaagaaac tgttgaatta 540
gacccgtttc ctatagatga gaaaccatac aagctgtggt atttatgagc ctccatttct 600
tatactactg cagtgaacca acattggatg tgaaaattgc cttttgtcag gtgtgtgttc 660
cttacaggta aaacaaggga ttcgataaac aagtggatgt gtcatatatt gccaaacatt 720
acaacatg 728

<210> SEQ ID NO 1102
<211> LENGTH: 143
<212> TYPE: DNA
<213> ORGANISM: Homo sapiens

<400> SEQUENCE: 1102
cgtcctcccc gccgccgccg gtcccggtgc gcgcccatcc ctgcccgcag ccccgcgcgc 60
cggccgagtc gctgagccgc ggctgccgga cgggacggga ccggctaggc tgggcgcgcc 120
ccccgggccc cgccgtgggc atg 143

<210> SEQ ID NO 1103
<211> LENGTH: 170
<212> TYPE: DNA
<213> ORGANISM: Homo sapiens

<400> SEQUENCE: 1103
acgccttttc cgctagtcgc cccgctctat cccatagtct cgctgccctg agcctcccgt 60
gccggccggc cggccggggg aacaggcggg cgctcggggg gcgctcgggg ggcgggggga 120
gttccggttc cggttctttg tgcggctgca tcggcggctc cgggaagatg 170

<210> SEQ ID NO 1104
<211> LENGTH: 35
<212> TYPE: DNA
<213> ORGANISM: Homo sapiens

<400> SEQUENCE: 1104
cgtcctcttg tgtagcctga ggcggcggta gcatg 35

<210> SEQ ID NO 1105
<211> LENGTH: 90
<212> TYPE: DNA
<213> ORGANISM: Homo sapiens

<400> SEQUENCE: 1105
aggcctcttt tgaaagatgc ggccctgacc ctgtgaacct cgcgcagagc ggcctgaagc 60
gagaggttga ggctgggagg tgagaaaatg 90

<210> SEQ ID NO 1106
<211> LENGTH: 102
<212> TYPE: DNA
<213> ORGANISM: Homo sapiens

<400> SEQUENCE: 1106
gcccctctac ggaggccccg cctctagttc ggcctgtttt ctcagtcccg gcacccgccg 60
cgaccgcaaa ggcggccgcg gttctaggaa cttgacgtga tg 102

<210> SEQ ID NO 1107
<211> LENGTH: 79
<212> TYPE: DNA
<213> ORGANISM: Homo sapiens

<400> SEQUENCE: 1107
cttcccttac tcaccggtgt ccggaaaggt gaacgctgcg ctcgggctgc ctcgcctgtt 60
acctccgccg ccgggcatg 79

<210> SEQ ID NO 1108
<211> LENGTH: 97
<212> TYPE: DNA
<213> ORGANISM: Homo sapiens

<400> SEQUENCE: 1108
gctccttttc agctagtggg tggaacccca ggagggaaaa ctcagggaag cccagggccc 60
gtgttgtgct tttggcccag gtaggtggac agacatg 97

<210> SEQ ID NO 1109
<211> LENGTH: 280
<212> TYPE: DNA
<213> ORGANISM: Homo sapiens

<400> SEQUENCE: 1109
agttccttca gtctcagccg ccaactccgg aggcgcggtg ctcggcccgg gagcgcgagc 60
gggaggagca gagacccgca gccgggagcc cgagcgcggg cgatgcaggc tccgcgagcg 120
gcacctgcgg ctcctctaag ctacgaccgt cgtctccgcg gcagcagcgc gggccccagc 180
agcctcggca gccacagccg ctgcagccgg ggcagcctcc gctgctgtcg cctcctctga 240
tgcgcttgcc ctctcccggc cccgggactc cgggagaatg 280

<210> SEQ ID NO 1110
<211> LENGTH: 396
<212> TYPE: DNA
<213> ORGANISM: Homo sapiens

<400> SEQUENCE: 1110
cattctttca tactgcctcc tcccttgttt ttctgtctca gagagatagt ctgtcctaaa 60
tatcccatgt agcccaggcc actgaattaa aacggagcgt attcgttctc tgccccaccc 120
cgcaactcct gaaagcggcg caactcaatt acttgatcct tatatgcccc acgcgggact 180
catactacgt ttcccgtgaa cacgtgcagt ccaaaccccg cccctgatat ttatctcagt 240
ggacggtggc cggaaaagga caatggtttc catgtcagcg gataaacgct ctcccctcgg 300
ctcccggacg cgacggaggt cgtagtagta gtgagtacgt gctgaggagc aaaggagtaa 360
ccaagagatc cagtgaccga cagagcaaga gccatg 396

<210> SEQ ID NO 1111
<211> LENGTH: 132
<212> TYPE: DNA
<213> ORGANISM: Homo sapiens

<400> SEQUENCE: 1111
tctcctcctt tgcttcataa aaagagggac aagtggctgg tgctgtggac agagaagctt 60
tatttttagt atgagacaac ctctattttc tttcaggaga gggaagttgg attatcaatt 120
cttttgtaaa tg 132

<210> SEQ ID NO 1112
<211> LENGTH: 103
<212> TYPE: DNA
<213> ORGANISM: Homo sapiens

<400> SEQUENCE: 1112
cccccccttt ccccccttcgc ctcctgacag gaaaggttta agggggacag agccctggga 60
ggccgggccg ggctcggggg ccaccccggg ggcccgggcc atg 103

<210> SEQ ID NO 1113
<211> LENGTH: 119
<212> TYPE: DNA
<213> ORGANISM: Homo sapiens

<400> SEQUENCE: 1113
ggttctctgc tctggacttg ggaggctccg ttgcctgctc ccggagggag acgcgctgcc 60
gaggagaacc cagcgggaga acatttcagg ataggaatag gccaagtgct gagaagatg 119

<210> SEQ ID NO 1114
<211> LENGTH: 225
<212> TYPE: DNA
<213> ORGANISM: Homo sapiens

<400> SEQUENCE: 1114
ccatctcttc cagcaggaga gggctctact ctgagctcct attttccaag gctccgggcc 60
gcgctcggcg ctggcctgct gccccggcgg gtccgccggc cggaggcggg agtcacagga 120
agagccctcc acaaaaggag gcctcggcgg atcaggacag ctgcaggtgg gtgtgcagac 180
tggtgagctg ccagcagggg cccagacgcg ccaggcctgg agatg 225

<210> SEQ ID NO 1115
<211> LENGTH: 105
<212> TYPE: DNA
<213> ORGANISM: Homo sapiens

<400> SEQUENCE: 1115
cggtctctca gcggccggtt tctgcgtccg ctgccgcagg ttccaccgcg ctccaggtat 60 tttttttct gaaggaaagc tgcttcctca tatgtttcaa gaatg 105

<210> SEQ ID NO 1116
<211> LENGTH: 271
<212> TYPE: DNA
<213> ORGANISM: Homo sapiens

<400> SEQUENCE: 1116
cctccttttc cgttgtccct tcgcgcccca aaccacatcc tggagcgcac tctccagcgt 60
ggctggcagc ggggacggtg cgccggggcg caggcccaag agtcgcgtgc gcggcccctt 120
gcaccatccc cccgggccca cccccgggcc gcgctgattg ggcaggtagg gactctgccc 180
agcggaaagt tttgggtgcc gggaggaagt ctaacctttg ggagactcca agacagcagc 240
tccgaggtcg gcgggggtct gggtggccat g 271

<210> SEQ ID NO 1117
<211> LENGTH: 252
<212> TYPE: DNA
<213> ORGANISM: Homo sapiens

<400> SEQUENCE: 1117
acttcttttc cgtgggagta aggaagtgct tttgaatgag gtactgaggg ccaaggtgtt 60
ggaagttcct aattctttcc tcggttaact gtgaaactct gcgtattggg aaggcctggc 120
ctcagtcatc aggccaggag aggtactgga cgccgcgcac gcactcgtct gccagcgagg 180
cccaaagggg aagcctagcg gagctcagtg tggcagctgc tggcctctgg gccgctactt 240
gtcaatacca tg 252

<210> SEQ ID NO 1118
<211> LENGTH: 638
<212> TYPE: DNA
<213> ORGANISM: Homo sapiens

<400> SEQUENCE: 1118
ccgccttcct cctcctcctc tcgccgctac cgccgtcgcc gccgccgcag ccgccgccgg 60
tccgcgcggc ctcgggtggc cggagctcag cctgcgcgcg ccgcgccctg tgtctccggg 120
tggggcagaa gactcgcccc ttgaacctcc cgcggggact ctccgtggtg tggcggccct 180
ggggctcttt cttaatagcc ccggactgag tcccctccag tcgaggaccc tctcctagtc 240
cactgacgag cggtggacac ctgccgctgt atctccccca aaccgagtcc ttgccctgct 300
gcctcctcat acccacacgg cggcagagac cttcaccata gcgttcgctc aactccagaa 360
ccttccgacc tccgctagtt cctgcgggcc tttgcccgct tcccggtgca ccctccccgg 420
gagacacctc agacccccga cagcctgggc aggctcggtg cctgcgggtg cgttcctgat 480
cacccctccc ctcttccctc cccctcatcc tccattccct tgttttcacc ctctgtcctc 540
tgcccgtcac tccccttgtc acctcttgga gccccctcct aaccagcggc cagtgggttt 600
cccatacccc aggatgtgag cctctttaac ctgtaatg 638

<210> SEQ ID NO 1119
<211> LENGTH: 107
<212> TYPE: DNA
<213> ORGANISM: Homo sapiens

<400> SEQUENCE: 1119
cactcttctt tagcatgcta ttatggggaa agtgaccact cctgggagcg ggggtggtcg 60
gggcggtttg gtggcgggga agcggctgta acttctacgt gaccatg 107

<210> SEQ ID NO 1120
<211> LENGTH: 90
<212> TYPE: DNA
<213> ORGANISM: Homo sapiens

<400> SEQUENCE: 1120
cttcctctgc tctgcttccc ttcggaggaa aatttcaggc tgaaggttta gcgggtgccg 60
cctctaaaga gagcaatcac tacacttatg 90

<210> SEQ ID NO 1121
<211> LENGTH: 271
<212> TYPE: DNA
<213> ORGANISM: Homo sapiens

<400> SEQUENCE: 1121
gctcctcttc ctgccggcat ccgggatccc tacgtcccgc gtcccccgag cgctcggagc 60
ctacgcgccc agcgctaccg aaacccagag tcctgcgccc tggagtcccc gcgcccccgga 120 gcccgagcac ccgggagtcc cgagcctcgc gccccggagt gcccgagcct gcgccgccgc 180
acccggatac cccgcgtccc cgcgagctgc cgaggccgcc cgccgccgcc ccgcggacag 240
taccgccttc ctcccctctg tccgcgccat g 271

<210> SEQ ID NO 1122
<211> LENGTH: 159
<212> TYPE: DNA
<213> ORGANISM: Homo sapiens

<400> SEQUENCE: 1122
ctccctccct agctgacttg ctccctcccg ggctgcggct gctgcaaaag ccagcagcgg 60
cagcgggagc tgtccggagg ccggcgtcga gggtttgccg ctgtctctgc tattccatcc 120
tccccatagg ggctctctcc cctctcccat ctcaagatg 159

<210> SEQ ID NO 1123
<211> LENGTH: 136
<212> TYPE: DNA
<213> ORGANISM: Homo sapiens

<400> SEQUENCE: 1123
cggcctttgt ctctcgctgc agtcagagct ccaggtctgg ttcttctcct aaaggcccag 60
gctgtgtggc cccgtgtcct gcaggtattg ggagatccac agctaagaca ccgggacctc 120
ctggaagcca aaaatg 136

<210> SEQ ID NO 1124
<211> LENGTH: 31
<212> TYPE: DNA
<213> ORGANISM: Homo sapiens

<400> SEQUENCE: 1124
cggtcttccg ggcccgggtc ggggctcgat g 31

<210> SEQ ID NO 1125
<211> LENGTH: 78
<212> TYPE: DNA
<213> ORGANISM: Homo sapiens

<400> SEQUENCE: 1125
ggctctctga cgaaggactg gaaggtggcg gtggtgaagg tgcaggccgt tggggcggct 60
cagaggcagg tgactatg 78

<210> SEQ ID NO 1126
<211> LENGTH: 148
<212> TYPE: DNA
<213> ORGANISM: Homo sapiens

<400> SEQUENCE: 1126
ctgcctctac ccccgccacg gatcgccggg tagtaggact gcgcggctcc aggctgaggg 60
tcggtccgga ggcgggtggg cgcgggtctc acccggattg tccgggtggc accgttcccg 120
gccccaccgg gcgccgcgag ggatcatg 148

<210> SEQ ID NO 1127
<211> LENGTH: 93
<212> TYPE: DNA
<213> ORGANISM: Homo sapiens

<400> SEQUENCE: 1127
ctttctcttt gtcggaggag ctcctctgtt tcctgtgcag tagctcccgt tgcggcggca 60
cccgtggcag ccctggcgga cgcaggagcg atg 93

<210> SEQ ID NO 1128
<211> LENGTH: 248
<212> TYPE: DNA
<213> ORGANISM: Homo sapiens

<400> SEQUENCE: 1128
ctgcctctcc tcggccaggc ggaacctctc tgctgggccc ggtggccgca aaagaacttt 60
ctttctcccg cccgaacggt cgccgcggcc aactgcctcg cccgcctggc agcctaaccc 120
tccttctctt cttctcctct ccggcttcgc gcggccctgc ctccctctcg cccggcggca 180
tccgcttgct gctgccaccg cctcctcatc ttctgcccgg ccaaccggcc tgccccgctg 240
cagtgatg 248

<210> SEQ ID NO 1129
<211> LENGTH: 495
<212> TYPE: DNA
<213> ORGANISM: Homo sapiens

<400> SEQUENCE: 1129
ccctcccttg cactgcctct ggcacctggg gcagccgcgc ccgcggagtt ttccgcccgg 60
cgctgacggc tgctgcgccc gcggctcccc agtgccccga gtgccccgcg ggccccgcga 120
gcgggagtgg gacccagccc ctaggcagaa cccaggcgcc gcgcccggga cgcccgcgga 180
gagagccact cccgcccacg tcccatttcg cccctcgcgt ccggagtccc cgtggccagg 240
gattattgga cctgcctggt ttaaactatt gtcttagtta attttgtgct gctctaacaa 300
aatatcacag actgagtaat ttataagcaa tagtagctta tttggctcac agttctggag 360
gctgagaaga tcgtgaggct gcatctggca agggccttct tgctgcttca taacatggca 420
gaagacatca tgcgggtgtg tgtctgggga agagacttac agaagtggag ttgctgagtc 480
aaagatctaa ccatg 495

<210> SEQ ID NO 1130
<211> LENGTH: 164
<212> TYPE: DNA
<213> ORGANISM: Homo sapiens

<400> SEQUENCE: 1130
ttttctttct ttcctctccc ggcgttgatg agtgcttggc tcctgacaga agggatttgg 60
ctcccagctt tgtagttcgg aagaagttgg gtctatagat ttccccctaa ctctccattg 120
atgtgttgag cttcagaggg aataataact ctacgtaaag catg 164

<210> SEQ ID NO 1131
<211> LENGTH: 33
<212> TYPE: DNA
<213> ORGANISM: Homo sapiens

<400> SEQUENCE: 1131
cttcctcttc gttaagtcgg ccttcccaac atg 33

<210> SEQ ID NO 1132
<211> LENGTH: 256
<212> TYPE: DNA
<213> ORGANISM: Homo sapiens

<400> SEQUENCE: 1132
cgctcttttt aagctcccct gagccggtgc tgcgctcctc taattgggac tccgagccgg 60
ggctatttct ggcgctggcg cggctccaag aaggcatccg catttgctac cagcggcggc 120
cgcggcggag ccaggccggt cctcagcgcc cagcaccgcc gctcccggca acccggagcg 180
cgcaccgcag gccggcggcc gagctcgcgc atcccagcca tcactcttcc acctgctcct 240
tagagaaggg aagatg 256

<210> SEQ ID NO 1133
<211> LENGTH: 173
<212> TYPE: DNA
<213> ORGANISM: Homo sapiens

<400> SEQUENCE: 1133
cggcctttgc ggttgatcgg tcattggggt gctgcagccc cgccacctgt tccgtagctt 60
gccggtgccc cgaaggtgtc ttctcctaag gaagattaaa tcagaaaatt ttaaatcaca 120
gttatccctt tacttaaagc cagagtaagc cttccaaatt aaccccagga atg 173

<210> SEQ ID NO 1134
<211> LENGTH: 485
<212> TYPE: DNA
<213> ORGANISM: Homo sapiens

<400> SEQUENCE: 1134
ctttctcttc tcttagcagc acccagcttg cccacccatg ctcaagatgg gcgggatgcc 60
agcctgttac ataaatgtgc caaaagcctg gccatgcctg gaaaatggac caatccgccc 120
gccaagaggt tgggtctcgt tccctagaga gaaggaagtt tcctctcctt gaagtgagag 180
ctagaatcgc actttctgtc aagctgagag aaagactctt ttccagaggc taaaaggaca 240
agaaaatctg atttgcttgc ttctaacttt gcgttttaaa gggggaagga ggaaaggaaa 300
gagggggagg gtggttctgc ttagccccac ccctccggct accccaggtc cagccgtcca 360
ttccggtgga ggcagaggca gtcctggggc tctggggctc gggctttgtc accgggaccc 420
gcaggagcca gaaccactcg gcgccgcctg gtgcatggga ggggagccgg gccaggaaca 480
atatg 485

<210> SEQ ID NO 1135
<211> LENGTH: 79
<212> TYPE: DNA
<213> ORGANISM: Homo sapiens

<400> SEQUENCE: 1135
ccgcctcccc gcgggttccg ttggctgtgg cggcagctga cgcttgtggc ggcggtggct 60
tcggggtggg cgtaagatg 79

<210> SEQ ID NO 1136
<211> LENGTH: 115
<212> TYPE: DNA
<213> ORGANISM: Homo sapiens

<400> SEQUENCE: 1136
tgttcttcta cttacctggg cccggagaag gtggagggag acgagaagcc gccgagagcc 60
gactaccctc cgggcccagt ctgtctgtcc gtggtggatc taagaaacta gaatg 115

<210> SEQ ID NO 1137
<211> LENGTH: 101
<212> TYPE: DNA
<213> ORGANISM: Homo sapiens

<400> SEQUENCE: 1137
ggtccttcac gttccattcc caggctggtc tgagctccgg ggccgtggtc ccgctgcctc 60
ctccggtcgt cgtgcggaag ctgcgacgca ggcagaccat g 101

<210> SEQ ID NO 1138
<211> LENGTH: 87
<212> TYPE: DNA
<213> ORGANISM: Homo sapiens

<400> SEQUENCE: 1138
cattcttccg gtggagatgg ctgcggccgt ggcggggatg ctgcgagggg gtctcctgcc 60
ccaggcgggc tagagtgcag tggcatg 87

<210> SEQ ID NO 1139
<211> LENGTH: 94
<212> TYPE: DNA
<213> ORGANISM: Homo sapiens

<400> SEQUENCE: 1139
acttctctgt agatcgctga gcgatacttt cggcagcacc tccttgattc tcagttttgc 60
tggaggccgc aaccaggccc gcgccgccac catg 94

<210> SEQ ID NO 1140
<211> LENGTH: 134
<212> TYPE: DNA
<213> ORGANISM: Homo sapiens

<400> SEQUENCE: 1140
cggtctttct ctagacgcgt cttgctggga gagtgtccgt tgcttcccgt ccgtgtcgcg 60
gccctgcggt tggcggcctc ctcgtggagc ggagcaaggc caggcggccc ctgctcgagt 120
cccgcgtcgc catg 134

<210> SEQ ID NO 1141
<211> LENGTH: 301
<212> TYPE: DNA
<213> ORGANISM: Homo sapiens

<400> SEQUENCE: 1141
gggccccctc cgcgcgtact gcgggcccca cgggtgttag tggcgggggc ggcagagtcc 60
gggtgggttg tcgcgacgga gccgggcctc ttcgccgtct tgagacgggg ctggcgagaa 120
gggcccctca cggagttgcc atgggcgtct aaccgcggca gccaggcccc tctctacgtg 180
agaccccggc ccccctcccc tttctgcagc ccgcccgcca cctgcgcgcc gcgtggcctc 240
cgccggcgcc tgcccgcccc gcgcctccgt ctcccacgga gcaggccggg ctctcgccat 300
g 301

<210> SEQ ID NO 1142
<211> LENGTH: 204
<212> TYPE: DNA
<213> ORGANISM: Homo sapiens

<400> SEQUENCE: 1142
ccatcttttc cggcgctggc tcctctccgt cagtgcggtt tcgcctttat ggtggtggag 60
tctgcccagg ctgtggaccg caaataaccc tgtacaaaga ggaatggaga ttgcctctat 120
ccacctagat tcataagctg gcctgaggtg atcttggcat caaggaaggg atgcacatca 180
tcacaccatc agcttcagag aatg 204

<210> SEQ ID NO 1143
<211> LENGTH: 117
<212> TYPE: DNA
<213> ORGANISM: Homo sapiens

<400> SEQUENCE: 1143
ctttctcttc ttttgcttct agttaccatc ctcaaaggat tggctaaaag caagcaactg 60
gattgaacac cctaagaaga aagattcaca ctgcaccagg agacatcaga aagaatg 117

<210> SEQ ID NO 1144
<211> LENGTH: 134
<212> TYPE: DNA
<213> ORGANISM: Homo sapiens

<400> SEQUENCE: 1144
gcgcctttcg attgcatcag ctggtccagc cgaggccaag tcccgggcgc tagcccacct 60
cccacccgcc tcttggctcc tctcctctag gccgtcgctt tcgggttctc tcatcgcttc 120
gtcgttcgcc aatg 134

<210> SEQ ID NO 1145
<211> LENGTH: 158
<212> TYPE: DNA
<213> ORGANISM: Homo sapiens

<400> SEQUENCE: 1145
cagcctctgt gcggtgggac caacggacgg acggacggac gcgcgcacct accgaggcgc 60
gggcgctgca gaggctccca gcccaagcct gagcctgagc ccgccccgag gtccccgccc 120
cgcccgcctg gctctctcgc cgcggagccg ccaagatg 158

<210> SEQ ID NO 1146
<211> LENGTH: 174
<212> TYPE: DNA
<213> ORGANISM: Homo sapiens

<400> SEQUENCE: 1146
cgtcctctca gtggtagcgc ggggactggc tgggaagcgg tcggtcgagt gtggcctgtg 60
tggactcgca tcttgcccga agccgggcgg aggagagctc aagctaaggg tgatcagccc 120
atgacctaaa cctccagaca aaataaaacg gaaaatttgc tagaatcaag aatg 174

<210> SEQ ID NO 1147
<211> LENGTH: 112
<212> TYPE: DNA
<213> ORGANISM: Homo sapiens

<400> SEQUENCE: 1147 tgacctttc attcccgttg ttatggaggt aggctctcta ggaatctggg agtagtagct 60
ggggggcaag agcaaataaa gagctcgagc ttctgtggtc tctggggaga tg 112

<210> SEQ ID NO 1148
<211> LENGTH: 1859
<212> TYPE: DNA
<213> ORGANISM: Homo sapiens

<400> SEQUENCE: 1148
gggccttctg gcagtttctg ggagctgcga acgcgccgcc ccggggctcg gcggccggaa 60
acgctggctt cggagcctta ggcgccgcgg cctttccttg ttttccgccc agtccacgcc 120
gccatggcca agtggggcca ggggaacccc cactggatcg tggaggagcg ggaggacggg 180
accaacgtga acaactggcg ctggcgcggc tggcggcggc ctccttccgg gatctgggga 240
gggccgggcc gcgggagccg gggctgccct ggggtctgtg cggggccgcg gggccagggg 300
gtcagggggc cgccccccct cagctgctgg acgcagggct cggccttcgc ctctcggctc 360
gggagagtcc ttgagtacgg agaccggcta ggagggttgc agctgcctct ttttgaaagt 420
tgggttgggc cccaagagtg acttccgaca gacctttcca ctcccaccgt ctgtggcctg 480
agggccttcc cttctcctcc cgcccacccc tctggatgtt tcggggagtt agaagggagc 540
tggattgaga gactgtgtta ggggcggggg tatggaacgt agtggaaagg gcagaaattt 600
ggatctcagt tcgcgcccac cccgcaggcg cctcccgcga gccgggccct ctgtgagtga 660
gacaagctcc ccttccttta cgcgcctcac ctggcgcgtg gggagaggtc ggcagccctc 720
cgccgcagaa cctccggaag ggatgtcctc tgccctgcgc ctctggccgg ggctgtggtc 780
cctccaggcc gtcgagggga tgctgaggcc ggtccccaga ggagcatgac ttggctggtc 840
cggaggagct ctgagggcat gggcaatctt ggctcgctgc aacctcagct tccagagttc 900
aagcgagtct cctgcttcag cctcatgagt agctgggact acagatgcgt gccactacgt 960
ccgtctgatg tttgtatttt tagtagagac agggtttcac catgttggtc aggctgctct 1020
cgaactccag atctcgtgat ccgcccgcct gggcctacta aagtgctggg attacaggcg 1080
tgagctagat ctgactttct agtgtcctag ccttggcccg atggacatgt catttctctc 1140
agctcgtttc tgtcccctaa agtgagaata ttgcctggga agattacatt agacgatgta 1200
tatgcgaaga cacttgatag ctggtattgt catgattctg attagttcac tactgctact 1260
ttccctgtgg cctaggcttt gcctatttcc agtgggcgag ctagctagat cctcctccct 1320
taaataagcc agtgttttta agacagaata ctacttgcat agtggacaat aatatcttaa 1380
agaactgagc aggatgaaaa gaatttgata gaaagcaggt ttgaggagca cattggaggt 1440
tggcaggttt cgaggctgct tgagaggact tgggccgatc tgggctgggc ttggacgtga 1500
ccctggcacc caggcaggtg gatcccagct ggggcttcca ttcacgactt tctggtccct 1560
ggcaggacag agcgggatgc caccagcttg tccaaaggga agttccagga gctcctggtg 1620
ggcatcgttg tggagaatga cgctggccgc ggcgagatca acgagttgaa gcaggtggaa 1680
ggggaggctt cgtgcagcag ccgcaaagga aagctgattt tcttctatga gtggaacatc 1740
aaactgggct ggaaaggcat cgttaaagaa tctggagtga agcacaaggg attgattgaa 1800
atacccaatc tttctgagga aaatgaagta gatgacactg agaatttaca acgggaatg 1859

<210> SEQ ID NO 1149

<211> LENGTH: 28
<212> TYPE: DNA
<213> ORGANISM: Homo sapiens

<400> SEQUENCE: 1149
ctgcctctca gcccaaattg gaaacatg 28

<210> SEQ ID NO 1150
<211> LENGTH: 115
<212> TYPE: DNA
<213> ORGANISM: Homo sapiens

<400> SEQUENCE: 1150
ccgccccttt catggccgcc gcctggcgcc ggggctaagt ggccgccggc gtccgggtac 60
ccgagggctc tcccgcgttg ctggcaccgc tggcgccgcg gtctcgtagc gcatg 115

<210> SEQ ID NO 1151
<211> LENGTH: 110
<212> TYPE: DNA
<213> ORGANISM: Homo sapiens

<400> SEQUENCE: 1151
cctcctctgg ctgctgcctc cgcagctccc tcctcctacc ccacctcctc catctgggga 60
gcgtctgcgg gggcctgagg ggcggcggcg gcggcggcgg ctgcgatatg 110

<210> SEQ ID NO 1152
<211> LENGTH: 98
<212> TYPE: DNA
<213> ORGANISM: Homo sapiens

<400> SEQUENCE: 1152
ccctcctttg cgctgggctg agcccagagc cgagagcagg ggtcggctct gagttccctg 60
cttggttttt gggtggcagc agccagagga ggaatatg 98

<210> SEQ ID NO 1153
<211> LENGTH: 112
<212> TYPE: DNA
<213> ORGANISM: Homo sapiens

<400> SEQUENCE: 1153 caccccttctc tgtctacctc tgggcgggac tgccgggtga tgagatactc ggtcggcgac 60
ggtagaacgg gcgacggcga caaccgcaat cacatccacg acggtgatca tg 112

<210> SEQ ID NO 1154
<211> LENGTH: 213
<212> TYPE: DNA
<213> ORGANISM: Homo sapiens

<400> SEQUENCE: 1154
ggcccctttc ggtccaacgg caggacctgg gggctgtggc cgggggcggc cgttgacctg 60
gtgaccgcgg cgccgcccca gaccgggggc gcagtcccac tcgctccgag ccccggtccc 120
ccaagcctcc ctcccgggta cctggggccg cgcccgccct gcgcccagct ccgccctccg 180
tcggcccagg cctgacagag cccggcagcc atg 213

<210> SEQ ID NO 1155
<211> LENGTH: 294
<212> TYPE: DNA
<213> ORGANISM: Homo sapiens

<400> SEQUENCE: 1155
cttcctctct agccgccagt gctctatgct ccgcggtcgc gggccgccag cctccagccg 60
gccagccgcg aggggtgcgc agagggaggc ggggcggaaa ggcgagaggt gtctcctcca 120
ccggagccag gggagacccg agcaagctcc gtgacagcac gtcggccgcc atgtcgccga 180
gtggggctgg aaacagaccc ggcgcccagc ggtagccctc cttgcgcctc cgattcccag 240
acatggaagg tctttaatgt aactttaaat ggttcaccaa aggatgctct aatg 294

<210> SEQ ID NO 1156
<211> LENGTH: 154
<212> TYPE: DNA
<213> ORGANISM: Homo sapiens

<400> SEQUENCE: 1156
gggcctttgt ctctcgctgc agccggcgct ccacgtctag tcttcactgc tctgcgtcct 60
gtgctgataa aggctcgccg ctgtgaccct gttacctgca agaacttgga ggttcacagc 120
taagacgcca ggaccccctg gaagcctaga aatg 154

<210> SEQ ID NO 1157
<211> LENGTH: 66
<212> TYPE: DNA
<213> ORGANISM: Homo sapiens

<400> SEQUENCE: 1157 ccccttctc tttcagcctc gggcacgggg gaggctcggc ggacctgctg attgggaacc 60
gatatg 66

<210> SEQ ID NO 1158
<211> LENGTH: 137
<212> TYPE: DNA
<213> ORGANISM: Homo sapiens

<400> SEQUENCE: 1158
cctcctccct ccttccgtcc tccgcgcctt ccgtcggtcg gtccttgctt cctgcttcgc 60
ctccgcgcct cgcgctatgg gacagagccc ccgatccgcc agcaccacct gaggatccag 120
aaaccgcccc agcgatg 137

<210> SEQ ID NO 1159
<211> LENGTH: 437
<212> TYPE: DNA
<213> ORGANISM: Homo sapiens

<400> SEQUENCE: 1159
acctccctcc cctcccaggc gccgccgcag ccggagcggc tcccgggccc tgggccgccg 60
ccggccagga agaaatactt gtgttggctg catttccagg gatgctacca gagctcaagg 120
ctgtcacctg gtcttgccca gaagagccgt tcttagaggc aggacttgat gaaggctttc 180
ctgctgatgg aataggtttg ctagagctgg ccttggaatt agaacccttc atgtggcctt 240
tataaatatg cgtttgagac agagttatat gcagaagttg aaaatgcctg gaagatttct 300
ggtttctttc actacttatc ctgccttttt gcatcgctgc cagatttgga tgatatgata 360
ttcagagggg caccttaatc aaagccattc ttcaacaaga cccacctggc ataagattgc 420
acacataatt caagatg 437

<210> SEQ ID NO 1160
<211> LENGTH: 68
<212> TYPE: DNA

<213> ORGANISM: Homo sapiens

<400> SEQUENCE: 1160
cctcctctgt ggattctggc caggccgggt tcggcggttg ctgtgagagc gggcttccca 60
acaccatg 68

<210> SEQ ID NO 1161
<211> LENGTH: 595
<212> TYPE: DNA
<213> ORGANISM: Homo sapiens

<400> SEQUENCE: 1161
aggcctctct gccgcgcgcg caggtacggg gcagaagtcg caggtaccca gctgctgccc 60
acatttctgg tccagagtcc cgaaccccga gcactgggat gcctggctac tccgagccaa 120
ggcactgatg tttgaactgg aaacttcaaa acgtttaata agagtcttca ggatgggttt 180
gaactagaca agctagaaat ttctttagaa caccagctct agcatgcatc tcccactttt 240
ggctttcctg gagaggagct tgaagaggtg gttctgcaga cagccacagt gatacttagg 300
aaaccagagg aatggatttg acttttctgc taggattctc tgttatagtt tctccctgag 360
ttgtaagagg catggaaata tacatgaaac tgaagaacct gcaaggaagg gaagtggaac 420
tttccatgct gagtgaaaac taaccaagtg gcagttgtga ctgaaaacac tgaaacctac 480
cacgtccaga ttcactggat tgggggatag aggaacggtc acagctaggg agaaagaagt 540
gataccggaa aagaaaacct aaatgaagag aatgaggatg actgcacagt agatg 595

<210> SEQ ID NO 1162
<211> LENGTH: 28
<212> TYPE: DNA
<213> ORGANISM: Homo sapiens

<400> SEQUENCE: 1162
agctcctttt cctgagcccg ccgcgatg 28

<210> SEQ ID NO 1163
<211> LENGTH: 311
<212> TYPE: DNA
<213> ORGANISM: Homo sapiens

<400> SEQUENCE: 1163
agttctcctg ggcgcctagc attgtcgccc acgctgcagt agcggcttct gcggctccaa 60
gccagcgggt cctgtgaagg cgagcagacg cggagaaagg acgcgggagt gagagagggt 120
gagtcagcca ctgtctaaac gataacggga ggcggctctg cggggtaggg ttgaattcag 180
taaatgggct cgtgctgctg tctcttcgga gacgctgcta tcttagcgtc agcgagggaa 240
ggttgaggag gagccagagc cgggtcctgc agcgtttctc gccatcagcg cccgtcgcca 300
tctccaccat g 311

<210> SEQ ID NO 1164
<211> LENGTH: 127
<212> TYPE: DNA
<213> ORGANISM: Homo sapiens

<400> SEQUENCE: 1164
ctttctttga ctggagcgga cccgccggac gcaaccgcct cgccagccgg agccagcgcg 60
agctcggcac ggtggacacc cggtccgagg ccggcaagcc ggctggtgcc cgagtcggcc 120
aagcatg 127

<210> SEQ ID NO 1165
<211> LENGTH: 137
<212> TYPE: DNA
<213> ORGANISM: Homo sapiens

<400> SEQUENCE: 1165
ggtcccctta tttggatctg cgggaatgtg ggctggagag gtcctgccgt ggtaccagcc 60
tccagcctgc ccccaggact gcccctgacc caggcgcgcc cgctgctcgg tggcaggagg 120
gccggcggag cgccatg 137

<210> SEQ ID NO 1166
<211> LENGTH: 90
<212> TYPE: DNA
<213> ORGANISM: Homo sapiens

<400> SEQUENCE: 1166
gattctcttt gttccgcagc catttcaggc cccggacagg aggcagtgcc gcttcggccg 60
aaggcccgag cgcccgaggc gtctgggatg 90

<210> SEQ ID NO 1167
<211> LENGTH: 43
<212> TYPE: DNA
<213> ORGANISM: Homo sapiens

<400> SEQUENCE: 1167
cttccttcgt tattggagcc aggcctacac cccagcaacc atg 43

<210> SEQ ID NO 1168
<211> LENGTH: 329
<212> TYPE: DNA
<213> ORGANISM: Homo sapiens

<400> SEQUENCE: 1168
ggctccttcc tccaggagtc tctggtgcag ctggggtgga atctggccag gccctgctta 60
ggcccccatc ctggggtcag gaaatttgga ggataaggcc cttcagcccc aaggacatcc 120
tggctgccat acctgctcct gacttctcag ggctggcagt catcgactgg gaggcatggc 180
gcccacgctg ggccttcaac tgggacacca aggacattta ccggcagcgc tcacgggcac 240
tggtacaggc acagcaccct gattggccag ctcctcaggt ggaggcagta gcccaggacc 300
agttccaggg agctgcacgg gcctggatg 329

<210> SEQ ID NO 1169
<211> LENGTH: 182
<212> TYPE: DNA
<213> ORGANISM: Homo sapiens

<400> SEQUENCE: 1169
agtcctcccg gtcgccccac tgcgcatggc acgttgcgta ctcccctccc agcaaccggt 60
ctggcggcgg cgcggcagta aaactgagga ggcggagcca agacggtcgg ggctgcttgc 120
taactccagg aacaggttta agtttttgaa actgaagtag gcctacacag taggaactca 180
tg 182

<210> SEQ ID NO 1170
<211> LENGTH: 113
<212> TYPE: DNA
<213> ORGANISM: Homo sapiens

<400> SEQUENCE: 1170
ccctctcttt cgctgtttga gagtctctcg gctcaaggac cgggaggtaa gaggtttggg 60
actgccccgg caactccagg gtgtctggtc cacgacctat cctaggcgcc atg 113

<210> SEQ ID NO 1171
<211> LENGTH: 79
<212> TYPE: DNA
<213> ORGANISM: Homo sapiens

<400> SEQUENCE: 1171
ggctctttcc agctcctggc agccgggcac ccgaaggaac gggtcgtgca acgacgcagc 60
tggacctggc ccagccatg 79

<210> SEQ ID NO 1172
<211> LENGTH: 115
<212> TYPE: DNA
<213> ORGANISM: Homo sapiens

<400> SEQUENCE: 1172
cagtcttttc tccttgctca gcttcaatgt gttccggagt ggggacgggg tggctgaacc 60
tcgcaggtgg cagagaggct cccctggggc tgtggggctc tacgtggatc cgatg 115

<210> SEQ ID NO 1173
<211> LENGTH: 145
<212> TYPE: DNA
<213> ORGANISM: Homo sapiens

<400> SEQUENCE: 1173
atcccttcct ctcttttctg ttcgccctct tctccctgct ctttttccct ttccaccccc 60
ctcctctgtt ctccctcacc tcctgcgccc cctccccctt cccgggttct gacagtacga 120
tgagctgccc cattacggcg ggatg 145

<210> SEQ ID NO 1174
<211> LENGTH: 169
<212> TYPE: DNA
<213> ORGANISM: Homo sapiens

<400> SEQUENCE: 1174
ttttcttttc gtttagatac attgcctttt gcctaggctg gcgtcgagac ttgaggccgt 60
tgcagacttt ggcgcggctc gcgcctcctg cttcaagagc ccagcggtga gagctggcct 120
gcggcacgcg gcctaatgcc agacagtaac agtttggagg atcaagatg 169

<210> SEQ ID NO 1175
<211> LENGTH: 238
<212> TYPE: DNA
<213> ORGANISM: Homo sapiens

<400> SEQUENCE: 1175
gagcctttgc cccggcgtcg gtgactcagt gttcgcggga gcgccgcacc tacaccagcc 60
aacccagatc ccgaggtccg acagcgcccg gcccagatcc ccacgcctgc caggagcaag 120
ccgagagcca gccggccggc gcactccgac tccgagcagt ctctgtcctt cgacccgagc 180
cccgcgccct ttccgggacc cctgccccgc gggcagcgct gccaacctgc cggccatg 238

<210> SEQ ID NO 1176
<211> LENGTH: 677
<212> TYPE: DNA
<213> ORGANISM: Homo sapiens

<400> SEQUENCE: 1176
cgctctttct ctcgccgcgc cgtcttgaag ccgcgcgggc tcgtgagcag cgcgaggccg 60
ccaaggtgcc tcgcttcgcc ggagccgctg ccgcccgccg gagggaagcc ggcctcgggc 120
gcgcacgctc gtcggagccc cggcgcgccc cgcgcctgag cctgctgaca gcggccgctg 180
ggctcaggct gtccgctctg ggctccgcgg cctcggcccc gctgcactcc acctccgccc 240
cctcggactc cctcccctct gcttctactc ctcctgctcc agtgcggatc gtttcgcaac 300
tgcttgccac tcgtcccgtg cctggctgtt tttccatttc ccggccccct cttcttgagt 360
actttacccc ctgcatttgg ggacagggac tggaaaaggg gcgggtggag cgtccagtgg 420
agaagaagga agcgaggccc gcaggaggag gaggatcggc ggactgtggg gaggagaccc 480
cacgccaccc tttctggtca tctcccctcc cgccccgccc ctgcgcacac tccctcgcgg 540
gcgagctact ttcggaccag gaaagtaaga gcggccctgg gtgacagcgc cgcggggcca 600
gtcccggggt tagccgcgcg tctgctcgct tctggtccgt cgcgctccca gccagggcac 660
agcccggacc gaggatg 677

<210> SEQ ID NO 1177
<211> LENGTH: 95
<212> TYPE: DNA
<213> ORGANISM: Homo sapiens

<400> SEQUENCE: 1177
ccgtctcctc ctcttgctcc ctcggccggg cggcggtgac tgtgcaccga cgtcggcgcg 60
ggctgcaccg ccgcgtccgc ccgcccgcca gcatg 95

<210> SEQ ID NO 1178
<211> LENGTH: 796
<212> TYPE: DNA
<213> ORGANISM: Homo sapiens

<400> SEQUENCE: 1178
ttttcttttc gccaggggtt gggactccgg gtggcaggcg cccgggggaa tcccagctga 60
ctcgctcact gccttcgaag tccggcgccc cccgggaggg aactgggtgg ccgcaccctc 120
ccggctgcgg tggctgtcgc cccccaccct gcagccagga ctcgatggag aatccattcc 180
aatatatggc catgtggctc tttggagcaa tgttccatca tgttccatgc tgctgacgtc 240
acatggagca cagaaatcaa tgttagcaga tagccagccc atacaagatc gttttcaact 300
agtggcccca ctgtgtccgg aattgatggg ttcttggtct cactgacttc aagaatgaag 360
ccgcggaccc tcgcggtgag tgttacagct cttaaggtgg cgcatctgga gtttgttcct 420
tctgatgttc ggatgtgttc ggagtttctt ccttctggtg ggttcgtggt ctcgctggct 480
caggagtgaa gctacagacc ttcgcggagg cattgtggat ggatggctgc tggaaacccc 540
ttgccatagc cagctcttct tcaatactta aggatttacc gtggctttga gtaatgagaa 600
tttcgaaacc acatttgaga agtatttcca tccagtgcta cttgtgttta cttctaaaca 660
gtcattttct aactgaagct ggcattcatg tcttcatttt gggatgcagc taatataccc 720
agttggccca aagcacctaa cctatagtta tataatctga ctctcagttc agttttactc 780
tactaatgcc ttcatg 796

<210> SEQ ID NO 1179
<211> LENGTH: 59
<212> TYPE: DNA

<213> ORGANISM: Homo sapiens

<400> SEQUENCE: 1179
gtccctcctt ccctccccga ctgtgcgccg cggctggctc gggttcccgg gccgacatg 59

<210> SEQ ID NO 1180
<211> LENGTH: 309
<212> TYPE: DNA
<213> ORGANISM: Homo sapiens

<400> SEQUENCE: 1180
cactctcttt ctctctccct ctggcatgca tgctgctggt aggagacccc caagtcaaca 60
ttgcttcaga aatcctttag cactcatttc tcaggagaac ttatggcttc agaatcacag 120
ctcggttttt aagatggaca taacctgtac gaccttctga tgggctttca actttgaact 180
ggatgtggac acttttctct cagatgacag aattactcca acttcccctt tgcagttgct 240
tcctttcctt gaaggtagct gtatcttatt ttctttaaaa agctttttct tccaaagcca 300
cttgccatg 309

<210> SEQ ID NO 1181
<211> LENGTH: 173
<212> TYPE: DNA
<213> ORGANISM: Homo sapiens

<400> SEQUENCE: 1181
agccctttta ctcagccaca gcctccggag ccgttgcaca cctacctgcc cggccgactt 60
acctgtactt gccgccgtcc cggctcacct ggcggtgccc gaggagtagt cgctggagtc 120
cgcgcctccc tgggactgca atgtgccgat cttagctgct gcctgagagg atg 173

<210> SEQ ID NO 1182
<211> LENGTH: 666
<212> TYPE: DNA
<213> ORGANISM: Homo sapiens

<400> SEQUENCE: 1182
cttccttcct tctccagtcc cttccactgt gcgtcttctg tcccccgttc ttccccagcg 60
gacccctctt tcgagactcc ctagtggggt ccccagctcc cgggcgatcc tgcccttgcc 120
gagcgcgttt tctggagtca cctgggggag gggagtcctg ggcagggccg ggctggggaa 180
gacgcctggg gcactgcccg gcgttaacaa agggagccga taccgaccgg cgtgggcgcg 240
gagcgggcgg ccgccaccga gcgtgctgag caaccgcagc ctccgcggcc gagagtgcag 300
cgagcaaggg gagagccagt tgcgcagagc cctgcaacca gcagtccagg gagaagtggt 360
gaatgtcatg gagcccagct gaaatggact ggccccccttg agcctgtccc aagccctggt 420
gccaggtgtc catccccgtg ctgagatgag ttttgatcat cctgagaaaa atgggccttg 480
gcctgcagac ccaataaacc ttccctccca tggataatag tgctaattcc tgaggacctg 540
aagggcctgc cgcccctggg ggattagcca gaagcagatg atcatgacgc agtcctgagg 600
tttaatgggg cacccacagc caacttccaa caagatgtgg gcacaaaaac taccattcgc 660
ctgatg 666

<210> SEQ ID NO 1183
<211> LENGTH: 60
<212> TYPE: DNA
<213> ORGANISM: Homo sapiens

<400> SEQUENCE: 1183
ctccccttcc gcgcccggct ccccttccgc gcccctcccg ccggagatga ggggaagatg 60

<210> SEQ ID NO 1184
<211> LENGTH: 37
<212> TYPE: DNA
<213> ORGANISM: Homo sapiens

<400> SEQUENCE: 1184
gcttcttttg ctgggctgct gctccttcgg catcatg 37

<210> SEQ ID NO 1185
<211> LENGTH: 420
<212> TYPE: DNA
<213> ORGANISM: Homo sapiens

<400> SEQUENCE: 1185
cggtcttccg ggtgtctttg acagggtttt ctacgccgct ttttcggcga ctttttgctc 60
ttccgctttt tgccaccgcc cccaaccttc tatatccttg cagcccctac cttttcttgt 120
gttgctcctc ccctggcagc cgtgaggggg gttagatctc agccggagcc ggagctgggc 180
ctagctgtcc cacgggccac cactacctcc tttggttcgg gagaaagcta cgaccaagta 240
cgcccagctc gggccttaga acttctgaac gggcagtgcg ggtaggccct gcttagccct 300
tcccggagga cacctgacca aaagaggaag atagtcttgg gacccttgca tggtgtttca 360
aagggtggtg aagaactaag gtagaagaat acatgttcac ttccagtgaa caagagcatg 420

<210> SEQ ID NO 1186
<211> LENGTH: 120
<212> TYPE: DNA
<213> ORGANISM: Homo sapiens

<400> SEQUENCE: 1186
ctcccttctg gtgtactggg tgggaggtgg aactagtcgg acaaagccct cgcgtcggac 60
ccttgccaga actcaattaa tggatgcctc gaagttgacg tacatatata ttcagaaatg 120

<210> SEQ ID NO 1187
<211> LENGTH: 230
<212> TYPE: DNA
<213> ORGANISM: Homo sapiens

<400> SEQUENCE: 1187
cgcccctttg cgcggctggc gcggccagcc ggccaggctc ccctcggcaa acctgtctaa 60
ttggggcggg gagcggagct tcctcctctg agggccgtgc cgcgctgcca gatttgttct 120
tccgcccctg cctccgcggc tcggaggcga gcggaaggtg ccccggggcc gaggcccgtg 180
acggggcggg cgggagcccc ggcagtccgg ggtcgccggc gagggccatg 230

<210> SEQ ID NO 1188
<211> LENGTH: 114
<212> TYPE: DNA
<213> ORGANISM: Homo sapiens

<400> SEQUENCE: 1188
ctacctctac ccacagccag tgcctttggc gcactgaggt gcacagggtc ccttagccgg 60
gcgcagggcg cgcagcccag gctgagatcc gcggcttccg tagaagtgag catg 114

<210> SEQ ID NO 1189
<211> LENGTH: 162
<212> TYPE: DNA

<213> ORGANISM: Homo sapiens

<400> SEQUENCE: 1189
cctcctctcg ctctctgccc gctaactttc ccgagccccg accggcggcg cagagctccg 60
gggtagcttt gtggccgaac gccgacctcg ggcggagagc gcggctgtgc ccagtatccc 120
atccccgcga cccccgcgcg ctccggagag aacaggacta tg 162

<210> SEQ ID NO 1190
<211> LENGTH: 206
<212> TYPE: DNA
<213> ORGANISM: Homo sapiens

<400> SEQUENCE: 1190
tcccctctgc ctcccggtgg ctcctcgctc tccttccatc tctctcgccc cctctccctc 60
cgtcccgtcc tcgccgctcc cctcaccccg cctctctccc cctcccccag cccctcctct 120
cctcacccca cccggcctcc ctccctccct cgcccgcccg gcgctcgcag agccgacacc 180 agggggctc tcgatgtagc accatg 206

<210> SEQ ID NO 1191
<211> LENGTH: 119
<212> TYPE: DNA
<213> ORGANISM: Homo sapiens

<400> SEQUENCE: 1191
ttcccttcct tggatccctg tgcacctact ggagccaggt tactctgggt cctggacctg 60
actgcctcat tctggaggct tccagacagc cacagttagt gcccaaacct gagaggatg 119

<210> SEQ ID NO 1192
<211> LENGTH: 52
<212> TYPE: DNA
<213> ORGANISM: Homo sapiens

<400> SEQUENCE: 1192
cgccctctct tcctgcagcc tgggaacttc agccggctgg agccccacca tg 52

<210> SEQ ID NO 1193
<211> LENGTH: 248
<212> TYPE: DNA
<213> ORGANISM: Homo sapiens

<400> SEQUENCE: 1193
cattctcttt ccttttcctt ctctcctgag cgctcctgca gttcctgggg cgtagtaggg 60
gatccacaag cgtttgtgac cagtgaagtt ctttacaagg gtgagatctg cacgggagga 120
cccgagcgag ggtctcggct tgccaggaag ccggggttcc ccgggaagcg tggagttcac 180
ccgcgcactc gaagtgcctt tgcaaaatta tatctgggtg ttggcaccca gccactattc 240
tgccaatg 248

<210> SEQ ID NO 1194
<211> LENGTH: 89
<212> TYPE: DNA
<213> ORGANISM: Homo sapiens

<400> SEQUENCE: 1194
agctcttttc cttcttcctc cacttcccct accctccacc gtccgggagc cgccgccacc 60
gccgccgagg agtcaggaag ttcaagatg 89

<210> SEQ ID NO 1195
<211> LENGTH: 693
<212> TYPE: DNA
<213> ORGANISM: Homo sapiens

<400> SEQUENCE: 1195
gcgcctttgc ggccgtgatt cggtcccgct gtcctaggcg ggatggtgcc gctgtgccag 60
gtaagggtgg cgggtgtgcg tgcgggcctg ggtgcggagc cctcctcgac gtgtctctcc 120
cgccctttcc ctccacatac ccagccttgg tcagtcggac ctccccacta gcccccaacc 180
tggccggcgt cttgggttcg ggggcgcccc cgcccccgcc cccgggccct tcctgtctcc 240
gggctttact gcgactgccc cagcagaagt cgggtcctct ccgagaactc ttgtcagctc 300
acggcagcaa ggacggactc gttctgaagg cgcctccacc ttttatgacc acctctttcc 360
cagattattc gttttgatga agctaaaatt ttaatctaaa aagaaatgca cctcatggag 420
aattcttgtg aagaactgtg cttcatctgt ggatttctac acccttgatc atttgcaaac 480
ctgtaattat ttcgtaaaga gttgtttgca cggagtgaca ggttgaagta ttgtattttg 540
caaaaagtgc tgaaataaca ggagttcgtt cagagaccat ttctgtgcct caagaaataa 600
aagcgttgca gctgtggaag gagatagaaa ctcgacatcc tggattggct gatgttagaa 660
atcagataat atttgctgtt cgtcaagaat atg 693

<210> SEQ ID NO 1196
<211> LENGTH: 24
<212> TYPE: DNA
<213> ORGANISM: Homo sapiens

<400> SEQUENCE: 1196 tttcctttt ccggagggga gatg 24

<210> SEQ ID NO 1197
<211> LENGTH: 45
<212> TYPE: DNA
<213> ORGANISM: Homo sapiens

<400> SEQUENCE: 1197
ctgcccctca ctcgtctcgc ccgccagtct ccctcccgcg cgatg 45

<210> SEQ ID NO 1198
<211> LENGTH: 512
<212> TYPE: DNA
<213> ORGANISM: Homo sapiens

<400> SEQUENCE: 1198
agtccttctt gtcctggtcg ttgttcccgt ctgagtacca gctccccact gccctgaggg 60
cgggccggcc tgcggcggag ggaaaaagga agaggagaag gaaattgtcc cgaatccctg 120
cagtgggtcc aagcctctcc cgggtggcca gtctttctgt aggttgcggc acaacgccag 180
gcaaaagaag aggaaggaat ttaatcctaa tcggtggagg tcgatttgag ggtctgctgt 240
agcaggtggc tccgcttgaa gcgagggagg aagtttcctc cgatcagtag agattggaaa 300
gattgttggg agtggcacac cactagggaa aagaagaagg ggcgaactgc ttgtcttgag 360
gaggtcaacc cccagaatca gctcttgtgg ccttgaagtg gctgaagacg atcaccctcc 420
acaggcttga gcccagtccc acagccttcc tcccccagcc tgagtgacta ctctattcct 480
tggtccctgc tattgtcggg gacgattgca tg 512

<210> SEQ ID NO 1199

<211> LENGTH: 518
<212> TYPE: DNA
<213> ORGANISM: Homo sapiens

<400> SEQUENCE: 1199
cgtcctcctc tgggtaccaa ctctattgcg cagctcgctg ccgtgcgttt aacccaggcg 60
aggaggagga ggagaaaatt cccccagatt cgggcaggcc cgcaccccac attccgtcct 120
gttttgagag gaggagggaa gagaaataaa cgtggcagcg catagaaggc cagcagggag 180
actgctttcc agacacctcc ggcccacaca gccgttcacc ccccgtcttt tcagtcctgg 240
aaaaggaatt cggtctgtcc ttaggatgaa gctctaactg aactgaagta aggagaaaca 300
gccttgaatc tttggagggt ctgtcttcct tttgggctct gtgcaactgc agctacagtg 360
gaaaaaagca aactgctctt gatcccaggc cctgcctaag cctcagcaga acttgtaagc 420
ctaaactgaa gagcctcacc cggacgagca ggcatccctt aaccttaagc aatccagttc 480
cacgccctgg atcagtgaat aaccccagct gcaccatg 518

<210> SEQ ID NO 1200
<211> LENGTH: 537
<212> TYPE: DNA
<213> ORGANISM: Homo sapiens

<400> SEQUENCE: 1200
cgccctctgg ggctccgagc ccggcgggac catgttcacc agcaccggct ccagtgggct 60
ctgtgagtac cggcctccgc catcctggct gccccctaca cgccacccta ggcacctctt 120
tgaggaggct ggggcagcgg ggaccctcgg gtttgccgga ggtggtgggg ccgaccctcc 180
agacccgcgt ccgaaccctg ctagttcccg gtcttggggg tcagcggaaa ccgcccccat 240
ttcggcctgg aggggcgaat ggggacaaag ccccgccgcc cgccccgacc ccacctggta 300
tccccaggtg ctctgcccag gagtctcttg gggccgctgc aagtgggcag gtgccctggt 360
gttctcgtgg gccggcccca ggccctttgc ggagcgtgtg ccgcgctgaa ggaaggggcc 420
gtccccctta ccatgcccca ttcttttagg cttgggggac cgaactaact ccccccgccc 480
ccacttgcaa agttcagcct ccgctttaga agctgacctc tcagtttcac ttggatg 537

<210> SEQ ID NO 1201
<211> LENGTH: 119
<212> TYPE: DNA
<213> ORGANISM: Homo sapiens

<400> SEQUENCE: 1201
cctcctccct cggccggccc tggggccgtg tccgccgggc aactccagcc gaggcctggg 60
cttctgcctg caggtgtctg cggcgaggcc cctagggtac agcccgattt ggccccatg 119

<210> SEQ ID NO 1202
<211> LENGTH: 181
<212> TYPE: DNA
<213> ORGANISM: Homo sapiens

<400> SEQUENCE: 1202
cgctccctca cagctcccgt cccgttaccg cctcctggcc ggcctcgcgc ctttcaccgg 60
caccttgcgt cggtcgcgcc gcggggcctg ctcctgccgc gcgcaccccc ggggcttcgg 120
ctccggcacg ggtcgcgccc agctttcctg cacctgaggc cgccggccag ccgccgccat 180
g 181

<210> SEQ ID NO 1203
<211> LENGTH: 130
<212> TYPE: DNA
<213> ORGANISM: Homo sapiens

<400> SEQUENCE: 1203
ctttcttttt aaaaatcgct gggtctgttg agctgtcctg ggctgggtgc cttgctcttt 60
gactgagact ggagacagac ggcaacagcc acaggcagac tgaggtggca ataggaaatc 120
tgccgagatg 130

<210> SEQ ID NO 1204
<211> LENGTH: 239
<212> TYPE: DNA
<213> ORGANISM: Homo sapiens

<400> SEQUENCE: 1204
gattctcccg cctcccagcc ccggcgcacg cgcgccccgc ccagcctgct ttccctccgc 60
gccctcccct ctcctttctc cctctcagaa ccttcctgcc gtcgcgtttg cacctcgctg 120
ctccagcctc tggggcgcat tccaaccttc cagcctgcga cctgcggaga aaaaaaatta 180
cttattttct tgccccatac ataccttgag gcgagcaaaa aaattaaatt ttaaccatg 239

<210> SEQ ID NO 1205
<211> LENGTH: 146
<212> TYPE: DNA
<213> ORGANISM: Homo sapiens

<400> SEQUENCE: 1205
tttccttctt cccgcgagtc agaagcttcg cgagggccca gagaggcggt ggggtgggcg 60
accctacgcc agctccgggc gggagaaagc ccaccctctc ccgcgcccca ggaaaccgcc 120
ggcgttcggc gctgcgcaga gccatg 146

<210> SEQ ID NO 1206
<211> LENGTH: 235
<212> TYPE: DNA
<213> ORGANISM: Homo sapiens

<400> SEQUENCE: 1206
ttttctttct ctcagcatct ccacccaacc agcagaaaac cggtgagtgg ggcttttaag 60
tgattttcaa gaagaatgta acagatgtca aacgggaaaa gcacaaggca aagcctgctc 120
tctctgtctc tctgtctcct cttctccttt tttgccttat tctatccgat tttttcccta 180
agcttctacc tgggattttc ctttggaaaa gtctctgagg ttccaccaaa atatg 235

<210> SEQ ID NO 1207
<211> LENGTH: 82
<212> TYPE: DNA
<213> ORGANISM: Homo sapiens

<400> SEQUENCE: 1207
ttgtcttttt ttttttaaac taaaatggag gctggtttct tgccttaagg agcccattgc 60
ctttcccgct gaagtctaga tg 82

<210> SEQ ID NO 1208
<211> LENGTH: 440
<212> TYPE: DNA
<213> ORGANISM: Homo sapiens

<400> SEQUENCE: 1208

```
ccacctttcc gggggaagcc acgcgcacca ggcatcgcac gcggctctgc acccgcgccg     60

ccggacctga aacccggcgg agggcacacg gggctgccgc tgcgggcccc ggaccaaccc    120

atgcttactc cggagcctgt accggcgccg acgggtcgga cctccctgcg cggtgtcgcc    180

cagcgggttc gtgcgaaagg cggggccgac tacacgcggt gccgcgccct gagaccgttt    240

atctgcagtc aacgcagcct cccggctcag cctgggaaga tgcgcgaatc gggaacccca    300

gagcgcggtg gctagaccgg gctccgccgc ctcccccaca gcccctttcc taatcgttca    360

gacggagcct ggtcgacttc gccggagact gccagatctc gttcctcttc cctgtgtcat    420

cttcttaatt ataaataatg                                                440
```

<210> SEQ ID NO 1209
<211> LENGTH: 257
<212> TYPE: DNA
<213> ORGANISM: Homo sapiens

<400> SEQUENCE: 1209

```
caccctcttc gtcgcttcgg ccagtgtgtc gggctgggcc ctgacaagcc acctgaggag     60

aggctcggag ccgggcccgg accccggcga ttgccgcccg cttctctcta gtctcacgag    120

gggtttcccg cctcgcaccc ccacctctgg acttgccttt ccttctcttc tccgcgtgtg    180

gagggagcca gcgcttaggc cggagcgagc ctgggggccg cccgccgtga agacatcgcg    240

gggaccgatt caccatg                                                   257
```

<210> SEQ ID NO 1210
<211> LENGTH: 555
<212> TYPE: DNA
<213> ORGANISM: Homo sapiens

<400> SEQUENCE: 1210

```
cctcctcttc ctccccactc tgcacatgcg gctgggtggc agccagcggc ctcagacaga     60

cccactggcg tctctctgct gagtgaccgt aagctcggcg tctggccctc tgcctgcctc    120

tccctgagtg tggctgacag ccacgcagct gtgtctgtct gtctgcggcc cgtgcatccc    180

tgctgcggcc gcctggtacc ttccttgccg tctctttcct ctgtctgctg ctctgtggga    240

cacctgcctg gaggcccagc tgcccgtcat cagagtgaca ggtcttatga cagcctgatt    300

ggtgactcgg gctgggtgtg gattctcacc ccaggcctct gcctgctttc tcagaccctc    360

atctgtcacc cccacgctga acccagctgc cacccccaga agcccatcag actgccccca    420

gcacacggaa tggatttctg agaaagaagc cgaaacagaa gatgaggcaa tgaggctgcg    480

agaggtagag tgattttccc tcggtgactc aactgggacg tagcaggtcg ggcagtcaag    540

ccaggtgacc ccatg                                                     555
```

<210> SEQ ID NO 1211
<211> LENGTH: 295
<212> TYPE: DNA
<213> ORGANISM: Homo sapiens

<400> SEQUENCE: 1211

```
tggtctttcc gggtccttgc acgcttcgct ccaactcctg cagagctgag ccggagggga     60

atccggaagg gacacgctga acaggtctga ctcccgggca gcacagcccg ctcacgattc    120

cggccacggt gatgacgagt ctccgtcaac ctcgtctggc acagctggga cctcctctgt    180

gccagagcta cctgggtttt actttgaccc tgaaaagaaa cgctacttcc gcttgctccc    240

tggacataac aactgcaacc ccctgacgaa agagagcatc cggcagaagg agatg         295
```

<210> SEQ ID NO 1212
<211> LENGTH: 138
<212> TYPE: DNA
<213> ORGANISM: Homo sapiens

<400> SEQUENCE: 1212
ccgcctcttg tgaggcgcgc ggagccgcct cccctgggtc aggtctgatg ggccggtggg 60
cgcgctagtg gtggccgcca ccgccgaaac cgtcgacctc ctgggcccca gttccgcgtc 120
cagccccgcg gcagcatg 138

<210> SEQ ID NO 1213
<211> LENGTH: 47
<212> TYPE: DNA
<213> ORGANISM: Homo sapiens

<400> SEQUENCE: 1213
ccccctctct atcagccgct cactccgtct caatatgtct caagatg 47

<210> SEQ ID NO 1214
<211> LENGTH: 173
<212> TYPE: DNA
<213> ORGANISM: Homo sapiens

<400> SEQUENCE: 1214
ctcccttttc ctccccactc cttcccacca gcgccacagc aacatcctca gagtctgagc 60
gaactgcgcc cagcgcgggc acggagcctc ccaccgccag caacctgcgg ccccggagaa 120
ggcagcgagc gcagtgacag cgcctcaccg ccaccagctc ctggaccacc atg 173

<210> SEQ ID NO 1215
<211> LENGTH: 162
<212> TYPE: DNA
<213> ORGANISM: Homo sapiens

<400> SEQUENCE: 1215
ctgccttctc tcccggggcc ctgtgggcaa gcctcctgct tcactttcag gtttctcgaa 60
gtgccttctt gctcctgtct gtttccccat cctgccagat ttctgtttct cttgctgggc 120
ttttggcagt agggggctgt gttggtgggc cctacgaaga tg 162

<210> SEQ ID NO 1216
<211> LENGTH: 225
<212> TYPE: DNA
<213> ORGANISM: Homo sapiens

<400> SEQUENCE: 1216
aggccttttc cgcttctctt ttacctcccc aggtccgccc gtctgcgccc ctcacaggaa 60
gccggagggt cgctctgatc ccgaatctcc cacaggcgtg aacctgctct gctgtgtatc 120
tttgcggggt ggcctgcgct gaggcctgcc gcgcgcggtg agtccgcgca gacctgaccc 180
tgcgtctcgc agctcggttg aggccgccgc cgccttctcg ggatg 225

<210> SEQ ID NO 1217
<211> LENGTH: 633
<212> TYPE: DNA
<213> ORGANISM: Homo sapiens

<400> SEQUENCE: 1217
cttcctttac cttcctccca tggtctcctt ccggttctcg atgcttctct gagcctaagg 60

-continued

```
gtttccgcca ctcgttcacc ctccccccag ctcatgatcc tcctccctcc cccgccctcc    120

tggtccaatc tccgatctgt ttagtaagaa ggtgctgttc cgagaagaag gaaaagggct    180

tgacacgtat tcactcggcc ccggacgtgg gaagcaagcc gtctggcttc ggcctcacat    240

cggtcttgtg ctcgggacgg cggcgttggc ggactgatcc gcggcggtga agagaggccg    300

ggaagttaaa cttgtagcca ccacctccgc tcttcccgtc accctcgccc ccacttcggg    360

ccgaaagcac ggtacagagg ctgttggtgg ctttgccacg ccaccccacc caccccggat    420

cgcggctgtc ttaagggacc tggattcatc aggggctctt cggggcctgt gcgagtgctg    480

atctgctccg tttttgcaaa aggcgcctgt gtctggcaga gctggtgtga gacgagacaa    540

tcctgccccg ccgccgggat aatcaagagt tttggccgga cctttgagca tacaccgaga    600

gagtgaggag ccagacgaca agcacacact atg                                 633
```

<210> SEQ ID NO 1218
<211> LENGTH: 169
<212> TYPE: DNA
<213> ORGANISM: Homo sapiens

<400> SEQUENCE: 1218

```
tttcctctgg ctcctgcgag ggcttggttt agggcttcag ctctctgcgt tctcggctcc     60

gggaggcctc ggtgattcag ccacagcctc tgcctcccgt tgctctgtga cctgagggta    120

ttggacaatt tgtagctaag actcccggat accctgaagt cgggaaatg                169
```

<210> SEQ ID NO 1219
<211> LENGTH: 143
<212> TYPE: DNA
<213> ORGANISM: Homo sapiens

<400> SEQUENCE: 1219

```
tgctctcttc caaggctgta ggagttctgg agctgctggc tggagaggag ggtggacgaa     60

gctctctcca gaaagacatc ctgagaggac ttggcagcct gcagatggcc tattgtggga    120

ccttgtgatc atgcctgaac atg                                            143
```

<210> SEQ ID NO 1220
<211> LENGTH: 190
<212> TYPE: DNA
<213> ORGANISM: Homo sapiens

<400> SEQUENCE: 1220

```
tttcccttta tagcaccatt gaatcccagt cctaacagaa gtactgcgaa tcttgtggcc     60

tcattctgaa caaaagggat tagagaagaa aaatctcttg atataaggct tgaaagcaag    120

ggcaggcaat cttggttgtg aatattttct gatttttcca gaaatcaagc agaagattga    180

gctgctgatg                                                           190
```

<210> SEQ ID NO 1221
<211> LENGTH: 93
<212> TYPE: DNA
<213> ORGANISM: Homo sapiens

<400> SEQUENCE: 1221

```
tgcccttcct cgccaccggg ctgctctggt ctcgtcggtc ccctcctccg ccccgtcgtc     60

ctgactctct ctccctcctt tcctcagagg atg                                  93
```

<210> SEQ ID NO 1222
<211> LENGTH: 378

<212> TYPE: DNA
<213> ORGANISM: Homo sapiens

<400> SEQUENCE: 1222 aacccttca cctcagtttt cttcactccg gcatttgcag cagagcgaaa ggtggtcgag 60
tcctgaagga gggcctgatg tcttcatcat tctcaaattc ttgtaagctc tgcgtcgggt 120
gaaaccagac aaagccgcga gcccagggat gggagcacgc gggggacggc ctgccggcgg 180
ggacgacagc attgcgcctg ggtgcagcag tgtgcgtctc ggggaaggga agatatttta 240
aggcgtgtct gagcagacgg ggaggctttt ccaaacccag gcagcttcgt ggcgtgtgcg 300
gtttcgaccc ggtcacacaa agcttcagca tgtcatgtgg cttatcagga gggcagactt 360
caaaagctac taaaaatg 378

<210> SEQ ID NO 1223
<211> LENGTH: 1104
<212> TYPE: DNA
<213> ORGANISM: Homo sapiens

<400> SEQUENCE: 1223
tgtccttccg cgcggcggcc gcggagagag ctgcggcccg ggggggcgtg cctgggatcc 60
ggagcttcgc tcgggcccgg gaaaggcggc agtgggctgg gatcgcggtg tctctgggtg 120
tgatggccaa tggctggact ggctcccgcc ctgggcggag gaatcccgag ctgtgaagcg 180
gctggaatcc gggcccatgt gcttctttgt ttactaagag cggaagcgat ggcgggagcg 240
ggggtggggt gcggtggcgg ggtgcggtgg cggaggtccc ggtgaaatca ggggctaagg 300
ggacccaaag aaggcggggg atcatagggg tggaaagaaa gctgagaacc ttgagaccgg 360
agtgtgaggg gccaacgggg aagggcgcta gaattttaaa ctaaagtagg gaccggaatt 420
cccctgggga gatgttggat ggccctgtgc actgccacgg gctctttatt cttcgctggt 480
tagaaacaga cttgtgaaaa agagttatgc ccactttggg gagacttcga aaaggttaag 540
aagttcttac aagagttcta ccaggatgat gaactcggga agaagcagtt caagtatggg 600
aaccagttgg ttcggctggc tcatcgggaa caggtggctc tgtatgtgga cctggacgac 660
gtagccgagg atgaccccga gttggtggac tcaatttgtg agaatgccag gcgctacgcg 720
aagctctttg ctgatgccgt acaagagctg ctgcctcagt acaaggagag ggaagtggta 780
aataaagatg tcctggacgt ttacattgag catcggctaa tgatggagca gcggagtcgg 840
gaccctggga tggtccgaag cccccagaac cagtaccctg ctgaactcat gcgcagattg 900
tgagtggtct ctgtcgggaa agatgtaggg attggttctc caggatcttg tttgtgactg 960
ttttctcccc ttagtgagct gtattttcaa ggccctagca gcaacaagcc tcgtgtgatc 1020
cgggaagtgc gggctgactc tgtggggaag ttggtaactg tgcgtggaat cgtcactcgt 1080
gtctctgaag tcaaacccaa gatg 1104

<210> SEQ ID NO 1224
<211> LENGTH: 135
<212> TYPE: DNA
<213> ORGANISM: Homo sapiens

<400> SEQUENCE: 1224
tttccccctc tccccctcct ccgccgaccg agcagtgact taagcaacgg agcgcggtga 60
agctcatttt tctccttcct cgcagccgcg ccagggagct cgcggcgcgc ggcccctgtc 120
ctccggcccg agatg 135

<210> SEQ ID NO 1225
<211> LENGTH: 463
<212> TYPE: DNA
<213> ORGANISM: Homo sapiens

<400> SEQUENCE: 1225
ctttctttcc ctctccgttt tggtgggctg gttgaagatg aaatccactg aggagggaag 60
tccagcaccc tgtgtgccag tccagaactg gcccatctgt agaccccctg aaaatcatat 120
gggcttggat ttggatattc tcaacagaaa gggttaaagg ctgatggtac ctaaagcctg 180
gtacttgaat tttgatcaag ataagctgcc ttaagttctc ttcattacac aaatgatcct 240
agataattga tagatcctgt ggttcaactg gatttctaga tagaagctgg attcatgtga 300
tgccagagga gtaaaatttc aagagactga aaccagatct gagtttcgct gttccagtct 360
ggacctcttt ggtgctgtaa atcctggata tactgtagat gagtactgcg tttttctttt 420
atggcctctc ttcagcttct ggagacctca ctatcctatt atg 463

<210> SEQ ID NO 1226
<211> LENGTH: 453
<212> TYPE: DNA
<213> ORGANISM: Homo sapiens

<400> SEQUENCE: 1226
ccgccttcgc cgcggacctt cagctgccgc ggtcgctccg agcggcgggc cgcagagatg 60
acatttattc attttatgca tcctgggttc tactggtcgt cccacctcag ttcctgtagc 120
aaagagactt gagtctgagc cactaattat cacccgtgag gtttcctccc cgagcaggaa 180
gcagcaggcc agagctgcgc tctctcagtg cactctccaa ccaagcatca gtcaccactc 240
ccggtccagc ccctgtggcc aagagctggc gtgcaggctg cgggaggcag ctggctgtgc 300
aagaccctgg cagggccctc gcctcctgag aaaccgagag tcagaaccaa agccaggctg 360
tcctggttgg agactgagcc agaaagggtg gctcacctca cggtgaggct gtcgagtgac 420
ctgagagcct cagaccctca cgtcagccgg atg 453

<210> SEQ ID NO 1227
<211> LENGTH: 169
<212> TYPE: DNA
<213> ORGANISM: Homo sapiens

<400> SEQUENCE: 1227
tgttcttccg ggttggaggc gcagcgccgc ggggcccaag cccgggtctg ccagcgcgac 60
gtcctctcgc ggccctcagg gcacagccca aggctgtcag cctcccggcc cagtgatttg 120
ccttcaagga aactggggag tcagaaaatt gggaactcat atcaacatg 169

<210> SEQ ID NO 1228
<211> LENGTH: 149
<212> TYPE: DNA
<213> ORGANISM: Homo sapiens

<400> SEQUENCE: 1228
gtccctctcc ctccccagga cttctgtgac tcctgggcca cagaggtcca accaggctaa 60
gggcctgggg ataccccctg cctggccccc ttgcccaaac tggcaggggg gccaggctgg 120
gcagcagccc ctctttcacc tcaactatg 149

<210> SEQ ID NO 1229
<211> LENGTH: 52

<212> TYPE: DNA
<213> ORGANISM: Homo sapiens

<400> SEQUENCE: 1229
cggcccttcc agaccgtctc tcctcagggt tggagacttc ggggccaaga tg 52

<210> SEQ ID NO 1230
<211> LENGTH: 771
<212> TYPE: DNA
<213> ORGANISM: Homo sapiens

<400> SEQUENCE: 1230
tcgcctcttt agtaggtcgg gtgagtgtag tgtgcaggga agagacgcgt cagcgccagg 60
gccaggcccg cccgggggca gcccggcagc cgaatcttgg gctactctgt cccaacagcc 120
ggagcagatc agaccgaccg gccctgcccg ctcggtcccg cgccctccag accctacggt 180
ctccgtttct aggggcacat ggttagcggc aggcgcccac agccaatcca ctttgccagc 240
ctgccccttc ctctgccaag agcagcttct tcagccgcgc tccagttccg cagacgcctg 300
ccccaccctg ctcttccctt ccagggaaga cggatcacgc ggccaagaac gagactcgca 360
aactgggcat ttctccgagc cgggctagag caagtagcga gactccgcgt gagagtggga 420
aagagcctta acaggcaacc atgttgccca gtgggttttc tgtgcctttg ggtgcggacc 480
aatgaggcgc gtggggcggg acttccgctt cgcctaggtg ttgtcgtccc tgctagtact 540
ccgggctgtg gggtcggtg cggatattca gtcatgaaat cagggtaggg acttctcccg 600
cagcgacgcg gctggcaaga ctgtttgtgt tgcgggggcc ggacttcaag agagaaagag 660
agagtgggca gacatcgaag ccaaacagca gtatcccgga agcactcatg caactttggt 720
ggcggccact cagttttctc tgccagtgtc tggtgatttt acaacgagat g 771

<210> SEQ ID NO 1231
<211> LENGTH: 190
<212> TYPE: DNA
<213> ORGANISM: Homo sapiens

<400> SEQUENCE: 1231
ccgcctcctg cgccgcccct tccgaggcta aatcggctgc gttcctctcg gaacgcgccg 60
cagaaggggt cctggtgacg agtcccgcgt tctctccttg aatccactcg ccagcccgcc 120
gccctctgcc gccgcaccct gcacacccgc ccctctcctg tgccaggaac ttgctactac 180
cagcaccatg 190

<210> SEQ ID NO 1232
<211> LENGTH: 208
<212> TYPE: DNA
<213> ORGANISM: Homo sapiens

<400> SEQUENCE: 1232
cgctccttcc ctgagctccc gggctccggc agcgcgctgg cggggcgccg cattgcacac 60
tctgggggcg ccgcagtgtt cgtgggatgg ggcagcgggc tgcagctggc ggccggaatc 120
cgcgcgcagc ccgggtgcaa gttctctcct gttgccctga gtgcccactc ccaggccctc 180
tgtatgagtg acacttcagt ctgccatg 208

<210> SEQ ID NO 1233
<211> LENGTH: 314
<212> TYPE: DNA
<213> ORGANISM: Homo sapiens

<400> SEQUENCE: 1233
cagtctctgc tttctttttc ctttcttcca gaaggagatt taaccatagt agaaagaatg 60
gagaactatt aactgccttt cttctgtggg ctgtgatttt cagaggggaa tgctaagagg 120
tgattttcaa tgttgggact caaaggtgaa gacactgaag gacagaattt ttggcagagg 180
aaagatcttc ttcggtcacc atacttgagt tagctctagg gaagtggagg tttccatttg 240
gaattctata gcttcttcca ggtcatagtg tctgcccccc accttccagt atctcctgat 300
atgcagcatg aatg 314

<210> SEQ ID NO 1234
<211> LENGTH: 65
<212> TYPE: DNA
<213> ORGANISM: Homo sapiens

<400> SEQUENCE: 1234
ctgtcctttc ccgggagtta gcgatccctc aacccctgca ctgcgctagt cctaaagagg 60
aaatg 65

<210> SEQ ID NO 1235
<211> LENGTH: 91
<212> TYPE: DNA
<213> ORGANISM: Homo sapiens

<400> SEQUENCE: 1235
gattctcttt tgtccacaga cagtcatctc aggagcagaa agaaaagagc tcccaaatgc 60
tatatctatt caggggctct caagaacaat g 91

<210> SEQ ID NO 1236
<211> LENGTH: 81
<212> TYPE: DNA
<213> ORGANISM: Homo sapiens

<400> SEQUENCE: 1236
actccttttc tcctaaccgt cccggccacc gctgcctcag cctctgcctc ccagcctctt 60
tctgagggaa aggacaagat g 81

<210> SEQ ID NO 1237
<211> LENGTH: 510
<212> TYPE: DNA
<213> ORGANISM: Homo sapiens

<400> SEQUENCE: 1237
aagcctttct ccattttgcg gtctaggaag tagcagaggc cccttcctgt agggagttgc 60
catggagacg cggtggggca ccgacggagt tctaatgacg gccgtgattg gtgcaggatc 120
ctgctaatct caggaaggcc cgtagagaag tgaggaaaac gtggtggggg gcatgcgcga 180
tctggtaggc ggtgctgccg tctgttgtac ctgagaggct tgcgcatgcc gacgcacgga 240
ttcgaggcgg ggagcatggg aagaagcggc caggagtatg acctgatcat tgcgaccacc 300
gctaggggaa gggaggagag ggtgtagaaa cggggacgag ggtgggggaa gggcaaggag 360
gcgctcgagc tggtgcgcgg agcatcctgg gagacgtagt ccagcgggag ggggaagtcg 420
aagactgcgc gtgctcagga gcgcggagcg gcccgctgag cgcagagggg cagacactgg 480
cctcagatac ctgacctggt accctctatg 510

<210> SEQ ID NO 1238
<211> LENGTH: 228

<212> TYPE: DNA
<213> ORGANISM: Homo sapiens

<400> SEQUENCE: 1238
cctcctcttt ttccgtctgc gtcgggagct cccgggcacg tgaggccgtg ccgcgtttac 60
tggcgggcgg gacggcctag ccgggcggcg cctcggagga agccgcggac cccttaggtg 120
ctgggccctt ggaaatcggc gcgtgggggg cggtgctcga gctgagcgcg agagggcggg 180
agagctcgtg gggtgcgagg ggagcaggac gcccggccgg gcagcatg 228

<210> SEQ ID NO 1239
<211> LENGTH: 327
<212> TYPE: DNA
<213> ORGANISM: Homo sapiens

<400> SEQUENCE: 1239
cttcctcttt caacaacaaa tgtgtcagtt atcagcagga tccatgccgc cagagtaaag 60
ctttctaccc tttactccct gcaaagaaac aagagtgctt atcccagcta agctccaggg 120
taatgttatc atgacagctt caacttttag accacaggca aatgctttgt taaaactcta 180
tgctggtcat tcccttcagg atttggcact caccaacata cccttctttc aagtgaaaag 240
gcatctcttt taatggtcct gacctttgga ataggaagca tgtaccctgg acagagcact 300
tcaaactaga ggaaccataa atccatg 327

<210> SEQ ID NO 1240
<211> LENGTH: 48
<212> TYPE: DNA
<213> ORGANISM: Homo sapiens

<400> SEQUENCE: 1240
catccttttg cctgctcccg gcgaggggtg gctttgattt cggcgatg 48

<210> SEQ ID NO 1241
<211> LENGTH: 26
<212> TYPE: DNA
<213> ORGANISM: Homo sapiens

<400> SEQUENCE: 1241
cgtccccttt ccggccggtc cccatg 26

<210> SEQ ID NO 1242
<211> LENGTH: 305
<212> TYPE: DNA
<213> ORGANISM: Homo sapiens

<400> SEQUENCE: 1242
ccctcccctc cgcccgtcac cgcctccttg aagctgccgc tgtcgctgct gctcgttcga 60
gtcgcagatc cttgccagca cattacagaa tatttttgtt gaaccttctt gagaattcag 120
agaaactgct gagtgaccac tgaacgaaaa gatctaatct taaggcttac gcctcacttt 180
gatgcccagg ctggagtgct gtggctcaat cacagctcat cgcaacctcg acctcccggg 240
ctcaagtgat cctctcacct cagcgtcccg aacaggcgtg ttccatccac cacatcagaa 300
caatg 305

<210> SEQ ID NO 1243
<211> LENGTH: 414
<212> TYPE: DNA
<213> ORGANISM: Homo sapiens

<400> SEQUENCE: 1243
tcctctctcc acttcctgct actgcaggcc tctcctccga gaacagaggc caggtcatga 60
ctcactggct tcctgcaacc tgacgatggc ccagccagaa gacaaggcac ctgaagtccc 120
cacagagggg gtgaggtgaa caaagcagac aggacccctc taggggtcct cagcacccta 180
gagccactta ctcgcctgca gaggacatgg ggggtgtggc atgtgccaga gctggatacc 240
caggatgcgg aggcccttgt ggggctgtgg ccactaggga gtttcttggt cacaggacgt 300
gaccccagcc aggccctggt gttgaggtca ggacctttac caggagaagt caatacctac 360
cagatccaga agattcccag aggtgtgtcc ctggaatcct ccaacctctg catg 414

<210> SEQ ID NO 1244
<211> LENGTH: 144
<212> TYPE: DNA
<213> ORGANISM: Homo sapiens

<400> SEQUENCE: 1244
ccgccttttc ttcagcgtcc tacccgcggc actggctgcg agcgccgggc cacctgcgag 60
tgtgcgcagg gactctggac acccgcggcg gcgagctgag ggagcagtct ccacgaggac 120
ccaggcggac cctctggcgc catg 144

<210> SEQ ID NO 1245
<211> LENGTH: 313
<212> TYPE: DNA
<213> ORGANISM: Homo sapiens

<400> SEQUENCE: 1245
ccgcctttcc ggagcgcggg cgcgcggtgg cgggaatttc gcctgtttgc ggtttagacc 60
ccaaagattc ctgttggtgg tctgggtcac aggaggcagg tttcgggagc tggaaatgtg 120
agcgggtacg acaggcaccg cgggtaaccg acgccccggg tccttgctgc agccgggtac 180
gcgggatacc ggcaccccgc cttctccgcc cgagtgctgc caggcgtggg cctggaatct 240
cttcacacct tctctttgga gcccttaatg atacgacgaa ccccaagtgt ttcagaacat 300
gaagtaaaca atg 313

<210> SEQ ID NO 1246
<211> LENGTH: 367
<212> TYPE: DNA
<213> ORGANISM: Homo sapiens

<400> SEQUENCE: 1246
actcctttcc tttttccagt ggttatcgcg gcgcccaccg gcctctgatc tctgagtctt 60
ctccaaccca cagacgtttt ttgttgctct ggttccagga ccttctccac aactaggcca 120
ttttccctgc caggtgtcct ttttgacctc ttgacctctg actcaaaggg cctgctcccc 180
ctcatgtctt cggcctggag aagagccagc tcctgaagga ggcctttgat aaggccggcc 240
cggtccccaa gggcagagaa gatgtgaaga ggcttctgaa actacacaag gaccggttcc 300
gaggtgacct gcggtggatc ctcttctgtg cagacctgcc gtccctcatc caagaaggcc 360
ctcaatg 367

<210> SEQ ID NO 1247
<211> LENGTH: 384
<212> TYPE: DNA
<213> ORGANISM: Homo sapiens

<400> SEQUENCE: 1247
cgcccttccg gctcggcctt tagttagtga ccagctcctc ggcgttctgc agagcgtggg 60
tttcagcgag ttctacgtgc caggtccgcc cggtgccggc ttcctcgctg cccctggcgg 120
ctcgtcagcc cccactaccc ctgaacttgg tcccaatggc ggcccgcccc tccttcaccc 180
ggaccgtggg catctgggcc tcgccgaagc cgtcaaggtg gctgctcggg cttctagagc 240
ccgtgtccag ccctttgcca ccgaggcctg atcctctttt ctgccctaaa gaacttgccc 300
tgacagcctc tggctcccgc tcttgaggat cttgcttgtc caaacccaga agacagtgca 360
tgaagccagg ggacatccgc catg 384

<210> SEQ ID NO 1248
<211> LENGTH: 14
<212> TYPE: DNA
<213> ORGANISM: Homo sapiens

<400> SEQUENCE: 1248
ccgccttctc catg 14

<210> SEQ ID NO 1249
<211> LENGTH: 143
<212> TYPE: DNA
<213> ORGANISM: Homo sapiens

<400> SEQUENCE: 1249
ccgccctttt cttcgtagcc tccaagggag ctggaacaaa aaacgaaacc aaaacctgcc 60
tgctcgctcc tctccccatc gcctgcgttc cgctggttgt gggctttctg cggccgctga 120
gggcgcgtct cccctccgcc atg 143

<210> SEQ ID NO 1250
<211> LENGTH: 97
<212> TYPE: DNA
<213> ORGANISM: Homo sapiens

<400> SEQUENCE: 1250
caccctcctt cagcccaggc aaggcctggg gccctgggca gcctccaggt gcagtgccct 60
cccgtgggcc gcacccttgc cactgcccca gggcatg 97

<210> SEQ ID NO 1251
<211> LENGTH: 31
<212> TYPE: DNA
<213> ORGANISM: Homo sapiens

<400> SEQUENCE: 1251
ctttctcttc cttccacccc gagggaccat g 31

<210> SEQ ID NO 1252
<211> LENGTH: 91
<212> TYPE: DNA
<213> ORGANISM: Homo sapiens

<400> SEQUENCE: 1252
cgctctccgc ctcggcagtg ccagccgcca gtggtcgcac ttggagggtc tcgccgccag 60
tggaaggagc caccgccccc gcccgaccat g 91

<210> SEQ ID NO 1253
<211> LENGTH: 117
<212> TYPE: DNA
<213> ORGANISM: Homo sapiens

<400> SEQUENCE: 1253
atttcctttc cctttttttcg ctcgtgtccc gccgggtggc gctcaccacc tccccggaac 60
acgcgagtct cctgtcgcgg ttccggtcgg aattaccccg tggagcacgc cgatatg 117

<210> SEQ ID NO 1254
<211> LENGTH: 63
<212> TYPE: DNA
<213> ORGANISM: Homo sapiens

<400> SEQUENCE: 1254
gagtctttcc ttagtaacct gggcgatagc tgtggatgtt tccaaggatt gtcttcagtc 60
atg 63

<210> SEQ ID NO 1255
<211> LENGTH: 211
<212> TYPE: DNA
<213> ORGANISM: Homo sapiens

<400> SEQUENCE: 1255
cttcctccat aacaagccaa acgccagacc gagagtgcct ccgtgcgcga gtgcccggtg 60
tgtgcgcgcc ggcgagagca ggggcccgcc cggctccccg cccgccgcgg cccgaactca 120
tgcagctccg agcgagcgag cggcgcccag cccagcgcct cggccgaacc cctccgcagc 180
aggctgcctg ctgtttcccg gggagatcat g 211

<210> SEQ ID NO 1256
<211> LENGTH: 49
<212> TYPE: DNA
<213> ORGANISM: Homo sapiens

<400> SEQUENCE: 1256
cctccttttc gccctcccac ccgcactgca gtctccagcc tgagccatg 49

<210> SEQ ID NO 1257
<211> LENGTH: 164
<212> TYPE: DNA
<213> ORGANISM: Homo sapiens

<400> SEQUENCE: 1257
aagccctttt cattgcagga gaagaggaca aagatactca gagagaaaaa gtaaaagacc 60
gaagaaggag gctggagaga ccaggatcct tccagctgaa caaagtcagc cacaaagcag 120
actagccagc cggctacaat tggagtcaga gtcccaaaga catg 164

<210> SEQ ID NO 1258
<211> LENGTH: 832
<212> TYPE: DNA
<213> ORGANISM: Homo sapiens

<400> SEQUENCE: 1258
cagccttctc actcctcact gagtccactc tgaacgtgct aaaatgggaa ggaggcggtg 60
ttttgctgat ctgttaaatt cttagtgaag tttccttgat ttccagtggc tgctgttgtt 120
tgagtttggt ttggagcaaa actgaggtag tcctaacatt tctgggactg aatccaggca 180
agagaaagaa gaaaaagaag aagaaaaaga ggaggaaaaa ggtagggaga aataaaggga 240
ggagagaagc acagtgaaag aaaaaaaaag tcccttttcg acatcacatt cctgtgtttt 300
ccctcagcct ggaaaacata ttaatcccag tgcttttacg cccggaaaca aagagactaa 360
gccagactat gggggaaagg gagataagaa ggatcctgga actttaaaga gggaaagagt 420
gagattcaga aatcgccagg actggacttt aagggacgtc ctgtgtcagc acaagggact 480
ggcacacaca gacacacgag accgaggaga aactgcagac aaatggagat acaaagactt 540
agaaggacag ctcctttcac ctcatcctac ttgtccagaa ggtaaaaaga cacagccaga 600
aagaaaaggc atcggctcag ctctcagatc aggacaggct gtggatctgt ggcggtactc 660
tgaaagctgg agctgcagca caccccttt gtattgctca ccctcggtaa agagagagag 720
ggctgggagg aaaagtagtt catctaggaa actgtcctgg gaaccaaact tctgatttct 780
tttgcaaccc tctgcattcc atctctatga gccaccattg gattacacaa tg 832

<210> SEQ ID NO 1259
<211> LENGTH: 114
<212> TYPE: DNA
<213> ORGANISM: Homo sapiens

<400> SEQUENCE: 1259
cgacctcttt gcgcctgcgc ccccccttgcc agtctttcgc cggcaaaagg aggacgtaga 60
aaaggggaca ccggaaactc actcttcacc cggaaatggt tattgaggaa catg 114

<210> SEQ ID NO 1260
<211> LENGTH: 16
<212> TYPE: DNA
<213> ORGANISM: Homo sapiens

<400> SEQUENCE: 1260
cgcccttctc aagatg 16

<210> SEQ ID NO 1261
<211> LENGTH: 440
<212> TYPE: DNA
<213> ORGANISM: Homo sapiens

<400> SEQUENCE: 1261
ctttccctgt gctgcccctg ccgcgcgatg gagaagagct cgagctgcga gagtcttggc 60
tcccagccgg cggcggctcg gccgcccagc gtggactcct tgtccagtta atgtgttaag 120
agccattgac atttgaagat catcagaagt gaagataaaa catctcaaaa attataattg 180
cctccacttc tcattcagag aattcagtgc atacaaaatc agcttctgtt gtatcatcag 240
attccatttc aacttctgcc gacaactttt ctcctgattt gaggagggag tctcgctcta 300
tcccctaggc tggagtgcat tggcgccatc tcggctcatt tgcaacctct gtctcccggg 360
ttcaagcgat tctcctgcct cagcttcccg aggagctggg attacaggtc ctgagggagt 420
ctaacaagtt agcagaaatg 440

<210> SEQ ID NO 1262
<211> LENGTH: 171
<212> TYPE: DNA
<213> ORGANISM: Homo sapiens

<400> SEQUENCE: 1262
cgccctctag ctgcgctcgg ctgagtcagt cagtctgtcg gagtctgtcc tcggagcagg 60
cggagtaaag ggacttgagc gagccagttg ccggattatt ctatttcccc tccctctctc 120
ccgccccgta tctcttttca cccttctccc accctcgctc gcgtagccat g 171

<210> SEQ ID NO 1263
<211> LENGTH: 347
<212> TYPE: DNA

<213> ORGANISM: Homo sapiens

<400> SEQUENCE: 1263
gtccctccct ctccgcacta gctgtctgcc ctgccctgcc gtaggagatg ggctgggagc 60
ctcccacgct ctccagctca ctcggcaggc agcggggacc agggctggca ggttaagcct 120
ctgggggtgg atcctgaaag gtggtccagc cgcctggccc tgcgtgggac cctccacctg 180
gcagcagaca gggtctcgct ctgtcacaca ggctggagtg cagtggtgtg atcttggctc 240
atcgtaacct ccacctcccg ggttcaagtg attctcatgc ctcagcctcc cgagtagctg 300
ggattacagg tggtgacttc caagagtgac tccgtcggag gaaaatg 347

<210> SEQ ID NO 1264
<211> LENGTH: 240
<212> TYPE: DNA
<213> ORGANISM: Homo sapiens

<400> SEQUENCE: 1264
gctcctccct gccgcctcct ctcagtggat ggttccaggc accctgtctg ggcagggag 60 ggcacaggcc tgcacatcga aggtggggtg ggaccaggct gcccctcgcc ccagcatcca 120
agtcctccct tgggcgcccg tggccctgca gactctcagg gctaaggtcc tctgttgctt 180
tttggttcca ccttagaaga ggctccgctt gactaagagt agcttgaagg aggcaccatg 240

<210> SEQ ID NO 1265
<211> LENGTH: 405
<212> TYPE: DNA
<213> ORGANISM: Homo sapiens

<400> SEQUENCE: 1265
atttcttttc cccattttaa atgcaaagca agacttgtga atcatagtgt ctctgctcct 60
gggattcaga ccaaatttcc ccccaaaatt ctcaggctat ttgtttgaat acctgcttac 120
agtggtacac aatgggcagc tttgagaaga aaaattgata atcttcacgg aagagtaatt 180
tgaatgaaat tacacttgac agcctgtctc caagcaaaca agaggaacga gggagcctga 240
gctaagctct gaggacttgc ccaagccact gctgttggag cttcccagga aaaaaaaaaa 300
aaaaaaaaaa aaaaaaaaaa aaaaaaaaac accagttttt ccaacatcta attgagcttt 360
tgattaattc cgtgtaccag attctactga agaaaggtag ccatg 405

<210> SEQ ID NO 1266
<211> LENGTH: 163
<212> TYPE: DNA
<213> ORGANISM: Homo sapiens

<400> SEQUENCE: 1266
ctccctcttt gtgcgtctcg cgccgccgcc gcccgccgcg tgagaggacg ggctccgcgc 60
gctccggcag cgcattcggg tcccctcccc ccgggaggct tgcgaaggag aagccgccgc 120
agaggaaaag caggtgccgg tgcctgtccc cgggggcgcc atg 163

<210> SEQ ID NO 1267
<211> LENGTH: 207
<212> TYPE: DNA
<213> ORGANISM: Homo sapiens

<400> SEQUENCE: 1267
ccgcccctcg cgacccagag ggctgctggc tggctaagtc cctcccgctc ccggctctcg 60
cctcactagg agcggctctc ggtgcagcgg gacagggcga agcggcctgc gcccacggag 120
cgcgcgacac tgcccggaag ggaccgccac ccttgccccc tcagctgccc actcgtgatt 180
tccagcggcc tccgcgcgcg cacgatg 207

<210> SEQ ID NO 1268
<211> LENGTH: 327
<212> TYPE: DNA
<213> ORGANISM: Homo sapiens

<400> SEQUENCE: 1268
ctgccctctt gcgtgccccg gccacccccg ggcggcttgt agccggtgcg cggggtggct 60
ggggctacgt gcagagctgt cgcggagccg gaacagcagc ggtgaagccc ctcggctcgg 120
ccgagaccgc cgtgcccatt gctcgcctcg gttgccgccg ctttagccgc agccgctgct 180
gccgccgccg ggggagaggc agcctattgt ctttctccgc ggcgaaggtg aggagctgtc 240
tcggctcggc ccgcggggga gccccgggag ccgcacggag atggaggagg acatctggac 300
agtgagcagg aggcgcctcg gcccatg 327

<210> SEQ ID NO 1269
<211> LENGTH: 183
<212> TYPE: DNA
<213> ORGANISM: Homo sapiens

<400> SEQUENCE: 1269
cgccctctcc ccgcctcctt ttcgggcgtc ccgaggccgc tccccaaccg acaaccaaga 60
ccccgcaggc cacgcagccc tggagccgag gccccccgac ggcggaggcg cccgcgggtc 120
ccctacagcc aaggtccctg agtgccagag gtggtggtgt tgcttatctt ctggaacccc 180
atg 183

<210> SEQ ID NO 1270
<211> LENGTH: 106
<212> TYPE: DNA
<213> ORGANISM: Homo sapiens

<400> SEQUENCE: 1270
ctccctctca accacaataa caggcggagg gtcggcgtag gtactttgaa ctcaagtaaa 60
caaaagggaa gattttctcg ttgatactgg agactgcaca acaatg 106

<210> SEQ ID NO 1271
<211> LENGTH: 74
<212> TYPE: DNA
<213> ORGANISM: Homo sapiens

<400> SEQUENCE: 1271
agatcttttc cagcagctgc tgcctgccag agaggcgcct tcagagaccc agcgcttaca 60
caatacccac catg 74

<210> SEQ ID NO 1272
<211> LENGTH: 62
<212> TYPE: DNA
<213> ORGANISM: Homo sapiens

<400> SEQUENCE: 1272
cctcctctcc ggcggcggcg gcggcggcgg cgggcggagt gagctgcgga gcctggaata 60
tg 62

<210> SEQ ID NO 1273

<211> LENGTH: 233
<212> TYPE: DNA
<213> ORGANISM: Homo sapiens

<400> SEQUENCE: 1273
gggcctctct tgtttattta tttattttcc gtgggtgcct ccgagtgtgc gcgcgctctc 60
gctacccggc ggggaggggg tggggggagg gcccgggaaa agggggagtt ggagccgggg 120
tcgaaacgcc gcgtgacttg taggtgagag aacgccgagc cgtcgccgca gcctccgccg 180
ccgagaagcc cttgttcccg ctgctgggaa ggagagtctg tgccgacaag atg 233

<210> SEQ ID NO 1274
<211> LENGTH: 76
<212> TYPE: DNA
<213> ORGANISM: Homo sapiens

<400> SEQUENCE: 1274
cagcctctac cccgctccgg atccgggatc tgagcgccgg ccgcggtgcc caggcactcc 60
cttggcgggc cggatg 76

<210> SEQ ID NO 1275
<211> LENGTH: 205
<212> TYPE: DNA
<213> ORGANISM: Homo sapiens

<400> SEQUENCE: 1275
cggccttctc ggcttctcca gcttcggtag gagaggatcc ggcgccgaat cactgactgg 60
cacaggtgtt gggatagtgt ctcacttggt cacccaggct ggagtgcagt ggcgcaatct 120
tagctctcta cagcgtcgat cttcctcctg ggctcaagca attctcctgc ttcatcctcc 180
tgagtaccta ggactacaga aaatg 205

<210> SEQ ID NO 1276
<211> LENGTH: 957
<212> TYPE: DNA
<213> ORGANISM: Homo sapiens

<400> SEQUENCE: 1276
cagtcttttc actgcagctg aatgagttgt ggcgcccaca atgctcccat gacaaggagc 60
tgacaagttc cattttccgt cgcgggcatc ttggaatcat gactcccaca atgccttggg 120
cacttggtcg acagtggggc cgcctctgaa aaaaaaatgt gagaggttgg tactaagaag 180
tgcctttcct gacgtctctg ctgcttggaa ccgcttctag agcagtctct gcttttgcct 240
tgcttgctgc cagctagact gtgacgacag cacatccacc ctccacctct agcccagaca 300
cccccatttc tacttataat caagagaaaa gctctaagta tctggcattg ccctaggctg 360
ctttagtgtt aaaagaaaag tttgctgaaa aagtaagata tcttctgcca ggaaatcaag 420
gaggaaaaaa aaaatcattt tctcgatttt gctctaaact gctgcatctg tctatgccaa 480
actaatcaat accgattgca ccaccaaact ccattgcaaa ttcagctgtg aggagattcc 540
ctttcagaca actttgctga aagcagcttg gaaattcggt gtcgaagggt ctgccacgtt 600
ttcatgcttg cattttgggc tccaaattgg cactgggaag gggttactga gagcacaagg 660
ctgataccag gccctacttt taaacgttca tctacttaca atcctagtat ttctctaaaa 720
accaaaacct ctttgaatta acagtttcat gctgtgaatt tctagtggga gatcttttcc 780
ttgatattga cgacacaatt ttccatgtac ttttaaagca gggagtgggg aaaagtattt 840
tgaggggaca ttttcatcat cagttcagct tttttttttt ggttgttgct cttttttggg 900
ggggttgggt ttgttggttt cactgaaaca tttaactacc tgtaaaatct aaacatg 957

<210> SEQ ID NO 1277
<211> LENGTH: 425
<212> TYPE: DNA
<213> ORGANISM: Homo sapiens

<400> SEQUENCE: 1277
cagccttttg ctctttcctt tcattaaaca aacaggagat cctgaaacct ggaccctgtg 60
caagctgcag cgccaggagg aggcagcgga ggaagcagag cgcgggatgg gcgcccagcg 120
gcatctgtga tcccgcgcac ctccgcccca cgggcgcgcg cacaaacacg gacacacaca 180
tacacacact cgcgcacaca ctcgcacaaa cacacactcg tacacgcccg cgccgctcgc 240
tcgccggctt gctctcccac gcaagcggaa tgcagcagcg cctggagagc gtgtctcgga 300
ccgccgcctg aatgtacctc gctcccggga gccggacggc ccagtagggc gcactggagg 360
acgctccgct gcgggagcct ggacagtttt tgacggtgca gtcttgctat atggtgtgag 420
aaatg 425

<210> SEQ ID NO 1278
<211> LENGTH: 803
<212> TYPE: DNA
<213> ORGANISM: Homo sapiens

<400> SEQUENCE: 1278
ctgtctttgc ttcatcatct gaaggtaaaa ttttccagat acggcagacg gctttcagag 60
tacaataaac agggaatgag aactatttac atggaagttt ctttctcatg atgcggtgga 120
gaagcctcgg ccacttggtt ctgccagatg ttcctggggt tactgtaaat gggaaggaca 180
ggcagagcta aacaaggttt atcatttaaa agtgcctgtg tgaagtcact tttgctggaa 240
aactgcagct tgggagcttt ctttgtattc acatcccact cttctgtcaa gtacacttta 300
ccctgacctt atgagtggat gaagatacct cagttgtctg actttgccaa ttgcttaatt 360
tcagaattta aaaaggggaa agaaaaacat cctgctaaaa tatgaacatc tgagtgtctt 420
attttccaac atcgtcaata gctgtgagcg tcagcattaa atattctccc aaggagtgcc 480
atgatattga agtcacttta ttaataacag ctgtatctgc aaaacagtca agagactcgg 540
acgttgaaag ccagagatga cactgagcat gcttttattg cggcctacca tctttaagtg 600
ggacatattg attgatgagt gattgcctgt ccatacactc tctcatcatc ctgttccttg 660
gattggactt cactaagcaa tttatcactc accttcagac ttacatgtgg gagttttcac 720
aacagtagtt ttggaatcat tagaacttgg attgatttca tcatttaaca gaaacaaaca 780
gcccaaatta ctttatcacc atg 803

<210> SEQ ID NO 1279
<211> LENGTH: 123
<212> TYPE: DNA
<213> ORGANISM: Homo sapiens

<400> SEQUENCE: 1279
gcgcctttcg cacgacttgg agttacggtt tatctgatac cgcggtaccc ctacgcaagc 60
aagcccacat cgacacacat tcacacacgc ccttcagcac cccctcccag caccacgacc 120
atg 123

<210> SEQ ID NO 1280

<211> LENGTH: 320
<212> TYPE: DNA
<213> ORGANISM: Homo sapiens

<400> SEQUENCE: 1280
cctcctcctt tccctgggtg cccacatgaa cagagacacc aggatgctct cctgagacca 60
cagcaactgc agaagctgaa gacatttcca gaagttcaag cttccaccct ctgcaggtcc 120
ccactgagct gggacccagg tcatccaccc caccccaaat ccctggatag gaaacccctt 180
tctcctcctg ctccttgtcc ccttcatccc tgccgcccag catcctactg gcctcagcac 240
ctgtggccag accgtccaag atcctctgaa ggcccagctc ttgctgtcca ccccggcagt 300
aggcaggcag cctggccatg 320

<210> SEQ ID NO 1281
<211> LENGTH: 240
<212> TYPE: DNA
<213> ORGANISM: Homo sapiens

<400> SEQUENCE: 1281
gcctccctcc cccgcagctg gggccagcgg tgccaagcgc agctggacga gcggcagcag 60
ctgggcgagt gacagccccg gctccgcgcg ccgcggccgc cagagccggc gcaggggaag 120
cgcccgcggc cccgggtgca gcagcggccg ccgcctcccg cgcctccccg gcccgcagcc 180
cgcggtcccg cggccccggg gccggcacct ctcgggctcc ggctccccgc gcgcaagatg 240

<210> SEQ ID NO 1282
<211> LENGTH: 45
<212> TYPE: DNA
<213> ORGANISM: Homo sapiens

<400> SEQUENCE: 1282
ccctccctcc gcgcggggac ccctggcggg cggcaggagg acatg 45

<210> SEQ ID NO 1283
<211> LENGTH: 242
<212> TYPE: DNA
<213> ORGANISM: Homo sapiens

<400> SEQUENCE: 1283
ccttctctgg ttccctgacc tcagtgagac agcagccggc ctggggacct gggggagaca 60
cggaggaccc cctggctgga gctgacccac agagtaggga atcatggctg gagaattgga 120
tagcagagta atgtttgacc tctggaaaca tcacttacag ggcttccggt caaaattcac 180
taggtaggag ggtcatcagc tgggaagaac cggcgcctgg gaaacctggc tggataggta 240
tg 242

<210> SEQ ID NO 1284
<211> LENGTH: 33
<212> TYPE: DNA
<213> ORGANISM: Homo sapiens

<400> SEQUENCE: 1284
cgttctttct ttgctgcgtc tactgcgaga atg 33

<210> SEQ ID NO 1285
<211> LENGTH: 33
<212> TYPE: DNA
<213> ORGANISM: Homo sapiens

<400> SEQUENCE: 1285
cggcctctac cggcgggatt tgatggcgtg atg 33

<210> SEQ ID NO 1286
<211> LENGTH: 64
<212> TYPE: DNA
<213> ORGANISM: Homo sapiens

<400> SEQUENCE: 1286
acttcctttt cctgtggcag cagccgggct gagaggagcg tggctgtctc ctctctccgc 60
catg 64

<210> SEQ ID NO 1287
<211> LENGTH: 82
<212> TYPE: DNA
<213> ORGANISM: Homo sapiens

<400> SEQUENCE: 1287
tggccctttt cccacccccct agcgccgctg ggcctgcagg tctctgtcga gcagcggacg 60
ccggtctctg ttccgcagga tg 82

<210> SEQ ID NO 1288
<211> LENGTH: 26
<212> TYPE: DNA
<213> ORGANISM: Homo sapiens

<400> SEQUENCE: 1288
aattctcttt cccatcttgc aagatg 26

<210> SEQ ID NO 1289
<211> LENGTH: 27
<212> TYPE: DNA
<213> ORGANISM: Homo sapiens

<400> SEQUENCE: 1289
cttcctcttt ttccggctgg aaccatg 27

<210> SEQ ID NO 1290
<211> LENGTH: 34
<212> TYPE: DNA
<213> ORGANISM: Homo sapiens

<400> SEQUENCE: 1290
ctttcctttc tctctcctcc cgccgcccaa gatg 34

<210> SEQ ID NO 1291
<211> LENGTH: 25
<212> TYPE: DNA
<213> ORGANISM: Homo sapiens

<400> SEQUENCE: 1291
ctttctcttc ctgctctcca tcatg 25

<210> SEQ ID NO 1292
<211> LENGTH: 95
<212> TYPE: DNA
<213> ORGANISM: Homo sapiens

<400> SEQUENCE: 1292
cggcctctcg gctttcggct cggaggaggc caaggtgcaa cttccttcgg tcgtcccgaa 60
tccgggttca tccgacacca gccgcctcca ccatg 95

<210> SEQ ID NO 1293
<211> LENGTH: 59
<212> TYPE: DNA
<213> ORGANISM: Homo sapiens

<400> SEQUENCE: 1293
gcttcctttc cgctcggctg ttttcctgcg caggagccgc agggccgtag gcagccatg    59

<210> SEQ ID NO 1294
<211> LENGTH: 34
<212> TYPE: DNA
<213> ORGANISM: Homo sapiens

<400> SEQUENCE: 1294
acttcctttt ttcttttttc cggcgttcaa gatg    34

<210> SEQ ID NO 1295
<211> LENGTH: 44
<212> TYPE: DNA
<213> ORGANISM: Homo sapiens

<400> SEQUENCE: 1295
cgttctctct ttccggacct ggccgagcag gaggcgccat catg    44

<210> SEQ ID NO 1296
<211> LENGTH: 43
<212> TYPE: DNA
<213> ORGANISM: Homo sapiens

<400> SEQUENCE: 1296
acttcctttt gcgggtggcg gcgaacgcgg agagcacgcc atg    43

<210> SEQ ID NO 1297
<211> LENGTH: 35
<212> TYPE: DNA
<213> ORGANISM: Homo sapiens

<400> SEQUENCE: 1297
agctctttcc tttcgctgct gcggccgcag ccatg    35

<210> SEQ ID NO 1298
<211> LENGTH: 51
<212> TYPE: DNA
<213> ORGANISM: Homo sapiens

<400> SEQUENCE: 1298
gcctctttcc tttcggccgg aaccgccatc ttccagtaat tcgccaaaat g    51

<210> SEQ ID NO 1299
<211> LENGTH: 30
<212> TYPE: DNA
<213> ORGANISM: Homo sapiens

<400> SEQUENCE: 1299
acctcccttt ctaactccgc tgccgccatg    30

<210> SEQ ID NO 1300
<211> LENGTH: 19
<212> TYPE: DNA
<213> ORGANISM: Homo sapiens

<400> SEQUENCE: 1300
agaccctttt cacaagatg    19

<210> SEQ ID NO 1301
<211> LENGTH: 295
<212> TYPE: DNA
<213> ORGANISM: Homo sapiens

<400> SEQUENCE: 1301
cgctcttcct ctttccctaa gcagcctgag ggttgactgg attggtgagg cccgtgtggc 60
tacttctgtg gaagcagtgc tgtagttact ggaagataaa agggaaagca agcccttggt 120
gggggaaagt atggctgcga tgatggcatt tcttaggaca cctttggatt aataatgaaa 180
acaactactc tctgagcagc tgttcgaatc atctgatatt tatactgaat gagttactgt 240
aagtacgtat tgacagaatt acactgtact ttcctctagg tgatctgtga aaatg 295

<210> SEQ ID NO 1302
<211> LENGTH: 51
<212> TYPE: DNA
<213> ORGANISM: Homo sapiens

<400> SEQUENCE: 1302
ttctctcttt cttttcgcca tcttttgtct ttccgtggag ctgtcgccat g 51

<210> SEQ ID NO 1303
<211> LENGTH: 49
<212> TYPE: DNA
<213> ORGANISM: Homo sapiens

<400> SEQUENCE: 1303
agttctcttc ccttttgcgg ccatcaccga agcgggagcg gccaaaatg 49

<210> SEQ ID NO 1304
<211> LENGTH: 43
<212> TYPE: DNA
<213> ORGANISM: Homo sapiens

<400> SEQUENCE: 1304
ctttcctttt tgctggtagg gccgggtggt tgctgccgaa atg 43

<210> SEQ ID NO 1305
<211> LENGTH: 81
<212> TYPE: DNA
<213> ORGANISM: Homo sapiens

<400> SEQUENCE: 1305
aagtctttcc tttctcgttc cccggccatc ttagcggctg ctgttggttg ggggccgtcc 60
cgctcctaag gcaggaagat g 81

<210> SEQ ID NO 1306
<211> LENGTH: 30
<212> TYPE: DNA
<213> ORGANISM: Homo sapiens

<400> SEQUENCE: 1306
ccttcctttt tcgtctgggc tgccaacatg 30

<210> SEQ ID NO 1307
<211> LENGTH: 49
<212> TYPE: DNA
<213> ORGANISM: Homo sapiens

<400> SEQUENCE: 1307

-continued cttcctcttt ccgtctcagg tcgccgctgc gaagggagcc gccgccatg 49

<210> SEQ ID NO 1308
<211> LENGTH: 60
<212> TYPE: DNA
<213> ORGANISM: Homo sapiens

<400> SEQUENCE: 1308
cagccccttt ctcttccggt tctaggcgct tcgggagccg cggcttatgg tgcagacatg 60

<210> SEQ ID NO 1309
<211> LENGTH: 34
<212> TYPE: DNA
<213> ORGANISM: Homo sapiens

<400> SEQUENCE: 1309
cgctcttcct ttccaacttg gacgctgcag aatg 34

<210> SEQ ID NO 1310
<211> LENGTH: 65
<212> TYPE: DNA
<213> ORGANISM: Homo sapiens

<400> SEQUENCE: 1310
ccgtcccttc tctcttcctc ggcgctgcct acggaggtgg cagccatctc cttctcggca 60
tcatg 65

<210> SEQ ID NO 1311
<211> LENGTH: 71
<212> TYPE: DNA
<213> ORGANISM: Homo sapiens

<400> SEQUENCE: 1311
cgtccttctc ttaccgccat cttggctcct gtggaggcct gctgggaacg ggacttctaa 60
aaggaactat g 71

<210> SEQ ID NO 1312
<211> LENGTH: 44
<212> TYPE: DNA
<213> ORGANISM: Homo sapiens

<400> SEQUENCE: 1312
ccttctcttc cggtctttct ggtctcggcc gcagaagcga gatg 44

<210> SEQ ID NO 1313
<211> LENGTH: 44
<212> TYPE: DNA
<213> ORGANISM: Homo sapiens

<400> SEQUENCE: 1313
gcgtctcttc ctttctgggc tcggacctag gtcgcggcga catg 44

<210> SEQ ID NO 1314
<211> LENGTH: 113
<212> TYPE: DNA
<213> ORGANISM: Homo sapiens

<400> SEQUENCE: 1314
cgttcttttt cgtccttttc cccggttgct gcttgctgtg agtgtctcta gggtgatacg 60
tgggtgagaa aggtcctggt ccgcgccaga gcccagcgcg cctcgtcgcc atg 113

<210> SEQ ID NO 1315
<211> LENGTH: 57
<212> TYPE: DNA
<213> ORGANISM: Homo sapiens

<400> SEQUENCE: 1315
ccctcctctt cctttctccg ccatcgtggt gtgttcttga ctccgctgct cgccatg 57

<210> SEQ ID NO 1316
<211> LENGTH: 84
<212> TYPE: DNA
<213> ORGANISM: Homo sapiens

<400> SEQUENCE: 1316
aggcccttct ctcgccaggc gtcctcgtgg aagtgacatc gtctttaaac cctgcgtggc 60
aatccctgac gcaccgccgt gatg 84

<210> SEQ ID NO 1317
<211> LENGTH: 105
<212> TYPE: DNA
<213> ORGANISM: Homo sapiens

<400> SEQUENCE: 1317
cggtccttcc gaggaagcta aggctgcgtt ggggtgaggc cctcacttca tccggcgact 60
agcaccgcgt ccggcagcgc cagccctaca ctcgcccgcg ccatg 105

<210> SEQ ID NO 1318
<211> LENGTH: 81
<212> TYPE: DNA
<213> ORGANISM: Homo sapiens

<400> SEQUENCE: 1318
ccttcctttt cctccctgtc gccaccgagg tcgcacgcgt gagacttctc cgccgcctcc 60
gccgcagacg ccgccgcgat g 81

<210> SEQ ID NO 1319
<211> LENGTH: 37
<212> TYPE: DNA
<213> ORGANISM: Homo sapiens

<400> SEQUENCE: 1319
acttcctttc ctttcagcgg agcgcggcgg caagatg 37

<210> SEQ ID NO 1320
<211> LENGTH: 31
<212> TYPE: DNA
<213> ORGANISM: Homo sapiens

<400> SEQUENCE: 1320
ccgccctttt ggctctctga ccagcaccat g 31

<210> SEQ ID NO 1321
<211> LENGTH: 30
<212> TYPE: DNA
<213> ORGANISM: Homo sapiens

<400> SEQUENCE: 1321
ggtcctcttt ccttgcctaa cgcagccatg 30

<210> SEQ ID NO 1322
<211> LENGTH: 30
<212> TYPE: DNA

-continued

<213> ORGANISM: Homo sapiens

<400> SEQUENCE: 1322
gattctcttc cgtcgcagag tttcgccatg 30

<210> SEQ ID NO 1323
<211> LENGTH: 115
<212> TYPE: DNA
<213> ORGANISM: Homo sapiens

<400> SEQUENCE: 1323
ttttcttccc agttaaaagt gttggcccgc ggcgcgcggc ctcttcctgt ctgtaccagg 60
gcggcgcgtg gtctacgccg agtgacagag acgctcaggc tgtgttctca ggatg 115

<210> SEQ ID NO 1324
<211> LENGTH: 48
<212> TYPE: DNA
<213> ORGANISM: Homo sapiens

<400> SEQUENCE: 1324
ggccctcttt tccgtggcgc ctcggaggcg ttcagctgct tcaagatg 48

<210> SEQ ID NO 1325
<211> LENGTH: 51
<212> TYPE: DNA
<213> ORGANISM: Homo sapiens

<400> SEQUENCE: 1325
gggtctcttc ctaagccggc gctcggcaag ttctcccagg agaaagccat g 51

<210> SEQ ID NO 1326
<211> LENGTH: 30
<212> TYPE: DNA
<213> ORGANISM: Homo sapiens

<400> SEQUENCE: 1326
gtttctcttt ccagccagcg ccgagcgatg 30

<210> SEQ ID NO 1327
<211> LENGTH: 63
<212> TYPE: DNA
<213> ORGANISM: Homo sapiens

<400> SEQUENCE: 1327
gcgcctcttt ctcagtgacc gggtggtttg cttaggcgca gacggggaag cggagccaac 60
atg 63

<210> SEQ ID NO 1328
<211> LENGTH: 48
<212> TYPE: DNA
<213> ORGANISM: Homo sapiens

<400> SEQUENCE: 1328
gctccttcct ttccagcccc ggtaccggac cctgcagccg cagagatg 48

<210> SEQ ID NO 1329
<211> LENGTH: 36
<212> TYPE: DNA
<213> ORGANISM: Homo sapiens

<400> SEQUENCE: 1329
ctgccccttt cttttttca ggcggccggg aagatg 36

<210> SEQ ID NO 1330
<211> LENGTH: 89
<212> TYPE: DNA
<213> ORGANISM: Homo sapiens

<400> SEQUENCE: 1330
aggcctcttt ccctgccgcc gccgagtcgc gcggaggcgg aggcttgggt gcgttcaaga 60
ttcaacttca cccgtaaccc accgccatg 89

<210> SEQ ID NO 1331
<211> LENGTH: 35
<212> TYPE: DNA
<213> ORGANISM: Homo sapiens

<400> SEQUENCE: 1331
cgctctcctt tcgttgcctg atcgccgcca tcatg 35

<210> SEQ ID NO 1332
<211> LENGTH: 28
<212> TYPE: DNA
<213> ORGANISM: Homo sapiens

<400> SEQUENCE: 1332
cgatctcttc tgaggatccg gcaagatg 28

<210> SEQ ID NO 1333
<211> LENGTH: 103
<212> TYPE: DNA
<213> ORGANISM: Homo sapiens

<400> SEQUENCE: 1333
cgtcctcttt ccgccatctt tccgcgccgg tgagtagcac tctctgagag ctccaatttc 60
atccgtctgc catcggcgcc atcctgcaat ctaagccaca atg 103

<210> SEQ ID NO 1334
<211> LENGTH: 61
<212> TYPE: DNA
<213> ORGANISM: Homo sapiens

<400> SEQUENCE: 1334
ctttcctttt ccggttgcgg cgccgcgcgg tgaggttgtc tagtccacgc tcggagccat 60
g 61

<210> SEQ ID NO 1335
<211> LENGTH: 42
<212> TYPE: DNA
<213> ORGANISM: Homo sapiens

<400> SEQUENCE: 1335
cgttcccttt cccctggctg gcagcgcgga ggccgcacga tg 42

<210> SEQ ID NO 1336
<211> LENGTH: 136
<212> TYPE: DNA
<213> ORGANISM: Homo sapiens

<400> SEQUENCE: 1336 ccacccettt ctttttgagg aagacgcggt cgtaagggct gaggattttt ggtccgcacg 60
ctcctgctcc tgactcaccg ctgttcgctc tcgccgagga acaagtcggt caggaagccc 120
gcgcgcaaca gccatg 136

<210> SEQ ID NO 1337
<211> LENGTH: 59
<212> TYPE: DNA
<213> ORGANISM: Homo sapiens

<400> SEQUENCE: 1337
gcttcctttc tctctcgcgc gcggtgtggt ggcagcaggc gcagcccagc ctcgaaatg 59

<210> SEQ ID NO 1338
<211> LENGTH: 40
<212> TYPE: DNA
<213> ORGANISM: Homo sapiens

<400> SEQUENCE: 1338
gcttctctct ttcgctcagg cccgtggcgc cgacaggatg 40

<210> SEQ ID NO 1339
<211> LENGTH: 67
<212> TYPE: DNA
<213> ORGANISM: Homo sapiens

<400> SEQUENCE: 1339
gcttcctttt tgtccgacat cttgacgagg ctgcggtgtc tgctgctatt ctccgagctt 60
cgcaatg 67

<210> SEQ ID NO 1340
<211> LENGTH: 34
<212> TYPE: DNA
<213> ORGANISM: Homo sapiens

<400> SEQUENCE: 1340
ccgtctcctc tctccggtcc gtgcctccaa gatg 34

<210> SEQ ID NO 1341
<211> LENGTH: 42
<212> TYPE: DNA
<213> ORGANISM: Homo sapiens

<400> SEQUENCE: 1341
cgctcctttc cggcggtgac gacctacgca cacgagaaca tg 42

<210> SEQ ID NO 1342
<211> LENGTH: 38
<212> TYPE: DNA
<213> ORGANISM: Homo sapiens

<400> SEQUENCE: 1342
actcctctcc gccagaccgc cgccgcgccg ccatcatg 38

<210> SEQ ID NO 1343
<211> LENGTH: 41
<212> TYPE: DNA
<213> ORGANISM: Homo sapiens

<400> SEQUENCE: 1343
gcttcttcct tttacctcgt tgcactgctg agagcaagat g 41

<210> SEQ ID NO 1344
<211> LENGTH: 30
<212> TYPE: DNA
<213> ORGANISM: Homo sapiens

<400> SEQUENCE: 1344
cgttcttctt ttccgacaaa acaccaaatg 30

<210> SEQ ID NO 1345
<211> LENGTH: 30
<212> TYPE: DNA
<213> ORGANISM: Homo sapiens

<400> SEQUENCE: 1345
cgttcttctt ttccgacaaa acaccaaatg 30

<210> SEQ ID NO 1346
<211> LENGTH: 36
<212> TYPE: DNA
<213> ORGANISM: Homo sapiens

<400> SEQUENCE: 1346
gggtcttctt ccttctcgcc taacgccgcc aacatg 36

<210> SEQ ID NO 1347
<211> LENGTH: 42
<212> TYPE: DNA
<213> ORGANISM: Homo sapiens

<400> SEQUENCE: 1347
ctctctttcc ggtgtggagt ctggagacga cgtgcagaaa tg 42

<210> SEQ ID NO 1348
<211> LENGTH: 48
<212> TYPE: DNA
<213> ORGANISM: Homo sapiens

<400> SEQUENCE: 1348
gcgcctcttt cccttcggtg tgccactgaa gatcctggtg tcgccatg 48

<210> SEQ ID NO 1349
<211> LENGTH: 38
<212> TYPE: DNA
<213> ORGANISM: Homo sapiens

<400> SEQUENCE: 1349
tagtctcttt tccggttagc gcggcgtgag aagccatg 38

<210> SEQ ID NO 1350
<211> LENGTH: 50
<212> TYPE: DNA
<213> ORGANISM: Homo sapiens

<400> SEQUENCE: 1350
tcctctttcc ctcggagcgg gcggcggcgt tggcggcttg tgcagcaatg 50

<210> SEQ ID NO 1351
<211> LENGTH: 32
<212> TYPE: DNA
<213> ORGANISM: Homo sapiens

<400> SEQUENCE: 1351
cctcctcctt ttccaagcgg ctgccgaaga tg 32

<210> SEQ ID NO 1352
<211> LENGTH: 42
<212> TYPE: DNA

<213> ORGANISM: Homo sapiens

<400> SEQUENCE: 1352
cagcccttcc gccacggccg tctctggaga gcagcagcca tg 42

<210> SEQ ID NO 1353
<211> LENGTH: 40
<212> TYPE: DNA
<213> ORGANISM: Homo sapiens

<400> SEQUENCE: 1353
gtttctttct ttccgcgccg atagcgctca cgcaagcatg 40

<210> SEQ ID NO 1354
<211> LENGTH: 51
<212> TYPE: DNA
<213> ORGANISM: Homo sapiens

<400> SEQUENCE: 1354
tcgcctttct ctcggcctta gcgccatttt tttggaaacc tctgcgccat g 51

<210> SEQ ID NO 1355
<211> LENGTH: 52
<212> TYPE: DNA
<213> ORGANISM: Homo sapiens

<400> SEQUENCE: 1355
cgctctctct tccacaggag gcctacacgc cgccgcttgt gctgcagcca tg 52

<210> SEQ ID NO 1356
<211> LENGTH: 46
<212> TYPE: DNA
<213> ORGANISM: Homo sapiens

<400> SEQUENCE: 1356
ggttctcttt tcctccttgg ctgtctgaag atagatcgcc atcatg 46

<210> SEQ ID NO 1357
<211> LENGTH: 58
<212> TYPE: DNA
<213> ORGANISM: Homo sapiens

<400> SEQUENCE: 1357
tttcctcttt cggccgcgct ggtgaacagg taggtcatcc ttgcggcctt gcggcatg 58

<210> SEQ ID NO 1358
<211> LENGTH: 33
<212> TYPE: DNA
<213> ORGANISM: Homo sapiens

<400> SEQUENCE: 1358
cttcctcttc cggggacgtt gtctgcaggt atg 33

<210> SEQ ID NO 1359
<211> LENGTH: 32
<212> TYPE: DNA
<213> ORGANISM: Homo sapiens

<400> SEQUENCE: 1359
gtttcctctt ttaccaagga cccgccaaca tg 32

<210> SEQ ID NO 1360
<211> LENGTH: 85

<212> TYPE: DNA
<213> ORGANISM: Homo sapiens

<400> SEQUENCE: 1360
ctgtcttttc cgtgctacct gcagaggggt ccatacggcg ttgttctgga ttcccgtcgt 60
aacttaaagg gaaattttca caatg 85

<210> SEQ ID NO 1361
<211> LENGTH: 91
<212> TYPE: DNA
<213> ORGANISM: Homo sapiens

<400> SEQUENCE: 1361
cttctctctc ggcgtttccg ctgtcagggc cctgcggtgt gactcgcggg ctcagctggt 60
ccggccgtag cacctccgcg ccgtcgccat g 91

<210> SEQ ID NO 1362
<211> LENGTH: 62
<212> TYPE: DNA
<213> ORGANISM: Homo sapiens

<400> SEQUENCE: 1362
cgctctcctc ctctcacgga aaggtcgcgg cctgtggccc tgcgggcagc cgtgccgaga 60
tg 62

<210> SEQ ID NO 1363
<211> LENGTH: 241
<212> TYPE: DNA
<213> ORGANISM: Homo sapiens

<400> SEQUENCE: 1363
cactcccttc caaaagcatg acaggcagaa agcagagaag ggccaggact ggctgagggc 60
ggggagctgg gcctctgggg tggacacacc cttggtcaca ttgtgagggt agcttggttg 120
gccagtccca ccactgcagt gaccacagtt gtgttgggct cacaccagtg aaccgaagct 180
ctggattctg agagtctgag gattccgtga agatctcaga cttgggctca gagcaaggat 240
g 241

<210> SEQ ID NO 1364
<211> LENGTH: 1810
<212> TYPE: DNA
<213> ORGANISM: Artificial Sequence
<220> FEATURE:
<223> OTHER INFORMATION: PpLuc(GC) A64N64

<400> SEQUENCE: 1364
gggagaaagc ttgaggatgg aggacgccaa gaacatcaag aagggcccgg cgcccttcta 60
cccgctggag gacgggaccg ccggcgagca gctccacaag gccatgaagc ggtacgccct 120
ggtgccgggc acgatcgcct tcaccgacgc ccacatcgag gtcgacatca cctacgcgga 180
gtacttcgag atgagcgtgc gcctggccga ggccatgaag cggtacggcc tgaacaccaa 240
ccaccggatc gtggtgtgct cggagaacag cctgcagttc ttcatgccgg tgctgggcgc 300
cctcttcatc ggcgtggccg tcgccccggc gaacgacatc tacaacgagc gggagctgct 360
gaacagcatg gggatcagcc agccgaccgt ggtgttcgtg agcaagaagg gcctgcagaa 420
gatcctgaac gtgcagaaga agctgcccat catccagaag atcatcatca tggacagcaa 480
gaccgactac cagggcttcc agtcgatgta cacgttcgtg accagccacc tcccgccggg 540
cttcaacgag tacgacttcg tcccggagag cttcgaccgg gacaagacca tcgccctgat 600
catgaacagc agcggcagca ccggcctgcc gaagggggtg gccctgccgc accggaccgc 660
ctgcgtgcgc ttctcgcacg cccgggaccc catcttcggc aaccagatca tcccggacac 720
cgccatcctg agcgtggtgc cgttccacca cggcttcggc atgttcacga ccctgggcta 780
cctcatctgc ggcttccggg tggtcctgat gtaccggttc gaggaggagc tgttcctgcg 840
gagcctgcag gactacaaga tccagagcgc gctgctcgtg ccgaccctgt tcagcttctt 900
cgccaagagc accctgatcg acaagtacga cctgtcgaac ctgcacgaga tcgccagcgg 960
gggcgccccg ctgagcaagg aggtgggcga ggccgtggcc aagcggttcc acctcccggg 1020
catccgccag ggctacggcc tgaccgagac cacgagcgcg atcctgatca cccccgaggg 1080
ggacgacaag ccgggcgccg tgggcaaggt ggtcccgttc ttcgaggcca aggtggtgga 1140
cctggacacc ggcaagaccc tgggcgtgaa ccagcggggc gagctgtgcg tgcgggggcc 1200
gatgatcatg agcggctacg tgaacaaccc ggaggccacc aacgccctca tcgacaagga 1260
cggctggctg cacagcggcg acatcgccta ctgggacgag gacgagcact tcttcatcgt 1320
cgaccggctg aagtcgctga tcaagtacaa gggctaccag gtggcgccgg ccgagctgga 1380
gagcatcctg ctccagcacc ccaacatctt cgacgccggc gtggccgggc tgccggacga 1440
cgacgccggc gagctgccgg ccgcggtggt ggtgctggag cacggcaaga ccatgacgga 1500
gaaggagatc gtcgactacg tggccagcca ggtgaccacc gccaagaagc tgcggggcgg 1560
cgtggtgttc gtggacgagg tcccgaaggg cctgaccggg aagctcgacg cccggaagat 1620
ccgcgagatc ctgatcaagg ccaagaaggg cggcaagatc gccgtgtaag actagtagat 1680
ctaaaaaaaa aaaaaaaaaa aaaaaaaaaa aaaaaaaaaa aaaaaaaaaa aaaaaaaaaa 1740
aaaaaatgca tccccccccc cccccccccc cccccccccc ccaaaggctc ttttcagagc 1800
caccagaatt 1810

<210> SEQ ID NO 1365
<211> LENGTH: 1997
<212> TYPE: DNA
<213> ORGANISM: Artificial Sequence
<220> FEATURE:
<223> OTHER INFORMATION: PpLuc(GC) albumin7 - A64N64

<400> SEQUENCE: 1365
gggagaaagc ttgaggatgg aggacgccaa gaacatcaag aagggcccgg cgcccttcta 60
cccgctggag gacgggaccg ccggcgagca gctccacaag gccatgaagc ggtacgccct 120
ggtgccgggc acgatcgcct tcaccgacgc ccacatcgag gtcgacatca cctacgcgga 180
gtacttcgag atgagcgtgc gcctggccga ggccatgaag cggtacggcc tgaacaccaa 240
ccaccggatc gtggtgtgct cggagaacag cctgcagttc ttcatgccgg tgctgggcgc 300
cctcttcatc ggcgtggccg tcgccccggc gaacgacatc tacaacgagc gggagctgct 360
gaacagcatg gggatcagcc agccgaccgt ggtgttcgtg agcaagaagg gcctgcagaa 420
gatcctgaac gtgcagaaga agctgcccat catccagaag atcatcatca tggacagcaa 480
gaccgactac cagggcttcc agtcgatgta cacgttcgtg accagccacc tcccgccggg 540
cttcaacgag tacgacttcg tcccggagag cttcgaccgg gacaagacca tcgccctgat 600
catgaacagc agcggcagca ccggcctgcc gaagggggtg gccctgccgc accggaccgc 660
ctgcgtgcgc ttctcgcacg cccgggaccc catcttcggc aaccagatca tcccggacac 720
cgccatcctg agcgtggtgc cgttccacca cggcttcggc atgttcacga ccctgggcta 780

```
cctcatctgc ggcttccggg tggtcctgat gtaccggttc gaggaggagc tgttcctgcg    840
gagcctgcag gactacaaga tccagagcgc gctgctcgtg ccgaccctgt tcagcttctt    900
cgccaagagc accctgatcg acaagtacga cctgtcgaac ctgcacgaga tcgccagcgg    960
gggcgccccg ctgagcaagg aggtgggcga ggccgtggcc aagcggttcc acctcccggg   1020
catccgccag ggctacggcc tgaccgagac cacgagcgcg atcctgatca cccccgaggg   1080
ggacgacaag ccgggcgccg tgggcaaggt ggtcccgttc ttcgaggcca aggtggtgga   1140
cctggacacc ggcaagaccc tgggcgtgaa ccagcggggc gagctgtgcg tgcgggggcc   1200
gatgatcatg agcggctacg tgaacaaccc ggaggccacc aacgccctca tcgacaagga   1260
cggctggctg cacagcggcg acatcgccta ctgggacgag gacgagcact tcttcatcgt   1320
cgaccggctg aagtcgctga tcaagtacaa gggctaccag gtggcgccgg ccgagctgga   1380
gagcatcctg ctccagcacc ccaacatctt cgacgccggc gtggccgggc tgccggacga   1440
cgacgccggc gagctgccgg ccgcggtggt ggtgctggag cacggcaaga ccatgacgga   1500
gaaggagatc gtcgactacg tggccagcca ggtgaccacc gccaagaagc tgcggggcgg   1560
cgtggtgttc gtggacgagg tcccgaaggg cctgaccggg aagctcgacg cccggaagat   1620
ccgcgagatc ctgatcaagg ccaagaaggg cggcaagatc gccgtgtaag actagtgcat   1680
cacatttaaa agcatctcag cctaccatga gaataagaga aagaaaatga agatcaatag   1740
cttattcatc tctttttctt tttcgttggt gtaaagccaa caccctgtct aaaaaacata   1800
aatttcttta atcattttgc ctcttttctc tgtgcttcaa ttaataaaaa atggaaagaa   1860
cctagatcta aaaaaaaaaa aaaaaaaaaa aaaaaaaaaa aaaaaaaaaa aaaaaaaaaa   1920
aaaaaaaaaa aaatgcatcc cccccccccc cccccccccc cccccccccca aaggctcttt   1980
tcagagccac cagaatt                                                  1997
```

<210> SEQ ID NO 1366
<211> LENGTH: 1848
<212> TYPE: DNA
<213> ORGANISM: Artificial Sequence
<220> FEATURE:
<223> OTHER INFORMATION: 32L PpLuc(GC) A64N64

<400> SEQUENCE: 1366

```
ggggcgctgc ctacggaggt ggcagccatc tccttctcgg catcaagctt gaggatggag     60
gacgccaaga acatcaagaa gggcccggcg cccttctacc cgctggagga cgggaccgcc    120
ggcgagcagc tccacaaggc catgaagcgg tacgccctgg tgccgggcac gatcgccttc    180
accgacgccc acatcgaggt cgacatcacc tacgcggagt acttcgagat gagcgtgcgc    240
ctggccgagg ccatgaagcg gtacggcctg aacaccaacc accggatcgt ggtgtgctcg    300
gagaacagcc tgcagttctt catgccggtg ctgggcgccc tcttcatcgg cgtggccgtc    360
gccccggcga acgacatcta caacgagcgg gagctgctga acagcatggg gatcagccag    420
ccgaccgtgg tgttcgtgag caagaagggc ctgcagaaga tcctgaacgt gcagaagaag    480
ctgcccatca tccagaagat catcatcatg gacagcaaga ccgactacca gggcttccag    540
tcgatgtaca cgttcgtgac cagccacctc ccgccgggct tcaacgagta cgacttcgtc    600
ccggagagct tcgaccggga caagaccatc gccctgatca tgaacagcag cggcagcacc    660
ggcctgccga agggggtggc cctgccgcac cggaccgcct gcgtgcgctt ctcgcacgcc    720
cgggacccca tcttcggcaa ccagatcatc ccggacaccg ccatcctgag cgtggtgccg    780
```

-continued

```
ttccaccacg gcttcggcat gttcacgacc ctgggctacc tcatctgcgg cttccgggtg    840

gtcctgatgt accggttcga ggaggagctg ttcctgcgga gcctgcagga ctacaagatc    900

cagagcgcgc tgctcgtgcc gaccctgttc agcttcttcg ccaagagcac cctgatcgac    960

aagtacgacc tgtcgaacct gcacgagatc gccagcgggg gcgccccgct gagcaaggag   1020

gtgggcgagg ccgtggccaa gcggttccac ctcccgggca tccgccaggg ctacggcctg   1080

accgagacca cgagcgcgat cctgatcacc cccgaggggg acgacaagcc gggcgccgtg   1140

ggcaaggtgg tcccgttctt cgaggccaag gtggtggacc tggacaccgg caagaccctg   1200

ggcgtgaacc agcggggcga gctgtgcgtg cgggggccga tgatcatgag cggctacgtg   1260

aacaacccgg aggccaccaa cgccctcatc gacaaggacg gctggctgca cagcggcgac   1320

atcgcctact gggacgagga cgagcacttc ttcatcgtcg accggctgaa gtcgctgatc   1380

aagtacaagg gctaccaggt ggcgccggcc gagctggaga gcatcctgct ccagcacccc   1440

aacatcttcg acgccggcgt ggccgggctg ccggacgacg acgccggcga gctgccggcc   1500

gcggtggtgg tgctggagca cggcaagacc atgacggaga aggagatcgt cgactacgtg   1560

gccagccagg tgaccaccgc caagaagctg cggggcggcg tggtgttcgt ggacgaggtc   1620

ccgaagggcc tgaccgggaa gctcgacgcc cggaagatcc gcgagatcct gatcaaggcc   1680

aagaagggcg gcaagatcgc cgtgtaagac tagtagatct aaaaaaaaaa aaaaaaaaaa   1740

aaaaaaaaaa aaaaaaaaaa aaaaaaaaaa aaaaaaaaaa aaaatgcatc cccccccccc   1800

cccccccccc cccccccccc aaaggctctt ttcagagcca ccagaatt                1848
```

<210> SEQ ID NO 1367
<211> LENGTH: 2035
<212> TYPE: DNA
<213> ORGANISM: Artificial Sequence
<220> FEATURE:
<223> OTHER INFORMATION: 32L PpLuc(GC) albumin 7 A64N64

<400> SEQUENCE: 1367

```
ggggcgctgc ctacggaggt ggcagccatc tccttctcgg catcaagctt gaggatggag     60

gacgccaaga acatcaagaa gggcccggcg cccttctacc cgctggagga cgggaccgcc    120

ggcgagcagc tccacaaggc catgaagcgg tacgccctgg tgccgggcac gatcgccttc    180

accgacgccc acatcgaggt cgacatcacc tacgcggagt acttcgagat gagcgtgcgc    240

ctggccgagg ccatgaagcg gtacggcctg aacaccaacc accggatcgt ggtgtgctcg    300

gagaacagcc tgcagttctt catgccggtg ctgggcgccc tcttcatcgg cgtggccgtc    360

gccccggcga acgacatcta caacgagcgg gagctgctga acagcatggg gatcagccag    420

ccgaccgtgg tgttcgtgag caagaagggc ctgcagaaga tcctgaacgt gcagaagaag    480

ctgcccatca tccagaagat catcatcatg gacagcaaga ccgactacca gggcttccag    540

tcgatgtaca cgttcgtgac cagccacctc ccgccgggct tcaacgagta cgacttcgtc    600

ccggagagct tcgaccggga caagaccatc gccctgatca tgaacagcag cggcagcacc    660

ggcctgccga agggggtggc cctgccgcac cggaccgcct gcgtgcgctt ctcgcacgcc    720

cgggacccca tcttcggcaa ccagatcatc ccggacaccg ccatcctgag cgtggtgccg    780

ttccaccacg gcttcggcat gttcacgacc ctgggctacc tcatctgcgg cttccgggtg    840

gtcctgatgt accggttcga ggaggagctg ttcctgcgga gcctgcagga ctacaagatc    900

cagagcgcgc tgctcgtgcc gaccctgttc agcttcttcg ccaagagcac cctgatcgac    960

aagtacgacc tgtcgaacct gcacgagatc gccagcgggg gcgccccgct gagcaaggag   1020
```

gtgggcgagg ccgtggccaa gcggttccac ctcccgggca tccgccaggg ctacggcctg 1080
accgagacca cgagcgcgat cctgatcacc cccgaggggg acgacaagcc gggcgccgtg 1140
ggcaaggtgg tcccgttctt cgaggccaag gtggtggacc tggacaccgg caagaccctg 1200
ggcgtgaacc agcggggcga gctgtgcgtg cgggggccga tgatcatgag cggctacgtg 1260
aacaacccgg aggccaccaa cgccctcatc gacaaggacg gctggctgca cagcggcgac 1320
atcgcctact gggacgagga cgagcacttc ttcatcgtcg accggctgaa gtcgctgatc 1380
aagtacaagg gctaccaggt ggcgccggcc gagctggaga gcatcctgct ccagcacccc 1440
aacatcttcg acgccggcgt ggccgggctg ccggacgacg acgccggcga gctgccggcc 1500
gcggtggtgg tgctggagca cggcaagacc atgacggaga aggagatcgt cgactacgtg 1560
gccagccagg tgaccaccgc caagaagctg cggggcggcg tggtgttcgt ggacgaggtc 1620
ccgaagggcc tgaccgggaa gctcgacgcc cggaagatcc gcgagatcct gatcaaggcc 1680
aagaagggcg gcaagatcgc cgtgtaagac tagtgcatca catttaaaag catctcagcc 1740
taccatgaga ataagagaaa gaaaatgaag atcaatagct tattcatctc tttttctttt 1800
tcgttggtgt aaagccaaca ccctgtctaa aaaacataaa tttctttaat cattttgcct 1860
cttttctctg tgcttcaatt aataaaaaat ggaaagaacc tagatctaaa aaaaaaaaaa 1920
aaaaaaaaaa aaaaaaaaaa aaaaaaaaaa aaaaaaaaaa aaaaaaaaaa atgcatcccc 1980
cccccccccc cccccccccc cccccccaaa ggctcttttc agagccacca gaatt 2035

<210> SEQ ID NO 1368
<211> LENGTH: 42
<212> TYPE: DNA
<213> ORGANISM: Artificial Sequence
<220> FEATURE:
<223> OTHER INFORMATION: 5-UTR of human ribosomal protein Large 32
lacking the 5 terminal oligopyrimidine tract

<400> SEQUENCE: 1368
ggcgctgcct acggaggtgg cagccatctc cttctcggca tc 42

<210> SEQ ID NO 1369
<211> LENGTH: 186
<212> TYPE: DNA
<213> ORGANISM: Homo sapiens

<400> SEQUENCE: 1369
catcacattt aaaagcatct cagcctacca tgagaataag agaaagaaaa tgaagatcaa 60
aagcttattc atctgttttt ctttttcgtt ggtgtaaagc caacaccctg tctaaaaaac 120
ataaatttct ttaatcattt tgcctctttt ctctgtgctt caattaataa aaaatggaaa 180
gaatct 186

<210> SEQ ID NO 1370
<211> LENGTH: 110
<212> TYPE: DNA
<213> ORGANISM: Homo sapiens

<400> SEQUENCE: 1370
gctggagcct cggtggccat gcttcttgcc ccttgggcct ccccccagcc cctcctcccc 60
ttcctgcacc cgtacccccg tggtctttga ataaagtctg agtgggcggc 110

<210> SEQ ID NO 1371
<211> LENGTH: 108

<212> TYPE: DNA
<213> ORGANISM: Homo sapiens

<400> SEQUENCE: 1371
gctggagcct cggtagccgt tcctcctgcc cgctgggcct cccaacgggc cctcctcccc 60
tccttgcacc ggcccttcct ggtctttgaa taaagtctga gtgggcag 108

<210> SEQ ID NO 1372
<211> LENGTH: 132
<212> TYPE: DNA
<213> ORGANISM: Homo sapiens

<400> SEQUENCE: 1372
gctcgctttc ttgctgtcca atttctatta aaggttcctt tgttccctaa gtccaactac 60
taaactgggg gatattatga agggccttga gcatctggat tctgcctaat aaaaaacatt 120
tattttcatt gc 132

<210> SEQ ID NO 1373
<211> LENGTH: 304
<212> TYPE: DNA
<213> ORGANISM: Homo sapiens

<400> SEQUENCE: 1373
gtgcacggcg tccctgaggg cccttcccaa cctcccctgg tcctgcactg tcccggagct 60
caggccctgg tgaggggctg ggtcccgggt gccccccatg ccctccctgc tgccaggctc 120
ccactgcccc tgcacctgct tctcagcgca acagctgtgt gtgcccgtgg tgaggttgtg 180
ctgcctgtgg tgaggtcctg tcctggctcc cagggtcctg ggggctgctg cactgccctc 240
cgcccttccc tgacactgtc tgctgcccca atcaccgtca caataaaaga aactgtggtc 300
tcta 304

<210> SEQ ID NO 1374
<211> LENGTH: 674
<212> TYPE: DNA
<213> ORGANISM: Homo sapiens

<400> SEQUENCE: 1374
gcgtcgccac cctttggtta tttcagcccc catcacccaa gccacaagct gaccccttcg 60
tggttatagc cctgccctcc caagtcccac cctcttccca tgtcccaccc tccctagagg 120
ggcacctttt catggtctct gcacccagtg aacacatttt actctagagg catcacctgg 180
gaccttactc ctctttcctt ccttcctcct ttcctatctt ccttcctctc tctcttcctc 240
tttcttcatt cagatctata tggcaaatag ccacaattat ataaatcatt tcaagactag 300
aataggggga tataatacat attactccac accttttatg aatcaaatat gatttttttg 360
ttgttgttaa gacagagtct cactttgaca cccaggctgg agtgcagtgg tgccatcacc 420
acggctcact gcagcctcag cgtcctgggc tcaaatgatc ctcccacctc agcctcctga 480
gtagctggga ctacaggctc atgccatcat gcccagctaa tattttttta ttttcgtgga 540
gacggggcct cactatgttg cctaggctgg aaataggatt ttgaacccaa attgagttta 600
acaataataa aaagttgttt tacgctaaag atggaaaaga actaggactg aactatttta 660
aataaaatat tggc 674

<210> SEQ ID NO 1375
<211> LENGTH: 1406
<212> TYPE: DNA

<213> ORGANISM: Homo sapiens

<400> SEQUENCE: 1375
actccctcca tcccaacctg gctccctccc acccaaccaa ctttcccccc aacccggaaa 60
cagacaagca acccaaactg aaccccctca aaagccaaaa aatgggagac aatttcacat 120
ggactttgga aaatattttt ttcctttgca ttcatctctc aaacttagtt tttatctttg 180
accaaccgaa catgaccaaa aaccaaaagt gcattcaacc ttaccaaaaa aaaaaaaaaa 240
aaaagaataa ataaataact ttttaaaaaa ggaagcttgg tccacttgct tgaagaccca 300
tgcgggggta agtccctttc tgcccgttgg gcttatgaaa ccccaatgct gccctttctg 360
ctcctttctc cacacccccc ttggggcctc ccctccactc cttcccaaat ctgtctcccc 420
agaagacaca ggaaacaatg tattgtctgc ccagcaatca aaggcaatgc tcaaacaccc 480
aagtggcccc caccctcagc ccgctcctgc ccgcccagca cccccaggcc ctgggggacc 540
tggggttctc agactgccaa agaagccttg ccatctggcg ctcccatggc tcttgcaaca 600
tctccccttc gtttttgagg gggtcatgcc gggggagcca ccagcccctc actgggttcg 660
gaggagagtc aggaagggcc acgacaaagc agaaacatcg gatttgggga acgcgtgtca 720
atcccttgtg ccgcagggct gggcgggaga gactgttctg ttccttgtgt aactgtgttg 780
ctgaaagact acctcgttct tgtcttgatg tgtcaccggg gcaactgcct gggggcgggg 840
atgggggcag ggtggaagcg gctccccatt ttataccaaa ggtgctacat ctatgtgatg 900
ggtggggtgg ggagggaatc actggtgcta tagaaattga gatgcccccc caggccagca 960
aatgttcctt tttgttcaaa gtctattttt attccttgat atttttcttt tttttttttt 1020 tttttgtgg atggggactt gtgaattttt ctaaaggtgc tatttaacat gggaggagag 1080
cgtgtgcggc tccagcccag cccgctgctc actttccacc ctctctccac ctgcctctgg 1140
cttctcaggc ctctgctctc cgacctctct cctctgaaac cctcctccac agctgcagcc 1200
catcctcccg gctccctcct agtctgtcct gcgtcctctg tccccgggtt tcagagacaa 1260
cttcccaaag cacaaagcag tttttccccc taggggtggg aggaagcaaa agactctgta 1320
cctattttgt atgtgtataa taatttgaga tgtttttaat tattttgatt gctggaataa 1380
agcatgtgga aatgacccaa acataa 1406

<210> SEQ ID NO 1376
<211> LENGTH: 186
<212> TYPE: DNA
<213> ORGANISM: Homo sapiens

<400> SEQUENCE: 1376
catcacattt aaaagcatct cagcctacca tgagaataag agaaagaaaa tgaagatcaa 60
tagcttattc atctcttttt ctttttcgtt ggtgtaaagc caacaccctg tctaaaaaac 120
ataaatttct ttaatcattt tgcctctttt ctctgtgctt caattaataa aaaatggaaa 180
gaacct 186

<210> SEQ ID NO 1377
<211> LENGTH: 256
<212> TYPE: DNA
<213> ORGANISM: Artificial Sequence
<220> FEATURE:
<223> OTHER INFORMATION: Human albumin 3'UTR + poly(A)

<400> SEQUENCE: 1377
catcacattt aaaagcatct cagcctacca tgagaataag agaaagaaaa tgaagatcaa 60
aagcttattc atctgttttt ctttttcgtt ggtgtaaagc caacaccctg tctaaaaaac 120
ataaatttct ttaatcattt tgcctctttt ctctgtgctt caattaataa aaaatggaaa 180
gaatctagat ctaaaaaaaa aaaaaaaaaa aaaaaaaaaa aaaaaaaaaa aaaaaaaaaa 240
aaaaaaaaaa aaaaaa 256

<210> SEQ ID NO 1378
<211> LENGTH: 155
<212> TYPE: DNA
<213> ORGANISM: Homo sapiens

<400> SEQUENCE: 1378
aaaagcatct cagcctacca tgagaataag agaaagaaaa tgaagatcaa aagcttattc 60
atctgttttt ctttttcgtt ggtgtaaagc caacaccctg tctaaaaaac ataaatttct 120
ttaatcattt tgcctctttt ctctgtgctt caatt 155

<210> SEQ ID NO 1379
<211> LENGTH: 110
<212> TYPE: DNA
<213> ORGANISM: Homo sapiens

<400> SEQUENCE: 1379
catcacattt aaaagcatct cagcctacca tgagaataag agaaagaaaa tgaagatcaa 60
aagcttattc atctgttttt ctttttcgtt ggtgtaaagc caacaccctg 110

<210> SEQ ID NO 1380
<211> LENGTH: 110
<212> TYPE: DNA
<213> ORGANISM: Homo sapiens

<400> SEQUENCE: 1380
aaaagcatct cagcctacca tgagaataag agaaagaaaa tgaagatcaa aagcttattc 60
atctgttttt ctttttcgtt ggtgtaaagc caacaccctg tctaaaaaac 110

<210> SEQ ID NO 1381
<211> LENGTH: 110
<212> TYPE: DNA
<213> ORGANISM: Homo sapiens

<400> SEQUENCE: 1381
cagcctacca tgagaataag agaaagaaaa tgaagatcaa aagcttattc atctgttttt 60
ctttttcgtt ggtgtaaagc caacaccctg tctaaaaaac ataaatttct 110

<210> SEQ ID NO 1382
<211> LENGTH: 110
<212> TYPE: DNA
<213> ORGANISM: Homo sapiens

<400> SEQUENCE: 1382
tgagaataag agaaagaaaa tgaagatcaa aagcttattc atctgttttt ctttttcgtt 60
ggtgtaaagc caacaccctg tctaaaaaac ataaatttct ttaatcattt 110

<210> SEQ ID NO 1383
<211> LENGTH: 110
<212> TYPE: DNA
<213> ORGANISM: Homo sapiens

<400> SEQUENCE: 1383
agaaagaaaa tgaagatcaa aagcttattc atctgttttt ctttttcgtt ggtgtaaagc 60
caacaccctg tctaaaaaac ataaatttct ttaatcattt tgcctctttt 110

<210> SEQ ID NO 1384
<211> LENGTH: 110
<212> TYPE: DNA
<213> ORGANISM: Homo sapiens

<400> SEQUENCE: 1384
tgaagatcaa aagcttattc atctgttttt ctttttcgtt ggtgtaaagc caacaccctg 60
tctaaaaaac ataaatttct ttaatcattt tgcctctttt ctctgtgctt 110

<210> SEQ ID NO 1385
<211> LENGTH: 110
<212> TYPE: DNA
<213> ORGANISM: Homo sapiens

<400> SEQUENCE: 1385
aagcttattc atctgttttt ctttttcgtt ggtgtaaagc caacaccctg tctaaaaaac 60
ataaatttct ttaatcattt tgcctctttt ctctgtgctt caattaataa 110

<210> SEQ ID NO 1386
<211> LENGTH: 110
<212> TYPE: DNA
<213> ORGANISM: Homo sapiens

<400> SEQUENCE: 1386
atctgttttt ctttttcgtt ggtgtaaagc caacaccctg tctaaaaaac ataaatttct 60
ttaatcattt tgcctctttt ctctgtgctt caattaataa aaaatggaaa 110

<210> SEQ ID NO 1387
<211> LENGTH: 151
<212> TYPE: DNA
<213> ORGANISM: Homo sapiens

<400> SEQUENCE: 1387
cagcctacca tgagaataag agaaagaaaa tgaagatcaa aagcttattc atctgttttt 60
ctttttcgtt ggtgtaaagc caacaccctg tctaaaaaac ataaatttct ttaatcattt 120
tgcctctttt ctctgtgctt caattaataa a 151

<210> SEQ ID NO 1388
<211> LENGTH: 121
<212> TYPE: DNA
<213> ORGANISM: Homo sapiens

<400> SEQUENCE: 1388
tgaagatcaa aagcttattc atctgttttt ctttttcgtt ggtgtaaagc caacaccctg 60
tctaaaaaac ataaatttct ttaatcattt tgcctctttt ctctgtgctt caattaataa 120
a 121

<210> SEQ ID NO 1389
<211> LENGTH: 91
<212> TYPE: DNA
<213> ORGANISM: Homo sapiens

<400> SEQUENCE: 1389
ctttttcgtt ggtgtaaagc caacaccctg tctaaaaaac ataaatttct ttaatcattt 60
tgcctctttt ctctgtgctt caattaataa a 91

<210> SEQ ID NO 1390
<211> LENGTH: 60
<212> TYPE: DNA
<213> ORGANISM: Homo sapiens

<400> SEQUENCE: 1390
aagcttattc atctgttttt ctttttcgtt ggtgtaaagc caacaccctg tctaaaaaac 60

<210> SEQ ID NO 1391
<211> LENGTH: 320
<212> TYPE: DNA
<213> ORGANISM: Artificial Sequence
<220> FEATURE:
<223> OTHER INFORMATION: Albumin7 3'UTR poly(A) poly(C) HL

<400> SEQUENCE: 1391
catcacattt aaaagcatct cagcctacca tgagaataag agaaagaaaa tgaagatcaa 60
tagcttattc atctcttttt ctttttcgtt ggtgtaaagc caacaccctg tctaaaaaac 120
ataaatttct ttaatcattt tgcctctttt ctctgtgctt caattaataa aaaatggaaa 180
gaacctagat ctaaaaaaaa aaaaaaaaaa aaaaaaaaaa aaaaaaaaaa aaaaaaaaaa 240
aaaaaaaaaa aaaaaatgca tccccccccc cccccccccc cccccccccc ccaaaggctc 300
ttttcagagc caccagaatt 320

<210> SEQ ID NO 1392
<211> LENGTH: 292
<212> TYPE: DNA
<213> ORGANISM: Artificial Sequence
<220> FEATURE:
<223> OTHER INFORMATION: Albumin7 3'UTR poly(A) poly(C)

<400> SEQUENCE: 1392
catcacattt aaaagcatct cagcctacca tgagaataag agaaagaaaa tgaagatcaa 60
tagcttattc atctcttttt ctttttcgtt ggtgtaaagc caacaccctg tctaaaaaac 120
ataaatttct ttaatcattt tgcctctttt ctctgtgctt caattaataa aaaatggaaa 180
gaacctagat ctaaaaaaaa aaaaaaaaaa aaaaaaaaaa aaaaaaaaaa aaaaaaaaaa 240
aaaaaaaaaa aaaaaatgca tccccccccc cccccccccc cccccccccc cc 292

<210> SEQ ID NO 1393
<211> LENGTH: 44
<212> TYPE: DNA
<213> ORGANISM: Artificial Sequence
<220> FEATURE:
<223> OTHER INFORMATION: Center, alpha-complex-binding portion of the
3UTR of an alpha-globin gene

<400> SEQUENCE: 1393
gcccgatggg cctcccaacg ggccctcctc ccctccttgc accg 44

<210> SEQ ID NO 1394
<211> LENGTH: 24
<212> TYPE: DNA
<213> ORGANISM: Artificial Sequence
<220> FEATURE:
<223> OTHER INFORMATION: Histone stem-loop

<400> SEQUENCE: 1394
caaaggctct tttcagagcc acca 24

<210> SEQ ID NO 1395
<211> LENGTH: 75
<212> TYPE: DNA
<213> ORGANISM: Artificial Sequence
<220> FEATURE:
<223> OTHER INFORMATION: ATP synthase lipid-binding protein,
      mitochondrial (atp5g2)

<400> SEQUENCE: 1395
tagtttctcc tctcgaacgc caggtggagc aaccggccgg ataccgccac agccctggca 60
ggcggcgctg tgatg 75

<210> SEQ ID NO 1396
<211> LENGTH: 2027
<212> TYPE: DNA
<213> ORGANISM: Artificial Sequence
<220> FEATURE:
<223> OTHER INFORMATION: RPL35  PpLuc(GC) albumin7 A64N64

<400> SEQUENCE: 1396
ggggagcggg cggcggcgtt ggcggcttgt gcagcaaagc ttgaggatgg aggacgccaa 60
gaacatcaag aagggcccgg cgcccttcta cccgctggag gacgggaccg ccggcgagca 120
gctccacaag gccatgaagc ggtacgccct ggtgccgggc acgatcgcct tcaccgacgc 180
ccacatcgag gtcgacatca cctacgcgga gtacttcgag atgagcgtgc gcctggccga 240
ggccatgaag cggtacggcc tgaacaccaa ccaccggatc gtggtgtgct cggagaacag 300
cctgcagttc ttcatgccgg tgctgggcgc cctcttcatc ggcgtggccg tcgccccggc 360
gaacgacatc tacaacgagc gggagctgct gaacagcatg gggatcagcc agccgaccgt 420
ggtgttcgtg agcaagaagg gcctgcagaa gatcctgaac gtgcagaaga agctgcccat 480
catccagaag atcatcatca tggacagcaa gaccgactac cagggcttcc agtcgatgta 540
cacgttcgtg accagccacc tcccgccggg cttcaacgag tacgacttcg tcccggagag 600
cttcgaccgg gacaagacca tcgccctgat catgaacagc agcggcagca ccggcctgcc 660
gaagggggtg gccctgccgc accggaccgc ctgcgtgcgc ttctcgcacg cccgggaccc 720
catcttcggc aaccagatca tcccggacac cgccatcctg agcgtggtgc cgttccacca 780
cggcttcggc atgttcacga ccctgggcta cctcatctgc ggcttccggg tggtcctgat 840
gtaccggttc gaggaggagc tgttcctgcg gagcctgcag gactacaaga tccagagcgc 900
gctgctcgtg ccgaccctgt tcagcttctt cgccaagagc accctgatcg acaagtacga 960
cctgtcgaac ctgcacgaga tcgccagcgg gggcgccccg ctgagcaagg aggtgggcga 1020
ggccgtggcc aagcggttcc acctcccggg catccgccag ggctacggcc tgaccgagac 1080
cacgagcgcg atcctgatca cccccgaggg ggacgacaag ccgggcgccg tgggcaaggt 1140
ggtcccgttc ttcgaggcca aggtggtgga cctggacacc ggcaagaccc tgggcgtgaa 1200
ccagcggggc gagctgtgcg tgcgggggcc gatgatcatg agcggctacg tgaacaaccc 1260
ggaggccacc aacgccctca tcgacaagga cggctggctg cacagcggcg acatcgccta 1320
ctgggacgag gacgagcact tcttcatcgt cgaccggctg aagtcgctga tcaagtacaa 1380
gggctaccag gtggcgccgg ccgagctgga gagcatcctg ctccagcacc ccaacatctt 1440
cgacgccggc gtggccgggc tgccggacga cgacgccggc gagctgccgg ccgcggtggt 1500
ggtgctggag cacggcaaga ccatgacgga gaaggagatc gtcgactacg tggccagcca 1560
ggtgaccacc gccaagaagc tgcggggcgg cgtggtgttc gtggacgagg tcccgaaggg 1620
cctgaccggg aagctcgacg cccggaagat ccgcgagatc ctgatcaagg ccaagaaggg 1680

```
cggcaagatc gccgtgtaag actagtgcat cacatttaaa agcatctcag cctaccatga   1740

gaataagaga aagaaaatga agatcaatag cttattcatc tctttttctt tttcgttggt   1800

gtaaagccaa caccctgtct aaaaaacata aatttcttta atcattttgc ctcttttctc   1860

tgtgcttcaa ttaataaaaa atggaaagaa cctagatcta aaaaaaaaaa aaaaaaaaaa   1920

aaaaaaaaaa aaaaaaaaaa aaaaaaaaaa aaaaaaaaaa aaatgcatcc cccccccccc   1980

cccccccccc cccccccccca aaggctcttt tcagagccac cagaatt               2027
```

```
<210> SEQ ID NO 1397
<211> LENGTH: 2027
<212> TYPE: DNA
<213> ORGANISM: Artificial Sequence
<220> FEATURE:
<223> OTHER INFORMATION: RPL21 PpLuc(GC) albumin7 A64N64

<400> SEQUENCE: 1397

ggggccggaa ccgccatctt ccagtaattc gccaaaaagc ttgaggatgg aggacgccaa     60

gaacatcaag aagggcccgg cgcccttcta cccgctggag gacgggaccg ccggcgagca    120

gctccacaag gccatgaagc ggtacgccct ggtgccgggc acgatcgcct tcaccgacgc    180

ccacatcgag gtcgacatca cctacgcgga gtacttcgag atgagcgtgc gcctggccga    240

ggccatgaag cggtacggcc tgaacaccaa ccaccggatc gtggtgtgct cggagaacag    300

cctgcagttc ttcatgccgg tgctgggcgc cctcttcatc ggcgtggccg tcgccccggc    360

gaacgacatc tacaacgagc gggagctgct gaacagcatg gggatcagcc agccgaccgt    420

ggtgttcgtg agcaagaagg gcctgcagaa gatcctgaac gtgcagaaga agctgcccat    480

catccagaag atcatcatca tggacagcaa gaccgactac cagggcttcc agtcgatgta    540

cacgttcgtg accagccacc tcccgccggg cttcaacgag tacgacttcg tcccggagag    600

cttcgaccgg gacaagacca tcgccctgat catgaacagc agcggcagca ccggcctgcc    660

gaagggggtg gccctgccgc accggaccgc ctgcgtgcgc ttctcgcacg cccgggaccc    720

catcttcggc aaccagatca tcccggacac cgccatcctg agcgtggtgc cgttccacca    780

cggcttcggc atgttcacga ccctgggcta cctcatctgc ggcttccggg tggtcctgat    840

gtaccggttc gaggaggagc tgttcctgcg gagcctgcag gactacaaga tccagagcgc    900

gctgctcgtg ccgaccctgt tcagcttctt cgccaagagc accctgatcg acaagtacga    960

cctgtcgaac ctgcacgaga tcgccagcgg gggcgccccg ctgagcaagg aggtgggcga   1020

ggccgtggcc aagcggttcc acctcccggg catccgccag ggctacggcc tgaccgagac   1080

cacgagcgcg atcctgatca cccccgaggg ggacgacaag ccgggcgccg tgggcaaggt   1140

ggtcccgttc ttcgaggcca aggtggtgga cctggacacc ggcaagaccc tgggcgtgaa   1200

ccagcggggc gagctgtgcg tgcgggggcc gatgatcatg agcggctacg tgaacaaccc   1260

ggaggccacc aacgccctca tcgacaagga cggctggctg cacagcggcg acatcgccta   1320

ctgggacgag gacgagcact tcttcatcgt cgaccggctg aagtcgctga tcaagtacaa   1380

gggctaccag gtggcgccgg ccgagctgga gagcatcctg ctccagcacc ccaacatctt   1440

cgacgccggc gtggccgggc tgccggacga cgacgccggc gagctgccgg ccgcggtggt   1500

ggtgctggag cacggcaaga ccatgacgga gaaggagatc gtcgactacg tggccagcca   1560

ggtgaccacc gccaagaagc tgcggggcgg cgtggtgttc gtggacgagg tcccgaaggg   1620

cctgaccggg aagctcgacg cccggaagat ccgcgagatc ctgatcaagg ccaagaaggg   1680
```

cggcaagatc gccgtgtaag actagtgcat cacatttaaa agcatctcag cctaccatga 1740
gaataagaga aagaaaatga agatcaatag cttattcatc tctttttctt tttcgttggt 1800
gtaaagccaa caccctgtct aaaaaacata aatttcttta atcattttgc ctcttttctc 1860
tgtgcttcaa ttaataaaaa atggaaagaa cctagatcta aaaaaaaaaa aaaaaaaaaa 1920
aaaaaaaaaa aaaaaaaaaa aaaaaaaaaa aaaaaaaaaa aaatgcatcc cccccccccc 1980
cccccccccc cccccccccca aaggctcttt tcagagccac cagaatt 2027

<210> SEQ ID NO 1398
<211> LENGTH: 2068
<212> TYPE: DNA
<213> ORGANISM: Artificial Sequence
<220> FEATURE:
<223> OTHER INFORMATION: ATP5A1 PpLuc(GC) albumin7 A64N64

<400> SEQUENCE: 1398
gggcggctcg gccattttgt cccagtcagt ccggaggctg cggctgcaga agtaccgcct 60
gcggagtaac tgcaaagaag cttgaggatg gaggacgcca agaacatcaa gaagggcccg 120
gcgcccttct acccgctgga ggacgggacc gccggcgagc agctccacaa ggccatgaag 180
cggtacgccc tggtgccggg cacgatcgcc ttcaccgacg cccacatcga ggtcgacatc 240
acctacgcgg agtacttcga gatgagcgtg cgcctggccg aggccatgaa gcggtacggc 300
ctgaacacca accaccggat cgtggtgtgc tcggagaaca gcctgcagtt cttcatgccg 360
gtgctgggcg ccctcttcat cggcgtggcc gtcgccccgg cgaacgacat ctacaacgag 420
cgggagctgc tgaacagcat ggggatcagc cagccgaccg tggtgttcgt gagcaagaag 480
ggcctgcaga agatcctgaa cgtgcagaag aagctgccca tcatccagaa gatcatcatc 540
atggacagca agaccgacta ccagggcttc cagtcgatgt acacgttcgt gaccagccac 600
ctcccgccgg gcttcaacga gtacgacttc gtcccggaga gcttcgaccg ggacaagacc 660
atcgccctga tcatgaacag cagcggcagc accggcctgc cgaagggggt ggccctgccg 720
caccggaccg cctgcgtgcg cttctcgcac gcccgggacc ccatcttcgg caaccagatc 780
atcccggaca ccgccatcct gagcgtggtg ccgttccacc acggcttcgg catgttcacg 840
accctgggct acctcatctg cggcttccgg gtggtcctga tgtaccggtt cgaggaggag 900
ctgttcctgc ggagcctgca ggactacaag atccagagcg cgctgctcgt gccgaccctg 960
ttcagcttct tcgccaagag caccctgatc gacaagtacg acctgtcgaa cctgcacgag 1020
atcgccagcg gggggcgccc gctgagcaag gaggtgggcg aggccgtggc caagcggttc 1080
cacctcccgg gcatccgcca gggctacggc ctgaccgaga ccacgagcgc gatcctgatc 1140
acccccgagg gggacgacaa gccgggcgcc gtgggcaagg tggtcccgtt cttcgaggcc 1200
aaggtggtgg acctggacac cggcaagacc ctgggcgtga accagcgggg cgagctgtgc 1260
gtgcgggggc cgatgatcat gagcggctac gtgaacaacc cggaggccac caacgccctc 1320
atcgacaagg acggctggct gcacagcggc gacatcgcct actgggacga ggacgagcac 1380
ttcttcatcg tcgaccggct gaagtcgctg atcaagtaca agggctacca ggtggcgccg 1440
gccgagctgg agagcatcct gctccagcac cccaacatct tcgacgccgg cgtggccggg 1500
ctgccggacg acgacgccgg cgagctgccg gccgcggtgg tggtgctgga gcacggcaag 1560
accatgacgg agaaggagat cgtcgactac gtggccagcc aggtgaccac cgccaagaag 1620
ctgcggggcg gcgtggtgtt cgtggacgag gtcccgaagg gcctgaccgg gaagctcgac 1680
gcccggaaga tccgcgagat cctgatcaag gccaagaagg gcggcaagat cgccgtgtaa 1740

-continued

```
gactagtgca tcacatttaa aagcatctca gcctaccatg agaataagag aaagaaaatg   1800

aagatcaata gcttattcat ctctttttct ttttcgttgg tgtaaagcca acaccctgtc   1860

taaaaaacat aaatttcttt aatcattttg cctcttttct ctgtgcttca attaataaaa   1920

aatggaaaga acctagatct aaaaaaaaaa aaaaaaaaaa aaaaaaaaaa aaaaaaaaaa   1980

aaaaaaaaaa aaaaaaaaaa aaaatgcatc cccccccccc cccccccccc cccccccccc   2040

aaaggctctt ttcagagcca ccagaatt                                      2068
```

<210> SEQ ID NO 1399
<211> LENGTH: 2055
<212> TYPE: DNA
<213> ORGANISM: Artificial Sequence
<220> FEATURE:
<223> OTHER INFORMATION: HSD17B4 PpLuc(GC) albumin7 A64N64

<400> SEQUENCE: 1399

```
gggtcccgca gtcggcgtcc agcggctctg cttgttcgtg tgtgtgtcgt tgcaggcctt     60

attcaagctt gaggatggag gacgccaaga acatcaagaa gggcccggcg cccttctacc    120

cgctggagga cgggaccgcc ggcgagcagc tccacaaggc catgaagcgg tacgccctgg    180

tgccgggcac gatcgccttc accgacgccc acatcgaggt cgacatcacc tacgcggagt    240

acttcgagat gagcgtgcgc ctggccgagg ccatgaagcg gtacggcctg aacaccaacc    300

accggatcgt ggtgtgctcg gagaacagcc tgcagttctt catgccggtg ctgggcgccc    360

tcttcatcgg cgtggccgtc gccccggcga acgacatcta caacgagcgg gagctgctga    420

acagcatggg gatcagccag ccgaccgtgg tgttcgtgag caagaagggc ctgcagaaga    480

tcctgaacgt gcagaagaag ctgcccatca tccagaagat catcatcatg gacagcaaga    540

ccgactacca gggcttccag tcgatgtaca cgttcgtgac cagccacctc ccgccgggct    600

tcaacgagta cgacttcgtc ccggagagct tcgaccggga caagaccatc gccctgatca    660

tgaacagcag cggcagcacc ggcctgccga agggggtggc cctgccgcac cggaccgcct    720

gcgtgcgctt ctcgcacgcc cgggacccca tcttcggcaa ccagatcatc ccggacaccg    780

ccatcctgag cgtggtgccg ttccaccacg gcttcggcat gttcacgacc ctgggctacc    840

tcatctgcgg cttccgggtg gtcctgatgt accggttcga ggaggagctg ttcctgcgga    900

gcctgcagga ctacaagatc cagagcgcgc tgctcgtgcc gaccctgttc agcttcttcg    960

ccaagagcac cctgatcgac aagtacgacc tgtcgaacct gcacgagatc gccagcgggg   1020

gcgccccgct gagcaaggag gtgggcgagg ccgtggccaa gcggttccac ctcccgggca   1080

tccgccaggg ctacggcctg accgagacca cgagcgcgat cctgatcacc cccgaggggg   1140

acgacaagcc gggcgccgtg ggcaaggtgg tcccgttctt cgaggccaag gtggtggacc   1200

tggacaccgg caagaccctg ggcgtgaacc agcggggcga gctgtgcgtg cgggggccga   1260

tgatcatgag cggctacgtg aacaacccgg aggccaccaa cgccctcatc gacaaggacg   1320

gctggctgca cagcggcgac atcgcctact gggacgagga cgagcacttc ttcatcgtcg   1380

accggctgaa gtcgctgatc aagtacaagg gctaccaggt ggcgccggcc gagctggaga   1440

gcatcctgct ccagcacccc aacatcttcg acgccggcgt ggccgggctg ccggacgacg   1500

acgccggcga gctgccggcc gcggtggtgg tgctggagca cggcaagacc atgacggaga   1560

aggagatcgt cgactacgtg gccagccagg tgaccaccgc caagaagctg cggggcggcg   1620

tggtgttcgt ggacgaggtc ccgaagggcc tgaccgggaa gctcgacgcc cggaagatcc   1680
```

```
gcgagatcct gatcaaggcc aagaagggcg gcaagatcgc cgtgtaagac tagtgcatca   1740
catttaaaag catctcagcc taccatgaga ataagagaaa gaaaatgaag atcaatagct   1800
tattcatctc tttttctttt tcgttggtgt aaagccaaca ccctgtctaa aaaacataaa   1860
tttctttaat cattttgcct cttttctctg tgcttcaatt aataaaaaat ggaaagaacc   1920
tagatctaaa aaaaaaaaaa aaaaaaaaaa aaaaaaaaaa aaaaaaaaaa aaaaaaaaaa   1980
aaaaaaaaaa atgcatcccc cccccccccc cccccccccc cccccccaaa ggctcttttc   2040
agagccacca gaatt                                                    2055
```

```
<210> SEQ ID NO 1400
<211> LENGTH: 2024
<212> TYPE: DNA
<213> ORGANISM: Artificial Sequence
<220> FEATURE:
<223> OTHER INFORMATION: AIG1 PpLuc(GC) albumin7 A64N64

<400> SEQUENCE: 1400
```

```
gggccgccca gccggtccag gcctctggcg aacaagcttg aggatggagg acgccaagaa     60
catcaagaag ggcccggcgc ccttctaccc gctggaggac gggaccgccg gcgagcagct    120
ccacaaggcc atgaagcggt acgccctggt gccgggcacg atcgccttca ccgacgccca    180
catcgaggtc gacatcacct acgcggagta cttcgagatg agcgtgcgcc tggccgaggc    240
catgaagcgg tacggcctga acaccaacca ccggatcgtg gtgtgctcgg agaacagcct    300
gcagttcttc atgccggtgc tgggcgccct cttcatcggc gtggccgtcg ccccggcgaa    360
cgacatctac aacgagcggg agctgctgaa cagcatgggg atcagccagc cgaccgtggt    420
gttcgtgagc aagaagggcc tgcagaagat cctgaacgtg cagaagaagc tgcccatcat    480
ccagaagatc atcatcatgg acagcaagac cgactaccag ggcttccagt cgatgtacac    540
gttcgtgacc agccacctcc cgccgggctt caacgagtac gacttcgtcc cggagagctt    600
cgaccgggac aagaccatcg ccctgatcat gaacagcagc ggcagcaccg gcctgccgaa    660
gggggtggcc ctgccgcacc ggaccgcctg cgtgcgcttc tcgcacgccc gggaccccat    720
cttcggcaac cagatcatcc cggacaccgc catcctgagc gtggtgccgt tccaccacgg    780
cttcggcatg ttcacgaccc tgggctacct catctgcggc ttccgggtgg tcctgatgta    840
ccggttcgag gaggagctgt tcctgcggag cctgcaggac tacaagatcc agagcgcgct    900
gctcgtgccg accctgttca gcttcttcgc caagagcacc ctgatcgaca agtacgacct    960
gtcgaacctg cacgagatcg ccagcggggg cgccccgctg agcaaggagg tgggcgaggc   1020
cgtggccaag cggttccacc tcccgggcat ccgccagggc tacggcctga ccgagaccac   1080
gagcgcgatc ctgatcaccc ccgaggggga cgacaagccg ggcgccgtgg gcaaggtggt   1140
cccgttcttc gaggccaagg tggtggacct ggacaccggc aagaccctgg gcgtgaacca   1200
gcggggcgag ctgtgcgtgc gggggccgat gatcatgagc ggctacgtga acaacccgga   1260
ggccaccaac gccctcatcg acaaggacgg ctggctgcac agcggcgaca tcgcctactg   1320
ggacgaggac gagcacttct tcatcgtcga ccggctgaag tcgctgatca agtacaaggg   1380
ctaccaggtg gcgccggccg agctggagag catcctgctc cagcacccca acatcttcga   1440
cgccggcgtg gccgggctgc cggacgacga cgccggcgag ctgccggccg cggtggtggt   1500
gctggagcac ggcaagacca tgacggagaa ggagatcgtc gactacgtgg ccagccaggt   1560
gaccaccgcc aagaagctgc ggggcggcgt ggtgttcgtg gacgaggtcc cgaagggcct   1620
gaccgggaag ctcgacgccc ggaagatccg cgagatcctg atcaaggcca agaagggcgg   1680
```

caagatcgcc gtgtaagact agtgcatcac atttaaaagc atctcagcct accatgagaa 1740
taagagaaag aaaatgaaga tcaatagctt attcatctct tttcttttt cgttggtgta 1800 aagccaacac cctgtctaaa aaacataaat ttctttaatc attttgcctc ttttctctgt 1860
gcttcaatta ataaaaaatg gaaagaacct agatctaaaa aaaaaaaaaa aaaaaaaaaa 1920
aaaaaaaaaa aaaaaaaaaa aaaaaaaaaa aaaaaaaaaa tgcatccccc cccccccccc 1980
cccccccccc ccccccaaag gctcttttca gagccaccag aatt 2024

<210> SEQ ID NO 1401
<211> LENGTH: 2049
<212> TYPE: DNA
<213> ORGANISM: Artificial Sequence
<220> FEATURE:
<223> OTHER INFORMATION: COX6C PpLuc(GC) albumin7 A64N64

<400> SEQUENCE: 1401
ggagtcagga aggacgttgg tgttgaggtt agcatacgta tcaaggacag taactaccaa 60
gcttgaggat ggaggacgcc aagaacatca agaagggccc ggcgcccttc tacccgctgg 120
aggacgggac cgccggcgag cagctccaca aggccatgaa gcggtacgcc ctggtgccgg 180
gcacgatcgc cttcaccgac gcccacatcg aggtcgacat cacctacgcg gagtacttcg 240
agatgagcgt gcgcctggcc gaggccatga agcggtacgg cctgaacacc aaccaccgga 300
tcgtggtgtg ctcggagaac agcctgcagt tcttcatgcc ggtgctgggc gccctcttca 360
tcggcgtggc cgtcgccccg gcgaacgaca tctacaacga gcgggagctg ctgaacagca 420
tggggatcag ccagccgacc gtggtgttcg tgagcaagaa gggcctgcag aagatcctga 480
acgtgcagaa gaagctgccc atcatccaga agatcatcat catggacagc aagaccgact 540
accagggctt ccagtcgatg tacacgttcg tgaccagcca cctcccgccg ggcttcaacg 600
agtacgactt cgtcccggag agcttcgacc gggacaagac catcgccctg atcatgaaca 660
gcagcggcag caccggcctg ccgaaggggg tggccctgcc gcaccggacc gcctgcgtgc 720
gcttctcgca cgcccgggac cccatcttcg gcaaccagat catcccggac accgccatcc 780
tgagcgtggt gccgttccac cacggcttcg gcatgttcac gaccctgggc tacctcatct 840
gcggcttccg ggtggtcctg atgtaccggt tcgaggagga gctgttcctg cggagcctgc 900
aggactacaa gatccagagc gcgctgctcg tgccgaccct gttcagcttc ttcgccaaga 960
gcaccctgat cgacaagtac gacctgtcga acctgcacga gatcgccagc gggggcgccc 1020
cgctgagcaa ggaggtgggc gaggccgtgg ccaagcggtt ccacctcccg ggcatccgcc 1080
agggctacgg cctgaccgag accacgagcg cgatcctgat caccccccgag ggggacgaca 1140 agccgggcgc cgtgggcaag gtggtcccgt tcttcgaggc caaggtggtg gacctggaca 1200
ccggcaagac cctgggcgtg aaccagcggg gcgagctgtg cgtgcggggg ccgatgatca 1260
tgagcggcta cgtgaacaac ccggaggcca ccaacgccct catcgacaag gacggctggc 1320
tgcacagcgg cgacatcgcc tactgggacg aggacgagca cttcttcatc gtcgaccggc 1380
tgaagtcgct gatcaagtac aagggctacc aggtggcgcc ggccgagctg gagagcatcc 1440
tgctccagca ccccaacatc ttcgacgccg gcgtggccgg gctgccggac gacgacgccg 1500
gcgagctgcc ggccgcggtg gtggtgctgg agcacggcaa gaccatgacg gagaaggaga 1560
tcgtcgacta cgtggccagc caggtgacca ccgccaagaa gctgcggggc ggcgtggtgt 1620
tcgtggacga ggtcccgaag ggcctgaccg ggaagctcga cgcccggaag atccgcgaga 1680

```
tcctgatcaa ggccaagaag ggcggcaaga tcgccgtgta agactagtgc atcacattta   1740
aaagcatctc agcctaccat gagaataaga gaaagaaaat gaagatcaat agcttattca   1800
tctctttttc tttttcgttg gtgtaaagcc aacaccctgt ctaaaaaaca taaatttctt   1860
taatcatttt gcctcttttc tctgtgcttc aattaataaa aaatggaaag aacctagatc   1920
taaaaaaaaa aaaaaaaaaa aaaaaaaaaa aaaaaaaaaa aaaaaaaaaa aaaaaaaaaa   1980
aaaaatgcat cccccccccc cccccccccc cccccccccc caaaggctct tttcagagcc   2040
accagaatt                                                           2049
```

<210> SEQ ID NO 1402
<211> LENGTH: 2035
<212> TYPE: DNA
<213> ORGANISM: Artificial Sequence
<220> FEATURE:
<223> OTHER INFORMATION: ASAH1 PpLuc(GC) albumin7 A64N64

<400> SEQUENCE: 1402

```
gggcctctgc tggagtccgg ggagtggcgt tggctgctag agcgaagctt gaggatggag     60
gacgccaaga acatcaagaa gggcccggcg cccttctacc cgctggagga cgggaccgcc    120
ggcgagcagc tccacaaggc catgaagcgg tacgccctgg tgccgggcac gatcgccttc    180
accgacgccc acatcgaggt cgacatcacc tacgcggagt acttcgagat gagcgtgcgc    240
ctggccgagg ccatgaagcg gtacggcctg aacaccaacc accggatcgt ggtgtgctcg    300
gagaacagcc tgcagttctt catgccggtg ctgggcgccc tcttcatcgg cgtggccgtc    360
gccccggcga acgacatcta caacgagcgg gagctgctga acagcatggg gatcagccag    420
ccgaccgtgg tgttcgtgag caagaagggc ctgcagaaga tcctgaacgt gcagaagaag    480
ctgcccatca tccagaagat catcatcatg gacagcaaga ccgactacca gggcttccag    540
tcgatgtaca cgttcgtgac cagccacctc ccgccgggct tcaacgagta cgacttcgtc    600
ccggagagct tcgaccggga caagaccatc gccctgatca tgaacagcag cggcagcacc    660
ggcctgccga agggggtggc cctgccgcac cggaccgcct gcgtgcgctt ctcgcacgcc    720
cgggacccca tcttcggcaa ccagatcatc ccggacaccg ccatcctgag cgtggtgccg    780
ttccaccacg gcttcggcat gttcacgacc ctgggctacc tcatctgcgg cttccgggtg    840
gtcctgatgt accggttcga ggaggagctg ttcctgcgga gcctgcagga ctacaagatc    900
cagagcgcgc tgctcgtgcc gaccctgttc agcttcttcg ccaagagcac cctgatcgac    960
aagtacgacc tgtcgaacct gcacgagatc gccagcgggg gcgccccgct gagcaaggag   1020
gtgggcgagg ccgtggccaa gcggttccac ctcccgggca tccgccaggg ctacggcctg   1080
accgagacca cgagcgcgat cctgatcacc cccgaggggg acgacaagcc gggcgccgtg   1140
ggcaaggtgg tcccgttctt cgaggccaag gtggtggacc tggacaccgg caagaccctg   1200
ggcgtgaacc agcggggcga gctgtgcgtg cgggggccga tgatcatgag cggctacgtg   1260
aacaacccgg aggccaccaa cgccctcatc gacaaggacg gctggctgca cagcggcgac   1320
atcgcctact gggacgagga cgagcacttc ttcatcgtcg accggctgaa gtcgctgatc   1380
aagtacaagg gctaccaggt ggcgccggcc gagctggaga gcatcctgct ccagcacccc   1440
aacatcttcg acgccggcgt ggccgggctg ccggacgacg acgccggcga gctgccggcc   1500
gcggtggtgg tgctggagca cggcaagacc atgacggaga aggagatcgt cgactacgtg   1560
gccagccagg tgaccaccgc caagaagctg cggggcggcg tggtgttcgt ggacgaggtc   1620
ccgaagggcc tgaccgggaa gctcgacgcc cggaagatcc gcgagatcct gatcaaggcc   1680
```

aagaagggcg gcaagatcgc cgtgtaagac tagtgcatca catttaaaag catctcagcc 1740
taccatgaga ataagagaaa gaaaatgaag atcaatagct tattcatctc tttttctttt 1800
tcgttggtgt aaagccaaca ccctgtctaa aaaacataaa tttctttaat cattttgcct 1860
cttttctctg tgcttcaatt aataaaaaat ggaaagaacc tagatctaaa aaaaaaaaaa 1920
aaaaaaaaaa aaaaaaaaaa aaaaaaaaaa aaaaaaaaaa aaaaaaaaaa atgcatcccc 1980
cccccccccc cccccccccc cccccccaaa ggctcttttc agagccacca gaatt 2035

<210> SEQ ID NO 1403
<211> LENGTH: 2027
<212> TYPE: DNA
<213> ORGANISM: Artificial Sequence
<220> FEATURE:
<223> OTHER INFORMATION: mRPL21 PpLuc(GC) albumin7 A64N64

<400> SEQUENCE: 1403
ggggccgccg cagccatctt ccagtaactc gccaaaaagc ttgaggatgg aggacgccaa 60
gaacatcaag aagggcccgg cgcccttcta cccgctggag gacgggaccg ccggcgagca 120
gctccacaag gccatgaagc ggtacgccct ggtgccgggc acgatcgcct tcaccgacgc 180
ccacatcgag gtcgacatca cctacgcgga gtacttcgag atgagcgtgc gcctggccga 240
ggccatgaag cggtacggcc tgaacaccaa ccaccggatc gtggtgtgct cggagaacag 300
cctgcagttc ttcatgccgg tgctgggcgc cctcttcatc ggcgtggccg tcgccccggc 360
gaacgacatc tacaacgagc gggagctgct gaacagcatg gggatcagcc agccgaccgt 420
ggtgttcgtg agcaagaagg gcctgcagaa gatcctgaac gtgcagaaga agctgcccat 480
catccagaag atcatcatca tggacagcaa gaccgactac cagggcttcc agtcgatgta 540
cacgttcgtg accagccacc tcccgccggg cttcaacgag tacgacttcg tcccggagag 600
cttcgaccgg gacaagacca tcgccctgat catgaacagc agcggcagca ccggcctgcc 660
gaagggggtg gccctgccgc accggaccgc ctgcgtgcgc ttctcgcacg cccgggaccc 720
catcttcggc aaccagatca tcccggacac cgccatcctg agcgtggtgc cgttccacca 780
cggcttcggc atgttcacga ccctgggcta cctcatctgc ggcttccggg tggtcctgat 840
gtaccggttc gaggaggagc tgttcctgcg gagcctgcag gactacaaga tccagagcgc 900
gctgctcgtg ccgaccctgt tcagcttctt cgccaagagc accctgatcg acaagtacga 960
cctgtcgaac ctgcacgaga tcgccagcgg gggcgccccg ctgagcaagg aggtgggcga 1020
ggccgtggcc aagcggttcc acctcccggg catccgccag ggctacggcc tgaccgagac 1080
cacgagcgcg atcctgatca cccccgaggg ggacgacaag ccgggcgccg tgggcaaggt 1140
ggtcccgttc ttcgaggcca aggtggtgga cctggacacc ggcaagaccc tgggcgtgaa 1200
ccagcggggc gagctgtgcg tgcgggggcc gatgatcatg agcggctacg tgaacaaccc 1260
ggaggccacc aacgccctca tcgacaagga cggctggctg cacagcggcg acatcgccta 1320
ctgggacgag gacgagcact tcttcatcgt cgaccggctg aagtcgctga tcaagtacaa 1380
gggctaccag gtggcgccgg ccgagctgga gagcatcctg ctccagcacc ccaacatctt 1440
cgacgccggc gtggccgggc tgccggacga cgacgccggc gagctgccgg ccgcggtggt 1500
ggtgctggag cacggcaaga ccatgacgga gaaggagatc gtcgactacg tggccagcca 1560
ggtgaccacc gccaagaagc tgcggggcgg cgtggtgttc gtggacgagg tcccgaaggg 1620
cctgaccggg aagctcgacg cccggaagat ccgcgagatc ctgatcaagg ccaagaaggg 1680

-continued

```
cggcaagatc gccgtgtaag actagtgcat cacatttaaa agcatctcag cctaccatga   1740

gaataagaga aagaaaatga agatcaatag cttattcatc tctttttctt tttcgttggt   1800

gtaaagccaa caccctgtct aaaaaacata aatttcttta atcattttgc ctcttttctc   1860

tgtgcttcaa ttaataaaaa atggaaagaa cctagatcta aaaaaaaaaa aaaaaaaaaa   1920

aaaaaaaaaa aaaaaaaaaa aaaaaaaaaa aaaaaaaaaa aaatgcatcc cccccccccc   1980

cccccccccc cccccccccca aaggctcttt tcagagccac cagaatt               2027
```

<210> SEQ ID NO 1404
<211> LENGTH: 2046
<212> TYPE: DNA
<213> ORGANISM: Artificial Sequence
<220> FEATURE:
<223> OTHER INFORMATION: mRPL35A PpLuc(GC) albumin7 A64N64

<400> SEQUENCE: 1404

```
gggccatctt ggcgcctgtg gaggcctgct gggaacagga cttctaacag caagtaagct     60

tgaggatgga ggacgccaag aacatcaaga agggcccggc gcccttctac ccgctggagg    120

acgggaccgc cggcgagcag ctccacaagg ccatgaagcg gtacgccctg gtgccgggca    180

cgatcgcctt caccgacgcc cacatcgagg tcgacatcac ctacgcggag tacttcgaga    240

tgagcgtgcg cctggccgag gccatgaagc ggtacggcct gaacaccaac caccggatcg    300

tggtgtgctc ggagaacagc ctgcagttct tcatgccggt gctgggcgcc ctcttcatcg    360

gcgtggccgt cgccccggcg aacgacatct acaacgagcg ggagctgctg aacagcatgg    420

ggatcagcca gccgaccgtg gtgttcgtga gcaagaaggg cctgcagaag atcctgaacg    480

tgcagaagaa gctgcccatc atccagaaga tcatcatcat ggacagcaag accgactacc    540

agggcttcca gtcgatgtac acgttcgtga ccagccacct cccgccgggc ttcaacgagt    600

acgacttcgt cccggagagc ttcgaccggg acaagaccat cgccctgatc atgaacagca    660

gcggcagcac cggcctgccg aagggggtgg ccctgccgca ccggaccgcc tgcgtgcgct    720

tctcgcacgc ccgggacccc atcttcggca accagatcat cccggacacc gccatcctga    780

gcgtggtgcc gttccaccac ggcttcggca tgttcacgac cctgggctac ctcatctgcg    840

gcttccgggt ggtcctgatg taccggttcg aggaggagct gttcctgcgg agcctgcagg    900

actacaagat ccagagcgcg ctgctcgtgc cgaccctgtt cagcttcttc gccaagagca    960

ccctgatcga caagtacgac ctgtcgaacc tgcacgagat cgccagcggg ggcgccccgc   1020

tgagcaagga ggtgggcgag gccgtggcca agcggttcca cctcccgggc atccgccagg   1080

gctacggcct gaccgagacc acgagcgcga tcctgatcac ccccgagggg gacgacaagc   1140

cgggcgccgt gggcaaggtg gtcccgttct tcgaggccaa ggtggtggac ctggacaccg   1200

gcaagaccct gggcgtgaac cagcggggcg agctgtgcgt gcgggggccg atgatcatga   1260

gcggctacgt gaacaacccg gaggccacca acgccctcat cgacaaggac ggctggctgc   1320

acagcggcga catcgcctac tgggacgagg acgagcactt cttcatcgtc gaccggctga   1380

agtcgctgat caagtacaag ggctaccagg tggcgccggc cgagctggag agcatcctgc   1440

tccagcaccc caacatcttc gacgccggcg tggccgggct gccggacgac gacgccggcg   1500

agctgccggc cgcggtggtg gtgctggagc acggcaagac catgacggag aaggagatcg   1560

tcgactacgt ggccagccag gtgaccaccg ccaagaagct gcggggcggc gtggtgttcg   1620

tggacgaggt cccgaagggc ctgaccggga agctcgacgc ccggaagatc cgcgagatcc   1680

tgatcaaggc caagaagggc ggcaagatcg ccgtgtaaga ctagtgcatc acatttaaaa   1740
```

gcatctcagc ctaccatgag aataagagaa agaaaatgaa gatcaatagc ttattcatct 1800
ctttttcttt ttcgttggtg taaagccaac accctgtcta aaaaacataa atttctttaa 1860
tcattttgcc tcttttctct gtgcttcaat taataaaaaa tggaaagaac ctagatctaa 1920
aaaaaaaaaa aaaaaaaaaa aaaaaaaaaa aaaaaaaaaa aaaaaaaaaa aaaaaaaaaa 1980
aatgcatccc cccccccccc cccccccccc cccccccaa aggctctttt cagagccacc 2040
agaatt 2046

<210> SEQ ID NO 1405
<211> LENGTH: 1840
<212> TYPE: DNA
<213> ORGANISM: Artificial Sequence
<220> FEATURE:
<223> OTHER INFORMATION: RPL35 PpLuc(GC) A64N64

<400> SEQUENCE: 1405
ggggagcggg cggcggcgtt ggcggcttgt gcagcaaagc ttgaggatgg aggacgccaa 60
gaacatcaag aagggcccgg cgcccttcta cccgctggag gacgggaccg ccggcgagca 120
gctccacaag gccatgaagc ggtacgccct ggtgccgggc acgatcgcct tcaccgacgc 180
ccacatcgag gtcgacatca cctacgcgga gtacttcgag atgagcgtgc gcctggccga 240
ggccatgaag cggtacggcc tgaacaccaa ccaccggatc gtggtgtgct cggagaacag 300
cctgcagttc ttcatgccgg tgctgggcgc cctcttcatc ggcgtggccg tcgccccggc 360
gaacgacatc tacaacgagc gggagctgct gaacagcatg gggatcagcc agccgaccgt 420
ggtgttcgtg agcaagaagg gcctgcagaa gatcctgaac gtgcagaaga agctgcccat 480
catccagaag atcatcatca tggacagcaa gaccgactac cagggcttcc agtcgatgta 540
cacgttcgtg accagccacc tcccgccggg cttcaacgag tacgacttcg tcccggagag 600
cttcgaccgg gacaagacca tcgccctgat catgaacagc agcggcagca ccggcctgcc 660
gaagggggtg gccctgccgc accggaccgc ctgcgtgcgc ttctcgcacg cccgggaccc 720
catcttcggc aaccagatca tcccggacac cgccatcctg agcgtggtgc cgttccacca 780
cggcttcggc atgttcacga ccctgggcta cctcatctgc ggcttccggg tggtcctgat 840
gtaccggttc gaggaggagc tgttcctgcg gagcctgcag gactacaaga tccagagcgc 900
gctgctcgtg ccgaccctgt tcagcttctt cgccaagagc accctgatcg acaagtacga 960
cctgtcgaac ctgcacgaga tcgccagcgg gggcgccccg ctgagcaagg aggtgggcga 1020
ggccgtggcc aagcggttcc acctcccggg catccgccag ggctacggcc tgaccgagac 1080
cacgagcgcg atcctgatca cccccgaggg ggacgacaag ccgggcgccg tgggcaaggt 1140
ggtcccgttc ttcgaggcca aggtggtgga cctggacacc ggcaagaccc tgggcgtgaa 1200
ccagcggggc gagctgtgcg tgcgggggcc gatgatcatg agcggctacg tgaacaaccc 1260
ggaggccacc aacgccctca tcgacaagga cggctggctg cacagcggcg acatcgccta 1320
ctgggacgag gacgagcact tcttcatcgt cgaccggctg aagtcgctga tcaagtacaa 1380
gggctaccag gtggcgccgg ccgagctgga gagcatcctg ctccagcacc ccaacatctt 1440
cgacgccggc gtggccgggc tgccggacga cgacgccggc gagctgccgg ccgcggtggt 1500
ggtgctggag cacggcaaga ccatgacgga gaaggagatc gtcgactacg tggccagcca 1560
ggtgaccacc gccaagaagc tgcggggcgg cgtggtgttc gtggacgagg tcccgaaggg 1620
cctgaccggg aagctcgacg cccggaagat ccgcgagatc ctgatcaagg ccaagaaggg 1680
cggcaagatc gccgtgtaag actagtagat ctaaaaaaaa aaaaaaaaaa aaaaaaaaaa 1740
aaaaaaaaaa aaaaaaaaaa aaaaaaaaaa aaaaaatgca tccccccccc cccccccccc 1800
cccccccccc ccaaaggctc ttttcagagc caccagaatt 1840

<210> SEQ ID NO 1406
<211> LENGTH: 1840
<212> TYPE: DNA
<213> ORGANISM: Artificial Sequence
<220> FEATURE:
<223> OTHER INFORMATION: RPL21 PpLuc(GC) A64N64

<400> SEQUENCE: 1406
ggggccggaa ccgccatctt ccagtaattc gccaaaaagc ttgaggatgg aggacgccaa 60
gaacatcaag aagggcccgg cgcccttcta cccgctggag gacgggaccg ccggcgagca 120
gctccacaag gccatgaagc ggtacgccct ggtgccgggc acgatcgcct tcaccgacgc 180
ccacatcgag gtcgacatca cctacgcgga gtacttcgag atgagcgtgc gcctggccga 240
ggccatgaag cggtacggcc tgaacaccaa ccaccggatc gtggtgtgct cggagaacag 300
cctgcagttc ttcatgccgg tgctgggcgc cctcttcatc ggcgtggccg tcgccccggc 360
gaacgacatc tacaacgagc gggagctgct gaacagcatg gggatcagcc agccgaccgt 420
ggtgttcgtg agcaagaagg gcctgcagaa gatcctgaac gtgcagaaga agctgcccat 480
catccagaag atcatcatca tggacagcaa gaccgactac cagggcttcc agtcgatgta 540
cacgttcgtg accagccacc tcccgccggg cttcaacgag tacgacttcg tcccggagag 600
cttcgaccgg gacaagacca tcgccctgat catgaacagc agcggcagca ccggcctgcc 660
gaagggggtg gccctgccgc accggaccgc ctgcgtgcgc ttctcgcacg cccgggaccc 720
catcttcggc aaccagatca tcccggacac cgccatcctg agcgtggtgc cgttccacca 780
cggcttcggc atgttcacga ccctgggcta cctcatctgc ggcttccggg tggtcctgat 840
gtaccggttc gaggaggagc tgttcctgcg gagcctgcag gactacaaga tccagagcgc 900
gctgctcgtg ccgaccctgt tcagcttctt cgccaagagc accctgatcg acaagtacga 960
cctgtcgaac ctgcacgaga tcgccagcgg gggcgccccg ctgagcaagg aggtgggcga 1020
ggccgtggcc aagcggttcc acctcccggg catccgccag ggctacggcc tgaccgagac 1080
cacgagcgcg atcctgatca cccccgaggg ggacgacaag ccgggcgccg tgggcaaggt 1140
ggtcccgttc ttcgaggcca aggtggtgga cctggacacc ggcaagaccc tgggcgtgaa 1200
ccagcggggc gagctgtgcg tgcgggggcc gatgatcatg agcggctacg tgaacaaccc 1260
ggaggccacc aacgccctca tcgacaagga cggctggctg cacagcggcg acatcgccta 1320
ctgggacgag gacgagcact tcttcatcgt cgaccggctg aagtcgctga tcaagtacaa 1380
gggctaccag gtggcgccgg ccgagctgga gagcatcctg ctccagcacc ccaacatctt 1440
cgacgccggc gtggccgggc tgccggacga cgacgccggc gagctgccgg ccgcggtggt 1500
ggtgctggag cacggcaaga ccatgacgga gaaggagatc gtcgactacg tggccagcca 1560
ggtgaccacc gccaagaagc tgcggggcgg cgtggtgttc gtggacgagg tcccgaaggg 1620
cctgaccggg aagctcgacg cccggaagat ccgcgagatc ctgatcaagg ccaagaaggg 1680
cggcaagatc gccgtgtaag actagtagat ctaaaaaaaa aaaaaaaaaa aaaaaaaaaa 1740
aaaaaaaaaa aaaaaaaaaa aaaaaaaaaa aaaaaatgca tccccccccc cccccccccc 1800
cccccccccc ccaaaggctc ttttcagagc caccagaatt 1840

<210> SEQ ID NO 1407
<211> LENGTH: 1881
<212> TYPE: DNA
<213> ORGANISM: Artificial Sequence
<220> FEATURE:
<223> OTHER INFORMATION: ATP5A1 PpLuc(GC) A64N64

<400> SEQUENCE: 1407

```
gggcggctcg gccattttgt cccagtcagt ccggaggctg cggctgcaga agtaccgcct     60
gcggagtaac tgcaaagaag cttgaggatg gaggacgcca agaacatcaa gaagggcccg    120
gcgcccttct acccgctgga ggacgggacc gccggcgagc agctccacaa ggccatgaag    180
cggtacgccc tggtgccggg cacgatcgcc ttcaccgacg cccacatcga ggtcgacatc    240
acctacgcgg agtacttcga gatgagcgtg cgcctggccg aggccatgaa gcggtacggc    300
ctgaacacca accaccggat cgtggtgtgc tcggagaaca gcctgcagtt cttcatgccg    360
gtgctgggcg ccctcttcat cggcgtggcc gtcgccccgg cgaacgacat ctacaacgag    420
cgggagctgc tgaacagcat ggggatcagc cagccgaccg tggtgttcgt gagcaagaag    480
ggcctgcaga agatcctgaa cgtgcagaag aagctgccca tcatccagaa gatcatcatc    540
atggacagca agaccgacta ccagggcttc cagtcgatgt acacgttcgt gaccagccac    600
ctcccgccgg gcttcaacga gtacgacttc gtcccggaga gcttcgaccg ggacaagacc    660
atcgccctga tcatgaacag cagcggcagc accggcctgc cgaagggggt ggccctgccg    720
caccggaccg cctgcgtgcg cttctcgcac gcccgggacc ccatcttcgg caaccagatc    780
atcccggaca ccgccatcct gagcgtggtg ccgttccacc acggcttcgg catgttcacg    840
accctgggct acctcatctg cggcttccgg gtggtcctga tgtaccggtt cgaggaggag    900
ctgttcctgc ggagcctgca ggactacaag atccagagcg cgctgctcgt gccgaccctg    960
ttcagcttct tcgccaagag caccctgatc gacaagtacg acctgtcgaa cctgcacgag   1020
atcgccagcg gggcgccccc gctgagcaag gaggtgggcg aggccgtggc caagcggttc   1080
cacctcccgg gcatccgcca gggctacggc ctgaccgaga ccacgagcgc gatcctgatc   1140
acccccgagg gggacgacaa gccgggcgcc gtgggcaagg tggtcccgtt cttcgaggcc   1200
aaggtggtgg acctggacac cggcaagacc ctgggcgtga accagcgggg cgagctgtgc   1260
gtgcgggggc cgatgatcat gagcggctac gtgaacaacc cggaggccac caacgccctc   1320
atcgacaagg acggctggct gcacagcggc gacatcgcct actgggacga ggacgagcac   1380
ttcttcatcg tcgaccggct gaagtcgctg atcaagtaca agggctacca ggtggcgccg   1440
gccgagctgg agagcatcct gctccagcac cccaacatct tcgacgccgg cgtggccggg   1500
ctgccggacg acgacgccgg cgagctgccg gccgcggtgg tggtgctgga gcacggcaag   1560
accatgacgg agaaggagat cgtcgactac gtggccagcc aggtgaccac cgccaagaag   1620
ctgcggggcg gcgtggtgtt cgtggacgag gtcccgaagg gcctgaccgg gaagctcgac   1680
gcccggaaga tccgcgagat cctgatcaag gccaagaagg gcggcaagat cgccgtgtaa   1740
gactagtaga tctaaaaaaa aaaaaaaaaa aaaaaaaaaa aaaaaaaaaa aaaaaaaaaa   1800
aaaaaaaaaa aaaaaaatgc atcccccccc cccccccccc cccccccccc cccaaaggct   1860
cttttcagag ccaccagaat t                                             1881
```

<210> SEQ ID NO 1408
<211> LENGTH: 1868
<212> TYPE: DNA
<213> ORGANISM: Artificial Sequence
<220> FEATURE:

<223> OTHER INFORMATION: HSD17B4 PpLuc(GC) A64N64

<400> SEQUENCE: 1408
gggtcccgca gtcggcgtcc agcggctctg cttgttcgtg tgtgtgtcgt tgcaggcctt 60
attcaagctt gaggatggag gacgccaaga acatcaagaa gggcccggcg cccttctacc 120
cgctggagga cgggaccgcc ggcgagcagc tccacaaggc catgaagcgg tacgccctgg 180
tgccgggcac gatcgccttc accgacgccc acatcgaggt cgacatcacc tacgcggagt 240
acttcgagat gagcgtgcgc ctggccgagg ccatgaagcg gtacggcctg aacaccaacc 300
accggatcgt ggtgtgctcg gagaacagcc tgcagttctt catgccggtg ctgggcgccc 360
tcttcatcgg cgtggccgtc gccccggcga acgacatcta caacgagcgg gagctgctga 420
acagcatggg gatcagccag ccgaccgtgg tgttcgtgag caagaagggc ctgcagaaga 480
tcctgaacgt gcagaagaag ctgcccatca tccagaagat catcatcatg gacagcaaga 540
ccgactacca gggcttccag tcgatgtaca cgttcgtgac cagccacctc ccgccgggct 600
tcaacgagta cgacttcgtc ccggagagct tcgaccggga caagaccatc gccctgatca 660
tgaacagcag cggcagcacc ggcctgccga agggggtggc cctgccgcac cggaccgcct 720
gcgtgcgctt ctcgcacgcc cgggacccca tcttcggcaa ccagatcatc ccggacaccg 780
ccatcctgag cgtggtgccg ttccaccacg gcttcggcat gttcacgacc ctgggctacc 840
tcatctgcgg cttccgggtg gtcctgatgt accggttcga ggaggagctg ttcctgcgga 900
gcctgcagga ctacaagatc cagagcgcgc tgctcgtgcc gaccctgttc agcttcttcg 960
ccaagagcac cctgatcgac aagtacgacc tgtcgaacct gcacgagatc gccagcgggg 1020
gcgccccgct gagcaaggag gtgggcgagg ccgtggccaa gcggttccac ctcccgggca 1080
tccgccaggg ctacggcctg accgagacca cgagcgcgat cctgatcacc cccgaggggg 1140
acgacaagcc gggcgccgtg ggcaaggtgg tcccgttctt cgaggccaag gtggtggacc 1200
tggacaccgg caagaccctg ggcgtgaacc agcggggcga gctgtgcgtg cgggggccga 1260
tgatcatgag cggctacgtg aacaacccgg aggccaccaa cgccctcatc gacaaggacg 1320
gctggctgca cagcggcgac atcgcctact gggacgagga cgagcacttc ttcatcgtcg 1380
accggctgaa gtcgctgatc aagtacaagg gctaccaggt ggcgccggcc gagctggaga 1440
gcatcctgct ccagcacccc aacatcttcg acgccggcgt ggccgggctg ccggacgacg 1500
acgccggcga gctgccggcc gcggtggtgg tgctggagca cggcaagacc atgacggaga 1560
aggagatcgt cgactacgtg gccagccagg tgaccaccgc caagaagctg cggggcggcg 1620
tggtgttcgt ggacgaggtc ccgaagggcc tgaccgggaa gctcgacgcc cggaagatcc 1680
gcgagatcct gatcaaggcc aagaagggcg gcaagatcgc cgtgtaagac tagtagatct 1740
aaaaaaaaaa aaaaaaaaaa aaaaaaaaaa aaaaaaaaaa aaaaaaaaaa aaaaaaaaaa 1800
aaaatgcatc cccccccccc cccccccccc cccccccccc aaaggctctt ttcagagcca 1860
ccagaatt 1868

<210> SEQ ID NO 1409
<211> LENGTH: 1837
<212> TYPE: DNA
<213> ORGANISM: Artificial Sequence
<220> FEATURE:
<223> OTHER INFORMATION: AIG1 PpLuc(GC) A64N64

<400> SEQUENCE: 1409
gggccgccca gccggtccag gcctctggcg aacaagcttg aggatggagg acgccaagaa 60
catcaagaag ggcccggcgc ccttctaccc gctggaggac gggaccgccg gcgagcagct 120
ccacaaggcc atgaagcggt acgccctggt gccgggcacg atcgccttca ccgacgccca 180
catcgaggtc gacatcacct acgcggagta cttcgagatg agcgtgcgcc tggccgaggc 240
catgaagcgg tacggcctga acaccaacca ccggatcgtg gtgtgctcgg agaacagcct 300
gcagttcttc atgccggtgc tgggcgccct cttcatcggc gtggccgtcg ccccggcgaa 360
cgacatctac aacgagcggg agctgctgaa cagcatgggg atcagccagc cgaccgtggt 420
gttcgtgagc aagaagggcc tgcagaagat cctgaacgtg cagaagaagc tgcccatcat 480
ccagaagatc atcatcatgg acagcaagac cgactaccag ggcttccagt cgatgtacac 540
gttcgtgacc agccacctcc cgccgggctt caacgagtac gacttcgtcc cggagagctt 600
cgaccgggac aagaccatcg ccctgatcat gaacagcagc ggcagcaccg gcctgccgaa 660
gggggtggcc ctgccgcacc ggaccgcctg cgtgcgcttc tcgcacgccc gggaccccat 720
cttcggcaac cagatcatcc cggacaccgc catcctgagc gtggtgccgt tccaccacgg 780
cttcggcatg ttcacgaccc tgggctacct catctgcggc ttccgggtgg tcctgatgta 840
ccggttcgag gaggagctgt tcctgcggag cctgcaggac tacaagatcc agagcgcgct 900
gctcgtgccg accctgttca gcttcttcgc caagagcacc ctgatcgaca agtacgacct 960
gtcgaacctg cacgagatcg ccagcggggg cgccccgctg agcaaggagg tgggcgaggc 1020
cgtggccaag cggttccacc tcccgggcat ccgccagggc tacggcctga ccgagaccac 1080
gagcgcgatc ctgatcaccc ccgaggggga cgacaagccg ggcgccgtgg gcaaggtggt 1140
cccgttcttc gaggccaagg tggtggacct ggacaccggc aagaccctgg gcgtgaacca 1200
gcggggcgag ctgtgcgtgc gggggccgat gatcatgagc ggctacgtga acaacccgga 1260
ggccaccaac gccctcatcg acaaggacgg ctggctgcac agcggcgaca tcgcctactg 1320
ggacgaggac gagcacttct tcatcgtcga ccggctgaag tcgctgatca agtacaaggg 1380
ctaccaggtg gcgccggccg agctggagag catcctgctc cagcacccca acatcttcga 1440
cgccggcgtg gccgggctgc cggacgacga cgccggcgag ctgccggccg cggtggtggt 1500
gctggagcac ggcaagacca tgacggagaa ggagatcgtc gactacgtgg ccagccaggt 1560
gaccaccgcc aagaagctgc ggggcggcgt ggtgttcgtg gacgaggtcc cgaagggcct 1620
gaccgggaag ctcgacgccc ggaagatccg cgagatcctg atcaaggcca agaagggcgg 1680
caagatcgcc gtgtaagact agtagatcta aaaaaaaaaa aaaaaaaaaa aaaaaaaaaa 1740
aaaaaaaaaa aaaaaaaaaa aaaaaaaaaa aaatgcatcc cccccccccc cccccccccc 1800
ccccccccca aaggctcttt tcagagccac cagaatt 1837

<210> SEQ ID NO 1410
<211> LENGTH: 1862
<212> TYPE: DNA
<213> ORGANISM: Artificial Sequence
<220> FEATURE:
<223> OTHER INFORMATION: COX6C PpLuc(GC) A64N64

<400> SEQUENCE: 1410
ggagtcagga aggacgttgg tgttgaggtt agcatacgta tcaaggacag taactaccaa 60
gcttgaggat ggaggacgcc aagaacatca agaagggccc ggcgcccttc tacccgctgg 120
aggacgggac cgccggcgag cagctccaca aggccatgaa gcggtacgcc ctggtgccgg 180
gcacgatcgc cttcaccgac gcccacatcg aggtcgacat cacctacgcg gagtacttcg 240

-continued

```
agatgagcgt gcgcctggcc gaggccatga agcggtacgg cctgaacacc aaccaccgga    300

tcgtggtgtg ctcggagaac agcctgcagt tcttcatgcc ggtgctgggc gccctcttca    360

tcggcgtggc cgtcgccccg gcgaacgaca tctacaacga gcgggagctg ctgaacagca    420

tggggatcag ccagccgacc gtggtgttcg tgagcaagaa gggcctgcag aagatcctga    480

acgtgcagaa gaagctgccc atcatccaga agatcatcat catggacagc aagaccgact    540

accagggctt ccagtcgatg tacacgttcg tgaccagcca cctcccgccg ggcttcaacg    600

agtacgactt cgtcccggag agcttcgacc gggacaagac catcgccctg atcatgaaca    660

gcagcggcag caccggcctg ccgaaggggg tggccctgcc gcaccggacc gcctgcgtgc    720

gcttctcgca cgcccgggac cccatcttcg gcaaccagat catcccggac accgccatcc    780

tgagcgtggt gccgttccac cacggcttcg gcatgttcac gaccctgggc tacctcatct    840

gcggcttccg ggtggtcctg atgtaccggt tcgaggagga gctgttcctg cggagcctgc    900

aggactacaa gatccagagc gcgctgctcg tgccgaccct gttcagcttc ttcgccaaga    960

gcaccctgat cgacaagtac gacctgtcga acctgcacga gatcgccagc gggggcgccc   1020

cgctgagcaa ggaggtgggc gaggccgtgg ccaagcggtt ccacctcccg ggcatccgcc   1080

agggctacgg cctgaccgag accacgagcg cgatcctgat cacccccgag ggggacgaca   1140

agccgggcgc cgtgggcaag gtggtcccgt tcttcgaggc caaggtggtg gacctggaca   1200

ccggcaagac cctgggcgtg aaccagcggg gcgagctgtg cgtgcggggg ccgatgatca   1260

tgagcggcta cgtgaacaac ccggaggcca ccaacgccct catcgacaag gacggctggc   1320

tgcacagcgg cgacatcgcc tactgggacg aggacgagca cttcttcatc gtcgaccggc   1380

tgaagtcgct gatcaagtac aagggctacc aggtggcgcc ggccgagctg gagagcatcc   1440

tgctccagca ccccaacatc ttcgacgccg gcgtggccgg gctgccggac gacgacgccg   1500

gcgagctgcc ggccgcggtg gtggtgctgg agcacggcaa gaccatgacg gagaaggaga   1560

tcgtcgacta cgtggccagc caggtgacca ccgccaagaa gctgcggggc ggcgtggtgt   1620

tcgtggacga ggtcccgaag ggcctgaccg ggaagctcga cgcccggaag atccgcgaga   1680

tcctgatcaa ggccaagaag ggcggcaaga tcgccgtgta agactagtag atctaaaaaa   1740

aaaaaaaaaa aaaaaaaaaa aaaaaaaaaa aaaaaaaaaa aaaaaaaaaa aaaaaaaatg   1800

catccccccc cccccccccc cccccccccc ccccaaaggc tcttttcaga gccaccagaa   1860

tt                                                                  1862
```

<210> SEQ ID NO 1411
<211> LENGTH: 1848
<212> TYPE: DNA
<213> ORGANISM: Artificial Sequence
<220> FEATURE:
<223> OTHER INFORMATION: ASAH1 PpLuc(GC) A64N64

<400> SEQUENCE: 1411

```
gggcctctgc tggagtccgg ggagtggcgt tggctgctag agcgaagctt gaggatggag     60

gacgccaaga acatcaagaa gggcccggcg cccttctacc cgctggagga cgggaccgcc    120

ggcgagcagc tccacaaggc catgaagcgg tacgccctgg tgccgggcac gatcgccttc    180

accgacgccc acatcgaggt cgacatcacc tacgcggagt acttcgagat gagcgtgcgc    240

ctggccgagg ccatgaagcg gtacggcctg aacaccaacc accggatcgt ggtgtgctcg    300

gagaacagcc tgcagttctt catgccggtg ctgggcgccc tcttcatcgg cgtggccgtc    360

gccccggcga acgacatcta caacgagcgg gagctgctga acagcatggg gatcagccag    420
```

-continued

```
ccgaccgtgg tgttcgtgag caagaagggc ctgcagaaga tcctgaacgt gcagaagaag    480

ctgcccatca tccagaagat catcatcatg gacagcaaga ccgactacca gggcttccag    540

tcgatgtaca cgttcgtgac cagccacctc ccgccgggct tcaacgagta cgacttcgtc    600

ccggagagct tcgaccggga caagaccatc gccctgatca tgaacagcag cggcagcacc    660

ggcctgccga agggggtggc cctgccgcac cggaccgcct gcgtgcgctt ctcgcacgcc    720

cgggacccca tcttcggcaa ccagatcatc ccggacaccg ccatcctgag cgtggtgccg    780

ttccaccacg gcttcggcat gttcacgacc ctgggctacc tcatctgcgg cttccgggtg    840

gtcctgatgt accggttcga ggaggagctg ttcctgcgga gcctgcagga ctacaagatc    900

cagagcgcgc tgctcgtgcc gaccctgttc agcttcttcg ccaagagcac cctgatcgac    960

aagtacgacc tgtcgaacct gcacgagatc gccagcgggg gcgccccgct gagcaaggag   1020

gtgggcgagg ccgtggccaa gcggttccac ctcccgggca tccgccaggg ctacggcctg   1080

accgagacca cgagcgcgat cctgatcacc cccgaggggg acgacaagcc gggcgccgtg   1140

ggcaaggtgg tcccgttctt cgaggccaag gtggtggacc tggacaccgg caagaccctg   1200

ggcgtgaacc agcggggcga gctgtgcgtg cgggggccga tgatcatgag cggctacgtg   1260

aacaacccgg aggccaccaa cgccctcatc gacaaggacg gctggctgca cagcggcgac   1320

atcgcctact gggacgagga cgagcacttc ttcatcgtcg accggctgaa gtcgctgatc   1380

aagtacaagg gctaccaggt ggcgccggcc gagctggaga gcatcctgct ccagcacccc   1440

aacatcttcg acgccggcgt ggccgggctg ccggacgacg acgccggcga gctgccggcc   1500

gcggtggtgg tgctggagca cggcaagacc atgacggaga aggagatcgt cgactacgtg   1560

gccagccagg tgaccaccgc caagaagctg cggggcggcg tggtgttcgt ggacgaggtc   1620

ccgaagggcc tgaccgggaa gctcgacgcc cggaagatcc gcgagatcct gatcaaggcc   1680

aagaagggcg gcaagatcgc cgtgtaagac tagtagatct aaaaaaaaaa aaaaaaaaaa   1740

aaaaaaaaaa aaaaaaaaaa aaaaaaaaaa aaaaaaaaaa aaaatgcatc cccccccccc   1800

cccccccccc cccccccccc aaaggctctt ttcagagcca ccagaatt                1848
```

<210> SEQ ID NO 1412
<211> LENGTH: 34
<212> TYPE: DNA
<213> ORGANISM: Artificial Sequence
<220> FEATURE:
<223> OTHER INFORMATION: 5'UTR of human RPL35 lacking the 5' terminal oligopyrimidine tract

<400> SEQUENCE: 1412

```
ggagcgggcg gcggcgttgg cggcttgtgc agca                                 34
```

<210> SEQ ID NO 1413
<211> LENGTH: 34
<212> TYPE: DNA
<213> ORGANISM: Artificial Sequence
<220> FEATURE:
<223> OTHER INFORMATION: 5'UTR of human RPL21 lacking the 5' terminal oligopyrimidine tract

<400> SEQUENCE: 1413

```
ggccggaacc gccatcttcc agtaattcgc caaa                                 34
```

<210> SEQ ID NO 1414
<211> LENGTH: 75
<212> TYPE: DNA

<213> ORGANISM: Artificial Sequence
<220> FEATURE:
<223> OTHER INFORMATION: 5'UTR of human ATP5A1 lacking the 5' terminal
      oligopyrimidine tract

<400> SEQUENCE: 1414
gcggctcggc cattttgtcc cagtcagtcc ggaggctgcg gctgcagaag taccgcctgc     60
ggagtaactg caaag                                                      75

<210> SEQ ID NO 1415
<211> LENGTH: 62
<212> TYPE: DNA
<213> ORGANISM: Artificial Sequence
<220> FEATURE:
<223> OTHER INFORMATION: 5'UTR of human HSD17B4 lacking the 5' terminal
      oligopyrimidine tract

<400> SEQUENCE: 1415
gtcccgcagt cggcgtccag cggctctgct tgttcgtgtg tgtgtcgttg caggccttat     60
tc                                                                    62

<210> SEQ ID NO 1416
<211> LENGTH: 31
<212> TYPE: DNA
<213> ORGANISM: Artificial Sequence
<220> FEATURE:
<223> OTHER INFORMATION: 5'UTR of human AIG1 lacking the 5' terminal
      oligopyrimidine tract

<400> SEQUENCE: 1416
gccgcccagc cggtccaggc ctctggcgaa c                                    31

<210> SEQ ID NO 1417
<211> LENGTH: 56
<212> TYPE: DNA
<213> ORGANISM: Artificial Sequence
<220> FEATURE:
<223> OTHER INFORMATION: 5'UTR of human COX6C lacking the 5' terminal
      oligopyrimidine tract

<400> SEQUENCE: 1417
agtcaggaag gacgttggtg ttgaggttag catacgtatc aaggacagta actacc         56

<210> SEQ ID NO 1418
<211> LENGTH: 42
<212> TYPE: DNA
<213> ORGANISM: Artificial Sequence
<220> FEATURE:
<223> OTHER INFORMATION: 5'UTR of human ASAH1 lacking the 5' terminal
      oligopyrimidine tract

<400> SEQUENCE: 1418
gcctctgctg gagtccgggg agtggcgttg gctgctagag cg                        42

<210> SEQ ID NO 1419
<211> LENGTH: 34
<212> TYPE: DNA
<213> ORGANISM: Artificial Sequence
<220> FEATURE:
<223> OTHER INFORMATION: 5'UTR of mouse mRPL21 lacking the 5' terminal
      oligopyrimidine tract

<400> SEQUENCE: 1419
ggccgccgca gccatcttcc agtaactcgc caaa                                 34

-continued

```
<210> SEQ ID NO 1420
<211> LENGTH: 53
<212> TYPE: DNA
<213> ORGANISM: Artificial Sequence
<220> FEATURE:
<223> OTHER INFORMATION: 5'UTR of mouse mRPL35A lacking the 5' terminal
      oligopyrimidine tract

<400> SEQUENCE: 1420

gccatcttgg cgcctgtgga ggcctgctgg gaacaggact tctaacagca agt           53


<210> SEQ ID NO 1421
<211> LENGTH: 73
<212> TYPE: DNA
<213> ORGANISM: Artificial Sequence
<220> FEATURE:
<223> OTHER INFORMATION: 5' UTR of mouse ribosomal protein Large 21
      (mRPL21)

<400> SEQUENCE: 1421

tcctcctttc ggccgccgca gccatcttcc agtaactcgc caaaatgcca tcttccagta     60

actcgccaaa atg                                                        73


<210> SEQ ID NO 1422
<211> LENGTH: 68
<212> TYPE: DNA
<213> ORGANISM: Artificial Sequence
<220> FEATURE:
<223> OTHER INFORMATION: 5'UTR of mouse ribosomal protein large 35A
      (mRPL35A)

<400> SEQUENCE: 1422

cttcctcttt ccgccatctt ggcgcctgtg gaggcctgct gggaacagga cttctaacag     60

caagtatg                                                              68
```